US011332791B2

(12) United States Patent
Tynan et al.

(10) Patent No.: US 11,332,791 B2
(45) Date of Patent: May 17, 2022

(54) PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES

(71) Applicant: SEQUENOM, INC., San Diego, CA (US)

(72) Inventors: John Allen Tynan, San Diego, CA (US); Grant Hogg, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 15/261,457

(22) Filed: Sep. 9, 2016

(65) Prior Publication Data

US 2017/0058350 A1    Mar. 2, 2017

Related U.S. Application Data

(63) Continuation of application No. 13/940,162, filed on Jul. 11, 2013.

(60) Provisional application No. 61/721,929, filed on Nov. 2, 2012, provisional application No. 61/671,628, filed on Jul. 13, 2012.

(51) Int. Cl.
| | |
|---|---|
| *C12Q 1/68* | (2018.01) |
| *C12P 19/34* | (2006.01) |
| *C12Q 1/6883* | (2018.01) |
| *C12Q 1/6886* | (2018.01) |
| *C12Q 1/6881* | (2018.01) |

(52) U.S. Cl.
CPC ......... *C12Q 1/6883* (2013.01); *C12Q 1/6881* (2013.01); *C12Q 1/6886* (2013.01); *C12Q 2600/154* (2013.01); *C12Q 2600/156* (2013.01); *C12Q 2600/16* (2013.01)

(58) Field of Classification Search
CPC .......... C12Q 2600/16; C12Q 2537/165; C12Q 1/6827; C12Q 1/6844; C12Q 2537/143
See application file for complete search history.

(56) References Cited

U.S. PATENT DOCUMENTS

| | | |
|---|---|---|
| 4,109,496 A | 8/1978 | Allemann et al. |
| 4,179,337 A | 12/1979 | Davis et al. |
| 4,458,066 A | 7/1984 | Caruthers et al. |
| 4,469,863 A | 9/1984 | Ts'o et al. |
| 4,522,811 A | 6/1985 | Eppstein et al. |
| 4,656,127 A | 4/1987 | Mundy |
| 4,676,980 A | 6/1987 | Segal et al. |
| 4,683,195 A | 7/1987 | Mullis et al. |
| 4,683,202 A | 7/1987 | Mullis |
| 4,851,331 A | 7/1989 | Vary et al. |
| 4,868,103 A | 9/1989 | Stavrianopoulos et al. |
| 4,873,316 A | 10/1989 | Meade et al. |
| 4,965,188 A | 10/1990 | Mullis et al. |
| 5,048,530 A | 9/1991 | Hurwitz et al. |
| 5,075,212 A | 12/1991 | Rotbart et al. |
| 5,118,937 A | 6/1992 | Hillenkamp et al. |
| 5,210,015 A | 5/1993 | Gelfand et al. |
| 5,272,071 A | 12/1993 | Chappel et al. |
| 5,283,317 A | 2/1994 | Saifer et al. |
| 5,487,972 A | 1/1996 | Gelfand et al. |
| 5,492,806 A | 2/1996 | Drmanac et al. |
| 5,525,464 A | 6/1996 | Drmanac et al. |
| 5,536,821 A | 7/1996 | Agrawal et al. |
| 5,541,306 A | 7/1996 | Agrawal et al. |
| 5,547,835 A | 8/1996 | Köster et al. |
| 5,589,330 A | 12/1996 | Shuber |
| 5,605,798 A | 2/1997 | Koester et al. |
| 5,614,622 A | 3/1997 | Iyer et al. |
| 5,631,169 A | 5/1997 | Lakowicz et al. |
| 5,637,683 A | 6/1997 | Usher et al. |
| 5,637,684 A | 6/1997 | Cook et al. |
| 5,656,493 A | 8/1997 | Mullis et al. |
| 5,679,524 A | 10/1997 | Nikiforov et al. |
| 5,691,141 A | 11/1997 | Koester et al. |
| 5,695,940 A | 12/1997 | Drmanac et al. |
| 5,700,922 A | 12/1997 | Cook |
| 5,717,083 A | 2/1998 | Cook et al. |
| 5,719,262 A | 2/1998 | Buchardt et al. |
| 5,720,928 A | 2/1998 | Schwartz |
| 5,739,308 A | 4/1998 | Kandimalla et al. |
| 5,739,314 A | 4/1998 | Roy et al. |

(Continued)

FOREIGN PATENT DOCUMENTS

| | | |
|---|---|---|
| AU | 2009293232 B2 | 9/2015 |
| AU | 2010295968 B2 | 12/2015 |

(Continued)

OTHER PUBLICATIONS

William Brockman et al., "Quality scores and SNP detection in sequencing-by-synthesis systems" Genome research 18.5 (2008): 763-770. (Year: 2008).*
AU 2013290102, "First Examination Report", dated Apr. 19, 2018, 3 pages.
EP 13739590.1, "Communication Pursuant to Article 94(3) EPC", dated Jun. 18, 2018, 5 pages.
JP 2015-521823, "Office Action", dated Apr. 19, 2018, 10 pages.
JP 2016-199141, "Office Action", dated May 28, 2018, 18 pages.
U.S. Appl. No. 14/735,477, Final Office Action dated Mar. 21, 2019, 11 pages.

(Continued)

*Primary Examiner* — Stephen T Kapushoc
(74) *Attorney, Agent, or Firm* — Kilpatrick Townsend & Stockton LLP

(57) ABSTRACT

Provided are compositions and processes that utilize genomic regions that are differentially methylated between a mother and her fetus to separate, isolate or enrich fetal nucleic acid from a maternal sample. The compositions and processes described herein are particularly useful for non-invasive prenatal diagnostics, including the detection of chromosomal aneuploidies.

5 Claims, 49 Drawing Sheets

Specification includes a Sequence Listing.

(56) References Cited

U.S. PATENT DOCUMENTS

| | | |
|---|---|---|
| 5,766,849 A | 6/1998 | McDonough et al. |
| 5,773,601 A | 6/1998 | Agrawal |
| 5,786,146 A | 7/1998 | Herman et al. |
| 5,834,189 A | 11/1998 | Stevens et al. |
| 5,849,483 A | 12/1998 | Shuber |
| 5,849,497 A | 12/1998 | Steinman |
| 5,849,542 A | 12/1998 | Reeve et al. |
| 5,849,546 A | 12/1998 | Sousa et al. |
| 5,851,770 A | 12/1998 | Babon et al. |
| 5,869,242 A | 2/1999 | Kamb et al. |
| 5,876,934 A | 3/1999 | Duthie et al. |
| 5,886,165 A | 3/1999 | Kandimalla et al. |
| 5,891,625 A | 4/1999 | Buchardt et al. |
| 5,908,755 A | 6/1999 | Kumar et al. |
| 5,912,118 A | 6/1999 | Ansorge et al. |
| 5,928,906 A | 7/1999 | Koester et al. |
| 5,929,226 A | 7/1999 | Padmapriya et al. |
| 5,952,174 A | 9/1999 | Nikiforov et al. |
| 5,955,599 A | 9/1999 | Iyer et al. |
| 5,958,692 A | 9/1999 | Cotton et al. |
| 5,962,674 A | 10/1999 | Iyer et al. |
| 5,976,802 A | 11/1999 | Ansorge et al. |
| 5,977,296 A | 11/1999 | Nielsen et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Solderlund et al. |
| 6,013,499 A | 1/2000 | Narumiya et al. |
| 6,017,702 A | 1/2000 | Lee et al. |
| 6,018,041 A | 1/2000 | Drmanac et al. |
| 6,024,925 A | 2/2000 | Little et al. |
| 6,043,031 A | 3/2000 | Köster et al. |
| 6,045,996 A | 4/2000 | Cronin et al. |
| 6,046,005 A | 4/2000 | Ju et al. |
| 6,057,134 A | 5/2000 | Lader et al. |
| 6,057,143 A | 5/2000 | Meyer et al. |
| 6,087,095 A | 7/2000 | Rosenthal et al. |
| 6,107,037 A | 8/2000 | Sousa et al. |
| 6,110,684 A | 8/2000 | Kemper et al. |
| 6,117,992 A | 9/2000 | Iyer et al. |
| 6,136,541 A | 10/2000 | Gulati |
| 6,140,053 A | 10/2000 | Koester |
| 6,140,054 A | 10/2000 | Wittwer et al. |
| 6,140,482 A | 10/2000 | Iyer et al. |
| 6,142,681 A | 11/2000 | Gulati |
| 6,143,496 A | 11/2000 | Brown et al. |
| 6,156,501 A | 12/2000 | McGall et al. |
| 6,183,958 B1 | 2/2001 | Stanton et al. |
| 6,194,144 B1 | 2/2001 | Köster et al. |
| 6,194,180 B1 | 2/2001 | Joyce et al. |
| 6,197,506 B1 | 3/2001 | Fodor et al. |
| 6,210,574 B1 | 4/2001 | Sammons et al. |
| 6,210,891 B1 | 4/2001 | Nyren et al. |
| 6,214,556 B1 | 4/2001 | Olek et al. |
| 6,214,560 B1 | 4/2001 | Yguerabide et al. |
| 6,223,127 B1 | 4/2001 | Berno et al. |
| 6,225,625 B1 | 5/2001 | Pirrung et al. |
| 6,229,911 B1 | 5/2001 | Balaban et al. |
| 6,239,273 B1 | 5/2001 | Pease et al. |
| 6,251,638 B1 | 6/2001 | Umansky et al. |
| 6,258,538 B1 | 7/2001 | Köster et al. |
| 6,258,540 B1 | 7/2001 | Lo et al. |
| 6,297,028 B1 | 10/2001 | Taniguchi et al. |
| 6,326,174 B1 | 12/2001 | Joyce et al. |
| 6,368,834 B1 | 4/2002 | Senapathy et al. |
| 6,440,706 B1 | 8/2002 | Vogelstein et al. |
| 6,468,748 B1 | 10/2002 | Monforte et al. |
| 6,610,492 B1 | 8/2003 | Stanton, Jr. et al. |
| 6,664,056 B2 | 12/2003 | Lo et al. |
| 6,723,513 B2 | 4/2004 | Lexow |
| 6,759,217 B2 | 7/2004 | Kopreski |
| 6,818,394 B1 | 11/2004 | O'Donnell-Maloney et al. |
| 6,884,586 B2 | 4/2005 | Van Ness et al. |
| 6,916,634 B2 | 7/2005 | Kopreski |
| 6,927,028 B2 | 8/2005 | Dennis et al. |
| 6,929,911 B2 | 8/2005 | Oefner et al. |
| 7,081,339 B2 | 7/2006 | Slepnev et al. |
| 7,169,314 B2 | 1/2007 | Quake et al. |
| 7,244,567 B2 | 7/2007 | Chen et al. |
| 7,253,259 B2 | 8/2007 | Otagiri et al. |
| 7,285,422 B1 | 10/2007 | Little et al. |
| 7,468,249 B2 | 12/2008 | Xie et al. |
| 7,655,399 B2 | 2/2010 | Cantor et al. |
| 7,709,194 B2 | 5/2010 | Lo et al. |
| 7,709,262 B2 | 5/2010 | Cantor et al. |
| 7,754,428 B2 | 7/2010 | Lo et al. |
| 7,785,798 B2 | 8/2010 | Cantor et al. |
| 7,901,884 B2 | 3/2011 | Lo et al. |
| 8,195,415 B2 | 6/2012 | Fan et al. |
| 8,476,013 B2 | 7/2013 | Ehrich et al. |
| 8,962,247 B2 | 2/2015 | Ehrich et al. |
| 9,074,013 B2 | 7/2015 | Rehli |
| 9,249,464 B2 | 2/2016 | Rehli |
| 9,926,593 B2 | 3/2018 | Ehrich et al. |
| 10,612,086 B2 | 4/2020 | Ehrich et al. |
| 10,738,358 B2 | 8/2020 | Ehrich et al. |
| 2001/0008615 A1 | 7/2001 | Little et al. |
| 2001/0051341 A1 | 12/2001 | Lo et al. |
| 2002/0006621 A1 | 1/2002 | Bianchi et al. |
| 2003/0022207 A1 | 1/2003 | Balasubramanian et al. |
| 2003/0082600 A1 | 5/2003 | Olek et al. |
| 2003/0087276 A1 | 5/2003 | Kopreski et al. |
| 2003/0096426 A1 | 5/2003 | Little et al. |
| 2003/0180748 A1 | 9/2003 | Braun et al. |
| 2003/0180779 A1 | 9/2003 | Lofton-Day et al. |
| 2003/0211483 A1 | 11/2003 | Schroeder et al. |
| 2003/0211522 A1 | 11/2003 | Landes et al. |
| 2004/0014105 A1 | 1/2004 | Schroeder et al. |
| 2004/0081993 A1 | 4/2004 | Cantor et al. |
| 2004/0115684 A1 | 6/2004 | Costa et al. |
| 2004/0137470 A1 | 7/2004 | Dhallan |
| 2004/0203037 A1 | 10/2004 | Lo et al. |
| 2005/0009059 A1 | 1/2005 | Shapero et al. |
| 2005/0019762 A1 | 1/2005 | Olek et al. |
| 2005/0037388 A1 | 2/2005 | Antonarakis et al. |
| 2005/0059003 A1 | 3/2005 | Enoki et al. |
| 2005/0064406 A1 | 3/2005 | Zabarovsky et al. |
| 2005/0064428 A1 | 3/2005 | Berlin et al. |
| 2005/0069879 A1 | 3/2005 | Berlin et al. |
| 2005/0079521 A1 | 4/2005 | Beaulieu et al. |
| 2005/0112590 A1 | 5/2005 | Boom et al. |
| 2005/0153316 A1 | 7/2005 | Jeddeloh et al. |
| 2005/0153347 A1 | 7/2005 | Shapero et al. |
| 2005/0164241 A1 | 7/2005 | Hahn |
| 2005/0266473 A1 | 12/2005 | Zhang et al. |
| 2005/0272070 A1 | 12/2005 | Ehrich et al. |
| 2005/0287592 A1 | 12/2005 | Kless et al. |
| 2006/0019278 A1 | 1/2006 | Lo et al. |
| 2006/0094039 A1 | 5/2006 | Rosenfeld et al. |
| 2006/0136142 A1 | 6/2006 | Berlin et al. |
| 2006/0160105 A1 | 7/2006 | Dhallan et al. |
| 2006/0166228 A1 | 7/2006 | Page et al. |
| 2006/0210992 A1 | 9/2006 | van den Boom et al. |
| 2006/0252068 A1 | 11/2006 | Lo |
| 2006/0252071 A1 | 11/2006 | Lo et al. |
| 2007/0048755 A1 | 3/2007 | Di Fiore et al. |
| 2007/0059707 A1 | 3/2007 | Cantor et al. |
| 2007/0065823 A1 | 3/2007 | Dressman et al. |
| 2007/0111233 A1 | 5/2007 | Bianchi et al. |
| 2007/0202525 A1 | 8/2007 | Quake et al. |
| 2007/0207466 A1 | 9/2007 | Cantor et al. |
| 2007/0212689 A1 | 9/2007 | Bianchi |
| 2007/0243549 A1 | 10/2007 | Bischoff et al. |
| 2007/0275402 A1 | 11/2007 | Lo |
| 2008/0020390 A1 | 1/2008 | Mitchell |
| 2008/0026390 A1 | 1/2008 | Stoughton et al. |
| 2008/0070792 A1 | 3/2008 | Stoughton et al. |
| 2008/0096766 A1 | 4/2008 | Lee |
| 2008/0299562 A1 | 12/2008 | Oeth et al. |
| 2008/0305479 A1 | 12/2008 | Van et al. |
| 2009/0026082 A1 | 1/2009 | Rothberg et al. |
| 2009/0029377 A1 | 1/2009 | Lo et al. |
| 2009/0061425 A1 | 3/2009 | Lo et al. |
| 2009/0111712 A1 | 4/2009 | Van et al. |

(56) References Cited

U.S. PATENT DOCUMENTS

| | | |
|---|---|---|
| 2009/0142755 A1 | 6/2009 | Albitar et al. |
| 2009/0202984 A1 | 8/2009 | Cantor et al. |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0184046 A1 | 7/2010 | Klass et al. |
| 2010/0203529 A1 | 8/2010 | Kuslich et al. |
| 2010/0216153 A1 | 8/2010 | Lapidus et al. |
| 2010/0227320 A1 | 9/2010 | Fu et al. |
| 2010/0240054 A1 | 9/2010 | Bischoff et al. |
| 2010/0273165 A1 | 10/2010 | Ehrich et al. |
| 2010/0279295 A1 | 11/2010 | Roy et al. |
| 2011/0033851 A1 | 2/2011 | Rand et al. |
| 2011/0039724 A1 | 2/2011 | Lo et al. |
| 2011/0105353 A1 | 5/2011 | Lo et al. |
| 2011/0151460 A1 | 6/2011 | Klass et al. |
| 2011/0177517 A1 | 7/2011 | Rava et al. |
| 2011/0178719 A1 | 7/2011 | Rabinowitz et al. |
| 2011/0201507 A1 | 8/2011 | Rava et al. |
| 2011/0212846 A1 | 9/2011 | Spier et al. |
| 2011/0224087 A1 | 9/2011 | Quake et al. |
| 2011/0244451 A1 | 10/2011 | Cantor et al. |
| 2011/0276277 A1 | 11/2011 | Lo et al. |
| 2011/0288780 A1 | 11/2011 | Rabinowitz et al. |
| 2012/0065076 A1 | 3/2012 | Peters et al. |
| 2012/0184449 A1 | 7/2012 | Hixson et al. |
| 2012/0264618 A1 | 10/2012 | Nygren et al. |
| 2012/0276542 A1 | 11/2012 | Nygren et al. |
| 2012/0277119 A1 | 11/2012 | Ehrich et al. |
| 2012/0282613 A1 | 11/2012 | Patsalis et al. |
| 2013/0012399 A1 | 1/2013 | Myers et al. |
| 2013/0085681 A1 | 4/2013 | Deciu et al. |
| 2013/0130923 A1 | 5/2013 | Ehrich et al. |
| 2013/0143211 A1 | 6/2013 | Ehrich et al. |
| 2013/0150249 A1 | 6/2013 | Ehrich et al. |
| 2013/0230858 A1 | 9/2013 | Cantor et al. |
| 2013/0295564 A1 | 11/2013 | Ehrich et al. |
| 2013/0296180 A1 | 11/2013 | Ehrich et al. |
| 2013/0310260 A1 | 11/2013 | Kim et al. |
| 2014/0093873 A1 | 4/2014 | Tynan et al. |
| 2015/0267263 A1 | 9/2015 | Rehli |
| 2015/0275304 A1 | 10/2015 | Ehrich et al. |
| 2016/0145685 A1 | 5/2016 | Jensen et al. |
| 2016/0201113 A1 | 7/2016 | Rehli |
| 2017/0058350 A1 | 3/2017 | Tynan et al. |
| 2017/0314071 A1 | 11/2017 | Ehrich et al. |

FOREIGN PATENT DOCUMENTS

| | | |
|---|---|---|
| AU | 2015252141 A1 | 12/2015 |
| AU | 2013290102 B2 | 2/2019 |
| AU | 2017251674 | 11/2019 |
| CA | 2737200 A1 | 3/2010 |
| CA | 2774342 C | 1/2019 |
| EP | 264166 | 4/1988 |
| EP | 0401384 | 12/1990 |
| EP | 1373561 | 2/2009 |
| EP | 1524321 | 7/2009 |
| EP | 2271772 B1 | 7/2014 |
| EP | 2872648 A1 | 5/2015 |
| EP | 2329021 B1 | 8/2016 |
| EP | 3103871 A1 | 12/2016 |
| EP | 2478119 B1 | 7/2017 |
| EP | 2650666 | 1/2018 |
| EP | 3330382 A1 | 6/2018 |
| GR | 2329021 | 8/2016 |
| HK | 1229846 | 11/2017 |
| JP | 2005-514956 | 5/2005 |
| JP | 2006-508632 | 3/2006 |
| JP | 2007-505641 | 3/2007 |
| JP | 2007-508017 A | 4/2007 |
| JP | 2008-518639 A | 6/2008 |
| JP | 2008-521389 | 6/2008 |
| JP | 2009/529330 | 8/2009 |
| JP | 2010/534068 | 11/2010 |
| JP | 5727375 | 6/2015 |
| JP | 2015-126748 | 7/2015 |
| JP | 5923571 | 5/2016 |
| JP | 6039034 | 12/2016 |
| JP | 2017000165 A | 1/2017 |
| JP | 5873434 | 3/2017 |
| JP | 6447765 B1 | 3/2018 |
| JP | 2018038438 | 3/2018 |
| JP | 6513622 B2 | 5/2019 |
| JP | 6634105 | 1/2020 |
| WO | 1991/006667 | 5/1991 |
| WO | 1994/010300 | 5/1994 |
| WO | 1997/012058 | 4/1997 |
| WO | 1997/035589 | 10/1997 |
| WO | 1997/037041 | 10/1997 |
| WO | 1998/020020 | 5/1998 |
| WO | 1998/022489 | 5/1998 |
| WO | 1998/039352 | 9/1998 |
| WO | 1998/039474 | 9/1998 |
| WO | 1998/054364 | 12/1998 |
| WO | 1999/057318 | 11/1999 |
| WO | 2000/052625 | 9/2000 |
| WO | 2000/056746 | 9/2000 |
| WO | 2000/066771 | 11/2000 |
| WO | 2000/075372 | 12/2000 |
| WO | 2001/014398 | 3/2001 |
| WO | 2001/020039 | 3/2001 |
| WO | 2001/025485 | 4/2001 |
| WO | 2001/027326 | 4/2001 |
| WO | 2001/027327 | 4/2001 |
| WO | 2001027329 | 4/2001 |
| WO | 2001029259 | 4/2001 |
| WO | 2002018616 | 3/2002 |
| WO | 2002086163 | 10/2002 |
| WO | 2003000919 | 1/2003 |
| WO | 2003/020974 | 3/2003 |
| WO | 2003/057909 | 7/2003 |
| WO | 2003/062441 A1 | 7/2003 |
| WO | 03074723 A2 | 9/2003 |
| WO | 2003/080863 | 10/2003 |
| WO | 2004/013284 | 2/2004 |
| WO | 2004/076653 | 9/2004 |
| WO | 2004/078999 | 9/2004 |
| WO | 2004/079011 | 9/2004 |
| WO | 2005/012578 | 2/2005 |
| WO | 2005/021793 | 3/2005 |
| WO | 2005/023091 | 3/2005 |
| WO | 2005/035725 | 4/2005 |
| WO | 2005/040399 | 5/2005 |
| WO | 2005/098050 | 10/2005 |
| WO | 2005/118852 | 12/2005 |
| WO | 2006/056480 | 6/2006 |
| WO | 2006/097049 | 9/2006 |
| WO | 2006/097051 | 9/2006 |
| WO | 2007/016668 | 2/2007 |
| WO | 2007/028155 | 3/2007 |
| WO | 2007/092473 | 8/2007 |
| WO | 2007/100911 | 9/2007 |
| WO | 2007/103910 | 9/2007 |
| WO | 2007/121276 | 10/2007 |
| WO | 2007/132166 | 11/2007 |
| WO | 2007/132167 | 11/2007 |
| WO | 2007132167 | 11/2007 |
| WO | 2007/140417 | 12/2007 |
| WO | 2007/147063 | 12/2007 |
| WO | 2008/098142 | 8/2008 |
| WO | 2008/103761 | 8/2008 |
| WO | 2008/103763 | 8/2008 |
| WO | 2008/118988 | 10/2008 |
| WO | 2008/157264 | 12/2008 |
| WO | 2009/030100 | 3/2009 |
| WO | 2009/032779 | 3/2009 |
| WO | 2009/039507 | 3/2009 |
| WO | 2009032781 | 3/2009 |
| WO | 2009/046445 | 4/2009 |
| WO | 2009/091934 | 7/2009 |
| WO | 2009114543 | 9/2009 |
| WO | 2010/004265 | 1/2010 |
| WO | 2010/065470 | 6/2010 |

(56) References Cited

FOREIGN PATENT DOCUMENTS

| WO | 2010/115016 | 10/2010 |
| --- | --- | --- |
| WO | 2010/033639 | 2/2011 |
| WO | 2011/018600 | 2/2011 |
| WO | 2011/034631 | 3/2011 |
| WO | 2011/054936 | 5/2011 |
| WO | 2011/057094 | 5/2011 |
| WO | 2011/087760 | 7/2011 |
| WO | 2011/091063 | 7/2011 |
| WO | 2011/092592 | 8/2011 |
| WO | 2011/143659 | 11/2011 |
| WO | 2011/142836 | 1/2012 |
| WO | 2012/012703 | 1/2012 |
| WO | 2012/118745 | 9/2012 |
| WO | 2012/149339 | 11/2012 |
| WO | 2013/052913 | 4/2013 |
| WO | 2013/055817 | 4/2013 |
| WO | 2013176958 A1 | 11/2013 |
| WO | 2013177086 A1 | 11/2013 |
| WO | 2014/011928 | 1/2014 |
| WO | 2014/168711 | 10/2014 |
| WO | 2015/138774 | 9/2015 |
| WO | 2017045654 A1 | 3/2017 |

OTHER PUBLICATIONS

U.S. Appl. No. 15/428,659, Non-Final Office Action dated Jan. 11, 2019, 9 pages.
Australian Application No. 2009293232, First Examination Report dated Mar. 11, 2014, 3 pages.
Australian Application No. 2009293232, Notice of Acceptance dated Apr. 30, 2015, 2 pages.
Australian Application No. 2010295968, First Examination Report dated Jul. 17, 2014, 4 pages.
Australian Application No. 2010295968, Notice of Acceptance dated Aug. 10, 2015, 3 pages.
Australian Application No. 2013290102, Notice of Acceptance dated Nov. 6, 2018, 3 pages.
Australian Application No. 2017251674, First Examination Report dated Sep. 14, 2018, 6 pages.
Canadian Application No. 2,878,979, Office Action dated Feb. 7, 2019, 4 pages.
European Application No. 09815148.3, Notice of Decision to Grant dated Jul. 14, 2016, 3 pages.
European Application No. 09815148.3, Office Action dated Nov. 13, 2014, 4 pages.
European Application No. 09815148.3, Office Action dated May 14, 2014, 5 pages.
European Application No. 09815148.3, Office Action dated Jan. 3, 2013, 7 pages.
European Application No. 10817598.5, Notice of Decision to Grant dated Jun. 29, 2017, 3 pages.
European Application No. 10817598.5, Office Action dated Jan. 29, 2014, 5 pages.
European Application No. 13739590.1, Office Action dated Feb. 1, 2016, 5 pages.
European Application No. 13739590.1, Office Action dated Nov. 26, 2018, 5 pages.
European Application No. 16173137.7, Office Action dated Oct. 1, 2018, 6 pages.
Indian Application No. 3139/DELNP/2012, First Examination Report dated Oct. 25, 2017, 8 pages.
Japanese Application No. 2011-527069, Notice of Decision to Grant dated Mar. 4, 2015, 6 pages (3 pages for the original document and 3 pages for the English translation).
Japanese Application No. 2011-527069, Office Action dated Mar. 7, 2014, 14 pages (8 pages for the original document and 6 pages for the English translation).
Japanese Application No. 2012-529756, Notice of Decision to Grant dated Dec. 24, 2015, 5 pages (3 pages for the original document and 2 pages for the English translation).
Japanese Application No. 2012-529756, Office Action dated Jul. 14, 2014, 14 pages (8 pages for the original document and 6 pages for the English translation).
Japanese Application No. 2012-529756, Office Action dated Jun. 2, 2015, 17 pages (10 pages for the original document and 7 pages for the English translation).
Japanese Application No. 2014-180865, Notice of Decision to Grant dated Apr. 1, 2016, 6 pages (3 pages for the original document and 3 pages for the English translation).
Japanese Application No. 2014-180865, Office Action dated Oct. 9, 2015, 7 pages (4 pages for the original document and 3 pages for the English translation).
Japanese Application No. 2015-005024, Office Action dated Jan. 25, 2016, 5 pages (3 pages for the original document and 2 pages for the English translation).
Japanese Application No. 2015-076001, Office Action dated Feb. 10, 2016, 6 pages (3 pages for the original document and 3 pages for the English translation).
Japanese Application No. 2015-076001, Office Action dated Nov. 11, 2016, 9 pages (5 pages for the original document and 4 pages for the English translation).
Japanese Application No. 2015-195591, Notice of Decision to Grant dated Oct. 26, 2016, 6 pages (3 pages for the original document and 3 pages for the English translation).
Japanese Application No. 2015-195591, Office Action dated Jul. 15, 2016, 6 pages (3 pages for the original document and 3 pages for the English translation).
Japanese Application No. 2017-241844, Office Action dated Oct. 19, 2018, 4 pages (2 pages for the original document and 2 pages for the English translation).
Japanese Application No. 2018-017348, Office Action dated Feb. 6, 2019, 15 pages (6 pages for the original document and 9 pages for the English translation).
Japanese Application No. 2018-017349, Office Action dated Dec. 26, 2018, 4 pages (2 pages for the original document and 2 pages for the English translation).
Lo, Y. M. D. et al., "Maternal plasma DNA sequencing reveals the genome-wide genetic and mutational profile of the fetus," Science Translation Medicine 2(61):61ra91, pp. 1-13 (2010).
U.S. Appl. No. 15/428,659, "Final Office Action," dated Sep. 20, 2019, 5 pages.
U.S. Appl. No. 15/428,659 , "Notice of Allowance", dated Dec. 18, 2019, 5 pages.
CA2,878,979 , "Office Action", dated Feb. 24, 2020, 3 pages.
CA3,024,967 , "Office Action", dated Nov. 25, 2019, 4 pages.
EP17182863.5 , "Notice of Decision to Grant", dated Feb. 13, 2020, 1 page.
JP2017-241844 , "Office Action", dated Sep. 20, 2019, 9 pages.
JP2018-17349 , "Office Action", dated Sep. 12, 2019, 5 pages.
Old et al., "Candidate Epigenetic Biomarkers for Non-Invasive Prenatal Diagnosis of Down Syndrome", Reproductive BioMedicine Online, vol. 15, No. 2, Jun. 21, 2007, pp. 227-235.
U.S. Appl. No. 12/561,241, "Non-Final Rejection", dated Jun. 15, 2012, 8 Pages.
U.S. Appl. No. 12/727,198, "Non-Final Rejection", dated Apr. 12, 2013, 5 Pages.
U.S. Appl. No. 12/727,198, "Non-Final Rejection," dated Dec. 31, 2013, 8 Pages.
U.S. Appl. No. 13/517,508, "Final Office Action," dated Jan. 7, 2014, 14 Pages.
U.S. Appl. No. 13/517,508, "Final Office Action," dated Feb. 5, 2014, 15 Pages.
U.S. Appl. No. 13/517,508 , "Non-Final Rejection," dated Aug. 13, 2013, 11 Pages.
U.S. Appl. No. 13/517,508, "Non-Final Rejection," dated Dec. 18, 2014, 7 Pages.
U.S. Appl. No. 13/517,532 , "Final Rejection," dated Sep. 20, 2013, 20 Pages.
U.S. Appl. No. 13/517,532 , "Non-Final Rejection," dated Apr. 5, 2013, 18 Pages.
U.S. Appl. No. 13/518,368, "Non-Final Rejection," dated Jan. 30, 2015, 16 Pages.

(56) References Cited

OTHER PUBLICATIONS

U.S. Appl. No. 13/782,857, "Non-Final Rejection," dated Jun. 26, 2014, 12 Pages.
U.S. Appl. No. 13/782,901, "Non-Final Rejection," dated Aug. 8, 2014.
U.S. Appl. No. 13/791,466, "Final Office Action," dated Aug. 3, 2015, 10 Pages.
U.S. Appl. No. 13/791,466, "Final Office Action," dated Aug. 12, 2016, 10 Pages.
U.S. Appl. No. 13/791,466, "Non-Final Rejection", dated Nov. 7, 2014, 8 Pages.
U.S. Appl. No. 13/801,384, "Final Rejection", dated Dec. 22, 2014, 9 Pages.
U.S. Appl. No. 13/801,384, "Non-Final Rejection," dated Mar. 7, 2014, 11 Pages.
U.S. Appl. No. 13/940,162, "Final Office Action," dated Mar. 17, 2016, 17 Pages.
U.S. Appl. No. 13/940,162, "Non-Final Rejection," dated Aug. 20, 2015, 12 Pages.
U.S. Appl. No. 14/735,477, "Final Office Action," dated Dec. 22, 2017, 10 pages.
U.S. Appl. No. 14/735,477, "Non Final Office Action," dated May 15, 2017, 8 pages.
Adinolfi, "Rapid detection of aneuploidies by micro satellite and the quantitative fluorescent polymerase chain Yeaction", Prenatal Diagnosis, vol. 17, No. 13, Dec. 1997, pp. 1299-1311.
Agresti, "Categorical Data Analysis", $2^{nd}$ Edition, 2002, Wiley, 13 pages.
Altschul et al., "Basic local alignment search tool", J Mol Biol., vol. 215, No. 3, 1990, pp. 403-410.
Altschul et al., "Gapped BLAST and PSI-BLAST: a new generation of protein database search programs", 1997, Nucleic Acids Res., vol. 25, No. 17, pp. 3389-3402.
Amicucci et al., Clin. Chemical, 2000, vol. 46 pp. 301-302.
Amir et al., "Rett syndrome is caused by mutations in X-linked MECP2, encoding methyl-CpG-binding protein 2", Nature Genetics; vol. 23, 1999, pp. 185-188.
Anantha et al., "Porphyrinbinding to quadrupled T4G4", Biochemistry 37(9), Mar. 1998, vol. 37, No. 9, 2709-2714.
Anders et al., "Clin Chem", Oct. 2010, vol. 56, No. 10, pp. 1627-1635, Epub Aug. 20, 2010.
Anderson, "Shotgun DNA sequencing using cloned Dnase !-generated fragments", Nucl. Acids Res. 9, 1981, vol. 9, pp. 3015-3027.
Antonarakis et al., Am J Hum Genet, Mar. 1992, vol. 50, No. 3, pp. 544-550.
Antonarakis et al., "Nat Genet.", Feb. 1993, vol. 3, No. 2, pp. 146-150.
Aoki, "Methylation status of the p15INK4B gene in hematopoietic progenitors and peripheral blood cells in myelodysplastic syndromes", Leukemia, vol. 14, No. 4, pp. 2000, 586-593.
Armour et al., "Measurement of locus copy number by hybridization with amplifiable probes", Nucleic Acids Research, vol. 28, No. 2, Jan. 2000, pp. 605-609.
Armour et al., "The detection of large deletions or duplications in genomic DNA", Human Mutation vol. 20, No. 5, Nov. 2002, pp. 325-337.
Asimakopoulos et al., "ABL 1 methylation is a distinct molecular event associated with clonal evolution of chronic myeloid leukemia", Blood, vol. 94, No. 7, 1999, pp. 2452-2460.
Aston et al., Methods Enzymol, 1999, vol. 303, pp. 55-73.
Aston et al., Trends Biotechnol, 1999, vol. 17, No. 7, pp. 297-302.
AU 2015252141, "First Examination Report," dated Oct. 28, 2016, 4 pages.
AU 2015252141, "Second Examination Report," dated Oct. 3, 2017, 3 pages.
Ausubel et al., Current Protocols in Molecular Biology, 1994.
Banerji et al., "A lymphocyte-specific cellular enhancer is located downstream of the joining region in immunoglobulin heavy chain genes", Cell, vol. 33, No. 3, Jul. 1983, pp. 729-740.
Bartel et al., Biotechniques, 1993, vol. 14, pp. 920-924.
Batey et al., Nucl. Acids Res, 1992, vol. 20, pp. 4515-4523.
Batey et al., Nucl. Acids Res, 1996, vol. 24, pp. 4836-4837.
Batzer et al., Nucleic Acid Res, vol. 19, 1991, p. 5081.
Beaucage et al., Tetrahedron Lett., vol. 22, 1981, pp. 1859-1862.
Beaudet, "Progress toward noninvasive prenatal diagnosis," Clinical Chemishy, vol. 57, No. 6, Jun. 2011, pp. 802-804.
Benson, "Tandem repeats finder: a program to analyze DNA sequences," Nucleic Acids Research, vol. 27, No. 2, Jan. 15, 1999, pp. 573-580.
Bianchi, "Fetal cells in the mother: from genetic diagnosis to diseases associated with fetal cell microchimerism," European Journal of Obstetrics & Gynecology and Reproductive Biology, vol. 92, No. 1, Sep. 2000, pp. 103-108.
Bock et al., "CpG island methylation in human lymphocytes is highly correlated with DNA sequence, repeats, and predicted DNA structure," PLOS Genetics, vol. 2, No. 3, 2006, pp. e26.
Boguski et al., "Identification of a cytidine-specific ribonuclease from chicken liver," J. Biology Chemishy vol. 255, No. 5, Mar. 10, 1980, pp. 2160-2163.
Boom et al., "J. Clin. Microbial 28," vol. 28, 1990, pp. 495-503.
Boom et al., "J. Clin. Microbial 29," vol. 29, 1991, pp. 1804-1811.
Boyer et al., "Polycomb complexes repress developmental regulators in murine embryonic stem cells," Nature, 2006, vol. 441, pp. 349-353.
Braslavsky et al., "Sequence information can be obtained from single DNA molecules," Proc Natl Acad Sci US A., Apr. 1, vol. 100, No. 7, 2003, pp. 3960-3964, Epub Mar. 21, 2003.
Brizot et al., "Maternal serum hCG an fetal nuchal translucency thickness for the prediction of fetal trisomies in the first trimester of pregnancy", British Journal of Obstetrics Gynaecology, vol. 102, No. 2, Feb. 1995, pp. 127-132.
Bullinger et al., "Use of gene-expression profiling to identifying prognostic subclasses in adult acute myeloid leukemia", New England Journal of Medicine, vol. 350, No. 16, Apr. 15, 2004, pp. 1605-1616.
Burlingame et al., Anal. Chem., vol. 70, 1998, pp. 647R-716R.
Burnier et al., "Cell-derived microparticles in haemostasis and vascular medicine", Thromb Haemost, 2009, vol. 101, pp. 439-451.
Byrne et al., "Multiplex gene regulation: a two-tiered approach to transgene regulation in transgenic mice", Proc Natl Acad Sci U.S.A., Jul. 1989, vol. 86, No. 14, pp. 5473-5477.
CA 2,737,200, "Office Action", dated Dec. 11, 2017, 3 pages.
CA 2,774,342, "Office Action", dated Mar. 28, 2017.
Calame et al., "Transcriptional controlling elements in the immunoglobulin and T cell receptor loci", Adv Immunol., 1988, vol. 43, pp. 235-275.
Caliper LifeSciences, Products and Contract Services, LabChip GX 2010, printed from the internet on Mar. 15, 2011 (http://www.caliperl.com/products/labchip-gx.htm).
Camper et al., "Postnatal repression of the alpha-fetoprotein gene is enhancer independent.", Genes Dev., Apr. 1989, vol. 3, No. 4, pp. 537-546.
Cell Death Detection ELISA PLUS Cat. No. 11 774 425 001 "Detection of Post-translational Modifications on Native Intact Nucleosomes by ELISA," Version 11.0, Roche, Content Version: Sep. 2010, pp. 1-19.
Chan et al., Clin. Chem., vol. 50, 2004, pp. 88-92.
Chan et al., "Hypermethylated RASSFIA in Maternal Plasma: A Universal Fetal DNA Marker that Improves the Reliability of Noninvasive Prenatal Diagnosis", Clin. Chem., 2006, 2211-2218.
Chan et al., Oncogene, vol. 22, 2003, pp. 924-934.
Chang et al., "LIBSVM: a library for Support Vector Machines", 2001.
Chen et al., "Fluorescence energy transfer detection as a homogeneous DNA diagnostic method", Proc Natl Acad Sci U.S.A., Sep. 30, 1997, vol. 94, No. 20, pp. 10756-10761.
Chen et al., "Template-directed dye-terminator incorporation (TDI) assay: a homogeneous DNA diagnostic method based on fluorescence resonance energy transfer", Nucleic Acids Res, Jan. 15, 1997, vol. 25, No. 2, pp. 347-353.
Cheson et al., "Report of the National Cancer Institute-sponsored workshop on definitions of diagnosis and response in acute myeloid leukemia", J Clin Oneal, vol. 8, 1990, pp. 813-819.

(56) References Cited

OTHER PUBLICATIONS

Cheung et al., J. Clin Microbial, vol. 32, 1994, pp. 2593-2597.
Chirgwin et al., Biochem, vol. 18, 1979, pp. 5294-5299.
Chitty et al., Br Med Bull, vol. 54, 1998, pp. 839-856.
Chiu et al., "Effects of blood-processing protocols on fetal and total DNA quantification in maternal plasma", Clin Chem., Sep. 2001, vol. 47, No. 9, pp. 1607-1613.
Chiu et al., Lancet, vol. 360, 2002, pp. 998-1000.
Chomczynski et al., Anal. Biochem, vol. 225, 1995, pp. 163-164.
Chomczynski et al., Analytical Biochem, vol. 162, 1987, p. 156-159.
Chomczynski, Biotech, vol. 15, 1993, pp. 532-537.
Chomczynski et al., Biotechniques, Vlo. 19, 1995, pp. 942-945.
Chow et al., "Mass Spectrometric detection of a SNP panel as an internal positive control for fetal DNA analysis in maternal plasma". Clin. Chem., vol. 53, 2007, pp. 141-142.
Chu et al., "A novel approach toward the challenge of accurately quantifying fetal DNA in maternal plasma", Prenatal Diagnosis, vol. 30, 2010, pp. 1226-1229.
Colella et al., Biotechniques, vol. 35, Jul. 2003, pp. 146-150.
Costa et al., N. Engl. J. Med., vol. 346, 2002, p. 1502.
Costello et al., "Restriction Landmark Genomic Scanning (RLGS): Analysis of CpG Islands in genomes by 2D Gel Electrophoresis", Methods in Molecular Biology, DNA Methylation, 2 Methods and Protocols, vol. 507, $2^{nd}$ eds, 2000, pp. 131-148.
Coulter, "Introduction to Capillary Electrophoresis", Beckman Coulter, 1991, 47 pages.
Craig et al., "Gen-Probe Transcription-Mediated Amplification: System Principles", httl://www.gen-probe.com/pdfs/tma whiteppr.pdf, Jan. 1996.
Cross et al., "Purification of CpG islands using a methylated DNA binding column", Nature Genetics, 1994, vol. 6, No. 3, pp. 236-244.
Cruikshank et al., "A lipidated anti-Tat antibody enters living cells and blocks HIV-1 viral replication", J. Acquired Immune Deficiency Syndromes and Human Retrovirology, Mar. 1, 1997, vol. 14, No. 3, pp. 193-203.
Dai et al., "Detection of Post-translational Modifications on Native Intact Nucleosomes by ELISA", Journal of Visualized Experiments, 2011, pp. 1-4.
D'Alton, "Prenatal diagnostic procedures", Semin Perinatal., Jun. 1994, vol. 18, No. 3, pp. 140-162.
Das et al., Proc Natl Acad Sci U S A, vol. 103, 2006, pp. 10713-10716.
Davison, "Sedimentation of deoxyribonucleic acid isolated under low hydrodynamic shear", Nature, Mar. 26, 1960, vol. 185, pp. 918-920.
Davison, "The Effect of Hydrodynamic Shear on the Deoxyribonucleic Acid From T(2) and T(4) Bacteriophages", Proc Natl Acad Sci USA vol. 45, No. 11, Nov. 1959, 1560-1568.
Dayie et al., J. Mag. Reson, vol. 130, pp. 1998, 97-101.
Dear, "One by one: Single molecule tools for genomics: Brief Funct Genomic Proteomic.", Jan. 2003, vol. 1, No. 4, pp. 397-416.
Deininger et al., "Random subcloning of sonicated DNA: application to shotgun DNA sequence analysis", Anal. Biochem, vol. 129, No. 1, 1983, 216-223.
Deininger et al., "Random subcloning of sonicated DNA: application to shotgun DNA sequence analysis", Anal. Biochem, vol. 129, No. 1, 1983, pp. 216-223.
Dembo et al., Ann. Prob vol. 22, 1994, pp. 2022-2039.
Ding et al., "A high-throughput gene expression analysis technique using competitive PCR and matrix-assisted laser desorption ionization time-of-flight", MS. Proc Natl Acad Sci USA, vol. 100, 2003, pp. 3059-3064.
Donis-Keller et al., Nucl. Acids Res., vol. 4, 1977, pp. 2527-2537.
Donis-Keller., "Phy M: an RNase activity specific for U and A residues useful in RNA sequence analysis." Nucleic Acids Res., Jul. 25, 1980, vol. 8, No. 14, pp. 3133-3142.
Dupont, et al., Anal Biochem, Oct. 2004, vol. 333, No. 1. pp. 119-127.
Eads et al., Cancer Res., vol. 59, 1999, pp. 2302-2306.

Eckhardt et al., Nat Genet, vol. 38, 2006, pp. 1378-1385.
Eckstein, "Oligonucleotides and Analogues, A Practical Approach", IRL Press, Oxford, 1991.
Edlund et al., "Cell-specific expression of the rat insulin gene: evidence for role of two distinct 5' flanking elements", Science, Nov. 22, 1985, vol. 230, No. 4728, pp. 912-916.
Egger et al., "Reverse transcription multiplex PCR for differentiation between polio-and enteroviruses from clinical and environmental samples", J Clin Microbial, Jun. 1995, vol. 33, No. 6, pp. 1442-1447.
Ehrich et al., "A new method for accurate assessment of DNA quality after bisulfite treatment", Nucl. Acids Res., 2007, vol. 35, No. 5, pp. e29 1-8.
Ehrich et al., "Cytosine methylation profiling of cancer cell lines." Proc Natl Acad Sci, USA, vol. 105, 2008, pp. 4844-4848.
Ehrich et al., "Noninvasive detection of fetal trisomy 21 by sequencing of DNA in maternal blood: a study in a clinical setting", Reports of Major Impact, American Journal of Obstetrics and Gyenocology, Mar. 2011,pp. 205e1-205e11.
Ehrich et al., "Quantitative high-throughput analysis of DNA methylation patterns by base specific cleavage and mass spectrometry", Proc Natl Acad Sci USA, 2005, vol. 102, pp. 15785-15790.
Eiben et al., "First-trimester screening: an overview", J Histochem Cytochem, Mar. 2005, vol. 53, No. 3, pp. 281-283.
ELISA, "Detection of Posttranslational Modifications on Native Intact Nucleosomes", Cell Death Detection ELISA PLUS Cat. No. 11 774 425 001 Version 11.0, Roche, Content Version, Sep. 2010, pp. 1-19.
EP 09720284, "Supplementary European Search Report dated", dated Jul. 14, 2011.
EP 09815148, "Extended European Search Report dated", dated Apr. 19, 2012.
EP 10817598.5, "Extended European Search Report dated", dated Jan. 4, 2012.
EP 10843520, "Extended European Search Report dated", dated Apr. 22, 2013.
EP 13739590.1, "Office Action", dated Aug. 1, 2017, 4 pages.
EP16173137.7, "Extended European Search Report", dated Nov. 14, 2016, 8 pages.
EP 17182863.5, "Extended European Search Report", dated Feb. 26, 2018, 9 pages.
Ernani et al., "Agilent's SureSelect Target Enrichment System: Bringing Cost and Process Efficiency to Next-Generation Sequencing Product Note", Agilent Technologies, Mar. 16, 2009.
Eva et al. Nature, vol. 316, 1985, pp. 273-275.
Fajkusova et al., "Detailed Mapping of Methylcytosine Positions at the CpG Island Surrounding the Pa Promoter at the bcr-abl Locus in CML Patients and in Two Cell Lines K562 and BV173", Blood Cells Mol. Dis. vol. 26, No. 3, 2000, pp. 193-204.
Fan et al., "Analysis of the size distributions of fetal and maternal cell-free DNA by paired end sequencing", Clinical Chemistry, vol. 56, No. 8, 2010, pp. 1279-1286.
Fan et al., "Molecular Counting: From Noninvasive Prenatal Diagnostics to Whole-Genome Haplotyping", Dissertation, Stanford University, Nov. 2010.
Fan et al., "Noninvasive diagnosis of fetal aneuploidy by shotgun sequencing DNA from maternal blood", Proc Natl Acad Sci USA, Oct. 21, 2008, vol. 105, No. 42, pp. 16266-16271.
Fan et al., "Working Set Selection Using the Second Order Information for Training SVM", Journal of Machine Learning Research, vol. 6, 2005, pp. 1889-1918.
Feinberg, "Methylation meets Genomics", Nat Genet., vol. 27, No. 1, Jan. 2001, pp. 9-10.
Ferguson et al., "Placental mRNA in maternal plasma: Prospects for fetal screening", PNAS, vol. 100, No. 8, Apr. 15, 2003, pp. 4360-4362.
Fournie et al., Anal. Biochem. 158, 1986, pp. 250-256.
Frommer et al., "Proc. Natl. Acad. Sci.", USA, vol. 89, 1992, pp. 1827-1831.
Futreal et al., "Nat Rev Cancer 4", vol. 4, 2004, pp. 177-183.
Gardiner et al., "CpG islands invertebrate genomes", J Mol Bioi., vol. 196, No. 2, Jul. 20, 1987, pp. 261-282.

(56) References Cited

OTHER PUBLICATIONS

Gebhard et al., "Genomewide profiling of CpG methylation identifies novel targets of aberrant hypermethylation in myeloid leukemia", Cancer Res, vol. 66, 2006, pp. 6118-6128.
Gebhard et al., "Rapid and sensitive detection of CpG-methylation using methyl-binding (MB)-PCR", Nucleic Acids Res, vol. 34, 2006, p. e82.
Giles et al., "Acute myeloid leukemia", Hematology Am Soc Hematol Educ Program, 2002, pp. 73-110.
Go et al., "Clin Chem", vol. 53, No. 12, Dec. 2007, pp. 2223-2224.
Go et al., "Non-invasive aneuploidy detection using free fetal DNA and RNA in maternal plasma recent progress and future possibilities", Human Reproduction Update, vol. 17, No. 3, 2011, pp. 372-382.
Goeddel et al., "Gene Expression Technology: Methods in Enzymology 185", Academic Press, San Diego, California, 1990.
Gonzalgo et al., Nucleic Acids Res., vol. 25, 1997, pp. 2529-2531.
Gottesman, "Gene Expression Technology: Methods in Enzymology", Academic Press, San Diego, California, vol. 185, 1990, pp. 119-129.
Grompe et al., Proc. Natl. Acad. Sci USA, vol. 86, 1989, pp. 5855-5892.
Grompe, "The rapid detection of unknown mutations in nucleic acids", Nat Genet., vol. 5, No. 2, Oct. 1993, pp. 111-117.
Grunau et al., "Bisulfite genomic sequencing: systematic investigation of critical experimental parameters", Nucleic Acids Res., vol. 29, No. 13, Jul. 2001, pp. E65-5.
Gupta et al., "Use of specific endonuclease cleavage in RNA sequencing", Nucleic Acids Res., vol. 4, No. 6, Jun. 1977, pp. 1957-1978.
Haase et al., Methods in Virology, 1984, pp. 189-226.
Haddow et al., "Screening of maternal serum for fetal Down's syndrome in the first trimester", The New England Journal of Medicine, vol. 338, No. 14, Apr. 2, 1998, pp. 955-961.
Hage et al., J. Chromatogr. B Biomed. Sci. Appl., vol. 699, No. 1-2, Oct. 10, 1997, pp. 499-525.
Hahn et al., Placenta 32 Suppl, 2011, pp. S17-S20.
Hahner et al., "Matrix-assisted laser desorption/ionization mass spectrometry (MALDI) of endonuclease digests of RNA", Nucleic Acids Res., vol. 25, No. 10, May 15, 1997, pp. 1957-1964.
Hames et al., Nucleic Acid Hybridization: A Practical Approach, IRL Press, 1985.
Hannish et al., "Activity of DNA modification and resuiction enzymes in KGB, a potassium glutamate buffer", Gene Anal. Tech, vol. 5, 1988, p. 105.
Harris et al., "Single-molecule DNA sequencing of a viral genome", Science. vol. 320, No. 5872, Apr. 4, 2008, pp. 106-109.
Hart et al., J.Bioi. Chem. 269, 1994, pp. 62-65.
Hasan et al., Nucl. Acids Res., vol. 24, 1996, pp. 2150-2157.
Health Screen Inc, "The Cancer Test, Cell Free DNA", http://www.thecancertest.com/science-of-cell-free-dna/, via the internet on Mar. 20, 2011.
Heegaard, J Mol. Recognit., Winter; vol. 11 No. 1-6, 1998, pp. 141-148.
Hennig et al., J. Am Chem. Soc. 129, 2007, pp. 14911-14921.
Herman et al., Proc. Nat. Acad. Sci. USA, vol. 93, 1996, pp. 9821-9826.
Hershey, E. J. Mol. Bioi, vol. 2, 1960, pp. 143-152.
Homer et al., Prenat Diagn, vol. 23, 2003, pp. 566-571.
Hook, "E. B. Lancet 2", 1981, 169-172.
Hromandnikova et al., "Quantification of Fetal and Total Circulatory DNA in Maternal Plasma Samples Before and After Size Fractionation by Agarose Gel Electrophoresis", DNA and Cell Biology, vol. 25. No. 11, 2006, pp. 635-640.
Hu et al., "Aneuploidy detection in single cells using DNA array-based comparative genomic hybridization", Mol Hum Reprod, vol. 10, 2004, pp. 283-289.
Hua et al., "Quantitative methylation analysis of multiple genes using methylationsensitive restriction enzyme-based quantitative PCR for the detection of hepatocellular carcinoma", Experimental and Molecular Pathology, 2011, vol. 91, pp. 455-460.
Huang et al., "Mechanism of ribose 2'-group discrimination by an RNA polymerase", Biochemistry, vol. 36 No. 27, Jul. 8, 1997, pp. 8231-8242.
Hulten et al., "Rapid and simple prenatal diagnosis of common chromosome disorders: advantages and disadvantages of the molecular methods FISH and QF-PCR Reproduction", Sep. 2003, 279-97.
Hunkapiller et al., "A microchemical facility for the analysis and synthesis of genes and proteins", Nature 310(5973), Jul. 12-18, 1984, 105-11.
Hyrup et al., "Peptide nucleic acids (PNA): synthesis, properties and potential applications", BioorQ Med Chem. 4 (1), 1996, 5-23.
Iliumina Inc, "Hi Seq 2000 Sequencing System Specification Sheet", 2010.
Imai et al., "J. Viral. Methods 36", 1992, 181-184.
Imamura et al., "Prenatal diagnosis of adrenoleukodystrophy by means of mutation analysis", Prenat Diagn 16(3), Mar. 1996, 259-61.
Innis et al., "PCR Protocols: A Guide to Methods and Applications", Academic Press, Inc., N.Y., 1990.
Iverson et al., "Prenat. Diagn 9", 1981, 31-48.
Jammes et al., "Anal Biochem 333(1)", Oct. 2004, 119-27.
Jensen et al., "Detection of microdeletion 22q11.2 in a fetus by next-generation sequencing of maternal plasma", Clin Chem vol. 58, 2012, pp. 1148-1151.
Jensen et al., "High-throughput massively parallel sequencing for fetal aneuploidy detection from maternal plasma", PloS One, 2013, 8:e57381.
Jing et al., Proc Natl Acad Sci, USA., vol. 95, No. (14), 1998, 8046-51.
Johansen et al., "An investigation of methods for enriching trophoblast from maternal blood", Prenat Diagn. 15(10), Oct. 1995, 921-31.
JP 2015-076001, "Office Action", dated Oct. 2, 2017, 4 pages.
JP 2015-521823, "Office Action", dated Jun. 28, 2017, 15 pages.
JP 2016-199141, "Office Action", dated Jun. 16, 2017, 2 pages.
Jurinke et al., "MALDI-TOF mass spectrometry: a versatile tool for high-performance DNA analysis", Mol. Biotechnol., vol. 26, 2004, pp. 147-164.
Kalinina et al., "Nanoliter scale PCR with TaqMan detection", Nucleic Acids Res., vol. 25 No. 10, May 15, 1997, pp. 1999-2004.
Kaneko et al., "Gut 52", 2003, pp. 641-646.
Karlin et al., "Methods for assessing the statistical significance of molecular sequence features by using general scoring schemes", Proc Natl Acad Sci USA 87(6), Mar. 1990, pp. 2264-2268.
Keller et al., "Nucl. Acids Res. 4", 1977, pp. 2527-2537.
Keller et al., "Phy M: an Rnase activity specific for U and A residues useful in RNA sequence analysis", Nucleic Acids Res., Jul. 25, 1980, pp. 3133-3142.
Kent, "BLAT—the BLAST-like alignment tool," Genome Res. 12(4), Apr. 2002, pp. 656-664.
Kessel et al., "Murine developmental control genes", Science.249 (4967), Jul. 27, 1990, pp. 374-379.
Kidd et al., "Mapping and sequencing of structural variation from eight human genomes nature", 453 (7191), May 1, 2008, pp. 56-64.
Kitzman et al., "Noninvasive Whole-Genome Sequencing of a Human Fetus", Science Translation Medicine 4(137-140), 2012, pp. 115-122.
Kriegier, "Gene Transfer and Expression: A Laboratory Manual", 1990.
Kristensen et al., "PCR-Based Methods for Detecting Single-Locus DNA Methylation Biomarkers in Cancer Diagnostics, Prognostics, and Response to Treatment", Clinical Chemistry, Washington DC, vol. 55, No. 8, Aug. 1, 2009, pp. 1471-1483.
Krueger et al., "Bismark: a flexible aligner and methylation caller for Bisulfite-Seq applications", Bioinformatics, 2011, vol. 27, pp. 1571-1572.
Kuchino et al., "Enzymatic RNA sequencing", Methods Enzymol, 1989, vol. 180, pp. 154-163.
Kuhn et al., "DNA Helicases", Cold Spring Harb Symp Quant Bioi, 1979, vol. 1, pp. 63-67.

(56) References Cited

OTHER PUBLICATIONS

Kulkarmi et al., "Global DNA methylation patterns in placenta and its association with maternal hypertension in pre-eclampsia", DNA Cell Bioi, vol. 30, No. 2, 2011, pp. 79-84.
Kumps et al., "Rmeseuarlcthi aprtilcelex Amplicon Quantification (MAO), a fast and efficient method for the simultaneous detection of copy number alterations in neuroblastoma", BMC Genomics 11 :298, 2010, pp. 1-10.
LabChip, "Caliper LifeSciences, Products and Contract Services", GX 2010 (http://www.caliperl.com/products/labchip-gx.htm), Mar. 15, 2011.
Lai et al., Nat Genet., vol. 23, No. 3, 1999, pp. 309-313.
Laird, "P. W. Nature Reviews Cancer 3", 2003, pp. 253-266.
Langmead et al., "Ultrafast and memory-efficient alignment of short DNA sequences to the human genome", Genome Bioi. vol. 10, No. 3, R25, 2009.
Larkin et al., "Ciustal W and Clustal X version 2.0", Bioinformatics, vol. 23, No. 21, Sep. 10, 2007, pp. 2947-2948.
Lee et al., "Control of developmental regulators by Polycomb in human embryonic stem cells", Cell, vol. 25, 2006, pp. 301-313.
Lee et al., "Fetal Nucleic Acids in Maternal Plasma", ln:Fetal and Maternal Medicine Review vol. 17, No. 2, 2006, pp. 125-137.
Leung et al., "An efficient algorithm for identifying matches with errors in multiple long molecular sequences", J Mol Bioi., vol. 221, No. 4, Oct. 20, 1991, pp. 1367-1378.
Li et al., "Dynamic Distribution of Linker Histone H1.5 in Cellular Differentiation, PLOS Genetics", vol. 8, No. 8, e 1002879, Aug. 2012, pp. 1-13.
Li et al., "Genotyping fetal paternally inherited SNPs by MALDI-TOF MS using cell-free fetal DNA in maternal plasma: Influence of size fractionation", Electrophoresis 27, 2006, pp. 3889-3896.
Li et al., "Mapping short DNA sequencing reads and calling variants using mapping quality scores", Genome Res. vol. 18, No. 11, 2008, pp. 1851-1858.
Li et al., Nucl. Acids Res. 23, 1995, pp. 4495-4501.
Li et al., "Size separation of circulatory DNA in maternal plasma permits ready detection of fetal DNA polymorphisms", Clin Chem, vol. 50, No. 6, Apr. 8, 2004, pp. 1002-1011.
Li et al., "Targeted mutation of the DNA methyltransferase gene results in embryonic lethality", Cell, vol. 69, No. 6, Jun. 1996, pp. 915-926.
Lingbeek et al., M. Cell, vol. 118, 2004, pp. 409-418.
Lingbeek et al., "Stem cells and cancer; the polycomb connection", Cell, vol. 118, No. 4, Aug. 20, 2004, pp. 409-418.
Little et al., Nat Med 3, 1997, pp. 1413-1416.
Litz et al., "Methylation status of the major breakpoint cluster region in Philadelphia chromosome negative Teukemias", Leukemia, vol. 6, No. 1, 1992, pp. 35-41.
Liu et al., "Quantification of regional DNA methylation by liquid chromatography/tandem mass spectrometry", Analytical Biochemistry, Academic Press Inc, New York, vol. 391, No. 2, Aug. 15, 2009, pp. 106-113.
Liu et al., "The ribosomal small-subunit protein S28 gene from *Helianthus annuus* (asteraceae) is down-regulated in response to drought, high salinity, and abscisic acid", American Journal of Botany, vol. 90, No. 4, Apr. 1, 2003, pp. 526-531.
Lo et al., Clin. Chem. vol. 45, 1999, pp. 1747-1751.
Lo et al., Clin. Chem., vol. 45, 1999, pp. 184-188.
Lo et al., "Maternal Plasma DNA Sequencing Reveals the Genome-Wide Genetic and Mutational Profile of the Fetus", Prenatal Diagnosis, Science Translational Medicine vol. 2, No. 61, Dec. 8, 2010, pp. 1-13.
Lo et al., N. Engl. J. Med., vol. 339, 1998, pp. 1734-1738.
Lo et al., Nat Med, vol. 13, No. 2, 2007, pp. 218-223.
Lo et al., "Prenatal diagnosis: progress through plasma nucleic acids", Nature Reviews Genetics, 2007, vol. 8, pp. 71-77.
Lo et al., "Presence of fetal DNA in maternal plasma and serum", Lancet, vol. 350, No. 9076, Aug. 16, 1997, pp. 485-487.

Lo et al., "Quantitative analysis of fetal DNA in maternal plasma and serum: implications for noninvasive prenatal diagnosis", Am J Hum Genet, Apr. 1998, pp. 768-775.
Lo, "Recent advances in fetal nucleic acids in maternal plasma", J Histochem Cytochem, Mar. 2005, pp. 293-296.
LSSA, "CpG island methylator phenotype in cancer", Nat Rev Cancer, vol. 4, No. 12, Dec. 2004, pp. 988-993.
Lun et al., "Microfluidics digital PCR reveals a higher than expected fraction of fetal DNA in maternal plasma", Clin Chem., vol. 54, No. 10, Epub, Oct. 2008, pp. 1664-1672.
Lun et al., "Noninvasive prenatal diagnosis of monogenic diseases by digital size selection and relative mutation dosage on DNA in maternal plasma", PNAS, vol. 1 05, No. 50, Dec. 16, 2008, pp. 19920-19925.
Lun et al., "Noninvasive prenatal diagnosis of monogenic diseases by digital size selection and relative mutation dosage on DNA in maternal plasma", Available Online at:- http://www.pnas.org/content/105/50/19920.full.pdf PNAS, 2008, vol. 105, No. 50, Dec. 16, 2008, pp. 19920-19925.
Lwabuchi et al., Oncogene 8, 1993, pp. 1693-1696.
Madura et al., J. Bioi. Chem. 268, 1993, pp. 12046-12054.
Majlessi et al., Nucleic Acids Research. vol. 26, No. 9, 1998, pp. 2224-2229.
Malik et al., "Polyethylene glycol (PEG)-modified granulocyte-macrophage colony stimulating factor (GM-CSF) with conserved biological activity", Exp Hematol, Sep. 1998, pp. 1028-1035.
Mann et al., "Development and implementation of a new rapid aneuploidy diagnostic service within the UK National Health Service and implications for the future of prenatal diagnosis", Sep. 2001, pp. 1057-1061.
Mann, Methods Mol Med, vol. 9, 2004, pp. 141-156.
Mao et al., Nucl. Acids Res., vol. 27, 1999, pp. 4059-4070.
Marais et al., EMBO Journal, vol. 14, 1995, pp. 3136-3145.
Marais et al., J. Bioi. Chem., vol. 272, 1997, pp. 4378-4383.
Margulies et al.., "Genome sequencing in microfabricated high-density picolitre reactors", Nature, vol. 437, No. 7057, Epub Jul. 31, 2005, Sep. 2005, pp. 376-380.
Mason et al., EMBO Journal, vol. 18, 1999, pp. 2137-2148.
McClelland et al., "A single buffer for all restriction endonucleases", Nucl. Acids Res, 1988, 16-364.
McConnell et al., Science, vol. 257, 1992, pp. 1906-1912.
Meller, Clin Chem, vol. 53, 2007, pp. 1996-2001.
Metzker, Nature Rev, vol. 11, 2010, pp. 31-46.
Meyers et al., CABIOS, vol. 4, 1989, pp. 11-17.
Millipore, QIA25 Nucleosome ELISA Kit, Information Brochure Calbiochem, Feb. 26, 2013.
Mito et al., S. Nat Genet ., vol. 37, 2005, pp. 1090-1097.
Molecular Cloning of PCR Products Unit 15.4, Current Protocols in Molecular Biology, (2001 John Wiley & Sons, Inc.) Supplement 56, 2001, 15.4.1-15.4.11.
Moudrianakis et al., Proc Natl Acad Sci USA, Mar. 1965, vol. 53, pp. 564-571.
Mouliere et al., "High fragmentation characterizes tumour-derived circulating DNA", PLOS ONE, vol. 6, No. 9 e23418, Sep. 6, 2011, pp. 1-10.
Nakamaye et al., Nucl. Acids Res., vol. 23, 1988, pp. 9947-9959.
Nakano et al., "Single-molecule PCR using water-in-oil emulsion", Journal of Biotechnology, vol. 102, 2003, pp. 117-124.
"NCBI dbSNP cluster report record for rs 16139", Sep. 16, 2013.
Needham et al., "Characterization of an adduct between CC-1065 and a defined oligodeoxynucleotide duplex", Nucleic Acids Res., vol. 12, No. 15, Aug. 10, 1984, pp. 6159-6168.
Needleman et al., "A general method applicable to the search for similarities in the amino acid sequence of two proteins", J Mol Bioi., vol. 48, No. 3, Mar. 1970, pp. 444-453.
Ng et al., Clin. Chem., vol. 48, 2002, pp. 1212-1217.
Ng et al., Proc. Natl. Acad. Sci. USA, vol. 100, 2003, pp. 4748-4753.
Nicolaides et al., "One-stop clinic for assessment of risk of chromosomal defects at 12 weeks of gestation", J Matern Fetal Neonatal Med., vol. 12, No. 1, Jul. 2002, pp. 9-18.
Nicolaides et al., PrenatDiagn, vol. 22, 2002, pp. 308-315.

(56) References Cited

OTHER PUBLICATIONS

Nicolaidis et al., "Origin and mechanisms of non-disjunction in human autosomal trisomies". Hum Reprod., vol. 13, No. 2, Feb. 1998, pp. 313-319.
Nishizuka et al., "Proteomic profiling of the NCI-60 cancer cell lines using new high-density reverse-phase lysate microarrays", Proc Natl Acad Sci USA, Nov. 25, 2003, Epub, Nov. 17, 2003, vol. 100, No. 24, pp. 14229-14234.
Nolte, "Branched DNA signal amplification for direct quantitation of nucleic acid sequences in clinical specimens", Adv Clin Chem, 1998, vol. 33, pp. 201-235.
Nosaka et al., "Increasing methylation of the CDKN2A gene is associated with the progression of adult T-cell leukemia", Cancer Res., vol. 60, No. 4, 2000, pp. 1043-1048.
Nygren et al., "Quantification of Fetal DNA by Use of Methylation-Based DNA Discrimination", Clinical Chemistry, vol. 56, No. 10, Sep. 2010, pp. 1627-1635.
Oefner et al., "Efficient random subcloning of DNA sheared in a recirculating pointsink flow system", Nucl. Acids Res., vol. 24, No. 20, 1996, pp. 3879-3886.
Oeth et al., "iPLEX™≠Assay: Increased Plexing Efficiency and Flexibility for MassARRAY® System through single base primer extension with mass-modified Terminators", SEQUENOM Application Note, 2005.
Oeth et al., "Qualitative and quantitative genotyping using single base primer extension coupled with matrix-assisted laser desorption/ionization time-of-flight mass spectrometry", Methods Mol Bioi., 2009, vol. 578, pp. 307-343.
Ohm et al., "A stem cell-like chromatin pattern may predispose tumor suppressor genes to DNA hypermethylation and heritable silencing", Nat Genet., vol. 39, 2007, pp. 237-242.
Ohtsuka et al., J. Bioi. Chem., vol. 260,1985, pp. 2605-2608.
Okano et al., "DNA methyltransferases Dnmt3a and Dnmt3b are essential for de novo methylation and mammalian development", Oct. 1999, vol. 99, No. 3, pp. 247-257.
Old et al., "Candidate Epigenetic Biomarkers for Non-invasive Prenatal Diagnosis of Down Syndrome", Reprod Biomed., vol. 15, No. 2, Jan. 1, 2007, pp. 227-235.
Olek et al., "A modified and improved method for bisulphite based cytosine methylation analysis", Nucleic Acids Res., Dec. 1996, vol. 24, No. 24, pp. 5064-5066.
Oligonucleotides and Analogues, A Practical Approach, IRL Press, Oxford, 1991.
Orita et al., Proc. Natl. Acad. Sci. USA, vol. 86, 1989, pp. 27776-2770.
Osborne et al., Curr. Opin. Chem. Biol., vol. 1, No. 1, 1997, pp. 5-9.
Oudejans et al., Prenatal Diagnosis, vol. 23, 2003, pp. 111-116.
Padilla et al., "Efficient synthesis of nucleic acids heavily modified with non-canonical ribose 2'-groups using a mutantT7 RNA polymerase (RNAP)", Nucleic Acids Res, vol. 27, No. 6, Mar. 1999, pp. 1561-1563.
Palomaki et al., "DNA sequencing of maternal plasma to detect Down syndrome: an international clinical validation study", Expanded Methods Appendix A, Genet Med, 2011. vol. 13, No. 913-920, 2011, pp. 1-65.
Palomaki et al., "Maternal serum screening for Down syndrome in the United States: a 1995 survey", Am J Obstet Gynecol., vol. 176, No. 5, May 1997, pp. 1046-1051.
Pandya et al., "Screening for fetal trisomies by maternal age and fetal nuchal translucency thickness at 10 to 14 weeks of gestation", Br J Obstet Gynaecol., vol. 102, No. 12, Dec. 1995, pp. 957-962.
Papageorgiou et al., "Fetal-specific DNA methylation ratio permits noninvasive prenatal diagnosis of trisomy 21", Nature Medicine, 2011, vol. 17, pp. 510-513.
Papageorgiou et al., "Sites of differential DNA methylation between placenta and peripheral blood molecular markers for noninvasive prenatal diagnosis of aneuploidies", The American Journal of Pathology, 2009, vol. 174, No. 5, pp. 1609-1618.
Patel et al., "Curr. Opin. Chem. Biol.", Jun. 1997, vol. 1, No. 1, pp. 32-46.
Paulin et al., Nucleic Acids Res., vol. 26, 1998, pp. 5009-5010.
PCT/US2008/054468, "International Preliminary Report on Patentability", dated Sep. 3, 2009.
PCT/US2008/066791, "International Preliminary Report on Patentability", dated Dec. 30, 2009.
PCT/US2008/066791, "International Search Report and Written Opinion", dated Dec. 22, 2008.
PCT/US2008/54468, "International Search Report and Written Opinion", dated Sep. 23, 2008.
PCT/US2008/54470, "International Preliminary Report on Patentability", dated Feb. 18, 2010.
PCT/US2008/54470, "International Search Report and Written Opinion", dated Aug. 18, 2008.
PCT/US2009/036683, "International Preliminary Report on Patentability", dated Sep. 23, 2010.
PCT/US2009/036683, "International Search Report and Written Opinion," dated Feb. 24, 2010.
PCT/US2009/036683, "Invitation to Pay Additional Fees and Partial International Search Report," dated Dec. 28, 2009.
PCT/US2009/057215, "International Preliminary Report on Patentability," dated Mar. 31, 2011.
PCT/US2009/057215, "International Search Report and Written Opinion," dated Dec. 29, 2010.
PCT/US2010/027879, "International Preliminary Report on Patentability," dated Mar. 29, 2012.
PCT/US2010/027879, "International Search Report and Written Opinion," dated Dec. 30, 2010.
PCT/US2010/061319, "International Preliminary Report on Patentability," dated Jul. 5, 2012.
PCT/US2010/061319, "International Search Report and Written Opinion," dated Sep. 21, 2011.
PCT/US2012/035479, "International Preliminary Report on Patentability," dated Nov. 7, 2013.
PCT/US2012/035479, "International Search Report and Written Opinion," dated Jan. 10, 2012.
PCT/US2013/028699, "International Preliminary Report on Patentability," dated Sep. 12, 2014.
PCT/US2013/028699, "International Search Report and Written Opinion," dated Jul. 1, 2013.
PCT/US2013/041354, "International Search Report and Written Opinion", dated Aug. 14, 2013.
PCT/US2013/041906, "International Preliminary Report on Patentability," dated Dec. 4, 2014.
PCT/US2013/041906, "International Search Report and Written Opinion," dated Jul. 16, 2013.
PCT/US2013/050145, "International Preliminary Report on Patentability," dated Jan. 22, 2015.
PCT/US2013/050145, "International Search Report and Written Opinion," dated Oct. 23, 2013.
PCT/US2014/025132, "International Preliminary Report on Patentability," dated Sep. 24, 2015.
PCT/US2014/025132, "International Search Report and Written Opinion†", dated Jul. 30, 2014.
PCT/US2015/020250, "International Preliminary Report on Patentability," dated Sep. 22, 2016.
Pearson et al., J. Chrom., vol. 255, 1983, pp. 137-149.
Pearson et al., Proc. Natl. Acad. Sci. USA, vol. 85, No. 5, 1998, pp. 2444-2448.
Perry-O'Keefe et al., "Peptide nucleic acid pre-gel hybridization: an alternative to southern hybridization", Proc Natl Acad Sci US A., Dec. 1996, vol. 93, No. 25, pp. 14670-14675.
Pertl et al., "Rapid molecular method for prenatal detection of Down's syndrome", Lancet., May 14, 1994, vol. 343, No. 8907, pp. 1197-1198.
Peters et al., "Noninvasive Prenatal Diagnosis of a Fetal Microdeletion Syndrome", New England Journal of Medicine, Nov. 10, 2011, pp. 1847-1848.
Petersen et al., Cytogenet Cell Genet., 2000, vol. 91, No. 1-4, pp. 199-203.
Pinkert et al., Genes Dev., 1987, vol. 1, pp. 268-277.
Poon et al., Clin. Chem., vol. 46, 2000, pp. 1832-1834.

(56) References Cited

OTHER PUBLICATIONS

Poon et al., "Differential DNA methylation between fetus and mother as a strategy for detecting fetal DNA in maternal plasma", Clin Chem., Jan. 2002, vol. 48, No. 1, pp. 35-41.
Porter et al., Biochemistry, vol. 34, 1995, pp. 11963-11969.
Qu et al., "Analysis of drug-DNA binding data", Methods Enzymol., 2000, vol. 321, pp. 353-369.
Queen et al., "Immunoglobulin gene transcription is activated by downstream sequence elements", Cell, Jul. 1983, vol. 33, No. 3, pp. 741-748.
Radding , "Homologous pairing and strand exchange in genetic recombination", Annu Rev Genet, 1982, vol. 16, pp. 405-437.
Randen et al., "Prenatal genotyping of RHO and SRY using maternal blood", Vox Sanguinis, vol. 85, No. 4, Nov. 2003, pp. 300-306.
Rashtchian, PCR Methods Applic 4, 1994, pp. S83-S91.
Rivas et al., Trends Biochem Sci, Aug. 1993, vol. 18, No. 8, pp. 284-287.
Roach et al., "Association between the abnormal expression of matrix-degrading enzymes by human osteoarthritic chondrocytes and demethylation of specific CpG sites in the promoter regions", Arthritis & Rheumatism, 2005, vol. 52, No. 10, pp. 3110-3124.
Robert et al., "Candidate Epigenetic 1-9 Biomarkers for Non-Invasive Prenatal Diagnosis of Down Syndrome", Reproductive Biomedicine Online, Reproductive Healthcare ltd,GB, vol. 15, No. 2, Jan. 1, 2007, pp. 227-235.
Robertson et al., Nature Rev. Genet., vol. 1, 2000, pp. 11-19.
Robinson et al., "A comparison of Affymetrix gene expression arrays", BMC Bioinformatics, 2007, vol. 8, p. 449.
Rojo et al., "Cusativin, a new cytidine-specific ribonuclease accumulated in seeds of *Cucumis sativus* L.", Planta., 1994, vol. 194, No. 3, pp. 328-338.
Rollins et al., "Large-scale structure of genomic methylation patterns", Genome Res., Feb. 2006, Epub Dec. 19, 2005, vol. 16, No. 2, pp. 157-163.
Romero et al., "Diagnostic Molecular Biology: Principles and Applications", Mayo Foundation, Rochester, Minn, 1993, pp. 401-406.
Roschke et al., "Karyotypic complexity of the NCI-60 drug-screening panel", Cancer Res., vol. 63, No. 24, Dec. 15, 2003, vol. 63, No. 24, pp. 8634-8647.
Rosenberg et al., A. J. Am. Chem. Soc., vol. 82, 1960, pp. 3198-3201.
Rossolini et al., Mol. Cell. Probes, vol. 8, 1994, pp. 91-98.
Sadri et al., Nucl. Acids Res., vol. 24, 1996, pp. 5058-5059.
Saito et al., Lancet, vol. 356, 2000, 1170.
Salgame et al., "An ELISA for detection of apoptosis", Nucleic Acids Research, vol. 25, No. 3, 1997, 680-681.
Sambrook et al., Molecular Biology: A laboratory Approach, Cold Spring Harbor, N.Y., 1989.
Sambrook et al., Molecular Cloning, A Laboratory Manual, 3$^{rd}$ edition, 2001.
Sanchez et al., "Effects of Sulpiride on Prolactin and mRNA Levels of Steroid 5areductase Isozymes in Adult Rat Brain", Neurochem Res., vol. 33, 2008, pp. 820-825.
Santoro et al., "A general purpose RNA-cleaving DNA enzyme", Proc. Natl. Acad. Sci. USA, Vo. 94, 1997, pp. 4262-4266.
Sargent et al., Meth. Enz., 1988, pp. 152:432.
Sayres et al., "Cell-free fetal nucleic acid testing: A review of the technology and its applications", Obstetrical and Gynecological Survey, vol. 66, No. 7, 2011, pp. 431-442.
Schlesinger et al., "Polycomb-mediated methylation on Lys27 of histone H3 pre-marks genes for de novo methylation in cancer", Nat Genet., vol. 39, No. 2, Epub Dec. 31, 2006, Feb. 2007, pp. 232-236.
Schouten et al., "Relative quantification of 40 nucleic acid sequences by multiplex ligationdependent probe amplification", Nucleic Acids Res., vol. 30, No. 12, Jun. 15, 2002, p. e57.
Schriefer et al., "Low pressure DNA shearing: a method for random DNA sequence analysis", Nucl. Acids Res. vol. 18, 1990, pp. 7455-7456.

Schroeder et al., "The human placenta methylome", PNAS USA, vol. 110, No. 15, 2013, pp. 6037-6042.
Schuler , "Sequence mapping by electronic PCR.", Genome Res., vol. 7, No. 5, May 1997, pp. 541-550.
Scott et al., J. Am. Chem. Soc., vol. 126, 2004, pp. 11776-11777.
Sekizawa et al., Clin. Chem., vol. 47, 2001, pp. 2164-2165.
Sharma et al., "Mass spectrometric based analysis, characterization and applications of circulating cell free DNA isolated from human body fluids", International Journal of Mass Spectrometry, vol. 304, 2011, pp. 172-183.
Sheffield et al., "Identification of novel rhodopsin mutations associated with retinitis pigmentosa by GC-clamped denaturing gradient gel electrophoresis", Am J Hum Genet., Oct. 1991, vol. 49, No. 4, pp. 699-706.
Silverman et al., "Methylation inhibitor therapy in the treatment of myelodysplastic syndrome", Nat Clin Pract Oneal. 2 Suppl 1, Dec. 2005, pp. S12-S23.
Simoncsits et al., "New rapid gel sequencing method for RNA", Nature. vol. 269, No. 5631, Oct. 27, 1977, pp. 833-866.
Singer et al., Biotechniques, vol. 4, 1986, p. 230.
Sjolander et al., Anal. Chem, vol. 63, 1991, pp. 2338-2345.
Slater et al., "Rapid, high throughput prenatal detection of aneuploidy using a novel quantitative method (MLPA)", J Med Genet., vol. 40, No. 12, Dec. 2003, pp. 907-912.
Smith et al., "Identification of common molecular subsequences", J Mol Bioi., vol. 147, No. 1, Mar. 25, 1981, pp. 195-197.
Smith et al., "Single-step purification of polypeptides expressed in *Escherichia coli* as fusions with Qlutathione S-transferase", Gene., vol. 67, No. 1, Jul. 15, 1988, pp. 31-40.
Snijders et al., "Assembly of microarrays for genome-wide measurement of DNA copy number", Nat Genet., vol. 29, No. 3, Nov. 2001, pp. 263-264.
Snijders et al., "First-trimester ultrasound screening for chromosomal defects", Ultrasound Obstet Gynecol., vol. 7, No. 3, Mar. 1996, pp. 216-226.
Snijders et al., "UK 41ulticenter project on assessment of risk of trisomy 21 by maternal age and fetal nuchal-translucency thickness at 10-14 weeks of gestation. Fetal Medicine Foundation First Trimester Screening Group", Lancet. 352(9125) :X, Aug. 1, 1998, pp. 343-346.
Soni et al., "Progress toward ultrafast DNA sequencing using solid-state nanopores", Clin Chem., vol. 53, No. 11, Epub Sep. 21, 2007, Nov. 2007, pp. 1996-2001.
Sousa et al., "A mutant T7 RNA polymerase as a DNA polymerase", EMBO J., vol. 14, No. 18, Sep. 15, 1995, pp. 4609-4621.
Spetzler et al., "Enriching for Rare Subpopulations of Circulating Microvesicles by the Depletion of Endothelial-and Leukocyte-Derived Microvesicles", CARIS Life Sciences, Carisome Posters, Papers, Abstracts and Presentations, American Academy of Cancer Research, AACR 2011.
Stanssens et al., "High-throughput MALDI-TOF discovery of genomic sequence polymorphisms", Genome Res. vol. 14, No. 1, Jan. 2004, pp. 126-133.
Staunton et al., "Chemosensitivity prediction by transcriptional profiling", Proc Natl Acad Sci USA, vol. 98, No. 19, Sep. 11, 2001, pp. 10787-10792.
Strachan, "The Human Genome", BIOS Scientific Publishers, 1992.
Strathdee et al., Am J. Pathol., vol. 158, 2001, pp. 1121-1127.
Strohmeier et al., "A New High-Performance Capillary Electrophoresis Instrument", Hewlett-Packard Journal, Jun. 1995, pp. 10-19.
Szabo et al., Curr. Opin. Struct. Biol., vol. 5, 1995, pp. 699-705.
Tabor et al., "Non-Invasive Fetal Genome Sequencing: Opportunities and Challenges", American Journal of Medical Genetics Part A, vol. 158A, No. 10, 2012, pp. 2382-2384.
Takai et al., Proc. Natl. Acad. Sci. U.S.A., vol. 99, 2002, pp. 3740-3745.
Tang et al., Analytical Chemistry, vol. 74, 2002, pp. 226-331.
Terme et al., "Histone H1 Variants Are Differentially Expressed and Incorporated into Chromatin during Differentiation and Reprogramming to Pluripotency", The Journal of Clinical Chemistry, vol. 286, No. 41, Oct. 14, 2011, pp. 35347-35357.

(56) References Cited

OTHER PUBLICATIONS

Thorsienson et al., "An Automated Hydrodynamic Process for Controlled, Unbiased DNA Shearing", Genome Research, vol. 8, 1998, pp. 848-855.
Tolbert et al., J. Am. Chem. Soc. 118, 1996, pp. 7929-7940.
Tolbert et al., J. Am. Chem. Soc. 119, 1997, pp. 12100-12108.
Tong et al., "Noninvasive Prenatal Detection of Fetal Trisomy 18 by Epigenetic Allelic Ratio Analysis in Maternal Plasma: Theoretical and Empirical Considerations", Clinical Chemishy, vol. 52, No. 12, pp. 2149-2202.
Tooke et al., M. IVDT., Nov. 2004, p. 41.
Tost et al., Nucl. Acids Res. 37, 2003, p. e50.
Toyota et al., Cancer Res., vol. 59, 1999, pp. 2307-2312.
Toyota et al., "Methylation profiling in acute myeloid leukemia", Blood, May 1, 2001, vol. 97 No. 9, pp. 2823-2829.
Tsaliki et al., "MeDIP real-time qPCR of maternal peripheral blood reliably identifies trisomy 21", Prenat. Diagn., vol. 32, 2012, pp. 996-1001.
Tsui et al., "Systemic Identification of Placental Epigenetic Signatures for the Noninvasive Prenatal Detection of Edwards Syndrome", PLOS One, vol. 5, No. 11, 2010, p. e15069.
Tungwiwat et al., "Non-invasive fetal sex determination using a conventional nested PCR analysis of fetal DNA in maternal plasma", Clinica Chimica Acta, vol. 334, No. 1-2, Aug. 2003, pp. 173-177.
Tynan et al., "Fractional DNA quantification by massively parallel shotgun sequencing implications for fetal fraction measurement in maternal plasma", (Sequenom MME) ASHG Poster, 2011.
Uhlmann et al., Electrophoresis, vol. 23, 2002, pp. 4072-4079.
Valk et al., "Prognostically useful gene-expression profiles in acute myeloid leukemia", N Engl J Med., vol. 350, No. 16, Apr. 15, 2004, pp. 1617-1628.
Van Der Schoot et al., "Real-time PCR of bi-allelic insertion/deletion polymorphisms can serve as a reliable positive control for cell-free fetal DNA in non-invasive prenatal Qenotyping", abstract, Blood, vol. 102, 2003, p. 93a.
Veltman et al., "High-throughput analysis of subtelomeric chromosome rearrangements by use of array-based comparative genomic hybridization", Am J Hum Genet., vol. 70, No. 5, Epub Apr. 9, 2002, May 2002, pp. 1269-1276.
Venter et al., "The sequence of the human genome", Science, vol. 291, No. 5507, Feb. 16, 2001, pp. 1304-1351.
Verbeck et al., The Journal of Biomolecular Technques, vol. 13, No. 2, 2002, pp. 56-61.
Verma et al., "Rapid and simple prenatal DNA diagnosis of Down's syndrome", Lancet, vol. 352, No. 9121, Jul. 4, 1998, pp. 9-12.
Vincenet et al., "Helicase-Dependent isothermal DNA Amplification", EMBO reports, vol. 5, No. 8, 2004, pp. 795-800.
Vire et al., "The Polycomb group protein EZH2 directly controls DNA methylation", Nature, vol. 439, No. 7078, Epub Dec. 14, 2005, Feb. 16, 2006, pp. 871-874.
Vogelstein et al., "Digital PCR", Proc Natl Acad Sci USA, vol. 96, No. 16, Aug. 3, 1999, pp. 9236-9241.
Volkerding et al., Clin Chem, vol. 55, 2009, pp. 641-658.
Vu et al., "Symmetric and asymmetric DNA methylation in the human IGF2-H19 imprinted region", Genomics, vol. 64, No. 2, Mar. 1, 2000, pp. 132-143.
Wada et al., "Codon usage tabulated from the GenBank genetic sequence data", Nucleic Acids Res., 20 Suppl., May 11, 1992, pp. 2111-2118.
Wald et al., Prenat Diagn, vol. 17, No. 9, 1997, pp. 821-829.
Wang et al., BMC Genomics 7, 2006, p. 166.
Wapner et al., "First-trimester screening for trisomies 21 and 18", N Engl J Med., vol. 349, No. 15, Oct. 9, 2003, pp. 1405-1413.
Waterman et al., J. Mol. Biol., vol. 147, 1980, pp. 195-197.
Weber et al., Oncogene, vol. 19, 2000, pp. 169-176.
Weisenberger et al., Nat Genet, vol. 38, 2006, pp. 787-793.
Weiss et al., "H1 variant-specific lysine methylation by G9a/KMT1 C and Glp1 /KMT1 D", Epigenetics & Chromatin, Mar. 24, 2010, vol. 3, No. 7, pp. 1-13.
White et al., "Detecting single base substitutions as heteroduplex polymorphisms", Genomics, vol. 12, No. 2, Feb. 1992, pp. 301-306.
Who, "The World Health Organization histological typing of lung tumours". Am J Clin Pathol., 1982, vol. 77, pp. 123-136.
Widschwendter et al., "Epigenetic stem cell signature in cancer", Nat Genet, vol. 39, 2007, pp. 157-158.
Wiley & Sons, "Current Protocols in Molecular Biology", 1989, 6.3.1-6.3.6.
Wilkinson, "In situ Hybridization", Wilkinson ed., IRL Press, Oxford University Press, Oxford, 1998.
Winoto et al., "A novel, inducible and T cell-specific enhancer located at the 3' end of the T cell receptor alpha locus", Embo J., vol. 8, No. 3, Mar. 1989, pp. 729-733.
Xiong et al., Nucleic Acids Res., vol. 25, 1997, pp. 2532-2534.
Yamada et al., Genome Research, vol. 14, 2004, pp. 247-266.
Yamada et al., "Suppressive effect of epigallocatechin gallate (EGCg) on DNA methylation in mice: Detection by methylation sensitive resuiction endonuclease digestion and PCR", Journal of Food, Agriculture & Environment, 2005, vol. 3, No. 2, pp. 73-76.
Yan et al., "A novel diagnostic strategy for trisomy 21 using short tandem repeats", Electrophoresis, vol. 27, 2006, pp. 416-422.
Zahra et al., "Plasma microparticles are not elevated in fresh plasma from patients with gynaecologicalmalignancy—An observational study", Gynecol Onco, vol. 123, No. 1, Oct. 2011, pp. 152-156.
Zervos et al., Cell, vol. 72, 1993, pp. 223-232.
Zhang et al., "Histone H1 Depletion Impairs Embryonic Stem Cell Differentiation", PLOS Genetics, vol. 8, No. 5, e1 002691, May 2012, pp. 1-14.
Zhao et al., Pretat Diag, vol. 30, No. 8, 2010, pp. 778-782.
Zheng et al., "Nonhematopoietically Derived DNA Is Shorter than Hematopoietically Derived DNA in Plasma: A Transplantation Model", Clin Chem., vol. 58, No. 2, Nov. 3, 2011.
Zhong et al., Am. J. Obstet. Gynecol, 2001, vol. 184, pp. 414-419.
Zhong et al., Prenat. Diagn. vol. 20, 2000, pp. 795-798.
Zimmermann et al., Clin Chem, Vo. 48, 2002, pp. 362-363.
Zimmermann et al., "Serum parameters and nuchal translucency in first trimester screening for fetal chromosomal abnormalities", In: BJOG: An International Journal of Obstetrics & Gynaecology, vol. 103, No. 10, 1996, pp. 1009-1014.
Zuker et al., "Mfold web server for nucleic acid folding and hybridization prediction", Nucleic Acids Res. vol. 31, No. 13, pp. 3406-3415, (2003).
EP 16173137.7, "Office Action," dated Jun. 26, 2019, 5 pages.
EP 17182863.5, "Office Action," dated Jul. 19, 2019, 4 pages.
AU 2019257485, "First Examination Report", dated Mar. 15, 2021, 3 pages.
CA 3,024,967, Notice of Allowance, dated Feb. 9, 2021, 1 page.
CA 3,073,079, Office Action, dated Feb. 18, 2021, 4 pages.
Gottesman, S., "Minimizing Proteolysis in *Escherichia coli*:Genetic Solutions", Methods in Enzymology, 185:119-129 (1990).
EP 20155147.0, Extended European Search Report, dated Sep. 11, 2020, 7 pages.
EP 20187954.1 , Extended European Search Report, dated Dec. 1, 2020, 8 pages.
CA 2,878,979, Notice of Allowance, dated Mar. 22, 2021, 1 page.
EP 20155147.0, Office Action, dated Oct. 5, 2021, 6 pages.
JP 2020-131448, Office Action, dated Jul. 1, 2021, 2 pages.
JP 2020-174625, Office Action, dated Sep. 14, 2021, 2 pages.

\* cited by examiner

Fractionating DNA
Based on Methylation

FIGURE 10
1. Assay Design
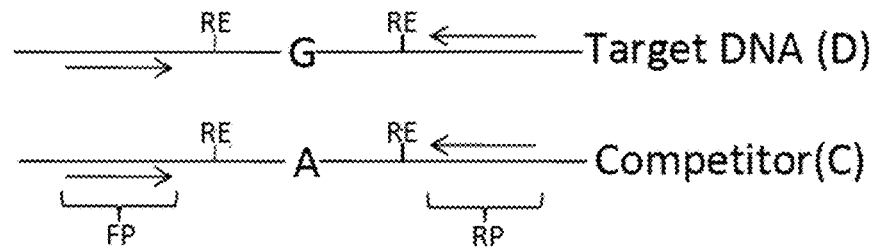
| 2. CCF DNA isolation | 3. DNA digestion |
|---|---|
| 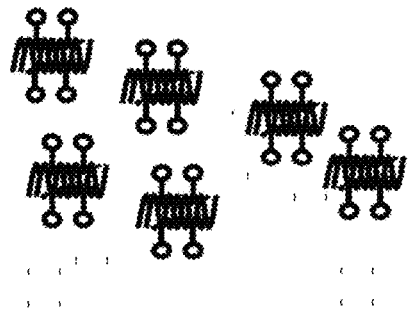 | 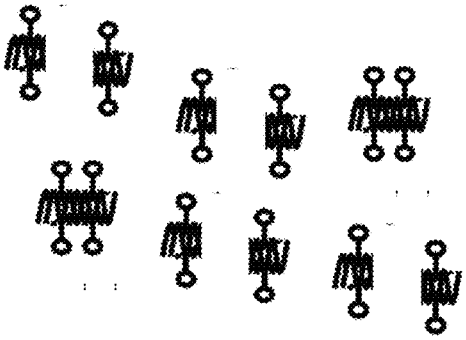 |
4. Addition of primers and known amount of competitor oligonucleotide Followed by PCR
5. Primer extension
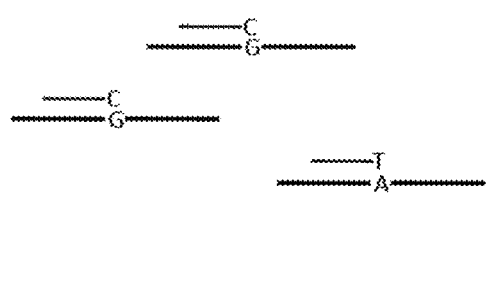
6. Analyte separation
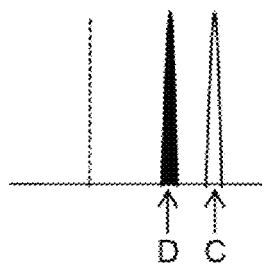

FIGURE 11
1. Selection of differentially methylated targets for specific DNA sequence capture
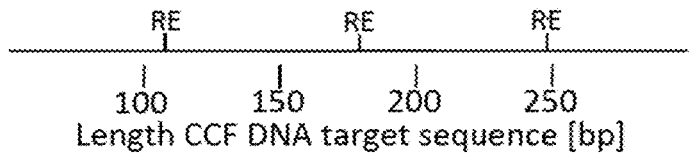
2. Distribution of CCF DNA after capture
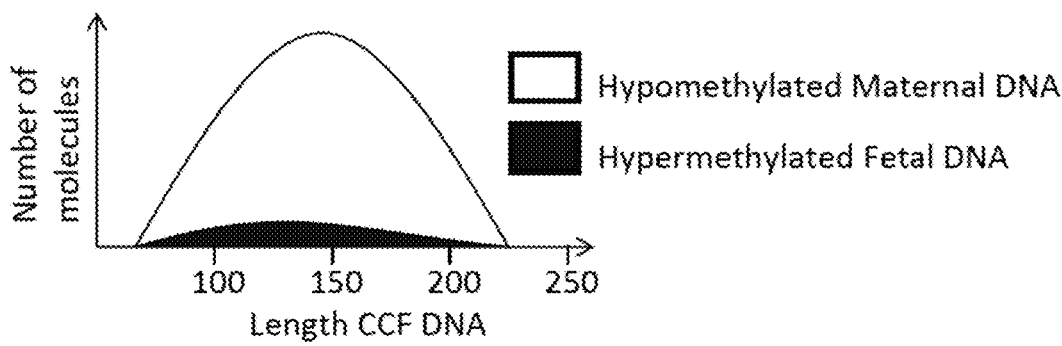
3. Distribution of CCF DNA after digestion
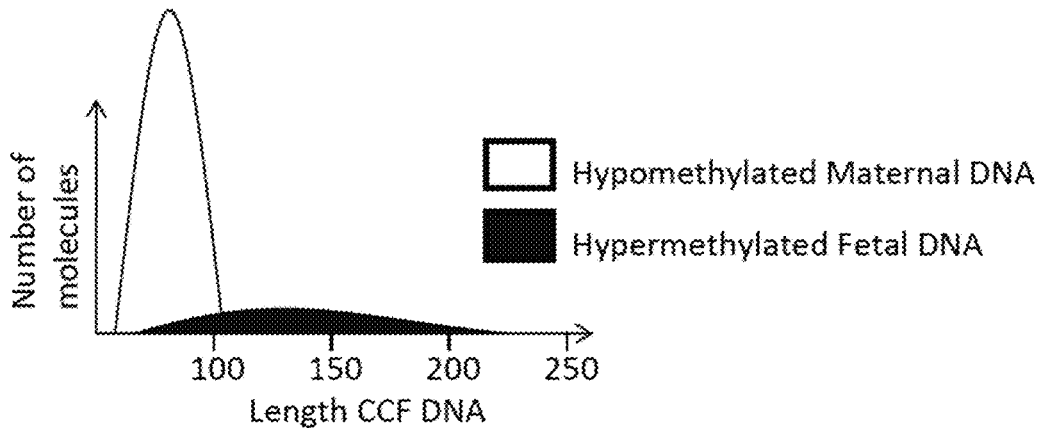
4. Quantification of non-digested DNA molecules
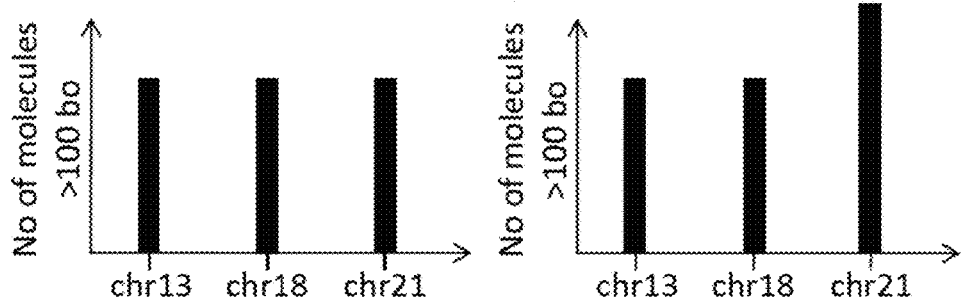

| 0.24 likelihood of informative fetal/maternal genotype combination with SNP minor allele frequency of 0.4 | Maternal Genotype | | |
|---|---|---|---|
| | AA (p=0.36) | Aa (p=0.48) | aa (p=0.16) |
| Paternal Genotype AA (p=0.36) | AA | AA Aa | Aa (p=0.058) |
| Aa (p=0.48) | AA Aa (p=0.086) | AA Aa aa | Aa (p=0.038) aa |
| aa (p=0.16) | Aa (p=0.058) | Aa aa | aa |

Detected SNPs have high minor allele population frequency

Maternal genotype
GG

Paternal genotype
GA

Fetal genotype
GA

CCF DNA from plasma of pregnant mother

Maternal CCF copies of GG = 900
Fetal CCF copies of GA = 100
Total CCF DNA copies = 1000

Figure 28
Perform multiplex PCR of 67 SNPs (one amplicon shown)
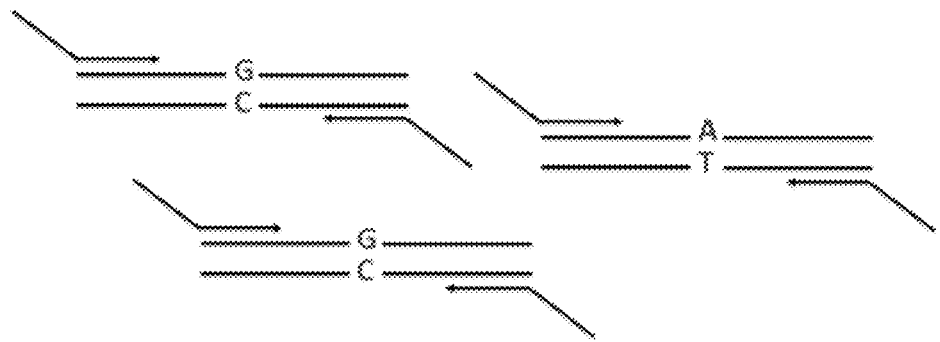
Amplicon sequencing and alignment
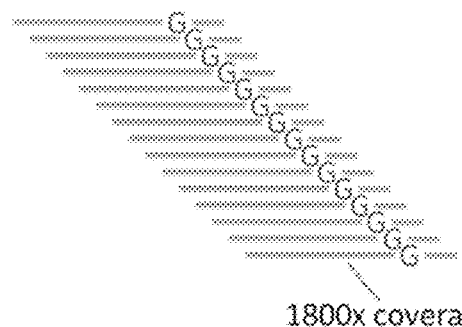
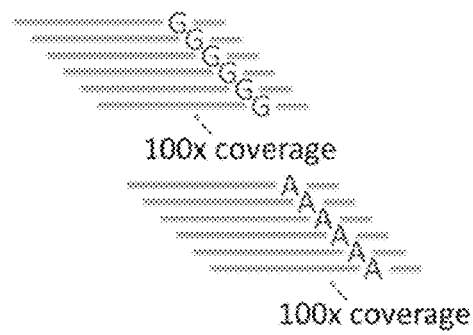
$$\text{Fetal fraction} = \frac{\text{\# of reads allele A}}{(\text{\# of reads allele A} + \text{\# of reads allele G})} \times 2 = 10\%$$

Graph probabilities assume 0.4 MAF SNPs

SEQUENCE LISTING

```
<160> NUMBER OF SEQ ID NOS: 388

<210> SEQ ID NO 1
<211> LENGTH: 305
<212> TYPE: DNA
<213> ORGANISM: Homo sapiens

<400> SEQUENCE: 1
cagcaggcgc gctcccggcg aatctgcctg aatcgccgtg aatgcggtgg ggtgcagggc     60
aggggctggt tttctcagcc ggtcttggct tttctctttc tctcctgctc caccagcagc    120
ccctccgcgg gtcccatggg ctccgcgctc agaacagccc ggaaccaggc gccgctcgcc    180
gctcgctggg ggccacccgc ctctcccgg aacagcctcc cgcgggcctc ttggcctcgc     240
actggcgccc tcacccacac atcgtccctt tatccgctca gacgctgcaa agggccttct    300
gtctc                                                                305

<210> SEQ ID NO 2
<211> LENGTH: 336
<212> TYPE: DNA
<213> ORGANISM: Homo sapiens

<400> SEQUENCE: 2
gctttggatt tatcctcatt ggctaaatcc ctcctgaaac atgaaactga aacaaagccc     60 tgaacccct caggctgaaa agacaaaccc cgcctgaggc cgggtcccgc tccccacctg    120
```

```
gagggaccca attctgggcg ccttctggcg acggtccctg ctagggacgc tgcgctctcc    180
gagtgcgagt tttcgccaaa ctgataaagc acgcagaacc gcaatcccca aactaacact    240
gaacccggac ccgcgatccc caaactgaca agggacccgg aacagcgacc cccaaaccga    300
cacgggactc gggaaccgct atctccaaag ggcagc                              336

<210> SEQ ID NO 3
<211> LENGTH: 139
<212> TYPE: DNA
<213> ORGANISM: Homo sapiens

<400> SEQUENCE: 3
tttccacaac agggagccag cattgaggcg cccagatggc atctgctgga aatcacgggc     60
cgctggtgaa gcaccacgcc ttacccgacg tggggaggtg atcccccacc tcatcccacc    120
cccttctgtc tgtctcctt                                                 139

<210> SEQ ID NO 4
<211> LENGTH: 292
<212> TYPE: DNA
<213> ORGANISM: Homo sapiens

<400> SEQUENCE: 4
gctggacaag gagcgctcac tgtagctctg ctgtggattg tgttggggcg aagagatggg     60
taagaggtca aagtcgtagg attctggcga ccgcctacca agggattggg tccacagcac    120
agaggtctga tcgcttcctt ctctgctctg ccacctccag acagcagctc taaccagctg    180
cccagcagca agaggatgcg cacggctttc accagcacgc agctgctaga gctggagcgc    240
gagttcgctt ctaatatgta cctgtcccgc ctacgtcgca tcgagatcgc ga            292

<210> SEQ ID NO 5
<211> LENGTH: 190
<212> TYPE: DNA
<213> ORGANISM: Homo sapiens

<400> SEQUENCE: 5
tgcctgacac tgaccccagg cgcagccagg aggggctttg tgcgggagag ggaggggac      60 cccagcttgc ctggggtcca cgggactctc ttcttcctag ttcactttct tgctaaggcg    120
aaggtcctga ggcaggacga gggctgaact gcgctgcaat cgtccccacc tccagcgaaa    180
cccagttgac                                                           190

<210> SEQ ID NO 6
<211> LENGTH: 706
<212> TYPE: DNA
<213> ORGANISM: Homo sapiens

<400> SEQUENCE: 6
tcggcggaga gacctcgagg agagtatggg gaaaggaatg aatgctgcgg agcgcccctc     60
tgggctccac ccaagcctcg gaggcgggac ggtgggctcc gtcccgaccc cttaggcagc    120
tggaccgata cctcctggat cagacccac aggaagactc gcgtggggcc cgatatgtgt     180
acttcaaact ctgagcggcc accctcagcc aactggccag tggatgcgaa tcgtgggccc    240
tgaggggcga gggcgctcgg aactgcatgc ctgtgcacgg tgccgggctc tccagagtga    300
gggggccgta aggagatctc caaggaagcc gaaaaaagca gccagttggg cttcgggaaa    360
gacttttctg caaaggaagt gatctggtcc cagaactcca gggttgaccc cagtacctga    420
```

```
cttctccggg agctgtcagc tctcctctgt tcttcgggct tggcgcgctc ctttcataat    480
ggacagacac cagtggcctt caaaaggtct ggggtggggg aacggaggaa gtggccttgg    540
gtgcagagga agagcagagc tcctgccaaa gctgaacgca gttagcccta cccaagtgcg    600
cgctggctcg gcatatgcgc tccagagccg gcaggacagc ccggccctgc tcaccccgag    660
gagaaatcca acagcgcagc ctcctgcacc tccttgcccc agagac                  706

<210> SEQ ID NO 7
<211> LENGTH: 325
<212> TYPE: DNA
<213> ORGANISM: Homo sapiens

<400> SEQUENCE: 7
agatcccggt gcatttaaag gccggcgtga tctgcaccac gtacctatct cggattctca     60
gtttcacttc gctggtgtct gccaccatct ttaccacatc ccggtagcta catttgtcta    120
ccgcttgagc caccagcgtc tgaaacctgg accggatttt gcgcgccgag aggtagccgg    180
aggcggtaat gaattccacc cagagggaca tgctcctctt gcgcccgtcg ctcaacttca    240
gcaccgcgca gccgggcagt gagccatcgt ccacgaagtt gaacaccccc atttggttga    300
gataaagcac cacttcaaat tcggt                                         325

<210> SEQ ID NO 8
<211> LENGTH: 663
<212> TYPE: DNA
<213> ORGANISM: Homo sapiens

<400> SEQUENCE: 8
actatgcctt gagggtcaaa acgtctggat ttcctgatcg atgctgtcgt cgctgtccac     60
ggagctactg tcgccgtcag agcgggaagg cacgttcagg gagtagaagc gtgggcttgc    120
agaaagggac ctgttgctgc cttacatggg ggccggcagg gtagtcttgg aaatgcccaa    180
gattgcttcc gcgcgcgtca gttcagcgga cgtgtctgcc tggcacgagg accgttctac    240
aaactcgttc ctggaagccg ggctcgctgg aggcggagct ttggtttcct tcgggagctt    300
gtggggaatg gtcagcgtct aggcaccccg ggcaagggtc tgtggccttg gtggccactg    360
gcttcctcta gctgggtgtt ttcctgtggg tctcgcgcaa ggcactttt tgtggcgctg    420 cttgtgctgt gtgcggggtc aggcgtcctc tctcctcccg gcgctgggcc ctctggggca    480
ggtccccgtt ggcctccttg cgtgtttgcc gcagctagta cacctggatg gcctcctcag    540
tgccgtcgtt gctgctggag tctgacgcct cgggcgcctg cgccgcactt gtgacttgct    600
ttccccttct cagggcgcca gcgctcctct tgacccccgct tttattctgt ggtgcttctg    660
aag                                                                 663

<210> SEQ ID NO 9
<211> LENGTH: 1985
<212> TYPE: DNA
<213> ORGANISM: Homo sapiens

<400> SEQUENCE: 9
gcaagtcggg tagctaccgg gtgctggaga actccgcacc gcacctgctg gacgtggacg     60
cagacagcgg gctcctctac accaagcagc gcatcgaccg cgagtccctg tgccgccaca    120
atgccaagtg ccagctgtcc ctcgaggtgt tcgccaacga caaggagatc tgcatgatca    180
aggtagagat ccaggacatc aacgacaacg cgccctcctt ctcctcggac cagatcgaaa    240
tggacatctc ggagaacgct gctccgggca cccgcttccc cctcaccagc gcacatgacc    300
```

```
ccgacgccgg cgagaatggg ctccgcacct acctgctcac gcgcgacgat cacggcctct    360
ttggactgga cgttaagtcc cgcggcgacg gcaccaagtt cccagaactg gtcatccaga    420
aggctctgga ccgcgagcaa cagaatcacc atacgctcgt gctgactgcc ctggacggtg    480
gcgagcctcc acgttccgcc accgtacaga tcaacgtgaa ggtgattgac tccaacgaca    540
acagcccggt cttcgaggcg ccatcctact tggtggaact gcccgagaac gctccgctgg    600
gtacagtggt catcgatctg aacgccaccg acgccgatga aggtcccaat ggtgaagtgc    660
tctactcttt cagcagctac gtgcctgacc gcgtgcggga gctcttctcc atcgacccca    720
agaccggcct aatccgtgtg aagggcaatc tggactatga ggaaaacggg atgctggaga    780
ttgacgtgca ggcccgagac ctggggccta accctatccc agcccactgc aaagtcacgg    840
tcaagctcat cgaccgcaac gacaatgcgc cgtccatcgg tttcgtctcc gtgcgccagg    900
gggcgctgag cgaggccgcc cctcccggca ccgtcatcgc cctggtgcgg gtcactgacc    960
gggactctgg caagaacgga cagctgcagt gtcgggtcct aggcggagga gggacgggcg   1020
gcggcggggg cctgggcggg cccggggggtt ccgtcccctt caagcttgag gagaactacg   1080
acaacttcta cacggtggtg actgaccgcc cgctggaccg cgagacacaa gacgagtaca   1140
acgtgaccat cgtggcgcgg gacggggggct ctcctcccct caactccacc aagtcgttcg   1200
cgatcaagat tctagacgag aacgacaacc cgcctcggtt caccaaaggg ctctacgtgc   1260
ttcaggtgca cgagaacaac atcccgggag agtacctggg ctctgtgctc gcccaggatc   1320
ccgacctggg ccagaacggc accgtatcct actctatcct gccctcgcac atcggcgacg   1380
tgtctatcta cacctatgtg tctgtgaatc ccacgaacgg ggccatctac gccctgcgct   1440
cctttaactt cgagcagacc aaggcttttg agttcaaggt gcttgctaag gactcggggg   1500
cgcccgcgca cttggagagc aacgccacgg tgagggtgac agtgctagac gtgaatgaca   1560
acgcgccagt gatcgtgctc cccacgctgc agaacgacac cgcggagctg caggtgccgc   1620
gcaacgctgg cctgggctat ctggtgagca ctgtgcgcgc cctagacagc gacttcggcg   1680
agagcgggcg tctcacctac gagatcgtgg acggcaacga cgaccacctg tttgagatcg   1740
acccgtccag cggcgagatc cgcacgctgc acccttttctg ggaggacgtg acgcccgtgg   1800
tggagctggt ggtgaaggtg accgaccacg gcaagcctac cctgtccgca gtggccaagc   1860
tcatcatccg ctcggtgagc ggatcccttc ccgagggggg accacgggtg aatggcgagc   1920
agcaccactg ggacatgtcg ctgccgctca tcgtgactct gagcactatc tccatcatcc   1980
tccta                                                               1985

<210> SEQ ID NO 10
<211> LENGTH: 213
<212> TYPE: DNA
<213> ORGANISM: Homo sapiens

<400> SEQUENCE: 10
atgcgccctc tgcaccccta gagccagaag acgctaggtg ggctgcgcgc tctgccaggc     60
gaaggctgga gcgcagacgg caaagccgcg cgtttcagcc gtggtcgggt ccgcaggacc    120
tgggcgtggg gacaccacca ggcaggagca gaggcaggac tgggacgcca aaagctgaga    180
atcctcgatg cccgcgcgag agccccgtgt tat                                 213

<210> SEQ ID NO 11
<211> LENGTH: 1558
<212> TYPE: DNA
```

<213> ORGANISM: Homo sapiens

<400> SEQUENCE: 11

```
ttctggaaac cgggccccac ttgcaggccc ggccaccttg ggttctggtg gccgaagccg      60
gagctgtgtt tctcgcagac tcggggagct acattgtgcg taggcaattg tttagtttga     120
aaggaggcac atttcaccac gcagccagcg ccctgcatgc aggagaagcc cccagggccc     180
agggtcggct ggctttagag gccacttagg ttgttttaag cacatgtgaa agggcagaca     240
gcagggagc aggatatggg taagatcttc gggtctcaga acaggggctg cccttgggct     300
gtcccggcgc cctgggctct gacactgaag ggtggaatgg aggaaggaat ggagaaagga     360
cggtggaact ttcgcttccc ctctgggccg ccttcccagg gtcatgcctg agctgctttg     420
atcccagtgt cgcgcatctt ggtccgctac ctcccaggcg atagctactg gctcctcgc      480
tggcctcact gggggccatc ccgggcagtg gcctgccctc cgaggcccgc gggacccagc     540
ccagagctga ggttggagtt ctccgggcca cgttccgggt cgcttaggct cggagatttc     600
ccggagaccg tcgtcctccc tttctgcttg gcactgcgga gctccctcgg cctctctcct     660
cctctggtcc ctaaggcccg gagtggttgg cggtactggg gcccgtcgtc atctctgctt     720
ctaaggcatt cagactgggc tccagctggg accggcagag gaggttctca aggaaactgg     780
tgggaaatat agttttcttt cgtctggtcg tttaatttaa atgcaacttc ccttggggac     840
attttcctgg acgttaacca gaccaccttg agatgtcgtt gatgacctag agacccagat     900
gatgcgtccc aggaaagttc actgctgact attgtcactc ttggcgttat atctatagat     960
atagacctat gtacatatct ccaccctgat ctctccgtgg acatgaaacc cacctacctt    1020
gtgaaagccc tacgggtgac acatgactac tacgtctctg tcccaacagg ggctgggcct    1080
cccctgccta atagttgcca ggagtttcgc agcccaagtg aataatgtct tatggctgaa    1140
cgtggccaag gactcctgtg atttaggtcc caggaggagc agagacgtcc ccgccccgcc    1200
tgggccctgc cgcattcaaa gctggaagaa ggcgctgatc agagaagggg cttccaggtc    1260
ctgggttaga acaacaacaa acaaacgaaa ctccacaaca gacacgcctg cccatgaccc    1320
cacgcaagga cataggaagt tctgtcgcct tcctgctccg cggatagccg cctgccgtct    1380
gctgccacca gaacgcacgg acgctcgggg tggaggtagt caatgggcag caggggaccc    1440
ccagccccca agcgcggc tccgaggacc tggaagcggg tgcctgtcgc tctccgcagg     1500
ctccgctctg cctccaggag caagatcccc aaaagggtct ggaagctgtg gagaaaac     1558
```

<210> SEQ ID NO 12
<211> LENGTH: 1264
<212> TYPE: DNA
<213> ORGANISM: Homo sapiens

<400> SEQUENCE: 12

```
tttttaaac acttcttttc cttctcttcc tcgttttgat tgcaccgttt ccatctgggg      60
gctagaggag caaggcagca gccttcccag ccagcccttg ttggcttgcc atcgtccatc     120
tggcttataa aagtttgctg agcgcagtcc agagggctgc gctgctcgtc ccctcggctg     180
gcagaagggg gtgacgctgg gcagcggcga ggagcgcgcc gctgcctctg gcgggctttc    240
ggcttgaggg gcaaggtgaa gagcgcaccg gccgtggggt ttaccgagct ggatttgtat    300
gttgcaccat gccttcttgg atcggggctg tgattcttcc cctcttgggg ctgctgctct    360
cccctcccgc cggggcggat gtgaaggctc ggagctgcgg agaggtccgc caggcgtacg    420
gtgccaaggg attcagcctg gcggacatcc cctaccagga gatcgcaggt aagcgcgggc    480
```

```
gcgctgcagg ggcaggctgc agccctcggc tgccgcacgt cccactggcc gcccggcgtc    540
cccttccttc ccctgttgc tgagttggtg ctcactttct gccaccgcta tgggactccg     600
cgtctccgtg ttgggcggcg gatgctcctg cggcttcttc ggcgggggaa ggtgtgcgtc    660
tccgccgcct cattgtgtgc acacgcggga gcacctggc tcccgcctcc cgctgctctc     720
gcgcccttct acccttagt tgatggctca ggcccggctg gccagggagc ccgggtcact     780
ccggggcggc tgcaaggcgc agacggagag ccgagccggg cgctcactcc gcgttctggt    840
tcgggcaaac ttggaagaac tgcgaccgca gtttgcccag cgccacagtc tgagtggcgc    900
cttctccact cccgcccttg cgccggcagg ggcggtggag agacgcggag ggctcccca    960 gcccctctct ccctatccg tccttcgggc gacagagcgc ccggcgctcg gccgggggc     1020 gggcaaggct gggagggacc ctcgccgggg acctggcctc tggacgccgg cgtttcaagg   1080
ctggtttggg gacttcacgg gctgcctgtt tcagatgtgg ggcgggcttt cccgttaggg   1140
ttcctcagtg cttccccagt tgctgttggc cactcagggc ccggggacac cctgccaccc   1200
ggtctggagc cggcctcgtc tgccagcgaa cagccaactt tagcgggtgg ctcagctggg   1260
gatt                                                               1264

<210> SEQ ID NO 13
<211> LENGTH: 761
<212> TYPE: DNA
<213> ORGANISM: Homo sapiens

<400> SEQUENCE: 13
cactcagtgt gtgcatatga gagcggagag acagcgacct ggaggccatg ggtggggcg     60 ggtggtgaag ctgccgaagc ctacacatac acttagcttt gacacttctc gtaggttcca   120
aagacgaaga cacggtggct tcaggagac aagtcgcaag ggcgactttt ccaagcggga    180
gatggtgaag tctttggacg tgtagtgggt aggtgatgat ccccgcagcc gcctgtaggc   240
ccgcagactt cagaaaacaa gggccttctg tgagcgctgt gtcctccccg gaatccgcgg   300
cttaacacat tctttccagc tgcggggcca ggatctccac cccgcgcatc cgtggacaca   360
cttagggtcg cctttgtttt gcgcagtgat tcaagttggg taacccttgc tcaacacttg   420
ggaaatgggg agaatctccc ccacccgcaa cctcccgcac cccaggttcc caaaatctga   480
atctgtatcc tagagtggag gcagcgtcta gaaagcaaag aaacggtgtc caaagacccc   540
ggagagttga gtgagcgcag atccgtgacg cctgcggtac gctagggcat ccaggctagg   600
gtgtgtgtgt gcgggtcggg gggcgcacag agaccgcgct ggtttaggtg gacccgcagt   660
cccgcccgca tctggaacga gctgcttcgc agttccggct cccggcgccc cagagaagtt   720
cggggagcgg tgagcctagc cgccgcgcgc tcatgtttat t                        761

<210> SEQ ID NO 14
<211> LENGTH: 1198
<212> TYPE: DNA
<213> ORGANISM: Homo sapiens

<400> SEQUENCE: 14
agtcactcca ggatcagagg ccgcgtcggt tctgcttggg gcatgggcag agggaggctg     60
ctggggccaa gccccggctg gacgcgaggg aagaaactcg tcccaggacc cgcacgccca   120
tacctggctg tcccagagct cttccctagg ccggcacctt cgctcttcct cttcccacc    180 ccctagccct tttgtctctt tttcagacgg atgttttcag tctcaagtgg ttttattttc   240
```

| | |
|---|---:|
| cgcacaaaac cctgagatca agggcagatc acagactgta ccggaggctc gggtttccct | 300 |
| ggactctgtg ctgttctgcg tcccagggtt ggctaggaag gaaggcctgg gccggcgagg | 360 |
| tgacgggtct cccgcccagg tcggcaggac gggggaggt gtgtcccggt aggtccctgg | 420 |
| tgagctcacc cgtggcatcg gggacccgcg ggaacccacc gggcgcccac tagagactcg | 480 |
| ggtcctaccc tcccccacac tactccaccg aaatgatcgg aagggcgcgc taggcctgct | 540 |
| tccaagggct cagtgataaa ggcctcaaaa tcacactcca tcaagacttg gttgaagctt | 600 |
| tgggtaggtt tgttgttgtt gttgttgttg tttgtttgtt tgttttagca gacacgtcct | 660 |
| ggaaagaggt cctcagaacc caaaggttca ataatgattt gtggatggat tgattatagt | 720 |
| ctgatatcgc tctggttcca cagaaacccg gagctccttg gcccactgtt accccagcag | 780 |
| acctaaatgg acggtttctg tttttcactg gcagctcaga actggaccgg aagaagttcc | 840 |
| cctccacttc ccccctcccg acaccagatc attgctgggt ttttattttc ggggaaaaa | 900 |
| caacaacaac aacaacaaaa aaaacactag gtccttccag actggatcag gtgatcgggc | 960 |
| aaaaaccctc aggctagtcc ggctgggtgc ccgagcatga aaaggcctcc gtggccgttt | 1020 |
| gaacagggtg ttgcaaatga gaacttttgt aagccataac cagggcatcc tgagggtctg | 1080 |
| agttcacggt caaggctgtg ggctactagg tccagcgagt ccaggcctcg ccccgccccc | 1140 |
| gagctgccac agccaagatc ttcggcaggg aattcgagac cagggtcctc ccactcct | 1198 |

<210> SEQ ID NO 15
<211> LENGTH: 377
<212> TYPE: DNA
<213> ORGANISM: Homo sapiens

<400> SEQUENCE: 15

| | |
|---|---:|
| tttcgtgccg ctgttttcaa tgcgctaacg aggcacgtta ttcttagccg cgtccgggag | 60 |
| gggatcacat tcctgcgcag ttgcgctgct ggcggaagtg acttgttttc taacgaccct | 120 |
| cgtgacagcc agagaatgtc cgtttctcgg agcgcagcac agcctgtccc atcgagaagc | 180 |
| ctcgggtgag gggcccggtg ggcgcccgga ggccgctgga gggctgtggg agggacggtg | 240 |
| gctcccccact cccgtggcga agggcaggca aaccagaagc ctcttttgag agccgtttgg | 300 |
| gattgagacg agtaagccac agcgagtggt tagaagtagg ttaggaagaa ggggaggtaa | 360 |
| gaaagccgag tagggtt | 377 |

<210> SEQ ID NO 16
<211> LENGTH: 256
<212> TYPE: DNA
<213> ORGANISM: Homo sapiens

<400> SEQUENCE: 16

| | |
|---|---:|
| gttcggtgga caagggggca gcgcccacag caagccggaa agagggaggc gcggggccgc | 60 |
| gcttggggcc tgccgctgca cgccagcctg ggcaaagagc tgccaccttc tgcgggcgaa | 120 |
| gcgggtcggg acgcaggacg gcagcgggc tggaggcagc tacgtgggtc cacacccca | 180 |
| tgccctgcaa ggctccttgg ccctgcttct cctctgtctc ggcgggagag gagcagcctc | 240 |
| ggttttacag aatttc | 256 |

<210> SEQ ID NO 17
<211> LENGTH: 189
<212> TYPE: DNA
<213> ORGANISM: Homo sapiens

<400> SEQUENCE: 17

```
tgtgccattt agtgagaggt gttttgggca aagaatcaat ttaactgtga ctgaccgacg    60
ggcttgactg tattaattct gctaccgaaa aaaaaaaaaa aaaaaaagca atgagccgca   120
agccttggac tcgcagagct gccggtgccc gtccgagagc cccaccagcg cggctcacgc   180
ctcagtctc                                                          189
```

```
<210> SEQ ID NO 18
<211> LENGTH: 707
<212> TYPE: DNA
<213> ORGANISM: Homo sapiens

<400> SEQUENCE: 18
agagtcccag ttctgcaggc cgctccaggg ctaggggtag agatggtggc aggtggtgcg    60
tcaactctct agggaagagg aacttgcatt acaaagactt gtctttctga gctgaagtca   120 aaacggggc gtcaagcgcg ctccgtttgg cggcggtgga ggggccgcgc gcccgcgctg   180
tcccagccgg agctgccctg gctggtgatt ggaggtttaa cgtccggaat tcaggcgctt   240
ctgcagctca gatttgccgg ccaaggggcc tcagttgcaa cttttcaaaa tggtgtttct   300
ggaaaataac aaattcagac tcaactggtg acagcttttg gctatagaga atgaaactgc   360
ttccctttgg cggtggaact cttaaacttc gaagagtgaa agaatacaat gaaataaaat   420
gccataagat cactggatt ttcagaaaaa ggaagacccc aaattactcc caaaatgagg   480
ctttgtaaat tcttgttaaa aatctttaaa tctcgaattt cccctacaa catctgatga    540 gtgctttaag agcaaacgag caaatcccac ctcgagaatc aacaaaccca agctctggcc   600
aaggctctcc ccgcgttttc ttctcgtgac ctggggaatg tcccgcccca tcgctcacct   660
ggctcttgtc atctcgctca tcttgaagtg accgtggac aatgctg                 707
```

```
<210> SEQ ID NO 19
<211> LENGTH: 182
<212> TYPE: DNA
<213> ORGANISM: Homo sapiens

<400> SEQUENCE: 19
agctgccctc tgtggccatg agcgggtgtc cagcccttc caaggctgca ccggggagac    60
gctggttttc tgctcgctgt gaccgaacaa agccctaag agtcagtgcg cggaacagaa   120
gagccggacc ccgacgggcc gagtcccaac gtgaggcacc cggcagagaa aacacgttca   180
cg                                                                 182
```

```
<210> SEQ ID NO 20
<211> LENGTH: 179
<212> TYPE: DNA
<213> ORGANISM: Homo sapiens

<400> SEQUENCE: 20
cctcggcagc accggcatgg ctggaggcca gtacggccag gtgtggcggg agggagcgcc    60
gtctggcttg ggtcgtccat cctgacagga cgctgcaagg gcaggagccc cgcgccccgt   120
gtcctgcgcc cccgctcgag gacaagcccc agccgccggt ctccgctggg ttccgacag   179
```

```
<210> SEQ ID NO 21
<211> LENGTH: 369
<212> TYPE: DNA
<213> ORGANISM: Homo sapiens

<400> SEQUENCE: 21
```

```
ctttaagagg ctgtgcaggc agacagacct ccaggcccgc tagggatcc gcgccatgga      60 ggccgcccgg gactatgcag gagccctcat caggcgagtg cccgcgtcc cctgattgc      120 cgtgcgcttc caatcgcctt gcgttcggtg gcctcatatt ccctgtgcg cctctagtac    180 cgtaccccgc tcccttcagc ccctgctcc ccgcattctc ttgcgctccg cgaccccgcg     240
cacacaccca tccgcccac tggtgcccaa gccgtccagc cgcgcccgcg ggcagagccc     300
aatcccgtcc cgcgcctcct caccctcttg cagctgggca caggtaccag gtgtggctct    360
tgcgaggtg                                                             369

<210> SEQ ID NO 22
<211> LENGTH: 176
<212> TYPE: DNA
<213> ORGANISM: Homo sapiens

<400> SEQUENCE: 22
agacttgcag aactcgggcc ccctggagga gacctaaccg ccacggtctt ggggaggttc     60
cggagggcct cggttgtctg cactcccaac accaagaaac ccctgagacg cgaagctgcc    120
agcgtgctgc cctcagagca gggcgacgca aagccagcgg accccggggt ggcggg         176

<210> SEQ ID NO 23
<211> LENGTH: 167
<212> TYPE: DNA
<213> ORGANISM: Homo sapiens

<400> SEQUENCE: 23
tgctcggctg gggggctcgc tccgcacttt cggtgccaga aaatgcccag aggagcgggg    60 cggcccaga gcctcctttc ggggcgcgag gccggcgcg tgtgtacgga gtccagtccc     120
cccagggagt gggggtgccg caccttcccc tccgcgctcg gagccac                   167

<210> SEQ ID NO 24
<211> LENGTH: 1205
<212> TYPE: DNA
<213> ORGANISM: Homo sapiens

<400> SEQUENCE: 24
tcttgcacac ctgcttgtag ttctgcaccg agatctggtc gttgaggaac tgcacgcaga     60
gcttggtgac ctgggggatg tgcaggatct tgctgaccga cagcacctcc tccaccgtgt    120
ccagggacag ggtcacgttg gccgtgtaga ggtactcgag caccaggcgc agcccgatgg    180
acgagcagcc ctgcagcacc aggttgttga tggcccgggg gctggtcagc agcttgtcgt    240
cgggggagga agaaggagtc ccgggctcct cctgcggcgg cggctgctgc tgctgtgacg    300
gctgctgctg cggcggctgc tgctggtcct tgggggcccc caggccgtcc tggccgccga    360
cccctccccc gagaggggggg tggctggaga agagcgatcg gaagtactgc gagcaggagg    420
ccagcacggc cttgtggcaa tggaactgct ggccctgggc cgtcagggtc acgtcgcaaa    480
acagctgctt cctccacagc aggttgaggc cgtgcagcag gttgtcgctg tggctggggt    540
cgaaggtgga ggtcctgtcc ccggatctgg acatggcgag ctgactcggt gcacctggct    600
ttaaaccctc ctccaacctg gcagacaggg gtggggatg ggaggagggg gagcagggtg     660
gtggagcggg tggggtgtgg tcggggtggg aagggtgtg gaggggaggg gagggcgaag    720
aacaagaatc aaggctcagc ttgactccct cctggcgcgc tccggacccc gaccctagga    780
ggaaagtccg aagacgctgg atccgtgagc gccaccagaa gggccctgtc tggggtcccg    840
gcgccggttc tgcgccctgc ggctcctctc gccacctccc acacacttcg tccctcactt    900
```

| | |
|---|---|
| tcctaaaacc aaccacctca gctcggctgt tggcagcaac agcagtggca gcagcgacgg | 960 |
| caaagtggcg gctgaggccg aggcacctcg tgggctcgtg tccatgccgg gccagatgaa | 1020 |
| gggaaaggcc gggaagtggg gagccggggg tgccctgaaa gctcagaggc gaccgacggc | 1080 |
| gaaggttcca ggtcaacttg tgcccgaagc tttgcttttc gcagttggcc cagtttgggg | 1140 |
| gaggggggtag gaacaggggc ccgaccagcg tgcggggtgt gcgaatctta gctctccaaa | 1200 |
| agctg | 1205 |

<210> SEQ ID NO 25
<211> LENGTH: 44
<212> TYPE: DNA
<213> ORGANISM: Homo sapiens

<400> SEQUENCE: 25

| | |
|---|---|
| cctctgtgtt agtgccctcg ggaatttggt tgatggggtg tttg | 44 |

<210> SEQ ID NO 26
<211> LENGTH: 5002
<212> TYPE: DNA
<213> ORGANISM: Homo sapiens

<400> SEQUENCE: 26

| | |
|---|---|
| tgatgtcgca cctgaacggc ctgcaccacc cgggccacac tcagtctcac gggccggtgc | 60 |
| tggcacccag tcgcgagcgg ccaccctcgt cctcatcggg ctcgcaggtg ccacgtcgg | 120 |
| gccagctgga agaaatcaac accaaagagg tggcccagcg catcacagcg gagctgaagc | 180 |
| gctacagtat cccccaggcg atctttgcgc agagggtgct gtgccggtct caggggactc | 240 |
| tctccgacct gctccggaat ccaaaaccgt ggagtaaact caaatctggc agggagacct | 300 |
| tccgcaggat gtggaagtgg cttcaggagc ccgagttcca gcgcatgtcc gccttacgcc | 360 |
| tggcaggtaa ggccggggct agccaggggc caggctgctg ggaagagggc tccgggtccg | 420 |
| gtgcttgtgg cccaagtctg cgcgccgagt cacttctctt gattcttttcc ttctctttcc | 480 |
| tatacacgtc ctctttcttc tcgtttttat ttcttcttcc attttctctt tctcttccgc | 540 |
| tcttccccta ctttcccttc tccctttttct ttttctttct tactctctcc ttgtccctga | 600 |
| gctttcattg accgaccccc ccccatttca ttcgccctcc cctcaatgtg ccaacctttg | 660 |
| ccctatttcc gatcttccca ggtactggga ggcgggatgg gggtgtgcgt tttcctctag | 720 |
| gagccctgtc tttccaagac ccacagaaac caggacctgc ccttattcaa aaccccatgc | 780 |
| acttcaagtc tcttttagac aacacatttc aattttccgg gctgactagt ctccctgtgc | 840 |
| agaggcagtt gagaggcttt gctctgcaga gggaaaagag ctctctactc tcccacccac | 900 |
| catataggca aacttatttg gtcattggct gaaggcacag ccttgccccc gcggggaacc | 960 |
| ggcggccagg atacaacagc gctcctggag cccatctctg gccttggcgt tggcgcaggg | 1020 |
| actttctgac cgggcttgag gggctcgggc cagctccaat gtcactacct acagcgaggg | 1080 |
| cagggtgtaa ggttgagaag gtcacattca ccgctttggg aggacgtggg agaagagact | 1140 |
| gaggtggaaa gcgctttgcc ttgctcaccg gccgtccttg ccccggtccc agcgtttgct | 1200 |
| gggatttgcc aggatttgcc ggggctccgg gagaccctga gcactcgcag gaagaggtgc | 1260 |
| tgagaaatta aaaattcagg ttagttaatg catccctgcc gccggctgca ggctccgcct | 1320 |
| ttgcattaag cggcgctga ttgtgcgcgc ctggcgaccg cggggaggac tggcggcccg | 1380 |
| cgggagggga cgggtagagg cgcgggttac attgttctgg agccggctcg gctctttgtg | 1440 |

```
cctcctctag cggccaagct gcgaggtaca gccctctatt gttctaggag cacagaaacc    1500
tcctgtgtgg gcggcgggtg cgcgagctag agggaaagat gcagtagtta ctgcgactgg    1560
cacgcagttg cgcgcttttg tgcgcacgga ccccgcgcgg tgtgcgtggc gactgcgctg    1620
cccctaggag caagccacgg gcccagaggg gcaaaatgtc caggtccccc gctgggaagg    1680
acacactata ccctatggca agccagggtg ggcgacttcc catggatcgg gtggagggggg   1740 gtatctttca ggatcggcgg gcggtctagg ggaacaattc gtggtggcga tgatttgcat    1800
agcgcgggtc ttgggatgcg cgcggttccg agccagcctc gcacagctcg cttccggagc    1860
tgcgagctca ggtttccacc cccgatcccc cgggctttcc tcgcaccgct gagcccagct    1920
tgtggggtgc actcgaccaa cgcccgacag ggctgtggga tgtgacaggc agcaggttca    1980
cccgggcttg ggaggggga gtttccgctt tgacagcatt ttcctttgcc gtctgctggt    2040
ggattcctat tcccagtcgg taatcgcccc gcagtgttga tctaagaagg taaagaaaac    2100
taggtttccc tgcaaagagc ctcccccaaa tcggcggact ccggatactt tgagtggatt    2160
tagaaattta tgtaatcttt ctcctttagt ttattttttca tcctctccta cagttttctc    2220
tgatttgctg ttggttcggg gcaagataaa gcagccagta gagagcgata ataatagcgg    2280
cgggaaatga actggagact ggctgacagt tcttaacatt ttgtcataga tccccccgaa    2340
tgtcccaggc tgtctctggt gggttttagt acccgccggc ttcttgggca ccggggacca    2400
gaaggaactt ggcagctggt cttaggggta cagttaaagg caggatgaca gctattctcc    2460
tgctcatctc agagcgctgc cgccccctca tgccggtcgc gcaaagaaca cagcttttaa    2520
aaaacacgtg ccttctgccc ataggtct gaaagtgatg aggaaagtaa tgcttcgcct     2580
attagcgagt ttcagctttt aaaatgatcc caagcgttgc tgagatgaga aagcgtggca    2640
tcccgggggt cctcagcccc acccgcgccc atggtgcaag tctgcaggga caggcccggg    2700
acagcactgc ccacgctgct agattttccg cagaggatcg ctgaagctgc cttcgtggga    2760
gacagaatgc ctcctccagc gagtggaaaa ggcctgctga ggaccccgct ttgctcgagc    2820
attcaaatgt gtgtctgttt tattaccctg ggttgaaaag ggacaagagc tttagccttt    2880
ttatctggcc atttttatcag caactacaag tgtgttgagt ggttattatt acataggagg    2940
cttttcagtt tggggtcagt agatcagtct cttcagacac tgatgcagaa gctgggactg    3000
gtaagtaggt attatgtgct cggagcgcta gggacagga gcaaatggag aagaaaagcg     3060
gaggctttct ccgcccggag tatcgatcgg aatccccgcc ggtacgccgc agagggccct    3120
cgccgttggg ccccggggt ttaacaagcc cagccgctcc gcaggcggct cggccggact     3180
ctcagaccgg tgcctggaag acaccgtccc tgccccctc ccgccaaacc tgcctcttct     3240
ctttctctca taggttatag gttcccttttc tctctcattt tggccccgcc ccgggtcct    3300 gccaaacagc caagcaggcc ggggtttagg gggctcagaa tgaagaggtc tgatttggcc    3360
agcgccggca aagctcaccc ttaggcgagg tcacaacaga ggcaggtcct tcctgcccag    3420
cctgccggtg tagtcacagc caagggtggc acttgaaagg aaaagggaga aaacttcgga    3480
gaaatttaga ttgccccaac gttagatttc agagaaattg actccaaatg cacggattcg    3540
ttcggaaagg gcggctaagt ggcaggtggt tgcaacccg cccggtcggg ccttcgcaga     3600
ggttccccaa gaccagccct tgcagggcgg ttttcagcaa cctgacaaga ggcggccaag    3660
acaaatttct gcgggttcga gcacacactc tcgggcgttg ggcccagag acctctaaac     3720 caagcacaaa caagaaggga gtgagagaac ccaggctaga acttgcacgg gcatcccact    3780
gaggaaaagc gaggcctcgg tggcaggcat gttttcttcc gacgcccgaa aatcgagccg    3840
```

```
agcgcccgac tacatttact gcagaggttt ccgcctccag tgagcccgga tcccccagcg    3900
gcctgcccgg agctggtctc cagtcccgc cgtagtccga cgcacggccc tctcctggca    3960
gcaagctccc agcggccagt ctgaagccaa ttctgttcag cggccgagg gcccttagcc     4020 aacccaccat gatgtcgcct gggccacctg atgcccgcag cggcgggaca cggcccgggc    4080
agtgcgcagt ggctcctgct aggggcaccg cgtgcgtgct tgtctcccgc tgcgccgggg    4140
acgtccttgg gtgacacggg ccgctgggca cctcccaagc cgaggaaacg acccccttc    4200 gcagagtctc gcgcccaccc cccaacctcc cacctcgttt ctcgctgcta gggctcccga    4260
ctcagcccac ctctcctggc ggtttagtta gggatcagag ctggagaggc tgaacgcaac    4320
ccgtgccagt acggaacaga cgatatgttt gcctgctagc tgcttggatg aataattgaa    4380
aagttcgctg cagtctgtgc ttcgtcaagt cccgggtgcc gggagaacac cttcccaaca    4440
cgcatcaggg tgggcgggag cgggcagagg aggcgggacc cgagggagga gagtgaaccc    4500
gagcaggaga agcagcccag gcagccaggc gccctcgatg cgagaggctg ggcatttatt    4560
tttattccag gctttccact gtgtggttat gtcactttct caaacaaatg tgtatatgga    4620
gggagatcga tgctgataat gtttagaaga ttaaaagagc attaatgctg caacaataa     4680 cgtaaacgtg tggacccaga tttcattgat ctggaacttg atccggcgcg tttccagtaa    4740
gcccgacggc gcgctcttcc cagcagagcg ctcaccagcg ccacggcccc gcggttttcc    4800
agcggtgccg cttcgccagc tctgcgcggg ttctcccgtc tgaccgcagc tcctcccccg    4860
cgaggcccca gcccgcctta cttccccgag gtttctcct cctctcgcgg ggctctctgc     4920
cctctgcacc ccctcccccg acctctgcac caccgcccc tgtgcgcaca caccgctact    4980
tgcgcttccg gcgatccgcc tg                                              5002

<210> SEQ ID NO 27
<211> LENGTH: 150
<212> TYPE: DNA
<213> ORGANISM: Homo sapiens

<400> SEQUENCE: 27
aaccggagat ctgcttggtg aactgagagg agtccttagg agagcgggga cgccaggggc      60
cgggggacac ttcgctctcg ccctagggaa ggtggtcttg acgctttcta ttgaagtcaa     120
acttgaaaat atcagctgcc gctggactat                                      150

<210> SEQ ID NO 28
<211> LENGTH: 339
<212> TYPE: DNA
<213> ORGANISM: Homo sapiens

<400> SEQUENCE: 28
cgtgagcaga acgcccgccc tggagcagtt aggaccgaag gtctccggag agtcgccggc      60
ggtgccaggt aacgcagagg gctcgggtcg ggccccgctt ctgggcttg ggactccggg      120 cgcgcggagc cagccctctg gggcgaaatc cccgggcggc gtgcgcggtc cctctccgcg     180
ctgtgctctc ccagcaactc cctgccacct cgacgagcct accggccgct ccgagttcga    240
cttcctcgga cttagtggga gaaggggttg gaaatgggct gccgggactg ggggagctgc    300
tctctggaag cagggaagct ggggcgcacc ggggcaggt                            339

<210> SEQ ID NO 29
<211> LENGTH: 1961
<212> TYPE: DNA
```

<213> ORGANISM: Homo sapiens

<400> SEQUENCE: 29

| | | | | | |
|---|---|---|---|---|---|
| tagaagagga | agactcctct | ggccccacta | ggtatcatcc | gcgctctccc | gctttccacc | 60 |
| tgcgccctcg | cttgggccaa | tctctgccgc | acgtgtccat | ccctgaactg | cacgctatcc | 120 |
| tccaccccg | gggggttcct | gcgcactgaa | agaccgttct | ccggcaggtt | ttgggatccg | 180 |
| gcgacggctg | accgcgcgcc | gccccacgc | ccggttccac | gatgctgcaa | tacagaaagt | 240 |
| ttacgtcggc | cccgacccgc | gcgggactgc | agggtccgcc | ggagcgcggc | gcagaggctt | 300 |
| ttcctgcgcg | ttcggccccg | ggaaaggggc | gggagggctg | gctccgggag | cgcacgggcg | 360 |
| cggcggggag | ggtactcact | gtgaagcacg | ctgcgcccat | ggatcatgtc | tgtgcgttac | 420 |
| accagaggct | ccgggctcca | ctaattccat | ttagagacgg | gaagacttcc | agtggcgggg | 480 |
| ggaggacagg | gtcgagaggt | gttaaagacg | caaagcaaga | aggaaataaa | gggggccga | 540 |
| gagggagacc | gagaggaagg | gggagctccg | agcccacgct | gcagccagat | ccggatgagt | 600 |
| ccgtcctccg | ccccgggcgg | gctctcgctc | tcgctggccc | tcagcgccgc | gcagccagca | 660 |
| gcatccccac | cgtgacgctc | gcatcacacc | cgggcgccgg | ccgccaccat | ccgcgccgcc | 720 |
| gccgtcagga | ccctcctccc | gggcatcgtc | gccgccgcgg | ggtcgggagg | acgcggcgcg | 780 |
| cgggaggcgg | cggtcgcagg | gcgagccccg | ggacgccccg | agccggggcc | ggggccgggg | 840 |
| agagggcgca | gcgaggtggg | ggccagtcca | gaccgacggc | agcgacggag | cgggcggcgg | 900 |
| cggcggcgcc | ggcggcggcg | gggtggctca | gtccccagtc | tcagacgcgc | gcgcagcag | 960 |
| gtcggagcag | cctccccggg | aggatgtcca | gcggcagcgc | tcctcgctcc | agcccttggg | 1020 |
| gatcttccgc | tgaggcattg | aaggcaggaa | gaagggggtcc | gtcatcggct | cgccgggctg | 1080 |
| cgcgccacct | ctgctatctt | gcggaaagag | gagcgggtgg | gtgggcgtct | gggaggcggg | 1140 |
| ctggagggcg | gtgcagggga | gcggggcggc | cgggggggg | gccgggggc | gggaaggga | 1200 |
| gggaggagaa | aggagccgga | agagggcaga | gttaccaaat | gggctcctta | gtcatggctt | 1260 |
| ggggctccac | gaccctcctg | gaagcccgga | gcctgggtgg | gatagcgagg | ctgcgcgcgg | 1320 |
| ccggcgcccc | ggggctggtg | cgcggcagaa | tggggccgcg | gcggcggcag | caaggacatc | 1380 |
| ccagccgcgc | ggatctgggg | gagggggggg | gaggggtga | ggacccggct | gggatccgcg | 1440 |
| gctcggcccg | ccagggcgca | gagagaggat | gcagccgcaa | atcccgagcc | ggatcctcgt | 1500 |
| gccggacgga | aggcgtggaa | gcgggagggg | ccttcgtgtg | aaaatccctt | gtggggtttg | 1560 |
| gtgtttcact | tttaaaggt | tagaccttgc | gggctctctg | cctcccaccc | cttcttttcc | 1620 |
| atccgcgtaa | aggaactggg | cgccccctct | ccctccctcc | ctggggcgca | ggtttcgccg | 1680 |
| cggactccgc | gctcagcttg | ggagacacgg | caggggcgcg | cccagggaa | aggcggccgt | 1740 |
| aaaagtttcg | cggttgagca | ctgggcctga | tgtccagtcc | ccccaccaaa | ttactcctgc | 1800 |
| aaagacgcgg | gcttcttgca | attgagcccc | ccacctcgag | gtatttaaaa | ccaccccaag | 1860 |
| gcacacacgg | accccgttc | ccccgcgcca | cttcctccta | caggctcgcg | cggcgcgtta | 1920 |
| aagtctggga | gacacgagtt | gcggggaaac | agcaccggaa | g | | 1961 |

<210> SEQ ID NO 30
<211> LENGTH: 314
<212> TYPE: DNA
<213> ORGANISM: Homo sapiens

<400> SEQUENCE: 30

| | | | | | |
|---|---|---|---|---|---|
| aagaaacagc | tcatttcgga | gctgaggaca | aggcgtggga | agaagacgcg | tttggtttca | 60 |

```
cccaggcggg tggcggcaaa gctgtgggat gcgcgctgca cactccttcc gtcatcccgt    120
tcccaccttc cacacacacc tgcgggaggt cggacatgtc ctgattgcgt gttcatcacg    180
atggcaaacc gaacatgagg agaacgccac tgacgctggg tgcgccggct ttcccagccc    240
tcgtgcataa cggggaggga gatgcagaag ttttttccaa catcggtgca aaggggaagc    300
tgaggttttc ctat                                                      314

<210> SEQ ID NO 31
<211> LENGTH: 584
<212> TYPE: DNA
<213> ORGANISM: Homo sapiens

<400> SEQUENCE: 31
tctgtcagct gctgccatgg ggcagcggga aggccctgga gggtgcctgg gctgtgtctg     60
gtcccggcca cgcgtccctg cagcgtctga gaccttgtgg aacacacttg accgggcgct    120
gggacggggt cggcccacac gcaccgccag cccgcaggag tgaggtgcag gctgccgctg    180
gctccttagg cctcgacagc tctcttgagg tcggccctcc tccctcccg agagctcagc     240 agccgcagac ccaggcagag agagcaaagg aggctgtggt ggcccccgac gggaacctgg    300
gtggccgggg gacacaccga ggaactttcc gccccccgac gggctctccc accgaggctc    360
aggtgctcgt gggcagcaag gggaagcccc atggccatgc cgcttccctt tcaccctcag    420
cgacgcgccc tcctgtgccc gcggggaaca agacggctct cggcggccat gcaggcggcc    480
tgtcccacga acacgatgga gacctcgac gccgtcccca cctgtcact gtcaccatca      540 cccatcctgt cccctcacgc ctccccacat cccatcatta ctac                    584

<210> SEQ ID NO 32
<211> LENGTH: 349
<212> TYPE: DNA
<213> ORGANISM: Homo sapiens

<400> SEQUENCE: 32
gaagtagaat cacagtaaat gaggagttag ggaatttagg gtagagatta aagtaatgaa     60
cagaggagga ggcctgagac agctgcagag agaccctgtg ttccctgtga ggtgaagcgt    120
ctgctgtcaa agccggttgg cgctgagaag aggtaccggg ggcagcaccc gcctcctggg    180
agagggatgg ggcctgcggc acctggggga accgcacgga cacagacgac actataaacg    240
cgggcgagac atcagggacc gggaaacaga aggacgcgcg tttcgagcag ctgcccagtg    300
ggccacaagc cccgccacgc cacagcctct tcccctcagc acgcagaga               349

<210> SEQ ID NO 33
<211> LENGTH: 3510
<212> TYPE: DNA
<213> ORGANISM: Homo sapiens

<400> SEQUENCE: 33
tactccggcg acgggaggat gttgagggaa gcctgccagg tgaagaaggg gccagcagca     60
gcacagagct tccgactttg ccttccaggc tctagactcg cgccatgcca agacgggccc    120
ctcgactttc accctgact cccaactcca gccactggac cgagcgcgca aagaacctga    180
gaccgcttgc tctcaccgcc gcaagtcggt cgcaggacag acaccagtgg gcagcaacaa    240
aaaaagaaac cgggttccgg gacacgtgcc ggcggctgga ctaacctcag cggctgcaac    300
caaggagcgc gcacgttgcg cctgctggtg tttattagct acactggcag gcgcacaact    360
```

-continued

```
ccgcgccccg actggtggcc ccacagcgcg caccacacat ggcctcgctg ctgttggcgg      420
ggtaggcccg aaggaggcat ctacaaatgc ccgagccctt tctgatcccc accccccgc      480 tccctgcgtc gtccgagtga cagattctac taattgaacg gttatgggtc atccttgtaa     540
ccgttggacg acataacacc acgcttcagt tcttcatgtt ttaaatacat atttaacgga     600
tggctgcaga gccagctggg aaacacgcgg attgaaaaat aatgctccag aaggcacgag     660
actggggcga aggcgagagc gggctgggct tctagcggag accgcagagg gagacatatc     720
tcagaactag gggcaataac gtgggtttct ctttgtattt gtttattttg taactttgct     780
acttgaagac caattattta ctatgctaat ttgtttgctt gttttaaaa ccgtacttgc      840 acagtaaaag ttccccaaca acggaagtaa cccgacgttc ctcacactcc ctaggagact     900
gtgtgcgtgt gtgcccgcgc gtgcgctcac agtgtcaagt gctagcatcc gagatctgca     960
gaaacaaatg tctgaattcg aaatgtatgg gtgtgagaaa ttcagctcgg ggaagagatt    1020
agggactggg ggagacaggt ggctgcctgt actataagga accgccaacg ccagcatctg    1080
tagtccaagc agggctgctc tgtaaaggct tagcaatttt ttctgtaggc ttgctgcaca    1140
cggtctctgg cttttcccat ctgtaaaatg ggtgaatgca tccgtacctc agctacctcc    1200
gtgaggtgct tctccagttc gggcttaatt cctcatcgtc aagagttttc aggtttcaga    1260
gccagcctgc aatcggtaaa acatgtccca acgcggtcgc gagtggttcc atctcgctgt    1320
ctggcccaca gcgtggagaa gccttgccca ggcctgaaac ttctctttgc agttccagaa    1380
agcaggcgac tgggacggaa ggctcttttgc taaccttttta cagcggagcc ctgcttggac   1440
tacagatgcc agcgttgccc ctgccccaag gcgtgtggtg atcacaaaga cgacactgaa    1500
aatacttact atcatccggc tcccctgcta ataaatggag gggtgtttaa ctacaggcac    1560
gaccctgccc ttgtgctagc gcggttaccg tgcggaaata actcgtccct gtacccacac    1620
catcctcaac ctaaggaga gttgtgaatt cttttcaaaac actcttctgg agtccgtccc    1680
ctccctcctt gcccgccctc tacccctcaa gtccctgccc ccagctgggg gcgctaccgg    1740
ctgccgtcgg agctgcagcc acggccatct cctagacgcg cgagtagagc accaagatag    1800
tggggacttt gtgcctgggc atcgtttaca tttggggcgc caaatgccca cgtgttgatg    1860
aaaccagtga gatgggaaca ggcggcggga aaccagacag aggaagagct agggaggaga    1920
ccccagcccc ggatcctggg tcgccagggt tttccgcgcg catcccaaaa ggtgcggctg    1980
cgtggggcat caggttagtt tgttagactc tgcagagtct ccaaaccatc ccatccccca    2040
acctgactct gtggtggccg tattttttac agaaatttga ccacgttccc tttctccctt    2100
ggtcccaagc gcgctcagcc ctccctccat cccccttgag ccgcccttct cctcccccctc   2160 gcctcctcgg gtccctcctc cagtccctcc ccaagaatct cccggccacg ggcgcccatt    2220
ggttgtgcgc agggaggagg cgtgtgcccg gcctggcgag tttcattgag cggaattagc    2280
ccggatgaca tcagcttccc agccccccgg cgggcccagc tcattggcga ggcagccct    2340 ccaggacacg cacattgttc cccgccccg ccccgccac cgctgccgcc gtcgccgctg       2400
ccaccgggct ataaaaaccg gccgagcccc taaaggtgcg gatgcttatt atagatcgac    2460
gcgacaccag cgcccggtgc caggttctcc cctgaggctt tcggagcga gctcctcaaa     2520 tcgcatccag agtaagtgtc cccgccccac agcagccgca gcctagatcc cagggacaga    2580
ctctcctcaa ctcggctgtg acccagaatg ctccgataca ggggtctgg atccctactc     2640 tgcgggccat ttctccagag cgactttgct ctttctgtcct cccacactc accgctgcat    2700 ctccctcacc aaaagcgaga agtcggagcg acaacagctc tttctgccca gccccagtc    2760
```

```
agctggtgag ctccccgtgg tctccagatg cagcacatgg actctgggcc ccgcgccggc    2820
tctgggtgca tgtgcgtgtg cgtgtgtttg ctgcgtggtg tcgatggaga taaggtggat    2880
ccgtttgagg aaccaaatca ttagttctct atctagatct ccattctccc caaagaaagg    2940
ccctcacttc ccactcgttt attccagccc gggggctcag ttttcccaca cctaactgaa    3000
agcccgaagc tctagaatg ccacccgcac cccgagggtc accaacgctc cctgaaataa     3060
cctgttgcat gagagcagag gggagataga gagagcttaa ttataggtac ccgcgtgcag    3120
ctaaaaggag ggccagagat agtagcgagg gggacgagga gccacgggcc acctgtgccg    3180
ggaccccgcg ctgtggtact gcggtgcagg cgggagcagc ttttctgtct ctcactgact    3240
cactctctct ctctctccct ctctctctct ctcattctct ctcttttctc ctcctctcct    3300
ggaagttttc gggtccgagg aaggaggac cctgcgaaag ctgcgacgac tatcttcccc     3360
tggggccatg gactcggacg ccagcctggt gtccagccgc ccgtcgtcgc cagagcccga    3420 tgacttttt ctgccggccc ggagtaaggg cagcagcggc agcgccttca ctgggggcac     3480
cgtgtcctcg tccaccccga gtgactgccc                                     3510
```

```
<210> SEQ ID NO 34
<211> LENGTH: 333
<212> TYPE: DNA
<213> ORGANISM: Homo sapiens

<400> SEQUENCE: 34
ttaattcgaa aatggcagac agagctgagc gctgccgttc ttttcaggat tgaaaatgtg     60
ccagtgggcc aggggcgctg ggacccgcgg tgcggaagac tcggaacagg aagaaatagt    120
ggcgcgctgg gtgggctgcc ccgccgccca cgccggttgc cgctggtgac agtggctgcc    180
cggccaggca cctccgagca gcaggtctga gcgttttgg cgtcccaagc gttccgggcc     240
gcgtcttcca gagcctctgc tcccagcggg gtcgctgcgg cctggcccga aggatttgac    300
tctttgctgg gaggcgcgct gctcagggtt ctg                                 333
```

```
<210> SEQ ID NO 35
<211> LENGTH: 385
<212> TYPE: DNA
<213> ORGANISM: Homo sapiens

<400> SEQUENCE: 35
ccggtcccca gtttggaaaa aggcgcaaga agcgggcttt tcagggaccc cggggagaac     60
acgagggctc cgacgcggga gaaggattga agcgtgcaga ggcgccccaa attgcgacaa    120
tttactggga tccttttgtg gggaaaggag gcttagaggc tcaagctata ggctgtccta    180
gagcaactag gcgagaacct ggccccaaac tccctcctta cgccctggca caggttcccg    240
gcgactggtg ttcccaaggg agcccctga gcctaccgcc cttgcagggg gtcgtgctgc     300
ggcttctggg tcataaacgc cgaggtcggg ggtggcggag ctgtagaggc tgcccgcgca    360
gaaagctcca ggatcccaat atgtg                                          385
```

```
<210> SEQ ID NO 36
<211> LENGTH: 105
<212> TYPE: DNA
<213> ORGANISM: Homo sapiens

<400> SEQUENCE: 36
gcgcaggtcc ccccagtccc cgagggagtg cgcccgacgg aaacgcccct agcccgcggg     60
```
cctcgctttc ctctcccggg ttcctgggtc acttcccgct gtctc         105

<210> SEQ ID NO 37
<211> LENGTH: 147
<212> TYPE: DNA
<213> ORGANISM: Homo sapiens

<400> SEQUENCE: 37
ttccctcgcg gctttggaaa ggggggtgcaa atgcacccctt ctgcgggccc gctacccgct    60
gcaacacctg tgtttccttt ctgggcacct tctaggtttc tagatattgc tgtgaatacg   120
gtcctccgct gtacagttga aaacaaa                                       147

<210> SEQ ID NO 38
<211> LENGTH: 365
<212> TYPE: DNA
<213> ORGANISM: Homo sapiens

<400> SEQUENCE: 38
tgggaattta ggtcgggcac tgccgatatg tcgccttcca caaggcgggc ccggggcctct    60 gctgaccgtg caccggtcct ggggctgggt aattctgcag cagcagcgca gcccatgccg   120
gggaatttgc gggcagagga gacagtgagg cccgcgttct gtgcgggaac tcccgagctc   180
acagagccca agaccacacg gctgcatctg cttggctgac tgggccaggc ccacgcgtag   240
taacccggac gtctctctct cacagtcccc ttgcgtctgg ccaggagct gccaggctgc    300 accccgcggt ggggatcggg agaggggcag tgtcgcccat ccccggaagg ctgagcctgg   360
tgcag                                                              365

<210> SEQ ID NO 39
<211> LENGTH: 418
<212> TYPE: DNA
<213> ORGANISM: Homo sapiens

<400> SEQUENCE: 39 cggtttttctc ctggaggact gtgttcagac agatactggt ttccttatcc gcaggtgtgc    60
gcggcgctcg caagtggtca gcataacgcc gggcgaattc ggaaagcccg tgcgtccgtg   120
gacgacccac ttggaaggag ttgggagaag tccttgttcc cacgcgcgga cgcttccctc   180
cgtgtgtcct tcgagccaca aaaagcccag accctaaccc gctccctttct cccgccgcgt   240 ccatgcagaa ctccgccgtt cctgggaggg aagcccgcg aggcgtcggg agaggcacgt    300
cctccgtgag caaagagctc ctccgagcgc gcggcgggga cgctgggccg acaggggacc   360
gcgggggcag ggcggagagg acccgccctc gagtcggccc agccctaaca ctcaggac    418

<210> SEQ ID NO 40
<211> LENGTH: 906
<212> TYPE: DNA
<213> ORGANISM: Homo sapiens

<400> SEQUENCE: 40
agggaatcgg gctgaccagt cctaaggtcc cacgctcccc tgacctcagg gcccagagcc    60
tcgcattacc ccgagcagtg cgttggttac tctccctgga agccgcccc cgccggggca   120 agtgggagtt gctgcactgc ggtctttgga ggcctaggtc gcccagagta ggcggagccc   180
tgtatccctc ctggagccgg cctcggtgact ggtcggtacc cagtacttag ggagggagga   240
cgcgcttggt gctcagggta ggctgggccg ctgctagctc ttgatttagt ctcatgtccg   300
cctttgtgcc ggcctctccg atttgtgggt ccttccaaga aagagtcctc tagggcagct   360

```
agggtcgtct cttgggtctg gcgaggcggc aggccttctt cggacctatc cccagaggtg    420
taacggagac tttctccact gcagggcggc ctggggcggg catctgccag gcagggagc    480 tgccctgccg ccgagattgt ggggaaacgg cgtggaagac accccatcgg agggcaccca    540
atctgcctct gcactcgatt ccatcctgca acccaggaga aaccatttcc gagttccagc    600
cgcagaggca cccgcggagt tgccaaaaga actcccgcg aggtcgctcg gaaccttgac    660
cctgacacct ggacgcgagg tctttcagga ccagtctcgg ctcggtagcc tggtccccga    720
ccaccgcgac caggagttcc ttcttccctt cctgctcacc agccggccgc cggcagcggc    780
tccaggaagg agcaccaacc cgcgctgggg cggaggttc aggcggcagg aatggagagg    840
ctgatcctcc tctagccccg gcgcattcac ttaggtgcgg gagccctgag gttcagcctg    900
actttc                                                              906
```

<210> SEQ ID NO 41
<211> LENGTH: 860
<212> TYPE: DNA
<213> ORGANISM: Homo sapiens

<400> SEQUENCE: 41

```
cactacggat ctgcctggac tggttcagat gcgtcgttta aaggggggg ctggcactcc     60 agagaggagg gggcgctgca ggttaattga tagccacgga agcacctagg cgccccatgc    120
gcggagccgg agccgccagc tcagtctgac ccctgtcttt tctctcctct tccctctccc    180
acccctcact ccgggaaagc gagggccgag gtagggcag atagatcacc agacaggcgg    240
agaaggacag gagtacagat ggagggacca ggacacagaa tgcaaaagac tggcaggtga    300
gaagaaggga gaaacagagg gagagagaaa gggagaaaca gagcagaggc ggccgccggc    360
ccggccgccc tgagtccgat ttccctcctt ccctgaccct tcagtttcac tgcaaatcca    420
cagaagcagg tttgcgagct cgaataccttt tgctccactg ccacgcgcag caccgggact    480
gggcgtctgg agcttaagtc tggggtctg agcctgggac cggcaaatcc gcgcagcgca    540
tcgcgcccag tctcggagac tgcaaccacc gccaaggagt acgcgcggca ggaaacttct    600
gcggcccaat ttcttcccca gctttggcat ctccgaaggc acgtacccgc cctcggcaca    660
agctctctcg tcttccactt cgacctcgag gtggagaaag aggctggcaa gggctgtgcg    720
cgtcgctggt gtgggagg cagcaggctg ccctccccg cttctgcagc gagttttccc    780
agccaggaaa agggaggggag ctgtttcagg aatttcagtg ccttcaccta gcgactgaca    840
caagtcgtgt gtataggaag                                                860
```

<210> SEQ ID NO 42
<211> LENGTH: 452
<212> TYPE: DNA
<213> ORGANISM: Homo sapiens

<400> SEQUENCE: 42

```
ggagcctgaa gtcagaaaag atggggcctc gttactcact ttctagccca gcccctggcc     60
ctgggtcccg cagagccgtc atcgcaggct cctgcccagc ctctgggtc gggtgagcaa    120 ggtgttctct tcggaagcgg gaagggctgc gggtcgggga cgtcccttgg ctgccacccc    180
tgattctgca tcctttttcgc tcgaatccct gcgctaggca tcctccccga tcccccaaaa    240
gcccaagcac tgggtctggg ttgaggaagg gaacgggtgc ccaggccgga cagaggctga    300
aaggaggcct caaggttcct ctttgctaca aagtggagaa gttgctctac tctggagggc    360
```

-continued

| agtggccttt tccaaacttt tccacttagg tccgtaagaa aagcaattca tacacgatca | 420 |
| gcgctttcgg tgcgaggatg gaaagaaact tc | 452 |

<210> SEQ ID NO 43
<211> LENGTH: 1992
<212> TYPE: DNA
<213> ORGANISM: Homo sapiens
<400> SEQUENCE: 43

| ttttcctgtt acagagctga gcccactcat gtggtgccaa gtagcgacta tctctcggcc | 60 |
| acctccaccc agagcaatgt gggcgccccc agcgggtggg agcgattgcc gagcggcgca | 120 |
| agggcgttta acgcctaacc ccctcctcct gggttgccaa gccgctaggt cgccgtttcc | 180 |
| aacgtggctg cgcgggactg aagtccgacg actcctcgtc ctcagtagga gacacacctc | 240 |
| ccactgcccc cagccacgcg agctatgggc agaatcgggg caacggtaat atctggatgg | 300 |
| ggcaggctcc cctgaggctg tgcttaagaa aaaggaatc tggagtagcc tgaggggccc | 360 |
| cacgaggggg cctcctttgc gatcgtctcc cagccttagg ccaaggctac ggaggcaggc | 420 |
| ggccgagtgt tggcgcccag cccggccgag gactggatgg aggacgagaa gcagcctgcc | 480 |
| tctgggcgac agctgcggac gcagcctcgc cgcctcgccg cctcagcctc ggtcccagcg | 540 |
| tctctaaagc cgcgcccatt ttacagatgc agggcaggga gacaagaggc atccgggg | 600 |
| gccgagtaga atgatggcgc gggttctccc ggcgccctga tttcgaggct cgcgcccggg | 660 |
| ccctacatgc aggcggggag gcctgggccg aaggcgtctg caaggagggg cgagtctgcc | 720 |
| cggtccgggg agggagtgag gccacagtca gttctcccta ggaggccgcg cagcgggtag | 780 |
| ggtatgggac tggggacgc aacggggacc tggccgaatc agagccctca gcagagaacg | 840 |
| ccgaaaactc tggggccggc cgctcgcttc ccgctagtgg gaatggtttc cggtcatccg | 900 |
| ttcccagtcc agccccgggt agggagctct gatttgcaat gcacagcact tgcgaggttc | 960 |
| gaatgccccc gcaatttgca gatggaaata ctaagcctag gccgggcgtg gtggctcaag | 1020 |
| cctatcatct cagccctttg ggaggccaag ccgggaggat tgtttgagcc caagaattca | 1080 |
| aaaccagcct gagcaacata gcgacccgt ctctacaaaa taaataaaa taaattatcc | 1140 |
| gggcgtggtg gcacgcgcct gtggttccag ctactccgga ggctgaggtg gaggatcgc | 1200 |
| ttgagtccgg gaggtcgagg ctacagtgag ccgtgatcgc accactgcac tccagcctgg | 1260 |
| gcgacagagt gagaccttgt ctcaaaaaag gaaaaaaga aaagaaagt aagcttcaaa | 1320 |
| gaagctctga taatagttct gggtcgtgca gcggtggcgg ccccgcgctc tcgcccctaa | 1380 |
| agcaagcgct ctttgtactg ggtggaggag ctttgagtag tgagggtgga gatgcagctt | 1440 |
| cggggtggcg cagccaccct gacactaggc ccggggtcgc agtgggacag aagagtctgc | 1500 |
| cgctctgact tgggctctga gttccaaggg cgcccggcac ttctagcctc ccaggcttgc | 1560 |
| gcgctggcgc ctttgccatc cgtgccgaag tggggagacc tagccgcgac caccacgagc | 1620 |
| gcagcggtga cacccagagg tcccaccggg ccctgggca gggtaacctt agcctgtccg | 1680 |
| cttcggcagc tttgcgaaga gtggcgcgca gctagggctg aggctcttgc ggacctgcgg | 1740 |
| tcgaagcagg cggctgagcc agttcgatcg ccaaggcctg gctgccgac agtggtgcgc | 1800 |
| gctctgttcc gccgcggccg ggccaggcgc tctggaatag cgatgggggg acacggcctc | 1860 |
| caactttctg cagagaccat cgggcagctc cgggcctaag cagcgacctc accgaaggtt | 1920 |
| cctgggaacc tttgccaaaa tcccagcctc tgcctcggtc cagctaaacc gtgtgtaaac | 1980 |
| aagtgcacca ag | 1992 |

<210> SEQ ID NO 44
<211> LENGTH: 448
<212> TYPE: DNA
<213> ORGANISM: Homo sapiens

<400> SEQUENCE: 44
ataaaggacc gggtaatttc gcggaatgcg gattttgaga caggcccaga cggcggcgga      60
ttccctgtgt cccccaactg gggcgatctc gtgaacacac ctgcgtccca ccccgatcct     120
aggttggggg gaaagggtat gggaaccctg agcccagagc gcgccccgct ctttcctttg     180
ctccccggct tccctggcca gcccctccc ggctggtttc ctcgctcact cggcgcctgg      240
cgtttcgggc gtctggagat caccgcgtgt ctggcacccc aacgtctagt ctccccgcag     300
gttgaccgcg gcgcctggag ccgggaatag gggtggggag tccggagaac caaacccgag     360
cctgaagttg ccattcgggt gactcccgag aaagcccggg agcattttgg ccaatgcggg     420
tttttacctg aacttcagca tcttcacc                                       448

<210> SEQ ID NO 45
<211> LENGTH: 395
<212> TYPE: DNA
<213> ORGANISM: Homo sapiens

<400> SEQUENCE: 45
aattggaaaa ccctggtatt gtgcctgttt gggggaagaa aacgtcaata aaaattaatt     60
gatgagttgg cagggcgggc ggtgcgggtt cgcggcgagg cgcagggtgt catggcaaat    120
gttacggctc agattaagcg attgttaatt aaaaagcgac ggtaattaat actcgctacg    180
ccatatgggc ccgtgaaaag gcacaaaagg tttctccgca tgtggggttc cccttctctt    240
ttctccttcc acaaaagcac cccagcccgt gggtccccc tttggcccca aggtaggtgg     300
aactcgtcac ttccggccag ggaggggatg gggcggtctc cggcgagttc caagggcgtc    360
cctcgttgcg cactcgcccg cccaggttct ttgaa                              395

<210> SEQ ID NO 46
<211> LENGTH: 491
<212> TYPE: DNA
<213> ORGANISM: Homo sapiens

<400> SEQUENCE: 46
gggaagcgat cgtctcctct gtcaactcgc gcctgggcac ttagcccctc ccgtttcagg     60
gcgccgcctc cccggatggc aaacactata aagtggcggc gaataaggtt cctcctgctg    120
ctctcggttt agtccaagat cagcgatatc acgcgtcccc cggagcatcg cgtgcaggag    180
ccatggcgcg ggagctatac cacgaagagt tcgcccgggc gggcaagcag gcggggctgc    240
aggtctggag gattgagaag ctggagctgg tgcccgtgcc ccagagcgct cacggcgact    300
tctacgtcgg ggatgcctac ctggtgctgc acacggccaa gacgagccga ggcttcacct    360
accacctgca cttctggctc ggtaagggac ggcggcggc gggaccccga cgcaccaagg     420
ccggcgaggg gagggcgtag gggtctgaga tttgcaggcg tgggagtaaa ggggaccgca    480
aactgagcta g                                                         491

<210> SEQ ID NO 47
<211> LENGTH: 1284
<212> TYPE: DNA
<213> ORGANISM: Homo sapiens

<400> SEQUENCE: 47

```
ctcaggggcg ggaagtggcg ggtgggagtc acccaagcgt gactgcccga ggcccctcct        60
gccgcggcga ggaagctcca taaaagccct gtcgcgaccc gctctctgca ccccatccgc       120
tggctctcac ccctcggaga cgctcgcccg acagcatagt acttgccgcc cagccacgcc       180
cgcgcgccag ccaccgtgag tgctacgacc cgtctgtcta ggggtgggag cgaacggggc       240
gcccgcgaac ttgctagaga cgcagcctcc cgctctgtgg agccctgggg ccctgggatg       300
atcgcgctcc actcccccagc ggactatgcc ggctccgcgc cccgacgcgg accagccctc       360
ttggcggcta aattccactt gttcctctgc tcccctctga ttgtccacgg cccttctccc       420
gggcccttcc cgctgggcgg ttcttctgag ttaccttta gcagatatgg agggagaacc       480
cgggaccgct atcccaaggc agctggcggt ctccctgcgg gtcgccgcct tgaggcccag       540
gaagcggtgc gcggtaggaa ggtttccccg gcagcgccat cgagtgagga atccctggag       600
ctctagagcc ccgcgccctg ccacctccct ggattcttgg gctccaaatc tctttggagc       660
aattctggcc cagggagcaa ttctctttcc ccttccccac cgcagtcgtc accccgaggt       720
gatctctgct gtcagcgttg atcccctgaa gctaggcaga ccagaagtaa cagagaagaa       780
acttttcttc ccagacaaga gtttgggcaa gaagggagaa aagtgaccca gcaggaagaa       840
cttccaattc ggttttgaat gctaaactgg cggggccccc accttgcact ctcgccgcgc       900
gcttcttggt ccctgagact tcgaacgaag ttgcgcgaag ttttcaggtg gagcagaggg       960
gcaggtcccg accggacggc gcccggagcc cgcaaggtgg tgctagccac tcctgggttc      1020
tctctgcggg actgggacga gagcggattg ggggtcgcgt gtggtagcag gaggaggagc      1080
gcggggggca gaggagggag gtgctgcgcg tgggtgctct gaatccccaa gcccgtccgt      1140
tgagccttct gtgcctgcag atgctaggta acaagcgact ggggctgtcc ggactgaccc      1200
tcgccctgtc cctgctcgtg tgcctgggtg cgctggccga ggcgtacccc tccaagccgg      1260
acaacccggg cgaggacgca ccag                                             1284
```

<210> SEQ ID NO 48
<211> LENGTH: 554
<212> TYPE: DNA
<213> ORGANISM: Homo sapiens

<400> SEQUENCE: 48

```
tggagaacct tgggctctgt ggcctcaaag gtaggggtga tttcgagggg ccggcacctc        60
acagggcagg ttccaccgcg gaaacgcagt catcgcccag cgaccctgct cctggccctc       120
agcctccccc caggtttctt tttctcttga atcaagccga ggtgcgccaa tggccttcct       180
tgggtcggat ccggggggcc agggccagct tacctgcttt caccgagcag tggatatgtg       240
ccttggactc gtagtacacc cagtcgaagc cggcctccac cgccaggcgg ccagcatgc       300
cgtacttgct gcggtcgcgg tcagacgtgg tgatgtccac tgcgcggccc tcgtagtgca       360
gagactcctc tgagtggtgg ccatcttcgt cccagccctc ggtcaccgc agtttcactc       420
ctggccactg gttcatcacc gagatggcca aagcgttcaa cttgtcctta cacctctgcg       480
aagacaaggg gaccccacc gacggacacg ttagcctggg caaccgccac ccctcccggc       540
ccctccatca gcct                                                         554
```

<210> SEQ ID NO 49
<211> LENGTH: 772
<212> TYPE: DNA
<213> ORGANISM: Homo sapiens

<400> SEQUENCE: 49

```
tctcacgacc catccgttaa cccaccgttc ccaggagctc cgaggcgcag cggcgacaga        60
ggttcgcccc ggcctgctag cattggcatt gcggttgact gagcttcgcc taacaggctt       120
ggggagggtg ggctgggctg ggctgggctg ggctgggtgc tgcccggctg tccgcctttc       180
gttttcctgg gaccgaggag tcttccgctc cgtatctgcc tagagtctga atccgacttt       240
cttcctttg  ggcacgcgct cgccagtgga gcacttcttg ttctggcccc gggctgatct       300
gcacgcggac ttgagcaggt gccaaggtgc cacgcagtcc cctcacggct ttcgggggt        360
cttggagtcg ggtggggagg gagacttagg tgtggtaacc tgcgcaggtg ccaaagggca       420
gaaggagcag ccttggatta tagtcacggt ctctccctct cttccctgcc attttaggg        480
cttcctctac gtgctgttgt ctcactgggt ttttgtcgga gccccacgcc ctccggcctc       540
tgattcctgg aagaaagggt tggtcccctc agcaccccca gcatcccgga aaatggggag       600
caaggctctg ccagcgccca tcccgctcca cccgtcgctg cagctcacca attactcctt       660
cctgcaggcc gtgaacacct tcccggccac ggtggaccac ctgcagggcc tgtacggtct       720
cagcgcggta cagaccatgc acatgaacca ctggacgctg ggtatccca at                 772
```

<210> SEQ ID NO 50
<211> LENGTH: 1362
<212> TYPE: DNA
<213> ORGANISM: Homo sapiens

<400> SEQUENCE: 50

```
tggtttcctt tcgcttctcg cctcccaaac acctccagca agtcggaggg cgcgaacgcg        60
gagccagaaa cccttcccca aagtttctcc cgccaggtac ctaattgaat catccatagg       120
atgacaaatc agccagggcc aagatttcca gacacttgag tgacttcccg gtccccgagg       180
tgacttgtca gctccagtga gtaacttgga actgtcgctc ggggcaaggt gtgtgtctag       240
gagagagccg gcggctcact cacgctttcc agagagcgac ccgggccgac ttcaaaatac       300
acacagggtc atttataggg actggagccg cgcgcaggac aacgtctccg agactgagac       360
attttccaaa cagtgctgac attttgtcgg gccccataaa aaatgtaaac gcgaggtgac       420
gaacccggcg gggagggttc gtgtctggct gtgtctgcgt cctggcggcg tgggaggtta       480
tagttccaga cctggcggct gcggatcgcc gggccggtac ccgcgaggag tgtaggtacc       540
ctcagcccga ccacctcccg caatcatggg gacaccggct tggatgagac acaggcgtgg       600
aaaacagcct tcgtgaaact ccacaaacac gtggaacttg aaaagacaac tacagccccg       660
cgtgtgcgcg agagacctca cgtcacccca tcagttccca cttcgccaaa gtttcccttc       720
agtggggact ccagagtggt gcgccccatg cccgtgcgtc ctgtaacgtg ccctgattgt       780
gtaccctct  gcccgctcta cttgaaatga aaacacaaaa actgttccga attagcgcaa       840
ctttaaagcc ccgttatctg tcttctacac tgggcgctct taggccactg acagaaacat       900
ggtttgaacc ctaattgttg ctatcagtct cagtcagcgc aggtctctca gtgacctgtg       960
acgccgggag ttgaggtgcg cgtatcctta aacccgcgcg aacgccaccg gctcagcgta      1020
gaaaactatt tgtaatccct agtttgcgtc tctgagcttt aactccccca cactctcaag      1080
cgcccggttt ctcctcgtct ctcgcctgcg agcaaagttc ctatggcatc cacttaccag      1140
gtaacccggga tttccacaac aaagcccggc gtgcgggtcc cttccccggg ccggccagcg     1200
cgagtgacag cgggcggccg gcgctggcga ggagtaactt ggggctccag cccttcagag     1260
```

| | |
|---|---|
| cgctccgcgg gctgtgcctc cttcggaaat gaaaaccccc atccaaacgg ggggacggag | 1320 |
| cgcggaaacc cggcccaagt gccgtgtgtg cgcgcgcgtc tg | 1362 |

<210> SEQ ID NO 51
<211> LENGTH: 476
<212> TYPE: DNA
<213> ORGANISM: Homo sapiens

<400> SEQUENCE: 51

| | |
|---|---|
| gaaagccatc cttaccattc ccctcaccct ccgccctctg atcgcccacc cgccgaaagg | 60 |
| gtttctaaaa atagcccagg gcttcaaggc cgcgcttctg tgaagtgtgg agcgagcggg | 120 |
| cacgtagcgg tctctgccag gtggctggag ccctggaagc gagaaggcgc ttcctccctg | 180 |
| catttccacc tcaccccacc cccggctcat ttttctaaga aaaagttttt gcggttccct | 240 |
| ttgcctccta cccccgctgc cgcgcggggt ctgggtgcag accctgcca ggttccgcag | 300 |
| tgtgcagcgg cggctgctgc gctctcccag cctcggcgag ggttaaaggc gtccggagca | 360 |
| ggcagagcgc cgcgcgccag tctattttta cttgcttccc ccgccgctcc gcgctccccc | 420 |
| ttctcagcag ttgcacatgc cagctctgct gaaggcatca atgaaaacag cagtag | 476 |

<210> SEQ ID NO 52
<211> LENGTH: 300
<212> TYPE: DNA
<213> ORGANISM: Homo sapiens

<400> SEQUENCE: 52

| | |
|---|---|
| atcgaaaatg tcgacatctt gctaatggtc tgcaaacttc cgccaattat gactgacctc | 60 |
| ccagactcgg ccccaggagg ctcgtattag gcagggaggc cgccgtaatt ctgggatcaa | 120 |
| aagcgggaag gtgcgaactc ctctttgtct ctgcgtgccc ggcgcgcccc cctcccggtg | 180 |
| ggtgataaac ccactctggc gccggccatg cgctgggtga ttaatttgcg aacaaacaaa | 240 |
| agcggcctgg tggccactgc attcgggtta acattggcc agcgtgttcc gaaggcttgt | 300 |

<210> SEQ ID NO 53
<211> LENGTH: 1246
<212> TYPE: DNA
<213> ORGANISM: Homo sapiens

<400> SEQUENCE: 53

| | |
|---|---|
| atcaacatcg tggctttggt cttttccatc atggtgagtg aatcacggcc agaggcagcc | 60 |
| tgggaggaga gacccgggcg gctttgagcc cctgcagggg agtccgcgcg ctctctgcgg | 120 |
| ctcccttcct cacggcccgg cccgcgctag gtgttctttg tcctcgcacc tcctcctcac | 180 |
| ctttctcggg ctctcagagc tctccccgca atcatcagca cctcctctgc actcctcgtg | 240 |
| gtactcagag ccctgatcaa gcttccccca ggctagcttt cctcttcttt ccagctccca | 300 |
| gggtgcgttt cctctccaac ccggggaagt tcttccgtgg actttgctga ctcctctgac | 360 |
| cttcctaggc acttgcccgg ggcttctcaa ccctcttttc tagagcccca gtgcgcgcca | 420 |
| ccctagcgag cgcagtaagc tcataccccg agcatgcagg ctctacgttc ctttccctgc | 480 |
| cgctccgggg gctcctgctc tccagcgccc aggactgtct ctatctcagc ctgtgctccc | 540 |
| ttctctcttt gctgcgccca agggcaccgc ttccgccact ctccgggggg tcccaggcg | 600 |
| attcctgatg cccctccctt gatccgtttt ccgcgctttg gcacggcacg ctctgtccag | 660 |
| gcaacagttt cctctcgctt cttcctacac ccaacttcct ctccttgcct ccctccggcg | 720 |
| cccccttttt aacgcgcccg aggctggctc acacccacta cctctttagg cctttcttag | 780 |

| | |
|---|---:|
| gctccccgtg tgccccctc accagcaaag tgggtgcgcc tctcttactc tttctaccca | 840 |
| gcgcgtcgta gttcctcccc gtttgctgcg cactggccct aacctctctt ctcttggtgt | 900 |
| cccccagagc tcccaggcgc cctccaccg ctctgtcctg cgcccggggc tctcccggga | 960 |
| atgaactagg ggattccacg caacgtgcgg ctccgcccgc cctctgcgct cagacctccc | 1020 |
| gagctgcccg cctctctagg agtggccgct ggggcctcta gtccgccctt ccggagctca | 1080 |
| gctccctagc cctcttcaac cctggtagga acacccgagc gaaccccacc aggagggcga | 1140 |
| cgagcgcctg ctaggccctc gccttattga ctgcagcagc tggcccgggg gtggcggcgg | 1200 |
| ggtgaggttc gtaccggcac tgtcccggga caacccttgc agttgc | 1246 |

<210> SEQ ID NO 54
<211> LENGTH: 984
<212> TYPE: DNA
<213> ORGANISM: Homo sapiens

<400> SEQUENCE: 54

| | |
|---|---:|
| acaaataaaa caccctctag cttcccctag actttgttta actggccggg tctccagaag | 60 |
| gaacgctggg gatgggatgg gtggagagag ggagcggctc aaggacttta gtgaggagca | 120 |
| ggcgagaagg agcacgttca ggcgtcaaga ccgatttctc cccctgcttc gggagacttt | 180 |
| tgaacgctcg gagaggcccg gcatctcacc actttacttg gccgtagggg cctccggcac | 240 |
| ggcaggaatg agggaggggg tccgattgga cagtgacggt ttgggccgt tcggctatgt | 300 |
| tcagggacca tatggtttgg ggacagcccc agtagttagt aggggacggg tgcgttcgcc | 360 |
| cagtccccgg atgcgtaggg aggcccagtg gcaggcagct gtcccaagca gcgggtgcgc | 420 |
| gtccctgcgc gctgtgtgtt cattttgcag agccagcctt cggggaggtg aaccagctgg | 480 |
| gaggagtgtt cgtgaacggg aggccgctgc ccaacgccat ccggcttcgc atcgtggaac | 540 |
| tggcccaact gggcatccga ccgtgtgaca tcagccgcca gctacgggtc tcgcacggct | 600 |
| gcgtcagcaa gatcctggcg cgatacaacg agacgggctc gatcttgcca ggagccatcg | 660 |
| ggggcagcaa gccccgggtc actacccca ccgtggtgaa acacatccgg acctacaagc | 720 |
| agagagaccc cggcatcttc gcctgggaga tccgggaccg cctgctggcg gacggcgtgt | 780 |
| gcgacaagta caatgtgccc tccgtgagct ccatcagccg cattctgcgc aacaagatcg | 840 |
| gcaacttggc ccagcagggt cattacgact catacaagca gcaccagccg acgccgcagc | 900 |
| cagcgctgcc ctacaaccac atctactcgt accccagccc tatcacggcg gcggccgcca | 960 |
| aggtgcccac gccacccggg gtgc | 984 |

<210> SEQ ID NO 55
<211> LENGTH: 545
<212> TYPE: DNA
<213> ORGANISM: Homo sapiens

<400> SEQUENCE: 55

| | |
|---|---:|
| aggaggcgca acgcgctgcc agggcggctt tatcctgccg ccacagggcg gggaccagcc | 60 |
| cggcagccgg gtgtccagcg ccgctcacgt gcctcgcctg gagcttagct ctcagactcc | 120 |
| gaagagggcg actgagactt gggcctggga gttggcttcg gggtacccaa ggcgacgaca | 180 |
| gctgagttgt accacgaagc tcaggccgag gcctcctccc ttgtctggcc ttcgaatcca | 240 |
| tactggcagc ctctcctctc aggcactccg cgggccgggc cactaggccc cctgctcctg | 300 |
| gagctgcgct atgatccggg tcttgagatg cgcgcgattc tctctgaacc ggtggagagg | 360 |

| | |
|---|---|
| aggctctgcc ccgcgcggag cgaggacagc ggcgcccgag cttcccgcgc ctctccaggg | 420 |
| cccaatggca agaacagcct ccgaagtgcg cggatgacag gaaaagatct tcagttcttc | 480 |
| tgccgctaga gaagtgcggg atacaagcct ctattggatc cacaacctgg agtcctgcct | 540 |
| tcgga | 545 |

<210> SEQ ID NO 56
<211> LENGTH: 1533
<212> TYPE: DNA
<213> ORGANISM: Homo sapiens

<400> SEQUENCE: 56

| | |
|---|---|
| atctgcgtgc cctttctgg gcgagccctg ggagatccag ggagaactgg gcgctccaga | 60 |
| tggtgtatgt ctgtaccttc acagcaaggc ttcccttgga tttgaggctt cctattttgt | 120 |
| ctgggatcgg ggtttctcct tgtcccagtg gcagccccgc gttgcgggtt ccgggcgctg | 180 |
| cgcggagccc aaggctgcat ggcagtgtgc agcgcccgcc agtcgggctg gtgggttgtg | 240 |
| cactccgtcg gcagctgcag aaaggtggga gtgcaggtct tgcctttcct caccgggcgg | 300 |
| ttggcttcca gcaccgaggc tgacctatcg tggcaagttt gcggccccg cagatcccca | 360 |
| gtggagaaag agggctcttc cgatgcgatc gagtgtgcgc ctccccgcaa agcaatgcag | 420 |
| accctaaatc actcaaggcc tggagctcca gtctcaaagg tggcagaaaa ggccagacct | 480 |
| aactcgagca cctactgcct tctgcttgcc ccgcagagcc ttcagggact gactgggacg | 540 |
| cccctggtgg cgggcagtcc catccgccat gagaacgccg tgcagggcag cgcagtggag | 600 |
| gtgcagacgt accagccgcc gtggaaggcg ctcagcgagt tgccctcca gagcgacctg | 660 |
| gaccaacccg ccttccaaca gctggtgagg ccctgcccta cccgccccga cctcgggact | 720 |
| ctgcgggttg ggatttagc cacttagcct ggcagagagg ggaggggtg gccttgggct | 780 |
| gagggctgg gtacagccct aggcggtggg ggagggggaa cagtggcggg ctctgaaacc | 840 |
| tcacctcggc ccattacgcg ccctaaacca ggtctccctg gattaaagtg ctcacaagag | 900 |
| aggtcgcagg attaaccaac ccgctccccc gccctaatcc ccccctcgtg cgcctgggga | 960 |
| cctggcctcc ttctccgcag ggcttgctct cagctggcgg ccggtcccca agggacactt | 1020 |
| tccgactcgg agcacgcggc cctggagcac cagctcgcgt gcctcttcac ctgcctcttc | 1080 |
| ccggtgtttc cgccgcccca ggtctccttc tccgagtccg gctccctagg caactcctcc | 1140 |
| ggcagcgacg tgacctccct gtcctcgcag ctcccggaca cccccaacag tatggtgccg | 1200 |
| agtcccgtgg agacgtgagg gggaccccctc cctgccagcc cgcggacctc gcatgctccc | 1260 |
| tgcatgagac tcacccatgc tcaggccatt ccagttccga aagctctctc gccttcgtaa | 1320 |
| ttattctatt gttatttatg agagagtacc gagagacacg gtctggacag cccaaggcgc | 1380 |
| caggatgcaa cctgctttca ccagactgca gaccctgct ccgaggactc ttagtttttc | 1440 |
| aaaaccagaa tctgggactt accagggtta gctctgccct ctcctctcct ctctacgtgg | 1500 |
| ccgccgctct gtctctccac gccccacctg tgt | 1533 |

<210> SEQ ID NO 57
<211> LENGTH: 702
<212> TYPE: DNA
<213> ORGANISM: Homo sapiens

<400> SEQUENCE: 57

| | |
|---|---|
| aggtctcttc agactgccca ttctccgggc ctcgctgaat gcgggggctc tatccacagc | 60 |
| gcgcggggcc gagctcaggc aggctggggc gaagatctga ttctttcctt cccgccgcca | 120 |

| | | |
|---|---|---|
| aaccgaatta atcagtttct tcaacctgag ttactaagaa agaaaggtcc ttccaaataa | 180 |
| aactgaaaat cactgcgaat gacaatacta tactacaagt tcgttttggg gccggtgggt | 240 |
| gggatggagg agaaagggca cggataatcc cggagggccg cggagtgagg aggactatgg | 300 |
| tcgcggtgga atctctgttc cgctggcaca tccgcgcagg tgcggctctg agtgctggct | 360 |
| cggggttaca gacctcggca tccggctgca ggggcagaca gagacctcct ctgctagggc | 420 |
| gtgcggtagg catcgtatgg agcccagaga ctgccgagag cactgcgcac tcaccaagtg | 480 |
| ttaggggtgc ccgtgataga ccgccaggga aggggctggt tcggagggaa ttcccgctac | 540 |
| cgggaaggtc ggaactcggg gtgatcaaac aaggaatgca tctcacctcc gtgggtgctt | 600 |
| gtgctgcgca aggaattatt accggagcgg ttgcgatggc ctttgcccgg cgacccaaga | 660 |
| agagtaagca aactaccgtc cacccagcgg atcaggtcca at | 702 |

```
<210> SEQ ID NO 58
<211> LENGTH: 3180
<212> TYPE: DNA
<213> ORGANISM: Homo sapiens

<400> SEQUENCE: 58
```

| | | |
|---|---|---|
| gatgtcctgt ttctagcagc ctccagagcc aagctaggcg agaggcgtag gaggcagaga | 60 |
| gagcgggcgc gggaggccag ggtccgcctg ggggcctgag gggacttcgt ggggtcccgg | 120 |
| gagtggccta gaaacaggga gctgggaggg ccggaagag cttgaggctg agcgggggac | 180 |
| gaacgggcag cgcaaagggg agatgaacgg aatggccgag gagccacgca ttcgccttgt | 240 |
| gtccgcggac ccttgttccc gacaggcgac caagccaagg ccctccggac tgacgcggcc | 300 |
| tgagcagcag cgagtgtgaa gtttggcacc tccggcggcg agacggcgcg ttctggcgcg | 360 |
| cggctcctgc gtccggctgg tggagctgct gcgccctatg cggcctgccg agggcgccgc | 420 |
| cgagggcccg cgagctccgt ggggtcgggg tgggggacc cggagcgga cagcgcggcc | 480 |
| cgaggggcag gggcaggggc gcgcctggcc tggggtgtgt ctgggccccg gctccgggct | 540 |
| cttgaaggac cgcgagcagg aggcttgcgc aatcccttgg ctgagcgtcc acggagaaag | 600 |
| aaaaagagca aaagcagagc gagagtggag cgagggatgg gggcgggcaa agagccatcc | 660 |
| gggtctccac caccgccctg acacgcgacc cggctgtctg ttggggaccg cacgggggct | 720 |
| cgggcgagca gggagggag gagcctgcgc ggggctcgtg ttcgcccagg aatcccggag | 780 |
| aagctcgaag acggtctggt gttgaacgca cacgtggact ccatttcatt accaccttgc | 840 |
| agctcttgcg ccacggaggc tgctgctgcc cggcggctgc tacccaccga gacccacgtg | 900 |
| gcccctcccc aggggtgtag gggtgacggt tgtcttctgg tgacagcaga ggtgttgggt | 960 |
| ttgcgactga tctctaacga gcttgaggcg caaacctagg attccctgag tgttggggtg | 1020 |
| cggcgggggg gcaagcaagg tgggacgacg cctgcctggt ttccctgact agttgcgggg | 1080 |
| ggtgggggcc ggctctcagg ggccaccaga agctgggtgg gtgtacagga aaatattttt | 1140 |
| ctcctgccgt gttttggcttt tcctggcat ttttgcccag ggcgaagaac tgtcgcgcgg | 1200 |
| ggcagctcca ccgcggaggg agaggggtcg cgaggctggc gcgggaagcg ctgtaggtgg | 1260 |
| cagtcatccg tccacgccgc acaggccgtc tgcgccgtcg gaccatcggg aggtctgcag | 1320 |
| caactttgtc ccggccagtc cccttgtccg ggaagggggct gagcttcccg acactctacc | 1380 |
| ctccccctct tgaaaatccc ctggaaaatc tgtttgcaat gggtgtttcc gcggcgtcca | 1440 |
| ggtctgggct gccgggggag gccgagcggc tgctgcagcc tccctgctgc caggggcgtc | 1500 |

```
ggactccgct tcgctcacta cgcccaggcc cctcagggc  ccacgctcag gacttcgggg   1560
ccacacagca ggacccggtg ccccgacgac gagtttgcgc aggacccggg ctgggccagc   1620
cgcggagctg gggaggaagg ggcggggtc  ggtgcagcgg atcttttctg ttgctgcctg   1680
tgcggcggca ggaagcgtct tgaggctccc caagactacc tgaggggccg cccaagcact   1740
tcagaagccc aaggagcccc cggccacccc cgctcctggc cttttgcca  acgactttga   1800 aagtgaaatg cacaagcacc agcaattgac ttcccttccg tggttattta ttttgtcttt   1860
gtggatggtg ggcagatggg gagagaggcc cctacctaac ctcggtggct ggtccctaga   1920
ccacccctgc cagccggtgt ggggaggagc tcaggtccgc gggagagcga atgggcgcca   1980
ggaggtggga cagaatcctg ggaaggtaca gcggacgccc tggaagctcc cctgatgccc   2040
cagagggccc ttcctgggaa acctcccggg ggggtgcccc ataccatccc acccggctgt   2100
cttggcccct cccagggagc cgcaggagaa actagccta  cacctgggat cccagagcc   2160 ttctgctggg gctcctgccc ccgacttcgg ataaccagct ccgcacaggt ccccgagaag   2220
ggccgctggc ctgcttattt gatactgccc cctcccagac aggggctggt cgagcccctg   2280
gttctgctgc cagactgaag ccttccagac gccacctcgg tttgggcccc cagggcctc   2340 aggggcccca ggagaggaga gctgctatct agctcagcca caggctcgct cctggtgggg   2400
gccaggctga aggagtggac cctggagagg tcgggaacct tttaacagcc gtgggctgga   2460
gggtggctac taagtgttcg gtctgggaag aggcatgacc cgcaccatcc cggggaaata   2520
aacgacttct taagggaatc ttctcgctga gcgggtgctc tgggccagga gattgccacc   2580
gccagcccac ggaacccaga tttgggctct gccttgagcg ggccgcctgt ggcttcccgg   2640
gtcgctcccc cgactcagaa agctctcaag ttggtatcgt tttcccggcc ctcggaggtg   2700
gattgcagat caccgagagg ggatttacca gtaaccacta cagaatctac ccgggcttta   2760
acaagcgctc atttctctcc cttgtcctta gaaaaacttc gcgctggcgt tgatcatatc   2820
gtacttgtag cggcagctta ggggcagcgg aactggtggg gttgtgcgtg caggggagg   2880 ctgtgaggga gccctgcact ccgcccctcc accttctgg  aggagtggct tgttctaa    2940 gggtgccccc ccaaccccg  ggtccccact tcaatgtttc tgctcttgt  cccaccgccc   3000 gtgaaagctc ggctttcatt tggtcggcga agcctccgac gcccccgagt cccaccctag   3060
cgggccgcgc ggcactgcag ccgggggttc ctgcggactg gcccgacagg gtgcgcggac   3120
ggggacgcgg gccccgagca ccgcgacgcc agggtccttt ggcagggccc aagcacccct   3180

<210> SEQ ID NO 59
<211> LENGTH: 1038
<212> TYPE: DNA
<213> ORGANISM: Homo sapiens

<400> SEQUENCE: 59
tggcggccgg cgggcacagc cggctcattg ttctgcacta caaccactcg ggccggctgg     60
ccgggcgcgg ggggccggag gatggcggcc tgggggccct gcggggctg  tcggtggccg    120 ccagctgcct ggtggtgctg gagaacttgc tggtgctggc ggccatcacc agccacatgc    180
ggtcgcgacg ctgggtctac tattgcctgg tgaacatcac gctgagtgac ctgctcacgg    240
gcgcggccta cctggccaac gtgctgctgt cggggggccg caccttccgt ctggcgcccg    300 ccagtggtt  cctacgggag ggctgctct  tcaccgccct ggccgcctcc accttcagcc    360
tgctcttcac tgcaggggag cgctttgcca ccatggtgcg gccggtggcc gagagcgggg    420
ccaccaagac cagccgcgtc tacggcttca tcggcctctg ctggctgctg gccgcgctgc    480
```

```
tggggatgct gcctttgctg ggctggaact gcctgtgcgc ctttgaccgc tgctccagcc      540
ttctgcccct ctactccaag cgctacatcc tcttctgcct ggtgatcttc gccggcgtcc      600
tggccaccat catgggcctc tatggggcca tcttccgcct ggtgcaggcc agcgggcaga      660
aggccccacg cccagcggcc cgccgcaagg cccgccgcct gctgaagacg gtgctgatga      720
tcctgctggc cttcctggtg tgctggggcc cactcttcgg gctgctgctg gccgacgtct      780
ttggctccaa cctctgggcc caggagtacc tgcggggcat ggactggatc ctggccctgg      840
ccgtcctcaa ctcggcggtc aaccccatca tctactcctt ccgcagcagg gaggtgtgca      900
gagccgtgct cagcttcctc tgctgcgggt gtctccggct gggcatgcga gggcccgggg      960
actgcctggc ccgggccgtc gaggctcact ccggagcttc caccaccgac agctctctga     1020
ggccaaggga cagctttc                                                   1038

<210> SEQ ID NO 60
<211> LENGTH: 374
<212> TYPE: DNA
<213> ORGANISM: Homo sapiens

<400> SEQUENCE: 60
tagtaaggca ccgaggggtg gctcctctcc ctgcagcggc tgtcgcttac catcctgtag       60
accgtgacct cctcacacag cgccaggacg aggatcgcgg tgagccagca ggtgactgcg      120
atcctggagc tggtcgcagc aggccatcct gcacgcggtg gaggcgcccc ctgcaggccg      180
cagcgcatcc ccagcttctg gacgcactgt gagcggttat gcagcagcac gctcatatga      240
gatgccccgc agggtgctat gcaggcccac gtccccacaa agcccatggc aggcgcccgg      300
gtgccggagc acgcacttgg ccccatggat ctctgtgccc agggctcagc caggcatctg      360
gccgctaaag gttt                                                       374

<210> SEQ ID NO 61
<211> LENGTH: 246
<212> TYPE: DNA
<213> ORGANISM: Homo sapiens

<400> SEQUENCE: 61
tctcatctga gcgctgtctt tcaccagagc tctgtaggac tgaggcagta gcgctggccc       60
gcctgcgaga gcccgaccgt ggacgatgcg tcgcgcccct cccatcgcgg cctgggcggg      120
cccgcctgcc ctcggctgag cccggtttcc ctaccccggg gcacctcccc tcgcccgcac      180
ccggccccag tccctcccag gcttgcgggt agagcctgtc tttgcccaga aggccgtctc      240
caagct                                                                246

<210> SEQ ID NO 62
<211> LENGTH: 222
<212> TYPE: DNA
<213> ORGANISM: Homo sapiens

<400> SEQUENCE: 62
cagtccccga ggccctcccc ggtgactcta accagggatt tcagcgcgcg gcgcggggct       60
gcccccaggc gtgacctcac ccgtgctctc tccctgcaga atctcctacg acccggcgag      120
gtaccccagg tacctgcctg aagcctactg cctgtgccgg ggctgcctga ccgggctgtt      180
cggcgaggag gacgtgcgct tccgcagcgc ccctgtctac at                        222

<210> SEQ ID NO 63
```

<211> LENGTH: 2209
<212> TYPE: DNA
<213> ORGANISM: Homo sapiens

<400> SEQUENCE: 63

```
agagagacat tttccacgga ggccgagttg tggcgcttgg ggttgtgggc gaaggacggg      60
gacacggggg tgaccgtcgt ggtggaggag aaggtctcgg aactgtggcg gcggcggccc     120
ccctgcgggt ctgcgcggat gaccttggcg ccgcggtggg ggtccggggg ctggctggcc     180
tgcaggaagg cctcgactcc cgacacctgc tccatgaggc tcagcctctt cacgcccgac     240
gtcgggctgg ccacgcgggc agcttctggc ttcggggggg ccgcgatagg ttgcggcggg     300
gtggcggcca caccaaaagc catctcggtg tagtcaccat tgtccccggt gtccgaggac     360
aacgatgagg cggcgcccgg gccctgggcg gtggcaacgg ccgaggcggg gggcaggcgg     420
tacagctccc ccggggccgg cggcggtggc ggcggctgca gagacgacga cggggacgcg     480
gacggacgcg ggggcaacgg cggatacggg gaggaggcct cggggacag gaggccgtcc      540
aaggagccca cggggtggcc gctcggggcg cccggcttag gagacttggg ggagctgaag     600
tcgaggttca tgtagtcgga gagcggagac cgctgccggc tgtcgctgct ggtgcccggg     660
gtgcctgagc ccagcgacga ggccgggctg ctggcggaca agagcgagga ggacgaggcc     720
gccgacgcca gcggggagg cgcgggcggc gacaggcggg ccccgggctc gccaaagtcg      780
atgttgatgt actcgccggg gctcttgggc tccgtggca gtgggtactc gtgcatgctg      840
ggcaggctgg gcagcccctc cagggacagg gcgtgggcc tcaccgcccg gccgcgctgg      900
cccaagaagc cctccgggcg gccgccgcta ggccgcacgg gcgaaggcac tacagggtga     960
gggggctgcg tggggccggc cccgaaggcg ctggccgcct ggctgggccc tggcgtggcc    1020
tgaggctcca gacgctcctc ctccaggatg cgccccacgg gggagctcat gagcacgtac    1080
tggtcgctgt ccccgccaca ggtgtagggg gccttgtagg agcggggcaa ggagctgtag    1140
cagcagccgg gaacgcccct gagcggctcc ccgccgggt gcagggctgc ggagaagaag     1200
tcgggcgggg tgcccgtggt gaccgcgtcg ctggggggaca cgttgaggta gtccccgttg    1260
ggcagcagct tgccatctgc atgctccatg gacagcttgg aaccgcacca catgcgcatg    1320
tacccactgt cctcggggga gctctcggcg ggcgagctgg ccttgtagcc gccccgctc     1380
gccgggaatg tcctgcccgc cgcagaggtg ggtgctggcc ccgcaggccc cgcagaaggc    1440
acggcggcgg cggcggcggc ggcggccctg ggctgcaaga tctgcttggg ggcggacacg    1500
ctggcggggc tcatgggcat gtagtcgtcg ctcctgcagc tgccgctccc actgcccgcg    1560
agggccgcgc cgggcgtcat gggcatgtag ccgtcgtctg cccccaggtt gctgctggag    1620
ctcctgtggg agccgatctc gatgtctccg tagtcctctg ggtaggggtg gtaggccacc    1680
ttgggagagg acgcggggca ggacgggcag aggcggcccg cgctgcccga aaggtggcc     1740
cgcatcaggg tgtattcatc cagcgaggca gaggagggct ggggcaccgg ccgctgccgg    1800
gctggcgtgg tcagggagta ggtcctcttg cgcagccctc ggtccaggtc ctgggccgcg    1860
tcccccgaga cccggcggta ggagcggcca cagtggctca ggggcctgtc catggtcatg    1920
tacccgtaga actcaccgcc gccgccgccg tctcggccg ggggcgtctc cgcgatggac     1980
tcgggcgtgt tgcttcggtg gctgcagaag gcgcgcaggt cgcctgggct ggagccgtac    2040
tcgtccaggg acatgaagcc ggggtcgctg ggggagcccg aggcggaggc gctgccgctg    2100
gagggccgct ggccggggcc gtggtgcagc ggatgcggca gaggcgggtg cgggccgggc    2160
ggcggcgggt aggagcccga gccgtggccg ctgctggacg acagggagc                2209
```

<210> SEQ ID NO 64
<211> LENGTH: 149
<212> TYPE: DNA
<213> ORGANISM: Homo sapiens

<400> SEQUENCE: 64
taacctaaag aatgaagtca tgccccggcc tgcacccggg aaactgcaca cagcgaaaga     60
tcgccactga gataaagagc tgaaagctat tccccaattc agctgtttca gccgtgcggt    120
ctcacaatgg gctcacagac ggcagcatc                                      149

<210> SEQ ID NO 65
<211> LENGTH: 832
<212> TYPE: DNA
<213> ORGANISM: Homo sapiens

<400> SEQUENCE: 65
gtttccacaa tccacctcgt agctggggcg tgccgcttgc ctcggcttgt cccggcagaa     60
cactcttacc tttaatggcg actgaaaagt tgccacgagt tcctgatcat tgtggtaggt    120
gctgcgtgaa gctgagacgt gcgtgagcca catcccaggg ggctttgagc ccccaccgcg    180
gcggcggctg aggggaggct tgtcgtactc gcacaggagg acacagggct gcagtgttca    240
ctccagggcc tcttatcatt gggatctgag gaattttccg agaggaagtg cgaattaaca    300
atgatgaaag gtttgtgagt gagtgacagg cacgttctat tgagcactgc atggggcatt    360
atgtgccacc agagacgggg gcagaggtca agagccctcg agggctggga gagttcggag    420
gatagaagtc atcagagcac aatgaagcca gaccctgcag ccgccttccc cttcggggc     480 ttccttagaa tgcagcattg cggggactga gctgtcccag gtgaagggg gccgtcacgg    540 tgtgtggacg cccctcggct cagccctcta agagactcgg cagccaggat gggctcaagg    600
catgagccct caaaggaggt taggaaggag cgagggagaa aagatatgct tgtgtgacgt    660
cctggccgaa gtgagaacaa ttgtatcaga taatgagtca tgtcccattg aggggtgccg    720
acaaggactc ggaggaggc cacggagccc tgtactgagg agacgcccac agggagcctc    780
gggggcccag cgtcccggga tcactggatg gtaaagccgc cctgcctggc gt            832

<210> SEQ ID NO 66
<211> LENGTH: 256
<212> TYPE: DNA
<213> ORGANISM: Homo sapiens

<400> SEQUENCE: 66
tccagctgca gcgagggcgg ccaggccccc ttctccgacc tgcagggta gcgcggcctc      60 ggcgccggag acccgcgcgc tgtctggggc tgcggtggcg tggggagggc gcggcccccg    120
gacgccccga ggaaggggca cctcaccgcc cccacccaga gcgcctggcc gtgcgggctg    180
cagaggaccc ctccggggca gaggcaggtt ccacggaaga ccccggcccg ctggggcttc    240
cccggagact ccagag                                                    256

<210> SEQ ID NO 67
<211> LENGTH: 184
<212> TYPE: DNA
<213> ORGANISM: Homo sapiens

<400> SEQUENCE: 67
acttactgct tccaaaagcg ctgggcacag ccttatatga ctgaccccgc cccgagtcc      60

| | |
|---|---|
| caggccgccc catgcaaccg cccaaccgcc caaccgccac tccaaaggtc accaaccact | 120 |
| gctccaggcc acgggctgcc tctccccacg gctctagggc ccttcccctc caccgcaggc | 180 |
| tgac | 184 |

<210> SEQ ID NO 68
<211> LENGTH: 118
<212> TYPE: DNA
<213> ORGANISM: Homo sapiens

<400> SEQUENCE: 68

| | |
|---|---|
| tgccacaccc aggtaccgcc cgcccgcgcg agagccgggc aggtgggccg cggatgctcc | 60 |
| cagaggccgg cccagcagag cgatggactt ggacaggcta agatggaagt gacctgag | 118 |

<210> SEQ ID NO 69
<211> LENGTH: 1534
<212> TYPE: DNA
<213> ORGANISM: Homo sapiens

<400> SEQUENCE: 69

| | |
|---|---|
| tcgccagcgc agcgctggtc catgcaggtg ccacccgagg tgagcgcgga ggcaggcgac | 60 |
| gcggcagtgc tgccctgcac cttcacgcac ccgcaccgcc actacgacgg gccgctgacg | 120 |
| gccatctggc gcgcgggcga gccctatgcg ggcccgcagg tgttccgctg cgctgcggcg | 180 |
| cggggcagcg agctctgcca gacgcgctg agcctgcacg gccgcttccg gctgctgggc | 240 |
| aacccgcgcc gcaacgacct ctcgctgcgc gtcgagcgcc tcgccctggc tgacgaccgc | 300 |
| cgctacttct gccgcgtcga gttcgccggc gacgtccatg accgctacga gagccgccac | 360 |
| ggcgtccggc tgcacgtgac aggcgaggcg gcgtgggagc gggtccccgg cctcccttcc | 420 |
| cgccctcccg cctgccccgc cccaagggct acgtgggtgc caggcgctgt gctgagccag | 480 |
| gaagggcaac gagacccagc cctctcctct accccaggga tctcacacct gggggtagtt | 540 |
| taggaccacc tgggagcttg acacaaatgc agaatccagg tcccaggaag ggctgaggtg | 600 |
| ggcccgggaa taggcattgc cgtgactctc gtagagtgac tgtccccagt ggctctcaga | 660 |
| cgaagaggcg agaaagacaa gtgaatggca atcctaaata tgccaagagg tgcaatgtgg | 720 |
| tgtgtgctac cagcccggaa agacactcgc agccctcta cccaggggtg cacagacagc | 780 |
| ccaccaagta gtgcctagca cttgtccaga ccctgatata caaagatgcc tgaaccaggg | 840 |
| tcccgtccct agagcagtgg ctctccactc tagcccccac cctgctctgc gacaataatg | 900 |
| gccacttagc atttgctagg gagccgggac ctagtccaag cacccacaag catgaatttg | 960 |
| ccaaatcttt tcagcaacct cttaaggcaa ctgctatcat gatcctcact ttacacatgg | 1020 |
| agaagcagaa gcagagatga tagaatcttt cgcccaaggc cacatctgta ttgggacggg | 1080 |
| ggcagcctgg cacccaagtg cccattcctc ccttctgacc agcccccacc cctccggctc | 1140 |
| tggcgtccaa agggctaagg ggaggggtgc ccttgtgaca gtcacccgcc ttctcccctg | 1200 |
| cagccgcgcc gcggatcgtc aacatctcgg tgctgcccag tccggctcac gccttccgcg | 1260 |
| cgctctgcac tgccgaaggg gagccgccgc ccgccctcgc ctggtccggc ccggccctgg | 1320 |
| gcaacagctt ggcagccgtg cggagcccgc gtgagggtca cggccaccta gtgaccgccg | 1380 |
| aactgcccgc actgacccat gacggccgct acacgtgtac ggccgccaac agcctgggcc | 1440 |
| gctccgaggc cagcgtctac ctgttccgct tccatggcgc cagcggggcc tcgacggtcg | 1500 |
| ccctcctgct cggcgctctc ggcttcaagg cgct | 1534 |

<210> SEQ ID NO 70
<211> LENGTH: 269
<212> TYPE: DNA
<213> ORGANISM: Homo sapiens

<400> SEQUENCE: 70

| | | | | | |
|---|---|---|---|---|---|
| atgaacttca | agggcgacat | catcgtggtc | tacgtcagcc | agacctcgca | ggagggcgcg | 60 |
| gcggcggctg | cggagcccat | gggccgcccg | gtgcaggagg | agaccctggc | gcgccgagac | 120 |
| tccttcgcgg | ggaacggccc | gcgcttcccg | gacccgtgcg | gcggcccga | ggggctgcgg | 180 |
| gagccggaga | aggcctcgag | gccggtgcag | gagcaaggcg | gggccaaggc | ttgagcgccc | 240 |
| cccatggctg | ggagcccgaa | gctcggagc | | | | 269 |

<210> SEQ ID NO 71
<211> LENGTH: 282
<212> TYPE: DNA
<213> ORGANISM: Homo sapiens

<400> SEQUENCE: 71

| | | | | | |
|---|---|---|---|---|---|
| tcagtgttat | gtggggagcg | ctagatcgtg | cacacagtag | gcgtcaggaa | gtgttttccc | 60 |
| cagtaattta | ttctccatgg | tactttgcta | aagtcatgaa | ataactcaga | ttttgttttc | 120 |
| caaggaagga | gaaaggccca | gaatttaaga | gcaggcagac | acacaaccgg | gcaccccag | 180 |
| accctggccc | ttccagcagt | caggaattga | cttgccttcc | aaagcccag | cccggagctt | 240 |
| gaggaacgga | ctttcctgcg | caggggatc | ggggcgcact | cg | | 282 |

<210> SEQ ID NO 72
<211> LENGTH: 142
<212> TYPE: DNA
<213> ORGANISM: Homo sapiens

<400> SEQUENCE: 72

| | | | | | |
|---|---|---|---|---|---|
| gtggaaacac | aacctgcctt | ccattgtctg | cgcctccaaa | acacaccccc | cgcgcatccg | 60 |
| tgaagctgtg | tgtttctgtg | ttactacagg | ggccggctgt | ggaaatccca | cgctccagac | 120 |
| cgcgtgccgg | gcaggcccag | cc | | | | 142 |

<210> SEQ ID NO 73
<211> LENGTH: 741
<212> TYPE: DNA
<213> ORGANISM: Homo sapiens

<400> SEQUENCE: 73

| | | | | | |
|---|---|---|---|---|---|
| tccacacctc | gggcagtcac | taggaaaagg | gtcgccaact | gaaaggcctg | caggaaccag | 60 |
| gatgatacct | gcgtcagtcc | cgcggctgct | gcgagtgcgc | gctctcctgc | caggggggacc | 120 |
| tcagaccctc | ctttacagca | caccgagggc | cctgcagaca | cgcgagcggg | ccttcagttt | 180 |
| gcaaaccctg | aaagcgggcg | cggtccacca | ggacgatctg | gcagggctct | gggtgaggag | 240 |
| gccgcgtctt | tatttggggt | cctcgggcag | ccacgttgca | gctctggggg | aagactgctt | 300 |
| aaggaacccg | ctctgaactg | cgcgctggtg | tcctctccgg | ccctcgcttc | cccgaccccg | 360 |
| cacaggctaa | cggagacgc | gcaggcccac | cccaccggct | ggagacccg | gcacggcccg | 420 |
| catccgccag | gattgaagca | gctggcttgg | acgcgcgcag | ttttccttg | gcgacattgc | 480 |
| agcgtcggtg | cggccacaat | ccgtccactg | gttgtgggaa | cggttggagg | tccccaaga | 540 |
| aggagacacg | cagagctctc | cagaaccgcc | tacatgcgca | tggggcccaa | acagcctccc | 600 |
| aaggagcacc | caggtccatg | cacccgagcc | caaaatcaca | gacccgctac | gggcttttgc | 660 |

```
acatcagctc caaacacctg agtccacgtg cacaggctct cgcacagggg actcacgcac    720
ctgagttcgc gctcacagat c                                             741

<210> SEQ ID NO 74
<211> LENGTH: 4498
<212> TYPE: DNA
<213> ORGANISM: Homo sapiens

<400> SEQUENCE: 74
ctgccctcgc ggatctcccc cggcctcgcc ggcctccgcc tgtcctccca ccaccctctc     60
cgggccagta ccttgaaagc gatgggcagg gtcttgttgc agcgccagtg cgtaggcagc    120
acggagcaga ggaagttggg gctgtcggtg cgcaccagct cgcccgggtg gtcggccagc    180
acctccacca tgctgcggtc gccgctcctc agcttgccgg ccagggcagc gccggcgtcc    240
ggggcgccca gcggcaacgc ctcgctcatc ttgcctgggc tcagcgcggt ggaaggcggc    300
gtgaagcggc ggctcgtgct ggcatctacg gggatacgca tcacaacaag ccgattgagt    360
taggaccctg caaacagctc ctaccagacg gcgacagggg cgcggatctt cagcaagcag    420
ctcccgggag accaacatac acgttcaggg gcctttatta ctgcgggggg tggggggggg    480 cggggtggt taggggagga gggagactaa gttactaaca gtccaggagg ggaaaacgtt    540
ctggttctgc ggatcggcct ctgacccagg atgggctcct agcaaccgat tgcttagtgc    600
attaaaaagt ggagactatc ttccacgaat cttgcttgca gaggttaagt tctgtctttg    660
gctgttagaa aagttcctga aggcaaaatt ctcatacact tcctaaaata tttatgcgaa    720
gagtaaaacg atcagcaaac acattatttg gaagttccag tagttaatgc ctgtcagttt    780
tttgcaggtg agttttgtct aaagtcccaa cagaacacaa ttatctcccg taacaaggcc    840
acttttatca tgcaaaactg gcttcagtcc gaaaagcaa gagctgagac ttccaaaggt    900
agtgctacta atgtatgtgc acgtatatat aaatatatac atatgctcta cttcataaaa    960
tatttacaat acaatctgtg gagaatttaa acacaacaga aatccattaa tgtacgctgc   1020 agatttttt aagtagcctt gaaaatcagc ttcagtagtt ggagcagtgc tgagctagaa   1080
gtacttgtca tgttctctgt tctctcaatg aattctgtca aaacgctcag tgcagaaaat   1140
tcagcgtttc agagatcttc agctaatctt aaaacaacaa tcataagaag gcccagtcga   1200
tgacactcag ggttctacag ctctcccaca tctgtgaact cgggtttggg gatgttggtt   1260
aagtttgtgg ctggtcctct ggtttgttgg gagttgagca gccgcagagt cacacacatg   1320
caaacacgca ctcttcggaa ggcagccact gtctacatca gctgggtgac tcagccctga   1380
ctcgggcagc agcgagacga tactcctcca ccgtcgccca gcacccgccg gttagctgct   1440
ccgaggcacg aacacccacg agcgccgcgt aaccgcagca ggtggagcgg gccttgaggg   1500
agggctccgc ggcgcagatc gaaacagatc gggcggctcg ggttacacac gcacgcacat   1560
cctgccacgc acactgccac gcacacgcaa cttcacggct cgcctcggac cacagagcac   1620
tttctccccc tgttgtaaaa ggaaaacaat tggggaaaag ttcgcagcca ggaaagaagt   1680
tgaaaacatc cagccaagaa gccagttaat tcaaaggaa gaagggggaa aaacaaaaaa   1740
aaacaacaaa aaaggaagg tccaacgcag gccaaggaga agcagcagag gttgacttcc   1800
ttctggcgtc cctaggagcc ccggaaagaa gtgcctggcg gcgcagggcc gggcagcgtg   1860
gtgccctggc tgggtccggc cgcggggcgc ccgtcccgcc cgcgcccgct ggctctatga   1920
atgagagtgc ctggaaatga acgtgctttt actgtaagcc cggccggagg aattccattc   1980
cctcagctcg tttgcatagg ggcggccggc ggccaatcac aggccttttcc ggtatcagcc   2040
```

```
agggcgcggc tcgccgccgc cggctcctgg aattggcccg cgcgccccccg ccgccgcgcc   2100
gcgcgctact gtacgcagcc cgggcgggga gtcggaggcc accccgcgc cccgcatcca    2160
agcctgcatg ctggcccggg gccccgcccg cgtgcggacc cctttccgca gccacacgca   2220
ggcttgtgcg gctccgcgag tggccacggt ccggagacct ggaaaaagaa agcaggcccc   2280
gccggcccga ggaggacccg gccggcgcgc cgcacccgga gaggcccggc cccgcgagcc   2340
gctgcaggca ggcgcagtgg ccgccacgag gctcccgaac cgggctgcag cccgcggacg   2400
gccccagatc ctgcgcggcc gcccagggcc aggcctccgc ttccagggcg ggggtgcgat   2460
ttggccgcgg ggcccggggg agccactccg cgctcctgca ccgtccggct ggcagctgcg   2520
gcgaagcggc gctgattcct tgcatgaggc cggacggcgt ccgcgcgtgc cgtttgctct   2580
cagcgtcttc ccttgggtcg gtttctgtaa tgggtgtttt ttaccgctgc gcccgggccg   2640
cggctcgatc cctccgcgcg tctcacttgc tgcgtgcgtc agcggccagc gaagagtttc   2700
ctagtcagga aagaccccaa gaacgcgcgg ctggaaggaa agttgaaagc agccacgcgg   2760
cttgctcccg ggccttgtag cgccggcacc cgcagcagcc ggacagcctg cccgggcccc   2820
gcgtctcccc tccggctccc cggaagcggc ccccgctcct ctccccgccc ccgtgcgctc   2880
gagcggcccc aggtgcggaa cccaccccgg cttcgcgtgc gggcggccgc ttccccctgc   2940
gccggtcccc gcggtgctgc gggcattttc gcggagctcg gagggccccg ccccccggtcc  3000
ggcgtgcgct gccaactccg accccgcccg gcggggctcc ctcccagcgg aggctgctcc   3060
cgtcaccatg agtccctcca cgccctccct gccgggccct gcacctcccg gggcctctca   3120
tccaccccgg ggctgcaacc cagtccccgg atcccggccc cgttccaccg cgggctgctt   3180
tgtggtcccc gcggagcccc tcaattaagc tccccggcgc gggggtccct cgccgacctc   3240
acggggcccc tgacgcccgc tcctccctcc cccagggcta gggtgctgtg gccgctgccg   3300
cgcagggact gtccccgggc gttgccgcgg gcccggacgc aggaggggc cggggttgac    3360
tggcgtggag gccttttcccg ggcgggcccg gactgcgcgg agctgtcggg acgcgccgcg   3420
ggctctggcg gacgccaggg ggcagcagcc gccctccctg gacgccgcgc gcagtccccg   3480
gagctcccgg aacgcccccg acggcgcggg gctgtgcggc ccgcctcgtg gccttcgggt   3540
cgcccgggaa gaactagcgt tcgaggataa aagacaggaa gccgcccag agcccacttg    3600
agctggaacg gccaaggcgc gtttccgagg ttcaatatata gagtcgcagc cggccaggtg   3660
gggactctcg gaccaggcct ccccgctgtg cggcccggtc ggggtctctt cccgaagccc   3720
ctgttcctgg ggcttgactc gggccgctct tggctatctg tgcttcagga gcccgggctt   3780
ccgggggggct aaggcgggcg gcccgcggcc tcaaccctct ccgcctccgc tccccctggg   3840
cactgccagc acccgagttc agttttgttt taatggacct ggggtctcgg aaagaaaact   3900
tactacattt ttcttttaaa atgatttttt taagcctaat tccagttgta aatccccccc   3960
tccccccgcc caaacgtcca ctttctaact ctgtccctga aagagtgca tcgcgcgcgc    4020
ccgcccgccc gcaggggccg cagcgccttt gcctgcgggt tcggacgcgg cccgctctag   4080
aggcaagttc tggcaagggg aaaccttttc gcctggtctc caatgcattt ccccgagatc   4140
ccacccaggg ctcctgggc cacccccacg tgcatccccc ggaaccccg agatgcggga    4200
gggagcacga gggtgtggcg gctccaaaag taggctttg actccagggg aaatagcaga    4260
ctcgggtgat ttgcccctcg gaaaggtcca gggaggctcc tctgggtctc gggccgcttg   4320
cctaaaaccc taaaccccgc gacgggggct gcgagtcgga ctcgggctgc ggtctcccag   4380
```

| | |
|---|---|
| gagggagtca agttccttta tcgagtaagg aaagttggtc ccagccttgc atgcaccgag | 4440 |
| tttagccgtc agaggcagcg tcgtgggagc tgctcagcta ggagtttcaa ccgataaa | 4498 |

<210> SEQ ID NO 75
<211> LENGTH: 453
<212> TYPE: DNA
<213> ORGANISM: Homo sapiens

<400> SEQUENCE: 75

| | |
|---|---|
| ttcggaagtg agagttctct gagtcccgca cagagcgagt ctctgtcccc agcccccaag | 60 |
| gcagctgccc tggtgggtga gtcaggccag gcccggagac ttcccgagag cgagggaggg | 120 |
| acagcagcgc ctccatcaca gggaagtgtc cctgcgggag gccctggccc tgattgggcg | 180 |
| ccggggcgga gcggcctttg ctctttgcgt ggtcgcgggg gtataacagc ggcgcgcgtg | 240 |
| gctcgcagac cggggagacg ggcgggcgca cagccggcgc ggaggcccca cagcccgcc | 300 |
| gggacccgag gccaagcgag gggctgccag tgtcccggga ccaccgcgt ccgcccagc | 360 |
| cccgggtccc cgcgcccacc ccatggcgac ggacgcggcg ctacgccggc ttctgaggct | 420 |
| gcaccgcacg gagatcgcgg tggccgtgga cag | 453 |

<210> SEQ ID NO 76
<211> LENGTH: 560
<212> TYPE: DNA
<213> ORGANISM: Homo sapiens

<400> SEQUENCE: 76

| | |
|---|---|
| acgcacactg ggggtgtgat ggaaaggggg acgcgatgga tagggggtggg cgcacactgg | 60 |
| gggacgcgac ggggagggggt gagcacacac tgggggtgtg atggagaggg cgacgcaata | 120 |
| gggaggggtg ggcgcacacc agggacgcga tgatggggac gggtgggcgc acaccaggtg | 180 |
| gcatgatggg gaggagtggg tacacaccat ggggggcgtg atggggaggc gtgggcgtac | 240 |
| accggggggc gcgatgggga ggggtgggcg cacaccgggg gacgcgatgg aggcggtggg | 300 |
| tgcacacggg gcgcgatggg tgggagtagg tgcacactga gggcacgatt ggggagacac | 360 |
| gaaggagagg ggtgggcgca cactgggggga cgcgatggcc gggacacgat gcggagaagt | 420 |
| gggtgaatac cggggtcgcg atgggcgccc tggaaggacg gcagtgctgc tcacagggggc | 480 |
| caggcccctc agagcgcgcc ccttgggggt aaccccagac gcttgttccc gagccgactc | 540 |
| cgtgcactcg acacaggatc | 560 |

<210> SEQ ID NO 77
<211> LENGTH: 157
<212> TYPE: DNA
<213> ORGANISM: Homo sapiens

<400> SEQUENCE: 77

| | |
|---|---|
| ccacagggtg gggtgcgccc acctgccctg tccatgtggc cttgggcctg cgggggagag | 60 |
| ggaatcagga cccacagggc gagccccctc cgtagcccgc ggcaccgact ggatctcagt | 120 |
| gaacacccgt cagcccatcc agaggctaga aggggga | 157 |

<210> SEQ ID NO 78
<211> LENGTH: 114
<212> TYPE: DNA
<213> ORGANISM: Homo sapiens

<400> SEQUENCE: 78

| | |
|---|---|
| ttgaggtctc tgtgcatgct tgtgcgtacc ctggactttg ccgtgagggg tggccagtgc | 60 |

```
tctgggtgcc tttgccagac aactggtctg ccgggccgag cattcatgct ggtc          114
```

<210> SEQ ID NO 79
<211> LENGTH: 104
<212> TYPE: DNA
<213> ORGANISM: Homo sapiens

<400> SEQUENCE: 79

```
tgacgcgccc ctctccccgc agctccacct ggttgcgctc aacagccccc tgtcaggcgg     60
catgcggggc atccgcgggg ccgacttcca gtgcttccag cagg                     104
```

<210> SEQ ID NO 80
<211> LENGTH: 659
<212> TYPE: DNA
<213> ORGANISM: Homo sapiens

<400> SEQUENCE: 80

```
aacacactgt ctcgcactag gtgctcgcgg aagagcgcgg cgtcgatgct gcggctcagg     60
ttgatgggcg atggcggccg cagatccagc tcgctcagcg atggcgccgg tcccacaccg    120
ttgcgggaca gtcccgggcc accctggggt ccgcgaccca acgacgcagc cgagccccag    180
gcgcctgaac tgggcgtggc cagctgccca ctctccgccg ggttgcggat gaggctcttg    240
ctgatgtcca agctgcctgc accaacgttg ctgggccctg catagcagtt attgggtcgc    300
tccggcacct cgctctttcc tgacggcgcc gggcacgcca gacgcatcag cttagcccag    360
caagcgtgct ccgtgggcgg cctgggtctc gcggcagcca ccgcggccaa cgccagggcg    420
agcgcccatg tcagctccag gaggcgcagc cagaagtgga cccccacca ggcccacgag     480 aagcggccca cgcggcctgg gcccgggtac agccagagcg cagccgccag ctgcaagccg    540
ctagccagca gccccagcgc gcccgccaca gccaacagcc gagggccggg gctggcatcc    600
cagccccgtg ggccgtccag caggcggcga cggcacaggc agagcgtgcc cagagccac    659
```

<210> SEQ ID NO 81
<211> LENGTH: 813
<212> TYPE: DNA
<213> ORGANISM: Homo sapiens

<400> SEQUENCE: 81

```
gtctgcacga agcccgcggc ggcctgcagg gggcccagcg actcgtccag ggaaccggtg     60
cgcaggagca gccgggggcg cggcgcgccg gccgcccttg ggggactctg gggccggggg    120
cgcagctcga tctgacgctt gggcactgtc cggggcctgg cgggcgcggc gccctcctcc    180
agagccacct ccacacactc gaactgcgct ggggcggcag gacttggccc acggggccgc    240
agctctaggt aggtggccca gcgggagcca ccatcgggga cctgggactg gcgtgggacc    300
gcggcgggag acgctggccc cggcggcaag gggctgatga aggccggctc cgtgaactgt    360
tgttgcgcct cgcgatcgtc tgcgccgag cagccgaaca ggggtccgac gccgaagatg     420
acttccatct ccccgacgg cagcgtgcgc agctggggct ggggtggccg tgggccggaa    480
cctgggcctc gcgggaaacc cgagccggcc ccgtgccgct ggcggctatt ctgggcgctg    540
acggacaggc gaggctgcgc gcccgccccc cgcccaggag ccaccagggg ccaattcgct    600
gggcctttcg cgtccggccc aacgtccggg ggctccggag aacctggagc cgtgtagtag    660
gagcctgacg aaccggagga gtcctggcgc cgcgcggggg ccgtgggcag ctgcctcggg    720
atcccaggca gggctggcgg ggcgagcgcg gtcagcatgg tggggccgga cgccgtgcac    780
```

```
tatctccctc gcattcgcct ccgctggtgg cgc                                   813
```

<210> SEQ ID NO 82
<211> LENGTH: 440
<212> TYPE: DNA
<213> ORGANISM: Homo sapiens

<400> SEQUENCE: 82

```
ctggagagaa ctatacgggc tgtgggagtc accgggcgac tatcaccggg cctcctttcc      60
acatcctcct ccgggaaggg accccgttcc gggcctcgac cggcgcagac tgggctgacc     120
cactttcttg ggcccactga gtcacctcga aacctccagg ccggtagcgg ggaggagagg     180
aggagcaggc gggggtgcca aggtgtgggc tgcgccctgg ttaggggcg agcccggctt      240
gtttatgagg aggagcgcgg aggaggatcc agacacacag gcttgcgcgc ccagactcgc     300
ccggccagcg gctggcggcc tccgacgtca ccaaaccggt tgggtgagag gcagagagc      360
aggggggaagg gccgcagtcc cgcccgcgcc ccccggcacg caccgtacat cttgccctcg    420
tctgacagga tgatcttccg                                                 440
```

<210> SEQ ID NO 83
<211> LENGTH: 252
<212> TYPE: DNA
<213> ORGANISM: Homo sapiens

<400> SEQUENCE: 83

```
gagtgcggag tgaaggggtg cactgggcac tcagcgcggc ccttgggagg cagggccgcc      60
ccagcctgcc ctcctgtctg ggaaggccgt ccagaagcag gagccccggg gaaaacaact     120
ggctggacgg ggcggccttc agtgtctctc ccagcctgag agtcgcttcc caccacctgg     180
gcacgaacct gctctgcgat ctccggcaag ttcctgcgcc tcctgtcggt aaaatgcaga     240
tcgtggcgtc tt                                                         252
```

<210> SEQ ID NO 84
<211> LENGTH: 1539
<212> TYPE: DNA
<213> ORGANISM: Homo sapiens

<400> SEQUENCE: 84

```
tcttctttcc gccccctaggg ggcacaagcg ggcatgtcca agcgcctagg agcccgtacc      60
gctggggacc tccccttccg cgaaccccga gcgggtagac ccagagcaat ccgagtgtgg     120
aaacaatgga gaggggcgt gttgagctgg ggtctccatg cctcgttggg gagagggagg      180
tgagtttgtg tcttctggaa ggcgtggggg ctgtgccctc gtggggtag gaagtgctcc      240
cgtggggcgg ggtgcggatc ggagaggtga gtgggtgcgt ctgtccagcg gtccgccccgg    300
tgtggtcgtg cccggcccgc gtggggatgg gggtgtctct cccgctgggc aactatacca     360
gcgcaaccgg ggcgtcggcg cggcccacgc tagcggcgct gctccggcgg cggggggctgg    420
gcgtggcggt gatgctgggc gtggtggccg cgctgggcgt ggtggccgcg ctgccgccct     480
cacccgggca gccgtgctgg agaaggatgt cggcgcacag ctggcttcca gcctggcggg    540
cgtagaacag cgccgtgcgg ccctgggcgt cacgggccgc cacgtccgcg ccgtactaga     600
gggcggaaac ggccgcgtga ccgcgcgtcc ccagggcgcc cacacccggc gccgcctccc     660
ccacatggcc aagcctactt ccggggtccc tctgggaatt cgggcttttc ccgcgccagg     720
cgttttccga gatgaagcct caaagacccc ctttcctccc cccagctcac gtacccacag     780
cagcagttgc gtgatgacga cgtgggcgag ctcggccgcc aggtggagtg gggagcgcag     840
```

| | |
|---|---|
| ctgtgggtcc tctacgctgg tgtcgagcgg cccgtgtcgc gcatgggcca aaagcaggag | 900 |
| aacggtagcc acgtcctggg cctgcacggc ggcccacagc tggcggccca gcggctcctc | 960 |
| cgaggtgctc agcggcgcca ggaacagtag ctgctcgtac ttggcgcgaa tccacgactc | 1020 |
| gcgctcctcc ctgcaagacc agggatcaac ggaaaaggct ctaggaccc ccagccagga | 1080 |
| cttctgcccc tacccacggg accgtctcag gttcgcacac cctcagcaac cctcccccg | 1140 |
| ctctgttccc tcacgcttac cgcgaagagt cccgcgaggg cttggcacgg cctcgcgtgt | 1200 |
| cgctttccca cacgcggttg gccgtgtcgt tgccaatagc cgtcagcacc agggtcagct | 1260 |
| cccgtggcca gtcgtccaag tccagcgagc gaacgcggga caggtgtgtg cccaggttgc | 1320 |
| ggtggatgcc agaacactcg atgcagatga gggcgcccag gttcaagctg gcccacgtgg | 1380 |
| ggtctgcgga aggagcgtag aggtcggctc ccagccgggc agcacaggca ccccggcatt | 1440 |
| cactacactc cctagcccct ccgctgcctc ctggcactca ctgggggccc cgcagtccac | 1500 |
| gcagattgaa ttccccttgg cgttccggat cgcctggat | 1539 |

<210> SEQ ID NO 85
<211> LENGTH: 2648
<212> TYPE: DNA
<213> ORGANISM: Homo sapiens

<400> SEQUENCE: 85

| | |
|---|---|
| agccaggtcc agcccccgcg cctgacaccg gccggacgtt cccggggcgc cgcagctgcg | 60 |
| gcgggaactc tgggatccgg agccatctgc tcccacccgc tccggagcca aaccccgggg | 120 |
| gccgcctccg ctcccggacc cgcctcctct cccgggagtg tgagccgaac caagagtctc | 180 |
| ctgcctatct cctccagtag gaaaatagta ataataatag acaccctgcc cccgtaaaaa | 240 |
| acactacctt ccccgtaccg cctcccaagt ctcccggggt acggattgcc tttgcagcag | 300 |
| ttccgcccca cctgactcac tcagggtca gccccgggtg ggtttcaatg cggctctggg | 360 |
| gaggggtgg gcagtggggg aagtgaggct tcctatccgc ccctctcac ttcacattta | 420 |
| aatattctgc acgttccagc ccccgcggac tcgcgtaccg cccaatccgc cttcaccgca | 480 |
| cgaaaaacat cactagcctg ctctcagccc aggggacgac tagtccctgg cgagaagctg | 540 |
| cctgcaaggt cactgtcatg ccacctgccc caagtgctca ggggaaactg aggcttcctc | 600 |
| atcccttca ccttcaacgt cgctctaaac acggcaaagc cccgtttcca tgctcccaga | 660 |
| gttcagctga ggctggaagt ggggtcctgg gcttctctgg gagcaatttt ctagtcactc | 720 |
| tgatcaagga cgttactttc ccagaaagct ctgaggctga gtccctctga aatcaagtcc | 780 |
| tttctcctgt cgcacaatgt agctactcgc cccgcttcag gactcctatt ctttgcccca | 840 |
| atccttgaca gaggggtgag cttggttcat ccgcccaccc cagagaaaag cttccctagt | 900 |
| ttcctggacc tcgctcctcc accccaagct gagcattcca ggtacccttc cctccctgtt | 960 |
| ctcaagccct gactcaactc actagggaa gcgcggagct cggcgcccag cagctccctg | 1020 |
| gacccgctgc cagaagacag gctgggggt ccgggaaggg gccggagcc aggaggccct | 1080 |
| cctgtgctct tggtgaagat gccgctgata aacttgagca tcttgcggtc acgagtggat | 1140 |
| gctcggcccc cctccggcc ccgtttcagc cccgagctg gaggctccag agtgattgga | 1200 |
| ggtgcaggcc cgggggctg cgcggaagca gcggtgacag cagtggctgg actcggagtt | 1260 |
| ggtgggaggg ttagcggagg aggagagccg cggcggtc ccggatgcaa gtcactgttg | 1320 |
| tccaaggtct tactcttgcc tttccgaggg gacaacttcc ctcgggctcc agccccagcc | 1380 |

```
ccgaccccac cagaggtcga agctgtagag cccccteccc cggcggcggc ggcggtggcg    1440
gcggcagaga ccgaagctcc agtcccggcg ctgctctttg accccttgac cctgggcttg    1500
ccctcgcttt cgggccatga caggcggcta cccgcgccct tgccccgcc ggctttggct    1560 ccactcgtgg tcacggtctt gcaaggcttg ggagccggcg gaggaggcgc caccttgagc    1620
ctccggctgc cggtgccagg gtgcggagag gatgagccag ggatgccgcc gcccgcccgg    1680
ccttcgggct ccgggccgcc ccagctcggg ctgctgagca ggggggcgccg ggaggaggtg    1740 ggggcgcccc caggcttggg gtcggggctc agtcccccgg agagcggggg tcccggaggg    1800
acggcccaga gggagaggcg gcggccggga gcggggagag ctgggcgggc cggactggcc    1860
ggagccgggg acagggctgg gggctccgcg ccccccggtgc ccgcgctgct cgtgctgatc    1920
cacagcgcat cctgccggtg aagagacgt tcgtgccgct tcttgcccgg ctcctccgcg    1980 cctcggggc tgccaggatc cccagtctcg gagcctctgg caccggcggc gccggccgcg    2040
gccgcagacg gagaaggcgg cggcggaggc accgactcga gcttaaccag ggtcagcgag    2100
atgaggtagg tcgttgtccg gcgctgaagc gcgcccgcgc cccggctcat ggggcccgga    2160 gaccccgag ctggggaggg gaggggactc ccccggactg cctcaggggg gcccggccat    2220 ggggccgcc tgctcgctgc ccccagcccc cggaccccgc tgagccccg gcccggctcc    2280 gctgtcgccg ccgcctccgc cgcctccgct tgcgccccccc tcccatcaca tggggcgccc    2340 cctcccatg ctccccgccc tgcgccccca ccctcttgga gccccgggac cttggtgctg    2400
ctccagggag gcgcgccgga ccgtccaccc cggcctgggt gggggcgctg agatgggtgg    2460
gggagggcgg ggaggacagt agtgggggca aatgggggag agagaggaaa agggagcaga    2520 aaagggacc ggaggctagg ggaaacgaac ctgtgcgggg gaggcagggg cggggaattg    2580
ggactcaagg gacaggggcc gcggatgcgg tcggaaagag ggtctagagg agggtgggaa    2640
gctagtgg                                                             2648
```

<210> SEQ ID NO 86
<211> LENGTH: 452
<212> TYPE: DNA
<213> ORGANISM: Homo sapiens

<400> SEQUENCE: 86

```
aggagcgcaa ggcttgcagg gcatgctggg agagcgcagg gaacgctggg agagcgcggg     60
aaatactggg attggctccc gagggctgtg aggagggcac gaggggacac tccgatgaag    120
gcagggcacg cggggcgagc cgggagcgtc tcctgagggc agcgaggagg gagctgaggc    180
acgcgggctc tcaatcgacg ccccacagag accaagaggc ctggccttgg ggggcagctg    240
cttgaaggag gcagagcgga agcgaggggag actgctggag gccctgccgc ccacccgccc    300
tttcctcccc ctgaggagac gcctgacgca tctgcagtgc aggaggccgt gggcgttaga    360
agtgttgctt ttccagtttg taagaccatt ttcctgattc tcttcccac ggttgcggag    420 gagcaggtca gggccgccat gagggcagga tc                                  452
```

<210> SEQ ID NO 87
<211> LENGTH: 232
<212> TYPE: DNA
<213> ORGANISM: Homo sapiens

<400> SEQUENCE: 87

```
tcgaccgcta ctattatgaa aacagcgacc agcccattga cttaaccaag tccaagaaca     60
agccgctggt gtccagcgtg gctgattcgg tggcatcacc tctgcgggag agcgcactca    120
```

| | | |
|---|---|---|
| tggacatctc cgacatggtg aaaaacctca caggccgcct gacgcccaag tcctccacgc | 180 |
| cctccacagt ttcagagaag tccgatgctg atggcagcag ctttgaggag gc | 232 |

<210> SEQ ID NO 88
<211> LENGTH: 221
<212> TYPE: DNA
<213> ORGANISM: Homo sapiens

<400> SEQUENCE: 88

| | |
|---|---|
| tgtgccgtcg cacacagacg ccctcaacgt cggagagctg tgagcggggc cgtgctcttg | 60 |
| ggatgggagc cccgggaga gctgccgcc aacaccactc cgacgtgatc catgctggac | 120 |
| ataaagtgct cttccctccg ctagtcatcg gccgagcggg cccctcgctc ctgggtgtaa | 180 |
| gttctttctg tgcgtccttc tcccatctcc gtgcagttca g | 221 |

<210> SEQ ID NO 89
<211> LENGTH: 477
<212> TYPE: DNA
<213> ORGANISM: Homo sapiens

<400> SEQUENCE: 89

| | |
|---|---|
| ccatgcgccg ctgcgcgcgc gagttcgggc tgctgctgct gttcctctgc gtggccatgg | 60 |
| cgctcttcgc gccactggtg cacctggccg agcgcgagct gggcgcgcgc cgcgacttct | 120 |
| ccagcgtgcc cgccagctat tggtgggccg tcatctccat gaccaccgtg ggctacggcg | 180 |
| acatggtccc gcgcagcctg cccgggcagg tggtggcgct cagcagcatc ctcagcggca | 240 |
| tcctgctcat ggccttcccg gtcacctcca tcttccacac cttttcgcgc tcctactccg | 300 |
| agctcaagga gcagcagcag cgcgcggcca gccccgagcc ggccctgcag gaggacagca | 360 |
| cgcactcggc cacagccacc gaggacagct cgcagggccc cgacagcgcg ggcctggccg | 420 |
| acgactccgc ggatgcgctg tgggtgcggg cagggcgctg acgcctgcgc cgcccac | 477 |

<210> SEQ ID NO 90
<211> LENGTH: 1200
<212> TYPE: DNA
<213> ORGANISM: Homo sapiens

<400> SEQUENCE: 90

| | |
|---|---|
| gtcctaacat cccaggtggc ggcgcgctgg ctccctggag cggggcggga cgcggccgcg | 60 |
| cggactcacg tgcacaaccg cgcgggacgg ggccacgcgg actcacgtgc acaaccgcgg | 120 |
| gaccccagcg ccagcgggac cccagcgcca gcggaccccc agcgcagcg gaccccagc | 180 |
| gccagcggga ccccagcgcc agcgggaccc cagcgccagc gggacccag cgccagcggg | 240 |
| tctgtggccc agtggagcga gtggagcgct ggcgacctga gcgagactg cgccctggac | 300 |
| gccccagcct agacgtcaag ttacagcccg cgcagcagca gcaaagggga aggggcagga | 360 |
| gccgggcaca gttggatccg gaggtcgtga cccaggggaa agcgtgggcg gtcgacccag | 420 |
| ggcagctgcg gcggcgaggc aggtgggctc cttgctccct ggagccgccc ctccccacac | 480 |
| ctgccctcgg cgccccagc agttttcacc ttggccctcc gcggtcactg cgggattcgg | 540 |
| cgttccgcc agcccagtgg ggagtgaatt agcgccctcc ttcgtcctcg gcccttccga | 600 |
| cggcacgagg aactcctgtc ctgccccaca gaccttcggc ctccgccgag tgcggtactg | 660 |
| gagcctgccc cgccagggcc ctggaatcag agaaagtcgc tctttggcca cctgaagcgt | 720 |
| cggatcccta cagtgcctcc cagcctgggc gggagcggcg gctgcgtcgc tgaaggttgg | 780 |

| | |
|---|---|
| ggtccttggt gcgaaaggga ggcagctgca gcctcagccc caccccagaa gcggccttcg | 840 |
| catcgctgcg gtgggcgttc tcgggcttcg acttcgccag cgccgcgggg cagaggcacc | 900 |
| tggagctcgc agggcccaga cctgggttgg aaaagcttcg ctgactgcag gcaagcgtcc | 960 |
| gggaggggcg gccaggcgaa gccccggcgc tttaccacac acttccgggt cccatgccag | 1020 |
| ttgcatccgc ggtattgggc aggaaatggc agggctgagg ccgaccctag gagtataagg | 1080 |
| gagccctcca tttcctgccc acatttgtca cctccagttt tgcaacctat cccagacaca | 1140 |
| cagaaagcaa gcaggactgg tggggagacg gagcttaaca ggaatatttt ccagcagtga | 1200 |

<210> SEQ ID NO 91
<211> LENGTH: 900
<212> TYPE: DNA
<213> ORGANISM: Homo sapiens

<400> SEQUENCE: 91

| | |
|---|---|
| caccttcccc gaggtaatta ttttctgggg ggtaggggtg ggggttggga gggtgaagaa | 60 |
| aggaagaaaa agaaggccga tcacactggg caccggcgga ggaagcgtgg agtccattga | 120 |
| tctaggtact tgtggggagg ggagaacccg agcagcagct gcaaacggaa gggctgtgag | 180 |
| cgagcgggcg gcgggtggc tggcagcgag gccaccagca ggggggggccc gggccgaggc | 240 |
| cgcgccacct cggcaccacg cgggcagccg gtgcggcggg gtcgccacgg ccaggggagc | 300 |
| gctgggtgcc caccatggca gttatgcaag cggtgacccc ctggtcttgc ctccccgccg | 360 |
| ccctgcactc cttcctcccc gctgccgaca cttggatctc tctagctctt tctctcccct | 420 |
| gtgttttcaa acaggaagtg cacggctgtc tataacgtgc tgcccgggtct caggatggag | 480 |
| gagtgaagtc tcctgtcgcc gtggttccag cctccggagc tcgcccaagc cgcgtcccca | 540 |
| gagagcgccc tgagagaaca gggtggccgc ttggtccagg tgcgcggggt cgggtctggg | 600 |
| tccagggagc gggtcgggaa gtctgcggca cggagcactg ctagtgtcgg atctgcatct | 660 |
| ccagctctgt gctgcagctt cacttgcccg ccccccacca ctggcttctc acccggggtc | 720 |
| tctgccaaac tctggctgct gccgccctgg gttcgggccg gcggaaggcc ctgggcgtgc | 780 |
| gctgcggagc cgcctgcgag gactccacta gggcgctttc caggctggac tgccccgggc | 840 |
| tgcgctggag ctgccagtgc tcggggagtc ttcctggagt ccccagctgc cctctccacc | 900 |

<210> SEQ ID NO 92
<211> LENGTH: 200
<212> TYPE: DNA
<213> ORGANISM: Homo sapiens

<400> SEQUENCE: 92

| | |
|---|---|
| ctcttcccaa gttacgccac cggtcgagga cggcaggaga cccccgagtg cagagaaagc | 60 |
| tcaaaccggc agcgaagtcg gtcctagcca agctgaaaaa acgtctcgga tttcgcggac | 120 |
| agcggcctag acacagcccg atcttccagt cctagtgccc tggtcgagac ggttctatcc | 180 |
| ttttgcaaag aagccggaaa | 200 |

<210> SEQ ID NO 93
<211> LENGTH: 400
<212> TYPE: DNA
<213> ORGANISM: Homo sapiens

<400> SEQUENCE: 93

| | |
|---|---|
| tctcggttgc aatccccacc ctcctcaccc agcagggcag gaggcaccca acttggagga | 60 |
| gaaaggggtg ggggaggtga aacagagacc ggagagtcac gagggctggg ccgccgagag | 120 |

| | |
|---|---|
| caggagaata taccgtgtca cacacctcca ttctctcaca cacgttgcag acacaaatca | 180 |
| ctgacggttt ccacgtgctg cgctcgtgag cggaggtgtt caaagagggg gcagatgagt | 240 |
| tacttcccga gacggaaccg ggggtcccac gtccgccgcc ttcagtagca caaccaatct | 300 |
| ctgaacactc aaaccgcgca tctctggcgc atcaccatcc tatttaaggc cacgggctcc | 360 |
| gcccttttcc tcccctccct tcttttccac tctttttcca | 400 |

<210> SEQ ID NO 94
<211> LENGTH: 700
<212> TYPE: DNA
<213> ORGANISM: Homo sapiens

<400> SEQUENCE: 94

| | |
|---|---|
| ctgccagaga tgtgtctgtc ttgcgccccg catgcactgc ctgcggggct gcgctgcact | 60 |
| ccccggcggc gccacgggtc tggccccgc gcttctacgt gttgggggga tgcatggacc | 120 |
| ttggagatcc gtagttggcc ctaaccttct cggaatctcc tctgcacgcg ctgcctgttc | 180 |
| ctcctctgca cgctctgtcc gttcctttgc aacttctgtg ggaattgtcc tggcgtggga | 240 |
| aacgcccccg cgctctttgg cacttagggt gtgagtgttg cgccccttgc cgcagcgctc | 300 |
| agggcagcat cccgctcgag gatgcagggt tctcaccaag cagtgagggg gactcacgcg | 360 |
| ccgccgggga gcggagccag gctccgagaa gggagcaggc tcgagccgct gggttttcgc | 420 |
| aagccttggg gcctctggcc gcccttccat gcctccgggc gcgggcggct cagcaggtcc | 480 |
| ccggcttcgg gaagttttgt gcgcggatcg ctggtgggga gggcgcgcgg gccagtggct | 540 |
| gagcttgcag cgaagtttcc gtgaaggaaa ctgcatgtgc ctttggaggc gactcgggac | 600 |
| tgctgtaggg tggactgggt gtctatggag ttgcgggtca gagcgagtag ggtgggtcct | 660 |
| ttcctgggac aggactggga attggggctc gaagtagggg | 700 |

<210> SEQ ID NO 95
<211> LENGTH: 200
<212> TYPE: DNA
<213> ORGANISM: Homo sapiens

<400> SEQUENCE: 95

| | |
|---|---|
| aggggtgtcc tccaacatct ctgaaccgcc ttcccttcct cctcactggc gccctcttgc | 60 |
| ctcagtcgtc ggagatggag aggcggctga agattggcag gcggcggcca gggtcgaggc | 120 |
| tgggagactc agagccgctg aggctgccgg agctcaggga gccgcttagg tagctgtcgc | 180 |
| ggtccgacag cgagtccggg | 200 |

<210> SEQ ID NO 96
<211> LENGTH: 5000
<212> TYPE: DNA
<213> ORGANISM: Homo sapiens

<400> SEQUENCE: 96

| | |
|---|---|
| tctgactctc gggctggagc agccgagaca gcgctcccca gcgggactac agaatcccgg | 60 |
| gtgtcggcct gggggccctg gattggcagt ggtggagtct tctgagccta acagctacta | 120 |
| ggaatgacag agttgcagat ggctttgtcg cccgcggggc ggctcaagcg tcctgggtcc | 180 |
| caggcctctg tcctacggcc aggccgccgg ctcaacgggc cgaagggaat cgggctgacc | 240 |
| agtcctaagg tccacgctc ccctgacctc agggcccaga gcctcgcatt accccgagca | 300 |
| gtgcgttggt tactctccct ggaaagccgc ccccgccggg gcaagtggga gttgctgcac | 360 |

| | |
|---|---|
| tgcggtcttt ggaggcctag gtcgcccaga gtaggcggag ccctgtatcc ctcctggagc | 420 |
| cggcctgcgg tgaggtcggt acccagtact tagggaggga ggacgcgctt ggtgctcagg | 480 |
| gtaggctggg ccgctgctag ctcttgattt agtctcatgt ccgcctttgt gccggcctct | 540 |
| ccgatttgtg ggtccttcca agaaagagtc ctctagggca gctagggtcg tctcttgggt | 600 |
| ctggcgaggc ggcaggcctt cttcggacct atccccagag gtgtaacgga gactttctcc | 660 |
| actgcagggc ggcctgggc gggcatctgc caggcgaggg agctgccctg ccgccgagat | 720 |
| tgtggggaaa cggcgtggaa gacaccccat cggagggcac ccaatctgcc tctgcactcg | 780 |
| attccatcct gcaacccagg agaaaccatt tccgagttcc agccgcagag gcacccgcgg | 840 |
| agttgccaaa agagactccc gcgaggtcgc tcggaaccct gaccctgaca cctggacgcg | 900 |
| aggtctttca ggaccagtct cggctcggta gcctggtccc cgaccaccgc gaccaggagt | 960 |
| tccttcttcc cttcctgctc accagccggc cgccggcagc ggctccagga aggagcacca | 1020 |
| acccgcgctg ggggcggagg ttcaggcggc aggaatggag aggctgatcc tcctctagcc | 1080 |
| ccggcgcatt cacttaggtg cgggagccct gaggttcagc ctgactttcc cgactccgcc | 1140 |
| gggcgcttgg tgggctcctg ggcttctggg ctcacccctta cacctgtgta ctaaagggct | 1200 |
| gctaccctcc cgaggtgtac gtccgccgcc tcggcgctca tcggggtgtt ttttcaccct | 1260 |
| ctcgcggtgc acgcttttc tctcacgtca gctcacatct ttcagtacac agccactggg | 1320 |
| tctccctgcc cctccagcct ttcctaggca gctttgaggg cccagacgac tgaagtctta | 1380 |
| ctgctaggat gggaacacga tgaaaaagga aggggcccag tcaaaagtcc tctcctcttc | 1440 |
| ggttttctt caactgtcct tcacaaaaac atttatttct gtcccagcgc cctggcggat | 1500 |
| ttcggcagat gggccctagg gggttgtgga ggccaaattc ccaggatgct ggtcctgcct | 1560 |
| ttttcattgg ccaaaactgt atttcctaca acgactaaag ataaccaaga actgagtaga | 1620 |
| ccctgttctc tcaccagatc tccctggctc tgtttaactt ttcctggtgc aatgcgatgg | 1680 |
| caccaccagc tcccccaggca ggcaccactc cctcaagata ccatttgggg tagggatttg | 1740 |
| agtcctggag agggtcagcg gggcgccggg gtgggggtgg aaggagact gacagggaca | 1800 |
| caccgcgagc tccgcatact ctcctctgcc ccctgtagcc cggggcttta atgaccccaa | 1860 |
| gcagatttcc tgtctctggt ctagccagct gcccctaggg ctggatttta tttcttcatg | 1920 |
| gggtttcacc ctaaagggcc ccctggtcat gggacctggt tgggaacaaa tgaaagatgt | 1980 |
| cttgtagcaa atgctttcag gggagcagaa aagaagattg ggcacttcca gtcacttggt | 2040 |
| cactttaggt ggctggaaca aaactggtga ctttcacgac tgctacaggg tgaggggggtg | 2100 |
| aagggtggca gagaggtgac aagccactgg gaatcctatt cagtggggat gccgacaggg | 2160 |
| agtggctgta atcaactgag caacatcgtg tgaatgtta ttcacaggtc aggacagcag | 2220 |
| cttggtcttc ccaggtgagg aactgaggac tggcctgcat agatttgtgc agtaggtgag | 2280 |
| tagcttccaa atttattttc agaacttcca tgtagtacct gcctctccat ttaaatattt | 2340 |
| tttaaaattt tatttattta aatattttct tggttagctt tccaagaggg aggaaaagag | 2400 |
| gggagttgca acaagtagtg cccctatgct gggattcatt ttccagagta aagcctggga | 2460 |
| ctggcaccct gaccctacc ggcaggtgaa aactccaggc aaaactgctga gatcccacct | 2520 |
| gggctggctg agatagtgcc tggggtgcat ccctcagcag ctgccacctg gccctgggg | 2580 |
| ccatctcttt ctctggcatc aagcagccag gtgtcaaggc cttcccagca atccatgctg | 2640 |
| catggctggg tcttgttcta gcaggtcgat gggcaggac tggtagctta gccagggcac | 2700 |
| cagtgcgtgg ctgtgggttt gtgtgcttct gtggagaagc atgatgtgta tgtgtgtgtg | 2760 |

```
tgggcacagg catgaggaag ggttcatttg tgcaggtatc tcccatgtat atcagtgtgg    2820
gagagtgcct gaggatgtgt ttgtgtgtct gaaaatgggc ggagggtctg ttgtgctaat    2880
gtgtgcaggg gtgaacatgt gtgtgacagt ctgtgtgttt ccctgagtgg tggctgcgtg    2940
agagggtgag gggatttggt gttgtctacc atgcccggca catagcaggc tcttaataat    3000
cttgaattta attaatgtta aatgtgtatg ttcccatcct tgtggaagtt ggtatagagc    3060
ctgttttcct gtgattgtga gactggaaaa tgggggacgg gcagggggcga gacaggatac   3120 agaggctact gttttcttcc tccctagaag taagtacata aagagtgggg ctctggcacc    3180
tcacgggaca tcaccaagtc ctgtgtggct ggctaggctg tcccaaggtg gcttcaggca    3240
tcacttgaat cttttgagac cttcaggcag tagcctgcca ttcaccctgt cagtcagcag    3300
aagttgggcc cacacaggcc atagaaacac agagcagttc ccgggaggac ctgagctgtc    3360
cctgagagca gagcttccag gagaggccgc aggaactgcc ttgaccggaa ttcctcttgg    3420
ggtgcaaagg tggagggaca catggtgcga ccccaggcag aggactgcag ccactccgtg    3480
cagtcccagc ctctggggta gccccttgac ctccaggcct gcacagatcc aaggccgagg    3540
tccaggctcc agcgccaaat tagctggcct agcagcctgc agccgctcta atctcaacta    3600
ggaaggaatc cttgcgctta gaaagtccaa gcgaaagggt attctgattt tatcccggtt    3660
ttaccagaaa atgctgaaag gaaaagcccc gagaggacac agtgctctag gaactcgggg    3720
cgccacgagc gcctcatccc ctcccttccg cccggccgcg gtgccctggt cgctgaggga    3780
cgcggtcagt acctaccgcc actgcgaccc gagaagggaa agcctcaact tcttcctctc    3840
ggagtcctgc ccactacgga tctgcctgga ctggttcaga tgcgtcgttt aaagggggggg   3900 gctggcactc cagagaggag ggggcgctgc aggttaattg atagccacgg aagcacctag    3960 gcgcccatg cgcggagccg gagccgccag ctcagtctga cccctgtctt ttctctcctc     4020
ttccctctcc cacccctcac tccgggaaag cgagggccga ggtagggggca gatagatcac    4080 cagacaggcg gagaaggaca ggagtacaga tggagggacc aggacacaga atgcaaaaga    4140
ctggcaggtg agaagaaggg agaaacagag ggagagagaa agggagaaac agagcagagg    4200
cggccgccgg cccggccgcc ctgagtccga tttccctcct tccctgaccc ttcagtttca    4260
ctgcaaatcc acagaagcag gtttgcgagc tcgaatacct ttgctccact gccacacgca    4320
gcaccgggac tgggcgtctg gagcttaagt ctgggggtct gagcctggga ccggcaaatc    4380
cgcgcagcgc atcgcgccca gtctcggaga ctgcaaccac cgccaaggag tacgcgcggc    4440
aggaaacttc tgcggcccaa tttcttcccc agctttggca tctccgaagg cacgtacccg    4500
ccctcggcac aagctctctc gtcttccact tcgacctcga ggtggagaaa gaggctggca    4560
agggctgtgc gcgtcgctgg tgtggggagg gcagcaggct gcccctcccc gcttctgcag    4620
cgagttttcc cagccaggaa aagggaggga gctgtttcag gaatttcagt gccttcacct    4680
agcgactgac acaagtcgtg tgtataggaa ggcgtctggc tgtttcggga ctcaccagag    4740
agcatcgcca accagaacgg cccacccggg gtgtcgagtc ttggtaggga aatcagacac    4800
agctgcactc ccggcccgcg ggccttgtgg catataacca tttatatatt tatgatttct    4860
aattttatta taaaataaaa gcagaaatat ttcccgaaga acattcacat gagggcatta    4920
cggggagacg gcaagtcggc ggctcggggg gcgcgctcag ccgggagcgc tgtagtcaca    4980
gtcccgggag gaagagcgcg                                               5000
```

<210> SEQ ID NO 97

<211> LENGTH: 1500
<212> TYPE: DNA
<213> ORGANISM: Homo sapiens

<400> SEQUENCE: 97

```
tggaacaagt gtcagagagt aagcaaacga ctttctgagc tgtgactctg ctcctcgact      60
gcccacgtgc tctccgctgt ctgcactcct gcctcacctg ggctgactcg gactctccac     120
ctcctttgct gcttccggca tgagctaccc aggagcctaa ggcgtcctt cccgcaactc      180
cggtccccgc gccccgggac tgcaaatcct ttaaacagag gccccagagc taggggtttt     240
cccaggctct ggtgggcgtg ggctgacagt cgctgggagc cccgcaacag ggggatgtc     300
caggcaggta tgcacccagc tcccggcgtt tcccggagtc accacaatgt ttccctttct     360
ctctccccca cgtatgctgc taggggtact ccccagatag gattttcttt gtcttttctc     420
ctagtaacac cgaagccctc tcgtgcccgg ggactgcaga ggaacgccag accatccgga     480
ccttgcggga tggctcggtg tgtgtgtttt actgtgtgtc ggagtgtcgc gcatgtgtgc     540
gtgttggggc gcgttatcaa caggggccta gggcacccccc actctttctt gctctcttcc    600
cccatcactt catggacctc cgaggcgcaa agcgctcgac cctctcctgg gctcagtggc     660
ttgggtactc cgggctgagc tcagctgggg agtcccctta cccagcccgc accggcaccc     720
cgaagcttca aagttgcggc aaacagttgc ggggagcaga ggaactgagg tccaggccag     780
cgcgcccgcg gtcgctcgcc ttggggagca ggctgagccg agggtcgtgc gggtgcgcgg     840
cagaggcggt aggaggcgga ggagaggggg gagaaagagg gggcggtggg gaacagctgc     900
cggggtaggc gaggcgcaag gtggctcccc gcggccccgc gccccgcggc tctcggacgc     960
accaggcagc caatggctgc gcagaggtgt acagcagatg gcgtctgact gcgccgttcc    1020
ttcctcctcc tcctcctcct ccttctcttc ctcctcctcc ttctcttcct cctcctcctc    1080
cttcagtgct gaggagccag agtcgccgcc gggttgccag acgctggaat gggtggtctt    1140
ccgacacaca ccaccatctt tcttgcgctc gggaagctcg ggctcagcg gctcccagag     1200
gttacggcgg cggctctggc gagacgggtg agtgcaagca cgcggagccc cgagtcgggg    1260
atgccgggcc ccctggccgg ccgactgggg cgcggggtgg cagcgccggg gaaggggggcg    1320
cgctgccggc gcagactttg ctctttcctc gccggacagc catcgtcgcc ccttctccca    1380
gccagacgcg ggaacttgga agcggatctt tcggacgcc tctggcttgg ggctgcggga     1440
agcgtgggct gccggggcg cagtgtgcgg agaccctcta ggcgggcggg gacgccccac    1500
```

<210> SEQ ID NO 98
<211> LENGTH: 800
<212> TYPE: DNA
<213> ORGANISM: Homo sapiens

<400> SEQUENCE: 98

```
gttattatcc acggggtcct aattaaagct tgattaaaat gcccttcttt ctctaaaaaa      60
ttacgaacta ggcaacttca tacattttga atggcgcagt gtttcctctt ccaactgttt     120
agtttgtagt atactatgta agcaacatca attatcaacc cttgcaagat gacaacatga     180
gcctgtgggg gaagcacttg aggggaggga ggagaaactt ctctttttta ataatcagcc     240
ggaaacaatg tttaacaaga atctgatgag gtcactgcag taaatatttt tcctcttaca     300
gagccaatca tcacggaggg atcccctgaa tttaaagtcc tggaggatgc atggactgtg     360
gtctccctag acaatcaaag gtgtttgctt tctgctctgt tgcttttaaa ttgtatggga     420
aaggaagatt ggtccgacgg cgcgcttgtg gcccggccgg agcttgcgtg cgcgttctga     480
```

-continued

```
cggctgggtg ctgtgttaca ggtcggcgca gttcgagcac acggttctga tcacgtcgag    540
gggcgcgcag atcctgacca aactacccca tgaggcctga ggagccgccc gaaggtcgcg    600
gtgacctggt gccttttaa ataaattgct gaaatttggc tggagaactt ttagaagaaa     660
cagggaaatg accggtggtg cggtaacctg cgtggctcct gatagcgttt ggaagaacgc    720
gggggagact gaagagcaac tgggaactcg atctgaagc cctgctgggg tcgcgcggct     780
ttggaaaaac aaatcctggc                                                800
```

<210> SEQ ID NO 99
<211> LENGTH: 40
<212> TYPE: DNA
<213> ORGANISM: Homo sapiens

<400> SEQUENCE: 99

```
tccctgctgt gggacccgag gagaggagaa ctggttcgct                           40
```

<210> SEQ ID NO 100
<211> LENGTH: 500
<212> TYPE: DNA
<213> ORGANISM: Homo sapiens

<400> SEQUENCE: 100

```
tctctctctc tctcttgctt ggtttctgta atgaggaagt tctccgcagc tcagtttcct     60
ttccctcact gagcgcctga acaggaagt cagtcagtta agctggtggc agcagccgag     120
gccaccaaga ggcaacgggc ggcaggttgc agtggagggg cctccgctcc cctcggtggt    180
gtgtgggtcc tgggggtgcc tgccggcccg gccgaggagg cccacgccca ccatggtccc    240
ctgctggaac catggcaaca tcacccgctc caaggcggag gagctgcttt ccaggacagg    300
caaggacggg agcttcctcg tgcgtgccag cgagtccatc tcccgggcat acgcgctctg    360
cgtgctgtga gtacaacctg ctccctcccc gggcacagat atgacagagg ggcttagagg    420
gggcccagct ttgagatggg ttgttcttat gtcacaggac agagtgatct gacatgcaca    480
cttccccgcc accctgtcat                                                500
```

<210> SEQ ID NO 101
<211> LENGTH: 500
<212> TYPE: DNA
<213> ORGANISM: Homo sapiens

<400> SEQUENCE: 101

```
tgtcctcgaa gaagggcctg agcagcagca gaggacccca ggcgaccgtg cctgagccgg    60
gcgccgacga cgactgagca cctgatatgt ccccggcact cgcagccccg cggccggagt    120
cgctgtgggt gagcggtcgt cgagcttcac agaggccggg ctctgtgcca gggccccgac    180
agggcaggaa gcagatagag tcccacaagc acaagcccag tgcgcagaaa gggttactta    240
aaaaataagt tctgtgataa aatcaaacag ggtgaagggc tggaaacagg tcatgagggc    300
gcaaacaggt cgtgagggcg caaacaggtc gtgagggcgc aaacaggtcg tgagggcgca    360
aacaggtcgt gagggcgcaa acaggtcgtg agggcgcaaa cagatcgtga gggcgcaaac    420
aggtcgtgag ggcgcaaaca ggtcgtgagg gtgcaaacag gtcgtgaggg cgcaaacagg    480
tcgtgagggt gcaaacaggt                                                500
```

<210> SEQ ID NO 102
<211> LENGTH: 300
<212> TYPE: DNA

<213> ORGANISM: Homo sapiens

<400> SEQUENCE: 102

| | | | | | |
|---|---|---|---|---|---|
| aaatgagacc | tctggggaga | ctgtcaaccc | caggggtaaa | acaaaaattc | tgatcagaaa | 60
| ctgagtttcc | caaagaaggg | gctaaatgtt | ttccaacact | ttcggggctc | agggaagatg | 120
| actctgtaag | gacactgaga | atcttcctcg | cgtgccacgg | ggaggaggac | tgggggcgtt | 180
| tgaggggctc | agcgcaccag | aggagtgagg | tggaggaggg | cgttcccgcg | tcctcctctt | 240
| caatccagag | cagctcaacg | acgtggctcc | ctttctatgt | atccctcaaa | gccttcgcgt | 300

<210> SEQ ID NO 103
<211> LENGTH: 600
<212> TYPE: DNA
<213> ORGANISM: Homo sapiens

<400> SEQUENCE: 103

| | | | | | |
|---|---|---|---|---|---|
| taggctctag | tggacctagc | agtgggagag | ctacttgggc | tggtttcttt | cctgacgctg | 60
| cagggatggg | catcggcctg | gaaccagaag | cgcaggagct | gggccacggc | agagtaatta | 120
| agaaaataat | gaaattgatg | gcggatgggg | gcgctagaaa | tcctggggcg | tctacttaaa | 180
| accagagatt | cgcggtcggc | cccacggaat | cccggctctg | tgtgcgccca | ggttccgggg | 240
| cttgggcgtt | gccggttctc | acactaggaa | ggagcctgaa | gtcagaaaag | atggggcctc | 300
| gttactcact | ttctagccca | gcccctggcc | ctggtcccg | cagagccgtc | atcgcaggct | 360
| cctgcccagc | ctctggggtc | gggtgagcaa | ggtgttctct | tcggaagcgg | gaagggctgc | 420
| gggtcgggga | cgtcccttgg | ctgccacccc | tgattctgca | tccttttcgc | tcgaatccct | 480
| gcgctaggca | tcctccccga | tcccccaaaa | gcccaagcac | tgggtctggg | ttgaggaagg | 540
| gaacgggtgc | ccaggccgga | cagaggctga | aaggaggcct | caaggttcct | ctttgctaca | 600

<210> SEQ ID NO 104
<211> LENGTH: 800
<212> TYPE: DNA
<213> ORGANISM: Homo sapiens

<400> SEQUENCE: 104

| | | | | | |
|---|---|---|---|---|---|
| gaggttgctg | actcaggagc | caggagctga | gaaactccta | ggctagcagc | cgttgagcct | 60
| aattttattt | tctggctttc | tccgaaatgt | ctcgttcccc | tcatctttct | ggtccttttc | 120
| gtctctctta | ttttccccaa | aacgtctacc | tcacttcgtc | ttcctttctc | ctcccctccc | 180
| cctctctttc | ctctatactc | tcttcccatt | tagccttgca | ggcccctcct | ccccggtgtt | 240
| ggagagctca | agacgcgcg | aaactcaagg | atctggccct | gaccagggac | gggattaggc | 300
| gggaagtggt | gacggcctga | aaaggctggg | ctcgaacccg | tgccttcctg | aaaggactct | 360
| ccccgccaca | agtcacaccc | acccgcaggc | ctgctggcca | aagaaacaaa | ggagtcgggc | 420
| gtggatccag | gagaaacagg | ttttcgctct | cggatctccc | tgggcaaatc | agggatcctg | 480
| agcgctatac | cccgcagtcg | tacgagcct | ctgggaaagg | ggatttaagg | gtgacttcca | 540
| ctttcagctt | cggctacttg | ttgcctgcgg | tccaagcctt | ctctgcttcc | tcctacctcg | 600
| tcttaggcct | ctgtagaaag | tgcacgcgcg | gtttccccctt | ccaggctctg | agagggcctg | 660
| caggcccgtg | gccgcctccg | acaagatgcc | ttccagtgct | agggggccca | ctttggcggg | 720
| atgggggtcg | gttggttaaa | aaaaacttaa | gttctggctc | agtcgagtgt | ggcaaaagcc | 780
| gagggtcggg | ggttgggggg | | | | 800

<210> SEQ ID NO 105
<211> LENGTH: 2000
<212> TYPE: DNA
<213> ORGANISM: Homo sapiens

<400> SEQUENCE: 105

```
tactgacctg gtctccgcct caccggcctc ttgcggccgc tgcagaagcg cactttgctg      60
aacaccccga ggacgtgcct ctcgcacagg gagcgcccgt ctttgctggg gctggagcgg     120
cgcttggagg ccgacactcg gtcgctgttg gactccctcg cctgccgctt ctgccggatc     180
aaggagctgg ctatcgccgc agccatagct gctcagcgag ggcctcaggc cccagcctct     240
actgcgccct ccggcttgcg ctccgccggg gcgagggcag gacctgggcg gccagggaaa     300
gggcagtcgc ggggaggcag tgctaaaatt tgaggaggct gcagtatcga aacccggcg     360
ctcacaaggt tagtcaaagt ctgggcagtg gcgacaaaat gtgtgaaaat ccagatgtaa     420
acttccccaa cctctggcgg ccgggggggcg gggcggggcg gtcccaggcc ctcttgcgaa     480
gtagacgttt gcaccccaaa cttgcacccc aaggcgatcg gcgtccaagg ggcagtgggg     540
agtttagtca cactgcgttc ggggtaccaa gtggaagggg aagaacgatg cccaaaataa     600
caagacgtgc ctctgttgga gaggcgcaag cgttgtaagg tgtccaaagt atacctacac     660
atacatacat agaaaacccg tttacaaagc agagtctgga cccaggcggg tagcgcgccc     720
ccggtagaaa atactaaaaa gtgaataaaa cgttcctta gaaacaagc caccaaccgc     780
acgagagaag gagaggaagg cagcaattta actccctgcg gcccgcggtt ctgaagatta     840
ggaggtccgt cccagcaggg tgaggtctac agaatgcatc gcgccggctg cggctttcca     900
ggggccggcc acccgagttc tggaattccg agaggcgcga agtgggagcg gttacccgga     960
gtctgggtag gggcgcgggg cggggcagc tgtttccagc tgcggtgaga gcaactcccg    1020
gccagcagca ctgcaaagag agcgggaggc gaggaggg ggagggcgcg agggaggag    1080
ggagatcctc gagggccaag caccctcgg ggagaaacca gcgagaggcg atctgcgggg    1140
tcccaagagt gggcgctctt tctctttccg cttgctttcc ggcacgagac gggcacagtt    1200
ggtgattatt tagggaatcc taaatctgga atgactcagt agtttaaata agccccctca    1260
aaaggcagcg atgccgaagg tgtcctctcc agctcggcgc ccacacgcct ttaactggag    1320
ctccccgcca tggtccaccc ggggccgccg caccgagctg gtctccgcac aggctcagag    1380
ggagcgaggg aagggaggga aggaaggggc gccctggcgg gctcgggatc aggtcatcgc    1440
cgcgctgctg cccgtgcccc ctaggctcgc gcgccccggc agtcagcagc tcacaggcag    1500
cagatcagat ggggattacc cgccggacgc aaggccgatc actcagtccc gcgccgccca    1560
tcccggccga ggaaggaagt gacccgcgcg ctgcgaatac ccgcgcgtcc gctcgggtgg    1620
ggcgggggct ggctgcaggc gatgttggct cgcggcggct gaggcctctg gccggagctg    1680
cccaccatgg tctggcgcca ggggcgcagg cggggcccct aggcctcctg ggctacctc    1740
gcgaggcagc cgaggcgca acccgggcgc ttggggccgg aggcggaatc aggggccggg    1800
gccaggaggc aggtgcaggc ggctgccaac tcgcccaact tgctgcgcgg gtggccgctc    1860
agagccgcgg gcttgcgggg cgccccccgc cgccgcgccg ccgcctcccc aggcccggga    1920
gggggcgctc agggtggagt cccattcatg ggctgaggct ctgggcgcgc ggagccgccg    1980
ccgcccctcc ggctggctca                                                2000
```

<210> SEQ ID NO 106
<211> LENGTH: 800
<212> TYPE: DNA

<213> ORGANISM: Homo sapiens

<400> SEQUENCE: 106

| | | |
|---|---|---|
| gggggacaca gagaggaggg gttgcgggcc tgtgagaatg aagagcacag agcggagagg | 60 | |
| gggaggagga gggaaaggaa ggcgtggcag tgagagagaa gaggaagaag agaggaggag | 120 | |
| tggggagggg agggagagca agacagcagc gggtctggat tccccteega gecacatetg | 180 | |
| gtcaggttct aagtaattag aagatttcc cattggttta cccaagggct ctctctctga | 240 | |
| ttaattttcg aaagagttgg ccaatttaa tcatagcaaa cacgatgatc acggtgatca | 300 | |
| tggcctgaac agctaaaagc agaaaataaa accccagaa cggactatga tcttgacctt | 360 | |
| tgcccgtggt caccggctgg cccacaccc agggttctga gctgttggga gccaaggctg | 420 | |
| ggtggacagg ggcttccgag gagctgtccg cagcggggcg gggaggcggg ccccgggggc | 480 | |
| ccgggcactc cgcgtcaccc cccggcaggg cccagagcgg caggccggcg tgcgcccag | 540 | |
| ggcctgcgca ccgtggggc tcttccccgc ccacgaggcc taggtgctgc cgcagccacc | 600 | |
| ccaggaaggg ccccaggcca cagtcgcagc gccaggagtt gtgccccaac aggacctccg | 660 | |
| tcagccgggg cagagcccca aacacgtcgc caggcagggt ctccagctgg ttgtggtcga | 720 | |
| gctggacgct ctccaggctg ctgagattgc ggaagagggc acggggcagg gcgcgcagcc | 780 | |
| tgttgcggcg cagggacacc | 800 | |

<210> SEQ ID NO 107
<211> LENGTH: 550
<212> TYPE: DNA
<213> ORGANISM: Homo sapiens

<400> SEQUENCE: 107

| | | |
|---|---|---|
| gccccggtgc accgcgcgtc cagccggccc aactcgagct agaagcccca accactgccc | 60 | |
| agtgcctgag ttgcagtctt gggtccttta gaaacctgga gatgtgcgta aaattcagat | 120 | |
| gccggtattc ccgaacttcc ccaggcctca gcatatctcg gcggcctgtg acagatgggg | 180 | |
| aggctaccaa tcgctccggc gtccgcagcc cgacccctgc cgccagaccc cggacgtctt | 240 | |
| ccggataata aagttcccgc tctaattcat tttccctaat ctggacgccc ctaatctaca | 300 | |
| gcttttattg cgcccagtta aaagtcgagg gaattcgctg tccctccgcg ctcggataat | 360 | |
| taccctaaa tggccacggc agccccttgt gtttcctgga gattagaacc ccgcagtcat | 420 | |
| caatggcagg gccgagtgag ccgccaatca cctccgctca ctccctgaga gccgctggcc | 480 | |
| tgggccgcag gaggagaggc cataaagcga caggcgcaga aaatggccaa gccccgaccc | 540 | |
| cgcttcaggc | 550 | |

<210> SEQ ID NO 108
<211> LENGTH: 2000
<212> TYPE: DNA
<213> ORGANISM: Homo sapiens

<400> SEQUENCE: 108

| | | |
|---|---|---|
| agggtgcctc tgttcaaatt agaaaaaggc gccccctcag ggcagactca gcccagctgc | 60 | |
| caggggacaa gtcctggcta acgggagctg gagctgggtt tcacctccag gtgcctcctt | 120 | |
| ggcggggcgc ccgtgcagg ctacagccta cagctgtcag cgccggtccg gagccggagc | 180 | |
| gcgggaatca ctcgctgcct cagcccaagc gggttcactg ggtgcctgcg cagctgcgc | 240 | |
| aggtggagag cgcccagcct gggaggcagt agtacgggta atagtaggag ggctgcagtg | 300 | |
| gcagaagcga gggtggccgc agcacttcgc cgggcaggta ttgtctctgg tcgtcgcgca | 360 | |

| | |
|---|---|
| ccagcacctt tacggccacc ttcttggcgg cgggcgccga ggccagcagg tcggctgcca | 420 |
| tctgccggcg ctttgtcttg tagcgacggt tctggaacca gattttcacc tgcgtctcgg | 480 |
| tgagcttcag cgacgcggcc aggtctgcgc gctcgggccc ggacaggtag cgctggtggt | 540 |
| taaagcggcg ctccagctcg aagacctgcg cgtgggagaa agcggcccgc gagcgcttct | 600 |
| tgcgtggctt gggcgccgcc ggctcctcct cctcctccgc gacgcctgcc ggcccgctgc | 660 |
| cgcccccgcc gccggccccg ctgcacagcg cggacacgtg tgcacctctg ggccaacac | 720 |
| cgtcgtcctc ggtccttggg ctgcggtcgc ctgcggaccc cggtgggaac agaaacaaga | 780 |
| gactgtcagc gccacagacg aggtgaggcc gggcctcaac tgcaggggtc acgggagtgg | 840 |
| ggcggaaata cactttgatc ccactcaagc ggagcggagg tctgggaggc cctgggcccg | 900 |
| ggagaccagt cttagactct tgccccactg ggtatcccat ctaggcctct tctggggagg | 960 |
| gcggcagact cagccgctgt gtcaacgctg tgttgtcgag accagctccc caccctctct | 1020 |
| gggcccagg ctcccctcag taacttgggg cactcgaccc gagcatccgc gaaagccctc | 1080 |
| ccggctctca gcgttgagca ttgggattct agactgcatt tccgtctctc tgcttgggtt | 1140 |
| cacgcgcctc tccacactta gttcacacgc acacacgcgc gcgtcctcgc agcacacact | 1200 |
| tgtctggtgc aggtaaggga aggtggaggc ggatcctggg gccaaaggta tttagaatct | 1260 |
| ttcaccctca gccgctggg attgctgtga gagacatgga aacaggctga gccgaggcct | 1320 |
| tagatgagag gatggactgg agagtaaaga gggagggttg cccctgcatc gagttttggg | 1380 |
| accctgatcc cacaccagct tctcggtctc gtacccgccc ttccgaagaa ctccagcaga | 1440 |
| aaggtccagc ggtcccctgt gcttgaggcc tacagaagct tgtacccaac tagggcaggc | 1500 |
| acccgggtct tccagaccac aggacaggac aggccacggc tgaggaggcc tctctcctgc | 1560 |
| ctccaggatg aactaaagac ccaatccggg atcttcggcc tagggctgct ctcccagacc | 1620 |
| tggggtctga gaaagccaaa ccagcccttt ccccaaagct ctagttctgc agattctcag | 1680 |
| ctctggccca ctcggaggtg ttcttcacca cctatccacc tactgtgggg cccggccctg | 1740 |
| ggaccttgaa ctggcaggtc tctggtccag agctaggtca ctggctacct gaggtctctg | 1800 |
| aaccctcac ttttccgctt ccctgatttt ggggatttgg ggacagacac ggcagaaagc | 1860 |
| actggcgacg aactcaaaaa ctcccgaacg caaggggcag cggttctccc aacccagtct | 1920 |
| aatgcacatt ggcccaggat gtctcaggcc tcacccagg acgtagggct ctgaggagct | 1980 |
| actccggtct ctcgcgggct | 2000 |

<210> SEQ ID NO 109
<211> LENGTH: 1000
<212> TYPE: DNA
<213> ORGANISM: Homo sapiens

<400> SEQUENCE: 109

| | |
|---|---|
| gagaagggat gtggcggggg gctcctccgg ccctggactc cctgggtgga ctagaaaagg | 60 |
| gcaaagaagt ggtcacatct gtgggccaga ctggtgcgcg atctttggag gcgcagcagc | 120 |
| aaggccgcgc cagggctgag cccagaccgc ccacgaggag gcccgccagg cccggagcag | 180 |
| cggcgcgtgc gggggcgtgc cgagcgcagg ctctagggcc cctgcttcgc cccagctgga | 240 |
| ccccgcgggc ggtcggtgca gctcgagcgt gtgggctgcg atgccctgcc tgagacttcg | 300 |
| ggctagggat gcggcgggga agtggggtg cggcggcagc tgcagattag attccttttt | 360 |
| tttttggccg gagggacgtg caaacttcta gtgcccgggc caagagggcg accccggagg | 420 |

```
tgcgtaggtg gccctccggg ttcccgcttc tcctagtgcc tctgaaaata ccgtcagggt    480
aaagggagac aggcagtaag tcttaccacc accgcccttt ccccatgtca ttggccaaaa    540
actgaacatt aagataaagc agctgtttca gtcaatggaa agcggtaggg cgaggttgta    600
cccaaaaccc ggtttagacg gccaatgaag tcctaggaaa agccgccccg ggggcacgtt    660
caggtggagc ggctgcacct cgggtcgttc taagggatgg gctgcgtggt acccacggaa    720
ttcatgggtc caaaaggtcc tggtcacctg tccaaacatc catcccctgg cgcatggcgg    780
ttgacaagat ggcccggcca cccagaggaa ggaggatccg ggacggggaa cttcgcgccg    840
ggaagctgta gcccagagct gcagctcagc attcgcaaga gattcatctt ttttttctct    900
cgtgttcgga gaaacagata aacaagacac cgcctcatca gataagaacg tctccttcga    960
tgtcacggat ttcaagaggt agctggagaa actgacgtca                         1000

<210> SEQ ID NO 110
<211> LENGTH: 1300
<212> TYPE: DNA
<213> ORGANISM: Homo sapiens

<400> SEQUENCE: 110
caggtcaggc agaacttctg cccttcccgc tactggcacc ccaagcaggg atgcactggg     60
atgcgtggca ggggcgggat ctcctgggag cgtctcagcc cagcagggag tggggaagca    120
agagggaagg cttaccttcc tcggtggctg gcaggaggtg gtcgctgcta gcagggggga    180
tgcaaaggtc gttgtcctgg gggaaacggt cgcactcaag catgtcgggc aggggaagc     240 cgaaggcgga catgacgggg cgcagcggt ccttcacctg cacgcagagc gagtggcatg     300
gctggatggt ctcgtctagg tcatcgaggc agacggggc gaagagcgag cacaggaact    360
tcttggtgtc cgggtggcac tgcttcatga ccagcgggat ccaagcgccg gcctgctcca    420
gcacctcctt catggtctcg tgcccagca ggttgggcag ccgcatgttc tggtattcga     480
tgccgtggca cagctgcagg ttggcaggga tgggcttgca attgctgcgc ttgtaggaga    540
agtcgggctg gccaaagagg aagagcccgc gcgccgagcc caggcagcag tgcgaggcga    600
ggaagagcag cagcagcgag ccagggccct gcagcatcgt gggcgcgcga ccccgagggg    660
gcagagggag cggagccggg gaagggcgag gcggccggag ttcgagcttg tcccgggccc    720
gctctcttcg ctgggtgcga ctcggggccc cgaaaagctg gcagccggcg gctggggcgc    780
ggagaagcgg gacaccggga ggacagcgcg ggcgaggcgc tgcaagcccg cgcgcagctc    840
cggggggctc cgacccgggg gagcagaatg agccgttgct ggggcacagc cagagttttc    900
ttggcctttt ttatgcaaat ctggagggtg gggggagcaa gggaggagcc aatgaagggt    960
aatccgagga gggctggtca ctactttctg ggtctggttt tgcgttgaga atgcccctca   1020
cgcgcttgct ggaagggaat tctggctgcg cccctcccc tagatgccgc cgctcgcccg    1080
ccctaggatt tctttaaaca acaaacagag aagcctggcc gctgcgcccc cacagtgagc   1140
gagcagggcg cgggctgcgg gagtgggggg cacgcagggc accccgcgag cggcctcgcg   1200
accaggtact ggcgggaacg cgcctagccc cgcgtgccgc cggggcccgg gcttgttttg   1260
ccccagtccg aagtttctgc tgggttgcca ggcatgagtg                         1300

<210> SEQ ID NO 111
<211> LENGTH: 500
<212> TYPE: DNA
<213> ORGANISM: Homo sapiens

<400> SEQUENCE: 111
```

```
tgcgatcatt aaaatcagtt ccttccctcc tgtcctgagg gtaggggcgg gcagatttta    60
ttacttctct tttcctgata gcagaactga ggcggggttg tggaggagcg acggaggacc   120
acctctaact tcccttcact tcctggattt gaagcctcag ggccaccggc ctcagtcctg   180
ttacggtggc ggactcgcga ggttttccag cagctcattc cggacggcg gtgtctagtc    240 cagtccaggg taactgggct ctctgagagt ccgacctcca tcggtctggg agcgagtggt   300
tcgagttcag atgctgggaa ccgtcgcttc tccccggccg ggctcgctgt tttctcctcc   360
gctcgccgtc atcaagcccg gctatgagca gggctttaaa tcctccctcc ctcacccgca   420
ggtttaccga gcagcccgg agctctcaga catgctgcgc tgcggcggcc agaggagggg    480
tgggggcatt gccctctgca                                               500
```

<210> SEQ ID NO 112
<211> LENGTH: 500
<212> TYPE: DNA
<213> ORGANISM: Homo sapiens

<400> SEQUENCE: 112

```
gggcttgggc cgcaggcttc cctggacttc cgcagtcccc cttctcccca ttccagaacc    60
tgccgagccc ctgctgcatc tgggacccgc cttcaccgtt tcccaatccc agcggttagc   120
ccctgcgccc ccttttttggt ctccactttg ccgttcgaaa atgcctaggt tggtggatcg   180
accctccgcg gagcaaagac ggatggctgg caggagcagg ttcaggagct gggccaaggt   240
attctctgct tccgcctttg tgtccgcccc ccgccccct gctccccgct tcccgccagc    300
atctctcctt ttctgctcag gagtgtttgg cccggcggtc caccccggct tcccgagata   360
cgctagagtt gcccccacgt cctgtccgcc gcgcccctac ccaccgggtt gccttcgggg   420
cccttcggtg ctgtgtagtc ggcgtggcgc tgtgagctag gcgaacagga accccccaggc  480 ccgccacgtc tacgctatta                                               500
```

<210> SEQ ID NO 113
<211> LENGTH: 600
<212> TYPE: DNA
<213> ORGANISM: Homo sapiens

<400> SEQUENCE: 113

```
ttctggggcc tggatgggtg cgagcgggac ccgggggagt gggagtcgcc aggctctgag    60
caagcaaggg ctgcacctgc acctctgccg ggcatgaaga aaggtaagga aggaaggagc   120
tcacccgggt gggagacaga gccggggcgc gcgagcttgg tgtgggggcg ccactccggg   180
gcggagggga ggggctacca gtgacttctc cgagtcggga gctagaaaga ggcttccggc   240
caggttccct tggaacaggt gtcggagttg ttgggagagg gggctgcaag aaagaggggt   300
gcagaaactg gttcattaga tggaggctct gggcggaacc gcgaggacac cctggcagcg   360
cgctgtgcct gcgttaggcc gggagggag aggcctccgg acggcgaagt gtccctaggg   420
acccagacgc ctcgggagcg atccgggccg ctgcgaagcc ctgcccacca ggagtggatc   480
cccaggattc acctcccggc tgcctgctct gagctgagaa ggggatctgg ttcttcacaa   540
taccgtggat ggcggggaag gggaggggagc ctggggtaaa atcccatctt ggtttcctcg   600
```

<210> SEQ ID NO 114
<211> LENGTH: 1300
<212> TYPE: DNA
<213> ORGANISM: Homo sapiens

<400> SEQUENCE: 114

| | | | | | |
|---|---|---|---|---|---|
| tgtcacagaa | accccagcag | cgcagccacc | ggactgggtt | ctggaggccg | agccgcagtc | 60 |
| cgtgcggcgg | cgctgggaag | agaaggcgcc | ccggcagctc | cctgccacc | ggccccgagg | 120 |
| agcggctggc | tcccccagcc | cagcgccgcc | gccgcccgt | aactccaggc | gcaactgggc | 180 |
| gcaactgggg | cagctgcgac | accgaatccc | tcacatctgc | aacctgggtg | ctgcggccac | 240 |
| tgagaaaatg | gaggcgcaga | ccaacgagcg | gtgccgcgac | cgagagacct | cggctggcga | 300 |
| aatggtggtg | ccgggagcct | gcgagtgacg | ccagccggcg | gggttgtcaa | ggacaacatt | 360 |
| cgttttgacg | cagccaatgg | cgccgtcacc | aagaaaccat | cgactctgag | aaaaaagaga | 420 |
| ggttcggcca | ccgagaaact | ccgtacgaca | agtgctgtgg | cagaaaaacc | gcctactccg | 480 |
| cgccacaggc | aaaacagcca | atggaaaccc | caggtgctgc | gaccgtgaca | ccggcactag | 540 |
| agggtctcgg | atggagaaag | cggcgcacgg | agaccaggaa | actatgtgta | gcacaactag | 600 |
| cagaaaaccg | tctggtcggc | catccgggag | aaagcgcgga | tcagaaacaa | gcgacttcga | 660 |
| tgcagggaac | cgcgcagcca | ctgaagaaag | tgacccacgt | ggcagtggtg | ccagcgaaac | 720 |
| actgcagttt | ggacggcagc | tgtggggatg | ccacagagaa | acatgcactg | ccactgaagt | 780 |
| acatccagct | ccgcggagct | agtgttcata | tgatcaagaa | accgccagtt | gggctctgct | 840 |
| agaaactttt | agtcctccct | taacggctat | cctacccaca | acagacaatg | cctttaccca | 900 |
| gcacctagcg | gtgctgagac | ccgcctgggc | cagcacagag | cgcagagcag | tacgggtacg | 960 |
| gagaaacgcc | ggactcagtg | aaaccagcct | tgcctccagc | ggattccccg | gcttcgccgg | 1020 |
| acgccacagg | cagagtgccg | cggggaaacc | tctggctccc | taaaccgatt | agattgtggg | 1080 |
| agtgggggg | acactcacaa | gttgtgtgga | agggaaccag | cggcaatggg | acccggcgag | 1140 |
| cacttgcccg | cagcaaatgc | ctgcgctgct | gcaaaaaaaa | caacttttgg | cgcaaagaat | 1200 |
| gttgcggcca | gagagcatcc | gctgtcgctg | acaaaggagt | agcaatggca | atgagaaacc | 1260 |
| gccggcgcca | cggccgaccg | cggcggctca | cgcctatgat | | | 1300 |

<210> SEQ ID NO 115
<211> LENGTH: 2100
<212> TYPE: DNA
<213> ORGANISM: Homo sapiens

<400> SEQUENCE: 115

| | | | | | |
|---|---|---|---|---|---|
| caaacgctga | gagacaaaaa | gacaccaaca | cccaccagga | ctgcgtcctg | ccagctcttc | 60 |
| actccgctga | cctgaccttc | cacgcccta | gtcctcgagc | ggacttgacc | tgtgggggag | 120 |
| taccgaaccg | tccccatgag | gccctccaag | cggccaggtg | gcctccgcca | ctctctccac | 180 |
| ccccaccctcc | tccaccccc | agcccatcgg | tccatcttcg | atctgcaaaa | cacgccgggt | 240 |
| cagcgacgca | tcggtcccag | gcttgtgacc | acctcttct | ctgttacttg | gggagccagg | 300 |
| cccaccgctc | aggatcacag | tgaggagaaa | aagacacaa | acgccaggac | agggcggctg | 360 |
| gggaaggaaa | ctgctaggga | ccgctcattg | tcagcctggc | gtgtcccacg | gatcgcagga | 420 |
| cccgtcgagg | cttggctctc | tgcgacccga | atactcctgg | gcctctcgac | ctcctcctcg | 480 |
| gactcaggcg | tccgcgtctc | cggtcatcac | gggagaccaa | ttggtttaca | aatagtgatg | 540 |
| ataaacctgg | gaccgacctt | ggggctgtgt | aaaagtctac | tgacagatgt | aatggagggt | 600 |
| tgttagcagt | cacaaagcct | gtcggacccg | tagcattagt | tcaagagact | attttcgtgt | 660 |
| cgcaccaaaa | ttactgcgcg | tgtaaaccaa | tttcccgac | ggaagaataa | acagagattc | 720 |
| gtttgaagcg | cgagatgaaa | acagatgggg | tatcgcaaac | agttccccaa | aatacaacag | 780 |

```
acttctgggc caattacacg tggttagctc tgaatggcag aggaaatagt tttctttgct      840
gctaaatgtc acaaaagtca cctaaaggca cagaggaggc cgctctgttt ttgcgaaact      900
tgctaaaatt aatctgcgct gggccacttg cagaaagcag aaccacctcc cgcccccacc      960
tcgcctccag ccgccggggt tcaggcgttt gtgaaagaca gaacctttgg gctagggacc     1020
cgggcactgg tgcttcgaag tccgaatccg ccggccgaga aaacgacaag agaaagaaaa     1080
tccagcgggc gctctctcca cgccaggcc ggtgtaggag ggcgctgggg ctcggcctgc      1140
cacccctacc cgacattggg aagcagcccc tgcgctcccg cggcgcctca gcctccggtc     1200
cccgccccga ggtgcgcgtt cctcctcccg catgcccgtc tcgggcccca cggagcaaga     1260
agatagacga tgacgaggcg cgcccatcca tccgggccga cgaggtcagg cccgcgccac     1320
aggcaaaaat tgcgcaagcc cggccgcagg gatttcgcgg gcgcctgggt cccaggtgcg     1380
cggccgaaat cctcagggaa aatcccgagg ggccaacggt ctaggccaca gggctgctgg     1440
gcccgggcct ggctcagagc gcattcgggc ggggaggccg cacgccgcac ccgggcctct     1500
cctccgagcc cgaggcaggc actgagctcc gggccagcca ggtgcctccc ggctggtgcg     1560
agaccccggg cctgctggga ggcgtgggca gggcagggca gggctgaacc ccagcgactg     1620
aatctcgaag gcaggaggcc tcggaggtca tcggcccagc tcgcctgaaa ctgtccctgc     1680
tcgtgccagg gcgcgggcag aggagaaagg acagggcgga gcaagcccac tgcagaactg     1740
cggtcggtgg ctgcgaaggg tccgggtcac cgcgctcccg gacgccggaa gccgcgctgg     1800
cggggccgcg gggagggagg ctgggtaccg gggccgtccg gccggaggaa gcggctccgg     1860
ccgcgctgtc cgcgcttggg agccgcgtgc agggttcagc cgtgtttcag ttgccctctg     1920
acctgacccc gggcgcacaa aggcctcccg ggtgcgccgc catggcccag tcttccagtc     1980
gctgccaaat taatgagccc acgtcaggtt gggtttacag ctcggccggg aagcagccga     2040
gtggaaaatg agctcggggc cgctccagag gctcccgcac aactgcagag gctgcccgcg     2100
```

<210> SEQ ID NO 116
<211> LENGTH: 250
<212> TYPE: DNA
<213> ORGANISM: Homo sapiens

<400> SEQUENCE: 116

```
tttccaagac agaaggaggg aactaggcgc cttttttcca ctccgctgac cccaacgtct       60
gggctgtgcg ttgtaacgca gttggcgggg ccttcagctt gggatgaggg cgaaggggct      120
cgggatgggt gggaaagcaa ggaccgggca acaggtgggg aggtggcgga cttttgtctc      180
ggggaaggaa atcggctgtg ctgaaagggc ggaaagcagt agcgcacaga actagtgtct      240
gcggggtccc                                                            250
```

<210> SEQ ID NO 117
<211> LENGTH: 250
<212> TYPE: DNA
<213> ORGANISM: Homo sapiens

<400> SEQUENCE: 117

```
ccctcctgtg gctgcttggg cagacgcctg tggcctgtcg gatgcggccc acatcgagag       60
cctgcaggag aagtcgcagt gcgcactgga ggagtacgtg aggagccagt accccaacca      120
gcccagccgt tttggcaaac tgctgctgcg actgccctcg ctgcgcaccg tgtcctcctc      180
cgtcatcgag cagctcttct tcgtccgttt ggtaggtaaa accccatcg aaactctcat       240
```

```
ccgcgatatg                                                          250
```

<210> SEQ ID NO 118
<211> LENGTH: 2000
<212> TYPE: DNA
<213> ORGANISM: Homo sapiens

<400> SEQUENCE: 118

```
tcctcctttg tgtatgtcaa cccagaggat ggacggatct ttgcccagcg tacctttgac    60
tatgaattgc tgcagatgct gcagattgtg gtggggttc gagactccgg ctctccccca   120
ttgcatgcca acacatctct gcatgtgttt gtcctagacg agaatgataa tgccccagct   180
gtgctgcacc cacggccaga ctgggaacac tcagcccccc agcgtctccc tcgctctgct   240
cctcctggct ccttggtcac caaggtgaca gccgtggatg ctgatgcagg ccacaatgcg   300
tggctctcct actcactgtt gccacagtcc acagccccag actgttcct cgtgtctaca    360
cacactggtg aggtgcgcac agcccgggcc ttactggagg atgactctga cacccagcag   420
gtggtggtcc tggtgaggga caatggtgac ccttcactct cctccacagc cacagtgctg   480
ctggttctgg aggatgagga ccctgaggaa atgcccaaat ccagtgactt cctcatacac   540
cctcctgagc gttcagacct tacccttttac ctcattgtgg ctctagcgac cgtcagtctc  600
ttatccctag tcaccttcac cttctctgtca gcgaagtgcc ttcagggaaa cgcagacggg   660
gacgggggtg gagggcagtg ctgcaggcgc caggactcac cctccccgga cttctataag   720
cagtccagcc caacctgca ggtgagctcg gacggcacgc tcaagtacat ggaggtgacg    780
ctgcggccca cagactcgca gagccactgc tacaggacgt gcttttcacc ggcctcggac   840
ggcagtgact tcacttttct aagacccctc agcgttcagc agcccacagc tctggcgctg   900
gagcctgacg ccatccggtc ccgctctaat acgctgcggg agcggagcca ggtgaggggc   960
tcggcgccgc cccgggcgac ccctgggggc ggcactggag aagccgcccg tcctcataag  1020
ggattgaact tgcatccact cctctccggc cggcttggtc gctggctgcg ctccacccga  1080
ttctcgggat cattggaccg tttgcgcgaa accagagtgg ccgattaagg gatggggctc  1140
cgagcaccgg gggtggtggc gactgtggc gaggggaggt gggaccgacc cccaccccta   1200
cactcaaaaa aggccggggc ctccttcgag cttccggtga atttcgggcg atttccgcgg  1260
gtgtcggggg tcccgggagg aggcagtcac agatccaccc ctgcagccag cctcctaggc  1320
gccggctccg gcacgcttcg ccggtctgta gatttcctct tcgatttctc cccagctccc  1380
agcatctgtg acttcactgt taccctccct atccccgcat cacccaaccg cacctgtctg  1440
cgggacttag gtgtgcgcgc ggggctcatg cgtgtcctcc ctgctggcca cccccacggc  1500
ccacacaagt tgcacgggct cgccacgccc cgccaacacg tgcgcggacg cacgcacgca  1560
ctcctcgcac gtgggcttac gcgaatacca gctttcactg ccactcgctc gcggccagat  1620
tcacaggcct gttccggtcc actcgcagct cccctctgcc gctccctccg ccgggctcag  1680
gagtactcgt agctgattgt gcgcgcctga gggtcccaga tcgcggccgc ccaggaccag  1740
gcgaggactc cggagcctcc tctcacctct cccacctgcg ccccgggctg gccgggtcg    1800
cctgggggc ggcctgagcg aggcgcgggg ccaggagcgc tggagcgact gccgctctaa   1860
gtgccgggcg ggcaggactc tacgatcctt gggccagagg tccggatggt cccgggactc   1920
cgtctcaagg gtcggcgacc cctcaaccca gaagcctcga gcaggcggac aggcagagct  1980
gcccagtggc cgaggcgcgg                                              2000
```

<210> SEQ ID NO 119
<211> LENGTH: 1100
<212> TYPE: DNA
<213> ORGANISM: Homo sapiens

<400> SEQUENCE: 119

| | | | | | |
|---|---|---|---|---|---|
| atttgtcgtt | gtgccattgc | tgccactgtt | gttcttgtcc | agggaaacac | cggtggccaa | 60 |
| cccagatcgg | atacaatggt | gcggctctgg | actgagcctc | caaccacatt | agccatgggc | 120 |
| agcattgttg | ctgccgctgc | tgttatttta | attatgattg | tacgttaacc | accaccttcc | 180 |
| ttcctctgcc | tcccttcagc | tgcaatgatg | tatgttactt | tttggtaact | ggatttcatt | 240 |
| aacatttatg | aactctcata | agtagtaga | aaaagcaatt | tgtgtggaag | aattttccac | 300 |
| ctcattaaac | agtgttcttt | tggggtcaa | gctgatattt | tttttgttgt | tagatttttt | 360 |
| ttataggtcc | tttgtccttc | cctaagccct | ggggatgaa | aggagagccg | tccacccagc | 420 |
| gaggggcttg | tgtgccctag | agggcgctgg | gccccgcgcg | ctttcctggc | tgtccccgcc | 480 |
| ggctttccac | cctccccaaa | gcccaggtgc | ccaccgtggg | tcgctgcggc | ctttccccctt | 540 |
| cttggccaaa | tccgattact | tcgcagcctg | cagatggcat | cgccggctaa | gggcagcctg | 600 |
| cggcaggtcc | ccgagcctga | gcactcctcc | tatctggggc | ctgagaggac | gctctgggct | 660 |
| ttttcccagg | cccagggtgc | gcggcctgct | agcgcctttc | gaggcacagt | cccaagatag | 720 |
| gctcttgtcc | ttcgacgccc | ccttggcaca | agcgcactgg | cgccctccgc | tcaacccacc | 780 |
| ttgcctttgg | ggcgggcttc | aaccctggga | agacaggcct | ggggggaagcg | agaggagagg | 840 |
| cccgaataga | ggttccggct | caatctttcc | cagacggagg | cctggtgttt | ccagctcagt | 900 |
| tgcatcttcc | agccgcgggc | tcctggccca | aacagaatgt | gtttgctttc | acaccgggac | 960 |
| ggcaagcgga | gtccgcctca | gtgagcagcg | agctgcgcag | tccggacggg | tgtcgccccc | 1020 |
| agagactcgc | cagccgcccc | cagacactcg | ccagccgtcc | ccatctctaa | tccaccgtcc | 1080 |
| aggcccgggc | cctgggaaga | | | | | 1100 |

<210> SEQ ID NO 120
<211> LENGTH: 800
<212> TYPE: DNA
<213> ORGANISM: Homo sapiens

<400> SEQUENCE: 120

| | | | | | |
|---|---|---|---|---|---|
| ccgtgtctcc | cttaagaact | ggggcctcat | ctccactcca | gctgcgcgtg | cacgtgtgct | 60 |
| cccggcagga | cgcgcgccca | ggagcgcgct | ggggctgcc | ccgcccctct | ctccctcccc | 120 |
| cgcgggtaaa | ctccgggcat | ccatcagtct | gttaattgca | ctaattagag | atcgcagagg | 180 |
| tgttaattgg | aaaaccctgg | tattgtgcct | gtttggggga | agaaaacgtc | aataaaaatt | 240 |
| aattgatgag | ttggcagggc | gggcggtgcg | ggttcgcggc | gaggcgcagg | gtgtcatggc | 300 |
| aaatgttacg | gctcagatta | agcgattgtt | aattaaaaag | cgacggtaat | taatactcgc | 360 |
| tacgccatat | gggcccgtga | aaaggcacaa | aaggtttctc | cgcatgtggg | gttcccctttc | 420 |
| tcttttctcc | ttccacaaaa | gcaccccagc | ccgtgggtcc | ccccttttggc | cccaaggtag | 480 |
| gtggaactcg | tcacttccgg | ccaggggaggg | gatggggcgg | tctccggcga | gttccaaggg | 540 |
| cgtccctcgt | tgcgcactcg | cccgcccagg | ttctttgaag | agccaggagc | ctccggggaa | 600 |
| gtgggagccc | ccagcggccc | gcagactgcc | tcagagcgga | agaggcagcc | gcggctttga | 660 |
| cccagcttcc | ttccgacggc | atctgcagga | gcctctaggc | ctgacatagg | ctccgaggtg | 720 |
| ccctggctcc | cccacgggga | atgctgaggg | ttgggccact | aggtcctgcc | taagtgcagg | 780 | acctgagcct cagacaaatc 800

<210> SEQ ID NO 121
<211> LENGTH: 300
<212> TYPE: DNA
<213> ORGANISM: Homo sapiens

<400> SEQUENCE: 121
gggattgccg gctttgagaa aatatgaaga aaccgatttc tccttccact ttgccagtgc 60
actttccttc cactttcact ggtgctgggg gcggcgcact ctttacgaca tataagcgga 120
aaattctgca aaagtggccc ccggggatcc ccgcccgacc cctgtctgtc gctaatgtgg 180
gcctgtctcc ggaaattcga ggttgggcct ttgcctgaat ctgttgctat tgctcccctt 240
gctaccgctg acacttggca ccgccgcctc ctagcagcgg ccagacgcgg ggctggggc 300

<210> SEQ ID NO 122
<211> LENGTH: 400
<212> TYPE: DNA
<213> ORGANISM: Homo sapiens

<400> SEQUENCE: 122
gttgcgagcg cggcacaggt tgctggtagc ttctggactc tggaggcttg gccttccttc 60
taagccgatg gcggggaaag aacctcgttt ccacagcttc cccgaccccc gccgcttgcc 120
atttggggac gggaagcgcg cccgggtcgc ttcacgtccc tctgggccgg agccctttcc 180
atggctggct cctctggggg cccttgggcc tgtgagcagc gtctacttcc ctcagagaag 240 aatccttttcc ttcccccatc gaagtgtccc tttctgtatc ctgaaataac ccctcctggg 300
tgaggccagt tcccctctgt cgccctcctc ccgcaggcgt ccgggagcct cgtgaggacc 360
ccgtgcagtt gagtccaggc gacaggtgcc tccccaggtg 400

<210> SEQ ID NO 123
<211> LENGTH: 800
<212> TYPE: DNA
<213> ORGANISM: Homo sapiens

<400> SEQUENCE: 123
cagtgcgccc cttaccggag cacccatggc ctcccgcgtt accccaaatt ttgtaggcag 60
actgtcagag ttcgaagcca gctgtgtcct ctgcgggccg tgtgacccta ggctatctgg 120
gctgctcgga gccttagttt ccctagttgt gaagagggag ggtgtgacca tggcccggag 180
ctctccgaaa ggctgtgcgg attgctcggt ggcgggatgt ggagcgcgtc ttctatgatg 240
ccaggtgctg gccaagcgct cgatgcaggc tgctccagtt aggtcgatgc gatggcggga 300
agcactttcc tctgcaatgg agagacgccg acaccccgag cccgaaggct tgcaaggcgc 360
gctctcgcca ctggggtcgg ggatccgtgg gttctctatc ccgcttaccc actccatcct 420
tagcagctgt cgtcggtccc agacctctac cttggagaga ccaaggcggc ccagagccca 480
ggagactact gcgcggtacg ccaggatcca gaagtggatt ctgacttcta aagacccctc 540
ccaagccaac gctatcaggg tccctgcaag cggttgactg tggcggaggc agaaccaaaa 600
cctttgctct gcccgcggcg ctccagcctc tcacccagga cagtgctctg ggctccagcc 660
gctgcagtgg ggtcgggaca cagacgccga gttagaagcc ccgccgctgc aggtccctgc 720
ttggtcggcg cggtgacggt gtcgctggcg gcggcggggg ccttcctttg gctgcccggc 780
catttaatca gagctattat 800

<210> SEQ ID NO 124
<211> LENGTH: 1000
<212> TYPE: DNA
<213> ORGANISM: Homo sapiens

<400> SEQUENCE: 124
tttagtattt aaggagaaaa gcctcatttt ccagaatcga ataagcgaat taatcgcaca      60
attgtgtaga atggaactca gtctgtaaaa aatcaagacc aacgtacttt ttaatattct     120
aacatctcca gtagtagtt acaagtattg tacccatgaa gtccaggtaa ttaatttgtt     180
caatgtcaca ctgttaaaag tcaggtgggc tccaaagcac agtcctaacc agcatgctct     240
actgcctcct ctgaggcaac agccgaagtg cagaccactg ggaataaata gctgcccggt     300
cttccccact cctaaattct cccgacagac cccaaagcct ctctgagagc ctctctgacc     360
gccctgcggc ccaccccgag ttcccggcat cctctgggat ccctcttcct ggagccaaaa     420
cctacgcagg ctcctttcct ccgagctggt tgctaggtga tctccgaagg ctgtccgaag     480
tctcgcgagg gcggacccgt tgcctgatga cgagagttgg gagtgtggct ggggctgcgg     540
atctccagca gtggcgttac ttctagcggc tggataccgg gttctccgcg agatcgcgag     600
atcccgagat attctccccg cacggaagcg acgactggcc tggccagagg actcgcgtgg     660
gagcgaggtg ccggccccga caggacggtg aggtatgcag aagtaaggcg gggcgccccc     720
tgcgggaagc gagcgcgccc cggaaaatga gcgcctcccc acaccaaggt gtccaggagt     780
gagtgcggga aggaactcgg ccgcccggag ttgtggcctc atcgtgcttc ccgccaaaaa     840
cgccttggta ctgtcgggac gcggctaagc gtggacgcgc ccgcatctgc ccctcctccg     900
cagtggtgga agacacccgc ggagcgccgg tggataaggg ccgtttcctg agaccagagc     960
tgtatccgca gcaggtcagc acttcgtgcg ccctgtgtgc                          1000

<210> SEQ ID NO 125
<211> LENGTH: 300
<212> TYPE: DNA
<213> ORGANISM: Homo sapiens

<400> SEQUENCE: 125
agcggcgctg ttcccgggct gggtgcagct gctaaggaca aggcccctgc tccgaagaac      60
gcggtggctc ggggataccc tgaaagggac ggccatggcg cacatgggat gccctagggt     120
tcgtgggagg gcatgcaggc gcagcccccg caggggttgg cctgccagag aaggcagggg     180
agagcactcg gggctgcaca aatggtgtgg ccggagggaa ggtgcagcct tgtgtgtgtc     240
tggatgaggg ctgggcatag gagcttggta tttgatcctg aaagctctgc gtttccaaag     300

<210> SEQ ID NO 126
<211> LENGTH: 600
<212> TYPE: DNA
<213> ORGANISM: Homo sapiens

<400> SEQUENCE: 126
gagtcatact tgtagtcaca tccttttcct ttctccaacc cactggttaa tcatgaaagg      60
ctcttctgat tggctgcctc ctggcagtag tgcctcagcg cgacggttcg ggagcaaata     120
aataattccc gctgggaagc tgtttctcag acaggagcag cgacacccct gccacgcctg     180
ccgcctggag ttgagtgggg taagcacgcc ggcctccagg aatcgacggt gccacgtggt     240
tcttcttgca cttctcttct tctccagttt caggggacac cgtggggtgt gcgagcccgg     300
gggagcgcag ggaagggcgg gttgggctgc aggtgggaat gtgcggtcct tctgcgccct     360

```
caacagagct tccttccttt tgccaaggt ccccgtgccg ccttcagcgc gcctccttat    420
gcacctctac ctctgctgca gcgtacctct tccgcagccc tagcggcctc cccgaggggc    480
gccgcggcct cggctgtccc tccctgcct ggcacgacca cctgaccccc agcgacccaa    540
gaagcaagtt gtgtttgcag acgcaaaggg gctgtcgttg gtatcggtgc actggtttga    600
```

<210> SEQ ID NO 127
<211> LENGTH: 1700
<212> TYPE: DNA
<213> ORGANISM: Homo sapiens

<400> SEQUENCE: 127

```
acactttctg tgtgggaggg cacaagacat gggctatgac atggccagag accccacctt     60
ctttacacat gtaaaaacca accaaatcaa gatgcgtcaa cggtgattct tcctcccaca    120
ttgtttccct ttttaaactg ttatttttc aatccatgga gcagttgaga aacgggtatg    180
catctctcct cccctcccct tctatcaaag cctgtaagac ataaggaa atccaaagcc     240 acagtaatag agagagagag agagagagag agagagagag agagagagag agagaaaaca    300
gaacaaaaga atcctccctt ggcttgtttt tccagggtgg ccaggcaagg tgtgaaaatc    360
catatttccc tctgggctgg caggtagaag ttactgggaa ggctgcgctc ccttctctcc    420
caccggctct cacatccagg ctgttccctc accctcagcc tccccagcg ccagcttcct     480 cctccgcctc tctgcagcca ggcctcccct gcaaggcgga ccttggccca ccttggttcc    540
gggccaaggc ggcgggaaag gcaccgctac ctgcagccgc acgactccac caccatgtcc    600
tcgtactgct tgtagaccac attattgccc gcgtcgatgt atagaatgct gatgggagtc    660
aatttggtgg gcacgcagca gctgggcggg gtggagccgg ggtccatgga gttcatcagc    720
gtctggatga tggcgtggtt ggtgggctcc aggtgcgagc gcagcgggaa gtcgcataca    780
ccctcgcagt gataggcctc gtactccagg ggcgcgataa tccagtcgtc ccagcccagc    840
tccttgaagt tcacgtgcag gggcttcttg ctgcagcgta gcctggactt cttgccgtgc    900
cgcttgccat ggcgactggc gaaggccgtg cgccgccgcc ggcggccggg cgagggcagc    960
caaggcctgg catccggggc gcccgacggc ggcggccacg accctcggc gcccgcgccc    1020 gggcccgcag cctcggccga gccagctgc tcgcgcatct ctgcgaacag gttcttgcgc    1080
tgggatctgg tgaataccac cagcagggcc cgctcctggg gaggccgcac cctccggccg    1140
aagcccagac tccgcaggtc cggggcggc ggttgctggg gtccccgcgc gcgcgcctcg    1200
gcctccccgg cgtccagctc gccccatgcg cccgcagct ccaagcacag ctgcttccag    1260
ggctggtggc gcaggccctg ccacacgtcg aagacttccc agccggccgg cggcgccccc    1320
tgcgggtcca gggtccgcgc gtccagcagt aggggcgaaa ggcaagggaa gagctgcacg    1380
tggagcggcc cggctggtgg ccccaggc gctgagggcg cctggcgaaa gagccgcagc    1440
tccgcgccca ccagctcttc tttgtctgag agcatggaca catcaaacaa atacttctgt    1500
ctccggagag gagtgtgcga gagatcgtct gcgagataaa aaataattac agtcagtttc    1560
acttaagggg gagatcagcc cggtgctctt cggccgcccc gggaggaaaa gggcggggag    1620 tggggggcagg tcgccgggc agtccagctt gcccggccca gggcctgacc acccccggctc   1680 cccatctggc tggtgcatgg                                                 1700
```

<210> SEQ ID NO 128
<211> LENGTH: 2000
<212> TYPE: DNA
<213> ORGANISM: Homo sapiens

<400> SEQUENCE: 128

```
gcccgctgtg aatgtaggtg aggtgatccc gggaacctgg gtctgaaatc agacctgtgt    60
tgccattggg agcacggaga gaggggaagc gccctgctta ggcccaggcc gggcgtcctg   120
gtggtgggac cgcagccgca ctcacctcca ggccaacgga caaggttcct gcaagccagc   180
agggccactc tgtgcttggc ctactgcagc tcccctgcag ctcctttcct ctccctcccc   240
ggagcgctct cctctctcct ctcccctctc ttctctctcc tctctcgtct cctggggcat   300
cccgggtgga gggatgtagg ggtcgctcct cggtgccagg ccgggaagca gctcaggcct   360
cccaagagct tggcgctcag tctgggaaaa ggggttcctc tggcctcagg gacgttctcc   420
gcccccaccc caccccctgg gagcctgaac catctggaag ggatcttagt cggggggttgg   480
gaggagagcc cgtggatagg aggagggggc gattctaggc cgaatccagc ccctgaggtg   540
tcactttcct ttcctgcggc ccgtcaccgc tgatagatgg ggctgagggc agaggaagga   600
aaaagaaaac ctccgaggtc agtgcggggc gaggtgagcc cctcccaggg ccctctggcc   660
caggaggatg aagcgcgccg gcttcgctct tgcacgccgg cttgccatcc gggtaagcgc   720
gggaaaggcg gccacagggc gcggcggcag cgcagcgcgt gggatctcac gacccatccg   780
ttaacccacc gttcccagga gctccgaggc gcagcggcga cagaggttcg ccccggcctg   840
ctagcattgg cattgcggtt gactgagctt cgcctaacag gcttggggag ggtgggctgg   900
gctgggctgg gctgggctgg gtgctgcccg gctgtccgcc tttcgttttc ctgggaccga   960
ggagtcttcc gctccgtatc tgcctagagt ctgaatccga cttctctttcc tttgggcacg  1020
cgctcgccag tggagcactt cttgttctgg ccccgggctg atctgcacgc ggacttgagc  1080
aggtgccaag gtgccacgca gtcccctcac ggctttcggg gggtcttgga gtcgggtggg  1140
gagggagact taggtgtggt aacctgcgca ggtgccaaag ggcagaagga gcagccttgg  1200
attatagtca cggtctctcc ctctcttccc tgccattttt agggctttct ctacgtgctg  1260
ttgtctcact gggttttgt cggagcccca cgccctccgg cctctgattc ctggaagaaa  1320
gggttggtcc cctcagcacc cccagcatcc cggaaaatgg ggagcaaggc tctgccagcg  1380
cccatcccgc tccacccgtc gctgcagctc accaattact ccttcctgca ggccgtgaac  1440
accttcccgg ccacggtgga ccacctgcag ggcctgtacg gtctcagcgc ggtacagacc  1500
atgcacatga accactggac gctggggtat cccaatgtgc acgagatcac ccgctccacc  1560
atcacggaga tggcggcggc gcagggcctc gtggacgcgc gcttcccctt cccggccctg  1620
cctttttacca cccaccctatt ccaccccaag caggggggcca ttgcccacgt cctcccagcc  1680
ctgcacaagg accggccccg ttttgacttt gccaatttgg cggtggctgc cacgcaagag  1740
gatccgccta agatgggaga cctgagcaag ctgagcccag gactgggtag ccccatctcg  1800
ggcctcagta aattgactcc ggacagaaag ccctctcgag gaaggttgcc ctccaaaacg  1860
aaaaaagagt ttatctgcaa gttttgcggc agacacttta ccaaatccta caatttgctc  1920
atccatgaga ggacccacac ggacgagagg ccgtacacgt gtgacatctg ccacaaggcc  1980
ttccggaggc aagatcacct                                              2000
```

<210> SEQ ID NO 129
<211> LENGTH: 2000
<212> TYPE: DNA
<213> ORGANISM: Homo sapiens

<400> SEQUENCE: 129

```
cactcccccg ccgcctccgc ccctaaccct cggccccgtg cgcgagcgag cgagggagcg      60
aacgcagcgc aacaaaacaa actagtgccg gcttcctgtt gtgcaactcg ctcctgagtg     120
agtcgggggc cgaaagggtg ctgcggctgg gaagcccggg cgccggggac ctgcgcgcgc     180
tgcccggcct ggccggagcc tgtagccggg gggcgccacg gccgggctcg cagtcccccc     240
acgccggccc cccggtcccc gccgagccag tgtcctcacc ctgtggtttc ctttcgcttc     300
tcgcctccca acacctcca gcaagtcgga gggcgcgaac gcggagccag aaacccttcc      360
ccaaagtttc tcccgccagg tacctaattg aatcatccat aggatgacaa atcagccagg     420
gccaagattt ccagacactt gagtgacttc ccggtccccg aggtgacttg tcagctccag     480
tgagtaactt ggaactgtcg ctcggggcaa ggtgtgtgtc taggagagag ccggcggctc     540
actcacgctt tccagagagc gacccgggcc gacttcaaaa tacacacagg gtcatttata     600
gggactggag ccgcgcgcag gacaacgtct ccgagactga gacattttcc aaacagtgct     660
gacattttgt cgggcccat aaaaaatgta acgcgaggt gacgaacccg gcggggaggg      720
ttcgtgtctg gctgtgtctg cgtcctggcg gcgtgggagt ttatagttcc agacctggcg     780
gctgcggatc gccgggccgg tacccgcgag gagtgtaggt accctcagcc cgaccacctc     840
ccgcaatcat ggggacaccg gcttggatga gacacaggg tggaaaacag ccttcgtgaa      900
actccacaaa cacgtggaac ttgaaaagac aactacagcc ccgcgtgtgc gcgagagacc    960
tcacgtcacc ccatcagttc ccacttcgcc aaagtttccc ttcagtgggg actccagagt    1020
ggtgcgcccc atgcccgtgc gtcctgtaac gtgccctgat tgtgtacccc tctgcccgct    1080
ctacttgaaa tgaaaacaca aaaactgttc cgaattagcg caactttaaa gccccgttat    1140
ctgtcttcta cactgggcgc tcttaggcca ctgacagaaa catggtttga accctaattg    1200
ttgctatcag tctcagtcag cgcaggtctc tcagtgacct gtgacgccgg gagttgaggt    1260
gcgcgtatcc ttaaacccgc gcgaacgcca ccggctcagc gtagaaaact atttgtaatc    1320
cctagtttgc gtctctgagc tttaactccc ccacactctc aagcgcccgg tttctcctcg    1380
tctctcgcct gcgagcaaag ttcctatggc atccacttac caggtaaccg ggatttccac    1440
aacaaagccc ggcgtgcggg tcccttcccc cggccggcca gcgcgagtga cagcgggcgg    1500
ccggcgctgg cgaggagtaa cttggggctc cagcccttca gagcgctccg cgggctgtgc    1560
ctccttcgga aatgaaaacc cccatccaaa cgggggacg gagcgcggaa acccggccca    1620
agtgccgtgt gtgcgcgcgc gtctgcgagg gcagcggcgg caggggagg aggaggcaga    1680
ggcggggtgg ctggaccctc ggcatcagct cattctcccc tgctacacac atacacacac    1740
aaataatgtt tctaaaaagt tcagttgcga ctttgtgcct cgcctgtcct gttcatcctc    1800
gtcctgggcc ggggaatgct tctgggggcc gaccccggga tgctggctaa ttgctgccgg    1860
cgggttccgt cgccggtgtg accctggacg gcgcggacgg cgtacagggg gtcccgggag    1920
gggcagtggc cgcggcactc gccgccggtg cccgtgcgcg ccgcgctctg ggctgcccgg    1980
gcggcgcagt gtggacgcgg                                                 2000
```

<210> SEQ ID NO 130
<211> LENGTH: 800
<212> TYPE: DNA
<213> ORGANISM: Homo sapiens

<400> SEQUENCE: 130

```
ctgaaaagcc gtcagggaaa ccacacatgt tcaaccctg gcggctcccc caaacctctc      60
atttccagta actgtgtgtt tccgctcgtc aacagctgaa accgagcgga acttgggggg    120
```

| | |
|---|---|
| ccccaccacg cggccctgct gtgcggcacg gggctcatct gtccccggc tgcggggagt | 180 |
| cagctctcac cgcccacctc cttcccagat agtctctgtg cccactcgac ggcccggcaa | 240 |
| gcccagcccc tgcctgccac ggccacagca gcctcagaga gctgccctct ctggccaggg | 300 |
| tcagggcctg agctgctgcc tcccgcaggg tcgaggcag acacttgtc tgaggcttgg | 360 |
| gtggggcaat ggcacctcct cagggcctca gccccgggc aggctcggtg accatgggcc | 420 |
| tacagcaggg aaaattctgg gccaaaagct ccagcctcct actagggcat ctgtctgcaa | 480 |
| atgcacctta acctgaccgc ttgggctgtg ggggagcctg tttcagggaa agtgagggac | 540 |
| gcgccagttt cctcctttgg acttgatgag gcacgaacgc atctctaata aagccaggtc | 600 |
| tccccgccgt ggctccctgg gcgggtgcct gtggctcggg ccatgagtca cgctgggtaa | 660 |
| ccccactacg gggaagaggg caggaagctg ggagccaccg cctctgtgcc cggttgtcat | 720 |
| ctcggcacga gggcgaccgt cggcttcgtc ctgccctcat ggctgagggc ttttgggatg | 780 |
| tggcgggaga cgggggagtc | 800 |

<210> SEQ ID NO 131
<211> LENGTH: 500
<212> TYPE: DNA
<213> ORGANISM: Homo sapiens

<400> SEQUENCE: 131

| | |
|---|---|
| aaatcatcag aatggctaaa atgaaaaga cagacaacag caagtgctga caagggtgtg | 60 |
| gggcggccaa atgctcctgc actgctggca ggggacctga gaactgcagg gcattccctg | 120 |
| gcttcctgcc cctcctggga ctggggaccc ccagggaca gcctaaggga actgcattta | 180 |
| tcttcacgtc tgccaaaaga taacacgaag atgttcaaag ctaagccccc aggctggtaa | 240 |
| gagctccaag gcaccagcag tgtgtgcaga actgggggga gtctgttctc ccaggdatgc | 300 |
| tcccatcacc tgctgccagc agtgggggcat gccggtcccc tggggtgtgg ccaagggget | 360 |
| gtgtctcctg cccgggctgc cggcccctct caggttcact ttcccatctc taagcccacg | 420 |
| tctcgctgca gttcaagttt gccaggccac caacgggtga cacgcccggc gcagtggggg | 480 |
| actccgcact ttctgcgcac | 500 |

<210> SEQ ID NO 132
<211> LENGTH: 1200
<212> TYPE: DNA
<213> ORGANISM: Homo sapiens

<400> SEQUENCE: 132

| | |
|---|---|
| acccttgtg cctgggtccc ataaacaatg tgcttttaa aggggagccc cctcccagct | 60 |
| ccggcctttt tctccagcgt gggcagccaa tcagctgcgc agagctgcat agctggaccg | 120 |
| ctttccattc tgagtagcaa caacgtacta atttgatgca cacatggatg cctcgcgcac | 180 |
| tctgcaaatt catcacccgc atcttgcatt agtcatctga cggactgcca agtgtttcat | 240 |
| tttctttcca tgtgactta ttattaccac ctctctcctc tcttccaaaa acctcccaaa | 300 |
| aagggcggtg gggcgggggg cggggcaggg agagggagag aaatccagca gacatctagc | 360 |
| tctgcctttc tttcccagcc acagccaggg tagggctgat aaggcgctga tgcgttgatg | 420 |
| gcagccttgc agagctagac ctgcacttaa cttgcagctg cctcccgagc ctccaagatg | 480 |
| tccacgccct gggtgacagg cggcagggcg ctgcccgtg ctcccccggc tctgctcgac | 540 |
| agcagcacgc agtgagagcc tcgccgccgc cgaggagcaa ctcatggtgc ctccgctttg | 600 |

| | |
|---|---|
| ttttagttca tcaaatttct acgactcatt aggcactttg ccactgctct tcttcctcct | 660 |
| ccttccgcct ccccgctccc ccaccccac tattttttct tcctgtccct catcgtgccg | 720 |
| ccctaactct ggctcccggt tccgttttg acagtaacgg cacagccaac aagatgaacg | 780 |
| gagctttgga tcactcagac caaccagacc cagatgccat taagatgttt gtcggacaga | 840 |
| tcccccggtc atggtcggaa aaggagctga agaacttttt tgagccttac ggagccgtct | 900 |
| accagatcaa cgtcctccgg gaccggagtc agaaccctcc gcagagtaaa ggtacagagc | 960 |
| gcggggcggg ggtcgccagg cgtccaggtg ggcgtcgcgg ggcactgggg ctgtccgagc | 1020 |
| ccccagcctg caggaggaag ggcgggtagg caggagggct ggaagcagcc ggtgctggcg | 1080 |
| gcccctgtgc tccaggggct gctcccgact cctccccgca ccccgcccg cctgcccgcc | 1140 |
| gggacaggtt ggaggcggga gagggacc gaggcagggc gggagcgcag aggctcggtc | 1200 |

<210> SEQ ID NO 133
<211> LENGTH: 800
<212> TYPE: DNA
<213> ORGANISM: Homo sapiens

<400> SEQUENCE: 133

| | |
|---|---|
| taacaaataa gccgcccgtg gtccgcgctg tgggtgaccc ttggcgcctt cgaggtctgg | 60 |
| agccctaggg taaataagga aacggggcgc ctctagagtt ttaaatgaac tctgttattg | 120 |
| gaagcttcag tagggaccct gaaaacaatt aacgtcttaa ttagcatttt aatgtctcca | 180 |
| ttattacggc gcgggctcta gctcagccct ttaccttacc ttctcaccgt aacaggggga | 240 |
| gggggattgt attttagtt catctttta tgtttttgag ttgttatcct gtctgtctga | 300 |
| ttccagcctc gagggtttga tgatgcggcc cgagcctggc tgtggtcgcc tgtcggggct | 360 |
| ggagcgggac cctcagccgg gcggggcctg ggggctaacg ttttcacagt gcgccctgag | 420 |
| tttccttggg ttactgctgg gaccgcgcag gaggaagcaa agagtttttc gagctagacc | 480 |
| aacaggaaac acattgacgg aaatgttgcc atagcccatg gggtggcttt aactggccgc | 540 |
| ccccgcgggc tgggtgtgaa atcagaggag gccgcggctc ccccggccag gattggaggc | 600 |
| tcctcgcgca acctaatgcg ggtgtccggg cccgagcgct tcccgcgcag ccaggccttg | 660 |
| tcggtgcagc agccccgctc ctccccaaca cgcacacacc cggtgttcgc aagtgcggct | 720 |
| caccaaggga gatccaaggg ggcaaaaagt tatgtataaa tccgagagcc actggggaaa | 780 |
| gagggtcgtg gtattgtaag | 800 |

<210> SEQ ID NO 134
<211> LENGTH: 500
<212> TYPE: DNA
<213> ORGANISM: Homo sapiens

<400> SEQUENCE: 134

| | |
|---|---|
| ctaccctgtg ctatcctgag ctgtagtctt ctgaaatgat cgtttggctt cccagccaag | 60 |
| gcagggctcc cccaaagttc attcccactc ttgcagtttc acctcgggat gcttccgcag | 120 |
| aatttcagcg cctaagcaga caaggtcaaa gtaaaccgct tcaccgctgc ttctggcgca | 180 |
| ggggcccaga gcgcgtgcag ctccccagca cagaccaaca gcaggagagg ggtccgggcg | 240 |
| ggagccctgg gctgtagata agcaaaacgc acccattttc tctcctattt actccagagg | 300 |
| cacctctcct cccccactcc tggcatctct ttatcactgg ctccctctcc ctgtggcata | 360 |
| tttttgggta gtagaatgct gaggtcacag ggagcggctc tttatccaag cagtggggac | 420 |
| atcagcctgg agccctgagc atgaaccagc aagatgcaga ctctcgctct tgactttggg | 480 |

```
ctccaggagc tgccccgacc                                               500
```

<210> SEQ ID NO 135
<211> LENGTH: 1100
<212> TYPE: DNA
<213> ORGANISM: Homo sapiens

<400> SEQUENCE: 135

```
cagtgctccg ctccgggaaa ttgcatcgtc acgacaaacg ggaccgtgat aaaacgaccc    60
tttccgtcct tatttgtaga tcactcagac gagattgaac tgcacttgtt tcccttcga   120
ggggagccgc gttttcaggg tagccgaagg cttggggctg aggggggcc ctcaccaagg    180
cgcgggtggg ggccggagcc tcaactcgat gagaagtgac aggcgtttgg gggatctggg  240
ctccggccgg gaccagcgca agcagggact ttgcggggac accgcttctc caacagagca  300
aggcctggcc cacgtttccg gtttctccta acttcctttt attgccttcc tttgcttcgc  360
aagttccatc taccccctcca gctacagagc cccacctcta ggcacaggaa gcttcccgga  420
aaaagaaagg ctgtcccaga aagagaccga gagagacttt ccaaacttcg ggcatagcca  480
cggcaattcc cagtctgcta atgccaaggc gggcgcgtaa ggccgcctaa atctagacct  540
ccctcctcac tcatttcaaa aaataacaac gtgccagcca cctccgcaga taccgccggc  600
tggtgcttgc ccaggagacg ccagggccag agcgccactc ccagcatcga aatggcagag  660
agaaagcgca gctccaaatt cccccttcaga ggttaagcct caatcattgt gtcccttccc  720
tagggactgc tggcgctctc gcccactggc gatgattatg cgcctagaac tcgaccgcga  780
agcaactaat aggaaaacat atggtgtcaa tttggatgct ccgcgcctcg cgcacacccg  840
ggaacgagcg gcacaaagcc ctgccggccg gccgcgacc ccgcgcccct cggggcctgc   900
cagccgggcc gcagcgacaa acgctcaggg ctgcgcgccc tggctgggc cgccccgaga   960
gacagcctgc ggctggggag tctgagctcc aaggggagag cccagccgcc gaaggcgagc 1020
ctaccggcca agccctgggg tccggcaggt tctgcacaac tactcccgca aagctcgcca 1080
cctttgtgcc ctttcctcag                                              1100
```

<210> SEQ ID NO 136
<211> LENGTH: 500
<212> TYPE: DNA
<213> ORGANISM: Homo sapiens

<400> SEQUENCE: 136

```
gggccctcgc ggctcaagcg ccagcgctgg agagagagtc tgagggtacc acgggcgtgc    60
tggcctgggt gctcactccc gccctccttc atgagcggct ttcctctggg tgtgtccagg  120
gcatcacaga gctcttctgc ccaaacccgg aggcctacca gggcctgccc accttgcctc  180
cttccacact ctctgtagca gcagccgcag ccatggcggg gatgaagaca gcctccgggg  240
actacatcga ctcgtcatgg gagctgcggg tgtttgtggg agaggaggac ccagaggccg  300
agtcggtcac cctgcgggtc actggggagt cgcacatcgg cggggtgctc ctgaagattg  360
tggagcagat cagtgagtgt ccgctgcccg cttgctgaac tcggaccat gggcggccgc   420
cacgggtgtc tctgggcact tccggccat ccctgctgct cagctcccga taatggtgtc    480
acggtgactc aggcattagc                                              500
```

<210> SEQ ID NO 137
<211> LENGTH: 600
<212> TYPE: DNA

<213> ORGANISM: Homo sapiens

<400> SEQUENCE: 137

```
tgtttacgga atcgggatcg aggggccgat aagtagttta cacgccggcc agagcagagg    60
gctggaggtc ggagttgggg gctggaggaa cgggtggcgt ttttaggatt cagtaacagg   120
atcacagctt tttcttgtgg tggaagctat tggaatttgg ggagggtagc acgaggggtc   180
ctgcagctcc gcgtgtgaaa aagcgtttag gtaggcgatg aaagtagttg atctgagcca   240
tggcaggcga gccccgaatt tttgctgctt ccccctgaaa gtgtttcttt aggaggagag   300
gacttgggcc acacaggacc cggtcctaag agagcgattc cgggaagcgg acagatcgaa   360
gagaccttct gggcgaagcg gcagggcagc ctcgcggggc tgggagtgga tctgaggtcc   420
cgacccaggc ggctcggagt gctccaggag ccacctgggt ctgcgggcgc agcgcggcgg   480
ggcgggagcg gtggcccgca ggggccgcgg cctgcgatga aggccggggg gcagcgctag   540
cagcgaggtg ccacagtggg ccgaggagtc tgggctgtgg cccagggtag gaccggctca   600
```

<210> SEQ ID NO 138
<211> LENGTH: 150
<212> TYPE: DNA
<213> ORGANISM: Homo sapiens

<400> SEQUENCE: 138

```
acctaaacca agctctccct ccctgccgtc tccttccctg gcctgggtct gaaggagagg    60
aggtgcccag aagttcagag cggcataacc acagagatac tacctaatta acataccaga   120
agcataaaga actcatttgc attggagagt                                    150
```

<210> SEQ ID NO 139
<211> LENGTH: 900
<212> TYPE: DNA
<213> ORGANISM: Homo sapiens

<400> SEQUENCE: 139

```
ataactacgg gggtgggggt ggggaaggaa gagatccaag gaggcagaag gctgcggtca    60
aaatattttg gggtggcaga gtcacgtagg atgtggctgt gggttctggc agcccagaga   120
ttcagctccc gcctcctccc tcagagcgag tccatagcta ccctcacgtc ccccgtggcg   180
gtcctcgcca cgctccggag cgggttaccc atgagggtgc tagacctggg cagcgggaac   240
ctcgaagagg tggagattgc aggctggac tccagatttc gggcagggat gcggggaagg   300
gaagacgcct cgctggaggc ggaatggagg gcaaggcgaa ggaggatggt gcaggaaacg   360
gcgacaaggc gcccggccag gcccgcgagc taccgagacc cgggttccaa tcctcccccc   420
ttccgcaaac gcccgggttc gaggtacctg gcgggcaagg gccgcagcgg agcgaagcgg   480
gctggccatg ggggaggctgc ggggacgcgg ggctgcagag agcggcagtg gcacggagcg   540
cgcggctgga agcgaaagca ggcggtgtgg ccaagccccg gcgcacggcc catagggcgc   600
tgggtaccac gacctggggc cgcgcgccag ggccaggcgc agggtacgac gcaacccctc   660
cagcatccct tggggaggag cctccaaccg tctcgtccca gtctgtctgc agtcgctaaa   720
accgaagcgg ttgtccctgt caccggggtc gcttgcggag gcccgagaat gcgcgccacg   780
aacgagcgcc tttccaagcg cagatatttc gcgagcatcc ttgtttatta acaacctct   840
aggtgaatgg ccgggaagcg cccctcggtc aaggctaagg aaacctcgga gaaactacat   900
```

<210> SEQ ID NO 140
<211> LENGTH: 600

```
<212> TYPE: DNA
<213> ORGANISM: Homo sapiens

<400> SEQUENCE: 140
cagtccagcc gcttgcctca cttcttcccg cttgccttat ctccccgcag acgtggttcc      60
cctgcagccc gaggtgagca gctaccggcg cgggcgcaag aaacgcgtgc cctacactaa     120
ggtgcagctg aaggagctag agaaggaata cgcggctagc aagttcatca ccaaagagaa     180
gcgccggcgc atctccgcca ccacgaacct ctctgagcgc caggtaacca tctggttcca     240
gaaccggcgg gtcaaagaga agaaggtggt cagcaaatcg aaagcgcctc atctccactc     300
cacctgacca cccaccccgct gcttgcccca tctatttatg tctccgcttt gtaccataac     360
cgaacccacg gaaagacgct gcgcgggtgc agaagagtat ttaatgttaa ggaaagagaa     420
gaaccgcgcc gcccggaggc agagaggctc catggccgtg ctgctgggcc atccccaact     480
ccctatccca tccccagcct ccacccccat ccagatggga ctcacgtggc ttcaacagct     540
ttggaaatgg gtcccgagtg ggccgtgcga ggaaggctgt cgacctctac tcctccttgc     600

<210> SEQ ID NO 141
<211> LENGTH: 1500
<212> TYPE: DNA
<213> ORGANISM: Homo sapiens

<400> SEQUENCE: 141
caagatcgac tttcttagga aggggagag gagggaactc ttcacgaagg gaggtgggag       60
tccacctcag acctctattg gaaggaaatc gagttgttcc gggggactga ggtctcttgc     120
ataaggcatg ggatccttat tattattatt attattttta aatccccgc ggaggagctc      180
tgggcaaatg aataccgagg cgccgctcta gctggttagg cttgggatgc gataactcag     240
tgccctcttg cagacttgca tagaaataat tactgggttg tcgtggaggg gacacgagac     300
agagggagtt ctccgtaatg tgccttgcgg agagaaaggt ccaagaatgc aattcgtccc     360
agagtggccc ggcaggggcg gggtgcgagt gggtggtgga gtagggtgg gagtgggagag     420
aggtggtttc tgtagagaat aattattgta ccagggcccg ccgaggcacg aggcactcta     480
ttttgttttg taatcacgac gactattatt tttagtctga tcaatgggca caatttctaa     540
gcagcgcagt ggtggatgct cgcaaacttt tgcgcaccgc tggaaaccca ctaggttgag     600
ttgcaaaacg taccgcgtag acgccctggg tggcgccgag agaagagcta ggcctgccca     660
gcacagagcc ggagagcgtc gggccttccg gaagggtaag ttctccgcca aggggtcccg     720
agggagctgg acgtctgaat ctggacttgc ccccagcttc ggggttcgat tctgggtttt     780
gcgcgtcccc aaccccagg gctttccgaa gcatggcctg gctccaggcc cggtcctgta     840
aggactggaa cggcagcaaa atgtgcaggg aggcagtcgg ccgcagagc tgcggcggga      900
gccaaggtca ggcccgcggg gagagcgggc agcttccagc gccggccaca agctcccagg     960
ccagctgggc gcagacccc tttgcttcca gagagcacaa cccgcgtcct ttctctcagc    1020
caggctgcag tggctgcccc gagcttcgct ttcgtttccc aagctgttaa taacgatatg    1080
tccccaaatc cgaggctcgt gtttgctccc agatgccaag aacgcaaccc gaaatccttc    1140
tcccaaaccc taggtcgacg agatgagttc ctacttgacc tctgagccga ggtgggccgg    1200
aaaccgaggc ctaggccccg ccggggctgc aaggaaaagg ggaaactccg agcgtagcgt    1260
cttttccttg tggttccttt ctccggcatc ccggactgcg ggccctgcag ccacctggac    1320
cggcattcaa aggattctgc aagtccagct tcacagactg gctttcccag acgctccgaa    1380
```

| | |
|---|---|
| gcccgcacca cgaacagaat aaaggagaga cgagagatcg caactagatt tgagaatcct | 1440 |
| cgttctttc cccaatcgtt cgggcagtaa actccggagc cggctacagc gcgcatcctc | 1500 |

<210> SEQ ID NO 142
<211> LENGTH: 500
<212> TYPE: DNA
<213> ORGANISM: Homo sapiens

<400> SEQUENCE: 142

| | |
|---|---|
| actgtcctcc tccctcaatt gcctattttt tgcccatagc tctaacttaa ccctgtgatc | 60 |
| accccagatc gctacttctg accccatct cctctcccac accaacctcc agcgcgcgaa | 120 |
| gcagagaacg agaggaaagt ttgcggggtt cgaatcgaaa atgtcgacat cttgctaatg | 180 |
| gtctgcaaac ttccgccaat tatgactgac ctcccagact cggccccagg aggctcgtat | 240 |
| taggcaggga ggccgccgta attctgggat caaaagcggg aaggtgcgaa ctcctctttg | 300 |
| tctctgcgtg cccggcgcgc cccctcccg gtgggtgata acccactct ggcgccggcc | 360 |
| atgcgctggg tgattaattt gcgaacaaac aaaagcggcc tggtgccac tgcattcggg | 420 |
| ttaaacattg gccagcgtgt tccgaaggct tgtgctgggc ctggcctcca ggagaaccca | 480 |
| cgaggccagc gctccccgga | 500 |

<210> SEQ ID NO 143
<211> LENGTH: 900
<212> TYPE: DNA
<213> ORGANISM: Homo sapiens

<400> SEQUENCE: 143

| | |
|---|---|
| ctcagggaat cacatgtccg cctggcctgg cctggtacca aatgtttata gacaggacga | 60 |
| gggtcgctgg aatcgcctcg ctcctttcag cttggcgcta aggcgcgaat ctcgatcctc | 120 |
| ctagtatttc tctggcgtct gtctctatct cagtctctgc ttttgtctct ttctccctcc | 180 |
| ctccgcccca gtctttccgt ctctttttcc tcgaatgcac gtggaattcg gaattgaaaa | 240 |
| ttgaggtcag aatctcccctt tttcttccag ttatccgcgc cgctgcccca cgcctagcgg | 300 |
| cttggatctg catagacatc tatctacccg caacaagatc cgagctgcag aagcaaacct | 360 |
| aatctgtctc cgcaccatcc cctgctctgt agacccactg ccccatccca cgccacatcc | 420 |
| ttgaggttca agtagcgact ccagcggatg attcggagaa tgccctgctt tccaaaggcc | 480 |
| ccaacccgtg tttttatttt cttttcctt tgcccgcttg accaactttg gtttctttca | 540 |
| gggcccggag gtgcctgcgc cgcgcttggc tttgctttcc gccgcccag gagacccggg | 600 |
| actgtggttt ccgctcgcca catcccagcc tggtgcgcac acaagagcct ggcgagcttc | 660 |
| cctcgcgcgc ttacagtcaa ctactttggg cctcggtttc cctgctcctt gtagatcaga | 720 |
| gaagggacgg gcgaaatgcc tgcgagggag ggttggcgaa tgggttggtt ggtggcaaga | 780 |
| ctgcagttct tgtacatgga cggggggtgg ggggtcaaca ctggaagaac tcctgcctga | 840 |
| cgccaagagc cacccgcttt ccagctcgtc ccactccgcg gatgtttacc caccttcatg | 900 |

<210> SEQ ID NO 144
<211> LENGTH: 500
<212> TYPE: DNA
<213> ORGANISM: Homo sapiens

<400> SEQUENCE: 144

| | |
|---|---|
| tttgggggcac ccaacccttc ccaagcctcg gttttcccga tcttgtggga tccttgcggc | 60 |
| gcgaatgggg ttggaagcac cttggaagct acagagtacc gggtcgggac aatttccggc | 120 |

| | |
|---|---|
| actgccccag ttcagtggtt tatagaaaat ttctttctct ctctcaggtc cactaagacc | 180 |
| gagagagaga gagaagtcga ctctggcaca cccgggcgag gggctgccgg gattcgggag | 240 |
| ctggcgcggt tgattttttc cgagaatcct ccacttgggg tgacgtcggg cagcgcgcgc | 300 |
| gggccgtgag gttaatgccc aggcttttct ctaaagcgtc cgggaatgat ccggcgaata | 360 |
| aaacgggtgt ctgcaaagtt aatgaattgt acaaggaggc tgagggtggg gacttcgacc | 420 |
| cggggagcca gaggcggttc tggtggacgc ttccccgtgc gcctaggggt gcgctgggct | 480 |
| ttcccagccg aggtctgcag | 500 |

<210> SEQ ID NO 145
<211> LENGTH: 2000
<212> TYPE: DNA
<213> ORGANISM: Homo sapiens

<400> SEQUENCE: 145

| | |
|---|---|
| ccagacagtt aaggtaaaac gttgaagtca agaggaagta gtgagtctgt tgccaactgg | 60 |
| atagggttgg tcctgtccca tctaaatgta ttagaattaa gtggcttttta aaaatgagct | 120 |
| ggtcatcttc agcccacggg ctggccaatt tggaacttaa tgggcctttg cgtcctcctt | 180 |
| ccctgagcct cctttttattc cagacttctc agtgtgagtc tgtgcgtccc tccgacgatc | 240 |
| tcagggagtg gggtgccttc atctgcctgt tccctgttcc tcaggctgac gctcccgctg | 300 |
| tcctccccgc ctcccctcac tccttttctc cctcccttcc tcttgtggg gaggctcttg | 360 |
| gccagggtcc ctgagcccgg gcgggtgctg gcagaggacg cagaagggg gaggtcacgt | 420 |
| ctcccttgag ccccgagccg ctggcttttc agagcctcgc cacaagccgg cggccagagc | 480 |
| cccagaccac acagaccgtg cgctcctccg ccctcccggc gccgccggcc tcgcccatgt | 540 |
| ctcagtacgc ccctagcccg gacttcaaga gggctttgga cagcagtccc gaggccaaca | 600 |
| ctgaagatga caagaccgag gaggacgtgc ccatgcccaa gaactacctg tggctcacca | 660 |
| tcgtctcgtg ttttttgccct gcgtacccca tcaacatcgt ggctttggtc ttttccatca | 720 |
| tggtgagtga atcacggcca gaggcagcct gggaggagag accccgggcgg ctttgagccc | 780 |
| ctgcagggga gtccgcgcgc tctctgcggc tcccttcctc acggcccggc ccgcgctagg | 840 |
| tgttctttgt cctcgcacct cctcctcacc tttctcgggc tctcagagct ctccccgcaa | 900 |
| tcatcagcac ctcctctgca ctcctcgtgg tactcagagc cctgatcaag cttcccccag | 960 |
| gctagctttc ctcttctttc cagctcccag ggtgcgtttc ctctccaacc cggggaagtt | 1020 |
| cttccgtgga ctttgctgac tcctctgacc ttcctaggca cttgcccggg gcttctcaac | 1080 |
| cctctttttct agagccccag tgcgcgccac cctagcgagc gcagtaagct catacccccga | 1140 |
| gcatgcaggc tctacgttcc tttccctgcc gctccggggg ctcctgctct ccagcgccca | 1200 |
| ggactgtctc tatctcagcc tgtgctccct tctctctttg ctgcgcccaa gggcaccgct | 1260 |
| tccgccactc tccgggggt ccccaggcga ttcctgatgc cccctccttg atcccgtttc | 1320 |
| cgcgctttgg cacggcacgc tctgtccagg caacagtttc ctctcgcttc ttcctacacc | 1380 |
| caacttcctc tccttgcctc cctccggcgc cccctttttta acgcgcccga ggctggctca | 1440 |
| cacccactac ctctttaggc ctttcttagg ctccccgtgt gcccccctca ccagcaaagt | 1500 |
| gggtgcgcct ctcttactct ttctacccag cgcgtcgtag ttcctccccg tttgctgcgc | 1560 |
| actggcccta acctctcttc tcttggtgtc cccagagct cccaggcgcc cctccaccgc | 1620 |
| tctgtcctgc gcccggggct ctcccgggaa tgaactaggg gattccacgc aacgtgcggc | 1680 |

```
tccgcccgcc ctctgcgctc agacctcccg agctgcccgc ctctctagga gtggccgctg   1740
gggcctctag tccgcccttc cggagctcag ctccctagcc ctcttcaacc ctggtaggaa   1800
cacccgagcg aaccccacca ggagggcgac gagcgcctgc taggccctcg ccttattgac   1860
tgcagcagct ggcccggggg tggcggcggg gtgaggttcg taccggcact gtcccgggac   1920 aaccctttgca gttgcgctcc ctcccccacc ggctcacctc gcctgcagct gggccacgga   1980
actccccggc cacagacgca                                              2000

<210> SEQ ID NO 146
<211> LENGTH: 600
<212> TYPE: DNA
<213> ORGANISM: Homo sapiens

<400> SEQUENCE: 146
ctctctgggc cttaggaaaa tggaaatgac acctgtacct gcccttccag gactgacagg    60
aggggctgct ccatgaaacc tcactgctgc ggtcataatg tcattatctt ttgccttaaa   120
gggatttctt ctgcaccagc acctaaagtg gcagccccct tacccttggcc atcagctgga   180 ccctggtgct ctcctggagc ccaaaacctc tgttttgtgt tgcatcctgc tgaccagcca   240
cagtccacac ccatctgagt gtctgagcag aacagcccag aggccacacc aggatggctt   300
tccaccggtc accttccccc acccactcat aaaccctgcg tctctggggg agagggtggc   360
gaggtcccct cccacatag atggaaacac tgaggcctga ttcatggtgc ccctgtgaa    420 gcgcctcatg ccagcaccg ggggggcagca ggccagggcg gggacacata cccggttctc   480
gtcgtagatg atctgcacca ggctgcggtg cttcgactcg atgggcggcg gtgacacggg   540
cttctcaggc tcgggcggct tggcagcctc ctcctccagc tgttgctgtg gggagaggca   600

<210> SEQ ID NO 147
<211> LENGTH: 400
<212> TYPE: DNA
<213> ORGANISM: Homo sapiens

<400> SEQUENCE: 147
cttgaaaact cccagccccc tttgtccaga tggggatgga ggtggccagg ctgccccgtt    60
gattgtgtgc cgaggagccc tccccgggaa ggctgtgatt tatacgcgca ggcttgtcac   120
ggggtgaaag gaagggccac ttttttcattt tgatccaatg ttaggtttga aagccaccca   180
ctgctgtaaa ctcagctgga tccgcgggcc gtgattaaac acattgcccg ctttgttgcc   240
gagatggtgt ttcggaaggc gctgtgaatg cacttcccctt tgcggggctc acacagacaa   300
gatgtgtgtt gcaaggatga ggcgcctgct cggcctccag cccagggccg ggaagggaga   360
aggtgctgtg cgtcgctgcc tgtgtcgccc gcggctctcc                         400

<210> SEQ ID NO 148
<211> LENGTH: 1200
<212> TYPE: DNA
<213> ORGANISM: Homo sapiens

<400> SEQUENCE: 148
cgcgtcaggg ccgagctctt cactggcctg ctccgcgctc ttcaatgcca gcgccaggcg    60
ctcaccctgc agagcgtccc gcctctcaaa gaggggtgtg acccgcgagt ttagatagga   120
ggttcctgcc gtggggaaca cccgccgcc ctcggagctt tttctgtggc gcagcttctc   180
cgcccgagcc gcgcgcggag ctgccggggg ctccttagca cccgggcgcc ggggccctcg   240
cccttccgca gccttcactc cagccctctg ctcccgcacg ccatgaagtc gccgttctac   300
```

```
cgctgccaga acaccacctc tgtggaaaaa ggcaactcgg cggtgatggg cggggtgctc      360
ttcagcaccg gcctcctggg caacctgctg ccctggggc tgctggcgcg ctcgggctg       420 gggtggtgct cgcggcgtcc actgcgcccg ctgccctcgg tcttctacat gctggtgtgt     480
ggcctgacgg tcaccgactt gctgggcaag tgcctcctaa gcccggtggt gctggctgcc     540
tacgctcaga accggagtct gcgggtgctt gcgcccgcat ggacaactc gttgtgccaa      600 gccttcgcct tcttcatgtc cttctttggg ctctcctcga cactgcaact cctgccatg     660 gcactggagt gctggctctc cctagggcac cctttcttct accgacggca catcaccctg    720
cgcctgggcg cactggtggc cccggtggtg agcgccttct ccctggcttt ctgcgcgcta    780
cctttcatgg gcttcgggaa gttcgtgcag tactgccccg gcacctggtg ctttatccag    840
atggtccacg aggagggctc gctgtcggtg ctggggtact ctgtgctcta ctccagcctc    900
atggcgctgc tggtcctcgc caccgtgctg tgcaacctcg gcgccatgcg caacctctat    960
gcgatgcacc ggcggctgca gcggcacccg cgctcctgca ccagggactg tgccgagccg   1020
cgcgcggacg ggagggaagc gtcccctcag cccctggagg agctggatca cctcctgctg   1080
ctggcgctga tgaccgtgct cttcactatg tgttctctgc ccgtaattgt gagtccccgg   1140
gccccgaggc agcagggcac tgagactgtc cggccgcgga tgcggggcgg aagggtgga    1200

<210> SEQ ID NO 149
<211> LENGTH: 2000
<212> TYPE: DNA
<213> ORGANISM: Homo sapiens

<400> SEQUENCE: 149
cttccgccgc ggtatctgcg tgcccttttc tgggcgagcc ctgggagatc cagggagaac      60
tgggcgctcc agatggtgta tgtctgtacc ttcacagcaa ggcttccctt ggatttgagg     120
cttcctattt tgtctgggat cggggttttct ccttgtccca gtggcagccc cgcgttgcgg    180
gttccgggcg ctgcgcggag cccaaggctg catggcagtg tgcagcgccc gccagtcggg    240
ctggtgggtt gtgcactccg tcggcagctg cagaaaggtg ggagtgcagg tcttgccttt    300
cctcaccggg cggttggctt ccagcaccga ggctgaccta tcgtggcaag tttgcggccc    360
ccgcagatcc ccagtggaga aagagggctc ttccgatgcg atcgagtgtg cgcctccccg    420
caaagcaatg cagaccctaa atcactcaag gcctggagct ccagtctcaa aggtggcaga    480
aaaggccaga cctaactcga gcacctactg ccttctgctt gccccgcaga gccttcaggg    540
actgactggg acgcccctgg tggcgggcag tcccatccgc catgagaacg ccgtgcaggg    600
cagcgcagtg gaggtgcaga cgtaccagcc gccgtggaag gcgctcagcg agtttgccct    660
ccagagcgac ctggaccaac ccgccttcca acagctggtg aggccctgcc ctacccgccc    720
cgacctcggg actctgcggg ttggggattt agccacttag cctggcagag aggggagggg    780
gtggccttgg gctgagggggc tgggtacagc cctaggcgt gggggagggg gaacagtggc    840
gggctctgaa acctcacctc ggcccattac gcgccctaaa ccaggtctcc ctggattaaa    900
gtgctcacaa gagaggtcgc aggattaacc aacccgctcc cccgccctaa tccccccctc    960
gtgcgcctgg ggacctggcc tccttctccg cagggcttgc tctcagctgg cggccggtcc   1020
ccaagggaca ctttccgact cggagcacgc ggccctggag caccagctcg cgtgcctctt   1080
cacctgcctc ttcccggtgt ttccgccgcc ccaggtctcc ttctccgagt ccggctccct   1140
aggcaactcc tccggcagcg acgtgacctc cctgtcctcg cagctcccgg acacccccaa   1200
```

| | |
|---|---|
| cagtatggtg ccgagtcccg tggagacgtg aggggaccc ctccctgcca gcccgcggac | 1260 |
| ctcgcatgct ccctgcatga gactcaccca tgctcaggcc attccagttc gaaagctct | 1320 |
| ctcgccttcg taattattct attgttattt atgagagagt accgagagac acggtctgga | 1380 |
| cagcccaagg cgccaggatg caacctgctt tcaccagact gcagacccct gctccgagga | 1440 |
| ctcttagttt ttcaaaacca gaatctggga cttaccaggg ttagctctgc cctctcctct | 1500 |
| cctctctacg tggccgccgc tctgtctctc cacgcccac ctgtgtcccc atctcggccg | 1560 |
| gcccggagct cgcccacgcg daccccgcc ctgcccagc tcagcgctcc ctggcggctt | 1620 |
| cgccgggct cctagcgggg aaaaggaagg ggataactca gaggaacaga cactcaaact | 1680 |
| cccaaagcgc atgattgctg ggaaacagta gaaaccagac ttgccttgaa agtgtttaag | 1740 |
| ttattcgacg gaggacagag tatgtgagcc tttgccgaac aaacaaacgt aagttattgt | 1800 |
| tatttattgt gagaacagcc agttcatagt gggacttgta ttttgatctt aataaaaaat | 1860 |
| aataacccgg ggcgacgcca ctcctctgtg ctgttggcgc ggcgggaggg ccggcggagg | 1920 |
| ccagttcagg ggtcaggctg gcgtcggctg ccggggctcc gcgtgctgcg ggcggggcgg | 1980 |
| gcccggtggg gattgggcgc | 2000 |

<210> SEQ ID NO 150
<211> LENGTH: 1000
<212> TYPE: DNA
<213> ORGANISM: Homo sapiens

<400> SEQUENCE: 150

| | |
|---|---|
| agtttgggga gccttttctc catttgagaa aaaacaaact tacagcgagg ggtgaggggt | 60 |
| tagggtttgg gattggggaa aatgtgggtg gggagccccc ccaaggaagt gaggaggggg | 120 |
| ctgcaaggat tacacctggg catacgtttc cctagaaatc acattcattg tatttttata | 180 |
| atttattcta aatctttcat gcgaagaaag tcagtagtga gtgttagtac tggtggccct | 240 |
| cctgatcaca cttgcatctc ttgagtgtgc cttaaaggtc ttgggaatgg aaaatataaa | 300 |
| aactgcttcg tgatgcgtca tctttatccc ccactccccc acccattcca atatattttc | 360 |
| tacttccagc ctaaattcgg ggcccccstac cgaggccggc catgatcttg agggcggcat | 420 |
| aggggaggcc gcgctctgtc caccccagcc tggtgatgcc gttcgcttct tgtgcccggt | 480 |
| attgtgggct acatgccttt ccggcgtacg gagctgagcg tccaggccag tgcccctcaa | 540 |
| cctctcagta atgtttaccc gaggccgtcg tgcaatgaga ctattcgcat ggcattgtca | 600 |
| acgcggcggc gcgcgcgtct cggccctccg cggcttgcca gactgtcctg caaaccacct | 660 |
| cacccgtctc tttggcgcag gagactcagg ctgtaaccgg agaaaacact tcaccctgga | 720 |
| accctaactc aggtcctggc aaaagatgcg agaggaagac ttgctctctt aataaatctc | 780 |
| ggccgcccgc acatctggcc cctagacctg ctcggtagag gactggctgg tggatgcgcg | 840 |
| gtccaggccg tgggcactcg acccacctct attttccttc ccgaggcgcc cctggattac | 900 |
| cactttcggt ttgcgcttac atccgggatg tcgaatttcc cagggaatca taattatttt | 960 |
| atctataatt tattctaacc ccaaggttcc aagaaaatct | 1000 |

<210> SEQ ID NO 151
<211> LENGTH: 1100
<212> TYPE: DNA
<213> ORGANISM: Homo sapiens

<400> SEQUENCE: 151

| | |
|---|---|
| acattccttc taaaatgtgg gctttctgtg tacatgggcg cgcattccca ggactcggtt | 60 |

```
ccctgggtgg aattcaccca ggaatacaat cgattttctg aacctgcgta aggccacagg      120
cagctctgaa aatgaaagcg tttgctaagt gggggagatc tcaccgatcg aacgtttaaa      180
aatggctttg tcttcattca gctctcccga tttattctgt gttttacaaa tagaagctca      240
gagcttctgt cgcccagtcc ttgcatgact catggcggtg ccacacggg tttcagggat       300 aacgggatgt ttagaaaatc gctgcatatc ggagtttcct agcacgttcc atttatactg      360
aacgcaggcg gccgctgaaa atccagcctc gactcttgct aatgactggg taggaccctc      420
ggggtcctgc gacggtgctg gagggtgttc ccggctccga tgtggggagg cctgcgcggg      480
gactaggttc tcgagaggcg agcgggcgcg ccagagaacc cgagactgct gcggggccgg      540
atgcgggatc cctgggctgc ggttctacgc agaaacgcca atggccatgc ctccccagct      600
cctcccagcc ccagtcacta ggccggcgcc tggcccggag atcctcccag agccctggcg      660
gtgccatcat gccggagaag acaagctcgg ccccgctgga attcgctcca acacagatg      720 ctcatttttg gaatattcta gaaaataac aagatcttgt ttgtcgttat gattcacggg       780
aggtaactga tgggagggcc atttacatga gggcagacac tgtgggcga aggtgacttc       840 tggacgtagg cttaaagta ggaacggctc caaattccca atatctccgg ccttaccggt       900
tgcaaatcgg acccctgcgg gaaaaccaga cacttctgtt tcgtggcttt cgggctgcct      960
ccagcccacg caggctcgtt tagtccccgt ggagtcagcc ccgagccttc ctagtcctgg     1020
aacaagggct ccaggtcgcg gccgcgggaa gccgccaaga gggcggggag tagggattcc     1080
ctccagctcc gcagggcatc                                                 1100

<210> SEQ ID NO 152
<211> LENGTH: 1500
<212> TYPE: DNA
<213> ORGANISM: Homo sapiens

<400> SEQUENCE: 152
tcctcctcgg cctcagatgt cgtcccacct gcccacgagc agggaacctg gaacccactc       60
tcccggcagt ccccagcggg ttccgccacc cggcggccgc ccctgacacc gagtgggtgg      120
gaggaagagg cagctggcgg ggatgggcca ttgagacctc ttgaaaaata ttaaaagaca      180
ggatgggtag agatttctcc gggagaaagt tcgagggtgc atcgggtcgc ggctgggagg      240
agtacccgaa atgccagcag gagaaatgca acctgtttag gccacacctt caatccccga      300
ggctgtctgg agagactgcg tgcggggac ttgccggcgt tcccacaccg cgcctgcaat       360
ccactcccgc ggctgcctgg cctctgccac tcgcggcttg aagccagtgg ctctcaagcc      420
ctcggccccg cggcggcccg cgcagccttc accggcgcc ggcaccacga agcctggccg       480
cagtggactc cccgcagctc gctgcgccct ggcgtctccc gtcgaggagg agggacgga      540 ggcctgagcc gggagctccc tggcggtggt cgggccgccc ccttgaggc ctgctccccc       600 ctctcggcct cgccaaatcc ctgaaagccc agtcccctt cgtcacccg ggggcttcta       660 atcactcggt atcgatttcc ctaactcttt tcatcctgtt gaagacacat cttaaaacac      720
tccagcccgg agtgtgctct gggctttatc cacactaata aaatgattta cccttctctc      780
cgcgctctcc tcacagagga aaatcgttcg agccccggct atttgtgtgt gatcagtaaa      840
tatttagtgc gctgacatcc ttagctgggc ttcggatcga ttcggggccc accgggaggt      900
gcgcacggtc cggcggggc cgcgccgagc tcgccgaggg ggctcctccc gccctcgccg      960
ccggccgctg atttacggcc cctgcaacca gctaagggg gcgaaagcgc gcctggaaaa     1020
```

```
ttggctttc   aacctttac   ttttgacatt   cagccacttc   cccaggctct   aattctcgcc   1080
cgcactcctc   cctcccgccc   tactaagggt   tgccctgtgc   gccctgcgag   cccttccagc   1140
agcaacgcgc   ggcgctcgcg   cccctcggc    ccggggacca   cctatcacag   ccctgagccg   1200
cgacgcgggg   aggccccggc   ccctgctatg   ggggtcgcct   ccttcgagga   gagatgctct   1260
ccgcccgccc   acacctctga   gggaggagag   ggggtggaga   agcccagagc   tgcatctgct   1320
ggatgacgag   ccgctctccc   tgctacccttt  tctccgaccc   gtcggccttt   ctcctactct   1380
ggagactgat   cctcgacgtc   catcgggccg   gatggcgtcg   ggtggaagcg   ttactttcct   1440
cgcagaaaaa   ctcctcctct   ttcctaagat   cagaaaaagc   gcttagcttg   gaattgttag   1500
```

<210> SEQ ID NO 153
<211> LENGTH: 600
<212> TYPE: DNA
<213> ORGANISM: Homo sapiens

<400> SEQUENCE: 153

```
cctaggcatt   ctcagcccgt   tttgctggag   ggggcatttg   aggcctggcc   agcttagcca    60
gcctacaagg   agtgttactg   gggtgaaaac   agccagcggg   gaccagtctg   cttgtggccc   120
gccaggtgcc   tgggatgggg   aagcagcaaa   tgcccacctt   cctgcccaac   cccctcctcc   180
ctcttcatgg   ggggaactgg   gggtggcagc   ggctgccggg   tgcgagcggg   ctcaggcctg   240
tggccctgcc   tgacgttggt   ccccatcaag   ccatgtgacg   agaccaggcc   acaagaaaga   300
ggtttcaaca   agcgttatcg   tttcctggaa   ctccaactcg   gcgacttccc   cgaagaccgg   360
ctgtgcctgg   cgggcgggct   gcgcacagcg   ggacaaggc   tgccccttc    ctcctccgct   420 gcctccgcgg   ccgcgtctat   ctcagtctga   ctacctggaa   gcagcactcc   accctccagc   480 ccagcggcc    tcggctcagc   tgccaggtca   ccggcaaccc   cggagcggt    ggggcagggg   540 ctgctccgcc   agcctctgtg   atgttcaggc   cgggctgcac   cagcccggga   cccctaggtg   600
```

<210> SEQ ID NO 154
<211> LENGTH: 700
<212> TYPE: DNA
<213> ORGANISM: Homo sapiens

<400> SEQUENCE: 154

```
gcactggttc   ccctttacct   gagccaacaa   cctaccagga   agtttccatc   aagatgtcat    60
cagtgcccca   ggaaacccct   catgcaacca   gtcatcctgc   tgttcccata   acagcaaact   120
ctctaggatc   ccacaccgtg   acaggtggaa   ccataacaac   gaactctcca   gaaacctcca   180
gtaggaccag   tggagcccct   gttaccacgg   cagctagctc   tctggagacc   tccagaggca   240
cctctggacc   cctcttacc    atggcaactg   tctctctgga   gacttccaaa   ggcacctctg   300 gacccctgt    accatggca    actgactctc   tggagacctc   cactgggacc   actgaccccc   360
ctgttaccat   gacaactggc   tctctggagc   cctccagcgg   ggccagtgga   ccccaggtct   420
ctagcgtaaa   actatctaca   atgatgtctc   caacgacctc   caccaacgca   agcactgtgc   480
ccttccggaa   cccagatgag   aactcacgag   gcatgctgcc   agtggctgtg   cttgtggccc   540
tgctggcggt   catagtcctc   gtggctctgc   tcctgctgtg   gcgccggcgg   cagaagcggc   600
ggactggggc   cctcgtgctg   agcagaggcg   gcaagcgtaa   cggggtggtg   gacgcctggg   660
ctgggccagc   ccaggtccct   gaggaggggg   ccgtgacagt                             700
```

<210> SEQ ID NO 155
<211> LENGTH: 300

```
<212> TYPE: DNA
<213> ORGANISM: Homo sapiens

<400> SEQUENCE: 155
tgtccgacag gcacacagag cgccgccagg cacggccctc attcttcacc ccgagctccc      60
gcaaggtcgg cgaggaggct ggagcagcgg gtaggaagcg ggccgaggct cccccgacgc     120
tgggccgcaa ctgtcatcgc agatccctga aaaacgagct ctgtaatcgt tgccgtcagc    180
gggtgtacaa ttgcagcctt atgtttcctg ccgctgttta ccttcctgag cggcgcccag    240
agatgcacac acgctgccct gaagcgggac gtgacctctg ggcacctgtg aggtcctggg    300

<210> SEQ ID NO 156
<211> LENGTH: 500
<212> TYPE: DNA
<213> ORGANISM: Homo sapiens

<400> SEQUENCE: 156
gtcggctcct gcgctcccaa cggggtggcc gtttccttcc tcgcaccctc ttctctcccg      60
gtgcctgcgg tcccaccttc cagataccccc tcggagagtc cagctgagct ctcgccagag    120
ctttcccctt ccaacccgct cgacttgccc agatcccaag ctgggcttct ctctccatcg    180
ccccagaaag tgggtcttgg agaccgaggc aagaatttgg gcctccgctt ctgttccaga    240
ccccggaccc cttgccaaaa tgcggcagat gtgcagattg ggccgcgctt ggttcctggc    300
tgggtttatg gagcctgcgg ctgaggcagg ctccgcagac cccgagccag agtgggattt    360
aacggcggcc ggtgcgctgt gcttggtcaa ccccggtaac cgtcacgctg ctagtgatat    420
gaaaaaaacc tgccagcgtt ctgcttttct gccccgctgc agtctttagc acccgccagg    480
attctgtccg agtgtttgga                                                500

<210> SEQ ID NO 157
<211> LENGTH: 1000
<212> TYPE: DNA
<213> ORGANISM: Homo sapiens

<400> SEQUENCE: 157
tttagtgtgt gcataaaaca tcccagctaa tcctcaaatag acttttcctg agcagaggct      60
gaaatttgca agtaatgcaa agaagactcc gggagagcgt cgccgatggt ggagcgggag     120
acgggcgtgg ggagccccac tgcagtgctg ggatcgaagt ggtgctgacc ccaagacctc     180 tccctcctc ctcccccggg agcttctcca gggttatttg ggaaatgagg gggaactcca     240
atccctgaga aagcgctcag gggcttgctg aggtgagcgc aaatggaagc acaaggccgg    300
gctggccgtg ggctcagtaa ccagtcggct gcccggcttg cgccagcact aaatgctcga    360
tcagaaagag aaaaagaggc gcaataattc caaatttcag gaaaagtcaa atcggagagg    420
ggggacgcag gtctcttcag actgcccatt ctccgggcct cgctgaatgc ggggctcta    480 tccacagcgc gcggggccga gctcaggcag gctggggcga agatctgatt ctttccttcc    540
cgccgccaaa ccgaattaat cagtttcttc aacctgagtt actaagaaag aaaggtcctt    600
ccaaataaaa ctgaaaatca ctgcgaatga caatactata ctacaagttc gttttggggc    660
cggtgggtgg gatggaggag aaagggcacg gataatcccg gagggccgcg gagtgaggag    720
gactatggtc gcggtggaat ctctgttccg ctggcacatc cgcgcaggtg cggctctgag    780
tgctggctcg ggggttacaga cctcggcatc cggctgcagg ggcagacaga gacctcctct    840
gctagggcgt gcggtaggca tcgtatggag cccagagact gccgagagca ctgcgcactc    900
```

```
accaagtgtt aggggtgccc gtgatagacc gccagggaag gggctggttc ggagggaatt      960
cccgctaccg ggaaggtcgg aactcggggt gatcaaacaa                          1000
```

<210> SEQ ID NO 158
<211> LENGTH: 500
<212> TYPE: DNA
<213> ORGANISM: Homo sapiens

<400> SEQUENCE: 158

```
catggtgctt caggaaggga ggggacgaga gccctgggct tgtggtgtcc acgtggacag       60
ctaatgagga gccttgccga tgaggagcat gcgttcccga cggggcggcc gaatgcggaa      120
ggagccgcca ttctctccgc cctgaccgcg ggattctctg cagcagatga gaaacggcgc      180
tgactcagca gggtccctcc caggcccgga gcggtcatct ggtgaccccc gcgcttcccc      240
cacggcccag ccggagaagg gcaaagggaa gtcccggctc caaggcgcac ccagagatgc      300
ggtgcatgtg gcaggatggc ccagcccgt cggcagcccc agcttcctgc ccctggtttc       360
cttcctccca cgggctacag gcctctgatg agctttggaa agcaggaaac acacaggcta      420
gtaactatga atgggtccaa aaaacactcc ttattacttt aaactactta ggaagaagca      480
cagcgttgcc aaacgccaga                                                  500
```

<210> SEQ ID NO 159
<211> LENGTH: 1200
<212> TYPE: DNA
<213> ORGANISM: Homo sapiens

<400> SEQUENCE: 159

```
gcgcggggg ccggaggatg gcggcctggg ggccctgcgg gggctgtcgg tggccgccag         60
ctgcctggtg gtgctggaga acttgctggt gctggcggcc atcaccagcc acatgcggtc      120
gcgacgctgg gtctactatt gcctggtgaa catcacgctg agtgacctgc tcacgggcgc      180
ggcctacctg gccaacgtgc tgctgtcggg ggcccgcacc ttccgtctgg cgcccgccca      240
gtggttccta cgggagggcc tgctcttcac cgcccggcc gcctccacct tcagcctgct       300
cttcactgca ggggagcgct tgccaccat ggtgcggccg gtggccgaga gcggggccac       360
caagaccagc cgcgtctacg gcttcatcgg cctctgctgg ctgctggccg cgctgctggg      420
gatgctgcct ttgctgggct ggaactgcct gtgcgccttt gaccgctgct ccagccttct      480
gccctctac tccaagcgct acatcctctt ctgcctggtg atcttcgccg gcgtcctggc       540
caccatcatg ggcctctatg gggccatctt ccgcctggtg caggccagcg ggcagaaggc      600
cccacgccca gcggcccgcc gcaaggcccg ccgcctgctg aagacggtgc tgatgatcct      660
gctggccttc ctggtgtgct ggggcccact cttcggctg ctgctggccg acgtctttgg       720
ctccaacctc tgggccagg agtacctgcg gggcatggac tggatcctgg ccctggccgt      780
cctcaactcg gcggtcaacc ccatcatcta ctccttccgc agcagggagg tgtgcagagc      840
cgtgctcagc ttcctctgct gcgggtgtct ccggctgggc atgcgagggc ccggggactg      900
cctggcccgg gccgtcgagg ctcactccgg agcttccacc accgacagct ctctgaggcc      960
aagggacagc tttcgcggct cccgctgct cagctttcgg atgcgggagc ccctgtccag     1020
catctccagc gtgcggagca tctgaagttg cagtcttgcg tgtggatggt gcagccaccg     1080
ggtgcgtgcc aggcaggccc tcctggggta caggaagctg tgtgcacgca gcctcgcctg     1140
tatgggagc agggaacggg acaggccccc atggtcttcc cggtggcctc tcggggcttc     1200
```

<210> SEQ ID NO 160
<211> LENGTH: 600
<212> TYPE: DNA
<213> ORGANISM: Homo sapiens

<400> SEQUENCE: 160

```
gggcgggttg ccacactgtc ccctttctgc atgggaggaa gggggctcga gaactgagtc      60
agccacacaa aacgaggatg gacagaactc ctgagtagcg agggtgcctg ccgggcgcga     120
ggaggagggg gaagacgagg aagacgagga ggaggaatag ggagcaccac atgacagagg     180
ggctgcctca gaccacaaag cgcttcctca tcctttcctc gcccttttgat gccgccggca   240
acgtgactct gcgagcagcg gggcagacgc caggtctccc tcgcaggcgg gaaagggggct  300
ccaaggcggg tgctgccttg ctcgggtcac atggctacgt gggggccttg ctcaaattca     360
cttcctgcct tcattacaaa actgtcaaag gggatcgcac gtttgcaggg tgtcacccaa     420
gcattctggt tttgcaaacg acgctgtgcg gcaggcggtc tgatacctga tgagctcggt     480
gtggcggggt cggcagcatt tcctccgggg ttttgagctc tggccacttc tccttttgtt     540
ccacccaatc tcacccactt ctgggcttcg aggccagagt gtcttaacaa gggggcacgt     600
```

<210> SEQ ID NO 161
<211> LENGTH: 500
<212> TYPE: DNA
<213> ORGANISM: Homo sapiens

<400> SEQUENCE: 161

```
gagcgagact ttgtctcaaa aaaaaaaaaa accaaataaa ttgaaagctg agaaattcag      60
agcacaagaa gacaagcgcg cccctcttt tagctgtcaa catggcggag ccgtccctgg     120
tgacgcagcc tccaaaggcc tccctgtgcc ctcctgagac cgcaagaggg aaagtggcag     180
cgacagtgat cgtggtgtct ttgtggcggt tgtgttgacc tcactgaccc ccgaagtgcc    240
gctctagggt ctgtcctcag cggtgacccg gccgggtcga aggcagagt tccgctgtca     300
ctagccctcc accgtcctg tgtgctggga tgccctcgcg gcgccgtcca cgccaccgcc     360
gccccctctt gtgggttctg tctcctccgt gtctaggatc ctcctgcatc cgttttttcct   420
tcctccccttc tctccctccg tctgtcttgc ccgcacctga ggttgtcgca gaggcgctga  480
gacgggccag caggagctgt                                                 500
```

<210> SEQ ID NO 162
<211> LENGTH: 600
<212> TYPE: DNA
<213> ORGANISM: Homo sapiens

<400> SEQUENCE: 162

```
tgctgtcccg gtcctgtcgc agtcctcaaa gatgctagag tgacagtcct ctaggggtag      60
agatggtcgt cctcccagga gaaggtggcc cggagacttg gaggtgggat caatcctgcc    120
agtcctggat caggaggcct ctgtcggcg ccgccccct tcctcctcca tcagcaacag     180
gcggcgccgg ccagcctcat agtcagcctc atccacactg accagcaggc gaacagcctc    240
ccggcccaca gcctctcgca gggcctcagt caggaacacg ccccgcaggg cctgcagcag    300
ggcgccactc agtagtcgc cccagaaggc gtccagatag gagagctctg agaacttgat     360
gtcacaaacc acagagccca ggtcccttga gcgcagcact gcggtggcct gcccaaacac    420
gtccagctgc cgcgccagcg cctggggccg ccggatgcc acgccctgct ccaaggctgg    480
cccatgctcg cagtactctg ctcgaacccg gagccggatg tctgcagggg aaggagggat    540
```
ttgtcaggga gggggccaac actagacaca cttatggga acgccaccct tcctccctcc    600

<210> SEQ ID NO 163
<211> LENGTH: 500
<212> TYPE: DNA
<213> ORGANISM: Homo sapiens

<400> SEQUENCE: 163
tgatgcccgg cccccagggg ggcagaggcg ccgccaccat gagcctgggc aagctctcgc    60
ctgtgggctg ggtgtccagt tcacagggaa agaggcggct gactgcagac atgatcagcc   120
acccactcgg ggacttccgc cacaccatgc atgtgggccg tggcggggat gtcttcgggg   180
acacgtcctt cctcagcaac cacggtggca gctccgggag cacccatcgc tcaccccgca   240
gcttcctggc caagaagctg cagctggtgc ggagggtggg ggcgcccccc cggaggatgg   300
catctccccc tgcaccctcc ccggctccac cggccatctc cccatcatc aagaacgcca    360 tctccctgcc ccagctcaac caggccgcct acgacagcct cgtggttggc aagctcagct   420
tcgacagcag ccccaccagc tccacggacg gccactccag ctacggtgag ggcctgggcc   480
atcttggccc acttttcaga                                              500

<210> SEQ ID NO 164
<211> LENGTH: 200
<212> TYPE: DNA
<213> ORGANISM: Homo sapiens

<400> SEQUENCE: 164
ggccgggcaa aaagccgccg caacaaaaag ctgcgctgac gggcggaaaa agccgcggcg    60
gcggagccaa aaagccgggg cggcaaaaag ccacggtggc gggcgcaaac agccgcaaaa   120
agccgcggtg gtgggggcaa aatcagtggg agcaggggca aaaaaacaca aaaagccgcg   180
gcggcggggg caaaaagcca                                              200

<210> SEQ ID NO 165
<211> LENGTH: 400
<212> TYPE: DNA
<213> ORGANISM: Homo sapiens

<400> SEQUENCE: 165
tggctttgct ggagtgtgat gtgataggaa atgtgcagcc aaagacaaaa gaagatgtaa    60
gtaggcttga ctcattgcag ctaagaaccc agatgttacc ttgagggtat taactaataa   120
gcagtttaaa tcagaatggc acattctgat ttgttttttg tatgttcaca tttggcaggc   180
atagatactg tttgaaaaga gaaaagtcag tacatagagg taacaagctt aaatatgtgc   240
caagtctaga acaagagac tagggggata aggacctttc gaaattaaat gcaagatttg    300
aaaactgatt ggctggggga tgaggcaaag gcaggtcttt aaggtcaatc cctgttttgc   360
tttaagttgt tagcgggtgg ttttatcata tattgtagaa                         400

<210> SEQ ID NO 166
<211> LENGTH: 650
<212> TYPE: DNA
<213> ORGANISM: Homo sapiens

<400> SEQUENCE: 166
ttcctgggaa tgtcagctaa cctgagccta ggggcctgag cccaagggca gactgaggct    60 ccccagcac agggaggtgc tgcctgtgac aaggggtagt gctggcacag tgcaggctac   120
tccctagaaa gatcagcttg aatatgcagg aagagcagga ccctcgggct gaggcagagg   180

| | | |
|---|---|---|
| tggaatggga agtgcatggt ggtaatttag ttctccagag gccagaagta ggaggagcgg | 240 | |
| ttggaatgct gatggcccaa agggaaaccc tggactaccc tggcctccca caggactctc | 300 | |
| atagtaattg cggctccctg cagtggtgag gccagaagga gtgttgccca atgctgtcat | 360 | |
| catccagtcc acccccacc caccatcaac agatgagtat ggtcatgagt gtggtcacct | 420 | |
| catcagtcat ttgctcagtt gtgaaaaaga aattgttcag agaagagcaa agtgttttc | 480 | |
| catgagccaa aggtcagcca agttatgcta atgaggagga ctggagacag cgtgtcacag | 540 | |
| acaccgagaa ggagcactgg gcaagggcac ttctcccagg gcagagccca caagaagcgt | 600 | |
| cctggcacca gacactcagg gaactgaagg ctggcagggg cccgcccagt | 650 | |

<210> SEQ ID NO 167
<211> LENGTH: 5000
<212> TYPE: DNA
<213> ORGANISM: Homo sapiens

<400> SEQUENCE: 167

| | | |
|---|---|---|
| tccccccagc tgggtataag caaactttcc tgtctatggg ccgcagagac caccatctag | 60 | |
| ttccccccgcc aaaactttac atgattttaa ttctcctgat gaagatgaga ggataacagc | 120 | |
| caacagagag ggcagaggat gggatgggac tcccttgctc agagacctca cctctaggtc | 180 | |
| tttacctcct attgagaata agtcagttct gtagtaagaa ctctgtgtcc acggcaaccc | 240 | |
| caaacagaat cctagcgctc ttgtgattct tgtagaatgg ggaatagaac gagcttggcc | 300 | |
| caagactgca cagacttaaa aacatactat tctttgaaaa tggcaatcat taaaaagtca | 360 | |
| ggaaacaaca ggtgctggag aggatgtgga gaaataggaa cacttttaca ctgttggtgg | 420 | |
| gactgtaaac tagttcaacc atggtggaag tcagtgtggc gattcctcag ggatctagaa | 480 | |
| ctagaaatac catttgaccc agccatccca ttactgggta tatacccaaa ggactataaa | 540 | |
| tcatgctgct atacagacac atgcacacgt atgtttactg cagcactatt cacaatagca | 600 | |
| aagacttgga accaacccaa atgtccaaca atgatagact ggattaagaa aatgtggcac | 660 | |
| atatacacca tggaatacta tgcagccata aaaaatgatg agttcatgtc ctttgtaggg | 720 | |
| acatggatga aattggaaat cattctcagt aaactatcgc aagaacaaaa aaccaaacac | 780 | |
| tgcatattct cactcatagg tgggaactga acaatgagaa cacgtggacc caggaagggg | 840 | |
| aacatcacac tctggggact gttgtggggt gggggagggg gggagggata gcattgggag | 900 | |
| atataccaaa tgctagatga ggagtttgtg ggtgcagcgc accagcatgt cacacgttta | 960 | |
| catatgtaac taacctgcac attgtgcaca tgtaccctaa aacttaaagt ataataaaaa | 1020 | |
| aaatactgtt ctgccataca tacagatact cattaaagat gagggagaag ggcatggggt | 1080 | |
| gggggagaat gtaccaaaac caaagaccac aggataataa cctcagagca gagactatct | 1140 | |
| ctctagttat ttttcttttt gtatgtaatg gagaggatta ttatttactc tgatgaagaa | 1200 | |
| gtttacatca agtgttcagc ttcctttgtg ggttacagag aataaccaga gggctcagtt | 1260 | |
| atgctctctg aataactatg tttgcttagt gttttctaaa caatattaaa tttcactaaa | 1320 | |
| atagacaagg ttgataggac ttgggggcat aactcattga ctcaagctat cattttatag | 1380 | |
| gattgtgaga aaacaaatag atgaacattt aaaatacact catattctcg ctagaaaaga | 1440 | |
| ggattttgaa tattcttaca tcaaagacat ggtaaatgtt taaggcaatg aatatgctaa | 1500 | |
| ttaccatgat ttgatcatta tgcaatgtaa aatgtactga acatcacat tgtacctcat | 1560 | |
| aaatatgtac aatttattat gtgcgaatta aaattttgag tataagaaaa aataaacttc | 1620 | |

```
aattgtaaga aaacaacccca acttttaaaa aacgggcaaa atacgtgaac agatacttca    1680
ctaatagaga tttgcaactg gcaaataagc aaatgaaaaa ctggtcatca tcactatcta    1740
ttagagaaat gcagattaaa actacaataa gaaacaatgc tgcccgtcca gacgcattgt    1800
tttgaccgtt tccaacttgt cccagccctt cccggggcat cgctgggggac cctacgccga   1860
cgtccccct ccgcccgcgc cccaagggcc gactgggcaa attgggagac ccgccccgcg    1920
gggcgaccca acttttcgga acagcacccc accgcccacc cccgcagacc cccggacccc    1980
cgctcccggc ggagactcag ggaaccccgc accccaagcc cttctaaatc gtgcagcgtg    2040
agtgtgacgg ccaagagcgg atgcagcccg ggatcgcccg caccttcccg tgggcggaag    2100
cgcaggagcc agctggggag ggggcgccct agaggagcgg ctagaaagca gacacgggga    2160
actcaggtca tcctgggggg ggacaagaca acgagagccg ggcgcctcgg gggcggcgcg    2220
ggagcctccg caggaccggg cggcgcccc ggctggcgcg ggcgggggc gcgccccctt      2280
tacctgcggc tccggctcct aggccatttc ctcacgcggc ggcggccggg actgagctaa    2340
caccactcag gccggccggg tttgaatgag gaggagcggg cgcggagagg aggggacggg    2400
gagggcggag ggagggaggg aggcgtcgcg gagttttttct cggccttttg tgcggacacc   2460
tcccggattc cgcgcccgca cccggccccc caaaagacac ggggagccgc gggcgagggg    2520
ttcagccatc cgccgaggcg cctagtgcct tcgcgcctcc aagaccccc cccaacaaaa     2580
aggagcgtcc cccaccccta cccccgcccg gaggacttag ggcctgggct cacctcgggc    2640
gcggagctaa gtgtaggcgc cggggggtccc tagagccgcc ggggcgcagc gagtccggcg   2700
ctgggtaact gttgggtcag aaactgttca ggtagcagct gttgtgccct cccttggccc    2760
cgccgctcgg agacgccccg ccccctgcct tgaacggccg cccggccccg cccagcgcc     2820
cacgtgacta gcataggcgc gccccgttc cgcccgccgc cgcagactcc gcctccggga    2880
cgcgagcgag cggcgagcgc gcgcactacc agttcttgct cggcgactcc cgcgcacgcg    2940
cgcgccgtgc caccctcccc gcaccccctcc tcccgccatc cggcttaacg tggcgggcgc    3000
gcgccgcggc agtagccgtg acaggtaccc ggcggggcgg gggggaggg ggttggcccg     3060
cgagggtgtg cgcaggcaca gaccgggtc ctgtccccgc cgcccccctcc tctgcaaggt    3120
gtgcctgggc gaggggaggg gcccgcggcc cgaacccctg ggtcaccccc gaattacaaa    3180
caaaaacctt aacgcattg ctcgcgggtt agaaggcagc tgtgcgtgct caggaaaaga    3240
agccacgcac aagagaccgc acgcggcgtg gatacagtga cacgaaacac ccaaaatctc    3300
ttttgaaagg gaaaccaggc acagtggctc atgcctataa tcccagcact ttcgggggcc    3360
aaggcgctca cctaaacccg agagttcaag accagcctgg gcaatacagc gaaaccctgt    3420
ctctacgaaa aatataaaaa ttagctgggc atagggctgg gcacggtggc tcacgcctgt    3480
aatcccagca ttttggaggc cgaggcgggc ggatcacgag gtcaggagtt ccagaccatc    3540
ctggctaaca cagtgaaacc ttctctctac taaaaataca aaaaaatta gccgggcgtg    3600
gtggcaggtg cctgtagtcc tagcacttg ggaggttgag gcaggagaat ggcatgaatc    3660
agggagcgga ggctgcagtg agctgagatt gcgccactgc actccagcct gggggacaga   3720
gtgagactcc gtctcaaaaa aaaaaataat aattagctgg gcatggtggc tggcacacat    3780
ggtcccagct actcaggagg ctgaggtgga aggatctctt gatcccgggg aggtcaaggc    3840
tgcagtgagc caagatggca tcaccgcact ccagcctggg ccacagaccc tgtctcaaaa    3900
aaaaaagaga aagtggggaa gaaatgtaa tacaaattaa tataccaaca gcaattagtg    3960
agtactttt ccatggagct gggagaggga ataaatgttt gtaaaattaa aatgttctac    4020
```

-continued

```
gctagaaatc aactttcctt ctatgctttc tttacttcac cccttatagc tacttagtaa    4080
atctcacaaa tcctatcctt ctgatctctc tgaaatgtat gtacccttc ccttctattc     4140 tcaccaccca tgtttctttg tttccttcta gcctgtgtaa taatctcata atcgcacctc    4200
ctgtacctgc cttctttcta gtccagaata cgttttccta aattccacca ataaccatcc   4260
tgctactgct ttgtgtgaaa ttctccaaaa aaaatttac ttttccaaaa taagtcaggc     4320
tccctctctt aggatacaaa accacaccat ggtcccagcc aatctttcag cctgattcac   4380
tcagtatata tttattgacc tctcctttct cccaagcact tggctagata ataattaaag   4440
agtgcggcac aaaacaaatt ggattcctcc cctcatggag cttgtatttt cacaggaagc   4500
acagacatta ataaattaa acacaaaaa aatagacaag catataatta cagtatgtat    4560
cctagagaaa tatcactcat gcagaaagca tacacaagga tgcagcactg tttccaatag  4620
cgaaaagcta gaaacaacct acatgttcac caaagaaaa tggccacata aactatacca    4680
tatccaaatt atccaatttt tagaatatag acaacaggtt gggcgcggtg gctcacacct   4740
gtaatcccag cactttggga agccgaggcg ggtggatcac aaggtcagga gttcaagacc   4800
agcctggcca acatggtgaa accccgtctc tctaaaaaa acaaaaaaat cagctgggca   4860
ctgtggcagg agcctgtaat cccagctact gaggagactg aggcaggaga atcgcttgaa  4920
ccctggaggc agaggttgca gtgagccaag atcgcgccac tgcactctag cctgggtgac  4980
agagcaagac tccatctcag                                                5000
```

```
<210> SEQ ID NO 168
<211> LENGTH: 1500
<212> TYPE: DNA
<213> ORGANISM: Homo sapiens

<400> SEQUENCE: 168
```

```
tgtaggagtc ctccggtgct ggagtccaga gcacagtgag gctgggtcct cccgtgccat      60
agtgtagggc atggcgggac agggatcctg ccctgcgata gtccagtgct tgagtccgca    120
gtaaggcaat ggtcctccaa tgctggagtt cacggcgttg tggggtcggg gtccttggt     180 gacttagtcc agggcgtacc agggcggggg tccacagttg ccatagtgag gatcttggag   240
gaaggtggtt cctgccttgc tgtagtccgg ggagcagggg gcaggggtcc tctcttgtca   300
gagtctctgg cgcggggtgg gggtggaggt gggggttttc ctatgcgata gcccacgggt  360
cggtgaagcc gggtcctccc gtgcctttgt ccagggcgca gggggcgag gtcttcggt     420 ggtggagtcc gcggagcggc aggacggggg tcctccagtg ccatattcca gggcgcggcg  480
gagtggggga cctgtcctgc agtggtccag gcatgtggg agtggtggtc ctgctgtgcc   540
tcagtccagt gcgcggtggg acggcggtcc tgctgtgctg tagtgcagga cgcggtggcg   600
caggggtagt ccagagagcg ccgtggcagg gggtcctcca gtgctggaat ccagtgcaag  660
gcgggtcagg ggtcttaccg tgccgaagtc ggtggcaagg gtcctcccgt gccatagtct  720 aggggcgac ggggcagggt tctctagtgc aggtgtccag ggtgtggcag gcaggagtc    780 ctcttgtgca ggagtccagg acgtagccga ggagtcctcc aatgtcagag tccagggctc   840
tgcggggccg ggttccccca tgccagagtg tagggcgcgt tcaggtgagg gtcttggcgt   900
gcagtaatcc agggtgcggt ggggcagggg tagtccagac ctccatggcg ggcgtccctc   960
tgtgcaggag cccagtgcct ggcggatcgg gggtccttct gtgctgtagt ccagggcacc  1020
gcaaggtgtg ggtcctctgg tgccctagtc caggggggcgg cgagtcagag gttctcccgt  1080
```

```
gtctcagtct agggcctggt aggactgggg tcctggagtc cacgtggtag cccaagttgc   1140
cgcaggacca ggtactctgg aaccacagtc cagggcgctg aggggcagga gtagttcagg   1200
gcgagccggg gcccaggtcc tcgggagcca gagtccaggg tgtggagggg tgggggttct   1260
gcagtggcac agtccaggac accgcgggc gggacagggc ggggatcctc ccgtgcctta    1320
gtccagggct gagccgcggg agaggtcctt cagtagcaca gtctagcgca cggcgttgca   1380
ggtgtcctcc agtgcctgag gccacggcag gtcgcgggtc ccactgtgct ctagttcagg   1440
gcggagtggg tctgaggtct tctcctgcct cagtctaggg cgctggagag cggggatcct   1500
```

<210> SEQ ID NO 169
<211> LENGTH: 2500
<212> TYPE: DNA
<213> ORGANISM: Homo sapiens

<400> SEQUENCE: 169

```
gggttggtcc tagaaagcgt gaggatcgcc gagtgcactg ccctcccagc ctagggtcca     60
ctcttccttg gcccgagccc agagctcggg gtttcaggcg ctgggccctg tgcagctgcc    120
cagaataggc tgagcggcag gttcccgccc tggcaaggga tccagcagtg gaatcctcac    180
tgctgttggc tgcgggcaag gtcagcgggg tttccatcgc tgctggtggg agccacctgg    240
cggtggtagc tgcaagtgag cgcgtggcag agactggcag ggctggtccc agacaccctg    300
agggtctctg ggtgcatcgc cctaccaccc tagggtctgc tcttccttag cctgctccca    360
ggacgcggtg tacgagggct agactctgag cagcctccag gatggggctg agcagcggat    420
tcctgccctg ctgcagctac agtctgaatt aggcgccacc gcagtatctg ccctggggt     480 acgtgctact gggtggcatg gacagagatg ggggctgcca cagctgctat ggggctgagc    540
agccgattct cgccctgctg cagcgggcga ccgctgcaat cccagcgct atgggaccga    600 ccacctgact tagatgcctt ggaggcatcc ggtcctgggg tcttgctgct ggtgtctgcg    660
ggcagggtca cggctgccac tactactgct gtgcgccatg gcaggtgcc agctgcagct    720 gagtccgagg cagatgctgt cagggctggt ctgaggttgc ctaagggtgg ctgagtgcac    780
cacgcttcca ccccaggtc cgttattcct aggccggctc ccagattgca gggttgtggg    840
cgttggacac tgtgcagcca tgaggatctg gttgggtgca gattcccgcc ctcctgcagc    900
tgagaagcca atctcataac aggcgctgca gtgacctctg gctctgcggt ccgcgctgct    960
gctggagctg cagagaaca gagctgccac cgctgctgct tccaggagtg tgcagctggc   1020
agctgcagct gagcccgtgg cggaggctgg aaggccttat tccagaagcc ttgagggtcc   1080
ccgaatgcac cgccctccca ccctaaggtc cagtcttcct tgcccgcgcc cagagagttg   1140
gattgcaggc gctgagcaca gtgcaggtgc tgggatgggg ctaagctgaa agtttccgcc   1200
ctctggctgc tgcggggccg acagcctgag ttatgcgccg cggcggcttt tggtcatggg   1260
atccgcactg ccggtggctt gcacagggtc gggggctgcc acagctgcta tagttcaccg   1320
tgtgcacgtg gcagccgccc ctgagcccac cgctgaggct gcaggctgg tccggtccca    1380 gacggcctga gggccatttg cccgcgccca gatccgggtg gctgcgctgg gcactgtgca   1440
gcctcccgga atccgctgaa gggcacgttc ccgctctcct acagctgtgg gccgactgcc   1500
tgattttggc cactaggtgg agtctggctc tagggtttcg aggccgctgg tgttggtggg   1560
cggagtccgg gtttgccacc gctgcgctcc atgagcaggt agcagctgca gcggagcttt   1620
agaccgaggc tggcagggct ggccccagac ggcctgaggg tcaggagtg cagggtcctc    1680 ccaccctagg tccgctcttc ctttcccctt acccagagcg ggttgtgcgg gctctgggct   1740
```

-continued

| | |
|---|---|
| ctgtgccggc gctgggctct gtgcagccgc cgagatgggg ctgagcagcg gatttcctcc | 1800 |
| ctgctgcagc tggaggacga ttacctgcac tagccgctga ggcggcatct ggccctgggt | 1860 |
| tactgcagct ggtgacgcgg gcagggtcag ggttggttgc aggtggcagc tgctgctaaa | 1920 |
| cccattgcga gcctcagggt caccaagttc accgtccttt catcatagta tctgatcttt | 1980 |
| ggcccgcgcc cagagtgcgg actggcctgc gctggggact gcatagcttc tggggggccgg | 2040 |
| tcagcgccag tttcacgtcc tcctgcagct gcgtggccta aggtcttagg cgccgcggcg | 2100 |
| ctatctggcc ctgctgtcga cgctgctggt ggtggggaca gggtcaaggg ttgccactgc | 2160 |
| tgctcccgtg cgccatcggc aggtggcagt tgcagatgag cccacaattg aggctgttgg | 2220 |
| ggctgctccc aggttgttag agggtcgccg agttcaccga catgccaccc taggttacgc | 2280 |
| tcttggcccg cacccagagc gccgggttac gggtcctggg ccctgtgcag ccacggggat | 2340 |
| ggtgctgagt gcaggttccc gtcttcctga gatgcgggcc gaccactgga attagcctct | 2400 |
| gtggtggtat ctgaccctag ggtccgagct gctggtggcg tgggcggggt cgaagtcgcc | 2460 |
| tctgttgctg cggcgtgcca tttgcaccgt cctctggtac | 2500 |

<210> SEQ ID NO 170
<211> LENGTH: 1600
<212> TYPE: DNA
<213> ORGANISM: Homo sapiens

<400> SEQUENCE: 170

| | |
|---|---|
| aaatactcta ctgaaaaaac agaaatagta atgaataca gtaaagtttt agaatacaaa | 60 |
| atcagcatag aaaaatcagt cgcatttcta tacccaacag cataccatct gaaaaaggaa | 120 |
| tcaagaaacc aatcccattt aaaatagcta taaaaaaatg cctgggaata aactaagcca | 180 |
| aataaatatg tctaaaatga aaactataaa acattgataa aaatcaattg aaaaagatac | 240 |
| aaataaaggg aaagttatcc cattttatg aattagaagt attaatactg ttaaaatgac | 300 |
| catcatactc aaatcagtct ataggtccaa tacaatctct aacaaatttc caatgtaatt | 360 |
| cttcagagat gttaaaaaag gtttttaaaaa tcgttctgcg gatgttaaaa ggatttttaa | 420 |
| aacgcttttt tcgttctgca ggcgaaggct gtggccgtgc tcccgccggc cagttcccag | 480 |
| cagcagcgca ttgcccctgc tccacgcctt cgctccaggc ccgcaggggc gcagcccgc | 540 |
| gggaatcagc actgagccgg tcccgccgcc gccccagtgt ccgggctgcg actgcgggga | 600 |
| gccgatcgcc cagcgattgg aggagggcga cgaggccttc cgccagagcg agtaccagaa | 660 |
| agcagccggg ctcttccgct ccacgctggc ccggctggcg cagcccgacc gcggtcagtg | 720 |
| cctgaggctg gggaacgcgc tggcccgcgc cgaccgcctc ccggtggccc tgggcgcgtt | 780 |
| ctgtgtcgcc ctgcggctcg aggcgctgcg gccgaggag ctgggagagc tggcagagct | 840 |
| ggcgggcggc ctggtgtgcc ccggcctgcg cgaacggcca ctgttcacgg ggaagccggg | 900 |
| cggcgagctt gaggcgccag gctagggagg gccggccctg gagcccggcg cgccccgcga | 960 |
| cctgctcggc tgcccgcggc tgctgcacaa gccggtgaca ctgccctgcg ggctcacggt | 1020 |
| ctgcaagcgc tgcgtggagc cggggccgag cggccacagg cgctgcgcgt gaacgtggtg | 1080 |
| ctgagccgca agctggagag gtgcttcccg gccaagtgcc cgctgctcag gctggagggt | 1140 |
| caggcgcgga gcctgcagcg ccagcagcag cccgaggccg cgctgctcag gtgcgaccag | 1200 |
| gccctgtagc tgtgacttgg ctgtggggct ggccgcctc cctgaccct gtcaggcgga | 1260 |
| gcagctggag ctgacccacg ggcctgggct ttcgagcgct ttgtccaggc gctaatgatg | 1320 |

```
ggaaggtgaa aggtgggggt ggccacaccc tgcagtcagg gtggcaggtg tcagaggcca    1380
catgcaaccc actggttttg tcttttccag gatgctgata agtttcccgc ggccccggga    1440
gcagctctgt aaggccctgt aattgccttt cgttcccttc tgctctattg aggagtggga    1500
agatgacaaa gtgttttgc tcaacccgaa ggaaaatgca catgggagga cacaccgggt    1560
tactatttga gtagcccaga caggagagca gcggtctgct                         1600
```

<210> SEQ ID NO 171
<211> LENGTH: 1500
<212> TYPE: DNA
<213> ORGANISM: Homo sapiens

<400> SEQUENCE: 171

```
tgggtggatt gcttgagccc aggagttcga gaccagcctg gacaaaatgg cagaaactcc     60
atgtctacaa aaaatacaaa aattagccgg gcatgatgtt ctgcgcctgt agtcccagct    120
actcaggagg ctgaggtggg aggatcgctt gagcccagga ggcggagttt gcagtgagct    180
gagatgtcac tgcattccag cctgggagac agagccagac tctgtctcaa aagaaaaaaa    240
gaaaaaaaaa aagaaaaaga aaaacgaaaa ttgtattctg aatacatctt ctaaaacact    300
acatttactt gcactatatt aaactggttt tatcctgacc acaattgcag gtgaaagata    360
ccactgttgt tctattttc tggtaagtag agtgagccat gtcttcccca gggaaagacg    420
cctcctaaaa atttgtagga ccaccttgg ttttcttcca gatatttttt ttgtcatcgc     480
ttttcctgcg cccaattccc atctgtctag cccttctgcc tccgctggtc tttttcgcga    540
gcctctcccc agccgcaggt attcgtctgg gctgcagccc ctcccatctc ctggggcgtg    600
accacctgtc caggccccgc ccccgtccaa cccgcggaga cccgcccct tccccggaca     660 ccgggttcag cgcccgagcg tgcgagcgcg tccccgctcg tcgcccggct cggcgtcggg    720
agcgcgctct gtgtggtcgc tgctgcagtg ttgttgtggc tgtgagaagg cggcggcggc    780
ggcggagcag cagccggacc agactcccta gtagctcagg cgctgccctg cgccggccct    840
ggcagggagc ctggtgagat ggtggaggag gaggctgtgc cgtggctggc cttgctgtgt    900
cctgctgcct ggttagaacc ccatcccgt ccccgtctc ctccggggg tgaggaggag        960 ctggaagagg ggccggcctc tgtccggccc ggccaggcgg cagtcaccct ctgaggaggc   1020
agcgcccggg gaggggcctc ccaggcgcc ccgccgcca gggggaggcg ctgggagtgg     1080
gagtgggagc gggacctcag ctgccaagct cggcccggac cctaggtgcg ggggaggcgg   1140
ggtcccgggc tcgggctgcc tgcccggacc tggcgggat gggcccgtgc ggctccgggt    1200
gtgggacgta ccctcagagc gcccggggtt attcccactg actccaggga ggtgagtgtg   1260 cgccccttcgc tccctgccgt gtctgtgagg gtccatcgtt gccggagact ggaggtcggg   1320
ggccatggga gccccggggc gaacggtgcg gacatgggcc ttgtggaaag gaggagtgac    1380
cgcctgagcg tgcagcagga catcttcctg acctggtaat aattaggtga gaaggatggt    1440
tgggggcggt cggcgtaact cagggaacac tggtcaggct gctccccaaa cgattacggt    1500
```

<210> SEQ ID NO 172
<211> LENGTH: 1700
<212> TYPE: DNA
<213> ORGANISM: Homo sapiens

<400> SEQUENCE: 172

```
gtctctagga caccctaaga tggcggcgag ggagacggtg aaggttggct cccgcctgtc     60
tgggctctga tcctctgtct ccccctcccc ctgcggccgg ctcatggcct ggcggaggcc    120
```

```
cgaaccaaag acctccgcac cgccgtgtac aacgccgccc gtgacggcaa ggggcagct     180 gctccagaag ctgctcagca gccggagccg ggaggaactg gacgagctga ctggctaggt    240
ggccggcggg gggacgccgc tgctcatcgc cgcctgctac ggccacctgg acgtggtgga    300
gtacctggtg gacccgtgcg gcgcgagcgt ggaggccggt ggctcggtgc acttcgatgg    360
cgagaccatg gagggtgcgc cgccgctgtg ggcgcggacc acctggacgt ggtgcggagc    420
ctgctgcgcc gcggggcctc ggtgaactgc accacgcgca ccaactccac gcccctccgc    480
gccgcctgct tcgagggcct cctggaggtg gtgcgctacc tggtcggcga gcaccaggcc    540
aacctggagg tggccaaccg gcacggccac atgtgcctca tgatctcgtg ctacaagggc    600
caccgtgaga tcgcccgcta cctgctggag cagggcgccc aggtgaactg gcgcagcgcc    660
aagggcaaca cggcccctgca caactgtgcc gagaccagca gcctggagat cctgcagctg    720
ctgctggggt gcaaggccag catggaacgt gatagctacg gcatgacccc gttgctcccg    780
gccagcgtga cgggccacac caacatcgtg gagtacctca tccaggagca gcccggccag    840
gagcagctca taggggtaga ggctcagctt aggctgcccc aagaaggctc ctccaccagc    900 cagggggtgtg cgcagcctca gggggctccg tgctgcatct tctcccctga ggtactgaac    960
ggggaatctt accaaagctg ctgtcccacc agccgggaag ctgccatgga agccttggaa   1020
ttgctgggat ctacctatgt ggataagaaa cgagatctgc ttggggccct taaacactgg   1080
aggcgggcca tggagctgcg tcaccagggg ggtgagtacc tgcccaaact ggagccccca   1140
cagctggtcc tggcctatga ctattccagg gaggtcaaca ccaccgagga gctggaggcg   1200
ctgatcaccg acgccgatga gatgcgtatg caggccttgt tgatccggga gcgcatcctc   1260 agtcctcgc accccgacac ttcctattgt atccgttaca ggggcgcagt gtacgccgac   1320
tcggggaata tcgagtgcta catccgcttg tggaagtacg ccctggacat gcaacagagc   1380
aacctggagc ctctgagccc catgagcgcc agcagcttcc tctccttcgc cgaactcttc   1440
tcctacgtgc tgcaggaccc ggctgccaaa ggcagcctgg gcacccagat cggctttgca   1500
gacctcatgg gggtcctcac caaaggggtc cgggaagtgg aatgggccct gcagctgctc   1560
agggagccta gagactcggc ccagttcaac aaggcgctgg ccatcatcct ccacctgctc   1620
tacctgctgg agaaagtgga gtgcacccccc agccaggagc acctgaagca ccagaccatc   1680
tatcgcctgc tcaagtgcgc                                                1700

<210> SEQ ID NO 173
<211> LENGTH: 300
<212> TYPE: DNA
<213> ORGANISM: Homo sapiens

<400> SEQUENCE: 173
taaaaataaa ttgtaataaa tatgccggcg gatggtagag atgccgaccc taccgaggag     60
cagatggcag aaacagagag aaacgacgag gagcagttcg aatgccagga acggctcaag    120
tgccaggtgc aggtgggggc ccccgaggag gaggaggagg acgcgggcct ggtggccaag    180
gccgaggccg tggctgcagg ctggatgctc gatttcctcc gcttctctct ttgccgagct    240
ttccgcgacg gccgctcgga ggacttctgc aggatccgca acagggcaga ggctattatt    300

<210> SEQ ID NO 174
<211> LENGTH: 600
<212> TYPE: DNA
<213> ORGANISM: Homo sapiens
```

<400> SEQUENCE: 174

| | | | | | |
|---|---|---|---|---|---|
| cgccaccacg | tgcgggtagc | gccgcatcgc | cccagccgtg | ttccttggtc | tccgtctccg | 60 |
| ccgcgcccgc | ctggtgaact | ggagcacagg | gaccatagtt | ctggaaattt | atccttttc | 120 |
| tctccatgga | ttcagcagca | gtgtctaaaa | gaaaaaaatt | catcaatcat | ttatgtatat | 180 |
| tttaatataa | aggtaaaaca | ctgcgaacca | gtggaaccgg | atagaaagta | attcagtttt | 240 |
| acagaacaca | actgttttc | aggctctttt | attaaatata | aaagagccat | atatatttct | 300 |
| gtggaattcc | ccttttactt | aagaattcat | tatcagcgaa | ttagtttaag | gaggctgttt | 360 |
| tgttagaggc | tgtggttgca | ttcaaaaatt | ggaataggaa | caatgacttg | taaaaattca | 420 |
| acatttatt | ttattttga | gatggagtct | cgctctgtcg | cccaggctgt | agtgcagtgg | 480 |
| cgcgatctcg | gctcactgca | acctcagcct | cccgggttta | aggaattctc | tgcttcagcc | 540 |
| tcctgaatag | ctgggattac | aggcgcatgc | caccaagccc | agctaatttt | ttttgtattt | 600 |

<210> SEQ ID NO 175
<211> LENGTH: 1300
<212> TYPE: DNA
<213> ORGANISM: Homo sapiens

<400> SEQUENCE: 175

| | | | | | |
|---|---|---|---|---|---|
| ccctgaacag | tcagagttta | ctgcccactt | ttgctggagg | agaagctcct | gaacaactag | 60 |
| agagactgtg | gttcccaaag | agcagcctgt | aggcctgagg | actgctctat | gaccggcgtc | 120 |
| agtccctgcc | tcctcccctc | cgtccctcct | tccctccttc | cttcccaggc | cttctctgac | 180 |
| taccagatcc | agcagatgac | ggccaacttt | gtggatcagt | ttggcttcaa | tgatgaggag | 240 |
| tttgcagacc | atgacaacaa | catcaagtga | gtccacttgg | atgccccctg | cacgaggcac | 300 |
| gactccccct | cctcgctgct | gaagtcccat | ggggcagct | cccttagtcc | ttgccgggag | 360 |
| ataacaggtg | tttccagttg | catgagggtg | ctgaggcccc | cagtgagaac | caggggagga | 420 |
| gcactgaggc | ctcagatgag | caccggggga | ggagccctga | ggcccagat | gagcaccagg | 480 |
| ggaggagcac | tgaggcccca | gatgagcacc | ggggaggag | cgttgaagcc | ccagatgagc | 540 |
| accagaggag | gagagctgag | gccccagatg | agccccgggg | gaggagctct | gaggcccag | 600 |
| acgagcaccg | ggggaggagc | gccgaggccc | cagatgagca | ccgggggagg | agcgccgagg | 660 |
| ccccagatga | gcagtggggg | aggagccccg | aggcccccag | atgagcagtg | ggcggggcag | 720 |
| ggagcgccga | ggccatcccc | cttgctcttg | cagcgcccca | tttgacagga | tcgcggagat | 780 |
| caacttcaac | atcgcacactg | acgaggacag | tgtgagcgag | cggggctgtg | cggggtcatg | 840 |
| caggcaccct | gttcccaggc | agctcaggcc | gcgcccatgg | ctcggtctgt | ggtgggcctg | 900 |
| tgcggtgggg | ctgggagagg | ccctctgtg | gagctaggaa | cagtcgcttt | tcttgaccct | 960 |
| ccccatcatg | ccctccagcc | catggcgccc | acatcctgaa | ctaagcccct | ctgggagccc | 1020 |
| tgtggggaga | gcgcctcctg | tctccccag | accctctgga | aactgacctt | ggcgttttac | 1080 |
| tctgcagccc | agcgcggctc | tgaggcctgc | tgcagcgacc | gcatccagca | ctttgatgag | 1140 |
| aacgaggaca | tctcggagga | cagcgacact | tgctgtgctg | cccaggtgaa | ggccagagcc | 1200 |
| aggtgcgggg | cctgcccatc | cccccaaagc | ctctgccgag | gaggtgcagc | cccagaaca | 1260 |
| cccgtcagat | gcccagacgc | cctgctgttt | gttatgccgg | | | 1300 |

<210> SEQ ID NO 176
<211> LENGTH: 110
<212> TYPE: DNA
<213> ORGANISM: Homo sapiens

<400> SEQUENCE: 176
tttgggccac gaggcaagtt caaagcggga gacttttgtt ttataaaatg atggtgagca    60
gctccggttt tatgtcaaac atcagggttt cgtgcaggat ataaacattt              110

<210> SEQ ID NO 177
<211> LENGTH: 1500
<212> TYPE: DNA
<213> ORGANISM: Homo sapiens

<400> SEQUENCE: 177
attgccgtac tttgcttccc tttgtatgta tttcttgtat gctgccgagt cactgatggc    60
tagctctgtc tggcaagtaa ttcaaaaatg ctgtttatgt agaaaggaaa ggtagggact   120
ttaccacact ctgtcattaa agggagcaat tgaagaacaa aggaactgag taaataccta   180
tatattgcct tttgtgttgc gaaacactgt agcacaaaca catttgtgtt cagccaaatg   240
ttttacttcc ttttgtaata acgcatatag taggttgtct ccacatatgt acaagaatcc   300 atatttatt taaacgtata tagtcaattg ttcatattta taggctgcaa acatttctca    360
atctcaaaga cttttacata tccactccca cacagctatt tgttattatt ttaaaagttc   420
ttaaattaaa aaaaaaata aaatatacta atatctctgt tggttgattt tattaagcaa    480
cttaggattt caacacagtt taaatcatat tgatgactca gatcctggca ggtcttacaa   540
ttcctgtgaa atgagagcac agctaataaa aatattaagc aattacttt attaaaatca    600 tagggttttt ttcattatca catagaaatg attgatctat acagattggt ctcactcatg   660
tgtcttttgg gctgcttggg agcttcatgt agaagtggaa agtccccttt gctcttcctt   720
cgaccaaggt ggggaaaatg aaggcataga atacaatcta gggctattaa agaattgctg   780
gcattacttc tctctatcac gtgtgagcct ggctgcctgc ttcctgaggt aggggatcca   840
ggatgagact gtgccggagc ctgttttccac aactgcattt ggagatccgt cttattgatt   900
agcgggggaa aggggtgggg atcaggagtg tgaggtgagg ggaggaccaa ctgacgactg   960
gctcaatgaa gcacaagaca ttttcttccg gaaagatgtc aaacaactga gaaacagcca  1020
gagaggaagt agaaaggtgg aaaaatgagg agacctggga agaaatgaag gcatttccta  1080
tgagacagcc ttggggcttt tttcttttct ttcttttttt ttgcttccat catctgacct  1140
gcaaaggcta gagtgacagc gtcatgcaaa tgctgcagtc cagcaggtct gggagagggt  1200
ggatgctaga ctgtgagtta atgttaatga tgagcgcagt gaaaatacca gccgctgcca  1260
ccccctgctc acagaagcgc tctgagtcag catcagatgc tttgcctcgc ctctcgctgt  1320
gtatctgtat gcctgtgtgc gcgcgcgtgc tcgctcgggc atccgtgtct agccgagggg  1380 aggggggtggc gtgtgagtgc gtggagggta aaagccagtc agtcagtgag aagcaaaggt  1440
acgttggaga gcaactaaaa tctgactgat ttccatcttt ggagcatcag atgtattccc  1500

<210> SEQ ID NO 178
<211> LENGTH: 200
<212> TYPE: DNA
<213> ORGANISM: Homo sapiens

<400> SEQUENCE: 178
gcagcctcct cctgaaaaat gtaagccatt tccactttgt aaagctacgt ttatattcca    60
ccacgatacg atgaaaaga aacccaagg caatttaata tacgggttgg gaagaaagtt    120
ttgctgatgg aactacatta gcctccactc cagcaaagca aacaaggaac cacactaaag   180
aaatgtactg aatctttaa       200

<210> SEQ ID NO 179
<211> LENGTH: 800
<212> TYPE: DNA
<213> ORGANISM: Homo sapiens

<400> SEQUENCE: 179
tgcctgagcg cagagcggct gctgctgctg tgatccagga ccagggcgca ccggctcagc     60
ctctcacttg tcagaggccg gggaagagaa gcaaagcgca acggtgtggt ccaagccggg    120
gcttctgctt cgcctctagg acatacacgg accccctaa cttcagtccc caaacgcgc     180
accctcgaag tcttgaactc cagccccgca catccacgcg cggcacaggc gcggcaggcg    240
gcaggtcccg gccgaaggcg atgcgcgcag ggggtcgggc agctgggctc gggcggcggg    300
agtagggccc ggcagggagg cagggaggct gcagagtcag agtcgcgggc tgcgccctgg    360
gcagaggccg ccctcgctcc acgcaacacc tgctgctgcc accgcgccgc gatgagccgc    420
gtggtctcgc tgctgctggg cgccgcgctg ctctgcggcc acgagccctt ctgccgccgc    480
gtggtcagcg gtgagtcagg ggccgtctcc ccgaagaacg agcggggaga ggggaccacg    540
gggcgcggcg ggcagcctgt tctcgggcgg aggctctccg gggcgttgga aacctgcatg    600
gtgtaaggac ccgggaggag gcggggagaa attgattgtg ctgttctcct ccctctcttc    660
tctaacacac acgcagaaaa gtttaaattt ttgtgaagcg cttgcttacg tagctgcgga    720
gcgagcctct gcttcattac gagcggcata gccttttca ggagtgattt ccactttctt     780
tgtgagagag ttgaccacac    800

<210> SEQ ID NO 180
<211> LENGTH: 600
<212> TYPE: DNA
<213> ORGANISM: Homo sapiens

<400> SEQUENCE: 180
ttcaatttac actcgcacac gcgggtacgt gggtgttcgg ggtagggcac tgatctgggg     60
aaggtctccc ccccgcgacc caactcatct ttgcacattt gcagtcctcc ctcggtgcac    120
tcctggcggg gatctggcca gtgcagcgca ctgggaccga gggcagagcc cgcggagtga    180
ggccaggaga gacttcaggc ctctaaggac acagctgagg ctaaggctga gttgaacgca    240
gccccctcccg cggctcgtcc cctctccagt gtctctcccg taaggtgccg ctcccaacag    300
caatgggtcg agatgtagag gaaacactct gtacgttatt tttccgccca ccctttagcg    360
cctgaggaga cagacagtgt agactttagg gtacaattgc ttcccctctg tcgcggcggg    420
gtggggagcg tgggaagggg acagccgcgc aaggggccag cctgctccag gtttgagcga    480
gagagggaga aggaggtcca cggagagaca agaatctccc tcctcccacg cccaaaagga    540
ataagctgcg gggcacaccg cccgcctcca gatcccccat tcacgttgag ccggggcgcg    600

<210> SEQ ID NO 181
<211> LENGTH: 600
<212> TYPE: DNA
<213> ORGANISM: Homo sapiens

<400> SEQUENCE: 181
tcattatccg attgattttc ctggtatcac atcacttaag tttaagtagc tcttatgtta     60
cttagtaatg actgcaaaac acgagttgtg atgcgggcaa tttggataca acaaaaagaa    120
gccattaagt ttgttcgtta gttaacaggt gaaagctctc aagttattaa ggataaaaat    180

```
gctagtatat atatatatgg tttggaacta tactgcggat tttggatcat atccgccatg    240
gataagggag gaatactata atcaggtttg ttttaaattc catgtctaat gacttcgtta    300
tctagatcac ctgtagagct gttttttattg taggagtttt ccttggtttt aatcttttga   360
tttgtttttc atgttaatac tgaaattttt aaaaattgca tattgtactt cctatatgaa    420
aattttacta tgtatttta tttttatttt ccttttcctt taggaagaat tagtttgttc     480
cctgacagag ttagagtaag ggcaaattac ttgtctctat aaacaactca gatgttttga    540
gccggtgttg tagggttat cttttctgg ttttgcattt tattatagga catagtgctt      600
```

<210> SEQ ID NO 182
<211> LENGTH: 140
<212> TYPE: DNA
<213> ORGANISM: Homo sapiens

<400> SEQUENCE: 182

```
agaaagaaga aatccggtaa aaggatgtgt tattgagttt gcagttggtg tttgatcttg    60
cacagatttt ctcaggggcc ttaagaccgg tgccttggaa ctgccatctg ggcatagaca   120
gaagggagca tttatacgcc                                               140
```

<210> SEQ ID NO 183
<211> LENGTH: 900
<212> TYPE: DNA
<213> ORGANISM: Homo sapiens

<400> SEQUENCE: 183

```
cgaagatggc ggaggtgcag gtcctggtgc tcgatggtcg aggccatctc ctggtccgcc    60
tggcggccat cgtggctaaa caggtactgc tgggccggaa agtggtggtc gtacgctgcg   120
aaggcatcaa catttctggc aatttctaca gaaacaagtt gaagtacctg ggttcctcc    180 gcaagcggat gaacaccac ctttcccgag gtccctacca cttccgggcc cccagccgc    240 atcttctggc ggaccgtgcg aggtatgccg ccccacaaga ccaagcgagg ccaggcttct   300
ctggaccgcc tcaaggtgtt tgaccgcatc ccaccgccct acgacaagaa aaagcggatg   360
gtgttcctgc tccctcaagg ttgtgcgtct gaagcctaca agaaagtttg cctatctggg   420
gcgcctggct cacgaggttg gctggaagta ccaggcagtg acagccaccc tggaggagaa   480
gaggaaagag aaagccaaga tccactaccg gaagaagaaa cagctcatga ggctacggaa   540
acaggccgag aagaacatgg agaagaaaat tgacaaatac acagaggtcc tcaagaccca   600
cagactcctg gtctgagccc aataaagact gttaattcct catgcgtggc ctgcccttcc   660
tccatcgtcg ccctggaatg tacgggaccc aggggcagca gcagtccagg cgccacaggc   720
agcctcggac acaggaagct gggagcaagg aaagggtctt agtcactgcc tcccgaagtt   780
gcttgaaagc actcggagaa ctgtgcaggt gtcatttatc tatgaccaat aggaagagca   840
accagttact attagtgaaa gggagccaga agactgattg gagggcccta tcttgtgagc   900
```

<210> SEQ ID NO 184
<211> LENGTH: 1400
<212> TYPE: DNA
<213> ORGANISM: Homo sapiens

<400> SEQUENCE: 184

```
gcctgaagac catttcttcc tctcttaggg acctgctggt ctccagctga ttcggtccag    60
gaggaaaaac ctcccacttg ctcctctcgg gctccctgca aggagagagt agagacactc   120
```

```
ctgccaccca gttgcaagaa gtcgccactt cccccctccag ccgactgaaa gttcgggcga    180
cgtctgggcc gtcatttgaa ggcgtttcct tttctttaag aacaaaggtt ggagcccaag    240
ccttgcggcg cggtgcagga agtacacgg cgtgtgttga gagaaaaaaa atacacacac    300
gcaatgaccc acgagaaagg gaaggggaa aacaccaact acccgggcgc tgggctttttt    360 cgacttttcc tttaaaaaga aaaagttttt tcaagctgta ggttccaaga acaggcagga    420 gggggggagaa ggggggggggg gttgcagaaa aggcgcctgg tcggttatga gtcacaagtg    480
agttataaaa gggtcgcacg ttcgcaggcg cgggcttcct gtgcgcggcc gagcccgggc    540
ccagcgccgc ctgcagcctc gggaaggag cggatagcgg agcccgagc cgcccgcaga    600 gcaagcgcgg ggaaccaagg agacgctcct ggcactgcag gtacgccgac ttcagtctcg    660
cgctcccgcc cgccttcct ctcttgaacg tggcagggac gccggggac ttcggtgcga    720 gggtcaccgc cgggttaact ggcgaggcaa ggcgggggca gcgcgcacgt ggccgtggag    780
cccggcctgg tcccgcgcgc gcctgcgggt gcccctggg gactcagtgg tgtcgcctcg    840
cccgggacca gagattgcgc tggatggatt cccgcgggca gaggcagggg aaggagggg    900 tgttcgaaac ctaatacttg agcttctttg caaagtttcc ttggatggtt ggggacgtac    960
ctgtataatg gccctggacc agcttccctg ttggagtggc cagagaagtg tgtaaaacac   1020
actagagggg cagggtggaa aaagagactg ccttcaaaac ttgtatcttt tcgatttcat   1080
tttgaaaaat aactacaaat ctattttaat tttacaaagt tagactcata gcatttaga    1140 tatcaatgtc ttcatttaac agaagtgaag atggagcaaa cgctcaatca gcgtctgtat   1200
ttattcgctc ctgttgtgcc agggtgcgtt tttgccgagc ggttgccttt ctttactcac   1260
aaaaccccct tgatgtctgt cctccacgtt ttacgaggga gagccggatc ttttgaagtt   1320
tgtatcatct aaagcaggta tattgggatg actatggata gaatttaacc tgaaaacact   1380
gaagttgaca gctgacaaag                                                1400
```

<210> SEQ ID NO 185
<211> LENGTH: 200
<212> TYPE: DNA
<213> ORGANISM: Homo sapiens

<400> SEQUENCE: 185

```
cataacaaga gtcattctaa tgtgattata aaggacccga agctttgctt ttaaaattca     60
atacttaggt agaaagaaaa tgataacttt ttcccttga ttttttattca ctattttat    120 aacactagca gccctgagac accggattgg aaatatctat gcctcttgat gttacctggg    180
caccactgca tcacagtcct                                                 200
```

<210> SEQ ID NO 186
<211> LENGTH: 400
<212> TYPE: DNA
<213> ORGANISM: Homo sapiens

<400> SEQUENCE: 186

```
aatagtaatt gccaacagtc aagatatgta ctaccaccaa attccgtgtt atttgtgatc     60
aaaagatata cacagatact tgaaaactga tttctacgtt gcatatggga aaaataccctc   120 atttttctca gctgtccatt attttttgaga tattatgtgc agtgatagta agaacaagca   180
gatttggaac acatcagcaa taattttttc aatcagagtc ctgccaaaat gaaagaattt    240
gacagtatcc ggcaccctgt actcatgctt ggcttctgta gaaactgtgg cttgcaaaag    300
ggcagctggg tactgtgttt tggtacctca ttctttaaac gtataatggg aatctggttg    360
```

```
gttcaggaaa acccttgcct acttattatt actctgtttt                    400
```

<210> SEQ ID NO 187
<211> LENGTH: 250
<212> TYPE: DNA
<213> ORGANISM: Homo sapiens

<400> SEQUENCE: 187

```
ggcccatact taatgtattt ttaaacgttt taacatttac taatatagaa ccttctattg    60
cctatttcct tctggtttat tccctttcct tctgtcattg aagaaatggt tctagtggta   120
gaaatactcc acgattgaga agaatgtggg aagaaaggag ggctggtggg taagaattgc   180
tcatgatgtc tccctctgaa ttctgtgctc tcacaatgac actccaatgt gtggtttgac   240
gcctggaaga                                                          250
```

<210> SEQ ID NO 188
<211> LENGTH: 250
<212> TYPE: DNA
<213> ORGANISM: Homo sapiens

<400> SEQUENCE: 188

```
tgcttcaacc ggaaatgtgg ttgaattacc cttacagtga acctgatcag tggtaacagg    60
agatgctaga acaggaaaag acaagtttcc cctttcctcc ctatcccatc aattactttg   120
aggtgtattt tttctttgca accoctccag agaagtcggc aatgtttaac gagcatgcct   180
gccaagtggc ttgccttata cctcattatg aagtgatact cagggccact aacacatcgc   240
acagcattgc                                                          250
```

<210> SEQ ID NO 189
<211> LENGTH: 500
<212> TYPE: DNA
<213> ORGANISM: Homo sapiens

<400> SEQUENCE: 189

```
tatgattccc tcgatttccc tcaatcttaa ccattgtgga tcacagcagg agggccagaa    60
agtgagcttc agcctggcac cgggacctca gcctctccct taaactttcc ctaatcctcg   120
gagctagtgt tactcaagtg actccacagt gttgcccgat cccttcagac atggccttga   180
tgatctccaa aactcatgct accttt gcca gcctaaagca tccactctgt gcccaaaaac   240
gtgaatgtca ataccccttc aaggcagaag gctatttcta tttttgtttg ttt ctgttta   300
aggcaacaat caccaacatt tggtacacat gagccatcct gtgaaacatc aaggcgcttc   360
gttggcagca agtcaacttc ggtttcagaa gaaagctgca ctatttcctg aggttagagg   420
tttaaaccaa aacaagacaa ccacatttta accccaaatc tgccgactga gggtaaccat   480
gatccttcct tcacagcacc                                               500
```

<210> SEQ ID NO 190
<211> LENGTH: 150
<212> TYPE: DNA
<213> ORGANISM: Homo sapiens

<400> SEQUENCE: 190

```
tactaaatca acccaaaccc gagaacccgg tcatggagaa ataaatgata gtaatctatg    60
ctgttcatct gttccatcac tcactcactc tcttgctgaa caagaaaggg ccacccatgt   120
agcaaaccac atgtaaagag ccgggaagac                                    150
```

<210> SEQ ID NO 191
<211> LENGTH: 300
<212> TYPE: DNA
<213> ORGANISM: Homo sapiens

<400> SEQUENCE: 191

| | | | | | |
|---|---|---|---|---|---|
| tattattttg | ttcaaagtag | acgggtatac | taacatctgt | gggcaagttt | accacacgcc | 60 |
| acttaaaaca | ggctaacagg | gtcatatgcc | aaaacgttca | ggtttgcatt | tttgaaaagc | 120 |
| tcagagatct | gacagatgtg | ttccggccgc | gatttaacat | gcggctccag | tgagaaggaa | 180 |
| gcagatatga | caaatggttc | acttatttca | gaactaaaac | cccagaggag | cagcctgagc | 240 |
| caaaaaggga | agtgatcaat | ggaaaagacg | gtcgaatctg | ctcacaggca | aggcaagggg | 300 |

<210> SEQ ID NO 192
<211> LENGTH: 300
<212> TYPE: DNA
<213> ORGANISM: Homo sapiens

<400> SEQUENCE: 192

| | | | | | |
|---|---|---|---|---|---|
| aagacctgga | gtttccatta | caccgaattg | gcacttaata | actgttgtcg | gagcatttct | 60 |
| taagccacat | tttcgtaaag | tggctttaaa | attgctctgc | cagtaggcag | gttgctaaga | 120 |
| tggtcagaga | caaacttctg | aacgactctt | gtaaaatata | cagaaatatt | ttcagaactt | 180 |
| ttatcagtaa | aattacaaaa | cgtgttgcaa | ggaaggtgct | tgtgataaca | ctgtccccag | 240 |
| aaccttagtg | aagttaccaa | ctggtggaaa | attttctctt | gcactcggct | taaaaatcat | 300 |

<210> SEQ ID NO 193
<211> LENGTH: 400
<212> TYPE: DNA
<213> ORGANISM: Homo sapiens

<400> SEQUENCE: 193

| | | | | | |
|---|---|---|---|---|---|
| gcaggggtga | ctggtcctct | ctctctgcac | ctcgcaggat | ttctctggaa | gatctgagcc | 60 |
| cgagcgtcgt | gctgcacatg | accgagaagc | tgggttacaa | gaacagcgac | gtgatcaaca | 120 |
| ctgtgctctc | caaccgcgcc | tgccacatcc | tggccatcta | cttcctctta | aacaagaaac | 180 |
| tggagcgcta | tttgtcaggg | gtaagtgcga | ccctagaggc | gatcgtctct | gctgtctgtg | 240 |
| gaaaaaagag | ctcctacacc | caagtgcttc | tcagttgct | gacacttgat | ccaagctgct | 300 |
| aatttaatct | aatgtgaggc | tgagttttct | gaatgtggga | taaagtcgta | gctaaacctg | 360 |
| cttctcaggg | agtgcctttt | atctgcaatg | ttttttcaaat | | | 400 |

<210> SEQ ID NO 194
<211> LENGTH: 1100
<212> TYPE: DNA
<213> ORGANISM: Homo sapiens

<400> SEQUENCE: 194

| | | | | | |
|---|---|---|---|---|---|
| aagtaacggg | atcaaattaa | ttattatttt | ggtggccgcc | tctcttctcc | accccaagcc | 60 |
| aggcaagact | caccctcggc | cctgcccgcc | ccagcatttc | aaatggaata | cctaggtggc | 120 |
| ccaggggac | ccctgacccc | tatatcctgt | ttctttctgc | ctgctttgct | acttttctcc | 180 |
| ttgataaaag | gagagagtga | gagataatta | acaaaaaaca | tggccccagg | acaatgaaac | 240 |
| aactggcctt | ggccggccag | aaatgtatcc | tggttttcta | ggtgaacttt | ctcccatcaa | 300 |
| tctttccttt | aacctctctg | ttagtggaag | caataggaac | accctccccc | tcccctgagc | 360 |
| aaatgctttc | ttttgactgg | aaacaaaaca | ggggctcggc | gaaggctgag | gtgaaatctg | 420 |

-continued

```
ggtggcatgg gcgccgcaca atggggccgc tgttccccgg cccgggcttg tgttttacaa      480
caggggaggg gcgggcgtga atggtctgat gattggaaca atcccccga ttcaggccta       540 caaacgcatc ttctgttcca caccgagggg acagaaagga gaaagtgac aaagaacgcg       600 gggcgggggg aattaaaaca aaatgcgctc gactaaaaaa tctctcatat cctgcatatt     660
ccagaaagcg gctctatgga gagagccttc aggaggcctc agccatatct gaatggcttt     720
ctctggcctc tgatttattg atgaagctga agcgacttgc tggagaaagg cctggagcct      780
tctttgtctc cgagatgaag tacaataggc cacagggcgg agatctcttg tgatgctctc      840
gggtcctgcc tttctcttgc cctctcctcc ctgcaaatac cagcagcggt gacaaacgat      900
tggtggtgtg cctgggagag ccggtgacaa gactgggcca cttgaggtct ccttaagagg      960
gtattatggc cagggcgacg tttgtgctgt gaagatggca cactccattt tgtcaatggc     1020
tctcatcggc ccagataatc gcccctgcc tgcctgtcag gggcgcagcc ggccgattca     1080
tggcgccctc ggagaaagta                                                 1100
```

<210> SEQ ID NO 195
<211> LENGTH: 10000
<212> TYPE: DNA
<213> ORGANISM: Homo sapiens

<400> SEQUENCE: 195

```
gtctttcccg cccccttgtc taaactcaaa accgagtccg ggcgcgcctt gcagggcgcc       60
cgagctctgc agcggcgttg cgggctgaac ccatccggca caaactgcgg gccactggcc      120
cctcacacct gggagtttgc ggcgctggcc tgcagcccgg gcccacgtg gcggaagctt      180 tcccgggcgc gcgctgcgca gcccgcgggg gccggggaga caccgctcgg gagtcctccg      240
ctcggctgca gaatctttat cagctgcact ttaccgcagc cctggctagg acgctaggcg      300
gtggagcgcc ctatccaggt gcgccgccgc accatggatc accgcgcccg gtcccgcagt      360
cccgccatgg cctggggagg cccgaagccc ggggacagtg gccggcccat ctccggctcc      420
gcggaccccc ggctcaggcg ggagggcagg cgggtccctg caggccccca gggagcccgg      480
gagcctctct ctggcgtcat tcagtcccgg ggcaacctga agcgcggtag atattggaga      540
gggggcgtct gttgggggga cctggcgtca ttactgatgg ctagcaggga ggagggaacg     600
ggttgtcacc tcggcctcat aaggccgtga gtgagtagtc cagggcctct tcaggcattt      660
ttgaaactgg attaactagg ggggaaattg tagcactgaa gccaccgtga ctgtcttttg      720
cgctgtgtgg aaactccggt aaaactcttt gggcaacagt cttatcacca gctcttcaac     780
gtgtgcagcc cttctggtcc tgtccctgtt ctgggcccca ggaatgcaaa gcaggtccag     840
gcactgtgaa gaccctggcg gtggaggaag aggcttcccg gctgtggagg aagccagacc      900
cttacaacac aagacgagaa ccagacctgc gtggggagc tctggatgct acaggggctc      960
aaggaggggt ggaggggcct tcccaggcca cccctgaac ggcttggaca agatgctcag    1020
atggacggga ggaacggcgt gtgggatggg ggagctggag gcgggtgggt gggggggga    1080 ggatggggaa agcgctggcc cacccagtgt gggaggggta gaggaaaagc ccgcaggggc    1140
caggttggga ccccgtaggc cggggttagag ggcttggact tgatcctgac aggcgacagg    1200
gagacatatt gctacttatt atgtgcacag tggccagatc tctaaagaaa acaccatccc    1260
ccacccccac cccccatata gtaaaccagg tggtccgccc agtgctccca gggaggtgat    1320
gggaaatccc actccatacc ctgcggtgag gggttccatg ccctccacgt gtgcaactac    1380
```

```
tccgggccca gggaaacact gggccccatc cggtaacccc cggcccagtc gggtttccca    1440
gttcacatta taaccaaacg gtcttgccag ctagacagac agacacccct gacctgttta    1500
ccctgatcct ctgctctcag gattaatcac aacttgtcga agggggtggc ttccagtggg    1560
gtggaccgct ctgtcaatgc cagcgtgtgt ctagcatctc ctgggtgggg ggtgtgggga    1620
agggaggtgt aggatgaagc cctagaagcc tcaggcaatt gtgatccggt gggctggata    1680
ctgaagccca cccctgcctt gacctcaatt ttcagtatct tcatctgtaa aatgggaaca    1740
acctgccttc ctcctagccc taaggggct gctgtcaaga ttggctgaga tagctgtttg    1800
caagctgagc tcaatgaaag ttcattgtgt cccctcagt cctatcccaa tatcgtctca    1860
ctgcaaaggt gggggcagc ttaacttcaa gggcacttca aggatagcca ggtggctgtc    1920
agcccagctt tccaggatgg gagcaggatc ttgacagaag ggttgactgg gagggcagt    1980
tgctggtttg ggcttcgtta ggttgcattt ttgtttgttg tcctttcatt tccctggggc    2040
agcaccccctt cctgcaagct ccaggccttc ctctggaatg ctcctagagc ccaacctctg   2100
ctggtgcctg agcttaagcc aggccagcta aggggatcct ggattcacac ggcctcacag    2160
tcactcagat tgttagcaga agacaaaaat tacaagggga gggcgtcatg tgattcttac    2220
acaccctcca aatccagcag acaccttgga agccacaggt agcttcaaga aacccatttt    2280
acggatgaga acctgagatg gagaaaggac aactggagat ctctgagtct ctgagcccac    2340
actccctacc tccctgcacc tccaggcact ctgctggcag gatcttgggc aaatgccac    2400
agctctctga gagtcagttt tcctgtctgt aaaatgggag tcatacccttc ctcctatggc    2460
cggtgagaga ctaaattaaa ctatgtctgt caagacacct gaaactcctg gcacaattta    2520
ggttgccttc aagtggtcac agttgtcatt aggtggaagt caacacccca atcattgtaa    2580
aggtgcccat atccccaag atccagatta cagctctcac agtttattat atacagcgaa    2640
aaaacacata acacacccttt gcccacattt acatgtatt tacggaccat gtttcacatc    2700
agtccgcatg cacatctgca cgtgtgtgca ttcggcagta tttaccaagc acctgccaag    2760
tgccagggcc tgtcctccgc acccggcgtg aactgtcctg gaccagtccc gggagccgcg    2820
gttctgacca gccgtgctga cccctggacga ctccatgagc tgttttgtga aaagacacg     2880
ccattttgttt gcagagttct gacttctgag gggtcatgta gcacatgttt ggtagccaaa    2940
cgctgtcatt cacgaccagg agcgatggct gcaatgcctt tttctttgct ttgctttccg    3000
gtgccgggag ccttgcctcc cgccgccacc cctggtcagc tctgcgcaag aacgtcgttc    3060
tgtttggcag ccaggccgag acgcagcctg aatgtgagca ggaactcgga aagggaagg    3120
gagagaatca gaaagaaggc ccgggaggga cccgggaagc agtgggaggt ctgcgccctg    3180
gagccccgcg agagcccgcc ggtttggcac gggctcctcc cggccgccc ggcggtccaa     3240
caaaggccgg ccccgacacg cacccggtct tttgtgggag agaaacacaa agaagaggga    3300
aaaacacgga ggaggccaac agcaccagga cgcgggggcc aaccaggaac tcccggagcc    3360
ggggcccatt agcctctgca aatgagcact ccattcccca ggaagggccc ccagctgcgc    3420
gcgctggtgg gaaccgcagt gcctgggacc cgcccaggtc gcccaccccg ggcgccgggc    3480
gcaggacccg gacaagtcct ggggacgcct ccaggacgca ccaggcaag cttgggcacc     3540
gggatctaat ttctagttat tcctgggacg gggtggggag gcataggaga cacaccgaga    3600
ggtactcagc atccgattgg caccaggggcc aagggagccc aggggcgaca cagacctccc   3660
cgacctccca agctactccg gcgacgggag gatgttgagg gaagcctgcc aggtgaagaa    3720
ggggccagca gcagcacaga gcttccgact ttgccttcca ggctctagac tcgcgccatg    3780
```

```
ccaagacggg cccctcgact ttcacccctg actcccaact ccagccactg gaccgagcgc   3840
gcaaagaacc tgagaccgct tgctctcacc gccgcaagtc ggtcgcagga cagacaccag   3900
tgggcagcaa caaaaaaaga aaccgggttc cgggacacgt gccggcggct ggactaacct   3960
cagcggctgc aaccaaggag cgcgcacgtt gcgcctgctg gtgtttatta gctacactgg   4020
caggcgcaca actccgcgcc ccgactggtg gccccacagc gcgcaccaca catggcctcg   4080
ctgctgttgg cggggtaggc ccgaaggagg catctacaaa tgcccgagcc ctttctgatc   4140 cccaccccc cgctccctgc gtcgtccgag tgacagattc tactaattga acggttatgg   4200
gtcatccttg taaccgttgg acgacataac accacgcttc agttcttcat gttttaaata   4260
catatttaac ggatggctgc agagccagct gggaaacacg cggattgaaa ataatgctc    4320 cagaaggcac gagactgggg cgaaggcgag agcgggctgg gcttctagcg gagaccgcag   4380
agggagacat atctcagaac taggggcaat aacgtgggtt tctctttgta tttgtttatt   4440
ttgtaacttt gctacttgaa gaccaattat ttactatgct aatttgtttg cttgttttta   4500
aaaccgtact tgcacagtaa aagttcccca acaacggaag taacccgacg ttcctcacac   4560
tccctaggag actgtgtgcg tgtgtgcccg cgcgtgcgct cacagtgtca agtgctagca   4620
tccgagatct gcagaaacaa atgtctgaat tcgaaatgta tgggtgtgag aaattcagct   4680
cggggaagag attagggact gggggagaca ggtggctgcc tgtactataa ggaaccgcca   4740
acgccagcat ctgtagtcca agcagggctg ctctgtaaag gcttagcaat ttttctgta    4800 ggcttgctgc acacggtctc tggcttttcc catctgtaaa atgggtgaat gcatccgtac   4860
ctcagctacc tccgtgaggt gcttctccag ttcgggctta attcctcatc gtcaagagtt   4920
ttcaggtttc agagccagcc tgcaatcggt aaaacatgtc ccaacgcggt cgcgagtggt   4980
tccatctcgc tgtctggccc acagcgtgga gaagccttgc ccaggcctga aacttctctt   5040
tgcagttcca gaaagcaggc gactgggacg gaaggctctt tgctaacctt ttacagcgga   5100
gccctgcttg gactacagat gccagcgttg ccctgcccc aaggcgtgtg gtgatcacaa    5160 agacgcacact gaaaatactt actatcatcc ggctcccctg ctaataaatg gaggggtgtt   5220
taactacagg cacgaccctg cccttgtgct agcgcggtta ccgtgcggaa ataactcgtc   5280
cctgtaccca caccatcctc aacctaaagg agagttgtga attcttcaa aacactcttc     5340 tggagtccgt cccctccctc cttgcccgcc ctctacccct caagtccctg ccccagctg    5400 ggggcgctac cggctgccgt cggagctgca gccacggcca tctcctagac gcgcgagtag   5460
agcaccaaga tagtggggac tttgtgcctg ggcatcgttt acatttgggg cgccaaatgc   5520
ccacgtgttg atgaaaccag tgagatggga acaggcggcg ggaaaccaga cagaggaaga   5580
gctagggagg agacccagc cccggatcct gggtcgccag ggttttccgc gcgcatccca    5640
aaaggtgcgg ctgcgtgggg catcaggtta gtttgttaga ctctgcagag tctccaaacc   5700
atcccatccc ccaacctgac tctgtggtgg ccgtattttt tacagaaatt tgaccacgtt   5760
cccttcctcc cttggtccca agcgcgctca gccctccctc catccccctt gagccgccct   5820
tctcctcccc ctcgcctcct cgggtccctc ctccagtccc tccccaagaa tctcccggcc   5880
acgggcgccc attggttgtg cgcagggagg aggcgtgtgc ccggcctggc gagtttcatt   5940
gagcggaatt agcccggatg acatcagctt cccagccccc cggcgggccc agctcattgg   6000
cgaggcagcc cctccaggac acgcacattg ttccccgccc ccgcccccgc caccgctgcc   6060
gccgtcgccg ctgccaccgg gctataaaaa ccggccgagc ccctaaaggt gcggatgctt   6120
```

```
attatagatc gacgcgacac cagcgcccgg tgccaggttc tccccctgagg cttttcggag    6180
cgagctcctc aaatcgcatc cagagtaagt gtccccgccc cacagcagcc gcagcctaga    6240
tcccagggac agactctcct caactcggct gtgacccaga atgctccgat acaggggtc    6300
tggatcccta ctctgcgggc catttctcca gagcgacttt gctcttctgt cctccccaca    6360
ctcaccgctg catctccctc accaaaagcg agaagtcgga gcgacaacag ctctttctgc    6420
ccaagcccca gtcagctggt gagctccccg tggtctccag atgcagcaca tggactctgg    6480
gccccgcgcc ggctctgggt gcatgtgcgt gtgcgtgtgt ttgctgcgtg gtgtcgatgg    6540
agataaggtg gatccgtttg aggaaccaaa tcattagttc tctatctaga tctccattct    6600
ccccaaagaa aggccctcac ttcccactcg tttattccag cccgggggct cagttttccc    6660
acacctaact gaaagcccga agcctctaga atgccacccg caccccgagg gtcaccaacg    6720
ctccctgaaa taacctgttg catgagagca gaggggagat agagagagct taattatagg    6780
tacccgcgtg cagctaaaag gagggccaga gatagtagcg aggggacga ggagccacgg    6840
gccacctgtg ccgggacccc gcgctgtggt actgcgtgc aggcgggagc agcttttctg    6900
tctctcactg actcactctc tctctctctc cctctctctc tctctcattc tctctctttt    6960
ctcctcctct cctggaagtt ttcgggtccg agggaaggag gaccctgcga aagctgcgac    7020
gactatcttc ccctggggcc atggactcgg acgccagcct ggtgtccagc cgcccgtcgt    7080
cgccagagcc cgatgacctt tttctgccgg cccggagtaa gggcagcagc ggcagcgcct    7140
tcactggggg caccgtgtcc tcgtccaccc cgagtgactg cccgccggag ctgagcgccg    7200
agctgcgcgc cgctatgggc tctgcgggcg cgcatcctgg ggacaagcta ggaggcagtg    7260
gcttcaagtc atcctcgtcc agcacctcgt cgtctacgtc gtcggcggct cgtcgtcca    7320
ccaagaagga caagaagcaa atgacagagc cggagctgca gcagctgcgt ctcaagatca    7380
acagccgcga gcgcaagcgc atgcacgacc tcaacatcgc catggatggc ctccgcgagg    7440
tcatgccgta cgcacacggc ccttcggtgc gcaagctttc caagatcgcc acgctgctgc    7500
tggcgcgcaa ctacatcctc atgctcacca actcgctgga ggagatgaag cgactggtga    7560
gcgagatcta cggggggccac cacgctggct tccaccccgtc ggcctgcggc ggcctggcgc    7620
actccgcgcc cctgcccgcc gccaccgcgc acccggcagc agcagcgcac gccgcacatc    7680
accccgcggt gcaccacccc atcctgccgc ccgccgccgc agcggctgct gccgccgctg    7740
cagccgcggc tgtgtccagc gcctctctgc ccggatccgg gctgccgtcg gtcggctcca    7800
tccgtccacc gcacggccta ctcaagtctc cgtctgctgc cgcggccgcc ccgctggggg    7860
gcggggggcgg cggcagtggg gcgagcgggg gcttccagca ctggggcggc atgccctgcc    7920
cctgcagcat gtgccaggtg ccgccgccgc accaccacgt gtcggctatg ggcgccggca    7980
gcctgccgcg cctcacctcc gacgccaagt gagccgactg gcgccggcgc gttctggcga    8040
caggggagcc aggggccgcg gggaagcgag gactggcctg cgctgggctc gggagctctg    8100
tcgcgaggag gggcgcagga ccatggactg ggggtggggc atggtgggga ttccagcatc    8160
tgcgaaccca agcaatgggg gcgcccacag agcagtgggg agtgagggga tgttctctcc    8220
gggacctgat cgagcgctgt ctggctttaa cctgagctgg tccagtagac atcgttttat    8280
gaaaaggtac cgctgtgtgc attcctcact agaactcatc cgaccccga ccccacctc    8340
cgggaaaaga ttctaaaaac ttcttttccct gagagcgtgg cctgacttgc agactcggct    8400
tgggcagcac ttcggggggg gagggggtgt tatgggaggg ggacacattg gggccttgct    8460
cctcttcctc ctttcttggc gggtgggaga ctccgggtag ccgcactgca gaagcaacag    8520
```

```
cccgaccgcg ccctccaggg tcgtccctgg cccaaggcca ggggccacaa gttagttgga      8580
agccggcgtt cggtatcaga agcgctgatg gtcatatcca atctcaatat ctgggtcaat      8640
ccacaccctc ttagaactgt ggccgttcct ccctgtctct cgttgatttg ggagaatatg      8700
gttttctaat aaatctgtgg atgttccttc ttcaacagta tgagcaagtt tatagacatt      8760
cagagtagaa ccacttgtgg attggaataa cccaaaactg ccgatttcag gggcgggtgc      8820
attgtagtta ttattttaaa atagaaacta ccccaccgac tcatctttcc ttctctaagc      8880
acaaagtgat ttggttattt tggtacctga gaacgtaaca gaattaaaag gcagttgctg      8940
tggaaacagt ttgggttatt tggggttct gttggctttt taaaattttc tttttttggat      9000 gtgtaaattt atcaatgatg aggtaagtgc gcaatgctaa gctgtttgct cacgtgactg      9060
ccagccccat cggagtctaa gccggctttc ctctatttg gtttatttt gccacgttta      9120 acacaaatgg taaactcctc cacgtgcttc ctgcgttccg tgcaagccgc ctcggcgctg      9180
cctgcgttgc aaactgggct ttgtagcgtc tgccgtgtaa cacccttcct ctgatcgcac      9240 cgccctcgc agagagtgta tcatctgttt tattttgta aaacaaagt gctaaataat      9300 atttattact tgtttggttg caaaaacgga ataaatgact gagtgttgag atttaaata      9360 aaatttaaag taaagtcggg ggattccat ccgtgtgcca ccccgaaaag gggttcagga      9420
cgcgatacct tgggaccgga tttggggatc gttccccag tttggcacta gagacacaca      9480
tgcattatct ttcaaacatg ttccgggcaa atcctccggg tcttttttcac aacttgcttg      9540 tccttatttt tatttctga cgcctaaccc ggaactgcct ttctcttcag ttgagtattg      9600
agctccttta taagcagaca tttccttccc ggagcatcgg actttgggac ttgcagggtg      9660
agggctgcgc ctttggctgg gggtctggc tctcaggagt cctctactgc tcgatttttta     9720 gattttatt tcctttctgc tcagaggcgg tctcccgtca ccaccttccc cctgcgggtt      9780
tccttggctt cagctgcgga cctggattct gcggagccgt agcgttccca gcaaagcgct      9840
tggggagtgc ttggtgcaga atctactaac ccttccattc ctttttcagcc atctccacta     9900 ccctccccca gcggccaccc ccgccttgag ctgcaaagga tcaggtgctc cgcacctctg      9960
gaggagcact ggcagcgctt tggcctctgt gctcttttcct                        10000
```

<210> SEQ ID NO 196
<211> LENGTH: 500
<212> TYPE: DNA
<213> ORGANISM: Homo sapiens

<400> SEQUENCE: 196

```
ccggcacggc ccgcatccgc caggattgaa gcagctggct tggacgcgcg cagttttcct       60
ttggcgacat tgcagcgtcg gtgcggccac aatccgtcca ctggttgtgg gaacggttgg      120
aggtccccca agaaggagac acgcagagct ctccagaacc gcctacatgc gcatggggcc      180
caaacagcct cccaaggagc acccaggtcc atgcacccga gccaaaaatc acagacccgc      240
tacgggcttt tgcacatcag ctccaaacac ctgagtccac gtgcacaggc tctcgcacag      300
gggactcacg cacctgagtt cgcgctcaca gatccacgca caccggtgct tgcacacgca      360
agggcctaga actgcaaagc agcggcctct ctggaccgcc tccctccggc cctcctgagc      420
cctactgagc cctgctgagt cctggaggcc ctgtgacccg gtgtccttgg accgcaagca      480
tcctggttta ccatccctac                                                  500
```

<210> SEQ ID NO 197

<211> LENGTH: 1000
<212> TYPE: DNA
<213> ORGANISM: Homo sapiens

<400> SEQUENCE: 197

```
ggacgcggcc cgctctagag gcaagttctg ggcaagggaa accttttcgc ctggtctcca     60
atgcatttcc ccgagatccc acccagggct cctggggcca cccccacgtg catccccgg    120
aaccccgag atgcgggagg gagcacgagg gtgtggcggc tccaaaagta ggcttttgac    180
tccaggggaa atagcagact cgggtgattt gcccctcgga aaggtccagg gaggctcctc    240
tgggtctcgg gccgcttgcc taaaaccta accccgcga cggggctgc gagtcggact       300
cgggctgcgg tctcccagga gggagtcaag ttcctttatc gagtaaggaa agttggtccc    360
agccttgcat gcaccgagtt tagccgtcag aggcagcgtc gtgggagctg ctcagctagg    420
agtttcaacc gataaacccc gagtttgaag cccgacaaaa agctgatagc aatcacagct    480
tttgctcctt gactcgatgg gatcgcggga catttgggtt ccccggagc ggcgcaggct     540
gttaactgcg cagcgcggtg ccctcttgaa aagaagaaac agaccaacct ctgcccttcc    600
ttactgagga tctaaaatga atggaaagag gcagggctc cggggaaagg gaacccctta     660
gtcggccggg cattttacgg agcctgcact ttcaaggaca gccacagcgt gtacgaagtg    720
aggaattcct ttccaccaag agcgctcatt ttagcgacaa tacagaattc cccttccttt    780
gcctaaggga gaaggaaag gaaacattac caggttcatt cccagtgttt ccctggagta     840
atgctagaat ttacttttgt cataatgcaa aattaaaaaa aaaaaaaata caacgaagcg    900
atacgttggg cggatgctac gtgacagatt tttccaaatt ttgttgcggg gagagggagg    960
gaggagaatt gaaaacggct cacaacagga atgaaatgta                        1000
```

<210> SEQ ID NO 198
<211> LENGTH: 100
<212> TYPE: DNA
<213> ORGANISM: Homo sapiens

<400> SEQUENCE: 198

```
tttttaatgc tcagagaagt tcgtattact gattcgggaa cactgagttt ttcagctcct     60
gtaaaactat ttttcaggttt attttcaagt acattcttta                         100
```

<210> SEQ ID NO 199
<211> LENGTH: 400
<212> TYPE: DNA
<213> ORGANISM: Homo sapiens

<400> SEQUENCE: 199

```
caccctagag gcaaggacgg ggtctgtgtc aagaggcttc ccagagaagt gaaaactctg     60
caggtgcagc cgctgggaga gcatcaagaa gggcagggtg gaggggcagg gggcgaaggg    120
aggggggtgaa gcccgcaccc taccccacca tgaaactgat tccactaccc catctctgca    180
agcgtccaga ggcagagagg ccaacatttc ggggacagct tggaggcggg agatttaggc    240
agggctcctt aaacttttat gtgcatgaaa atcaggccaa tcacggggct cttgagcaaa    300
tggggacgat gattcagcag gtctgggctg aggcctcaga ttctgcactt ctaacaagtt    360
cccaggtggt agtgatgctg ccagtccaaa gaccacactg                         400
```

<210> SEQ ID NO 200
<211> LENGTH: 5000
<212> TYPE: DNA
<213> ORGANISM: Homo sapiens

<400> SEQUENCE: 200

```
tgcttcagtg gggtaaactt gaaccgctga gaagacaagc agggagtcgg tctcgctgag    60
atttttacct gtggttctag gaacgcagag gcatgtgagt gttcaggctt tgcatagacc   120
actaagccac ttctaagaac aaggctacct gagccatttt gcaaaaatat gtacgtgccg   180
aggcttttcc tccccacacc tacctcaact ctttctgccg acacactgca cttttcaagg   240
gaacccaagt ttgggttcgg caagaattgt acgttgcaca ccgtgtgtga taattccagg   300
gaatttcaat cgcatcttgt cttccttcct aagcaaattc ggtgggaacc tggtgtggtg   360
tgatagaaaa agccccgagt tctctgtggt agaccacatc aatttcatgt gccagtctct   420
cagactccgg cttgcctctc tcaaggaagg gaacaatggt ttgcttggct tcactcctct   480
cttcccccc aatttccaca tgggtatctg gctaaaaatg agttacaggt ttccttctgt   540
gagaattgca tggactgata aagtaccatc ccaggaagaa aacaaagatg ctgtcttccc   600
tttcggctca cagttgccgt tggggaggga acacacgctg taaattatag gcagccagaa   660
gtgaccgcat tgaccactgc gagtggccca gctatggcaa caggctgaga actctggggg   720
agagccattt gttggcaggg atggtgattc ttctagcatc aagctctaag atgatgacca   780
aacggtatca aaagaaatga tattttgcta cctctccggc ttgggtgaat gatgtggaca   840
gttaacctgg acaatttaaa cctttatgtt gatggatcac ttggatgaaa ttaaccagga   900
aattgccaag atttcacttg gccctctgac atcaaatctc aatattatat taccaaatta   960
gagattctaa agaaccctga gttcctttca ctgaaaggaa ggagtggaaa aacctttcca  1020
gatgatccct tttgagtctt ggtgcgagct caggccctcc ctacactgcc tccgtgaaag  1080
ctaaccgacc cttgttccta acctagcgca ggtcagctga gtgtccatcg ggcacaggag  1140
ccctgggctt gtccgggaga tagccagact cctgctattt cctgatgtct gcatagctca  1200
gcgtgtccct caccatcttt gccgttggcc agtaaggaga gccccagggg ccagcactgc  1260
acactgaaac ccaacctatt gctcaatgga atgcttaaaa atttcctgaa tctgccttcc  1320
tgagttgata aaataggaaa caatacacgt tctgagggg tactgaaagc agagtaaagc  1380
caggaagatc ttttttttct gttattctat acaaatattg cttcctctgc ttgttagcag  1440
cccagaggaa atgcagccag ggagccgttt gcagcttttc accagtggcc ggtgtctctg  1500
tgttaccaac caaacgacgc tgcaagacta gtgactaacg cacgtctgca tgattcaact  1560
tcactaaaat tccctctgct gccagtaaag aagcacttga aaactcttta atttgaaact  1620
tgagcttggt taatgacttg ttttcttctc tttctcttta acttctctct tgccatctcc  1680
aacacacaca cacacacaca cacacacaca cacacacact ctctctctct  1740
ctctctctct ctctctctct ctctcatcaa gttttttaat ttcagggacc cggaaacata  1800
cagccccgtg cattcacaat agcatttgct gtgataaagt ggccggcaag ccctctgcat  1860
tccccctgctc acttagctgt atgaataaat aatgagtcac agatacaatt tgggtgctca  1920
agagagtttg tagccagaaa attaattatt ctcccatccc agcccactcc atctcagctt  1980
tgccaaacca tcaagataca ctttgcaggc actggtcaga gtgcgtgccc cgacgcacac  2040
ggcaatgcct ttgagacatt ttatgttatt attttttgttt gtttaagcac agccctcttt  2100
taccacgaaa gatacacaag acgcacatgc acacacatac tcacacactc acagctcaac  2160
cacagctttg tccatttcaa gaggctggtt tcaaaaatgg agacaggttt tccaccctgg  2220
ctgttcctat tcataagcct gtaatctaac gacttaagct gcgagaatgc ttaactcggg  2280
```

| | | | | | |
|---|---|---|---|---|---|
| aaacttctct | attgccctttt | tccagagaga | cctcggtatg | ccacaatttg | cttcctttct | 2340 |
| ctcttgaaag | atgctggttg | tctctttgca | ttgaggctac | aaggaaaaac | acagcacagc | 2400 |
| cccatgctga | tgattttaac | ctaaccaagt | ctgtcagtct | cctgtactct | ctgccttata | 2460 |
| gagacagctg | ccttgccact | ttggccctga | agtcccagg | ctggtgcaag | gctatctgag | 2520 |
| agcctccgcc | tcctgcccca | cactggcacc | agccctcctg | gctggctctg | tgcatgtgcc | 2580 |
| tgctaagccc | cagggcaggc | tgcattctgg | gccacacagc | atgccgagtt | aaggataact | 2640 |
| cagacacagg | cattccgggc | aagggacagc | aaaataaaac | ccagggagct | cgtgcaagc | 2700 |
| ttcataatct | ctaagccttt | aaacaagacc | agcacaactt | actcgcactt | gacaaagttc | 2760 |
| tcacgcaccg | actgaacact | ccaacagcat | aactaagtat | ttattaaaac | atttctgaag | 2820 |
| agcttccatc | tgattagtaa | gtaatccaat | agacttgtaa | tcatatgcct | cagtttgaat | 2880 |
| tcctctcaca | aacaagacag | ggaactggca | ggcaccgagg | catctctgca | ccgaggtgaa | 2940 |
| acaagctgcc | atttcattac | aggcaaagct | gagcaaagt | agatattaca | agaccagcat | 3000 |
| gtactcacct | ctcatgaagc | actgtgggta | cgaaggaaat | gactcaaata | tgctgtctga | 3060 |
| agccatcgct | tcctcctgaa | aatgcaccct | cttctgaagg | cgggggactc | aatgatttct | 3120 |
| tttaccttcg | gagcgaaaac | caagacaggt | cactgtttca | gcctcacccc | tctagcccta | 3180 |
| catctctctt | tcttctcccc | tctgctggat | acctctggga | ctccccaagc | cctattaaaa | 3240 |
| aatgcacctt | tgtaaaaaca | aatattcaaa | ttgttaaaga | ttaaaaaaaa | aaaaaaagcc | 3300 |
| agcgccgcct | tggctgtggg | ttggtgatgc | tcaccacgct | gcgaaaccct | gtggtttgca | 3360 |
| ttcagtgtga | ttcgtcctgc | ctgctgacca | ctatgctggg | ttcagacttc | tgacactgcc | 3420 |
| aggctaccca | acttgtggtt | ctgtggttgt | ttatgaggcc | caaagaagtt | ttcacacaac | 3480 |
| ccaaattaca | aatttaactg | ttccccttc | cacagcccat | ctcaattggt | tcttgccaat | 3540 |
| catgtgactt | aagtgatgtc | aattttttt | tttcttttct | gagcaatgcc | cttccttccc | 3600 |
| tccacctgcc | ctcccccagg | ctgtgcaaga | aaatagccga | gtagactttg | caagaggggg | 3660 |
| ggatgtagaa | aaaagtgact | cagtcactta | ttatatctca | atggtctttg | ctgatttagt | 3720 |
| acaactcggc | tcctgttgtt | atttgtggtt | tttggaacta | ctgattattt | tgataaagat | 3780 |
| ttcattgctg | cttattcaat | agtaattcaa | cgctggcatc | aagccgctgc | tccgacagga | 3840 |
| tgtggatccc | atcattaaa | atgctaggca | tcagctccgg | gagagttaag | tccttggtaa | 3900 |
| cgtctatcat | ggcataagtg | aaactataaa | agggaaaaat | aaataaaaag | aaatgttttg | 3960 |
| gtgagagtct | gaccctaca | acgggctggc | aactcacagg | tatttaaag | cctgggaaag | 4020 |
| ggaaagaatt | ttacttttga | aataaaagga | ctgtttaat | gaaaccaaaa | ttatgtggtt | 4080 |
| ttattccccc | taaatggaca | actttagtat | gtatctcttt | cagtaaagag | ataaaatcat | 4140 |
| agtacagtct | taacacacac | acacacacac | acacacacac | acacacacac | acaaattagg | 4200 |
| aagctaaagg | aaaacaaagc | agagagaatt | tctgtatttg | ggacaaagca | gtggttactc | 4260 |
| tgcagatgtt | tatttgtatt | gtcacttggg | aaagctccct | gtattgcctt | tctctagttc | 4320 |
| aattcaaatc | aataggctaa | tttacacctg | taggtaaaac | tacactttga | gcacatgagg | 4380 |
| atgccacaat | agaaggggaa | ccaggaggag | acacttctcc | tggggctgac | taatgaatat | 4440 |
| tatatagcgc | gtcctctacc | ttagaaagac | atgcctgttt | gaagatgcta | aaaacaggat | 4500 |
| aattttgtaa | gtgggcaaac | cactgtggtc | acacgtattt | cattttccgg | ccccactggc | 4560 |
| tttacctgct | gacaactaaa | acgtcatttt | gttttgtagt | tccaagatga | agaaaggctt | 4620 |
| attttcctga | tttactacct | tattcatttg | gctctgctct | gcctacatcc | gccatagcac | 4680 |

```
tctgcgcacg tgaaatttcg acacataggg tcaagagaac ctgtgtgatg atgggttgta    4740
aatgccagtc ctggattcta agctgcagta gccagcacag gcacttcaga aaggctgaac    4800
tcccacaaca ctccctcggt tttccctcat ccacttaatt tcacacacac aaagacccac    4860
aacgatagta gcttccatgg cacaagtctt tcaaaaggaa cagacacaat ttttacttac    4920
tcctgttttg actaaagcag gaattgaaac tcaacagacc gctttctctt acacttgtga    4980
gaagttagct ggccacatgt                                                5000

<210> SEQ ID NO 201
<211> LENGTH: 500
<212> TYPE: DNA
<213> ORGANISM: Homo sapiens

<400> SEQUENCE: 201
agggaaaaga gataacgaaa gaaagaaaga aaaaaaaaag ggccggcaat tcatgtaca     60 tttgttttgg cattcgctga attctagaga tgaaaacaat ctcctgcttt taattcagtc    120
cacgtgcaac aaagttgtac gttgggagat ctggctttta ataagaacga ttaacaagcg    180
tttttgatca caggaagttg agaagagtcg ctgcttctaa gaatacaata aacattgact    240
agcagttaga cggtccatct ttctctatca gccgtttagc agcctctact ttgatttggg    300
gcaaatgcga gatgggacca ggagagagct ccccacaccc ccaccaccac gtgggcagtg    360
gttctgttcc agagcgcctt ccttcctgtc cagggaggca ggctgctgag gccgtttctg    420
ggcaagaggc cattgtcggg atatttgctt tagatagctt gcagctgggc tgagtgggtg    480
tttcattcag actcaacaca                                                500

<210> SEQ ID NO 202
<211> LENGTH: 700
<212> TYPE: DNA
<213> ORGANISM: Homo sapiens

<400> SEQUENCE: 202
agcctggcgc acccgcccta atttgagtca gggaccctag gcgcctgcag ctccggttcg     60
ggttgagtgc ctcctgtcag gatgtgaagc tgctgtcccc cccgggggcc tccagcactg    120
ctgaggactc agcagtcagc ctctcctccc acttgggctc atttacagag agcatctcca    180
ggaatcagtc atggggaaag gggaaacgcg gagtgacaac acaacacgta gaaagttctc    240
tgccgccttg gtcaggcttg tcagcctcac agcccatcct gctcctgcgg gaggaaaagt    300
gagcagaact cagcccggag atgagccgca ggccggcagc ccctgcctct gccctgcttg    360
ttgtgactgc aatgcaaggc tctctgtagg tgcgggggat tcgggttaaa tgggtctcca    420
gtggtccagc gctcccagca aaggccgacc acaagaatta gcgggctagt tatttaccat    480
aaccatatac aaaaccacaa gcatcagcgt tccctcaaat acatccgaga cgctgtatat    540
ctctttatta aagcctgtca gggtttgtta ttgcacagct tggccttgaa ccccaactaa    600
accaggctgc ttgagcaaag aaccaagcaa tgcaagcatt caggcaggac cattataacc    660
ctgaggccaa aggcagaagc agggagagga gacgtcttcc                          700

<210> SEQ ID NO 203
<211> LENGTH: 500
<212> TYPE: DNA
<213> ORGANISM: Homo sapiens

<400> SEQUENCE: 203
```

```
agaccagcct cggtcttcgg cctgcgggtt ctgcaaagtc aggctagctg gctctccgcc    60
tgctccgcac cccggcgagg ttccggtggg gaggggtagg gatggttcag ccccgccccg   120
ctagggcggg gcctgcgcct gcgcgctcag cggccgggcg tgtaacccac gggtgcgcgc   180
ccacgaccgc cagactcgag cagtctctgg aacacgctgc ggggctcccg ggcctgagcc   240
aggtctgttc tccacgcagg tgttccgcgc gccccgttca gccatgtcgt ccggcatcca   300
tgtagcgctg gtgactggag gcaacaaggg catcggcttg gccatcgtgc gcgacctgtg   360
ccggctgttc tcggggacg tggtgctcac ggcgcgggac gtgacgcggg gccaggcggc   420
cgtacagcag ctgcaggcgg agggcctgag cccgcgcttc caccagctgg acatcgacga   480
tctgcagagc atccgcgccc                                              500

<210> SEQ ID NO 204
<211> LENGTH: 1500
<212> TYPE: DNA
<213> ORGANISM: Homo sapiens

<400> SEQUENCE: 204
aaacgtttaa aatatatttc taaacagaat gggccaattc agtcacagta actgttgatc    60
tccatagcag agcaacccac aaagacagaa ctgattttttt tcccataatc aggggtgaaa   120
aatatacaac ttgtttctga accaaaacca caatttctgc agtttaaaat gtttcactgc   180
taatatggcc ctggtagaaa ttatgtagtt tcttttcttc tttaaaaaaa aaaaaaatta   240
aaaaaatttc ctaagacact aaatgctcca tctggaatgt agattctgat cacaaagcag   300
ctcagttaac ctaaaaaata aaaaattccc atcacctgtc tcagtagggc ctgagagtag   360
tgtggggaac cccagctttg gtatggagag tcatggcccc ttgaaccaga tagagacctt   420
gaatagccat agctggtgct ctctcagga taaactctga tgtaggaagt atcaccctca   480
tgagagtgga atttggtcat ccagttgacg cagggcatat tccatgtctt cttttctgag   540
acacccaacc atccccactc catccttctg cacatccgtg taacaggcat ccccagcttc   600
tcgcgtgtga tccttcaggt cctgccagct gcctgatgga agaagtccat tcttccata   660 aatagcatcc tctgcatctc gagggtcctc gaagcgcacg gaggcgaagg gcacaaggcc   720
gtaccggctc ttgagctcga tctcgcggat gcggctgtac ttgtagaaca ggtcctgcgg   780
ctccttctcg cgcacgtggg tcggaaggtt tccccacgta gatgcacccg tcgccctccc   840
agccgcgctc gtgtccgccc agccggacaa ccgcaccgcc cgacgctgct ggccagccgc   900
agcccgcatc cgcccgtatc gccgccgctg ccgcctcagc acggctgccc ccgcagcgtc   960
tgttttgttt tattctaaca gggtctctct ctgtcgccca ggctggagtg cagtggcgtg  1020
atcttggctc cctgcaacct ctgcctcccg ggttcaagcg attcacctgc ctcagcctcc  1080
caagtagtgg gcattatagg tgccagctaa ccatggccgg ctaattttttt ttttttttt  1140 ttttttttt tgagacagag tcttgctctg tcacccaggc tggagtgcag tggcgcgatc  1200
tcggctccct gcaacctccg cctcctgggt tcaagcgatt ctcctgcctc agcctcctga  1260
gtagctggga ttacagctat gtacagcgat gtctgcaaag atagggattt aacagcactc  1320
atatcttcat gttcataaaa aagtcctaca cgcgtgatgt acgtctagat cttttccttt  1380
gtcacaggat atagcacggt agttacggat atagtctccg cagtgcctgg gtttgactca  1440
gcttccccac gtactgtcct gcgcatattt tgtgtctcag tttcctcatc tttaaggtag  1500

<210> SEQ ID NO 205
<211> LENGTH: 17000
```

```
<212> TYPE: DNA
<213> ORGANISM: Homo sapiens

<400> SEQUENCE: 205
cacgcgcccc ggcctggctg gaggggccaa cccagcgggg cccgcctgcc cgccggcctt      60
tctgtaactt tctctctttta aacttccaat gaatgaacgt gcctcttctt acggatttgt    120
ttagattagg gaatagattc ctcgctgata gcgttgcttt gcaaataaga cctcctatat    180
tattcaaacc aaacgagttt gtgtctttaa aggactatag cagccccatt ctatgttaag    240
ggttggctat tacaattatt atatgcttag ggaaaaaatg taagcccgt agtttgtgct     300
tttcttgatg tacagaaagg tttatcttag gtggataggt tttgttttgt ttcttaaatg    360
ggattttttt ggttcgtgtc tttgaagggc tgtttcgcga cgtcattaat gaactaatcg    420
gttttcagat ttcaagacgg tgtgtaattg atgtaaccac tgaggaattt cagtgcacac    480
cagactaaga ctcttccagc gcagggggatt ccagatgctt cttgggccct ctggaagcca   540
tggggatgtt tccagaccga aaggagggct tgctgggga gcagatgtgc tgcctctccc     600
cgacccagga ttttgaggcc atgtttccgt taatctggac cgagagccct ctgggagagg    660
gaggcaggtc gtaggggcg gggtgaggg ggagcgagat gaggtcgtcg ctggacgctg      720
ggctcccttg tcgttgtcct tttccccaga atccatggtc aggcctaggg agccacccct    780
gggtgctcga gatgagtccc caccctcact gaaggtcggt cactggatgt ttgtgtgcat    840
cgtaagggc ccaccgaagt cccgaagcct tctcaggac cagcgagaaa gaggagcagg      900
cttgggagac agggaaggaa aatgcagggg aaagggctca cccctcgacc ccaggtaaaa    960
ttagaaggaa cgtgtggcaa cccaggtgca gctttggtcg ctcgctcaag gactttgcta   1020
gtcactacca ttaattaatt aatcactatc attaactacc aaggacaccg tttttattcc    1080
cctaaaagcg tcaccttgag gggaatggag aattgggcag cagctatgca aatcctggga   1140
caggagacac tgcctgagga ccctctctca ctcccaatcc cagaaccga agttatcccc    1200
gacaaccaag tccaagcaca tgaaccaaga cgatcagctt caggcagctc cttacccca    1260
caagcggccc aggaggtggg cattatcccc caccctggg atttctccat ccctccctct    1320
tctctcctgc gggagagaga gctgtggtca cccagttggg cgcgatggct ctggactaat    1380
ggggtctcta gacccagggc acaaaggcca atctgccagg ggttactgca tgtaatgaga   1440
taatcagaca tgttgaccaa cctaaaagaa aagactctcc cagggagtaa ctcccagtga    1500
aataatttat taaaaaagc aaaaagaga cataaatttc tctctactac ttgaggaaac     1560
agcaaacaga acgaattagg gtcttggcct ctgcaggaat aaattattc cgacttggtc    1620
tggatacctg taattatttg taagctgtgg gtagtaatac tgtaattgtc ccccggtcct   1680
ttctggaagt agcaatgacc ccaaggacaa ttggtgacgt ctccacaggg tttacacatg   1740
gaaaggagtg aaaaatcgag gaattctttc agatagccca gaccaaaaat cctctcagcc   1800
atgaaaggt catatatgtg atgctgggcc aagcggactt ttctggagta accatatcat    1860
aactgattgc ggatgtagac aagagcgtat aaaccaaata ggcttgaatc aacgcagtcc   1920
tggattttct gttgcctctg cttgctgggg cagtggaagt tcttaaactc cacttcagag   1980
gttgaaaatt cttccccctc ccccacctcc ttagtgacaa ggtctctgat ctcctgctgc   2040
cactgcaata gcctctccca tcccgcgggg aacggccgga gttcttccct tgatctctcc   2100
cgagtcggct tccgctgggg atggatcgca ggtaggcgcc ggcgcggcct ggggaagaac   2160
agttgcggag catctgaagc ggaaaatcca agcagatgtg aggcgatccg ggcccgcctc   2220
```

```
gttcctcttg ggqcctgaat ttcttccaga taagtttcct aatggaacat ttctaagagg    2280
tggggtacga ggcggcttgc tcgcacgcgc agtgggacag actgcgggtg ggacgtact     2340
gagaggtccg gacctcaatg cgtccgaccc gtctccacac cgccctttc cagcccccag     2400
tctcctttca ttccctactc ttcaggctcc tttggggcca gtgggtgaac cgccatttag    2460
aacggtgcct cggactcggg ggtcgtgcgc tccatctctg cctcccccct ggggcccgcg    2520
aggctggtcc gggctttctg agctgggcgt tcggctttag gcccaatacc tggaccagga    2580
atttcttctc cccgcgccag aagggaaaga cataggaggt gtcccaatct gcggtcaccg    2640
ccgatgctcc tgaccactct agtgagcacc tgcccggtac ttttccattc caacagagct    2700
tccagcttca tactaactat cccacatacg gcctgtgggt attagctcta agtgtccttt    2760
tccgagggcc cgaggctccc cctccagcag ggagagctcc gggacggccc ccaccaaggg    2820
ttgggttct tccttcacaa ttccacagag gcatccctgt ccttcctacc tgggaaacct    2880
cgaggtgcgg tgcccgtgta cttctggtac tttgcgtggt gccatcaggg accccagagc    2940
cacagctgcg tgtgtgtgtg gatgtgtgtg tgtgtgtgcg cgcgcgcgcg tgtacgcga     3000
aaggatgtgc ttgggggagc cgagtacaca acgtctgctt gggcagctgc tgggcaggcg    3060
ttgggcctgg aggtatctca cacccacgta tcttccagtc ttcaaacacg gcattgctct    3120
gcctcccgta gcgcgcttcg aacctgcctc gcggacacgt gaacagaggc tgtccctggg    3180
aagataagtg cgctttcccg taaaatccgg gaaatttgcc ttgaggaaag tttccgttct    3240
tgttacttgt cgggtttctc ccacttccac ttagccatgt ttctgcgatc tgggtaatcc    3300
ctttcaagcc caggaggaat tctcccgggt ccataattga gggtcggaag ccgtgggggt    3360
gagaaacgca ttaaatcctc ccgaagccca ggaggtgcca gagcgggctc aggggggccgc   3420
ctgcggaagc tgcggcaggg gctggttccg tagcctctaa ccccttggag ctccttctcc    3480
cagaggcccg gagccggcag ctgtcagcgc agccaggagc gggatcctgg gcgcggaggt    3540
gggtccgact cgccaggctt gggcattgga gacccgcgcc gctagcccat ggccctctgc    3600
tcaagccgct gcaacaggaa agcgctcctg gatccgaaac cccaaggaa agcgctgtta     3660
ctctgtgcgt ccggctcgcg tggcgtcgcg gtttcggagc accaagcctg cgagccctgg    3720
ccacgatgtg gactccgcaa ggggctaggg acaggcaggg ggagagcccg ggtttgcgca    3780
caccttccag cccctggagg gagcctgctc ggcttcgaac gccttcgaac tttttgacctt   3840
caaaggagtc cctggaaaag gtcaggagcg cctgctgcag gcacggttgc cgaaggccag    3900
gccttcctgg cgcaggggag ggccagggga gggaagcgga tactcagtcg ctgtccgacg    3960
gcgagttttc ggagcagcag gctcatgatc ccgggccagt ggcgagagca gtgacaccga    4020
gaacccaaat ctccgcgccc ccatccgcgg cccggtgtcc tcccggcccc tgctgacctc    4080
caggtcacgc acccccactgc tccacggctc tgcagcctgt ggcacacggc cgagagtccc    4140
cacatgatct cgacgccaag gtaaggaatt gccctgcgtc ctctgagcct gtctctggcc    4200
tgggggggccg ggaaagctgc actcctggaa gaggtggggt tatgtgaccg ccgctgcagg   4260
ggtgcgcgga ggactcctgg gccgcacacc catttccagg ctgcgggagc cggacagggg    4320
agggcagagg ggggacaaaa ggactctta ggtccaaaat gaccctgaag gagagtccag    4380
aatgcccagt ggccgcgtct gcaacggagt cttctttctc caattgcctt ctgccccatc    4440
accatgggcc ccacctgcgc cacctgcgcc caccctgtga ccctggctca gcgaccttgg    4500
cccttaatcg cccaacgccg attcctcaaa attccggctg cgctgaatcg ggctgctttt    4560
gccgccgccc cggcagttgg gccctgtttc cgccggcgcc ctgggagagg cctcaccact    4620
```

```
cggctgggct ccctggcccc tcccttcccc tggcctgagc gccccctgcgg cctcccgctc    4680 ctcctgagaa ggcgacaatc tctttgcacc ttagtgtttc gaggacagaa agggcagaag    4740
ggtcacttcg gagccactcg cgccgttttc acgtgtgtgt gtaatggggg agggggggct    4800
cccggctttc ccctttcag ctcttggacc tgcaacaccg ggagggcgag gacgcgggac    4860
cagcgcaccc tcggaaggct cgatcctccc cggcagggcg cctggccaac gagtcgcgcc    4920
gcctcctctc ggccgcgcct gctggtgacc ttcccgagag ccacaggggc ggcctcggca    4980 ccctccttc cctcgccctc cctgccgccc atcctagctc cggggtccgg cgaccggcgc     5040
tcaggagcgg gtccccgcgg cgccgcgtgt gcactcaccg cgacttcccc gaacccggga    5100
gcgcgcgggt ctctcccggg agagtccctg gaggcagcga cgcggaggcg cgcctgtgac    5160 tccaggccg cggcggggtc ggaggcaaga ttcgccgccc ccgcccccgc cgcggtccct      5220
cccccctccc gctccccct ccgggaccca ggcggccagt gctccgcccg aaggcgggtc     5280
tgccataaac aaacgcggct cggccgcacg tggacagcgg aggtgctgcg cctagccaca    5340
catcgcgggc tccggcgctg cgtctccagg cacagggagc cgccaggaag ggcaggagag    5400
cgcgcccggg ccagggcccg gccccagccg cctgcgactc gctccctcc gctgggctcc     5460 cgctccatgg ctccgcggcc accgccgccc ctgtcgccct ccggtccgga ggggccttgc    5520
cgcagccggt tcgagcactc gacgaaggag taagcagcgc ctccgcctcc gcgccggccg    5580 ccccacccc ccaggaaggc cgaggcagga gaggcaggag ggaggaaaca ggagcgagca     5640
ggaacggggc tccggttgct gcaggacggt ccagcccgga ggaggctgcg ctccgggcag    5700
cggcgggcgg cgccgccggg ttgctcggag ctcaggcccg gcggctgcgg ggaggcgtct    5760
cggaaccccg ggaggccccc cgcacctgcc cgcggcccac tccgcggact cacctggctc    5820
ccggctcccc cttccccatc cccgccgccg cagcccgagc ggggctccgc gggcctggag    5880
cacggccggg tctaatatgc ccggagccga ggcgcgatga aggagaagtc caagaatgcg    5940
gccaagacca ggagggagaa ggaaaatggc gagttttacg agcttgccaa gctgctcccg    6000
ctgccgtcgg ccatcacttc gcagctggac aaagcgtcca tcatccgcct caccacgagc    6060
tacctgaaga tgcgcgccgt cttccccgaa ggtgaggcct caggtgggcg gccggggacg    6120
ctggggagcc cggcggcccc ggcccaggcg ggaagcgcaa gccagcccgc ccagaggggt    6180
tgccgcggcc tggcgtccag agctgggcg tctgaggag gttgcgtgag ggtcttcggc       6240
ttcggcgctg gcttggggcg aggggccagg gccttggcgg cccaggcgac caaaccctct    6300
cctggtccag ggctgggtga gggcgaatta cgaattgttc caggggcagg cagtccccca    6360
gcccgcacgg ccagcgagtt ctttctggtt ttgttctttc tcccttcct ccttccttcc     6420 ttcgccagtg cattctggtt tggtttggat tttttctct cttctttcc tttctttctt      6480 tcttctctt tctttttctt tcttctcc tcttctttc attctcccct tccttccttc        6540 cttgccccc tctctccctc cctccttcct tccttccttt gccaatgcat tggtttgttt     6600
tcttcctttt tctgctttcc ttcctttctt tggaagttca ctctggtttt gctttctttc    6660 ttccccatc ccttccttc tttatccctc cttcccttcc tcctttcttt tctacgattc      6720
cctttatttt tccttcattc ctccctcttt ttgtctcttc tggaggaggt gaaggagggt    6780
cagcttcagg cgctgcgagt cagcggggat cacggtgagg cccaagcact gcaggctgag    6840
gccacagagc gaaacttgt gctgagccgg gccctctcgt gaggctgggg tgcgggaagt     6900
ccgggcagga gagacccgcc cccgccgttg ctgagctgag accggctga aagagagggg     6960
```

```
tccgattaat tcgaaaatgg cagacagagc tgagcgctgc cgttctttc  aggattgaaa    7020
atgtgccagt gggccagggg cgctgggacc cgcggtgcgg aagactcgga acaggaagaa    7080
atagtggcgc gctgggtggg ctgccccgcc gcccacgccg gttgccgctg gtgacagtgg    7140
ctgcccggcc aggcacctcc gagcagcagg tctgagcgtt tttggcgtcc caagcgttcc    7200
gggccgcgtc ttccagagcc tctgctccca gcggggtcgc tgcggcctgg cccgaaggat    7260
ttgactcttt gctgggaggc gcgctgctca gggttctggt gggtcctctg ggcccaggag    7320
ctgggagggc tgcgccggcc tctggagccc cgggagccag tgccgaggta gggagacaac    7380
ttccgccgca gggcgccgga cggtcggggc agagcaggcg acaggtgtcc ctaggccgca    7440
gggcgcttcc atagcgccat ccccaccagg cactctactc gaaatcggaa agctcgacct    7500
tttgcgttcg cctctgccaa gcctgttatt tgtgctggcc gctgggtctg gagctgcgct    7560
tctcggcccc tccccggtgg agcgcagagg gctggtctgc aagcgcggcc tccagccccg    7620
cggctccccg gcccaggagc caggcgcggg ctgacccggg agcacccggc agcggagggg    7680
gctggaagcg gaccctaggc ctctcctgtg ccacccggcc ctaccgcgcg gccgcggggc    7740
gctctcctct cggcgcagc  ggtccttcag cccagggcag gttcctccct ttcctactcg    7800
gaacgtggca aagataccc  agtcccagcc cctccagctg agagctgttg cccaaggtcg    7860
tcgctacttg tccgctcaat ggtgacccct tggcagagaa ctagggatga ttccactccg    7920
gttgatgttt taggggaaat taaaagaaca ttcggttttc tgagtctcct tccggggagg    7980
cgtggtggta actggtttgc tgggaagagc cgttccttaa ccgcatgcaa caaagcaggt    8040
gtggaatccg gacgagaggg cactcactgc cttctgcccc ctttggaaat agaaaaagcc    8100
ttcgaagcag caatccaaag atcaaatgat ttgcggtcaa tgatttcaat taaaccagaa    8160
attagtaagg gagggccgag aagacacggc tgctcagaag ctgttcgctg tttgagggat    8220
ttcccggaga gcctgttaaa agatgcgaag tggtgggtgt accgctcagc cacctttaaa    8280
ccggctctgt gcgttctggc tctggaaagc aagtctccag gcatttgggc tcagaattgc    8340
tgggccccga gtttgggcgg gggtggtcct tctgggggtc aggccttgag cagcttgcac    8400
tggtggcagg tttgggagca gttgaggggc ttcctgtgtg tcttttggag ggggtgaccc    8460
tggaagttgg cactctggaa gggagctgtt tggccctaga gttttggaaa gggccctgaa    8520
cctgttcggt cccctcgga  aagggaaggg agcagtggct tagtccctcc ctcctccatt    8580
cgtgcaatgc ctggggtagg ggtagacctg gagccggtgg actcatatcc ttggaattcg    8640
tcaggacagc tgctccgggg ccttggccct cagtcagtct ggggctgagg agtagggaag    8700
ctggaacttt ggggcagagg aagaagatgc gtttagaaag acctccatta tgcaaactgg    8760
agtccattta tgcaaactgg tcacccttcc agtagctcca aagagtggca gtggagtggc    8820
atcttgattg atttaacctc ttctcagggg acctgggtct gcgagggagg atatggctgc    8880
ggggttggaa taggatctgt ctgagctgcc agggtcaggg tggtggccct agggaggttt    8940
tagggccagg gtggtcccgg gctgtggcag gggctctcag atcgcctcgg gctctcagct    9000
gcaaggtgaa aaataccatg aggaattgat ctgccaaggg cggtcttgtc tcaaagcaag    9060
tggattgctg gggtaaagaa tctagagacc agcttaggac tctgggagga agaaaaaaaa    9120
aaaagaata  gcatagtcct aaggaactgc aaggatcacc agattaaccc ttcatacctg    9180
gggaaattaa ggccagacat gacacaggcc tttcccaagg ctctgtagca agggcaatag    9240
caggccagtt gctgccactg cggtcctgtg gggcatgttc tcactccact gcacccagga    9300
ggctgccagc ctctgttcct tttaacatag atctcctcag ttgttaagac agaaagagga    9360
```

```
actcagaggg gtccctgtgt gcaaggcaga gggagaccac cagaaccagg gtaagcaccc    9420
cacttggtag ccagttcaag gacttgggga tgttttcaac atttacagcg aggtttgagg    9480
ccccattgtc atgcagcgct actcggcctt ggtctcctta tctgtaaaat gggcccatta    9540
gcaatgcaca gggttgctgt gatgaagggt gaggtcccac aagcaaaagc tgtgcagtga    9600 gggggaatc ctaagcattg ttcctatgcc attcacccct tcctgtgagc tccccatatt    9660
ccctggctca aaggagtctt gaatggcagg gatggaggac tcactgcctg gactttgaag    9720 accctgctt tctgggtgac cacctttct tcctttgac agtgaactaa tacattggag    9780
gtagatagtg ctgggaagag gacaggagac cacggctgac tttggacatg ggctcgaaat    9840
tgataacttg atgagtcttg gagggtggtt aagataagct cggggctggg gcagcgctga    9900
ggtctgatgg tcagccagcc ctccccaaag tgtggccctc cgttctggag ataggggctt    9960
tggaaactgc aaaagcgtcc tggcaggcca gctctggttg ctccctggcc atagctgctc   10020
tgactacagg cagcaggacg caggtcggcc tctgcccatc ggaggtcaga ggcagggcct   10080
ccagcaccag actcagcagt gccactgcaa acctggcaca acaggctggt cccaggactc   10140
agctcagcag tgaagttgga aaccaaggtt gagtctcccc atctcccttt ccccaacccg   10200
aaagacccaa gatgggtgtg ggtgaaagag ggagaaagaa ttgctactcc agaaactgtc   10260
atttgcccac acgaaacgag gtggggttca aggtctgaac tcttccagtg cctgggtgcc   10320
tttgggttta aattcagctg caggtgcccc catcaccact tccacctgag cacaccacga   10380
gaagccaggt tatcttagaa actgtttccc ggaatcaaag cgacttgatt tggagagttg   10440
ggtgaggaga aactcacccc tatacccctc agggcgtcag agatgtgagg caattctcta   10500
cctccgctgg aaaaaatgca gatttattaa aggtcgactg tttagcagaa caacgtagat   10560
tttttacaac gctttcccc g tctctgcttt gaagcctgcc aggctgcagc tggggatcca   10620
ggagggaaag cccgcaggcg cagagggac aatccgggaa gtggtaaagg ggacacccgg   10680
gcacagggcc tgtgctttcg ttgcaggcga ggaagtggag cgcgcgctgc agattcagcg   10740
cggggctaga ggaggggacc tggatccctg aaccccgggg cggaaaggga gcctccgggc   10800
ggctgtgggt gccgcgctcc tcggagccag cagctgctgg ggcggcgtcc gaactcccca   10860
ggtctgcgca cggcaatggg ggcaccgggc cttctgtctg tcctcagaat acgtaggata   10920
cccgcgggcg acaagccggg ccaggctagg agcctccttc cctgccccct cccatcggcc   10980
gcgggaggct ttcttggggc gtccccacga ccacccctt ctcacccggt ccccagtttg   11040
gaaaaaggcg caagaagcgg gcttttcagg gaccccgggg agaacacgag ggctccgacg   11100
cgggagaagg attgaagcgt gcagaggcgc cccaaattgc gacaatttac tgggatcctt   11160
ttgtggggaa aggaggctta gaggctcaag ctataggctg tcctagagca actaggcgag   11220
aacctggccc caaactccct ccttacgccc tggcacaggt tcccggcgac tggtgttccc   11280
aagggagccc cctgagccta ccgccccttgc aggggtcgt gctgcggctt ctgggtcata   11340
aacgccgagg tcggggtgg cggagctgta gaggctgccc gcgcagaaag ctccaggatc   11400
ccaatatgtg cttgcgtgga gcagggagcg gaagaggcag ccggtcctca ccctcctctc   11460
ccgccacgca catatccttc ttgacttcga agtggtttgc aatccgaaag tgagaccttg   11520
agtcctcaga tggccggcaa cgcgccgagg tcacgctccc cagaaacacc cctctcccct   11580 ccctacccc agctcccct ggggcgggtg gtaattgggg gaggagaggc cgcaggcagg   11640 gaagggggtgg gaaagccaga gagggaggca caaagtgatg gcagcccggc aaacactggg   11700
```

```
gcttcgggct gggccgcgct cgtttaatcc cacaaaaatc ccattttgga ggtgagaaat   11760
agaggttaga ggtcgggccc ttctggagat cagaccgagg agacgggccc agctggcgtc   11820
ttaaagcaag gaggggagt cgggaggagg tgagaccct gcacccaggt ggggctccca    11880
aaccgttctg gatttaccac actcccaggt ccgattttcc atggagggct ggggttaggg   11940
actggcacct tcttgttgtt aaccgcattt gatattcaca agaaccctgt gaggagactt   12000
tgtcaccgtt tttagatgcc tgaggttgcc ggaggggcag tgagagaatc gtctaacctg   12060
gtgttcctac cacagtccag gccctgtgtc ctgggctgga cccacagccc ctgccaccac   12120
ccagaggaag gcgcgaagct ggctgcctcc tttacgggtc tcccttaggt gccctcatga   12180 aggggacgg ccacctcaca gtgcaggaac tatctcccg tttgctccca aatagtcttc      12240
ttggtgtggt gctgtctatg gtctgtgacc tgcatctgga gttaccccca ggaccagctt   12300
cggaagagga gggatcgctt ggaggccgtg cagtgtgagg aacggcaggc agggtgtggg   12360
accaacatgc acacactcgc aggtgctggg gccaggagg aatgaggcgc tggctcccctt    12420 tccctccatt tctccctggg ggtcccagca acctggccat ccctgacttc aacagcaca    12480 gcgtccccac aggtcctgca gtgctctgca ggggtgcagg gagctcccct ccccccagcc   12540
gcaacctcac cttcctcacc cccacccctc cggcaggaaa ccacaggctg ggttggggac   12600
ccctggtgct ccaagagagc agtgagtgct gggagccgct aaccccgagg cgcctagcac   12660
agactcttct caccccttat ttctgaaata agcccttcc ttaggtccag atgaggacca    12720
cgtgctcagt gcctcacttt cgtgggagtg tatatcactt tacagtatca agacaatttt   12780
ctttcgttac aaatctttat ttagtctctg cgtttagacc aaagtagatt tttatgggct   12840
gagtgaaaaa acctcgcccg cattggtttc tgatggaaca gctggcagcg ccacggcccc   12900
gggtggggtg gcctagaggc aggggtgctt ggaggaaca tctagcaccc gaccacctcc    12960
accaggtggg aaagggacgt ttgcaccaaa tctccgccgg caaagcagag gctttgggga   13020
attacagaaa aactataatg atctaaaaga gaacaagtta tcttgaactg tgcgggtatt   13080
tgaatcatac agaaaattgt cctgtgtgcc caatgcactt ttgcatgtag agccagggcc   13140
ttcgaggaag ctttcaggag atcccgggca gcggagtctg gtctggagtt tcatttccgt   13200
aggtgcagat ttctccccaa gtcttcccgc catgggcttt gcaagaagcc agggcccaga   13260
ggccacgctc accgttaaca ctgcacaggg caaaggtggc tccaggacaa ctgcccaacc   13320
ccaggaacga cccagcagca gagaaaagga cagctgccag ggtgcctttg tcgcttttttg   13380 gaaatcagaa ttcctgggtc cttagttaag tcttacttca ccaaatccca ggaccttcac   13440
attttggttc ttgccattgc taacagttgt aaatgctgcc gccacgaggc ctgggaggaa   13500
ggacccgctg gtgagagcac agggagtgct gctgtgatca cggtggtgat gcggggtgag   13560
cgcgatttcc cgggattaaa aagccaccgc tgccccgtg gtggaggctg ggggccccg      13620 aataatgagc tgtgattgta ttcccgggat cgtgtatgtg gaaattagcc acctcctcag   13680
ccaggataag cccctaattc cttgagccca ggaggagaaa ttaaaggtca tccctttta    13740 aattgaggaa tagtggtttt tttaactttt tttttttta ggttttagt tgccgaatag     13800 ggaagggttt gcgaagccgc tgccctggc cgaggtgcat tttacgcttc cagaggtcga   13860
ggcctccaga gaccgcgatg cccagggcgt tcccggggag gctgagagac ccagggtgct   13920
ctgggtgact gcacggcgac tcctcgggaa cccactcgtg gctcccgct tggaagggct    13980 ttgcggcccc gggaacgatc tccaggatct ccacggctgg tcaggttccc cgtccctcgt   14040
atcccgcgct gcccgggggc tcctgccttt ggttcagtgc tcgcggcacc accgcactca   14100
```

```
ggacggcagt gggggggctgg ggctggggct gggcctggcc cagcgtgggt tggggcgggg    14160
gacgcgccag cagcgcccgc agctcgctcc gcagggtcg cagccagggg tcgggagcta     14220
ggctcgtggg ccgggagacg ccgggcgcgt tgtcctccgg ggaggttggg gtgcaggcgg    14280
tgcaccgacc ctcgccatct ggcgctgcag ccaccagcca cggcgcttag tggagggtct    14340
gcggccaggc tcccggcgga aagattccgg ggagggctcg ggggttgtcc cagcccgcgc    14400
taagcgccgc agcctcgccc ggcttttcctg cttcctcgga ctgtgcaggg gaagcctggg   14460
gtctcgcggg gcgcagcagt caggtcgagg gtgcagcagg aggggagtcc tgacgggcag    14520
gtccctcttt cccctggtgc gcaacactgg ttggtagctt ttgcggaggt ggtgaagaag    14580
ggcaggaggc ctgttgagcg gaggagtccg gggatcccta attatgtgac aggagaccct    14640
ttccagttcg gcctgtggcc catccctctc tcaccgccgg cagattggag tctgctctcg    14700
gggagccccc aggtaaaccc ctcacaggga gaaggtttcg gattggaagg aggaccgcgc    14760
tcgtggggcg cctgtgagag ctgggaagcc caaggggtag cgtgtagggg gttttttatg    14820
cgggaggagc tgcctcctgg gcggcgggga cttctgtct cagcctgtct gccttggga     14880 aaacaaggag ttgccggaga agcagggaaa gaaggaggg agggaaggag ggtccttggg    14940
ggaatatttg cgggtcaaat cgatatcccc gtttggccac gagaatggcg atttcaaagc    15000
agattagatt actttgtggc atttcaaata aaacggcaat ttcagggcca tgagcacgtg    15060
ggcgacccgc gggagctgtg ggcctggcag gctcgcacag gcgcccgggc tgccggccgc    15120
tgcggggatt tctcccccag cctttctttt ttaacagagg gcaaaggggc gacggcgaga    15180
gcacagatgg cggctgcgga gccggggagg cggcgggag acgcgcggga ctcgtgggga    15240
gggctggcag ggtgcagggg ttccgcgtga cctgcccggc tcccaggcat cgggctgggc    15300
gctgcagttt accgatttgc tttcgtccct cgtccaggtt taggagacgc gtggggacag    15360
ccgagccgcg ccgggcccct ggacggcgtc gccaaggagc tgggatcgca cttgctgcag    15420
gtagagcggc ctcgccgggg gaggagcgca gccgccgcag gctcccttcc caccccgcca    15480
ccccagcctc caggcgtccc ttccccagga gcgccaggca gatccagagg ctgccggggg   15540
ctggggatgg ggtggtcccc actgcggagg gatgacgct tagcatgtcg gatgcggcct    15600
gcggccaacc ctaccctaac cctacgtctg cccccacacc ccgccgaagg ccccaggact   15660
ccccaggcca cctgagacct acgccagggg cgcctcccga gcgtggtcaa gtgctttcca   15720
atctcacttc cctcagcagg ttccacccag cgcttgctct gtgccaggcg ccagggctgg   15780
agcagcagaa atgattgggc tgctctgagc tctgaagcat tcggccgctg tgtgtgtgca   15840
aggggcgcaa ggacggagag acagcatcaa taatacaata ttaacaggag cacttgtcca   15900
gagcttactg caagccacat tcagttccgg accttattga cttcccctc ccatctagag    15960 tggattctgg ttttttcaatt tgttttgttt tgttttttgt ttgtttgttt gttttttgaga   16020 cggagtctca ctctgtggcc caggctagag tgcaatggcg cgatctcggc tcactccaac   16080
ctccgcctcc cgggttcaag cgattctccc gcttcagcct cccgagtagc caggattgca   16140
ggcacccgcc atcatgcctg gctaattttt gtagagacag ggtttcaccc aggctggtct   16200
cgatctcctg acctccgatg atccgcccac ctcagccttc caaagtgttg ggattacagg   16260
cgtgagccaa cgcgtcctgc cttgattctg tttttaactc cattttttag aggaggaaat   16320
tgaggcacag agaggttaaa taacatgtct aaggtcacac agcaagggt ggagcggagt     16380 tagcccactg gcctagctct agagcccacc cggataacca gaacttggtg aggcctccgg    16440
```

| | |
|---|---|
| gctcttgctt ggtttggagc caggtgctta gcgccccgag cccggggcca ttcaccctgc | 16500 |
| aggagctgca cgcgcccctg acctcggctt ttccctggca gcagagggc tttgcgggtc | 16560 |
| ggccgggtag ccctgagcac agctcgccac ttccaggtgg gctgttggcg ctggctgggg | 16620 |
| acacatcccg atctttcaaa tgcccttac agagcctcat caacgacccg attcattccc | 16680 |
| ccctcctgtc atttgtctct gccatcgaaa aatgcctacc gagagctgct ctgcatttcc | 16740 |
| gccctctatt ttgtgtttta ctttaaaata ataataaaaa aaatgttggc tgcaggacgc | 16800 |
| catgacttag gtcagcgagt cagccgctag ctctgcattt ccaaaaagca gatcttttca | 16860 |
| caactctctt gccccaagtg ccctggtgtg gtttattttt taaaatgcat gcctgcggaa | 16920 |
| gagaagaccc ggggaatatt cgaaaccccg agcttttaca acataaagcg catggtgtgg | 16980 |
| ccgcggcgag taatggcgct | 17000 |

<210> SEQ ID NO 206
<211> LENGTH: 1500
<212> TYPE: DNA
<213> ORGANISM: Homo sapiens

<400> SEQUENCE: 206

| | |
|---|---|
| caaatcactt gaactcaagt tcaagaccag cctgggcaac atggtgaaac cacatctcta | 60 |
| caaaagtaaa gaaaattagc caggcatggt gctgtgtgcc tgtagttcca gctactcctg | 120 |
| gggaggtcga ggctgcagtg agccgcaatc acgccacttg tactccagcc tgggcgacag | 180 |
| agcaagtccc catctcaaaa aaaaaaaaa aaaaaaaaa aaaaggctgg gtgtggtggt | 240 |
| cccagatact cagaggctga aaagggagga ttgcttgagc ccaggagttc aaggctgcag | 300 |
| tgagctgcga tcacatcaat gcactccatc cagcctgagc aatggagtga ccctgact | 360 |
| atatttaaaa aaaaaaaaa taggaagaaa caactcaacc acagggctag tatgttactc | 420 |
| ggttataaaa tgataaagcc ctaaacagag aattagcccg tttccagaag aggccaagaa | 480 |
| cagatgatac agctgaactg aactcctgcc tgtacagctc gttttctaca agattccaga | 540 |
| cctggaagat gatggcatcc agccccatt gaagcacctc gaacaagaaa acgccgagt | 600 |
| ccgaagagcc aggccttgaa cacacgattc ctgtctataa ataactcccc ctggggaata | 660 |
| aaaagcagga tccaaggcag gaaacccgag ccgtggaatc tggtaagttc ttaggaaacc | 720 |
| cactcacggg cctgagtccc ccgtggaagc ggcgacttcg gcacctggac acccgagtcc | 780 |
| ccagagcccc gggcggccgc gcgtccctac ctgcaggcct gataccggcc gcggagcgct | 840 |
| cctggccccg ctcccgccag gctccgggac cgctgaaacg cacccagggg ggtgaaggcg | 900 |
| tagtcgccaa ggacagcgca gatggcagcg gaggcatggg agccggaacc taccgtggca | 960 |
| aagggccagg tcgggacgcc cctcggcgca gccccaaatc ctgcccgcgc ccagccccg | 1020 |
| ctcaggccgc gcccctgcca cctctggcca cacgggctga gacgtctggc tcctgcacag | 1080 |
| cgcacttccc gctgcccttc tccactggct gctcaggccc tgcctcgcca gcacggcatc | 1140 |
| cgcgggggat ccctacctgt cctttagggc ttgcctcata ggtcaaacgt cacctcccag | 1200 |
| ggaggtatgg cctgcccct ggccaggtgg gccccttcca cgctcgcctg caacaccacc | 1260 |
| cacccacctt gataactgct tgtaaaggtt gtactgcttt ccccttgag actgcaaacc | 1320 |
| ttcaagggca ggaaatgggt ctgttttcct ggcaaaataa tgaagttggc ttaaggtttt | 1380 |
| gctgaataaa atgagtgaca gacaaaagta gccaaatttg gcactcctga tgggttattt | 1440 |
| gatgaaggag gtgcaatgta tgggcttaac tagttattct ggatttcttt ccccatgtta | 1500 |

<210> SEQ ID NO 207
<211> LENGTH: 200
<212> TYPE: DNA
<213> ORGANISM: Homo sapiens

<400> SEQUENCE: 207

| | | | | | |
|---|---|---|---|---|---|
| caaggccggt | gcacgcggac | ccgaggattc | ggtagatgtc | cccgaagacc cgctgccgct | 60 |
| ctaaggcggt | ggaagcgaga | ttctccggaa | acccagggaa | tccgatgctc gcacaggacc | 120 |
| aaagcccgag | gccgcgggga | ccacagaggg | acggagaagc | cgggactcct cacatcccac | 180 |
| atccggcagg | ggaagcccag | | | | 200 |

<210> SEQ ID NO 208
<211> LENGTH: 2000
<212> TYPE: DNA
<213> ORGANISM: Homo sapiens

<400> SEQUENCE: 208

| | | | | | |
|---|---|---|---|---|---|
| ctgataataa | agttttacca | ttttataatt | taaaaatgta | aatatggagt tgggcatggt | 60 |
| ggttgggagg | ctgagaccag | aagatcgctt | gagcccaggg | gtttgagacc agcctgggca | 120 |
| acatgcagaa | accctgtctc | tacaaataaa | aaattagcca | agcgtggtag cacgcacctg | 180 |
| taatcccagc | tactcgggag | gctgaggcag | agaatcgct  | tgagcctggg aggtggaggc | 240 |
| tgcagtgagc | tgagactgta | ccactgcact | ccagcctggg | tgacagagtg aggctctgtc | 300 |
| tcaaaaaaac | aaaacacaaa | aaaacaaaca | aaaaaagca  | aatatatgta aaaataggaa | 360 |
| gtgcggtttc | ccaaaatgag | gtctgtaaac | aactgatcta | gaaaatgttc tggaaaaagt | 420 |
| aaaaaaggat | caggatctga | ggtcaactga | cctctccctg | cgctctggac aggcaaacag | 480 |
| gcaaggttcc | ctctgaggcc | gtagcggctt | ctcgtgggcg | agtccctgtt cgcaggtgac | 540 |
| gtgtggacca | cgctcttccg | aagcgtctgg | cctgtgtgct | ctcggggagg ggacgcaggt | 600 |
| cagcccacct | agccgatggc | taacaagtca | gtttgttttc | tgaacggaag cttaaaccta | 660 |
| gaaaagtaac | tgggttgggg | tggggtgta  | gccacatgca | gtaaaagcac tgcctgtctg | 720 |
| tataacaacg | acctgatgaa | aaaaggaacg | cgtgaaatgg | ggagtgttag ggcgtcacaa | 780 |
| actccagtgt | ggttgaaatg | aaagcagaaa | gcaaatggca | agctggcttc cccttccagc | 840 |
| ttttcacaac | cctgccttgc | tcatggtcag | ccccaagcac | gggcggaaga aaggactgga | 900 |
| ggggagggaa | aggggtgggg | agcgagggta | ccagaggcgt | gggaggacgg ggacaaaggg | 960 |
| gcagcaaggg | accggcggaa | aggaaagtcg | gcgttagctg | gattggaaac agtccagaca | 1020 |
| gaacgatggg | ctctgctgcc | tccgggtggg | gcaccaagcg | gggagcgggg ccacgaggca | 1080 |
| ggggacagtg | aagcaccatg | cagcgcccac | cagccggcag | cgcccaccag cctgcgctgc | 1140 |
| gctgcacatg | gtacccgcgg | ccccagctgg | ccagtgtgtg | gcggagatga gaccctcgtg | 1200 |
| aagagactaa | gcggccacag | caggggggaag | ggttgctcac ataacccat  | actgctcaca | 1260 |
| ctacgaggtt | aactgccgtg | agatctgcct | gcagccagca | gaaacccgtt ctaggaaaac | 1320 |
| gttgcccagt | gacttcagtg | agtgccactg | acccgggcgc | ctccgccccg cgtccggca  | 1380 |
| gcagcaccga | ttgcgcagga | ggcaccttgc | aaacaacctt | tcctgatccg cgctgcagtt | 1440 |
| cccaggccgg | ttgcagccgt | ttcacagaga | ctgcgcacac | aaagcgtctc cgtgccctgc | 1500 |
| cattcacctt | tcgacacagc | cgcaaccccct | cttttcagtg | ttaaaacctg gcgccaaaag | 1560 |
| gaacatgcga | tgtgacgtgt | tacctctgcg | catgcgccgg | gcattcccag cgccccgaac | 1620 |
| ctgatgaacg | cgcggtgggg | accccaggct | tccgtgcttc | cgttttcctg gaagctacgt | 1680 |

| gtcctcagtc tacatattgt tacctggaaa ataaagtttt ctccttttt cttcctttgt | 1740 |
| taacaggcag aaggtgtagg ctgcaggttt cgggcctaag agagggcatg gctggcgaca | 1800 |
| cggagtagac tcctagatga cataacggag gcgagtctgc accggggact cggcattagg | 1860 |
| aggaggcaga ggaaaagccc accaccgtgg ccgagggaga tctagcaagc agcttgcagg | 1920 |
| gggtgaagtg tgtgcaaagc aggctgagac ctgtccagta tcgaaacacg ccgcggtggt | 1980 |
| caagcaggct ttaccatgct | 2000 |

<210> SEQ ID NO 209
<211> LENGTH: 700
<212> TYPE: DNA
<213> ORGANISM: Homo sapiens

<400> SEQUENCE: 209

| tgaggctcaa aacaggtgtc tgtgagcttc acaggcggta aggccgtgtc tacatggccg | 60 |
| ggacatgcat cccggggctg cccctgccgt gctgcccgag tgcacgggg atgaggacct | 120 |
| gacaaggcca ttgatcttgc gggagcttcc tgaactactc cagcgtgaaa atcttccaga | 180 |
| aggattctcc acagggcaat gaggcaagaa atttacagct tagcctgatt aatgggccag | 240 |
| gcagttaaga gttctttgcc aagctatgag cataatttat agtcatcacg gcaggaggaa | 300 |
| aggccacata actcacatcc ttaaagggcc cttagaacaa gagacacgcc ggatcattga | 360 |
| aaacgtctcc actcctggcg ccaaaagaga tcggcacgtt tctgggtatt ctggtcaaag | 420 |
| aacagggagt ctggattaat atacacggca gaaaaaagcg aagaaaagac acacaggtca | 480 |
| tatatttctg actgatattc cgtttgttgt tttcggaggg acttggtatt tatttaacca | 540 |
| cattctcact tgacacgccc cctccccaca ccttgtaaat gccttcctct ttagccgagt | 600 |
| cattttcat cacatagaat tgaaatgttg ccaggaaggc ggtttatgag attgtagaaa | 660 |
| tggcactaga gaaagcagtg tgaaaagagg cctagaacgt | 700 |

<210> SEQ ID NO 210
<211> LENGTH: 600
<212> TYPE: DNA
<213> ORGANISM: Homo sapiens

<400> SEQUENCE: 210

| tctctacatg ctatctacta aaaacttagg caaggaaatg catcagacca aacaccccac | 60 |
| agcacagaga accgaccggc cattgctttc caatctccgc aaacctaacc attgctggaa | 120 |
| gaaatcttac tcacagtgca cagacagtag gtatttttatt gaagataaac atatagtgga | 180 |
| acaaaccaaa ttaccccat ttgagttacg tgagcactca gttctcagcg tggatgtccc | 240 |
| acaaatcaag tcaacatttg cgtcccatta ccagcagcca cttgccgagt atctcttcgc | 300 |
| ttccactggg actgcctggc atccctgatg ctaaggagcc actgaagagc ctccaaatgt | 360 |
| ctgacattca caaacgcatc ttttgctttg acccgaccct tcaacctctc cgagtctgct | 420 |
| gcctttctc agacacacat ccaggcaccg ttagggatag ttagagaatc tgaaaattca | 480 |
| gaagcgctcc gaaaagcctt tccaaaagta atccacagca ctcaacagtg aatttagaaa | 540 |
| ccccaatttt tttctgagtt tgaagttttt aagccttgcg gatggttgga gtaggaaaaa | 600 |

<210> SEQ ID NO 211
<211> LENGTH: 1100
<212> TYPE: DNA
<213> ORGANISM: Homo sapiens

<400> SEQUENCE: 211

```
tcagacaagc tctgtgcagt cggaattttt taaagatgca ctgtcacttg aggaagacag    60
gtgatcttcc tgcggcacaa atagaagcaa agagatttct cttcttctct gtagagcaac   120
acaattgata aatggccgat aatctccacc aaattggcag cagtaggctg cccgaaggca   180
gcaggcatat tcgtctttgt gaattgtttt actatgatgc tgtcacattt ccaggaataa   240
gacggttaaa atgatatatt gttgtggttt ggcatttgca gctttgctct gacttccctg   300
gtaactgcca acatctgcaa attattatgt gcttaaaaaa aaaatcaacc gccaccgcag   360
gctgccccca cggtccctgg ctgggccagg cctcctgcca ggccacaggg cagagttctt   420
ggaccaggag gcagcagggt caaaacccag gttgcctagg aagcccccaa agacagttat   480
ggatagagct gggagcccga acacatgcg gcagtctctc agtttccagg taccggttct    540
cacatcatcc atgcatgtgt ttgaggaaaa acaaaaaaaa attgatggtt gccaaaaaca   600
aaaatgcttc catatcaaag tttatcagtg tcaatgtcaa gagacttctg gttcgtagac   660
tcattttggc ttgaggccac cagaagtgaa ctctggtttc taaatgcaga agcagaggca   720
ctggccgatc atggaagatg cagggaactg ttcaagaggc ccaagcctgg tgctcagaaa   780
cttggcagga tcaagcatct cgcccaggaa ttcatcccct gcttgtctaa gccggctggc   840
tctcgtgact gactcggaac aacagagcag atgtttgcgt gggaggcaag cctcacccaa   900
catctgtcct gcggcgggaa ggcctgggtg ttcacagata gagctggagt tccccggtgg   960
gtggcacaga caattagctg gggctgcctc acatgtaatc taattacagg ggaaacaggc  1020
tcaaacaccg ggtgataagc agcgcaactg tttcgggtga ctctgtaatt tttcctccat  1080
taattttctc cataacgcac                                              1100

<210> SEQ ID NO 212
<211> LENGTH: 250
<212> TYPE: DNA
<213> ORGANISM: Homo sapiens

<400> SEQUENCE: 212
gttgcctggg atatgcttat atcaaaaact tacgtgtcac ttacctagca tttgcatttc    60
actgggcctc ctaaattctg tgtggtaacc gactgccacc ggacatgctg tttacttctc   120
tatcctcacg cagccagttg ccacattcaa cataacactg caaatattgc cggtggatcc   180
tgacttcctc gtggacccta ctgtgtcggg aaaaacaaac aaacgaaccc tggaaggaaa   240
caccatgagt                                                          250

<210> SEQ ID NO 213
<211> LENGTH: 600
<212> TYPE: DNA
<213> ORGANISM: Homo sapiens

<400> SEQUENCE: 213
tcataaatat ttccaaatgt attcctattt gtctctacag agtctaacag acataaatag    60
cgaattgaag gttctgtctt aaaacccagc agaaagaaaa acaatgacca gaaaaaaaaa   120
acaattgtct ttggcttccc aagaacagca tcggatttca actggaacca cagatggtcc   180
gttgatagaa gcgactactt tttagctctg gaggacgaca aaaggaacca gcttcttcct   240
gtgggtgtca cagcgaggtc gcctggccac atcaggtacc agagcgagcg ccctcacctg   300
ataggccctg tacaacctca gccacagcac tgtcaggagg aacacgcgga actagcaacc   360
taggagggta aaggcggagt tgggagggaa cacgaggcag gcaggtcggc tggctgctga   420
```

| | |
|---|---|
| gctacaggct gcactcctag gacgtctacg tgtaattgag aaaaataaga caaaataac | 480 |
| ttactgtgca ggcaattaat tctggttggc atagcgatcc tcttaagtta aagggaatga | 540 |
| gcatgagatg aagagaagta agaggcagaa agaattatgc aagagcaaca tcagagtgga | 600 |

<210> SEQ ID NO 214
<211> LENGTH: 2000
<212> TYPE: DNA
<213> ORGANISM: Homo sapiens

<400> SEQUENCE: 214

| | |
|---|---|
| acgccgagcc gcctctgcag gggaaaccga agcagatgtg gtgagataat acatccaacc | 60 |
| ctgagtgcta ctctaacctg ccagaggcgg agggttctca gtgagatgaa agcattacag | 120 |
| atgcgttaga tctaagggag gggcctgcag atgcgcagct ggcagagaaa ccagggaggg | 180 |
| gctgaactgt cagtcgcgac caccagggat ctgaatcagt tcaccgacag ccttggggac | 240 |
| attccacttg ggctccacaa cctgtcagaa atgcccccaa gcccaaaggc gtcgagagaa | 300 |
| tggccaggtt gtttcagatt gacacatatc ctaatgtaca agtcagccca cacacccac | 360 |
| gtgcactgag cgtctcttgt tgttcacccc aaataaactc tgccggaact ggggcgggac | 420 |
| tcgcaggggc ggagaagggg ggagacgggc agagggcaga agtggatggt gagaagagcc | 480 |
| aatggagggg ccccgtgaga gtgagcaagg ctgcaccct aaccgacgtc ctggggctac | 540 |
| tgtacaaaca aagaaccaca ggctgggagg ctgaacaaca gacctgcact ctctcgcagc | 600 |
| tcggaggctg caggtctgaa atcgaggggc tgacagcgct ggtttcctct ggaggctgcg | 660 |
| agggagaaac cgtcccctgc ctctcccagg ctctggggtg agcccttcct ggcatcccgg | 720 |
| gctcattgta gatggatcac tccaatctcc atggcttctc agggcttccc tccatgcacc | 780 |
| tcaaatctct ctctccttcc ttttgtaagg atgccagtca ttggatttag gttcaccta | 840 |
| aatccaggat gatctcatct aaattacatc tgcaaaaaga ccctttttcc aagtaagttg | 900 |
| acattcacag gtacctgggg ttaggattgg acatatcttt tgcaggggtg caggggctg | 960 |
| ccactgagcc cgctgcacag ggtgacctgg gccaagggcc cttcactttc acttcctcat | 1020 |
| tggcaagctg ccctgtgttt ggactgggtc gaggctgtca accttgctgc ccctcggagt | 1080 |
| cccccctggt gtcccccaaa cagattctaa gctgctttcc tggggctgga ggccaggcat | 1140 |
| tgggattttt taaagagctt cccagcaggt gagcagcctt tcatgggtat caggagacct | 1200 |
| tcctggcaaa tgtggtgaag gtccttcctc ctgagcgatg ccttagaccc aggagcccag | 1260 |
| ggaggctgct cacctgatcg ttaggacagg agcagtggaa acctctggcc tcagacccc | 1320 |
| tggaggaatc cctccctcta agactctggg actggtgcac gcaaggagct atcgtgaaca | 1380 |
| ttgctcccaa ctggccgctt gcttgtcccc cggctcccct tggccccagt ggcggctttg | 1440 |
| cctgaattag agggcgtgag agccacctgt gtctcagcac tgcaattaaa gcaggaagcc | 1500 |
| ctttcggaag cagccgtgtg caccagcctc ccatgggtgg agcagagcaa accacccact | 1560 |
| tctgccctct gcccttcttc cctttttctcg acaccctgcg gccccccagt ttcagcagag | 1620 |
| tttatttggg gtgaaaaaca agagatgctc agcgcctgtg ggatgtgtgg gctgactcgt | 1680 |
| acattaggat gtgtgtcaat ctgaaataac ctggccgtta tatggatgcc ttggggcttg | 1740 |
| gggggtttct ggcagtctgt cgagcccgag gtgaatgtcc ccaaggctgc tggtgaatca | 1800 |
| gatccctggc gttctccgtt ggcagttcag cccaacagtt tctctgccgg ccgtgcctct | 1860 |
| gcaggtccct cctctgatct gattggatta atatttgaat caatagactg agtcaagcag | 1920 |
| aatgtgggtg ggcctcatgc aatcagctga agccctgaaa agagcaaaag ggctgcccct | 1980 |

```
tcccccgagg aggagagaac                                              2000
```

<210> SEQ ID NO 215
<211> LENGTH: 700
<212> TYPE: DNA
<213> ORGANISM: Homo sapiens

<400> SEQUENCE: 215

```
cacatttcag agctgaggtg ctggtgcggg caggtctcct gagctggggg gtcagctgtg    60
tggccagtga tggtgacgcc tcaggccgtg catggccggg gaggcggccc tgcctctgca   120
ctcttttgac tccatgacta ctggtgtctt cggacgccag agtcggggga gcaaccatgg   180
ggcaccgccc ctgcctgggg aggcagcacg aggcctgagc ccagcttaca ggggacatc    240
caccccgct gagagcccca ccttcacggc gaggatctgt agaagaagac atttgatatt    300
actcggcaaa aaaacaaga aacgaaaaca caaaagagc tcctctgaag aagaaaggt     360
atttgcgctg tggtccacct agaaataatg ttgttggcac aactagagca ttcctcagtc   420
attcaggagc actccctgcc ggtgcgtcca catgtcccaa ccccgataga tgaggcgctg   480
ttcgcccgtg gaggggtcag gttgtcgtga ccttatcttt acccttaggc cgtccatccc   540
ggggcctggg gtttcctgcg ccagtcacgg tgggctgtgt aggtggccat gtgttcggtc   600
tttccccagg aggtacgtac catgtgctgg gaggcctgga ggctgagccg ccccccgcgc   660
ctatgagttg caccctcaca gcggcggcca aacctcctgc                        700
```

<210> SEQ ID NO 216
<211> LENGTH: 200
<212> TYPE: DNA
<213> ORGANISM: Homo sapiens

<400> SEQUENCE: 216

```
caggcttgag cggtgactgg gagaccccgg gaatggaaat ggcgctcaaa tgctggtgtg    60
gtgtccgcag gggaacggcc cgcgggtgtg tggagtctgc gccctgtgg cttcagctgc   120
gtcgggggac tgcgggaatc ttccagactc cagtttaaat cagagaggtg tgtccacgaa   180
aagagtcaaa ctaaaacatt                                              200
```

<210> SEQ ID NO 217
<211> LENGTH: 1300
<212> TYPE: DNA
<213> ORGANISM: Homo sapiens

<400> SEQUENCE: 217

```
aacgagacag tgcaaaaagc cgctgcctgg tgacctggca tgcagactcg gccctcccac    60
ttgcacggtg atccactgaa gacaacagct gcctctgtac tcacgctccc ccacactccc   120
ctccttcctg ccctggtttc tccatcccta gatgccatcc catgccccaa accatccgcc   180
aagcacaata acctcgcccc cacccacccc atgaggtcac tcgagttgac aaccagataa   240
cagttttttgt tttgttttgt tttgttttgt tttgttttgtt tttgagacgg ggtctcgctc   300
tgttgcccag gctggagtgc aatgacgtta tctcggctca ccacaacctc cgcctcccgg   360
gttcaagaga ttcttctgcc tcagctgcct gagtagctgg gactacaggc gcgtgccacc   420
attctcagct aacttttgta ttttagtag agacagggtt tcattatatt ggccaggctg   480
gtctcgaact cctgacctct tgatccgccc acctcagcct ctcaaagtgc agggattaca   540
ggcgtgagcc accgcgccca atagcaattt gatgacccat cccctccact gctgggaaaa   600
```

| | |
|---|---|
| ggctgggcac cgcccacact ccatgcagct ctctttccct ggctcggaat cgctgcaggc | 660 |
| gccacagacc agacgcgcac tgttccccac tcctgcttat cggccgcgcg gcatcccctt | 720 |
| gtcgcagcac tccagcatcc atgcagccgc gcggcacccc gtcttcggag cactccagaa | 780 |
| tccatgcaga gcgcagcacc ccacatccag agcgctccag aatccatgaa gcacgcggca | 840 |
| cccctcgtc agagtgctcc agaatccatg aagtgcgcag cacccttaa tcggagcgct | 900 |
| ctagaacccg tgcagcgagc agcacccac acccggagcg ctccagaatc catgaagcca | 960 |
| gcagcacccc acacccggag tgctccagaa tccacgcagc acgtggcatc tcctcgtcat | 1020 |
| agcgttctag aatccatgca gcgagcagta ccccacaccg ggagcgctcc agaatccacg | 1080 |
| cagcgtctgg cacatcttta tcagagcgct ccagagtcca tgcagccaca gtcctccaac | 1140 |
| ggaccctgag attgtttctg caaaaggcca tgccttcata aatctgaaaa tttggaaaac | 1200 |
| atccttctac ttatatcctt acaacccacc attcaagctg tagaagcctt tctggaaccc | 1260 |
| caagcagaag gatatccaaa atgtaaaaac ggtgggcct | 1300 |

<210> SEQ ID NO 218
<211> LENGTH: 1000
<212> TYPE: DNA
<213> ORGANISM: Homo sapiens

<400> SEQUENCE: 218

| | |
|---|---|
| atagtgcgac tgttccgaag tctttatcac agttactggt gatgcttttt tccagatgtc | 60 |
| ctcgacgtgc acccatgaag ggctccacct gagagtgcca gggtcctccg tgggatgggg | 120 |
| ctggaggggg tgctcttgcc gtcctgggct cccaagcagc cataggaaca ataggggtgat | 180 |
| ggggtcccag agatagaggc cagtgacagc agcgctttga accctcaca cgggcacggg | 240 |
| ccctctggca gggatgggcg tcccggtcac acggagatgg gggctgctgc tgcctgcagg | 300 |
| tagaggaagg gacgtgtttg gcagtcctgt gaccctggg cacctcgcct cccccacggc | 360 |
| cggctctgct tgtaaacaga caagtgcaca agcgcagccc ggtgaaggca cagcggtccc | 420 |
| aggaggcatc tgggctgcac cccagcgagc cgcccataca cgtggagatg ccggccaagg | 480 |
| ccctgcagca cacggcagag gaaggcgcga tgggagccat gctgggcccg gaaggtgccg | 540 |
| ccgcccggag ctgtagccat cactccagct cttcttttaa gtgttcccag aaattgtgac | 600 |
| ccaccaaaat ctgagagcac ccgacagtaa gccagaggac cttgatgtga gatcccagca | 660 |
| cggtgtgggg gcggactgtg gtgggtgctg tctcggcccc caccccttcc acaggtcggt | 720 |
| gtgcacatcc cacggcgcct gctaagctgc agtcttctcc aaaggggtca ctctccgtgg | 780 |
| gaagggagcc acccgccccc gggtgatgtc cccagtcagt gactgacgac agtccccagc | 840 |
| cgaggtgagg gaccagctcc tgcatccctc actccgggc ttgcctgtgg gcagggtgg | 900 |
| gggcgagcct cagcagagac cgcgtccccc ttgcctgtcc tgccctgcct ccctgcctc | 960 |
| ccccgcgcct ctgctgagca cgcccagagg gagctgcttg | 1000 |

<210> SEQ ID NO 219
<211> LENGTH: 500
<212> TYPE: DNA
<213> ORGANISM: Homo sapiens

<400> SEQUENCE: 219

| | |
|---|---|
| cacttgaaaa gcacaactca tggtgccaaa gctctgacac ggactccact ggagctgtgg | 60 |
| gcaggggtg ccaaggtacc gagttccaag ccgttgttat ttgagagcgt gcccccgcc | 120 |
| atgagagcag gtgggggac ataaagtgac acaggatgga ctggccaaag gctgaggacg | 180 |

```
atcacttacc tcacaggatg atgccacccc cacggacagg caaggagctc tcaccttccc    240
caggacccca gctgccacca gagctccaga tggccctggg ggtgtctgta aagcctgtga    300
ccgtccacca ggtggagacc aggctggcca ggggagggag aggaagtgac cactggccct    360
ggcactggct ggccggctcc agcaggcccg aaggggaggg aggagcctgg gtgcaccaga    420
ctctctcaat aagcagcacc cagacactta acagatggaa agcggtggct tggaactcac    480
ttccaacgaa acaatagcac                                                500

<210> SEQ ID NO 220
<211> LENGTH: 1300
<212> TYPE: DNA
<213> ORGANISM: Homo sapiens

<400> SEQUENCE: 220
agcacctcct accccaccct ccccattcct gccatcccca gggtccaggg agcccagatt    60
ccagggaagg gttgcattag ctcccactcg gagtcctgat gcagcagaga cagacagagg    120
ccctgggaga agtgagcatg aattattaag acaagacaag ggtgaggccc cagagagggg    180
gtggcggaag ggtcatgttc atgcagcgag agttgcttcg agcttgaacc gcgtatccag    240
gagtcaagca gattgcaact ggcgagaggc cttcagaaat gccccgtgag agtcctgtgt    300
gcagagctcc atctcagcac acttcctgtt cttttggttc gtcgattttt gcattttcag    360 tccctgtga tccattattt ataacagtgg agattggcct cagacactag cagtgaggaa    420
aacaaaagcg aagctacgca gaaaaatgac aagagtgatg agcacagcag tcatgacaaa    480
tgagccctgt gcggaggccc gggatccgcg cagatgccgg cgcggggaa atgggccctg    540 aaatcccacc gtcaggccag gcagctctga gcgtgacctg gagggctgtt cagacggtct    600
gggtagccgt gtcctgcgca tgaacatcct ccgtcgggag aggaattccc cacggattat    660
cagagctgct ccctccaccc ccgccacgt cccacgcggg ccacatcaac tccctctgca    720
gcctctggcc agcggctgag ccctccgtgt ctcccctcgt taatgcctcc ttcaccatcc    780
cctcctgaag tttcccccat tgcatacacg cgctgaggcc cacccggtat caaggactcc    840
cattgcttgc gaaaaagatt ccacccctct tagaacagag accagggccg ctgtagcaaa    900
tggccataaa tgccacagct taaaacaaca gaaacggatt atctcgcagc tctggaggat    960
ggagtccaaa atctgaatcg ctgggctgaa atccaggtgt gggcagggcc gcgctccctc    1020
tagaggctcc cccggagatt cccttccttg cctcttccag ctgctggtgg ctgccagcag    1080
tttgggaatt gcgccgcat cacaccacct ttctgtttgt tgttgacatc cccgcctccc    1140
ctgcctgcgg ggtcttagat gtctctctcc ttcccactga gtttcactcc acatttgaat    1200
tggattaact catgccatgt taggcaaacg tgccctcaa atccttccac ttaacagaca    1260
tttattgaag gttcctgtgt gcggggccca agagaaggga                         1300

<210> SEQ ID NO 221
<211> LENGTH: 200
<212> TYPE: DNA
<213> ORGANISM: Homo sapiens

<400> SEQUENCE: 221
gaatgttcaa agaaagagcc ctccttgcct tcctcttctt ccacccctgc cctctgcaga    60
ctggggttct gtagacccc aaagtaagtc cgcacaccg gaaggaagtg agttacacag    120
gggcccacat gggaaccgct ttttgtcctg tcttggtggg aaaatggcca cgaccccagc    180
```

| | |
|---|---|
| ccaggctctg ccacgccaca | 200 |

<210> SEQ ID NO 222
<211> LENGTH: 1600
<212> TYPE: DNA
<213> ORGANISM: Homo sapiens

<400> SEQUENCE: 222

| | |
|---|---|
| ccatcttcct aggcctgcgt ttcccccaca ccggggactt gtgctggaaa gaaaagctgc | 60 |
| gttggcagcc aggagccggg gaaactgtcc agggaggcat cctctgcgat gaaggcgggg | 120 |
| cctcggcgtg gcccgttccg cgctctgtcc agccctggag aagccccacc ctcaccgagc | 180 |
| tcgaaatacc ccctccctga gagccgagac tcatggccgg gacccccttgg acagaagatg | 240 |
| cggatgctaa cccggcgctt ccaccacagc cccggcggca ctggggagcg agcgcggcca | 300 |
| tcccgcgcgt aggtggtgtt tctctgcagg cgccagtttc accgcgggcg cccaggatcc | 360 |
| tcaacggttc tgttgtgatg tgattcccct cttcgacttc gtcattcagc ctcagtccct | 420 |
| cagtccccaa ataccgaaag gcagtctttt tttttttttt ttgagacgga gtttcactct | 480 |
| tgttgcccag gctggagtgc aatggtgcga tctcggttca ctgcaacctc cgtctccctg | 540 |
| gctcaagcga ttctcccggc tcagcctccc gagtagctgg gattacaggc acctgccacc | 600 |
| acgcccggct aatttttttgt attttttagta gagacggggt ttcaccatgt tggccaggat | 660 |
| ggtctggaac tcctgatctc agtgatcca cccgcctctg cctcccaaag tgctgggatt | 720 |
| acaggcgtga gccaccgcgc ccggccttttt tttcttttttt cttttgaagt taatgaactt | 780 |
| gaattttatt ttatttacag aatagccccc atgagatact tgaagacccg gtgccaagcg | 840 |
| acagtgttga ccccaggtgg tcagtcctgc ctggccccctt ccgagggatg cgccttcacc | 900 |
| ataaccatgt cacggacagg cgtgtgggca agggggcatc gctgtatttt tcacaactct | 960 |
| ttccactgaa cacgacaatg acatttttca ccaccgtat gcatcaacca aatgaaaaga | 1020 |
| tgagcctgtg acattcccgt gcgtagagtt acagcttttc ttttcaaaac gaaccttcag | 1080 |
| tttggagccg aagcggaagc acgtggcgtc tgacgtctcc agggagaccc gccgccctcg | 1140 |
| ctgccgcctc accgcgcttc tgttttgcag gtaatcttca gcaagtactg caactccagc | 1200 |
| gacatcatgg acctgttctg catcgccacc ggcctgcctc ggtgagtgcg cgctgcgggc | 1260 |
| tctgcccggt gacgccacgc ggcctcctcg ccttttcggg atggctggga ggggcgggaa | 1320 |
| gaggcgctga agggcccgag gcaccggcct tctacaaggg gctcttcgaa atcaatcaat | 1380 |
| gcgcagaatc ccgagggagg ctcagccgcc ctccgggcct ctctgcctcc acaggtgatg | 1440 |
| gctgtgtcca caaggaggaa accgtcgggc tgaattaaac agaaccgccc tcctaagagt | 1500 |
| gtgggttttt ctgccggggcg tggtgtctca cacctgtaat cccaacactt tgagaggccg | 1560 |
| aggtgggcag atcacctgag gtcaggagtt cgagaccagc | 1600 |

<210> SEQ ID NO 223
<211> LENGTH: 400
<212> TYPE: DNA
<213> ORGANISM: Homo sapiens

<400> SEQUENCE: 223

| | |
|---|---|
| aggcagcagg gttaggactt caacatacaa cttttggggg gagatgtact tcagcccata | 60 |
| acacaccacg tgggaggata acaccgattt cagagcttgc agaggaagcc gccaggaact | 120 |
| ccagtgagac atcagccccc aggtgcctgt caggcacgcc gggctgtggg gggcacctgg | 180 |
| gcccatctga gtaacggagg cgcatccgca cttcccccag gagtacattt ttagaaccca | 240 |

```
cagcgccata aaccaaagac aaggagactt cctggtgccc cgtcagcttc tggaggcgac    300
gttctcggct gacagctctg gcagcctccc ctgtaggtga gagacaggta aatgggactc    360
ttgcttccaa aacggaacag ggtaaaaatt ctcaagcgtt                          400
```

<210> SEQ ID NO 224
<211> LENGTH: 700
<212> TYPE: DNA
<213> ORGANISM: Homo sapiens

<400> SEQUENCE: 224

```
tgctgcaccc ccgctgccct ccctcccgct ggccggcagc accttctcca cccgggcccc     60
tctgctcaca gcgctcccg ccccgtctc cccgaggggc ggggagccag acatggccc      120 tgaaagccta gccctggcct tgacctcccc agagcgccct ccccaccctc cgccctctgc    180
caaccctggc ccctgccctg gccccgtcct tgtcctctgc tgctggcctt ggggtcgcgc    240
cccgcagact gggctgtgcg tggggtcct ggcggcctgt gccgtcccac gcctacgggg     300
atgggcgagg tccttcttgg ggcttctctt acccactctc cagtcacctg agggcgctgc    360
ttccctgcgg ccaccccagg tttctgtgca gccgaagcct ctgcctctgc ggccgggtga    420
tcccaagacc ccggggtcca gggaggcacg ggatctgctc cccggtccc aaatgcaccg     480 gctgcgcctt aggagggacg gcctccaccc atggcgctgg cgcccagggg ccgctcctcg    540
gactacagca cttgctcgtc gccctgcgcc ctgtttagtt ctcatcacca gcagcctgga    600 ctagggcccct ggtccttctg gcctccttcc acagcccgct gcacatctca cccacttccc   660
cgaggtgctg tcattgttta gctgggcccc tcagcctccg                          700
```

<210> SEQ ID NO 225
<211> LENGTH: 300
<212> TYPE: DNA
<213> ORGANISM: Homo sapiens

<400> SEQUENCE: 225

```
ttaaagggga gtggttgtat gaagagttcc tcagtcaaag gtgtgcagct gggaagccca     60
ccccacctaa gagggaggtc tgacaaactg tccacactga accactcaga cctgcatcag    120
ggccccgttt cttccataag ccgccaagta cagccctgag tcaactgaac tcaggcctgg    180
gaggcttccc aaagctgact tgactcagct ttgaactgaa atgaccgtac catgacaacc    240
ctgatgaaaa gctaaactga gcccaattat tcaacagtaa aattcagttg gtctcactca    300
```

<210> SEQ ID NO 226
<211> LENGTH: 450
<212> TYPE: DNA
<213> ORGANISM: Homo sapiens

<400> SEQUENCE: 226

```
tgctaccagc tgcttgggct tgggcaagtc accctagctc tcagatgtca tctgtaaatg     60
atgacaatgc caatgtggca ctgttctgag agtcagacag aacgtatgtg tgcttcacat    120
atggtgctca tgaagtgcta tcattatcta aggaaaacag aaaacgaagt tcagagtctc    180
tctaaacgca tgacaccaga ccaacaggga gtttcaaaaa ataggtctga agtaaatcaa    240
ttctcctggt ctcaatacac tgaaaacaaa ctattagggg actgaccgaa cccaccttag    300
gaaccacctt acgtcacctt ctgtctctac tgcaaaaccc tcccttaata ctgttcaaat    360
acgctgacaa tccagatcca tatccaatgg aaccagcaat catgcctgtg tgccagcaat    420
```

```
gtcagggagg gaagccgatc tctgatgaat                                      450
```

```
<210> SEQ ID NO 227
<211> LENGTH: 1000
<212> TYPE: DNA
<213> ORGANISM: Homo sapiens

<400> SEQUENCE: 227
caggtgccgg ccaccacacc cggctaattt ttgtgttttt agtggagaca gggtttcgcc      60
atgttggccg ggctggtctc aaactcctga cctcatgtga tccacccgcc tcggccttcc    120
aaagtgctgg gattacaagt gtaagccact gcgcccggcc aagagtgaag ttctgatagc    180
tggggtaaga aaggccgtgg aacagccgg tttcagacac gctgggtcta agacgctgcg     240
tctggcgctg ctcggcatcc aatgggagcc gtggagaagc caggcgagtg cgtagggcgg    300
agccagcgca caggaaatag gacgtgatga ggtcaaccgg ctggtccaag tgtggacgga    360
agtagaggat gcaagcaccg agccccgggg ccccagcat tggcggggag gagctcgcgg     420
tgcgggagaa gcagggacc gcgcatcctg gagaccaggt ggagccagtg cgcccggaag     480
gggcgtggcc cgctgacagc cgcccaggag gccgggggag gcctggagcc gagggccgcg    540
cgtggcaatg tggagagaca ttttggtgga gtcatggggc cacagcctga ttggtgagaa    600
caggaaggga aattgcagat gggcctgggc cccctggctc ccgcatactc caggaccagg    660
gctgagtcat cgttcaccgt gtgtgaccag ggccccgtgt ggccggctgt cactcggtat    720
ccagttaccc tgggcagacc actggcggca ccccccagcc agaggccgca gcaacacaca    780
cgcctgcagg cgaccaggcc ggactgcatg ccccgtgggg gaactgaggg cgtttcagta    840
acagagtgtt aggggacacg ggttgggtgg cttggaaagg gcctaaggtg gggtttgttt    900
tagattgggg tggtgagggc gcaggggccc ggtaggattc tctaacaggg cagcagccac    960
tcatttagca acaggagagg cgtccagcgt ttcgtgggct                         1000
```

```
<210> SEQ ID NO 228
<211> LENGTH: 3100
<212> TYPE: DNA
<213> ORGANISM: Homo sapiens

<400> SEQUENCE: 228
acccaaccac aggcctcctc tctgagccac gggtgagcgg tgcaggttct gctgttctgg      60
agggcctgag tcccacccag cacctcataa acagggtcct ccccagggct gctgcagtag    120
gcatcaacgc cagggtgcaa aatgcctcag ggagccaagg ctgagccagg ggagtgagaa    180
ggagcatgtg gaagtgcgtt ttggagaggc agctgcgcag gctgtcagca ggctccggcc    240
gcttctatag acagcatgac accaagggca gtgacctcat tccacaggct gagtccagcc    300
agccagccaa gcatcaccag ccagacgatt gaccctaacg gaccaaccaa cccgtaacga    360
cccctcctac cataaccagt agccagccag cccataacca gccaacttat ctataaccag    420
ccacctgacc atagccaaac aaccagccgg cccaccagta gcattcagcc cctcagctgg    480
ccctgagggt ttggagacag gtcgagggtc atgcctgtct gtccaggaga cagtcacagg    540
cccccgaaag ctctgcccca cttggtgtgt gggagaagag gccggcaggt gaccgaagca    600
tctctgttct gataaccggg accgccctg tctctgccaa cccccagcagg gacggcaccc     660
tctgggcagc tccacatggc acgttttggat ttcaggttcg atccgaccgg gacaagttcg   720
tcatcttcct cgatgtgaag cacttctccc cggaggacct caccgtgaag gtgcaggacg    780
actttgtgga gatccacgga aagcacaacg agcgccaggt gagcccaggc actgagaggt    840
```

-continued

```
gggagagggg ggcgagttgg gcgcgaggac aagggggtca cggcgggcac gaccgggcct    900
gcacacctgc accatgcctt caaccctggg agagggacgc tctccagggg accccgaatc    960
aggcctggct tttccccaag ggaggggccg tgcccacctg agcacagcca gcccctcccg   1020
gtgacagagg tcaccattcc cgagctaatg tggctcaggg atccaggtta gggtcccttc   1080
ccgggctgca cccagccgtc gccagctcca tccctgtcac ctggatgcca gggtggtctt   1140
agaaagaacc ccaggaagtg ggagtgcccc gggtggccgc tcctagcca gtgtacatct    1200 tcacatgaac cctacctgag gaagccagtc cccgacggca tagctgcatc cgcttggaat   1260
gctttacagg cattgacacc ttcgcctcac agcagcactt tggaaccagt gtcctcatta   1320
ttccagggca cggctgggga caagggggt cctcagcctg ctgggtccca cagctagtac    1380
cgggcaggtg gacgggagct tctccccaca gtcaccctga tgccccgctc ttgctcggct   1440
ggaggcctcg gatctccgtg tgttgaggg agccggggca ctggagccct ggtgacctgc    1500
atctcctggc ggagccggga agagctcatg gactgtcaca gatggacagt gccccgcggg   1560
ggctggagag cagagtgggg ctggaaggtg gaactcttag ccaaagtctt ggtttctttt   1620
ggccagggtc ctctttcaat ggctggagaa ggtggtgctg gggggtgaac gctgacctcc   1680
tcatgtgctg cccctccctc gcctgggccc ggtaaagccc ccacgtagcc ccagccagcc   1740
tggaacatgc ttcctgagct cccagctctt ggtctttgca cccagtggag gaggaggtca   1800
gcccagggag ctgagtctgc ggtttagggc gtccagggga cgtggaagca tgtgggtcgt   1860
ctggccacat taggtagggc tgcagagacc tgggctagag cagtcctgcg gggtctggaa   1920
ggggaagact ggctgaggtg cggggcctgg tctggaatga tcctgcgatt ttggagtgaa   1980
gccatggagc gggaagagac aaccccccgc ggggaatagc ccggcaagtg gccacgaggc   2040
caggctgagg tccagagaag caggggcatg aatccataaa tcccaggggg cctggccatg   2100
ggatgtgctg gctgcacccg gcccctgtga gagcccccgc aggctggccc ccttctgcag   2160
tcagtggggc tggggcagct tctctggcat ggggcgaggc agccgcctgc acagtggccc   2220
ccctgactgt gcgcccccac cctctccagg acgaccacgg ctacatttcc cgtgagttcc   2280
accgccgcta ccgcctgccg tccaacgtgg accagtcggc cctctcttgc tccctgtctg   2340
ccgatggcat gctgaccttc tgtggcccca agatccagac tggcctggat gccacccacg   2400
ccgagcgagc catcccccgtg tcgcgggagg agaagcccac ctcggctccc tcgtcctaag   2460
caggcattgc ctcggctggc tcccctgcag ccctggccca tcatgggggg agcaccctga   2520
gggcggggtg tctgtcttcc tttgcttccc ttttttcctt tccaccttct cacatggaat   2580
gagggtttga gagagcagcc aggagagctt agggtctcag ggtgtccag accccgacac    2640 cggccagtgg cggaagtgac cgcacctcac actcctttag atagcagcct ggctcccctg   2700
gggtgcaggc gcctcaactc tgctgagggt ccagaaggag ggggtgacct ccggccaggt   2760
gcctcctgac acacctgcag cctccctccg cggcggccc tgcccacacc tcctggggcg    2820
cgtgaggccc gtggggccgg ggcttctgtg cacctgggct ctcgcggcct cttctctcag   2880
accgtcttcc tccaacccct ctatgtagtg ccgctcttgg ggacatgggt cgcccatgag   2940
agcgcagccc gcggcaatca ataaacagca ggtgatacaa gcaacccgcc gtctgctggt   3000
gctgtctcca tcaggggcgc gaggggcagg agggcggcgc cgggagggag gacagcgggg   3060
tctcctgctc gcgttggacc cggtggcctc ggaacgatgg                         3100
```

<210> SEQ ID NO 229

```
<211> LENGTH: 1000
<212> TYPE: DNA
<213> ORGANISM: Homo sapiens

<400> SEQUENCE: 229 ttttgtgtt tttagtagag atgggatttc accatgttgg ccaggctggt ctcaaactcc    60
tggcctcatg caatcctcct gcctcagtag tagtagttgg gattacaggt gtgagctgcc   120
atgcccagct gcaggtgcgg aagctggggg cctcagagac tgtggactcc tggccggtga   180
ggagcggcat gggccgggag agctgactct tcagcgggac tgaggtggct ggagcgtgac   240
cctttcctga gggcaaacag ggagggcctt ggagcccggc gctcaggaca gcccctgct    300 ggcccggcag cctgagcttc cacactttc cagggcgtct cgagttcgcc cacagagctg    360
ttgtttcagg ataaaaaatg cccttgtatt ccacgttcca gttcagaggc ccgtctgttc    420
ccaagagcgg aggcgtcagc cgcatgagtc ccaccggaag ccgggttgcc gggtccccgt   480
ccctgccctg cagacgacgc attccggagc cccttggga agctgcctgg ctctcccagg     540
cctggctgcc ttcgcacgag ggctccgagg catgctcatc ctacgtgact gcccgagtgt   600
gcacacgcct ggccgtgtgt gggcgtgtgc ctggggcccg agctcaggag caaggcctgc   660
gtggacctgt tgtctgaaac aagccagtag acagctgcgt caatgcaggc aagctgaaca   720
gggctgcttt ttcagcctga caaccccagg ggctgaacag gagctggggg aggagcaagg   780
ggccgttccc ctgccccaca gcacagcaca cgaccccgcc ttggaacctg ggggcccgggg  840 tgaatcgagg gtcctggagc aagaggggct gctccacagg agagcctgtc ccgccacccc   900
tcagccacca gattcggggc tgctggactt gttctcaaac ctgcacagtg agtgacagct   960
gctgagacgg aggtctcagg cagtgcaggt gaatcagcat                         1000

<210> SEQ ID NO 230
<211> LENGTH: 500
<212> TYPE: DNA
<213> ORGANISM: Homo sapiens

<400> SEQUENCE: 230
tccttatttt ttagttctca agccctgtag ggtgttttcg gtcgcagttg tttgggctgt    60
ggtcctgacc ctcctgagtt ccagtggctc tgttcaggag agctgcctgg ggccgggact   120
tctgaaacac acactgagcc acaggccggc ccggcggctt gggttcaccg ccgcctcttt   180
gtgtgtgatg tcctgggata ggcccgtgca cgttcagatg acactgtaca tataaataac   240
ttgtagccga gaacaggatg gggcggggag gaggggaggg cagaacgtac cacagcagca   300
gaagtcactg tggatgcctt cgtaagttgc atggaaggtt tttaaaccta gccctgccga   360
gcagccctct cctggtccgg gagaacgatg gggagagagc tggcgttcag ctttcatcac   420
tggagccgtt ccttcttccg gcccccgag ggcctgtcca tgatcacact ttgtcttgtt    480 tcggggtgg cccctgtgac                                                500

<210> SEQ ID NO 231
<211> LENGTH: 1300
<212> TYPE: DNA
<213> ORGANISM: Homo sapiens

<400> SEQUENCE: 231
caagcctgtg gtagggacca ggtcagagta aacaggaaga cagctttcgg ccaggcggtg    60 caccctcggtg ccggtgagtg tgagcgtgtg tgcgtgtgca cgtgtgcaga tgtgtgtgga   120
cgctcccttc tccgcagcag ctcctgaccc cctgcaggtg accctcagcc agccccaggg   180
```

-continued

```
ctgcccccac tctccctgt ggacacctac ctcatttggg gtgaagtggg gggactgggg      240 tgtgagggt gctttgggg gcacacttcg accctctct ctgcaggcca agtcctgagg       300
ctcagtttcc tcctctgtgc cccggcgacg tggtgcaggc ctcgcgagtg acgtgagggt    360
tcatgaccca ggtgtgggca gccagccctt cacgggaggc cacccacctg ccacagtgc     420 ctgggaattt aggtcgggca ctgccgatat gtcgccttcc acaaggcggg cccgggcctc    480
tgctgaccgt gcaccggtcc tggggctggg taattctgca gcagcagcgc agcccatgcc    540
ggggaatttg cgggcagagg agacagtgag gcccgcgttc tgtgcgggaa ctcccgagct    600
cacagagccc aagaccacac ggctgcatct gcttggctga ctgggccagg cccacgcgta    660
gtaacccgga cgtctctctc tcacagtccc cttgcgtctg gcagggagc tgccaggctg     720 cacccgcgg tggggatcgg gagaggggca gtgtcgccca tccccggaag gctgagcctg     780
gtgcagccag ggagtgaggg ggcgggaagc cggggtgctg ccctgagggt gccccgacac    840
gctctcctgg ggcctgagc ggctgccacg tgcgtccagg gttctggcca cagggtgggc     900
aggggccctg tgctcctcac tggaggcccc tgaggctctg gaactgagac catccacccg    960 ccggcccct ctcgccggct ccggcacccc tgcctactgt gacttcctgc cccgactcg     1020 ctctgccagc ttggggcaaa ccacttccct ctggggtttt cacttccctc tttcccaagt   1080
ggggaaagac cacctgtccc cgacccagaa agggcccctg cccgagggca gcagcagtgc    1140
caggctggca tgtgaggctt ggggcaggcc cggcccccag aggcacaggg cgatgctctg   1200
tgggacgctg tgtcgtttct aagtacaagg tcaggagagg agccccctga ccccggaggg   1260
gaggagaggc agggcaggaa accgccacca tctcagccca                          1300
```

<210> SEQ ID NO 232
<211> LENGTH: 200
<212> TYPE: DNA
<213> ORGANISM: Homo sapiens

<400> SEQUENCE: 232

```
gcccactgtg ggtgtgcccg tgtgtgtggc tgtgaggcgt gagtgcaggc gtgaagtgtc     60
tgggagtggg agcgggcatg agtgtgtgcc acgggcctgc tgttgggtcc ttggaggcca   120
cggttgcccc tgaagggact gcaagctctt ttttgatttg tagttatttg agaagtctat   180
acaggaagaa aattaaaccg                                                200
```

<210> SEQ ID NO 233
<211> LENGTH: 1000
<212> TYPE: DNA
<213> ORGANISM: Homo sapiens

<400> SEQUENCE: 233

```
agcgcccagc gcagggccgg gacccagagt ggactctacc gtgggctgc ctcaaagaaa      60 tctcagcaaa cacaggaagc cagcccaccc gtgcagccat ggggcaggaa agcccgccct   120
ttaccaagtc atttgggcat tttttctctg tgctaacagc ccagatggag ccatagcctc   180
aacctctgtg ttctgataac accaagctgg gacgccggag ccatgcaggg gacagtgccc   240
ggcctgaggc tgcagcctgg gtctggatgc ctttctaatt cagggcctcc tcatggcctg   300
gttccataaa tggtcaaatg cagcctgaca gcgcagcctc ctatcagcgc tgggctccgt   360
accgccacac agcccacata ccccgttccc caggagacgc ccgcaggtgg gcagcgtcac   420
tcccacccgc cgagcacacg ctgtcccgt ctcgtgtccc gaggagccgg aagcagctgc    480
```

```
ttcctcccag cctgaaagct gcacctcggg ctgcactcgg ctccccgaac ccgccctccg    540
ctgccctgca attcgccaag ggagctaccc ttcccatata aaaatttcac ctccatttcc    600
ttgtagagaa gaaacatttc tgacagcaag gaagattcta atttgaaaag caagtgattc    660
atctcccggt gccaaacagc agacgcaggc gttaccagtc tgggtggggc gcccgagctg    720
gggacctggg gtcctctggg aggggcaaga aggcagcgat gctggccccc gcctccatct    780
gcccatccca tctgcttcca cacccgccc tgccgtagct gcttgcagcc cttctctgtc    840
agtttctcca tcttttggtt tggtgataaa tgagagttcc catcgggtgt gccaccctct    900
gtgtgacggg gagcagagaa gaccctgcgt ccaagtcctc ctgggggaag agcgaagatg    960
ctgggaccag ccccagctgt caggggggtct ccaatcccag                        1000

<210> SEQ ID NO 234
<211> LENGTH: 1300
<212> TYPE: DNA
<213> ORGANISM: Homo sapiens

<400> SEQUENCE: 234
ggaacggaga gccgccaggc ccaaacctcc cagaatttgc gcagtattct cggcctagag    60
agcgaggagt ggccttggcg aggtccctct ttggctcttc tggcttagcc ggggttttaa   120
acttgttatc tgcaaagcag aaggaaagtc agcccctgat gtaagtgtca agtaaaataa   180
atcggatggg tcctttcctg tttggcgagg aatgctacac taaggggggac tgcgttcaaa   240
tgggcagtct ttgctggaaa cctcgcctcc gcgcgccttc cctcgctcgg attcaggcgc   300
ttttacgtta agggttgaat ttttgtgtca acaggcacct cggagggtcg cctagacaac   360
tgagcggagc aactgagata acccccgcta cgtgtggagt gacctagtcc attaacttgc   420
cccagcacgc ccgctgagtc cgcaaaatat aggatggcct cgggttttag atgaacccaa   480
agctaagatt tcttccctct ctggaattag caagcagccc gccctgccca actcccctgg   540
aagcgcgcgt gctcgccagg cctcgggacg cctgcgcggg cgcccttgca ctggcaccag   600
ggctccgggg tagggcgca ccgatctgcc caagcctctg caggcactgg aggaaggcga    660
gccctccacc cgctcaacag gccccagtgc cggccttttcc ttccagtctc aactccaccc   720
gggggcccgg gggctccaca gttaaaaact ccacgccacg gagatcgcag gtaagctgct   780
ggctcaacga ggtgtgctaa atgggattaa agatcctgga ccgtggccag gcgcggcggc   840
tcaagcctgt aatcccagcg atcagggagg ccgccgcggg aggattgctt gagcccagga   900
gtttgagacc agcttgggca acatagcgag acaccgtctc tacaaaaaaa taacaaatag   960
tggggcgtga tggcgcgcgc ctgtagtctc agctacttgg gcggtcgaga tgggaggatc   1020
gatcgagtct gggaggtcga ggctgcagtg agccaggatc accgccaaga tcgcgccact  1080
gcattccagc ctgggcgaca gagggagacc ctgtctcaaa acaaacaaa aaatcctaga   1140
ccgtttacaa acagccttcc gtctcttcct ggtcaagtcc taaccctggc taacctcgcc   1200
gtctacagcc tgaattttgg caaccgaaag gcagcgccgg cgccacgtgc acacgggctg   1260
ggccgctccg ccagctgcca gggccactgc cgcgctcact                         1300

<210> SEQ ID NO 235
<211> LENGTH: 300
<212> TYPE: DNA
<213> ORGANISM: Homo sapiens

<400> SEQUENCE: 235
cgcacacaca gcacagacgc ctgcatcttc ccatgcgtgg tttctgctct tgcctctctg    60
```

| | | |
|---|---|---|
| ggttttttgtt | tcacttcggt cgagttttg gtggtgttga gcggatagcc ggggaagttg | 120 |
| gagtcttgtt | tgtggccgcc tcgtgctcgt gtctgtatct aagatcctca ggctgctcct | 180 |
| ttttgggtaa | ggtctgttgc ttctctagga acagtgacgg tggcagagcc cgtggcccct | 240 |
| ctctcctgtc | ccagagccaa gctgtttcct ctccccactc ccgggcaccc tgcgggcaag | 300 |

<210> SEQ ID NO 236
<211> LENGTH: 1000
<212> TYPE: DNA
<213> ORGANISM: Homo sapiens

<400> SEQUENCE: 236

| | | |
|---|---|---|
| cacagcccag | cttcaagcct ggccgaccag gggtttggca tgaagacccc ggcagggctg | 60 |
| gggctgtgct | ggaatccacc cggaagtttc ctgccccttg gctgcccac caggtccccct | 120 |
| ttctgctctg | atcaagctgg acaaaacgtc gtggggccac agcacagggg gccaacgcaa | 180 |
| gctgggatcg | tcagacgtta ggaaatccca aggaagaaga gaaaggggac acattcggga | 240 |
| gacgtcggca | cacgctcgaa gcagcggaca ggcacctctc tgtggacaag gcagactggg | 300 |
| cggccgagat | tccgcataga tgcctgcttc ctccacgacc tccacgtgtg gctgcccag | 360 |
| tccgggtccc | cctcacctcc tctgtctgtc ttggtggcct cacgccgtgg gctgtgatgc | 420 |
| cggctacgct | gcttgggtgg ccaagggtct gagctgcaag acgcccagcc tgggtctctc | 480 |
| ccgagctctc | ccacgtcctg tctgctcctc ctccgagctc ccggttgact ctcacgactg | 540 |
| caccagcctc | tcccccagga aggcgtggaa acaacctcct tctcccaggc ccgctctgcc | 600 |
| tcctgcgttt | caaggcaaat ccgttcctcc aggagatgat gcaaccacat cctgttggag | 660 |
| cccagagaag | tgcggatgca gcccggggct ctttctttcc tagaaccctg cctgggagtg | 720 |
| gcttccctga | actaaggaca gagactttgt cttcgttgcc tctcggcctg tgggcactga | 780 |
| gcatacagta | ggtgctcagt aaatgcttgc aggccgatgc ccagagccat tagccctcat | 840 |
| catggtgagc | tcggcagccg gtgttggggc tgggctgggc ctaggtgtgc gtggggggcgg | 900 |
| tgctggtctg | ctttgctggg agccatggac accggaggaa cagggcccca tcagtgcggt | 960 |
| cagagtgcaa | actcggagcg tccttctctg gaaaacgaat | 1000 |

<210> SEQ ID NO 237
<211> LENGTH: 500
<212> TYPE: DNA
<213> ORGANISM: Homo sapiens

<400> SEQUENCE: 237

| | | |
|---|---|---|
| gggaggggc | gtggccagca ggcagctggg tggggctgag ccagggcgat ccgaccccga | 60 |
| accggagctt | ttagcacttt gagtcccctgt actcagaggt ctcctgcagc cgggaatccc | 120 |
| actgtgctgt | ggtccctggc agccagcacc caccccagc ttctccgtca aggttgagga | 180 |
| cggagcactc | ctgcctctga ttaactggac gcaggagaag cagttgcttt aatccggagc | 240 |
| cttgagttgg | gacagataat gagtcattca accagatttt ccaaggacac actaactttg | 300 |
| gtatgatgcg | tgtgtgcccc tgaatccacg tggtcaggaa agcccaggga acactggcct | 360 |
| gtgactcact | gagcaggttc ccttgttacc ccgagggtg atttactcct ctgacagtga | 420 |
| cacggacact | gtgcgtccat tcccggggcg ggcagaggac actcccagat gcccacgagg | 480 |
| ggcccagcaa | gcactggcca | 500 |

<210> SEQ ID NO 238

<211> LENGTH: 600
<212> TYPE: DNA
<213> ORGANISM: Homo sapiens

<400> SEQUENCE: 238

```
ctgcaggacc tgctcgttca cagatgttct cctagaagca gaagctgttt cttgttgcaa      60
acaaatttgc tgtgtcctgt cttaggagtc tcacctgaat ttaccaagga tgcatctgtg     120
cttggggatg gctcggtttg aggggtctga ggagcggctc ccctggatcc tttcctcccc     180
aggagcccac ctgccgagct gtcagcgtca gccccacatc tcaagatgag gaaatggagg     240
tcgaagccat gcacacgcag gcgtcctgct gacatgcagg ccaggcgggt gcctctgtat     300
tcagcagcct cagggctgtg gccagttcag gcagcagagg ggcctcatcc cggtgcttcc     360
ctgcaggcag ttgtggggcc ggcctgcagc aggggctcag acaggccctt gggagaggga     420
gggatcacag aggtgtccag tgacaggcag ggcgggcaga gcccatgggg ccttgggctc     480
ctcactcctt cggtcagtca gggtgacatc tggagccacc tccattaatg gtgggttatg     540
atttggttcc catgcagccc gtgccagctc gctgggagga ggacgaggac gcctgtgatc     600
```

<210> SEQ ID NO 239
<211> LENGTH: 5000
<212> TYPE: DNA
<213> ORGANISM: Homo sapiens

<400> SEQUENCE: 239

```
aagaggaaat tcccacctaa taaattttgg tcagaccggt tgatctcaaa accctgtctc      60
ctgataagat gttatcaatg acaatggtgc ccgaaacttc attagcaatt ttaatttcgc     120
cttggagctg tggtcctgtg atctcgccct gcctccactg gccttgtgat attctattac     180
cctgttaagt acttgctgtc tgtcacccac acctattcgc acactccttc ccctttttgaa    240
actccctaat aaaaacttgc tggttttttgc ggcttgtggg gcatcacaga tcctaccaac    300
gtgtgatgtc tcccccggac gcccagcttt aaaatttctc tcttttgtac tctgtccctt    360
tatttctcaa gccagtcgat gcttaggaaa atagaaaaga acctacgtga ttatcggggc    420
aggtcccccg ataaccccca gctgcagatc gaggcctagt gcgagcacag gtcccccag     480
acccttccca gtgcccacca accggcggcc taggccaggt agaactggca gcgcctcccc    540
tgctgcaaca ccaggctctg gtagaaactt cagaaaacat gcaccggcaa aaccaaggaa    600
gggtggctgc gtcccgggtt cttccgcgca gctgtgtgta cacgcatgca cacacccaca    660
cgcacacacc cacgtgcaca cccccatgca cacgcaccca cttgcacgcc catgcacgca    720
cacgcgcg tgcacccatg cgcacgcacc catgcacaca cacgcgcgca cacacccacg    780
tgcgcaccca catgtacaca cccacgtgca cacaccacg cgtacacacc cacgcgcaca    840
caccgctgtc cccagccgtg cagaacgatc ctccctgagt ccccggctcc gacccacacg    900
cagcactcgc taaacgcttc ccacgcagtc gttttgctgg gttgcgcttc acccacttct    960
cagagggggc ggccgaggca gaggtgtcgg ggatcgagca gctccgggcc tcaggggtcg   1020
cccccgccacc gttttccttt cccagatgct gggacggggg cagggagggg ctccccaggc   1080
tgaacccgac taggtcaccc tagaagcgag gcgagcttct cttctgtttt tcttcggcgc   1140
ccctgagccc ctgacagtgc caagctgcc catgggattg gattcgccag agcctcctac    1200
gcagacccca cccagggcca aagccaaccc caagccccac cacccttggtg gtgtgggatg   1260
aaaagtgagc catcgagaga tggggtcccc ccaccccaa cccctccaag acaaaggcg     1320
ggctgggaag cacccgcttt cacgtccgcc cctgcccggc tttcctagcg gaattggcgc    1380
```

```
cggcatcagt tgggggttgt gggatcagtg aggaatcccg tgggtcgcc tccatttatc      1440 agttgtgtgg ggttgggcga gcaccctag cccagccca ggcgatcagg gcgcgaagcc       1500
cactggacgc ggatttggga ttaggacggg ggtgacagcc aggaggaccg cacctgccct    1560
ccccactcct gccgctccac ccctgccccc accgcaacac caaggtctcc accaggaaga    1620 tggggtggg gaaaggacgc ggggtggggg ggggtgcggg gagagaggac acagggtcgg     1680
aagggtgagg ggtagtggca gaggcggagg ccgaggccac gcagctgcgg ggcgcaggga    1740
ggggcagagg aggggcgttc agatgggaac ctagtccaga cccgtcgggg ccctcgtgtg   1800
cggctcgtta tcctggaacc agagaggctg gagacccttg gcttgtctgg agcggaaccg    1860
tagtgtccaa tagagtgtgt ggggctcagc cctaaagcta acattctttt atttcctgat   1920
gaccatgggg gcggagcggg ggaaaagccc tggccttata gtttagaatt ttataaaagg    1980
aaaggcgtgg ccactgacaa tttgcgcttc aggagtccca gagtgaccgc ctggctcgga   2040
gcagggaatg aggggtcct taactctgag atttgttttc tgagagacaa aggtgatggg    2100
tgaggcggct aagcctctga ttctctatag gtggcggtca ttcatttcag aacatgaatg   2160
gattcagtaa ataaacatga tagaaaaatg ccacaagccc taggcccatt ggagtggact    2220
ggacagtctg ttcccagtgt gtccctcagc ctcggtcccc caccttccc ggagccctgg    2280 gggtcacaca catccctcct ggctgcctag cctgtgcccc ccgattcccc cctccccgc     2340 cccgcgcgtg cacacacaca cacacacaca cacacacaca cacacacacc acacagcacg    2400
aggcgacaga gatatgagag agagcgagcg agagaggacg ggagagagag ggagtgcaag   2460
tgtgcgctgg gggtaacccg tgcatgcatg cattgggggt aacaggctgg agctcagatc    2520
cctcccccag cccccagcag gggggactgc aggctcctgg tctgagtggg gagctgggcc    2580
ccctggacag aggactgggc tgcggggtca ggaatgggca cacttcctaa ctgcaggaca    2640
ctctaagggc tttggtcatg cacacgcagc caagagaagg tgtcgctggc acacagcctt    2700
ccaggagcgg acttggagac ctcgccaagg accaggactc cccagcactc acactccctt   2760
aggcgctgaa gtccagagga cagaggttga gggcagagct cctggagca ccagtggaag     2820 taggagggct gggctggaaa acctccccca acctcctatt gcaaagaggc tccagccagc    2880
agcctccaca ccccagtgat cttttaagat gcaaatctgc gccatcattt atttcctcag    2940
tgccttctcc agctcctggg atgcacactg cccgtcccca ggcccagaga cctgaccacc    3000
ctcattcctc cctcagccca ccctgggggtc tctccaccag ctgacagcct tcctgcagtc   3060
ccctccccga atgctgctcc ctgaggccct cctggacacc tgcagggcag gcacagcccg    3120
cgggacctca cagcacttgc tccgggcaga gctgcagttt ggccaagttg ccagctccgt     3180
gtgggcaggg gccctggcct gtggctgcca catcccgggt ggggcacgg cctttcctgg     3240 cgtggatgct gagcaaacgt aggggaagg ggagtgaatg aggagagcca ggtagctcag    3300 gggctgagge ctcactgagc agggtcccgc gtgaccggtc cccaccgctg acggttcctg    3360
gggtaacact caggacaggg agaggcaatg gaaagagacg tggccgccct cgcatcctgc    3420
agctcccgca ctcccagcct ccagcctcc cacccagccc ccagagccc accagtgacc       3480 ccgcccactg ggtcctcaga tggctcccac gggatctcct gccttgatct cctgtccaca    3540
tggaggtgaa gtgggttgct ctgaatgagg ggtgccgagc ctagggcgca gcccactctc    3600
ctgggtccgc agcatcacgc agcccggacc acaggtcctt tacaagaatc ggaagggtcc    3660
ctgcaatcgc ccttcgcact gaggcttcct actgtgtggt gtaaaaacac aggcttgtcc    3720
```

```
tcccttgctg cccacggggc tggagccgcc tgaaaatccc agcccacaac ttccccaaag    3780
cctggcagtc acttgaatag ccaaatgagt cctagaaagc gagagacgag aggggaatga    3840
gcgccgaaaa tcaaagcagg ttcccctcct gacaactcca gagaaggcgc atgggccccg    3900
tggcagaccc gaaccccag cctcgcgacc gcctgtgacc tgcgggtcaa ccacccgccg    3960
cggctccacg ccgtgggcac agactcaggg agcaggatga gaaagctgag acggcgcagc    4020
cacggcccgg tgccttcacg cgcacagcga cacagcccca gccagcgggg cccacgctaa    4080
ggcggaatcc cacagaagcc tacagagcga gcgcgcgcct gtgcttccca aaacggaatg    4140
gaaccaaggt gacttctaca gaacgatctg aagcccctggc tggcccttat gctagtctct    4200
tgggagcgtt ccaaatgcag ctcaatatta cttacttgac tttttatcttt cctccctggt    4260 tcgtggtatt tataactggg tcatctttta actatttgca acgtagcttc aggggagagg    4320
gggagggctt tataaataac ctgtattatt attatgcagg ttgattctgt tccctgagct    4380
aaagggaaca tgaaaataca tgtctgtgac tcatgccccc ccaccccac tccagggtgt    4440 gctgaggagt ctctcagctg ccccggggtc ctcgagcagg ggagggagaa aggctggcgc    4500
tgcgccctcc atcgcgtgaa gccaggggat tttgctctgc gacaagctga cttggctctc    4560
gtattgtttg cagaatcacc cagttccaag gcagtccctg cgggcaggtg cagctgtgcg    4620
ggagcttcag tcctgtcccc aacacccagg cagtaatggt tccagcacgg aaggtctacc    4680
tacctcccac tgcacagccc gagggctgtc ctggaggcac agccatccgt ccctgggtgg    4740
gcaggcacgt ttatgacccc caccccccac cccaccccc acgcgagtca gcacgttcca    4800
tactcgggtg atcgtgctca tcccctggtc atgtcatcgg gatctgagtg ccatccgagc    4860
agagagctgt ggcccggtgc cggggtgga cttcatctat tccagggaac caaggatgca    4920
tgatttgcaa acaaaaccag aagcgcaagc catctcctcg cctcccctga tagccgtgct    4980
gcggagcctg agtgctggag                                                5000
```

<210> SEQ ID NO 240
<211> LENGTH: 600
<212> TYPE: DNA
<213> ORGANISM: Homo sapiens

<400> SEQUENCE: 240

```
caggaaccac gggacctgct gcctagcggc cctgttccac ccttggccgc tcgcaaaatg      60
tttaggcttc ataaggtttg cccagggtca caaatttaac tcacagcaaa caatgaaatc     120
agcgcatgat tttcgagccc tcgtggtcac cctcccttcc tcctgccctt tcctgcatgg     180
gcagcagcag ggtgaggagc tgctctcccc aggcccaggc tggagtccct cagacgacct     240
gccggccagg gtacccccct gccccacac agcgcctgac agagccccccc acactgggg     300 aacgtgggga cccaagcagg ggcagcggcc tcaccgggca ggcggcgacc tgcatcatgg     360
cgtccagccc accctcgggt gcatccaggt ttccggaaat cagctgcttc ccgacctcgg     420
tctgaaactg gttggagttg ttggtcagct tcagcacgtg cctgaaggca aacgggggct     480
ggcactcttt ctccttgttg gggcatgggt ttcgcagctt atcagggtgc gtgttcacga     540
acggcagcac ggtcttgtcc acgaaggacc cgaagcctgc agggcacatg gaggggctgg     600
```

<210> SEQ ID NO 241
<211> LENGTH: 400
<212> TYPE: DNA
<213> ORGANISM: Homo sapiens

<400> SEQUENCE: 241

| | |
|---|---|
| tgcgtttagt gtaaaaatat caggtgtggc tgcacggagt gaaaaatcac aggctccacg | 60 |
| gagccgggag gcctgctgcc ctgccctctt gctttgatga ggaaatggcg accgcagaag | 120 |
| gaaatgtagc agcaccggca accggcatcc gtggggccac gccgggctgc ttcccagggc | 180 |
| cctccagcca agcagccaca ggaaagagta gatgttgatc ccaagctagg actgaggagt | 240 |
| ccgtccctaa gagccgaggg agtcaggtgg gcgaaactgg ccgcatgtct gggtacaact | 300 |
| gctcagggtt tctcatctgc tgaatcacca agctaggttc tgaagccagg cgtgagtgag | 360 |
| caggactgga gcaggattct gggaacaatc ttttccctcc | 400 |

<210> SEQ ID NO 242
<211> LENGTH: 2000
<212> TYPE: DNA
<213> ORGANISM: Homo sapiens

<400> SEQUENCE: 242

| | |
|---|---|
| gctggggaac tgaaggaagg gctgtggagc ctgaagcctg ggcctggcct gtgctgcggc | 60 |
| cgcaccgctg ggtgatgcag gagccactcc acctccctgg caccccagcc tcatccggca | 120 |
| acctgggagc gtgggcctcc tgcccctcca gggaggccct ggccgtgtcc tcatggggcc | 180 |
| cctccaggtc cttgtggctc aggtcggga cagtggctgt gagatctgac cctcccgttc | 240 |
| cccctccacc aagtaggaga aaccccggag catgagccct cgtccttcac cgtcccgggg | 300 |
| acaggggac ccccagatgc tgcacggctg acaggccaac gtggcagaag ctccagcttc | 360 |
| acaggaagcc agtgaccatg agagtctgta gctgtaacga agccacagag ctgtggcttt | 420 |
| ctttcccctt cagctctagg aaaggttatc tgccctgcac agatctccgg aggcctggct | 480 |
| gggctctgag agcatcagac tgattatcgt aagaaaataa tctctgcaga cacattcctt | 540 |
| gctagaagca ggggacaaag cccagcttca aagacaattc cacacacgcc ctccctgccc | 600 |
| tgcacagctg cctgccgggt gggagcagag cccttgcagc cgggctcagg ggcctgggca | 660 |
| gggacagcgt gtggcagggg cacagctgag acaggagcct caaagcgaca ccaacccgac | 720 |
| gtgaagctac agttgaggag acacagctgc ccccattccc gggcctcatc tccacagtga | 780 |
| gacgctggac tctctccctg acccaccgtc tcttagaacc tcccctccat ccggagcagt | 840 |
| tcggcagccc cagggcagcc aggggaaccc tgccgagtgc ctctgggccg ccacagaccg | 900 |
| cagagcccgc gggagccttg ctcacacagc ctcaggtcca ctgtggtctt ggggaaagc | 960 |
| cctgtcctgg acaggggag ccggggtcc tggccctgga ccaccatctg ggaccacgt | 1020 |
| tgtcacgcct gcaaagctcc ctgccccacc cccatgtgcc ggctggtgtt gacacctttg | 1080 |
| tagagtggga acctgcctcc gaccccagcc tgcagccaca gggcaggtta tagaccaggt | 1140 |
| gagagggcgc gcgcgcccaga accaaggagc acaagtccgc agtgcccatg agatcctcat | 1200 |
| gctggccggc gcaggagcca tcctcggcct ctgcaggtcc tcgtgggaaa ccgcggggc | 1260 |
| acgtggggcg gctgcagggt ccgcaaagcc ggctgtttgc gaaggcgca gctccacctg | 1320 |
| gaacagccga ggccgcccac gcgcttcccg cgggatcaga gcagcctcca cggctgttgt | 1380 |
| ctcaggcacc acgggatgcc tttcttcgtt tcaatagctg tgggaaagcc tcaatcggtc | 1440 |
| ctgaaagaac ccagatgtgc agcaatgaca aggccttctc tgagactcta gaaccttctg | 1500 |
| ccatctcaga caggagggag ccgtgaggca ggcgggagat ttgcagtcag caaaggacgg | 1560 |
| gcaggtgggg cagctgcaca cccagggccc tctccacggt cttccgggc caccccctcc | 1620 |
| cgcggtcctg ggtcatccac ctgctggcct cactctgccc acgcggccag gtcccaccgg | 1680 |

```
cccctgagct caacagacca aagctggccc gaccccaccc ccaagaagaa tgaaacaatt    1740 ttttttttacc tcttgcagaa aagtaaaaga tcatttattc attctgtttc tagatagcaa    1800
aactaagtgt caaaagcacc ttctgcacac agtctgcaca cactggccgg tggtcctgtt    1860
cccgcaaggt tgagctgtgt tccagagaca tgggtcctcc gggtgatgag gagccgctgg    1920
agggccctga gctgcacgtg ctaatgatta acgccccgtc cgtgctggcc ggtttctcaa    1980
atgcctcctg acgattgcgc                                                2000
```

<210> SEQ ID NO 243
<211> LENGTH: 2200
<212> TYPE: DNA
<213> ORGANISM: Homo sapiens

<400> SEQUENCE: 243

```
ggcctgagga gtcaaacggt gcaaaccctg ccccactctg tttgggaagc acctgctgtg      60
tggcaggcgc tgcgcttggt gctggggata gaccatgggg aagaaacaca cagaacctgc     120
cctgctctca aggaacaggc cctggggggcg gccaggggga gagacccaag gcagacaccc    180
acacagtggc gtaatgacag tgcttatggt ggggacctgg ctgcacagca ggtcagcaag     240
gggatgttca ggtgacactg ggggcacgga gacccagggg agagtggatt acagagggg     300 acgctgggca aatgtcccga ggctgaggtg gagttgcggg aaggaggagg ctgccgggca    360
gaggcgcaga gagctttgca ggtgttggca gagaccagca ggccctgcga ggcctggggt     420
gtgtcctcag ctgggagggc catagaagga tctgggcttg cagatgctgg tgcagactgg     480
aggcctgggg tgtgagagtc caggcggggc tcctgccaac acccagggga gtgggcctgg     540
gccaggtgga ccgggagctg gcacggtggt caggtgcttg gaggctgcgt gccacgctgg     600
ggacctggag gtgtgtgagg aggtgtctgt tgctcctggg gctgccgcct gcagggctgg     660
gtgtgcagca gtgcggggca atgaagtggg cgggttctgg gatggtggac gttcccttg     720 ttgggaacgt gttggtgcca agctgccatt tgagtttggc tctgagggt ctgggcaggg      780 gacacacagg gaatcacaca ggatggagtg agttcccagg gacccagggt ggcttggcct     840
gagaacagct cccactccca gatgtgtggg aagcccctcgg caccaagcct cagcctctcc    900
atctgtgaaa tggagacaac gtcactggac ttgcaggctg tccatgaggg tgatgcgatc    960
agaaagggtg gagttcctga acgccccggg gtcgggtct cacagcagga gcttagctgg      1020
tgtcggcatc tcctggaccc gtcctcagct ccgagcgccc agtcctgcca cctgtgtcca    1080
agtctgcact gtgcccacga ggccctcaag gccgcagaca gccccacact tctcggacgc    1140
cgccccagca cggtccttgt gtgaggtgga cactccttct ggacgccgcc ccagcacggt    1200
ccttgtgtga ggtggacact ccttctggac gccgcccag tacggtcctt gtgtgaggtg     1260
gacactcctt ctagggaagg agtagtaact cttgggtggt cgggtagttg ccatggaaag    1320
gggcagtaat gcccaggtat tgccgtggca accgtaaact gacatggcgc actggagggc     1380
gtgcctcatg gaaagctacc tgtgcccctg ccctgtgtta gctaggcctc aatgtggtcc    1440
agtatctgag caccgcctcc tgcctcagat gttcccgtct gtcaccccat taccagggcg    1500
gcacttcggg tcctttccag ccatcattgt cctggcattg ccacagtgga cactgccaca    1560
caggcttgtg tgcttgcgcg tacccaggtc ctcacctctc tgggataaac caggcacgtg    1620
gcggccgccc cattttccac ccgccagcgg tggaggagtt gcccagcctt gcaggaaaac    1680
agctctcatg ccagcagcgg agcatcctat tcaagtttc tcaggctgc cagcacaaat     1740 gctgcatgcc gggcggcttc ctcagcagac cgttgttct ctgcgtcctg gaggctggac    1800
```

```
gtcccaggtc ccgtgtggc aggcccggtt cctcccgcag cctctccttg gcttgtgggc    1860
ggcgtctcct ccctgggtcc tcgcagggcc acccctccgt gtgtctgtgt cctccctccc    1920
cttataagga ccccaggcag actggatcag ggcctgccct aaggactgaa ttttacctta    1980
atcacctctt taaaagctgt ctccaaatac agtcaccttc tggggtcctg gctgttaggg    2040
ctttgatgca tggatttggg ggacaccgct cagcccctaa cagccccat cctctgcctg    2100 cctttaccat ggggctgagc ccagccctgc aggagtcccc tggtttgatg tctgctgtgg    2160
ccacggcgac cctcaggctg ctccagccgc acttgtgctt                          2200

<210> SEQ ID NO 244
<211> LENGTH: 1600
<212> TYPE: DNA
<213> ORGANISM: Homo sapiens

<400> SEQUENCE: 244
ggggagtctc caggggctgg ggctggagcc gcatcagaga ggaaaggggt gtttgaaaaa      60
ggggcagggc ctgggaccca ggaaactgtt cttccagaga caccgtgaa gctgagcttt     120 gcctctcagg gaagctgtga ccccacgggt gctgccaga gagatcgggc caggtggagc     180
caagatggac tggaattccc cgacggggac aaggggccgg acgaggctga cttgccctgt     240
ctgatgaatg gtcaggtttg cttttctcc tgaaaacacg aggcagtgat cccggccagc     300
taattccagc agactggaga cgggatggtg agaatgagg ctgtgggcgg aagagcaga      360 tgggactcgc cagcatcctc acggcagggc gcgctattg ccctccctcc cctcctactc     420
tctggggtcc caggagcccc agatacgcaa tgctgccagg cgatttctgg cgccccgcag    480 accctgccc ctggagttgg gccaggtccc ggctggagca aaggggctc cttcaagccc      540 gctcctccct gtcaaacccg aggagcctga caggcgcagc gtcaccagcg tcaccgggcc    600
atagtgagcg gccaagccag cgtcaccggg ccatagtgag cggccaagcc agcgtcaccg    660
ggccatagtg agccgccaag ccagcgtcac cgggccatag tgagccgcca agccagtgtc    720
accgggccat agtgagcggc caagccttgg tctgccagag ccggccgcac cagaaggatt    780
tctgggtccc cagtcctgga ggagcacacg gtttacacca ggccttggga ggggaagagg    840
caaggcgtgg gcccagccct cactccccag gagaaaccct gtttgagcgg cagaggagac    900
tggagagacc ccagggcggg gatccctgag aggagagaaa cccggaattc atccacggag    960
gcgttcaccc agaggagacc cggagcttct ccaggagagg ctggattgct ccaacagggg   1020
ccctgaggag ctgatggcaa gagcggaagg cagctctgac tcgtgcgtct gactccaggt   1080
gtggccgttg ggctacagt gggaccagcc tgttgtcact gaacccacaa agtgcctccg    1140
agcgcgggtg gagagagggg gacctccac cgtctgctgg ccttgaatct tgaatctaat    1200
tcccgtctgt gctttgatgg gagaggcact gggagcgggc ggcttttca gttccttta     1260 tcttgaatgg cctttggggg attttcacag attctgagtt caaagcccag ggaggtgtgg   1320
gaacgtgaca ttcctcaccg cattcctcac cgcattcctc tgtaaaccag gcggtgttgg    1380
cacccatgag cctgtgtctt ctatgacatc aggagtttta tccctcacgt cagaaatcag    1440
ggttccaggc gccttggttt ttcttggcgc cagcggcttg gctatagaag aaaaactgaa   1500
ggggccaggt gcggtggctc acacctgtaa tcccagcact ttggaaggcc aaggcgggtg   1560
gatcacgagg tcaggggttc gagaccagcc aacatggcaa                         1600

<210> SEQ ID NO 245
```

<211> LENGTH: 7000
<212> TYPE: DNA
<213> ORGANISM: Homo sapiens

<400> SEQUENCE: 245

| | | | | | |
|---|---|---|---|---|---|
| gctcctcagg | gggaggttcg | gggcctttgg | tctctggact | tgggcagcag | aaaggaaaca | 60 |
| tccctggggg | cctgtggtga | cccccatcct | ccccagggtg | gtctggcagg | ggacactgtt | 120 |
| ttccaaagca | aagccagagc | gccaagggct | ctcgggattc | acgagatcca | catttatccc | 180 |
| aagttagaac | agcacatctg | tgcgtgcaaa | cttcattctg | acttcggccg | gctgtccttc | 240 |
| ttgcccaaag | caccgtgagg | cctcatccct | gcatccctgt | tgcttctttc | atgtgggatg | 300 |
| agaacccagg | aaggggctga | gtgtgactcc | tctggttttt | agagagcact | gccccgccc | 360 |
| cgcccctcc | tgcttcccca | ccttttcaca | gttgcctggc | tggggcgtaa | gtgaattgac | 420 |
| agcatttagt | ttgagtgact | ttcgagttac | ttttttttctt | ttttttgagac | agagtctcgc | 480 |
| tctgtcgccc | agggtggact | gcagtggtgt | aatcttggct | cactgcaacc | tctacctccc | 540 |
| gggttcaagc | gattctcaca | tctcagcctc | tggagtagct | ggaattacag | gcgcccgcca | 600 |
| ccacacctgg | ctaattttg | tgtttttagt | agagatgggg | tttcaccatg | ttggccaggc | 660 |
| tggtctcgaa | ctcctgacct | caggtgatcc | gcctgccttg | gcctcccaaa | gtgctgggat | 720 |
| tacaggtgtg | agccaccgag | cctggcctgg | agttattttg | ggagagggca | gcccctggtt | 780 |
| cagcgtggcg | aggctgcgct | tgctctcccg | ggcgggcgtc | cacaccctcc | tcgccgagat | 840 |
| ggagaagccc | aaaccctgc | agcgctcccc | catcacgtcc | ggccctggaa | gcccccggaa | 900 |
| accctgccac | gccctgagtg | ggagagcgca | ggtccctttc | cggccctgga | agcccccaga | 960 |
| aaccctggg | tgccaggcct | ggccgggaca | gcagcgacac | tgcatgctca | gcccttgcgt | 1020 |
| gagaccacgg | gagtgtccgc | cctctgcacg | tgctgctgat | tgcccacttc | gtccagcagg | 1080 |
| tttgggagct | tgtggctgca | tcctcctgca | gacacttgcc | cattctgggg | cctcctctct | 1140 |
| gtcttttctc | ctctgttgag | gggtctggga | gggaggcctt | ggagggtacc | catgctgctg | 1200 |
| ggactgatgc | tccccgcggt | ggaaggagct | gcctcttgaa | cagcaggggg | ctgagcagag | 1260 |
| gggaggggat | gcggggggtgc | cgtgcacaca | ggtgctctca | ggacgcaggg | gcttctcagc | 1320 |
| cctgctgtcc | cagggctgca | ctccagcagg | gcagactcct | gaggtgcaga | caccccagct | 1380 |
| tcacgctcac | acttctggaa | ggcgatgtct | gtgcgtttgc | tttctgctgc | agtttaaaaa | 1440 |
| gccgggctct | ctccggagcg | tgtgtagggc | ctggtcactg | gaatatctgg | actcagtgtt | 1500 |
| aatggcagcc | acgctggggg | ctgggcccag | ctttctgttc | tccgtgtggg | tgccatatcc | 1560 |
| acctccatcg | cagcccttc | tctctcgacc | ttttaaatca | cagtgtcacc | tccccctgct | 1620 |
| gtcctgccag | tggcccctgg | aggcttctcc | ccacccttt | cttctgggc | aattcttaag | 1680 |
| gctggcattg | aatcaggagg | ccagatgtgg | ccccctagtaa | ctcaccagca | gtccctgagg | 1740 |
| cttctggctc | ccctgcccca | ccagcctccc | atgtctgcct | caggcctctt | gacccgcctg | 1800 |
| gcactgacca | gactgtgtgc | ccgggtgccg | tgcccatggg | ctccgcctcc | cccaggcagg | 1860 |
| ccccctcttg | ctccgcggcc | accctgctc | ttgacctcac | acctctgcgg | tgtgtctgga | 1920 |
| cacaccagca | ccacgcgggg | cggggagcgg | aattctccag | gtggggtggg | caggccggcg | 1980 |
| ggtgttgagg | tctctgtgca | tgcttgtgcg | taccctggac | tttgccgtga | ggggtggcca | 2040 |
| gtgctctggg | tgcctttgcc | agacaactgg | tctgccgggc | cgagcattca | tgctggtcgc | 2100 |
| catcacgtga | ctcccatgcg | ccctggccct | ggggttgggg | ctgcaggact | gagaaccagc | 2160 |
| ggaagggggg | cgaggcctcg | ggaatgcgcc | ggcaactggc | gatgagctca | ggcctgacta | 2220 |

```
atgagcccag gtgactcata cacccggggc ctggatgagt ctgactgggt caggacttcc    2280
ctgcttgttc tgtcctggga gatgttgtcc ctggccctgc agagccggga ggacacgagg    2340
cctcctgggt cacagccaac gcagcctact cctgcccact gctcgcgccg gccaaggccc    2400
gtcggcacca cctcctccat gaagccttcc tgactgcccc catccctctg tgggcagctc    2460
gagtgtgcat cttgagtgct gtgcaggttg gggtccggcg ctcctgcagg caggcggcgt    2520
ctgggcctgg gggctctcag agtttgagga gcgtgtggtg agggtggcct cgggcctcaa    2580
agacgcagcg ctgtgggaac cgggagactg gctgagcccg ctctgaggaa ggtggggcca    2640
ggggcaccct cagctgaccc ggcgtgcagg ggtgaccagc caggcgtggc caaggatggg    2700
gtctctggga tcaggagact tcagtagcag ccaggaccga ggccaccagt ttccaccctg    2760
gcattttcca tcttttgaag gactggaaac gattggattc tttaactttt ttaagttgag    2820
gtgaaattca caacgcataa aattaaccat cttaaagcga acaattcggt gacatttagt    2880
acagccagaa ggctgtgcag ccatcaccac tgcccaactc tagaacattc acacgccgga    2940
gagagggagc cctgggccat cacgcagcca ccgcccggcc ccaagaacct gcgagtccac    3000
tttccacctc tggatcggcg gttctggacg ttcatgcagg tggttcccgc agtgcgaggc    3060
cttttgtttc gggctcctct cacaagcctc acgtttccag gtacgtcgtg gtgttgtgca    3120
gacccacaat tcatcccttt tcatgggtgt gtaaatagtcc accatagatt ctctacgttt    3180
taaagcatgt tttatgtgcc tgaaatgtct ctgcactcga gactatagct tgctttcttt    3240
cttttctttt tttttttta atttgagacg gagtcttgct ctgttttcag gctggagtgc    3300
agtggtgcga tctcggctca ctataacctc tgcctcccag gttcaactga ttcttttgcc    3360
tcagcctccc gagtagctgg gactataggc gcgccacccc acccggccaa ttttttttgta    3420
tttttagtag agatggggtt tcatcatgtt ggccaggatg gtctcgatct tccgaccttg    3480
tgatctgccc gcctcggcct cccaaattgt tgggattaca ggcgtgagcc accgcgccca    3540
gccgagacta cagcttttctt taactgcatc cctggaggga tctgagagtc tctttccctg    3600
tctcctttcc tttggaaaac atttcagcca gggctcccca agatgaaagg ccagagtccc    3660
aggcatgggc gttgcaggtg cacagttgcc acggggagct gtgggtgatg gtcgctgtca    3720
gcgatggctg ctgcaggtcc ctgtgaggaa ggggcagtgc cacagcagga ggagagggag    3780
tcagcggacg ttgattggca gtgcccgccc attccatcat tcagtcaccc actgtgcacc    3840
cagcacccag gctcggctgc atagaacatg gcccaggaag gctccacttc ctgtctcctc    3900
ttctccccctc tccagtctca tgatgggggct ggaggcatct tctagttttg agttctgagc    3960
taatgaacat gctcatgagc aggcggcagg atcccaggac ggtggagctg ggagcctgac    4020
tgcgggtgac ggacaggctc tggcagcccc tgtcagcatc ctctccaggg catgtgaaag    4080
ccagtgtgtc ctcagctgcc agtgcccccct ccccacctcc tctgggccca tgtgcacggg    4140
acctgggctc ccccaaccaa gcctgcccgc cttggttcag cagaacggct cctgtctcta    4200
cagcggtgcc aggccaggag tgctgtgtct gtgaagcggg gtcatggttt tggggccctc    4260
atctccctcg cgccctctca ttggggaccc cccgtctccc tagcgccctc tcgtcctctc    4320
ctgcatgtgc tgtgtctgtg aagcggggtc atggttttgg ggccccccgt ctccctagcg    4380
ttctctcgcc ctctccagca tgtgaagtgg ggtcatggtt tgggggcccc catctcccta    4440
gcgccctctc gttggggacc cccgtctccc tagcgccctc tcgccctcg cctgcatgtg    4500
ctgtgtccat gaagtggggt catggtttgg gggccccta tctttctagc accctctcgc    4560
```

```
cctctcctgt atgtgaagtg gggtcatggt ttgggggccg ccatctttct agcgccctct    4620
cgccttctcc tgagcgtgtg gaactctgtg gtggtcagag ctaaggttct gaataggtcg    4680
aagcacctcc ccggtgcctc tcaccctgaa tgctctggga ggacacagcc ttttcatagg    4740
ctacgactga catggcagga ggggcctgcc tgccacccgg gtcctctgct gcctgctgct    4800
tgctggggag ggggctcgag actgggatcc tgggcttctg ctccagctgt gcccaaggga    4860
gctgctgagg agggaccggg tggggcatcc actctgggca ggttcagggt cattcttggt    4920
gaccccgggt ccggttacaa aggctgatgg agcgcgtggg tggctgccta agtctctgga    4980
agcccaagaa tgtggagatg gcgcgtctcg gcccggggtc tcgtggctgg tctgggagaa    5040
cttgccttta tttctaggca ggaggctgca ctgcaaggga gcgtcagtgg cccggctggc    5100
tttccccggc cctcagcccg cactcgtcca ccaaagcaag ctcctttgtg gggctgccct    5160
gggaagccgg gatcacgagg ctctgccggc cgtggtcacc ccatgaggca gggtcagctc    5220
gggagcaagg cggatcagat ggaacagaac acgtagacca cctcgcccgc ccttagtcag    5280
ctgggccatt gaaaatcaag tccgtagaaa gacctagaaa taagtcccgg ggtgcccttg    5340
cctgttgacg ggcgggccga gcaggactgt tctcaggcag gcactggtct cttggcttcc    5400
aggtggtttg tttgctggtt tgaggctggg ggtgacgctc ctgtgcggga ggaggtcgca    5460
ttccattcat agcggcttat ctgggctgtc aggcaggcct gggagggagc ctgcctctgt    5520
gctctccaag ggtgggcgac ggacagacag ggtgtcccac cccttctggg ccaaggacag    5580
agggtcagtg tttgcagaga cctggggagg cccaggtgac ctccaccgag cacctgctgt    5640
gtgcagggcc agtgctggct gcagagacag cggagcgtgt gtggacccgg cggcccaggg    5700
gagggggggca ggcaggaccc ggcggcccag gggaggggg caggcaggac ccggcggccc    5760
aggggaggtg ggcaggcagg acccggcggc caggggaggg gggcaggca ggacccggcg    5820
gcccagggga ggggcaggc aggacccggc ggcccagggg agggggcag gcaggactcg    5880
gcggcccagg ggaggggggc aggcaggacc aggcggccct gggggtcagg ggtgaggcc    5940
aggcctagac ggcccacagg agggtggact cattctgacc gattcctgga agcccccgga    6000
aagtggtgat gttctggagg gcccagcaga ccccaaggcc cccaagacaa tcccagctgg    6060
ctctctgcgg ctctcggtgt ctgccatttg agacaatttg gcacaggca gggcaggccg    6120
tcgcggacgg tctaagccgc gcgcattggt gggggcagca gagcccctgc tctcagctcc    6180
tcggggtaca gcgggggtac caggcgggtg agtgggtggg tggtcactgc tcctgccaag    6240
ggcagccctg gtttggtttg cacttgctgc cctggtgacg gctgctctca ttcctgcccc    6300
attgctaaca agggtgtcat aagctacttt cccggcccac atcctattaa gcccatggag    6360
accctcccac agctgagcct gctgtgggct gcaggccctg gcggtgccc acctcggtcc    6420
ccactggcct ccttccagca ctttagagca gacacaggtt ggagataagg aaagttccag    6480
agcacagact ggaacaagcc ccaggcctct ccctgcccca gcagggcctc cctggatttg    6540
ggggacaggt gccctcatgg ggggtcctga aggtcagagc tggggctggg gctgggctgg    6600
cggaggtggc cttggcggag gccacattcc agggtctcag tgagagtctg tggcaggcag    6660
ccttgcagat gccgctgagg gaccccccac ttcatgttgt gggtgatgtg gtccattgat    6720
tgcctccagg tttaaatcag gtggatattt acctagcggc ctcctctccc tctgcacagg    6780
gcctggagtg ggatggactg gggtgctcag ctggaggctc tgcagacaca gcccctgggg    6840
ctatgcaggc cctgctggga gccacattgc catttttcat cacccacttt ttgggtgaga    6900
acccccctcga gtcctaacat ctgccgcatc tcagagcctg tggctccagt cagagcatct    6960
```

```
ggaccatact gctggggtca gagcgcggca ggacaatggc                          7000
```

<210> SEQ ID NO 246
<211> LENGTH: 1500
<212> TYPE: DNA
<213> ORGANISM: Homo sapiens

<400> SEQUENCE: 246

```
tgccaccacc atcttcaggt agagcttctc tctcctcctt gctgggcggg gcccctccct      60
ggggaagcct gcaggaccca gacagccaag gactctcgcc cgccgcagcc gctcccagcc     120
agcagctcca acgccctgac gtccgcctgc gcacgccact tctgcacccc ctggtgatgg     180
gctccctggg caagcacgcg gccccctccg ccttctcctc tgggctcccg ggcgcactgt     240
ctcaggtcgc agtcaccact ttaaccaggg acagcggtgc ttgggtctcc cacgtggcta     300
actctgtggg gccgggtctt gctaataact ctgccctgct cggggctgac cccgaggccc     360
ccgccggtcg ctgcctgccc ctgccaccct ccctgccagt ctgcgccac ctgggcatct      420
cacgcttctg gctgcccaac cacctccacc acgagagcgg cgagcaggtg cgggccgggg     480
cacgggcgtg ggggggcctg ctgcagacgc actgccaccc cttcctcgcc tggttcttct     540
gcctgctgct ggtcccccca tgcggcagcg tcccgccgcc cgccccgcca ccctgctgcc     600
agttctgcga ggccctgcag gatgcgtgtt ggagccgcct gggcggggc cggctgcccg       660
tcgcctgtgc ctcgctcccg acccaggagg atgggtactg tgtgctcatt gggccggctg     720
caggtaactg gccggccccg atctccccac cctttccttt ttgccttgcc aggtaagtgt     780
gggcggggct gacgtgagcc tggtacaggt tccccccaca tcgaatctct acgttcaggg     840
gcccgtggcc ctcgggaggt gggagagctg ggagtgaggc ctcctgtgtg ggaggaggc      900
cggcgtctgg acaggaagag ggctggatga accgcagccg atgtgtccag gtgccacctg     960
ggcctggagc tccctgagca ttttagcgca tttagtcctc agcacggtcc cgagataccc    1020
tgccatgccc cgagtcacag aggggaaact gaggcgtggg gcagtggcgt gactcacccc    1080
agggagccga gattcccgct caggtgtggc tgcatcgacc ttgctccggt cactaagctg    1140
cacggttcga tgcgcttcct gggagcccca gcgtgctcgg gccaagggtg ctgccgcgtg    1200
ggcagtgcag agaccctacc agcgtgggga ccagggaggt ctgcaggcc cgtcctgaga     1260
gggagccttt catgtccccc tccccatcct gaagcacaca gctccctgc cacagtgggg     1320
gccgcttctg ggcccagggg acgttgcccc atcaccgtgt ggcctggcct tgttgctggc    1380
tggacagttg ggggcaggaa gaggagggaa aggggactc tttaacctcc tggggcagg      1440
ggcagcccag aaaggacccc agcagatccc tcctctgtgt ccgggagtag acggggcccc    1500
```

<210> SEQ ID NO 247
<211> LENGTH: 2000
<212> TYPE: DNA
<213> ORGANISM: Homo sapiens

<400> SEQUENCE: 247

```
gggctccaca gcggcctgtc tcctcacagg gttcagccca gtctgctctc actcatttgc      60
tgattcattc tttcattcag ccagtcaata gtcatggccc ctcctgtgtg ccgggtggcc     120
atggatattg ccctgggtaa cacacagcct ggccctgtgg agcagacagt ggggacagcc     180
atgtggacag ggtgcaggtg gatggcaatg gcagctgggt caggagggc tgagggccgt      240
ggggaaaggt gcagaatcaa taggggcatc cggactgggg tgcaggcctg ggggctggga     300
```

| | |
|---|---|
| tttctagggt ggaggtcacc tctgagggag acagagcaag gccctggag attagaaggt | 360 |
| cgaaggtcgc cgtgttgagg tcaggggccc tgaattggag ccgcggcaaa ggagagggca | 420 |
| ggtcagggca cgtggtgagt gattgctgcg gcttctgagc acggctgggt ctgtggggcc | 480 |
| tgagcagagg tgaccgcgca tccggcgcca cggcaggcag gactccccac ccttgctgct | 540 |
| gcctacaccc ccagggcagc cccagagtcg ggggcgcagc tccctgcttg ccagttcaga | 600 |
| gcccagcccc tctcacccag cccagaggag gacacagatg gaggagggc acccggaggg | 660 |
| tcccccgcc gacaggcccc acgtctccca cctgcaggac aatgaagtgg ccgccttgca | 720 |
| gcccccgtg gtgcagctgc acgacagcaa cccctacccg cggcgggagc accccacccc | 780 |
| caccgcgcgg ccctggcggg cagatgacat cctggccagc cccctcgcc tgcccgagcc | 840 |
| ccagccctac cccggagccc cgcaccacag ctcctacgtg cacctgcggc cggcgcgacc | 900 |
| cacaagccca cccgcccaca gccaccgcga cttccagccg gtggtgagtg cccccccaaa | 960 |
| gtgggcttgg ctccatctag cccctcggct ctcggcagca aagagggcc cagcccctgc | 1020 |
| agagctgctg ggggtcccag gcttcggcca tgggtgggg tctggcggct cagggccact | 1080 |
| cagggcggct tggctggccc tgggacttgc cctctggtgg ccaagcagtg gtcatgaaag | 1140 |
| tccagccgct gtcacatcct tgaggaaccg gcgtacctcc gcctacagcg gcagctgggg | 1200 |
| gcacccacgt ggcccggggc tgctctgacc tggcagcgta tgggggctgc tgcctgggcc | 1260 |
| cctcagtgtg tcacttgcgc gcctcccgct cagcgcccct cggccgtgcc tgtccacaca | 1320 |
| ggtgcggggc cggggtggtg cgcccggggc ctgggtgcag ggggcagcgt gggacacagc | 1380 |
| ccgtgacgcg cccctctccc cgcagctcca cctggttgcg ctcaacagcc cctgtcagg | 1440 |
| cggcatgcgg ggcatccgcg gggccgactt ccagtgcttc cagcaggcgc gggccgtggg | 1500 |
| gctggcgggc accttccgcg ccttcctgtc ctcgcgcctg caggacctgt acagcatcgt | 1560 |
| gcgccgtgcc gaccgcgcag ccgtgcccat cgtcaacctc aaggtgggtc agtccagtcc | 1620 |
| tgagggcgcg ggctcctcgg ccccacttg acctctgggg tgaactccca gcggggagct | 1680 |
| cccctctagg gcctctggag gccaccatgt tacagacact ggcgcctagg ctggcgactt | 1740 |
| cagggcaggc tccgggtggg tcacaccct ccaggctcag gccaggcctc tgcatccctg | 1800 |
| ggcactgcca cgtcccccag ggcatcccat gaggcccccc cgtggccccc tgaccccccg | 1860 |
| ctcccccggc agtgccctc agagggtccc atgctgctgg accaagtgtc cacacaggtg | 1920 |
| atagggctca catacaagcc tggaatcagg aaccgtcctt tgggcctcta gtgccatgcg | 1980 |
| ggctggtggc ccctctgcca | 2000 |

<210> SEQ ID NO 248
<211> LENGTH: 2000
<212> TYPE: DNA
<213> ORGANISM: Homo sapiens

<400> SEQUENCE: 248

| | |
|---|---|
| gcctggagtg tagtcctgct gaaggccaga gaccacacac tccacccaga ctccggatct | 60 |
| ccctccccag caggggatg gaggccctgc cgctgggagt gctggtgtta tgtggaaggg | 120 |
| ctgggcttct ccaggctcc tgggaggcct aaacatcttg caaggttttg acgttaatta | 180 |
| ctattatgat tgctttctgt gtgttactgt tttccccaca ctttagccag ctaatgtgga | 240 |
| gctacagaag gccctcgccc ctaccctcc agatgtccca gcccatgaca agcaggaagg | 300 |
| ccgggtgctg ggagacttcc tggggctgga tctgacatca ttccaagcag atgataacct | 360 |
| gccttcccga tttccaaacc cacagcaaga caccctggag ttatttataa atgcgagccc | 420 |

-continued

```
ctgggtgcac ttctgacggg accagcaccc tgacggccat gagagggtgg agacagcgca      480
ccccgagctc agggaggcag gaaactctgg acctggaggc cggcaccat gagggacacg       540 ctgcaggccc agctgctgcc gcctgggcg gggctgccct gcaggctccg ggaaaaccca       600
gaaccaggcc ggatcagcgt gtgtcaagag gcggggcgtg agagatgagc tgctttttt      660 cttcacaggg ttggcaggaa ctgcaaataa tagaaagtct ttagggtcta acacgctgcc     720
ctgaaaacac tatcattact ttcctaatga ctaactgtgt ctttcagccg gcggggcagg     780
cagctgaggc cgcaggctcc cgcagaggac cggggaggc tggcagcctg taatctgggg      840
gcgctgacag tgctctgccc agaccctcgc gccagctcca gctccagcac agcagccctg     900
ggtccctctg gccccctgcc cgcagagtcc aggtgtggca gaggccgccc agtatccctt     960
ctcctcctcc ttttctaaaa acagagtctc acgatgtttc ccatgcgggt ctccaacgcc     1020
tgggctcaag cgatccttct gcctcggcct cccaaagcgt tgggattaag ggcgagcca     1080 ccgcgcccgg cccaccttcc cttctggttc atttccagta aggtcctgtc cacagcgtcc    1140
ttcccagcat tcccaccagg ctgcaggcct tggcctccct cccctccatt ctcattctcc    1200
ccgaaaccgc caagcgcgtc caaagcacgg gttcgccaag cgcccccccc gccccactcc    1260
acattccctt ccccgccgac tcagcctccg tagctcgcgg acggcccctc ctcacgccag    1320
cccaggcttt tttttttttt ttttcttcta ttttaaggtt gtcttttaat gacacaagcg    1380
acatttggag acaaaaggac acatctcttc ctgacccacc tccaaccca gctgacggcc     1440 gccctgagcc tggcgtagac ggcccggaac gttccctgcg tgggttccgt ccatcccgaa    1500
cccctgtccc cgcgccggct ccgggggtgc tcgggggcc gcgtggggtc tgtgacgtcg      1560
cctcgaggct gcatcccggt gacccggcag cccctggcgc tcgcgggagg cgggcgggcg    1620 cggacccag gctttagggc gcgattcctg cagctggctg ccggcccgag ttctggggt       1680 gtctgaggtc tcgggcgggg cgaggacgtt tctccggctc agcccccca cctcctgccc      1740 tgccgccccc cacacccagc tccccacgga cgccaagagg cgcctccac cccggcgagg      1800 acccgcgggg aaacgggcc caggcgcggc gactgcggag gacgcgcctc ggccccagcg      1860 cccctggtcct cggggcgtcc ggctgccctt gcccgaggcc ggggcgggcg ctcagcgccg    1920
cggaagaaac gcccgggcgg ggacgcacag cgaggcgggc tccgcgggaa gtaccgggaa    1980
aacggcgcgg agcggaacag                                                2000
```

<210> SEQ ID NO 249
<211> LENGTH: 3000
<212> TYPE: DNA
<213> ORGANISM: Homo sapiens

<400> SEQUENCE: 249

```
tggagcaatc ccagagaggc tgaggtgttc aggctggccc cagatgcaca cgagcgtgaa       60
gcctgttcag aagccagctc ctcacaccct ctcccctgcc agaggctcca gcaccccctc     120
ccctctcctc tcccctccct tccctgtggt cctcctgccc accccacccc cgtctgcatg     180
tgcaccgtca cggagatgcg tgtactaggg cggaggtcgg ggacagtcgt cagaaggaca    240
caggaaagaa gggaacagga atcccataac agaacattat ccggcaggag taattaacac    300
aggcaggact ggaggctttg ttttgttttg cttaaaaaac agtggtattt aaattaatgg     360
gcatgggaag actattcagt gaaagacatc ggtcattgag gtatctattc aaaaacacgg    420
tttagtactc tgccacacac cgaacgcaac gccacagcag ccatagaagc gtgtgtggct    480
```

```
gtttaacgtg gtcttttttgg ggagggcatc ctaggcagag caggcgtgga agggaaggcg    540
gcggacggaa caaaacgcgg gcacgcaacg gctgctgcgc cggatctgag gcagggccag    600
cctgtgggag cagcaacatc gctcgcagga cagcgatgga gcccccacga atccgcgtga    660
aagcagcaac cacctagaaa tgaacgtaca gctgcttaga aacagaatac ggatgacccg    720
aaagacttcc cgatggtagt caccagcata caggacctga cacgggcgtg cgggcagggt    780
gtgccgctac ggggtccctg gcgcacctgc tacccctgct acccgcattc accgcacgcg    840
gagggtgcgg gccgtgaagg ttatacatgc aaatatcctt ccaccagcca gttctccttc    900
caggaatctg ccacccgacc cttgtgttgt gcacagacat ggtccaggtg tttgcgacgt    960
gattgtttat cagagagaga aagggaaat ctccaggctc gctgtagctg caggagctct   1020
gggggctgcg cccatcgtgg agacggatag ctgtctctca tgaacacagg acagcaagtc   1080
cggctgcggc cacagaagac tcgccctcct ggacgcagcg tcttccttcc tcagccccac   1140
actggaggtg gccagtgcca tccacagcag aaggggccag ccgggaccag gctcacgccg   1200
tggaattctg ctctgtggta agaggaagag cgatagctgg aacccagcgc cgtcgcacac   1260
acagcgggga agagtctcag aaatgttact ttgagtcaaa agctggaca aaaaaaggcg   1320
caagccagat ggtgctgaag aggccacagg aggctggcag ccaggggtc tggcacctca   1380
ctcggaggcg cagtgggccc gtccggaatt agtggccata cggcaagtgc cgagtggaca   1440
tcaaaccgtc acttcagact cctgcgcttc actgcctgtc ggttatgcct gggttttgaa   1500
atcaagtcac agaacacctg gaatgtggtg tttacgcaga acaaagcggg tgcctcggag   1560
gagagagcct agggacaggg gcacctcccg gtgtgggtgc ccagggttgc agggtggctt   1620
cctctgtctg cgcggttttc agagccccag ggtcctgcct gcccggctgc ctggaggcgg   1680
cccacatcct gctctgcgcc gccgaatctc agcctgaaca gcttcgctgg tgtttgtgtt   1740
gacttatttg ttcttttttt tttttttttt ttttaaataa aggattccga tgctgttaca   1800
gtcaataaaa gccacaggtc tgggtgacct acaaatgtgt gtgtctgact ttctgcagtt   1860
taaatcgcca ctgagcctta aggcgtctgg cccgcgcatt gaggaatcca cgtgggtctc   1920
ggggtcccca tgcctgccca gctccctgct tcagcctggg cggtctggc gggcatttct   1980
gcgagcctgt ccctgggccc gcctcctggc cagacttcca gaaacattgt ccacatcccc   2040
gttgcacgtc cccccgtcac cggaaactgc agcccacagc actgggaaga acccgggagg   2100
caggcgttag gacggggtgg ccgagacagg gaagggagcc atggcggacg tcctcaccca   2160
agccagggct tcctgcccct gtggtactga caggagcccc gcaggacgtg gggttggctt   2220
tgggcagctc ggtggacact tctctttcag atcctgccac agcaaagctc acgagactca   2280
cttcttccca ttggaattca ctaagaacaa attcaacaat tcagacgccc cagctggagg   2340
tttatttat ggattttacc tgtgcggtat ttagggttgt gtttatgaat aaaggtgtgc   2400
gttctggcaa gtagaaatac agagcttgtc tttcacccaa gtatctgtaa ctttctccaa   2460
tgcagacact aaaatgcaat aaaaacaaac caaacccatt aaacatgaat tagatgaggc   2520
aggctgatgg gaggttgtgg gattaacagg ccgtcagcgg attgaagctg cgcacatcgc   2580
tgggatgctg ctgcgggagg attcggtcta atccggagc atctggctgg gcagtgggca   2640
gcgtctgcag tcgtggctgc ttgaaggtat gaaggttgtg gcctttgctt cccccсcatca   2700
ggctgcccca ccctggaccc cacccagacc cctcgggcac cctggggtca tcttcagctc   2760
ccccttctct tccttccttc tcttccgcct gggcccctac tgtgacccga ggtcagcaga   2820
ggaccctggc aggtggctgc tccctgggac tcgactgtgc aggtgaggct tggggtgacc   2880
```

```
gctgctcctg ctcctgctcc tctcgccgtc cccaccctcc tccatcatgc tgtcaacatg      2940
catgtgggct gcagccctca gcctgcagga cgctgtcagt gcagctcctc agtggccagg      3000

<210> SEQ ID NO 250
<211> LENGTH: 2500
<212> TYPE: DNA
<213> ORGANISM: Homo sapiens

<400> SEQUENCE: 250
atcttgtctt ccttgtccca gtcctggaac cagccactgc cccagcagct cctgtgtgtg        60
gtggcatgtt ctggaagcca ggatgcatgg tgctcctggg ctgctgtggg tcctgggctg       120
ctgtgggtcc cgagctgctg tgggtcctgg gctgcacccc tgcagaacac ttccttccat       180
gttcagctcc ctatatggaa ccccagttcc agcccacag cacagggtcc cccagttctt        240
cctgcctcag gtgtgcacca cgaggaatcc aactgccagt atctgtgcgt ggcctcccgc       300
cgggaggagg ctgccggagg ctctgagctc tagccccaca gcactggcac atcctagatt       360
tccgggaaga cacggcctcc tccccagggg aaggtggtgg tgcccacacc cagagcattc       420
attcctgcag tggagacaga gggacctgcc tctccaactg tgggtgtcag gagccaaggc       480
gcatggtaaa tggggctctc tgtgaggcca ggtgcacggc cccatctcca gcagcagcgg       540
ccatgccacc cagctgcact ctgtggggga ggtgccatga ttgacggggg cccctccctg       600
tgtccagtgt cctcctccct ccacgggccc ctctgcacac cgtcctcaca gtctccctct       660
gcacaccgtc ctcacagcct ccctctgcac accatcctca tggtctccct ctgcacaccg       720
tcctcacagc ctccctctgc acaccgtcct cacagcctcc ctgcacacac cgtcctcaca       780
gcctccctct gcacaccatc ctcatggtct ccctctcctt ccacagaccc ctctgctcgc       840
catcctgacg gcctccctct ccctccacgg accctctac acactgtcct cccagcctcc        900
ctctacacgc catcctcaca gcctccctct ccctccacgg gccctctac acaccgtcct        960 cacggcctcc ctctccctcc acgggcccct ctgcacaccg tcctcacagc ctccctctcc      1020
ctccacgggc ccctctgcac gccgtcctca cggcctccct ctgcctccac gggcccctct      1080
gcacgccgtc ctcacggcct ccctctgcct ccacgggccc ctctgcatgc cgtcctcacg      1140
gcctccctct ctccacggg gccctctgc acgccgtcct cacggcctcc ctctctctcc       1200
acgggcccct ctgcacgccg tcctcacagc cttcctcttt ttccacagac ccctctgcac      1260
gccgtcctca cggcctccct ctccctccac gggcccctct gcatgccgtc ctcacagcct      1320
caccgacgtc accattgctg gccccgcttc aggtgacagg ccacagtagc acctgtcagc      1380
tctgtcccgc tgctggacag ggagatactg ggccactcag cccagcgggg aacgtgtgtc      1440
ccgaaactgc cttgggctcg ccatcagaac tgtggcagca tcttccagcg ttccttttaa      1500
caggctgccg ttggaatagg agtcacggag caattgcagt gctaagtttt ctttaagtca      1560
cacaattgaa ggaggcttta tttttcacac atttcttcca gagtttcctg gtagcctgag      1620
tgcatgggtg atgcccccctg agttatttat caggggcagc cagctgccct ccccgggggc    1680
acttacagtc agcccatctc tgtcctggtc aggtgggcgc caaggaagac ccggctcagg      1740
gcctctgtat gggcagcctg gcttgtacac acaccctcc ccaccagcag attctgaatt       1800
ctcccttctt catgcacacc gggaaggtcc cttctgcact cataccggga aggtaggcag      1860
gtttcggtag tgtctgcctc cagtgttttc ctcctcctgc tctatgacat catctttctg      1920 tgatttttttt tttcttgcag gaagttggaa gcatcatcgg gaaggtaatt attgattgaa      1980
```

```
tctctgcctc tcctggggtc tctgtaaggg gatggtgagg atggcagcct ccctgggtac    2040
taggtggcac ccagtaggtg cgcctttccc agttggtggg tggtctgtgt tccatgaaga    2100 caggaccccca gaggtgtcgc ctttatgctg tatgacattg aagctggtcc ctggctctgc   2160
gtggcctgag gggaaggggt tcactccagc tggtcacctc gctgcccct gcccgtggcc     2220 ttggtggcca gtccttcttt cccggttgaa gaccccacga agaatgattt ctcacgcctt    2280
cttcagccgg ctgtgtagtc tgggtggtct ccaggagtgc cagtgaggc agcagccccc    2340 agacaattcc tttccaaatc agggctggcc cggggggaagt aaggcccagt ttggaagcct   2400
gctgccccgg gaggccgagc agtgagggcc acctccctgt cttcatcaca ttttcaccgc    2460
ttccgggggt ccttcccctc agtcccacca tgggggcgcc                          2500
```

<210> SEQ ID NO 251
<211> LENGTH: 6000
<212> TYPE: DNA
<213> ORGANISM: Homo sapiens

<400> SEQUENCE: 251

```
gctggacacc tctgagagcg tggccctgag gctgaagccc tacggggccc tcgtggacaa      60
agtcaagtcc ttcaccaagc gcttcatcga caacctgagg gacaggtagg agggacgccc    120
cgtgaccttc ctcctgtgct ctgggcctc ttggagggag gggtggggc ccaggggaac     180 acgggtgcga cggcctcaac ctcctaaggt tgggcgagcg ttgccctgac cggggcccct    240
cccggcgccc tccagagtga ggccggggcc ctttccggcg ccctccagag tgagctggtc    300
tgagcctctc ccagcgcctt ccagagtgag ctggtttgag accctgctcg cggggggtggc   360 acctgttcag cagggccgag gtgacagtga ggctgagatg tagggaagag aggctcccgc    420
aggctgaccg agagggctca gcgcactggc ccagacacgc agtcctgcct ggtgcgcggg    480
agcccctcac taaccacctg gaccctggtt tgttccgtgg gcagtgagag cctctacctg    540
ggtcctggat cccacgttct gaaggtcccc gactcgggag ccaggagggg tgtcgctctg    600
cagccccagg gcccccaggc ttggttctgg gcttgggaca cggcaccctc tgctccacgt    660
tcctccatct gtgcgtgtgg ctgaggacag accgggggga gaggggagtc ggtcctgtgg    720
gtgcacaggg ccgctgaggg gggggcatgt agaacggggc tcccccactg agacgggtcc    780
tggcagtggg gacacagctt agccggcgta ggaaccccg tcctccttga ccctgctgac     840
tggccgctgg gccggagcct cccgccacca gaaggggcac agtcagaggc tgccggtaac    900
agcagggtgg accttccagc ccacaccgtg cccagcagga gccattggta ccaggaaccc    960
tgagcttagt ggacatggcc aggcccgtgc ggcagtgttt ggggggggggt ctggctgtgg   1020 atggcaccgg ggaggggcgg ccgcgtggcc cagcgtcccc cgagtcgccc ttgttgcctt    1080
tactcagtct ccccatgact cagtttccca cctgtgaaat ggggcggagt catcccatg    1140 tcgctgccac tggattcctg caggcgccgt ggtcactctg ctgaatggat gggagggtgg   1200
gtggggcaga ggtgggccca cccccaggctg ggcagagca gaccctgag agcctcaggc    1260 tcaggtgctc agagggcagc gaggggctg ctcagatccc cggggtgcct ccttccccca    1320
ctgtcatgct gccccactgc aggcccaagg accccacccc agcagggcca cacactcagg   1380
gctcctggtc tgagggcctg agggatcggg gcgcaggtcg cttgctggcc acccgcct     1440 gcacagcctt ccaggagggc cggcctcagg gccacagggc aagtccagct gtgtgtcagc   1500
cacggccagg gtggggcagc ctgtccatct gggtgacgtc gcgccctggg acgggtagcg   1560
atggcgccag gggccgcccg cctcacgccc gccgtgcctg ttcctggcag gtactaccgc   1620
```

```
tgtgaccgaa acctggtgtg gaacgcaggc gcgctgcact acagtgacga ggtggagatc    1680
atccaaggcc tcacgcgcat gcctggcggc cgcgacgcac tcaaaagcag cgtggacgcg    1740
gtcaagtact ttgggaaggg cacctacacc gactgcgcta tcaagaaggg gctggagcag    1800
ctcctcgtgg ggtgagtggc ccccagcctc ctgcccacgc cagttctcac gcgtggtacc    1860
cagcctgggc tggggttggc ctggggtccc tgtgcggctt cagctgcagc ctccctgttc    1920
tcttggaggc tgcacggcct ccctgaccca ctttgtgggc aggaaagaga cggagacaga    1980
cagagacaga gagaaacaga aacagggaga aacagacaca gagagagaca gagacagaga    2040
gagatagaga cagagacaga gagagacaga gacaaagagt gacagaggga ccaagacagg    2100
cagacagaga caaacagaga cagagacaga gacacagaga gagacacaga gagacagaga    2160
cgggaacaga gacaggcaga cagagacaga gagagacaga gacagaaaca gagacagagg    2220
gacagagaca ggcagagaga gacagagaga cagagacaga gacagacaaa cagagacaga    2280
gagacagaaa cagggacaga gacagaaaga gagagagaca gagggaaaca gagagagaca    2340
gagacagata gaaaaagaca gaggcagaga gaagcagaga cagagaaaca aagacagtca    2400
gagacagaca gagacagaga cagaaacaga gacagagaga cagagacaga ggggcagaga    2460
caggcagaca gagagacaga gacagagaca gcgaaacaga gacagaaaca tacagagaca    2520
gagagacaga gagaagcaga gacagacaga ggcagagaga cagagagaag cagagacagg    2580
gacagagaca gagacagaaa tagagagata gagacagagg gacagagaca gagagataga    2640
gacagagagg gagacagaga gataagaagca gagagagaga gacaaagaca gaggcagaga    2700
gacagagaga gaagcacaga cagagacaga cagagagaca gggacagaca gagacagaga    2760
gaccggaaac agaggcagag agactgagag actgagagag acggggtggt tttccccaca    2820
gcatcaacac caagcagggc taggatcact gaaacagact catcagaccc gaagcatgcg    2880
cttttctcggg gttttttctgg actgagggggt ttcctctcat cccagtgtcc agctgtgggg    2940
acgcaggggc cgcaagcccc ggagtgtcca gaggggaacg tggcctcccc acacccagcc    3000
cttcacgagg cctcaggatc ccagtggggg tacccgaggc tgccctgtcc agccaggcgg    3060
tgcgggggt ttggggagag cctctccccg aggtcggtct cagagggcca catggccggt    3120
gtgggccgga cattcccttt ccaatggttg tgcccacttc cctccagagt tggtgccaag    3180
ctgggacctg ggggacttgg agtctcagga agtcgtccgc tgtctgcagg gggtgcatgg    3240
gggatgtggc cacacacgtc agagtgcggc cccctgtgga agccacagac agacacgact    3300
cccctaaatg agctcgccct tctggccgag atgctcagcg tccccagcag gctgcccgac    3360
tgccctgcga tactgccctc cttcctgctg ctcccacttt ccctttcggg gggttggatt    3420
tggggcattc agggatcgcc ctgttgtttg ctcatcacac ccatttcctg caagagccac    3480
ggtgaccgag cagccttgag ttgaggcagc ttgtgggtag acgcggcggg catctcggag    3540
gggcacgctc cctgccaccc tcagcctcca ctcactggtc aggggctttg cgccccaggg    3600
caccccagga accgagcctc ctttggggtc atgggtgcct ctcctgggag ggcgtggatt    3660
ttccaaagca gtttagagaa atgagaccca caggcgttat ttcccatggt gaggttcttt    3720
tcagtaaccc ccaccgtata gccaggatca gcaaagagag gcggctcctc ccggtgagac    3780
agggaccagc acctcccgga caggcttggg tctccctcca gttcccccac ctagtctcga    3840
ggtctcacgc tgccctctcc tgtccagggg ctcccacctg aaggagaata agtacctgat    3900
tgtggtgacc gacgggcacc ccctggaggg ctacaaggaa ccctgtgggg ggctggagga    3960
```

```
tgctgtgaac gaggccaagc acctgggcgt caaagtcttc tcggtggcca tcacacccga    4020
ccacctggta ggcaccggcc cccccggca gatgccccca accacaggga gtggcggctg    4080
caaggccccc ggcagctggg accgtctttt ggtcctcggg agggtgtggg ttctccagcc    4140
ggccacccett gccectgaga ggccagcccc tcctgctgag gagcctggag cgccccagcc    4200
cagcctcccc tctggccctg tgggaagcgg ccccggccgt caggggtccc agccctgctc    4260
agcccaccct gaacactgcc cccaggagcc gcgtctgagc atcatcgcca cggaccacac    4320
gtaccggcgc aacttcacgg cggctgactg gggccagagc cgcgacgcag aggaggccat    4380
cagccagacc atcgacacca tcgtggacat gatcgtgagg ccctgccca ggagacgggg    4440
aggcccgcgg cggccgcagg tggaaagtaa ttctgcgttt ccatttctct ttccagaaaa    4500
ataacgtgga gcaagtggta agagccctcc ccaccacccc cagccgtgag tctgcacacg    4560
tccacccaca cgtccacctg tgtgttcagg acgcatgtcc ctatgcatat ccgcccatgt    4620
gcccgggaca catgtcccct gcgtgtctgc ccgtgtgccc gggatgtgtg tcccctgcg    4680
tgtccacctg tgtgtctgcc catgtgcctg ggacatgtgt ccgcctgtgc gtccatccgt    4740
gtgtccgtct gcccatgtgc ctgggtcgca tgtcaccctg tgtcccagcc gtatgtccgt    4800
ggctttccca ctgactcgtc tccatgcttt cccccccacag tgctgctcct tcgaatgcca    4860
ggtgagtgtg ccccccgacc cctgaccccg cgccctgcac cctgggaacc tgagtctggg    4920
gtcctggctg accgtcccct ctgccttgca gcctgcaaga ggacctccgg ggctccgggg    4980
cgaccccggc tttgaggtga gtggtgactc ctgctcctcc catgtgttgt ggggcctggg    5040
agtgggggtg gcaggaccaa agcctcctgg gcacccaagt ccaccatgag gatccagagg    5100
ggacggcggg ggtccagatg gaggggacgg cgggggtcca gatggagggg acggcgggag    5160
tccagatgga ggggatggcg gggtccagat ggaggggacg gcggggtcca gatggagggg    5220
acggcggggt ccagatggag gggatggcgg ggtccagatg gaggggacgg cggggtccag    5280
atggagggga cggcggggtc cagatggagg ggacgtcggg gctccagatg gaggggacgg    5340
cgggagtcca gatggagggg acggcggggt ccagatggag gggacggcgg ggtccagatg    5400
gaggggacgg cggggtccag atggagggga cgtcggggct ccagatggag gggacggcgg    5460
gagtccagat ggaggggacg gcgtggtcca gatggagggg acggcggggt ccagatggag    5520
gggacgtcgg ggctccagat ggaggggacg gcggggtcc agatggaggg gacggcgggg    5580
tccagatgga ggggacggcg gggtccagat ggaggggacg gcggggtcca gatggagggg    5640
acggcggggt ccagatggag gggacggcgg ggtccagatg gaggggacgg cgggagtcca    5700
gatggagggg acggcgtggt ccagatggag gggacggcgg ggtccagatg gagggggacgt    5760
cggggctcca gatggagggg acggcggggt ccagatggag gggatgtcgg ggtccagatg    5820
gaagggacgg cggggtccag caggcaggct ccggccgtgc agggtgtgga ctgtcccggg    5880
ggcgctgggg gcttctgagg gtgtctctgt ccgccctgcc ctcagccgca ctctgttcag    5940
aaggaccttt ctggaggtag gagggtgaga atgtgggtcc cctgcttctg tgtggctcac    6000

<210> SEQ ID NO 252
<211> LENGTH: 7000
<212> TYPE: DNA
<213> ORGANISM: Homo sapiens

<400> SEQUENCE: 252
ggccggggag gcggggaggc tgccccaaga gtaaaagcct ttctgacgtg cgcaggacgc      60
ggccctgact ggtctaactg actctttctc ttctcctcag cttgctgtgg tgagacccag     120
```

```
gctctagctc ctgagagaat ggatcccggg ggtcggggag cgaggcctgg gtcccacaca    180
tgtcacagga cagcacatgg cactctggtc cccgcccgca gctccctgca cctgcccgcc    240
ccctctgggg cctgctccaa gccagcaggg ttcccgggtg ttgggctggg ccccgccctc    300
tttcacccat aactgaaata accaggagca ggcttggggg ggtccctgct ccatcattct    360
ggcccacagg ccccacccta gcctggctga gcaacgccag ccctgaccag ccgccggaca    420
gagcagcctt tacggggcca tgggaggggg tgggcttttc tggggctgag acggggggac    480
cccaacgtgt caggtgagga tgtggcagcc aaggaggggc cagggcggtg gaggggaggg    540
gccagggcac tggaggggag gggcgtgctc tgctgacacc gcccccgcct gcagaatgca    600
agtgcggccc catcgacctc ctgttcgtgc tggacagctc agagagcatt ggcctgcaga    660
acttcgagat tgccaaggac ttcgtcgtca aggtcatcga ccggctgagc cgggacgagc    720
tggtcaaggt gaggcctcgc cccgcccggc tttctcaagc ccaggtgcac cccgaccctg    780
ccggccgccc ctgcccgcgc cagacctcag cctcccgagg ccaccgctgc atccctgtga    840
cttccctact catgacaagg atgccaggca cgcgccagcc cgtccaggcc tccagctcca    900
cctggcgagg ctggcccatt gtacacaggc gccccagatg agggagggtc tcccctctc     960 cttgaagggc ggtagtctgg ggtcctgagt gctgggtgtg ggcttgtccc tcgtggacag   1020
aacccaggag ggcttcatcc accaaggaag attgctttgc agggtaccca ggtcccgggg   1080
gctgtgccac cctctgggca cccggagcca atcgcagggt acccaggtcc cgggggctgt   1140
gccaccctct gtgcacccag agccaatcgc aggggaccca ggtcctgagg tcctgggggc   1200
catgccaccc tctgggcacc cgcagccaat agagtcaccc ttgggaagct tatgcggacc   1260
tggggcagca ctcgcgtcct gaccccggtg ccggtccac agttcgagcc agggcagtcg    1320
tacgcgggtg tggtgcagta cagccacagc cagatgcagg agcacgtgag cctgcgcagc   1380
cccagcatcc ggaacgtgca ggagctcaag gagtgagtgc cccacgcggc caggaccctc   1440
ccacccctcg ccccgaccgc tgttcccacg gcaggtcggc cctgaccct gatcccaggt    1500 gggctcggcc ccgcgcagg cctggcccca accggccctt cctgcccttt gctatgcaga    1560
gccatcaaga gcctgcagtg gatggcgggc ggcaccttca cggggaggc cctgcagtac    1620 acgcgggacc agctgctgcc gcccagcccg aacaaccgca tcgccctggt catcactgac   1680
gggcgctcag acactcagag ggacaccaca ccgctcaacg tgctctgcag ccccggcatc   1740
caggtggggt ggccacccc aggctgcacc tgccccgcct agggcgcccc gccagccagg    1800 gtggcccttgt cccagaaag acgagggcag agcaggctgc gccacaccga tactgtctgt   1860
ccccacaggt ggtctccgtg ggcatcaaag acgtgtttga cttcatccca ggctcagacc   1920
agctcaatgt catttcttgc caaggcctgg caccatccca gggccggccc ggcctctcgc   1980
tggtcaagga gaactatgca gagctgctgg aggatgcctt cctgaagaat gtcaccgccc   2040
agatctgcat aggtgcgcat ggggccaccc gggcagtccc agatctgcgt aggtgcgcgc   2100
ggggccgccc gggcagtccc agatctgcgt aggtgcacgc ggggccgccc gggcagtccc   2160
agatctgcgt aggtgcacgc ggggccgccc agggccgtcc cagatctgtg taggtgcgcg   2220
caggcgccca gggctgtccc agaggcctcc tcccagctca ctgttacctc caggggcacg   2280
gccaccctgt aggtgcgcac ggggccgcct ggggctgtcc cacaggcatc ctcctcccgg   2340
ctcgctgtga cttccggggg cacggccacc cctgtgctcg gccggaggt cctgtgacat    2400 ctccttgcgg ggttataggt ggagcagtgg gctcacactg cacggctttt ctcttttaca   2460
```

```
gacaagaagt gtccagatta cacctgcccc agtgagtacc tcggcggccg ggacacgtgg    2520
ggaggagggc accgtggttg gggcgagggc tctgagagga cggggctctg ggaggagggc    2580
ctggcggtca cgagagtagg tgcatggctc actccggtgg ctgagcacca ccgtgccgtg    2640
ccctctctgg ggagcttaga cgctctctgg ccggcccact cgggctgcat caccagggcc    2700
tcatgctaac ggctgcccac cccgccccgc agtcacgttc tcctcccegg ctgacatcac    2760
catcctgctg gacggctccg ccagcgtggg cagccacaac tttgacacca ccaagcgctt    2820
cgccaagcgc ctggccgagc gcttcctcac agcgggcagg acggaccccg cccacgacgt    2880
gcgggtggcg gtggtgcagt acagcggcac gggccagcag cgcccagagc gggcgtcgct    2940
gcagttcctg cagaactaca cggccctggc cagtgccgtc gatgccatgg actttatcaa    3000
cgacgccacc gacgtcaacg atgccctggg ctatgtgacc cgcttctacc gcgaggcctc    3060
gtccggcgct gccaagaaga ggctgctgct cttctcagat ggcaactcgc agggcgccac    3120
gcccgctgcc atcgagaagg ccgtgcagga agcccagcgg gcaggcatcg agatcttcgt    3180
ggtggtcgtg ggccgccagg tgaatgagcc ccacatccgc gtcctggtca ccggcaagac    3240
ggccgagtac gacgtggcct acggcgagag ccacctgttc cgtgtcccca gctaccaggc    3300
cctgctccgg ggtgtcttcc accagacagt ctccaggaag gtggcgctgg gctagcccac    3360
cctgcacgcc ggaccaaaac cctgtcctcc caccccteec cactcatcac taaacagagt    3420
aaaatgtgat gcgaattttc ccgaccaacc tgattcgcta gattttttt aaggaaaagc    3480
ttggaaagcc aggacacaac gctgctgcct gctttgtgca gggtcctccg gggctcagcc    3540
ctgagttggc atcacctgcg cagggccctc tggggctcag ccctgagcta gtgtcacctg    3600
cacagggccc tctgaggctc agccctgagc tggcgtcacc tgtgcagggc cctctggggc    3660
tcagccctga gctggcctca cctgggttcc ccaccccggg ctctcctgcc ctgccctcct    3720
gcccgccctc cctcctgcct gcgcagctcc ttccctaggc acctctgtgc tgcatcccac    3780
cagcctgagc aagacgccct ctcggggcct gtgccgcact agcctccctc tcctctgtcc    3840
ccatagctgg tttttcccac caatcctcac ctaacagtta ctttacaatt aaactcaaag    3900
caagctcttc tcctcagctt ggggcagcca ttggcctctg tctcgttttg ggaaaccaag    3960
gtcaggaggc cgttgcagac ataaatctcg gcgactcggc cccgtctcct gagggtcctg    4020
ctggtgaccg gcctggacct tggccctaca gccctggagg ccgctgctga ccagcactga    4080
ccccgacctc agagagtact cgcaggggcg ctggctgcac tcaagaccct cgagattaac    4140
ggtgctaacc ccgtctgctc ctccctcccg cagagactgg ggcctggact ggacatgaga    4200
gccccttggt gccacagagg gctgtgtctt actagaaaca acgcaaacct ctccttcctc    4260
agaatagtga tgtgttcgac gttttatcaa aggccccctt tctatgttca tgttagtttt    4320
gctccttctg tgtttttttc tgaaccatat ccatgttgct gactttccca aataaaggtt    4380
ttcactcctc tccctgtggt tatcttcccc acaaagtaaa atcctgccgt gtgcccaaa    4440
ggagcagtca caggaggttg gggggcgtgt gcgtgcgtgc tcactcccaa cccccatcac    4500
caccagtccc aggccagaac cagggctgcc cttggctaca gctgtccatc catgcccctt    4560
atctgcgtct gcgtcggtga catggagacc atgctgcacc tgtggacaga gaggagctga    4620
gaaggcaaca ccctgggctt tggggtcggg agcagatcag gcctcagtgg gctggggccg    4680
gccacatcca ccgaggtcaa ccacagaggc cggccacagg ttctaggctt ggtactgaaa    4740
tacccctggg agctcggaag gggagttgag atactgcagg gccatagga agaagtcttg    4800
ggaggctcca cctttggggc agaggaagaa gtcttgggag gctccacctt tggggcagag    4860
```

```
caagaagagg gcggagggca gaggcagcga gggctcatcc tcaaaagaaa gaagttagtg    4920
gccccctgaat cccagaatcc ggggtgcacg gctgttctgg gggccgctag gggactaaga   4980
ggatcggccg agggctgggc tggaggaggg cagcagggat gggcggcgag ggtgagggtg    5040
gggcttcctg aaggccttca cctgcgggga ccccggcgag cccctcaggt gccacaggca    5100
gggacacgcc tcgctcgatg cgtcacacca tgtggccacc agagctgcgg gaaaatgctg    5160
gggaccctgc atttccgttt caggtggcga acaagcgccc ctcacagaac tgcaggtaga    5220
gacgggcccg gggcagacgc agtgaggcgg tgggcggggc ccggggcaga tgcagtgagg    5280
cggtgggcgg ggcccggggc agaggcagcg agcggtgggc ggggcccggg gcagacgcag    5340
tgaggcggtg gcggggcccc ggggcagagg cagcgggtgg tggccggggc ccggggcaga    5400
cgcagtgagg cggtgggcgg ggcccggggt agtcgcagta ggtggtgggc ggggcccggg    5460
gcagacgcag tgaggtggtg gcggggcccc ggggcagacg cagtgaggcg gtgggagggg    5520
cccggggcag acgcagtgag gcggtgggcg ggccccgggt cagaggcaac gggtggtggg    5580
cggggcccgg ggcagacgca gtgaggcggt gggcggggcc cggggcagat gcagtgaggc    5640
ggtgggcggg gcccggggca gatgcagtga ggcggtggga ggggcccggg gcagacgcag    5700
tgaggcggtg gcggggcccc ggggcagacg cagtgaggcg gtgggcgggg cccggggcag    5760
acgcagtgag gcagttgcca gcctctctca gctgcctcat gggattcgca ctgcagctgc    5820
ggccctggcg cgacaagggc tggacttggc cagcgggacg gtccctcacg gcgctgaggc    5880
ccacactctg cgtggagcct ccccgtgccc aggctaccct gcaaggtcct cggagaggct    5940
tcctccagcc ccagccccca cacagctccg gcccaggccc gctcttcccc atcccagttg    6000
ctttgcgctg tatacggcca ggtgaccccg agcggccct gagccctcgt cccggcttcc     6060
tcccctgtaa gctgggtgaa ggactccatg gcacccacct gagagggttg tggcgaggcc    6120
caggcccctc gtgcccacac ggccggcggc ccatgcctgg caggggctgg gaggaggctg    6180
gggcgaccag aggggagcgg cctgtcctgg aggaggccca gggaccctgg tgagagggtc    6240
tctcccaagt gctctctatg ggacccccctt cctctgcgcc cgtccttcac ggacctctcc   6300
gggtcacccc tgggctgcac actgggttca gggggggcctt gaggtggggc ccctgttccc   6360
aagtcccggc ggggtttctc ctgaacctca acccatcctc acctgcgggc attcccatcc    6420
cccaacgcct gggtcaccag gattccaggc aggaggggcg gtgggggtta ccaaggcccg    6480
ggttgccatg cagaaccccc agccaccacg cagaccccca cggggcccag ggaagctcct    6540
ggtctcacac tgcacctcac acttcctgtg ggggcagact ccaaggtccc ggcctctcat    6600
cttgtagaaa ctgaggcaca ggagggacac acactcccac ggccggtcac cgtggccccc    6660
acacctccca ctgactgac acctggccag gctccggaca cccgtggcac agcctcagcc     6720
cctgcggccc ctgctccgtg gccccaggc cccagctccc atgtgcacgt cctgcctcag     6780
gcctggaggc ccctcggccc caaataatca gacaattcaa cagcaaaact acttttttca    6840
ggctggcagg actctgggca accccctgca acagcccccct gccctatcac agccaccctt   6900
gcctcccagg cacggagacc ccaccatcag gtcccagcct tggttcatcc ccaagcaccc    6960
tgtgtgttgg gatggcgatg ctggctgagc ccctgcatcc                          7000
```

<210> SEQ ID NO 253
<211> LENGTH: 2500
<212> TYPE: DNA
<213> ORGANISM: Homo sapiens -continued

```
<400> SEQUENCE: 253
agggcgtttg ggaacacccc tcccggaggg gtgaggcggc ccagcctgcg gctgccagag    60
gacacaggtt ctgctgcgga acctgcagac atggccataa caggccacag tgctcgggcc   120
cacacagcct ggacccacat ggccctgtgt cacctcctca ggggcaggct tcagggcctc   180
gaccctagag gctgcccctc ggttctgctc catggacggc gcaggcaggc ccaggcctgt   240
gacgagttca cggaagctcc aggatgaccc ccgctctgcg ccctcctcca gcattccaga   300
ccacaaacca ctctgggcta aaacgaggca tcgccagagc atcccacttc ctcggaaagc   360
tgcggtctgg ggacgcgtct tggccctgaa gaggctccag atggctccca tcaggcctct   420
ccgcctacgt gcggccgaca tggagtgaca gagcgtcggg gacacagaat tcagagctgg   480
gcctggggct gctttgagat actgatggct gccaggggc acagagaccc gtcctgcaga    540
cagggctgtg agggccacag ggggcctcgg ggagaggcag tgggagggag gacagtgggg   600
gcctccagct gggtgagcag ctggagcgag ggggcccgg ggcttgtgat ggtgctgccg    660
accctagagg tgccggcccc acgatggaga gcacgtagtg cccccgga gtcaggaggc     720 cgggcctgac ctcggggct gcagccaggg gaggccggca ccccagataa ccccaaaga    780 actgcaggcc ctgaggcgag gccagagtgg gggcggggc aggtcccagc cgaggaggtg    840
ctccgtgctg cctcagcaga acccatgatg ggctggccca aggctctgaa ggtggaaagg   900
cctcacacat tctgccccgg ctgacgcctt ccttgggcca gtgctcgggg gtgtgtaaca   960
aacgccaaga cgcattgtaa agaaggaagc ctgcgtttcc atcaccggct taatatcaaa  1020
caaaagtgca attttgaaaa tgtagtccaa ggttttctgt ggtgcggaaa tggccaggcc  1080
agacctccgt gggtggtcct tcgtgtccac gtcagcgccc tacatccaca ctgtgggcac  1140
catgacctca catgcggagc ggagcagggc cggcgcccgg agagccaggc tggtcacgaa  1200
cgaggcctag agggcgtcag gccccaaagc actcacaggc ttctcctctg tcctcgggc   1260 cttcagacac ctgcatgcgc cgattcagcc cccgcgcgc gccgattccc ctggccatgg   1320
ggtttccaaa gtgtgtgctc agaggacagt ttcctccagg atgacctgtc agtggctctc  1380
tgtgccgggg acgtcgcgtg ctgggtcccg gtctgaatgc ttcctaacga tttacccagt  1440
tccttttctc cactcaggag gcgtttgctg agaggcacag gctgagcccc cgtgctgatg  1500
ccacgaccga gggaacgggt ctccctgtcg gcgtgaactg acccggccag gcgtccactg  1560
ccactcggac tgtctcccag gcacgtggcg cccacacggg cagaacacgc cctccacaca  1620
cgcggcttcg ggcagaacac gaggcgccct ccacacacgc ggcttcgggg cttgtcatga  1680
aaaaagctga atgctggggg tgcagctttc accaacagaa tcccgtttgg aagggacgcg  1740
gtgagacatg atccaccca agttgtgatc ctgggtgagc cgccgtccac accctgctga  1800
gggtcccttc acccacttta ttctccagaa accctgccc atcagggctg agtcccacgc   1860
cttccctctc cgtccaggcc tggctttgac ctctggggtc gtgtggggca caggggacac  1920
cctatccagg cagaggccct acggctatct ggaggaagtg gtgggagctg gcttctgcc   1980 tggaggatgc acccagaggg gtcacagtcc acacagagac acacgggtgc cttccagatg  2040
gctgagccag tccagcccag aagggcctgg gggttggggg ctgcacctgg cctgtcccca  2100
ccagcagggc tcagggcttc ccaaggtgtg tggggacgg ggcagcacct ctcaaccagg    2160
tcacctgaaa cccgaactga aaggcatcct aagttaagac attaactccc attgtcaagg  2220
tgccatcgtc aattctgtct ccaaatcctt ctttgttatt tcatgtattc acagagtgac  2280
gctccgtgtt tcgttcagcc tgcaggcctg cagaagctgc atctcgggat ggccaagagc  2340
```

| | | |
|---|---|---|
| ccggccaggc cccacggctg cacccaggac gggattcatg ccccatgcct ggcttctcac | 2400 | |
| gaccacagag tgcctttccc gggactggat ggaggcagag tgagagaaga gcctggagca | 2460 | |
| agtgttttgg accacagtga tcaaacacgg agcccgtggg | 2500 | |

<210> SEQ ID NO 254
<211> LENGTH: 700
<212> TYPE: DNA
<213> ORGANISM: Homo sapiens

<400> SEQUENCE: 254

| | |
|---|---|
| aagaaaggcc agaccgggca cggtggctca cgcctgtaat cccaacactt ggggaggccg | 60 |
| aggcgggcag atcacctgag gtcaggagtt cgagaccagc ctggccaaca gggtgaaacc | 120 |
| ccgtctctac taaaaataca aaaaaaatt agccgggcgt ggtggcaggc acctgtaatc | 180 |
| ccagctaatc gggaggctga ggcaggagaa aatcacttga acctggagg cggaggctgc | 240 |
| agtgagctga gatcgcgcca ctgcactcca gcctgggtga gggagcgaga ctgtctcaaa | 300 |
| aaaaaaaaa aaaaaaaaa aaaggaaag aaaggcccgg tgagatgctt tctcttaaac | 360 |
| acggccctgc acgttgagtt gctgcctcct gtggcctatt tcacgtttat gcaaagtcgg | 420 |
| gcgcctgatg cggggctcac ccgccacaag caggggtcct ggtgctgctc atggaagggg | 480 |
| ccctacccag cccgcgggc actggctggg acggggctgc ccaggtccgc ccaggatcca | 540 |
| aacacccagc cccgcccagc ggcccttcct ggcctgcagt ggaggctgta atgggcaggg | 600 |
| gtggtgggaa tcccagctca cagggcgcct gctcttagaa gggcggcatc tgggtccaga | 660 |
| ggtcagaaac gtcagatgcc catcccagaa gtggcgggga | 700 |

<210> SEQ ID NO 255
<211> LENGTH: 10000
<212> TYPE: DNA
<213> ORGANISM: Homo sapiens

<400> SEQUENCE: 255

| | |
|---|---|
| gggtgaatga gtagatgtat gggtgagtag gtgggtaggt gggtagatgg atgggtgggt | 60 |
| gggcgagtgt gtggttagat gatggatggc tgaatggatg agtgggggga tggatgggtg | 120 |
| agtgggtgta tgtatggatg ggttagtggg tgggtggatg aatggatggg tgcataaagg | 180 |
| atggatggat gaatgagtta gtgggttggc agatggatgg atgggtgagt cagtggatag | 240 |
| atggatgggt gggtggatag aggatggatg gttgggtagg tgatgggtgg atgagtggat | 300 |
| agatgggtat gtgagtgagt gggggatgg gtaggtgggt ggatggatgg ttaggtgaat | 360 |
| gagtggatgg acagacggac agtgggtgga tgatgagtg aacggatgga ccgatggatg | 420 |
| aatgggtggg tgggtagagg atggacggac aggtgagtgg gtgggtggat ggatagatgg | 480 |
| gtaagtgagt ggatagatag atgggtgggt ggacagagga tgggtggatg aatggatggg | 540 |
| ttagtgggtg gctgggtgga tgatgatgg atgggtgact gggtgatgg atggatgggt | 600 |
| tagtgggtgg ctgggtggat agatggatgg gtgattgggc gaatgggcga atgggtggat | 660 |
| gggtgggcgt ggagttggtg ggtacatgat aatggggtgg aatacccatg gattggaatg | 720 |
| agctgttttg gctgctattt ctgggacacc cagctctgcc aggcccctac ccctctggtg | 780 |
| ggccaggctc tgacggtggc cactcatggc ctttctagct ctggtgccag catagggaag | 840 |
| gaggaggcac agccttgtct tactccttgc acctgttagc cccccccccc gccaagggag | 900 |
| gacccgtggt tggggacagc acaggggggcc ctgctgtgtg cagggactgt ccctgggggcc | 960 |

```
actgaagccc acctgttctt gttccttctc aggcggatcc tggtccccct ggtgagccag   1020
gccctcgggg gccaagagga gtcccaggac ccgaggtagg ttggtggcca gtccccatgc   1080
cctcccccca acctgccagg ccaacacaca cccaagcctc gtggttctgc ccacggtgga   1140
cccacgtatc agtgggcagt ggcctgggag agactcagcc acccagcctt gccccagag    1200 tctcagcctc atccttcctt ccccagggtg agcccggccc cctggagac cccggtctca    1260 cggtaggtgt cacatggggc agaaccagtg tccttctcct gccaaaacta gacaccaaga   1320
gcagcagggg tgggggaagg tcagctggca cggtcagaga gcaagatcag tggaggaggt   1380
cagagggcaa ggtcagagag caagcttggt tggggaaggt cacagggcaa ggttggtggg   1440
gggaggaggg tggcagcgag gttggtaggg acaggacccg ccagcctccc cgcatggctg   1500
cctccacacg tgggctggaa tgtcccggga ccccaggcc aggaccttgc tgtgaaaact    1560
cttctggggc ccgggggga ctaccctgcc tgccgtgtgc attgcaggag tgtgacgtca    1620
tgacctacgt gagggagacc tgcgggtgct gcggtgaggc actgcccacg gcagggtcgg   1680
ggcccatgca ccgggtggag ggcggagtg cagcagggct gggtcatcgc tgggtcctgc    1740
atgtgcacgt gaccctaggg tctgaggtct cccggtacc ccccgatgac cctgccaccc    1800
ccccagactg tgagaagcgc tgtggcgccc tggacgtggt cttcgtcatc gacagctccg   1860
agagcattgg gtacaccaac ttcacactgg agaagaactt cgtcatcaac gtggtcaaca   1920
ggctgggtgc catcgctaag gaccccaagt ccgagacagg tcagcggggc aggggcgggt   1980
gcagcattgc gggggccgg gcggggcgtg ggaggcgatg agatgggaga agtccagacg    2040
cgtccctcca acgagggcct ctgcatggct ggggatgccc cagaccccga ggcctctggc   2100
aacgacctca cgcgtgcggc ttgcagggac gcgtgtgggc gtggtgcagt acagccacga   2160
gggcaccttt gaggccatcc agctggacga cgaacgtatc gactccctgt cgagcttcaa   2220
ggaggctgtc aagaacctcg agtggattgc gggcggcacc tggacaccct cagccctcaa   2280
gtttgcctac gaccgcctca tcaaggagag ccggcgccag aagacacgtg tgtttgcggt   2340
ggtcatcacg gacgggcgcc acgaccctcg ggacgatgac ctcaacttgc gggcgctgtg   2400
cgaccgcgac gtcacagtga cggccatcgg catcggggac atgttccacg agaagcacga   2460
gagtgaaaac ctctactcca tcgcctgcga caagccacag caggtgcgca acatgacgct   2520
gttctccgac ctggtcgctg agaagttcat cgatgacatg gaggacgtcc tctgcccggg   2580
tgagcgtgtg ggcgcggggc agtcggccga ggagcagcag gcccagccg ctgtctagcg     2640 tgagccccag ggacacccct cacctgaggg atgaatgtgc agcccaggat cttgggctgt   2700
gggtgggaag gggtcgggcc ctctcggggc tgcagggcag aggccagctg caccctgagc   2760
ctgtctaggc agatcagtga acggccgctg agggttcgct agggactgac cctggcctgg   2820
cccggcctct ctcctctctt ccagaccctc agatcgtgtg cccagacctt ccctgccaaa   2880
caggtaatgc agggcaccct gagccaccac cccagactag caaagcagcc ctggtgtcct   2940
tcctcctcga gggccgggct gggggagggg ccgtgcaggg accgggggg cggcggagcc     3000 actgcggagg ctgctcctta gggagatggc cccaggatgg cagcacaggg gaggaggggc   3060
ttggggaagg caggctccca ggaacgcagg aacagcatca cgaggccatg aggtgggtgc   3120
tgctagcctg gcgctgtgct cggcatgtgg ccactggtct tgaaggccca ccatgggcct   3180
tgcagtctcc ctcagctgcc gcccagctcc catgggctgg ccgtgcatgt gccactcgga   3240
ggaagccctg gattcagtga gtgaaaccat cccggggtgg aagcactgac acccccagc    3300 accagcaggt cttgctccaa ccctggcctg cctcggagct gcagctgcgg ctctcacatc   3360
```

-continued

```
tctgggagtg ggggagccca tgtcccggat gtggcccacg tgggtgtgaa gctggagctg    3420
ggggtgccgt ccaggctctg ctggacgtgg tgctgccccc atggtgcact gctgcaccgt    3480
acctgggccc acaggaggtc cccggggggcg ttaggagctg agtcccccctc agtgagccgt    3540 cccctccagg agtgtgaggg tagggatgcc atggagacag ggtgggaggg tccgacctgg    3600
aggaccacag ggaggaaacc tcagggtctg cggtacgaag tcagcgcttc ctcagcacgc    3660
gggtcgcggt gtgcgttcgg gcgttccatg gggagctccc ggtgggtgag ctgggccact    3720
gagcacattc acaggccctg aggctgcccc aggggaggag ccgtggactc agagccgagg    3780
ttccccatac gtgctgcgac agagaaccta gggcttgcac ctgggtctgg ctgcccttca    3840
gcaggcgggc agcctctggc cccacaacag tgggctgtgc ttctgccgcc aaggtgcagg    3900
cgtcctcccc cagggtccac atcagcagca ggggcacctg gaccctgagg gcaggaacca    3960
gaccttggct cctccaccca cccccctcgtt cctgatgggg cagggaagtc tcgggaccccc   4020 atgatgggcg acatggcgat ggtcactgtg ggtgctttgc tatcaggtgg ggggccttcc    4080
tctccactct gggtccagtg tgagtggccg ctatggcttc ccctccactc caggttctat    4140
cgtgagtggg tgggtgctgc gtctgtggat gtcacgtgac ctttcctctt tagcctatca    4200
ttgtagttgg gagttagtta gcccgttgag cgtcattgaa tttccagtgt tgagccagcc    4260
ctgcgtgccc gggataaacc cacctggccg tggtgtgtgg ccctgtttat gcacgtgggc    4320
cctgattcgc tgatgcctgc ctgagggttt gcgcttatcg gcgacatcag cctgcacttt    4380
tcttttctcg tgatctctct ggttctggcc tcagggtgac gtgggcctcg tagggtcctg    4440
tggtggctcc tccccagacg gtgacatgga gtgagcccat tctccctcct gggagtgggt    4500
cactcaggcc accagagcac cacagggaaa gcagccaggg aggacacgga ggcccttgaa    4560
gctctggcct cttctgaggc ctccaggacc tgacagtgag tgggagcagc cctggcagaa    4620
cccctcccct cctctcggcc gccctgacac ctcatccccg acactcagag ctcatcctcc    4680
ttcccagctg tttccaattt caaagtgaac tcgaccttgt ggctccagga gatgcagcag    4740
ggacagtgtt aaatcggctt tcaccagccc acacggccag gcatcctcct cggccctcct    4800
gggcactggg tggacaccac tggctgtggc ctggccctgg ccttctccag acagccctgt    4860
ccaccccaaa gcccagccac cctgggcctg cagcaggcct gtggagttct cagttgcgtg    4920
gggaccagag ggtgctggag aaacaaacca gacgcagctg aaggcagtca gggcagggcg    4980
caatcagcga taagagctgc ataggggcca cagcgtaacc tgagctccag tcggtggaaa    5040
gaaaaggcag agacgttgca gaggccaggt ctgctcaggg gaagacagtt ctgggtgtag    5100
aggactcaca tcccagagag gctgaggaag ggtttaccac cgcaagcttt ctcaggcggg    5160
ctcttgaggg gtggctgggg tcttcctggc gacgggcctg cggcactgga agccctactg    5220
gagtttggcc tgtctccggc acaggtttgg acggagctgt tttgtgctga aaggttttct    5280
cggggtccgt ggtgtccccc aaaggtgcca ccgtgcgggt ctcctagctc cctgccagct    5340
tcctgtccct gtgctcactg cccccacgcc tcctgccaag gccgagccac acacccgctc    5400
cacctgcatt tcctctaccg actcgccagc ccaaatgccg ctcttcactc tggcctcgct    5460
gagcggctgc ccgaggagga gctctaggcc gacgcccacc gcaggcctta cagtcttctc    5520
tggacgctcc cttgcagatg caccgtggcc tggcggcgag ccccggtca ccttcctccg    5580 cacggaagag gggccggacg ccaccttccc caggaccatt cccctgatcc aacagttgct    5640
aaacgccacg gagctcacgc aggacccggc cgcctactcc cagctggtgg ccgtgctggt    5700
```

| | |
|---|---|
| ctacaccgcc gagcgggcca agttcgccac cggggtagag cggcaggact ggatggagct | 5760 |
| gttcattgac acctttaagc tggtgcacag ggacatcgtg ggggaccccg agaccgcgct | 5820 |
| ggccctctgc taaagcccgg gcacccgccc agccgggctg ggccctccct gccacactag | 5880 |
| cttcccaggg ctgccccga caggctggct ctcagtggag gccagagatc tggaatcggg | 5940 |
| gtcagcgggg ctacagtcct tccaggggct ctggggcagc tcccagcctc ttcccatgct | 6000 |
| ggtggccacc gtgtcccttg ctgcggctgc atcttccagt ctctcctccg tcttcctgtg | 6060 |
| gccgctctct ttataagaac cctggtcatt gaatttaagg cccaccccaa gtccagaatg | 6120 |
| acctcgcaag acccttaact cactcccgtc tgcagagtcc ttctttgctg catcaggtca | 6180 |
| ccctcacagg ctccagggtt tgggtgtgga agtctttgga ggcccttact tagcggccca | 6240 |
| gctgggctgc cgtgcgtctg ggatgggct gagggagggt gctgcccagg tgctggagga | 6300 |
| tgttccagca ccaggttcca gcggagcctc ggaaacaggc cccagaggct ggtgagcctc | 6360 |
| gctgggtgtg ggcactaatc ccgtgcatgg tgactcgtgg gcgctcacgg cccacctggt | 6420 |
| ggcaggtgaa ggcttccggt tgggcagcag atagtcctgg gggaagctgg cagtcctggc | 6480 |
| accatgacgt atctgggctg gtgtcatgca cagtagggcg aatggccaca gctgcctgcc | 6540 |
| agcagccctg atcccggggt gtctgcaccc ttccagccca acctctgggt ctccaaaagc | 6600 |
| acagtcgggg gagcatccac caggcacaac ctctgcggtc ctcagaggac tgagcagaga | 6660 |
| atcccagggt ccacaatgtt ggggagcggc agggatcacc atccaaaggg agcggccccc | 6720 |
| acggcgagct gaccccgacg ttctgactgc aggagccctc atccaggctg ggctcctgcc | 6780 |
| gggcacggct gtgaccattt tcagggcca ggttctcgtc cccacaccca ctgcacaggg | 6840 |
| caggccaggc tggtcttccc actgtgggga tgaaggatcc tccacaggag gaggagagca | 6900 |
| gagtccacag acatcccaac agcctcagcc tccctgtgcc tggccggccc ccacagcttc | 6960 |
| cccgtctcct ccaggcccca cagacactga tgaatggaca gagaccccca aaaccagctg | 7020 |
| cccccttgcat gtctgtctcc atatgttttgg tgacagcagt gaaaatgtta ttagttttga | 7080 |
| gggggtttgg gaagcccagc ggtacctgag gagtttctgg acatttaagc cggttcctag | 7140 |
| gtgtggcctt aacagggagg ctgcccttcc tttcactgaa tgagctgcgt cactcataag | 7200 |
| ctcactgagg gaacccatc tgccagctcg tgcgtgctca gacggcgtcc atgtctcaag | 7260 |
| cgttctgtga aggctgcggt gcagcgtgag gtcaccctgc tgtgttcaga gctttgctca | 7320 |
| ctgcctgcgg ggctggaccg ttgcacctcc agggccccca gaaaccgagt ttcgggtcag | 7380 |
| ggtcctctgt gtgcattcct gggggtccat gtaccagctg tgacgacgtc caggggttgg | 7440 |
| gctgagaagc agacaccctt ggggaaactg gctctgtccc tcccctcccc catcccagga | 7500 |
| gctgaggtct tggtgaggcc acagggccag gtccacgcaa ggactgtccg tgtcctgtcc | 7560 |
| tgtggtctct ggccccacgt gacacccaca cgtgtggtag gcagcctggc ctgggttgtg | 7620 |
| gctatggcca ggcccccaag ctgtcccga tgcccagggc tggtgaccac ccaggcaggt | 7680 |
| gggggcccca cttggtaaca gagtcatagg gcagaaccca cctgggctgc cacagaaggt | 7740 |
| ctggctgccc ctgtgcccac tgctccccac catggccaat cagaagagtc aggggctcct | 7800 |
| ggtcttccg ggagggacgt ggcccagcca gctctaggtg ttctgagcag ctctgggacc | 7860 |
| cagcgattga ggggtcaggc tgggggtgtc agagccaggg tcctccttaa gtacctccca | 7920 |
| cactacacag acagtggccc ttttgtgggc agcaaattct tgagccatga aaggatgctt | 7980 |
| tgggcccctt ccctcccagg agggcagcct gtgcagggat ggtgctcagc aggtggacag | 8040 |
| ggcctggggc ctgtgtcagg gtctcaggcc tgggagcacc agcagaggag atggcggctc | 8100 |

```
ccagcagtgc cgcctgaaag tgtcttgggc taaggaccca cacccagggc tgccctgcag    8160
aaacgccccc gcagagccca gtggtctgtg aggttgcagg caggg tgcga atggaagggc    8220 acaggtgcgg ggctggcacc tgcccggtcc tgcccacctc ccctccgccc agcccgcacc    8280
tgcgtctccc cacagagctg tccgtggcac agtgcacgag gcggcccgtg gacatcgtct    8340
tcctgctgga cggctccgag cggctgggtg agcagaactt ccacaaggcc ggcgcttcg     8400 tggagcaggt ggcgcggcgg ctgacgctgg cccggaggga cgacgaccct ctcaacgcac    8460
gcgtggcgct gctgcagttt ggtggccccg gcgagcagca ggtggccttc ccgctgagcc    8520
acaacctcac ggccatccac gaggcgctgg agaccacaca atacctgaac tccttctcgc    8580
acgtgggcgc aggcgtggtg cacgccatca atgccatcgt gcgcagcccg cgtggcgggg    8640
cccggaggca cgcagagctg tccttcgtgt tcctcacgga cggcgtcacg ggcaacgaca    8700
gtctgcacga gtcggcgcac tccatgcgca agcagaacgt ggtacccacc gtgctggcct    8760
tgggcagcga cgtggacatg gacgtgctca ccacgctcag cctgggtgac cgcgccgccg    8820
tgttccacga gaaggactat gacagcctgg cgcaacccgg cttcttcgac cgcttcatcc    8880
gctggatctg ctagcgccgc cgcccggggcc ccgcagtcga gggtcgtgag cccaccccgt    8940
ccatggtgct aagcgggccc gggtcccaca cggccagcac cgctgctcac tcggacgacg    9000
ccctgggcct gcacctctcc agctcctccc acggggtccc cgtagcccg gccccgccc     9060 agccccaggt ctccccaggc cctccgcagg ctgcccggcc tccctccccc tgcagccatc    9120
ccaaggctcc tgacctacct ggcccctgag ctctggagca agccctgacc caataaaggc    9180
tttgaaccca ttgcgtgcct gcttgcgagc ttctgtgcgc aggagagacc tcaaaggtgt    9240
cttgtggcca ggagggaaac actgcagctg tcgctcgccc accagggtca atggctcccc    9300
cgggcccagc cctgacctcc taggacatca actgcaggtg ctggctgacc ccgcctgtgc    9360 agacccaca gccttgatca gcaaactctc cctccagccc cagccaggcc caaagtgctc    9420
taagaagtgt caccatggct gagggtcttc tgtgggtgga cgcatgatta acactagacg    9480
gggagacagc aggtgctgag cctgttgtgt tctgtgtgga gatctcagtg agttttgct     9540 gttcagaccc cagggtcctt caggctcagc tcaggagccc cacagtgaac cagaggctcc    9600
acaggcaggt gctgacctga caggagtggg cttggtggcc atcacagggc accacagaca    9660
cagcttgaac aactaccagt atcggccaca ggcctgagg catcagccgg ccatgcttc      9720 ctctggaggg ctagaggagg actagagaag ggcctgcccc ggcctctccc cagcatccca    9780
gggttcctga tctcctggat aaggatacaa gtcaccacac tggactgggg ctcagcctgc    9840
tctagaatac ctcacctaag tcacagtgga ccaggctcag cctgctctaa ggtgagctta    9900
cccgagacac tggaccagag atcagcctat cctgggataa gctcacccga gtcacactgg    9960
accagggctc agcctattcc gggatgagct caccc gagtc                        10000
```

<210> SEQ ID NO 256
<211> LENGTH: 800
<212> TYPE: DNA
<213> ORGANISM: Homo sapiens

<400> SEQUENCE: 256

```
gacacttcca tgactgcagc tgaccagtcc acctgccagc ggttgaccac tcccacttcg      60
ccagcgaccg aaggggaggg gaggggcctc acctgagggc aacagcagaa cccaccacct    120
ggtcttgctt tactcagacc tgagggtgtg aaaggtgccc gtgacctccc gcatcaggga    180
```

```
gctggccgcc accctcgact cccgggagc aggcgtcccg cgacccctc atctaccagg      240 ccatctgagc tgggcggcgc ctcacctccg ctcccggggg agccggcctc agggtaggca      300
tgcgccctgg gtgggagcag gtcgtggccg ccgcctcct ggcagctctg ctgagcagc      360 cgccgcagca tctgattctc cttcaggagg cgcacctgct tcttcaggtc cgcgttctcg      420
ctcaggagcc ggctcatcag ctcgccgcct tcagccatgg cgggtgcgtc cctccttgtc      480
cctcacggct cctgcagccc catggaggtg ggagcccaga gccgcaggc accacagaaa      540 cagcccaggc acggagttcc gtagccacca ccgccttcca cgccttgtga tgtcactgcc      600
ctagtgatga ggtgcccagc accctgcctg ccccgcgat ggctcatggc cccgttgagg      660
cagtgaagct ggaggcccgt ggcgtgcaca ggcagccact cccacattat gaccagggcc      720
cgagaatgcc aaggacatta ggcagctacg ggatgtagcg actgtactcc aagaggggcg      780
tccaagccac tccccattga                                                  800
```

<210> SEQ ID NO 257
<211> LENGTH: 293
<212> TYPE: DNA
<213> ORGANISM: Homo sapiens

<400> SEQUENCE: 257

```
aggtggaggt tgcagtgagc cctcctcccc tcctccccct tcccttccca cctcccatgc       60
ccccctttct tcctcccact cccctcccga ggccccgctt attctcccgg cctgtggcgg      120
ttcgtgcact cgctgagctc aggttctggt gaaggtgccc ggagccgggt cccgccttcg      180
gcctgagcta gagccgcgcg ggcggccggc ttcccccaaa ccctgtggga ggggcatccc      240
gaggaggcga ccccagagag tggggcgcgg acaccttccc tggggagggc cag            293
```

<210> SEQ ID NO 258
<211> LENGTH: 474
<212> TYPE: DNA
<213> ORGANISM: Homo sapiens

<400> SEQUENCE: 258

```
ccttccagat gttccagaag gagaaggcgg tgctggacga gctgggccga cgcacgggga       60
cccggctgca gcccctgacc cggggcctct tcggagggag ctgagggccg cgttccttct      120
gaaagcggga cgcggagggg gtggaggctg cgggagccg gggtcgcaca cgaataaata      180
acgaatgaac gtacgagggg aacctcctct tatttccttc acgttgcatc gggtatttt      240 cgttattgta aataaaacgg ttccgagccg tggcatcgag agggcgtctg gagttcaggg      300
aacgcgtggc cccgcccgg gagcaccgcg cagcgctcgc ctctcgccct tcaaggggt      360 ccctgcccgg agcctgcgcc cccggagagg aaggggctcg aggggcttgg gtgccgcagc      420
gcgtccttcc gtagaaaagg cttgcgtcag tatttcctgc ttttacctcc tgag            474
```

<210> SEQ ID NO 259
<211> LENGTH: 346
<212> TYPE: DNA
<213> ORGANISM: Homo sapiens

<400> SEQUENCE: 259

```
cagtatttcc tgcttttacc tcctgagtat tggaatattc gagtaaaccc tggagtttca       60
gcgccagcgc acgcctcttc atcagggcag cgcgtcgcga gcgcgctggt tccccggggc      120
ctcccggcca cggacaccgc tctagccagg gccacgcgca ggccgccgag cagcacctca      180
gagacctgcg tgagttctaa agcctggggc tactacaatt ctgctcatct gtttgtcctg      240
```

| | |
|---|---|
| tgaaatgatt cagggacatg aaaatgcctt cccactgact tgcgtcctgt cttagcctgg | 300 |
| acttgtcccc ttgggaacac gggccaggcc cctctgttcc tgaagt | 346 |

<210> SEQ ID NO 260
<211> LENGTH: 490
<212> TYPE: DNA
<213> ORGANISM: Homo sapiens

<400> SEQUENCE: 260

| | |
|---|---|
| atgtctgcag ggaagaagca gggggacccct gaataaagtt tccgtttttc ctatttgtta | 60 |
| aagtgataga gcattatagg accagagaac aggtgtgtct gtacactgtg caggtccccg | 120 |
| gggcaggctc tgagtccgtc tgcacacggt gcgggtcccc ggggcgcgcc ctgagcccgt | 180 |
| ctgcacacgg tgcgggtccc cggggcgcgc cctgagcccg tctgcacacg gtgcgggtcc | 240 |
| ccggggcgcg ccctgagccc gtctgcacac ggtgcgggtc ccggggcgcg ccctgagcc | 300 |
| cgtctgcaca cggtgcgggt ccccggggcg cgccctgagc ccgtctgcac acggtgcggg | 360 |
| tccccggggc gcgccctgag cccgtctgta cacggtgcgg tccccgggg cgcgccctga | 420 |
| gtctctacta aaaatacaaa aattagccag gcgtggtggt tcaagcctgt aatcccagct | 480 |
| ccttgggagg | 490 |

<210> SEQ ID NO 261
<211> LENGTH: 2000
<212> TYPE: DNA
<213> ORGANISM: Homo sapiens

<400> SEQUENCE: 261

| | |
|---|---|
| catacatggt tattagaaaa ggcatctcat ccaaatgtgg tggctcgtgc ttgtaatccc | 60 |
| agtgcttcag gaggccaagg gaggaggatt acttgagcct aagagtttga gaccagcctg | 120 |
| ggcaacacaa caagaccttg cctctacaaa aaacttaaaa actagctggg tatgatggtg | 180 |
| cacacctgta gtcccagcta cttgggaggc ggaggcgggc agatcgcctg aggtcaggag | 240 |
| ttcgagacca gcctggccaa catgatgaaa ccccgtctct actaaaaata caaaaattag | 300 |
| ccgagtgtgg tggtgcatgc ctgtaatccc agctactcag gaggctgagg caggagaatc | 360 |
| acttgaaccc gggaggcgga ggttgccatg agccgagatc acgtcactgc actccagcct | 420 |
| gggtgacaga gcacaaaaga caggcatgac tttgtactta actgctcagc tttgtaatca | 480 |
| ctgggggccc agatgctcac ttggattcta actttgttgg catctgggcc taaaagccgt | 540 |
| gatgcaggtg agcaatgatg cagagggctc tgtgcgcctg gcgggctctg tttgcctgct | 600 |
| gggctctgtg cgcctgctgg gctctgtgcg cccgggaagg tgcggccacc ctcacgcgga | 660 |
| aggcggccag cggatcccgg tgcgcgcagc tcccagcgct ggggttccag cgccccgcct | 720 |
| cttcctatag caaccagcgg gacctgccgt ccccggggc accccgaggg gtctgcgccc | 780 |
| gcttctttcc gaaacgggaa ggcgctgggg gctcggcagc cagagggacg ggttcaggga | 840 |
| gcgtccggtg agcctaagac gcgccttttgc cggggttgcc gggtgtctgc ctctcactta | 900 |
| ggtattagga accgtggcac aaatctgtag gttttcctct gggggtgggc ggaggctcca | 960 |
| aaccggacgg ttttctcctg gaggactgtg ttcagacaga tactggtttc cttatccgca | 1020 |
| ggtgtgcgcg cgctcgcaa gtggtcagca taacgccggg cgaattcgga aagcccgtgc | 1080 |
| gtccgtggac gacccacttg gaaggagttg ggagaagtcc ttgttcccac gcgcggacgc | 1140 |
| ttccctccgt gtgtccttcg agccacaaaa agcccagacc ctaacccgct cctttctccc | 1200 |

```
gccgcgtcca tgcagaactc cgccgttcct gggaggggaa gcccgcgagg cgtcgggaga      1260
ggcacgtcct ccgtgagcaa agagctcctc cgagcgcgcg gcggggacgc tgggccgaca      1320
ggggaccgcg ggggcagggc ggagaggacc cgccctcgag tcggcccagc cctaacactc      1380
aggaccgcct ccagccggag gtctgcgccc ttctgaggac cctgcctggg ggagcttatt      1440
gcggttcttt tgcaaatacc cgctgcgctt ggacggagga agcgcccacg cgtcgacccc      1500
ggaaacgaag gcctccctga tgggaacgca tgcgtccagg agcctttatt tactcttaat      1560
tctgcccgat gcttgtacgt gtgtgaaatg cttcagatgc ttttgggagc gaggtgttac      1620
ataaatcatg gaaatgcctc ctggtctcac cacacccagg gtgacagctg agatgcggct      1680
tctccagggt ggagcctcct cgttttccag agctgcttgt tgaagtcttc ccagggcccc      1740
tgacttgcac tggaaactgc tcaccttggc atcgggatgt ggagcaagaa atgcttttgt      1800
tttcattcat cctagtgttc ataaaatgga aaacaaataa ggacatacaa aaacattaat      1860
aaaataaatt aatggaacta gattttcag aaagcacaac aaacacaaaa tccaagtatt      1920
gccatgtcag caacacattc ctactttaag ttttatgaag ttaattggag tagtggagaa      1980
caaaagtgga tgtggggcag                                                 2000
```

<210> SEQ ID NO 262
<211> LENGTH: 88
<212> TYPE: DNA
<213> ORGANISM: Homo sapiens

<400> SEQUENCE: 262

```
gattgacagt ttctccttcc ccagactggc caatcacagg caggaagatg aaggttctgt       60
gggctgcgtt gctggtcaca ttcctggc                                          88
```

<210> SEQ ID NO 263
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263

```
acgttggatg ttgacagttt ctccttcccc                                        30
```

<210> SEQ ID NO 264
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264

```
acgttggatg gaatgtgacc agcaacgcag                                        30
```

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265

```
gcaggaagat gaaggtty                                                     18
```

<210> SEQ ID NO 266
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gattgacagt ttctccttcc ccagactggc caatcacagg caggaagatg aaggttttgt      60
gggctgcgtt gctggtcaca ttcctggc                                        88

<210> SEQ ID NO 267
<211> LENGTH: 90
<212> TYPE: DNA
<213> ORGANISM: Homo sapiens

<400> SEQUENCE: 267
gagttttgga tagtaaaata agtttcgaac tctggcacct ttcaattttg tcgcactctc      60
cttgtttttg acaatgcaat catatgcttc                                      90

<210> SEQ ID NO 268
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
acgtggatag taaaataagt ttcgaactct g                                    31

<210> SEQ ID NO 269
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
gaagcatatg attgcattgt caaaaac                                         27

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
atttcaattt tgtcgcacty                                                 20

<210> SEQ ID NO 271
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gagttttgga tagtaaaata agtttcgaac tctggcacct ttcaattttg tcgcactttc      60

```
cttgttttg acaatgcaat catatgcttc                                    90

<210> SEQ ID NO 272
<211> LENGTH: 97
<212> TYPE: DNA
<213> ORGANISM: Homo sapiens

<400> SEQUENCE: 272
gaactcctct tgtctctgc gtgcccggcg cgccccctc ccggtgggtg ataaacccac    60
tctggcgccg gccatgcgct gggtgattaa tttgcga                           97

<210> SEQ ID NO 273
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
acgttggatg tctttgtctc tgcgtgccc                                    29

<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
acgttggatg ttaatcaccc agcgcatggc                                   30

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
cccctcccgg tgggtgataa ay                                           22

<210> SEQ ID NO 276
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gaactcctct tgtctctgc gtgcccggcg cgccccctc ccggtgggtg ataaatccac    60
tctggcgccg gccatgcgct gggtgattaa tttgcga                           97

<210> SEQ ID NO 277
<211> LENGTH: 86
<212> TYPE: DNA
<213> ORGANISM: Homo sapiens

<400> SEQUENCE: 277
ccattggccg tccgccgtgg cagtgcgggc gggagcgcag ggagagaacc acagctggaa  60
tccgattccc accccaaaac ccagga                                       86
```

<210> SEQ ID NO 278
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
acgttggatg ccattggccg tccgccgtg                                    29

<210> SEQ ID NO 279
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
acgttggatg tcctgggttt tggggtggga a                                 31

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ttccagctgt ggttctctc                                               19

<210> SEQ ID NO 281
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ccattggccg tccgccgtgg cagtgcgggc gggagcgcag agagagaacc acagctggaa   60
tccgattccc accccaaaac ccagga                                       86

<210> SEQ ID NO 282
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
acgttggatg acatggtcgg ccccacggaa t                                 31

<210> SEQ ID NO 283
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
acgttggatg acccattggc cgtccgccgt					30

<210> SEQ ID NO 284
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
acgttggatg gaactcctct ttgtctctgc g					31

<210> SEQ ID NO 285
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
acgttggatg cgcagcaacg ggaccgctac a					31

<210> SEQ ID NO 286
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
acgttgcgta gcaacctgtt acatattaa						29

<210> SEQ ID NO 287
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
acgttggatg catagaggcc catgatggtg g					31

<210> SEQ ID NO 288
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
acgttggatg gtgtggtcag ctcttccctt cat					33

<210> SEQ ID NO 289
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
acgttggatg ctccttccta gtgtgagaac cg					32

<210> SEQ ID NO 290
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
acgttggatg ttttggggtg ggaatcggat t                              31

<210> SEQ ID NO 291
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
acgttggatg tggcatggcc ggcgccaga                                 29

<210> SEQ ID NO 292
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
acgttggcat ctaggtaggt ctttgtagcc aa                             32

<210> SEQ ID NO 293
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
acgttggatc tgagcaaagg caatcaacac cc                             32

<210> SEQ ID NO 294
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
acgttggatg accttctgcc cctctactcc aa                             32

<210> SEQ ID NO 295
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
acgttggccc acatgtaatg tgttgaaaaa gca                            33

<210> SEQ ID NO 296
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
caggttccgg ggcttggg                                              18

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
cgcagggaga gaaccacag                                             19

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
cccctcccgg tgggtgataa a                                          21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
aaagctgtag gacaatcggg t                                          21

<210> SEQ ID NO 300
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300 cattttcta catcctttgt tt                                          22

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
agaagatcac caggcagaag agg                                        23

```
<210> SEQ ID NO 302
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
acttggagaa caaaggacac cgtta                                           25

<210> SEQ ID NO 303
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
ggtcggcccc acggaatccc ggctctgtgt gcgcccaggt tccggggctt gggtgttgcc     60
ggttctcaca ctaggaagga g                                               81

<210> SEQ ID NO 304
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
ccattggccg tccgccgtgg cagtgcgggc gggagcgcag agagagaacc acagctggaa     60
tccgattccc accccaaaa                                                  79

<210> SEQ ID NO 305
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gaactcctct ttgtctctgc gtgcccggcg cgccccctc ccggtgggtg ataaatccac      60
tctggcgccg gccatgc                                                    77

<210> SEQ ID NO 306
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
gcagcaacgg gaccgctaca gccactggac aaagccgtag gacaatcggg taacattggc    60
tacaaagacc tacctagatg c                                               81

<210> SEQ ID NO 307
<211> LENGTH: 95
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 307
gcgtagcaac ctgttacata ttaaagtttt attatactac attttttctac atcctttgtt    60 tcagagtgtt gattgccttt gctcagtatc ttcag                                95

<210> SEQ ID NO 308
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ccttctgccc ctctactcca agcgctacac cctcttctgc ctggtgatct ttgccggcgt    60
cctggccacc atcatgggcc tctatg                                          86

<210> SEQ ID NO 309
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gtgtggtcag ctcttcccctt catcacatac ttggagaaca aggacaccg ttatccatgc    60 tttttcaaca cattacatgt ggg                                             83

<210> SEQ ID NO 310
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
acgttggatg ttctgcccct ctactccaag                                      30

<210> SEQ ID NO 311
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
acgttggatg tcagctcttc ccttcatcac                                      30

<210> SEQ ID NO 312
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
acgttggatg ttgacagttt ctccttcccc                                      30

<210> SEQ ID NO 313

<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 313
acgttggatg cggtcggccc cacggaat                                    28

<210> SEQ ID NO 314
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 314
acgtggatag taaaataagt ttcgaactct g                                31

<210> SEQ ID NO 315
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 315
acgttggatg cacagctcac cgcagcaacg                                  30

<210> SEQ ID NO 316
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 316
acgttggatg tctttgtctc tgcgtgccc                                   29

<210> SEQ ID NO 317
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 317
acgttggatg gactgagccc cagaactcg                                   29

<210> SEQ ID NO 318
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 318
acgttggatg aagccaagtt tccctccgc                                   29

<210> SEQ ID NO 319
<211> LENGTH: 30

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
acgttagcgt agcaacctgt tacatattaa                                    30

<210> SEQ ID NO 320
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
acgttggatg catagaggcc catgatggtg                                    30

<210> SEQ ID NO 321
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
acgttggatg cctacctccc acatgtaatg t                                  31

<210> SEQ ID NO 322
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
acgttggatg gaatgtgacc agcaacgcag                                    30

<210> SEQ ID NO 323
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
acgttggatg ctccttccta gtgtgagaac cg                                 32

<210> SEQ ID NO 324
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
gaagcatatg attgcattgt caaaaac                                       27

<210> SEQ ID NO 325
<211> LENGTH: 32
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 325
acgttggatg ctaggtaggt ctttgtagcc aa                                    32

<210> SEQ ID NO 326
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
acgttggatg ttaatcaccc agcgcatggc                                       30

<210> SEQ ID NO 327
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
acgttggatg gtgggtttgt gctttccacg                                       30

<210> SEQ ID NO 328
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
acgttggatg cttttgcttt cccagccagg                                       30

<210> SEQ ID NO 329
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
acgttggatg ctgagcaaag gcaatcaaca                                       30

<210> SEQ ID NO 330
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
ttctgcctgg tgatctt                                                     17

<210> SEQ ID NO 331
<211> LENGTH: 17
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 331
aacaaaggac accgtta                                                    17

<210> SEQ ID NO 332
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
gcaggaagat gaaggtt                                                    17

<210> SEQ ID NO 333
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
aaggttccgg ggcttggg                                                   18

<210> SEQ ID NO 334
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
atttcaattt tgtcgcact                                                  19

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
agctgtagga caatcgggt                                                  19

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
ccctcccggt gggtgataaa                                                 20

<210> SEQ ID NO 337
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 337
agggccgggg tctgcgcgtg                                                    20

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
gaggcactgc ccggacaaac c                                                  21

<210> SEQ ID NO 339
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
catttttcta catcctttgt tt                                                 22

<210> SEQ ID NO 340
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
ccttctgccc ctctactcca agcgctacac cctcttctgc ctggtgatct ttgccggcgt        60
cctggccacc atcatgggcc tctatg                                             86

<210> SEQ ID NO 341
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gtgtggtcag ctcttccctt catcacatac ttggagaaca aaggacaccg ttatccatgc        60
tttttcaaca cattacatgt gggaggtagg                                         90

<210> SEQ ID NO 342
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gattgacagt ttctccttcc ccagactggc caatcacagg caggaagatg aaggttttgt        60
gggctgcgtt gctggtcaca ttcctggc                                           88

```
<210> SEQ ID NO 343
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
aaaaccagag attcgcggtc ggccccacgg aatcccggct ctgtgtgcgc ccaggttccg    60
gggcttgggt gttgccggtt ctcacactag gaaggagc                           98

<210> SEQ ID NO 344
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gagttttgga tagtaaaata agtttcgaac tctggcacct ttcaattttg tcgcactttc    60
cttgtttttg acaatgcaat catatgcttc                                    90

<210> SEQ ID NO 345
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gcagccagct caccgcagca acgggaccgc tacagccact ggacaaagct gtaggacaat    60
cgggtgacat tggctacaaa gacctaccta gatgc                              95

<210> SEQ ID NO 346
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
gaactcctct tgtctctgc gtgcccggcg cgccccctc ccggtgggtg ataaatccac       60
tctggcgccg gccatgcgct gggtgattaa tttgcga                             97

<210> SEQ ID NO 347
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gtgggtttgt gctttccacg cgtgcacaca cacgcgcaga ccccggccct tgccccgcct    60
acctccccga gttctggggc tcagtc                                        86

<210> SEQ ID NO 348
<211> LENGTH: 89
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 348
gcgccagctt tgctttccc agccagggcg cggtgaggtt tgtccgggca gtgcctcgag      60
caactgggaa ggccaaggcg gagggaaac                                      89

<210> SEQ ID NO 349
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gcgtagcaac ctgttacata ttaaagtttt attatactac attttctac atcctttgtt     60 ttagggtgtt gattgccttt gctcagtatc ttcagc                              96

<210> SEQ ID NO 350
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 350
tagcugcgta gcaacctgtt acatatt                                        27

<210> SEQ ID NO 351
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 351
tagcucagtt tctccttccc cagac                                          25

<210> SEQ ID NO 352
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 352
tagcuggtca gctcttccct tcatc                                          25

<210> SEQ ID NO 353
<211> LENGTH: 24
<212> TYPE: DNA
<213> ORGANISM: Artificial Sequence
<220> FEATURE:

<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 353
tagcuagctg gtgcggaggg tggg                                            24

<210> SEQ ID NO 354
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 354
tagcuggcct ttgcaacaag gatcac                                          26

<210> SEQ ID NO 355
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 355
tagcutctgg tgaccccgc gcttc                                            25

<210> SEQ ID NO 356
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 356
tagcuccctc cacatcccgc catc                                            24

<210> SEQ ID NO 357
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 357
tagcuacgga atcccggctc tgtg                                            24

<210> SEQ ID NO 358
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 358
tagcuggccc tgctggcggt cata                                              24

<210> SEQ ID NO 359
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 359
tagcuagcaa cgggaccgct acag                                              24

<210> SEQ ID NO 360
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 360
tagcutaagt ttcgaactct ggcacc                                            26

<210> SEQ ID NO 361
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 361
tagcuctcct ctttgtctct gcgtg                                             25

<210> SEQ ID NO 362
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 362
tagcutgatg cccgatgccg ccctt                                             25

<210> SEQ ID NO 363
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 363
gatcuatact gagcaaaggc aatcaac                                          27

<210> SEQ ID NO 364
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 364
gatcugaatg tgaccagcaa cgcag                                            25

<210> SEQ ID NO 365
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 365
gatcucctcc cacatgtaat gtgttg                                           26

<210> SEQ ID NO 366
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 366
gatcuatggg ggagatggcc ggtgga                                           26

<210> SEQ ID NO 367
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 367
gatcucgcaa tactagaaac cagggc                                           26

<210> SEQ ID NO 368
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 368
gatcucatct ctgggtgcgc cttg                                          24

<210> SEQ ID NO 369
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 369
gatcucagcc gcctgctcca tcg                                           23

<210> SEQ ID NO 370
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 370
gatcuccttc ctagtgtgag aaccg                                         25

<210> SEQ ID NO 371
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 371
gatcutgctc agcacgaggg cccca                                         25

<210> SEQ ID NO 372
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 372
gatcutctag gtaggtcttt gtagcc                                        26

<210> SEQ ID NO 373
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 373
gatcugaagc atatgattgc attgtcaa                                          28

<210> SEQ ID NO 374
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 374
gatcuttaat cacccagcgc atggc                                             25

<210> SEQ ID NO 375
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 375
gatcugtctg tgctgggtgt ttttgc                                            26

<210> SEQ ID NO 376
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
aatgatacgg cgaccaccga gatctacact ctttccctac acgacgctct tccgatct        58

<210> SEQ ID NO 377
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
gctcttccga tctatagct                                                    19

<210> SEQ ID NO 378
<211> LENGTH: 65
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 378
gatcggaaga gcacacgtct gaactccagt cacagtcaac aatctcgtat gccgtcttct    60
gcttg    65

<210> SEQ ID NO 379
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
aatgatacgg cgaccaccga gatctacact ctttccctac acgacgctct tccgatct    58

<210> SEQ ID NO 380
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
acactctttc cctacacgac gctcttccga tct    33

<210> SEQ ID NO 381
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
gatcggaaga gcacacgtct gaactccagt cacagtcaaa tctcgtatgc cgtcttctgc    60
ttg    63

<210> SEQ ID NO 382
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
gatcggaaga gcacacgtct gaactccagt cac    33

<210> SEQ ID NO 383
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
tctttcccta cacgacgctc ttccgatct    29

<210> SEQ ID NO 384
<211> LENGTH: 34
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 384
gtgactggag ttcagacgtg tgctcttccg atct                                34

<210> SEQ ID NO 385
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
aatgatacgg cgaccaccga gatctacact ctttccctac acgacgctc                49

<210> SEQ ID NO 386
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
caagcagaag acggcatacg agatttgact gtgactggag ttcagacgtg               50

<210> SEQ ID NO 387
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
cgcaaccact                                                           10

<210> SEQ ID NO 388
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
cgcgaccact                                                           10
```

PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES

RELATED APPLICATIONS

This patent application is a continuation of U.S. patent application Ser. No. 13/940,164, filed on Jul. 11, 2013, entitled "PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES," naming John Allen TYNAN and Grant HOGG as inventors, which claims the benefit of U.S. Provisional Patent Application No. 61/671,628 filed on Jul. 13, 2012, entitled "PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES," naming John Allen TYNAN and Mengjia TANG as inventors, and claims the benefit of U.S. Provisional Patent Application No. 61/721,929, filed on Nov. 2, 2012, entitled "PROCESSES AND COMPOSITIONS FOR METHYLATION-BASED ENRICHMENT OF FETAL NUCLEIC ACID FROM A MATERNAL SAMPLE USEFUL FOR NON-INVASIVE PRENATAL DIAGNOSES," naming John Allen TYNAN and Grant HOGG as inventors. The entire content of each of the foregoing applications is incorporated herein by reference, including all text, tables and drawings.

SEQUENCE LISTING

The instant patent application contains a Sequence Listing that has been submitted in ASCII format via EFS-Web and is hereby incorporated by reference in its entirety. The ASCII copy, created on Sep. 3, 2013, is named SEQ-6022-UT2_SL.txt and is 437,311 bytes in size.

FIELD

The technology in part relates to prenatal diagnostics and enrichment methods.

BACKGROUND

Non-invasive prenatal testing is becoming a field of rapidly growing interest. Early detection of pregnancy-related conditions, including complications during pregnancy and genetic defects of the fetus is of crucial importance, as it allows early medical intervention necessary for the safety of both the mother and the fetus. Prenatal diagnosis has been conducted using cells isolated from the fetus through procedures such as chorionic villus sampling (CVS) or amniocentesis. However, these conventional methods are invasive and present an appreciable risk to both the mother and the fetus. The National Health Service currently cites a miscarriage rate of between 1 and 2 percent following the invasive amniocentesis and chorionic villus sampling (CVS) tests.

An alternative to these invasive approaches has been developed for prenatal screening, e.g., to detecting fetal abnormalities, following the discovery that circulating cell-free fetal nucleic acid can be detected in maternal plasma and serum (Lo et al., Lancet 350:485-487, 1997; and U.S. Pat. No. 6,258,540). Circulating cell free fetal nucleic acid (cffNA) has several advantages making it more applicable for non-invasive prenatal testing. For example, cell free nucleic acid is present at higher levels than fetal cells and at concentrations sufficient for genetic analysis. Also, cffNA is cleared from the maternal bloodstream within hours after delivery, preventing contamination from previous pregnancies.

Examples of prenatal tests performed by detecting fetal DNA in maternal plasma or serum include fetal rhesus D (RhD) genotyping (Lo et al., N. Engl. J. Med. 339:1734-1738, 1998), fetal sex determination (Costa et al., N. Engl. J. Med. 346:1502, 2002), and diagnosis of several fetal disorders (Amicucci et al., Clin. Chem. 46:301-302, 2000; Saito et al., Lancet 356:1170, 2000; and Chiu et al., Lancet 360:998-1000, 2002). In addition, quantitative abnormalities of fetal DNA in maternal plasma/serum have been reported in preeclampsia (Lo et al., Clin. Chem. 45:184-188, 1999 and Zhong et al., Am. J. Obstet. Gynecol. 184:414-419, 2001), fetal trisomy 21 (Lo et al., Clin. Chem. 45:1747-1751, 1999 and Zhong et al., Prenat. Diagn. 20:795-798, 2000) and hyperemesis gravidarum (Sekizawa et al., Clin. Chem. 47:2164-2165, 2001).

SUMMARY

The technology herein provides inter alia human epigenetic biomarkers that are useful for the noninvasive detection of fetal genetic traits, including, but not limited to, the presence or absence of fetal nucleic acid, the absolute or relative amount of fetal nucleic acid, fetal sex, and fetal chromosomal abnormalities such as aneuploidy. The human epigenetic biomarkers of the technology herein represent genomic DNA that display differential CpG methylation patterns between the fetus and mother. The compositions and processes of the technology herein allow for the detection and quantification of fetal nucleic acid in a maternal sample based on the methylation status of the nucleic acid in said sample. More specifically, the amount of fetal nucleic acid from a maternal sample can be determined relative to the total amount of nucleic acid present, thereby providing the percentage of fetal nucleic acid in the sample. Further, the amount of fetal nucleic acid can be determined in a sequence-specific (or locus-specific) manner and with sufficient sensitivity to allow for accurate chromosomal dosage analysis (for example, to detect the presence or absence of a fetal aneuploidy).

In the first aspect of the technology herein, a method is provided for enriching fetal nucleic acids from a maternal biological sample, based on differential methylation between fetal and maternal nucleic acid comprising the steps of: (a) binding a target nucleic acid, from a sample, and a control nucleic acid, from the sample, to a methylation-specific binding protein; and (b) eluting the bound nucleic acid based on methylation status, where differentially methylated nucleic acids elute at least partly into separate fractions. In an embodiment, the nucleic acid sequence includes one or more of the polynucleotide sequences of SEQ ID NOs: 1-261. SEQ ID NOs: 1-261 are provided in Tables 4A-4C. The technology herein includes the sequences of SEQ ID NOs: 1-261, and variations thereto. In an embodiment, a control nucleic acid is not included in step (a).

In a related embodiment, a method is provided for enriching fetal nucleic acid from a maternal sample, which comprises the following steps: (a) obtaining a biological sample from a woman; (b) separating fetal and maternal nucleic acid based on the methylation status of a CpG-containing genomic sequence in the sample, where the genomic sequence from the fetus and the genomic sequence from the woman are differentially methylated, thereby distinguishing the genomic sequence from the woman and the genomic sequence from the fetus in the sample. In an embodiment, the genomic sequence is at least 15 nucleotides in length, comprising at least one cytosine, further where the region consists of (1) a genomic locus selected from Tables 1A-1C; and (2) a DNA sequence of no more than 10 kb upstream and/or downstream from the locus. For this aspect and all aspects of the technology herein, obtaining a biological sample from a woman is not meant to limit the scope of the technology herein. Said obtaining can refer to actually drawing a sample from a woman (e.g., a blood draw) or to receiving a sample from elsewhere (e.g., from a clinic or hospital) and performing the remaining steps of the method.

In a related embodiment, a method is provided for enriching fetal nucleic acid from a maternal sample, which comprises the following steps: (a) obtaining a biological sample from the woman; (b) digesting or removing maternal nucleic acid based on the methylation status of a CpG-containing genomic sequence in the sample, where the genomic sequence from the fetus and the genomic sequence from the woman are differentially methylated, thereby enriching for the genomic sequence from the fetus in the sample. Maternal nucleic acid may be digested using one or more methylation sensitive restriction enzymes that selectively digest or cleave maternal nucleic acid based on its methylation status. In an embodiment, the genomic sequence is at least 15 nucleotides in length, comprising at least one cytosine, further where the region consists of (1) a genomic locus selected from Tables 1A-1C; and (2) a DNA sequence of no more than 10 kb upstream and/or downstream from the locus.

In a second aspect of the technology herein, a method is provided for preparing nucleic acid having a nucleotide sequence of a fetal nucleic acid, which comprises the following steps: (a) providing a sample from a pregnant female; (b) separating fetal nucleic acid from maternal nucleic acid from the sample of the pregnant female according to a different methylation state between the fetal nucleic acid and the maternal nucleic acid counterpart, where the nucleotide sequence of the fetal nucleic acid comprises one or more CpG sites from one or more of the polynucleotide sequences of SEQ ID NOs: 1-261 within a polynucleotide sequence from a gene or locus that contains one of the polynucleotide sequences of SEQ ID NOs: 1-261; and (c) preparing nucleic acid comprising a nucleotide sequence of the fetal nucleic acid by an amplification process in which fetal nucleic acid separated in part (b) is utilized as a template. In an embodiment, a method is provided for preparing nucleic acid having a nucleotide sequence of a fetal nucleic acid, which comprises the following steps: (a) providing a sample from a pregnant female; (b) digesting or removing maternal nucleic acid from the sample of the pregnant female according to a different methylation state between the fetal nucleic acid and the maternal nucleic acid counterpart, where the nucleotide sequence of the fetal nucleic acid comprises one or more CpG sites from one or more of the polynucleotide sequences of SEQ ID NOs: 1-261 within a polynucleotide sequence from a gene that contains one of the polynucleotide sequences of SEQ ID NOs: 1-261; and (c) preparing nucleic acid comprising a nucleotide sequence of the fetal nucleic acid. The preparing process of step (c) may be a hybridization process, a capture process, or an amplification process in which fetal nucleic acid separated in part (b) is utilized as a template. Also, in the above embodiment where maternal nucleic acid is digested, the maternal nucleic acid may be digested using one or more methylation sensitive restriction enzymes that selectively digest or cleave maternal nucleic acid based on its methylation status. In either embodiment, the polynucleotide sequences of SEQ ID NOs: 1-261 may be within a polynucleotide sequence from a CpG island that contains one of the polynucleotide sequences of SEQ ID NOs: 1-261. The polynucleotide sequences of SEQ ID NOs: 1-261 are further characterized in Tables 1-3 herein, including the identification of CpG islands that overlap with the polynucleotide sequences provided in SEQ ID NOs: 1-261. In an embodiment, the nucleic acid prepared by part (c) is in solution. In yet an embodiment, the method further comprises quantifying the fetal nucleic acid from the amplification process of step (c).

In a third aspect of the technology herein, a method is provided for enriching fetal nucleic acid from a sample from a pregnant female with respect to maternal nucleic acid, which comprises the following steps: (a) providing a sample from a pregnant female; and (b) separating or capturing fetal nucleic acid from maternal nucleic acid from the sample of the pregnant female according to a different methylation state between the fetal nucleic acid and the maternal nucleic acid, where the nucleotide sequence of the fetal nucleic acid comprises one or more CpG sites from one or more of the polynucleotide sequences of SEQ ID NOs: 1-261 within a polynucleotide sequence from a gene that contains one of the polynucleotide sequences of SEQ ID NOs: 1-261. In an embodiment, the polynucleotide sequences of SEQ ID NOs: 1-261 may be within a polynucleotide sequence from a CpG island that contains one of the polynucleotide sequences of SEQ ID NOs: 1-261. The polynucleotide sequences of SEQ ID NOs: 1-261 are characterized in Tables 1A-1C herein. In an embodiment, the nucleic acid separated by part (b) is in solution. In yet an embodiment, the method further comprises amplifying and/or quantifying the fetal nucleic acid from the separation process of step (b).

In a fourth aspect of the technology herein, a composition is provided comprising an isolated nucleic acid from a fetus of a pregnant female, where the nucleotide sequence of the nucleic acid comprises one or more of the polynucleotide sequences of SEQ ID NOs: 1-261. In one embodiment, the nucleotide sequence consists essentially of a nucleotide sequence of a gene, or portion thereof. In an embodiment, the nucleotide sequence consists essentially of a nucleotide sequence of a CpG island, or portion thereof. The polynucleotide sequences of SEQ ID NOs: 1-261 are further characterized in Tables 1A-1C. In an embodiment, the nucleic acid is in solution.

In an embodiment, the nucleic acid from the fetus is enriched relative to maternal nucleic acid. In an embodiment, the composition further comprises an agent that binds to methylated nucleotides. For example, the agent may be a methyl-CpG binding protein (MBD) or fragment thereof.

In a fifth aspect of the technology herein, a composition is provided comprising an isolated nucleic acid from a fetus of a pregnant female, where the nucleotide sequence of the nucleic acid comprises one or more CpG sites from one or more of the polynucleotide sequences of SEQ ID NOs: 1-261 within a polynucleotide sequence from a gene, or portion thereof, that contains one of the polynucleotide sequences of SEQ ID NOs: 1-261. In an embodiment, the nucleotide sequence of the nucleic acid comprises one or more CpG sites from one or more of the polynucleotide sequences of SEQ ID NOs: 1-261 within a polynucleotide sequence from a CpG island, or portion thereof, that contains one of the polynucleotide sequences of SEQ ID NOs: 1-261. The polynucleotide sequences of SEQ ID NOs: 1-261 are further characterized in Tables 1A-1C. In an embodiment, the nucleic acid is in solution. In an embodiment, the nucleic acid from the fetus is enriched relative to maternal nucleic acid. Hyper- and hypomethylated nucleic acid sequences of the technology herein are identified in Tables 1A-1C. In an embodiment, the composition further comprises an agent that binds to methylated nucleotides. For example, the agent may be a methyl-CpG binding protein (MBD) or fragment thereof.

In some embodiments, a nucleotide sequence of the technology herein includes three or more of the CpG sites. In an embodiment, the nucleotide sequence includes five or more of the CpG sites. In an embodiment, the nucleotide sequence is from a gene region that comprises a PRC2 domain (see Table 3). In an embodiment, the nucleotide sequence is from a gene region involved with development. For example, SOX14—which is an epigenetic marker of the present technology (See Table 1A)—is a member of the SOX (SRY-related HMG-box) family of transcription factors involved in the regulation of embryonic development and in the determination of cell fate.

In some embodiments, the genomic sequence from the woman is methylated and the genomic sequence from the fetus is unmethylated. In other embodiments, the genomic sequence from the woman is unmethylated and the genomic sequence from the fetus is methylated. In an embodiment, the genomic sequence from the fetus is hypermethylated relative to the genomic sequence from the mother. Fetal genomic sequences found to be hypermethylated relative to maternal genomic sequence are provided in SEQ ID NOs: 1-59, 90-163, 176, 179, 180, 184, 188, 189, 190, 191, 193, 195, 198, 199, 200, 201, 202, 203, 205, 206, 207, 208, 209, 210, 211, 212, 213, 214, 221, 223, 225, 226, 231, 232, 233, 235, 239, 241, 257, 258, 259, and 261. Alternatively, the genomic sequence from the fetus is hypomethylated relative to the genomic sequence from the mother. Fetal genomic sequences found to be hypomethylated relative to maternal genomic sequence are provided in SEQ ID NOs: 60-85, 164, 165, 166, 167, 168, 169, 170, 171, 172, 173, 174, 175, 177, 178, 181, 182, 183, 185, 186, 187, 192, 194, 196, 197, 204, 215, 216, 217, 218, 219, 220, 222, 224, 227, 228, 229, 230, 234, 236, 237, 238, 240, 242, 243, 244, 245, 246, 247, 248, 249, 250, 251, 252, 253, 254, 255, 256, and 260. Methylation sensitive restriction enzymes of the technology herein may be sensitive to hypo- or hyper-methylated nucleic acid.

In an embodiment, the fetal nucleic acid is extracellular nucleic acid. Generally the extracellular fetal nucleic acid is about 500, 400, 300, 250, 200 or 150 (or any number there between) nucleotide bases or less. In an embodiment, the digested maternal nucleic acid is less than about 90, 100, 110, 120, 130, 140 or 150 base pairs. In a related embodiment, the fetal nucleic acid is selectively amplified, captured or separated from or relative to the digested maternal nucleic acid based on size. For example, PCR primers may be designed to amplify nucleic acid greater than about 75, 80, 85, 90, 95, 100, 105, 110, 115 or 120 (or any number there between) base pairs thereby amplifying fetal nucleic acid and not digested maternal nucleic acid. In an embodiment, the nucleic acid is subjected to fragmentation prior to the methods of the technology herein. Examples of methods of fragmenting nucleic acid, include but are not limited to sonication and restriction enzyme digestion. In some embodiments the fetal nucleic acid is derived from the placenta. In other embodiments the fetal nucleic acid is apoptotic.

In some embodiments, the present technology provides a method in which the sample is a member selected from the following: maternal whole blood, maternal plasma or serum, amniotic fluid, a chorionic villus sample, biopsy material from a pre-implantation embryo, fetal nucleated cells or fetal cellular remnants isolated from maternal blood, maternal urine, maternal saliva, washings of the female reproductive tract and a sample obtained by celocentesis or lung lavage. In certain embodiments, the biological sample is maternal blood. In some embodiments, the biological sample is a chorionic villus sample. In certain embodiments, the maternal sample is enriched for fetal nucleic acid prior to the methods of the present technology. Examples of fetal enrichment methods are provided in PCT Publication Nos. WO/2007140417A2, WO2009/032781A2 and US Publication No. 20050164241.

In some embodiments, all nucleated and anucleated cell populations are removed from the sample prior to practicing the methods of the technology herein. In some embodiments, the sample is collected, stored or transported in a manner known to the person of ordinary skill in the art to minimize degradation or the quality of fetal nucleic acid present in the sample.

The sample can be from any animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may have a detectable pregnancy-associated disorder or chromosomal abnormality.

In some embodiments, the sample is treated with a reagent that differentially modifies methylated and unmethylated DNA. For example, the reagent may comprise bisulfite; or the reagent may comprise one or more enzymes that preferentially cleave methylated DNA; or the reagent may comprise one or more enzymes that preferentially cleave unmethylated DNA. Examples of methylation sensitive restriction enzymes include, but are not limited to, HhaI and HpaII.

In one embodiment, the fetal nucleic acid is separated from the maternal nucleic acid by an agent that specifically binds to methylated nucleotides in the fetal nucleic acid. In an embodiment, the fetal nucleic acid is separated or removed from the maternal nucleic acid by an agent that specifically binds to methylated nucleotides in the maternal nucleic acid counterpart. In an embodiment, the agent that binds to methylated nucleotides is a methyl-CpG binding protein (MBD) or fragment thereof.

In a sixth aspect of the technology herein, a method is provided for determining the amount or copy number of fetal DNA in a maternal sample that comprises differentially methylated maternal and fetal DNA. The method is performed by a) distinguishing between the maternal and fetal DNA based on differential methylation status; and b) quantifying the fetal DNA of step a). In a specific embodiment, the method comprises a) digesting the maternal DNA in a maternal sample using one or more methylation sensitive restriction enzymes thereby enriching the fetal DNA; and b) determining the amount of fetal DNA from step a). The amount of fetal DNA can be used inter alia to confirm the presence or absence of fetal nucleic acid, determine fetal sex, diagnose fetal disease or a pregnancy-associated disorder, or be used in conjunction with other fetal diagnostic methods to improve sensitivity or specificity. In one embodiment, the method for determining the amount of fetal DNA does not require the use of a polymorphic sequence. For example, an allelic ratio is not used to quantify the fetal DNA in step b). In an embodiment, the method for determining the amount of fetal DNA does not require the treatment of DNA with bisulfite to convert cytosine residues to uracil. Bisulfite is known to degrade DNA, thereby, further reducing the already limited fetal nucleic acid present in maternal samples. In one embodiment, determining the amount of fetal DNA in step b) is done by introducing one or more competitors at known concentrations. In an embodiment, determining the amount of fetal DNA in step b) is done by RT-PCR, primer extension, sequencing or counting. In a related embodiment, the amount of nucleic acid is determined using BEAMing technology as described in US Patent Publication No. US20070065823. In another related embodiment, the amount of nucleic acid is determined using the shotgun sequencing technology described in US Patent Publication No. US20090029377 (U.S. application Ser. No. 12/178,181), or variations thereof. In an embodiment, the restriction efficiency is determined and the efficiency rate is used to further determine the amount of fetal DNA. Exemplary differentially methylated nucleic acids are provided in SEQ ID NOs: 1-261.

In a seventh aspect of the technology herein, a method is provided for determining the concentration of fetal DNA in a maternal sample, where the maternal sample comprises differentially methylated maternal and fetal DNA, comprising a) determining the total amount of DNA present in the maternal sample; b) selectively digesting the maternal DNA in a maternal sample using one or more methylation sensitive restriction enzymes thereby enriching the fetal DNA; c) determining the amount of fetal DNA from step b); and d) comparing the amount of fetal DNA from step c) to the total amount of DNA from step a), thereby determining the concentration of fetal DNA in the maternal sample. The concentration of fetal DNA can be used inter alia in conjunction with other fetal diagnostic methods to improve sensitivity or specificity. In one embodiment, the method for determining the amount of fetal DNA does not require the use of a polymorphic sequence. For example, an allelic ratio is not used to quantify the fetal DNA in step b). In an embodiment, the method for determining the amount of fetal DNA does not require the treatment of DNA with bisulfite to convert cytosine residues to uracil. In one embodiment, determining the amount of fetal DNA in step b) is done by introducing one or more competitors at known concentrations. In an embodiment, determining the amount of fetal DNA in step b) is done by RT-PCR, sequencing or counting. In an embodiment, the restriction efficiency is determined and used to further determine the amount of total DNA and fetal DNA. Exemplary differentially methylated nucleic acids are provided in SEQ ID NOs: 1-261.

In an eighth aspect of the technology herein, a method is provided for determining the presence or absence of a fetal aneuploidy using fetal DNA from a maternal sample, where the maternal sample comprises differentially methylated maternal and fetal DNA, comprising a) selectively digesting the maternal DNA in a maternal sample using one or more methylation sensitive restriction enzymes thereby enriching the fetal DNA; b) determining the amount of fetal DNA from a target chromosome; c) determining the amount of fetal DNA from a reference chromosome; and d) comparing the amount of fetal DNA from step b) to step c), where a biologically or statistically significant difference between the amount of target and reference fetal DNA is indicative of the presence of a fetal aneuploidy. In one embodiment, the method for determining the amount of fetal DNA does not require the use of a polymorphic sequence. For example, an allelic ratio is not used to quantify the fetal DNA in step b). In an embodiment, the method for determining the amount of fetal DNA does not require the treatment of DNA with bisulfite to convert cytosine residues to uracil. In one embodiment, determining the amount of fetal DNA in steps b) and c) is done by introducing one or more competitors at known concentrations. In an embodiment, determining the amount of fetal DNA in steps b) and c) is done by RT-PCR, sequencing or counting. In an embodiment, the amount of fetal DNA from a target chromosome determined in step b) is compared to a standard control, for example, the amount of fetal DNA from a target chromosome from euploid pregnancies. In an embodiment, the restriction efficiency is determined and used to further determine the amount of fetal DNA from a target chromosome and from a reference chromosome. Exemplary differentially methylated nucleic acids are provided in SEQ ID NOs: 1-261.

In a ninth aspect of the technology herein, a method is provided for detecting the presence or absence of a chromosomal abnormality by analyzing the amount or copy number of target nucleic acid and control nucleic acid from a sample of differentially methylated nucleic acids comprising the steps of: (a) enriching a target nucleic acid, from a sample, and a control nucleic acid, from the sample, based on its methylation state; (b) performing a copy number analysis of the enriched target nucleic acid in at least one of the fractions; (c) performing a copy number analysis of the enriched control nucleic acid in at least one of the fractions; (d) comparing the copy number from step (b) with the copy number from step (c); and (e) determining if a chromosomal abnormality exists based on the comparison in step (d), where the target nucleic acid and control nucleic acid have the same or substantially the same methylation status. In a related embodiment, a method is provided for detecting the presence or absence of a chromosomal abnormality by analyzing the amount or copy number of target nucleic acid and control nucleic acid from a sample of differentially methylated nucleic acids comprising the steps of: (a) binding a target nucleic acid, from a sample, and a control nucleic acid, from the sample, to a binding agent; (b) eluting the bound nucleic acid based on methylation status, where differentially methylated nucleic acids elute at least partly into separate fractions; (c) performing a copy number analysis of the eluted target nucleic acid in at least one of the fractions; (d) performing a copy number analysis of the eluted control nucleic acid in at least one of the fractions; (e) comparing the copy number from step (c) with the copy number from step (d); and (f) determining if a chromosomal abnormality exists based on the comparison in step (e), where the target nucleic acid and control nucleic acid have the same or substantially the same methylation status. Differentially methylated nucleic acids are provided in SEQ ID NOs: 1-261.

In a tenth aspect of the technology herein, a method is provided for detecting the presence or absence of a chromosomal abnormality by analyzing the allelic ratio of target nucleic acid and control nucleic acid from a sample of differentially methylated nucleic acids comprising the steps of: (a) binding a target nucleic acid, from a sample, and a control nucleic acid, from the sample, to a binding agent; (b) eluting the bound nucleic acid based on methylation status, where differentially methylated nucleic acids elute at least partly into separate fractions; (c) performing an allelic ratio analysis of the eluted target nucleic acid in at least one of the fractions; (d) performing an allelic ratio analysis of the eluted control nucleic acid in at least one of the fractions; (e) comparing the allelic ratio from step c with the all from step d; and (f) determining if a chromosomal abnormality exists based on the comparison in step (e), where the target nucleic acid and control nucleic acid have the same or substantially the same methylation status. Differentially methylated nucleic acids are provided in SEQ ID NOs: 1-261, and SNPs within the differentially methylated nucleic acids are provided in Table 2. The methods may also be useful for detecting a pregnancy-associated disorder.

In an eleventh aspect of the technology herein, the amount of maternal nucleic acid is determined using the methylation-based methods of the technology herein. For example, fetal nucleic acid can be separated (for example, digested using a methylation-sensitive enzyme) from the maternal nucleic acid in a sample, and the maternal nucleic acid can be quantified using the methods of the technology herein. Once the amount of maternal nucleic acid is determined, that amount can subtracted from the total amount of nucleic acid in a sample to determine the amount of fetal nucleic acid. The amount of fetal nucleic acid can be used to detect fetal traits, including fetal aneuploidy, as described herein.

For all aspects and embodiments of the technology described herein, the methods may also be useful for detecting a pregnancy-associated disorder. In some embodiments, the sample comprises fetal nucleic acid, or fetal nucleic acid and maternal nucleic acid. In the case when the sample comprises fetal and maternal nucleic acid, the fetal nucleic acid and the maternal nucleic acid may have a different methylation status. Nucleic acid species with a different methylation status can be differentiated by any method known in the art. In an embodiment, the fetal nucleic acid is enriched by the selective digestion of maternal nucleic acid by a methylation sensitive restriction enzyme. In an embodiment, the fetal nucleic acid is enriched by the selective digestion of maternal nucleic acid using two or more methylation sensitive restriction enzymes in the same assay. In an embodiment, the target nucleic acid and control nucleic acid are both from the fetus. In an embodiment, the average size of the fetal nucleic acid is about 100 bases to about 500 bases in length. In an embodiment the chromosomal abnormality is an aneuploidy, such as trisomy 21. In some embodiments, the target nucleic acid is at least a portion of a chromosome which may be abnormal and the control nucleic acid is at least a portion of a chromosome which is very rarely abnormal. For example, when the target nucleic acid is from chromosome 21, the control nucleic acid is from a chromosome other than chromosome 21—preferably another autosome. In an embodiment, the binding agent is a methylation-specific binding protein such as MBD-Fc. Also, the enriched or eluted nucleic acid is amplified and/or quantified by any method known in the art. In an embodiment, the fetal DNA is quantified using a method that does not require the use of a polymorphic sequence. For example, an allelic ratio is not used to quantify the fetal DNA. In an embodiment, the method for quantifying the amount of fetal DNA does not require the treatment of DNA with bisulfite to convert cytosine residues to uracil.

In some embodiments, the methods of the technology herein include the additional step of determining the amount of one or more Y-chromosome-specific sequences in a sample. In a related embodiment, the amount of fetal nucleic acid in a sample as determined by using the methylation-based methods of the technology herein is compared to the amount of Y-chromosome nucleic acid present.

Methods for differentiating nucleic acid based on methylation status include, but are not limited to, methylation sensitive capture, for example using, MBD2-Fc fragment; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes. Except where explicitly stated, any method for differentiating nucleic acid based on methylation status can be used with the compositions and methods of the technology herein.

In some embodiments, methods of the technology herein may further comprise an amplification step. The amplification step can be performed by PCR, such as methylation-specific PCR. In an embodiment, the amplification reaction is performed on single molecules, for example, by digital PCR, which is further described in U.S. Pat. Nos. 6,143,496 and 6,440,706, both of which are hereby incorporated by reference. In other embodiments, the method does not require amplification. For example, the amount of enriched fetal DNA may be determined by counting the fetal DNA (or sequence tags attached thereto) with a flow cytometer or by sequencing means that do not require amplification. In an embodiment, the amount of fetal DNA is determined by an amplification reaction that generates amplicons larger than the digested maternal nucleic acid, thereby further enriching the fetal nucleic acid.

In some embodiments, the fetal nucleic acid (alone or in combination with the maternal nucleic acid) comprises one or more detection moieties. In one embodiment, the detection moiety may be any one or more of a compomer, sugar, peptide, protein, antibody, chemical compound (e.g., biotin), mass tag (e.g., metal ions or chemical groups), fluorescent tag, charge tag (e.g., such as polyamines or charged dyes) and hydrophobic tag. In a related embodiment, the detection moiety is a mass-distinguishable product (MDP) or part of an MDP detected by mass spectrometry. In a specific embodiment, the detection moiety is a fluorescent tag or label that is detected by mass spectrometry. In some embodiments, the detection moiety is at the 5' end of a detector oligonucleotide, the detection moiety is attached to a non-complementary region of a detector oligonucleotide, or the detection moiety is at the 5' terminus of a non-complementary sequence. In certain embodiments, the detection moiety is incorporated into or linked to an internal nucleotide or to a nucleotide at the 3' end of a detector oligonucleotide. In some embodiments, one or more detection moieties are used either alone or in combination. See for example US Patent Applications US20080305479 and US20090111712. In certain embodiments, a detection moiety is cleaved by a restriction endonuclease, for example, as described in U.S. application Ser. No. 12/726,246. In some embodiments, a specific target chromosome is labeled with a specific detection moiety and one or more non-target chromosomes are labeled with a different detection moiety, whereby the amount target chromosome can be compared to the amount of non-target chromosome.

For embodiments that require sequence analysis, any one of the following sequencing technologies may be used: a primer extension method (e.g., iPLEX®; Sequenom, Inc.), direct DNA sequencing, restriction fragment length polymorphism (RFLP analysis), real-time PCR, for example using "STAR" (Scalable Transcription Analysis Routine) technology (see U.S. Pat. No. 7,081,339), or variations thereof, allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, fluorescence tagged dNTP/ddNTPs, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader™ assay, hybridization using at least one probe, hybridization using at least one fluorescently labeled probe, electrophoresis, cloning and sequencing, for example as performed on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, or nanopore-based sequencing (Soni G V and Meller A. 2007 Clin Chem 53: 1996-2001), for example, using an Ion Torrent ion sensor that measures an electrical charge associated with each individual base of DNA as each base passes through a tiny pore at the bottom of a sample well, or Oxford Nanopore device that uses a nanopore to measure the electrical charge associated with each individual unit of DNA, and combinations thereof. Nanopore-based methods may include sequencing nucleic acid using a nanopore, or counting nucleic acid molecules using a nanopore, for example, based on size where sequence information is not determined.

The absolute copy number of one or more nucleic acids can be determined, for example, using mass spectrometry, a system that uses a competitive PCR approach for absolute copy number measurements. See for example, Ding C, Cantor C R (2003) A high-throughput gene expression analysis technique using competitive PCR and matrix-assisted laser desorption ionization time-of-flight MS. Proc Natl Acad Sci USA 100:3059-3064, and U.S. patent application Ser. No. 10/655,762, which published as US Patent Publication No. 20040081993, both of which are hereby incorporated by reference.

In some embodiments, the amount of the genomic sequence is compared with a standard control, where an increase or decrease from the standard control indicates the presence or progression of a pregnancy-associated disorder. For example, the amount of fetal nucleic acid may be compared to the total amount of DNA present in the sample. Or when detecting the presence or absence of fetal aneuploidy, the amount of fetal nucleic acid from target chromosome may be compared to the amount of fetal nucleic acid from a reference chromosome. Preferably the reference chromosome is another autosome that has a low rate of aneuploidy. The ratio of target fetal nucleic acid to reference fetal nucleic acid may be compared to the same ratio from a normal, euploid pregnancy. For example, a control ratio may be determined from a DNA sample obtained from a female carrying a healthy fetus who does not have a chromosomal abnormality. Preferably, one uses a panel of control samples. Where certain chromosome anomalies are known, one can also have standards that are indicative of a specific disease or condition. Thus, for example, to screen for three different chromosomal aneuploidies in a maternal plasma of a pregnant female, one preferably uses a panel of control DNAs that have been isolated from mothers who are known to carry a fetus with, for example, chromosome 13, 18, or 21 trisomy, and a mother who is pregnant with a fetus who does not have a chromosomal abnormality.

In some embodiments, the present technology provides a method in which the alleles from the target nucleic acid and control nucleic acid are differentiated by sequence variation. The sequence variation may be a single nucleotide polymorphism (SNP) or an insertion/deletion polymorphism. In some embodiments, the fetal nucleic acid should comprise at least one high frequency heterozygous polymorphism (e.g., about 2%, 3%, 4%, 5%, 6%, 7%, 8%, 9%, 10%, 11%, 12%, 13%, 14%, 15%, 16%, 17%, 18%, 19%, 20%, 25%, 35%, 40%, 45%, 50%, 55%, 60% or more frequency rate), which allows the determination of the allelic-ratio of the nucleic acid in order to assess the presence or absence of the chromosomal abnormality. Lists of example SNPs are provided in Table 2, Table 9 and Table 10, however, these do not represent a complete list of polymorphic alleles that can be used as part of the technology herein. In some embodiments, any SNP meeting the following criteria, for example, may also be considered: (a) the SNP has a heterozygosity frequency greater than about 2% (preferably across a range of different populations), (b) the SNP is a heterozygous locus; and (c)(i) the SNP is within a nucleic acid sequence described herein, or (c)(iii) the SNP is within about 5 to about 2000 base pairs of a SNP described herein (e.g., within about 5, 10, 15, 20, 25, 30, 40, 50, 60, 70, 80, 90, 100, 200, 300, 400, 500, 600, 700, 800, 900, 1000, 1250, 1500, 1750 or 2000 base pairs of a SNP described herein). In some cases, SNPs are selected by other criteria described in further detail herein.

In other embodiments, the sequence variation is a short tandem repeat (STR) polymorphism. In some embodiments, the sequence variation falls in a restriction site, whereby one allele is susceptible to digestion by a restriction enzyme and the one or more other alleles are not. In some embodiments, the sequence variation is a methylation site.

In some embodiments, performing an allelic ratio analysis comprises determining the ratio of alleles of the target nucleic acid and control nucleic acid from the fetus of a pregnant woman by obtaining an nucleic acid-containing biological sample from the pregnant woman, where the biological sample contains fetal nucleic acid, partially or wholly separating the fetal nucleic acid from the maternal nucleic acid based on differential methylation, discriminating the alleles from the target nucleic acid and the control nucleic acid, followed by determination of the ratio of the alleles, and detecting the presence or absence of a chromosomal disorder in the fetus based on the ratio of alleles, where a ratio above or below a normal, euploid ratio is indicative of a chromosomal disorder. In one embodiment, the target nucleic acid is from a suspected aneuploid chromosome (e.g., chromosome 21) and the control nucleic acid is from a euploid chromosome from the same fetus.

In some embodiments, the present technology is combined with other fetal markers to detect the presence or absence of multiple chromosomal abnormalities, where the chromosomal abnormalities are selected from the following: trisomy 21, trisomy 18 and trisomy 13, or combinations thereof. In some embodiments, the chromosomal disorder involves the X chromosome or the Y chromosome.

In some embodiments, the compositions or processes may be multiplexed in a single reaction. For example, the amount of fetal nucleic acid may be determined at multiple loci across the genome. Or when detecting the presence or absence of fetal aneuploidy, the amount of fetal nucleic acid may be determined at multiple loci on one or more target chromosomes (e.g., chromosomes 13, 18 or 21) and on one or more reference chromosomes. If an allelic ratio is being used, one or more alleles from Table 2, Table 9, and/or Table 10 can be detected and discriminated simultaneously. When determining allelic ratios, multiplexing embodiments are particularly important when the genotype at a polymorphic locus is not known. In some instances, for example when the mother and child are homozygous at the polymorphic locus, the assay may not be informative. In one embodiment, greater than 1, 2, 3, 4, 5, 6, 7, 8, 9, 10, 11, 12, 13, 14, 15, 16, 17, 18, 19, 20, 25, 30, 35, 40, 50, 100, 200, 300 or 500, and any intermediate levels, polynucleotide sequences of the technology herein are enriched, separated and/or examined according the methods of the technology. When detecting a chromosomal abnormality by analyzing the copy number of target nucleic acid and control nucleic acid, less than 3, 4, 5, 6, 7, 8, 9, 10, 11, 12, 13, or 14 polynucleotide sequences may need to be analyzed to accurately detect the presence or absence of a chromosomal abnormality. In an embodiment, the compositions or processes of the technology herein may be used to assay samples that have been divided into 2, 3, 4, 5, 6, 7, 8, 9, 10, 11, 12, 13, 14, 15, 16, 17, 18, 19, 20, 25, 30, 35, 40, 50, 100 or more replicates, or into single molecule equivalents. Methods for analyzing fetal nucleic acids from a maternal sample in replicates, including single molecule analyses, are provided in U.S. application Ser. No. 11/364,294, which published as US Patent Publication No. US 2007-0207466 A1, which is hereby incorporated by reference.

In a further embodiment, the present technology provides a method where a comparison step shows an increased risk of a fetus having a chromosomal disorder if the ratio of the alleles or absolute copy number of the target nucleic acid is higher or lower by 1 standard deviation from the standard control sequence. In some embodiments, the comparison step shows an increased risk of a fetus having a chromosomal disorder if the ratio of the alleles or absolute copy number of the target nucleic acid is higher or lower by 2 standard deviations from the standard control sequence. In some other embodiments, the comparison step shows an increased risk of a fetus having a chromosomal disorder if the ratio of the alleles or absolute copy number of the target nucleic acid is higher or lower by 3 standard deviations from the standard control sequence. In some embodiments, the comparison step shows an increased risk of a fetus having a chromosomal disorder if the ratio of the alleles or absolute copy number of the target nucleic acid is higher or lower than a statistically significant standard deviation from the control. In one embodiment, the standard control is a maternal reference, and in an embodiment the standard control is a fetal reference chromosome (e.g., non-trisomic autosome).

In some embodiments, the methods of the technology herein may be combined with other methods for diagnosing a chromosomal abnormality. For example, a noninvasive diagnostic method may require confirmation of the presence or absence of fetal nucleic acid, such as a sex test for a female fetus or to confirm an RhD negative female fetus in an RhD negative mother. In an embodiment, the compositions and methods of the technology herein may be used to determine the percentage of fetal nucleic acid in a maternal sample in order to enable another diagnostic method that requires the percentage of fetal nucleic acid be known. For example, does a sample meet certain threshold concentration requirements? When determining an allelic ratio to diagnose a fetal aneuploidy from a maternal sample, the amount or concentration of fetal nucleic acid may be required to make a diagnose with a given sensitivity and specificity. In other embodiments, the compositions and methods of the technology herein for detecting a chromosomal abnormality can be combined with other known methods thereby improving the overall sensitivity and specificity of the detection method. For example, mathematical models have suggested that a combined first-trimester screening program utilizing maternal age (MA), nuchal translucency (NT) thickness, serum-free beta-hCG, and serum PAPP-A will detect more than 80% of fetuses with Down's syndrome for a 5% invasive testing rate (Wald and Hackshaw, Prenat Diagn 17(9):921-9 (1997)). However, the combination of commonly used aneuploidy detection methods combined with the non-invasive free fetal nucleic acid-based methods described herein may offer improved accuracy with a lower false positive rate. Examples of combined diagnostic methods are provided in PCT Publication Number WO2008157264A2 (assigned to the Applicant), which is hereby incorporated by reference. In some embodiments, the methods of the technology herein may be combined with cell-based methods, where fetal cells are procured invasively or non-invasively.

In certain embodiments, an increased risk for a chromosomal abnormality is based on the outcome or result(s) produced from the compositions or methods provided herein. An example of an outcome is a deviation from the euploid absolute copy number or allelic ratio, which indicates the presence of chromosomal aneuploidy. This increase or decrease in the absolute copy number or ratio from the standard control indicates an increased risk of having a fetus with a chromosomal abnormality (e.g., trisomy 21). Information pertaining to a method described herein, such as an outcome, result, or risk of trisomy or aneuploidy, for example, may be transfixed, renditioned, recorded and/or displayed in any suitable medium. For example, an outcome may be transfixed in a medium to save, store, share, communicate or otherwise analyze the outcome. A medium can be tangible (e.g., paper) or intangible (e.g., electronic medium), and examples of media include, but are not limited to, computer media, databases, charts, patient charts, records, patient records, graphs and tables, and any other medium of expression. The information sometimes is stored and/or renditioned in computer readable form and sometimes is stored and organized in a database. In certain embodiments, the information may be transferred from one location to another using a physical medium (e.g., paper) or a computer readable medium (e.g., optical and/or magnetic storage or transmission medium, floppy disk, hard disk, random access memory, computer processing unit, facsimile signal, satellite signal, transmission over an internet or transmission over the world-wide web).

In practicing the present technology within all aspects mentioned above, a CpG island may be used as the CpG-containing genomic sequence in some cases, whereas in other cases the CpG-containing genomic sequence may not be a CpG island.

In some embodiments, the present technology provides a kit for performing the methods of the technology. One component of the kit is a methylation-sensitive binding agent.

Also provided, in some aspects, are methods for determining the amount of fetal nucleic acid in a sample comprising (a) contacting a sample nucleic acid with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid; (b) contacting under amplification conditions the differentially modified sample nucleic acid with: (i) a first set of amplification primers that specifically amplify a first region in sample nucleic acid comprising one or more loci that are differentially methylated between the fetal nucleic acid and maternal nucleic acid, and (ii) a second set of amplification primers that amplify a second region in the sample nucleic acid allowing for a determination of total nucleic acid in the sample, where the first region and the second region are different, thereby generating fetal nucleic acid amplification products and total nucleic acid amplification products; (c) incorporating adaptor oligonucleotides into the amplification products in (b); thereby generating adaptor-modified amplification products; (d) obtaining nucleotide sequences of the adaptor-modified amplification products in (c) by a sequencing process, thereby generating sequence reads; (e) quantifying the sequence reads; and (f) determining the amount of fetal nucleic acid in the sample based on a quantification of the sequence reads in (e).

Also provided, in some aspects, are methods for determining the amount of fetal nucleic acid in a sample comprising (a) contacting a sample nucleic acid with one or more methylation sensitive restriction enzymes, which sample nucleic acid comprises differentially methylated fetal nucleic acid and maternal nucleic acid, the combination of the fetal nucleic acid and the maternal nucleic acid comprising total nucleic acid in the sample, thereby generating differentially digested sample nucleic acid; (b) contacting under amplification conditions the digested sample nucleic acid with (i) a first set of amplification primers that specifically amplify a first region in sample nucleic acid comprising one or more loci that are differentially methylated between the fetal nucleic acid and maternal nucleic acid, and (ii) a second set of amplification primers that amplify a second region in the sample nucleic acid allowing for a determination of total nucleic acid in the sample, where the first region and the second region are different, thereby generating fetal nucleic acid amplification products and total nucleic acid amplification products; (c) incorporating adaptor oligonucleotides into the amplification products in (b); thereby generating adaptor-modified amplification products; (d) obtaining nucleotide sequences of the adaptor-modified amplification products in (c) by a sequencing process, thereby generating sequence reads; (e) quantifying the sequence reads; and (f) determining the amount of fetal nucleic acid in the sample based on a quantification of the sequence reads in (e).

Also provided, in some aspects, are methods for determining the copy number of fetal nucleic acid in a sample comprising (a) contacting a sample nucleic acid with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid; (b) contacting under amplification conditions the differentially modified sample nucleic acid with (i) a first set of amplification primers that specifically amplify a first region in sample nucleic acid comprising one or more loci that are differentially methylated between the fetal nucleic acid and maternal nucleic acid, and (ii) a predetermined copy number of one or more first competitor oligonucleotides that compete with the first region for hybridization of primers of the first amplification primer set, thereby generating fetal nucleic acid amplification products and competitor amplification products; (c) incorporating adaptor oligonucleotides into the amplification products in (b); thereby generating adaptor-modified amplification products; (d) obtaining nucleotide sequences of the adaptor-modified amplification products in (c) by a sequencing process, thereby generating sequence reads; (e) quantifying the sequence reads; and (f) determining the copy number of fetal nucleic acid in the sample based on a quantification of the sequence reads in (e) and the amount of competitor oligonucleotide used.

Also provided, in some aspects, are methods for detecting the presence or absence of a fetal aneuploidy in a sample comprising (a) contacting a sample nucleic acid with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid; (b) contacting under amplification conditions the differentially modified sample nucleic acid with (i) a first set of amplification primers that specifically amplify one or more loci in a target chromosome that are differentially methylated between the fetal nucleic acid and maternal nucleic acid, and (ii) a second set of amplification primers that specifically amplify one or more loci in a reference chromosome that are differentially methylated between the fetal nucleic acid and maternal nucleic acid, thereby generating target chromosome amplification products and reference chromosome amplification products; (c) incorporating adaptor oligonucleotides into the amplification products in (b); thereby generating adaptor-modified amplification products; (d) obtaining nucleotide sequences of the adaptor-modified amplification products in (c) by a sequencing process, thereby generating sequence reads; (e) quantifying the sequence reads; and (f) detecting the presence or absence of a fetal aneuploidy in the sample based on a quantification of the sequence reads in (e).

In some embodiments, the first region comprises one or more loci which each contain a restriction site for a methylation-sensitive restriction enzyme. In some embodiments, the one or more agents that differentially modify methylated nucleic acid and unmethylated nucleic acid comprise one or more methylation sensitive restriction enzymes. In some embodiments, the second region comprises one or more loci which do not contain a restriction site for a methylation-sensitive restriction enzyme. In some embodiments, the one or more agents that differentially modify methylated nucleic acid and unmethylated nucleic acid comprise bisulfite. In some embodiments, the target chromosome comprises one or more loci which each contain a restriction site for a methylation-sensitive restriction enzyme. In some embodiments, the reference chromosome comprises one or more loci which each contain a restriction site for a methylation-sensitive restriction enzyme.

In some embodiments, the adaptor oligonucleotides are incorporated into the amplification products by ligation. In some cases, the ligation is unidirectional ligation. In some embodiments, the adaptor oligonucleotides are incorporated into the amplification products using amplification primers comprising the adaptor oligonucleotide sequences. In some embodiments, the adaptor oligonucleotides comprise one or more index sequences. In some cases, the one or more index sequences comprise a sample-specific index. In some cases, the one or more index sequences comprise an aliquot-specific index.

In some embodiments, at least one of the one or more loci in the first region comprises a nucleotide sequence selected from among SEQ ID NOs:1-261, or a fragment thereof. In some cases, at least one of the one or more loci in the first region comprises a nucleotide sequence selected from among SEQ ID NOs:1-89, or a fragment thereof. In some cases, at least one of the one or more loci in the first region comprises a nucleotide sequence selected from among SEQ ID NOs:90-261, or a fragment thereof. In some cases, at least one of the one or more loci in the first region comprises a nucleotide sequence selected from among SEQ ID NOs: 1-59 and SEQ ID NOs:86-89, or a fragment thereof. In some cases, at least one of the one or more loci in the first region comprises a nucleotide sequence selected from among SEQ ID NOs:1-59, or a fragment thereof. In some cases, at least one of the one or more loci in the first region comprises a nucleotide sequence selected from among SEQ ID NO:42, SEQ ID NO:52, SEQ ID NO:154, SEQ ID NO:158 and SEQ ID NO:163.

In some embodiments, at least one of the one or more loci in the target chromosome comprises a nucleotide sequence selected from among SEQ ID NOs:1-261, or a fragment thereof. In some cases, at least one of the one or more loci in the target chromosome comprises a nucleotide sequence selected from among SEQ ID NOs:1-89, or a fragment thereof. In some cases, at least one of the one or more loci in the target chromosome comprises a nucleotide sequence selected from among SEQ ID NOs:90-261, or a fragment thereof. In some cases, at least one of the one or more loci in target chromosome comprises a nucleotide sequence selected from among SEQ ID NOs:1-59 and SEQ ID NOs: 86-89, or a fragment thereof. In some cases, at least one of the one or more loci in the target chromosome comprises a nucleotide sequence selected from among SEQ ID NOs:1-59, or a fragment thereof. In some cases, at least one of the one or more loci in the target chromosome comprises a nucleotide sequence selected from among SEQ ID NO:42, SEQ ID NO:52, SEQ ID NO:154, SEQ ID NO:158 and SEQ ID NO:163.

In some embodiments, at least one of the one or more loci in the reference chromosome comprises a nucleotide sequence selected from among SEQ ID NOs:1-261, or a fragment thereof. In some cases, at least one of the one or more loci in the reference chromosome comprises a nucleotide sequence selected from among SEQ ID NOs:1-89, or a fragment thereof. In some cases, at least one of the one or more loci in the reference chromosome comprises a nucleotide sequence selected from among SEQ ID NOs:90-261, or a fragment thereof. In some cases, at least one of the one or more loci in reference chromosome comprises a nucleotide sequence selected from among SEQ ID NOs:1-59 and SEQ ID NOs:86-89, or a fragment thereof. In some cases, at least one of the one or more loci in the reference chromosome comprises a nucleotide sequence selected from among SEQ ID NOs:1-59, or a fragment thereof. In some cases, at least one of the one or more loci in the reference chromosome comprises a nucleotide sequence selected from among SEQ ID NO:42, SEQ ID NO:52, SEQ ID NO:154, SEQ ID NO:158 and SEQ ID NO:163.

In some embodiments, the sequencing process is a sequencing by synthesis method. In some embodiments, the sequencing process is a reversible terminator-based sequencing method.

In some embodiments, the amount of fetal nucleic acid determined is the fraction of fetal nucleic acid in the sample based on the amount of each of the fetal nucleic acid amplification products and total nucleic acid amplification products. In some cases, the fraction of fetal nucleic acid is a ratio of fetal nucleic acid amplification product amount to total nucleic acid amplification product amount.

In some embodiments, a method further comprises contacting under amplification conditions the nucleic acid sample with a second set of amplification primers that amplify a second region in the sample nucleic acid allowing for a determination of total nucleic acid in the sample, where the first region and the second region are different. In some cases, the second region comprises one or more loci which do not contain a restriction site for a methylation-sensitive restriction enzyme.

In some embodiments, a method further comprises contacting under amplification conditions the nucleic acid sample with a third set of amplification primers that amplify a third region in the sample nucleic acid allowing for a determination of the presence or absence of fetal specific nucleic acid. In some cases, the fetal specific nucleic acid is Y chromosome nucleic acid. In some cases, the third region comprises one or more loci within chromosome Y.

In some embodiments, a method further comprises contacting under amplification conditions the nucleic acid sample with a fourth set of amplification primers that amplify a fourth region in the sample nucleic acid allowing for a determination of the amount of digested or undigested nucleic acid, as an indicator of digestion efficiency. In some cases, the fourth region comprises one or more loci present in both fetal nucleic acid and maternal nucleic acid and unmethylated in both fetal nucleic acid and maternal nucleic acid.

In some embodiments, a method further comprises contacting under amplification conditions the nucleic acid sample with a predetermined copy number of one or more first competitor oligonucleotides that compete with the first region for hybridization of primers of the first amplification primer set. In some embodiments, a method further comprises contacting under amplification conditions the nucleic acid sample with a predetermined copy number of one or more first competitor oligonucleotides that compete with the target chromosome for hybridization of primers of the first amplification primer set.

In some embodiments, a method further comprises contacting under amplification conditions the nucleic acid sample with a predetermined copy number of one or more second competitor oligonucleotides that compete with the second region for hybridization of primers of the second amplification primer set. In some embodiments, a method further comprises contacting under amplification conditions the nucleic acid sample with a predetermined copy number of one or more second competitor oligonucleotides that compete with the reference chromosome for hybridization of primers of the second amplification primer set.

In some embodiments, a method further comprises contacting under amplification conditions the nucleic acid sample with a predetermined copy number of one or more third competitor oligonucleotides that compete with the third region for hybridization of primers of the third amplification primer set.

In some embodiments, a method further comprises contacting under amplification conditions the nucleic acid sample with a predetermined copy number of one or more fourth competitor oligonucleotides that compete with the fourth region for hybridization of primers of the fourth amplification primer set.

In some embodiments, the amount of fetal nucleic acid determined is the copy number of fetal nucleic acid based on the amount of competitor oligonucleotide used. In some embodiments, the amount of fetal nucleic acid determined is the copy number of fetal nucleic acid based on a quantification of sequence reads.

In some embodiments, the sample nucleic acid is extracellular nucleic acid. In some cases, the nucleic acid sample is obtained from a pregnant female subject. In some cases, the subject is human. In some embodiments, the sample nucleic acid is from plasma or serum.

In some embodiments, two or more independent loci in the first region are assayed. In some embodiments, two or more independent loci in the target chromosome are assayed. In some embodiments, two or more independent loci in the reference chromosome are assayed. In some embodiments, the target chromosome is chromosome 13. In some embodiments, the target chromosome is chromosome 18. In some embodiments, the target chromosome is chromosome 21.

In some embodiments, the amount of fetal nucleic acid is substantially equal to the amount of fetal nucleic acid determined using a mass spectrometry method. In some embodiments, the amount of fetal nucleic acid is determined with an $R^2$ value of 0.97 or greater when compared to an amount of fetal nucleic acid determined using a mass spectrometry method. In some embodiments, the copy number of fetal nucleic acid is substantially equal to the copy number of fetal nucleic acid determined using a mass spectrometry method. In some embodiments, the copy number of fetal nucleic acid is determined with an $R^2$ value of 0.97 or greater when compared to a copy number of fetal nucleic acid determined using a mass spectrometry method.

Also provided, in some aspects, are methods for determining fetal fraction in a sample comprising (a) enriching a sample nucleic acid for a plurality of polymorphic nucleic acid targets, which sample nucleic acid comprises fetal nucleic acid and maternal nucleic acid; (b) obtaining nucleotide sequences for some or all of the nucleic acid targets by a sequencing process; (c) analyzing the nucleotide sequences of (b); and (d) determining fetal fraction based on the analysis of (c), where the polymorphic nucleic acid targets and number thereof result in at least five polymorphic nucleic acid targets being informative for determining the fetal fraction for at least 90% of samples.

In some embodiments, the enriching comprises amplifying the plurality of polymorphic nucleic acid targets. In some cases, the enriching comprises generating amplification products in an amplification reaction, and sometimes the amplification reaction is performed in a single vessel.

In some embodiments, the maternal genotype and the paternal genotype at each of the polymorphic nucleic acid targets are not known prior to (a). In some embodiments, polymorphic nucleic acid targets having a minor allele population frequency of about 40% or more are selected.

In some embodiments, a method comprises determining an allele frequency in the sample for each of the polymorphic nucleic acid targets. In some embodiments, determining which polymorphic nucleic acid targets are informative comprises identifying informative genotypes by comparing each allele frequency to one or more fixed cutoff frequencies. In some cases, the fixed cutoff for identifying informative genotypes from non-informative homozygotes is about a 2% or greater shift in allele frequency and sometimes is a 1% or greater shift in allele frequency. In some cases, the fixed cutoff for identifying informative genotypes from non-informative heterozygotes is about a 50% or greater shift in allele frequency and sometimes is a 25% or greater shift in allele frequency. In some embodiments, determining which polymorphic nucleic acid targets are informative comprises identifying informative genotypes by comparing each allele frequency to one or more target-specific cutoff frequencies. In some cases, the one or more target-specific cutoff frequencies are determined for each polymorphic nucleic acid target. In some cases, each target-specific cutoff frequency is determined based on the allele frequency variance for the corresponding polymorphic nucleic acid target.

In some embodiments, a method comprises determining an allele frequency mean. In some cases, fetal fraction is determined based, in part, on the allele frequency mean. In some embodiments, the fetal genotype at one or more informative polymorphic nucleic acid targets is heterozygous. In some embodiments, the fetal genotype at one or more informative polymorphic nucleic acid targets is homozygous. In some embodiments, fetal fraction is determined with a coefficient of variance (CV) of 0.20 or less. In some cases, fetal fraction is determined with a coefficient of variance (CV) of 0.10 or less, and sometimes fetal fraction is determined with a coefficient of variance (CV) of 0.05 or less.

In some embodiments, the polymorphic nucleic acid targets each comprise at least one single nucleotide polymorphism (SNP). In some cases, the SNPs are selected from: rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, rs985462, rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

In some cases, the SNPs are selected from: rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, and rs985462.

In some cases, the SNPs are selected from: rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

The polymorphic targets can comprise one or more of any of the single nucleotide polymorphisms (SNPs) listed above and any combination thereof.

In some embodiments, the polymorphic nucleic acid targets and number thereof result in at least five polymorphic nucleic acid targets being informative for determining the fetal fraction for at least 95% of samples. In some cases, the polymorphic nucleic acid targets and number thereof result in at least five polymorphic nucleic acid targets being informative for determining the fetal fraction for at least 99% of samples. In some cases, the polymorphic nucleic acid targets and number thereof result in at least ten polymorphic nucleic acid targets being informative for determining the fetal fraction for at least 90% of samples. In some cases, the polymorphic nucleic acid targets and number thereof result in at least ten polymorphic nucleic acid targets being informative for determining the fetal fraction for at least 95% of samples. In some cases, the polymorphic nucleic acid targets and number thereof result in at least ten polymorphic nucleic acid targets being informative for determining the fetal fraction for at least 99% of samples. Sometimes, 10 or more polymorphic nucleic acid targets are enriched, sometimes 50 or more polymorphic nucleic acid targets are enriched, sometimes 100 or more polymorphic nucleic acid targets are enriched, and sometimes 500 or more polymorphic nucleic acid targets are enriched. Sometimes, about 40 to about 100 polymorphic nucleic acid targets are enriched.

In some embodiments, the sequencing process comprises a sequencing by synthesis method. In some cases, the sequencing by synthesis method comprises a plurality of synthesis cycles. Sometimes, the sequencing by synthesis method comprises about 36 cycles and sometimes the sequencing by synthesis method comprises about 27 cycles. In some embodiments, the sequencing process comprises a sequencing by ligation method. In some embodiments, the sequencing process comprises a single molecule sequencing method.

In some embodiments, the sequencing process comprises sequencing a plurality of samples in a single compartment. In some cases, the fetal fraction is determined for 10 or more samples. In some cases, the fetal fraction is determined for 100 or more samples. In some cases, the fetal fraction is determined for 1000 or more samples.

In some embodiments, the sample nucleic acid is cell-free DNA. In some embodiments, the sample nucleic acid is obtained from a pregnant female subject. In some cases, the subject is human. In some cases, the sample nucleic acid is from plasma or serum.

Certain embodiments are described further in the following description, examples, claims and drawings.

BRIEF DESCRIPTION OF THE DRAWINGS

The drawings illustrate embodiments of the technology herein and are not limiting. For clarity and ease of illustration, the drawings are not made to scale and, in some instances, various aspects may be shown exaggerated or enlarged to facilitate an understanding of particular embodiments.

FIG. 10 shows one embodiment of the Fetal Quantifier Method. Maternal nucleic acid is selectively digested and the remaining fetal nucleic acid is quantified using a competitor of known concentration. In this schema, the analyte is separated and quantified by a mass spectrometer.

FIG. 11 shows one embodiment of the Methylation-Based Fetal Diagnostic Method. Maternal nucleic acid is selectively digested and the remaining fetal nucleic acid is quantified for three different chromosomes (13, 18 and 21). Parts 2 and 3 of the Figure illustrate the size distribution of the nucleic acid in the sample before and after digestion. The amplification reactions can be size-specific (e.g., greater than 100 base pair amplicons) such that they favor the longer, non-digested fetal nucleic acid over the digested maternal nucleic acid, thereby further enriching the fetal nucleic acid. The spectra at the bottom of the Figure show an increased amount of chromosome 21 fetal nucleic acid indicative of trisomy 21.

In FIG. 14A, the copy number for each sample is shown. Two samples (no 25 and 26) have a significantly higher total copy number than all the other samples. A mean of approximately 1300 amplifiable copies/ml plasma was obtained (range 766-2055). FIG. 14B shows a box-and-whisker plot of the given values, summarizing the results.

FIG. 26 shows an example of a likelihood chart for an informative fetal/maternal genotype combination.

FIG. 28 illustrates a method for calculating fetal fraction by MPSS.

DEFINITIONS

Figure 1:
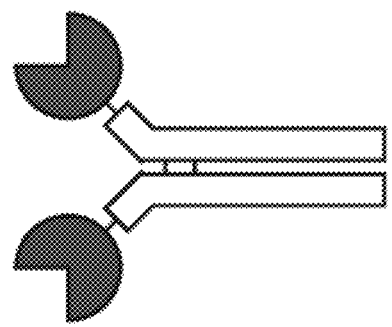
FIG. 1 shows the design of the recombinant MBD-Fc protein used to separate differentially methylated DNA.

The term "pregnancy-associated disorder," as used in this application, refers to any condition or disease that may affect a pregnant woman, the fetus, or both the woman and the fetus. Such a condition or disease may manifest its symptoms during a limited time period, e.g., during pregnancy or delivery, or may last the entire life span of the fetus following its birth. Some examples of a pregnancy-associated disorder include ectopic pregnancy, preeclampsia, pre-term labor, RhD incompatibility, fetal chromosomal abnormalities such as trisomy 21, and genetically inherited fetal disorders such as cystic fibrosis, beta-thalassemia or other monogenic disorders. The compositions and processes described herein are particularly useful for diagnosis, prognosis and monitoring of pregnancy-associated disorders associated with quantitative abnormalities of fetal DNA in maternal plasma/serum, including but not limited to, preeclampsia (Lo et al., Clin. Chem. 45:184-188, 1999 and Zhong et al., Am. J. Obstet. Gynecol. 184:414-419, 2001), fetal trisomy (Lo et al., Clin. Chem. 45:1747-1751, 1999 and Zhong et al., Prenat. Diagn. 20:795-798, 2000) and hyperemesis gravidarum (Sekizawa et al., Clin. Chem. 47:2164-2165, 2001). For example, an elevated level of fetal nucleic acid in maternal blood (as compared to a normal pregnancy or pregnancies) may be indicative of a preeclamptic pregnancy. Further, the ability to enrich fetal nucleic from a maternal sample may prove particularly useful for the noninvasive prenatal diagnosis of autosomal recessive diseases such as the case when a mother and father share an identical disease causing mutation, an occurrence previously perceived as a challenge for maternal plasma-based non-trisomy prenatal diagnosis.

The term "chromosomal abnormality" or "aneuploidy" as used herein refers to a deviation between the structure of the subject chromosome and a normal homologous chromosome. The term "normal" refers to the predominate karyotype or banding pattern found in healthy individuals of a particular species, for example, a euploid genome (in humans, 46XX or 46XY). A chromosomal abnormality can be numerical or structural, and includes but is not limited to aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. Chromosomal abnormality may also refer to a state of chromosomal abnormality where a portion of one or more chromosomes is not an exact multiple of the usual haploid number due to, for example, chromosome translocation. Chromosomal translocation (e.g. translocation between chromosome 21 and 14 where some of the 14th chromosome is replaced by extra 21st chromosome) may cause partial trisomy 21. A chromosomal abnormality can be correlated with presence of a pathological condition or with a predisposition to develop a pathological condition. A chromosomal abnormality may be detected by quantitative analysis of nucleic acid.

The terms "nucleic acid" and "nucleic acid molecule" may be used interchangeably throughout the disclosure. The terms refer to nucleic acids of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. For example, the nucleic acids provided in SEQ ID NOs: 1-261 (see Tables 4A-4C) can be in any form useful for conducting processes herein (e.g., linear, circular, super-coiled, single-stranded, double-stranded and the like) or may include variations (e.g., insertions, deletions or substitutions) that do not alter their utility as part of the present technology. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A template nucleic acid in some embodiments can be from a single chromosome (e.g., a nucleic acid sample may be from one chromosome of a sample obtained from a diploid organism). Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil. A template nucleic acid may be prepared using a nucleic acid obtained from a subject as a template.

A "nucleic acid comprising one or more CpG sites" or a "CpG-containing genomic sequence" as used herein refers to a segment of DNA sequence at a defined location in the genome of an individual such as a human fetus or a pregnant woman. Typically, a "CpG-containing genomic sequence" is at least 15 nucleotides in length and contains at least one cytosine. Preferably, it can be at least 30, 50, 80, 100, 150, 200, 250, or 300 nucleotides in length and contains at least 2, 5, 10, 15, 20, 25, or 30 cytosines. For anyone "CpG-containing genomic sequence" at a given location, e.g., within a region centering around a given genetic locus (see Tables 1A-1C), nucleotide sequence variations may exist from individual to individual and from allele to allele even for the same individual. Typically, such a region centering around a defined genetic locus (e.g., a CpG island) contains the locus as well as upstream and/or downstream sequences. Each of the upstream or downstream sequence (counting from the 5' or 3' boundary of the genetic locus, respectively) can be as long as 10 kb, in other cases may be as long as 5 kb, 2 kb, 1 kb, 500 bp, 200 bp, or 100 bp. Furthermore, a "CpG-containing genomic sequence" may encompass a nucleotide sequence transcribed or not transcribed for protein production, and the nucleotide sequence can be an inter-gene sequence, intra-gene sequence, protein-coding sequence, a non protein-coding sequence (such as a transcription promoter), or a combination thereof.

As used herein, a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring, however, for purposes herein, thymine is not considered a methylated nucleotide when present in DNA since thymine is a typical nucleotide base of DNA. Typical nucleoside bases for DNA are thymine, adenine, cytosine and guanine. Typical bases for RNA are uracil, adenine, cytosine and guanine. Correspondingly a "methylation site" is the location in the target gene nucleic acid region where methylation has, or has the possibility of occurring. For example a location containing CpG is a methylation site where the cytosine may or may not be methylated.

As used herein, a "CpG site" or "methylation site" is a nucleotide within a nucleic acid that is susceptible to methylation either by natural occurring events in vivo or by an event instituted to chemically methylate the nucleotide in vitro.

As used herein, a "methylated nucleic acid molecule" refers to a nucleic acid molecule that contains one or more methylated nucleotides that is/are methylated.

A "CpG island" as used herein describes a segment of DNA sequence that comprises a functionally or structurally deviated CpG density. For example, Yamada et al. (Genome Research 14:247-266, 2004) have described a set of standards for determining a CpG island: it must be at least 400 nucleotides in length, has a greater than 50% GC content, and an OCF/ECF ratio greater than 0.6. Others (Takai et al., Proc. Natl. Acad. Sci. U.S.A. 99:3740-3745, 2002) have defined a CpG island less stringently as a sequence at least 200 nucleotides in length, having a greater than 50% GC content, and an OCF/ECF ratio greater than 0.6.

The term "epigenetic state" or "epigenetic status" as used herein refers to any structural feature at a molecular level of a nucleic acid (e.g., DNA or RNA) other than the primary nucleotide sequence.

For instance, the epigenetic state of a genomic DNA may include its secondary or tertiary structure determined or influenced by, e.g., its methylation pattern or its association with cellular proteins.

The term "methylation profile" "methylation state" or "methylation status," as used herein to describe the state of methylation of a genomic sequence, refers to the characteristics of a DNA segment at a particular genomic locus relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation due to, e.g., difference in the origin of the alleles. The term "methylation" profile" or "methylation status" also refers to the relative or absolute concentration of methylated C or unmethylated C at any particular stretch of residues in a biological sample. For example, if the cytosine (C) residue(s) within a DNA sequence are methylated it may be referred to as "hypermethylated"; whereas if the cytosine (C) residue(s) within a DNA sequence are not methylated it may be referred to as "hypomethylated". Likewise, if the cytosine (C) residue(s) within a DNA sequence (e.g., fetal nucleic acid) are methylated as compared to another sequence from a different region or from a different individual (e.g., relative to maternal nucleic acid), that sequence is considered hypermethylated compared to the other sequence. Alternatively, if the cytosine (C) residue(s) within a DNA sequence are not methylated as compared to another sequence from a different region or from a different individual (e.g., the mother), that sequence is considered hypomethylated compared to the other sequence. These sequences are said to be "differentially methylated", and more specifically, when the methylation status differs between mother and fetus, the sequences are considered "differentially methylated maternal and fetal nucleic acid".

Figure 2:
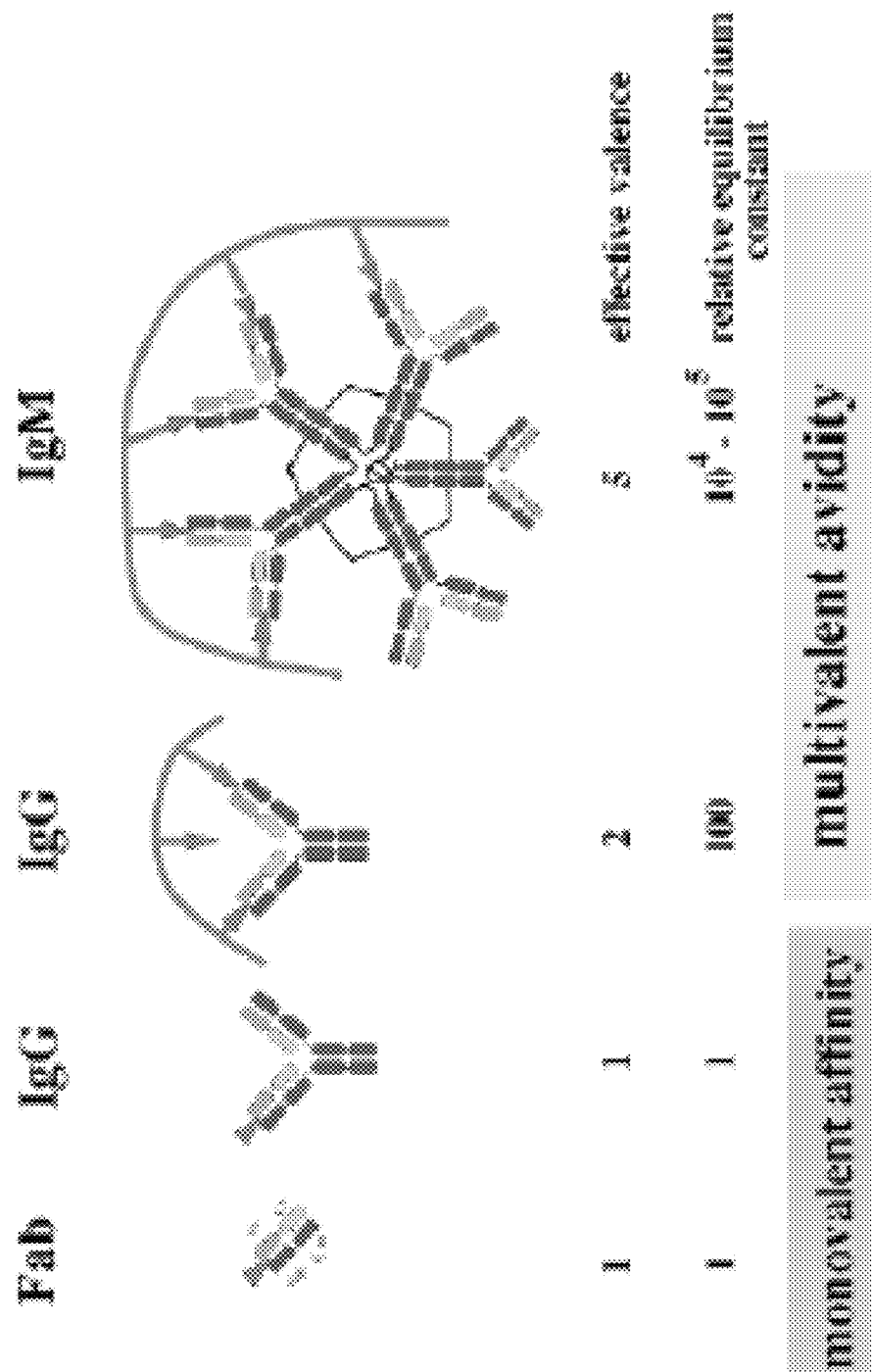
FIG. 2 shows the methyl-CpG-binding, antibody-like protein has a high affinity and high avidity to its "antigen", which is preferably DNA that is methylated at CpG dinucleotides.

The term "agent that binds to methylated nucleotides" as used herein refers to a substance that is capable of binding to methylated nucleic acid. The agent may be naturally-occurring or synthetic, and may be modified or unmodified. In one embodiment, the agent allows for the separation of different nucleic acid species according to their respective methylation states. An example of an agent that binds to methylated nucleotides is described in PCT Patent Application No. PCT/EP2005/012707, which published as WO06056480A2 and is hereby incorporated by reference. The described agent is a bifunctional polypeptide comprising the DNA-binding domain of a protein belonging to the family of Methyl-CpG binding proteins (MBDs) and an Fc portion of an antibody (see FIG. 1). The recombinant methyl-CpG-binding, antibody-like protein can preferably bind CpG methylated DNA in an antibody-like manner. That means, the methyl-CpG-binding, antibody-like protein has a high affinity and high avidity to its "antigen", which is preferably DNA that is methylated at CpG dinucleotides. The agent may also be a multivalent MBD (see FIG. 2).

The term "polymorphism" or "polymorphic nucleic acid target" as used herein refers to a sequence variation within different alleles of the same genomic sequence. A sequence that contains a polymorphism is considered a "polymorphic sequence". Detection of one or more polymorphisms allows differentiation of different alleles of a single genomic sequence or between two or more individuals. As used herein, the term "polymorphic marker" or "polymorphic sequence" refers to segments of genomic DNA that exhibit heritable variation in a DNA sequence between individuals. Such markers include, but are not limited to, single nucleotide polymorphisms (SNPs), restriction fragment length polymorphisms (RFLPs), short tandem repeats, such as di-, tri- or tetra-nucleotide repeats (STRs), deletions, duplications, and the like. Polymorphic markers according to the present technology can be used to specifically differentiate between a maternal and paternal allele in the enriched fetal nucleic acid sample.

The terms "single nucleotide polymorphism" or "SNP" as used herein refer to the polynucleotide sequence variation present at a single nucleotide residue within different alleles of the same genomic sequence. This variation may occur within the coding region or non-coding region (i.e., in the promoter or intronic region) of a genomic sequence, if the genomic sequence is transcribed during protein production. Detection of one or more SNP allows differentiation of different alleles of a single genomic sequence or between two or more individuals.

The term "allele" as used herein is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archeabacteria.

The terms "ratio of the alleles" or "allelic ratio" as used herein refer to the ratio of the population of one allele and the population of the other allele in a sample. In some trisomic cases, it is possible that a fetus may be tri-allelic for a particular locus. In such cases, the term "ratio of the alleles" refers to the ratio of the population of any one allele against one of the other alleles, or any one allele against the other two alleles.

The term "non-polymorphism-based quantitative method" as used herein refers to a method for determining the amount of an analyte (e.g., total nucleic acid, Y-chromosome nucleic acid, or fetal nucleic acid) that does not require the use of a polymorphic marker or sequence. Although a polymorphism may be present in the sequence, said polymorphism is not required to quantify the sequence. Examples of non-polymorphism-based quantitative methods include, but are not limited to, RT-PCR, digital PCR, array-based methods, sequencing methods, nanopore-based methods, nucleic acid-bound bead-based counting methods and competitor-based methods where one or more competitors are introduced at a known concentration(s) to determine the amount of one or more analytes. In some embodiments, some of the above exemplary methods (for example, sequencing) may need to be actively modified or designed such that one or more polymorphisms are not interrogated.

As used herein, a "competitor oligonucleotide" or "competitive oligonucleotide" or "competitor" is a nucleic acid polymer that competes with a target nucleotide sequence for hybridization of amplification primers. Often, a competitor has a similar nucleotide sequence as a corresponding target nucleotide sequence. In some cases, a competitor sequence and a corresponding target nucleotide sequence differ by one or more nucleotides. In some cases, a competitor sequence and a corresponding target nucleotide sequence are the same length. In some cases, the competitor optionally has an additional length of nucleotide sequence that is different from the target nucleotide sequence. In some embodiments, a known amount, or copy number, of competitor is used. In some embodiments, two or more competitors are used. In some cases, the two or more competitors possess similar characteristics (e.g. sequence, length, detectable label). In some cases, the two or more competitors possess different characteristics (e.g. sequence, length, detectable label). In some embodiments, one or more competitors are used for a particular region. In some cases, the competitor possesses a characteristic that is unique for each set of competitors for a given region. Often, competitors for different regions possess different characteristics.

A competitor oligonucleotide may be composed of naturally occurring and/or non-naturally occurring nucleotides (e.g., labeled nucleotides), or a mixture thereof. Competitor oligonucleotides suitable for use with embodiments described herein, may be synthesized and labeled using known techniques. Competitor oligonucleotides may be chemically synthesized according to any suitable method known, for example, the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of competitor oligonucleotides can be effected by any suitable method known, for example, native acrylamide gel electrophoresis or by anion-exchange high-performance liquid chromatography (HPLC), for example, as described in Pearson and Regnier, J. Chrom., 255:137-149, 1983.

The terms "absolute amount" or "copy number" as used herein refers to the amount or quantity of an analyte (e.g., total nucleic acid or fetal nucleic acid). The present technology provides compositions and processes for determining the absolute amount of fetal nucleic acid in a mixed maternal sample. Absolute amount or copy number represents the number of molecules available for detection, and may be expressed as the genomic equivalents per unit. The term "concentration" refers to the amount or proportion of a substance in a mixture or solution (e.g., the amount of fetal nucleic acid in a maternal sample that comprises a mixture of maternal and fetal nucleic acid). The concentration may be expressed as a percentage, which is used to express how large/small one quantity is, relative to another quantity as a fraction of 100. Platforms for determining the quantity or amount of an analyte (e.g., target nucleic acid) include, but are not limited to, mass spectrometery, digital PCR, sequencing by synthesis platforms (e.g., pyrosequencing), fluorescence spectroscopy and flow cytometry.

The term "sample" as used herein refers to a specimen containing nucleic acid. Examples of samples include, but are not limited to, tissue, bodily fluid (for example, blood, serum, plasma, saliva, urine, tears, peritoneal fluid, ascitic fluid, vaginal secretion, breast fluid, breast milk, lymph fluid, cerebrospinal fluid or mucosa secretion), umbilical cord blood, chorionic villi, amniotic fluid, an embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, embryonic tissues, lymph fluid, cerebrospinal fluid, mucosa secretion, or other body exudate, fecal matter, an individual cell or extract of the such sources that contain the nucleic acid of the same, and subcellular structures such as mitochondria, using protocols well established within the art.

Fetal DNA can be obtained from sources including but not limited to maternal blood, maternal serum, maternal plasma, fetal cells, umbilical cord blood, chorionic villi, amniotic fluid, urine, saliva, lung lavage, cells or tissues.

The term "blood" as used herein refers to a blood sample or preparation from a pregnant woman or a woman being tested for possible pregnancy. The term encompasses whole blood or any fractions of blood, such as serum and plasma as conventionally defined.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent or agent that "differentially modifies" methylated or non-methylated DNA encompasses any reagent that modifies methylated and/or unmethylated DNA in a process through which distinguishable products result from methylated and non-methylated DNA, thereby allowing the identification of the DNA methylation status. Such processes may include, but are not limited to, chemical reactions (such as a C→U conversion by bisulfite) and enzymatic treatment (such as cleavage by a methylation-dependent endonuclease). Thus, an enzyme that preferentially cleaves or digests methylated DNA is one capable of cleaving or digesting a DNA molecule at a much higher efficiency when the DNA is methylated, whereas an enzyme that preferentially cleaves or digests unmethylated DNA exhibits a significantly higher efficiency when the DNA is not methylated.

The terms "non-bisulfite-based method" and "non-bisulfite-based quantitative method" as used herein refer to any method for quantifying methylated or non-methylated nucleic acid that does not require the use of bisulfite. The terms also refer to methods for preparing a nucleic acid to be quantified that do not require bisulfite treatment. Examples of non-bisulfite-based methods include, but are not limited to, methods for digesting nucleic acid using one or more methylation sensitive enzymes and methods for separating nucleic acid using agents that bind nucleic acid based on methylation status.

The terms "methyl-sensitive enzymes" and "methylation sensitive restriction enzymes" are DNA restriction endonucleases that are dependent on the methylation state of their DNA recognition site for activity. For example, there are methyl-sensitive enzymes that cleave or digest at their DNA recognition sequence only if it is not methylated. Thus, an unmethylated DNA sample will be cut into smaller fragments than a methylated DNA sample. Similarly, a hyper-methylated DNA sample will not be cleaved. In contrast, there are methyl-sensitive enzymes that cleave at their DNA recognition sequence only if it is methylated. As used herein, the terms "cleave", "cut" and "digest" are used interchangeably.

The term "target nucleic acid" as used herein refers to a nucleic acid examined using the methods disclosed herein to determine if the nucleic acid is part of a pregnancy-related disorder or chromosomal abnormality. For example, a target nucleic acid from chromosome 21 could be examined using the methods of the technology herein to detect Down's Syndrome.

The term "control nucleic acid" as used herein refers to a nucleic acid used as a reference nucleic acid according to the methods disclosed herein to determine if the nucleic acid is part of a chromosomal abnormality. For example, a control nucleic acid from a chromosome other than chromosome 21 (herein referred to as a "reference chromosome") could be as a reference sequence to detect Down's Syndrome. In some embodiments, the control sequence has a known or predetermined quantity.

The term "sequence-specific" or "locus-specific method" as used herein refers to a method that interrogates (for example, quantifies) nucleic acid at a specific location (or locus) in the genome based on the sequence composition. Sequence-specific or locus-specific methods allow for the quantification of specific regions or chromosomes.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), where the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and 0-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Primers" as used herein refer to oligonucleotides that can be used in an amplification method, such as a polymerase chain reaction (PCR), to amplify a nucleotide sequence based on the polynucleotide sequence corresponding to a particular genomic sequence, e.g., one located within the CpG island CGI137, PDE9A, or CGI009 on chromosome 21, in various methylation status. At least one of the PCR primers for amplification of a polynucleotide sequence is sequence-specific for the sequence.

The term "template" refers to any nucleic acid molecule that can be used for amplification in the technology herein. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The term "amplification reaction" as used herein refers to a process for copying nucleic acid one or more times. In embodiments, the method of amplification includes but is not limited to polymerase chain reaction, self-sustained sequence reaction, ligase chain reaction, rapid amplification of cDNA ends, polymerase chain reaction and ligase chain reaction, Q-beta phage amplification, strand displacement amplification, or splice overlap extension polymerase chain reaction. In some embodiments, a single molecule of nucleic acid is amplified, for example, by digital PCR.

The term "sensitivity" as used herein refers to the number of true positives divided by the number of true positives plus the number of false negatives, where sensitivity (sens) may be within the range of $0 \leq sens \leq 1$. Ideally, method embodiments herein have the number of false negatives equaling zero or close to equaling zero, so that no subject is wrongly identified as not having at least one chromosome abnormality or other genetic disorder when they indeed have at least one chromosome abnormality or other genetic disorder. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of 0≤spec≤1. Ideally, methods embodiments herein have the number of false positives equaling zero or close to equaling zero, so that no subject wrongly identified as having at least one chromosome abnormality other genetic disorder when they do not have the chromosome abnormality other genetic disorder being assessed. Hence, a method that has sensitivity and specificity equaling one, or 100%, sometimes is selected.

One or more prediction algorithms may be used to determine significance or give meaning to the detection data collected under variable conditions that may be weighed independently of or dependently on each other. The term "variable" as used herein refers to a factor, quantity, or function of an algorithm that has a value or set of values. For example, a variable may be the design of a set of amplified nucleic acid species, the number of sets of amplified nucleic acid species, percent fetal genetic contribution tested, percent maternal genetic contribution tested, type of chromosome abnormality assayed, type of genetic disorder assayed, type of sex-linked abnormalities assayed, the age of the mother and the like. The term "independent" as used herein refers to not being influenced or not being controlled by another. The term "dependent" as used herein refers to being influenced or controlled by another. For example, a particular chromosome and a trisomy event occurring for that particular chromosome that results in a viable being are variables that are dependent upon each other.

One of skill in the art may use any type of method or prediction algorithm to give significance to the data of the present technology within an acceptable sensitivity and/or specificity. For example, prediction algorithms such as Chi-squared test, z-test, t-test, ANOVA (analysis of variance), regression analysis, neural nets, fuzzy logic, Hidden Markov Models, multiple model state estimation, and the like may be used. One or more methods or prediction algorithms may be determined to give significance to the data having different independent and/or dependent variables of the present technology. And one or more methods or prediction algorithms may be determined not to give significance to the data having different independent and/or dependent variables of the present technology. One may design or change parameters of the different variables of methods described herein based on results of one or more prediction algorithms (e.g., number of sets analyzed, types of nucleotide species in each set). For example, applying the Chi-squared test to detection data may suggest that specific ranges of maternal age are correlated to a higher likelihood of having an offspring with a specific chromosome abnormality, hence the variable of maternal age may be weighed differently verses being weighed the same as other variables.

In certain embodiments, several algorithms may be chosen to be tested. These algorithms can be trained with raw data. For each new raw data sample, the trained algorithms will assign a classification to that sample (i.e. trisomy or normal). Based on the classifications of the new raw data samples, the trained algorithms' performance may be assessed based on sensitivity and specificity. Finally, an algorithm with the highest sensitivity and/or specificity or combination thereof may be identified.

DETAILED DESCRIPTION

The presence of fetal nucleic acid in maternal plasma was first reported in 1997 and offers the possibility for non-invasive prenatal diagnosis simply through the analysis of a maternal blood sample (Lo et al., Lancet 350:485-487, 1997). To date, numerous potential clinical applications have been developed. In particular, quantitative abnormalities of fetal nucleic acid, for example DNA, concentrations in maternal plasma have been found to be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma represents a powerful mechanism for the monitoring of fetomaternal well-being.

However, fetal DNA co-exists with background maternal DNA in maternal plasma. Hence, most reported applications have relied on the detection of Y-chromosome sequences as these are most conveniently distinguishable from maternal DNA. Such an approach limits the applicability of the existing assays to only 50% of all pregnancies, namely those with male fetuses. Thus, there is much need for the development of sex-independent compositions and methods for enriching and analyzing fetal nucleic acid from a maternal sample. Also, methods that rely on polymorphic markers to quantify fetal nucleic acid may be susceptible to varying heterozygosity rates across different ethnicities thereby limiting their applicability (e.g., by increasing the number of markers that are needed).

It was previously demonstrated that fetal and maternal DNA can be distinguished by their differences in methylation status (U.S. Pat. No. 6,927,028, which is hereby incorporated by reference). Methylation is an epigenetic phenomenon, which refers to processes that alter a phenotype without involving changes in the DNA sequence. By exploiting the difference in the DNA methylation status between mother and fetus, one can successfully detect and analyze fetal nucleic acid in a background of maternal nucleic acid.

The present inventors provides novel genomic polynucleotides that are differentially methylated between the fetal DNA from the fetus (e.g., from the placenta) and the maternal DNA from the mother, for example from peripheral blood cells. This discovery thus provides a new approach for distinguishing fetal and maternal genomic DNA and new methods for accurately quantifying fetal nucleic which may be used for non-invasive prenatal diagnosis.

Methodology Practicing the technology herein utilizes routine techniques in the field of molecular biology. Basic texts disclosing the general methods of use in the technology herein include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, Tetrahedron Lett. 22: 1859-1862 (1981), using an automated synthesizer, as described in Van Devanter et. al., Nucleic Acids Res. 12: 6159-6168 (1984). Purification of oligonucleotides is performed using any art-recognized strategy, e.g., native acrylamide gel electrophoresis or anion-exchange high performance liquid chromatography (HPLC) as described in Pearson & Reanier, J. Chrom. 255: 137-149 (1983).

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods and apparatuses described herein often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman).

Nucleic acid may be isolated from any type of suitable biological specimen or sample. Non-limiting examples of specimens include fluid or tissue from a subject, including, without limitation, umbilical cord blood, chorionic villi, amniotic fluid, cerbrospinal fluid, spinal fluid, lavage fluid (e.g., bronchoalveolar, gastric, peritoneal, ductal, ear, athroscopic), biopsy sample (e.g., from pre-implantation embryo), celocentesis sample, fetal nucleated cells or fetal cellular remnants, washings of female reproductive tract, urine, feces, sputum, saliva, nasal mucous, prostate fluid, lavage, semen, lymphatic fluid, bile, tears, sweat, breast milk, breast fluid, embryonic cells and fetal cells (e.g. placental cells). In some embodiments, a biological sample is a cervical swab from a subject. In some embodiments, a biological sample may be blood and sometimes plasma or serum. As used herein, the term "blood" encompasses whole blood or any fractions of blood, such as serum and plasma as conventionally defined, for example. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to further preparation. A fluid or tissue sample from which nucleic acid is extracted may be acellular. In some embodiments, a fluid or tissue sample may contain cellular elements or cellular remnants. In some embodiments fetal cells or cancer cells may be included in the sample.

A sample often is heterogeneous, by which is meant that more than one type of nucleic acid species is present in the sample. For example, heterogeneous nucleic acid can include, but is not limited to, (i) fetally derived and maternally derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation).

Acquisition of Blood Samples and Extraction of DNA

The present technology relates to separating, enriching and analyzing fetal DNA found in maternal blood as a non-invasive means to detect the presence and/or to monitor the progress of a pregnancy-associated condition or disorder. Thus, the first steps of practicing the technology herein are to obtain a blood sample from a pregnant woman and extract DNA from the sample.

Acquisition of Blood Samples

A blood sample is obtained from a pregnant woman at a gestational age suitable for testing using a method of the present technology. The suitable gestational age may vary depending on the disorder tested, as discussed below. Collection of blood from a woman is performed in accordance with the standard protocol hospitals or clinics generally follow. An appropriate amount of peripheral blood, e.g., typically between 5-50 ml, is collected and may be stored according to standard procedure prior to further preparation. Blood samples may be collected, stored or transported in a manner known to the person of ordinary skill in the art to minimize degradation or the quality of nucleic acid present in the sample.

Preparation of Blood Samples

The analysis of fetal DNA found in maternal blood according to the present technology may be performed using, e.g., the whole blood, serum, or plasma. The methods for preparing serum or plasma from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation-following blood clotting. If centrifugation is used then it is typically, though not exclusively, conducted at an appropriate speed, e.g., 1,500-3,000 times g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

Extraction of DNA

There are numerous known methods for extracting DNA from a biological sample including blood. The general methods of DNA preparation (e.g., described by Sambrook and Russell, Molecular Cloning: A Laboratory Manual 3d ed., 2001) can be followed; various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

In some embodiments, the sample may first be enriched or relatively enriched for fetal nucleic acid by one or more methods. For example, the discrimination of fetal and maternal DNA can be performed using the compositions and processes of the present technology alone or in combination with other discriminating factors. Examples of these factors include, but are not limited to, single nucleotide differences between chromosome X and Y, chromosome Y-specific sequences, polymorphisms located elsewhere in the genome, size differences between fetal and maternal DNA and differences in methylation pattern between maternal and fetal tissues.

Other methods for enriching a sample for a particular species of nucleic acid are described in PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878 (assigned to the Applicant), (PCT Patent Application Number PCT/EP05/012707, filed Nov. 28, 2005) which are all hereby incorporated by reference. In certain embodiments, maternal nucleic acid is selectively removed (either partially, substantially, almost completely or completely) from the sample.

Nucleic Acid Isolation and Processing

Nucleic acid may be derived from one or more sources (e.g., cells, soil, etc.) by methods known in the art. Cell lysis procedures and reagents are known in the art and may generally be performed by chemical, physical, or electrolytic lysis methods. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

The terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome (e.g., a nucleic acid sample may be from one chromosome of a sample obtained from a diploid organism). Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid can include extracellular nucleic acid in certain embodiments. The term "extracellular nucleic acid" as used herein refers to nucleic acid isolated from a source having substantially no cells and also is referred to as "cell-free" nucleic acid and/or "cell-free circulating" nucleic acid. Extracellular nucleic acid often includes no detectable cells and may contain cellular elements or cellular remnants. Non-limiting examples of acellular sources for extracellular nucleic acid are blood plasma, blood serum and urine. As used herein, the term "obtain cell-free circulating sample nucleic acid" includes obtaining a sample directly (e.g., collecting a sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less).

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid may be extracted, isolated, purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. An isolated nucleic acid is provided with fewer non-nucleic acid components (e.g., protein, lipid) than the amount of components present in a source sample. A composition comprising isolated nucleic acid can be about 90%, 91%, 92%, 93%, 94%, 95%, 96%, 97%, 98%, 99% or greater than 99% free of non-nucleic acid components. The term "purified" as used herein refers to nucleic acid provided that contains fewer nucleic acid species than in the sample source from which the nucleic acid is derived. A composition comprising nucleic acid may be about 90%, 91%, 92%, 93%, 94%, 95%, 96%, 97%, 98%, 99% or greater than 99% free of other nucleic acid species. The term "amplified" as used herein refers to subjecting nucleic acid of a sample to a process that linearly or exponentially generates amplicon nucleic acids having the same or substantially the same nucleotide sequence as the nucleotide sequence of the nucleic acid in the sample, or portion thereof.

Nucleic acid also may be processed by subjecting nucleic acid to a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by any suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of nucleotide sequence information.

Nucleic acid fragments may contain overlapping nucleotide sequences, and such overlapping sequences can facilitate construction of a nucleotide sequence of the non-fragmented counterpart nucleic acid, or a portion thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

Nucleic acid can be fragmented by various methods known in the art, which include without limitation, physical, chemical and enzymatic processes. Non-limiting examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected to generate non-specifically cleaved fragments or specifically cleaved fragments. Non-limiting examples of processes that can generate non-specifically cleaved fragment nucleic acid include, without limitation, contacting nucleic acid with apparatus that expose nucleic acid to shearing force (e.g., passing nucleic acid through a syringe needle; use of a French press); exposing nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the portion of an amplified product thereof containing the corresponding nucleotide sequence of a nucleic acid template gene molecule. For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from portions of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel).

Nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often cleave specifically according to a particular nucleotide sequence at a particular site.

Examples of enzymatic specific cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I, Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind II, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I; glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Nucleic acid may be treated with a chemical agent, and the modified nucleic acid may be cleaved. In non-limiting examples, nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any form useful for conducting a sequence analysis or manufacture process described herein, such as solid or liquid form, for example. In certain embodiments, nucleic acid may be provided in a liquid form optionally comprising one or more other components, including without limitation one or more buffers or salts.

Nucleic acid may be single or double stranded. Single stranded DNA, for example, can be generated by denaturing double stranded DNA by heating or by treatment with alkali, for example. In some cases, nucleic acid is in a D-loop structure, formed by strand invasion of a duplex DNA molecule by an oligonucleotide or a DNA-like molecule such as peptide nucleic acid (PNA). D loop formation can be facilitated by addition of *E. Coli* RecA protein and/or by alteration of salt concentration, for example, using methods known in the art.

Genomic DNA Target Sequences

In some embodiments of the methods provided herein, one or more nucleic acid species, and sometimes one or more nucleotide sequence species, are targeted for amplification and quantification. In some embodiments, the targeted nucleic acids are genomic DNA sequences.

Certain genomic DNA target sequences are used, for example, because they can allow for the determination of a particular feature for a given assay. Genomic DNA target sequences can be referred to herein as markers for a given assay. In some cases, genomic target sequences are polymorphic, as described herein. In some embodiments, more than one genomic DNA target sequence or marker can allow for the determination of a particular feature for a given assay. Such genomic DNA target sequences are considered to be of a particular "region". As used herein, a "region" is not intended to be limited to a description of a genomic location, such as a particular chromosome, stretch of chromosomal DNA or genetic locus. Rather, the term "region" is used herein to identify a collection of one or more genomic DNA target sequences or markers that can be indicative of a particular assay. Such assays can include, but are not limited to, assays for the detection and quantification of fetal nucleic acid, assays for the detection and quantification of maternal nucleic acid, assays for the detection and quantification of total DNA, assays for the detection and quantification of methylated DNA, assays for the detection and quantification of fetal specific nucleic acid (e.g. chromosome Y DNA), and assays for the detection and quantification of digested and/or undigested DNA, as an indicator of digestion efficiency. In some embodiments, the genomic DNA target sequence is described as being within a particular genomic locus. As used herein, a genomic locus can include any or a combination of open reading frame DNA, non-transcribed DNA, intronic sequences, extronic sequences, promoter sequences, enhancer sequences, flanking sequences, or any sequences considered by one of skill in the art to be associated with a given genomic locus.

Assays for the Determination of Methylated DNA

In some embodiments of the methods provided herein, one or more genomic DNA target sequences are used that can allow for the determination of methylated DNA. Generally, genomic DNA target sequences used for the determination of methylated DNA are differentially methylated in fetal and maternal nucleic acid, and thus, differentially digested according to the methods provided herein for methylation-sensitive restriction enzymes. In some cases, a genomic DNA target sequence is a single copy gene. In some cases, a genomic DNA target sequence is located on chromosome 13, chromosome 18, chromosome 21, chromosome X, or chromosome Y. In some cases, a genomic DNA target sequence is not located on chromosome 13. In some cases, a genomic DNA target sequence is not located on chromosome 18. In some cases, a genomic DNA target sequence is not located on chromosome 21. In some cases, a genomic DNA target sequence is not located on chromosome X. In some cases, a genomic DNA target sequence is not located on chromosome Y. In some cases, a genomic DNA target sequence is typically methylated in one DNA species such as, for example, placental DNA (i.e. at least about 50% or greater methylation). In some cases, the genomic DNA target sequence is minimally methylated in another DNA species such as, for example, maternal DNA (i.e. less than about 1% methylation). In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some cases, the genomic DNA target sequence contains at least two restriction sites within the amplified region. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of methylated DNA is within the TBX3 locus. In some embodiments, the genomic DNA target sequence used for the determination of methylated DNA is within the SOX14 locus. Additional genomic targets that can be used for the determination of methylated DNA in conjunction with the methods provided herein are presented in Example 3.

Assays for the Determination of Total DNA

In some embodiments of the methods provided herein, one or more genomic DNA target sequences are used that can allow for the determination of total DNA. Generally, genomic DNA target sequences used for the determination of total DNA are present in every genome copy (e.g. is present in fetal DNA and maternal DNA, cancer DNA and normal DNA, pathogen DNA and host DNA). In some cases, a genomic DNA target sequence is a single copy gene. In some cases, a genomic DNA target sequence is located on chromosome 13, chromosome 18, chromosome 21, chromosome X, or chromosome Y. In some cases, a genomic DNA target sequence is not located on chromosome 13. In some cases, a genomic DNA target sequence is not located on chromosome 18. In some cases, a genomic DNA target sequence is not located on chromosome 21. In some cases, a genomic DNA target sequence is not located on chromosome X. In some cases, a genomic DNA target sequence is not located on chromosome Y. In some cases, a genomic DNA target sequence does not contain any known single nucleotide polymorphisms (SNPs) within the PCR primer hybridization sequences. In some cases, a genomic DNA target sequence does not contain any known mutations within the PCR primer hybridization sequences. In some cases, a genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of total DNA is within the ALB locus. In some embodiments, the genomic DNA target sequence used for the determination of total DNA is within the APOE or RNAseP locus.

Assays for the Determination of Fetal DNA

In some embodiments of the methods provided herein, one or more genomic DNA target sequences are used that can allow for the determination of fetal DNA. In some embodiments, genomic DNA target sequences used for the determination of fetal DNA are specific to the Y chromosome. In some cases, the genomic DNA target sequence is a single copy gene. In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some cases, the genomic DNA target sequence does not contain the restriction site GCGC within the amplified region. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of fetal DNA is within the UTY locus. In some embodiments, the genomic DNA target sequence used for the determination of fetal DNA is within the SRY1 or SRY2 locus.

Assays for the Determination of Digested and/or Undigested DNA

In some embodiments of the methods provided herein, one or more genomic DNA target sequences are used that can allow for the determination of the amount of digested or undigested nucleic acid, as an indicator of digestion efficiency. Such genomic DNA target sequences are present in every genome in the sample (e.g. maternal and fetal species genomes). Generally, genomic DNA target sequences used for the determination of digested or undigested DNA contain at least one restriction site present in a genomic DNA target sequence used in another assay. Thus, the genomic DNA target sequences used for the determination of digested or undigested DNA serve as controls for assays that include differential digestion. Generally, the genomic DNA target sequence is unmethylated in all nucleic acid species tested (e.g. unmethylated in both maternal and fetal species genomes). In some cases, the genomic DNA target sequence is a single copy gene. In some cases, the genomic DNA target sequence is not located on chromosome 13. In some cases, the genomic DNA target sequence is not located on chromosome 18. In some cases, the genomic DNA target sequence is not located on chromosome 21. In some cases, the genomic DNA target sequence is not located on chromosome X. In some cases, the genomic DNA target sequence is not located on chromosome Y. In some cases, the genomic DNA target sequence does not contain any known single nucleotide polymorphisms (SNPs) within the PCR primer hybridization sequences. In some cases, the genomic DNA target sequence does not contain any known mutations within the PCR primer hybridization sequences. In some cases, the genomic DNA target sequence does not contain any known insertion or deletions within the PCR primer hybridization sequences. In some cases, the melting temperature of the PCR primers that can hybridize to a genomic DNA target sequence is not below 65° C. In some cases, the melting temperature of the PCR primers that can hybridize to a genomic DNA target sequence is not above 75° C. In some embodiments, the genomic DNA target sequence length is about 50 base pairs to about 200 base pairs. In some cases, the genomic DNA target sequence length is 70 base pairs. In some cases, the genomic DNA target sequence does not possess any negative ΔG values for secondary structure of the complete amplicon prediction using mfold (M. Zuker, Mfold web server for nucleic acid folding and hybridization prediction. *Nucleic Acids Res.* 31 (13), 3406-15, (2003)). In some embodiments, the genomic DNA target sequence used for the determination of digested or undigested DNA is within the POPS locus. In some embodiments, the genomic DNA target sequence used for the determination of digested or undigested DNA is within the LDHA locus.

Methylation Specific Separation of Nucleic Acid

The methods provided herein offer an alternative approach for the enrichment of fetal DNA based on the methylation-specific separation of differentially methylated DNA. It has recently been discovered that many genes involved in developmental regulation are controlled through epigenetics in embryonic stem cells. Consequently, multiple genes can be expected to show differential DNA methylation between nucleic acid of fetal origin and maternal origin. Once these regions are identified, a technique to capture methylated DNA can be used to specifically enrich fetal DNA. For identification of differentially methylated regions, a novel approach was used to capture methylated DNA. This approach uses a protein, in which the methyl binding domain of MBD2 is fused to the Fc fragment of an antibody (MBD-FC) (Gebhard C, Schwarzfischer L, Pham T H, Schilling E, Klug M, Andreesen R, Rehli M (2006) Genome wide profiling of CpG methylation identifies novel targets of aberrant hypermethylation in myeloid leukemia. Cancer Res 66:6118-6128). This fusion protein has several advantages over conventional methylation specific antibodies. The MBD-FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC on the other hand binds all DNA molecules regardless of their methylation status. The strength of this protein—DNA interaction is defined by the level of DNA methylation. After binding genomic DNA, eluate solutions of increasing salt concentrations can be used to fractionate non-methylated and methylated DNA allowing for a more controlled separation (Gebhard C, Schwarzfischer L, Pham T H, Andreesen R, Mackensen A, Rehli M (2006) Rapid and sensitive detection of CpG-methylation using methyl-binding (MB)-PCR. Nucleic Acids Res 34:e82). Consequently this method, called Methyl-CpG immunoprecipitation (MCIP), cannot only enrich, but also fractionate genomic DNA according to methylation level, which is particularly helpful when the unmethylated DNA fraction should be investigated as well.

Methylation Sensitive Restriction Enzyme Digestion

The technology herein also provides compositions and processes for determining the amount of fetal nucleic acid from a maternal sample. The technology herein allows for the enrichment of fetal nucleic acid regions in a maternal sample by selectively digesting nucleic acid from said maternal sample with an enzyme that selectively and completely or substantially digests the maternal nucleic acid to enrich the sample for at least one fetal nucleic acid region. Preferably, the digestion efficiency is greater than about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Following enrichment, the amount of fetal nucleic acid can be determined by quantitative methods that do not require polymorphic sequences or bisulfite treatment, thereby, offering a solution that works equally well for female fetuses and across different ethnicities and preserves the low copy number fetal nucleic acid present in the sample.

For example, there are methyl-sensitive enzymes that preferentially or substantially cleave or digest at their DNA recognition sequence if it is non-methylated. Thus, an unmethylated DNA sample will be cut into smaller fragments than a methylated DNA sample. Similarly, a hypermethylated DNA sample will not be cleaved. In contrast, there are methyl-sensitive enzymes that cleave at their DNA recognition sequence only if it is methylated.

Methyl-sensitive enzymes that digest unmethylated DNA suitable for use in methods of the technology herein include, but are not limited to, HpaII, HhaI, MaeII, BstUI and AciI. An enzyme that can be used is HpaII that cuts only the unmethylated sequence CCGG. Another enzyme that can be used is HhaI that cuts only the unmethylated sequence GCGC. Both enzymes are available from New England BioLabs®, Inc. Combinations of two or more methyl-sensitive enzymes that digest only unmethylated DNA can also be used. Suitable enzymes that digest only methylated DNA include, but are not limited to, DpnI, which cuts at a recognition sequence GATC, and McrBC, which belongs to the family of AAA$^+$ proteins and cuts DNA containing modified cytosines and cuts at recognition site 5' . . . Pu$^m$C (N$_{40-3000}$) Pu$^m$C . . . 3' (New England BioLabs, Inc., Beverly, Mass.).

Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al., Molecular Biology: A laboratory Approach, Cold Spring Harbor, N.Y. 1989) provide a general description of methods for using restriction enzymes and other enzymes. Enzymes often are used under conditions that will enable cleavage of the maternal DNA with about 95%-100% efficiency, preferably with about 98%-100% efficiency.

Other Methods for Methylation Analysis

Various methylation analysis procedures are known in the art, and can be used in conjunction with the present technology. These assays allow for determination of the methylation state of one or a plurality of CpG islands within a DNA sequence. In addition, the methods maybe used to quantify methylated nucleic acid. Such assays involve, among other techniques, DNA sequencing of bisulfite-treated DNA, PCR (for sequence-specific amplification), Southern blot analysis, and use of methylation-sensitive restriction enzymes.

Genomic sequencing is a technique that has been simplified for analysis of DNA methylation patterns and 5-methylcytosine distribution by using bisulfite treatment (Frommer et al., Proc. Natl. Acad. Sci. USA 89:1827-1831, 1992). Additionally, restriction enzyme digestion of PCR products amplified from bisulfite-converted DNA may be used, e.g., the method described by Sadri & Hornsby (Nucl. Acids Res. 24:5058-5059, 1996), or COBRA (Combined Bisulfite Restriction Analysis) (Xiong & Laird, Nucleic Acids Res. 25:2532-2534, 1997).

COBRA analysis is a quantitative methylation assay useful for determining DNA methylation levels at specific gene loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the interested CpG islands, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

The MethyLight™ assay is a high-throughput quantitative methylation assay that utilizes fluorescence-based real-time PCR (TaqMan®) technology that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight assay may be used as a quantitative test for methylation patterns in the genomic DNA sample, where sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight process can by used with a "TaqMan" probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10.degree. C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific gene (or methylation-altered DNA sequence or CpG island); TaqMan® probes; optimized PCR buffers and deoxynucleotides; and Taq polymerase.

The Ms-SNuPE technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation status at CpG sites.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

MSP (methylation-specific PCR) allows for assessing the methylation status of virtually any group of CpG sites within a CpG island, independent of the use of methylation-sensitive restriction enzymes (Herman et al. Proc. Nat. Acad. Sci. USA 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

The MCA technique is a method that can be used to screen for altered methylation patterns in genomic DNA, and to isolate specific sequences associated with these changes (Toyota et al., Cancer Res. 59:2307-12, 1999). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Another method for analyzing methylation sites is a primer extension assay, including an optimized PCR amplification reaction that produces amplified targets for subsequent primer extension genotyping analysis using mass spectrometry. The assay can also be done in multiplex. This method (particularly as it relates to genotyping single nucleotide polymorphisms) is described in detail in PCT publication WO05012578A1 and US publication US20050079521A1. For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME) assays) in a single well to further increase the throughput and reduce the cost per reaction for primer extension reactions.

Four additional methods for DNA methylation analysis include restriction landmark genomic scanning (RLGS, Costello et al., 2000), methylation-sensitive-representational difference analysis (MS-RDA), methylation-specific AP-PCR (MS-AP-PCR) and methyl-CpG binding domain column/segregation of partly melted molecules (MBD/SPM).

Additional methylation analysis methods that may be used in conjunction with the present technology are described in the following papers: Laird, P. W. Nature Reviews Cancer 3, 253-266 (2003); Biotechniques; Uhlmann, K. et al. Electrophoresis 23:4072-4079 (2002)—PyroMeth; Colella et al. Biotechniques. 2003 July; 35(1): 146-50; Dupont J M, Tost J, Jammes H, and Gut I G. Anal Biochem, October 2004; 333(1): 119-27; and Tooke N and Pettersson M. IVDT. November 2004; 41.

Nucleic Acid Quantification

In some embodiments, the amount of fetal nucleic acid in a sample is determined. In some cases, the amount of fetal nucleic acid is determined based on a quantification of sequence read counts described herein. Quantification may be achieved by direct counting of sequence reads covering particular methylation sites and/or target sites, or by competitive PCR (i.e., co-amplification of competitor oligonucleotides of known quantity, as described herein). The term "amount" as used herein with respect to nucleic acids refers to any suitable measurement, including, but not limited to, absolute amount (e.g. copy number), relative amount (e.g. fraction or ratio), weight (e.g., grams), and concentration (e.g., grams per unit volume (e.g., milliliter); molar units).

Fraction Determination

In some embodiments, a fraction or ratio can be determined for the amount of one nucleic acid relative to the amount of another nucleic acid. In some embodiments, the fraction of fetal nucleic acid in a sample relative to the total amount of nucleic acid in the sample is determined. To calculate the fraction of fetal nucleic acid in a sample relative to the total amount of the nucleic acid in the sample, the following equation can be applied:

$$\text{The fraction of fetal nucleic acid} = (\text{amount of fetal nucleic acid})/[(\text{amount of total nucleic acid})].$$

Copy number Determination using Competitors

In some embodiments, the absolute amount (e.g. copy number) of fetal nucleic acid is determined. Often, the copy number of fetal nucleic acid is determined based on the amount of a competitor oligonucleotide used. In some embodiments, the copy number of maternal nucleic acid is determined. To calculate the copy number of fetal nucleic acid in a sample, the following equation can be applied:

$$\text{Copy number}(\text{fetal nucleic acid}) = [(\text{amount of the fetal nucleic acid})/(\text{amount of the fetal competitor})] \times C$$

where C is the number of competitor oligonucleotides added into the reaction. In some cases, the amounts of the fetal nucleic acid and fetal competitor are obtained in a readout generated by a sequencing reaction (e.g. sequence read counts).

Additional Methods for Determining Fetal Nucleic Acid Content

The amount of fetal nucleic acid (e.g., concentration, relative amount, absolute amount, copy number, and the like) in nucleic acid is determined in some embodiments. In some cases, the amount of fetal nucleic acid in a sample is referred to as "fetal fraction". In certain embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Polymorphism-Based Fetal Quantifier Assay

Determination of fetal nucleic acid content (e.g., fetal fraction) sometimes is performed using a polymorphism-based fetal quantifier assay (FQA), as described herein. This type of assay allows for the detection and quantification of fetal nucleic acid in a maternal sample based on allelic ratios of polymorphic sequences (e.g., single nucleotide polymorphisms (SNPs)). In some cases, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. In some cases, fetal alleles are identified, for example, by their relative minor contribution to the mixture of fetal and maternal nucleic acids in the sample when compared to the major contribution to the mixture by the maternal nucleic acids. In some cases, fetal alleles are identified by a deviation of allele frequency from an expected allele frequency, as described below. In some cases, the relative abundance of fetal nucleic acid in a maternal sample can be determined as a parameter of the total number of unique sequence reads mapped to a target nucleic acid sequence on a reference genome for each of the two alleles of a polymorphic site. In some cases, the relative abundance of fetal nucleic acid in a maternal sample can be determined as a parameter of the relative number of sequence reads for each allele from an enriched sample.

In some embodiments, determining fetal fraction comprises enriching a sample nucleic acid for one or more polymorphic nucleic acid targets. In some cases, a plurality of polymorphic targets is enriched. A plurality of polymorphic nucleic acid targets is sometimes referred to as a collection or a panel (e.g., target panel, SNP panel, SNP collection). A plurality of polymorphic targets can comprise two or more targets. For example, a plurality of polymorphic targets can comprise 2, 3, 4, 5, 6, 7, 8, 9, 10, 20, 30, 40, 50, 60, 70, 80, 90, 100, 200, 300, 400, 500, 600, 700, 800, 900, 1000, or more targets. In some cases, 10 or more polymorphic nucleic acid targets are enriched. In some cases, 50 or more polymorphic nucleic acid targets are enriched. In some cases, 100 or more polymorphic nucleic acid targets are enriched. In some cases, 500 or more polymorphic nucleic acid targets are enriched. In some cases, about 10 to about 500 polymorphic nucleic acid targets are enriched. In some cases, about 20 to about 400 polymorphic nucleic acid targets are enriched. In some cases, about 30 to about 200 polymorphic nucleic acid targets are enriched. In some cases, about 40 to about 100 polymorphic nucleic acid targets are enriched. In some cases, about 60 to about 90 polymorphic nucleic acid targets are enriched. For example, in certain embodiments, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 polymorphic nucleic acid targets are enriched.

In some embodiments, at least one polymorphic nucleic acid target of the plurality of polymorphic nucleic acid targets is informative for determining fetal fraction in a given sample. A polymorphic nucleic acid target that is informative for determining fetal fraction, sometimes referred to as an informative target, informative polymorphism, or informative SNP, typically differs in some aspect between the fetus and the mother. For example, an informative target may have one allele for the fetus and a different allele for the mother (e.g., the mother has allele A at the polymorphic target and the fetus has allele B at the polymorphic target site). Typically, a fetal allele that differs from either of the maternal alleles is paternally inherited (i.e., is from the father). Thus, paternally inherited alleles that differ from maternal alleles can be useful for identifying and/or quantifying fetal nucleic acid (e.g., determining fetal fraction).

In some cases, polymorphic nucleic acid targets are informative in the context of certain maternal/fetal genotype combinations. For a biallelic polymorphic target (i.e., two possible alleles (e.g., A and B)), possible maternal/fetal genotype combinations include: 1) maternal AA, fetal AA; 2) maternal AA, fetal AB; 3) maternal AB, fetal AA; 4) maternal AB, fetal AB; 5) maternal AB; fetal BB; 6) maternal BB, fetal AB; and 7) maternal BB, fetal BB. Genotypes AA and BB are considered homozygous genotypes and genotype AB is considered a heterozygous genotype. In some cases, informative genotype combinations (i.e., genotype combinations for a polymorphic nucleic acid target that may be informative for determining fetal fraction) include combinations where the mother is homozygous and the fetus is heterozygous (e.g., maternal AA, fetal AB; or maternal BB, fetal AB). Such genotype combinations may be referred to as Type 1 informative genotypes or informative heterozygotes. In some cases, informative genotype combinations (i.e., genotype combinations for a polymorphic nucleic acid target that may be informative for determining fetal fraction) include combinations where the mother is heterozygous and the fetus is homozygous (e.g., maternal AB, fetal AA; or maternal AB, fetal BB). Such genotype combinations may be referred to as Type 2 informative genotypes or informative homozygotes. In some cases, non-informative genotype combinations (i.e., genotype combinations for a polymorphic nucleic acid target that may not be informative for determining fetal fraction) include combinations where the mother is heterozygous and the fetus is heterozygous (e.g., maternal AB, fetal AB). Such genotype combinations may be referred to as non-informative genotypes or non-informative heterozygotes. In some cases, non-informative genotype combinations (i.e., genotype combinations for a polymorphic nucleic acid target that may not be informative for determining fetal fraction) include combinations where the mother is homozygous and the fetus is homozygous (e.g., maternal AA, fetal AA; or maternal BB, fetal BB). Such genotype combinations may be referred to as non-informative genotypes or non-informative homozygotes.

Figure 37:
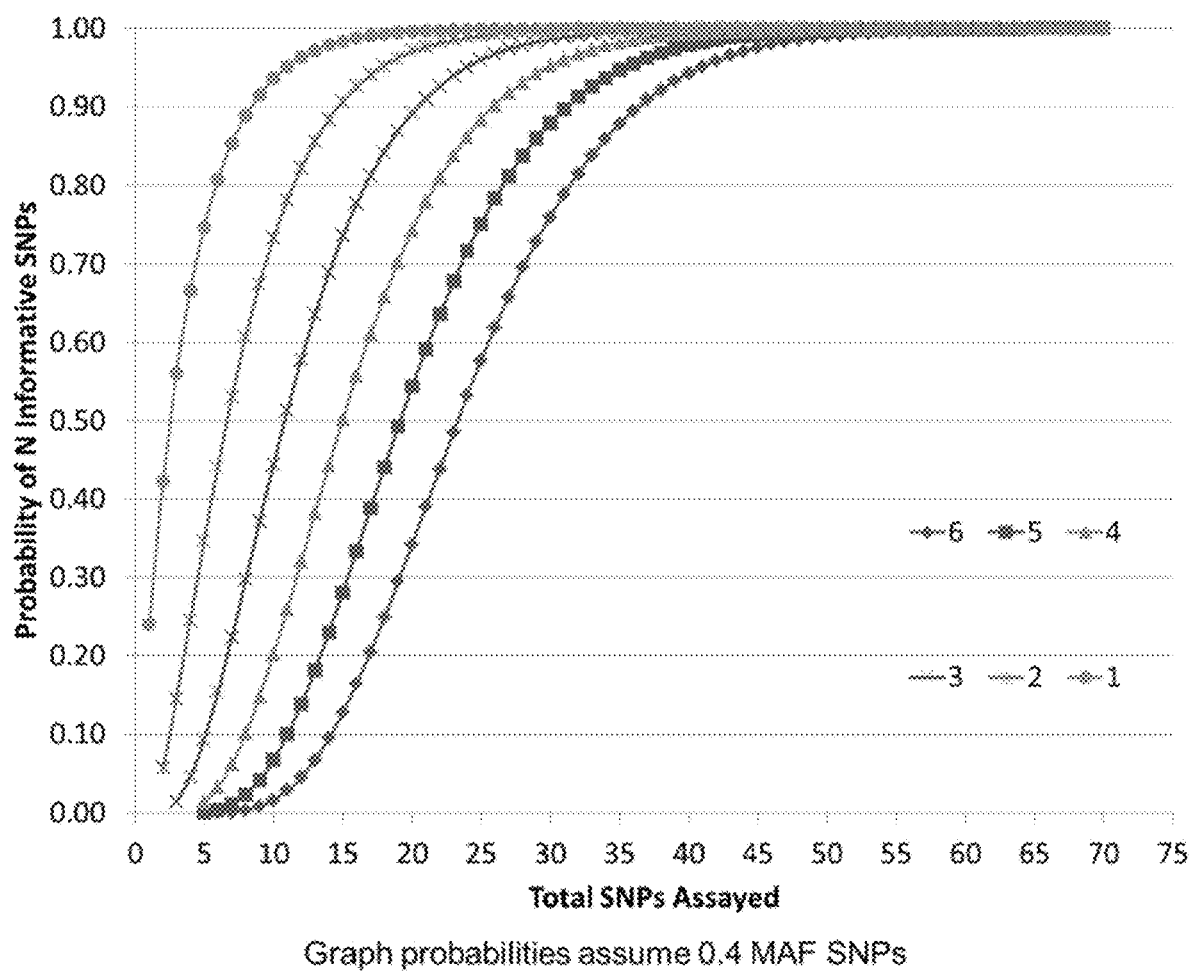
FIG. 37 shows probabilities of the number of informative SNPs for each of the selected thresholds (1-6 informative SNPs) at increasing numbers of total SNPs assayed.

In some embodiments, individual polymorphic nucleic acid targets and/or panels of polymorphic nucleic acid targets are selected based on certain criteria, such as, for example, minor allele population frequency, variance, coefficient of variance, MAD value, and the like. In some cases, polymorphic nucleic acid targets are selected so that at least one polymorphic nucleic acid target within a panel of polymorphic targets has a high probability of being informative for a majority of samples tested. Additionally, in some cases, the number of polymorphic nucleic acid targets (i.e., number of targets in a panel) is selected so that at least one polymorphic nucleic acid target has a high probability of being informative for a majority of samples tested. For example, selection of a larger number of polymorphic targets generally increases the probability that least one polymorphic nucleic acid target will be informative for a majority of samples tested (see, FIG. 37, for example). In some cases, the polymorphic nucleic acid targets and number thereof (e.g., number of polymorphic targets selected for enrichment) result in at least about 2 to about 50 or more polymorphic nucleic acid targets being informative for determining the fetal fraction for at least about 80% to about 100% of samples. For example, the polymorphic nucleic acid targets and number thereof result in at least about 5, 10, 15, 20, 25, 30, 35, 40, 45, 50 or more polymorphic nucleic acid targets being informative for determining the fetal fraction for at least about 81%, 82%, 83%, 84%, 85%, 86%, 87%, 88%, 89%, 90%, 91%, 92%, 93%, 94%, 95%, 96%, 97%, 98%, or 99% of samples. In some cases, the polymorphic nucleic acid targets and number thereof result in at least five polymorphic nucleic acid targets being informative for determining the fetal fraction for at least 90% of samples. In some cases, the polymorphic nucleic acid targets and number thereof result in at least five polymorphic nucleic acid targets being informative for determining the fetal fraction for at least 95% of samples. In some cases, the polymorphic nucleic acid targets and number thereof result in at least five polymorphic nucleic acid targets being informative for determining the fetal fraction for at least 99% of samples. In some cases, the polymorphic nucleic acid targets and number thereof result in at least ten polymorphic nucleic acid targets being informative for determining the fetal fraction for at least 90% of samples. In some cases, the polymorphic nucleic acid targets and number thereof result in at least ten polymorphic nucleic acid targets being informative for determining the fetal fraction for at least 95% of samples. In some cases, the polymorphic nucleic acid targets and number thereof result in at least ten polymorphic nucleic acid targets being informative for determining the fetal fraction for at least 99% of samples.

In some embodiments, individual polymorphic nucleic acid targets are selected based, in part, on minor allele population frequency. In some cases, polymorphic nucleic acid targets having minor allele population frequencies of about 10% to about 50% are selected. For example, polymorphic nucleic acid targets having minor allele population frequencies of about 15%, 20%, 25%, 30%, 35%, 36%, 37%, 38%, 39%, 40%, 41%, 42%, 43%, 44%, 45%, 46%, 47%, 48%, or 49% are selected. In some embodiments, polymorphic nucleic acid targets having a minor allele population frequency of about 40% or more are selected.

In some embodiments, individual polymorphic nucleic acid targets and/or panels of polymorphic nucleic acid targets are selected based, in part, on degree of variance for an individual polymorphic target or a panel of polymorphic targets. Variance, in come cases, can be specific for certain polymorphic targets or panels of polymorphic targets and can be from systematic, experimental, procedural, and or inherent errors or biases (e.g., sampling errors, sequencing errors, PCR bias, and the like). Variance of an individual polymorphic target or a panel of polymorphic targets can be determined by any method known in the art for assessing variance and may be expressed, for example, in terms of a calculated variance, an error, standard deviation, p-value, mean absolute deviation, median absolute deviation, median adjusted deviation (MAD score), coefficient of variance (CV), and the like. In some embodiments, measured allele frequency variance (i.e., background allele frequency) for certain SNPs (when homozygous, for example) can be from about 0.001 to about 0.01 (i.e., 0.1% to about 1.0%). For example, measured allele frequency variance can be about 0.002, 0.003, 0.004, 0.005, 0.006, 0.007, 0.008, or 0.009. In some cases, measured allele frequency variance is about 0.007.

In some cases, noisy polymorphic targets are excluded from a panel of polymorphic nucleic acid targets selected for determining fetal fraction. The term "noisy polymorphic targets" or "noisy SNPs" refers to (a) targets or SNPs that have significant variance between data points (e.g., measured fetal fraction, measured allele frequency) when analyzed or plotted, (b) targets or SNPs that have significant standard deviation (e.g., greater than 1, 2, or 3 standard deviations), (c) targets or SNPs that have a significant standard error of the mean, the like, and combinations of the foregoing. Noise for certain polymorphic targets or SNPs sometimes occurs due to the quantity and/or quality of starting material (e.g., nucleic acid sample), sometimes occurs as part of processes for preparing or replicating DNA used to generate sequence reads, and sometimes occurs as part of a sequencing process. In certain embodiments, noise for some polymorphic targets or SNPs results from certain sequences being over represented when prepared using PCR-based methods. In some cases, noise for some polymorphic targets or SNPs results from one or more inherent characteristics of the site such as, for example, certain nucleotide sequences and/or base compositions surrounding, or being adjacent to, a polymorphic target or SNP. A SNP having a measured allele frequency variance (when homozygous, for example) of about 0.005 or more may be considered noisy. For example, a SNP having a measured allele frequency variance of about 0.006, 0.007, 0.008, 0.009, 0.01 or more may be considered noisy.

In some embodiments, variance of an individual polymorphic target or a panel of polymorphic targets can be represented using coefficient of variance (CV). Coefficient of variance (i.e., standard deviation divided by the mean) can be determined, for example, by determining fetal fraction for several aliquots of a single maternal sample comprising maternal and fetal nucleic acid, and calculating the mean fetal fraction and standard deviation. In some cases, individual polymorphic nucleic acid targets and/or panels of polymorphic nucleic acid targets are selected so that fetal fraction is determined with a coefficient of variance (CV) of 0.30 or less. For example, fetal fraction may determined with a coefficient of variance (CV) of 0.25, 0.20, 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, 0.01 or less, in some embodiments. In some cases, fetal fraction is determined with a coefficient of variance (CV) of 0.20 or less. In some cases, fetal fraction is determined with a coefficient of variance (CV) of 0.10 or less. In some cases, fetal fraction is determined with a coefficient of variance (CV) of 0.05 or less.

In some embodiments, an allele frequency is determined for each of the polymorphic nucleic acid targets in a sample. This sometimes is referred to as measured allele frequency. Allele frequency can be determined, for example, by counting the number of sequence reads for an allele (e.g., allele B) and dividing by the total number of sequence reads for that locus (e.g., allele B+allele A). In some cases, an allele frequency average, mean or median is determined. Fetal fraction can be determined based on the allele frequency mean (e.g., allele frequency mean multiplied by two), in some cases.

In some embodiments, determining whether a polymorphic nucleic acid target is informative comprises comparing its measured allele frequency to a fixed cutoff frequency. In some cases, determining which polymorphic nucleic acid targets are informative comprises identifying informative genotypes by comparing each allele frequency to one or more fixed cutoff frequencies. Fixed cutoff frequencies may be predetermined threshold values based on one or more qualifying data sets, for example. In some cases, the fixed cutoff for identifying informative genotypes from non-informative genotypes is expressed as a percent (%) shift in allele frequency from an expected allele frequency. Generally, expected allele frequencies for a given allele (e.g., allele A) are 0 (for a BB genotype), 0.5 (for an AB genotype) and 1.0 (for an AA genotype), or equivalent values on any numerical scale. A deviation from an expected allele frequency that is beyond one or more fixed cutoff frequencies may be considered informative. The degree of deviation generally is proportional to fetal fraction (i.e., large deviations from expected allele frequency may be observed in samples having high fetal fraction).

In some cases, the fixed cutoff for identifying informative genotypes from non-informative homozygotes is about a 0.5% or greater shift in allele frequency. For example, a fixed cutoff may be about a 0.6%, 0.7%, 0.8%, 0.9%, 1%, 1.5%, 2%, 3%, 4%, 5%, 10% or greater shift in allele frequency. In some cases, the fixed cutoff for identifying informative genotypes from non-informative homozygotes is about a 1% or greater shift in allele frequency. In some cases, the fixed cutoff for identifying informative genotypes from non-informative homozygotes is about a 2% or greater shift in allele frequency. In some embodiments, the fixed cutoff for identifying informative genotypes from non-informative heterozygotes is about a 10% or greater shift in allele frequency. For example, a fixed cutoff may be about a 10%, 15%, 20%, 21%, 22%, 23%, 24%, 25%, 26%, 27%, 28%, 29%, 30%, 35%, 40%, 45%, 50%, 55%, 60%, 70%, 80% or greater shift in allele frequency. In some cases, the fixed cutoff for identifying informative genotypes from non-informative heterozygotes is about a 25% or greater shift in allele frequency. In some cases, the fixed cutoff for identifying informative genotypes from non-informative heterozygotes is about a 50% or greater shift in allele frequency.

In some embodiments, determining whether a polymorphic nucleic acid target is informative comprises comparing its measured allele frequency to a target-specific cutoff value. In some embodiments, target-specific cutoff frequencies are determined for each polymorphic nucleic acid target. Typically, target-specific cutoff frequency is determined based on the allele frequency variance for the corresponding polymorphic nucleic acid target. In some embodiments, variance of individual polymorphic targets can be represented by a median absolute deviation (MAD), for example. In some cases, determining a MAD value for each polymorphic nucleic acid target can generate unique (i.e., target-specific) cutoff values. To determine median absolute deviation, measured allele frequency can be determined, for example, for multiple replicates (e.g., 5, 6, 7, 8, 9, 10, 15, 20 or more replicates) of a maternal only nucleic acid sample (e.g., buffy coat sample).

Each polymorphic target in each replicate will typically have a slightly different measured allele frequency due to PCR and/or sequencing errors, for example. A median allele frequency value can be identified for each polymorphic target. A deviation from the median for the remaining replicates can be calculated (i.e., the difference between the observed allele frequency and the median allele frequency). The absolute value of the deviations (i.e., negative values become positive) is taken and the median value of the absolute deviations is calculated to provide a median absolute deviation (MAD) for each polymorphic nucleic acid target. A target-specific cutoff can be assigned, for example, as a multiple of the MAD (e.g., 1×MAD, 2×MAD, 3×MAD, 4×MAD or 5×MAD). Typically, polymorphic targets having less variance have a lower MAD and therefore a lower cutoff value than more variable targets.

In some embodiments, enriching comprises amplifying the plurality of polymorphic nucleic acid targets. In some cases, the enriching comprises generating amplification products in an amplification reaction. Amplification of polymorphic targets may be achieved by any method described herein or known in the art for amplifying nucleic acid (e.g., PCR). In some cases, the amplification reaction is performed in a single vessel (e.g., tube, container, well on a plate) which sometimes is referred to herein as multiplexed amplification.

In some embodiments, certain parental genotypes are known prior to the enriching of polymorphic nucleic acid targets. In some cases, the maternal genotype for one or more polymorphic targets is known prior to enriching. In some cases, the paternal genotype for one or more polymorphic targets is known prior to enriching. In some cases, the maternal genotype and the paternal genotype for one or more polymorphic targets are known prior to enriching. In some embodiments, certain parental genotypes are not known prior to the enriching of polymorphic nucleic acid targets. In some cases, the maternal genotype for one or more polymorphic targets is not known prior to enriching. In some cases, the paternal genotype for one or more polymorphic targets is not known prior to enriching. In some cases, the maternal genotype and the paternal genotype for one or more polymorphic targets are not known prior to enriching. In some embodiments, parental genotypes are not known for any of the polymorphic nucleic acid targets prior to enriching. In some cases, the maternal genotype for each of the polymorphic targets is not known prior to enriching. In some cases, the paternal genotype for each of the polymorphic targets is not known prior to enriching. In some cases, the maternal genotype and the paternal genotype for each of the polymorphic targets are not known prior to enriching.

In some embodiments, the polymorphic nucleic acid targets each comprise at least one single nucleotide polymorphism (SNP). In some embodiments, the SNPs are selected from: rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, rs985462, rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

In some embodiments, the SNPs are selected from: rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, and rs985462.

In some embodiments, SNPs are selected from: rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

The polymorphic targets can comprise one or more of any of the single nucleotide polymorphisms (SNPs) listed above and any combination thereof.

SNPs may be selected from any SNP provided herein or known in the art that meets any one or all of the criteria described herein for SNP selection. In some cases, SNPs can be located on any chromosome (e.g., chromosome 1, 2, 3, 4, 5, 6, 7, 8, 9, 10, 11, 12, 13, 14, 15, 16, 17, 18, 19, 20, 21, 22, X and/or Y). In some cases, SNPs can be located on autosomes (e.g., chromosome 1, 2, 3, 4, 5, 6, 7, 8, 9, 10, 11, 12, 13, 14, 15, 16, 17, 18, 19, 20, 21, 22), and not on chromosome X or chromosome Y. In some cases, SNPs can be located on certain autosomes (e.g., chromosome 1, 2, 3, 4, 5, 6, 7, 8, 9, 10, 11, 12, 14, 15, 16, 17, 19, 20, 22 and not chromosome 13, 18 or 22). In some cases, SNPs can be located on certain chromosomes suspected of having a genetic variation (e.g., aneuploidy), such as, for example, chromosome 13, 18, 21, X and/or Y (i.e., test chromosome(s)). In some cases, SNPs are located on a reference chromosome. In some cases, fetal fraction and the presence or absence of a genetic variation (e.g., aneuploidy) are determined simultaneously using a method provided herein.

In some embodiments, enriched (e.g., amplified) polymorphic nucleic acid targets are sequenced by a sequencing process. In some cases, the sequencing process is a sequencing by synthesis method, as described herein. Typically, sequencing by synthesis methods comprise a plurality of synthesis cycles, whereby a complementary nucleotide is added to a single stranded template and identified during each cycle. The number of cycles generally corresponds to read length. In some cases, polymorphic targets are selected such that a minimal read length (i.e., minimal number of cycles) is required to include amplification primer sequence and the polymorphic target site (e.g., SNP) in the read. In some cases, amplification primer sequence includes about 10 to about 30 nucleotides. For example, amplification primer sequence may include about 11, 12, 13, 14, 15, 16, 17, 18, 19, 20, 21, 22, 23, 24, 25, 26, 27, 28, or 29 nucleotides, in some embodiments. In some cases, amplification primer sequence includes about 20 nucleotides. In some embodiments, a SNP site is located within 1 nucleotide base position (i.e., adjacent to) to about 30 base positions from the 3' terminus of an amplification primer. For example, a SNP site may be within 2, 3, 4, 5, 6, 7, 8, 9, 10, 11, 12, 13, 14, 15, 16, 17, 18, 19, 20, 21, 22, 23, 24, 25, 26, 27, 28, or 29 nucleotides of an amplification primer terminus. Read lengths can be any length that is inclusive of an amplification primer sequence and a polymorphic sequence or position. In some embodiments, read lengths can be about 10 nucleotides in length to about 50 nucleotides in length. For example, read lengths can be about 15, 20, 21, 22, 23, 24, 25, 26, 27, 28, 29, 30, 31, 32, 33, 34, 35, 36, 37, 38, 39, 40, or 45 nucleotides in length. In some cases, read length is about 36 nucleotides. In some cases, read length is about 27 nucleotides. Thus, in some cases, the sequencing by synthesis method comprises about 36 cycles and sometimes comprises about 27 cycles.

In some embodiments, a plurality of samples is sequenced in a single compartment (e.g., flow cell), which sometimes is referred to herein as sample multiplexing. Thus, in some embodiments, fetal fraction is determined for a plurality of samples in a multiplexed assay. For example, fetal fraction may be determined for about 10, 20, 30, 40, 50, 60, 70, 80, 90, 100, 200, 300, 400, 500, 600, 700, 800, 900, 1000, 2000 or more samples. In some cases, fetal fraction is determined for about 10 or more samples. In some cases, fetal fraction is determined for about 100 or more samples. In some cases, fetal fraction is determined for about 1000 or more samples.

Methylation-Based Fetal Quantifier Assay

Determination of fetal nucleic acid content (e.g., fetal fraction) sometimes is performed using a methylation-based fetal quantifier assay (FQA) as described herein and, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. In some cases, the amount of fetal nucleic acid from a maternal sample can be determined relative to the total amount of nucleic acid present, thereby providing the percentage of fetal nucleic acid in the sample. In some cases, the copy number of fetal nucleic acid can be determined in a maternal sample. In some cases, the amount of fetal nucleic acid can be determined in a sequence-specific (or locus-specific) manner and sometimes with sufficient sensitivity to allow for accurate chromosomal dosage analysis (for example, to detect the presence or absence of a fetal aneuploidy).

A fetal quantifier assay (FQA) can be performed in conjunction with any of the methods described herein. Such an assay can be performed by any method known in the art and/or described herein and in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching the fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In some cases, the restriction efficiency can be determined and the efficiency rate is used to further determine the amount of fetal DNA.

In some cases, a fetal quantifier assay (FQA) can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. In some cases, the absolute copy number of fetal nucleic acid in a maternal sample can be determined, for example, using mass spectrometry and/or a system that uses a competitive PCR approach for absolute copy number measurements. See for example, Ding and Cantor (2003) Proc Natl Acad Sci USA 100:3059-3064, and U.S. Patent Application Publication No. 2004/0081993, both of which are hereby incorporated by reference.

Determining Fetal Nucleic Acid Content in Conjunction with Other Methods

The amount of fetal nucleic acid in extracellular nucleic acid (e.g., fetal fraction) can be quantified and used in conjunction with other methods for assessing a genetic variation (e.g., fetal aneuploidy, fetal gender). Thus, in certain embodiments, methods for determining the presence or absence of a genetic variation, for example, comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call).

The determination of fetal nucleic acid content (e.g., fetal fraction) can be performed before, during, at any one point in a method for assessing a genetic variation (e.g., aneuploidy detection, fetal gender determination), or after such methods. For example, to achieve a fetal gender or aneuploidy determination method with a given sensitivity or specificity, a fetal nucleic acid quantification method may be implemented prior to, during or after fetal gender or aneuploidy determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for fetal gender or aneuploidy determination, or the presence or absence of aneuploidy or genetic variation, for example. In certain embodiments, determinations of, for example, fetal gender or the presence or absence of aneuploidy are selected (e.g., selected and communicated to a patient) only for samples having a certain threshold amount of fetal nucleic acid (e.g., about 15% or more fetal nucleic acid; about 4% or more fetal nucleic acid).

Additional Methods for Enriching for a Subpopulation of Nucleic Acid

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with the methods provided herein. Thus, in certain embodiments, methods of the technology herein comprise an additional step of enriching for a subpopulation of nucleic acid in a sample, such as, for example, fetal nucleic acid. In some cases, a method for determining fetal fraction described above also can be used to enrich for fetal nucleic acid. In certain embodiments, maternal nucleic acid is selectively removed (partially, substantially, almost completely or completely) from the sample. In some cases, enriching for a particular low copy number species nucleic acid (e.g., fetal nucleic acid) may improve quantitative sensitivity. Methods for enriching a sample for a particular species of nucleic acid are described herein and, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, all of which are incorporated by reference herein.

In some embodiments, nucleic acid is enriched for certain target fragment species and/or reference fragment species. In some cases, nucleic acid is enriched for a specific nucleic acid fragment length or range of fragment lengths using one or more length-based separation methods described below. In some cases, nucleic acid is enriched for fragments from a select genomic region (e.g., chromosome) using one or more sequence-based separation methods described herein and/or known in the art. Certain methods for enriching for a nucleic acid subpopulation (e.g., fetal nucleic acid) in a sample are described in detail below.

Some methods for enriching for a nucleic acid subpopulation (e.g., fetal nucleic acid) that can be used with the methods described herein include methods that exploit epigenetic differences between maternal and fetal nucleic acid. For example, fetal nucleic acid can be differentiated and separated from maternal nucleic acid based on methylation differences. Methylation-based fetal nucleic acid enrichment methods are described herein and, for example, in U.S. Patent Application Publication No. 2010/0105049, which is incorporated by reference herein. Such methods sometimes involve binding a sample nucleic acid to a methylation-specific binding agent (methyl-CpG binding protein (MBD), methylation specific antibodies, and the like) and separating bound nucleic acid from unbound nucleic acid based on differential methylation status. Such methods also can include the use of methylation-sensitive restriction enzymes (as described above; e.g., HhaI and HpaII), which allow for the enrichment of fetal nucleic acid regions in a maternal sample by selectively digesting nucleic acid from the maternal sample with an enzyme that selectively and completely or substantially digests the maternal nucleic acid to enrich the sample for at least one fetal nucleic acid region.

Another method for enriching for a nucleic acid subpopulation (e.g., fetal nucleic acid) that can be used with the methods described herein is a restriction endonuclease enhanced polymorphic sequence approach, such as a method described in U.S. Patent Application Publication No. 2009/0317818, which is incorporated by reference herein. Such methods include cleavage of nucleic acid comprising a non-target allele with a restriction endonuclease that recognizes the nucleic acid comprising the non-target allele but not the target allele; and amplification of uncleaved nucleic acid but not cleaved nucleic acid, where the uncleaved, amplified nucleic acid represents enriched target nucleic acid (e.g., fetal nucleic acid) relative to non-target nucleic acid (e.g., maternal nucleic acid). In some cases, nucleic acid may be selected such that it comprises an allele having a polymorphic site that is susceptible to selective digestion by a cleavage agent, for example.

Some methods for enriching for a nucleic acid subpopulation (e.g., fetal nucleic acid) that can be used with the methods described herein include selective enzymatic degradation approaches. Such methods involve protecting target sequences from exonuclease digestion thereby facilitating the elimination in a sample of undesired sequences (e.g., maternal DNA). For example, in one approach, sample nucleic acid is denatured to generate single stranded nucleic acid, single stranded nucleic acid is contacted with at least one target-specific primer pair under suitable annealing conditions, annealed primers are extended by nucleotide polymerization generating double stranded target sequences, and digesting single stranded nucleic acid using a nuclease that digests single stranded (i.e. non-target) nucleic acid. In some cases, the method can be repeated for at least one additional cycle. In some cases, the same target-specific primer pair is used to prime each of the first and second cycles of extension, and in some cases, different target-specific primer pairs are used for the first and second cycles.

Some methods for enriching for a nucleic acid subpopulation (e.g., fetal nucleic acid) that can be used with the methods described herein include massively parallel signature sequencing (MPSS) approaches. MPSS typically is a solid phase method that uses adapter (i.e. tag) ligation, followed by adapter decoding, and reading of the nucleic acid sequence in small increments. Tagged PCR products are typically amplified such that each nucleic acid generates a PCR product with a unique tag. Tags are often used to attach the PCR products to microbeads. After several rounds of ligation-based sequence determination, for example, a sequence signature can be identified from each bead. Each signature sequence (MPSS tag) in a MPSS dataset is analyzed, compared with all other signatures, and all identical signatures are counted.

In some cases, certain MPSS-based enrichment methods can include amplification (e.g., PCR)-based approaches. In some cases, loci-specific amplification methods can be used (e.g., using loci-specific amplification primers). In some cases, a multiplex SNP allele PCR approach can be used. In some cases, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In some cases, a multiplex SNP allele PCR approach can be used in combination with a three-primer system and indexed sequencing. For example, such an approach can involve the use of multiplex PCR (e.g., MASSARRAY system) with primers having a first capture probe incorporated into certain loci-specific forward PCR primers and adapter sequences incorporated into loci-specific reverse PCR primers, to thereby generate amplicons, followed by a secondary PCR to incorporate reverse capture sequences and molecular index barcodes for sequencing using, for example, the Illumina MPSS system. In some cases, a multiplex SNP allele PCR approach can be used in combination with a four-primer system and indexed sequencing. For example, such an approach can involve the use of multiplex PCR (e.g., MASSARRAY system) with primers having adaptor sequences incorporated into both loci-specific forward and loci-specific reverse PCR primers, followed by a secondary PCR to incorporate both forward and reverse capture sequences and molecular index barcodes for sequencing using, for example, the Illumina MPSS system. In some cases, a microfluidics approach can be used. In some cases, an array-based microfluidics approach can be used. For example, such an approach can involve the use of a microfluidics array (e.g., Fluidigm) for amplification at low plex and incorporation of index and capture probes, followed by sequencing. In some cases, an emulsion microfluidics approach can be used, such as, for example, digital droplet PCR.

In some cases, universal amplification methods can be used (e.g., using universal or non-loci-specific amplification primers). In some cases, universal amplification methods can be used in combination with pull-down approaches. In some cases, the method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In some cases, pull-down approaches can be used in combination with ligation-based methods. In some cases, the method can include biotinylated ultramer pull down with sequence specific adapter ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In some cases, pull-down approaches can be used in combination with extension and ligation-based methods. In some cases, the method can include molecular inversion probe (MIP) extension and ligation. For example, such an approach can involve the use of molecular inversion probes in combination with sequence adapters followed by universal amplification and sequencing. In some cases, complementary DNA can be synthesized and sequenced without amplification.

In some cases, extension and ligation approaches can be performed without a pull-down component. In some cases, the method can include loci-specific forward and reverse primer hybridization, extension and ligation. Such methods can further include universal amplification or complementary DNA synthesis without amplification, followed by sequencing. Such methods can reduce or exclude background sequences during analysis, in some cases.

In some cases, pull-down approaches can be used with an optional amplification component or with no amplification component. In some cases, the method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In some cases, the method can include a biotinylated pull-down assay with extension and ligation of adaptor sequence in combination with circular single stranded ligation. For example, such an approach can involve the use of selector probes to capture regions of interest (i.e. target sequences), extension of the probes, adaptor ligation, single stranded circular ligation, optional amplification, and sequencing. In some cases, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments typically are isolated away from the remaining fragments in the nucleic acid sample. In some cases, the separated target fragments and the separated reference fragments also are isolated away from each other (e.g., isolated in separate assay compartments). In some cases, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, Wis.); Illumina BEADARRAY platform (Illumina, San Diego, Calif.); Affymetrix GENECHIP platform (Affymetrix, Santa Clara, Calif.); Agilent SureSelect Target Enrichment System (Agilent Technologies, Santa Clara, Calif.); and related platforms. Such methods typically involve hybridization of a capture oligonucleotide to a portion or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome).

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In some cases, length-based separation approaches can include fragment circularization, chemical treatment (e.g., formaldehyde, polyethylene glycol (PEG)), mass spectrometry and/or size-specific nucleic acid amplification, for example.

Certain length-based separation methods that can be used with methods described herein employ a selective sequence tagging approach, for example. In such methods, a fragment size species (e.g., short fragments) nucleic acids are selectively tagged in a sample that includes long and short nucleic acids. Such methods typically involve performing a nucleic acid amplification reaction using a set of nested primers which include inner primers and outer primers. In some cases, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Nucleic Acid Amplification and Detection

Following separation of nucleic acid in a methylation-differential manner, nucleic acid may be amplified and/or subjected to a detection process (e.g., sequence-based analysis, mass spectrometry). Furthermore, once it is determined that one particular genomic sequence of fetal origin is hypermethylated or hypomethylated compared to the maternal counterpart, the amount of this fetal genomic sequence can be determined. Subsequently, this amount can be compared to a standard control value and serve as an indication for the potential of certain pregnancy-associated disorder.

Nucleotide sequences, or amplified nucleic acid sequences, or detectable products prepared from the foregoing, can be detected by a suitable detection process. Non-limiting examples of methods of detection, quantification, sequencing and the like include mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), direct DNA sequencing, Molecular Inversion Probe (MIP) technology from Affymetrix, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization using at least one probe, hybridization using at least one fluorescently labeled probe, cloning and sequencing, electrophoresis, the use of hybridization probes and quantitative real time polymerase chain reaction (QRT-PCR), digital PCR, nanopore sequencing, chips and combinations thereof. In some embodiments the amount of each amplified nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

Nucleic acid detection and/or quantification also may include, for example, solid support array based detection of fluorescently labeled nucleic acid with fluorescent labels incorporated during or after PCR, single molecule detection of fluorescently labeled molecules in solution or captured on a solid phase, or other sequencing technologies such as, for example, sequencing using ION TORRENT or MISEQ platforms or single molecule sequencing technologies using instrumentation such as, for example, PACBIO sequencers, HELICOS sequencer, or nanopore sequencing technologies.

In some cases, nucleotide sequences, or amplified nucleic acid sequences, or detectable products prepared from the foregoing, are detected using a sequencing process (e.g., such as a sequencing process described herein). Nucleic acid quantifications generated by a method comprising a sequencing detection process may be compared to nucleic acid quantifications generated by a method comprising a different detection process (e.g., mass spectrometry). Such comparisons may be expressed using an $R^2$ value, which is a measure of correlation between two outcomes (e.g., nucleic acid quantifications). In some cases, nucleic acid quantifications (e.g., fetal copy number quantifications) are highly correlated (i.e., have high $R^2$ values) for quantifications generated using different detection processes (e.g., sequencing and mass spectrometry). In some cases, $R^2$ values for nucleic acid quantifications generated using different detection processes may be between about 0.90 and about 1.0. For example, $R^2$ values may be about 0.91, 0.92, 0.93, 0.94, 0.95, 0.96, 0.97, 0.98, or 0.99.

Amplification of Nucleotide Sequences

In many instances, it is desirable to amplify a nucleic acid sequence of the technology herein using any of several nucleic acid amplification procedures which are well known in the art (listed above and described in greater detail below). Specifically, nucleic acid amplification is the enzymatic synthesis of nucleic acid amplicons (copies) which contain a sequence that is complementary to a nucleic acid sequence being amplified. Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a polynucleotide sequence is typically used in practicing the present technology, one of skill in the art will recognize that the amplification of a genomic sequence found in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of the technology herein, which represents a particular methylation pattern, or to quantitatively determine the amount of this particular genomic sequence in the maternal blood. For a review of branched-DNA signal amplification for direct quantitation of nucleic acid sequences in clinical samples, see Nolte, Adv. Clin. Chem. 33:201-235, 1998.

The compositions and processes of the technology herein are also particularly useful when practiced with digital PCR. Digital PCR was first developed by Kalinina and colleagues (Kalinina et al., "Nanoliter scale PCR with TaqMan detection." Nucleic Acids Research. 25; 1999-2004, (1997)) and further developed by Vogelstein and Kinzler (Digital PCR. Proc Natl Acad Sci USA. 96; 9236-41, (1999)). The application of digital PCR for use with fetal diagnostics was first described by Cantor et al. (PCT Patent Publication No. WO05023091A2) and subsequently described by Quake et al. (US Patent Publication No. US 20070202525), which are both hereby incorporated by reference. Digital PCR takes advantage of nucleic acid (DNA, cDNA or RNA) amplification on a single molecule level, and offers a highly sensitive method for quantifying low copy number nucleic acid. Fluidigm® Corporation offers systems for the digital analysis of nucleic acids.

The terms "amplify", "amplification", "amplification reaction", or "amplifying" refer to any in vitro process for multiplying the copies of a nucleic acid. Amplification sometimes refers to an "exponential" increase in nucleic acid. However, "amplifying" as used herein can also refer to linear increases in the numbers of a select nucleic acid, but is different than a one-time, single primer extension step. In some embodiments a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions, for example, and also may reduce amplification biases due to nucleotide sequence or abundance of the nucleic acid. In some embodiments a one-time primer extension may be performed as a prelude to linear or exponential amplification.

Any suitable amplification technique can be utilized. Amplification of polynucleotides include, but are not limited to, polymerase chain reaction (PCR); ligation amplification (or ligase chain reaction (LCR)); amplification methods based on the use of Q-beta replicase or template-dependent polymerase (see US Patent Publication Number US20050287592); helicase-dependant isothermal amplification (Vincent et al., "Helicase-dependent isothermal DNA amplification". EMBO reports 5 (8): 795-800 (2004)); strand displacement amplification (SDA); thermophilic SDA nucleic acid sequence based amplification (3SR or NASBA) and transcription-associated amplification (TAA). Non-limiting examples of PCR amplification methods include standard PCR, AFLP-PCR, Allele-specific PCR, Alu-PCR, Asymmetric PCR, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcriptase PCR (RT-PCR), Real Time PCR, Single cell PCR, Solid phase PCR, digital PCR, combinations thereof, and the like. For example, amplification can be accomplished using digital PCR, in certain embodiments (see e.g. Kalinina et al., "Nanoliter scale PCR with TaqMan detection." Nucleic Acids Research. 25; 1999-2004, (1997); Vogelstein and Kinzler (Digital PCR. Proc Natl Acad Sci USA. 96; 9236-41, (1999); PCT Patent Publication No. WO05023091A2; US Patent Publication No. US 20070202525). Digital PCR takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation). Reagents and hardware for conducting PCR are commercially available.

A generalized description of an amplification process is presented herein. Primers and nucleic acid are contacted, and complementary sequences anneal to one another, for example. Primers can anneal to a nucleic acid, at or near (e.g., adjacent to, abutting, and the like) a sequence of interest. In some embodiments, the primers in a set hybridize within about 10 to 30 nucleotides from a nucleic acid sequence of interest and produce amplified products. In some embodiments, the primers hybridize within the nucleic acid sequence of interest.

A reaction mixture, containing components necessary for enzymatic functionality, is added to the primer-nucleic acid hybrid, and amplification can occur under suitable conditions. Components of an amplification reaction may include, but are not limited to, e.g., primers (e.g., individual primers, primer pairs, primer sets and the like) a polynucleotide template, polymerase, nucleotides, dNTPs and the like. In some embodiments, non-naturally occurring nucleotides or nucleotide analogs, such as analogs containing a detectable label (e.g., fluorescent or colorimetric label), may be used for example. Polymerases can be selected by a person of ordinary skill and include polymerases for thermocycle amplification (e.g., Taq DNA Polymerase; Q-Bio™ Taq DNA Polymerase (recombinant truncated form of Taq DNA Polymerase lacking 5'-3'exo activity); SurePrime™ Polymerase (chemically modified Taq DNA polymerase for "hot start" PCR); Arrow™ Taq DNA Polymerase (high sensitivity and long template amplification)) and polymerases for thermostable amplification (e.g., RNA polymerase for transcription-mediated amplification (TMA) described at World Wide Web URL "gen-probe.com/pdfs/tma_whiteppr.pdf"). Other enzyme components can be added, such as reverse transcriptase for transcription mediated amplification (TMA) reactions, for example.

PCR conditions can be dependent upon primer sequences, abundance of nucleic acid, and the desired amount of amplification, and therefore, one of skill in the art may choose from a number of PCR protocols available (see, e.g., U.S. Pat. Nos. 4,683,195 and 4,683,202; and PCR Protocols: A Guide to Methods and Applications, Innis et al., eds, 1990. Digital PCR is also known in the art; see, e.g., United States Patent Application Publication no. 20070202525, filed Feb. 2, 2007, which is hereby incorporated by reference). PCR is typically carried out as an automated process with a thermostable enzyme. In this process, the temperature of the reaction mixture is cycled through a denaturing step, a primer-annealing step, and an extension reaction step automatically. Some PCR protocols also include an activation step and a final extension step. Machines specifically adapted for this purpose are commercially available. A non-limiting example of a PCR protocol that may be suitable for embodiments described herein, is treating the sample at 95° C. for 5 minutes; repeating thirty-five cycles of 95° C. for 45 seconds and 68° C. for 30 seconds; and then treating the sample at 72° C. for 3 minutes. A completed PCR reaction can optionally be kept at 4° C. until further action is desired. Multiple cycles frequently are performed using a commercially available thermal cycler. Suitable isothermal amplification processes known and selected by the person of ordinary skill in the art also may be applied, in certain embodiments.

In some embodiments, an amplification product may include naturally occurring nucleotides, non-naturally occurring nucleotides, nucleotide analogs and the like and combinations of the foregoing. An amplification product often has a nucleotide sequence that is identical to or substantially identical to a nucleic acid sequence herein, or complement thereof. A "substantially identical" nucleotide sequence in an amplification product will generally have a high degree of sequence identity to the nucleotide sequence species being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of infidelity of the polymerase used for extension and/or amplification, or additional nucleotide sequence(s) added to the primers used for amplification.

Primers

Primers useful for detection, amplification, quantification, sequencing and analysis of nucleic acid are provided. The term "primer" as used herein refers to a nucleic acid that includes a nucleotide sequence capable of hybridizing or annealing to a target nucleic acid, at or near (e.g., adjacent to) a specific region of interest. Primers can allow for specific determination of a target nucleic acid nucleotide sequence or detection of the target nucleic acid (e.g., presence or absence of a sequence or copy number of a sequence), or feature thereof, for example. A primer may be naturally occurring or synthetic. The term "specific" or "specificity", as used herein, refers to the binding or hybridization of one molecule to another molecule, such as a primer for a target polynucleotide. That is, "specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "primer", "oligo", or "oligonucleotide" may be used interchangeably throughout the document, when referring to primers.

A primer nucleic acid can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein, may be synthesized and labeled using known techniques. Primers may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of primers can be effected by native acrylamide gel electrophoresis or by anion-exchange high-performance liquid chromatography (HPLC), for example, as described in Pearson and Regnier, J. Chrom., 255:137-149, 1983.

All or a portion of a primer nucleic acid sequence (naturally occurring or synthetic) may be substantially complementary to a target nucleic acid, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are target and primer sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complimentary to a target nucleic acid sequence are also substantially identical to the compliment of the target nucleic acid sequence. That is, primers are substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Primer sequences and length may affect hybridization to target nucleic acid sequences. Depending on the degree of mismatch between the primer and target nucleic acid, low, medium or high stringency conditions may be used to effect primer/target annealing. As used herein, the term "stringent conditions" refers to conditions for hybridization and washing. Methods for hybridization reaction temperature condition optimization are known to those of skill in the art, and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6x sodium chloride/sodium citrate (SSC) at about 45° C., followed by one or more washes in 0.2×SSC, 0.1% SDS at 50° C.

Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Often, stringent hybridization conditions are hybridization in 6× sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile. Features of primers can be applied to probes and oligonucleotides, such as, for example, the competitive and inhibitory oligonucleotides provided herein.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

In some embodiments primers can include a nucleotide subsequence that may be complementary to a solid phase nucleic acid primer hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). A primer may contain a nucleotide subsequence not complementary to or not substantially complementary to a solid phase nucleic acid primer hybridization sequence (e.g., at the 3' or 5' end of the nucleotide subsequence in the primer complementary to or substantially complementary to the solid phase primer hybridization sequence).

A primer, in certain embodiments, may contain a modification such as one or more inosines, abasic sites, locked nucleic acids, minor groove binders, duplex stabilizers (e.g., acridine, spermidine), Tm modifiers or any modifier that changes the binding properties of the primers or probes. A primer, in certain embodiments, may contain a detectable molecule or entity (e.g., a fluorophore, radioisotope, colorimetric agent, particle, enzyme and the like, as described above for labeled competitor oligonucleotides).

A primer also may refer to a polynucleotide sequence that hybridizes to a subsequence of a target nucleic acid or another primer and facilitates the detection of a primer, a target nucleic acid or both, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

In some embodiments, the primers are complementary to genomic DNA target sequences. In some cases, the forward and reverse primers hybridize to the 5' and 3' ends of the genomic DNA target sequences. In some embodiments, primers that hybridize to the genomic DNA target sequences also hybridize to competitor oligonucleotides that were designed to compete with corresponding genomic DNA target sequences for binding of the primers. In some cases, the primers hybridize or anneal to the genomic DNA target sequences and the corresponding competitor oligonucleotides with the same or similar hybridization efficiencies. In some cases the hybridization efficiencies are different. The ratio between genomic DNA target amplicons and competitor amplicons can be measured during the reaction. For example if the ratio is 1:1 at 28 cycles but 2:1 at 35, this could indicate that during the end of the amplification reaction the primers for one target (i.e. genomic DNA target or competitor) are either reannealing faster than the other, or the denaturation is less effective than the other.

In some embodiments primers are used in sets. As used herein, an amplification primer set is one or more pairs of forward and reverse primers for a given region. Thus, for example, primers that amplify genomic targets for region 1 (i.e. targets 1a and 1b) are considered a primer set. Primers that amplify genomic targets for region 2 (i.e. targets 2a and 2b) are considered a different primer set. In some embodiments, the primer sets that amplify targets within a particular region also amplify the corresponding competitor oligonucleotide(s). A plurality of primer pairs may constitute a primer set in certain embodiments (e.g., about 2, 3, 4, 5, 6, 7, 8, 9, 10, 15, 20, 25, 30, 35, 40, 45, 50, 55, 60, 65, 70, 75, 80, 85, 90, 95 or 100 pairs). In some embodiments a plurality of primer sets, each set comprising pair(s) of primers, may be used.

Determination of Polynucleotide Sequences

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present technology. Additional means suitable for detecting changes in a polynucleotide sequence for practicing the methods of the present technology include but are not limited to mass spectrometry, primer extension, polynucleotide hybridization, real-time PCR, and electrophoresis.

Use of a primer extension reaction also can be applied in methods of the technology herein. A primer extension reaction operates, for example, by discriminating the SNP alleles by the incorporation of deoxynucleotides and/or dideoxynucleotides to a primer extension primer which hybridizes to a region adjacent to the SNP site. The primer is extended with a polymerase. The primer extended SNP can be detected physically by mass spectrometry or by a tagging moiety such as biotin. As the SNP site is only extended by a complementary deoxynucleotide or dideoxynucleotide that is either tagged by a specific label or generates a primer extension product with a specific mass, the SNP alleles can be discriminated and quantified.

Reverse transcribed and amplified nucleic acids may be modified nucleic acids. Modified nucleic acids can include nucleotide analogs, and in certain embodiments include a detectable label and/or a capture agent. Examples of detectable labels include without limitation fluorophores, radioisotopes, colormetric agents, light emitting agents, chemiluminescent agents, light scattering agents, enzymes and the like. Examples of capture agents include without limitation an agent from a binding pair selected from antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) pairs, and the like. Modified nucleic acids having a capture agent can be immobilized to a solid support in certain embodiments Mass spectrometry is a particularly effective method for the detection of a polynucleotide of the technology herein, for example a PCR amplicon, a primer extension product or a detector probe that is cleaved from a target nucleic acid. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. For a review of genotyping methods using Sequenom® standard iPLEX™ assay and MassARRAY® technology, see Jurinke, C., Oeth, P., van den Boom, D., "MALDI-TOF mass spectrometry: a versatile tool for high-performance DNA analysis." Mol. Biotechnol. 26, 147-164 (2004); and Oeth, P. et al., "iPLEX™ Assay: Increased Plexing Efficiency and Flexibility for MassARRAY® System through single base primer extension with mass-modified Terminators." SEQUENOM Application Note (2005), both of which are hereby incorporated by reference. For a review of detecting and quantifying target nucleic using cleavable detector probes that are cleaved during the amplification process and detected by mass spectrometry, see U.S. patent application Ser. No. 11/950, 395, which was filed Dec. 4, 2007, and is hereby incorporated by reference.

Sequencing technologies are improving in terms of throughput and cost. Sequencing technologies, such as that achievable on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001), allow the sequencing of many nucleic acid molecules isolated from a specimen at high orders of multiplexing in a parallel fashion (Dear Brief Funct Genomic Proteomic 2003; 1: 397-416).

Each of these platforms allow sequencing of clonally expanded or non-amplified single molecules of nucleic acid fragments. Certain platforms involve, for example, (i) sequencing by ligation of dye-modified probes (including cyclic ligation and cleavage), (ii) pyrosequencing, and (iii) single-molecule sequencing. Nucleotide sequence species, amplification nucleic acid species and detectable products generated there from can be considered a "study nucleic acid" for purposes of analyzing a nucleotide sequence by such sequence analysis platforms.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled with more than one fluorescent label (e.g., 1 fluorescent label, 2,3, or 4 fluorescent labels). An example of a system that can be used by a person of ordinary skill based on sequencing by ligation generally involves the following steps. Clonal bead populations can be prepared in emulsion microreactors containing study nucleic acid ("template"), amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag. Such a system can be used to exponentially amplify amplification products generated by a process described herein, e.g., by ligating a heterologous nucleic acid to the first amplification product generated by a process described herein and performing emulsion amplification using the same or a different solid support originally used to generate the first amplification product. Such a system also may be used to analyze amplification products directly generated by a process described herein by bypassing an exponential amplification process and directly sorting the solid supports described herein on the glass slide.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Study nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination.

An example of a system that can be used by a person of ordinary skill based on pyrosequencing generally involves the following steps: ligating an adaptor nucleic acid to a study nucleic acid and hybridizing the study nucleic acid to a bead; amplifying a nucleotide sequence in the study nucleic acid in an emulsion; sorting beads using a picoliter multiwell solid support; and sequencing amplified nucleotide sequences by pyrosequencing methodology (e.g., Nakano et al., "Single-molecule PCR using water-in-oil emulsion;" Journal of Biotechnology 102: 117-124 (2003)). Such a system can be used to exponentially amplify amplification products generated by a process described herein, e.g., by ligating a heterologous nucleic acid to the first amplification product generated by a process described herein.

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair", in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a study nucleic acid to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslaysky et al., PNAS 100(7): 3960-3964 (2003)). Such a system can be used to directly sequence amplification products generated by processes described herein. In some embodiments the released linear amplification product can be hybridized to a primer that contains sequences complementary to immobilized capture sequences present on a solid support, a bead or glass slide for example. Hybridization of the primer—released linear amplification product complexes with the immobilized capture sequences, immobilizes released linear amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as nonspecific fluorescence. Following immobilization of the primer—released linear amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting sample nucleic acid and solid support under conditions in which a single molecule of sample nucleic acid hybridizes to a single molecule of a solid support. Such conditions can include providing the solid support molecules and a single molecule of sample nucleic acid in a "microreactor." Such conditions also can include providing a mixture in which the sample nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons sometimes are performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis is facilitated by sequence analysis apparatus and components known to the person of ordinary skill in the art.

Methods provided herein allow for high-throughput detection of nucleic acid species in a plurality of nucleic acids (e.g., nucleotide sequence species, amplified nucleic acid species and detectable products generated from the foregoing). Multiplexing refers to the simultaneous detection of more than one nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of nucleic acid species (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction.

In certain embodiments, the number of nucleic acid species multiplexed include, without limitation, about 1 to about 500 (e.g., about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501).

Design methods for achieving resolved mass spectra with multiplexed assays can include primer and oligonucleotide design methods and reaction design methods. See, for example, the multiplex schemes provided in Tables X and Y. For primer and oligonucleotide design in multiplexed assays, the same general guidelines for primer design applies for uniplexed reactions, such as avoiding false priming and primer dimers, only more primers are involved for multiplex reactions. For mass spectrometry applications, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. In some embodiments multiplex analysis may be adapted to mass spectrometric detection of chromosome abnormalities, for example. In certain embodiments multiplex analysis may be adapted to various single nucleotide or nanopore based sequencing methods described herein. Commercially produced micro-reaction chambers or devices or arrays or chips may be used to facilitate multiplex analysis, and are commercially available.

Additional Methods for Obtaining Nucleotide Sequence Reads

In some embodiments, nucleic acids (e.g., nucleic acid fragments, sample nucleic acid, cell-free nucleic acid) may be sequenced. In some cases, a full or substantially full sequence is obtained and sometimes a partial sequence is obtained. Sequencing, mapping and related analytical methods are known in the art (e.g., United States Patent Application Publication US2009/0029377, incorporated by reference). Certain aspects of such processes are described hereafter.

As used herein, "reads" are short nucleotide sequences produced by any sequencing process described herein or known in the art. Reads can be generated from one end of nucleic acid fragments ("single-end reads"), and sometimes are generated from both ends of nucleic acids ("double-end reads"). In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

In some embodiments, one nucleic acid sample from one individual is sequenced. In certain embodiments, nucleic acid samples from two or more biological samples, where each biological sample is from one individual or two or more individuals, are pooled and the pool is sequenced. In the latter embodiments, a nucleic acid sample from each biological sample often is identified by one or more unique identification tags.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.1-fold to about 100-fold coverage, about 0.2-fold to 20-fold coverage, or about 0.2-fold to about 1-fold coverage (e.g., about 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In certain embodiments, a fraction of a nucleic acid pool that is sequenced in a run is further sub-selected prior to sequencing. In certain embodiments, hybridization-based techniques (e.g., using oligonucleotide arrays) can be used to first sub-select for nucleic acid sequences from certain chromosomes (e.g., a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected pool of nucleic acids is sequenced randomly. In some embodiments, the nucleic acid is amplified prior to sequencing. In some embodiments, a portion or subset of the nucleic acid is amplified prior to sequencing.

In some cases, a sequencing library is prepared prior to or during a sequencing process. Methods for preparing a sequencing library are known in the art and commercially available platforms may be used for certain applications. Certain commercially available library platforms may be compatible with certain nucleotide sequencing processes described herein. For example, one or more commercially available library platforms may be compatible with a sequencing by synthesis process. In some cases, a ligation-based library preparation method is used (e.g., ILLUMINA TRUSEQ, Illumina, San Diego Calif.). Ligation-based library preparation methods typically use a methylated adaptor design which can incorporate an index sequence at the initial ligation step and often can be used to prepare samples for single-read sequencing, paired-end sequencing and multiplexed sequencing. In some cases, a transposon-based library preparation method is used (e.g., EPICENTRE NEXTERA, Epicentre, Madison Wis.). Transposon-based methods typically use in vitro transposition to simultaneously fragment and tag DNA in a single-tube reaction (often allowing incorporation of platform-specific tags and optional barcodes), and prepare sequencer-ready libraries.

Any sequencing method suitable for conducting methods described herein can be utilized. In some embodiments, a high-throughput sequencing method is used. High-throughput sequencing methods generally involve clonally amplified DNA templates or single DNA molecules that are sequenced in a massively parallel fashion within a flow cell (e.g. as described in Metzker M Nature Rev 11:31-46 (2010); Volkerding et al. Clin Chem 55:641-658 (2009)). Such sequencing methods also can provide digital quantitative information, where each sequence read is a countable "sequence tag" or "count" representing an individual clonal DNA template or a single DNA molecule. High-throughput sequencing technologies include, for example, sequencing-by-synthesis with reversible dye terminators, sequencing by oligonucleotide probe ligation, pyrosequencing and real time sequencing.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

In some embodiments, first generation technology, such as, for example, Sanger sequencing including the automated Sanger sequencing, can be used in the methods provided herein. Additional sequencing technologies that include the use of developing nucleic acid imaging technologies (e.g. transmission electron microscopy (TEM) and atomic force microscopy (AFM)), also are contemplated herein. Examples of various sequencing technologies are described below.

A nucleic acid sequencing technology that may be used in the methods described herein is sequencing-by-synthesis and reversible terminator-based sequencing (e.g. Illumina's Genome Analyzer; Genome Analyzer II; HISEQ 2000; HISEQ 2500 (Illumina, San Diego Calif.)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

In certain sequencing by synthesis procedures, for example, template DNA (e.g., circulating cell-free DNA (ccfDNA)) sometimes is fragmented into lengths of several hundred base pairs in preparation for library generation. In some embodiments, library preparation can be performed without further fragmentation or size selection of the template DNA (e.g., ccfDNA). Sample isolation and library generation may be performed using automated methods and apparatus, in certain embodiments. Briefly, template DNA is end repaired by a fill-in reaction, exonuclease reaction or a combination of a fill-in reaction and exonuclease reaction. The resulting blunt-end repaired template DNA is extended by a single nucleotide, which is complementary to a single nucleotide overhang on the 3' end of an adapter primer, and often increases ligation efficiency. Any complementary nucleotides can be used for the extension/overhang nucleotides (e.g., A/T, C/G), however adenine frequently is used to extend the end-repaired DNA, and thymine often is used as the 3' end overhang nucleotide.

In certain sequencing by synthesis procedures, for example, adapter oligonucleotides are complementary to the flow-cell anchors, and sometimes are utilized to associate the modified template DNA (e.g., end-repaired and single nucleotide extended) with a solid support, such as the inside surface of a flow cell, for example. In some embodiments, the adapter also includes identifiers (i.e., indexing nucleotides, or "barcode" nucleotides (e.g., a unique sequence of nucleotides usable as an identifier to allow unambiguous identification of a sample and/or chromosome)), one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). Identifiers or nucleotides contained in an adapter often are six or more nucleotides in length, and frequently are positioned in the adaptor such that the identifier nucleotides are the first nucleotides sequenced during the sequencing reaction. In certain embodiments, identifier nucleotides are associated with a sample but are sequenced in a separate sequencing reaction to avoid compromising the quality of sequence reads. Subsequently, the reads from the identifier sequencing and the DNA template sequencing are linked together and the reads de-multiplexed. After linking and de-multiplexing the sequence reads and/or identifiers can be further adjusted or processed as described herein.

In certain sequencing by synthesis procedures, utilization of identifiers allows multiplexing of sequence reactions in a flow cell lane, thereby allowing analysis of multiple samples per flow cell lane. The number of samples that can be analyzed in a given flow cell lane often is dependent on the number of unique identifiers utilized during library preparation and/or probe design. Non limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively). The methods described herein can be performed using any number of unique identifiers (e.g., 4, 8, 12, 24, 48, 96, or more). The greater the number of unique identifiers, the greater the number of samples and/or chromosomes, for example, that can be multiplexed in a single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell.

In certain sequencing by synthesis procedures, adapter-modified, single-stranded template DNA is added to the flow cell and immobilized by hybridization to the anchors under limiting-dilution conditions. In contrast to emulsion PCR, DNA templates are amplified in the flow cell by "bridge" amplification, which relies on captured DNA strands "arching" over and hybridizing to an adjacent anchor oligonucleotide. Multiple amplification cycles convert the single-molecule DNA template to a clonally amplified arching "cluster," with each cluster containing approximately 1000 clonal molecules. Approximately $50 \times 10^6$ separate clusters can be generated per flow cell. For sequencing, the clusters are denatured, and a subsequent chemical cleavage reaction and wash leave only forward strands for single-end sequencing. Sequencing of the forward strands is initiated by hybridizing a primer complementary to the adapter sequences, which is followed by addition of polymerase and a mixture of four differently colored fluorescent reversible dye terminators. The terminators are incorporated according to sequence complementarity in each strand in a clonal cluster. After incorporation, excess reagents are washed away, the clusters are optically interrogated, and the fluorescence is recorded. With successive chemical steps, the reversible dye terminators are unblocked, the fluorescent labels are cleaved and washed away, and the next sequencing cycle is performed. This iterative, sequencing-by-synthesis process sometimes requires approximately 2.5 days to generate read lengths of 36 bases. With $50 \times 10^6$ clusters per flow cell, the overall sequence output can be greater than 1 billion base pairs (Gb) per analytical run.

Another nucleic acid sequencing technology that may be used with the methods described herein is 454 sequencing (Roche). 454 sequencing uses a large-scale parallel pyrosequencing system capable of sequencing about 400-600 megabases of DNA per run. The process typically involves two steps. In the first step, sample nucleic acid (e.g. DNA) is sometimes fractionated into smaller fragments (300-800 base pairs) and polished (made blunt at each end). Short adaptors are then ligated onto the ends of the fragments. These adaptors provide priming sequences for both amplification and sequencing of the sample-library fragments. One adaptor (Adaptor B) contains a 5'-biotin tag for immobilization of the DNA library onto streptavidin-coated beads. After nick repair, the non-biotinylated strand is released and used as a single-stranded template DNA (sstDNA) library. The sstDNA library is assessed for its quality and the optimal amount (DNA copies per bead) needed for emPCR is determined by titration. The sstDNA library is immobilized onto beads. The beads containing a library fragment carry a single sstDNA molecule. The bead-bound library is emulsified with the amplification reagents in a water-in-oil mixture. Each bead is captured within its own microreactor where PCR amplification occurs. This results in bead-immobilized, clonally amplified DNA fragments.

In the second step of 454 sequencing, single-stranded template DNA library beads are added to an incubation mix containing DNA polymerase and are layered with beads containing sulfurylase and luciferase onto a device containing pico-liter sized wells. Pyrosequencing is performed on each DNA fragment in parallel. Addition of one or more nucleotides generates a light signal that is recorded by a CCD camera in a sequencing instrument. The signal strength is proportional to the number of nucleotides incorporated.

Pyrosequencing exploits the release of pyrophosphate (PPi) upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed (see, for example, Margulies, M. et al. Nature 437:376-380 (2005)).

Another nucleic acid sequencing technology that may be used in the methods provided herein is Applied Biosystems' SOLiD™ technology. In SOLiD™ sequencing-by-ligation, a library of nucleic acid fragments is prepared from the sample and is used to prepare clonal bead populations. With this method, one species of nucleic acid fragment will be present on the surface of each bead (e.g. magnetic bead). Sample nucleic acid (e.g. genomic DNA) is sheared into fragments, and adaptors are subsequently attached to the 5' and 3' ends of the fragments to generate a fragment library. The adapters are typically universal adapter sequences so that the starting sequence of every fragment is both known and identical. Emulsion PCR takes place in microreactors containing all the necessary reagents for PCR. The resulting PCR products attached to the beads are then covalently bound to a glass slide. Primers then hybridize to the adapter sequence within the library template. A set of four fluorescently labeled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n−1 position for a second round of ligation cycles. Often, five rounds of primer reset are completed for each sequence tag. Through the primer reset process, each base is interrogated in two independent ligation reactions by two different primers. For example, the base at read position 5 is assayed by primer number 2 in ligation cycle 2 and by primer number 3 in ligation cycle 1.

Another nucleic acid sequencing technology that may be used in the methods described herein is the Helicos True Single Molecule Sequencing (tSMS). In the tSMS technique, a polyA sequence is added to the 3' end of each nucleic acid (e.g. DNA) strand from the sample. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into a sequencing apparatus and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step (see, for example, Harris T. D. et al., Science 320:106-109 (2008)).

Another nucleic acid sequencing technology that may be used in the methods provided herein is the single molecule, real-time (SMRT™) sequencing technology of Pacific Biosciences. With this method, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is then repeated.

Another nucleic acid sequencing technology that may be used in the methods described herein is ION TORRENT (Life Technologies) single molecule sequencing which pairs semiconductor technology with a simple sequencing chemistry to directly translate chemically encoded information (A, C, G, T) into digital information (0, 1) on a semiconductor chip. ION TORRENT uses a high-density array of micro-machined wells to perform nucleic acid sequencing in a massively parallel way. Each well holds a different DNA molecule. Beneath the wells is an ion-sensitive layer and beneath that an ion sensor. Typically, when a nucleotide is incorporated into a strand of DNA by a polymerase, a hydrogen ion is released as a byproduct. If a nucleotide, for example a C, is added to a DNA template and is then incorporated into a strand of DNA, a hydrogen ion will be released. The charge from that ion will change the pH of the solution, which can be detected by an ion sensor. A sequencer can call the base, going directly from chemical information to digital information. The sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection (i.e. detection without scanning, cameras or light), each nucleotide incorporation is recorded in seconds.

Another nucleic acid sequencing technology that may be used in the methods described herein is the chemical-sensitive field effect transistor (CHEMFET) array. In one example of this sequencing technique, DNA molecules are placed into reaction chambers, and the template molecules can be hybridized to a sequencing primer bound to a polymerase. Incorporation of one or more triphosphates into a new nucleic acid strand at the 3' end of the sequencing primer can be detected by a change in current by a CHEMFET sensor. An array can have multiple CHEMFET sensors. In another example, single nucleic acids are attached to beads, and the nucleic acids can be amplified on the bead, and the individual beads can be transferred to individual reaction chambers on a CHEMFET array, with each chamber having a CHEMFET sensor, and the nucleic acids can be sequenced (see, for example, U.S. Patent Application Publication No. 2009/0026082).

Another nucleic acid sequencing technology that may be used in the methods described herein is electron microscopy.

In one example of this sequencing technique, individual nucleic acid (e.g. DNA) molecules are labeled using metallic labels that are distinguishable using an electron microscope. These molecules are then stretched on a flat surface and imaged using an electron microscope to measure sequences (see, for example, Moudrianakis E. N. and Beer M. Proc Natl Acad Sci USA. 1965 March; 53:564-71). In some cases, transmission electron microscopy (TEM) is used (e.g. Halcyon Molecular's TEM method). This method, termed Individual Molecule Placement Rapid Nano Transfer (IM-PRNT), includes utilizing single atom resolution transmission electron microscope imaging of high-molecular weight (e.g. about 150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA (see, for example, International Patent Application No. WO 2009/046445).

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number. In sequencing by hybridization, the method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in the methods described herein. Nanopore sequencing is a single-molecule sequencing technology whereby a single nucleic acid molecule (e.g. DNA) is sequenced directly as it passes through a nanopore. A nanopore is a small hole or channel, of the order of 1 nanometer in diameter. Certain transmembrane cellular proteins can act as nanopores (e.g. alpha-hemolysin). In some cases, nanopores can be synthesized (e.g. using a silicon platform). Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree and generates characteristic changes to the current. The amount of current which can pass through the nanopore at any given moment therefore varies depending on whether the nanopore is blocked by an A, a C, a G, a T, or in some cases, methyl-C. The change in the current through the nanopore as the DNA molecule passes through the nanopore represents a direct reading of the DNA sequence. In some cases a nanopore can be used to identify individual DNA bases as they pass through the nanopore in the correct order (see, for example, Soni G V and Meller A. Clin Chem 53: 1996-2001 (2007); International Patent Application No. WO2010/004265).

There are a number of ways that nanopores can be used to sequence nucleic acid molecules. In some embodiments, an exonuclease enzyme, such as a deoxyribonuclease, is used. In this case, the exonuclease enzyme is used to sequentially detach nucleotides from a nucleic acid (e.g. DNA) molecule. The nucleotides are then detected and discriminated by the nanopore in order of their release, thus reading the sequence of the original strand. For such an embodiment, the exonuclease enzyme can be attached to the nanopore such that a proportion of the nucleotides released from the DNA molecule is capable of entering and interacting with the channel of the nanopore. The exonuclease can be attached to the nanopore structure at a site in close proximity to the part of the nanopore that forms the opening of the channel. In some cases, the exonuclease enzyme can be attached to the nanopore structure such that its nucleotide exit trajectory site is orientated towards the part of the nanopore that forms part of the opening.

In some embodiments, nanopore sequencing of nucleic acids involves the use of an enzyme that pushes or pulls the nucleic acid (e.g. DNA) molecule through the pore. In this case, the ionic current fluctuates as a nucleotide in the DNA molecule passes through the pore. The fluctuations in the current are indicative of the DNA sequence. For such an embodiment, the enzyme can be attached to the nanopore structure such that it is capable of pushing or pulling the target nucleic acid through the channel of a nanopore without interfering with the flow of ionic current through the pore. The enzyme can be attached to the nanopore structure at a site in close proximity to the part of the structure that forms part of the opening. The enzyme can be attached to the subunit, for example, such that its active site is orientated towards the part of the structure that forms part of the opening.

In some embodiments, nanopore sequencing of nucleic acids involves detection of polymerase bi-products in close proximity to a nanopore detector. In this case, nucleoside phosphates (nucleotides) are labeled so that a phosphate labeled species is released upon the addition of a polymerase to the nucleotide strand and the phosphate labeled species is detected by the pore. Typically, the phosphate species contains a specific label for each nucleotide. As nucleotides are sequentially added to the nucleic acid strand, the bi-products of the base addition are detected. The order that the phosphate labeled species are detected can be used to determine the sequence of the nucleic acid strand.

The length of the sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median or average length of about 15 bp to 900 bp long (e.g. about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130 bp, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp or more.

In some embodiments, nucleic acids may include a fluorescent signal or sequence tag information. Quantification of the signal or tag may be used in a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

Adaptors

In some embodiments, nucleic acids (e.g., PCR primers, PCR amplicons, sample nucleic acid) may include an adaptor sequence and/or complement thereof. Adaptor sequences often are useful for certain sequencing methods such as, for example, a sequencing-by-synthesis process described herein. Adaptors sometimes are referred to as sequencing adaptors or adaptor oligonucleotides. Adaptor sequences typically include one or more sites useful for attachment to a solid support (e.g., flow cell). Adaptors also may include sequencing primer hybridization sites (i.e. sequences complementary to primers used in a sequencing reaction) and identifiers (e.g., indices) as described below. Adaptor sequences can be located at the 5' and/or 3' end of a nucleic acid and sometimes can be located within a larger nucleic acid sequence. Adaptors can be any length and any sequence, and may be selected based on standard methods in the art for adaptor design.

One or more adaptor oligonucleotides may be incorporated into a nucleic acid (e.g., PCR amplicon) by any method suitable for incorporating adaptor sequences into a nucleic acid. For example, PCR primers used for generating PCR amplicons (i.e., amplification products) may comprise adaptor sequences or complements thereof. Thus, PCR amplicons that comprise one or more adaptor sequences can be generated during an amplification process. In some cases, one or more adaptor sequences can be ligated to a nucleic acid (e.g., PCR amplicon) by any ligation method suitable for attaching adaptor sequences to a nucleic acid. Ligation processes may include, for example, blunt-end ligations, ligations that exploit 3' adenine (A) overhangs generated by Taq polymerase during an amplification process and ligate adaptors having 3' thymine (T) overhangs, and other "sticky-end" ligations. Ligation processes can be optimized such that adaptor sequences hybridize to each end of a nucleic acid and not to each other.

In some cases, adaptor ligation is bidirectional, which means that adaptor sequences are attached to a nucleic acid such that both ends of the nucleic acid are sequenced in a subsequent sequencing process. In some cases, adaptor ligation is unidirectional, which means that adaptor sequences are attached to a nucleic acid such that one end of the nucleic acid is sequenced in a subsequent sequencing process. Examples of unidirectional and bidirectional ligation schemes are discussed in Example 4 and shown in FIGS. 21 and 22.

Identifiers

In some embodiments, nucleic acids (e.g., PCR primers, PCR amplicons, sample nucleic acid, sequencing adaptors) may include an identifier. In some cases, an identifier is located within or adjacent to an adaptor sequence. An identifier can be any feature that can identify a particular origin or aspect of a genomic target sequence. For example, an identifier (e.g., a sample identifier) can identify the sample from which a particular genomic target sequence originated. In another example, an identifier (e.g., a sample aliquot identifier) can identify the sample aliquot from which a particular genomic target sequence originated. In another example, an identifier (e.g., chromosome identifier) can identify the chromosome from which a particular genomic target sequence originated. An identifier may be referred to herein as a tag, index, barcode, identification tag, index primer, and the like. An identifier may be a unique sequence of nucleotides (e.g., sequence-based identifiers), a detectable label such as the labels described below (e.g., identifier labels), and/or a particular length of polynucleotide (e.g., length-based identifiers; size-based identifiers) such as a stuffer sequence. Identifiers for a collection of samples or plurality of chromosomes, for example, may each comprise a unique sequence of nucleotides. Identifiers (e.g., sequence-based identifiers, length-based identifiers) may be of any length suitable to distinguish certain target genomic sequences from other target genomic sequences. In some embodiments, identifiers may be from about one to about 100 nucleotides in length. For example, identifiers independently may be about 1, 2, 3, 4, 5, 6, 7, 8, 9, 10, 20, 30, 40, 50, 60, 70, 80, 90 or 100 nucleotides in length. In some embodiments, an identifier contains a sequence of six nucleotides. In some cases, an identifier is part of an adaptor sequence for a sequencing process, such as, for example, a sequencing-by-synthesis process described in further detail herein. In some cases, an identifier may be a repeated sequence of a single nucleotide (e.g., poly-A, poly-T, poly-G, poly-C). Such identifiers may be detected and distinguished from each other, for example, using nanopore technology, as described herein.

In some embodiments, the analysis includes analyzing (e.g., detecting, counting, processing counts for, and the like) the identifier. In some embodiments, the detection process includes detecting the identifier and sometimes not detecting other features (e.g., sequences) of a nucleic acid. In some embodiments, the counting process includes counting each identifier. In some embodiments, the identifier is the only feature of a nucleic acid that is detected, analyzed and/or counted.

Detection of Fetal Aneuploidy

For the detection of fetal aneuploidies, some methods rely on measuring the ratio between maternally and paternally inherited alleles. However, the ability to quantify chromosomal changes is impaired by the maternal contribution of cell free nucleic acids, which makes it necessary to deplete the sample from maternal DNA prior to measurement. Promising approaches take advantage of the different size distribution of fetal and maternal DNA or measure RNA that is exclusively expressed by the fetus (see for example, U.S. patent application Ser. No. 11/384,128, which published as US20060252071 and is hereby incorporated by reference). Assuming fetal DNA makes up only about 5% of all cell free DNA in the maternal plasma, there is a decrease of the ratio difference from 1.6% to only about 1.2% between a trisomy sample and a healthy control. Consequently, reliable detection of allele ratio changes requires enriching the fetal fraction of cell free DNA, for example, using the compositions and methods of the present technology.

Some methods rely on measuring the ratio of maternal to paternally inherited alleles to detect fetal chromosomal aneuploidies from maternal plasma. A diploid set yields a 1:1 ratio while trisomies can be detected as a 2:1 ratio. Detection of this difference is impaired by statistical sampling due to the low abundance of fetal DNA, presence of excess maternal DNA in the plasma sample and variability of the measurement technique. The latter is addressed by using methods with high measurement precision, like digital PCR or mass spectrometry. Enriching the fetal fraction of cell free DNA in a sample is currently achieved by either depleting maternal DNA through size exclusion or focusing on fetal-specific nucleic acids, like fetal-expressed RNA. Another differentiating feature of fetal DNA is its DNA methylation pattern. Thus, provided herein are novel compositions and methods for accurately quantifying fetal nucleic acid based on differential methylation between a fetus and mother. The methods rely on sensitive absolute copy number analysis to quantify the fetal nucleic acid portion of a maternal sample, thereby allowing for the prenatal detection of fetal traits. The methods of the technology herein have identified approximately 3000 CpG rich regions in the genome that are differentially methylated between maternal and fetal DNA. The selected regions showed highly conserved differential methylation across all measured samples. In addition the set of regions is enriched for genes important in developmental regulation, indicating that epigenetic regulation of these areas is a biologically relevant and consistent process (see Table 3). Enrichment of fetal DNA can now be achieved by using the MBD-FC protein to capture all cell free DNA and then elute the highly methylated DNA fraction with high salt concentrations. Using the low salt eluate fractions, the MBD-FC is equally capable of enriching non-methylated fetal DNA.

The present technology provides 63 confirmed genomic regions on chromosomes 13, 18 and 21 with low maternal and high fetal methylation levels. After capturing these regions, SNPs can be used to determine the aforementioned allele ratios. When high frequency SNPs are used around 10 markers have to be measured to achieve a high confidence of finding at least one SNP where the parents have opposite homozygote genotypes and the child has a heterozygote genotype.

In an embodiment, a method for chromosomal abnormality detection is provided that utilizes absolute copy number quantification. A diploid chromosome set will show the same number of copies for differentially methylated regions across all chromosomes, but, for example, a trisomy 21 sample would show 1.5 times more copies for differentially methylated regions on chromosome 21. Normalization of the genomic DNA amounts for a diploid chromosome set can be achieved by using unaltered autosomes as reference (also provided herein—see Table 1B). Comparable to other approaches, a single marker is less likely to be sufficient for detection of this difference, because the overall copy numbers are low. Typically there are approximately 100 to 200 copies of fetal DNA from 1 ml of maternal plasma at 10 to 12 weeks of gestation. However, the methods of the present technology offer a redundancy of detectable markers that enables highly reliable discrimination of diploid versus aneuploid chromosome sets.

Data Processing and Identifying Presence or Absence of a Chromosome Abnormality

The term "detection" of a chromosome abnormality as used herein refers to identification of an imbalance of chromosomes by processing data arising from detecting sets of amplified nucleic acid species, nucleotide sequence species, or a detectable product generated from the foregoing (collectively "detectable product"). Any suitable detection device and method can be used to distinguish one or more sets of detectable products, as addressed herein. An outcome pertaining to the presence or absence of a chromosome abnormality can be expressed in any suitable form, including, without limitation, probability (e.g., odds ratio, p-value), likelihood, percentage, value over a threshold, or risk factor, associated with the presence of a chromosome abnormality for a subject or sample. An outcome may be provided with one or more of sensitivity, specificity, standard deviation, coefficient of variation (CV) and/or confidence level, or combinations of the foregoing, in certain embodiments.

Detection of a chromosome abnormality based on one or more sets of detectable products may be identified based on one or more calculated variables, including, but not limited to, sensitivity, specificity, standard deviation, coefficient of variation (CV), a threshold, confidence level, score, probability and/or a combination thereof. In some embodiments, (i) the number of sets selected for a diagnostic method, and/or (ii) the particular nucleotide sequence species of each set selected for a diagnostic method, is determined in part or in full according to one or more of such calculated variables.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome determined by an algorithm is not due to chance) in certain embodiments is expressed as a p-value, and sometimes the p-value is about 0.05 or less (e.g., about 0.05, 0.04, 0.03, 0.02 or 0.01, or less than 0.01 (e.g., about 0.001 or less, about 0.0001 or less, about 0.00001 or less, about 0.000001 or less)).

For example, scoring or a score may refer to calculating the probability that a particular chromosome abnormality is actually present or absent in a subject/sample. The value of a score may be used to determine for example the variation, difference, or ratio of amplified nucleic detectable product that may correspond to the actual chromosome abnormality. For example, calculating a positive score from detectable products can lead to an identification of a chromosome abnormality, which is particularly relevant to analysis of single samples.

In certain embodiments, simulated (or simulation) data can aid data processing for example by training an algorithm or testing an algorithm. Simulated data may for instance involve hypothetical various samples of different concentrations of fetal and maternal nucleic acid in serum, plasma and the like. Simulated data may be based on what might be expected from a real population or may be skewed to test an algorithm and/or to assign a correct classification based on a simulated data set. Simulated data also is referred to herein as "virtual" data. Fetal/maternal contributions within a sample can be simulated as a table or array of numbers (for example, as a list of peaks corresponding to the mass signals of cleavage products of a reference biomolecule or amplified nucleic acid sequence), as a mass spectrum, as a pattern of bands on a gel, or as a representation of any technique that measures mass distribution. Simulations can be performed in most instances by a computer program. One possible step in using a simulated data set is to evaluate the confidence of the identified results, i.e. how well the selected positives/negatives match the sample and whether there are additional variations. A common approach is to calculate the probability value (p-value) which estimates the probability of a random sample having better score than the selected one. As p-value calculations can be prohibitive in certain circumstances, an empirical model may be assessed, in which it is assumed that at least one sample matches a reference sample (with or without resolved variations). Alternatively other distributions such as Poisson distribution can be used to describe the probability distribution.

In certain embodiments, an algorithm can assign a confidence value to the true positives, true negatives, false positives and false negatives calculated. The assignment of a likelihood of the occurrence of a chromosome abnormality can also be based on a certain probability model.

Simulated data often is generated in an in silico process. As used herein, the term "in silico" refers to research and experiments performed using a computer. In silico methods include, but are not limited to, molecular modeling studies, karyotyping, genetic calculations, biomolecular docking experiments, and virtual representations of molecular structures and/or processes, such as molecular interactions.

As used herein, a "data processing routine" refers to a process, that can be embodied in software, that determines the biological significance of acquired data (i.e., the ultimate results of an assay). For example, a data processing routine can determine the amount of each nucleotide sequence species based upon the data collected. A data processing routine also may control an instrument and/or a data collection routine based upon results determined. A data processing routine and a data collection routine often are integrated and provide feedback to operate data acquisition by the instrument, and hence provide assay-based judging methods provided herein.

As used herein, software refers to computer readable program instructions that, when executed by a computer, perform computer operations. Typically, software is provided on a program product containing program instructions recorded on a computer readable medium, including, but not limited to, magnetic media including floppy disks, hard disks, and magnetic tape; and optical media including CD-ROM discs, DVD discs, magneto-optical discs, and other such media on which the program instructions can be recorded.

Different methods of predicting abnormality or normality can produce different types of results. For any given prediction, there are four possible types of outcomes: true positive, true negative, false positive, or false negative. The term "true positive" as used herein refers to a subject correctly diagnosed as having a chromosome abnormality. The term "false positive" as used herein refers to a subject wrongly identified as having a chromosome abnormality. The term "true negative" as used herein refers to a subject correctly identified as not having a chromosome abnormality. The term "false negative" as used herein refers to a subject wrongly identified as not having a chromosome abnormality. Two measures of performance for any given method can be calculated based on the ratios of these occurrences: (i) a sensitivity value, the fraction of predicted positives that are correctly identified as being positives (e.g., the fraction of nucleotide sequence sets correctly identified by level comparison detection/determination as indicative of chromosome abnormality, relative to all nucleotide sequence sets identified as such, correctly or incorrectly), thereby reflecting the accuracy of the results in detecting the chromosome abnormality; and (ii) a specificity value, the fraction of predicted negatives correctly identified as being negative (the fraction of nucleotide sequence sets correctly identified by level comparison detection/determination as indicative of chromosomal normality, relative to all nucleotide sequence sets identified as such, correctly or incorrectly), thereby reflecting accuracy of the results in detecting the chromosome abnormality.

EXAMPLES

The following examples are provided by way of illustration only and not by way of limitation. Thus, the examples set forth below illustrate certain embodiments and do not limit the technology. Those of skill in the art will readily recognize a variety of non-critical parameters that could be changed or modified to yield essentially the same or similar results.

In Example 1 below, the Applicants used a new fusion protein that captures methylated DNA in combination with CpG Island array to identify genomic regions that are differentially methylated between fetal placenta tissue and maternal blood. A stringent statistical approach was used to only select regions which show little variation between the samples, and hence suggest an underlying biological mechanism. Eighty-five differentially methylated genomic regions predominantly located on chromosomes 13, 18 and 21 were validated. For this validation, a quantitative mass spectrometry based approach was used that interrogated 261 PCR amplicons covering these 85 regions. The results are in very good concordance (95% confirmation), proving the feasibility of the approach.

Next, the Applicants provide an innovative approach for aneuploidy testing, which relies on the measurement of absolute copy numbers rather than allele ratios.

Example 1

Figure 3:
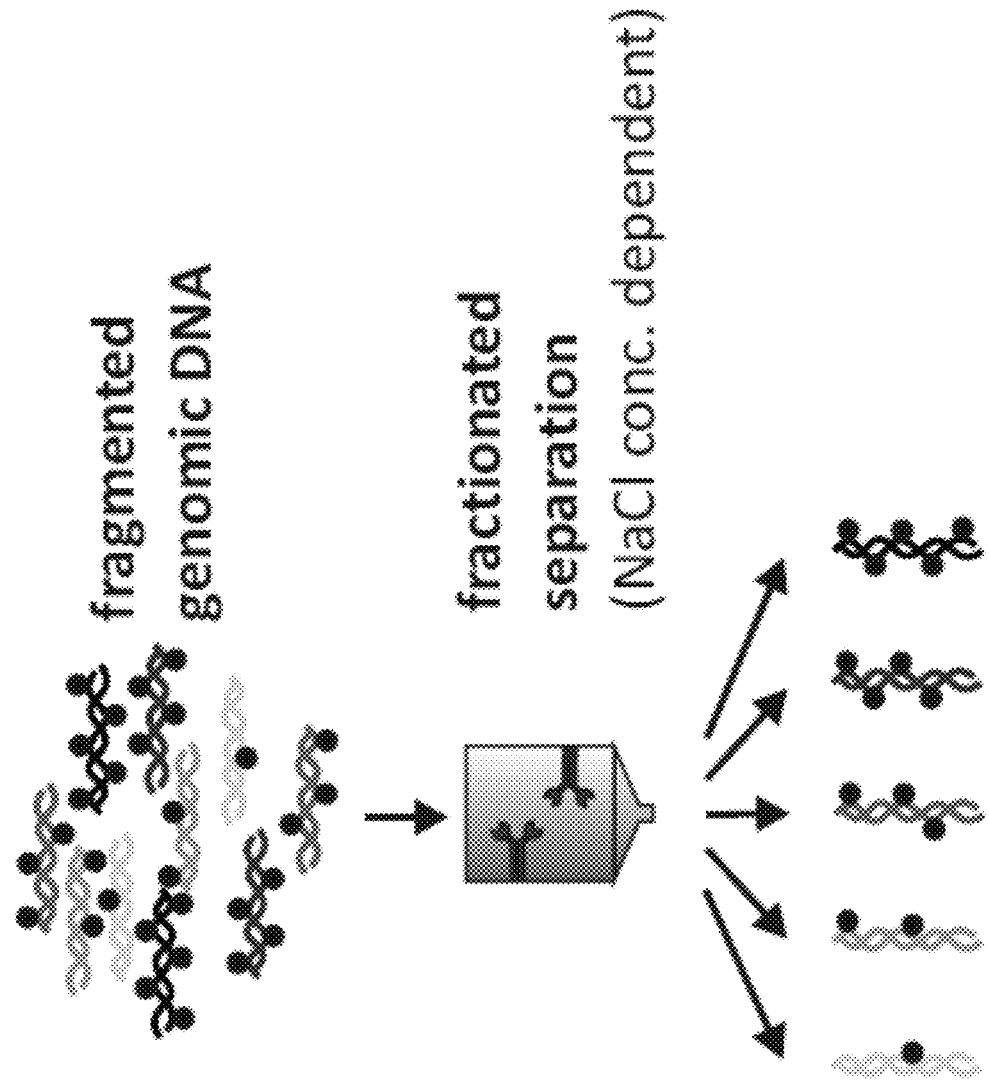
FIG. 3 shows the methyl binding domain of MBD-FC binds all DNA molecules regardless of their methylation status. The strength of this protein/DNA interaction is defined by the level of DNA methylation. After binding genomic DNA, eluate solutions of increasing salt concentrations can be used to fractionate non-methylated and methylated DNA allowing for a controlled separation.
Figure 4:
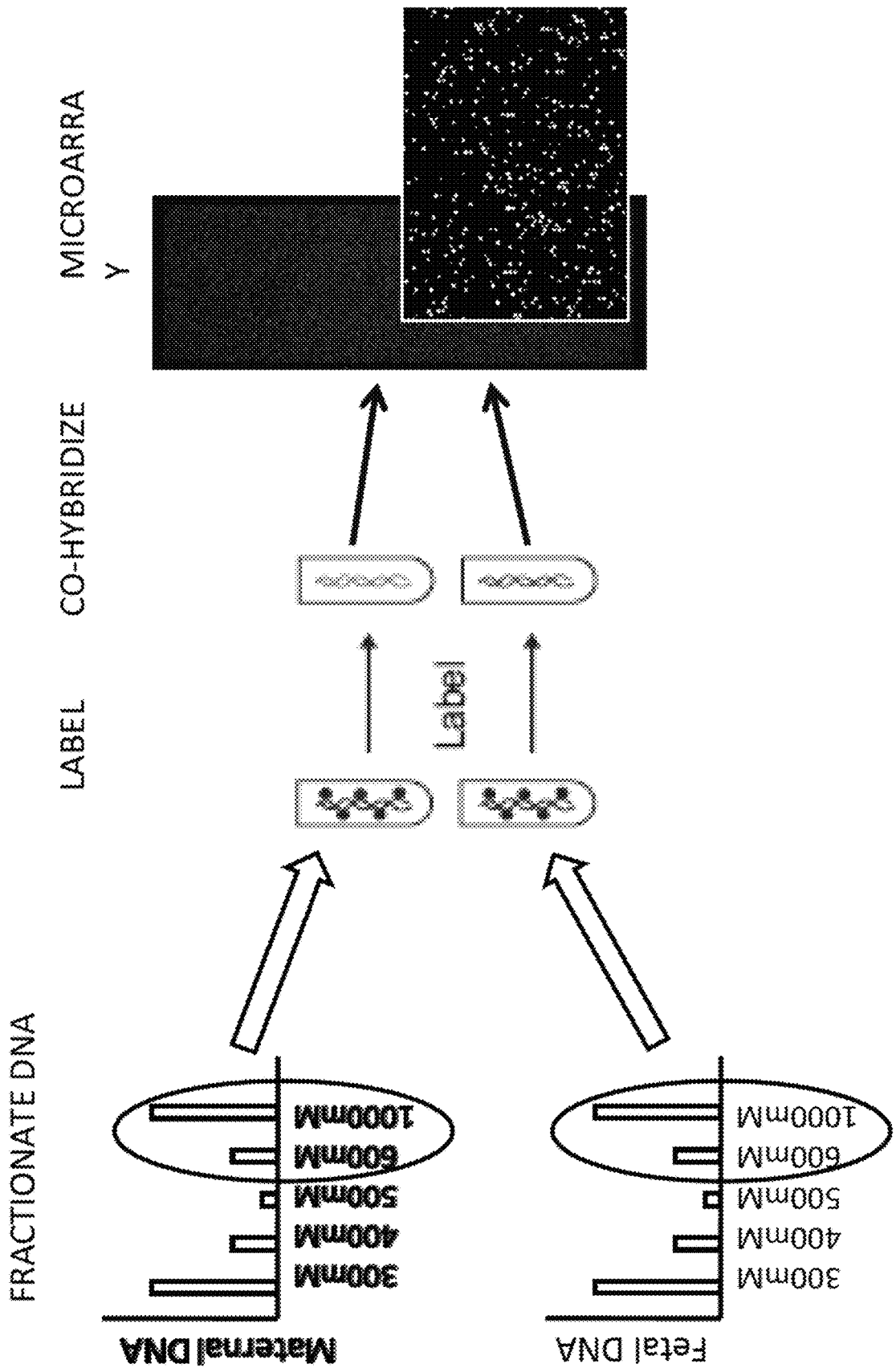
FIG. 4 shows the experiment used to identify differentially methylated DNA from a fetus and mother using the recombinant MBD-Fc protein and a microarray.
Figure 5:
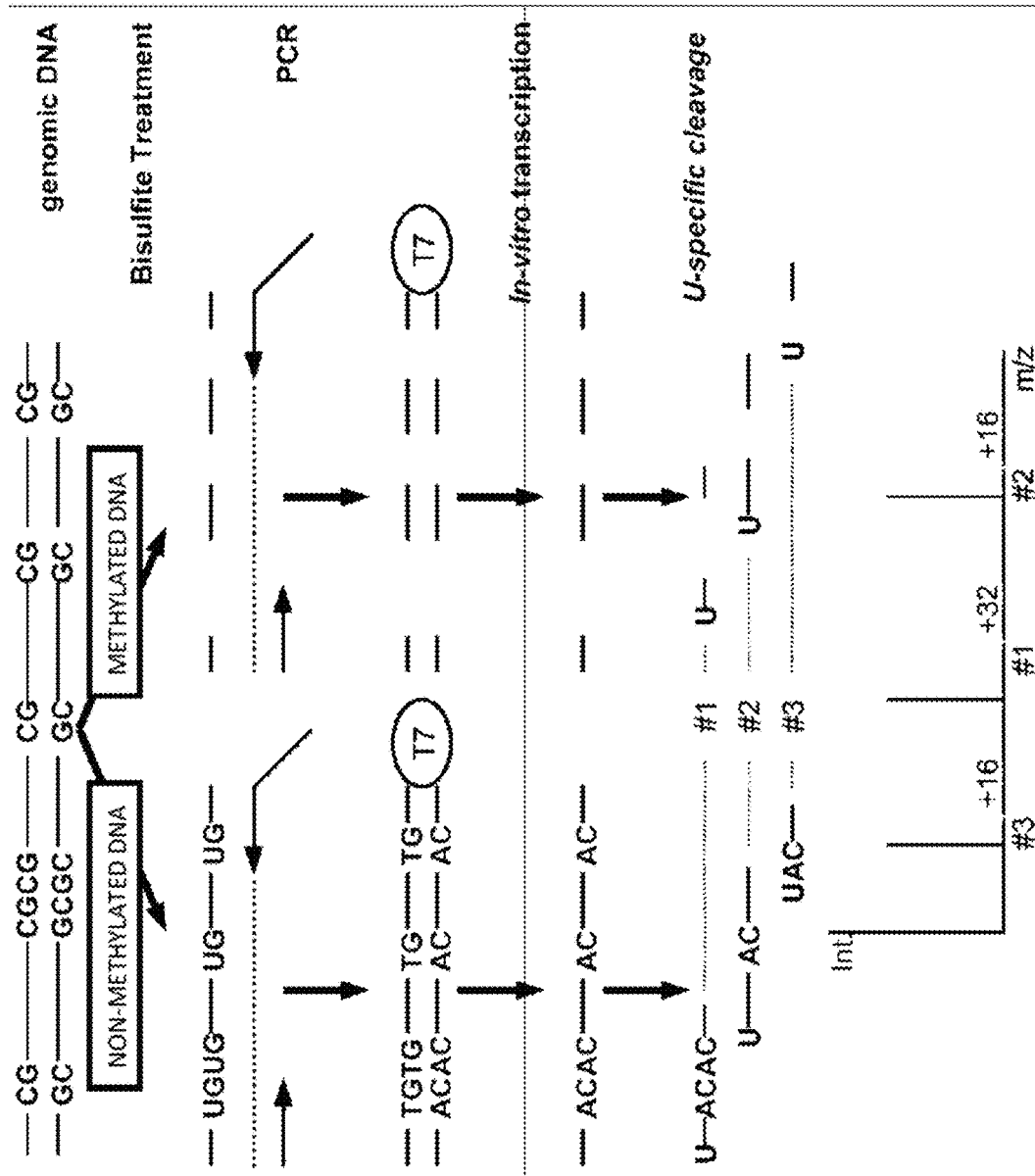
FIG. 5 shows typical results generated by Sequenom® EpiTYPER™ method, which was used to validate the results generated from the experiment illustrated in FIG. 4.
Figure 6:
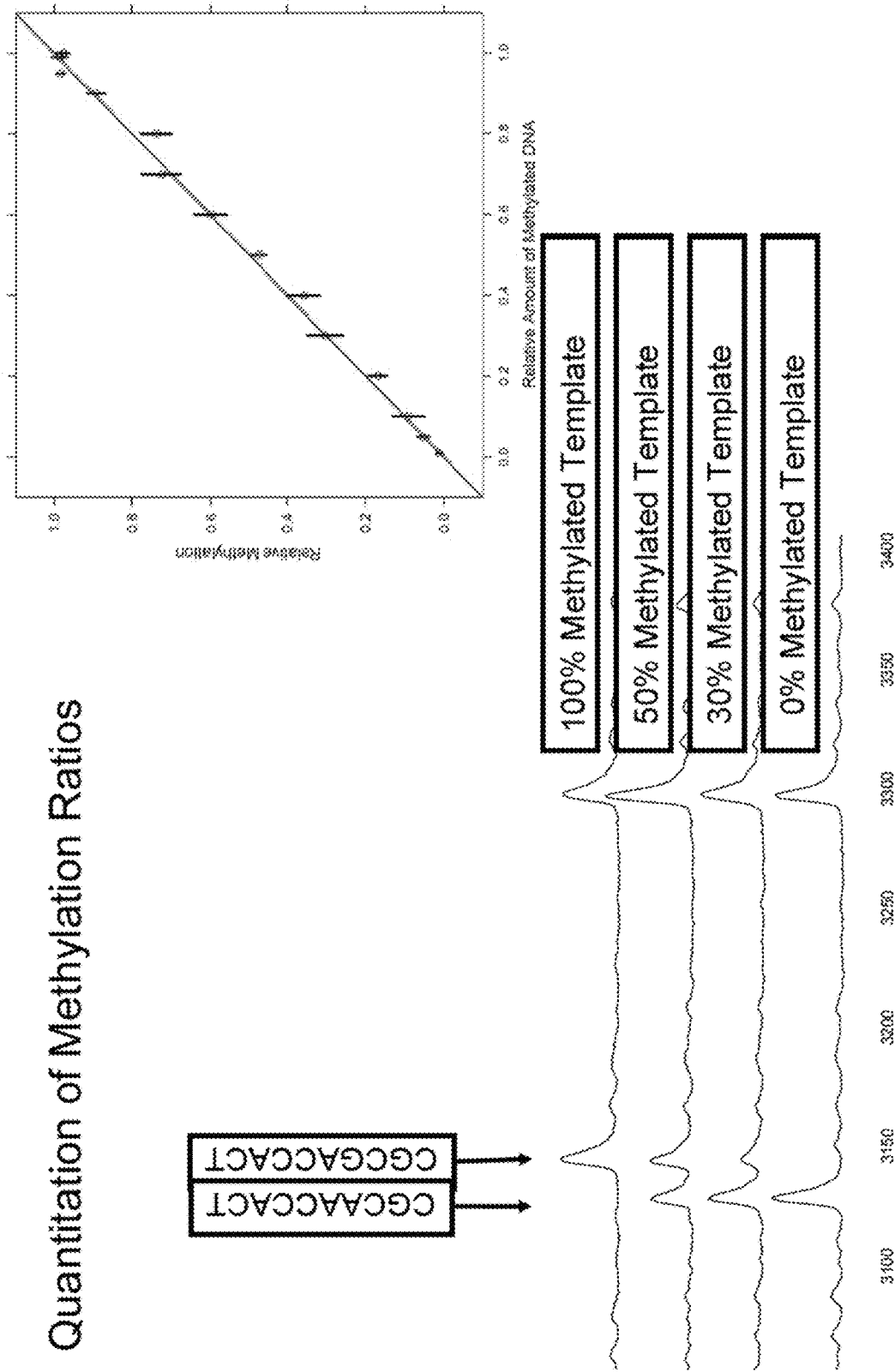
FIG. 6 shows the correlation between the log ratios derived from microarray analysis (x axis) and methylation differences obtained by EpiTYPER™ analysis (y axis). Each data point represents the average for one region across all measured samples. The microarray analysis is comparative in nature because the highly methylated fraction of the maternal DNA is hybridized together with the highly methylated fraction of placenta DNA. Positive values indicate higher methylation of the placenta samples. In mass spectrometry each samples is measured individually. The difference in methylation was calculated by subtracting the maternal methylation values from the placenta methylation value. To compare the results with the microarray data the average of the differences for all maternal/placenta DNA pairs was calculated. Figure discloses SEQ ID NOS 387 and 388, respectively, in order of appearance.

In the below Example, ten paired maternal and placental DNA samples were used to identify differentially methylated regions. These results were validated using a mass spectrometry-based quantitative methylation assay. First, genomic DNA from maternal buffy coat and corresponding placental tissue was first extracted. Next the MBD-FC was used to capture the methylated fraction of each DNA sample. See FIGS. 1-3. The two tissue fractions were labeled with different fluorescent dyes and hybridized to an Agilent® CpG Island microarray. See FIG. 4. This was done to identify differentially methylated regions that could be utilized for prenatal diagnoses. Therefore, two criteria were employed to select genomic regions as potential enrichment markers: the observed methylation difference had to be present in all tested sample pairs, and the region had to be more than 200 bp in length.

DNA Preparation and Fragmentation

Genomic DNA (gDNA) from maternal buffy coat and placental tissue was prepared using the QIAamp DNA Mini Kit™ and QIAamp DNA Blood Mini Kit™, respectively, from Qiagen® (Hilden, Germany). For MCIp, gDNA was quantified using the NanoDrop ND1000™ spectrophotometer (Thermo Fisher®, Waltham, Mass., USA). Ultrasonication of 2.5 µg DNA in 500 µl TE buffer to a mean fragment size of 300-500 bp was carried out with the Branson Digital Sonifier 450™ (Danbury, Conn., USA) using the following settings: amplitude 20%, sonication time 110 seconds, pulse on/pulse off time 1.4/0.6 seconds. Fragment range was monitored using gel electrophoresis.

Methyl-CpG Immunoprecipitation

Per sample, 56 µg purified MBD-Fc protein and 150 µl of Protein A Sepharose 4 Fast Flow beads (Amersham Biosciences®, Piscataway, N.J., USA) were rotated in 15 ml TBS overnight at 4° C. Then, the MBD-Fc beads (150 µl/assay) were transferred and dispersed in to 2 ml Ultrafree-CL centrifugal filter devices (Millipore®, Billerica, Mass., USA) and spin-washed three times with Buffer A (20 mM Tris-HCl, pH8.0, 2 mM MgCl2, 0.5 mM EDTA 300 mM NaCl, 0.1% NP-40). Sonicated DNA (2 µg) was added to the washed MBD-Fc beads in 2 ml Buffer A and rotated for 3 hours at 4° C. Beads were centrifuged to recover unbound DNA fragments (300 mM fraction) and subsequently washed twice with 600 µl of buffers containing increasing NaCl concentrations (400, 500, 550, 600, and 1000 mM). The flow through of each wash step was collected in separate tubes and desalted using a MinElute PCR Purification Kit™ (Qiagen®). In parallel, 200 ng sonicated input DNA was processed as a control using the MinElute PCR Purification Kit™ (Qiagen®).

Microarray Handling and Analysis

To generate fluorescently labeled DNA for microarray hybridization, the 600 mM and 1M NaCl fractions (enriched methylated DNA) for each sample were combined and labeled with either Alexa Fluor 555-aha-dCTP (maternal) or Alexa Fluor 647-aha-dCTP (placental) using the BioPrime Total Genomic Labeling System™ (Invitrogen®, Carlsbad, Calif., USA). The labeling reaction was carried out according to the manufacturer's manual. The differently labeled genomic DNA fragments of matched maternal/placental pairs were combined to a final volume of 80 µl, supplemented with 50 µg Cot-1 DNA (Invitrogen®), 52 µl of Agilent 10× blocking reagent (Agilent Technologies®, Santa Clara, Calif., USA), 78 µl of deionized formamide, and 260 µl Agilent 2× hybridization buffer. The samples were heated to 95° C. for 3 min, mixed, and subsequently incubated at 37° C. for 30 min. Hybridization on Agilent CpG Island Microarray Kit™ was then carried out at 67° C. for 40 hours using an Agilent SureHyb™ chamber and an Agilent hybridization oven. Slides were washed in Wash I (6×SSPE, 0.005% N-lauroylsarcosine) at room temperature for 5 min and in Wash II (0.06×SSPE) at 37° C. for an additional 5 min. Next, the slides were submerged in acetonitrile and Agilent Ozone Protection Solution™, respectively, for 30 seconds. Images were scanned immediately and analyzed using an Agilent DNA Microarray Scanner™. Microarray images were processed using Feature Extraction Software v9.5 and the standard CGH protocol.

Bisulfite Treatment

Genomic DNA sodium bisulfite conversion was performed using EZ-96 DNA Methylation Kit™ (ZymoResearch, Orange County, Calif.). The manufacturer's protocol was followed using 1 ug of genomic DNA and the alternative conversion protocol (a two temperature DNA denaturation).

Quantitative Methylation Analysis

Sequenom's MassARRAY® System was used to perform quantitative methylation analysis. This system utilizes matrix-assisted laser desorption ionization time-of-flight (MALDI-TOF) mass spectrometry in combination with RNA base specific cleavage (Sequenom® MassCLEAVE™). A detectable pattern is then analyzed for methylation status. PCR primers were designed using Sequenom® EpiDESIGNER™ (www.epidesigner.com). A total of 261 amplicons, covering 85 target regions, were used for validation (median amplification length=367 bp, min=108, max=500; median number of CpG's per amplicon=23, min=4, max=65). For each reverse primer, an additional T7 promoter tag for in-vivo transcription was added, as well as a 10mer tag on the forward primer to adjust for melting temperature differences. The MassCLEAVE™ biochemistry was performed as previously described (Ehrich M, et al. (2005) Quantitative high-throughput analysis of DNA methylation patterns by base specific cleavage and mass spectrometry. Proc Natl Acad Sci USA 102:15785-15790). Mass spectra were acquired using a MassARRAY™ Compact MALDI-TOF (Sequenom®, San Diego) and methylation ratios were generated by the EpiTYPER™ software v1.0 (Sequenom®, San Diego).

Statistical Analysis

All statistical calculations were performed using the R statistical software package (www.r-project.org). First, the array probes were grouped based on their genomic location. Subsequent probes that were less than 1000 bp apart were grouped together. To identify differentially methylated regions, a control sample was used as reference. In the control sample, the methylated fraction of a blood derived control DNA was hybridized against itself. Ideally this sample should show log ratios of the two color channels around 0. However because of the variability in hybridization behavior, the probes show a mean log ratio of 0.02 and a standard deviation of 0.18. Next the log ratios observed in the samples were compared to the control sample. A two way, paired t-test was used to test the NULL hypothesis that the groups are identical. Groups that contained less than 4 probes were excluded from the analysis. For groups including four or five probes, all probes were used in a paired t-test. For Groups with six or more probes, a sliding window test consisting of five probes at a time was used, whereby the window was moved by one probe increments. Each test sample was compared to the control sample and the p-values were recorded. Genomic regions were selected as being differentially methylated if eight out of ten samples showed a p value <0.01, or if six out of ten samples showed a p value <0.001. The genomic regions were classified as being not differentially methylated when the group showed less than eight samples with a p value <0.01 and less than six samples with a p value <0.001. Samples that didn't fall in either category were excluded from the analysis. For a subset of genomic regions that have been identified as differentially methylated, the results were confirmed using quantitative methylation analysis.

The Go analysis was performed using the online GOstat tool (http://gostat.wehi.edu.au/cgibin/-goStat.pl). P values were calculated using Fisher's exact test.

Microarray-Based Marker Discovery Results

To identify differentially methylated regions a standard sample was used, in which the methylated DNA fraction of monocytes was hybridized against itself. This standard provided a reference for the variability of fluorescent measurements in a genomic region. Differentially methylated regions were then identified by comparing the log ratios of each of the ten placental/maternal samples against this standard. Because the goal of this study was to identify markers that allow the reliable separation of maternal and fetal DNA, the target selection was limited to genes that showed a stable, consistent methylation difference over a contiguous stretch of genomic DNA. This focused the analysis on genomic regions where multiple probes indicated differential methylation. The selection was also limited to target regions where all samples showed differential methylation, excluding those with strong inter-individual differences. Two of the samples showed generally lower log ratios in the microarray analysis. Because a paired test was used for target selection, this did not negatively impact the results.

Based on these selection criteria, 3043 genomic regions were identified that were differentially methylated between maternal and fetal DNA. 21778 regions did not show a methylation difference. No inter-chromosomal bias in the distribution of differentially methylated regions was observed. The differentially methylated regions were located next to or within 2159 known genes. The majority of differentially methylated regions are located in the promoter area (18%) and inside the coding region (68%), while only few regions are located downstream of the gene (7%) or at the transition from promoter to coding region (7%). Regions that showed no differential methylation showed a similar distribution for promoter (13%) and downstream (5%) locations, but the fraction of regions located in the transition of promoter to coding region was higher (39%) and the fraction inside the coding region was lower (43%).

It has been shown in embryonic stem cells (ES) that genes targeted by the polycomb repressive complex2 (PRC2) are enriched for genes regulating development (Lee T I, et al. (2006) Control of developmental regulators by Polycomb in human embryonic stem cells. Cell 125:301-313). It has also been shown that differentially methylated genes are enriched for genes targeted by PRC2 in many cancer types (Ehrich M, et al. (2008) Cytosine methylation profiling of cancer cell lines. Proc Natl Acad Sci USA 105:4844-48). The set of genes identified as differentially methylated in this study is also enriched for genes targeted by PRC2 (p-value <0.001, odds ratio=3.6, 95% Cl for odds ratio=3.1-4.2). A GO analysis of the set of differentially methylated genes reveals that this set is significantly enriched for functions important during development. Six out of the ten most enriched functions include developmental or morphogenic processes [anatomical structure morphogenesis (GO:0009653, p value=0), developmental process (GO:0032502, p value=0), multicellular organismal development (GO:0007275, p value=0), developmental of an organ (GO:0048513, p value=0), system development (GO:0048731, p value=0) and development of an anatomical structure (GO:0048856, p value=0)].

Validation Using Sequenom® EpiTYPER™

Figure 7:
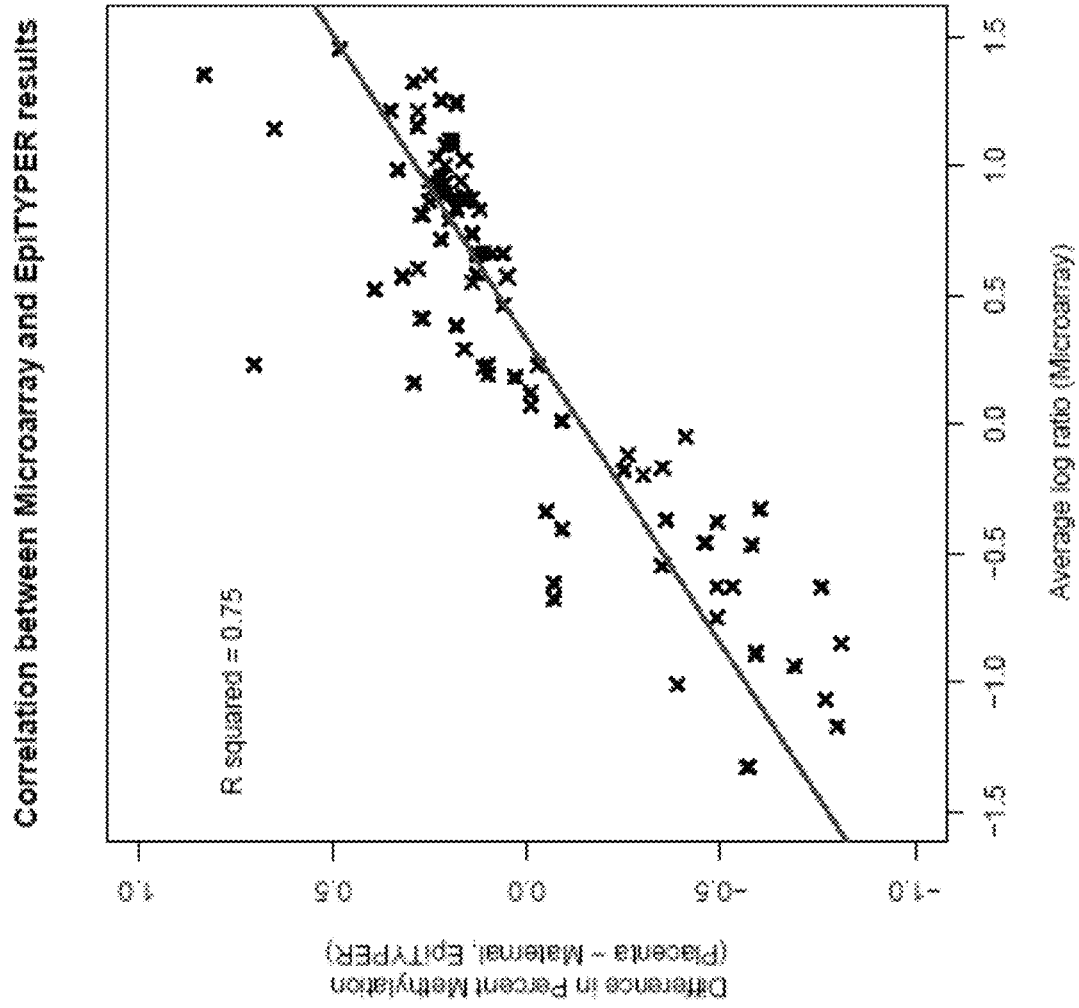
FIG. 7 shows a correlation between microarray and Epi-TYPER™ results.

To validate the microarray findings, 63 regions from chromosomes 13, 18 and 21 and an additional 26 regions from other autosomes were selected for confirmation by a different technology. Sequenom EpiTYPER™ technology was used to quantitatively measure DNA methylation in maternal and placental samples. For an explanation of the EpiTYPER™ methods, see Ehrich M, Nelson M R, Stanssens P, Zabeau M, Liloglou T, Xinarianos G, Cantor C R, Field J K, van den Boom D (2005) Quantitative high-throughput analysis of DNA methylation patterns by base specific cleavage and mass spectrometry. Proc Natl Acad Sci USA 102:15785-15790). For each individual CpG site in a target region the average methylation value across all maternal DNA samples and across all placenta samples was calculated. The difference between average maternal and placenta methylation was then compared to the microarray results. The results from the two technologies were in good concordance (see FIG. 7). For 85 target regions the quantitative results confirm the microarray results (95% confirmation rate). For 4 target regions, all located on chromosome 18, the results could not be confirmed. The reason for this discrepancy is currently unclear.

In contrast to microarrays, which focus on identification of methylation differences, the quantitative measurement of DNA methylation allowed analysis of absolute methylation values. In the validation set of 85 confirmed differentially methylated regions, a subset of 26 regions is more methylated in the maternal DNA sample and 59 regions are more methylated in the placental sample (see Table 1A). Interestingly, genes that are hypomethylated in the placental samples tend to show larger methylation differences than genes that are hypermethylated in the placental sample (median methylation difference for hypomethylated genes=39%, for hypermethylated genes=20%).

Example 2

Example 2 describes a non-invasive approach for detecting the amount of fetal nucleic acid present in a maternal sample (herein referred to as the "Fetal Quantifier Method"), which may be used to detect or confirm fetal traits (e.g., fetal sex of RhD compatibility), or diagnose chromosomal abnormalities such as Trisomy 21 (both of which are herein referred to as the "Methylation-Based Fetal Diagnostic Method"). FIG. 10 shows one embodiment of the Fetal Quantifier Method, and FIG. 11 shows one embodiment of the Methylation-Based Fetal Diagnostic Method. Both processes use fetal DNA obtained from a maternal sample. The sample comprises maternal and fetal nucleic acid that is differentially methylated. For example, the sample may be maternal plasma or serum. Fetal DNA comprises approximately 2-30% of the total DNA in maternal plasma. The actual amount of fetal contribution to the total nucleic acid present in a sample varies from pregnancy to pregnancy and can change based on a number of factors, including, but not limited to, gestational age, the mother's health and the fetus' health.

As described herein, the technical challenge posed by analysis of fetal DNA in maternal plasma lies in the need to be able to discriminate the fetal DNA from the co-existing background maternal DNA. The methods of the present technology exploit such differences, for example, the differential methylation that is observed between fetal and maternal DNA, as a means to enrich for the relatively small percentage of fetal DNA present in a sample from the mother. The non-invasive nature of the approach provides a major advantage over conventional methods of prenatal diagnosis such as, amniocentesis, chronic villus sampling and cordocentesis, which are associated with a small but finite risk of fetal loss. Also, because the method is not dependent on fetal cells being in any particular cell phase, the method provides a rapid detection means to determine the presence and also the nature of the chromosomal abnormality. Further, the approach is sex-independent (i.e., does not require the presence of a Y-chromosome) and polymorphic-independent (i.e., an allelic ratio is not determined). Thus, the compositions and methods of the technology herein represent improved universal, noninvasive approaches for accurately determining the amount of fetal nucleic acid present in a maternal sample.

Assay Design and Advantages

There is a need for accurate detection and quantification of fetal DNA isolated noninvasively from a maternal sample. The present technology takes advantage of the presence of circulating, cell free fetal nucleic acid (ccfDNA) in maternal plasma or serum. In order to be commercially and clinically practical, the methods of the technology herein should only consume a small portion of the limited available fetal DNA. For example, less than 50%, 40%, 30%, 25%, 20%, 15%, 10%, 5% or less of the sample. Further, the approach should preferably be developed in a multiplex assay format in which one or more (preferably all) of the following assays are included:

Assays for the detection of total amount of genomic equivalents present in the sample, i.e., assays recognizing both maternal and fetal DNA species;

Assays for the detection of fetal DNA isolated from a male pregnancy, i.e., sequences specific for chromosome Y;

Assays specific for regions identified as differentially methylated between the fetus and mother; or Assays specific for regions known to be hypomethylated in all tissues to be investigated, which can serve as a control for restriction efficiency.

Other features of the assay may include one or more of the following:

For each assay, a target-specific, competitor oligonucleotide that is identical, or substantially identical, to the target sequence apart from a distinguishable feature of the competitor, such as a difference in one or more nucleotides relative to the target sequence. This oligonucleotide when added into the PCR reaction will be co-amplified with the target and a ratio obtained between these two PCR amplicons will indicate the number of target specific DNA sequences (e.g., fetal DNA from a specific locus) present in the maternal sample.

The amplicon lengths should preferably be of similar length in order not to skew the amplification towards the shorter fragments. However, as long as the amplification efficiency is about equal, different lengths may be used.

Differentially methylated targets can be selected from Tables 1A-1C or from any other targets known to be differentially methylated between mother and fetus. These targets can be hypomethylated in DNA isolated from non-pregnant women and hypermethylated in samples obtained from fetal samples. These assays will serve as controls for the restriction efficiency.

The results obtained from the different assays can be used to quantify one or more of the following:

Total number of amplifiable genomes present in the sample (total amount of genomic equivalents);

The fetal fraction of the amplifiable genomes (fetal concentration or percentage); or Differences in copy number between fetally-derived DNA sequences (for example, between fetal chromosome 21 and a reference chromosome such as chromosome 3).

Examples of Assays Used in the Test

Below is an outline of the reaction steps used to perform a method of the technology herein, for example, as provided in FIG. 10. This outline is not intended to limit the scope of the technology herein. Rather it provides one embodiment of the technology herein using the Sequenom® MassARRAY® technology.

1) DNA isolation from plasma samples.
2) Digestion of the DNA targets using methylation sensitive restriction enzymes (for example, HhaI and HpaII).

For each reaction the available DNA was mixed with water to a final volume of 25 ul.

10 ul of a reaction mix consisting of 10 units HhaI, 10 units HpaII and a reaction buffer were added. The sample was incubated at an optimal temperature for the restriction enzymes. HhaI and HpaII digest non-methylated DNA (and will not digest hemi- or completely methylated DNA). Following digestion, the enzymes were denatured using a heating step.

3) Genomic Amplification—PCR was performed in a total volume of 50 ul by adding PCR reagents (Buffer, dNTPs, primers and polymerase). Exemplary PCR and extend primers are provided below. In addition, synthetic competitor oligonucleotide was added at known concentrations.

4) Replicates (optional)—Following PCR the 50 ul reaction was split into 5 ul parallel reactions (replicates) in order to minimize variation introduced during the post PCR steps of the test. Post PCR steps include SAP, primer extension (MassEXTEND® technology), resin treatment, dispensing of spectrochip and MassARRAY.

5) Quantification of the Amplifiable Genomes—Sequenom MassARRAY® technology was used to determine the amount of amplification product for each assay. Following PCR, a single base extension assay was used to interrogate the amplified regions (including the competitor oligonucleotides introduced in step 3). Specific extend primers designed to hybridize directly adjacent to the site of interest were introduced. See extend primers provided below. These DNA oligonucleotides are referred to as iPLEX® MassEXTEND® primers. In the extension reaction, the iPLEX primers were hybridized to the complementary DNA templates and extended with a DNA polymerase. Special termination mixtures that contain different combinations of deoxy- and dideoxynucleotide triphosphates along with enzyme and buffer, directed limited extension of the iPLEX primers. Primer extension occurs until a complementary dideoxynucleotide is incorporated.

The extension reaction generated primer products of varying length, each with a unique molecular weight. As a result, the primer extension products can be simultaneously separated and detected using Matrix Assisted Laser Desorption/Ionization, Time-Of-Flight (MALDI-TOF) mass spectrometry on the MassARRAY® Analyzer Compact. Following this separation and detection, SEQUENOM's proprietary software automatically analyzes the data.

Figure 18:
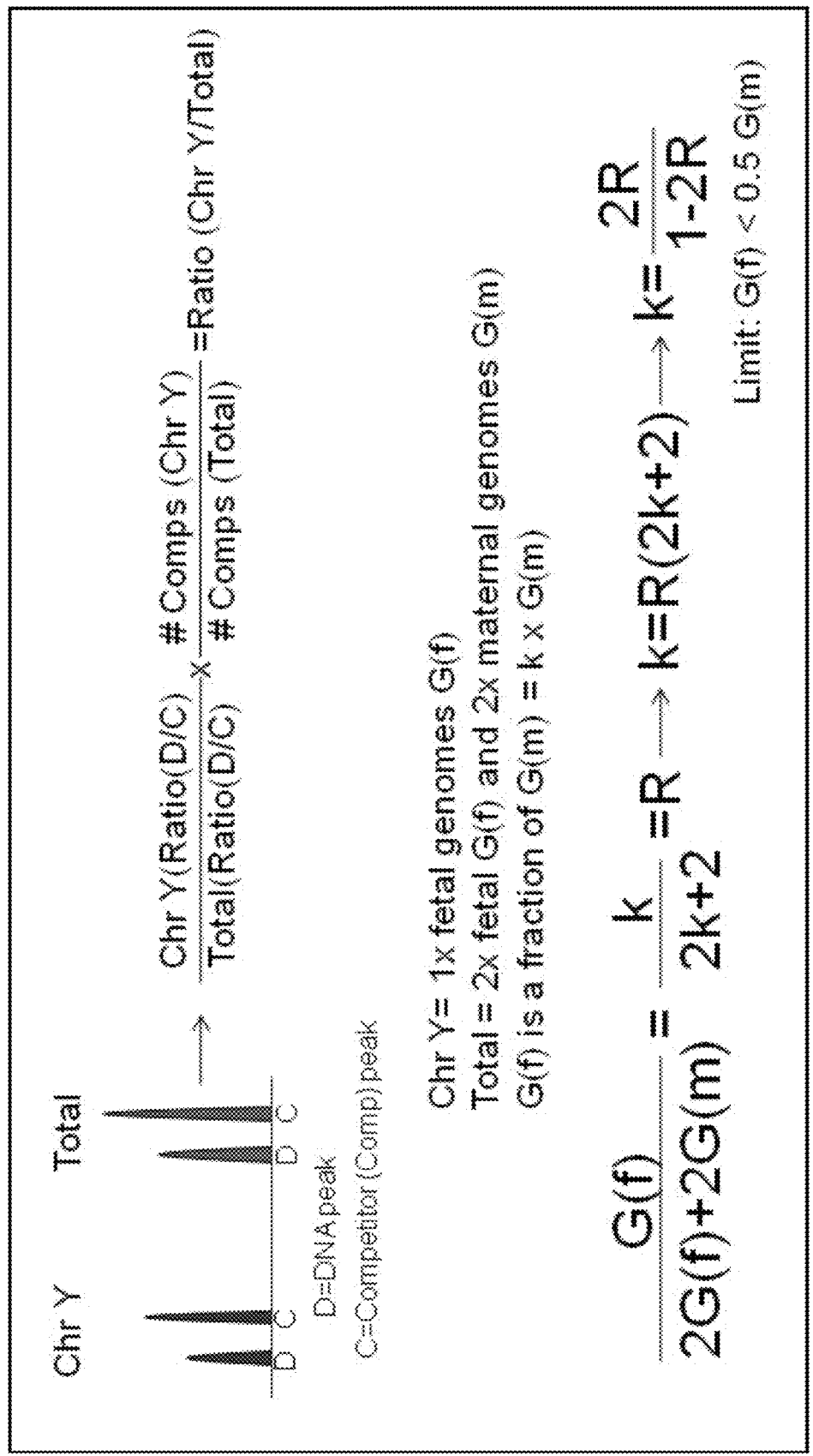
FIG. 18 provides a specific method for calculating fetal DNA fraction (or concentration) in a sample using the Y-chromosome-specific markers for male pregnancies and the mean of the methylated fraction for all pregnancies (regardless of fetal sex).

6) Calculating the amount and concentration of fetal nucleic acid—Methods for calculating the total amount of genomic equivalents present in the sample, the amount (and concentration) of fetal nucleic acid isolated from a male pregnancy, and the amount (and concentration) of fetal nucleic based on differentially methylated targets are provided below and in FIGS. 18 and 19.

The above protocol can be used to perform one or more of the assays described below. In addition to the sequences provided immediately below, a multiplex scheme that interrogates multiple targets is provided in Table X below.

1) Assay for the Quantification of the Total Number of Amplifiable Genomic Equivalents in the Sample.

Targets were selected in housekeeping genes not located on the chromosomes 13, 18, 21, X or Y. The targets should be in a single copy gene and not contain any recognition sites for the methylation sensitive restriction enzymes.

Underlined sequences are PCR primer sites, italic is the site for the single base extend primer and bold letter (C) is the nucleotide extended on human DNA ApoE Chromosome 19:45409835-45409922 DNA target sequence with interrogated nucleotide C in bold. All of the chromosome positions provided in this section are from the February 2009 UCSC Genome Build.

(SEQ ID NO: 262)
GA<u>TTGACAGTTTCTCCTTCCCC</u>AGACTGGCCAATCACAGG*CAGGAAGATG*

AA<u>GGTTCTGTGGG</u><u>CTGCGTTGCTGGTCACATTCC</u>TGGC

-continued

ApoE Forward Primer:
(SEQ ID NO: 263)
5'-ACGTTGGATG-TTGACAGTTTCTCCTTCCCC (Primer contains a 5' 10 bp MassTag separated by a dash)

ApoE Reverse Primer:
(SEQ ID NO: 264)
5'-ACGTTGGATG-GAATGTGACCAGCAACGCAG (Primer contains a 5' 10 bp MassTag separated by a dash)

ApoE Extension Primer:
(SEQ ID NO: 265)
5'-GCAGGAAGATGAAGGTT [C/T]

Primer extends C on human DNA targets and T on synthetic DNA targets

ApoE synthetic competitor oligonucleotide:
(SEQ ID NO: 266)
5'-GATTGACAGTTTCTCCTTCCCCAGACTGGCCAATCACAGGCAGGAAG

ATGAAGGTTTTGTGGGCTGCGTTGCTGGTCACATTCCTGGC (Bold T at position 57 is different from human DNA)

2) Assay for the Quantification of the Total Number of Chromosome Y Sequences in the Sample.

Targets specific for the Y-chromosome were selected, with no similar or paralog sequences elsewhere in the genome. The targets should preferably be in a single copy gene and not contain any recognition sites for the methylation sensitive restriction enzyme(s).

Underlined sequences are PCR primer sites, and italic nucleotide(s) is the site for the single-base extend primer and bold letter (C) is the nucleotide extended on human DNA.

SRY on chrY: 2655628-2655717 (reverse complement)
(SEQ ID NO: 267)
GAGTTT<u>TGGATAGTAAAATAAGTTTCGAACTCTGGCACC</u>*TTTCAATTTTG*

*TCGCACT*C*TCCTT*<u>GTTTTTGACAATGCAATCATATGCTTC</u>

SRY Forward Primer:
(SEQ ID NO: 268)
5'-ACG-TGGATAGTAAAATAAGTTTCGAACTCTG (Primer contains a 5' 3 bp MassTag separated by a dash)

SRY Reverse Primer:
(SEQ ID NO: 269)
5'- GAAGCATATGATTGCATTGTCAAAAAC

SRY Extension Primer:
(SEQ ID NO: 270)
5'-aTTTCAATTTTGTCGCACT [C/T]

Primer extends C on human DNA targets and T on synthetic DNA targets. 5' Lower case "a" is a non-complementary nucleotide SRY synthetic competitor oligonucleotide:
(SEQ ID NO: 271)
5'-GAGTTTTGGATAGTAAAATAAGTTTCGAACTCTGGCACCTTTCAATT

TTGTCGCACTTTCCTTGTTTTTGACAATGCAATCATATGCTTC

3) Assay for the Quantification of Fetal Methylated DNA Sequences Present in the Sample.

Targets were selected in regions known to be differentially methylated between maternal and fetal DNA. Sequences were selected to contain several restriction sites for methylation sensitive enzymes. For this study the HhaI (GCGC) and HpaII (CCGG) enzymes were used.

Underlined sequences are PCR primer sites, italic is the site for the single base extend primer and bold letter (C) is the nucleotide extended on human DNA, lower case letter are recognition sites for the methylation sensitive restriction enzymes.

TBX3 on chr12: 115124905-115125001
(SEQ ID NO: 272)
GAACTCC<u>TCTTTGTCTCTGCGTGC</u>ccggcgcgc*CCCCCTCccgg*TGGGTG

*ATAAAC*CCACTCTGgcgccgg<u>CCATgcgcTGGGTGATTAATTTGCGA</u>

TBX3 Forward Primer:
(SEQ ID NO: 273)
5'- ACGTTGGATG-TCTTTGTCTCTGCGTGCCC (Primer contains a 5' 10 bp MassTag separated by a dash)

TBX3 Reverse Primer:
(SEQ ID NO: 274)
5'- ACGTTGGATG-TTAATCACCCAGCGCATGGC (Primer contains a 5' 10 bp MassTag separated by a dash)

TBX3 Extension Primer:
(SEQ ID NO: 275)
5'- CCCCTCCCGGTGGGTGATAAA [C/T]

Primer extends C on human DNA targets and T on synthetic DNA targets. 5' Lower case "a" is a non-complementary nucleotide TBX3 synthetic competitor oligonucleotide:
(SEQ ID NO: 276)
5'-GAACTCCTCTTTGTCTCTGCGTGCCCGGCGCGCCCCCCTCCCGGTGG

GTGATAAATCCACTCTGGCGCCGGCCATGCGCTGGGTGATTAATTTGCGA

4) Control Assay for the Enzyme Restriction Efficiency.

Targets were selected in regions known not to be methylated in any tissue to be investigated. Sequences were selected to contain no more than one site for each restriction enzyme to be used.

Underlined sequences are PCR primer sites, italic nucleotide(s) represent the site for the single-base extend primer and bold letter (G) is the reverse nucleotide extended on human DNA, lower case letter are recognition sites for the methylation sensitive restriction enzymes.

CACNA1G chr17: 48637892-48637977 (reverse complement)
(SEQ ID NO: 277)
<u>CCATTGGCCGTCCGCCGTGGCAGTGCGGGCGGGA</u>gcgcAGG*GAGAGAACC*

*ACAGCTGGAATCCGA*<u>TTCCCACCCCAAAACCCAGGA</u>

HhaI Forward Primer:
(SEQ ID NO: 278)
5'- ACGTTGGATG-CCATTGGCCGTCCGCCGTG (Primer contains a 5' 10 bp MassTag separated by a dash)

HhaI Reverse Primer:
(SEQ ID NO: 279)
5'- ACGTTGGATG-TCCTGGGTTTTGGGGTGGGAA

-continued (Primer contains a 5' 10 bp MassTag separated by a dash)

Hhal Extension Primer:
(SEQ ID NO: 280)
5'- TTCCAGCTGTGGTTCTCTC

Hhal synthetic competitor oligonucleotide:
(SEQ ID NO: 281)
5'-<u>CCATTGGCCGTCCGCCGTGGCAGTGCGGGCGGGAGCGC</u>AGAGAGAGA
*ACCACAGCTGGAATCCGA*<u>TTCCCACCCCAAAACCCAGGA</u>

Validation Experiments

The sensitivity and accuracy of the present technology was measured using both a model system and clinical samples. In the different samples, a multiplex assay was run that contains 2 assays for total copy number quantification, 3 assays for methylation quantification, 1 assay specific for chromosome Y and 1 digestion control assay. See Table X. Another multiplex scheme with additional assays is provided in Table Y.

TABLE X

PCR Primers and Extend Primers

| Gene ID | First Primer *(SEQ ID NOS 282-288) | Second Primer (SEQ ID NOS 289-295) | Extend Primer (SEQ ID NOS 296-302) |
|---|---|---|---|
| SOX14 | M ACGTTGGATGACATGGTCGGCCCCACGGAAT | ACGTTGGATGCTCCTTCCTAGTGTGAGAACCG | CAGGTTCCGGGGCTTGGG |
| Hhal_CTRL | D ACGTTGGATGACCCATTGGCCGTCCGCCGT | ACGTTGGATGTTTTGGGGTGGGAATCGGATT | CGCAGGGAGAGAACCACAG |
| TBX3 | M ACGTTGGATGGAACTCCTCTTTGTCTCTGCG | ACGTTGGATGTGGCATGGCCGGCGCCAGA | CCCCTCCCGGTGGGTGATAAA |
| SRY | Y ACGTTGGATGCGCAGCAACGGGACCGCTACA | ACGTTGGCATCTAGGTAGGTCTTTGTAGCCAA | AAAGCTGTAGGACAATCGGGT |
| ALB | T ACGTTGCGTAGCAACCTGTTACATATTAA | ACGTTGGATCTGAGCAAAGGCAATCAACACCC | CATTTTTCTACATCCTTTGTTT |
| EDG6 | M ACGTTGGATGCATAGAGGCCCATGATGGTGG | ACGTTGGATGACCTTCTGCCCCTCTACTCCAA | agAAGATCACCAGGCAGAAGAGG |
| RNaseP | T ACGTTGGATGGTGTGGTCAGCTCTTCCCTTC AT | ACGTTGGCCCACATGTAATGTTGAAAAAGCA | ACTTGGAGAACAAAGGACACCGT TA |

Competitor Oligonucleotide Sequence

| Gene ID | *Competitor Oligonucleotide Sequence (SEQ ID NOS 303-309) |
|---|---|
| SOX14 | M GGTCGGCCCCACGGAATCCCGGCTCTGTGTGCGCCCAGGTTCCGGGGCTTGGGTGTTGCCGGTTCTCACACTAGGAAGGAG |
| Hhal_CTRL | D CCATTGGCCGTCCGCCGTGGCAGTGCGGGCGGGAGCGCAGAGAGAGAACCACAGCTGGAATCCGATTCCCACCCCAAAA |
| TBX3 | M GAACTCCTCTTTGTCTCTGCGTGCCCGGCGCGCCCCCCTCCCGGTGGGTGATAAATCCACTCTGGCGCCGGCCATGC |
| SRY | Y GCAGCAACGGGACCGCTACAGCCACTGGACAAAGCCGTAGGACAATCGGGTAACATTGGCTACAAAGACCTACCTAGATGC |
| ALB | T GCGTAGCAACCTGTTACATATTAAAGTTTTATTATACTACATTTTTCTACATCCTTTGTTTCAGAGTGTTGATTGCCTTTG CTCAGTATCTTCAG |
| EDG6 | M CCTTCTGCCCCTCTACTCCAAGCGCTACACCCTCTTCTGCCTGGTGATCTTTGCCGGCGTCCTGGCCACCATCATGGGCCTCTATG |
| RNaseP | T GTGTGGTCAGCTCTTCCCTTCATCACATACTTGGAGAACAAAGGACACCGTTATCCATGCTTTTTCAACACATTACATGTGGG |

TABLE Y

PCR Primers and Extend Primers

| Gene ID | First Primer (SEQ ID NOS *310-319) | Second Primer (SEQ ID NOS 320-329) | Extend Primer (SEQ ID NOS 330-339) |
|---|---|---|---|
| EDG6 | M ACGTTGGATGTTCTGCCCCTCTACTCCAAG | ACGTTGGATGCATAGAGGCCCATGATGGTG | TTCTGCCTGGTGATCTT |
| RNAseP | T ACGTTGGATGTCAGCTCTTCCCTTCATCAC | ACGTTGGATGCCTACCTCCCACATGTAATGT | AACAAAGGACACCGTTA |
| ApoE | T ACGTTGGATGTTGACAGTTTCTCCTTCCCC | ACGTTGGATGGAATGTGACCAGCAACGCAG | GCAGGAAGATGAAGGTT |
| SOX14 | M ACGTTGGATGCGGTCGGCCCCACGGAAT | ACGTTGGATGCTCCTTCCTAGTGTGAGAACCG | aAGGTTCCGGGGCTTGGG |
| SRY no2 | Y ACGTGGATAGTAAAATAAGTTTCGAACTCTG | GAAGCATATGATTGCATTGTCAAAAAC | aTTTCAATTTTGTCGCACT |
| SRY no1 | Y ACGTTGGATGCACAGCTCACCGCAGCAACG | ACGTTGGATGCTAGGTAGGTCTTTGTAGCCAA | AGCTGTAGGACAATCGGGT |
| TBX3 | M ACGTTGGATGTCTTTGTCTCTGCGTGCCC | ACGTTGGATGTTAATCACCCAGCGCATGGC | CCCTCCCGGTGGGTGATAAA |
| CACNA1G dig CTRL 1 | D ACGTTGGATGGACTGAGCCCCAGAACTCG | ACGTTGGATGGTGGGTTTGTGCTTTCCACG | AGGGCCGGGGTCTGCGCGTG |
| DAPK1 dig CTRL 2 | D ACGTTGGATGAAGCCAAGTTTCCCTCCGC | ACGTTGGATGCTTTTGCTTTCCCAGCCAGG | GAGGCACTGCCCGGACAAACC |
| ALB | T ACGTTAGCGTAGCAACCTGTTACATATTAA | ACGTTGGATGCTGAGCAAAGGCAATCAACA | CATTTTTCTACATCCTTTGTTT |

Competitor Oligonucleotide Sequence

| Gene ID | *Competitor (SEQ ID NOS 340-349) |
|---|---|
| EDG6 | M CCTTCTGCCCCTCTACTCCAAGCGCTACACCCTCTTCTGCCTGGTGATCTTTGCCGGCGTCCTGGCCACCATCATGGGCCTCTATG |
| RNAseP | T GTGTGGTCAGCTCTTCCCTTCATCACATACTTGGAGAACAAAGGACACCGTTATCCATGCTTTTTCAACACATTACATGTGGGAGGTAGG |
| ApoE | T GATTGACAGTTTCTCCTTCCCCAGACTGGCCAATCACAGGCAGGAAGATGAAGGTTTTGTGGGCTGCGTTGCTGGTCACATTCCTGGC |
| SOX14 | M AAAACCAGAGATTCGCGGTCGGCCCCACGGAATCCCGGCTCTGTGTGCGCCCAGGTTCCGGGGCTTGGGTGTTGCCGGTTCTCACACTAG GAAGGAGC |

TABLE Y-continued

| | | |
|---|---|---|
| SRY n02 | Y | GAGTTTTGGATAGTAAAATAAGTTTCGAACTCTGGCACCTTTCAATTTTGTCGCACTTTCCTTGTTTTTGACAATGCAATCATATGCTTC |
| SRY no1 | Y | GCAGCCAGCTCACCGCAGCAACGGGACCGCTACAGCCACTGGACAAAGCTGTAGGACAATCGGGTGACATTGGCTACAAAGACCTACCTAGATGC |
| TBX3 | M | GAACTCCTCTTTGTCTCTGCGTGCCCGGCGCGCCCCCCTCCCGGTGGGTGATAAATCCACTCTGGCGCCGGCCATGCGCTGGGTGATTAATTTGCGA |
| CACNA1G dig CTRL 1 | D | GTGGGTTTGTGCTTTCCACGCGTGCACACACACGCGCAGACCCCGGCCCTTGCCCCGCCTACCTCCCGAGTTCTGGGGCTCAGTC |
| DAPK1 dig CTRL 2 | D | GCGCCAGCTTTTGCTTTCCCAGCCAGGGCGCGGTGAGGTTTGTCCGGGCAGTGCCTCGAGCAACTGGGAAGGCCAAGGCGGAGGGAAAC |
| ALB | T | GCGTAGCAACCTGTTACATATTAAAGTTTTATTATACTACATTTTTCTACATCCTTTGTTTTAGGGTGTTGATTGCCTTTGCTCAGTATCTTCAGC |

Figure 12:
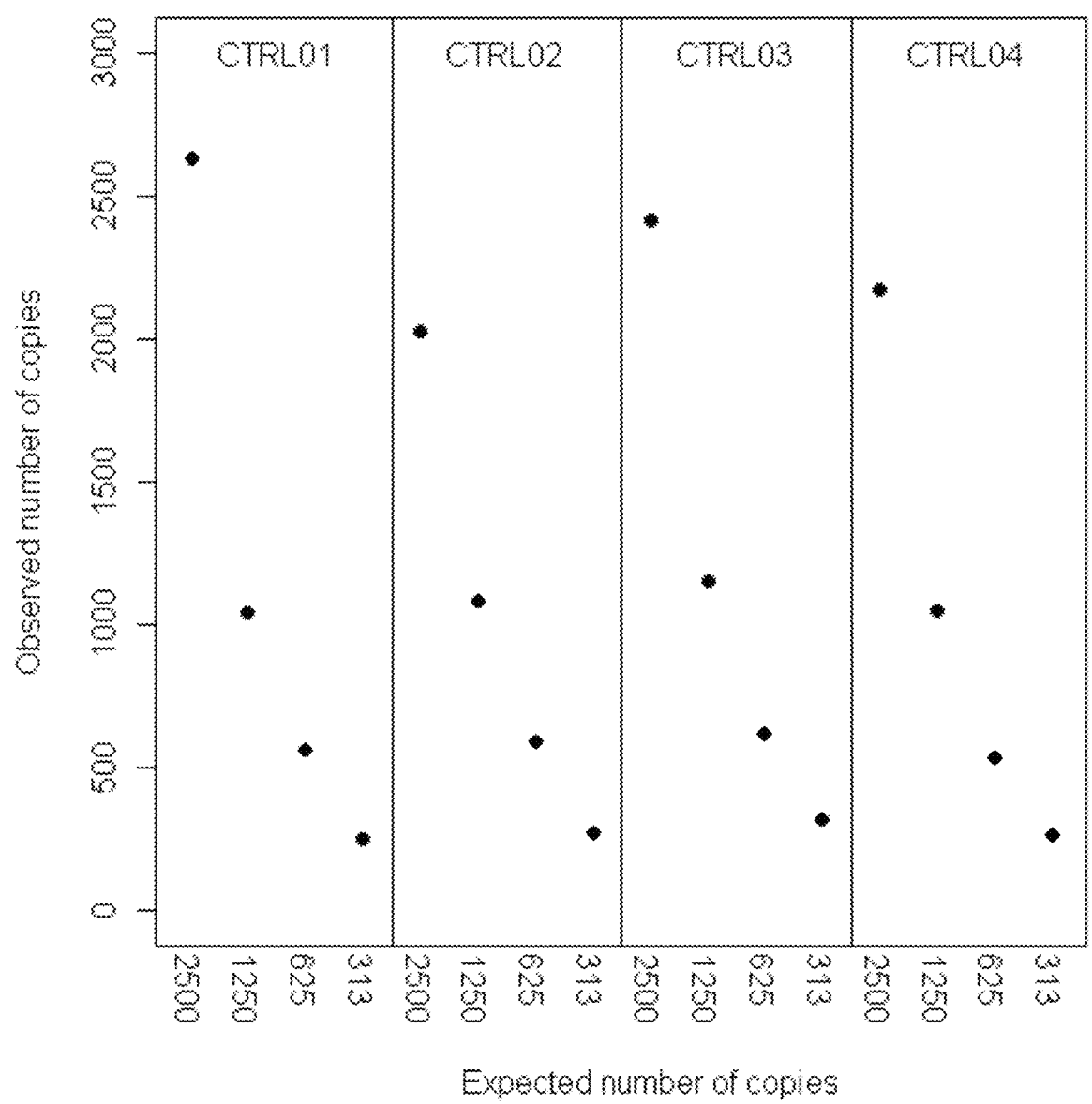
FIG. 12 shows the total number of amplifiable genomic copies from four different DNA samples isolated from the blood of non-pregnant women. Each sample was diluted to contain approximately 2500, 1250, 625 or 313 copies per reaction. Each measurement was obtained by taking the mean DNA/competitor ratio obtained from two total copy number assays (ALB and RNAseP in Table X). As FIG. 12 shows, the total copy number is accurate and stable across the different samples, thus validating the usefulness of the competitor-based approach.

T = Assay for Total Amount
M = Assay for Methylation quantification
Y = Y-Chromosome Specific Assay
D = Digestion control Model System Using Genomic DNA In order to determine the sensitivity and accuracy of the method when determining the total number of amplifiable genomic copies in a sample, a subset of different DNA samples isolated from the blood of non-pregnant women was tested. Each sample was diluted to contain approximately 2500, 1250, 625 or 313 copies per reaction. The total number of amplifiable genomic copies was obtained by taking the mean DNA/competitor ratio obtained from the three total copy number assays. The results from the four different samples are shown in FIG. 12.

Figure 13A:
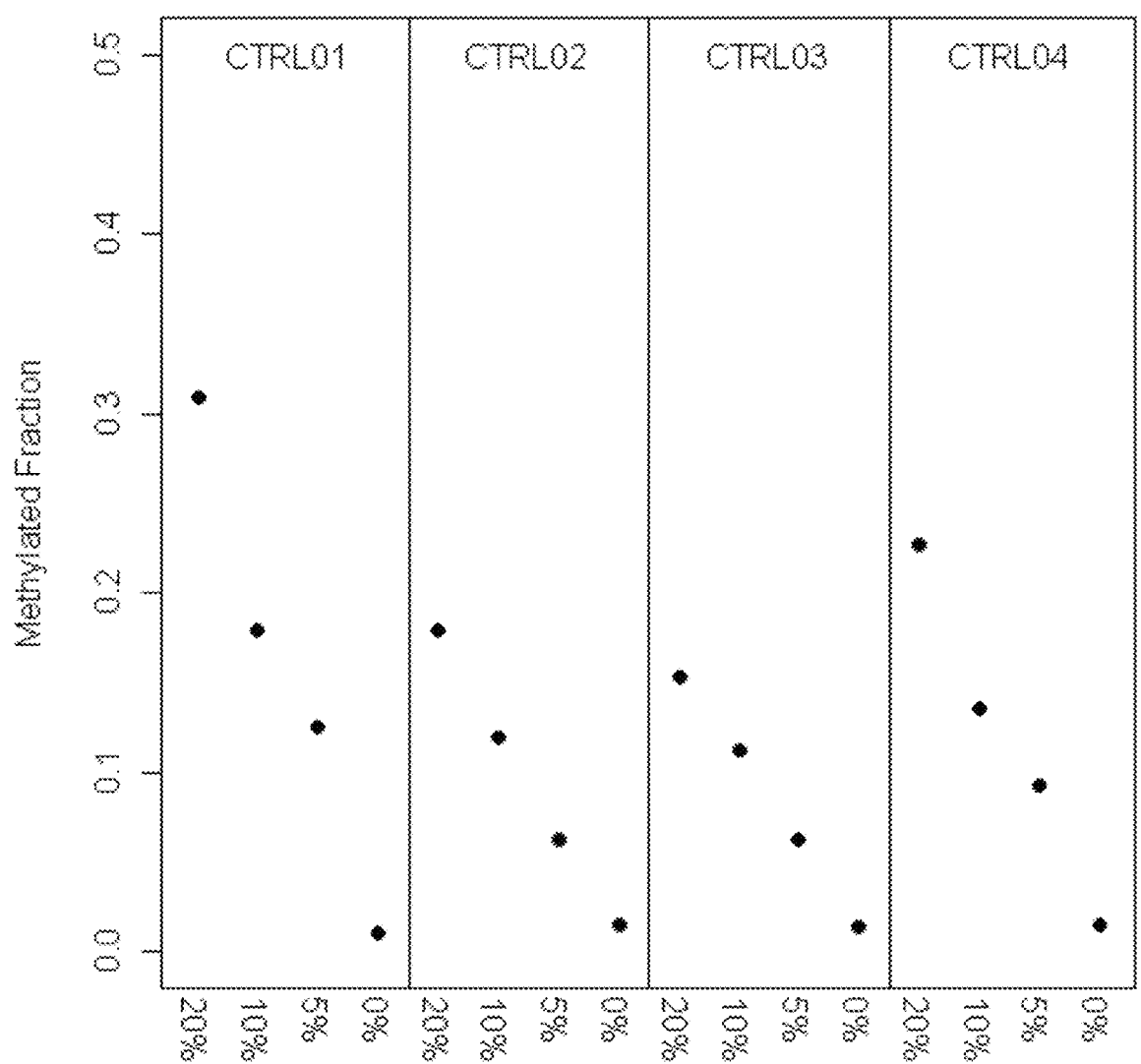
FIGS. 13A and 13B show a model system that was created that contained a constant number of maternal non-methylated DNA with varying amounts of male placental methylated DNA spiked-in. The samples were spiked with male placental amounts ranging from approximately 0 to 25% relative to the maternal non-methylated DNA. The fraction of placental DNA was calculated using the ratios obtained from the methylation assays (FIG. 13A) and the Y-chromosome marker (FIG. 13B) as compared to the total copy number assay. The methylation and Y-chromosome markers are provided in Table X.
Figure 13B:
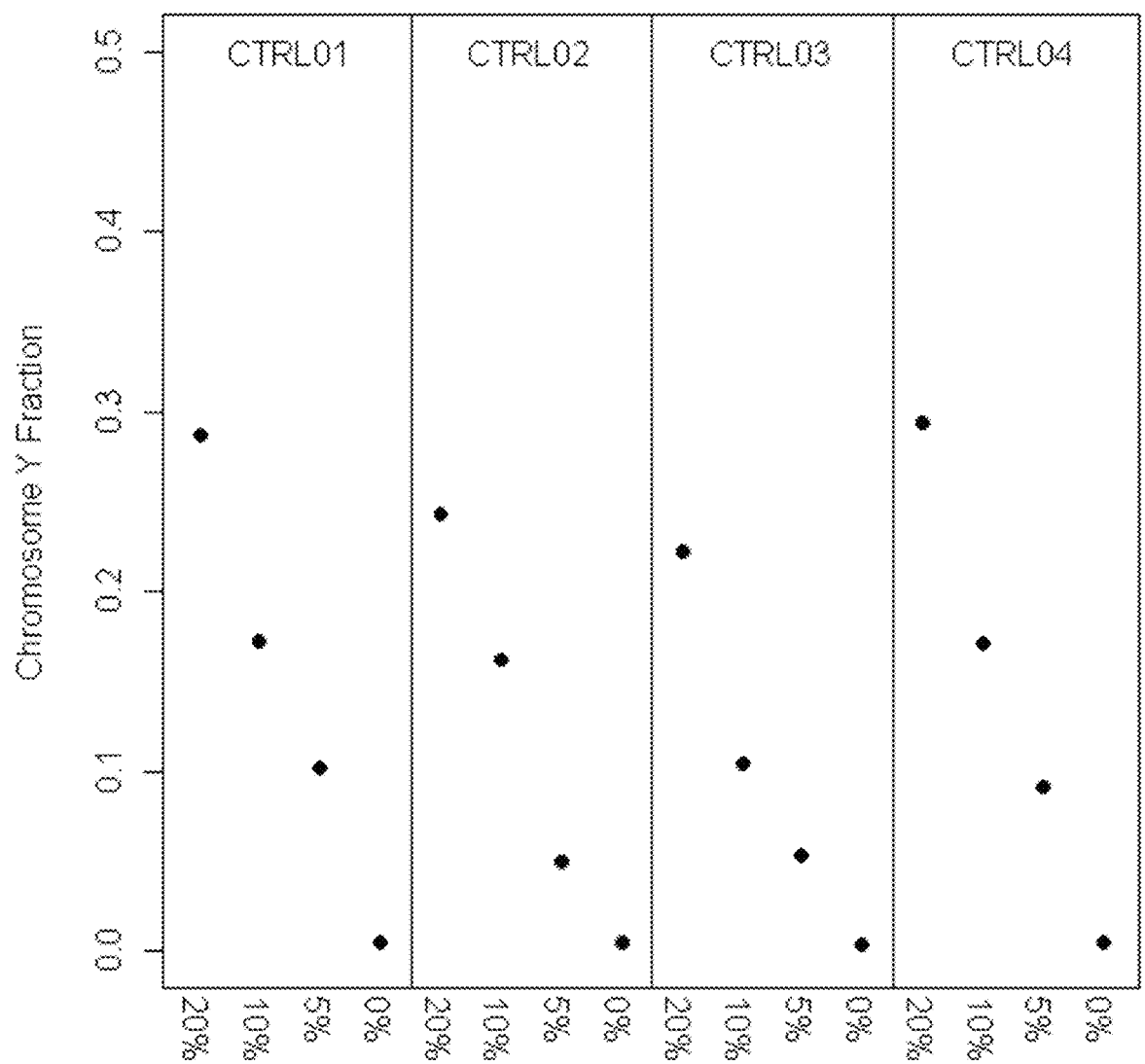

To optimize the reaction, a model system was developed to simulate DNA samples isolated from plasma. These samples contained a constant number of maternal non-methylated DNA and were spiked with different amounts of male placental methylated DNA. The samples were spiked with amounts ranging from approximately 0 to 25% relative to the maternal non-methylated DNA. The results are shown in FIGS. 13A and B. The fraction of placental DNA was calculated using the ratios obtained from the methylation assays (FIG. 13A), the SRY markers (FIG. 13B) and the total copy number assays. The primer sequences for the methylation assays (TBX), Y-chromosome assays (SRY) and total copy number (APOE) are provided above. The model system demonstrated that the methylation-based method performed equal to the Y-chromosome method (SRY markers), thus validating the methylation-based method as a sex-independent fetal quantifier.

Plasma Samples

To investigate the sensitivity and accuracy of the methods in clinical samples, 33 plasma samples obtained from women pregnant with a male fetus were investigated using the multiplex scheme from Table X. For each reaction, a quarter of the DNA obtained from a 4 ml extraction was used in order to meet the important requirement that only a portion of the total sample is used.

Total Copy Number Quantification

Figures 14A, 14B:
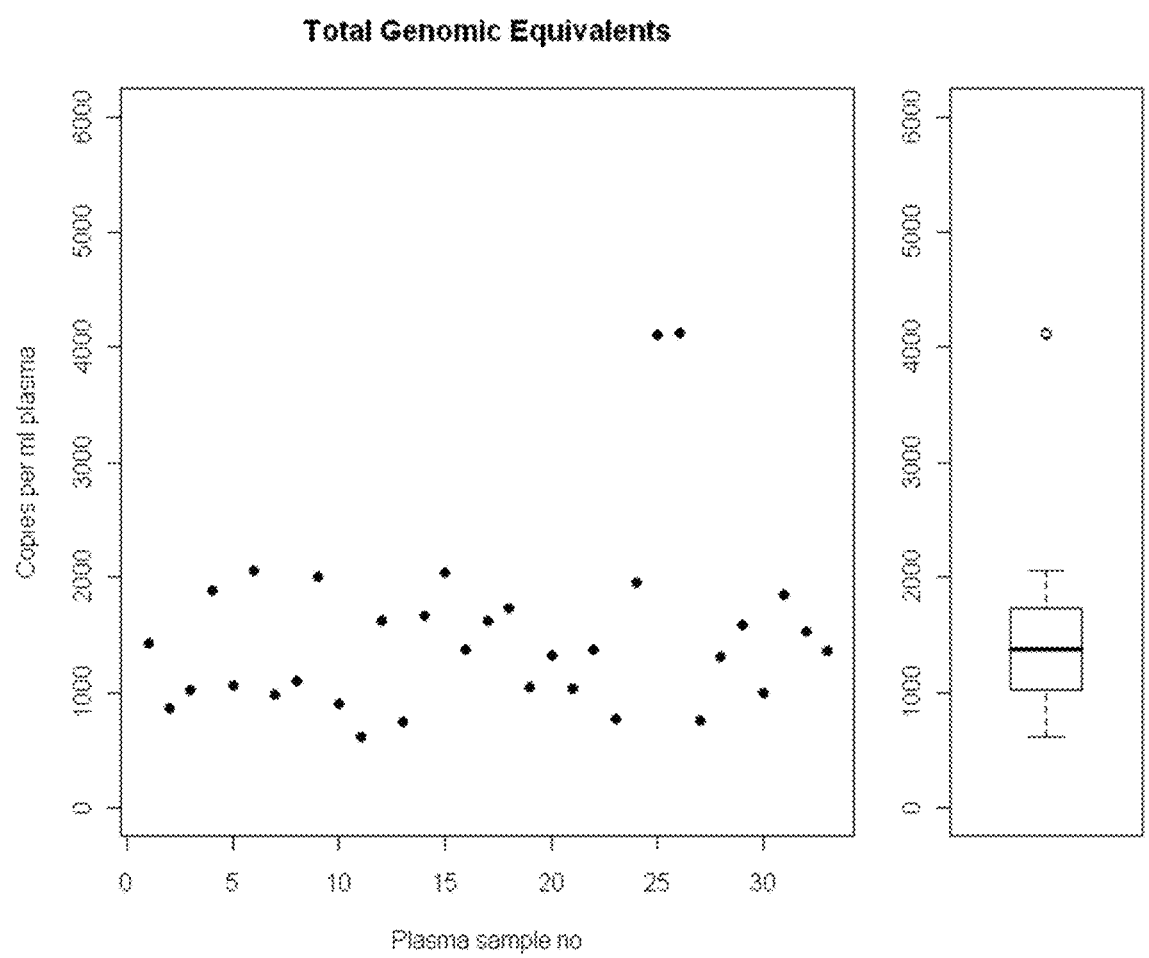
FIGS. 14A and 14B show the results of the total copy number assay from plasma samples.

The results from the total copy number quantification can be seen in FIGS. 14A and B. In FIG. 14A, the copy number for each sample is shown. Two samples (nos. 25 and 26) have a significantly higher total copy number than all the other samples. In general, a mean of approximately 1300 amplifiable copies/ml plasma was obtained (range 766-2055). FIG. 14B shows a box-and-whisker plot of the given values, summarizing the results.

Figures 15A, 15B:
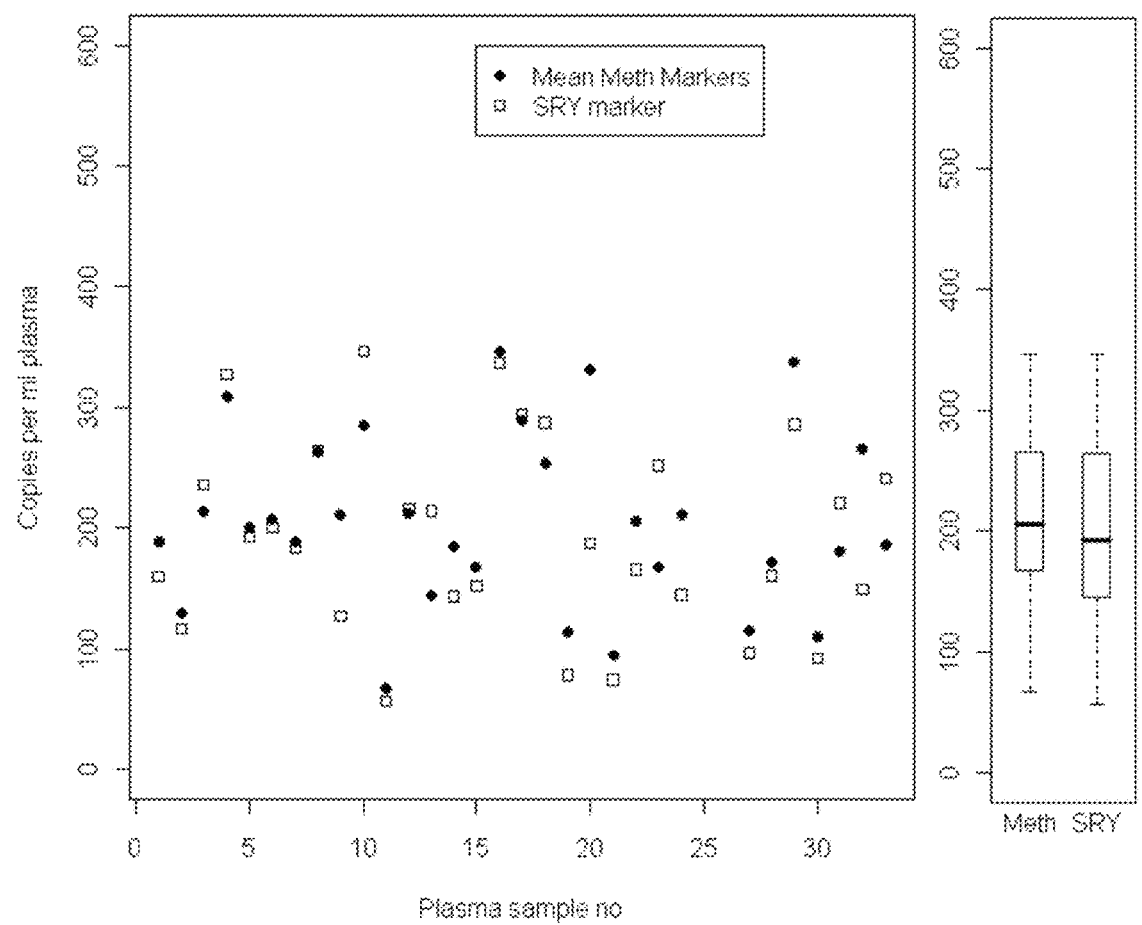
FIGS. 15A and 15B show the amount (or copy numbers) of fetal nucleic acid from 33 different plasma samples taken from pregnant women with male fetuses plotted. The copy numbers obtained were calculated using the methylation markers and the Y-chromosome-specific markers using the assays provided in Table X. As can be seen in FIG. 15B, the box-and-whisker plot of the given values indicated minimal difference between the two different measurements, thus validating the accuracy and stability of the method.

Correlation Between Results Obtained from the Methylation Markers and the Y-Chromosome Marker In FIGS. 15A and B, the numbers of fetal copies for each sample are plotted. As all samples were from male pregnancies. The copy numbers obtained can be calculated using either the methylation or the Y-chromosome-specific markers. As can be seen in FIG. 15B, the box-and-whisker plot of the given values indicated minimal difference between the two different measurements.

Figure 16:
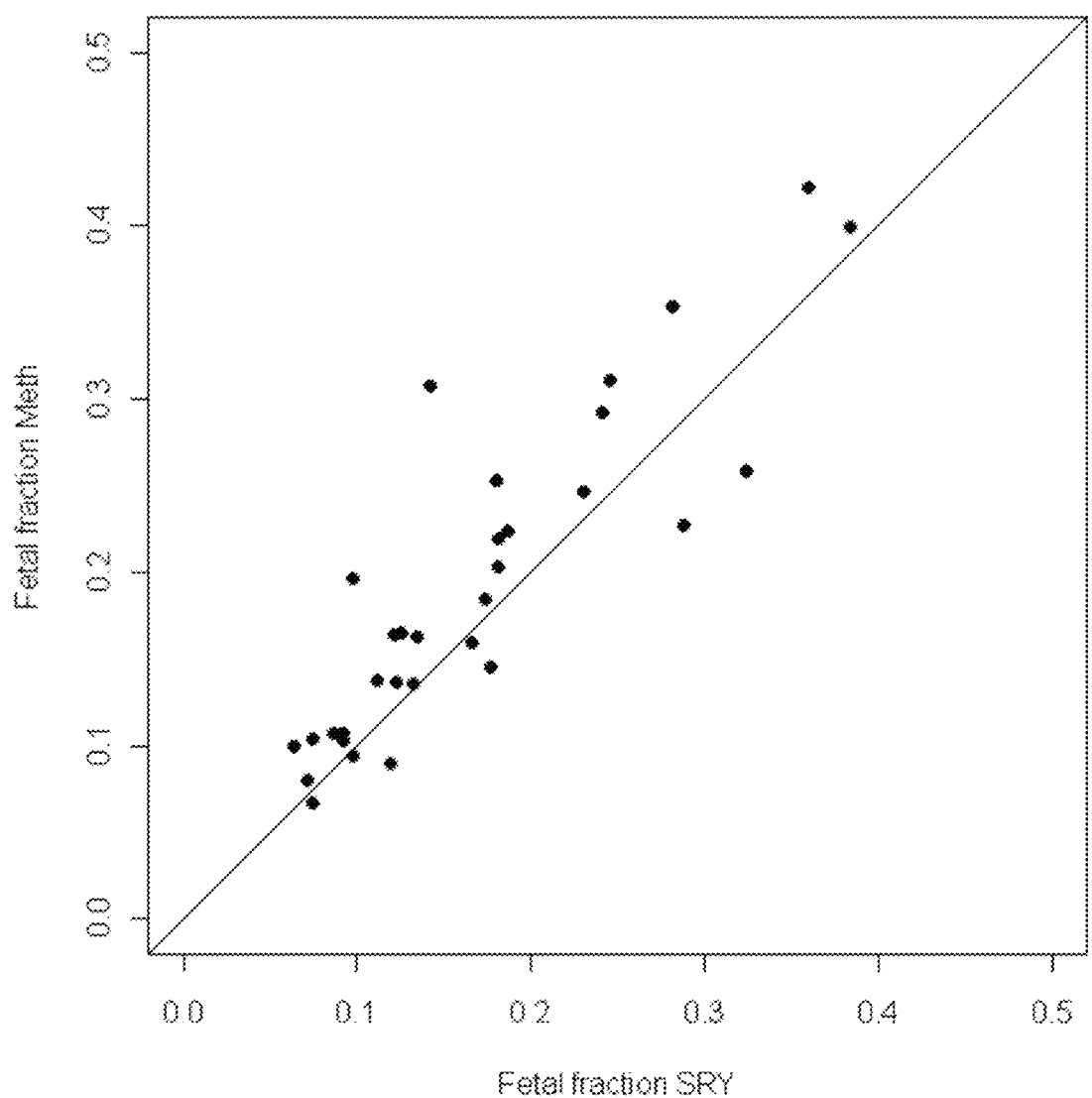
FIG. 16 shows a paired correlation between the results obtained using the methylation markers versus the Y-chromosome marker from FIG. 15A.

The results showing the correlation between results obtained from the methylation markers and the Y-chromosome marker (SRY) is shown in FIG. 16. Again, the methylation-based method performed equal to the Y-chromosome method (SRY markers), further validating the methylation-based method as a sex-independent and polymorphism-independent fetal quantifier. The multiplexed assays disclosed in Table X were used to determine the amount fetal nucleic.

Figure 17:
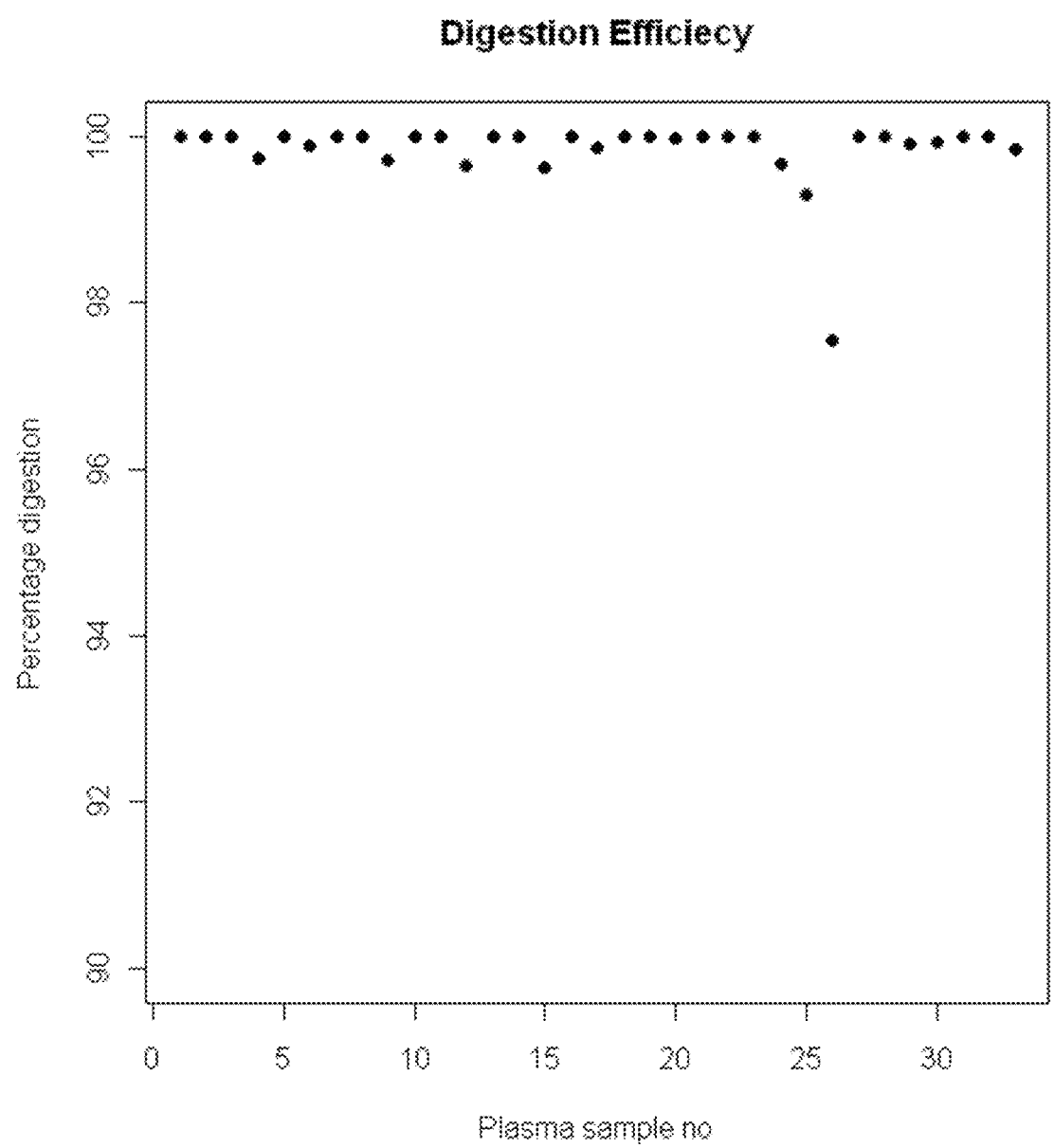
FIG. 17 shows the digestion efficiency of the restriction enzymes using the ratio of digestion for the control versus the competitor and comparing this value to the mean total copy number assays. Apart from sample 26 all reactions indicate the efficiency to be above about 99%.

Finally, the digestion efficiency was determined by using the ratio of digestion for the control versus the competitor and comparing this value to the mean total copy number assays. See FIG. 17. Apart from sample 26 all reactions indicate the efficiency to be above 99%.

Data Analysis

Mass spectra analysis was done using Typer 4 (a Sequenom software product). The peak height (signal over noise) for each individual DNA analyte and competitor assay was determined and exported for further analysis.

The total number of molecules present for each amplicon was calculated by dividing the DNA specific peak by the competitor specific peak to give a ratio. (The "DNA" Peak in FIGS. 18 and 19 can be thought of as the analyte peak for a given assay). Since the number of competitor molecules added into the reaction is known, the total number of DNA molecules can be determined by multiplying the ratio by the number of added competitor molecules.

The fetal DNA fraction (or concentration) in each sample was calculated using the Y-chromosome-specific markers for male pregnancies and the mean of the methylated fraction for all pregnancies. In brief, for chromosome Y, the ratio was obtained by dividing the analyte (DNA) peak by the competitor peak and multiplying this ratio by the number of competitor molecules added into the reaction. This value was divided by a similar ratio obtained from the total number of amplifiable genome equivalents determination (using the Assay(s) for Total Amount). See FIG. 18. Since the total amount of nucleic acid present in a sample is a sum of maternal and fetal nucleic acid, the fetal contribution can be considered to be a fraction of the larger, background maternal contribution. Therefore, translating this into the equation shown in FIG. 18, the fetal fraction (k) of the total nucleic acid present in the sample is equal to the equation: $k = 2 \times R/(1-2R)$, where R is the ratio between the Y-chromosome amount and the total amount. Since the Y-chromosome is haploid and Assays for the Total Amount are determined using diploid targets, this calculation is limited to a fetal fraction smaller than 50% of the maternal fraction.

Figure 19:
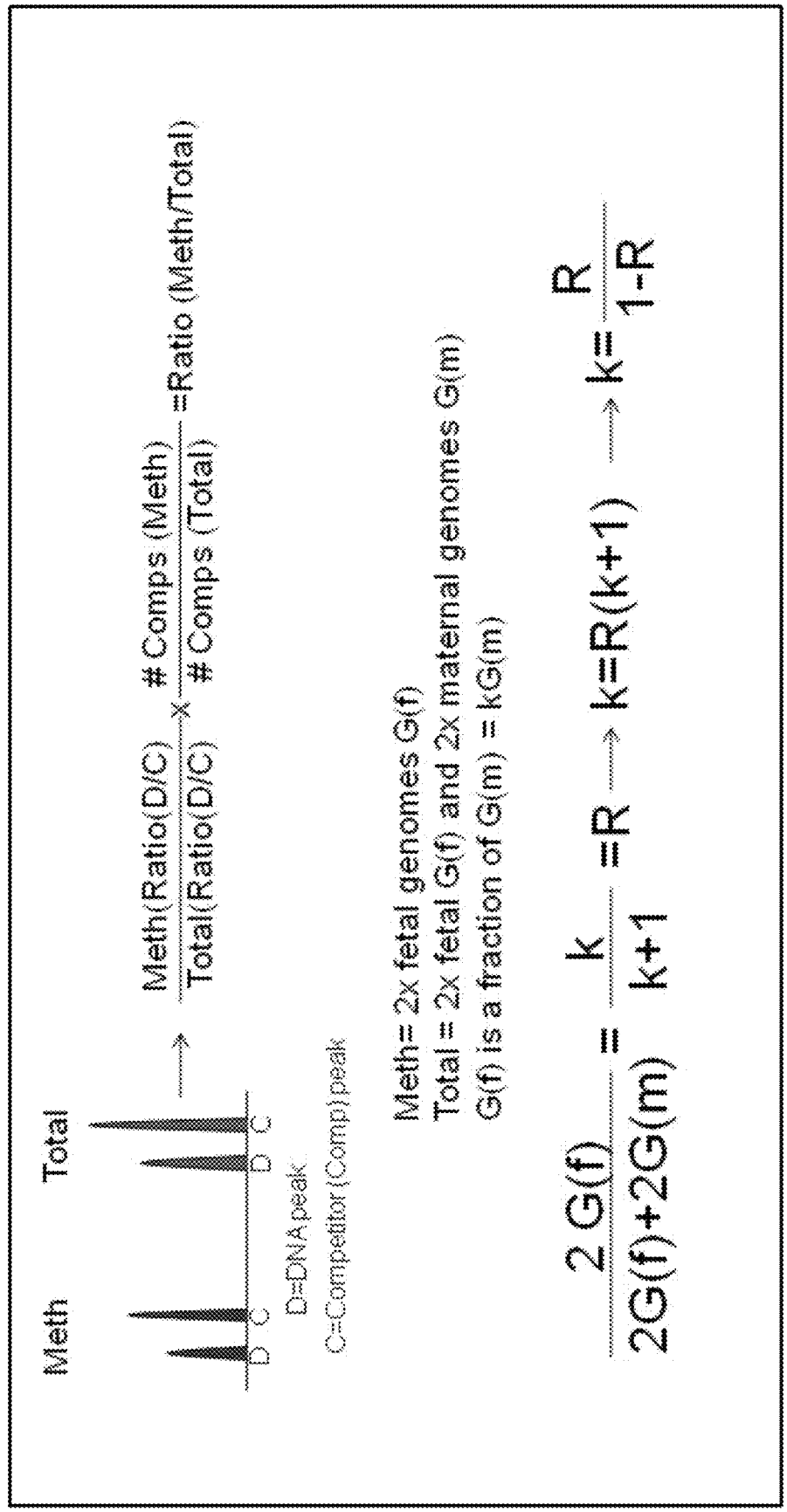
FIG. 19 provides a specific method for calculating fetal DNA fraction (or concentration) in a sample without the Y-chromosome-specific markers. Instead, only the Assays for Methylation Quantification were used to determine the concentration of fetal DNA.

In FIG. 19, a similar calculation for the fetal concentration is shown by using the methylation specific markers (see Assays for Methylation Quantification). In contrast to Y-chromosome specific markers, these markers are from diploid targets, therefore, the limitations stated for the Y-Chromosome Specific Assay can be omitted. Thus, the fetal fraction (k) can be determined using the equation: k=R(1-R), where R is the ratio between the methylation assay and the total assay.

Simulation

Figure 8:
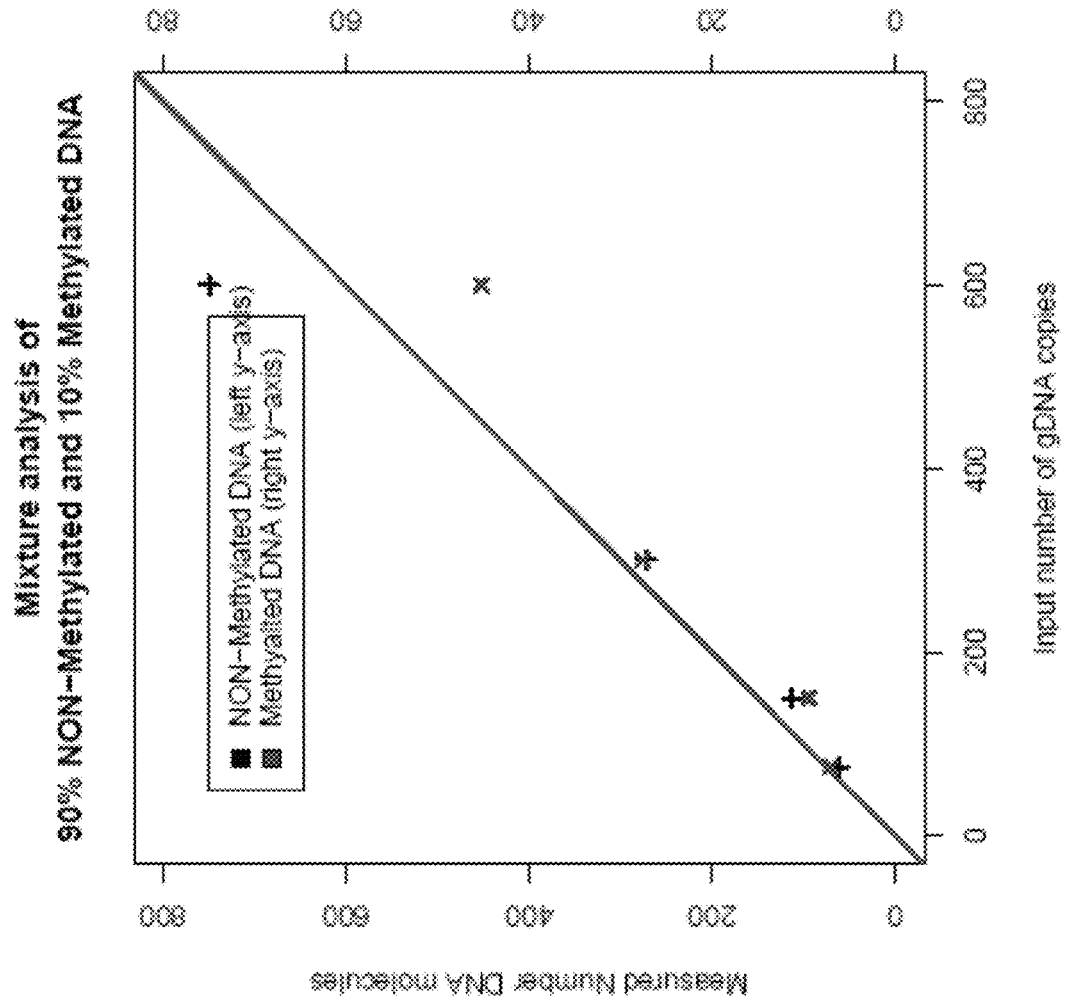
FIG. 8 shows the correlation between the number of gDNA molecules that were expected and the number of molecules measured by competitive PCR in combination with mass spectrometry analysis. In this experiment, DNA derived from whole blood (black plus signs) was used and commercially available fully methylated DNA (red crosses) was used in a 90 to 10 ratio. The MBD-FC fusion protein was used to separate the non-methylated and the methylated fraction of DNA. Each fraction was subject to competitive PCR analysis with mass spectrometry readout. The method has been described earlier for the analysis of copy number variations and is commercially available for gene expression analysis. The approach allows absolute quantification of DNA molecules with the help of a synthetic oligonucleotides of know concentration. In this experiment the MGMT locus was targeted, which was not methylated in the whole blood sample used here. Using an input of 300 total gDNA copies, 270 copies of non-methylated DNA and 30 copies of methylated DNA was expected. The measured copy numbers are largely in agreement with the expected values. The data point at 600 copies of input DNA indicates a bias in the reaction and shows that this initial proof of concept experiment needs to be followed up with more development work, before the assay can be used. However, this initial data indicates the feasibility of the approach for capturing and quantifying of a few copies of methylated DNA in the presence of an excess of unmethylated DNA species.
Figure 9A:
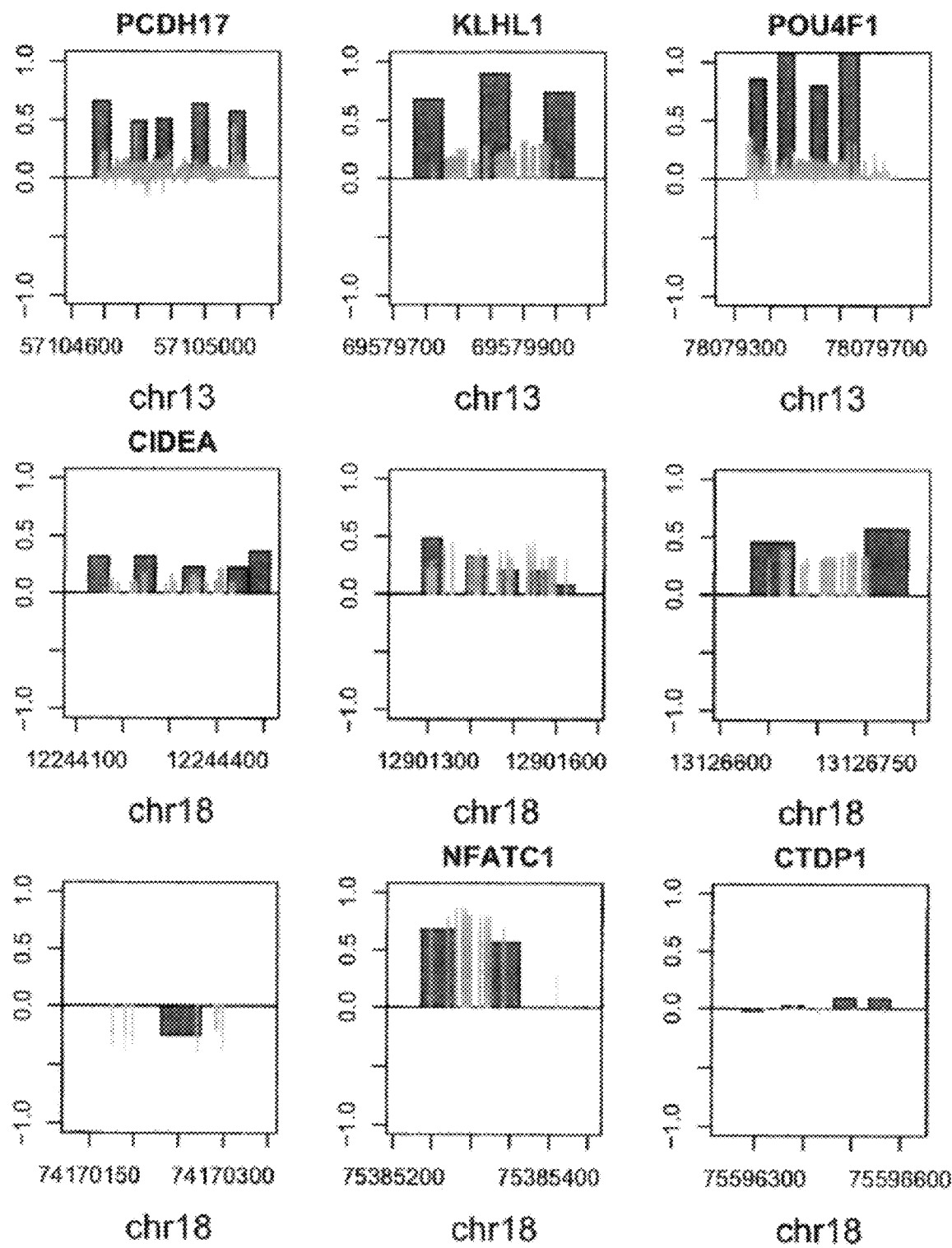
FIG. 9A-9L show bar graph plots of the methylation differences obtained from the microarray analysis (dark bars) and the mass spectrometry analysis (light grey bars) with respect to their genomic location. For each of the 85 regions that were identified to be differentially methylated by microarray an individual plot is provided. The x axis for each plot shows the chromosomal position of the region. The y axis depicts the log ration (in case of the microarrays) and the methylation differences (in case of the mass spectrometry results). For the microarrays each hybridization probe in the area is shown as a single black (or dark grey) bar. For the mass spectrometry results each CpG site, is shown as a light grey bar. Bars showing values greater than zero indicate higher DNA methylation in the placenta samples compared to the maternal DNA. For some genes the differences are small (i.e. RB1 or DSCR6) but still statistically significant. Those regions would be less suitable for a fetal DNA enrichment strategy.
Figure 9B:
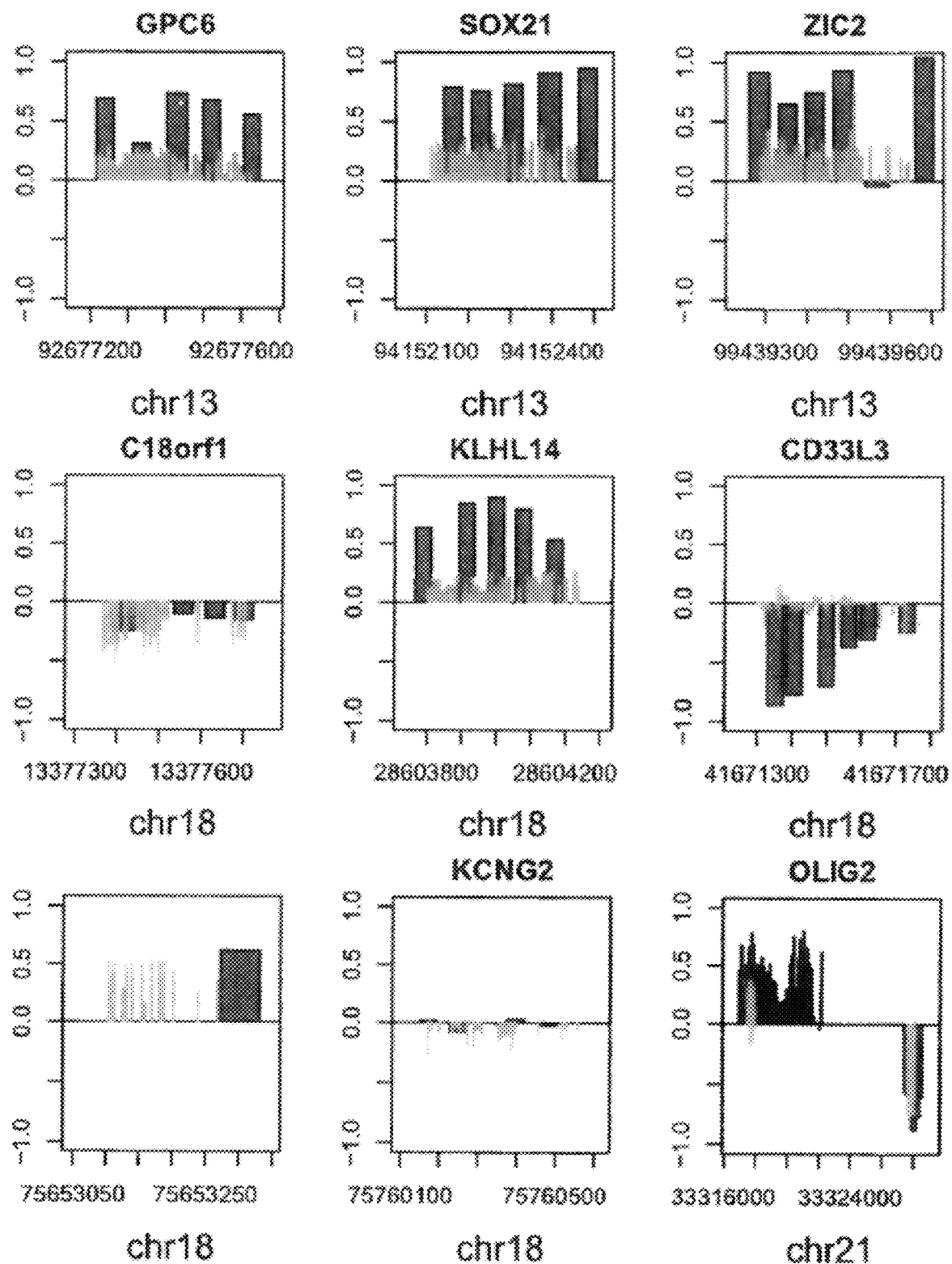
Figure 9C:
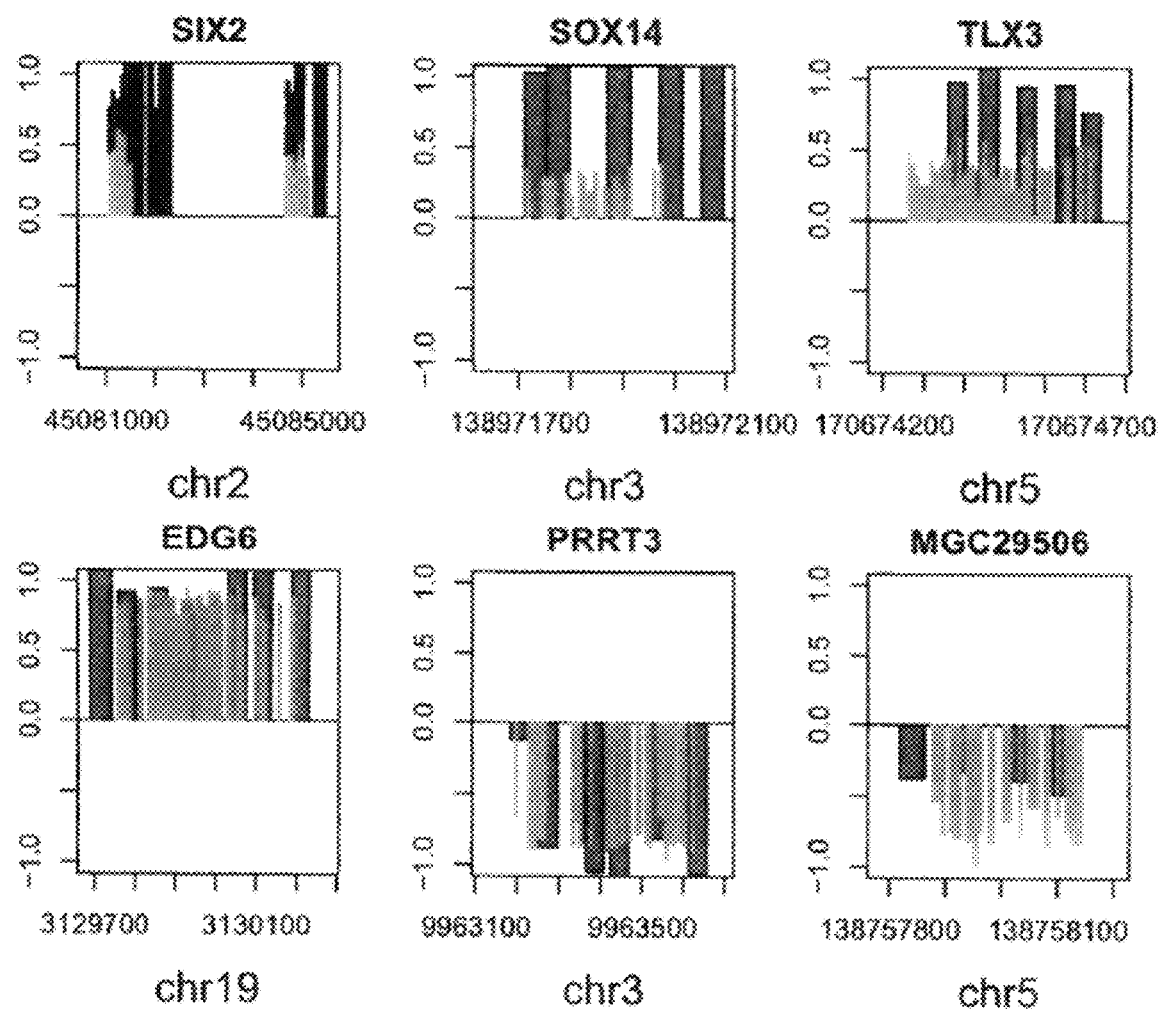
Figure 9D:
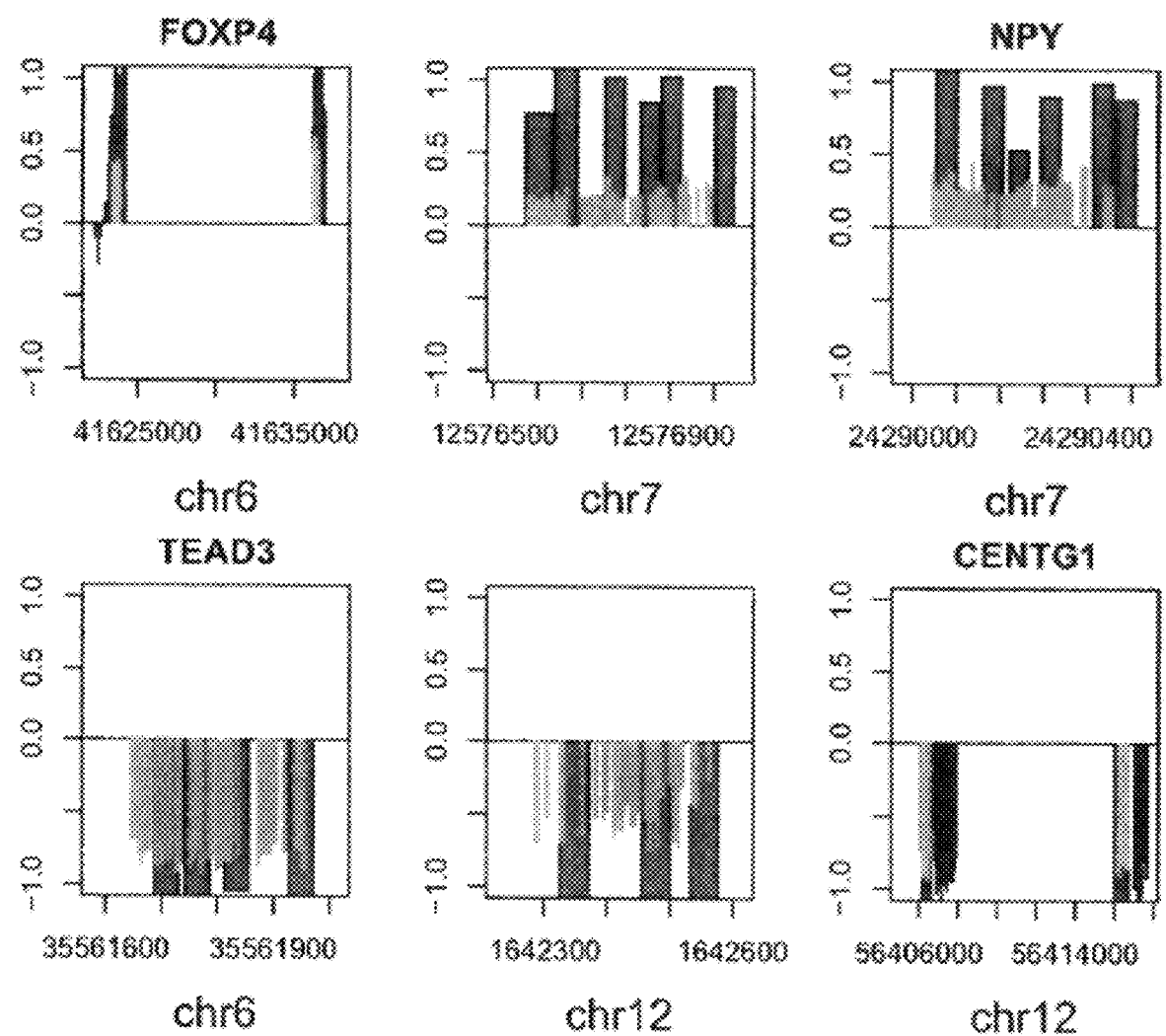
Figure 9E:
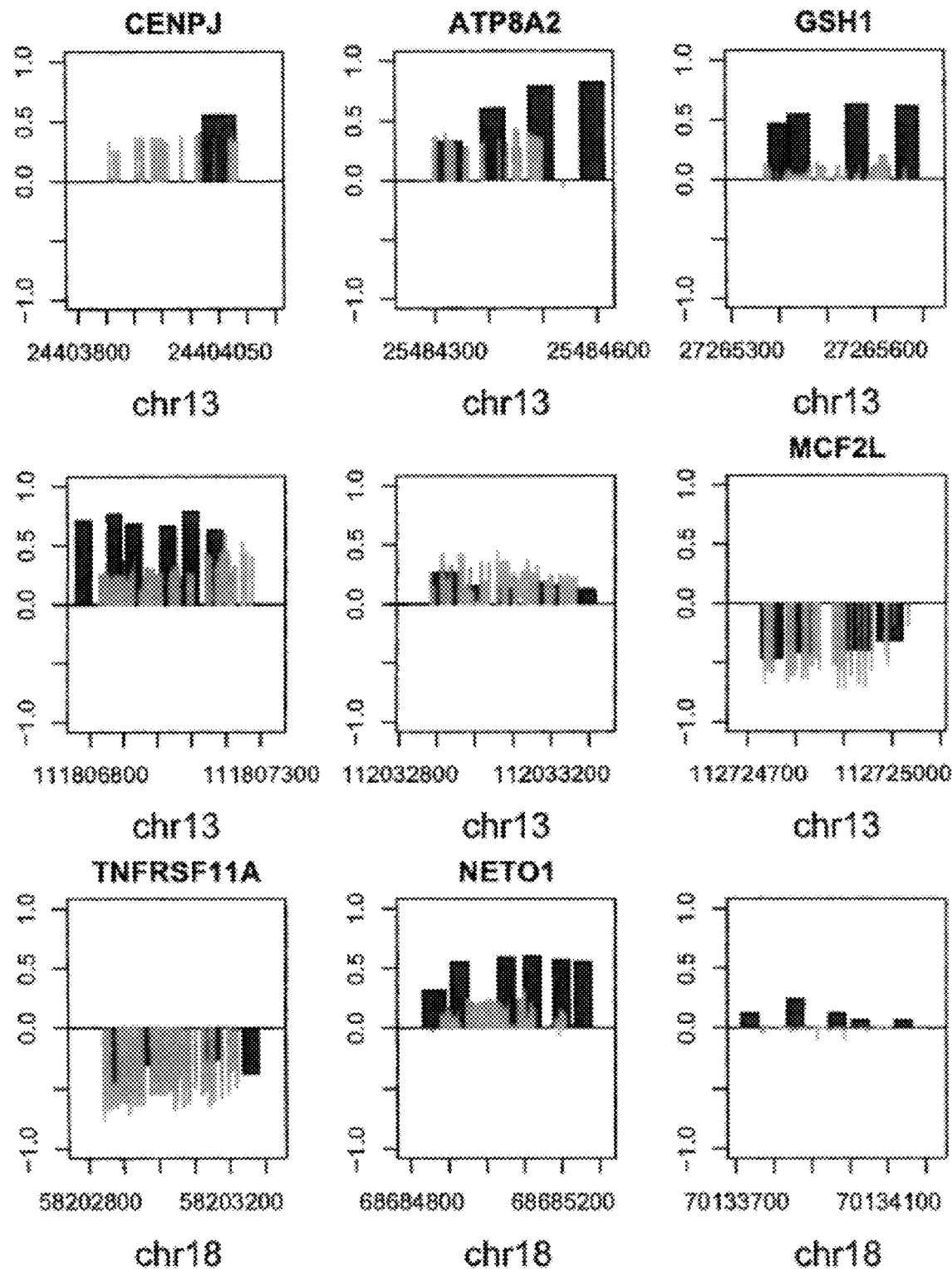
Figure 9F:
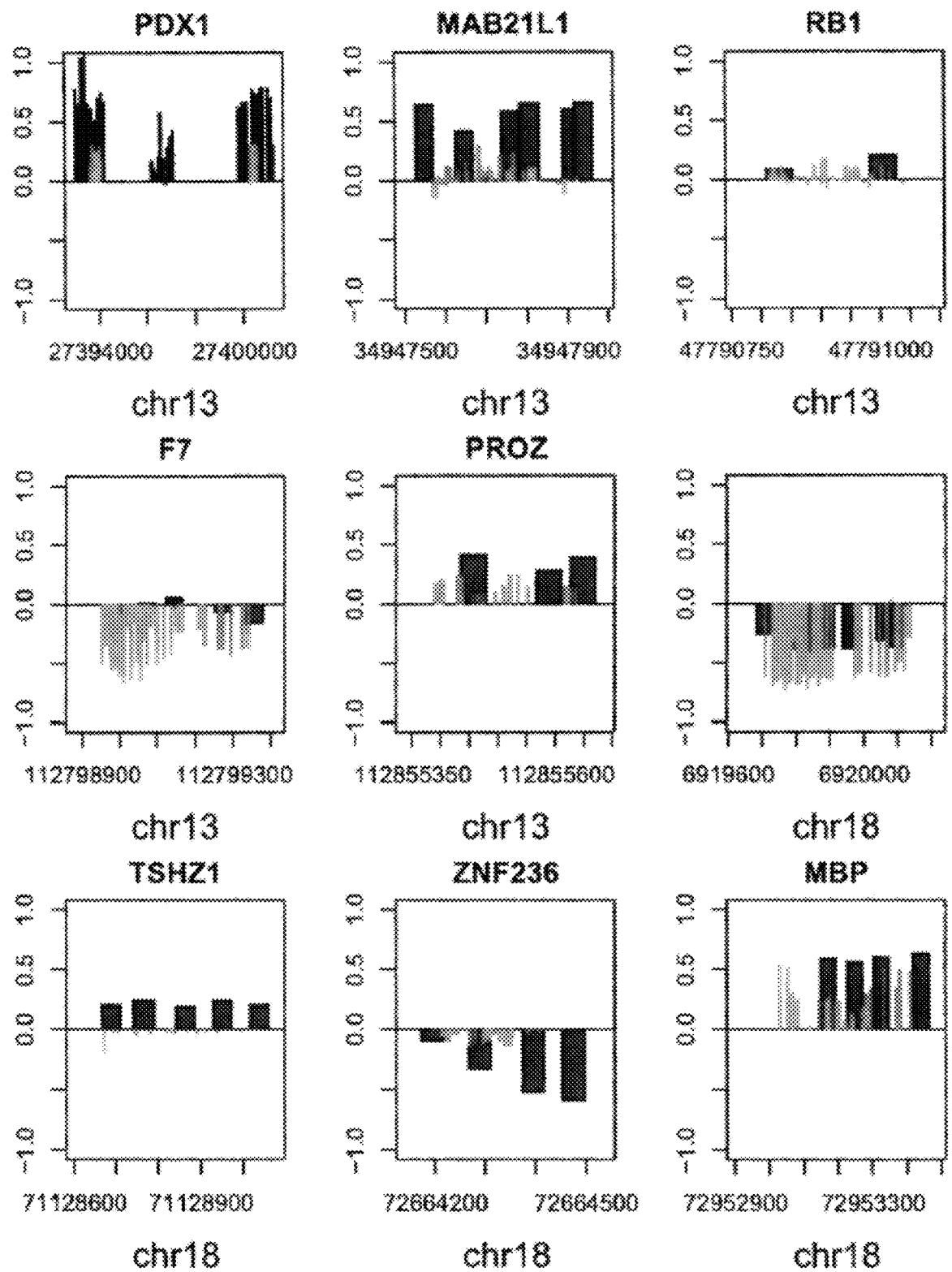
Figure 9G:
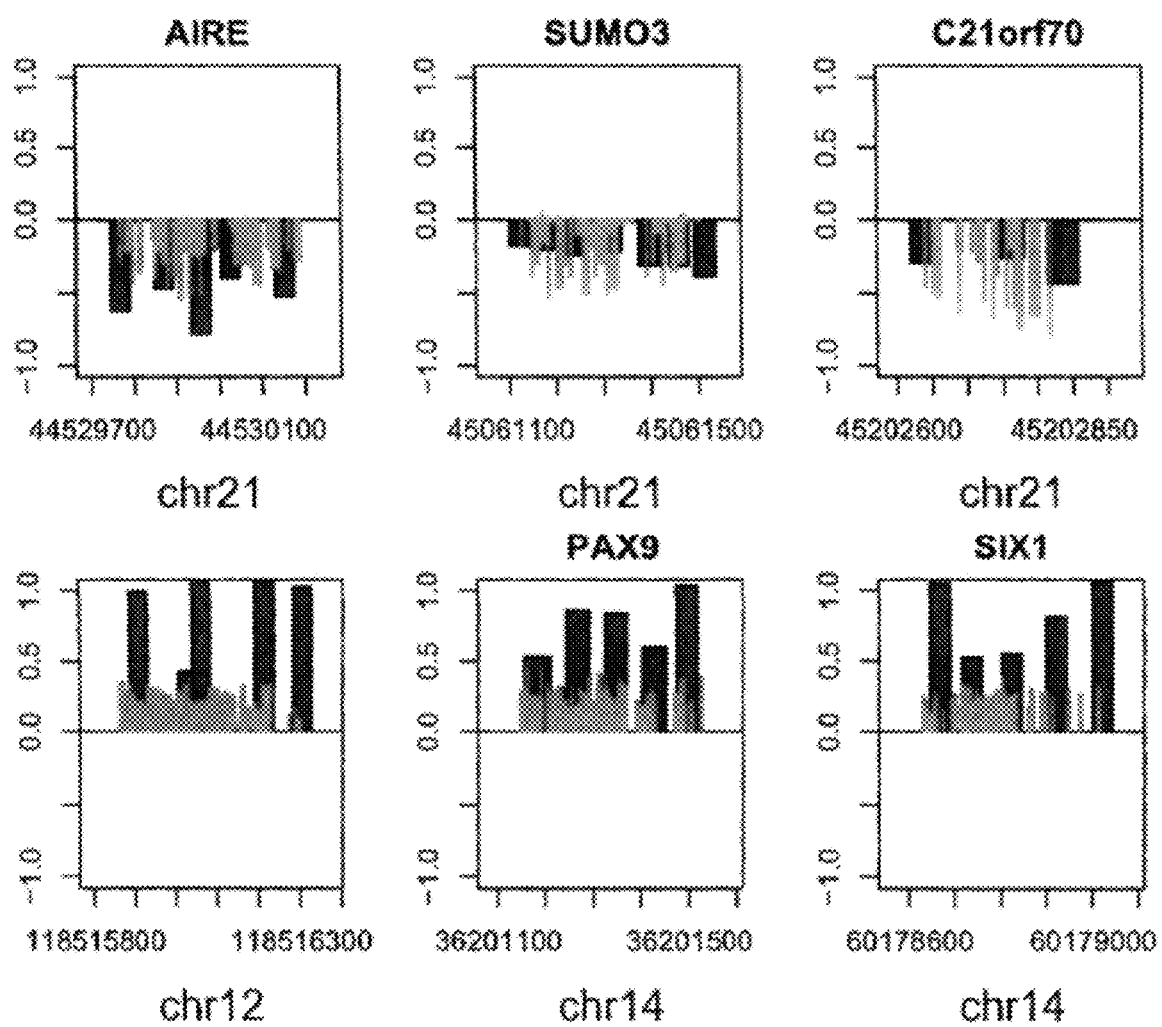
Figure 9H:
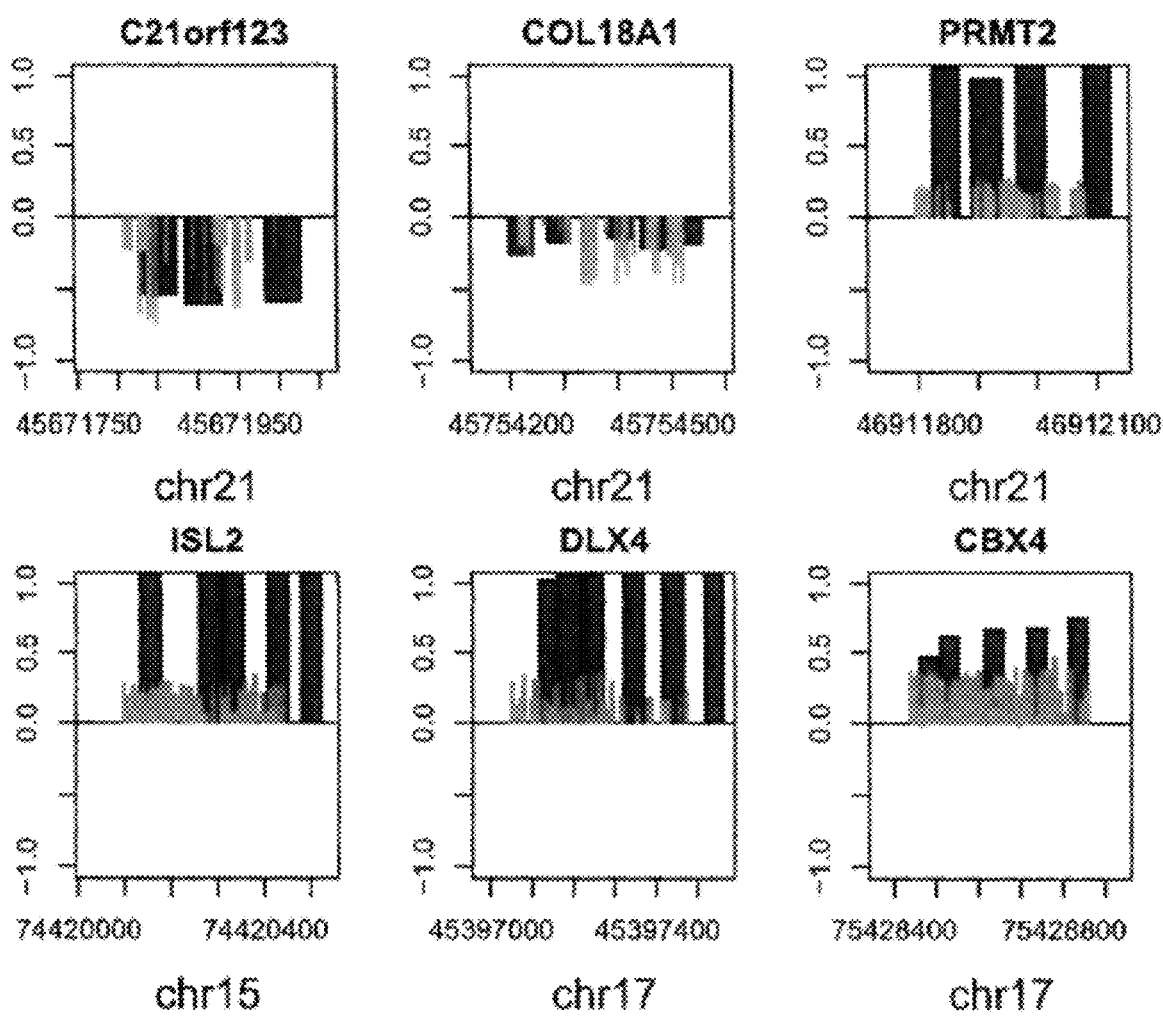
Figure 9I:
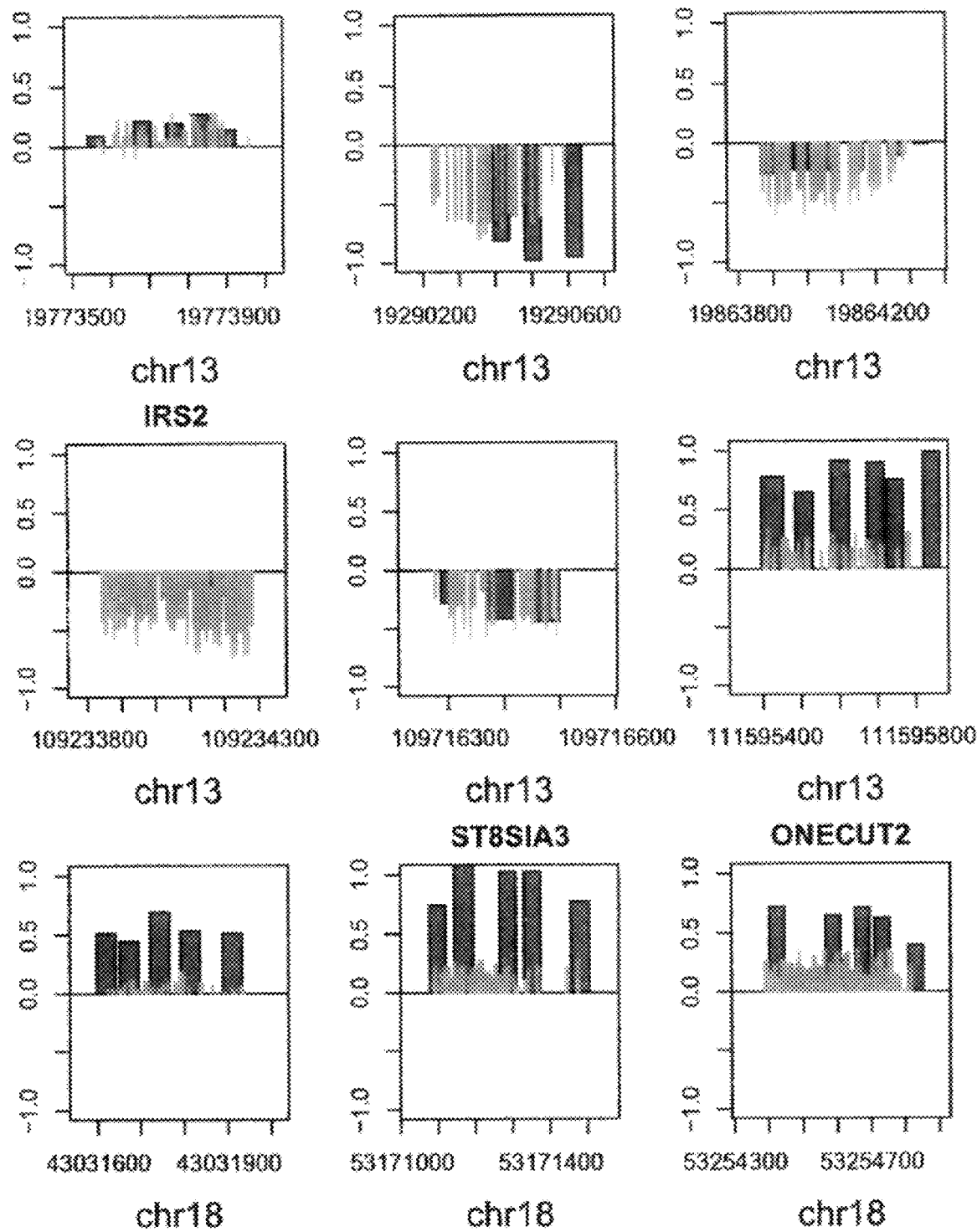
Figure 9J:
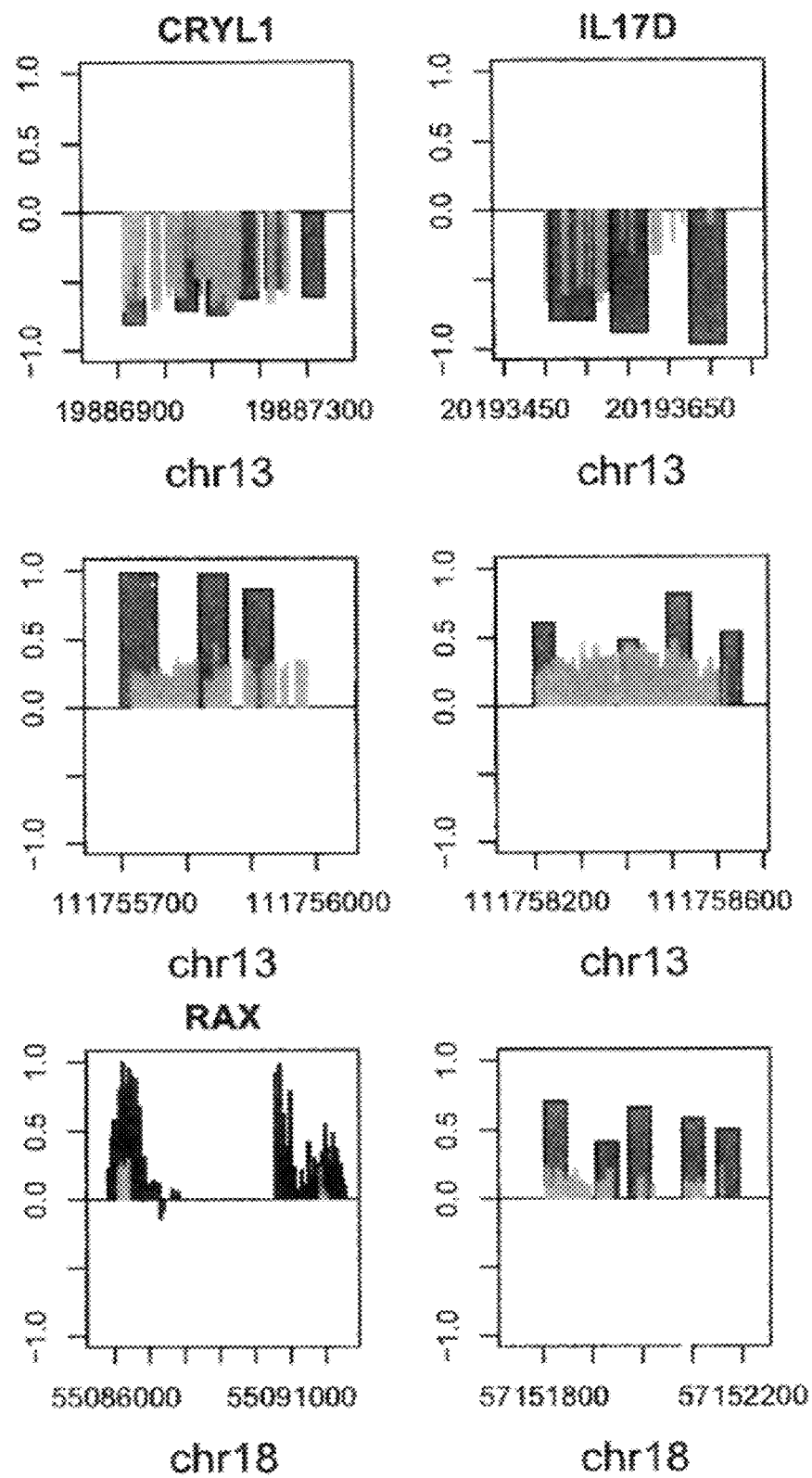
Figure 9K:
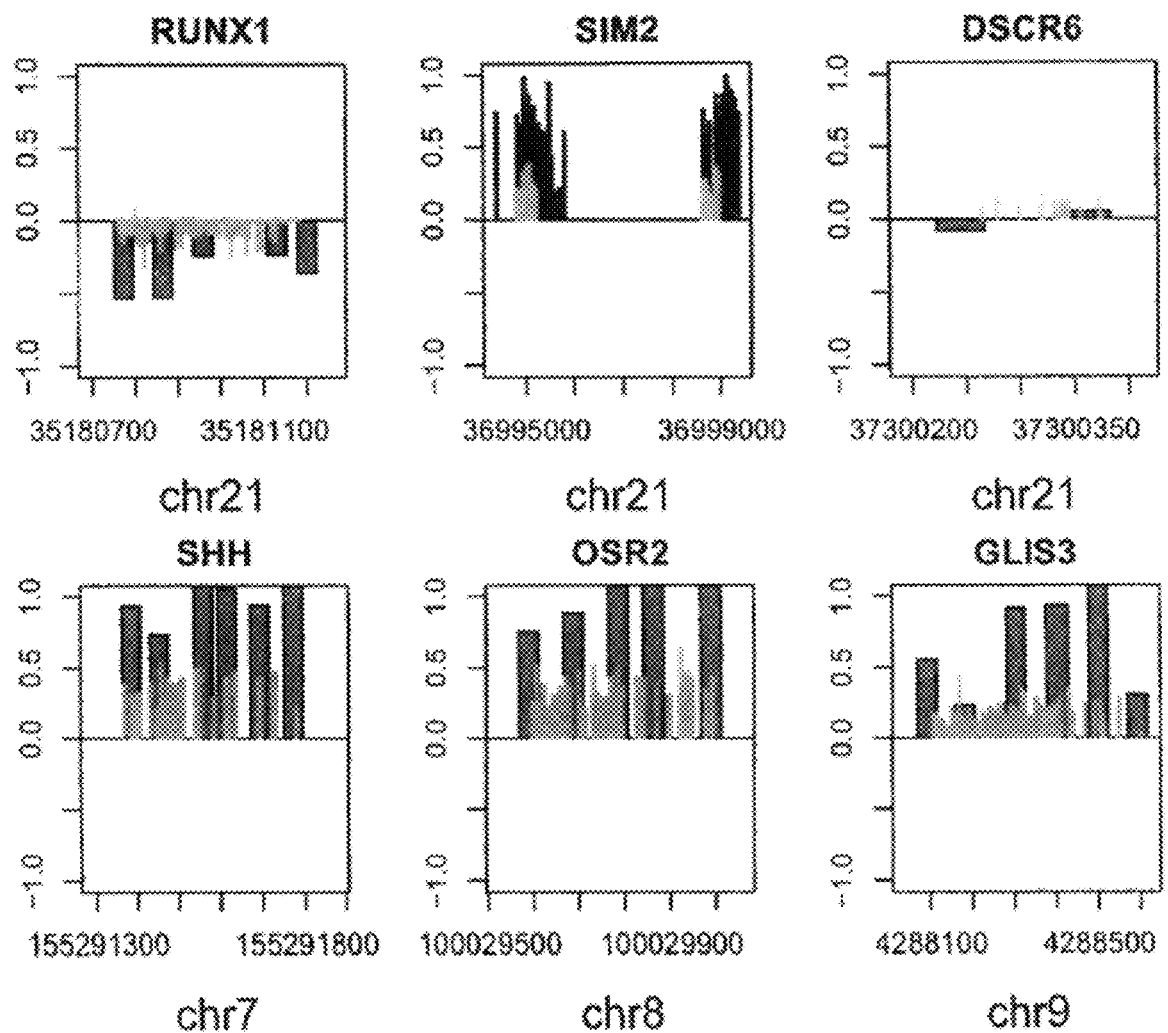
Figure 9L:
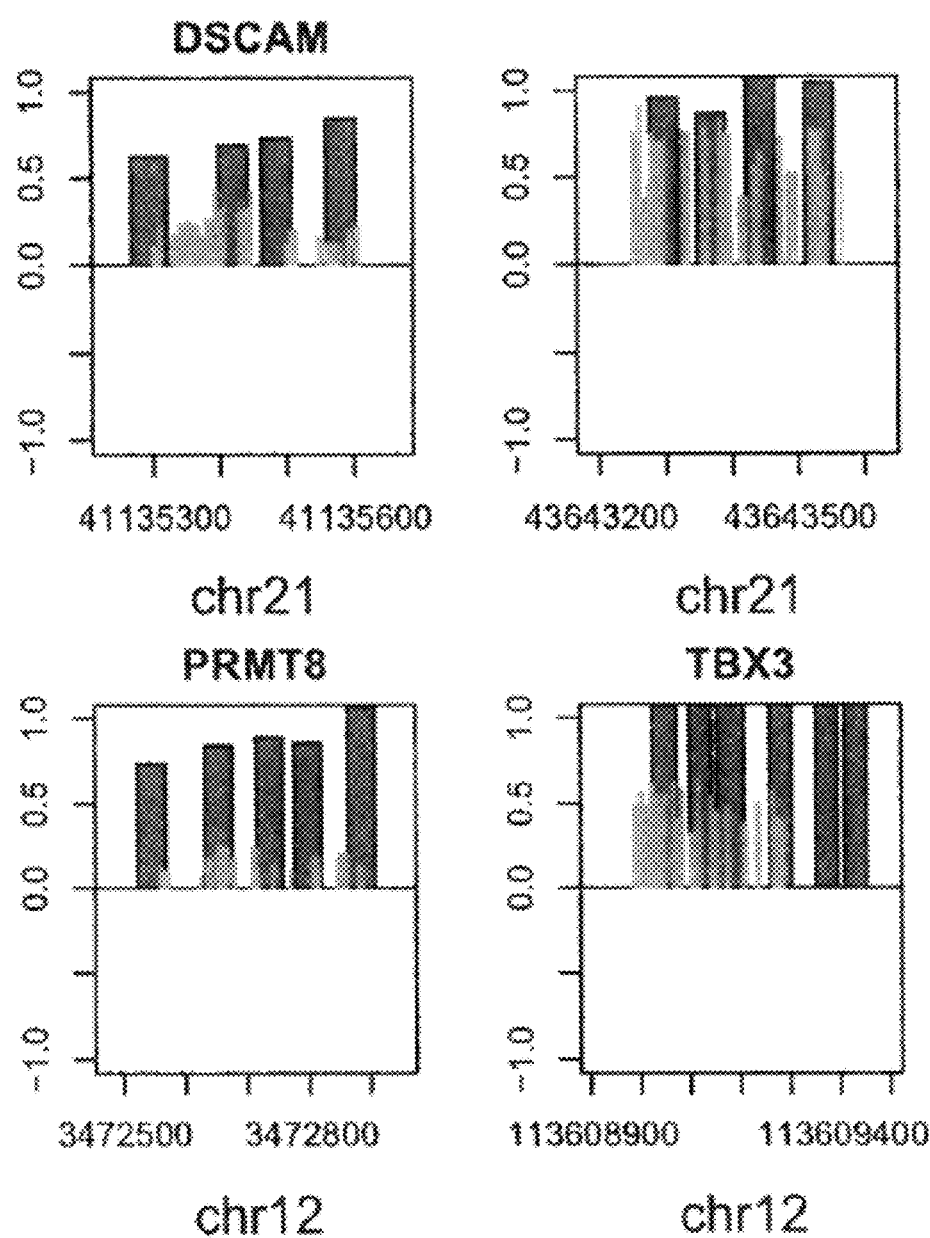

A first simple power calculation was performed that assumes a measurement system that uses 20 markers from chromosome 21, and 20 markers from one or more other autosomes. Starting with 100 copies of fetal DNA, a measurement standard deviation of 25 copies and the probability for a type I error to be lower than 0.001, it was found that the methods of the technology herein will be able to differentiate a diploid from a triploid chromosome set in 99.5% of all cases. The practical implementation of such an approach could for example be achieved using mass spectrometry, a system that uses a competitive PCR approach for absolute copy number measurements. The method can run 20 assays in a single reaction and has been shown to have a standard deviation in repeated measurements of around 3 to 5%. This method was used in combination with known methods for differentiating methylated and non-methylated nucleic acid, for example, using methyl-binding agents to separate nucleic acid or using methylation-sensitive enzymes to digest maternal nucleic acid. FIG. 8 shows the effectiveness of MBD-FC protein (a methyl-binding agent) for capturing and thereby separating methylated DNA in the presence of an excess of unmethylated DNA (see FIG. 8).

A second statistical power analysis was performed to assess the predictive power of an embodiment of the Methylation-Based Fetal Diagnostic Method described herein. The simulation was designed to demonstrate the likelihood of differentiating a group of trisomic chromosome 21 specific markers from a group of reference markers (for example, autosomes excluding chromosome 21). Many parameters influence the ability to discriminate the two populations of markers reliably. For the present simulation, values were chosen for each parameter that have been shown to be the most likely to occur based on experimentation. The following parameters and respective values were used:

Copy Numbers
  Maternal copy numbers=2000
  Fetal copy numbers for chromosomes other than 21, X and Y=200
  Fetal copy numbers for chromosome 21 in case of euploid fetus=200
  Fetal copy numbers for chromosome 21 in case of aneuploid T21 fetus=300
  Percent fetal DNA (before methylation-based enrichment)=10% (see above)
  Methylation Frequency
  Average methylation percentage in a target region for maternal DNA=10%
  Average methylation percentage in a target region for fetal DNA=80%
  Average percentage of non-methylated and non-digested maternal DNA (i.e., a function of restriction efficiency among other things)=5%
  Number of assays targeting chromosome 21=10
  Number of assays targeting chromosomes other than 21, X and Y=10

Figure 20:
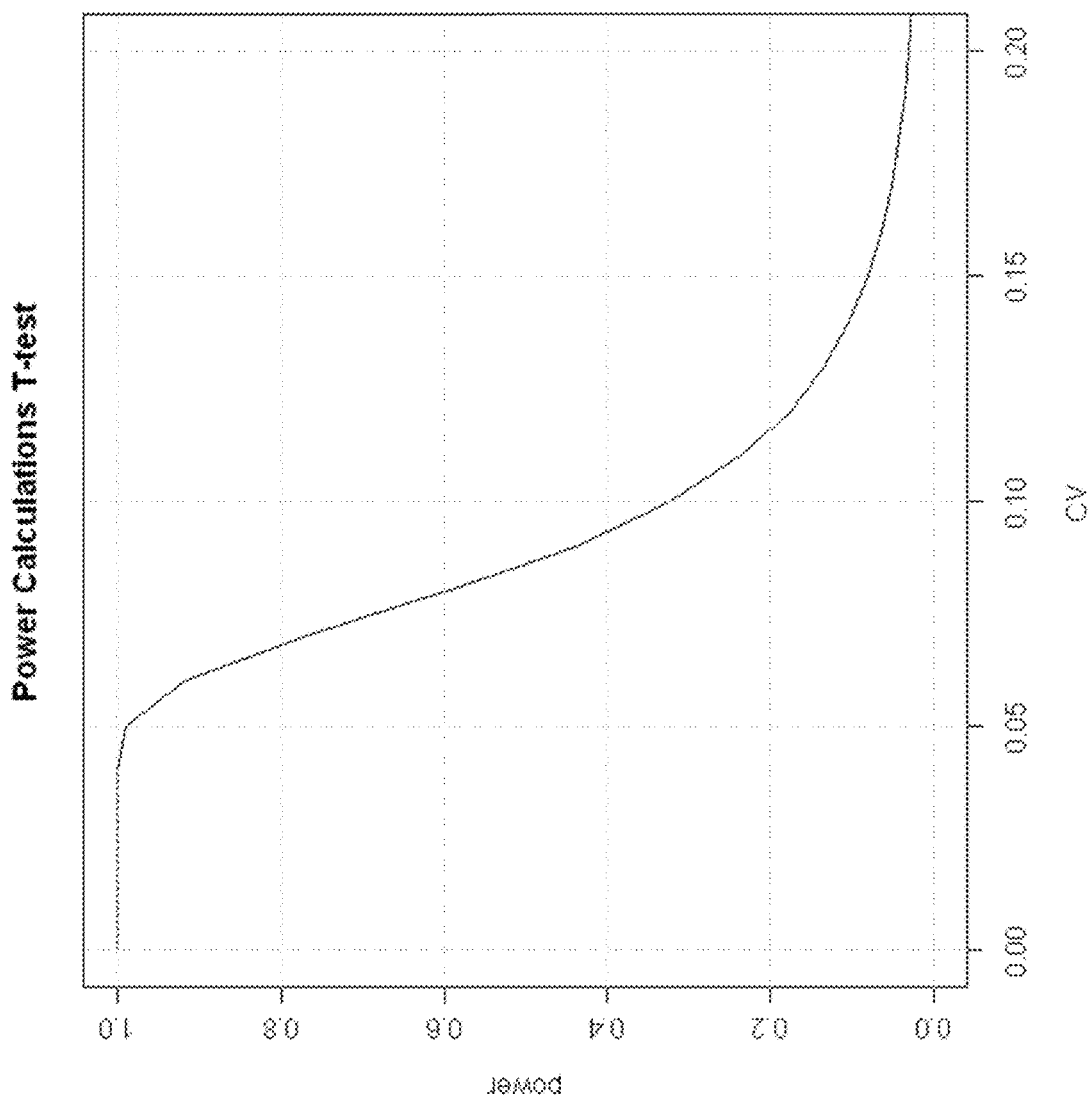
FIG. 20 shows a power calculation t-test for a simulated trisomy 21 diagnosis using the methods of the technology herein. The Figure shows the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less.

The results are displayed in FIG. 20. Shown is the relationship between the coefficient of variation (CV) on the x-axis and the power to discriminate the assay populations using a simple t-test (y-axis). The data indicates that in 99% of all cases, one can discriminate the two population (euploid vs. aneuploid) on a significance level of 0.001 provided a CV of 5% or less. Based on this simulation, the method represents a powerful noninvasive diagnostic method for the prenatal detection of fetal aneuploidy that is sex-independent and will work in all ethnicities (i.e., no allelic bias).

Example 3

Additional Differentially-Methylated Targets

Differentially-Methylated Targets not Located on Chromosome 21

Additional differentially-methylated targets were selected for further analysis based upon previous microarray analysis. See Example 1 for a description of the microarray analysis. During the microarray screen, differentially methylated regions (DMRs) were defined between placenta tissue and PBMC. Regions were selected for EpiTYPER confirmation based upon being hypermethylated in placenta relative to PBMC. After directionality of the change was selected for, regions were chosen based upon statistical significance with regions designed beginning with the most significant and working downward in terms of significance. These studies were performed in eight paired samples of PBMC and placenta. Additional non-chromosome 21 targets are provided in Table 1B, along with a representative genomic sequence from each target in Table 4B.

Differentially-Methylated Targets Located on Chromosome 21

The microarray screen uncovered only a subset of DMRs located on chromosome 21. The coverage of chromosome 21 by the microarray, however, was insufficient. Therefore a further analysis was completed to examine all 356 CpG islands on chromosome 21 using the standard settings of the UCSC genome browser. As shown in Table 1C below, some of these targets overlapped with those already examined in Table 1A. More specifically, CpG sites located on chromosome 21 including ~1000 bp upstream and downstream of each CpG was investigated using Sequenom's EpiTYPER® technology. See Example 1, "Validation using Sequenom® EpiTYPER™" for a description of Sequenom's EpiTYPER® technology. These studies were performed in eight paired samples of PBMC and placenta. In addition, since DMRs may also be located outside of defined CpG islands, data mining was performed on publicly available microarray data to identify potential candidate regions with the following characteristics: hypermethylated in placenta relative to maternal blood, not located in a defined CpG island, contained greater than 4 CpG dinucleotides, and contained a recognition sequence for methylation sensitive restriction enzymes. Regions that met these criteria were then examined using Sequenom's EpiTYPER® technology on eight paired PBMC and placenta samples. Additional chromosome 21 targets are provided in Table 10, along with a representative genomic sequence from each target in Table 4C.

Tables 1B and 10 provide a description of the different targets, including their location and whether they were analyzed during the different phases of analysis, namely microarray analysis, EpiTYPER 8 analysis and EpiTYPER 73 analysis. A "YES" indicates it was analyzed and a "NO" indicates it was not analyzed. The definition of each column in Table 1B and 10 is listed below.

- Region Name: Each region is named by the gene(s) residing within the area defined or nearby. Regions where no gene name is listed but rather only contain a locus have no refseq genes in near proximity.
- Gene Region: For those regions contained either in close proximity to or within a gene, the gene region further explains the relationship of this region to the nearby gene.
- Chrom: The chromosome on which the DMR is located using the hg18 build of the UCSC genome browser.
- Start: The starting position of the DMR as designated by the hg18 build of the UCSC genome browser.
- End: The ending position of the DMR as designated by the hg18 build of the UCSC genome browser.
- Microarray Analysis: Describes whether this region was also/initially determined to be differentially methylated by microarray analysis. The methylated fraction of ten paired placenta and PBMC samples was isolated using the MBD-Fc protein. The two tissue fractions were then labeled with either Alexa Fluor 555-aha-dCTP (PBMC) or Alexa Fluor 647-aha-dCTP (placental) using the BioPrime Total Genomic Labeling System™ and hybridized to Agilent® CpG Island microarrays. Many regions examined in these studies were not contained on the initial microarray.
- EpiTYPER 8 Samples: Describes whether this region was analyzed and determined to be differentially methylated in eight paired samples of placenta and peripheral blood mononuclear cells (PBMC) using EpiTYPER technology. Regions that were chosen for examination were based on multiple criteria. First, regions were selected based on data from the Microarray Analysis. Secondly, a comprehensive examination of all CpG islands located on chromosome 21 was undertaken. Finally, selected regions on chromosome 21 which had lower CpG frequency than those located in CpG islands were examined.
- EpiTYPER 73 Samples: Describes whether this region was subsequently analyzed using EpiTYPER technology in a sample cohort consisting of 73 paired samples of placenta and PBMC. All regions selected for analysis in this second sample cohort were selected based on the results from the experimentation described in the EpiTYPER 8 column. More specifically, the regions in this additional cohort exhibited a methylation profile similar to that determined in the EpiTYPER 8 Samples analysis. For example, all of the regions listed in Tables 1B-1C exhibit different levels of DNA methylation in a significant portion of the examined CpG dinucleotides within the defined region. Differential DNA methylation of CpG sites was determined using a paired T Test with those sites considered differentially methylated if the p-value (when comparing placental tissue to PBMC) is $p<0.05$.
- Previously Validated EpiTYPER: Describes whether this region or a portion of this region was validated using EpiTYPER during previous experimentation. (See Examples 1 and 2).
- Relative Methylation Placenta to Maternal: Describes the direction of differential methylation. Regions labeled as "hypermethylation" are more methylated within the designated region in placenta samples relative to PBMC and "hypomethylation" are more methylated within the designated region in PBMC samples.

TABLE 1A

| GENE NAME | CHROM | START | END | CpG ISLAND | MEAN LOG RATIO MICRO-ARRAY |
|---|---|---|---|---|---|
| chr13 group00016 | chr13 | 19773745 | 19774050 | chr13:19773518-19774214 | 0.19 |
| chr13 group00005 | chr13 | 19290394 | 19290768 | :- | −0.89 |
| CRYL1 | chr13 | 19887090 | 19887336 | chr13:19887007-19887836 | −0.63 |
| IL17D | chr13 | 20193675 | 20193897 | chr13:20193611-20194438 | −1.01 |
| CENPJ | chr13 | 24404023 | 24404359 | :- | 0.57 |
| ATP8A2 | chr13 | 25484475 | 25484614 | chr13:25484287-25484761 | 0.81 |
| GSH1 | chr13 | 27265542 | 27265834 | chr13:27264549-27266505 | 0.57 |
| PDX1 | chr13 | 27393789 | 27393979 | chr13:27392001-27394099 | 0.55 |
| PDX1 | chr13 | 27400459 | 27401165 | chr13:27400362-27400744; chr13:27401057-27401374 | 0.73 |
| MAB21L1 | chr13 | 34947737 | 34948062 | chr13:34947570-34948159 | 0.66 |
| RB1 | chr13 | 47790983 | 47791646 | chr13:47790636-47791858 | 0.18 |
| PCDH17 | chr13 | 57104856 | 57106841 | chr13:57104527-57106931 | 0.46 |
| KLHL1 | chr13 | 69579933 | 69580146 | chr13:69579733-69580220 | 0.79 |
| POU4F1 | chr13 | 78079515 | 78081073 | chr13:78079328-78079615; chr13:78080860-78081881 | 0.66 |
| GPC6 | chr13 | 92677402 | 92678666 | chr13:92677246-92678878 | 0.66 |
| SOX21 | chr13 | 94152286 | 94153047 | chr13:94152190-94153185 | 0.94 |
| ZIC2 | chr13 | 99439660 | 99440858 | chr13:99439335-99440189; chr13:99440775-99441095 | 0.89 |
| IRS2 | chr13 | 109232856 | 109235065 | chr13:109232467-109238181 | −0.17 |
| chr13 group00350 | chr13 | 109716455 | 109716604 | chr13:109716325-109716726 | −0.37 |
| chr13 group00385 | chr13 | 111595578 | 111595955 | chr13:111595459-111596131 | 0.87 |
| chr13 group00390 | chr13 | 111756337 | 111756593 | chr13:111755805-111756697 | 0.71 |
| chr13 group00391 | chr13 | 111759856 | 111760045 | chr13:111757885-111760666 | 0.86 |
| chr13 group00395 | chr13 | 111808255 | 111808962 | chr13:111806599-111808492; chr13:111808866-111809114 | 0.96 |
| chr13 group00399 | chr13 | 112033503 | 112033685 | chr13:112032967-112033734 | 0.38 |
| MCF2L | chr13 | 112724910 | 112725742 | chr13:112724782-112725121; chr13:112725628-112725837 | −0.47 |
| F7 | chr13 | 112799123 | 112799379 | chr13:112798487-112799566 | −0.05 |
| PROZ | chr13 | 112855566 | 112855745 | chr13:112855289-112855866 | 0.29 |
| chr18 group00039 | chr18 | 6919797 | 6919981 | chr18:6919450-6920088 | −0.38 |

TABLE 1A-continued

| | | | | | |
|---|---|---|---|---|---|
| CIDEA | chr18 | 12244327 | 12244696 | chr18:12244147-12245089 | 0.23 |
| chr18 group00091 | chr18 | 12901467 | 12901643 | chr18:12901024-12902704 | 0.16 |
| chr18 group00094 | chr18 | 13126819 | 13126986 | chr18:13126596-13127564 | 0.41 |
| C18orf1 | chr18 | 13377536 | 13377654 | chr18:13377385-13377686 | −0.12 |
| KLHL14 | chr18 | 28603978 | 28605183 | chr18:28603688-28606300 | 0.83 |
| CD33L3 | chr18 | 41671477 | 41673011 | chr18:41671386-41673101 | −0.34 |
| ST8SIA3 | chr18 | 53171265 | 53171309 | chr18:53170705-53172603 | 1.02 |
| ONECUT2 | chr18 | 53254808 | 53259850 | chr18:53254152-53259851 | 0.74 |
| RAX | chr18 | 55086286 | 55086436 | chr18:55085813-55087807 | 0.88 |
| chr18 group00277 | chr18 | 57151972 | 57152311 | chr18:57151663-57152672 | 0.58 |
| TNFRSF11A | chr18 | 58203013 | 58203282 | chr18:58202849-58203367 | −0.33 |
| NETO1 | chr18 | 68685099 | 68687060 | chr18:68684945-68687253 | 0.65 |
| chr18 group00304 | chr18 | 70133945 | 70134397 | chr18:70133732-70134724 | 0.12 |
| TSHZ1 | chr18 | 71128742 | 71128974 | chr18:71128638-71129076 | 0.23 |
| ZNF236 | chr18 | 72664454 | 72664736 | chr18:72662797-72664893 | −0.62 |
| MBP | chr18 | 72953150 | 72953464 | chr18:72953137-72953402 | 0.6 |
| chr18 group00342 | chr18 | 74170347 | 74170489 | chr18:74170210-74170687 | −0.2 |
| NFATC1 | chr18 | 75385424 | 75386008 | chr18:75385279-75386532 | 0.23 |
| CTDP1 | chr18 | 75596358 | 75596579 | chr18:75596009-75596899 | 0.07 |
| chr18 group00430 | chr18 | 75653272 | 75653621 | :- | 0.52 |
| KCNG2 | chr18 | 75760343 | 75760820 | chr18:75759900-75760988 | 0.01 |
| OLIG2 | chr21 | 33317673 | 33321183 | chr21:33316998-33322115 | 0.66 |
| OLIG2 | chr21 | 33327593 | 33328334 | chr21:33327447-33328408 | −0.75 |
| RUNX1 | chr21 | 35180938 | 35185436 | chr21:35180822-35181342; chr21:35182320-35185557 | −0.68 |
| SIM2 | chr21 | 36994965 | 36995298 | chr21:36990063-36995761 | 0.83 |
| SIM2 | chr21 | 36999025 | 36999410 | chr21:36998632-36999555 | 0.87 |
| DSCR6 | chr21 | 37300407 | 37300512 | chr21:37299807-37301307 | 0.22 |
| DSCAM | chr21 | 41135559 | 41135706 | chr21:41135380-41135816 | 1.03 |
| chr21 group00165 | chr21 | 43643421 | 43643786 | chr21:43643322-43643874 | 1.14 |
| AIRE | chr21 | 44529935 | 44530388 | chr21:44529856-44530472 | −0.55 |
| SUMO3 | chr21 | 45061293 | 45061853 | chr21:45061154-45063386 | −0.41 |
| C21orf70 | chr21 | 45202815 | 45202972 | chr21:45202706-45203073 | −0.46 |
| C21orf123 | chr21 | 45671984 | 45672098 | chr21:45671933-45672201 | −0.63 |
| COL18A1 | chr21 | 45754383 | 45754487 | chr21:45753653-45754639 | −0.18 |
| PRMT2 | chr21 | 46911967 | 46912385 | chr21:46911628-46912534 | 1.08 |
| SIX2 | chr2 | 45081223 | 45082129 | chr2:45081148-45082287 | 1.15 |
| SIX2 | chr2 | 45084851 | 45085711 | chr2:45084715-45084986; chr2:45085285-45086054 | 1.21 |
| SOX14 | chr3 | 138971870 | 138972322 | chr3:138971738-138972096; chr3:138972281-138973691 | 1.35 |
| TLX3 | chr5 | 170674439 | 170676431 | chr5:170674208-170675356; chr5:170675783-170676712 | 0.91 |
| FOXP4 | chr6 | 41623666 | 41624114 | chr6:41621630-41624167 | 1.1 |
| FOXP4 | chr6 | 41636384 | 41636779 | chr6:41636244-41636878 | 1.32 |
| chr7 group00267 | chr7 | 12576755 | 12577246 | chr7:12576690-12577359 | 0.94 |
| NPY | chr7 | 24290224 | 24291508 | chr7:24290083-24291605 | 0.93 |
| SHH | chr7 | 155291537 | 155292091 | chr7:155288453-155292175 | 0.98 |
| OSR2 | chr8 | 100029764 | 100030536 | chr8:100029673-100030614 | 1.21 |
| GLIS3 | chr9 | 4288283 | 4289645 | chr9:4287817-4290182 | 1.24 |
| PRMT8 | chr12 | 3472714 | 3473190 | chr12:3470227-3473269 | 0.86 |
| TBX3 | chr12 | 113609153 | 113609453 | chr12:113609112-113609535 | 1.45 |
| chr12 group00801 | chr12 | 118516189 | 118517435 | chr12:118515877-118517595 | 1.1 |
| PAX9 | chr14 | 36201402 | 36202386 | chr14:36200932-36202536 | 0.89 |
| SIX1 | chr14 | 60178801 | 60179346 | chr14:60178707-60179539 | 0.95 |
| ISL2 | chr15 | 74420013 | 74421546 | chr15:74419317-74422570 | 1.08 |
| DLX4 | chr17 | 45397228 | 45397930 | chr17:45396281-45398063 | 1.25 |
| CBX4 | chr17 | 75428613 | 75431793 | chr17:75427586-75433676 | 1 |
| EDG6 | chr19 | 3129836 | 3130874 | chr19:3129741-3130986 | 1.35 |
| PRRT3 | chr3 | 9963364 | 9964023 | chr3:9962895-9964619 | −0.85 |
| MGC29506 | chr5 | 138757911 | 138758724 | chr5:138755609-138758810 | −0.63 |
| TEAD3 | chr6 | 35561812 | 35562252 | chr6:35561754-35562413 | −1.17 |
| chr12 group00022 | chr12 | 1642456 | 1642708 | chr12:1642195-1642774 | −1.33 |
| CENTG1 | chr12 | 56406249 | 56407788 | chr12:56406176-56407818 | −1.07 |
| CENTG1 | chr12 | 56416146 | 56418794 | chr12:56416095-56416628; chr12:56418745-56419001 | −0.94 |

| GENE NAME | MEAN MATERNAL METHYLATION EPITYPER | MEAN PLACENTA METHYLATION EPITYPER | METHYLATION DIFFERENCE PLACENTA − MATERNAL | RELATIVE METHYLATION PLACENTA TO MATERNAL |
|---|---|---|---|---|
| chr13 group00016 | 0.22 | 0.32 | 0.1 | HYPERMETHYLATION |
| chr13 group00005 | 0.94 | 0.35 | −0.59 | HYPOMETHYLATION |
| CRYL1 | 0.74 | 0.21 | −0.53 | HYPOMETHYLATION |
| IL17D | 0.53 | 0.13 | −0.39 | HYPOMETHYLATION |
| CENPJ | 0.17 | 0.49 | 0.32 | HYPERMETHYLATION |
| ATP8A2 | 0.16 | 0.43 | 0.27 | HYPERMETHYLATION |
| GSH1 | 0.13 | 0.19 | 0.05 | HYPERMETHYLATION |
| PDX1 | 0.06 | 0.2 | 0.14 | HYPERMETHYLATION |

TABLE 1A-continued

| | | | | |
|---|---|---|---|---|
| PDX1 | 0.12 | 0.26 | 0.14 | HYPERMETHYLATION |
| MAB21L1 | 0.11 | 0.17 | 0.06 | HYPERMETHYLATION |
| RB1 | 0.45 | 0.48 | 0.03 | HYPERMETHYLATION |
| PCDH17 | 0.15 | 0.21 | 0.06 | HYPERMETHYLATION |
| KLHL1 | 0.09 | 0.28 | 0.2 | HYPERMETHYLATION |
| POU4F1 | 0.12 | 0.23 | 0.11 | HYPERMETHYLATION |
| GPC6 | 0.06 | 0.19 | 0.13 | HYPERMETHYLATION |
| SOX21 | 0.16 | 0.4 | 0.25 | HYPERMETHYLATION |
| ZIC2 | 0.13 | 0.35 | 0.22 | HYPERMETHYLATION |
| IRS2 | 0.73 | 0.38 | −0.35 | HYPOMETHYLATION |
| chr13 group00350 | 0.77 | 0.41 | −0.36 | HYPOMETHYLATION |
| chr13 group00385 | 0.06 | 0.2 | 0.14 | HYPERMETHYLATION |
| chr13 group00390 | 0.12 | 0.34 | 0.22 | HYPERMETHYLATION |
| chr13 group00391 | 0.11 | 0.36 | 0.25 | HYPERMETHYLATION |
| chr13 group00395 | 0.13 | 0.35 | 0.22 | HYPERMETHYLATION |
| chr13 group00399 | 0.26 | 0.43 | 0.18 | HYPERMETHYLATION |
| MCF2L | 0.91 | 0.33 | −0.58 | HYPOMETHYLATION |
| F7 | 0.97 | 0.55 | −0.41 | HYPOMETHYLATION |
| PROZ | 0.15 | 0.3 | 0.16 | HYPERMETHYLATION |
| chr18 group00039 | 0.88 | 0.39 | −0.49 | HYPOMETHYLATION |
| CIDEA | 0.14 | 0.23 | 0.1 | HYPERMETHYLATION |
| chr18 group00091 | 0.15 | 0.43 | 0.29 | HYPERMETHYLATION |
| chr18 group00094 | 0.07 | 0.34 | 0.27 | HYPERMETHYLATION |
| C18orf1 | 0.95 | 0.69 | −0.26 | HYPOMETHYLATION |
| KLHL14 | 0.07 | 0.19 | 0.12 | HYPERMETHYLATION |
| CD33L3 | 0.49 | 0.44 | −0.05 | HYPOMETHYLATION |
| ST8SIA3 | 0.09 | 0.25 | 0.16 | HYPERMETHYLATION |
| ONECUT2 | 0.09 | 0.23 | 0.14 | HYPERMETHYLATION |
| RAX | 0.11 | 0.26 | 0.16 | HYPERMETHYLATION |
| chr18 group00277 | 0.08 | 0.21 | 0.13 | HYPERMETHYLATION |
| TNFRSF11A | 0.88 | 0.28 | −0.6 | HYPOMETHYLATION |
| NETO1 | 0.09 | 0.22 | 0.13 | HYPERMETHYLATION |
| chr18 group00304 | 0.93 | 0.92 | −0.01 | NOT CONFIRMED |
| TSHZ1 | 0.95 | 0.92 | −0.03 | NOT CONFIRMED |
| ZNF236 | 0.17 | 0.1 | −0.07 | HYPOMETHYLATION |
| MBP | 0.44 | 0.72 | 0.28 | HYPERMETHYLATION |
| chr18 group00342 | 0.78 | 0.48 | −0.3 | HYPOMETHYLATION |
| NFATC1 | 0.14 | 0.84 | 0.7 | HYPERMETHYLATION |
| CTDP1 | 0.97 | 0.96 | −0.01 | NOT CONFIRMED |
| chr18 group00430 | 0.24 | 0.62 | 0.39 | HYPERMETHYLATION |
| KCNG2 | 0.84 | 0.75 | −0.09 | NOT CONFIRMED |
| OLIG2 | 0.11 | 0.2 | 0.09 | HYPERMETHYLATION |
| OLIG2 | 0.77 | 0.28 | −0.49 | HYPOMETHYLATION |
| RUNX1 | 0.14 | 0.07 | −0.07 | HYPOMETHYLATION |
| SIM2 | 0.08 | 0.26 | 0.18 | HYPERMETHYLATION |
| SIM2 | 0.06 | 0.24 | 0.18 | HYPERMETHYLATION |
| DSCR6 | 0.04 | 0.14 | 0.11 | HYPERMETHYLATION |
| DSCAM | 0.06 | 0.29 | 0.23 | HYPERMETHYLATION |
| chr21 group00165 | 0.16 | 0.81 | 0.65 | HYPERMETHYLATION |
| AIRE | 0.62 | 0.27 | −0.35 | HYPOMETHYLATION |
| SUMO3 | 0.55 | 0.46 | −0.09 | HYPOMETHYLATION |
| C21orf70 | 0.96 | 0.51 | −0.46 | HYPOMETHYLATION |
| C21orf123 | 0.92 | 0.43 | −0.49 | HYPOMETHYLATION |
| COL18A1 | 0.97 | 0.72 | −0.25 | HYPOMETHYLATION |
| PRMT2 | 0.04 | 0.25 | 0.21 | HYPERMETHYLATION |
| SIX2 | 0.08 | 0.36 | 0.28 | HYPERMETHYLATION |
| SIX2 | 0.07 | 0.35 | 0.28 | HYPERMETHYLATION |
| SOX14 | 0.08 | 0.33 | 0.25 | HYPERMETHYLATION |
| TLX3 | 0.11 | 0.35 | 0.24 | HYPERMETHYLATION |
| FOXP4 | 0.07 | 0.27 | 0.2 | HYPERMETHYLATION |
| FOXP4 | 0.04 | 0.33 | 0.29 | HYPERMETHYLATION |
| chr7 group00267 | 0.08 | 0.26 | 0.17 | HYPERMETHYLATION |
| NPY | 0.09 | 0.3 | 0.21 | HYPERMETHYLATION |
| SHH | 0.19 | 0.52 | 0.33 | HYPERMETHYLATION |
| OSR2 | 0.08 | 0.43 | 0.35 | HYPERMETHYLATION |
| GLIS3 | 0.06 | 0.24 | 0.18 | HYPERMETHYLATION |
| PRMT8 | 0.07 | 0.23 | 0.16 | HYPERMETHYLATION |
| TBX3 | 0.09 | 0.56 | 0.48 | HYPERMETHYLATION |
| chr12 group00801 | 0.06 | 0.25 | 0.19 | HYPERMETHYLATION |
| PAX9 | 0.11 | 0.32 | 0.21 | HYPERMETHYLATION |
| SIX1 | 0.1 | 0.33 | 0.22 | HYPERMETHYLATION |
| ISL2 | 0.08 | 0.27 | 0.19 | HYPERMETHYLATION |
| DLX4 | 0.1 | 0.32 | 0.22 | HYPERMETHYLATION |
| CBX4 | 0.07 | 0.27 | 0.21 | HYPERMETHYLATION |
| EDG6 | 0.04 | 0.87 | 0.83 | HYPERMETHYLATION |
| PRRT3 | 0.9 | 0.09 | −0.81 | HYPOMETHYLATION |
| MGC29506 | 0.93 | 0.17 | −0.76 | HYPOMETHYLATION |
| TEAD3 | 0.92 | 0.13 | −0.8 | HYPOMETHYLATION |
| chr12 group00022 | 0.66 | 0.09 | −0.57 | HYPOMETHYLATION |

TABLE 1A-continued

| | | | | |
|---|---|---|---|---|
| CENTG1 | 0.95 | 0.19 | −0.77 | HYPOMETHYLATION |
| CENTG1 | 0.85 | 0.16 | −0.69 | HYPOMETHYLATION |

Information in Table 1A based on the March 2006 human reference sequence (NCBI Build 36.1), which was produced by the International Human Genome Sequencing Consortium.

TABLE 1B

Non-Chromosome 21 differentially methylated regions

| Region Name | Gene Region | Chrom | Start | End | Micro-array Analysis | EpiTYPER 8 Samples | EpiTYPER 73 Samples | Previously Validated EpiTYPER | Relative Methylation Placenta to Maternal |
|---|---|---|---|---|---|---|---|---|---|
| TFAP2E | Intron | chr1 | 35815000 | 35816200 | YES | YES | NO | NO | Hypermethylation |
| LRRC8D | Intron/Exon | chr1 | 90081350 | 90082250 | YES | YES | NO | NO | Hypermethylation |
| TBX15 | Promoter | chr1 | 119333500 | 119333700 | YES | YES | NO | NO | Hypermethylation |
| C1orf51 | Upstream | chr1 | 148520900 | 148521300 | YES | YES | NO | NO | Hypermethylation |
| chr1:179553900-179554600 | Intergenic | chr1 | 179553900 | 179554600 | YES | YES | NO | NO | Hypermethylation |
| ZFP36L2 | Exon | chr2 | 43304900 | 43305100 | YES | YES | NO | NO | Hypermethylation |
| SIX2 | Downstream | chr2 | 45081000 | 45086000 | YES | YES | NO | YES | Hypermethylation |
| chr2:137238500-137240000 | Intergenic | chr2 | 137238500 | 137240000 | YES | YES | NO | NO | Hypermethylation |
| MAP1D | Intron/Exon | chr2 | 172652800 | 172653600 | YES | YES | NO | NO | Hypermethylation |
| WNT6 | Intron | chr2 | 219444250 | 219444290 | YES | YES | NO | NO | Hypermethylation |
| INPP5D | Promoter | chr2 | 233633200 | 233633700 | YES | YES | YES | NO | Hypermethylation |
| chr2:241211100-241211600 | Intergenic | chr2 | 241211100 | 241211600 | YES | YES | YES | NO | Hypermethylation |
| WNT5A | Intron | chr3 | 55492550 | 55492850 | YES | YES | NO | NO | Hypermethylation |
| chr3:138971600-138972200 | Intergenic | chr3 | 138971600 | 138972200 | YES | YES | YES | YES | Hypermethylation |
| ZIC4 | Intron | chr3 | 148598200 | 148599000 | YES | YES | NO | NO | Hypermethylation |
| FGF12 | Intron/Exon | chr3 | 193608500 | 193610500 | YES | YES | NO | NO | Hypermethylation |
| GP5 | Exon | chr3 | 195598400 | 195599200 | YES | YES | NO | NO | Hypermethylation |
| MSX1 | Upstream | chr4 | 4910550 | 4911100 | YES | YES | NO | NO | Hypermethylation |
| NKX3-2 | Intron/Exon | chr4 | 13152500 | 13154500 | YES | YES | NO | NO | Hypermethylation |
| chr4:111752000-111753000 | Intergenic | chr4 | 111752000 | 111753000 | YES | YES | YES | NO | Hypermethylation |
| SFRP2 | Promoter | chr4 | 154928800 | 154930100 | YES | YES | NO | NO | Hypermethylation |
| chr4:174664300-174664800 | Intergenic | chr4 | 174664300 | 174664800 | YES | YES | NO | NO | Hypermethylation |
| chr4:174676300-174676800 | Intergenic | chr4 | 174676300 | 174676800 | YES | YES | NO | NO | Hypermethylation |
| SORBS2 | Intron | chr4 | 186796900 | 186797500 | YES | YES | NO | NO | Hypermethylation |
| chr5:42986900-42988200 | Intergenic | chr5 | 42986900 | 42988200 | YES | YES | NO | NO | Hypermethylation |
| chr5:72712000-72714100 | Intergenic | chr5 | 72712000 | 72714100 | YES | YES | NO | NO | Hypermethylation |
| chr5:72767550-72767800 | Intergenic | chr5 | 72767550 | 72767800 | YES | YES | NO | NO | Hypermethylation |
| NR2F1 | Intron/Exon | chr5 | 92955000 | 92955250 | YES | YES | NO | NO | Hypermethylation |
| PCDHGA1 | Intron | chr5 | 140850500 | 140852500 | YES | YES | YES | NO | Hypermethylation |
| chr6:10489100-10490200 | Intergenic | chr6 | 10489100 | 10490200 | YES | YES | YES | NO | Hypermethylation |
| FOXP4 | Intron | chr6 | 41636200 | 41637000 | YES | YES | NO | YES | Hypermethylation |
| chr7:19118400-19118700 | Intergenic | chr7 | 19118400 | 19118700 | YES | YES | NO | NO | Hypermethylation |
| chr7:27258000-27258400 | Intergenic | chr7 | 27258000 | 27258400 | YES | YES | NO | NO | Hypermethylation |
| TBX20 | Upstream | chr7 | 35267500 | 35268300 | YES | YES | NO | NO | Hypermethylation |
| AGBL3 | Promoter | chr7 | 134321300 | 134322300 | YES | YES | NO | NO | Hypermethylation |
| XPO7 | Downstream | chr8 | 21924000 | 21924300 | YES | YES | NO | NO | Hypermethylation |
| chr8:41543400-41544000 | Intergenic | chr8 | 41543400 | 41544000 | YES | YES | NO | NO | Hypermethylation |
| GDF6 | Exon | chr8 | 97225400 | 97227100 | YES | YES | NO | NO | Hypermethylation |
| OSR2 | Intron/Exon | chr8 | 100029000 | 100031000 | YES | YES | YES | YES | Hypermethylation |
| GLIS3 | Intron/Exon | chr9 | 4288000 | 4290000 | YES | YES | NO | YES | Hypermethylation |
| NOTCH1 | Intron | chr9 | 138547600 | 138548400 | YES | YES | YES | NO | Hypermethylation |
| EGFL7 | Upstream | chr9 | 138672350 | 138672850 | YES | YES | NO | NO | Hypermethylation |
| CELF2 | Intron/Exon | chr10 | 11246700 | 11247900 | YES | YES | NO | NO | Hypermethylation |
| HHEX | Intron | chr10 | 94441000 | 94441800 | YES | YES | NO | NO | Hypermethylation |
| DOCK1/FAM196A | Intron/Exon | chr10 | 128883000 | 128883500 | YES | YES | NO | NO | Hypermethylation |
| PAX6 | Intron | chr11 | 31782400 | 31783500 | YES | YES | NO | NO | Hypermethylation |
| FERMT3 | Intron/Exon | chr11 | 63731200 | 63731700 | YES | YES | YES | NO | Hypermethylation |
| PKNOX2 | Intron | chr11 | 124541200 | 124541800 | YES | YES | NO | NO | Hypermethylation |
| KIRREL3 | Intron | chr11 | 126375150 | 126375300 | YES | YES | NO | NO | Hypermethylation |
| BCAT1 | Intron | chr12 | 24946700 | 24947600 | YES | YES | NO | NO | Hypermethylation |
| HOXC13 | Intron/Exon | chr12 | 52625000 | 52625600 | YES | YES | NO | NO | Hypermethylation |

TABLE 1B-continued

Non-Chromosome 21 differentially methylated regions

| Region Name | Gene Region | Chrom | Start | End | Microarray Analysis | EpiTYPER 8 Samples | EpiTYPER 73 Samples | Previously Validated EpiTYPER | Relative Methylation Placenta to Maternal |
|---|---|---|---|---|---|---|---|---|---|
| TBX5 | Promoter | chr12 | 113330500 | 113332000 | YES | YES | NO | NO | Hypermethylation |
| TBX3 | Upstream | chr12 | 113609000 | 113609500 | YES | YES | NO | YES | Hypermethylation |
| chr12:113622100-113623000 | Intergenic | chr12 | 113622100 | 113623000 | YES | YES | YES | NO | Hypermethylation |
| chr12:113657800-113658300 | Intergenic | chr12 | 113657800 | 113658300 | YES | YES | NO | NO | Hypermethylation |
| THEM233 | Promoter | chr12 | 118515500 | 118517500 | YES | YES | NO | YES | Hypermethylation |
| NCOR2 | Intron/Exon | chr12 | 123516200 | 123516800 | YES | YES | YES | NO | Hypermethylation |
| THEM132C | Intron | chr12 | 127416300 | 127416700 | YES | YES | NO | NO | Hypermethylation |
| PTGDR | Promoter | chr14 | 51804000 | 51805200 | YES | YES | NO | NO | Hypermethylation |
| ISL2 | Intron/Exon | chr15 | 74420000 | 74422000 | YES | YES | NO | YES | Hypermethylation |
| chr15:87750000-87751000 | Intergenic | chr15 | 87750000 | 87751000 | YES | YES | NO | NO | Hypermethylation |
| chr15:87753000-87754100 | Intergenic | chr15 | 87753000 | 87754100 | YES | YES | NO | NO | Hypermethylation |
| NR2F2 | Upstream | chr15 | 94666000 | 94667500 | YES | YES | YES | NO | Hypermethylation |
| chr16:11234300-11234900 | Intergenic | chr16 | 11234300 | 11234900 | YES | YES | NO | NO | Hypermethylation |
| SPN | Exon | chr16 | 29582800 | 29583500 | YES | YES | YES | NO | Hypermethylation |
| chr16:85469900-85470200 | Intergenic | chr16 | 85469900 | 85470200 | YES | YES | NO | NO | Hypermethylation |
| SLFN11 | Promoter | chr17 | 30725100 | 30725600 | YES | YES | NO | NO | Hypermethylation |
| DLX4 | Upstream | chr17 | 45396800 | 45397800 | YES | YES | NO | YES | Hypermethylation |
| SLC38A10 (MGC15523) | Intron | chr17 | 76873800 | 76874300 | YES | YES | YES | NO | Hypermethylation |
| S1PR4 | Exon | chr19 | 3129900 | 3131100 | YES | YES | YES | YES | Hypermethylation |
| MAP2K2 | Intron | chr19 | 4059700 | 4060300 | YES | YES | YES | NO | Hypermethylation |
| UHRF1 | Intron | chr19 | 4867300 | 4867800 | YES | YES | YES | NO | Hypermethylation |
| DEDD2 | Exon | chr19 | 47395300 | 47395900 | YES | YES | YES | NO | Hypermethylation |
| CDC42EP1 | Exon | chr22 | 36292300 | 36292800 | YES | YES | YES | NO | Hypermethylation |

TABLE 1C

Chromosome 21 differentially methylated regions

| Region Name | Gene Region | Chrom | Start | End | Microarray Analysis | Epi TYPER 8 Samples | Epi TYPER 73 Samples | Previously Validated Epi TYPER | Relative Methylation Placenta to Maternal |
|---|---|---|---|---|---|---|---|---|---|
| chr21:9906600-9906800 | Intergenic | chr21 | 9906600 | 9906800 | NO | YES | NO | NO | Hypomethylation |
| chr21:9907000-9907400 | Intergenic | chr21 | 9907000 | 9907400 | NO | YES | NO | NO | Hypomethylation |
| chr21:9917800-9918450 | Intergenic | chr21 | 9917800 | 9918450 | NO | YES | NO | NO | Hypomethylation |
| TPTE | Promoter | chr21 | 10010000 | 10015000 | NO | YES | NO | NO | Hypomethylation |
| chr21:13974500-13976000 | Intergenic | chr21 | 13974500 | 13976000 | NO | YES | NO | NO | Hypomethylation |
| chr21:13989500-13992000 | Intergenic | chr21 | 13989500 | 13992000 | NO | YES | NO | NO | Hypomethylation |
| chr21:13998500-14000100 | Intergenic | chr21 | 13998500 | 14000100 | NO | YES | NO | NO | Hypomethylation |
| chr21:14017000-14018500 | Intergenic | chr21 | 14017000 | 14018500 | NO | YES | NO | NO | Hypomethylation |
| chr21:14056400-14058100 | Intergenic | chr21 | 14056400 | 14058100 | NO | YES | NO | NO | Hypomethylation |
| chr21:14070250-14070550 | Intergenic | chr21 | 14070250 | 14070550 | NO | YES | NO | NO | Hypomethylation |
| chr21:14119800-14120400 | Intergenic | chr21 | 14119800 | 14120400 | NO | YES | NO | NO | Hypomethylation |
| chr21:14304800-14306100 | Intergenic | chr21 | 14304800 | 14306100 | NO | YES | NO | NO | Hypomethylation |
| chr21:15649340-15649450 | Intergenic | chr21 | 15649340 | 15649450 | NO | YES | YES | NO | Hypermethylation |
| C21orf34 | Intron | chr21 | 16881500 | 16883000 | NO | YES | NO | NO | Hypomethylation |
| BTG3 | Intron | chr21 | 17905300 | 17905500 | NO | YES | NO | NO | Hypomethylation |
| CHODL | Promoter | chr21 | 18539000 | 18539800 | NO | YES | YES | NO | Hypomethylation |
| NCAM2 | Upstream | chr21 | 21291500 | 21292100 | NO | YES | NO | NO | Hypomethylation |
| chr21:23574000-23574600 | Intergenic | chr21 | 23574000 | 23574600 | NO | YES | NO | NO | Hypomethylation |

TABLE 1C-continued

Chromosome 21 differentially methylated regions

| Region Name | Gene Region | Chrom | Start | End | Micro-array Analysis | Epi TYPER 8 Samples | Epi TYPER 73 Samples | Previously Validated Epi TYPER | Relative Methylation Placenta to Maternal |
|---|---|---|---|---|---|---|---|---|---|
| chr21:24366920-24367060 | Intergenic | chr21 | 24366920 | 24367060 | NO | YES | NO | NO | Hypomethylation |
| chr21:25656000-25656900 | Intergenic | chr21 | 25656000 | 25656900 | NO | YES | NO | NO | Hypomethylation |
| MIR155HG | Promoter | chr21 | 25855800 | 25857200 | NO | YES | YES | NO | Hypermethylation |
| CYYR1 | Intron | chr21 | 26830750 | 26830950 | NO | YES | NO | NO | Hypomethylation |
| chr21:26938800-26939200 | Intergenic | chr21 | 26938800 | 26939200 | NO | YES | NO | NO | Hypomethylation |
| GRIK1 | Intron | chr21 | 30176500 | 30176750 | NO | YES | NO | NO | Hypomethylation |
| chr21:30741350-30741600 | Intergenic | chr21 | 30741350 | 30741600 | NO | YES | NO | NO | Hypermethylation |
| TIAM1 | Intron | chr21 | 31426800 | 31427300 | NO | YES | YES | NO | Hypermethylation |
| TIAM1 | Intron | chr21 | 31475300 | 31475450 | NO | YES | NO | NO | Hypermethylation |
| TIAM1 | Intron | chr21 | 31621050 | 31621350 | NO | YES | YES | NO | Hypermethylation |
| SOD1 | Intron | chr21 | 31955000 | 31955300 | NO | YES | NO | NO | Hypomethylation |
| HUNK | Intron/Exon | chr21 | 32268700 | 32269100 | NO | YES | YES | NO | Hypermethylation |
| chr21:33272200-33273300 | Intergenic | chr21 | 33272200 | 33273300 | NO | YES | NO | NO | Hypomethylation |
| OLIG2 | Promoter | chr21 | 33314000 | 33324000 | YES | YES | NO | YES | Hypermethylation |
| OLIG2 | Downstream | chr21 | 33328000 | 33328500 | YES | YES | NO | NO | Hypomethylation |
| RUNX1 | Intron | chr21 | 35185000 | 35186000 | NO | YES | NO | NO | Hypermethylation |
| RUNX1 | Intron | chr21 | 35320300 | 35320400 | NO | YES | NO | NO | Hypermethylation |
| RUNX1 | Intron | chr21 | 35321200 | 35321600 | NO | YES | NO | NO | Hypermethylation |
| RUNX1 | Intron/Exon | chr21 | 35340000 | 35345000 | NO | YES | YES | NO | Hypermethylation |
| chr21:35499200-35499700 | Intergenic | chr21 | 35499200 | 35499700 | NO | YES | YES | NO | Hypermethylation |
| chr21:35822800-35823500 | Intergenic | chr21 | 35822800 | 35823500 | NO | YES | YES | NO | Hypermethylation |
| CBR1 | Promoter | chr21 | 36364000 | 36364500 | NO | YES | NO | NO | Hypermethylation |
| DOPEY2 | Downstream | chr21 | 36589000 | 36590500 | NO | YES | NO | NO | Hypomethylation |
| SIM2 | Promoter | chr21 | 36988000 | 37005000 | YES | YES | YES | YES | Hypermethylation |
| HLCS | Intron | chr21 | 37274000 | 37275500 | YES | YES | YES | NO | Hypermethylation |
| DSCR6 | Upstream | chr21 | 37300200 | 37300400 | YES | YES | NO | YES | Hypermethylation |
| DSCR3 | Intron | chr21 | 37551000 | 37553000 | YES | YES | YES | NO | Hypermethylation |
| chr21:37841100-37841800 | Intergenic | chr21 | 37841100 | 37841800 | NO | YES | YES | NO | Hypermethylation |
| ERG | Intron | chr21 | 38791400 | 38792000 | NO | YES | YES | NO | Hypermethylation |
| chr21:39278700-39279800 | Intergenic | chr21 | 39278700 | 39279800 | NO | YES | YES | NO | Hypermethylation |
| C21orf129 | Exon | chr21 | 42006000 | 42006250 | NO | YES | YES | NO | Hypermethylation |
| C2CD2 | Intron | chr21 | 42188900 | 42189500 | NO | YES | YES | NO | Hypermethylation |
| UMODL1 | Upstream | chr21 | 42355500 | 42357500 | NO | YES | YES | NO | Hypermethylation |
| UMODL1/C21orf128 | Intron | chr21 | 42399200 | 42399900 | NO | YES | NO | NO | Hypomethylation |
| ABCG1 | Intron | chr21 | 42528400 | 42528600 | YES | YES | NO | NO | Hypomethylation |
| chr21:42598300-42599600 | Intergenic | chr21 | 42598300 | 42599600 | YES | YES | NO | NO | Hypomethylation |
| chr21:42910000-42911000 | Intergenic | chr21 | 42910000 | 42911000 | NO | YES | NO | NO | Hypomethylation |
| PDE9A | Upstream | chr21 | 42945500 | 42946000 | NO | YES | NO | NO | Hypomethylation |
| PDE9A | Intron | chr21 | 42961400 | 42962700 | NO | YES | NO | NO | Hypomethylation |
| PDE9A | Intron | chr21 | 42977400 | 42977600 | NO | YES | NO | NO | Hypomethylation |
| PDE9A | Intron/Exon | chr21 | 42978900 | 42979800 | YES | YES | NO | NO | Hypomethylation |
| PDE9A | Intron | chr21 | 43039800 | 43040200 | NO | YES | YES | NO | Hypermethylation |
| chr21:43130800-43131500 | Intergenic | chr21 | 43130800 | 43131500 | NO | YES | NO | NO | Hypomethylation |
| U2AF1 | Intron | chr21 | 43395500 | 43395800 | NO | YES | NO | NO | Hypermethylation |
| U2AF1 | Intron | chr21 | 43398000 | 43398450 | NO | YES | YES | NO | Hypermethylation |
| chr21:43446600-43447600 | Intergenic | chr21 | 43446600 | 43447600 | NO | YES | NO | NO | Hypermethylation |
| CRYAA | Intron/Exon | chr21 | 43463000 | 43466100 | NO | YES | NO | NO | Hypomethylation |
| chr21:43545000-43546000 | Intergenic | chr21 | 43545000 | 43546000 | YES | YES | NO | NO | Hypomethylation |
| chr21:43606000-43606500 | Intergenic | chr21 | 43606000 | 43606500 | NO | YES | NO | NO | Hypomethylation |
| chr21:43643000-43644300 | Intergenic | chr21 | 43643000 | 43644300 | YES | YES | YES | YES | Hypermethylation |
| C21orf125 | Upstream | chr21 | 43689100 | 43689300 | NO | YES | NO | NO | Hypermethylation |
| C21orf125 | Downstream | chr21 | 43700700 | 43701700 | NO | YES | NO | NO | Hypermethylation |
| HSF2BP | Intron/Exon | chr21 | 43902600 | 43903800 | YES | YES | NO | NO | Hypermethylation |
| AGPAT3 | Intron | chr21 | 44161100 | 44161400 | NO | YES | YES | NO | Hypermethylation |
| chr21:44446500-44447500 | Intergenic | chr21 | 44446500 | 44447500 | NO | YES | NO | NO | Hypomethylation |
| TRPM2 | Intron | chr21 | 44614500 | 44615000 | NO | YES | NO | NO | Hypomethylation |
| C21orf29 | Intron | chr21 | 44750400 | 44751000 | NO | YES | NO | NO | Hypomethylation |

TABLE 1C-continued

Chromosome 21 differentially methylated regions

| Region Name | Gene Region | Chrom | Start | End | Microarray Analysis | Epi TYPER 8 Samples | Epi TYPER 73 Samples | Previously Validated Epi TYPER | Relative Methylation Placenta to Maternal |
|---|---|---|---|---|---|---|---|---|---|
| C21orf29 | Intron | chr21 | 44950000 | 44955000 | NO | YES | YES | NO | Hypermethylation |
| ITGB2 | Intron/Exon | chr21 | 45145500 | 45146100 | NO | YES | NO | NO | Hypomethylation |
| POFUT2 | Downstream | chr21 | 45501000 | 45503000 | NO | YES | NO | NO | Hypomethylation |
| chr21:45571500-45573700 | Intergenic | chr21 | 45571500 | 45573700 | NO | YES | NO | NO | Hypomethylation |
| chr21:45609000-45610600 | Intergenic | chr21 | 45609000 | 45610600 | NO | YES | NO | NO | Hypomethylation |
| COL18A1 | Intron | chr21 | 45670000 | 45677000 | YES | YES | NO | YES | Hypomethylation |
| COL18A1 | Intron/Exon | chr21 | 45700500 | 45702000 | NO | YES | NO | NO | Hypomethylation |
| COL18A1 | Intron/Exon | chr21 | 45753000 | 45755000 | YES | YES | NO | YES | Hypomethylation |
| chr21:45885000-45887000 | Intergenic | chr21 | 45885000 | 45887000 | NO | YES | NO | NO | Hypomethylation |
| PCBP3 | Intron | chr21 | 46111000 | 46114000 | NO | YES | NO | NO | Hypomethylation |
| PCBP3 | Intron/Exon | chr21 | 46142000 | 46144500 | NO | YES | NO | NO | Hypomethylation |
| COL6A1 | Intron/Exon | chr21 | 46227000 | 46233000 | NO | YES | NO | NO | Hypomethylation |
| COL6A1 | Intron/Exon | chr21 | 46245000 | 46252000 | NO | YES | NO | NO | Hypomethylation |
| chr21:46280500-46283000 | Intergenic | chr21 | 46280500 | 46283000 | NO | YES | NO | NO | Hypomethylation |
| COL6A2 | Intron | chr21 | 46343500 | 46344200 | NO | YES | NO | NO | Hypomethylation |
| COL6A2 | Intron/Exon | chr21 | 46368000 | 46378000 | NO | YES | NO | NO | Hypomethylation |
| C21orf56 | Intron/Exon | chr21 | 46426700 | 46427500 | NO | YES | NO | NO | Hypomethylation |
| C21orf57 | Intron | chr21 | 46541568 | 46541861 | NO | YES | NO | NO | Hypermethylation |
| C21orf57 | Exon | chr21 | 46541872 | 46542346 | NO | YES | NO | NO | Hypermethylation |
| C21orf57 | Downstream | chr21 | 46542319 | 46542665 | NO | YES | NO | NO | Hypermethylation |
| C21orf58 | Intron | chr21 | 46546914 | 46547404 | NO | YES | NO | NO | Hypermethylation |
| PRMT2 | Downstream | chr21 | 46911000 | 46913000 | YES | YES | NO | YES | Hypermethylation |
| ITGB2 | Intron | chr21 | 45170700 | 45171100 | NO | YES | YES | NO | Hypermethylation |

TABLE 2

| GENE NAME | CHROM | START | END | SNPs |
|---|---|---|---|---|
| chr13 group00016 | chr13 | 19773745 | 19774050 | rs7996310; rs12870878 |
| chr13 group00005 | chr13 | 19290394 | 19290768 | rs11304938 |
| CENPJ | chr13 | 24404023 | 24404359 | rs7326661 |
| ATP8A2 | chr13 | 25484475 | 25484614 | rs61947088 |
| PDX1 | chr13 | 27400459 | 27401165 | rs58173592; rs55836809; rs61944011 |
| RB1 | chr13 | 47790983 | 47791646 | rs2804094; rs4151432; rs4151433; rs4151434; rs4151435 |
| PCDH17 | chr13 | 57104856 | 57106841 | rs35287822; rs34642962; rs41292834; rs45500496; rs45571031; rs41292836; rs28374395; rs41292838 |
| KLHL1 | chr13 | 69579933 | 69580146 | rs3751429 |
| POU4F1 | chr13 | 78079515 | 78081073 | rs11620410; rs35794447; rs2765065 |
| GPC6 | chr13 | 92677402 | 92678666 | rs35689696; rs11839555; rs55695812; rs35259892 |
| SOX21 | chr13 | 94152286 | 94153047 | rs41277652; rs41277654; rs35276096; rs5805873; rs35109406 |
| ZIC2 | chr13 | 99439660 | 99440858 | rs9585309; rs35501321; rs9585310; rs7991728; rs1368511 |
| IRS2 | chr13 | 109232856 | 109235065 | rs61747993; rs1805097; rs9583424; rs35927012; rs1056077; rs1056078; rs34889228; rs1056080; rs1056081; rs12853546; rs4773092; rs35223808; rs35894564; rs3742210; rs34412495; rs61962699; rs45545638; rs61743905 |
| chr13 group00395 | chr13 | 111808255 | 111808962 | rs930346 |
| MCF2L | chr13 | 112724910 | 112725742 | rs35661110; rs2993304; rs1320519; rs7320418; rs58416100 |
| F7 | chr13 | 112799123 | 112799379 | rs2480951; rs2476320 |
| CIDEA | chr18 | 12244327 | 12244696 | rs60132277 |
| chr18 group00091 | chr18 | 12901467 | 12901643 | rs34568924; rs8094284; rs8094285 |
| C18orf1 | chr18 | 13377536 | 13377654 | rs9957861 |
| KLHL14 | chr18 | 28603978 | 28605183 | rs61737323; rs61737324; rs12960414 |
| CD33L3 | chr18 | 41671477 | 41673011 | rs62095363; rs2919643 |
| ONECUT2 | chr18 | 53254808 | 53259810 | rs35685953; rs61735644; rs8084084; rs35937482; rs35427632; rs7232930; rs3786486; rs34286480; rs3786485; rs28655657; rs4940717; rs4940719; rs3786484; rs34040569; rs35542747; rs33946478; rs35848049; rs7231349; rs7231354; rs34481218; rs12962172; rs3911641 |
| RAX | chr18 | 55086286 | 55086436 | rs58797899; rs45501496 |
| chr18 group00277 | chr18 | 57151972 | 57152311 | rs17062547 |
| TNFRSF11A | chr18 | 58203013 | 58203282 | rs35114461 |
| NETO1 | chr18 | 68685099 | 68687060 | rs4433898; rs34497518; rs35135773; rs6566677; rs57425572; rs36026929; rs34666288; rs10627137; rs35943684; rs9964226; rs4892054; rs9964397; rs4606820; rs12966677; rs8095606 |

TABLE 2-continued

| GENE NAME | CHROM | START | END | SNPs |
|---|---|---|---|---|
| chr18 group00304 | chr18 | 70133945 | 70134397 | rs8086706; rs8086587; rs8090367; rs999332; rs17806420; rs58811193 |
| TSHZ1 | chr18 | 71128742 | 71128974 | rs61732783; rs3744910; rs1802180 |
| chr18 group00342 | chr18 | 74170347 | 74170489 | rs7226678 |
| NFATC1 | chr18 | 75385424 | 75386008 | rs28446281; rs56384153; rs4531815; rs3894049 |
| chr18 group00430 | chr18 | 75653272 | 75653621 | rs34967079; rs35465647 |
| KCNG2 | chr18 | 75760343 | 75760820 | rs3744887; rs3744886 |
| OLIG2 | chr21 | 33317673 | 33321183 | rs2236618; rs11908971; rs9975039; rs6517135; rs2009130; rs1005573; rs1122807; rs10653491; rs10653077; rs35086972; rs28588289; rs7509766; rs62216114; rs35561747; rs7509885; rs11547332 |
| OLIG2 | chr21 | 33327593 | 33328334 | rs7276788; rs7275842; rs7275962; rs7276232; rs16990069; rs13051692; rs56231743; rs35931056 |
| RUNX1 | chr21 | 35180938 | 35185436 | rs2843956; rs55941652; rs56020428; rs56251824; rs13051109; rs13051111; rs3833348; rs7510136; rs743289; rs5843690; rs33915227; rs11402829; rs2843723; rs8128138; rs8131386; rs2843957; rs57537540; rs13048584; rs7281361; rs2843965; rs2843958 |
| SIM2 | chr21 | 36994965 | 36995298 | rs2252821 |
| SIM2 | chr21 | 36999025 | 36999410 | rs58347144; rs737380 |
| DSCAM | chr21 | 41135559 | 41135706 | rs35298822 |
| AIRE | chr21 | 44529935 | 44530388 | rs35110251; rs751032; rs9978641 |
| SUMO3 | chr21 | 45061293 | 45061853 | rs9979741; rs235337; rs7282882 |
| C21orf70 | chr21 | 45202972 | 45203525 | rs61103857; rs9979028; rs881318; rs881317 |
| COL18A1 | chr21 | 45754383 | 45754487 | rs35102708; rs9980939 |
| PRMT2 | chr21 | 46911967 | 46912385 | rs35481242; rs61743122; rs8131044; rs2839379 |
| SIX2 | chr2 | 45081223 | 45082129 | rs62130902 |
| SIX2 | chr2 | 45084851 | 45085711 | rs35417092; rs57340219 |
| SOX14 | chr3 | 138971870 | 138972322 | rs57343003 |
| TLX3 | chr5 | 170674439 | 170676431 | rs11134682; rs35704956; rs2964533; rs35601828 |
| FOXP4 | chr6 | 41623666 | 41624114 | rs12203107; rs1325690 |
| FOXP4 | chr6 | 41636384 | 41636779 | rs56835416 |
| chr7 group00267 | chr7 | 12576755 | 12577246 | rs56752985; rs17149965; rs6948573; rs2240572 |
| NPY | chr7 | 24290224 | 24291508 | rs2390965; rs2390966; rs2390967; rs2390968; rs3025123; rs16146; rs16145; rs16144; rs13235842; rs13235935; rs13235938; rs13235940; rs13235944; rs36083509; rs3025122; rs16143; rs16478; rs16142; rs16141; rs16140; rs16139; rs2229966; rs1042552; rs5571; rs5572 |
| SHH | chr7 | 155291537 | 155292091 | rs9333622; rs1233554; rs9333620; rs1233555 |
| GLIS3 | chr9 | 4288283 | 4289645 | rs56728573; rs12340657; rs12350099; rs35338539; rs10974444; rs7852293 |
| PRMT8 | chr12 | 3472714 | 3473190 | rs12172776 |
| TBX3 | chr12 | 113609153 | 113609453 | rs60114979 |
| chr12 group00801 | chr12 | 118516189 | 118517435 | rs966246; rs17407022; rs970095; rs2711748 |
| PAX9 | chr14 | 36201402 | 36202386 | rs17104893; rs12883298; rs17104895; rs35510737; rs12882923; rs12883049; rs28933970; rs28933972; rs28933971; rs28933373; rs61734510 |
| SIX1 | chr14 | 60178801 | 60179346 | rs761555 |
| ISL2 | chr15 | 74420013 | 74421546 | rs34173230; rs11854453 |
| DLX4 | chr17 | 45397228 | 45397930 | rs62059964; rs57481357; rs56888011; rs17638215; rs59056690; rs34601685; rs17551082 |
| CBX4 | chr17 | 75428613 | 75431793 | rs1285243; rs35035500; rs12949177; rs3764374; rs62075212; rs62075213; rs3764373; rs3764372; rs55973291 |
| EDG6 | chr19 | 3129836 | 3130874 | rs34728133; rs34573539; rs3826936; rs34914134; rs61731111; rs34205484 |
| MGC29506 | chr5 | 138757911 | 138758724 | rs11748963; rs7447765; rs35262202 |
| CENTG1 | chr12 | 56406249 | 56407788 | rs61935742; rs12318065; rs238519; rs238520; rs238521; rs808930; rs2640595; rs2640596; rs2640597; rs2640598; rs34772922 |
| CENTG1 | chr12 | 56416146 | 56418794 | rs11830475; rs34482618; rs2650057; rs2518686; rs12829991 |

TABLE 3

| GENE NAME | RELATIVE METHYLATION PLACENTA TO MATERNAL | PRC2 TARGET |
|---|---|---|
| CRYL1 | HYPOMETHYLATION | TRUE |
| IL17D | HYPOMETHYLATION | TRUE |
| GSH1 | HYPERMETHYLATION | TRUE |
| MAB21L1 | HYPERMETHYLATION | TRUE |
| PCDH17 | HYPERMETHYLATION | TRUE |
| KLHL1 | HYPERMETHYLATION | TRUE |
| POU4F1 | HYPERMETHYLATION | TRUE |
| SOX21 | HYPERMETHYLATION | TRUE |
| ZIC2 | HYPERMETHYLATION | TRUE |
| CIDEA | HYPERMETHYLATION | TRUE |
| KLHL14 | HYPERMETHYLATION | TRUE |
| ONECUT2 | HYPERMETHYLATION | TRUE |
| RAX | HYPERMETHYLATION | TRUE |
| TNFRSF11A | HYPOMETHYLATION | TRUE |
| OLIG2 | HYPERMETHYLATION | TRUE |
| OLIG2 | HYPOMETHYLATION | TRUE |
| SIM2 | HYPERMETHYLATION | TRUE |
| SIM2 | HYPERMETHYLATION | TRUE |
| SIX2 | HYPERMETHYLATION | TRUE |
| SIX2 | HYPERMETHYLATION | TRUE |
| SOX14 | HYPERMETHYLATION | TRUE |
| TLX3 | HYPERMETHYLATION | TRUE |
| SHH | HYPERMETHYLATION | TRUE |
| OSR2 | HYPERMETHYLATION | TRUE |
| TBX3 | HYPERMETHYLATION | TRUE |
| PAX9 | HYPERMETHYLATION | TRUE |
| SIX1 | HYPERMETHYLATION | TRUE |
| ISL2 | HYPERMETHYLATION | TRUE |

TABLE 3-continued

| GENE NAME | RELATIVE METHYLATION PLACENTA TO MATERNAL | PRC2 TARGET |
|---|---|---|
| DLX4 | HYPERMETHYLATION | TRUE |
| CBX4 | HYPERMETHYLATION | TRUE |
| CENTG1 | HYPOMETHYLATION | TRUE |
| CENTG1 | HYPOMETHYLATION | TRUE |

TABLE 4A

| SEQ ID NO | GENE NAME | SEQUENCE |
|---|---|---|
| 1 | chr13 group-00016 | CAGCAGGCGCGCTCCCGGCGAATCTGCCTGAATCGCCGTGAATGCGGTGGGGTGCAGGGCAGGGGCTGGTTTTCTCAGCCGGTCTTGG CTTTTCTCTTTCTCTCCTGCTCCACCAGCAGCCCCTCCGCGGGTCCCATGGGCTCCGCGCTCAGAACAGCCCGGAACCAGGCGCCGCTC GCCGCTCGCTGGGGGCCACCCGCCTCTCCCCGGAACAGCCTCCCGCGGGCCTCTTGGCCTCGCACTGGCGCCCTCACCCACACATCGT CCCTTTATCCGCTCAGACGCTGCAAAGGGCCTTCTGTCTC |
| 2 | CENPJ | GCTTTGGATTTATCCTCATTGGCTAAATCCCTCCTGAAACATGAAACTGAAACAAAGCCCTGAACCCCCTCAGGCTGAAAAGACAAACCCC GCCTGAGGCCGGGTCCCGCTCCCCACCTGGAGGGACCCAATTCTGGGCGCCTTCTGGCGACGGTCCCTGCTAGGGACGCTGCGCTCTC CGAGTGCGAGTTTTCGCCAAACTGATAAAGCACGCAGAACCGCAATCCCCAAACTAACACTGAACCCGGACCCGCGATCCCCAAACTGAC AAGGGACCCGGAACAGCGACCCCCAAACCGACACGGGACTCGGGAACCGCTATCTCCAAAGGGCAGC |
| 3 | ATP8A2 | TTTCCACAACAGGGAGCCAGCATTGAGGCGCCCAGATGGCATCTGCTGGAAATCACGGGCCGCTGGTGAAGCACCACGCCTTACCCGAC GTGGGGAGGTGATCCCCCACCTCATCCCACCCCCTTCTGTCTGTCTCCTT |
| 4 | GSH1 | GCTGGACAAGGAGCGCTCACTGTAGCTCTGCTGTGGATTGTGTTGGGGCGAAGAGATGGGTAAGAGGTCAAAGTCGTAGGATTCTGGCG ACCGCCTACCAAGGGATTGGGTCACAGCACAGAGGTCTGATCGCTTCCTTCTCTGCTCTGCCACCTCCAGACAGCAGCTCTAACCAGCT GCCCAGCAGCAAGAGGATGCGCACGGCTTTCACCAGCACGCAGCTGCTAGAGCTGGAGCGCGAGTTCGCTTCTAATATGTACCTGTCCC GCCTACGTCGCATCGAGATCGCGA |
| 5 | PDX1 | TGCCTGACACTGACCCCAGGCGCAGCCAGGAGGGGCTTTGTGCGGGAGAGGGAGGGGGACCCCAGCTTGCCTGGGGTCCACGGGACT CTCTTCTTCCTAGTTCACTTTCTTGCTAAGGCGAAGGTCCTGAGGCAGGACGAGGGCTGAACTGCGCTGCAATCGTCCCCACCTCCAGCG AAACCCAGTTGAC |
| 6 | PDX1 | TCGGCGGAGAGACCTCGAGGAGAGTATGGGGAAAGGAATGAATGCTGCGGAGCGCCCCTCTGGGCTCCACCCAAGCCTCGGAGGCGG GACGGTGGGCTCCGTCCCGACCCCTTAGGCAGCTGGACCGATACCTCCTGGATCAGACCCCACAGGAAGACTCGCGTGGGGCCCGATA TGTGTACTTCAAACTCTGAGCGGCCACCCTCAGCCAACTGGCCAGTGGATGCGAATCGTGGGCCCTGAGGGGCGAGGGCGCTCGAAC TGCATGCCTGTGCACGGTGCCGGGCTCTCCAGAGTGAGGGGCCGTAAGGAGATCTCCAAGGAAGCCGAAAAAAGCAGCCAGTTGGGC TTCGGGAAAGACTTTTCTGCAAAGGAAGTGATCTGGTCCCAGAACTCCAGGGTTGACCCCAGTACCTGACTTCTCCGGGAGCTGTCAGCT CTCCTCTGTTCTTCGGGCTTGGCGCGCTCCTTTCATAATGGACAGACACCAGTGGCCTTCAAAAGGTCTGGGGTGGGGAACGGAGGAA GTGGCCTTGGGTGCAGAGGAAGAGCAGAGCTCCTGCCAAAGCTGAACGCAGTTAGCCCTACCCAAGTGCGCGCTGGCTCGGCATATGC GCTCCAGAGCCGGCAGGACAGCCCGGCCCTGCTCACCCCGAGGAGAAATCCAACAGCGCAGCCTCCTGCACCTCCTTGCCCCAGAGAC |
| 7 | MAB21L1 | AGATCCCGGTGCATTTAAAGGCCGGCGTGATCTGCACCACGTACCTATCTCGGATTCTCAGTTTCACTTCGCTGGTGTCTGCCACCATCTT TACCACATCCCGGTAGCTACATTTGTCTACCGCTTGAGCCACCAGCGTCTGAAACCTGGACCGGATTTTGCGCGCCGAGAGGTAGCCGG AGGCGGTAATGAATTCCACCCAGAGGGACATGCTTCCTCTTGCGCCCGTCGCTCAACTTCAGCACCGCGCAGCCGGGCAGTGAGCCATCG TCCACGAAGTTGAACACCCCCATTTGGTTGAGATAAAGCACCACTTCAAATTCGGT |
| 8 | RB1 | ACTATGCCTTGAGGGTCAAAACGTCTGGATTTCCTGATCGATGCTGTCGTCGCTGTCCACGGAGCTACTGTCGCCGTCAGAGCGGGAAG GCACGTTCAGGGAGTAGAAGCGTGGGCTTGCAGAAAGGGACCTGTTGCTGCCTTACATGGGGCCGGCAGGGTAGTCTTGGAAATGCC CAAGATTGCTTCCGCGCGCGTCAGTTCAGCGGACGTGTCTGCCTGGCACGAGGACCGTTCTACAAACTCGTTCCTGGAAGCCGGGCTCG CTGGAGGCGGAGCTTTGGTTTCCTTCGGGAGCTTGTGGGGAATGGTCAGCGTCTAGGCACCCCGGGCAAGGGTCTGTGGCCTTGGTGG CCACTGGCTTCCTCTAGCTGGGTGTTTTCCTGTGGGTCTCGCGCAAGGCACTTTTTTGTGGCGCTGCTTGTGCTGTGTGCGGGTCAGGC GTCCTCTCTCCTCCCGGCGCTGGGCCTCTGGGGCAGGTCCCCGTTGGCCTCCTTGCGTGTTTGCCGCAGCTAGTACACCTGGATGGCC TCCTCAGTGCCGTCGTTGCTGCTGGAGTTCTGACGCCTCGGGCGCCTGCGCCGCACTTGTGACTTGCTTTCCCCTTCTCAGGGCGCCAGC GCTCCTCTTGACCCCGCTTTTATTCGTGGTGCTTCTGAAG |
| 9 | PCDH17 | GCAAGTCGGGTAGCTACCGGGTGCTGGAGAACTCCGCACCGCACCTGCTGGACGTGGACGCAGACAGCGGGCTCCTCTACACCAAGCA GCGCATCGACCGCGAGTCCCTGTGCCGCCACAATGCCAAGTGCCAGCTGTCCCTGAGGTGTTCGCCAACGACAAGGAGATCTGCATGA TCAAGGTAGAGATCCAGGACATCAACGACAACGCGCCCTCCTTCTCCTCGGACCAGATCGAAATGGACATCTCGGAGAACGCTGCTCCG GGCACCCGCTTCCCCCTCACCAGCGCACATGACCCCGACGCCGGCGAGAATGGGCTCCGCACCTACCTGCTCACGCGCGACGATCACG GCCTCTTTGGACTGGACGTTAAGTCCCGCGGCGACGGCACCAAGTTCCCAGAACTGGTCATCCAGAAGGCTCTGGACCGCGAGCAACAG AATCACCATACGCTCGTGCTGACTGCCCTGGACGGTGGCGAGCTCCACGTTCCGCCACCGTACAGATCAACGTGAAGGTGATTGACTC CAACGACAACAGCCCGGTCTTCGAGGCGCCATCCTACTTGGTGGAACTGCCCGAGAACGCTCCGCTGGGTACAGTGGTCATCGATCTGA ACGCCACCGACGCCGATGAAGGTCCCAATGGTGAAGTGCTCTACTCTTTCAGCAGCTACGTGCCTGACCGCGTGCGGGAGCTCTTCTCC ATCGACCCCAAGACCGGCCTAATCCGTGTGAAAGGCAATCTGGACTATGAGGAAAACGGGATGCTGGAGATTGACGTGCAGGCCCAGAA CCTGGGCCTAACCCTATCCCAGCCCACTGCAAAGTCACGGTCAAGCTCATCGACCGCAACGACAATGCGCCGTCCATCGGTTTCGTCTC CGTGCGCCAGGGGGCGCTGAGCGAGGCCGCCCCTCCCGGCACCGTCATCGCCCTGGTGCGGGTCACTGACCGGGACTCTGGCAAGAA CGGACAGCTGCAGTGTCGGGTCCTAGGCGGAGGAGGGACGGGCGGCGGCGGGGCCTGGGCGGGCCCGGGGGTTCCGTCCCCTTCA AGCTTGAGGAGAACTACGACAACTTCTACACGCGTGGTGACTGACCGCCCGCTGGACCGCGAGACACAAGACGAGTACAACGTGACCATC GTGGCGCGGGACGGGGGCTCTCCTCCCCTCAACTCCAACCAAGTCGTTCGCGATCAAGATTCTAGACGAAGACACAACCCGCCTCGGTT CACCAAAGGGCTCTACGTGCTTCAGGTGCACGAGAACAACAACTCCGGGAGAGTACCTGGGCTCTGTGCTCGCCCAGGATCCCGACCTGG GCCAGAACGGCACCGTATCCTACTCTATCCTGCCCTCGACACATCGGCGACGTGTCTATCTACACCTATGTGTCTGTGAATCCCACGAACG GGCCATCTACGCCCTGCGCTCCTTTAACTTCGAGCAGACCAAGGCTTTTGAGTTCAAGGTGCTTGCTAAGGACTCGGGGGCGCCCGCG CACTTGGAGAGCAACGCCACGGTGAGGGTGACAGTGCTAGACGTGAATGACAACGCGCCAGTGATCGTGCTCCCCACGCTGCAGAACGA CACCGGGAGCTGCAGGTGCCGCGCAACGCTGGCCTGGGCTATCTGGTGAGCACTGTGCGCGCCCTAGACAGCGACTTCGGCGAGAGC GGGCGTCTCACCTACGAGATCGTGGACGGCAACGACGACCACCTGTTTGAGATCGACCCGTCCAGCGGCGAGATCCGCACGCTGCACC |

TABLE 4A-continued

| SEQ ID NO | GENE NAME | SEQUENCE |
|---|---|---|
| | | CTTTCTGGGAGGACGTGACGCCCGTGGTGGAGCTGGTGGTGAAGGTGACCGACCACGGCAAGCCTACCCTGTCCGCAGTGGCCAAGCT<br>CATCATCCGCTCGGTGAGCGGATCCCTTCCCGAGGGGGTACCACGGGTGAATGGCGAGCAGCACCACTGGGACATGTCGCTGCCGCTC<br>ATCGTGACTCTGAGCACTATCTCCATCATCCTCCTA |
| 10 | KLHL1 | ATGCGCCCTCTGCACCCCTAGAGCCAGAAGACGCTAGGTGGGCTGCGCGCTCTGCCAGGCGAAGGCTGGAGCGCAGACGGCAAAGCC<br>GCGCGTTTCAGCCGTGGTCGGGTCCGCAGGACCTGGGCGTGGGGACACCACCAGGCAGGAGCAGAGGCAGGACTGGGACGCCAAAAG<br>CTGAGAATCCTCGATGCCCGCGCGAGAGCCCCGTGTTAT |
| 11 | POU4F1 | TTCTGGAAACCGGGCCCCACTTGCAGGCCCGGCCACCTTGGGTTCTGGTGGCCGAAGCCGGAGCTGTGTTTCTCGCAGACTCGGGGAG<br>CTACATTGTGCGTAGGCAATTGTTTAGTTTGAAAGGAGGCACATTTCACCACGCAGCCAGCGCCCTGCATGCAGGAGAAGCCCCCAGGG<br>CCCAGGGTCGGCTGGCTTTAGAGGCCACTTAGGTTGTTTTAAGCACATGTGAAAGGGCAGACAGCAGGGGAGCAGGATATGGGTAAGAT<br>CTTCGGGTCTCAGAACAGGGGCTGCCCTTGGGCTGTCCCGGCGCCCTGGGCTCTGACACTGAAGGGTGGAATGGAGGAAGGAATGGAG<br>AAAGGACGGTGGAACTTTCGCTTCCCCTCTGGGCGCCTTCCCAGGGTCATGCCTGAGCTGCTTTGATCCCAGTGTCGCGCATCTTGTC<br>CGCTACCTCCCAGGCGATAGCTACTGGGCTCCTCGCTGGCCTCACTGGGGGCCATCCCGGGCAGTGGCCTGCCCTCCGAGGCCCGCGG<br>GACCCAGCCCAGAGCTGAGGTTGGAGTTCTCCGGGCCACGTTCCGGGTCGCTTAGGCTCGGAGATTTCCCGGAGACCGTCGTCCTCCCT<br>TTCTGCTTGGCACTGCGGAGCTCCCTCGGCCTCTCTCCTCCTCTGGTCCCTAAGGCCCGGAGTGGTTGGCGGTACTGGGGCCCGTCGTC<br>ATCTCTGCTTCTAAGGCATTCAGACTGGGCTCCAGCTGGGACCGGCAGAGGAGGTTCTCAAGGAAACTGGTGGGAAATATAGTTTTCTTT<br>CGTCTGGTCGTTTAATTTAAATGCAACTTCCCTTGGGGACATTTTCCTGGACGTTAACCAGACCACCTTGAGATGTCGTTGATGACCTAGA<br>GACCCAGATGATGCGTCCCAGGAAAGTTCACTGCTGACTATTGTCACTCTTGGCGTTATATCTATAGATATAGACCTATGTACATATCTCCA<br>CCCTGATCTCTCCGTGGACATGAAACCCACCTACCTTGTGAAAGCCCTACGGGTGACACATGACTACTACGTCTCTGTCCCAACAGGGGC<br>TGGGCCTCCCCTGCCTAATAGTTGCCAGGAGTTTCGCAGCCAAGTGAATAATGTCTTATGGCTGAACGTGGCCAAGGACTCCTGTGATT<br>TAGGTCCCAGGAGGAGCAGAGACGTCCCCGCCCCGCCTGGGCCTGCCGCATTCAAAGCTGGAAGAAGGCGCTGATCAGAGAAGGGGC<br>TTCCAGGTCCTGGGTTAGAACAACAACAAACAAACGAAACTCCACAACAGACACGCCTGCCCATGACCCCACGCAAGGACATAGGAAGTT<br>CTGTCGCCTTCCTGCTCCGCGGATAGCCGCCTGCCGTCTGCTGCCACCAGAACGCACGGACGCTCGGGGTGGAGGTAGTCAATGGGCA<br>GCAGGGGACCCCCAGCCCCCACAAGCGCGGCTCCGAGGACCTGGAAGCGGGTGCCTGTCGCTCTCCGCAGGCTCCGCTCTGCCTCCA<br>GGAGCAAGATCCCCAAAAGGGTCTGGAAGCTGTGGAGAAAAC |
| 12 | GPC6 | TTTTTTAAACACTTCTTTTCCTTCTCTTCCTCGTTTTGATTGCACCGTTTCCATCTGGGGGCTAGAGGAGCAAGGCAGCAGCCTTCCCAGCC<br>AGCCCTTGTTGGCTTGCCATCGTCCATCTGGCTTATAAAAGTTTGCTGAGCGCAGTCCAGAGGGCTGCCTGCTCGTCCCCTCGGCTGGC<br>AGAAGGGGTGACGCTGGGCAGCGGCGAGGAGCGCGCCGCTGCCTCTGGCGGGCTTTCGGCTTGAGGGGCAAGGTGAAGAGCGCACC<br>GGGCGTGGGGTTTACCGAGCTGGATTTGTATGTTGCACCATGCCTTCTTGGATCGGGGCTGTGATTCTTCCCCTCTTGGGGCTGCTGCTC<br>TCCCTCCCCGCCGGGGCGGATGTGAAGGCTCGGAGCTGCGGAGAGGTTCCGCCAGGCGTACGGTGCCAAGGGATTCAGCCTGGCGGAC<br>ATCCCCTACCAGGAGATCGCAGGTAAGCGCGGGCGCGCTGCAGGGGCAGGCTGCAGCCCTCGGCTGCCGCACGTCCCACTGGCCGCC<br>CGGCGTCCCCTTCCTTCCCCCTGTTGCTGAGTTGGTGCTCACTTTCTGCCACCGCTATGGGACTCCGCGTCTCCGTGTTGGGCGGCGGA<br>TGCTCCTGCGGCTTCTTCGGCGGGGAAGGTGTGCGTCTCCGCCGCCTCATTGTGTGCACACGCGGGAGCACCCTGGCTCCCGCCTCC<br>CGCTGCTCTCGCGCCCTTCTACCCCTTAGTTGATGGCTCAGGCCCGGCTGGCCAGGGAGCCCGGGTCACTCCGGGGCGGCTGCAAGGC<br>GCAGACGGAGAGCCGAGCCGGGCGCTCACTCGCGTTCTGGTTCGGGCAAACTTGGAAGAACTGCGACCGCAGTTTGCCCAGCGCCAC<br>AGTCTGAGTGGCGCCTTCTCCACTCCCGCCCTTGCGCCGGCAGGGGCGGTGGAGAGACGCGGAGGGCTCCCCAGCCCCTCTCTCCCC<br>TATCCGTCCTTCGGGCGACAGAGCCCCGGCGCTCGGGCCGGGGCGGGCAAGGCTGGGAGGGACCCTCGCCGGGGACCTGGCCTC<br>TGGACGCCGGCGTTTCAAGGCTGGTTTGGGGACTTCACGGGCTGCCTGTTTCAGATGTGGGGCGGGCTTTCCCGTTAGGGTTCCTCAGT<br>GCTTCCCCAGTTGCTGTTGGCCACTCAGGGCCCGGGGACACCCTGCCACCCGGTCTGGAGCCGGCCTCGTCTGCCAGCGAACAGCCAA<br>CTTTAGCGGGTGGCTCAGCTGGGGATT |
| 13 | SOX21 | CACTCAGTGTGTGCATATGAGAGCGGAGAGACAGCGACCTGGAGGCCATGGGTGGGGCGGGTGGTGAAGCTGCCGAAGCCTACACAT<br>ACACTTAGCTTTGACACTTCTCGTAGGTTCCAAAGACGAAGACACGGTGGCTTCAGGGAGACAAGTCGCAAGGGCGACTTTTCCAAGCGG<br>GAGATGGTGAAGTCTTTGGACGTGTAGTGGGTAGGTGATGATCCCCGCCAGCCGCCTGTAGGCCCGCAGACTTCAGAAAACAAGGGCCTT<br>CTGTGAGCGCTGTGTCCTCCCCGGAATCCGCGGCTTAACACATTCTTTCCAGCTGCGGGGCCAGGATCTCCACCCCGCGCATCCGTGGA<br>CACACTTAGGGTCGCCTTTGTTTTGCGCAGTGATTCAAGTTGGGTAACCCTTGCTCAACACTTGGGAAATGGGGAGAATCTCCCCCACCC<br>GCAACCTCCCGCACCCCAGGTTCCCAAAATCTGAATCTGTATCCTAGAGTGGAGGCAGCGTCTAGAAAGCAAAGAAACGGTGTCCAAAGA<br>CCCCGGAGAGTTGAGTGAGCGCAGATCCGTGACGCCTGCGGTACGCTAGGGCATCCAGGCTAGGGTGTGTGTGTGCGGGTCGGGGGG<br>CGCACAGAGACCGCGCTGGTTTAGGTGGACCCGCAGTCCCGCCCGCATCTGGAACGAGCTGCTTCGCAGTTCCGGCTCCCGGCGCCCC<br>AGAGAAGTTCGGGGAGCGGTGAGCCTAGCCGCCGCGCGCTCATGTTTATT |
| 14 | ZIC2 | AGTCACTCCAGGATCAGAGGCCGCGTCGGTTCTGCTTGGGGCATGGGCAGAGGGAGGCTGCTGGGGCAAGCCCCGGCTGGACGCGA<br>GGGAAGAAACTCGTCCCAGGACCCGCACGCCCATACCTGGCTGTCCCAGAGCTCTTCCCTAGGCCGGCACCTTCGCTCTTCCTCTTCCC<br>CACCCCCTAGCCCTTTTGTCTCTTTTTCAGACGGATGTTTTCAGTCTCAAGTGGTTTTATTTTCCGCACAAAACCCTGAGATCAAGGGCAGA<br>TCACAGACTGTACCGGAGCTCGGGTTTCCCTGGACTCTGTGCTGTTCTGCGTCCAGGGTTGGCTAGGAAGGAAGGCCTGGGCCGG<br>GAGGTGACGGGTCTCCCGCCCAGGTCGGCAGGACGGGGAGGTGTGTCCCGGTAGGTCCCTGGTGAGCTCACCCGTGGCATCGGGG<br>ACCCGCGGGAACCCACCGGGCGCCCACTAGAGACTCGGGTCCTACCCTCCCCACACTACTCCACCGAAATGATCGGAAGGGCGCGCT<br>AGGCCTGCTTCCAAGGGCTCAGTGATAAAGGCCTCAAAATCACACTCCATCAAGACTTGGTTGAAGCTTTGGGTAGGTTTGTTGTTGTTGT<br>TGTTGTTGTTTGTTTGTTTTAGCAGACACGTCCTGGAAAGAGGTCCTCAGAACCCAAAGGTTCAATAATGATTTGTGGATGGATTGAT<br>TATAGTCTGATATCGCTCTGGTTCCACAGAAACCCGGAGCTCCTTGGCCCACTGTTACCCCAGCAGACCTAAATGGACGGTTTCTGTTTTT<br>CACTGGCAGCTCAGAACTGGACCGGAAGAAGTTCCCCTCCACTTCCCCCCTCCCGACACCAGATCATTGCTGGGTTTTATTTTCGGGGG<br>AAAAACAACAACAACAACAAAAAAAAACACTAGGTCCTTCCAGACTGGATCAGGTGATCGGGCAAAAACCCTCAGGCTAGTCCGGCTG<br>GGTGCCCGAGCATGAAAAGGCCTCCGTGGCCGTTTGAACAGGGTGTTGCAAATGAGAACTTTTGTAAGCCATAACCAGGGCATCCTGAG<br>GGTCTGAGTTCACGGTCAAGGCTGTGGGCTACTAGGTCCAGCGAGTCCAGGCCTCGCCCCGCCCCGAGCTGCCACAGCCAAGATCTTC<br>GGCAGGGAATTCGAGACCAGGGTCCTCCCACTCCT |
| 15 | chr13<br>group-<br>00385 | TTTCGTGCCGCTGTTTTCAATGCGCTAACGAGGCACGTTATTCTTAGCCGCGTCCGGGAGGGGATCACATTCCTGCGCAGTTGCGCTGCT<br>GGCGGAAGTGACTTGTTTTCTAACGACCCTCGTGACAGCCAGAGAATGTCCGTTTCTCGGAGCGCAGCACAGCCTGTCCCATCGAGAAG<br>CCTCGGGTGAGGGGCCCGGTGGGCGCCCGGAGGCCGCTGGAGGGCTGTGGGAGGGACGGTGGCTCCCCACTCCCGTGCGAAGGGC<br>AGGCAAACCAGAAGCCTCTTTTGAGAGCCGTTTGGGATTGAGACGAGTAAGCCACAGCGAGTGGTTAGAAGTAGGTTAGGAAGAAGGGG<br>AGGTAAGAAAGCCGAGTAGGGTT |

TABLE 4A-continued

| SEQ ID NO | GENE NAME | SEQUENCE |
|---|---|---|
| 16 | chr13 group-00390 | GTTCGGTGGACAAGGGGGCAGCGCCCACAGCAAGCCGGAAAGAGGGAGGCGCGGGCCGCGCTTGGGGCCTGCCGCTGCACGCCAG CCTGGGCAAAGAGCTGCCACCTTCTGCGGGCGAAGCGGGTCGGGACGCAGGACGGCAGCGGGGCTGGAGGCAGCTACGTGGGTCCAC ACCCCCATGCCCTGCAAGGCTCCTTGGCCCTGCTTCTCCTCTGTCTCGGCGGGAGAGGAGCAGCCTCGGTTTTACAGAATTTC |
| 17 | chr13 group-00391 | TGTGCCATTTAGTGAGAGGTGTTTGGGCAAAGAATCAATTTAACTGTGACTGACCGACGGGCTTGACTGTATTAATTCTGCTACCGAAAA AAAAAAAAAAAAAAAAAGCAATGAGCCGCAAGCCTTGGACTCGCAGAGCTGCCGGTGCCCGTCCGAGAGCCCCACCAGCGCGGCTCACGC CTCAGTCTC |
| 18 | chr13 group-00395 | AGAGTCCCAGTTCTGCAGGCCGCTCCAGGGCTAGGGGTAGAGATGGTGGCAGGTGGTGCGTCAACTCTCTAGGGAAGAGGAACTTGCAT TACAAAGACTTGTCTTTCTGAGCTGAAGTCAAAACGGGGGCGTCAAGCGCGCTCCGTTTGGCGGCGGTGGAGGGGCCGCGCGCCCGCG CTGTCCCAGCCGGAGCTGCCCTGGCTGGTGATTGGAGGTTTAACGTCCGGAATTCAGGCGCTTCTGCAGCTCAGATTTGCCGGCCAAGG GGCCTCAGTTGCAACTTTTCAAAATGGTGTTTCTGGAAAATACAATGGTGACAGCTTTTGGCTATAGAGAATGAAACT GCTTCCCTTTGGCGGTGGAACTCTTAAACTTCGAAGAGTGAAAGAATACAATGAAATAAAATGCCATAAGATCACTGGATTTTTCAGAAAAA GGAAGACCCCAAATTACTCCCAAATGAGGCTTTGTAAATTCTTGTTAAAAATCTTTAAATCTCGAATTTCCCCCTACAACATCTGATGAGTG CTTTAAGAGCAAACGAGCAAATCCCACCTCGAGAATCAACAAACCCAAGCTCTGGCCAAGGCTCTCCCCGCGTTTCTTCTCGTGACCTG GGGAATGTCCCGCCCATCGCTCACCTGGCTCTTGTCATCTCGCTCATCTTGAAGTGACCCGTGGACAATGCTG |
| 19 | chr13 group-00399 | AGCTGCCCTCTGTGGCCATGAGCGGGTGTCCAGCCCCTTCCAAGGCTGCACCGGGGAGACGCTGGTTTTCTGCTCGCTGTGACCGAACA AAGCCCCTAAGAGTCAGTGCGCGGAACAGAAGAGCCGGACCCCGACGGGCCGAGTCCCAACGTGAGGCACCCGGCAGAGAAAACACGT TCACG |
| 20 | PROZ | CCTCGGCAGCACCGGCATGGCTGGAGGCCAGTACGGCCAGGTGTGGCGGGAGGGAGCGCCGTCTGGCTTGGGTCGTCCATCCTGACA GGACGCTGCAAGGGCAGGAGCCCCGCGCCCCGTGTCCTGCGCCCCGCTCGAGGACAAGCCCCAGCCGCCGGTCTCCGCTGGGTTCC GACAG |
| 21 | CIDEA | CTTTAAGAGGCTGTGCAGGCAGACAGACCTCCAGGCCCGCTAGGGGATCCGCGCCATGGAGGCCGCCCGGGACTATGCAGGAGCCCTC ATCAGGCGAGTGCCCCGCGTCCCCCTGATTGCCGTGCGCTTCCAATCGCCTTGCGTTCGGTGGCCTCATATTCCCCTGTGCGCCTCTAGT ACCGTACCCCGCTCCCTTCAGCCCCTGCTCCCCGCATTCTTGCGCTCCGCGACCCCGCGCACACACCCATCGCCCCACTGGTGCC CAAGCCGTCCAGCCGCGCCCGCGGGCAGAGCCCAATCCCGTCCCGCGCCTCCTCACCCTCTTGCAGCTGGGCACAGGTACCAGGTGTG GCTCTTGCGAGGTG |
| 22 | chr18 group-00091 | AGACTTGCAGAACTCGGGCCCCTGGAGGAGACCTAACCGCCACGGTCTTGGGGAGGTTCCGGAGGGCCTCGGTTGTCTGCACTCCCA ACACCAAGAAACCCTGAGACGCGAAGCTGCCAGCGTGCTGCCCTCAGAGCAGGGCGACGCAAAGCCAGCGGACCCCGGGGTGGCGG G |
| 23 | chr18 group-00094 | TGCTCGGCTGGGGGGCTCGCTCCGCACTTTCGGTGCCAGAAAATGCCCAGAGGAGCGGGGCGGCCCCAGAGCCTCCTTTCGGGCGC GAGGCCCGGCGCGTGTGTACGGAGTCCAGTCCCCCAGGGAGTGGGGTGCCCGCACCTTCCCCTCCGCGCTCGGAGCCAC |
| 24 | KLHL14 | TCTTGCACACCTGCTTGTAGTTCTGCACCGAGATCTGGTCGTTGAGGAACTGCACGCAGAGCTTGGTGACCTGGGGGATGTGCAGGATCT TGCTGACCGACAGCACCTCCTCCACCGTGTCCAGGGACAGGGTCACGTTGGCCGTGTAGAGGTACTCGAGCACCAGGCGCAGCCCGAT GGACGAGCAGCCCTGCAGCACCAGGTTGTTGATGGCCCGGGGCTGGTCAGCAGCTTGTCGTCGGGGAGGAAGAAGGAGTCCCGGG CTCCTCCTGCGGCGGCGGCTGCTGCTGTGACGGCTGCTGCTGCGGCGGCTGCTGCTGGTCCTTGGGGGCCCCAGGCCGTCCTG GCCGCCGACCCCTCCCCCGAGAGGGGGGTGGCTGGAGAAGAGCGATCGGAAGTACTGCGAGCAGGAGGCCAGCACGGCCTTGTGGCA ATGGAACTGCTGGCCCTGGGCCGTCAGGGTCACGTCGCAAAACAGCTGCTTCCTCCACAGCAGGTTGAGGCCGTGCAGCAGGTTGTCGC TGTGGCTGGGGTCGAAGGTGGAGGTCCTGTCCCCGGATCTGGACATGGCGAGCTGACTCGGTGCACCTGGCTTTAAACCCTCCTCCAAC CTGGCAGACAGGGGTGGGGATGGAGGGAGGGGAGCAGGGTGGTGGAGCGGGTGGGGTGTGGTCGGGGTGGGAAGGGTGTGGA GGGGAGGGGAGGCGAAGAACAAGAATCAAGGCTCAGCTTGACTCCTCCTGGCGCGCTCCGGACCCCGACCCTAGGAGGAAAGTCCG AAGACGCTGGATCCGTGAGCGCCACCAGAAGGGCCCTGTCTGGGGTCCCGGCGCCGGTTCTGCGCCCTGCAGCTCCTCTCGCCACCTC CCACACACTTCGTCCCTCACTTTCCTAAAACCAACCACCTCAGCTCGGCTGCGTTGGCAGCAACAGCAGTGGCAGCAGCGACGGCAAAGTG GCGCTGAGGCCGAGGCACCTCGTGGGCTCGTGTCCATGCCGGGCAGATGAAGGGAAAGGCCGGGAAGTGGGGAGCCGGGGGTGC CCTGAAAGCTCAGAGGCGACCGACGGCGAAGGTTCCAGGTCAACTTGTGCCCGAAGCTTTGCTTTTCGCAGTTGGCCCAGTTTGGGGGA GGGGGTAGGAACAGGGGCCCGACCAGCGTGCGGGTGTGCGAATCTTAGCTCTCCAAAAGCTG |
| 25 | ST8SIA3 | CCTCTGTGTTAGTGCCCTCGGGAATTTGGTTGATGGGGTGTTTG |
| 26 | ONECUT2 | TGATGTCGCACCTGAACGGCCTGCACCACCCGGGCCACACTCAGTCTCACGGGCCGGTGCTGGCACCCAGTCGCGAGCGGCCACCCTC GTCCTCATCGGGCTCGCAGGTGGCCACGTCGGGCCAGCTGGAAGAAATCAACACCAAAGAGGTGGCCCAGCGCATCACAGCGGAGCTG AAGCGCTACAGTATCCCCCAGGCGATCTTTGCGCAGAGGGTGCTGTGCCGGTCTCAGGGGACTCTCTCCGACCTGCTCCGGAATCCAAA ACCGTGGAGTAAACTCAAATCTGGCAGGGAGACCTTCCGCAGGATGTGGAAGTGGCTTCAGGAGCCCGAGTTCCAGCGCATGTCCGCCT TACGCCTGGCAGGTAAGGCCGGGGCTAGCCAGGGGCCAGGCTGCTGGGAAGAGGGCTCCGGGTCCGGTGCTTGTGGCCCAAGTCTGC GCGCCGAGTCACTTCTCTTGATTCTTCTCCTTTCCTATACACGTCCTCTTTCTTCTCGTTTTTATTTCTTCTTCCATTTTCTCTTTCTC TTCCGCTCTTCCCCTACTTTCCCTTCTCCCTTTTCTTTTTCTTCTTACTCTCCTTGTCCCTGAGCTTTCATTGACCGACCCCCCCCATT TCATTCGCCCTCCCCTCAATGTGCCAACCTTTGCCCTATTTCCGATCTTCCCAGGTACTGGGAGGCGGGATGGGGGTGTGCGTTTTCCTCTA GGAGCCCTGTCTTTCCAAGACCCACAGAAACCAGGACCTGCCCTTATTCAAAACCCCATGCACTTCAAGTCTCTTTTAGACAACACATTTC AATTTTCCGGGCTGACTAGTCTCCTCGTGCAGAGCAGTTGAGAGGCTTTGCTCTGCAGAGGGAAAAGAGCTCTCTACTCTCCCACCCAC CATATAGGCAAACTTATTTGGTCATTGGCTGAAGGCACAGCCTTGCCCCGCGGGGAAACGGCGGCCAGGATCAACAGCGCTCCTGGA GCCCATCTCTGGCCTTGGCGTTGGCGCAGGGACTTTCTGACCGGGCTTGAGGGGCTCGGGCCAGCTCCAATGTCACTACCTACAGCGAG GGCAGGGTGTAAGGTTGAGAAGGTCACATTCACCGCTTTGGGAGGACGTGGGAGAAGAGACTGAGGTGGAAAGCGCTTTGCCTTGCTCA CCGGCCGTCCTTGCCCCGGTCGTGAGCGCCACCAGAAGGGCCGTTTGCTGGGATTTGCAGGATTTGCCGGGGCTCCGGGAGACCCTGGCACTCGCAGGAAGA GGTGCTGAGAAATTAAAAATTCAGGTTAGTTAATGCATCCCTGCCGCCGGCTGCAGGCTCCGCCTTTGCATTAAGCGGGCGCTGATTGTG CGCGCCTGGCGACCGCGGGAGGACTGGCGGCCCGGGAGGGACGGGTAGAGGCGCGGGTTACATTGTTCTGGAGCGGCTCGG CTCTTTGTGCCTCCTCTAGCGGCAAGCTGCGAGGTACAGCCCTCTATTGTTCTAGGAGCACAGAAACCTCCTGTGTGGGCGGGGTG CGCGAGCTAGAGGGGAAAGATGCAGTAGTTACTGCGACTGGCACGCAGTTGCGCGCTTTTGTGCGCACGGACCCCGCGGTGTGCGTG GCGACTGCGCTGCCCCTAGGAGCAAGCCACGGGCCCAGAGGGGCAAAATGTCCAGGTCCCCCGCTGGGAAGGACACACTATACCCTAT |

TABLE 4A-continued

| SEQ ID NO | GENE NAME | SEQUENCE |
|---|---|---|
| | | GGCAAGCCAGGGTGGGCGACTTCCCATGGATCGGGTGGAGGGGGGTATCTTTCAGGATCGGCGGGCGGTCTAGGGGAACAATTCGTGG<br>TGGCGATGATTTGCATAGCGCGGGTCTTGGGATGCGCGCGGTTCCGAGCCAGCCTCGCACAGCTCGCTTCCGGAGCTGCGAGCTCAGG<br>TTTTCCACCCCCGATCCCCCGGGCTTTCCTCGCACCGCTGAGCCCAGCTTGTGGGGTGCACTCGACCAACGCCCGACAGGGCTGGGGAA<br>TGTGACAGGCAGCAGGTTCACCCGGGCTTGGGGAGGGGGAGTTTCCGCTTTGACAGCATTTTCCTTTGCCGTCTGCTGGTGGATTCCTAT<br>TCCCAGTCGGTAATCGCCCCGCAGTGTTGATCTAAGAAGGTAAAGAAAACTAGGTTTCCCTGCAAAGAGCCTCCCCCAAATCGGCGGACT<br>CCGGATACTTTGAGTGGATTTAGAAATTTATGTAATCTTTCTCCTTTAGTTTATTTTTCATCCTCTCCTACAGTTTTCTCTGATTTGCTGTT<br>GGTTCGGGGCAAGATAAAGCAGCCAGTAGAGAGCGATAATAATAGCGGCGGGAAATGAACTGGAGACTGGCTGACAGTTCTTAACATTTTGT<br>CATAGATCCCCCGAATGTCCCAGGCTGTCTCTGGTGGGTTTTAGTACCCGCCGGCTTCTTGGGCACCGGGGACCAGAAGGAACTTGGC<br>AGCTGGTCTTAGGGGTACAGTTAAAGGCAGGATGACAGCTATTCTTCCTGCTCATCTCAGAGCGCTGCCGCCCCCTCATGCCGGTCGCGC<br>AAAGAACACAGCTTTTAAAAAACACGTGCCTTCTGCCCATATAGGTCTGAAAGTGATGAGGAAAGTAATGCTTCGCCTATTAGCGAGTTTCA<br>GCTTTTAAAATGATCCCAAGCGTTGCTGAGATGAGAAAGCGTGGCATCCCGGGGGTCCTCAGCCCCACCCGCGCCCATGGTGCAAGTCT<br>GCAGGGACAGGCCCGGGACAGCACTGCCCACGCTGCTAGATTTTCCGCAGAGGATCGCTGAAGCTGCCTTCGTGGGAGACAGAATGCC<br>TCCTCCAGCGAGTGGAAAAGGCCTGCTGAGGACCCCGCTTTGCTGAGGCATTCAAATGTGTGTCTGTTTTATTACCCTGGGTTGAAAAGG<br>GACAAGAGCTTTAGCCTTTTTATCTGGCCATTTTATCAGCAACTACAAGTGTGTTGAGTGGTTATTATTACATAGGAGGCTTTTCAGTTTGG<br>GGTCAGTAGATCAGTCTCTTCAGACACTGATGCAGAAGCTGGGACTGGTAAGTAGGTATTATGTGCTCGGAGCGCTAGGGGACAGGAGC<br>AAATGGAGAAGAAAAGCGGAGGCTTTCTCCGCCCGGAGTATCGATCGGAATCCCCGCCGGTACGCCGCAGAGGGCCCTCGCCGTTGGG<br>CCCCGGGGGTTTAACAAGCCCAGCCGCTCGCAGGCGGCTCGGCCGGACTCTCAGACCGGTGCCTGGAAGACACCGTCCCTGCCCCCC<br>TCCCGCCAAACCTGCCTCTTCTCTTTCTCTCATAGGTTATAGGTTCCCTTTCTCTCTCATTTTGGCCCGCCCCGGGTCCTGCCAAACAG<br>CCAAGCAGGCCGGGGTTTAGGGGGCTCAGAATGAAGAGGTCTGATTTGGCCAGCGCCGGCAAAGCTCACCCTTAGGCGAGGTCACAAC<br>AGAGGCAGGTCCTTCCTGCCCAGCCTGCCGGTGTAGTCACAGCCAAGGGTGGCACTTGAAAGGAAAAGGGAGAAAACTTCGGAGAAATT<br>TAGATTGCCCCAACGTTAGATTTCAGAGAAATTGACTCCAAATGCACGGATTCGTTCGGAAAGGGCGGCTAAGTGGCAGGTGGTTGCAAC<br>CCCGCCCGGTCGGGCCTTCGCAGAGGTTCCCCAAGACCAGCCCTTGCAGGGCGGTTTTCAGCAACCTGACAAGAGGCGGCCAAGACAA<br>ATTTCTGCGGGTTCGAGCACACACTCTCGGGCGTTGGGCCCCAGAGACCTCTAAACAAGCACAAACAAGAAGGGAGTGAGAGAACCCA<br>GGCTAGAACTTGCACGGGCATCCCACTGAGGAAAAGCGAGGCCTCGGTGGCAGGCATGTTTTCTTCCGACGCCCGAAAATCGAGCCGAG<br>CGCCCGACTACATTTACTGCAGAGGTTTCCGCCTCCAGTGAGCCCGGATCCCCCAGCGGCCTGCCCGGAGCTGGTCTCCAGGTCCCCGCC<br>GTAGTCCGACGCACGGCCCTCTCCTGGCAGCAAGCTCCCAGCGGCCAGTCTGAAGCCAATTCTGTTCAGGCGGCCGAGGGCCCTTAGC<br>CAACCCACCATGATGTCGCCTGGGCCACCTGATGCCCGCAGCGGCGGGACACGGCCCGGGCAGTGCGCAGTGGCTCCTGCTAGGGGC<br>ACCGCGTGCGTGCTTGTCTCCCGCTGCGCCGGGGACGTCCTTGGGTGACACGGGCCGCTGGGCACCTCCCAAGCCGAGGAAACGGAC<br>CCCCTTCGCCAGAGTCTCGCGCCCACCCCCAAACCTCCCACCTCGTTTCTCGCTGCTAGGGCTCCCGACTCAGCCCACCTCTCCTGGCGG<br>TTTAGTTAGGGATCAGAGCTGGAGAGGCTGAACGCAACCCGTGCCAGTAGGAACAGACGATATGTTTGCCTGCTAGCTGCTTGGATGAA<br>TAATTGAAAAGTTCGCTGCAGTCTGTGCTTCGTCAAGTCCCGGGTGCCGGGAGAACACCTTCCCAACACGCATCAGGGTGGGCGGGAGC<br>GGGCAGAGGAGGCGGGACCCGAGGGAGGAGAGTGAACCCGAGCAGGAGAAGCAGCCCAGGCAGCCAGGCGCCCTCGATGCGAGAGG<br>CTGGGCATTTATTTTTATTCCAGGCTTTCCACTGTGTGGTTATGTCACTTTCTCAAACAAATGTGTATATGGAGGGAGATCGATGCTGATAA<br>TGTTTAGAAGATTAAAAGAGCATTAATGCTGGCAACAATAACGTAAACGTGTGGACCCAGATTTCATTGATCTGGAACTTGATCCGGCGCG<br>TTTCCAGTAAGCCCGACGGCGCGCTCTTCCCAGCAGAGCGCTCACCAGCGCCACGGCCCCGGTTTTCCAGCGGTGCCGCTTCGCCA<br>GCTCTGCGCGGGTTCTCCCGTCTGACCGCAGCTCCTCCCCCGCGAGGCCCCAGCCCGCCTTACTTCCCCGAGGTTTTCTCCTCCTCTCG<br>CGGGGCTCTCTGCCCTCTGCACCCCCTCCCCCGACCTCTGCACCACCCGCCCCTGTGCGCACACACCGCTACTTGCGCTTCCGGCGATC<br>CGCCTG |
| 27 | RAX | AACCGGAGATCTGCTTGGTGAACTGAGAGGAGTCCTTAGGAGAGCGGGACGCCAGGGGCCGGGGACACTTCGCTCTCGCCCTAGGG<br>AAGGTGGTCTTGACGCTTTCTATTGAAGTCAAACTTGAAAATATCAGCTGCCGCTGGACTAT |
| 28 | chr18 group-00277 | CGTGAGCAGAACGCCCGCCCTGGAGCAGTTAGGACCGAAGGTCTCCGGAGAGTCGCCGGCGGTGCCAGGTAACGCAGAGGGCTCGGG<br>TCGGGCCCCGCTTCTGGGGCTTGGGACTCCGGGCGCGGAGCCAGCCCTCTGGGGCGAAATCCCCGGGCGGCGTGCGCGGTCCCTC<br>TCCGCGCTGTGCTCTCCCAGCAACTCCCTGCCACCTCGACGAGCCTACCGGCCGCTCCGAGTTCGACTTCCTCGGACTTAGTGGGAGAA<br>GGGGTTGGAAATGGGCTGCCGGGACTGGGGAGCTGCTCTCTGGAAGCAGGGAAGCTGGGGCGCACCGGGGCAGGT |
| 29 | NETO1 | TAGAAGAGGAAGACTCCTCTGGCCCCACTAGGTATCATCCGCGCTCTCCCGCTTTCCACCTGCGCCCTCGCTTGGGCCAATCTCTGCCGC<br>ACGTGTCCATCCCTGAACTGCACGCTATCCTCCACCCCCGGGGGTTCCTGCGCACTGAAAGACCGTTCTCCGGCAGGTTTTGGGATCC<br>GGCGACGGCTGACCGCGCGCCCCCACGCCCGGTTCCACGATCGTGCAATACAGAAAGTTTACGTCGGCCCCGACCCGCGCGGGAC<br>TGCAGGGTCCGCCGGAGCGCGGCCAGAGGCTTTTCCTGCGCGTTCGGCCCCGGGAAAGGGCGGGAGGGCTGGCTCCGGGAGCGC<br>ACGGGCGCGGCGGGAGGGTACTCACTGTGAAGCACGCTGCGCCCATGGATCATGTCTGTGCGTTACACCAGAGGCTCCGGGCTCCAC<br>TAATTCCATTTAGAGACGGGAAGACTTCCAGTGGCGGGGGGAGGACAGGGTCGAGAGGTGTTAAAGACGCAAAGCAAGAAGGAAATAAA<br>GGGGGGCCGAGGGGAGACCGAGAGGGAAGGGGGACTCCGAGCCCACGCTGCAGCAGATCCGGATGAGTCCGTCCTCCGCCCCGG<br>GCGGGCTCTCGCTCTCGCTGGCCCTCAGCGCCGCGCAGCCAGCAGCATCCCCACCGTGACGCTCGCATCACACCCGGGCGCCGCCG<br>CCACCATCCGCGCCGCCGCCGTCAGGACCCTCCTCCCGGGCATCGTCGCCGCCGCGGGTCGGGAGGACGCGGCGCGCGGGAGGCG<br>GCGGTCGCAGGGCGAGCCCCGGGACGCCCCGAGCCGGGGCCGGGGCCGGGAGAGGGCGCAGCGAGGTGGGGGCCAGTCCAGACC<br>GACGGCAGCGACGGAGCGGGCGGCGGCGGCGCGCGGCGGCGCGGGGTGGCTCAGTCCCCAGTCTCAGACGCGCGCGCAGCA<br>GGTCGGAGCAGCCTCCCCGGGAGGATGTCCAGCGGCAGCGCTCCTCGCTCCCGCCCTTGGGGATCTTCCGCTGAGGCATTGAAGGCAG<br>GAAGAAGGGGTCCGTCATCGGCTCGCCGGGCTGCGCGCCACCTCTGCTATCTTGCGGAAAGAGGAGCGGGTGGGTGGCGTCTGGGA<br>GGCGGGCTGGAGGGCGGTGCAGGGGAGCGGGCGGCGGGGGGGGCGGGGCGGGAAGGGAGGGAGGAGAAAGGAGCCG<br>GAAGAGGGCAGAGTTACCAAATGGGCTCCTTAGTCATGGCTTGGGGCTCCACGACCCTCCTGGAAGCCCGGAGCCTGGGTGGGATAGC<br>GAGGCTGCGCGCGCCGGCGCCCCGGGGCTGGTGCGGCAGAATGGGGCGCGGCGGCAGCAAGGACATCCCAGCCGCGCG<br>GATCTGGGGGAGGGCGGGAGGGGGTGAGGACCCGGCTGGGATCCGGGCTCGGCCCGCCAGGGCGCAGAGAGAGGATGCAGCCG<br>CAAATCCCGAGCCGGATCCTCGTGCCGACGGAAGGCGTGGAAGCGGGAGGGGCCTTCGTGTGAAATCCCTTGTGGGGTTTGGTGTTT<br>CACTTTTTAAAGGTTAGACCTTGCGGGCTCTCTGCCTCCCACCCCTTCTTTTCCATCCGCGTAAAGGAACTGGGCGCCCCCTCTCCCTCCC<br>TCCCTGGGGCGCAGGTTTCGCCGCGGACTCCGCGCTCAGCTTGGGAGACACGGCAGGGGCGCCCCAGGGAAAGCGGCCGTAAA<br>GTTTCGCGGTTGAGCACTGGGCCTGATGTCCAGTCCCCCCACCAAATTACTCCTGCAAAGACGCGGGCTTCTTGCAATTGAGCCCCCAC<br>CTCGAGGTATTTAAAACCACCCCAAGGCACACACGGACCCCGTTCCCCCGCGCCACTTCCTCCTACAGGCTCGCGCGGCGCGTTAAAG<br>TCTGGGAGACACGAGTTGCGGGGAAACAGCACCGGAAG |
| 30 | MBP | AAGAAACAGCTCATTTCGGAGCTGAGGACAAGGCGTGGGAAGAAGACGCGTTTGGTTTCACCCAGGCGGGTGGCGGCAAAGCTGTGGG<br>ATGCGCGCTGCACACTCTTCCGTCATCCCGTTCCCACCTTCCACACACACCTGCGGGAGGTCGGACATGTCCTGATTGCGTGTTCATCA<br>CGATGGCAAACCGAACATGAGGAGAACGCCACTGACGCTGGGTGCGCCGGCTTTCCCAGCCCTCGTGCATAACGGGGAGGGAGATGCA<br>GAAGTTTTTTCCAACATCGGTGCAAAGGGGAAGCTGAGGTTTTCCTAT |

TABLE 4A-continued

| SEQ ID NO | GENE NAME | SEQUENCE |
|---|---|---|
| 31 | NFATC1 | TCTGTCAGCTGCTGCCATGGGGCAGCGGGAAGGCCCTGGAGGGTGCCTGGGCTGTGTCTGGTCCCGGCCACGCGTCCCTGCAGCGTCT<br>GAGACCTTGTGGAACACACTTGACCCGGCGCTGGGACGGGGTCGGCCCACACGCACCGCCAGCCCGCAGGAGTGAGGTGCAGGCTGC<br>CGCTGGCTCCTTAGGCCTCGACAGCTCTCTTGAGGTCGGCCCTCCTCCCCTCCCGAGAGCTCAGCAGCCGCAGACCCAGGCAGAGAGA<br>GCAAAGGAGGCTGTGGTGGCCCCCGACGGGAACCTGGGTGGCCGGGGGACACACCGAGGAACTTTCCGCCCCCCGACGGGCTCTCCC<br>ACCGAGGCTCAGGTGCTCGTGGGCAGCAAGGGGAAGCCCCATGGCCATGCCGCTTCCCTTTCACCCTCAGCGACGCGCCCTCCTGTGC<br>CCGCGGGGAACAAGACGGCTCTCGGCGGCCATGCAGGCGGCCTGTCCCACGAACACGATGGAACCTCAGACGCGTCCCCACCCTGT<br>CACTGTCACCATCACCCATCCTGTCCCCTCACGCCTCCCCACATCCCATCATTACTAC |
| 32 | chr18 group-00430 | GAAGTAGAATCACAGTAAATGAGGAGTTAGGGAATTTAGGGTAGAGATTAAAGTAATGAACAGAGGAGGAGGCCTGAGACAGCTGCAGAG<br>AGACCCTGTGTTCCCTGTGAGGTGAAGCGTCTGCTGTCAAAGCCGGTTGGCGCTGAGAAGAGGTACCGGGGGCAGCACCCGCCTCCTG<br>GGAGAGGGATGGGCCTGCGGGCACCTGGGGGAACCGCACGGACACAGACGACACTATAAACGCGGGCGAGACATCAGGGACCGGGAA<br>ACAGAAGGACGCGCGTTTCGAGCAGCTGCCCAGTGGGCCACAAGCCCCGCCACGCCACAGCCTCTTCCCCTCAGCACGCAGAGA |
| 33 | OLIG2 | TACTCCGGCGACGGGAGGATGTTGAGGGAAGCCTGCCAGGTGAAGAAGGGGCCAGCAGCAGCACAGAGCTTCCGACTTTGCCTTCCAG<br>GCTCTAGACTCGCGCCATGCCAAGACGGGCCCCTCGACTTTCACCCCTGACTCCCAACTCCAGCCACTGGACCGAGCGCGCAAAGAACC<br>TGAGACCGCTTGCTCTCACCGCCGCAAGTCGGTCGCAGGACAGACACCAGTGGGCAGCAACAAAAAAAGAAACCGGGTTCCGGGACAC<br>GTGCCGGCGGCTGGACTAACCCTCAGCGGCTGCAACCAAGGAGCGCGCAGTTGCGCCTGCTGGTGTTTATTAGCTACACTGGCAGGCG<br>CACAACTCCGCGCCCCGACTGGTGGCCCCACAGCGCGCACCACACATGGCTCGCTGCTGTTGGCGGGGTAGGCCCGAAGGAGGCATC<br>TACAAATGCCCGAGCCCTTTCTGATCCCCACCCCCCGCTCCCTGCGTCGTCCGAGTGACAGATTCTACTAATTGAACGGTTATGGGTCA<br>TCCTTGTAACCGTTGGACGACATAACACCACGCTTCAGTTCTTCATGTTTTAAATACATATTTAACGGATGGCTGCAGAGCCAGCTGGGAA<br>ACACGCGGATTGAAAAATAATGCTCCAGAAGGCACAGAGCTGGGACGGAAGGCGAGGCGGGCTGGGCTTCTAGCGGAGACGCAGAGG<br>GAGACATATCTCAGAACTAGGGGCAATAACGTGGGTTTCTCTTTGTATTTGTTTATTTTGTAACTTTGCTACTTGAAGACCAATTATTTACT<br>ATGCTAATTTGTTTGCTTGTTTTTAAAACCGTACTTGCACAGTAAAAGTTCCCCAACAACGGAAGTAACCCGACGTTCCTCACACTCCCTAG<br>GAGACTGTGTGCGTGTGTGCCCGCGCGTGCGCTCACAGTGTCAAGTGCTAGCATCCGAGATCTGCAGAAACAAATGTCTGAATTCGAAATG<br>TATGGGTGTGAGAAATTCAGCTCGGGGAAGAAGATTAGGGACTGGGGAGGACAGGTGGCTGCCTGTACTATAAGGAACCGCCAACGCCAG<br>CATCTGTAGTCCAAGCAGGGCTGCTCTGTAAAGGCTTAGCAATTTTTTCTGTAGGCTTGCTGCACACGGTCTCTGGCTTTTCCCATCTGTA<br>AAATGGGTGAATGCATCCGTACCTCAGCTACCTCCGTGAGGTGCTTCTCCAGTTCGGGCTTAATTCCTCATCGTCAAGAGTTTTCAGGTTT<br>CAGAGCCAGCCTGCAATCGGTAAAACATGTCCCAACGCGGTCGCGAGTGGTTCCATCTCGCTGTCTGGCCCACAGCGTGGAGAAGCCTT<br>GCCCAGGCCTGAAACTTCTCTTTGCAGTTCCAGAAAGCAGGCGACTGGGACGGAAGGCTCTTTGCTAACCTTTTACAGCGGAGCCCTGCT<br>TGGACTACAGATGCCAGCGTTGCCCCTGCCCAAGGCGTGGTGATCACAAAGACGACACTGAAATACTTACTATCATCCGGCTCCCC<br>TGCTAATAAATGGAGGGGTGTTTAACTACAGGCACGACCCTGCCCTTGTGCTAGCGCGGTTACCGTCGGAAATAACTCGTCCTGTACC<br>CACACCATCCTCAACCTAAAGGAGAGTTGTGAATTCTTTCAAAACACTCTTCTGGAGTCCGTCCCCTCCCTCCTTGCCCGCCCTCTACCCC<br>TCAAGTCCCTGCCCCCAGCTGGGGGCGCTACCGGCTGCCGTCGGAGCTGCAGCCACGGCCATCTCCTAGACGCGCGAGTAGAGCACCA<br>AGATAGTGGGGACTTTGTGCCTGGGCATCGTTTACATTTGGGGCGCCAAATGCCCACGTGTTGATGAAACCAGTGAGATGGGAACAGGC<br>GGCGGGAAACCAGACAGAGGAAGAGCTAGGGAGGAGACCCCAGCCCCGGATCCTGGGTCGCCAGGGTTTTCCGCGCGCATCCCAAAAG<br>GTGCGGCTGCGTGGGGCATCAGGTTAGTTTGTTAGACTCTGCAGAGTCTCCAAACCATCCCATCCCCCAACCTGACTCTGTGGTGGCCGT<br>ATTTTTTACAGAAATTTGACCACGTTCCCTTTCTCCCTTGGTCCCAAGCGCGCTCAGCCCTCCCTCCATCCCCCTTGAGCCGCCCTTCTCC<br>TCCCCCCTCGCCTCCTCGGGTCCCTCCTCCAGTCCCTCCCCAAGAATCTCCCGGCCACGGGCGCCCATTGGTTGTGCGCAGGGAGGAGG<br>CGTGTGCCCGGCCTGGCGAGTTTCATTGAGCGGAATTAGCCCGGATGACATCAGCTTCCCAGCCCCCGGCGGGCCCAGCTCATTGGC<br>GAGGCAGCCCCTCCAGGACACGCACATTGTTCCCGCCCCCGCCCCGCCACCGCTGCCGCCGTCGCCGCTGCCACCGGGCTATAAA<br>ACCGGCCGAGCCCCTAAAGGTGCGGATGCTTATTATAGATCGACGCGACACCAGCGCCCGGTGCCAGGTTCTCCCCTGAGGCTTTTCGG<br>AGCGAGCTCCTCAAATCGCATCCAGAGTAAGTGTCCCCGCCCCACAGCCGCAGCCTAGATCCCAGGGACAGACTCTCCTCAACTCG<br>GCTGTGACCCAGAATGCTCCGATACAGGGGGTCTGGATCCCTACTCTGCGGGCCATTTCTCCAGAGCGACTTTGCTCTTCTGTCCTCCCC<br>ACACTCACCGCTGCATCTCCCTCACCAAAAGCGAGAAGTCGGAGCGACAACAGCTCTTTCTGCCCAAGCCCCAGTCAGCTGGTGAGCTC<br>CCCGTGGTCTCCAGATGCAGCACATGGACTCTGGGCCCCGCGCGGCTCTGGGTGCATGTGCGTGTGCGTGTTTGCTGCGTGGTGT<br>CGATGGAGATAAGGTGGATCCGTTTGAGGAACCAAATCATTTGTCTATCTAGATCTCCATTCTCCCCAAAGAAAGGCCCTCACTTCCC<br>ACTCGTTTATTCCAGCCCGGGGCTCAGTTTTCCCACACCTAACTGAAAGCCCGAAGCCTCTAGAATGCACCCGACACCCCGAGGGTCAC<br>CAACGCTCCCTGAAATAACCTGTTGCATGAGAGCAGAGGGGAGATAGAGAGCTTAATTATAGGTACCCGCGTGCAGCTAAAAGGAGG<br>GCCAGAGATAGTAGCGAGGGGACGAGGAGCCACGGGCCACCTGTGCCGGGACCCCGCGCTGTGGTACTGCGGTGCAGGCGGGAGCA<br>GCTTTTCTGTCTCACTGACTCACTCTCTCTCTCCCTCTCTCTCTCTCATTCTCTCTTTTCCTCCCTCTCCTCCTGGAAGTTTT<br>CGGGTCCGAGGGAAGGAGGACCCTGCGAAAGCTGCGACGACTATCTTCCCCTGGGGCCATGGACTCGGACGCCGACTGGTGTCCAGCCG<br>CCCGTCGTCGCCAGAGCCCGATGACCTTTTTCTGCCGGCCCGGAGTAAGGGCAGCAGCGGCAGCGCCTTCACTGGGGGCACCGTGTCC<br>TCGTCCACCCCGAGTGACTGCCC |
| 34 | SIM2 | TTAATTCGAAAATGGCAGACAGAGCTGAGCGCTGCCGTTCTTTTCAGGATTGAAAATGTGCCAGTGGGCCAGGGGCGCTGGGACCCGCG<br>GTGCGGAAGACTCGGAACAGGAAGAAATAGTGGCGCGCTGGGTGGGCTGCCCGCCGCCCACGCCGGTTGCCGCTGGTGACAGTGGC<br>TGCCCGGCCAGGCACCTCCGAGCAGCAGGTCTGAGCGTTTTTGGCGTCCCAAGCGTTCCGGGCGCGTCTTCCAGAGCCTCTGCTCCCA<br>GCGGGGTCGCTGCGGCCTGGCCCGAAGGATTTGACTCTTTGCTGGGAGGCGCGCTGCTCAGGGTTCTG |
| 35 | SIM2 | CCGGTCCCCAGTTTGGAAAAAGGCGCAAGAAGCGGGCTTTTCAGGGACCCCGGGGAGAACACGAGGGCTCCGACGCGGGAGAAGGATT<br>GAAGCGTGCAGAGGCGCCCCAAATTGCGACAATTTACTGGGATCCTTTTGTGGGGAAAGGAGGCTTAGAGGGCTCAAGCTATAGGCTGTC<br>CTAGAGCAACTAGGCGAGAACCTGGCCCCAAACTCCCTCCTTACGCCCTGGCACAGGTTCCCGGCGACTGGTGTTCCCAAGGGAGCCCC<br>CTGAGCCTACCCCTTGCAGGGGGTCGTGCTGCGGCTTCGGGTCATAAACGCCGAGGTCGGGGTGGCGGAGCTGTAGAGGCTGCC<br>CGCGCAGAAAGCTCCAGGATCCCAATATGTG |
| 36 | DSCR6 | GCGCAGGTCCCCCAGTCCCCGAGGGAGTGCGCCCGACGGAAACGCCCCTAGCCCGCGGGCCTCGCTTTCCTCTCCCGGGTTCCTGG<br>GTCACTTCCCGCTGTCTC |
| 37 | DSCAM | TTCCCTCGCGGCTTTGGAAAGGGGTGCAAATGCACCCTTCTGCGGGCCCGCTACCCGCTGCAACACCTGTGTTTCCTTTCTGGGCACCT<br>TCTAGGTTTCTAGATATTGCTGTGAATACGGTCCTCCGCTGTACAGTTGAAAACAAA |
| 38 | chr21 group-00165 | TGGGAATTTAGGTCGGGCACTGCCGATATGTCGCCTTCCACAAGGCGGGCCCGGGCCTCTGCTGACCGTGCACCGGTCCTGGGGCTGG<br>GTAATTCTGCAGCAGCAGCGCAGCCATGCCGGGGAATTTGCGGGCAGAGGGAGACAGTGAGGCCCGCGTTCTGTGCGGGAACTCCGA<br>GCTCACAGAGCCCAAGACCACACGCGTGCATCTGCTTGGCTGACTGGGCCAGGCCCACGCGTAGTAACCCGGACGTCTCTCTCTCACAG<br>TCCCCTTGCGTCTGGCCAGGGAGCTGCCAGGCTGCACCCCGCGGTGGGGATCGGGAGAGGGGCAGTGTCGCCCATCCCCGGAAGGCT<br>GAGCCTGGTGCAG |

TABLE 4A-continued

| SEQ ID NO | GENE NAME | SEQUENCE |
|---|---|---|
| 39 | PRMT2 | CGGTTTTCTCCTGGAGGACTGTGTTCAGACAGATACTGGTTTCCTTATCCGCAGGTGTGCGCGGCGCTCGCAAGTGGTCAGCATAACGCC<br>GGGCGAATTCGGAAAGCCCGTGCGTCCGTGGACGACCCACTTGGAAGGAGTTGGGAGAAGTCCTTGTTCCCACGCGCGGACGCTTCCC<br>TCCGTGTGTCCTTCGAGCCACAAAAAGCCCAGACCCTAACCCGCTCCTTTCTCCCGCCGCGTCCATGCAGAACTCCGCCGTTCCTGGGA<br>GGGGAAGCCCGCGAGGCGTCGGGAGAGGCACGTCCTCCGTGAGCAAAGAGCTCCTCCGAGCGCGCGGCGGGGACGCTGGGCCGACA<br>GGGGACCGCGGGGGCAGGGCGGGAGAGGACCCGCCCTCGAGTCGGCCCAGCCCTAACACTCAGGAC |
| 40 | SIX2 | AGGGAATCGGGCTGACCAGTCCTAAGGTCCCACGCTCCCCTGACCTCAGGGCCCAGAGCCTCGCATTACCCCGAGCAGTGCGTTGGTTA<br>CTCTCCCTGGAAAGCCGCCCCGCCGGGGCAAGTGGGAGTTGCTGCACTGCGGTCTTTGGAGGCCTAGGTCGCCCAGAGTAGGCGGAG<br>CCCTGTATCCCTCCTGGAGCCGGCCTGCGGTGAGGTCGGTACCCAGTACTTAGGGAGGGAGGACGCGCTTGGTGCTCAGGGTAGGCTG<br>GGCCGCTGCTAGCTCTTGATTTAGTCTCATGTCCGCCTTTGTGCCGGCCTCTCCGATTTGTGGGTCCTTCCAAGAAAGAGTCCTCTAGGG<br>CAGCTAGGGTCGTCTCTTGGGTCTGGCGAGGCGGCAGGCCTTCTTCGGACCTATCCCCAGAGGTGTAACGGAGACTTTCTCCACTGCAG<br>GGCGGCCTGGGGCGGGCATCTGCCAGGCGAGGGAGCTGCCGTGCCGCCGAGATTGTGGGGAAACGGCGTGGAAGACACCCCATCGGA<br>GGGCACCCAATCTGCCTCTGCACTCGATTCCATCCTGCAACCCAGGAGAAACCATTTCCGAGTTCCAGCCGCAGAGGCACCCGCGGAGT<br>TGCCAAAAGAGACTCCCGCGAGGTCGCTCGGAACCTTGACCCTGACACCTGGACGCGAGGTCTTTCAGGACCAGTCTCGGCTCGGTAGC<br>CTGGTCCCCGACCACCGCGACCAGGAGTTCCTTCTTCCCTTCCTGCTCACCAGCCGGCCGCCGGCAGCGGCTCCAGGAAGGAGCACCA<br>ACCCGCGCTGGGGGCGGAGGTTCAGGCGGCAGGAATGGAGAGGCTGATCCTCCTCTAGCCCCGGCGCATTCACTTAGGTGCGGAGCC<br>CTGAGGTTCAGCCTGACTTTC |
| 41 | SIX2 | CACTACGGATCTGCCTGGACTGGTTCAGATGCGTCGTTTAAAGGGGGGGGCTGGCACTCCAGAGAGGAGGGGCGCTGCAGGTTAATT<br>GATAGCCACGGAAGCACCTAGGCGCCCCATGCGCGGACCGGAGCCGCCAGCTCAGTCTGACCCCTGTCTTTTCTCTCTTCCCTCT<br>CCCACCCCTCACTCCGGGAAAGCGAGGGCCGAGGTAGGGGCAGATAGATCACCAGACAGGCGGAGAAGGACAGGAGTACAGATGGAG<br>GGACCAGGACACAGAATGCAAAAGACTGGCAGGTGAGAAGAAGGGAGAAACAGAGGGAGAGAGAAAGGGAGAAACAGAGCAGAGGCGG<br>CCGCCGGCCCGGCCGCCCTGAGTCCGATTTCCCTCCTTCCCTGACCCTTCAGTTTCACTGCAAATCCACAGAAGCAGGTTTGCGAGCTCG<br>AATACCTTTGCTCCACTGCCACACGCAGCACCGGGACTGGGCGTCTGGAGCTTAAGTCTGGGGGTCTGAGCCTGGGACCGGCAAATCCG<br>CGCAGCGCATCGCGCCCAGTCTCGGAGACTGCAACCACCGCCAAGGAGTACGCGCGGCAGGAAACTTCTGCGGCCCAATTTCTTCCCCA<br>GCTTTGGCATCTCCGAAGGCACGTACCCGCCCTCGGCACAAGCTCTCTCGTCTTCCACTTCGACCTCGAGGTGGAGAAAGAGGCTGGCA<br>AGGGCTGTGCGCGTCGCTGGTGTGGGGAGGGCAGCAGGCTGCCCCTCCCCGCTTCTGCAGCGAGTTTTCCCAGCCAGGAAAAGGGAGG<br>GAGCTGTTTCAGGAATTTCAGTGCCTTCACCTAGCGACTGACACAAGTCGTGTGTATAGGAAG |
| 42 | SOX14 | GGAGCCTGAAGTCAGAAAAGATGGGGCCTCGTTACTCACTTTCTAGCCCAGCCCCTGGCCCTGGGTCCCGCAGAGCCGTCATCGCAGGC<br>TCCTGCCCAGCCTCTGGGTCGGGTGAGCAAGGTGTTCTCTTCGGAAGCGGGAAGGGCTGCGGGTCGGGGACGTCCCTTGGCTGCCAC<br>CCCTGATTCTGCATCCTTTTCGCTCGAATCCCTGCGCTAGGCATCCTCCCCGATCCCCAAAAGCCCAAGCACTGGGTCTGGGTTGAGGA<br>AGGGAACGGGTGCCCAGGCCGGACAGAGGCTGAAAGGAGGCCTCAAGGTTCCTCTTTGCTACAAAGTGGAGAAGTTGCTCTACTCTGGA<br>GGGCAGTGGCCTTTTCCAAACTTTTCCACTTAGGTCCGTAAGAAAAGCAATTCATACACGATCAGCGCTTTCGGTGCGAGGATGGAAAGAA<br>ACTTC |
| 43 | TLX3 | TTTTCCTGTTACAGAGCTGAGCCCACTCATGTGGTGCCAAGTAGCGACTATCTCTCGGCCACCTCCACCCAGAGCAATGTGGGCGCCCCC<br>AGCGGGTGGGAGCGATTGCCGAGCGGCGCAAGGGCGTTTAACGCCTAACCCCCTCCTCCTGGGTTGCCAAGCCGCTAGGTCGCCGTTT<br>CCAACGTGGCTGCGCGGGACTGAAGTCCGACGACTCCTCGTCCTCAGTAGGAGACACACCTCCCACTGCCCCAGCCACGCGAGCTATG<br>GGCAGAATCGGGGCAACGGTAATATCTGGATGGGGCAGGCTCCCTGAGGCTGTGCTTAAGAAAAAAGGAAATCTGGAGTAGCTGAGGG<br>GCCCCACGAGGGGGCCTCCTTTGCGATCGTCTCCCAGCCTTAGGCCAAGGCTACGGAGGCAGGCGGCCGAGTGTTGGCGCCCAGCCC<br>GGCCGAGGACTGGATGGAGGACGAGAAGCAGCCTGCCTCTGGGCGACAGCTGCGGACGCAGCCTCGCCGCCTCGCCGCCTCAGCCTC<br>GGTCCCAGCGTCTCTAAAGCCGCGCCCATTTTACAGATGCAGGGCAGGGAGACAAGAGGCATCTCCGGGGGCCGAGTAGAATGATGGC<br>GCGGGTTCTCCCGGCGCCCTGATTTCGAGGCTGCGCCCGGGGCCCTACATGCAGGCGGGGAGGCCTGGGCCGAAGGCGTCTGCAAGG<br>AGGGGCGAGTCTGCCCGGTCCGGGCAGGGAGTGAGGCCACAGTCAGTTCTCCCTAGGAGGCCGCGCAGCGGGTAGGGTATGGGACTG<br>GGGGACGCAACGGGGACCTGGCCGAATCAGAGCCCTCAGCAGAGAACGCCGAAAACTCTGGGGCGGCCGCTCGTTCCCGCTAGTG<br>GGAATGGTTTCCGGTCATCCGTTCCCAGTCCAGCCCCGGGTAGGGAGCTCTGATTTGCAATGCACAGCACTTGCGAGGTTCGAATGCCC<br>CCGCAATTTGCAGATGGAAATACTAAGCCTAGGCCGGGCGTGGTGGCTCAAGCCTATCATCTCAGCCCTTTGGGAGGCCAAGCCGGGAG<br>GATTGTTTGAGCCCAAGAATTCAAAACCAGCCTGAGCAACATAGCGACCCCGTCTCTACAAAATAAAATAAAATAAATTATCCGGGCGTGG<br>TGGCACGCGCCTGTGGTTCCAGCTACTCCGGAGGCTGAGGTGGGAGGATCGCTTGAGTCCGGGAGGTCGAGGCTACAGTGAGCCGTGA<br>TCGCCACCACTGCACTCCAGCCTGGGCGACAGATGAGACTTTGCTCAAAAAAGGAAAAAAAGAAAAAAAGAAAAGTAAGCTTCAAAGAAGCT<br>CTGATAATAGTTCTGGGTCGTGCAGCGGTGGCGGCCCCGCGCTCTCGCCCTAAAGCAAGCGCTCTTTGTACTGGGTGGAGGAGCTTTG<br>AGTAGTGAGGGTGGAGATGCAGCTTCGGGGTGCGCAGCCACCCTGACACTAGGCCCGGGGTCGCAGTGGGACAGAAGAGTCTGCCG<br>CTCTGACTTGGGCTCTGAGTTCCAAGGGCGCCCGGCACTTCTAGCCTCCCAGGCTTGCGCGCTGGCGCCTTTGCCATCCGTGCCGAAGT<br>GGGGAGACCTAGCCGCGACCACCACGAGCGCAGCGGTGACACCCAGAGGTCCCACCGGGCCCCTGGGCAGGGTAACCTTAGCCTGTC<br>CGCTTCGGCAGCTTTGCGAAGAGTGCGCGGGCGCAGCTAGGGCTGAGGCTCTTGCGGACCTGCGGTCGAAGCAGGCGGCTGAGCCAGTTCG<br>ATCGCCAAGGCCTGGGCTGCCGACAGTGGTGCGCGCTCTGTTCCGCCGCGGCCGGGCCAGGCGCTCTGGAATGCGATGGGGGACA<br>CGGCCTCCAACTTTCTGCAGAGACCATCGGGCAGCTCCGGGCCTAAGCAGCGACCTCACCGAAGGTTCCTGGGAACCTTTGCCAAAATC<br>CCAGCCTCTGCCTCGGTCCAGCTAAACCGTGTGTAAACAAGTGCACCAAG |
| 44 | FOXP4 | ATAAAGGACCGGGTAATTTCGCGGAATGCGGATTTTGAGACAGGCCCAGACGGCGGCGGATTCCCTGTGTCCCCAACTGGGGCGATCT<br>CGTGAACACACCTGCGTCCCACCCCGATCCTAGGTTGGGGGGAAAGGGTATGGGAACCCTGAGCCCAGAGCGCGCCCCGCTCTTTCCTT<br>TGCTCCCCGGCTTCCCTGGCCAGCCCCTCCCGGCTGGTTTCCTCGCTCACTCGGCGCCTGGCGTTTCGGGCGTCTGGAGATCACCGC<br>GTGTCTGGCACCCCAACGTCTAGTCTCCCCGCAGGTTGACCGCGGCGCCTGGAGCCGGGAATAGGGTGGGGAGTCCGGAGAACCAAA<br>CCCGAGCCTGAAGTTGCCATTCGGGTGACTCCCGAGAAAGCCCGGGAGCATTTTGGCCAATGCGGGTTTTTACCTGAACTTCAGCATCTT<br>CACC |
| 45 | FOXP4 | AATTGGAAACCCTGGTATTGTGCCTGTTTGGGGGAAGAAAACGTCAATAAAAATTAATTGATGAGTTGGCAGGGCGGGCGGTGCGGGTT<br>CGCGGCGAGGCGCAGGGTGTCATGGCAAATGTTACGGCTCAGATTAAGCGATTGTTAATTAAAAGCGACGGTAATTAATACTCGCTACG<br>CCATATGGGCCCGTGAAAAGGCACAAAAGGTTTCTCCGCATGTGGGGTTCCCCTTCTCTTTTCTCCTTCCACAAAAGCACCCCAGCCCGT<br>GGGTCCCCCCTTTGGCCCCAAGGTAGGTGGAACTCGTCACTTCCGGCCAGGGAGGGGATGGGCGGTCTCCGGCGAGTTCCAAGGGC<br>GTCCCTCGTTGCGCACTCGCCCGCCCAGGTTCTTTGAA |

TABLE 4A-continued

| SEQ ID NO | GENE NAME | SEQUENCE |
|---|---|---|
| 46 | chr7 group-00267 | GGGAAGCGATCGTCTCCTCTGTCAACTCGCGCCTGGGCACTTAGCCCCTCCCGTTTCAGGGCGCCGCCTCCCCGGATGGCAAACACTAT<br>AAAGTGGCGGCGAATAAGGTTCCTCCTGCTGCTCTCGGTTTAGTCCAAGATCAGCGATATCACGCGTCCCCCGGAGCATCGCGTGCAGG<br>AGCCATGGCGCGGGAGCTATACCACGAAGAGTTCGCCCGGGCGGGCAAGCAGGCGGGGCTGCAGGTCTGGAGGATTGAGAAGCTGGA<br>GCTGGTGCCCGTGCCCCAGAGCGCTCACGGCGACTTCTACGTCGGGGATGCCTACCTGGTGCTGCACACGGCCAAGACGAGCCGAGGC<br>TTCACCTACCACCTGCACTTCTGGCTCGGTAAGGGACGGCGGGCGGCGGGACCCCGACGCACCAAGGCCGGCGAGGGGAGGCGTAG<br>GGGTCTGAGATTTGCAGGCGTGGGAGTAAAGGGGACCGCAAACTGAGCTAG |
| 47 | NPY | CTCAGGGGCGGGAAGTGGCGGGTGGGAGTCACCCAAGCGTGACTGCCCGAGGCCCCTCCTGCCGCGGCGAGGAAGCTCCATAAAAGC<br>CCTGTCGCGACCCGCTCTCTGCACCCCATCCGCTGGCTCTCACCCCTCGGAGACGCTCGCCCGACAGCATAGTACTTGCCGCCCAGCCA<br>CGCCCGCGCGCCAGCCACCGTGAGTGCTACGACCCGTCTGTCTAGGGGTGGGAGCGAACGGGGCGCCCGCGAACTTGCTAGAGACGC<br>AGCCTCCCGCTCTGTGGAGCCCTGGGGCCCTGGGATGATCGCGCTCCACTCCCCAGCGGACTATGCCGGCTCCGCGCCCCGACGCGGA<br>CCAGCCCTCTTGGCGGCTAAATTCCACTTGTTCCTCTGCTCCCCTCTGATTGTCCACGGCCCTTCTCCCGGGCCTTCCCGCTGGGCGGT<br>TCTTTCTGAGTTACCTTTTAGCAGATATGGAGGGAGAACCCGGGACCGCTATCCCAAGGCAGCTGGCGGTCTCCCTGCGGGTCGCCGCCT<br>TGAGGCCCAGGAAGCGGTGCGCGGTAGGAAGGTTTCCCCGGCAGCGCCATCGAGTGAGGAATCCCTGGAGCTCTAGAGCCCCGCGCCC<br>TGCCACCTCCCTGGATTCTTGGGCTCCAAATCTCTTTGGAGCAATTCTGGCCCAGGGAGCAATTCTCTTTCCCCTTCCCCACCGCAGTCGT<br>CACCCCGAGGTGATCTCTGCTGTCAGCGTTGATCCCCTGAAGCTAGGCAGACCAGAAGTAACAGAGAAGAAACTTTTCTTCCCAGACAAG<br>AGTTTGGGCAAGAAGGGAGAAAAGTGACCCAGCAGGAAGAACTTCCAATTCGGTTTTGAATGCTAAACTGGCGGGGCCCCCACCTTGCAC<br>TCTCGCCGCGCGCTTCTTGGTCCCTGAGACTTCGAACGAAGTTGCGCGAAGTTTTCAGGTGGAGCAGAGGGGCAGGTCCCGACCGGAC<br>GGCGCCCGGAGCCCGCAAGGTGGTGCTAGCCACTCCTGGGTTCTCTCTGCGGGACTGGGACGAGAGCGGATTGGGGGTCGCGTGTGG<br>TAGCAGGAGGAGGAGCGCGGGGGGCAGAGGAGGGAGGTGCTGCGCGTGGGTGCTCTGAATCCCCAAGCCCGTCCGTTGAGCCTTCTG<br>TGCCTGCAGATGCTAGGTAACAAGCGACTGGGGCTGTCCGGACTGACCCTCGCCCTGTCCCTGCTCGTGTGCCTGGGTGCGCTGGCCG<br>AGGCGTACCCCTCCAAGCCGGACAACCCGGGCGAGGACGCACCAG |
| 48 | SHH | TGGAGAACCTTGGGCTCTGTGGCCTCAAAGGTAGGGGTGATTTCGAGGGGCCGGCACCTCACAGGGCAGGTTCCACCGCGGAAACGCA<br>GTCATCGCCCAGCGACCCTGCTCCTGGCCCTCAGCCTCCCCCAGGTTTCTTTTTCTCTTGAATCAAGCCGAGGTGCGCCAATGGCCTTC<br>CTTGGGTCGGATCCGGGGGGCCAGGGCCAGCTTACCTGCTTTCACCGAGCAGTGGATATGTGCCTTGGACTCGTAGTACACCCAGTCGA<br>AGCCGGCCTCCACCGCCAGGCGGGCCAGCATGCCGTACTTGCTGCGGTCGCGGTCAGACGTGGTGATGTCCACTGCGCGGCCCTCGTA<br>GTGCAGAGACTCCTCTGAGTGGTGGCCATCTTCGTCCCAGCCCTCGGTCACCCGCAGTTTCACTCCTGGCCACTGGTTCATCACCGAGAT<br>GGCCAAGCGTTCAACTTGTCCTTACACCTCTGCGAAGACAAGGGGACCCCCACCGACGGACACGTTAGCCTGGGCAACCGCCACCCCT<br>CCCGGCCCCTCCATCAGCCT |
| 49 | OSR2 | TCTCACGACCCATCCGTTAACCCACCGTTCCCAGGAGCTCCGAGGCGCAGCGGCGACAGAGGTTCGCCCCGGCCTGCTAGCATTGGCAT<br>TGCCGTTGACTGAGCTTCGCCTAACAGGCTTGGGGAGGGTGGGCTGGGCTGGGCTGGGCTGGGCTGGGTGCTGCCCGGCTGTCCGCC<br>TTTCGTTTTCCTGGGACCGAGGAGTCTTCCGCTCCGTATCTGCCTAGAGTCTGAATCCGACTTTCTTTCCTTTGGGCACGCGCTCGCCAGT<br>GGAGCACTTCTTGTTCTGGCCCCGGGCTGATCTGCACGCGGACTTGAGCAGGTGCCAAGGTGCCACGCAGTCCCCTCACGGCTTTCGGG<br>GGGTCTTGGAGTCGGGTGGGAGGGAGACTTAGGTGTGGTAACCTGCGCAGGTGCCAAAGGGCAGAAGGAGCAGCCTTGGATTATAGT<br>CACGGTCTCTCCCTCTCTTCCCTGCCATTTTTAGGGCTTTCTTCTACGTGCTGTTGTCTCACTGGGTTTTTGTCGGAGCCCACGCCCTCCG<br>GCCTCTGATTCCTGGAAGAAAGGGTTGGTCCCCTCAGCACCCCCAGCATCCCGGAAATGGGGAGCAAGGCTCTGCCAGCGCCCATCCC<br>GCTCCACCCGTCGCTGCAGCTCACCAATTACTCCTTCCTGCAGGCCGTGAACACCTTCCCGGCCACGGTGGACCACCTGCAGGGCCTGT<br>ACGGTCTCAGCGCGGTACAGACCATGCACATGAACCACTGGACGCTGGGGTATCCCAAT |
| 50 | GLIS3 | TGGTTTCCTTTCGCTTCTCGCCTCCCAAACACCTCCAGCAAGTCGGAGGGCGCGAACGCGGAGCCAGAAACCCTTCCCCAAAGTTTCTCC<br>CGCCAGGTACCTAATTGAATCATCCATAGGATGACAAATCAGCCAGGGCCAAGATTTCCAGACACTTGAGTGACTTCCCGGTCCCCGAGG<br>TGACTTGTCAGCTCCAGTGAGTAACTTGGAACTGTCGCTCGGGGCAAGGTGTGTGTCTAGGAGAGAGCCGGCGGCTCACTCACGCTTTC<br>CAGAGAGCGACCCGGGCCGACTTCAAAATACACACAGGGTCATTTATAGGGACTGGAGCCGCGCGCAGGACAACGTCTCCGAGACTGAG<br>ACATTTTCCAAACAGTGCTGACATTTTGTCGGGCCCCATAAAAAATGTAAACGCGAGGTGACGAACCCGGCGGGAGGGTTCGTGTCTGG<br>CTGTGTCTGCGTCCTGGCGGCGTGGGAGGTTATAGTTCCAGACCTGGCGGCTGCGGATCGCCGGGCCGGTACCCGCGAGGAGTGTAGG<br>TACCCTCAGCCCGACCACCTCCCGCAATCATGGGGACACCGGCTTGGATGAGACACAGGCGTGGAAAACAGCCTTCGTGAAACTCCACA<br>AACACGTGGAACTTGAAAAGACAACTACAGCCCCGCGTGTGCGCGAGAGACCTCACGTCACCCCATCAGTTCCCACTTCGCCAAAGTTTC<br>CCTTCAGTGGGGACTCCAGAGTGGTGCGCCCCATGCCCGTGCGTCCTGTAACGTGCCCTGATTGTGTACCCCTCTGCCCGCTCTACTTG<br>AAATGAAAACACAAAAACTGTTCCGAATTAGCGCAACTTTAAAGCCCGTTATCTGTCTTCTACACTGGGCGCTCTTAGGCCACTGACAGA<br>AACATGGTTTGAACCCTAATTGTTGCTATCAGTCTCAGTCAGCGCAGGTCTCTCAGTGACCTGTGACGCCGGGAGTTGAGGTGCGCGTAT<br>CCTTAAACCCGCGGAACGCCACCGGCTCAGCGTAGAAAACTATTTGTAATCCCTAGTTTGCGTCTCTGAGCTTTAACTCCCCCACACTCT<br>CAAGCGCCCGGTTTCTCCTCGTCTCTCGCCTGCGAGCAAAGTTCCTATGGCATCCACTTACCAGGTAACCGGGATTTCCACAACAAAGCC<br>CGGCGTGCGGGTCCCTTCCCCCGGCCGGCCAGCGCGAGTGACAGCGGGCGGCCGGCGCTGGCGAGGAGTAACTTGGGGCTCCAGCC<br>CTTCAGAGCGCTCCGCGGGCTGTGCCTCCTTCGGAAATGAAAACCCCCATCCAAACGGGGGGACGGAGCGCGGAAACCCGGCCCAAGT<br>GCCGTGTGTGCGCGCGCGTCTG |
| 51 | PRMT8 | GAAAGCCATCCTTACCATTCCCCTCACCCTCCGCCCTCTGATCGCCCACCCGCCGAAAGGGTTTCTAAAAATAGCCCAGGGCTTCAAGGC<br>CGCGCTTCTGTGAAGTGTGGAGCGAGCGGGCACGTAGCGGTCTCTGCCAGGTGGCTGGAGCCCTGGAAGCGAGAAGGCGCTTCCTCCC<br>TGCATTTCCACCTCACCCCACCCCGGCTCATTTTTCTAAGAAAAGTTTTTGCGGTTCCCTTTGCCTCCTACCCCCGCTGCCGCGCGGG<br>GTCTGGGTGCAGACCCCTGCCAGGTTCCGCAGTGTGCAGCGGCGGCTGCTGCGCTCTCCCAGCCTCGGCGAGGGTTAAAGGCGTCCGG<br>AGCAGGCAGAGCGCCGGAACTGCTCTATTTTACTTGCTTCCCCCGCCGCTCCGCGCTCCCCCTTCTCAGCAGTTGCACATGCCAGCT<br>CTGCTGAAGGCATCAATGAAAACAGCAGTAG |
| 52 | TBX3 | ATCGAAAATGTCGACATCTTGCTAATGGTCTGCAAACTTCCGCCAATTATGACTGACCTCCCAGACTCGGCCCCAGGAGGCTCGTATTAGG<br>CAGGGAGGCCGCCGTAATTCTGGGATCAAAAGCGGGAAGGTGCGAACTCCTCTTTGTCTCTGCGTGCCCGGCGCGCCCCCTCCCGGT<br>GGGTGGATAAACCCACTCTGGCGCCGGCCATGCGCTGGGTGATTAATTTGCGAACAAACAAAGCGGCCTGGTGGCCACTGCATTCGGGT<br>TAAACATTGGCCAGCGTGTTCCGAAGGCTTGT |
| 53 | chr12 group-00801 | ATCAACATCGTGGCTTTGGTCTTTTCCATCATGGTGAGTGAATCACGGCCAGAGGCAGCCTGGGAGGAGAGACCCGGGCGGCTTTGAGC<br>CCTGCAGGGGAGTCCGCGCGCTCTCTGCGGCTCCCTTCCTCACGGCCCGGCCCGCGCTAGGTGTTCTTTTGTCCTCGCACCTCCTCCTC<br>ACCTTTCTCGGGCTCTCAGAGCTCTCCCCGCAATCATCAGCACCTCCTCTGCACTCCTCGTGGTACTCAGAGCCCTGATCAAGCTTCCCC<br>CAGGCTAGCTTTCCTCTTCTTTCCAGCTCCCAGGGTGCGTTTCCTCTCCAACCCGGGGAAGTTCTTCCGTGGACTTTGCTGACTCCTCTGA<br>CCTTCCTAGGCACTTGCCCGGGGCTTCTCAACCCTCTTTTCTAGAGCCCCAGTGCGCGCCACCCTAGCGAGCGCAGTAAGCTCATACCCC |

TABLE 4A-continued

| SEQ ID NO | GENE NAME | SEQUENCE |
|---|---|---|
| | | GAGCATGCAGGCTCTACGTTCCTTTCCCTGCCGCTCCGGGGGCTCCTGCTCTCCAGCGCCCAGGACTGTCTCTATCTCAGCCTGTGCTC CCTTCTCTCTTTGCTGCGCCCAAGGGCACCGCTTCCGCCACTCTCCGGGGGGTCCCCAGGCGATTCCTGATGCCCCTCCTTGATCCCG TTTCCGCGCTTTGGCACGGCACGCTCTGTCCAGGCAACAGTTTCCTCTCGCTTCTTCCTACACCCAACTTCCTCTCCTTGCCTCCCTCCGG CGCCCCTTTTTAACGCGCCGAGGCTGGCTCACACCCACTACCTCTTTAGGCCTTTCTTAGGCTCCCCGTGCTGCCCCCCTCACCAGCAA AGTGGGTGCGCCTCTCTTACTCTTTCTACCCAGCGCGTCGTAGTTCCTCCCCGTTTGCTGCGCACTGGCCCTAACCTCTCTTCTTGGTG TCCCCCAGAGCTCCCAGGCGCCCCTCCACCGCTCTGTCCTGCGCCCGGGGGCTCTCCCGGGAATGAACTAGGGGATTCCACGCAACGTG CGGCTCCGCCCGCCCTCTGCGCTCAGACCTCCCGAGCTGCCCGCCTCTCTAGGAGTGGCCGCTGGGGCCTCTAGTCCGCCCTTCCGGA GCTCAGCTCCCTAGCCCTCTTCAACCCTGGTAGGAACACCCGAGCGAACCCCACCAGGAGGGCGACGAGCGCCTGCTAGGCCCTCGCC TTATTGACTCAGCAGCTGGCCCGGGGGTGGCGGCGGGGTGAGGTTCGTACCGGCACTGTCCCGGGACAACCCTTGCAGTTGC |
| 54 | PAX9 | ACAAATAAAACACCCTCTAGCTTCCCCTAGACTTTGTTTAACTGGCCGGGTCTCCAGAAGGAACGCTGGGGATGGGATGGGTGGAGAGAG GGAGCGGCTCAAGGACTTTAGTGAGGAGCAGGCGAGAAGGAGCACGTTCAGGCGTCAAGACCGATTTCTCCCCCTGCTTCGGGAGACTT TTGAACGCTCGGAGAGGCCCGGCATCTCACCACTTTACTTGGCGTGTAGGGGCCTCCGGCACGGCAGGAATGAGGGAGGGGGTCCGATT GGACAGTGACGGTTTGGGGCCGTTCGGCTATGTTCAGGGACCCATATGGTTTGGGGACAGCCCCAGTAGTTAGTAGGGGACGGGTGCGTT CGCCCAGTCCCCGGATGCGTAGGGAGGCCCAGTGGCAGGCAGCTGTCCCAAGCAGCGGGTGCGCGTCCTGCGCGCTGTGTGTTCATT TTGCAGAGCCAGCCTTCGGGGAGGTGAACCAGCTGGGAGGAGTGTTCGTGAACGGGAGGCCGCTGCCCAACGCCATCCGGCTTCGCAT CGTGGAACTGGCCCAACTGGGCATCCGACCGTGTGACATCAGCCGCCAGCTACCAGGGTCTCGCACGGCTGCGTCAGCAAGATCCTGGCG CGATACAACGAGACGGGCTCGATCTTGCCAGGAGCCATCGGGGGCAGCAAGCCCCGGGTCACTACCCCCACCGTGGTGAAACACATCC GGACCTACAAGCAGAGAGACCCCGGCATCTTCGCCTGGGAGATCCGGGACCGCCTGCTGGCGACGGCGTGTGCGACAAGTACAATGT GCCCTCCGTGAGCTCCATCAGCCGCATTCTGCGCAACAAGATCGGCAACTTGGCCCAGCAGGGTCATTACGACTCATACAAGCAGCACC AGCCGACGCCGCAGCCAGCGCTGCCCTACAACCACATCTACTCGTACCCCAGCCCTATCACGGCGGCGGCCGCCAAGGTGCCCACGCC ACCCGGGGTGC |
| 55 | SIX1 | AGGAGGCGCAACGCGCTGCCAGGGCGGCTTTATCCTGCCGCCACAGGGCGGGGACCAGCCCGGCAGCCGGGTGTCCAGCGCCGCTCA CGTGCCTCGCCTGGAGCTTAGCTCTCAGACTCCGAAGAGGGCGACTGAGACTTGGGCCTGGGAGTTGGCTTCGGGGTACCCAAGGCGA CGACAGCTGAGTTGTACCACGAAGCTCAGGCCGAGGCTTCCTCCCCTTGTCTGGCCTTTCGAATCCATACTGGCAGCCTCTCCTCTCAGGCA CTCCGCGGGCCGGGCCACTAGGCCCCCTGCTCCTGGAGCTGCGCTATGATCCGGTCTTGAGATGCGCGCGATTCTCTCTGAACCGGT GGAGAGGAGGCTCTGCCCCGCGCGGAGCGAGGACAGCGGCGCCCGAGCTTCCCGCGCCTCTCCAGGGCCCAATGGCAAGAACAGCCT CCGAAGTGCGCGGATGACAGGAAAAGATCTTCAGTTCTTCTGCCGCTAGAAGTGCGGGATACAAGCCTCTATTGGATCCACAACCTGG AGTCCTGCCTTCGGA |
| 56 | ISL2 | ATCTGCGTGCCCTTTCTGGGCGAGCCCTGGGAGATCCAGGGAGAACTGGGCGCTCCAGATGGTGTATGTCTGTACCTTCACAGCAAGG CTTCCCTTGGATTTGAGGCTTCCTATTTTGTCTGGGATCGGGTTTCTCCTTGTCCCAGTGGCAGCCCCGCGTTGCGGGTTCCGGGCGCT GCGCGGAGCCCAAGGCTGCATGGCAGTGTGCAGCGCCCGCCAGTCGGGCTGGTGGGTTGTGCACTCCGTCGGCAGCTGCAGAAAGGT GGGAGTGCAGGTCTTGCCTTTCCTCACCGGGCGGTTGGCTTCCAGCACCGAGGCTGACCTATCGTGGCAAGTTTGCGGCCCCGCAGAT CCCCAGTGGAGAAAGAGGGCTCTTCCGATGCGATCGAGTGTGCGCCTCCCCGCAAAGCAATGCAGACCCTAAATCACTCAAGGCCTGGA GCTCCAGTCTCAAAGGTGGCAGAAAAGGCCAGACCTAACTCGAGCACCTACTGCCTTCTGCTTGCCCCGCAGAGCCTTCAGGGACTGAC TGGGACGCCCTGGTGGCGGGCAGTCCCATCCGCCATGAGAACGCCGTGCAGGGCAGCGCAGTGGAGGTGCAGCAGGTACCAGCCGCC GTGGAAGGCGCTCAGCGAGTTTGCCCTCCAGAGCGACCTGGACCAACCCGCCTTCCAACAGCTGGTGAGGCCCTGCCCTACCCGCCCC GACCTCGGGACTCTGCGGGTTGGGGATTTAGCCACTTAGCCTGGCAGAGAGGGGAGGGGGTGGCCTTGGGCTGAGGGGCTGGGTACA GCCCTAGGCGGTGGGGAGGGGAACAGTGGCGGGCTCTGAAACCTCACCTCGGCCCATTACGCGCCCTAAACCAGGTCTCCCTGGAT TAAAGTGCTCACAAGAGAGGTCGCAGGATTAACCAACCCGCTCCCCCGCCCTAATCCCCCCCTCGTGCGCCTGGGGACCTGGCCTCCTT CTCCGCAGGGCTTGCTCTCAGCTGGCGGCCGGTCCCCAAGGGACACTTTCCGACTCGGAGCACGCGGCCCTGGAGCACCAGCTCGCGT GCCTCTTCACCTGCCTCTTCCCGTGTTTCCGCCGCCCCAGGTCTCCTTCTCCGAGTCCGCTCCCTAGGCAACTCCTCCGGCAGCGAC GTGACCTCCTGTCCTCGCAGCTCCCGGACACCCCAACAGTATGGTGCCGAGTCCCGTGGAGACGTGAGGGGGACCCCTCCCTGCCA GCCCGCGGACCTCGCATGCTCCCTGCATGAGACTCACCCATGCTCAGGCCATTCCAGTTCCGAAAGCTCTCTCGCCTTCGTAATTATTCT ATTGTTATTTATGAGAGAGTACCGAGAGACACGGTCTGGACAGCCCAAGGCGCCAGGATGCAACCTGCTTTCACCAGACTGCAGACCCT GCTCCGAGGACTCTTAGTTTTTCAAAACCAGAATCTGGGACTTACCAGGGTTAGCTGCCCTCCTCTCCTCTCTACGTGGCCGCCGCT CTGTCTCTCCACGCCCCACCTGTGT |
| 57 | DLX4 | AGGTCTCTTCAGACTGCCCATTCTCCGGGCCTCGCTGAATGCGGGGGCTCTATCCACAGCGCGCGGGGCCGAGCTCAGGCAGGCTGGG GCGAAGATCTGATTCTTTCCTTCCCGCCGCCAAACCGAATTAATCAGTTTCTTCAACCTGAGTTACTAAGAAAGAAAGGTCCTTCCAAATAA AACTGAAAATCACTGCGAATGACAATACTATACTACAAGTTCGTTTTGGGGCCGGTGGGTGGGATGGAGGAGAAAGGGCACGGATAATCC CGGAGGGCGCGGAGTGAGGAGGACTATGGTCGCGGTGGAATCTCTGTTCCGCTGGCACATCCGCGCAGGTGCGGCTCTGAGTGCTGG CTCGGGGTTACAGAACCTCGGCATCCGGCTGCAGGGGCAGACAGAGACCTCCTCTGCTAGGGCGTGCGGTAGGCATCGTATGGAGCCCA GAGACTGCCGAGAGCACTGCGCACTCACCAAGTGTTAGGGGTGCCCGTGATAGACCGCCAGGGAAGGGCTGGTTCGGAGGGAATTCC CGCTACCGGGAAGGTCGGAACTCGGGTGATCAAACAAGGAATGCATCTCACCTCCGTGGGTGCTTGTGCTGCGCAAGGAATTATTACC GGAGCGGTTGCGATGGCCTTTGCCCGGCGACCCAAGAAGAGTAAGCAAACTACCGTCCACCCAGCGGATCAGGTCCAAT |
| 58 | CBX4 | GATGTCCTGTTTCTAGCAGCCTCCAGAGCCAAGCTAGGCGAGAGGCGTAGGAGGCAGAGAGAGCGGGCGCGGGAGGCCAGGGTCCGC CTGGGGGCCTGAGGGGACTTCGTGGGGTCCCGGGAGTGGCCTAGAAACAGGGAGCTGGGAGGGCCGGAAGAGCTTGAGGCTGAGCG GGGGACGAACGGGCAGCGCAAAGGGGAGATGAACGGAATGGCCGAGGAGCCACGCATTCGCCTTGTGTCCGCGGACCCTTGTTCCCGA CAGGCGACCAAGCCAAGGCCCTTCCGGACTGACGCGGCCGGCGAGTGTGAAGTTTGGCACCTCCGGCGGCGAGACGGCGC GTTCTGGCGCGCGGCTCCTGCGTCCGGCTGGTGGAGCTGCTGCGCCCTATGCGGCCTGCCGAGGGCGCCGCGAGGGCCCGCGAGCT CCGTGGGGTCGGGTGGGGGGCCCGGGAGCGGACAGCGCGGCCCGAGGGCAGGGCAGGGGCGCGCCTGGCCTGGGTGTGTC TGGGCCCCGGCTCCGGGTCTTGAAGGACCGCGAGCAGGAGGCTTGCGCAATCCCTTGGCTGAGCGTCCACGGAGAAAGAAAAAGAGC AAAAGCAGACGCAGGTGGACGAGGATGGGGCGGGCAAAGAGCCATCCGGGTCTCACCACCGCCCTGACACGCGACCCGGCTG TCTGTTGGGGACCGCACGGGGCTCGGGCGAGCAGGGAGGGAGGGAGCCTGCGCGGGGCTCGTGTTCGCCAGGAATCCCGGAGAA GCTCGAAGACGGTCTGGTGTTGAACGCACACGTGGACTCCATTTCATTACCACCTTGCAGCTCTTGCGCCACGGAGGCTGCTGCTGCCC GGCGGCTGCTACCCACCGAGACCCACGTGGCCCCTCCCCAGGGGTGTAGGGGTGACGGTTGTCTTCTGGTGACAGCAGAGGTGTTGGG TTTGCGACTGATCTCTAACGAGCTTGAGGCGCAAACCTAGGATTCCCTGGAGTTTGGGGTGCGGCGGGGGGGCAAGGAGCAAGGTGAG ACGCCTGCCTGGTTTCCCTGACTAGTTGCGGGGGTGGGGGCCGGCTCTCAGGGGCCACCAGAAGCTGGGTGGGTGTACAGGAAAATA TTTTTTCTCCTGCCGTGTTTGGCTTTTTCCTGGCATTTTTGCCCAGGGCGAAGAACTGTCGCGCGGGGCAGCTCCACCGCGGAGGGAGAG GGGTCGCGAGGCTGGCGCGGGAAGCGCTGTAGGTGGCAGTCATCCGTCCACGCCGCACAGGCCGTCTGCGCCGTCGGACCATCGGGA GGTCTGCAGCAACTTTGTCCCGGCCAGTCCCCTTGTCCGGGAAGGGGCTGAGCTTCCCGACACTCTACCCTCCCCCTCTTGAAAATCCCC TGGAAAATCTGTTTGCAATGGGTGTTTCCGCGGCGTCCAGGTCTGGGCTGCCGGGGGAGGCCGAGCGGCTGCTGCAGCCTCCCTGCTG |

TABLE 4A-continued

| SEQ ID NO | GENE NAME | SEQUENCE |
|---|---|---|
| | | CCAGGGGCGTCGGACTCCGCTTCGCTCACTACGCCCAGGCCCCTCAGGGGCCCACGCTCAGGACTTCGGGGCCACACAGCAGGACCC<br>GGTGCCCCGACGACGAGTTTGCGCAGGACCCGGGCTGGGCCAGCCGCGGAGCTGGGGAGGAAGGGGCGGGGTCGGTGCAGCGGAT<br>CTTTTCTGTTGCTGCCTGTGCGGCGGCAGGAAGCGTCTTGAGGCTCCCCAAGACTACCTGAGGGGCCGCCCAAGCACTTCAGAAGCCCA<br>AGGAGCCCCGGCCACCCCCGCTCCTGGCCTTTTTGCCAACGACTTTGAAAGTGAAATGCACAAGCACCAGCAATTGACTTCCCTTCCGT<br>GGTTATTTATTTTTGTCTTTGTGGATGGTGGGCAGATGGGGAGGAGAGGCCCCTACCTAACCTCGGTGGCTGGTCCCTAGACCACCCCTGCC<br>AGCCGGTGTGGGGAGGAGCTCAGGTCCGCGGGAGAGCGAATGGGCGCCAGGAGGTGGGACAGAATCCTGGGAAGGTACAGCGGACGC<br>CCTGGAAGCTCCCCTGATGCCCCAGAGGGCCCTTCCTGGGAAACCTCCCGGGGGGTGCCCCATACCATCCCACCCGGCTGTCTTGGC<br>CCCTCCCAGGGAGCCGCAGGAGAAACTAGCCCTACACCTGGGATTCCCAGAGCCTTCTGCTGGGGCTCCTGCCCCCGACTTCGGATAAC<br>CAGCTCCGCACAGGTCCCCGAGAGATTGCCACCGCCGCTGGCCTGCTTATTTGATACTGCCCCCCTCCCAGACAGGGGCTGGTCGAGCCCCTGGTTC<br>TGCTGCCAGACTGAAGCCTTCCAGACGCCACCTCGGTTTGGGCCCCCAGGGCCCTCAGGGGCCCCAGGAGAGGAGAGCTGCTATCTAG<br>CTCAGCCACAGGCTCGCTCCTGGTGGGGGCCAGGCTGAAGGAGTGGACCCTGGAGAGGTCGGGAACCTTTTAACAGCCGTGGGCTGGA<br>GGGTGGCTACTAAGTGTTCGGTCTGGGAAGAGGCATGACCCGCACCATCCCGGGGAAATAAACGACTTCTTAAGGGAATCTTCTCGCTGA<br>GCGGGTGCTCTGGGCCAGGAGATTGCCACCGCCAGCCCAGCAGCCCAGATTTGGGCTCTGCCTTGAGCGGGCCGCCTGTGGCTTCCC<br>GGGTCGCTCCCCCGACTCAGAAAGCTCTCAAGTTGGTATCGTTTTCCCGGCCCTCGGAGGTGGATTGCAGATCACCGAGAGGGGATTTA<br>CCAGTAACCACTACAGAATCTACCCGGGCTTTAACAAGCGCTCATTTCTCTCCCTTGTCCTTAGAAAACTTCGCGCTGGCGTTGATCATAT<br>CGTACTTGTAGCGGCAGCTTAGGGGCAGCGGAACTGTGGGGTTGTGCGTGCAGGGGGAGGCTGTGAGGGAGCCCTGCACTCCGCCC<br>CTCCACCCTTCTGGAGGAGTGGCTTTGTTTCTAAGGGTGCCCCCCAACCCCGGGTCCCCACTTCAATGTTTCTGCTCTTTGTCCCACC<br>GCCCGTGAAAGCTCGGCTTTCATTTGGTCGGCGAAGCCTCCGACGCCCCCGAGTCCCACCCTAGCGGGCCGCGCGGCACTGCAGCCGG<br>GGGTTCCTGCGGACTGGCCCGACAGGGTGCGCGACGGGGACGCGGGCCCCGAGCACCGCGACGCCAGGGTCCTTTGGCAGGGCCC<br>AAGCACCCCT |
| 59 | EDG6 | TGGCGGCCGGCGGGCACAGCCGGCTCATTGTTCTGCACTACAACCACTCGGGCCGGCTGGCCGGGCGCGGGGGCCGGAGGATGGC<br>GGCCTGGGGCCCTGCGGGGCTGTCGGTGGCCGCCAGCTGCCTGGTGGTGCTGGAGAACTTGCTGGTGCTGGCCGGCCATCACCAGC<br>CACATGCGGTCGCGACGCTGGGTCTACTATTGCCTGGTGAACATCACGCTGAGTGACCTGCTCACGGGCGCGGCCTACCTGGCCAACGT<br>GCTGCTGTCGGGGGCCCGCACCTTCCGTCTGCGGCCCCGCCAGTGGTTCCTACGGGAGGGCCTGCTCTTCACCGCCCTGGCCGCCTCC<br>ACCTTCAGCCTGCTCTTCACTGCAGGGGAGCGCTTTGCCACCATGGTGGCGGCCGGTGGCCGAGAGCGGGGCCACCAAGACCAGCCGCG<br>TCTACGGCTTCATCGGCCTCTGCTGGCTGCTGGCCGCGCTGCTGGGGATGCTGCCTTTGCTGGGCTGGAACTGCCTGTGCGCCTTTGAC<br>CGCTGCTCCAGCCTTCTGCCCCTCTACTCCAAGCGCTACATCCTCTTCTGCCTGGTGATCTTCGCCGGCGTCCTGGCCACCATCATGGGC<br>CTCTATGGGGCCATCTTCCGCCTGGTGCAGGCCAGCGGGCAGGAAGGCCCCACGCCCAGCGGCCCGCCGCCAAGGCCCGCCGCCTGCTG<br>AAGACGGTGCTGATGATCCTGCTGGCCTTCCTGGTGTGCTGGGGGCCCACTCTTCGGGCTGCTGCTGGCCGACGTCTTTGGCTCCAACCT<br>CTGGGCCCAGGAGTACCTGCGGGGCATGGACTGGATCCTGGCCCTGGCCGTCCTCAACTCGGCGGTCAACCCCATCATCTACTCCTTCC<br>GCAGCAGGGAGGTGTGCAGAGCCGTGCTCAGCTTCCTCTGCTGCGGGTGTCTCCGGCTGGGCATGCGAGGGCCCGGGACTGCCTGG<br>CCCGGGCCGTCGAGGCTCACTCCGGAGCTTCCACCACCGACAGCTCTGAGGCCAAGGGACAGCTTTC |
| 60 | chr13<br>group-<br>00005 | TAGTAAGGCACCGAGGGGTGGCTCCTCTCCCTGCAGCGGCTGTCGCTTACCATCCTGTAGACCGTGACCTCCTCACACAGCGCCAGGAC<br>GAGGATCGCGGTGAGCCAGCAGGTGACTGCGATCTGGAGCTGGTCGCAGCAGGCCATCCTGCACGCGGTGGAGGCGCCCCCTGCAG<br>GCCGCAGCGCATCCCCAGCTTCTGGACGCACTGTGAGCGGTTATGCAGCAGCACGCTCATATGAGATGCCCCGCAGGGTGCTATGCAGG<br>CCCACGTCCCCACAAAGCCCATGGCAGGCGCCCGGGTGCCGGAGCACGCACTTGGCCCCATGGATCTCTGTGCCCAGGGCTCAGCCAG<br>GCATCTGGCCGCTAAAGGTTT |
| 61 | CRYL1 | TCTCATCTGAGCGCTGTCTTTCACCAGAGCTCTGTAGGACTGAGGCAGTAGCGCTGGCCCGCCTGCGAGAGCCCGACCGTGGACGATGC<br>GTCGCGCCCTTCCCATCGCGGCCTGGGCGGGCCCGCCTGCCCTCGGCTGAGCCCGGTTTCCCTACCCCGGGGCACCTCCCCTCGCCC<br>GCACCCGGCCCCAGTCCCTCCCAGGCTTGCGGGTAGAGCCTGTCTTTGCCCAGAAGGCCGTCTCCAAGCT |
| 62 | IL17D | CAGTCCCCGAGGCCCTCCCCGGTGACTCTAACCAGGGATTTCAGCGCGCGGCGCGGGGCTGCCCCAGGCGTGACCTCACCCGTGCTC<br>TCTCCCTGCAGAATCTCCTACGACCCGGCGAGGTACCCCAGGTACCTGCCTGAAGCCTACTGCCTGTGCCGGGGCTGCCTGACCGGGCT<br>GTTCGGCGAGGAGGACGTGCGCTTCCGCAGCGCCCCTGTCTACAT |
| 63 | IRS2 | AGAGAGACATTTTCCACGGAGGCCGAGTTGTGGCGCTTGGGGTTGTGGGCGAAGGACGGGACACGGGGGTGACCGTCGTGGTGGAG<br>GAGAAGGTCTCGGAACTGTGGCGGCGGCGGCCCCCCTGCGGGTCTGCGCGGATGACCTTGGCGCCGCGGTGGGGGTCCGGGGGCTG<br>GCTGGCCTGCAGGAAGGCCTCGACTCCCGACACCTGCTCCATGAGGCTCAGCCTCTTCACGCCCGACGTCGGGCTGGCCACGCGGGCA<br>GCTTCTGGCTTCGGGGGGCCGCGATAGGTTGCGGCGGGGTGGCGGCCACACCAAAAGCCATCTCGGTGTAGTCACCATTGTCCCCGG<br>TGTCCGAGGACAACGATGAGGCGGCGCCCGGGCCCTGGGCGGTGGCAGCGCGAGGCGGGGGCAGGCGGTACAGCTCCCCGGG<br>GCCGGCGGCCGGTGGCGGCGGCTGCAGAGACGACGACGGGGACGGGACGGACGACGCGGGGCAACGGCGGATACGGGGAGGAGGCCT<br>CGGGGGACAGGAGGCCGTCCAAGGAGCCCACGGGTGGCCGCTCGGGCGGCCCGGCTTAGGAGACTTGGGGGAGCTGAAGTCGAGG<br>TTCATGTAGTCGGAGAGCGGAGACCGCTGCCGGCTGTCGCTGCTGGTGCCCGGGGTGCCTGAGCCCAGCGACGAGGCCGGGCTGCTG<br>GCGGACAAGAGCGAGGAGGACGAGGCCGCCGACGCCAGCAGGGGAGGCGCGGGCGGCGACAGGCGGGCCCCGGGCTCGCCAAAGT<br>CGATGTTGATGTACTCGCCGGGGCTCTTGGGCTCCGGTGGCAGTTGCTCGTGCATGCTGGGCAGGCTGGGCAGCCCCTCCAGGGA<br>CAGGCGCGTGGGCCTCACCGCCCGGCCGCGCTGGCCAAGAAGCCCTCCGGGCGGCCGCGCTAGGCCGCACGGGCGAAGGCACTA<br>CAGGGTGAGGGGCTGCGTGGGGCCGGCCCCGAAGGCGCTGGCCGCCTGGCTGGGCCCTGGCGTGGCTGAGGCTCCAGACGCTCC<br>TCCTCCAGGATGCGCCCCACGGGGGAGCTCATGAGCACGTACTGGTCGCTGTCCCCGCCACAGGTGTAGGGGCCTTGTAGGAGCGGG<br>GCAAGGAGCTGTAGCAGCAGCCGGGAACGCCCTGAGCGGCTCCCCGCCGGGGTGCAGGGCTGCGAGAAGAAGTCGGCGGGGTG<br>CCCGTGGTGACCGCGTCGCTGGGGGACACGTTGAGGTAGTCCCGTTTGGGCAGCAGCTTGCCATCTGCATGCTCATGACAGCTTGG<br>AACCGCACCACATGCGCATGTACCCACTGTCCTCGGGGGAGCTCTCGGCGGGCGAGCTGGCCTTGTAGCCGCCCCGCTCGCCGGGAA<br>TGTCCTGCCCGCCGCAGAGGTGGGTGCTGGCCCCGCAGGCCCGCAGAAGGCACGGCGGCGGCGGCGGCGGCCTGGGCT<br>GCAAGATCTGCTTGGGGCGGACACGCTGGCGGGGCTCATGGGCATGTAGTCGTCGCTCCTGCAGCTGCCGCTCCCACTGCCCGCGAG<br>GGCCGCGCCGGGCGTCATGGGCATGTAGCCGTCGTCTGCCCCCAGGTTGCTGCTGGAGCTCCTGTGGGAGCGATCTCGATGTCTCCG<br>TAGTCCTCTGGGTAGGGGTGTAGGCCACCTTGGGAGAGGACGCGGGAGGACGCGAGAGGCGGCCCGCTGCCCGAGAAGGTG<br>GCCCGCATCAGGGTGTATTCATCCAGCGAGGCAGAGGAGGCTGGGGCACCGGCCGCTGCCGGGCTGGCGTGGTCAGGGAGTAGGTC<br>CTCTTGCGCAGCCCTCGGTCCAGGTCCTGGGCGCGTCCCCCGAGACCCGGCGGTAGGAGCGGCCACAGTGGCTCAGGGGCCTGTCC<br>ATGGTCATGTACCCGTAGAACTCACCGCCGCCGCCGCCGTCTCGGGCGGGGGCGTCTCCGCGATGGACTCGGGCGTGTTGCTTCGGT<br>GGCTGCAGAAGGCGCGCAGGTCGCCTGGGCTGGAGCCGTACTCGTCCAGGGACATGAAGCGGGGTCGCTGGGGGAGCCCGAGGCG<br>GAGGCGCTGCCGCTGGAGGGCCGCTGGCCGGGGCCGTGGTGCAGCGGATGCGGCAGAGGCGGGTGCGGGCCGGGCGGCGGCGGGT<br>AGGAGCCCGAGCCGTGGCCGCTGCTGGACGACAGGGAGC |

TABLE 4A-continued

| SEQ ID NO | GENE NAME | SEQUENCE |
|---|---|---|
| 64 | chr13 group-00350 | TAACCTAAAGAATGAAGTCATGCCCCGGCCTGCACCCGGGAAACTGCACACAGCGAAAGATCGCCACTGAGATAAAGAGCTGAAAGCTAT<br>TCCCCAATTCAGCTGTTTCAGCCGTGCGGTCTCACAATGGGCTCACAGACGGCAGCATC |
| 65 | MCF2L | GTTTCCACAATCCACCTCGTAGCTGGGGCGTGCCGCTTGCCTCGGCTTGTCCCGGCAGAACACTCTTACCTTTAATGGCGACTGAAAAGT<br>TGCCACGAGTTCCTGATCATTGTGGTAGGTGCTGCGTGAAGCTGAGACGTGCGTGAGCCACATCCCAGGGGGCTTTGAGCCCCCACCGC<br>GGCGGCGGCTGAGGGGAGGCTTGTCGTACTCGCACAGGAGGACACAGGGCTGCAGTGTTCACTCCAGGGCCTCTTATCATTGGGATCT<br>GAGGAATTTTCCGAGAGGAAGTGCGAATTAACAATGATGAAAGGTTTTGTGAGTGAGTGACAGGCACGTTCTATTGAGCACTGCATGGGGC<br>ATTATGTGCCACCAGAGACGGGGGCAGAGGTCAAGAGCCCTCGAGGGCTGGGAGAGTTCGGAGGATAGAAGTCATCAGAGCACAATGAA<br>GCCAGACCCTGCAGCCGCCTTCCCCTTCGGGGGCTTCCTTAGAATGCAGCATTGCGGGGACTGAGCTGTCCCAGGTGAAGGGGGGCCG<br>TCACGGTGTGTGGACGCCCCTCGGCTCAGCCCTCTAAGAGACTCGGCAGCCAGGATGGGCTCAAGGCATGAGCCCTCAAAGGAGGTTA<br>GGAAGGAGCGAGGGAGAAAAGATATGCTTGTGTGACGTCCTGGCCGAAGTGAGAACAATTGTATCAGATAATGAGTCATGTCCCATTGAG<br>GGGTGCCGACAAGGACTCGGGAGGAGGCCACGGAGCCCTGTACTGAGGAGACGCCCACAGGGAGCCTCGGGGGCCCAGCGTCCCGG<br>GATCACTGGATGGTAAAGCCGCCCTGCCTGGCGT |
| 66 | F7 | TCCAGCTGCAGCGAGGGCGGCCAGGCCCCCTTCTCCGACCTGCAGGGGTAGCGCGGCCTCGGCGCCGGAGACCCGCGCGCTGTCTGG<br>GGCTGCGGTGGCGTGGGAGGGCGCGGCCCCCGGACGCCCCGAGGAAGGGGCACCTCACCGCCCCACCCAGAGCGCCTGGCCGTG<br>CGGGCTGCAGAGGACCCCTCCGGGGCAGAGGCAGGTTCCACGGAAGACCCCGGCCCGCTGGGGCTTCCCCGGAGACTCCAGAG |
| 67 | chr18 group-00039 | ACTTACTGCTTCCAAAAGCGCTGGGCACAGCCTTATATGACTGACCCCGCCCCCGAGTCCCAGGCCGCCCCATGCAACCGCCCAACCGC<br>CCAACCGCCACTCCAAAGGTCACCAACCACTGCTCCAGGCCACGGGCTGCCTCTCCCCACGGCTCTAGGGCCCTTCCCCTCCACCGCAG<br>GCTGAC |
| 68 | C18orf1 | TGCCACACCCAGGTACCGCCCGCCCGCGCGAGAGCCGGGCAGGTGGGCCGCGGATGCTCCCAGAGGCCGGCCCAGCAGAGCGATGG<br>ACTTGGACAGGCTAAGATGGAAGTGACCTGAG |
| 69 | CD33L3 | TCGCCAGCGCAGCGCTGGTCCATGCAGGTGCCACCCGAGGTGAGCGCGGAGGCAGGCGACGCGGCAGTGCTGCCCTGCACCTTCACG<br>CACCCGCACCGCCACTACGACGGGCCGCTGACGGCCATCTGGCGCGCGGGCGAGCCCTATGCGGGCCCGCCAGGTGTTCCGCTGCGCT<br>GCGGCGCGGGGCAGCGAGCTCTGCCAGACGGCGCTGAGCCTGCACGGCGCGCTTCCGGCTGCTGGGCAACCCGCGCCGCAACGACCTC<br>TCGCTGCGCGTCGAGCGCCTCGCCCTGGCTGACGACCGCCGCTACTTCTGCCGCGTCGAGTTCGCCGGCGACGTCCATGACCGCTACG<br>AGAGCCGCCACGGCGTCCGGCTGCACGTGACAGGCGAGGCGGCGTGGGAGCGGGTCCCGGCCTCCCTTCCCGCCCTCCCGCCTGCC<br>CCGCCCAAGGGCTACGTGGGTGCCAGGCGCTGTGCTGAGCCAGGAAGGGCAACGAGACCCAGCCCTCTCCTCTACCCCAGGGATCTC<br>ACACCTGGGGGTAGTTTAGGACCACCTGGGAGCTTGACACAAATGCAGAATCCAGGTCCCAGGAAGGGCTGAGGTGGGCCCGGGAATA<br>GGCATTGCCGTGACTCTCGTAGAGTGACTGTCCCCAGTGGCTCTCAGACGAAGAGGCGAGAAAGACAAGTGAATGGCAATCCTAAATATG<br>CCAAGAGGTGCAATGTGGTGTGTGCTACCAGCCCGGAAAGACACTCGCAGCCCCTCTACCCAGGGGTGCACAGACAGCCCACCAAGTAG<br>TGCCTAGCACTTTGCCAGACCCTGATATACAAAGATGCCTGAACCAGGGTCCCGTCCCTAGAGCAGTGGCTCTCCACTCTAGCCCCCACC<br>CTGCTCTGCGACAATAATGGCCACTTAGCATTTGCTAGGGAGCCGGGACTAGTCCAAGCACCCACAAGCATGAATTTGCCAAATCTTTTC<br>AGCAACCTCTTAAGGCAACTGCTATCATGATCCTCACTTTACACATGGAGAAGCAGAAGCAGAGATGATAGAATCTTTCGCCCAAGGCCAC<br>ATCTGTATTGGGACGGGGGCAGCCTGGCACCCAAGTGCCCATTCCTCCCTTCTGACCAGCCCCCACCCCTCCGGCTCTGGCGTCCAAAG<br>GGCTAAGGGGAGGGTGCCCTTGTGACAGTCACCCGCCTTCTCCCCTGCAGCCGCGCCGCGGATCGTCAACATCTCGGTGCTGCCCAG<br>TCCGGCTCACGCCTTCCGCGCGCTCTGCACTGCCGAAGGGGAGCCGCCGCCCGCCCTGGTCCGGCCCGGCCCTGGGCAACAG<br>CTTGGCAGCCGTGCGGAGCCCGCGTGAGGGTCACGGCCACCTAGTGCCGCCGAACTGCCCGCACTGACCCATGACGGCCGCTACACG<br>TGTACGGCCGCCAACAGCCTGGGCGCTCCGAGGCCAGCGTCTACCTGTTCCGCTTCATGGCGCCAGCGGGGCCTCGACGGTCGCCC<br>TCCTGCTCGGCGCTCTCGGCTTCAAGGCGCT |
| 70 | TNFRSF11A | ATGAACTTCAAGGGCGACATCATCGTGGTCTACGTCAGCCAGACCTCGCAGGAGGGCGCGGCGGCGGCTGCGGAGCCCATGGGCCGCC<br>CGGTGCAGGAGGAGACCCTGGCGCGCCCGAGACTCCTTCGCGGGGAACGGCCCGCGCTTCCCGGACCCGTGCGGCGGCCCCGAGGGG<br>CTGCGGGAGCCGGAGAAGGCCTCGAGGCCGGTGCAGGAGCAAGGCGGGGCAAGGCTTGAGCGCCCCCATGGCTGGGAGCCCGAA<br>GCTCGGAGC |
| 71 | ZNF236 | TCAGTGTTATGTGGGGAGCGCTAGATCGTGCACACAGTAGGCGTCAGGAAGTGTTTTCCCCAGTAATTTATTCTCCATGGTACTTTGCTAA<br>AGTCATGAAATAACTCAGATTTTGTTTTCCAAGGAAGGAGAAAGGCCCAGAATTTAAGAGCAGGCAGACACACAACCGGGCACCCCCAGA<br>CCCTGGCCCTTCCAGCAGTCAGGAATTGACTTGCCTTCCAAAGCCCCAGCCCGGAGCTTGAGGAACGGACTTTCCTGCGCAGGGGGATC<br>GGGGCGCACTCG |
| 72 | chr18 group-00342 | GTGGAAACACAACCTGCCTTCCATTGTCTGCGCCTCCAAAACACACCCCCGCGCATCCGTGAAGCTGTGTGTTTCTGTGTTACTACAGG<br>GGCCGGCTGTGGAAATCCCACGCTCCAGACCGCGTGCCGGGCAGGCCCAGCC |
| 73 | OLIG2 | TCCACACCTCGGGCAGTCACTAGGAAAAGGGTCGCCAACTGAAAGGCCTGCAGGAACCAGGATGATACCTGCGTCAGTCCCGCGGCTGC<br>TGCGAGTGCGCGCTCCTGCCAGGGGACCTCAGACCCTCCTTTACAGCACACCGAGGGCCCTGCAGACACGCGAGCGGGCCTTCAG<br>TTTGCAAACCTGAAAGCGGGCGCGTCCACCAGGACGATCTGGGTAGGGAGGCTCTGGGTGAGGAGGCCGCGTCTTTATTTGGGGTCCTCG<br>GGCAGCCACGTTCAGCTCTGGGGGAAGACTGCTTAAGGAACCCGCTCTGAACTGCGCGCTGGTGTCCTCTCCGGCCCTCGCTTCCCCG<br>ACCCCGCACAGGCTAACGGGAGACGCGCAGGCCCACCCCACCGGCTGGAGACCCCGGCACGGCCCGCATCCGCCAGGATTGAAGCAG<br>CTGGCTTGGACGCGCAGTTTTCCTTTGGCGACATTGCAGCGTCGGTGCGGCCACAATCCGTCCACTGGTTGTGGGAACGGTTGGAGG<br>TCCCCAAGAAGGAGACGCAGAGCTCTCCAGAACGCCTACATGCGCATGGGGCCCAAACAGCCTCCCAAGGAGCACCCAGGTCCAT<br>GCACCCCGAGCCCAAAATCACAGACCCGCTACGGGCTTTTGCACATCAGCTCCAAACACCTGAGTTCCACGTGCACAGGCTCTCGCACAGG<br>GGACTCACGCACCTGAGTTCGCGCTCACAGATC |
| 74 | RUNX1 | CTGCCCTCGCGGATCTCCCCCGGCCTCGCCGGCCTCCGCCTGTCCTCCCACCACCCTCTCCGGGCAGTACCTTGAAAGCGATGGGCA<br>GGGTCTTGTTGCAGCGCCAGTGCGTAGGCAGCACGGAGCAGAGGAAGTTGGGGCTGTCGGTGCGCACCAGCTCGCCCGGGTGGTCGG<br>CCAGCACCTCCACCATGCTGCGGTCGCCGCTCCTCAGCTTGCCGGCCAGGCAGCGCCGGCGTCCGGGGCGCCCAGCGGCAACGCCT<br>CGCTCATCTTGCCTGGGCTCAGCGCGGTGGAAGGCGGCGTGAAGCGGCGGCTCGTGCTGGCATCTACGGGGATACGCATCACAACAAG<br>CCGATTGAGTTAGGACCCTGCAAACAGCTCCTACCAGACGGCGACAGGGGCGCGGATCTTCAGCAAGCAGCTCCCGGGAGACCAACATA<br>CACGTTCAGGGGCCTTTATTACTGCGGGGGGTGGGGGGGGCGGGGGTTGGTTAGGGGAGGAGGGAGACTAAGTTACTAACAGTCCAGG |

TABLE 4A-continued

| SEQ ID NO | GENE NAME | SEQUENCE |
|---|---|---|
| | | AGGGGAAAACGTTCTGGTTCTGCGGATCGGCCTCTGACCCAGGATGGGCTCCTAGCAACCGATTGCTTAGTGCATTAAAAAGTGGAGACT ATCTTCCACGAATCTTGCTTGCAGAGGTTAAGTTCTGTCTTTGGCTGTTAGAAAAGTTCCTGAAGGCAAAATTCTCATACACTTCCTAAAAT ATTTATGCGAAGAGTAAAACGATCAGCAAACACATTATTTGGAAGTTCCAGTAGTTAATGCCTGTCAGTTTTTTGCAGGTGAGTTTTGTCTA AAGTCCCAACAGAACACAATTATCTCCCGTAACAAGGCCACTTTTATCATGCAAAACTGGCTTCAGTCCCGAAAAGCAAGAGCTGAGACTTC CAAAGGTAGTGCTACTAATGTATGTGCACGTATATATAAATATATACATATGCTCTACTTCATAAAATATTTACAATACAATCTGTGGAGAA TTTAAACACAACAGAAATCCATTAATGTACGCTGCAGATTTTTTTAAGTAGCCTTGAAAATCAGCTTCAGTAGTTGGAGCAGTGCTGAGCTA GAAGTACTTGTCATGTTCTCTGTTCTCAATGAATTCTGTCAAAACGCTCAGTGCAGAAAATTCAGCGTTTCAGAGATCTTCAGCTAATCT TAAAACAACAATCATAAGAAGGCCCAGTCGATGACACTCAGGGTTCTACAGCTCTCCCACATCTGTGAACTCGGGTTTGGGGATGTTGGTTA AGTTTGTGGCTGGTCCTCTGGTTTGTTGGGAGTTGAGCAGCCGCAGAGTCACACACATGCAAACACGCACTCTTCGGAAGGCAGCCACTGT CTACATCAGCTGGGTGACTCAGCCCTGACTCGGGCAGCAGCGAGACGATACTCCTCCACCGTCGCCCAGCACCCGCCGGTTAGCTGCTC CGAGGCACGAACACCCACGAGCGCCGCGTAACCGCAGCAGGTGGAGCGGGCCTTGAGGGAGGGCTCCGCGGCGCAGATCGAAACAGA TCGGGCGGCTCGGGTTACACACGCACGCACATCCTGCCACGCACACTGCCACGCACACGCAACTTCACGGCTCGCCTCGGACCACAGA GCACTTTCGCCCCCTGTTGTAAAAGGAAAACAATTGGGGAAAAGTTTCGCAGCCAGGAAAGAAGTTGAAAACATCCAGCCAAGAAGCCAGT TAATTCAAAAGGAAGAAAGGGGAAAAACAAAAAAAACAACAAAAAAAGGAAGGTCCAACGCAGGCCAAGGAGAAGCAGCAGAGGTTGAC TTCCTTCTGGCGTCCCTAGGAGCCCCGAAAGAAGTGCCTGGCGGCGCAGGGCCGGGCAGCGTGGTGCCCTGGCTGGGTCCGGCCGC GGGGCGCCCGTCCCGCCCGCGCCCGCTGGCTCTATGAATGAGAGTGCCTGGAAATGAACGTGCTTTTACTGTAAGCCCGGCCGGAGGA ATTCCATTCCCTCGACTCGTTTGCATAGGGGCGGCCGGCGGCCAATCACAGGCCTTTCCGGTATCAGCCAGGGCGGCTCGCCGCCG CCGGCTCCTGGAATTGGCCGCGCGCCCCCGCCGCCGCGCCGCGCTACTGTACGCAGCCCGGGCGGGGAGTCGGAGGCCACCCC CGCGCCCGCATCCAAGCCTGCATGCTGGCCGGGGCCCCGCCCGCGTGCGGACCCCTTTCCGCAGCCACACGCAGGCTTGTGCGGC TCCGCGAGTGGCCACGGTCCGGAGACCTGGAAAAAGAAAGCAGGCCCCGCCGGCCCGAGGAGGACCCGGCCGGCGCGCCGCACCCG GAGAGGCCCGGCCCGCGAGCCGCTGCAGGCAGGCGCAGTGGCGCCACGAGGCTCCCGAACCGGGCTGCAGCCCGCGACGGCCC CAGATCCTGCGCGGCCGCCCAGGGCCAGGCCTCCGCTTCCAGGGCGGGGTGCGATTTGGCCGCGGGGCCCGGGGAGCCACTCCG CGCTCCTGCACCGTCCGGCTGGCAGCTGCGGCGAAGCGGCGCTGATTCCTGCATGAGGCCGGACGGCGTCCGCGCGTGCCGTTTGCT CTCAGCGTCTTCCCTTGGGTCGGTTTCTGTAATGGGTGTTTTTTACCGCTGCGCCCGGGCGCGGCTCGATCCCTCCGCGTCTCACTT GCTGCGTGCGTCAGCGGCCAGCGAAGAGTTTCCTAGTCAGGAAAGACCCCAAGAACGCGCGGCTGGAAGGAAAGTTGAAAGCAGCCAC GCGGCTTGCTCCCGGGCCTTGTAGCGCCGGCACCCGCAGCAGCCGGACAGCCTGCCCGGGCCCCGCGTCTCCCCTCCGGCTCCCCGG AAGCGGCCCCGCTCCTCTCCCCGCCCCGTGCGCTCGAGCGGCCCCAGGTGCGGAACCCACCCCGGCTTCGCGTGCGGGCGGCCGC TTCCCCCTGCGCCGGTCCCGCGGTGCTGCGGGCATTTTCGCGGAGCTCGGAGGGCCCCGCCCCGGTCCGGCGTGCGCTGCCAACT CCGACCCCGCCCGGCGGGGCTCCCTCCCAGCGGAGGCTGCTCCCGTCACCATGAGTCCCTCCACGCCCTCCCTGCCGGGCCCTGCAC CTCCCGGGGCCTCTCATCCACCCCGGGGCTGCAACCCAGTCCCCGGATCCCGGCCCCGTTCCACCGCGGGCTGCTTTGTGGTCCCGC GGAGCCCCTCAATTAAGCTCCCGGCGCGGGGGTCCTCGCCGACCTCACGGGGCCCCTGACGCCCGCTCCTCCTCCCCCAGGGCTA GGGTGCTGTGGCCGCTGCCGCGCAGGGACTGTCCCCGGGCGTTGCCGCGGGCCCGGACGCAGGAGGGGGCCGGGGTTGACTGGCGT GGAGGCCTTTCCCGGGCGGGCCCGGACTGCGCGGAGCTGTCGGGAGCGCCGGCTCGGCGGACGCCAGGGGGCAGCAGCCGC CCTCCCTGGACGCGCGCGCAGTCCCCGGAGCTCCGGAACGCCCCCGACGGCGCGGGGCTGTGCGGGCCGCCTCGTGGCCTTCGG GTCGCCCGGGAAGAACTAGCGTTCGAGGATAAAAGACAGGAAGCGCCCCAGAGCCCACTTGAGCTGGAACGGCCAAGGCGCGTTTCC GAGGTTCAATATAGAGTCGCAGCCGGCCAGGTGGGACTCTCGGACCAGGCCTCCCGCTGTGCGGCCCGGTCGGGGTCTCTTCCCG AAGCCCCTGTTCCTGGGGCTTGACTCGGGCCGCTCTTGGCTATCTGTGCTTCAGGAGCCCGGGCTTCCGGGGGCTAAGGCGGGCGGC CCGCGGCCTCAACCCTCTCCCGCTCCCGCTCCCCCTGGGCACTGCTGCAGCACCCGAGTTCAGTTTTGTTTTTAATGGACCTGGGGTCTCGGA AAGAAAACTTACTACATTTTTCTTTTAAAATGATTTTTTTAAGCTCTAATTCCAGTTGTAAATCCCCCCCTCCCCCGCCCAAACGTCCACT TTCTAACTCTGTCCCTGAGAAGAGTGCATCGCGCGCGCCCGCCCGCCCGCAGGGGCGCAGCGCCTTTGCCTGCGGGTTCGGACGGC CCGCTCTAGAGGCAAGTTCTGGGCAAGGGAAACCTTTTCGCCTGGTCTCCAATGCATTTCCCCGAGATCCCACCCAGGGCTCCTGGGGC CACCCCCACGTGCATCCCCCGGAACCCCCGAGATGCGGGAAGGGAGCACGAGGGTGTGGCGGCTCAAAAGTAGGCTTTTGACTCCAGG GGAAATAGCAGACTCGGGTGATTTGCCCCTCGGAAAGGTCCAGGGAGGCTCCTCTGGGTCTCGGGCGCTTGCCTAAAACCCTAAACCC CGCGACGGGGCTGCGAGTCGGACTCGGGCTGCGGTCTCCCAGGAGGGAGTCAAGTTCCTTTATCGAGTAAGGAAAGTTGGTCCCAGC CTTGCATGCACCGAGTTTAGCCGTCAGAGGCAGCGTCGTGGGAGCTGCTCAGCTAGGAGTTTCAACCGATAAA |
| 75 | AIRE | TTCGGAAGTGAGAGTTCTCTGAGTCCCGCACAGAGCGAGTCTCTGTCCCCAGCCCCAAGGCAGCTGCCCTGGTGGGTGAGTCAGGCCA GGCCCGGAGACTTCCCGAGAGCGAGGGAGGGACAGCAGCGCCTCCATCACAGGGAAGTGTCCCTGCGGGAGGCCCTGGCCCTGATTG GGCGCCGGGGCGGAGCGGCCTTTGCTCTTTGCGTGGTCGCGGGGGTATAACAGCGGCGCGCGTGGCTCGCAGACCGGGGAGACGGG CGGGCGCACAGCCGGCGCGGAGGCCCCACAGCCCCGCCGGGACCCGAGGCCAAGCGAGGGGCTGCCAGTGTCCCGGGACCCACCGC GTCCGCCCCAGCCCCGGGTCCCCGCGCCCACCCCATGGCGACGACGCGGCGCTACGCCGGCTTCTGAGGCTGCACCGCACGGAGAT CGCGGTGGCCGTGGACAG |
| 76 | SUMO3 | ACGCACACTGGGGGTGTGATGGAAAGGGGGACGCGATGGATAGGGTGGGCGCACACTGGGGGACGCGACGGGGAGGGGTGAGCAC ACACTGGGGGTGTGATGGAGAGGGCGACGCAATAGGGAGGGGTGGGCGCACACCAGGGACGCGATGATGGGGACGGGTGGGCGCAC ACCAGGTGGCATGATGGGGAGGAGTGGGTACACACCATGGGGGCGTGATGGGGAGGCGTGGGCGTACACCGGGGGCGCGATGGG GAGGGGTGGGCGCACACCGGGGGACGCGATGGAGGCGGTGGGTGCACACGGGGCGCGATGGGTGGGAGTAGGTGCACACTGAGGGC ACGATTGGGGAGAACACGAAGGAGAGGGGTGGGCGCACACTGGGGGACGCGATGGCCGGGACACGATGCGGAGAAGTGGGTGAATACC GGGGTCGCGATGGGCGCCCTGGAAGGACGGCAGTGCTGCTCACAGGGGCCAGGCCCCTCAGAGCGCGCCCCTTGGGGGTAACCCCAG ACGCTTGTTCCCGAGCCGACTCCGTGCACTCGACACAGGATC |
| 77 | C21orf70 | CCACAGGGTGGGGTGCGCCCACCTGCCCTGTCCATGTGGCCTTGGGCCTGCGGGGAGAGGGAATCAGGACCCACAGGGCGAGCCCC CTCCGTAGCCCGCGGCACCGACTGGATCTCAGTGAACACCCGTCAGCCCATCCAGAGGCTAGAAGGGGA |
| 78 | C21orf-123 | TTGAGGTCTCTGTGCATGCTTGTGCGTACCCTGGACTTTGCCGTGAGGGGTGGCCAGTGCTCTGGGTGCCTTTGCCAGACAACTGGTCT GCCGGGCCGAGCATTCATGCTGGTC |
| 79 | COL18A1 | TGACGCGCCCCTCTCCCCGCAGCTCCACCTGGTTGCGCTCAACAGCCCCCTGTCAGGCGGCATGCGGGGCATCCGCGGGGCCGACTTC CAGTGCTTCCAGCAGG |
| 80 | PRRT3 | AACACACTGTCTCGCACTAGGTGCTCGCGGAAGAGCGCGGCGTCGATGCTGCGGCTCAGGTTGATGGGCGATGGCGGCCGCAGATCCA GCTCGCTCAGCGATGGCGCCGGTCCCACACCGTTGCGGGACAGTCCCGGGCCACCCTGGGGTCCGCGACCCAACGACGCAGCCGAGC CCCAGGCGCCTGAACTGGGCGTGGCCAGCTGCCCACTCTCCGCGGGTTGCGGATGAGGCTCTTGCTGATGTCCAAGCTGCCTGCACC AACGTTGCTGGGCCCTGCATAGCAGTTATTGGGTCGCTCCGGCACCTCGCTCTTTCCTGACGGCGCCGGGCACGCCAGACGCATCAGCT TAGCCCAGCAAGCGTGCTCCGTGGGCGGCCTGGGTCTCGCGGCAGCCACCGCGGCCAACGCCAGGGCGAGCGCCCATGTCAGCTCCA GGAGGCGCAGCCAGAAGTGGACACCCCACCAGGCCCACGAGAAGCGGCCCACGCGGCCTGGGCCCGGGTACAGCCAGAGCGCAGCC |

TABLE 4A-continued

| SEQ ID NO | GENE NAME | SEQUENCE |
|---|---|---|
| | | GCCAGCTGCAAGCCGCTAGCCAGCAGCCCCAGCGCGCCCGCCACAGCCAACAGCCGAGGGCCCGGGCTGGCATCCCAGCCCCGTGGG<br>CCGTCCAGCAGGCGGCGACGGCACAGGCAGAGCGTGCCCAGAGCCAC |
| 81 | MGC29506 | GTCTGCACGAAGCCCGCGGCGGCCTGCAGGGGGCCCAGCGACTCGTCCAGGGAACCGGTGCGCAGGAGCAGCCGGGGGCGCGGCGC<br>GCCGGCCGCCCTTGGGGGACTCTGGGGCCGGGGGCGCAGCTCGATCTGACGCTTGGGCACTGTCCGGGGCCTGGCGGGCGCGGCGC<br>CCTCCTCCAGAGCCACCTCCACACACTCGAACTGCGCTGGGGCGGCAGGACTTGGCCCACGGGGCCGCAGCTCTAGGTAGGTGGCCCA<br>GCGGGAGCCACCATCGGGGACCTGGGACTGGCGTGGGACCGCGGCGGGAGACGCTGGCCCCGGCGGCAAGGGGCTGATGAAGGCCG<br>GCTCCGTGAACTGTTGTTGCGCCTCGCGATCGTCTGCGCCGGAGCAGCCGAACAGGGGTCCGACGCCGAAGATGACTTCCATCTCCCCC<br>GACGGCAGCGTGCGCAGCTGGGGCTGGGGTGGCCGTGGGCCGGAACCTGGGCCTCGCGGGAAACCCGAGCCGGGCCCGTGCCGCTG<br>GCGGCTATTCTGGGCGCTGACGGACAGGCGAGGCTGCGCGCCCGCCCCCGCCCAGGAGCCACCCAGGGCCAATTCGCTGGGCCTTT<br>CGCGTCCGGCCCAACGTCCGGGGGCTCCGGAGAACCTGGAGCCGTGTAGTAGGAGCCTGACGAACCGGAGGAGTCCTGGCGCCGCG<br>GGGGGCCGTGGGCAGCTGCCTCGGGATCCCAGGCAGGGCTGGCGGGCGAGCGCGGTCAGCATGGTGGGGCCGGACGCCGTGCACT<br>ATCTCCCTCGCATTCGCCTCCGCTGGTGGCGC |
| 82 | TEAD3 | CTGGAGAGAACTATACGGGCTGTGGGAGTCACCGGGCGACTATCACCGGGCCTCCTTTCCACATCCTCCTCCGGGAAGGGACCCCGTTC<br>CGGGGCCTCGACCGGCGCAGACTGGGCTGACCCACTTTCTTGGGCCCACTGAGTCACCTCGAAACCTCCAGGCCGGTAGCGGGGAGGAG<br>AGGAGGAGCAGGCGGGGGTGCCAAGGTGTGGGCTGCGCCTCGGTTAGGGGGCGAGCCCGGCTTGTTTATGAGGAGGAGCGCGGAGGA<br>GGATCCAGACACACAGGCTTGCGCGCCCAGACTCGCCCGGCCAGCGGCTGGCGGCCTCCGACGTCACCAAACCGGTTGGGTGAGAGG<br>GCAGAGAGCAGGGGGAAGGGCCGCAGTCCCGCCCCGCCCCCCGGCACGCACCGTACATCTTGCCCTCGTCTGACAGGATGATCTTCC<br>G |
| 83 | chr12<br>group-<br>00022 | GAGTGCGGAGTGAAGGGGTGCACTGGGCACTCAGCGCGGCCCTTGGGAGGCAGGGCCGCCCAGCCTGCCCTCCTGTCTGGGAAGGC<br>CGTCCAGAAGCAGGAGCCCCGGGGAAAACAACTGGCTGGACGGGGCGGCCTTCAGTGTCTCTCCCAGCCTGAGAGTCGCTTCCCACCA<br>CCTGGGCACGAACCTGCTCTGCGATCTCCGGCAAGTTCCTGCGCCTCCTGTCGGTAAAATGCAGATCGTGGCGTCTT |
| 84 | CENTG1 | TCTTCTTTCCGCCCCTAGGGGGCACAAGCGGGCATGTCCAAGCGCCTAGGAGCCCGTACCGCTGGGGACCTCCCCTTCCGCGAACCCC<br>GAGCGGGTAGACCCAGAGCAATCCGAGTGTGGAAACAATGGAGAGGGGGCGTGTTGAGCTGGGGTCTCCATGCCTCGTTGGGGAGAGG<br>GAGGTGAGTTTGTGTCTTCTGGAAGGCGTGGGGGCTGTGCCCTCGTGGGGGTAGGAAGTGCTCCCGTGGGCGGGGTGCGGATCGGA<br>GAGGTGAGTGGGTGCGTCTGTCCAGCGGTCCGCCCGGTGGTCGTGCCCGGCCCGCGTGGGGATGGGGTGTCTCTCCGCTGGGC<br>AACTATACCAGCGCAACCGGGGCGTCGGCGGCCCACGCTAGCGGCGCTGCTCCGGCGGCGGGGCTGGGCGTGGCGGTGATGCT<br>GGGCGTGGTGGCCGCGCTGGGCGTGGTGGCCGCGCTGCCGCCCTCACCCGGGCAGCCGTGCTGGAGAAGGATGTCGGCGCACAGCT<br>GGCTTCCAGCCTGGCGGGCGTAGAACAGCGCCGTGCGCCCTGGGCGTCACGGGCCGCCACGTCCGCGCCGTACTAGAGGGCGGAAA<br>CGGCCGCGTGACCGCCGCGTCCCCAGGGCGCCCACACCCGGCGCCGCCTCCCCCACATGGCCAAGCCTACTTCCGGGGTCCCTCTGGG<br>AATTTCGGGCTTTCCCGCGCCAGGCGTTTTCCAGGATGAAGCCTCAAAGACCCCCTTTCCTCCCCCCAGCTCACGTACCCACAGCAGCAG<br>TTGCGTGATGACGACGTGGGCGAGCTCGGCCGCCAGGTGGAGTGGGGAGCGCAGCTGTGGGTCCTCTACGCTGGTGTCGAGCGGCCC<br>GTGTCGCGCATGGGCCAAAAGCAGGAGAACGGTAGCCACGTCCTGGGCCTGCACGGCGGCCCACAGCTGGCGCCCAGCGGCCTC<br>CGAGGTGCTCAGCGGCGCCAGGAACAGTAGCTGCTCGTACTTGGCGCGAATCCACGACTCGCGCTCCTCCCTGCAAGACCAGGGATCAA<br>CGGAAAAGGCTCTAGGGACCCCCAGCCAGGACTTCTGCCCCTACCCACGGGACCGTCTCAGGTTCGCACACCCTCAGCAACCCTCCCCC<br>CGCTCTGTTCCCTCACGCTTACCGCGAAGAGTCCCGCGAGGGCTTGGCACGGCCTCGCGTGTCGCTTTCCCACACGCGGTTGGCCGTGT<br>CGTTGCCAATAGCCGTCAGCACCAGGGTCAGCTCCCGTGGCCAGTCGTCCAAGTCCAGCGAGCGAACGCGGGACAGGTGTGTGCCCAG<br>GTTGCGGTGGATGCCAGAACACTCGATGCAGATGAGGGCGCCCAGGTTCAAGCTGGCCCACGTGGGGTCTGCGGAAGGAGCGTAGAGG<br>TCGGCTCCCAGCCGGGCAGCACAGGCACCCCGGCATTCACTACACTCCCTAGCCCCTCCGCTGCCTCCTGGCACTCACTGGGGGCCCC<br>GCAGTCCACGCAGATTGAATTCCCCTTGGCGTTCCGGATCGCCTGGAT |
| 85 | CENTG1 | AGCCAGGTCCAGCCCCCGCGCCTGACACCGGCCGGACGTTCCCGGGGCGCCGCAGCTGCGGCGGGAACTCTGGGATCCGGAGCCATC<br>TGCTCCCACCCGCTCCGGAGCCAAACCCCGGGGGCCGCTCTCGCTCCCGGACCCGCCTCCTCTCCCGGGAGTGTGAGCCGAACCAAGA<br>GTCTCCTGCCTATCTCCTCCAGTAGGAAAATAGTAATAATAATAGACACCCTGCCCCGTAAAAAACACTACCTTCCCCGTACCGCCTCCC<br>AAGTCTCCCGGGGTACGGATTGCCTTTGCAGCAGTTCCGCCCCACCTGACTCACTCCAGGGTCAGCCCCGGGTGGGTTTCAATGCGGCT<br>CTGGGGAGGGGTGGGCAGTGGGGAAGTGAGGCTTCCTATCCGCCCCCTCTCACTTCACATTTAAATATTCTGCACGTTCCAGCCCCC<br>GCGGACTCGCGTACCGCCCAATCCGCCTTCACCGCACAGAAAACATCACTAGCCTGCTCTCAGCCCAGGGAGCAGTAGTCCCTGGCGA<br>GAAGCTGCCTGCAAGGTCACTGTCATGCCACCTGCCCCAAGTGCTCAGGGGAAACTGAGGCTTCCTCATCCCCTTCACCTTCAACGTCGC<br>TCTAAACACGGCAAAGCCCCGTTTCCATGCTCCCAGAGTTCAGCTGAGGCTGGAAGTGGGGTCCTGGGCTTCTCTGGGAGCAATTTTCTA<br>GTCACTCTGATCAAGGACGTTACTTTCCCAGAAAGCTCTGAGGCTGAGTCCCTCTGAAATCAAGTCCTTTCTCCTGTCGCACAATGTAGCT<br>ACTCGCCCCGCTTCAGGACTCCTATTCTTTGCCCCAATCCTTGACAGAGGGGTGAGCTTGGTTCATCCGCCCACCCCAGAGAAAAGCTTC<br>CCTAGTTTCCTGGACCTCGCTCCTCCACCCCAAGCTGAGCATTCCAGGTACCCTTCCCTCCCTGTTCTCAAGCCCTGACTCAACTCACTAG<br>GGGAAGCGCGGAGCTCGGCGCCCAGCAGCTCCCTGGACCCGCTGCCAGAAGCAGGCTGGGGGGTCCGGAAGGGGCCCGGAGCCA<br>GGAGGCCCTCCTGTGCTCTTGGTGAAGATGCCGCTGATAAACTTGAGCATCTTGCGGTCACGAGTGGATGCTCGGCCCCCTCCCGGCC<br>CCGTTTCAGCCCCGGAGCTGGAGGCTCCAGAGTGATTGGAGGTGCAGGCCCGGGGGGCTGCGCGGAAGCAGCAGTGACAGCAGTGGC<br>TGGACTCGGAGTTGGTGGGAGGGTTAGCGGAGGAGGAGGCCGGCAGGCGGTCCCGGATCGCAAGTCACTGTTGTCCAAGGTCTTACTC<br>TTGCCTTTCCGAGGGGACAACTTCCCTCGGGCTCCAGCCCCAGCCCCGACCCCACCAGAGGTCGAAGCTGTAGAGCCCCTCTCCCCGG<br>CGGCGGCGGCGGTGCGGCGGCAGAGACCGAAGCTCCAGTCCCGGCGCTGCTCTTTGACCCCTTGACCCTGGGCTTGCCCTCGCTTTC<br>GGGCCATGACAGGCGGCTACCCGCGCCCTTGCCCCGCCGGTTTGGCTCCACTCGTGGTCACGGTCTTGCAAGGCTTGGGAGCCGGC<br>GGAGGAGGCGCCACCTTGAGCCTTCGGCTGCCGGTGCCAGGGTGCGGAGGATGAGCCAGGGATGCGCCGCCCGCCCGGCCTTCG<br>GGCTCCGGGCCGCCCAGCTCGGGCTGCTGAGCAGGGGGCGCCGGAGGAGGTGGGGGCGCCCCAGGCTTGGGGTCGGGGCTCAG<br>TCCCCCGGAGAGCGGGGTCCCGGAGGGACGGCCCAGGGGAGGGCGGCGGCCGGGAGCGGGGAGACTGGGCGGCCGGACTG<br>GCCGGAGCCGGGGACAGGGCTGGGGGCTCCGCGCCCCCGGTGCCCGCGCTGCTCGTGCTGATCCACAGCGCATCCTGCCGGTGGAAG<br>AGACGTTCGTGCCGCTTCTTGCCCGGCTCCTCCGCGCCTCGGGGGCTGCCAGGATCCCCAGTCTCGGAGCCTCTGGCACCGGCGGCGC<br>CGGCCGCGGCCGCAGACGGAGAAGGCGCGGCGGAGGCACCGACTCGAGCTTAACCAGGGTCAGCAGATGAGGTAGGTCGTTGTCC<br>GGCGCTGAAGCGCGCCCGCGCCCCGGCTCATGGGGCCGGAGACCCCGAGCTGGGAGGGGAGGGGAGACTCCCCCGGACTGCCTCA<br>GGGGGGCCCGGCCATGGGGCCGCCCTGCTGCTGCCCCAGCCCCGGGACCCCGCTGAGCCCCGGCCCCGGCTCCGCTGTCGCCGC<br>CGCCTCCGCCGCGCCTTGCTGCGCCCCTCCCCATCACATGGGGCGCCCCTCCCCATGCTCCCCGCCCTGCCCCCACCCTCTTGG<br>AGCCCCGGGACCTTGGTGCTGCTCCAGGGAGCGCGCCGGACCGTCCACCCCGCCTGGGTGGGGCGCTGAGATGGGTGGGGAG<br>GGCGGGGAGGACAGTAGTGGGGCAAATGGGGAGAGAGAGGAAAAGGGAGCAGAAAGGGGACCGGAGGCTAGGGGAAACGAACCT<br>GTGCGGGGAGGCAGGGGCGGGGAATTGGGACTCAAGGGACAGGGGCGCGGATGCGGTCGGAAAGAGGGTCTAGAGGAGGGTGGG<br>AAGCTAGTGG |

TABLE 4A-continued

| SEQ ID NO | GENE NAME | SEQUENCE |
|---|---|---|
| 86 | chr18 group-00304 | AGGAGCGCAAGGCTTGCAGGGCATGCTGGGAGAGCGCAGGGAACGCTGGGAGAGCGCGGGAAATACTGGGATTGGCTCCCGAGGGCT GTGAGGAGGGCACGAGGGGACACTCCGATGAAGGCAGGGCACGCGGGGCGAGCCGGGAGCGTCTCCTGAGGGCAGCGAGGAGGGAG CTGAGGCACGCGGGCTCTCAATCGACGCCCCACAGAGACCAAGAGGCCTGGCCTTGGGGGGCAGCTGCTTGAAGGAGGCAGAGCGGA AGCGAGGGAGACTGCTGGAGGCCCTGCCGCCCACCCGCCCTTTCCTCCCCCTGAGGAGACGCCTGACGCATCTGCAGTGCAGGAGGCC GTGGGCGTTAGAAGTGTTGCTTTTCCAGTTTGTAAGACCATTTTCCTGATTCTCTTCCCCACGGTTGCGGAGGAGCAGGTCAGGGCCGCC ATGAGGGCAGGATC |
| 87 | TSHZ1 | TCGACCGCTACTATTATGAAAACAGCGACCAGCCCATTGACTTAACCAAGTCCAAGAACAAGCCGCTGGTGTCCAGCGTGGCTGATTCGG TGGCATCACCTCTGCGGGAGAGCGCACTCATGGACATCTCCGACATGGTGAAAAACCTCACAGGCCGCCTGACGCCCAAGTCCTCCACG CCCTCCACAGTTTCAGAGAAGTCCGATGCTGATGGCAGCAGCTTTGAGGAGGC |
| 88 | CTDP1 | TGTGCCGTCGCACACAGACGCCCTCAACGTCGGAGAGCTGTGAGCGGGCCGTGCTCTTGGGATGGGAGCCCCCGGGAGAGCTGCCC GCCAACACCACTCCGACGTGATCCATGCTGGACATAAAGTGCTCTTCCCTCCGCTAGTCATCGGCCGAGCGGGCCCCTCGCTCCTGGGT GTAAGTTCTTTCTGTGCGTCCTTCTCCCATCTCCGTGCAGTTCAG |
| 89 | KCNG2 | CCATGCGCCGCTGCGCGCGCGAGTTCGGGCTGCTGCTGCTGTTCCTCTGCGTGGCCATGGCGCTCTTCGCGCCACTGGTGCACCTGGC CGAGCGCGAGCTGGGCGCGCGCCGCGACTTCTCCAGCGTGCCCGCCAGCTATTGGTGGGCCGTCATCTCCATGACCACCGTGGGCTAC GGCGACATGGTCCCGCGCAGCCTGCCCGGGCAGGTGGTGGCGCTCAGCAGCATCCTCAGCGGCATCCTGCTCATGGCCTTCCCGGTCA CCTCCATCTTCCACACCTTTTCGCGCTCCTACTCCGAGCTCAAGGAGCAGCAGCAGCGCGCGGCCAGCCCCGAGCCGGCCCTGCAGGA GGACAGCACGCACTCGGCCACAGCCACCGAGGACAGCTCGCAGGGCCCCGACAGCGCGGGCCTGGCCGACGACTCCGCGGATGCGCT GTGGGTGCGGGCAGGGCGCTGACGCCTGCGCCGCCCAC |

TABLE 4B

| SEQ ID NO | GENE NAME | SEQUENCE |
|---|---|---|
| 90 | TFAP2E | GTCCTAACATCCCAGGTGCGCGGCGCGTCTGGCTCCCTGGAGCGGGGCGGGACGGGCGGCCGGCGGACTCACGTGCACAACCCGCGGGA CGGGCCACGCGGACTCACGTGCACAACCGCGGACCCCAGCGCCCAGCGCCCAGCGGACCCAGCCGGCACCCCAGCCCAGCGGAC CCCAGCGCCAGCGGGACCCCAGCGCCCAGCGCCCAGCGCCCAGCGCCCAGCCCCTGACGCGCCCAGCGCCCAGCGGTCTGTGCCCAGTGAGCGAG TGAGCGCTGGCGACCTGGCGACAGTTGGATCCGGAGCTCGCCTGAGGCCCCTGAGGCGCGACCTAGACGTGCAAGTTACAGCCCGGCAGCAGCAGTGCGCGCG AAGGGGCAGGAGTGCGGGCACTTCCTTGCCTCCCGAGGTCGTCGACCCAGGGAAAGCGTGGGCGTCGACCCAGCGCAGCAGTGCGGCGCG AGGCAGGTGGGATTCGGGCTTGCCCTGCCGCCCTCGGCGCCTCCGGGAGTGCGGTACTGAGGCCTGCCGCCAGCCTGCCTCGGGCGGACGGCGTGGAATTAGCGCCCTCCGACGGCACGAGGAACT CACTGCGGGATTCGGGCTTGCCCAGCCAGCCTCCGCCAGTGCCTCCGCAGGGCTCCCGCCAGGGCCTGCCTCGTCGGGCCCTGCCTCGGCGCCTCCCCGGCCCCTTTCAACCTTGGCCCTCCGCGGT CCTGTCTCCTGAAGCGTCGACCTTCGGGATCCTACACCCCCCAGACGCGGCTCCCCAGAAGCGGCCCTGCGCGGCTTCGACTTCGGGCAAGCCCCCAGACGCGCTCCCCCGCCCCAGAAGCGGCCCTCGCATCGCCAGTGCCATCCGGTATTGGGCAGGAAGTCCCGGAGCGTCCGCTCGCCGAAAGCGG TTGGCCACCTGAAGCGTCGACGCTCAGCCCTGCAATCGGGATCCTCGGGATGGCCCTTGGCTCGCAGCACCCAGCCATCGCCCAGCAGCCCCCAGCTTCCCGCAGCCATCGCCCAGCAGGTTCCGGAAAGCTTCGCGGCTTCGACTTGGTGC GAAAGGGGCAGGCAGCTGCAGCCTTCGACCCCCAGAGGCGGCCCACACTTCGGGTCCGATCCCATGCCAGTTGCAATCCCAGTGTGAAAAAGCTTGCATCCGCCAGTGCCAGTGCCCGTATTGGGCAGGAAATGCAGGGGCTGA GCCAGGCGGAAGCCCCTAGGAGTATAAGGGAGCGGAGCTTAACCAGAAGCGGAGCTTAACAGGAATATTTTCCAGCAGTGA AGCAGGACTGGTGGGAGACGGAGCTTAACAGGAATATTTTCCAGCAGTGA |
| 91 | LRRC8D | CACCTTCCCCAGGTAATTATTTTCTGGGGGTAGGGTGGGGTTGGGAGGGTGAAGAAAGAAAAAGAAGGCCGATCACACTGG GCACCGGCGGAGAAGCGTGGAGTCCATTGATCTAGGTACTGTGGGGAGGAGAACCCGAGCAGCAGTGCAAACGGAAGGCTGTG AGCGAGCCGGCCGGCTGCAGCAGGGCGTGCCACCAGGAGCTCCGGTGCCGGGGGCGTGCCGGCGACCCCCGGCGCCGCCCACCACCGGG CAGCCGGTGGCTGCGCGGGGTCGCCACGCCAGGAGGCGCTGGGTGCCCACCATGGCAGTTGCTCTTTCGCCGTGGTTTCTCCCCCTGTGTTTCAAACAGGAAGTGCAC CCCGCCGCCCCTGCACTCCTTCTCCCCGCCGCCGACTTGACTTGCTAGCTCTTCGCCGTGGTTCGCCGAGCTCGCCCAAGCCG GGCTGTCTATAACGTGCTGCCGGGTCTCAGGATGCAGGAGTGAAGTCTCCTGTCGCCGTGGTTCGCCAGCCTCGCGCAGCGGGCCTCGGAA CGTCCCCAGAGAGCGCCCTGAGAGAACAGGGTTGGCCGCTGGTCGATCTGCATTCCAGCTCTGTGCTCAGCCTGCTGCCCACCACTGGCTCTC GTTGCGGCACCGGAGCACTGCTAGTGTCGAACAAACTCTGGCTGCTCCCGCCCCCTGACAGCCTGCCCCCGGCTGCGGGCCCCAGAACTGGGCGGTGCAGTGCTCGGGCTGCGGGCCAGTGCCTCGGGCTGCGGGCCAGTGCCTGCCGAGCCGCTGCG ACCCCGGGGTCTCTGCCAAACTCTGGCTGCTCCAGGCTGGCACTGCCCGGCGATGCCCAGCTGCCAGTGCGCGGCTGCGGGGAGTCCTGCCGAGCCGCCGG AGAGACTTCCACTAGGGCCGCTTTTTCAGCGGCTTTCTGTCGGAGCTCGACGGAGCTCCAGTGCCGGAGTCCTGGAGTCCGTCGAGACGGTTCTATCC TGCCCCTCTCCACC |
| 92 | TBX15 | CTCTTCCCAAGTTACGCCACCGGTCGAGGACGGCCAGGAGACCCCGAGTGCAGAGAACTCAAACCGGCAGCGAAGTCGTCCTAGCC AAGCTGAAAAACGTCTCGGATTTCGCGGACAGCGGCCTAGACACAGCCGATCTTCCAGTCCTAGTGCCCTGGTCGAGACGGTTCTATCC TTTTGCAAAGAAGCCGGAAA |
| 93 | C1orf51 | TCTCGGTTGCAATCCCCACCCTCCTACCCAGCAGGGCAGGAGGCACCAACTTGGAGGAGGAAAGGGTGGGGAGGTGAAACAGAGAC CGGAGAGTCACGAGGGCTGGGCCGCCGAGAGCAGGAGGAGAATATACCGTGTCACACACTCCATTCTCTCACACACGTTGCAGACACAAATC ACTGACGGTTCCACGTGCTCCAGTGACGACAGCACAACCAATCTCGAACCCAACCGGCAGTTACTCCCGAGACGGAACCGGGGGTCCC ACGTCCCTGCCTCAGTAGCACAATCTCGAACCTCTGGGCCATCACAACCATCCATTAAGGCCACGGCTC CGCCCTTTTCCTCCCCCCTCTTTTCCACTCTTTTCCA |
| 94 | chr1: 179553900- 179554600 | CTGCCAGAGATGTGTCTGTCTTGCGCCCAGCATGCAGTCGCCGGCTGCCGCTGCACTCCCCGGGCGGCCACGGTTCGGCCCC GCGCTTTCTACGTGTTGGGGGATGCATGGAGCCTTGAGATCCGTAGTTGGCCCCTAACCTCTCCTGCACGCGCCTGCTGTT CCTCCTCTGCACGCTCTCTCCGTTCCTTTGCCCAGCGCCTCAGGGCAGCAATCCCGCTGCTGGCTGGGAATTGTCCTGGTGGGGAAACGCCCCAGCAGTGAGGGGACTCACGC GTGAGTGTTGCCCCCTTTGCCACGCTCTCTCCCAGGCAGGATGCAGGGTTTCAGCGCTCGAGCCGCTCGGGTTTGTGCGGGATCGGTGGGGCCTTGGGGCCTTGGCCGCCCTTC CATGCCTCCGGAGCGGAGCCAGGCTCCGAGAAGGGAGCAGGCTCGGGAAGTTTTGTGCGGGATCGGTGGGGCTCTGGGGACTCGGGACTCGTGAGGGTGGACTGGGTGTCT GTGCCTGAGCTTGCGGGTCAGAGCGAGTAGGGTGGGTCCTTTCGGGACAGGTAGGGTGGGATTGGGAATTGGGAGACTGGGAATTGGGAGACTGGGAATTGGGAATTGGGAGACTGGGAATTGGGAGACTGGGAGTCAAGTAGGGG ATGGAGTTGCGGTCAGAGCGAGTAGGGTGGGTCCTTTCGGGACAGGTAGGGTGGGATTGGGAATTGGGAGACTGGGAGTCGAAGTAGGGG |

TABLE 4B-continued

| SEQ ID NO | GENE NAME | SEQUENCE |
|---|---|---|
| 95 | ZFP36L2 | AGGGGTGTCCTCCAAACATCTCTGAACCGCCTTCCCTTCCTCCTCACTGGCCGCCCCTCTTGCCTCAGTCGTCGGAGATGAGAGGCGGCTGA<br>AGATTGGCAGGCCGGCCGCCAGGTCGAGGCTGCAGGGAGACTCAGAGCCCGCTGAGGCTGCCGGAGCTCAGGGAGCCGCTTAGGTAGCTGTC<br>GCGGTCCCGACAGCGAGTCCGGG |
| 96 | SIX2 | TCTGACTCTCGGGCTGGAGCAGCCGAGACAGCGCTCCCCAGCGGGACTACACAGAATCCGGGTGTCGGCCTGGGGTGTGCGGCCCTGGATTGGCA<br>GTGGTGAGTCTTCTGAGCTCAAACAGCTACTAGGAATGACAGAGTTGCACAGATGCCTTTGTCGCCGCGGGGGCGGCTTCCTCAAGCGTCCTGGGT<br>CCCAGGCCTCTGTCTCCAGCCGCCCAGGCCCGGCTCAGCAGCCGCCGACAGTCGCACGCTGCCCCTGAC<br>CTCAGGGCCCAGAGCCTCGCATTACCCGAGCAGTGCCGTTGGTTACTCTCCTGGAAAGCCGCAGTCCCAGCCCCCCGGGGCAAGTGGGAGTTGCT<br>GCACTGCCGGTCTTTGGAGGCCTAGGTCGCCCAGAGTAGGCGGAGCGCTGTATCCCTCCTGGAGCCTGCGGTGAGGTCGGTACCCA<br>GTATCTAGGGAGGGAGGACGCGCTTGGTGCAGGGTAGGCTGGGCCTGGGCAGTGCTTTGATTGAGTCTCATGTCCGCCTTTGTGCCGG<br>CCTCTCCGATTTGTGGGGCTCCTTCCAAGAAGAGTCTTGGTGCTCTCTAGGGCAGCTAGGGTGCCTCAGCCGGAGGCGGCCGGCCTTCTTCG<br>GACCTATCCCAGAGGTGTAACGGACGTGAACACCCCATGGAGGGGCAACCAATCTGCCTCTGCACTCGATTCATCCCTGCAACCCAGGAGAA<br>CAGAGATTGTGGGGACAAACGGCGTGAAGACAGAGGCCGCCAAAAGAAGCTGCCAAAAGAAGATCGCTGGAACCCTTGACCCTGACACCTG<br>ACCATTTCCGAGTTTCCAGCCGCCAGGACCGCTCCGAGGCCGAGTTCCCCACCCCGGAGTCGCTCGGGAACCCTTGACCCTGACACCTG<br>GACGCGAGGTCTTCAGGACCGTCGGTAGCCTGGTTCCCGACACCAGGAGTTCCTTCCTTCTGCTCACCA<br>GCCCGGCCCGCCGAGCGCTCAGGAAGGAGCACCAACCCGCTGGGGGCTCAGGGTTCAGGCGGCCAGGAATGCAGAGGCTGATCCT<br>CCTCTAGCCCCGGCCATTCACTTAGGTGCGGAGCGCCTGAGGTTCAGCCTCCCGAGGTGTACGTCCGCTCGGCGTCATCGGGGTGTT<br>GGCTTCTCGGGCTCACCCCTTTCACACCTGTGTACTAAAGGGCTGCTACCCTGCCGAGGTGTACGTCCGCTCGGCGTCATCGGGGTGTT<br>TTTTCACCCTCTCGCGGTGCACGCTTTTCCTGCACCATCTTCAGTACACAGCCACTGGGTCTCCCTGCCCCTCCAGCCTTT<br>CCTAGGCAGCTTTGAGGGCCCAACTGCTCCTTCACAGACGACTGAAGTCTTACTGCTAGGATGGAACACGATGAAAAGGAAGGGCCAGTCAAAGTCCTC<br>TCCTCTTCCGTTTTTCTTGAGGCCAAATCCCAAGATGCTGCTCGCTGCTCCAAAACTGATTTCCAGCGAATAAGATAACCAAGATAACCAAGAACTGAG<br>TGTGGAGGCCAAATCCCAAGATGCTGCTCGCTGCTCCAAAACTGATTTCCAGCGAATAAGATAACCAAGAACTGAG<br>TAGACCTGCTCCCTCCTCCAGAGATCTCCAGCCAACTTTTCCCTGCTCAATGCGATGGACCACCAGCTGCCCCAGGCAGGCACCACCA<br>CTCCCTCAAGATACCATTTGGGGTAGGGATTGAGTCCTGAGAGGGGTCAGCGGGGCGCCCGGGGTGGGAGAGATTCTCTGCTCGGTCTTAGCC<br>GGACACACGGCGAGCTCCGCATATCTCCGATTTTATTTCTTCATGGGGTTTCACCTAAAGGGCCCTGGTCATGGACCCCTGTTGGGAACAAATGAAAGA<br>AGTCTGCCCTGCTAGGGCTGGATGTTGCAGTAGGCAGTAGGTTTAGCTTCCAAGAGAAGCATCAGAAAGAGTAGGTTGCAACAGTAGTGCCCTATGCTGGAT<br>TGTCTTGTAGCAAATGCTTTCACGGACTGCAGGAGAGAAGAGATTGGCACTTTCCCAGTCACTGGGTCACTTTAGGTGGCTGAACAAACTGGT<br>GACTTTCACGACTGCTACAGGGTGAGGGGTAGGGATTGGAGTCCTGAAGAGAGGTGACAGCCACTGGAGAATCCTATTCAGTGGGATGCGACA<br>GGGAGTGGCTGTAATCAACTGAGCAACATCGTGTGACAGTCTATTCACAGGTCAGGACAGCAGCTTGGTCTTCCCAGGTGAGGAACTGAGG<br>ACTGGCCTGACATAGATTGTGCAGTAGGTGAGTAGCTTCACCCCAAGAAGGGAAGAAAAGAGGGAGTTGCAACAAGTAGTGCCCCTATGCTGGGAT<br>TAAAATTTATTTATTTAAATATTTTTCTTGGGTTTAGCTTCACCCCAAGAGGAAGAAAAGAGGGAGTTGCAACAAGTAGTGCCCCTATGCTGGGAT<br>TCATTTTCCAGAGTAAAGCTCTGGCCATCCCTGACCTGAGCAGCTGGCTCTTGTTCTAGCAGTGCATGAGCAGCTGGTAGCTTAGCCAGGCACCAGTGTC<br>GGCTGAGATAGTGCCTGAGGGTGCATCCCTCAGCAGCTGGGTCTTGTTCTAGCAGTCGATGGCAGGAGCTGTAGCTTAGCCAGGCACCAGTGTC<br>AAGGCCTTGGGTTTCCAGCAATCCATGCTTCTGTGGAGAAGCATGATGTGTGTGGGACATGAGGAAGGTTCATTTGTGCAG<br>GTATCCCCATGTATATCAGTGTGCACAGTCTGTGTTCCCTGAGGTGTTGTGTGCTGTGAAAATGCGGAGGGTCTGTTGTCTAATGTGTGC<br>AGGGGTGAACATGTGTGTGACAGTCTGTGTGTTCCCTGAGGTGTTGTGTGCTGTGAAAATGCGGAGGGTCTGTTGTCTAATGTGTGC<br>GCCACATAGCAGGCTCTTAATAATCTTGAATTTAATTAATGTGATTGTATTGTGGAAGTGGTATGAAGCCTGTTTTCCT<br>GTGATTGTGAGACTGGAGAAATGGGGACAGGGACACCGGAGGGCGAGACAGGATACAGAGGCTACTGTTTTCCTCCCTAGAAGTAAGTACATA<br>GAAGAGTGGCCTCTGGCACCTCAAGTCCTCGTGTGCTAGCCTGTCAAGGTGGCTTCAGCGATCCATCACTTGAAT<br>CTTTTGAGACCTTCAGGACTTCTGAGGCAGTAGCCTGCCATTCAGCAGCCCTGTCAGCAGAAGCGCCCGCCATAGAACACAGAGCAGTTCC<br>CGGAGGACACATGGTGCACCCCAGGCAGCAGAGCTCCGTGCAGTCCGTCAGTGGTCCGGGCTCCTCCAGGGGCCAGCCAGGTGCAGGGCCAGTTTCCAGGCC<br>TGAAGGGACACATGGTGCACCCCAGGCAGCAGAGCTCCGTGCAGTCCGTCAGTCCAGCCCTCTGGGGTAGCCCTTGACCTTCCAGCC<br>TGCACAGATCCAAGCCGAGGTCCAAGCTCCAGCCAGGCTCCAACGCCCAAATTAGCTGCCTAGCCTGCGCCCGCTCTAATCTCAATTAGGAAGGAAT<br>CCTTGCGCTTAGAAGTCAAGCGAGACCTCGGGGCCACCAGAGCGCCACCAGAGCGCCCTATTCTGATTTTATCCGGTTTACCAGAAAATGTGAAAGGAAAAGCCCGAGGACGGGTCA<br>AGTGCTCTAGGAACTCGGGGCCACCAGAGGGCGGCCACGAGCGCGTCTGCTGTGCCCTGGTCGCTGAGGGACCGGGTCA<br>GATACCTACCGCCACTGCACTGCAGGCCCGAGAAGGGAAGGCTCAACTTCTTCCTCCGGAGTCCTGCCCACTACGGATCTGCTGGATTCA<br>GATCGTCGCGTTTAAAGGGGGGCCCTGGCACTCCAGAGCTGCAGGTTAATTGATAGCCCGAAGCACGAAGCACTGAGGCGCCC<br>ATGCGCGGAGCCGGAGCCCCAGTCAGTCTGACCCTGTCTTTTCTCTCTGTCTTTTCTCCTCCCACCCCTCACTCCGGAAAGCAGGGC |

TABLE 4B-continued

| SEQ ID NO | GENE NAME | SEQUENCE |
|---|---|---|
|  |  | CGAGGTAGGGGCAGATAGATCACCAGACAGGCGGAGAAGGAGGGAGAGAGTACAGAGGACCAGGACACAGAATGCAAAAGACTGGCA GGTGAGAGAAGGGAGAAACAGAGGGAGAGAAAACAGACCAGGAGAGTGAGGGCGCCCGCCCCCCCTGAGTCCGATTTC CCTCCTTCCCTGACCCTTCACTGCAGCTTAAGTCTGGGGGTCTGAGCTCAGAAGCAGGTTGCGAGCTCGAAATCCACAACGCAGCACC GGGACTGGGCGCTCTGAGCTAAGTCTGGGGGTCTGAGCTGGACCCCAATTTCTTCCGCCGCAAATCCGCAGCGCATCGCGCCCAGCTTGGCATCTCCGAAGGCACGTACCCGCCCT AACCACCCCAAGGAGTACGGCGCCGACAGGAGTACTTCGCGGCCAGGAAACTTCTGCGGCCAGAAACTTCTTCCCGCAGCTTTGGCATCTCCGAAGGCACGTACCCGCCCT CGGCACAAGCTCTCTGCTCCACTTCGACCTCGAGGTGAGAAGAGGCTGGAGCAAGGAGGCTGTGCGCTGCTGGTGGAGGCA GCAGGCTGCCCCCCGCTTCACAGGGCGTGATTCTCCAGGAGAGTTTTTCAGCGAGTTTCAGTGCCCTTCACCTAGC GACTGACACAAGTCGTGTGTATAGGAAGGCGTCTGGCTGTTTCCGGCCCTGCACTCCCGCCCTGTGCATATAACCATTTATATATTTATGATTTCTAATT GTCGAGTCTTGGTTGAGGAAATCAGACAGACCAGCTGCACTCCGAAGAACATTCACATGAGGGCATTACGGGAGACGGCAAGTCGGCTCGGGGCGC TTATTATAAAATAAAGCAGAAATATTTCCCGAAGAACATTCACATGAGGGCATTACGGGAGACGGCAAGTCGCGCTCGGGGGCGC GCTCAGGGAGCGCTGTAGTCACAGTCCCGGAGGAAGAGCGCG |
| 97 | chr2: 137238500- 137240000 | TGGAACAAGTGTCAGAGAGTAAGCAAACGACTTTCTGAGCTGTGACTCTGCTCCTGACTCTGCCCACGTGCTCTCCGTGCTGTGCACTCCTG CCTTCACTTCGGGCTGACTCGGACTTCCACCTCTTTGCTGTTTCCGGCATGAGCTTCCCAGGAGCCTAAGGCGCTCTTCCCGCAACTCC GGTCCCGGGACCTGCAAATCCTTAAACAGAGCCCCAGGTAGGGGTTTTCCCAGACTCTGTGGGCGTGGGCTGACAGT CGCTGGGAGCCCCACGTATGCTGCTAGGGGATGTCCAGATAGAGATTTTCTTGTCTTTTTCTCCTAGTAACACCGAAGCCCTCTGCTGCCGGG CTCTCCCCCACGTATGCTGCTAGGGGTACTCCGGACCTTGCGGGACCATCCGGACCCATTGCGGCCACATCTCTTTCTCCCCCACTCTTTGTCTGGTGTGTACTGTGTCGCAGTGTGCG TGTTGGGCGCGGTTATCACAGGGCGTTATCACAGGGCGCTGGGAGTTTCCACCCCACTCTTTCTTCCCCCACTCTTCATGACCTTCATGAGCCGAGGCGCAAAG CGTCGACCCCTTCTCTGGGCTTGCGGGAGCCCAGAGTTGCGGGAGCCAGAGGAACTGAGGTCCAGGCAGAGGAAACTGAGGTCCAGGCAGAGAGTCCCGCGTGCTGCCCTTGGGAGC GAAGCTTCAAAGTTGCGGCAAACAGTTGCGCGCGCAAGCCGTGCCGGTCGTGCCGGTGGAGGCGCAGAGGCCGGAAGAGGGGCGGTGGGAACA GCTGCCGGGTAGGCGAGGCGCAAGGTGGTCGACTGCGTCGTCAGCAGAAGCCCAGAGCCTCCGAGCCGCATGCCAATGGCTGCGC AGAGGTGTACAGACAGATGCGTGGTCGAGGCACAGATCGTCGACTGCGTCGACTGCGTCTTCCTCTCCTCTCCAGACGCGGCGGCTTCTTCCGAGAGCAGGGTGAGTGCAAGACACGGGAGCCCC CTCCTCCTTCAGTGCTGAGAGCCCAGCGGCTCCAGAGTTACCGCGGCGCGCTTGCAGATGGTCTTTCCTCCAGACGCGGCGGCTTCTTCCGACAGACTGCGGAGTCCGGCCCGGA GCGCTCGGAGAAGCTCGGGGCTCAGCGCTCCAGAGGTTACGGCGGCGCTTGCAGATGGTCTTCTCCAGACGCGGCGGCTTCTTCCGACAGACTGCGGAGTCCGGCCCGGA GAGTCCGGGATGCCGGATCTCGGGGCTCAGCGCTCCAGAGGTTACGGCGGCGCCTTGCAGATGGTCTTCTCCAGACGCGGCGGCTTCTTCCGACAGCCTGCTGGCCGGCGCAG TTGCTCTTTTCCTCGCGGAAGCGTGCGGCTGCGCAGCCAGCCATCGCGCCCCTCGCCCCGGGGCGGGCGCCCTCCCCCTCAGTGGCCTGCGGGCTCCTTCCGACGGCCTCTGCT TGGGGCTCGTGCGGAAGCGTGGGCTGCGCCGGGACGTGGGCTGCCCCGGGACCGTGCCAGCCGCCAGCCGCCCTCAGGCGCCCCTCAGGCGCCGGGACGCCCAC |
| 98 | MAP1D | GTTATTATCCACGGGGTCCTAATTAAAGCTTGATTAAAAATGCCCTTCTTCTTCTAAAAATTACGAACTAGGCAACTTCATACATTTTGAATGG CGCAGTGTTCTTTCCTCTTCCACTGTTTAGTTGTAGTAATATGAGGACCATCAATGTAACAACACATCAAATTATCAACCTTGCAAGATGACAACATGAGCCTGTG GGGGAAGCACTTGAGGGGAGGAGAACTTCCTTCTTTTTTAATAATCAGCCGGAAACAATGTTTAACAAGAATCTGATGAGGTCACTGC AGTAATACAAAGGTGTTTGCTTTTCTTGCTTGTTGCTTGTTACAGCTCCGAAGCCCTGAATTTAAGTCTGGAGGATGCATGGACTGTGTCTCCTAG ACAATCAAAGGTGTTTGCTTTGCTTCTTGCTTGTTGCTTGTTACAGCTCCGAAGCCCGAAATTAATAAGGAAAGGAAAGATTGGTCGACAGTTCTCGAGCCACCGAGCCCGGCCGGA GCTTGCGTGCGCATCAAGCGGTGGGTGCCCTCTCTCCGGAGCCGACCCGGTTCGATCAACAGCAGTTCGAGCACCTGTCTGATCACGTCAGGGCGCGCGAG ATCCTGACCAAACTACCCCCATGAGGGCCTGAGGAGCCCGGTGCGTGGCTCCGGTAACCTGCGTGCCGTAACCTGCGTGCCTGATAGCGTTTGAAGACGCGGGGAGACTG GAGAACTTTAGAAGAACAGGGAAATGACGGGATCTGAACCTGCGTCCGCGGGGATCTGAACGCCCTGCGCGCGGCTTTGAAAAACAAATCCCTGC AAGAGCAACTGGGAACTCGGATCTGAACGCCCTGCGCGCGGCTTTGAAAAACAAATCCCTGC |
| 99 | WNT6 | TCCCTGCTGTGGGACCCCGAGGAGGAGGAACTGGTTCGCT |
| 100 | INPP5D | TCTCTCTCTCTCTCTTGGTTTCGTAATGAGGAAGTTCCGCAGCTCAGTTCCTTCCCTGAGCGCCTGAAACAGGAGTCA GTCAGTTAAGCTGGTGGCAGCAGCCGAGGCCCACCAGGCAACGGGCCCGCCAGTTGCCAGTGGAGGGCCTCCCGTCCGCCCCGGTGT GTGTGGGTCCTGGGGTCCTGCCGCCCGGCCAGGAGGCCCCACCATGGCCCGAGGAGTCCCAGGAGCCTTCCTGCCAGCCATCTCCGGCATCACCCGC TCCAAGGCCGAGGAGAGCTGCTTTCCAGACACAGGCAAGACGGAAGCTTCCTCCGTGCCAGCCAGTCCATCTCCGGCATCACGCCT CATGCGCTGTGAGTACAACTGCTCCCTCGCCGGCACAGATATGACAGAGGGGCACAGATATGACAGAGGGCTTAGAGGGGCCCAGCTTTGAGATGGGTTGTTCT TATGTCACAGGACAGAGTGATCTGACATGCACACTTCCCCGCCACCCTGTCAT |

TABLE 4B-continued

| SEQ ID NO | GENE NAME | SEQUENCE |
|---|---|---|
| 101 | chr2: 241211100- 241211600 | TGTCCTCGAAGAGAAGGGCCTGAGCAGCAGCAGAGAGGACCCCAGGCGACCTGTCCTGCCTGAGCCGGGCGGCCGACGACGACTGAGCACCTGATAT<br>GTCCCCGGCACTGCAGCCCCGCGCCTGAGCCTGCCAGCTGTCAGCCGTTCAGCCGTTCACGAGGCCCGGCTCTGTGCCAGGGCCC<br>CGACAGGGGCAGGAAGCAGATAGAGTCCCACAGACAGTGCCAAGCCCAGTGCCAAGCCCAGCTGAGGGGTACTTAAAAATAAGTTCTGTGATAAAATCAAA<br>CAGGGTGAAGGCTGAAACAGTTCATGAGGGCGCAAACAGTTCGTGAGGGCGCAAACAGATCGTGAGGGCGCAAACAGTTCGTGAGGGCCGCAAACAGTT<br>GCCAAACAGTTCGTGAGGCGCAAACAGTTCGTGAGGGCGCAAACAGATCGTGAGGGCGCAAACAGTTCGTGAGGGCCGCAAACAGTT<br>CGTGAGGGTGCAAACAGTTCGTGAGGGCGCAAACAGTTCGTGAGGGTGCAAACAGTT |
| 102 | WNT5A | AAATGAGACCTCTTGGGGAGACTGTCAACCCCAGGGTAAAACAAAAATTCTGATCAGAACTGAGTTTCCAAAGAAGGGGCTAAATGTTT<br>CCAACACTTTCGGGGCTTCAGGGAAGATGACTTGTAAGGACACTGAGAATCTTCCTGCGTGCCACGGAGGAGACTGGGGGCGTTTG<br>AGGGGCTCAGGCGACCAGGAGTGAGGTGAGAGGAGGGCGTTCCCGGCGTTCCAATCCAGAGCAGCTCAACGACGTGGCTCCC<br>TTTTCTATGTATCCCTCAAAGCCTTCGCGT |
| 103 | chr3: 138971600- 138972200 | TAGGCTCTAGTGACTGACTAGCAGTGGAGAGCTACTTGGGCTGTGTTTTCTTCCTGACCGTCAGGGATGGGCATCGGCTGGAACCAGAAG<br>CCGAGAGCTGGACCACGGCACAGGAGTAATTAAGAAATATAATGAATTGATGAGCCGGATGGGCCTAGAAATCCTGGGCGTCTACTTAAA<br>ACCAGAGATTCGCGTGCCAGGAATCCCGGCTCTGTGTGCCCAGCTCGTTGGGCGGTTCCGCGGTTCCACACTAGGA<br>AGGAGCCTTGAAGTCAGAAAGATGGGGCTCGTTACTCACTTTCTAGCCAGCCGGGGAAGGCGTGGGGACGTCGCAGGC<br>TCCTGCCAGCTCTGGGGTCGGGTGGCTCAATCCCTGCGCTAGGCATCCTCCCGATCCCAAAGCCTCGGGTTCGGGTTGAGGAAG<br>CCTGATTCTGACTCTTTGTGGCGGCCTTCGCCTTCCTCGGCATCCTCTCGGACCACAAGCCTCGGGGTGCGCCACTTGGGCGATGGGG<br>GAACGGGTGCCCAGGCCGTGAAAGGAGGCCTGAAAGGAGGCCTCAAGTTCTCCTTTGCTACA |
| 104 | ZIC4 | GAGGTTGCTGACTCAGGAGCCAGGAGTGAGAAACTCCTAGCTGCTAGCAGCCGTTGAGCCTAATTTATTTCTGGCTTTCTCCTCCCCTCCCCTCTC<br>CGTTTCCTATACTCCTCTTGTCCTCATCTTGTGCTTCTATTTCGTCTCTATTTCCCCAAAACGTCTACCTCACTTCGTCTCTTCCTTTCTCCTCCCCCTCTC<br>TTTCTCCCTATACTCCTCTTCCCATTTAGCCTTGCAGCGCCCTCCCTGTGGGAGGCCGTTGAGAGGTCTGGGCTCAAAACGCGCGAAACTCAAGGATCTGGC<br>CCTGACCCAGGGACGGATTAGGCGGAAGTGGTGACGGCCAAGAAGTGGTGACGGCCAAGAAGCTCGGGCGTGCTGGGCTCCAGAAGGTTTTCGCTTCGATC<br>CACAAGTCACACACCCAGCGGTGCTGGCCCAATACCCGCAGCTCCTACCCCTCTACGAGCCCTGGAAACAAGAGAGAGAAAAGGTTTTAAGGTGACTTCACTTTCA<br>TCCCTGGGCAAATCAGGGATCCTGGGGGATCCAGGGATCGGCGGCTCTCTCTGCTCCAAGCCTTCTGCCCTTCCTCTCTCCCTCCCAGCTTCCGTCAAGAGAAAGTGCACGCCGCGTTTCCC<br>GCTTCAGGTCTACTTGTTGCCTGCGGTGTGTGCAGGGCGTCTCAGGCGCGTGCAGGCGCGTCAGGCCGCTCAGTGCACCATGCCTTACAGTGCTTTAGCGCTTACAGATCTACAGAATGCATCGCCGGCTGCGGCTT<br>CTTCAGGTCTGAGGGGCTCTGAGGGGCGTTCAGGCCGTGCAGGCGCGTCAGGCGCGTCAGGCCGCTCAGTGCACTGCTTAGGGGTCTTACAGAATGCATCGCCGGCTGCGGCTT<br>GTCGGTTGGTTAAAAAAACTTAAGTTCTGGCTCAGTCGAGTGTGGCCAAAAGCCGAGGGTCGGGGTTGGGGGG |
| 105 | FGF12 | TACTGACCTGGTCTCCGCTCGGTTGGTCTCCGGCCTCTCCTTGCCGGCCGCTCCGGCCGCGTCAGAAGACGTGCCACTTTGCTGAACACCCCGAGGACTGCCTCGCACAGG<br>GAGCGCCTCTTTGCTCGGGGCTGGAGCGGCGTTGGAGGCCGACACTCGGGTCTGCGGGGCGCTCGCCTGCCGCTTCTGCCGAT<br>CAAGGAGCTGGCTATCGCCGAGGCCTGGCTGGCAGGCTATCGCCGAGGCCTGGCTGGCAGGGAGAGGGATCGGCGGCCGGCGATCAACTCAAGGATCTGATCGCCCGCCCGCTCTACTGCGTCCTCCGGCTTCTGCCGCTTCTGCCGAT<br>GGGCAGGGCAGGACAGCCTGGCCGCCAGGAAAGGCCAGTGCGGCGAAAGACAGTGCGGCCAGGGAAACTGCTGTAAAATTGAGGAGCTGCAGTATCAGAAACCC<br>GGGCTGGCTCACAAGGTTAGTCAAAGTTCGAAGTTCCCAGTGCGGCAAGCCCTCTTGCGAAGTAGAAGAGTTGTGCCCACCCAAGATGTGAAAATCAGATGTAAACTTCCCCAACCTCTGGCCGCCGGG<br>GGCGGGCCGGGGGCGTTCAGTCAACTGGTTAGTCAACTCGTTCGGGGTAGTGGGCAAGTGTTGCACCCCAAACTTGCACCCAAAATGCCGAAGGGGCA<br>GTGGGAGTTTAGTCAACTGGTTCGGGGTACCAAGTGGAAGGGGAAGAACATGCGGAAGCCATCAGAAAGCCGAGAATCGGGAGGGAGGCCCTCGTTGAGAGG<br>CGCAAGGCTTGTAAGGTGTCCAAAGTATACCTACACATAAAAAGTTCCTTTAGAAAACAGAGTCTGGACCCAGGCGGAGGAAGGCAGCAA<br>CGCCCCCGTAGAAAATACTAAAAGTGAATAAAAGTTCCTTTAGAAAACAGAGTCTGGACCCAGGCGGAGGAAGGCAGCAA<br>TTTAACTCCTCGCCCCCGTTCTGAAGATTAGGAGGTCCGTCTACCAGGTTCTACAGAATGCATCGCCGGCTGCGGCTT<br>TCCAGGGCCGGCCGGCCCAGTCGCGTGAGGGCCAACTCCCGCCAGCAGCGCGAAGTGGAGGCGGGTTACCCGGAGTCTGGGTAGGGCGGAGGGCGCG<br>AGGGAGGAGGGAGAGTCCTCAGGGAGGAGCGGGCGATCTGCGGGGTTGCGGGCTCCAAGAGTGGCGCTC<br>TTTCTTTCCCGTTGCTTTCCGGACCACAGACCGACCAGTTGTCTCTCCAGGTTGCTCTCTCAGAGGAGAATCCTAAATCTCAGTAGTTTAAATAA<br>GCCCCTCAAAAGCAGCGATGCCAGGAGGCGAGCGGAGCGCGCCAGGAAGGAGAGGCCGCGCTCGGCCATGGCGTCCACC<br>GGGGCCCCCGACACCGGCCGAGCTGGTTCTCCCAGGCTGTCCCCCTAGGCCTGCGCGCGGGCAGCGGAAGGAGGAAGGAAGGAGCGCGCCCTGGCGCGGGCTCGGG<br>ATCAGGTCATCGCCGCAAGGCCCGCTACTCACTTCAGTCCCCGTGCCCATCCCGCCGGAGGAGAAGTGACTCAGGCAGCAGATCAGATGGGGAT<br>TACCCGCCGCGCCAAGCCCGCGATCACTCAGTCCCCGTGCCCATCCCGCCGGAGGAGAAGTGACTCAGGCAGCAGATCAGATGGGGAT<br>GCGTTCCGCTCGGGTTCGGGGCGGGGGGCTTGCCTGCAGAGGTGCTGCTCGGCGGCTGGCTCAGGCAGCAGATCAGATGGGGAT |

TABLE 4B-continued

| SEQ ID NO | GENE NAME | SEQUENCE |
|---|---|---|
| 106 | GP5 | CTGGCGCCAGGGGCAGGCGGGGCGGGGCCCCTAGGCCTCTCTGGGCTACCTCGCAGGCAGCCAGGGGCAGCCGAGGGCGCTTGGGCC<br>GGAGGCGGAATCAGGGGCCGGGGCCCCAGAGGCAGGTGCAGGCGGCTGCCAACTCGCCCAACTTGCTGCCGGGTGGCCGCTCAGAGC<br>CGCGGGCTTGCGGGGCGCCCCCGCGCCGCCCCTCCCAGCCCGGCCGCCTCCCCAGCCCGGAGGGGGCGCTCAGGGTGGAGTCCATTCATGGG<br>CTGAGGCTCTGGGCGCCGCGCGAGCCGCGCCGCCTCCGGCTGGCTCA<br>GGGGGACACAGAGGAGGGGTTGCGGCCTGTGAGAATGAAGAGCACAGAGCGAGGAGGGGAGGAGGAGGAAGGAAGGCGTGG<br>CAGTGAGGAGAAGAAGAAGAAGAGGAGGAGGAGGAAGACAGCAGCAGGGCTGGATTCCCCTCCGAGCCAC<br>AATCTGGTCAGGTTCTAAGTAATTAGAAGATTTTCCATTGGTTTACCCAAGGGCTCTCTCTGATTAATTTTCGAAAGAGTTGGCCAATTTTA<br>ATCATAGCAAACACGATGATCACGGTATCATGGCCTGAACAGCTAAAGCAGAAAATAAAACCCCAGAACGGACTATGATCTTGACCTTT<br>GCCCGTGGTCACCGGCTCGGGCCTGGCCCAGGGTTCTGAGCTGTTGGAGCCAAGGCTGGGTGGACAGGGCTTCCGAGGAGCTGTCC<br>GCAGCGGGGCGGGAGGGCGGCCACCCGTGGGGCTCTTCCCCACAGGAGCCTGGGTGTGCCGCAGAGCCCTAGTGTGCGCAGACCCAGGAAGGGTCCCAGGCCACAG<br>CCCAGGGCCTGCGCACCCGTGGGGGCTCTTCCCCACAGGACCTCCGTCAGCCGGGCAGACCCCAGCGGGCCAGGGGTCTCAGCTGGTT<br>TCGCAGGCGCCAGGAGTTGTGCCCCAACAGGACCTCCGTCAGCCGGGCAGACCCCAGCGCGGCCAGGGGTCTCAGCTGGTT<br>GTGGTCGAGCTGGACGCTCTCCAGGCTGCTCAGATTGCCGAAGAGGGCACGGCGCGTGTTGCGGCGCAGGGACACC |
| 107 | MSX1 | GCCCCGGTGCACCGCGGTCCAGCCGGCCCAACTCGAGCTAGAAGCCCAGTGCCTGAGTTGCAGTCTTGGGTCCTTTA<br>GAAACCTGGAGATGTGCTAAAATTCAGATGCCGGTATTCCCGAACTTCCCCAGGCTCAGCATATCTCGGCGGCTGTGACAGATGGG<br>AGGCTACCAATCGCTCCGCCGTCCCAGCCCAGACCCCCAGACCCCGCAGAGCGTCTTCCGCGACGTTCTCCGGATAATAAAGTTCCCGCTCTAATTCAT<br>TTTCCCTAATCTGACGCCCTAATCTACAGCTTTTATTCGCCAGTTAAAAGTTCGGGAATTCGCTGTCCCTCCGCGCTCGGATAATTA<br>CCCCTAAATGGCCACGGCAGCCCTGGCCTGGCCCTGGTGTTCCTGGAGATTAGAACCCCAGTCAGGGCCAGTGGAGGCGCCAATCACC<br>TCCGCTCACTCCTGAGAGCCGCTGGGCCTGGACTGGCGACCCCGCAGGCGCAGAAATGGCCAAGCCCGACCC<br>CGCTTCAGGC |
| 108 | NKX3-2 | AGGGTGCCTCTGTTCAATTAGAAAAGGCGCTCAGGGCAGACTCAGCCAGCTGCCAGGGACAAGTCTCGGCTAACGGGAGCT<br>GGAGCTGGGTTTCACCTCCCAGGTGCCTCTCAGCCCAAGGCTGGGTCACTGGTGCCCAGGTGGAGAGCGCCAGCCTGGGAG<br>AGCGCGGAGAATCACTCGCTGCTCAGCCCAACAGTCTTAGGAGCAGGCAGTCTCACTGGGTGCCAGGTGGAGAGCGCCCAGCCTGGGAG<br>GCAGTAGTACGGGTAATAGTAGGAGGGAGAGAGGAGCCAGCGGCAGAGCGAGGGTGCCGCCAGACTTCGCCGCCACTTGCTCTCGGTCGT<br>CGCGCACCAGCACCTTTACGCCCACCTTCTTGCGCGCCTCTGTCGGCGCGCCCAGCGCAGGTCGGCTCGCCATCGCCGCCAGCTTGCCGGCGATCCTGGGCCA<br>CGACGGTTCTGAACCAGATTTCACCTGCTCGAAGACCTGCCAGCTGGGAGCTTCAGCGAGCTTCAGCGGGACTTCTTGCCGCTGGGCGCCGC<br>CTGGTGGTTAAAAGGCGGCCGCTCCCAGCTCAGACGCGCTTCCCGGACCGCTGCCGTGCAGGACCTGTCCGTCGCCAGCTTCAGACGCGCTTCCACAGCCTGGCGCCGACAGCGTGCACCTCGCCGCCTCACACCGCCCCGAGGAGCTTCAGCGAGCTGTCCACCTTCACAGACGGGTCCAAACACCTGCGTCTCCCGCCGTCCTTGGCCGTCCTGTCGCTGGGACCCGGCGGACCGTCCGCCCACGCCACCCCGTGCAGGAACAAGAGATGTCAGCGCCACAG<br>ACGAGGTGAGGCCCGGGCCTCAACTGCAGGGGGTCACGCGGAGTGGGCCGGAAATACACTTTGATCCACTCAAGCGAGCGGAGTGCTGG<br>GAGGCCTGGGCCCTGGGAGACCAGTCTTAGACTCTTGCCCACTGGGTATCCCATCTAGGCCTCTTCTTGGGGAGGGGCGGCAGACTCAGC<br>CGCTGTGTCAACCGTGTTCACGACCAGCTCCGCAGTCATTGGGATTCTAGACTGCATTTCGCTGGTTCACGCGCCTCTCCAC<br>ATCCGCGAAGCCTCCCCGCCTCACGCGCGCGTCCTCCGCGCCTGGACACCTGTCTGTGCAGGTAAGGGAAGTGGAGGCGGATCCTGGGCCA<br>ACTTAGTTCACACACCACAGCTTTCACCTGCAGCGGGGTGGCCCCTGGGATTGCTGTGAGAGACATGCTGTGAGAGACACCTGATCCGACCGCCCTTCC<br>AAGGTAGAGTAAAGAGGGAGGGTTGCCCCTGAGCCCTGCCCCTGGGCCATCGAGTTTTTGGACCCCAACTAGGCAGGCAGGCCGAGCTTCTCGTTCGTACCCGCCTTCCA<br>GACTGGAGTAAAGAGGGAGGGTTGCCCCTGAGCCCGGTCGGCAGCCCGAGCCCAACTAGGCAGGCAGGCAGCCCGGGTCTTTCA<br>GAAGAACTCCAGACAAAAGTTCCAGCGGGTCTGAGAAAGTGTACCCCAACTAGGGCAGGCACCCCGGGTCTTCCA<br>GACCACAGACAGGACAGCCCCGGGTCTGAGAAAGCCAAACCAGCCCTTTCCCAGGGCTTTTGCCAGGGTCTGCCCAAGAACTAATAGACACCAATCGGGATCTTCGGCTAG<br>GGCTGCTCTCCCAGACTCGGGTCTGAGAAAGCCAAACCAGCCCTTTCCCCGGGGGGCTTGAGATGGTGCACCTGGCCCACTCG<br>GAGTGTTCTTCACCACCTATCCACCTACTGTGGGGCTTGAGATTTGGGATTTGGGATTTGGCCAGCAGAAAGCACTGGCCGACGAACTC<br>CTACCTGAGCTCTGAACCCCCACTTTCCCTTCCCTGATTTGGGATTTGGGACAGCAGCAGAAAGCACTGGCCGACGAACTC<br>AAAAACTCCCGAACGCAAGGGCAGCCGGTTCTCCAACCAGTCTAATGCACATTGGCCAGATGTCTCAGCCCCTCACCCCAGGACTA<br>GGGCTCTGAGGAGCTACTCCGGTCTCTCGCGGGCT |

TABLE 4B-continued

| SEQ ID NO | GENE NAME | SEQUENCE |
|---|---|---|
| 109 | chr4: 111752000- 111753000 | GAGAAGGGATGTGGCGGGGGGCTTCTCCTCCGGCCCTGGACTCCCTGGGTGACTAGAAAAGGGCAAAGAAGTGGTCACATCTGTGGGCCAG ACTGGTGCGCGATCTTTGGAGGCGCAGCAAGCCAGGCCCAGACCGCCAGACGGGCTGAGCCAGAGCCCCCAAGCAGGAGGCCCGCCCCGGA GCAGCGGCCGTGCGGCTGCCAGGCCAGGCAGCCTTAGGGCGCTCTGCCCCAGCTGACCCCCGGCGGTGGTCGAGCT CGAGCGTGTGGGCTGCGATGCCCTGCCTCGAGACTTCGGGCGCTGAGGATGCGGGCGGAAGTGGGGCTGCGGCGCAGCTGCAGATTAGA TTCCTTTTTTTTTTCCCTAGTGCCTTCTGCAAACTTCAGGTAGGGACAGACAGGCGTAAGGAGGACAGGCAGGGTCTTACCACCGCCCTTCCCATGTCATT GGCCAAAAACTGAACATTAAGATAAAAGCCGCTGTTTCAGTCAATGGAAAAAGCCGTAGGGCGAGGTTGTACCCAAAACCGGTTTAGACGGCC AATGAAGTTCTAGGAGAAAAGCCGTCTCAGGTGAGCGGCTTCTTAAGGGATGGCTGCGTGTAC CCACGGAATTCATGGGTCCAAAAGGTCCTGGTCACCTGTCGCCGGGAAGCTGTAGCCCAGAGCTGCAGCATTGCCAAGAGATTCATCTTTT CAGAGGAAGGAGGATCCGGAGCGGGAGAACTTGCGGGAGAAATAACAGAATAAACAGAACAGCGCCTCATCAGATAAGAACGTCTCCTTGATGTCAAGAGGTAGCT GGAGAAACTGACGTCA |
| 110 | SFRP2 | CAGGTCAGGCAGAACTTCTGCCTTCCCCTTCTGCCCCTCTGCTGCAGGAGGATGCTGCGCAGGGCGGGGATCTCCTGGGA GCGTCTCAGCCCCAGCAGGGAGGTGGGAACAGAAGGCTTACCTTCCTCCGGTGGCCAGGAGGTGGTCGCTGCTAGCGAGGG GGATGCAAAGGTCCTTGTCCTTGGGGGAAACGTGCCACTCAACGATGTCGGATGGTCTCGGGATCAGGCCAAGGCCGAACGCGGGGCGCA GCGGTCCTTCACCTGCACGCAGAGCGAGTGGCATGGCTCGATGGTCGGATTCCAAGCGCCGGATCCATCGAGGCAGAGGGGCGAAGAGCGAGCACA GGAACTTCTTGGTGTCCGGTGGCACTGCTGCTGCTTCATGACCAGCGGATCCAAGCGCGCTGCTCCAGCACCTGCTCCTTCATGGTCTCGTGGC CCAGCAGTTGGGCGCACCATGTTCTGTATTCGATGCCGTGGCACAGCTGCAGGTTTGGCAGTGTGTGTGCCCAGAGTGTGCCGCTGT AGGAGAAGTCGGGCTGGGCAAGAGAAGAGCCCGACCGTTCAGGTGAGCTGCGAGGCCGAGGGCAGCGAGGTTCGAGC CAGGGCCCTGCAGCATCGTGGGCGCGACCGTCGGGCCGACTCCGGGGAAAAGCTGGCACGTCCCGGGGGCCCTCCCAGAAAGGCGGGACAC TGTTCCCGGGCCCGCTCTCTTCCTGCTGGGTGCGACTCGGGGCCCCCGGGTTCCGGGCGAGAAGCGGAAGGTCAGCAGATGAGCCGTTGCTGG GGCACAGCCAGAGTTTCTTGGCCTTTTGCTTGGCCTTTGCGTTTGCGTTGAGAATGCCCCTCACGCGCTCTGAGGGGTGGGGGGAGCAAGGAGGAGCAATGAAGGGTAATCGAGGAGG GCTGGTCACTACTTTCTGCCTCCGCCCCTCCAGGATCTTTCTTAAACAACAACAAGAGAAGCTTGGCCGCTGCGCCCCCACAGTGAGCGAGCAGGGCGCG GCGCGGGGAGTTGGGGCCAGCGCCACACCGGGCCCACCAGTTGGCCGGGAACCGCCCTAGCCCGCTGCCG CCGGGGGCCCCCGGGCTTGTTTGCCCCAGTCGAAGTTTCTGCGAAGTTCTGCCCGCAGTCCAGCCAGTTGGGTTCCCAGCCATGAGTG |
| 111 | chr4: 174664300- 174664800 | TGCGATCATTAAAATCAGTTCTTCCCTCTGTCCTGAGGGTAGGGCGGCAGATTTATTACTTCTCTTTTCCTGATAGCAGAACTGAGG CGGGTGTGGAGGAGCCAGGAGCTCACTTCCTTCACTTCCTTGATTTGAAGCCTCAGGGCCACCGGCCTCAGTCCTGTT ACGTGGGCGACTTGCGAGGTTTCCAGGAGCTCATTCCGGACAGGCGTGTCTAGTCATGCTCATCATCCAGGTAACTGGGCTCTCAGAGTCC GACCTCCATCGTCGGGAGCGAGTGGTTCAGATGGTTCAGATGGTTCAGAGGGTCGTCTTTGGGAACCTGCTCGCTTCTCCCCCGGCTCTTCCAGGTTTACCCGAGCCACAGCCCGGAGCTTCAGACA TGCTGCGGCGGCCCAGGCGCAGAGAGGAGGGTGGGGGCATTGCCCTTCTGCA |
| 112 | chr4: 174676300- 174676800 | GGGCTTGGGCGCCCAGGCTTCCCCTGGACTTCCGCAGTCCCCCATTCCCCCATTCCAGAACCTGCCGAGCCCTGCTGCGATCTGGGACCCGC CTTCACCGTTTCCAATCCAGCGGTTAGCCCGTTAGCGGCCGGTTAGCCCACCTTGGTCCACTTTGGTCCTTGAGAAATGCCTAGGTTGGTGATCGA CCCTCCCCGGCAAAGACGGATTCTCCCCCCAGCCATCTCCTTTTCGTCGGGAGTCAGGGGGAGGCTAGGAGCTGTTGGCCCCCGGGTCTTCCCGAGATA CCCCCGGCGGCCCGGGAGTTGCCCGCCCGTGCCCCAGGCCCCGACGGCCCCCTACCCACGGGTTGCCTTCCGGGGGTGCCTTCGTGCTGTAGTCGGCGTGGCG CTGTGAGCTAGGCAGAACAGCGAACCCGGCACGTTACGCTATTA |
| 113 | SORBS2 | TTCTGGGCCTGATGGGGTGCGAGCGGGAGCCCGGCGGAGTGGAGTGCCCAGGCTCTGAGCCTGCTGAGCAAGCTGCACCTGCCACTCGC CGGGCATGAAGAAAGGGTAAGGAAGGAAGGAAGAAGAGCTTCACCCGGGTGGGGAGACAGAGCCGGGGCGCCGAGCTTGGTGTGGGGCCACTC CGGGGCCGAGGGGAGGGCTACCAGTGACTTCTCCGAGTCGGAGCTAGAAAGAGGCTTCCGCCAGGTTCCCTTGAACAGGTGTCG GAGTTGTTGGGAGAGGGGCTGCAAGAAGAGAGGGTGCAGAAAACTGGTTCATTAGATGAGGCTCTGGGCCGAACCCGAGGAGACCCCT |

TABLE 4B-continued

| SEQ ID NO | GENE NAME | SEQUENCE |
|---|---|---|
| 114 | chr5: 42986900- 42988200 | GGCAGCGGCGCTGTGCCTGCTGTTAGGCCGGAGGGGAGAGGCCTTCCGACGACGGAAGTGTCCTTAGGACCCAGACGCCTCGGGAGCG ATCCGGCCGCTGCGAAGCCGTGATGGCGGAGGGGAAGGGGAGGGAGCCTGCTGCTGGGGTAAAATCCCATCTTGGTTTCCTCG GTTCTTCACAATACCGTGATGGCGGAGGGGAAGGGGAGGGAGCCCTGGGGTAAAATCCCATCTTGGTTTCCTCG TGTCACAGAAGCCCAGCAGCCAGCACCGACTGGGTTCTGGAGGCCGAGCCGCAGTCCGTCCGTGCGGCGCAGTCCGTGCGGCGGCTGGGAAGAGAAGGCG CCCGGGCAGCTCCCCTGCCACCGGCCCGAGGAGGGGAATACCCTCACTCTGATCCCGGTCTCGAATCTCCAGGCGCAACT GGGGCAACTCAGGGGCAGCTGCGACCGGAATCCCTCACTCTGCAACCTGGGTGCTGCGGCACTGAGGAGCCGCAGACCAAC GAGCGGTTGCCCGGACCGAGAGACTTCGGCTGCGCGAAATGTGTGCCGGAGCTGCGCAGCCGCAGCCGGGGGTTGTCAAGGA CAACATTCGTTTTGACCGACAGCAGAAAAACCATCGACTCTGAGAAAAAGAGAGGTTCGGCCACGCACCGTGACACCG ACGCAAGTGCTGTGGCAGAAAAACCAGCCAATGCGAAAACCAGGTGCTGCGACCGTGACACCG GCACTAGAGGGTCTCGATGCGAGAACCGCGGCCACTGGTCCTGTAGCAGAAAACGCTCTGGTGCGCCAT CCCGGAGAAAGCGCGGATCAGAAACAAGCGACTTCGATGCAGGGAACCCAGCCACTGCCACTGCAGCATCCAGCTCCCGCAGGCTGTGTGCC AGCGAAACACTCCAGTTTGACGGCAGCTGGGCTCTGCTAGAAACTTTTAGTCTCTCCTTCACCGCTATCCTACCCACACAGACATGCCTTT ACCCAGCCTCAGCGGTGCTGAGACCCAGCAGCGGTACGGGTTGAGAGAACGCCGGACTCAGTGAAAC CAGCCTTGCCTCCAGGGCGGATTCCGCCGGACACTCACAAGTGTGTGGCACGAGTTGCCGCCAGAGGTACGGTTGAAGGAACCTTGGCTTCCCAGCAAATAGA TTGTGGAGTGGGGGGGACACTCACAAGTTTGGCGCAAAGAATGTTGCGCCAGAGAGCATCCGCTGTCGCTGACAAGGAGTAGCAATGGCAAT GCGCTGTCTGCAAAAAAAAAAACCGGCCACCCGGCCTGCCACCCGGACACTCACAAGTTTGGCGCAAAGAATGTTGCGCCAGAGAGCATCCGCTGTCGCTGACAAGGAGTAGCAATGGCAAT GAGAAACCCGCGCCACCCGGCCTGCCACCCGGACACTCACAAGTTTGGCGCAAAGAATGTTGCGCCAGAGAGCATCCGCTGTCGCTGACAAGGAGTAGCAATGGCAAT |
| 115 | chr5: 72712000- 72714100 | CAAACGTCTGAGAGACAAAAAGACACCAACACCACCAAGAAGACACCACTGCCTCCAGCTCTTCACTCCGCTGACCTGACCTTCACGCCCCTA GTCCTGAGCGGACTTGACCTGTGGGGAGTACCGACCAATCCCCATGAGGCCCTCCAAGCGGCCAGTGGGCCTCCGGCCACTCTCTCCA CCCGCCAACCTCCTCCACCCCAGCCACTCGATCTCGATCTGCAAAACGCTCAGCTCAGCGACGCATCCCAGGCTTGTGAC CACTCTTTCTCTGTTACTCTAGGGACCCGCTCCATTGTCAGCCTGCCAGGCCTGCCAGGGTCTGCAGCGTCCAAACGCAGGACAGGGCGCT GGGGAAGGAAACTGCTAGGGACCGCTCCAGCCTGCCCATGTCAGCCTGCCAGGCCGTCCCGCTGCGGGATCGAGGAGCGTCGGAGAACCGCGTTGCTTCTGCCACCC GAATACTCCTGGGCCTCTCGACCTCGTGTAAAAGTTGTCCGAATGATGTAAAAGTTCTACAGCGAGACGCCAATTGGTTTACAAATAGTGAT GATAAACTGGGACCGACTATTTCGTGTCGACCAAACAGTTGCCAAAGTCACAAAAGTCACAGAGGCACACCGGAGAAAGGCGACGAAGGACGTACTGACGAAGTCACTGAGGGTTGTTAGCAGTCAGGGAATAAACAGAGATTCGTT TAGCATTAGTTCAAGAGACTATTTCGTGTCGACCAAACAGTTGCCAAAGTCACAAAAGTCACAGAGGCACACCGGAGAAAGGCGACGAAGGACGTACTGACGAAGTCACTGAGGGTTGTTAGCAGTCAGGGAATAAACAGAGATTCGTT TGAAGGCGAGATGAAAACAGATGGGTATCGCTAAATGTCAAAAGTCACTAAAGGCACAGAGGAGGCCGCTCTGTTTTTGCGAAACTTGCTAA AATTAATCTGCGTGGGCCACTTGCAGAAAGCAGAACAGAACCACTTCAGGGCAAATCCGCCGCTGCGAAAATCCGAGGGCCACAAGGGCTGCT GACAGAACCTTTGCCTAGGGACCCGGCCACTGGTGCTTCAGAGAAATCCAGGGGGCCGAAAATCCGAGGGCCACAAGGGCTGCT GGGCCGCTCTCCAGGCCAGGCCGTGTAGGAGGGCCGGTGTAGGAGGGGCCGAGTGCGCGTTCTCGAGGCCCGTCTCGGGCCCCAGGAGCAGGA CTCCGCCGCGCCTCAGCCTGCCGTTCCGCCATCCGCCGGCCAGGCCGGCGCCGTGCCTGCGACGAGTTCAGGGGCGCCCAGGCGGCCGCGACGGCGACGCGACGACGAGCAGCGGGCCCGGGCCGCCTCATATAACTAAAGGCACCCGCCCACCGGCAAATTCCAGGCGCGAGTCGGCGGCCGCGACGCGACGCAGCCCCACCGGCGAAGCCGACGCGACGACCGCCGGTGTGTAGTCCCACCGGCGAAGCAGCCGCAGCCGACGCGACGGCCGGTGTGTAGCCAGCC ATAGACGATGACAAGCAGAACAGAACCATCCGCGGCCCGCCTCTCAGGAGTCAGGCCGGAAATGCCAAGCCCGGCCCGGCCACTGA GATTTCGCGGCCCTGGGGCTCCAGGCGGCTCAGAGGGCAGAAATCAGCCAGGACCCACCGGCCAGGCCAAGAGCCGCGGCAGCGTGCT GGGCCCCGGGCCTGCCTCAGAGCGCCATTCAGCGCTGGTGGGAGCGGTCCCGGGCTCTGCGAGGCCTCTCTCCCAGCCGGCACTGA GTCCGGCCCAGCCAGTGCCCTCGAAGCTGCAGGTGCCTCAGAGTGCGGCTCATCGCGGCTCGGCCAAACGTCCGCAAGCCGGGGCCACTGA AGCGACTGAATCTCGAAGCAGGCCTGCAAGCCCGCTGCGAGGGCATCGCGCGGCGAGCGCTGCGAGGCTCGGCCTAGGGCGCCGGACAGA GGAGAAAGGACAGGGGCCAAGCCCACTGGTGGCTGAGGCGCGTCGCGTCCGGGCCCTCGGCCCTCGGCCCGTCGCGGCCCGGA AGCCGCGCTGGCCGGGGCCGGGCCCTGGGGTACCGGCCCTGGGTACCGGTTTCAGTTTGCCCTCTGACCTGTTGGGTTTACAGTCGGCCCGGAAGCGCACAAAAGCGCTCCCGGGTCCCGCCATG TTGGGAGCCGCCGGTCAGGGGCCAGGGTTCGTGCCACACGTTAATGAGCCCAGGTTGGGTTTACAGTCGGCCCGGAAGCGCACAAAAGCGCTCCCGGGTCCCGCCATG GCCAGGTCTTCCAGTCGCTGCTTCCAGTCGCTGCTAAATTATAGAGCAAATTATAGAGCGCCGGAAGCGCACAAAAGCGCTCCCGGGTCCCGCCATG CGGGGAACTCTCCAGAGCTCCCACACTGCCACAACTGCGAGAGCTGCCCCG |
| 116 | chr5: 72767550- 72767800 | TTTCCAAGACAAGAGGAGGGAACTAGGCGCCCTTTTTTCCACTCCGCTGACCCCAACTCTCGGCTGTGCGTTGTAACGCAGTTGGCGGGG CCTTCAGCTTGGGATGAGGGCGAAGGGCTCGGGATGGGTGGGAAAGCAGGAACAAGGACCGGCAACAGGTGGGGAGGTGGCGGACTTTGTC TCGGGAAGGAAATCGGCTGCTGTGCTGAAAGGGCCGACAGCGCGCACAGAAGCCACAAGCAGAACTAGTGTCTGCGGGTCCC |

TABLE 4B-continued

| SEQ ID NO | GENE NAME | SEQUENCE |
|---|---|---|
| 117 | NR2F1 | CCCTCCTGTGGCTGCTTGGGCAGAGCGCCTCTGTGCCTGTCGGATGCGGCCCAATGAGAGCCTGCAGGAGAGTCGCAGTGCCACTGG AGGAGTACGTGAGGAGCCAGTACCCCACCAGCCGCCCAGCCGTTTGGCAAACTGCTGCGACTCGCTGCGCACCGTGTCCTCCT CCGTCATCGAGCGCTCTTCTGCGTCCCGTTGGTAGGTAAAACCCATGAAACTCTCATCCGCGATATG |
| 118 | PCDHGA1 | TCCTCCTTTGTGTATGTCAACCCAGAGGACGGATCTTTGCCCAGCGACCTTTGACTATGAATTGCTGCAGATTGTGGT GGGGGTTCGAGACTTCCGGCTCTCCCATTGCATGCCAACCAGCCGCCCGTTTGCATGTGTTTGTCCTAGACGAGAATGATATAGCCCAGCTGTG CTGCACCCGCAGACTCAGCCCCAGCGTGCCTCCTCCCGCTCTGCTTCGCTCCAGAGACGACCTGTTCCTCGTGTTCTACACACA GTGGATGCTGAGGCCACCAGGCCACAGCCCGGGCCCTTACTGAGGATGACTCTGACACCCAGCAGGTGGTGTCCAAATGCACTGACTTTCCATACACCCTC CTGGTGAGGTGCGCACAGCCCACAGCCAGTGCTTACCTTATTGTGGTTCTGGAGGATGAAGACGTGTGAGGAAATGACTTCCTAGCACCCCTC CTGAGGCGGTTCAGACCTTTACCCTATGTCAGTCTCTTATCCCTAGTACACTTCCACCTTTCTGTCAGCGAAG TGCCTTCAGGGAGAAACGAGAGGGGACGGACCAGTGCAGTGTCGCAGGACTGCCAAGTACATGAGGGTCTGCGGCCCAGAACTGCAGGCCACTGCTACA CAGCCCAACCTGCAGGTGAGTCTGGACGCGTCAGTAGACTTCACTTTTCTAAGACCTGGGCCCACAGACTGCAGAGCCACTGCTACA GAGCGTGCTTTCACCGCCTCCCGTCCTCTAATACGCTCCGGTAGGGGCTGCGGTGAGCACAGCCCCGTGGGGCG CTGACGCCATCCGGTCCCGTTCCCGAGCGAGGGAGGAGCCACCACACGGCCTGACTTTCGCTCGCCTGGCGATTCCCGC GCACTGGAGAAGCCCCTCATAAGGGATTGAACTTGCATCCACTCCTCCGTTGTCGCTGCCTCCACCCGAT TCTGGGATCATTGACCGTTTGCGCGAAACCAGAGTGCCACTGCAAAAAAGCGGGGATGGGCCCTCCTTCGAGCTTCCGGTGAATTTCGGCGATTTCCGG GAGGGGAGGTGGGACCCGACCCTACCACCGCCAGCAGCCGGAGCGCCTTAGGCGCGGCGTCGGACGCTTGCGGTCT GGTGTCGGGGCTCCCGGGAGAGGAGGCCGCCGGTCACAGATGCCAGCTCGAGGAGTACTCGTAGCTGATTGTCGCGCC GAATTCACAGCGCTGTTCCGGTGCACTCCGGTCGGAGGAACTCGGAGATTCCTCCTCACCCTCTAAGTTGCCGGGCGGGCAGGAGACTCTA GTAGATTTCCTCTTCGATTTCGCCGGGGCTCATCGGTGTCCTCCTGCCCACCGAGTGGCACAAGCCCCAACCGTTCCGATCACCGAGCACTGTCT TGAGGGTCCAGATGCGCCGCCCAGCAGCGAGGCGCTGAGGGAGGCCGTCCGTCTCCTAAGGTCAGCTGCCGGGCGGAGTCCCACCTTGCCCCTGTCGCCCGG GGTCGCCTGGGGGCCGCAGAGTCCGATGCTCCGAGACCTCGTCTCAAGGTCCTGAGCAGGCTCGAGCAGGCGGACA CGATCCTTGGGCCCAGAGTCCGATGCTCCGAGACCTCGTCTCAAGGTCCTGAGCAGGCTCGAGCAGGCGGACA GGCAGAGCTGCCCAGTGGCCCAGGCGCGG |
| 119 | chr6:10489100-10490200 | ATTTGTCGTTGTGCCATTGCTGCCACTGTTGTTCTTGTCCAGGAAACACCGTGGCCAACCCAGATTCGGATACAATGGTGCGGCTCTGGA CTGAGCCTCCAACCATTAGCCATCATGGGCAGCATTGTTGCTCGCCTGCTGTTATTTATGCTAGGTCCTGTCTGTAACCACCACCTTCCTTC TCTGCCTCCTCCCTTCAGCTGCCAATGATGTATGTAGTTTACTTTTTGGTAACTGGATTCATTAACATTTATGAACTCTCATAAGTAGTAGAAAAGCAA TTTGTGTGAAGAATTTTCCACCTCATTGAAACAGTGTCCTTTCTTTGGGGTCAAGCTGATATTTTTTGTGTGTGAGAATTTTTATAGGTCTCTTT GTCTTTCCCTAAGCCCTGCCCGGGGATGAAAGGAGAGCCGTTCCACCCTCCAAAGCCCAGGCTGCAGTCTCCGGAGTGCCACCGTGGTGCTGCGGAGCCTGGACCTGAGGCACTCCTATCTGGGC TTTCCTGCTGTCCGCCCCAGGGCTTTTCACCCTCCCAAAGCCCAGCCCAGGTGCCACCGTGGCAGCCTGAGCCTGAGCACTCCTATCTGGGGC CCGATTACTTCCAGCCCTGACCAAGCATCCGCCGGCCCTAAGGGCAGCCGGGAGCCTCAACCCACCTCACCACCCTCCACTCCTCCTATCTGGGC CTGAGAGACGCTCTGGGCTTTCCAACGCCACTGCCAAACCACACCACACTCTTCCCAGACGGAGGCTGGTGTTTCCAGCTCAGTTGCATCTTC TTCGACGCCCCCCTTGGCACAAGCACTGGCCGAATAGAGATGTGTTTGCTTTCACCGGACGCAAGCGAGTCCGCCTCATCCTCTAATCACCGTCCAGGCCCG TGGGGAAGCGACGGGGACGCGGACCTGCGCCAAACAGAATGTGTTGCTTTCACCGGACCGCAAGCGAGTCCGCCTCATCCTCTAATCACCGTCCAGGCCCG CAGCCGCCGGGGCCGCCCGGCGTGCGCCCCAGAGACTCGCCGCCCCCAGAGACTCGCCAGCCTCCCAGCCCGCGCCCAGGCCCG AGTCCGGACGGGTGTCGCCCCAGAGACTCGCCGCCCCCAGAGACTCGCCAGCCTGCTCCAATCCTAATCACCGTCCAGGCCCG GGCCCTGGGAAGA |
| 120 | FOXP4 | CCGTGTCTCCCTTAAGAACTGGGCCTCCATCTCCACTCCAGCTGCCGTCGCTGCCCAGGACGCGCCCAGGAGCGCGC TGGGGCTCCGGAAACCCTCCTCCCCCGGTAAACTCCGGGCATCCATCAGTCTGTTAATGCACTAATTAGAGATCGCAGAG GTGTTAATTGGAAAACCCTGGTATTGTGCCTGTTTGGGGAAGAAACGTCAATAAAATTAATTGATGAGTTGCAGGGCGGGTGCG GGTTCGCGGCGAGGCCGCAGGGTGCAATGTTACGGCTCAGATGTGGGTTCCCCTTCTTCCTTCCACAAAAGCACCCCAGCCT ACGCCATATGGGCCCCCTTGCCGCCCGTGAAAAAGGCACAAAGGTTTCCGCATGTGGGGATGGGAGCCTCCGGCAGTTCCAAGG GTGGTCCCCCTGTTGCCACTGCCCCCCCAGCGGATTGGGAACTGGAACTCACTTCCGGCAGGAGGATGGGAGCCTCCGGCAGTTCCAAGG CGTCCCCTGCTTGCGCACTGCCCCCCAGTTCTTTGCGGAAGCTCCGGGAAGTGGAGCCCCGGCCGCCGCCCAGACTGC |

TABLE 4B-continued

| SEQ ID NO | GENE NAME | SEQUENCE |
|---|---|---|
| 121 | chr7: 19118400-19118700 | CTCAGAGCGGAAGAGGCAGCCCGGGCTTTGACCCAGCTTCCTTCCGACGGCATCTGAGGAGGCCTCTAGGCCTGACATAGGCTCCGAGG TGCCCTGGCTCTCCCCACGGGGAATGCTGAGGGTTGGGCCACTAGGTCTGCCTAAGTGCAGAACCTGAGCCTCAGACCAAATC GGGATTGCCGGCTTTGAGAAATATGAAGAAACCGATTTCTCCTTCCACTTTGCCAGTGCACTTTCCACTGTGCTGGGGGC GGCGCACTCTTTTACGACATATAAGCGGAAAAATTCGCAAAGTGGCCCCGGGATCCCCGACCCTGTCTGTCGCTAATGTGGC CTGTCTCCGGAAATTCGAGGTTGGGCCTTTGCCTGAATCTGTTGCTATTGCTGCACTTGGCACACTTGGCACCGCCGCCTCTA GCAGCGGCCAGACGCGGGGGCTGGGGGC |
| 122 | chr7: 27258000-27258400 | GTTGCGAGCGGCGGCACAGGTTGCTGGTAGCTTCTGGACTTCTGGAGGGTTGGCCTTCTTCTAAGCCGATGGCGGGAAAGAACCTCGTTT CCACAGCTTCCCCGACCCCCGCCTTTGGGGACGGAAGCGCGCCAGAGCGCTGCGTTCACGTCCGTTCCGGGCCTGGGCCTTTC CATGGCTGCCTCCTCTGCCCTTGGGCCTGCTGCAGCGGCCAGCTTCCTCCAGAGAAGAATCCTTCTCTCCCATCGAAGTGTCCC TTTCTGTATCCTGAAATACCCCTCTGGGTGAGGCCAGTTCCCCTCGTCGCCCTGGAGGGCTCCCGGCGGTCCGGAGCCTCGTGAGGACC CCGTGCAGTTGAGTCCAGGCGCACCAGGTTGCCTCCCCAGGTG |
| 123 | TBX20 | CAGTGCGCCCCCTTACCGACGCACCCATGGCCTCCCGGTTACCCCAAATTTGTAGGCAGACTGTCAGAGTTCGAAGCAGCTGTGTCCT CTGCGGGCCTGTGTCACCCTAGGCTGCCCCAGCCTCCGGATGTGCGGGATGTGAGCCGTCTTCTATGATGCAGGGCTGCTGGCCCAAGCGCTCGATGCAG GCTCTCCGAAAGGCTGTGCCGATTGCTCGGTCGGCGGAAGCACTTTCGCCAATGGAAGAGCGCCGACACCCCGAGCCTCGAAGGCTTGCAAGG GTGCTCTCGCCACTGGGGGTCGGGATCCGTGGGTTCTCTATCCGCCCTTACCCCACTCCATCCCATCCTTAGCAGTCGTGTCGTCCCAGACCTC TACCTTGGAGAGACCAAGGCGGCCCAGGAGACTACTGTGCGCGGGGCCCCAGGAGCCCGGTTGACTGTGCGCGGAGTACTGACTGTCAAGAAGTCAGAAGCCTTTGACTTCTAAAGACCC CTCCAAGCCAACGCTATCAGGTGCTCTGGGCTCAGCCGCTCCAGGGAAGGACAGCAAAACCTTTGCTCTGGGGCTCAGC CTCACCCAGGACAGTGCTTGGGCTCCGGTGGGGATTAGAAGCCCCGCCGTCGAGGTCC CTGCTGGTCGGCGGTGACGTGCTGGGCTGCCTGGGTGTAAGCGAACTTGGCCCCGGCCTTTAATCAGAGCTATTAT |
| 124 | AGBL3 | TTTAGTATTTAAGGAGAAAAGCTCATTTTCAAGAATCGAATAAGCGAATTAATCGCACAATTGTGTAGAATCAGTCTGTAAAAAT CAAGACCAACGTACTTTTAATATTCTAACATCTCCAAGTAGTCAGTATTGTACCATGAACATATTGAAGTCCAGGTAATTAATTGTTCAATGTC ACACTGTTAAAAGTCAGGTGGGCTCCAAAGCACAGTCTTCCCCACTCTAACATTCTCCGACACCCCAAAGCTCTCCGAGAGCCTCTGAGAGCCTCCGAAGTGCAGACCAC TGGGAATAAATAGCTGCCCGGTTCCCGGCCATCCTCTGGGATCCCTCTAAATTCTCCGACCACCCCAAAAACCTACGCAGGCCTCCTTCCTGAGCTGGTTGCTAGGTG CCCACCCCGAGTTCCCCGGCCATCCTCTGGGATCCCTCTAAATTCTCCGACCACCCCAAAACCTACGCAGGCCTCCTTCCTGAGCTGGTTGCTAGGTG ATCTCCGAAGGCTGTCCGAAGTCTCGCGAGGGCGAATCCCGGTTCTCTGCAGGGTGGAGTGTGGCTGGGATCTCAG CAGTGGCTTACTTCTAGCGGCTGGGATCCGGATGCGCCCCAGGAAACCCGAGATCGCGAGATCCGAGATCCCGAGATCCGAGAAGCGACGACTGG CCTGGCCAGAGGACTCGCGTGGGAGCGAGGTGCCGCCCCCAGGTGCCGCCCCAGGTATGCAGAAGTAAGGCGGGCCCCCTGCGG GAAGCGAGCGCGCCCCGGAAATGAGCGCCTCCACCAAGGTGTCCAGAGTGCGGGAAGGAACTCGGCCGCCCCGAGTTG TGGCCTCATCGTGCTTCCGCCAAAACGCTTGGTACTGCTGGGACGCGGCTAAGCGTGGCACGCGCGTAAGCGTCCCCTCTCCGCA GTGCTGGAAGACACCCCGGGAGCGCGGTGGATAAGGGCCGTTTTCCTGAGACCCAGCTGTATCCGCAGCAGTCAGCACTCGTGCGC CCTGTGTGC |
| 125 | XPO7 | AGCGGCCTGTTCCCGGGCTGGGTGCAGCTGTCAGCTGTCTAAGGACAAAGGCCCTGCTCCGAAGAACGCGGTGGCTCGGGGATACCCTGAAAGGG ACGGCCATGGCGCACATGGGATGCCTCTAGGGTTCGGTGGGAGGGCATGCAGCCCGCCAAGGAGGAATCCTGCCAGAGAAGGCA GGGGAGAGCACTCGGGGCTGCACAAATGGTGGTCCGGAGGGAAGTGTCAGCCTTGTGTGCTGTCTGGATGAGGGCTGGGCATAGGAGC TTGGTATTTGATCCTGCAAAGCTCTGCGTTTCCAAAG |
| 126 | chr8: 41543400-41544000 | GAGTCATACTTGTAGTCACATCCTTTTCCTTTCCAACCCACTGGTTAATCATGAAAAGGCTCTTCTGATTGGTGCCTCCTGGCAGTAGTGC CTCAGCCGCACGTTCGGGAGCCAGTTGAGTGGGTAAGCACGCCGGCTCCACCCCGCCCTCCAGGAGGCAGCAGCAGCGACACCCTGCCACGCCTGCCG CCTGGAGTTGAGTGGGTAAGCACGCCGGCTCCACGTGGTTCTGCACTGGTTCTTCTGCACTTCCCAGTTTCAGG GGACACCGTGGGGTGTCGCGAGCCCAGGAGCCCAGGGAGGCCCGGCCTTCAGCGCGCCGTTCAGCCAGCGCCGTTCAGCGGGCCTTCTCAGCCAGCCTCTCC ACAGAGCTTCCTTCTCTTTTTGCCAAGGTCCCCAGGTCCCGCCTTCAGCGCGCCGTTCGCCCCGCCGTTCGCCGCCTTCAGCGCGAGCCACGCCTCTC GCGACCCTAGGCGTTCCCCAGGGCGGCCGCAAAGGGGCTGTCGTTGTATCGGTCACTGTTTGA AAGCAAGTTGTGTTTGCAGACCGCAAGGCAAAGGGGCTCGTTGTATCGGTCACTGTTTGA |

TABLE 4B-continued

| SEQ ID NO | GENE NAME | SEQUENCE |
|---|---|---|
| 127 | GDF6 | ACACTTTCTGTGTGGAGGGCACAAGACATGGCTATGACATGGCCAGAGACCCACCTTCTTTACACATGTAAAACCAACCAAATCAAG ATGCGTCAACGGTGATTCTTCCTCCACATTGTTCCCTTTTAAACTGTTATTTTCAATCATGAGCAGTTGAGAAACGGTATGCATC TCTCCCTCCCCTCCCTTCTATCAAAGCTGTAAGACATGAACACATAAGGAAATCCTCCTTGGCTTGTTTTCCACCGGCTCACATCCAGGTGAAATCCATATT GAGAGAGAGAGAGAGAAACAGAACAAAAGAAATCCTCCTTGGCTTGTTTTCCACCGGCTCACATCCAGGTGAAATCCATATT TCCCTCTGGGCTTGCAGGTAGAAGTTACTGGAAGAAGGCTTCCTCCGCTCACCACCATCCAGGCGACCTTGGCCCACCTTGGTTCGGGCCA GCTCCCCCCAGCCAGCCAGCCAGGCCCCACCACGACTCCACCACATGTCTCCGTACTGCTGTAGACCACATTATTGCCCGTCG AGGCGGCCGGAAAGGCACCCGCTACCTGCAGCTCAATTGGTGGGCACGCAGGAAGTCGCAGCCAGGAAGGTCCATGGAGTCATGAGTTCATCAGCGTCG ATGTATAGAATGCTGATGGGAGTCAATTGGTGGGCACGCAGGAAGTCGCATACACCCTCGACAGTGATACCCTCGTACTCCAGGGCG CGATAATGCGTGTTGGGTCTCCAGCCCCAGCTCTGTGACTCATGACGCACCGCTGGGCGATCGCACCCGGCGGAGGCCTCTGACCCTCCGTGCCGTCCT GCCATGGCCACTGCCGAAGGCCGTGCCGCGACCCCCGGACCGAGCCCACACACACCCTCCCTCGGAGCGACGTCACCCGTGACCCCCGCCGCCCGACCGG GCGGCCACGACCCCTCGGCGTCGAATACCACCAGCAGGGCCCGCTCGGGAGGCCCAGCTCTGCGAACTCCGGCGTTCCAGG CTGGGATCTGGTGAATACCACCAGCAGGGCCCGCTCGGGAGGCCCAGCTCTGCGAACTCCTGCAGGTCTGGGGC GGCGGTTCGTGGGTCCCCGCGGCTCCCCCGCGCTCCCACACGTCGAAGACTTCCTGCCCAGGCGCTCAAGCACAGTGCT TCCAGGGCTGGTGCGCAGGCCCTGCCACACGTCGAAGACTTCCTGCCCAGGCGCTCAAGCACAGTGCT CAGCAGTAGGGCCAAAGGCAAGGAGCAGTTGCACGTGGAGCGCATGAGCACACACAAACAAATACTTCGTCTCCGGAGGAGAGTGTGGCGAA GAGATCGTCGAGATAAAATAATTACAGTCAGTTTCACTTAAGGGCAGAATCAGCCGGTTCTTCTCGGCCCCCGGAGGAAA GGGCGGGGAGTGGGGCAGGTCGCCGGACCAGGCCAGCTCGTGCCCGTCCCCATCTGGCTGTGCAT GG |
| 128 | OSR2 | GCCCGCTGTGAATGTAGTGAGTGATCCCGGACCTGCTGAAATCAGACCTGTGTTCGCCATTGGACGACCCGAGGAGGGAAG CGCCCTGCTTAGCGCCGGGCCTGTGCTTGGCTCTGCGTCTCGGGGCACCCGCACACCGAACGACAAGGTTCTGCAAGCCA GCAGGGCCACTCTGTCCTCTCGCCTTCGGGGACATCGCCCTGCAGCTCCTTCTCCCTGCGCTCGCCGGGGATGTAGGGGTCGCCAACGACAAGGTTCTGCAAGCCA CTCGCCAAGAGCTTCAGTCTGGAAATGGGATCTGGGGGTTGGGAGGAGGAGGGCGATTCTAGGCGAAGCCAGGAACCTCAGGAAGCAGCTCAGGC AACCATCTGAAAGGATCTTAGTCGCGGCCCGTCACCCGTCGATAGATGGGCGTGAGGCAGAGGAGGAAGGAGAAAACCTCCGAGTCAGTGCG GGTGTCACTTTTCTTTCCTCGCGCAGGGCCTCTGCGCCAGGCCCTGCAGGGAGCCCCAGAGCCGCCAGCGCGATCCTCCGGCTTCACGACCCAGCGCCGGCTTGCCATCGGGT AAGCGGGAAAGGCCAGCGGCCACAGGGCCCACAGGCGGGGGATCTCACGACCGCGCCAGCGCCACCCCATCCGTTAACCACCGTTCCCAGGAGC TCCGAGGCCAGCGGGGACAGAGAGGTTCGCCCGCCAGCCAGCAGGCGCGTTGACTGACGTTCGCCTAACAGGCTTGGGAGG GTGGGCTCGGGCTGGGCTGGAGCTGGGAGGGCAGCCCCGGCCTTTCCGCCCTAAACAGGCTTGGGAGG TGCCTAGAGTCTGAATCCGACTTTCTTTCTCGGCACGCCTGCCAGTGGAGCACTTCTTGTTCTGGCCCGGGCTGATCGACGCG GACTTGAGCAGGTGCCAAAGGCAGGAGCAGAGGAGCAGCCTTGAGTCGGGCCCCTCCCCGGGGAGGGAGGAGACTTAGGTGTGT AACCTGCAGTCGTGTCTCACTGGGTTTTGTCGAAAATGGGGAGCAAGGCTCTGCCAGCGCTCTCGCCTCTTCCTGCCATTTTAGGGCTTTCTC TACGTGTCTGCTCCAGTCGAGCATCCGGGATCATGCCCCAGACTCCAGCGCCATGTCCGCCGCTCCACCGTCGATTCTGAAAGAAAGGCTTCCCTCAGAGACG CAGCACACATCCGGAAATGGGAGGCCAAGCTGCACGATGTCAACAACCTCCAGCGCGCTACTCATCGCGCGTACAGACGCCATGAACCACTGGACG CTGGGATATCCCGATGTCACGACACCCCGTCACATCATGTCCATCGACGCCAGGACCCAGCGCGCTACAGACGCCAGCGCGCTCCCCTT CCCGGCCCCTGGCTTTTTACCAATTTTGGCGGTGCGTGCTGCCAATTTGACTCCGGAATTGACACCACTTATTCACCCAAGAGAATCCGCTCAGTGGGAGAACCCCTCTGAGCAGCGTGCCCAAAACGAAAAAGAGTTATCTGCAAG TTTTGACTTTGCCATTGCCAATTGGCGTGGCTGCAATTGACTCCGGATCACCACGCGGAGTGCCCTGCAAAAACGAAAAAGAGTTATCTGCAAG TTTTGCGCAGACACTCCAGCACGTCACCACGCCACGTCCAGGCAAGCCGGACCCGCAGCCGCAGCCAGCCACCCGCAGCCGCGCGCGTCAACCGTCACCGTGACATCTGCC ACAAGGCCTTCCGGAGGCAAGATCACCT |
| 129 | GLIS3 | CACTCCCCCGCCGCCTCCGCCCTAACCCTCGCCCCGTCGCGGAGCGAGGGAGCCAACGACGCCAGGCGAACGACAGCCGCAACAAACAAACTAGTGCC GGCTTCCTTGTGTTGTCAACTCGCTGCTGTGAGTGAGTGCGCGGAAAGGGTGCTGCGGGCGGCCGGAACCTGCGG CGCTGCCCCGGCCTAGCCCGGAGCCCTGTAGCCCGGGAGCCCAGGGGCCCACGGCCCGGCTCGCAGTCCCGCAGTCCAGTCCCCGTCCCCGTCCCCCG |

TABLE 4B-continued

| SEQ ID NO | GENE NAME | SEQUENCE |
|---|---|---|
| | | AGCCAGTGTCCTCACCCTGTGGTTTCCTTTCGCTTCTCGCCTCCCAAACACCTTCCAGCAAGTCGGAGGGCGGGAACGCGGAGCCAGAAAC<br>CCTTCCCCAAAGTTCTCCCGAGGTACCTAATGAATCATCCATAGGATGACAAATCAGCCAGGGCCAAGATTTCCAGACACTTGAGTGA<br>CTTCCCGGTCCCCGAGGTGACTTGTCAGCTCCAGTGAACTGGAACTGTGTCTCGGGCAAGGTGTGTCTAGAGAGACCGGCG<br>GCTCACTCACGCTTTCCAGAGAGCGACCCGGGCGACCTCAAATACACAGGGTCATTTATAGGACTGAGCCGCGCAGGACCAAC<br>GTCTCCGAGACTGAGACATTTTCCAAACAGTGCTGACATTTTGTCGGCCCATAAAATGTAAACGCGAGTGACGAACCCGGCGGGGA<br>GGGTTCGTCTGTCTGCCTGCGTCTGCTCGCTCGGGAGTTATAGTTCAGAACCTGGCGGCTGCGGATCGCCGGTACCCG<br>CAGGAGTGTAGGTACCCTCGACCCGACCAGTCATGGAGCAATCATGAGCGCTTGGATGAGACAGGCGTGAAAACAGCCTTC<br>GTGAAACTTCCACAAACGTGGAACTTGAAAAGACAACTACAGACCCACGTGTGCGCGAGAGACCTCACGTCACCCATCAGTTCCCACTT<br>CGCCAAAGTTTCCCTTCAGTGGGACTTCAGAGTGGTGCGCCCCATGCCGTCGTCCTGTAACGTCGTCGATTGTGTACCCCCTCTGCC<br>CGTCTACTTGAATGAAAACAAAAGTTGTTCCGAATTAGCGCAACTTTAAAGCCCCGTTATCTGTCTTCTACACTGGGCGCTCTTAGGC<br>CACTGACAGAAACATGGTTTGAACTCTAATTGTGTCTATCAGCTGATGACTGACCTGGACCGCGGAGTTGAGG<br>TGCGCGTATCCTTAAACCCGCGAACGCCACCGCTCAGCCTAGAGAAAACATATTGTAATCCTAGTTTGCGTCTCTGAGCTTTAACTCCCC<br>CACACTTCAAGCGCCCGGTTTCTCCTCGTCTCGCCTGCGAGCAAAGTTCTATGGCATCCACTTACCAGGTAACCGGATTTCCACAA<br>CAAAGCCCCCGGCGTGCGGGTCCCTTCCCCGGCCCGGCCAGGCGCGCCAGCAGCAGCGTGACAGCGGCGGCTGGCGAGAGTAACTTGGGCT<br>CCAGCCCTTCAGAGCGCTCCGGCCGTGCGGCGCTGGCCCCGCCTTCGGAAAGATGAAAACCCATCCAAACGGGGACAGGCGGAAACCGGCC<br>CAAGTGCCCGTGTGTGCGCGCGCTGCGGAGGGCAGCGGCGCAGCACAATAATGTTTTAAAGTTCAGTTGCGACTTGTGCCCCTGTCCTGTTCATCC<br>CAGCTCATTCTCCGGCCTGGGCGCTTCTGGGGGCCGACCCGGGAATGCCTTCTGGGGCCGCCTAATTGCTGCCGGTCCGTCGCCGCTCTGG<br>GACGGCGCGACGCCGTACAGGGGCTCCGGAGGGGCAGTGCCCCGGGAGGGGCAGTGGCCACTGCGCCCGTGCCCGTGCCCGCGCTCTGG<br>CTGCCCGGCGGCCGGCCCAGTGTGGACGCGG |
| 130 | NOTCH1 | CTGAAAAGCCGTCAGGGAAACCACACATGTTCAACCTCAATTTCCAGTAACTCTCATTTCCAGTAACTCTCATTTCCAGTAATCTGTGTTCCGCTCGTCA<br>ACAGCTGAAACAGCCGAACTTGGGGCCCACCACTCTCTGGGCCTGGTGCGCCCTGCTGTGCGACGGCCCCTGTCCTGCCACGCCACAGC<br>TCAGCTCTCAGAGAGCTGCCCTCTCTGGCCAGGGCTCAGGGCCTCGCAGGATAGTCTCAGGGCAGCCTCAGGGTCAGGAACACTTGTCTGAGGCTT<br>AGCCTCTCAGAGAGCTGCCCTCTCTGGCCAGGGCTCAGGGCCTGTCAAATGCCATGGCGCATCGCCCGCTCGCCTCTGCTACAGGGCAGGAAAATTCTGGCCAAAA<br>GCTCCAGCCTCCTACTAGGGCCATCGTGCTCTTTTGACTTGATGAGGCACGAACAGGTCCTAATAAACCAGGTTCCCCGCCCGTCTGTTTCAGGAAAGTGAGG<br>GACGCGAGTTTCCTCCTTTGAAGCCCATGAGCGTCGGGTAACCCACTACGGGCCAGGAAGAGGGCAGGAAGCTGGGAAGCCAGGTTTTGGGATGTGCGGAGCACGGGTTG<br>CCTGTGCTCCGGCACCAGGGCGACCGTCGGCTTCGTCCTTCGTCCCCTATGGCTGAGGCTTTTGGGGATGTGCGGAGACGGGAGTC<br>TCATCTCGGCACGAGGCGACCGTGCTAAAATGAAAAGACAGACAGCAAGTGCTGACAAGGCTGTGGGCGGCCAAATGCTCTGCACTGCTGCA |
| 131 | EGFL7 | AAATCATCAGAATGCTAAAATGAAAAGACAGACAGCAAGTGCTGACAAGGCTGTGGGCGGCCAAATGCTCTGCACTGCTGCA<br>GGGGACCTGAGACTGCAGGGCATTCCTGGCTTCGCCCTCCCTGCCCTGCTGGCAAAGTGTTCAAAGTAAGCTGGTCAAGGGACCAGCCTAAGGGAACTGCATTT<br>ATCTTCACGTCTGCCAAAGATAACACGAAGATGTTCCCATCACGAGATGCTCCAAGTTGGGGCATGGCAAGTAGGGACTAAGCAGCCAGCATCCAAGGGC<br>ACTGGGGGAGTCTGTTCTCCCAGGGATGCCCCCCCCCGCAGCCATGGGTGGGCCATGCCCGGTCGCCAGTGCACTCGCTGCAGTTTGCCAGGCCAC<br>TGTGTCTCCGCCCCGGGAGTCCTTCCTCAGGGCTTCACTTTCCATCTCTAAGCCCACGTCTCGCTCAGTTCAAGTTTGCCAGGCCAC<br>CAACGGGTGACACCCCCGGCGCAGTGGGGGACTCGGGGGCACACTTTCTGCGCAC |
| 132 | CELF2 | ACCCTTTGTGCCTGGGTCCCATAAACAATGTCGTTTTAAAGGGGAGCCCCCCCCTTTTTCCAGCCTGGCCCAGCCAAT<br>CAGCTGCCCAGAGCTGCCATAGCTGGACATGTCCATCTGAGTAGCAACAACTGATAATTCTGATCCAACATGATGCTCGCGACTC<br>TGCAAATTTCATCACCCGCATCTTGCCAAAAACTCCAAAAGGGCGTTGGGCGCGGGGCGGACTCGCCAAGTTGGGATTGTTTCATTTCTTTCATGATGACTTTATTATTACCACCTCTCT<br>CCTCTCTTTCCAAAACCTCCAGGCCACGAGCTTCCGCCACAGCCAGGTAGGGCTGATAAGGCGTGATGCGTCAGCCTTGCAGAGCTAGACCTTGCACTTAACTTGCA<br>CTTGCCCGACCAGCCACGAGCCTGCTCTTCCTCCCGTCCGCGCCGAGGAGGACAACTCATGTGCCTCCACCCAACCTGAAAGGAGAGGACCTTGCAGAGCTAGACCTTGCACTTAACTTGCA<br>GCACGCAGTGAGAGCTCTGCGCCCAAGATGTCCACCGCCGCCGAGGAGGACAACTCATGTGCCTCCCACCCAACCTGAAAGGAGAAGACCCACTATTTTTTCTTCCTGTCCCTCATCCGTGCCGCCCTAAC<br>CTTTGCCACTGCGCTCTTCCCGTTCGTGTTTGGACAGTACCGCACAGTGTTCGGAAGAAGGATGAAGAACTTTTTGAGCCTTACGGAGCCGTCTACCAGATCA<br>ATTAAGATGTTGTCGGACAGATCCCCGATGTCCAGAGATGCATGGCTGGAAAGAAGATACAGAGCGCGGGGGGGGTCCAGGTGGGCGTG<br>ACGTCCTCCGACCGAGTCAGAACCCCTGGGCGCGCGGGCGTG |

| SEQ ID NO | GENE NAME | SEQUENCE |
|---|---|---|
| | | CGGGGCACTGGGGCTGTCCGAGCCCCCAGCCTGCAGGAGGAAGGGCGGGTAGCCAGGCAGGAGGCTGGAAGCAGCCGGTCGTGGCGGCCC CTGTGCTCCAGGGCTGCTTCCCGACTCCTCCCCGCACCCCGGCACCCCGCTGCCCGGCACCAGGTTGGAGGCGGGACAGAGGGACCGA GGCAGGGCGGGAGCGCAGAGGGCTGGTC |
| 133 | HHEX | TAACAAATAAGCCGCCCGTGGTCCGCGCTGTGGGTGACCCCTGGCCGCTCCTAGGGTGTCTGGAGCCTGAAATAAGGAAACGGGGCG CCTTCTAGAGTTTTAAATGAACTCGTTATTGGAAGCTTCAGTAGGGACCCTGAAAACAATTAACGTCTTAATTAGCATTTAATGTCTCCATTA TTACGGCGGGCCTTCTAGCCTTCAGCCCTTTCGATTCGAGTCCTTACCTTCCTCACCGTTAACAGGAGGGGGATTGTATTTTAGTTTCATCTTTTATGTTTT TGAGTTGTTATCCTGTCTGTCTGTCTGATTCCAGCCTCGAGGGTTTCACAGTGCGCCCTGAGTTCCTTGGGTTACTGCTGGGACCGCAGGAGCG GACCCCTCAGCGCCGGGCCGGGCTGGGGCTAGCTAGAACCAACAGGAAACATTGACGGAAATGTGCCATAGCCCATGGGGTGGCTTTAACTGGCCGCCCCGC AGCAAAGAGTTTTTCGAGCTGAAATCAGAGAGGCCGCGGCTCCGCGGCGAAATCGAGGCTCTCCGCAACCTAATGCGGGTGTCCGGCCCG GGGCTGGGGTGAAATCAGAGAGGCCGCGGCTCCGCGGCGAAATCGAGGCTCTCCGCAACCTAATGCGGGTGTCCGGCCCG AGCGCTTCCCGCAGCCAGGCCTTGTCGGTGCAGCCAGGCCAAAAAGTTATGTATAAATCCGAGAGCCACTGGGAAAGAGGGTCGTGTATTGTAAG |
| 134 | DOCK1/ FAM196A | CTACCCTGTGCTATCCTGAGCTGTAGTCTTCTGAAATGATCGTTTGGCTTCCCAGCCAAGGCAGGGCTCCCCCCAAAGTTCATTCCCACTCTT GCAGTTTCACCTCGGGATGCTTCCCAGCACACAGACCAACAGCAGGAGGGGTCAAAGTCAAAGTAAACCGTTCAGCTGCTTCTGGCGCAGG GGCCCAGAGCGCGTGCAGCTCCCCAGCACAGACCAACAGCAGGAGGGGTCGGGAGCCTCTTTATCACTGGCTCCCTCCCTGTGGCATATT ACCCATTTTCTCCTATTTACTCCAGAGGCACCTCTCCTCCCCCACCTCTCCTCCCCCACCTCTTTATCACTGGCTCCCTCCCTGTGGCATATT TTGGGTAGTAGAATGCTGAGGTCACAGGGACGGCTCTTGATCCAAGCAGTGGGACATCAGCCTGGACATGAACCAGCAAG ATGCAGACTCTCGCTCTTGACTTTGGGCTCCAGGAGCTGCCCCGACC |
| 135 | PAX6 | CAGTGCTCCCGCTCCGAGGGAAATTGCATCGTCACGACAACAAACGGGACCGTGATAAAACGAGACCCCTTTCTCCTTATTTGTAGATCACTCAGACG AGATTGAACTGCCACTTGTTCCCCTGGCCGTTTTCAGGGTAGCCAAGGCTTGAGGGGGCGTTGGGATCTCGGGCTCCGGGACCAGCCAAGCAGGGA CGGCGGGGTGGGGGCCGAACCGCTTCTCCAACTCCAACAGAGACAAGGCCTGGCCCACGTTTCCGGTTTCTGCTATTCCGGAACTTCCTTTATTGCTTCGC CTTTGCGGGGACAACCGCTTCTCCAACTCCAACAGAGACAAGGCCTGGCCCACGTTTCCGGTTTCTGCTATTCCGGAACTTCCTTTATTGCTTCGC AAGTTCATTCCACCCCTCACCCTCCAGTTCACAGCCATAGCCCATAGGCACAGGAAGCTTCCCGAAAAAGAAAGGTGTCCAGAAAGAGACCGA GAGAGACTTTCCAAACTTCGGGCATAGCCCAATCAAAAATAACAACGTGCCACACCTCCGCAGATACCGCGTGTGCTTCCAGGAGCGTCAGGGCCAG CCCTCCTCACTTCATTCAAAAATAACAACGTGCCACACCTCCGCAGATACCGCGTGTGCTTCCAGGAGCGTCAGGGCCAG AGCGCCCACTCCCAGCATCGAAATGCAGAGAGAAAGCCAGCTCCAGTTCGCCGAAGCAACTAATAGGAAAACATATGTGTCAATT AGGGACTGCTGGCGCTTCGCCCGCACCCGGAACGAGCGGCGAACGGAACCTGCCGCCCGGCCCCTGCGCTGCTGCTGCTGGGAGTCTGAG CCAGCCGCCGACGACAAACGTCAGCCGCTGCGCCCTTGGGCTGCGCGCCCCGCCCAGCAGCCGCTGCGCTGGGGAGTCTGAG CTCCAAGGGAGAGCCCAGCCGCGAAGGCGAGCCGAGCGCGAAGGCGAGCCAGCCTACCGGCCCAAGCCCTGGGGTTCTGCACAACTACTCCCGCAAAGCT CGCCACCTTTGTGCCCTTTCCTCAG |
| 136 | FERMT3 | GGGCCCTCGCGGCTCAAGCGCCAGCGCTGAGAGAGAGTCTGAGGATCAGCGTGTCTGCTGGTCTCACTCCCGCCCTCCT TCATGAGCCGCCTTTCCTCTGTAGCAGCAGCCCAGCCATGGCCGGGTGTCCAGGGCATCACAGAGACTCTTCACCTTGCCCACCTTGCC TCCTTCCACACTCTCTGTGGGAGGAGGGCATCACCAGGGATGAAGACAGCCTCCGGGGACTACATGCACTCGTCGTCATGGAGCTGCG GTGTTGTGGAGAGGAGGGCATCACCAGGGATGAAGACAGCCTCCGGGGACTACATCACTCGGGTCTCTGGGGACTTCGTCGTCATGGAGCTGCG ATTGTGGACAGATCAGTGAGTGCCCGCCCGTTCTGCTACCACCGCAACCGTCGCCACCGGTGTCTCTCGGGACTTCGAG ATTGTGGACAGATCAGTGAGTGCCCGCCCGTTCTGCTACCACCGCAACCGTCGCCACCGGTGTCTCTCGGGACTTCCGG GCCATCCCTGCTGCTCAGCTCCGCGATAATGGTGTCACGGTGACTCAGGCATTAGC |
| 137 | PKNOX2 | TGTTTACGGAATCGGGATCGAGGGCCATAAGGTGGGCCGATAAGTAGTTTACACGCCGGCCAGAGCAGGAGGGCTGGAGTTGGGGCTGGAGGA ACGGGTGGCGTTTTAGGATTCAGTAACAGGATCACAGATGAGCAGCTTTTCTTGTGTGGATGCGATTAGTGGATTCGGAGGTTAGCACGAGGGGTC CTGCAGCTTCCGCTGTGTTTAAGGAGGAGGACTTTAGTACCAGGGCCGATGAAAAGTAGTTGATCCAGGCATGCAGGCCGAGGCGCATCCGGCGATTCCGG AAGCCGGACGATCGAAG CCCCTTGAAAAGTGTTTCTTAAGGAGGAGGACTTGGGCCACACAGGACCCGGTTCTGCAGGAGGTCGAGGAAGCCGGAGTGGAGCCGGACAGATTCCG AGCACCTGGGCTCTGCGAGGCGCCAGCCAGGGCCAGCCTGCGCGGTCTGGTTGGCCCGCAGGGAGGCTGGGAGGTCCAGGA CCTAGCAGCGAGGTGCCACAGTGGGCCAGGGAGTCTGGGCGTGGCCCCAGGGTAGGACCGGCTCA |

TABLE 4B-continued

| SEQ ID NO | GENE NAME | SEQUENCE |
|---|---|---|
| 138 | KIRREL3 | ACTTAAACCAAGTCTCCTCCCTGCCTCTCCTTCCCTGGCTGGGTCTGAAGGAGGAGTGCCCAGAAGTTCAGAGCGGCATAACC ACAGAGATACTACCTAATTAACATAAGAAGCATAAAGAACTCATTTGCATTGGAAGAGT |
| 139 | BCAT1 | ATAACTACGGAGGGTGGGGTGGGGTTCGGCAGCCCAGAGATTCAGCTCCCGCCTCCCCTGAAGGAGGCAGAAGGCTGCGGTCAAAATATTTGGGGTGGCAGAGTCACGTAG GATGTGGCTGTGGGTTCGGCAGCCCAGAGATTCAGCTCCCGCCTCCCCTGAAGGAGGCAGAAGGCTGCGGTCAAAATATTTGGGGTGGCAGAGTCACGTAG GGTCCTCGCCACCGTCCCGAGCGGGTTACCCATGGAGGGTCTAGAACTCGGAGGGTCGAAGAGGTGAGATTGCAGGCTGG GACTCCAGATTTCGGGCAGGGATGCGGGAAGGGAAGACGCCTCGCTGGAGGCGGAATGCTCCCCCTTCCGCAAGGCAAGGAGGAAGGATGTGTCAGG AAACGGCACAAGGCGCCCGGCCAGGCCGCAGCGGAGCGAAGCGGACGGGCTGGCCATGGGAGCTGCGGGAGCTGCAGGAGCGGGGCTGCAGGAGCGCAGT GTACCTGCGGGCAAGGGCTGAAGCGAGGCAGGCAGGCGTGTGGCCAAGCCGCCCATAGGCGCTGGGTACCACGACCTG GGGCAGGAGCGGCGCCAGGGCGAAGCCAGGGCTACGACGCAACCCCTTCCAGCATCCCTTGCCTGGGAGGAGCCCAGAATGCGGCCACGAACGAGCGGCCTTT GTCTGCAGTCGTCAAAACCGAAGCGGTTGTCCCTGTCACCGGGGTGTCCGAGTAACACCTTCGGGTGAATGCCGGAAGCCTAAGGCTAAGGAAAAC CCAAGCCAGATATTTCGCGAGCATCCTTGTTTATTAAACAACCTTCGGGTGAATGCCGGAAGCCTAAGGCTAAGGAAAAC CTCGGAGGAAACTACAT |
| 140 | HOXC13 | CAGTCCAGCCGCTTGCCTCGCTCACTTCTTCCCGCTTGCCTTATCTCCCGCAGACGTGGTTCCCTGCAGCCCGAGGTGAGCAGCTACCGGCG CGGGCGCAAGAAACGCGTGCCCTACACTAAGGTGCCAGCTGAAGGAGCTAGAGAAGAATACGCGGCTAGCAAGTTCATCACCAAAGAGAA GCCCGGCCATCTCGCCACCAGACGAACCTCTTCGAGCGCCAGGTAACCATCTGGTTCCAGAACCGGCGGTCAAAGAAGAAGGTGG TCAGCAAATGCGAAAGACCGCTGCCGGGTGCAGAAGAGTATTTAATGTTAAGGAAAGACCGCGCCGCCTGGGACTCACGTGGCTTCAAACGCT GAACCCACCGTGCTGCTGGGCCATCCGAACCTCCTATCCGATCCCCAGCCTCCACCCCATCCCAGATGGGACTCACGTGGCTTCAAACGCT CATGGCCGTGCTGCTGGGCCATCCGAACCTCCTATCCGATCCCCAGCCTCCACCCCATCCCAGATGGGACTCACGTGGCTTCAAACGCT TTGGAAATGGGTCCCCAGTGGGCCTGCCAGGACTGTCGACCTGTCCTACTCCTTGC |
| 141 | TBX5 | CAAGATCGACTTTCTTAGGAAGGGGAGGAGGAACTCTTCACGAAGGAGGTGGAGTCCACCTCAGACTTCCACTCCTCAGAGCTCTCATTGAAGGAAATC GAGTTGTTCCGGGGGACTGAGGTTCTTGCATAAGGACATGGAATCCTTATTATTATTATTTAAATCCCCCGGCGGAGGAGCTCTG GGCAAAATGAATACGAGGCGCCCGCTCTAGCTGGTTAGGCTTGGAGCGATAATCAGTGCCCTCTTGCAGACTGCATAGAAATAATTAC TGGGTTGTGTGGAGGGGACACAGAGACAGAGGAGTTCTCGTAATGTCCTTGCGGAGAGAAGGTCAAGAATGCAATTCGTCCCAGA GTGGCCCGGCAGGGGCGGGGCGCAGCACTCTATTTTGTTTGTAATCACGACGACTATTATTTTAGTCTGATCAATGGGCACAATTTCTAAGCAG AGGGCCCGCCGAGCCACGATGTGGATGCTGGCCGCAGCAGCAAACTTTTGCCACCGCTGGAAAACCCACTAGGTTGAGTTGCAAAACGTACCGCGTAGGCCTGGTGGC GCCAGTGGGATGCTCCCAAACTTTTGCCACCGCTGGAAAACCCACTAGGTTGAGTTGCAAAACGTACCGCGTAGGCCTGGTGGC GCCAGAAGAGACTAGGCCTGCCCAGGGGTAAGTTCTCCCAAGGGGTCCGAG GGAGCTGACGTCTGAATCTGAACTCTGTAAGGACTGGAACGGCAGCAAATGTGCAGGAGGCAGTCGGCGGCAGACGGCTTTTCCGAAGC ATGGCCTGGCTCCAGGCCCCGGCCGGCTCTTCTCTTGCCTCGTAAGGACTGGAACGGCAGCAAATGTGCAGGAGGCAGTCGGCGGCAGACGGCTTTTCCGAAGC CAGAGCAACCAACCCGCGGCTTCCTTCTCCCGTGTTGCTCCAGGCCGAGTTGGGCCGGAAACCAGAGCCTAGGCGGGAATCCTTCTCCAAACCCTAGGTCGACGATGAGTTC CTACTTGACCCTCTGAGCCGAGGCTTCCTTGTGTTCCTCGGGATCCGAACTCCCGGAAACCAGAGCCTAGGCGGGAATCCTTCTCCAAACCCTAGGTCGACGATGAGTTC GTCTTTTCCTTGTGTTCCTCGGGATCCGAACTGTAAACTCCGGAGGCCAGTAACTCCGGAGCCATTCAAAGGATTCGCAAGTCCAGC TTCACAGACTGGCTTTCCCAGACGCTTCCCAGGACCACCACGACAGGAGCACCGAGAGATCGCAACTAGATTTGAGAATCCT CGTTCTTTTTCCCAATCGTTCGGGCAGTAAACTCCGGAGCCCGGCTACAGCGCGCATCCTC |
| 142 | TBX3 | ACTGTCCTTCCTCCCTCCCTCAATTGCCTATTTTTTGCCCATAGCTCTAACTGTAACCCTGTGATCACCCCAGATCGTCACTTCTGACCCCATCTCCT CTCCAACCTCAGCGCCGCAAGCGGCAGCCAATTATGACTGACCTCCCAGACTCGGCCCGACTCGGTCCTATTAGGCAGGAGGCTCGTATTAGGCAGCTAATCTTCGGATCAAA GCAAACTTCCGCCAATTATGACTGACCTCCCAGACTCGGCCCGACTCGGTCCTATTAGGCAGGAGGCTCGTATTAGGCAGCTAATCTTCGGATCAAA AGCGGAAGGTCGAACTCCTCTTTGTCTCTGCGTGCCGCCCCTCGTCCCGTGGGTGATAAACCACTCTGCGCCGGCCATG CGCTGGGTGATTAATTTGCAACAAAAACAAACCCAACACCGGCCTGGTGCCACTGCATTCGGGTTAAACATTGCCAGCGTGTTCCAGGCTTGTG CTGGGCCTGGCCTCCAGGAGAACCCACGAGGCCAGCGCTCCCCGGA |

TABLE 4B-continued

| SEQ ID NO | GENE NAME | SEQUENCE |
|---|---|---|
| 143 | chr12: 113622100-113623000 | CTCAGGGAATCACATGTCCGCTTGGCCTGGACTGGACCAAATGTTATAGACAGGACAGGAGGGTCGCTGGAATCGCCTCGCTCCTTTCAG CTTGGCGCTAAGGCGGAATCTGCATCTCCTAGTATTTCTGGCGTCTCTATCTCAGTCTGTCCTTTGCTTTTGTCCTCTTTCCCTCCCTC CGCCCAGTCTTTCCGTCTCTTTTTCCTGCAGCTGGCTTGGATCTGCATAGACATCTATTACCCGCAACAAGATCCGAGCTGCAGAAGCAACCTAATCTGT GCGCCCGCTGCCCACGCCTAGCGGCTTGGATCTGCATAGACATCTATTACCCGCAACAAGATCCGAGCTGCAGAAGCAACCTAATCTGT CTCCGCACCATCCGCTTCTGTAGAGGCCAACCCACTGCCCATCCACGCCACATCTGCCCATCCACGTTCAAGTAGCGACTCCAGCGACTGATTCGA GAATGCCCTGCTTTCCAAAGGCCAACCCACTGCCCATCCACGCCGTTTTTATTTTCTTTTCCGCTTGGACCAACTTTGGTTTCTTTCAGGGCCCGAG GTGCCTGCCGCCGTTGGCTTTGCTTTCCGCCGCGCTTACAGTCAACTACTTTGGTGTGGGCAAGACTGCAGTTCTTGTACATGGACGGGGGTTGGGGGGGTCAA CACAAGAGCCTGGCGAGCTTCCTGCGGGAGGGTTGGCGAATGGGTTGGTTGGTGGCAAGACTGCAGTTCTTGTACATGGACGGGGGTTGGGGGGGTCAA GGCGAAATGCCTGCAGGGAACTCCTGCCTGACGCCAAGAGCCGTCGTCCCACTCCGCGATGTTTACCCACCTTCATG |
| 144 | chr12: 113657800-113658300 | TTTGGGGCACCCAACCCTTCCCAAGCCTCGGTTTCCCGATCTGTGGATCCTTGCGCGCCGAATGGGTTGAAGCACTTGGAAGCT ACAGAGTTACGGGTCGGGACAATTCTCGGCACTGCCCCAGTTCAGTGTTTATAGAAAATTCTTTCTCTCTCAGTCCACTAAGACCGA GAGAGAGAGAAGAGTCTGGCACACCCGGGCGAGCGGTCTGAGGGATTGGAGGGGCTGGCGCCGGTTGATTTTTTCCGAGAATCTC CACTGGGGTGACGTCGGCAGCCGGCTGAGATGTGAGGTGAAGCGTTCTCTAAAGCGTCCGGAATGATCCGGCGAATA AAACGGGTGTCTGCAAAGTTAATGAATTGTACAAGGAGGCTGAGGGTGGGAGAGCCAGAGGCGGTTCTGTGGACG CTTCCCCCGTGCCCCTAGGGGTGCGCTGGGCTTTCCCAGCGAGGTCTGCAG |
| 145 | THEM233 | CCAGACAGTTAAGGTAAAACGTTGAAGTCAAGAGAAGAAGTTCAGCTCATCTGAGTCTGTTGCCAACTGGATAGGGTTGGTCTGCTCCATCTAAATGTATT AGAATTAAGTGGCTTTTATTCCAGACTTTCCCGCTGCTCAGTGTGAGTCTGTGCCTCCGAGATCTCTCCCCTCCCTCAGGGCTTAATGGGCTTTCGTCTCCTCCCT GAGCCTCTTCTTTATTCAGACTTTCCCGCTGCCAGTGAGTCTGTGCCTCCGAGATCTCTCCCCTCCCTCAGGGCTTAATGGGCTTTCATCTGCCTGTTCCT GTTCCTCAGGCTGACGTCCCCAGGACGCAGAGGGTGAGGTGATGCCCTCGAGCCCGCGAGCCGCTGGCTTTCAGAG CCTGCCACAAGGCGCGCCAGCCCCTAGCCCTGAGACTTCAAGAGGGCTTGAGACTGTCCACCGTGTTTTGACGAGTCCCCATCAACATCGTGGCTTTGGTCTTTCCATCATGG CAGTACGCCCTAGCCCTGAGACTTCAAGAGGGCTTGAGACTTGCCTCACCATGGTCCCATCAACATCGTGGCTTTGGTCTTTCCATCATGG TGAGTGAATCACGGCCGGCCGCCCGCCAGTGCACCGCCAGTTCTGTCTTTGTCCTCGAGGCCCTGACTATCCAACCCTCCGACTCTTCCCCGCAATC CCCTTCCTCACGGCCGGCCGCCCGCCAGTGCACCGCCAGTTCTGTCTTTGTCCTCGAGGCCCTGACTATCCAACCCTCCGACTCTTCCCCGCAATC ATCAGCACCTCTCTGCAACCCGGGAGTTCTTCCTGAGGCCACCTCGGGAAGTTCTTCTCAGAGCCCGTGAGCTTCAACTCCTC GCGTTTCTAGAGCCCCCAGTGCGCGCAACCCAGGCAGTTCTTCTCAGAGCCCGTGATGCCTCTATCCAGCAAAGTGGCGCCTCTTTACCGCGACCAGCCGTC CGGGGCCTCTGCTCTTCCCCAGGCGTCCCAGCCGATTCCCAGGAATGAACTAGGGCCTCTAGTGCGCTGGCGGCTCTCAGCTGCAGCAGCGCGTCACCGCCTTCG GTAGTTCTCCCCCGGTGCACTGCCCACTGCCCCAGGCAGTCCGCTACTGGCCCCAGAGCTCCAGCAGCTGCAGCAGCTCCCTCGTGTCC TGCGCCCCGGGCTCCCAGGAATGAACTAGGGCCTCTAGTGCGCTGGCGGCTCTCAGCTGCAGCAGCTCCCTCGTGTCC CGCCTCTCTAGGAGTGGCCGTGGGGGCGACGAGGGCCTGCTAGGCCCTGCCTTATTGACTGCAGCACCGGTCAGCCGTGTAGGAACACCCG AGGAGCCCACCAGGAGGGCGACCAGGGCCTGCCTCCCCAGGGCCTCCACCGGCTCACCTCCGCTGCAGCTGGCCACGGAACT GGTTCGTACCGCACTGTCCCGGACACACCCTTGCCGTCAGTGCGCTCGCTCCCGCTGGCGCCGGCCCACGGAACT CCCCGGCCACAGACGCA |
| 146 | NCOR2 | CTCTCTGAGCTCTTAGGAAGAAATGGAAATGACACCTGACCTGCCCTTCCAGGACTGACAGGAGGGGCTGCTCATGAAACCTCACTGTGC GGTCATAATGTCATTATCTTTGCCTTAAACAGGATTCTTGTCGACAGCCACCTAAAGTGGCACCCCTTAAACCTTGGCCATCAGCTGGACC CTGGTGCTCTCCTGGAGCCACACCAGGATGGCTTTCCACCGGTCATCCTGTCACCCACTCATTAAACCTGCTCTGGGAGAGGTGGCGA AGCCCAGGAGCCCCACAGGATGGCTTTCCACCGGTCATCCTGTCACCCACTCATTAAACCTGCTCTGGGAGAGGTGGCGA GGTCCCTGCCCCACATAGATGGAAACACTGAGGCTGTGAGATCTGCTAGATGATCTGCGCTGCCTTCGACTCAGTCGCGGTGACACGGG GCCAGGGCGGACACATACCCGGTTCTGCAGCCCTGGCTGCGGTTGCCCCAGGCTGCGTGCCTTCGACTCAGTCGCGGTGACACGGG CTTCTCAGCCTCGGGGCTTGGACGCTGCCTGGCAGCCCTGCTCAGTGACCTCCTTGGGAGCGTCGATGCGGCGGGTGACACGGG |

TABLE 4B-continued

| SEQ ID NO | GENE NAME | SEQUENCE |
|---|---|---|
| 147 | THEM132C | CTTGAAAACTCCAGCCCCTTTGTCCAGATGGGATGGAGGTGGCCAGGCTGCCCGTTGATTGTGCCAGAGAGCCCTCCCGGGA AGGCTGTGATTTATACGCCAGGCTTGTCACGGGCCGTGATTAAACACATTGCCCGGTCATTTTCATTTGATCCAATGTTAGTTGAAAGCCACCCAC TGCTGTAAACTCAGCTGGCTTGCGGGGCCCGTGATTAAACACATTGCCCGGTCATTTGTTGCCGAGATGGTGTTTCGGAAGGCGCTGTGAATGCA CTTCCCTTTGCGGGGCTCACACAGACAAGATGTGTTGCAAGGATGAGGCCCTGCTCGGCCTCAGCCCAGGGCCGGAAGGGAGAGA GGTGCTGTGCGTCGCGCTGCCTGTGTCGCCCGCGCTCTCC |
| 148 | PTGDR | CGCGTCAGGGCCGAGCTCTTCACTGGCCTCCGCGCTCTTCAATGCCAGGCGCCTCACCCTGCAGAGCGCTCCGCTCTCAA AGAGGGGTGTGACCCGGCAGTTTAGATAGGAGTTCTGCCTGGGGAACACCCCGCCTCGAGCTTTTCTGTGGCCCAGCTTCT CCGCCCGAGCCGCCGCGGGAGCTGGCTCCTTAGCACCCGGGGTCTCCGCCCTTCCGCAGCCTTCACTCCAGCCT CTGCTCCCGACGCCATGAAGTCCGTTCTACGCGCCTGTGTGCAGACAACTCCGGGTTCGCGTGAAAAAGCAACTCGCGTGATGGCGGGT GCTCTTCAGCACCTCCTGGGCAACCTGCTGGGCCCTGTGCGCGCCGCTCGGGCTGTGCTCCGCGGTCCACTG CGCCCGTTCGCCCTGCCTTCGGTTCTACATCGGAGTTCTGCGCCGCCATTGGACAACTCGTTGTGCCAAGCCTTCGCCCTTCTTGCCCTTCATGTCCTTCT GCTTCCTACGCTCAGAACCGGAGTTCTGCGCCATGGCACCAGAACTCGTTGCTGCGGCTGCTGCCCAACTCGTTGTCCGCCTCTTCTTCTACCGACGGCACAATCAC TTGGGCTTCCTCTGCACACTGCTGGGAACCTGCTGCCGAGCCCGCGCGGGCCCTCTTCGCCTTCTCTAGGGGCACCCTTTCTTCTACCGACGGCACAATCAC CCTGGCCCCTGGGCGGTCAGGGCCCACTGGTGCCCGTGGTCGTGCCGGCCCTTTATCCCAACCTGGCTTTCGGGGGTACTCGTGCTCTACTCCAG GCAGTACTGCCCCGGCCACCTGGTGCTTCTCCGCACCTGCTGTGCAACCTCGGCAACCTCGGCCATGCGCAACCTCTATGCGATGCACCGGGGATCACCT CCTTCATGGCGCTGCTGGTCCTGCCACCGTGACCCGTCTCTTCACTATGTGTTCTGCCGTAATTGTGAGTCCCGGCCCCAGGCAGGGCACTGA GACTGTCCGGCCGCGATGCGGGGCGGGAAGGGTGA |
| 149 | ISL2 | CTTCCGCCGCGTATCTGCCTGCCCTTTCTGCGGAGCCCTGGGAGATCCAGGGAGACTCGGGCGCTCCAGATGGTGTATCTGTACC TTCACAGCAAGGCTTCGCGCGGAGCCCAAGGCTGCGAGGTGCGCTCTATTTTGTCTGGGATCGGGTTTGTCCAGTGCAGCCCGGTTGCGGG TTCCGGCCGCTGCGCCGGAGCTGCATCGAGCTGATGGCAGTTGCAGCGCGCCAGTGCAGTGCAGCTGTTGCACTCCGTGCGGCAGCT GCAGAAGGTGGAGTGCCAGGCTTGCCTCTTGCTTGCCTTCCTCAGGGCGGTTGCTTCCAGCACCGAGCTGCCTATCGTGCCAAGTTGCCGCC CCGGCAGATCCCCAGTCTCAAAGTGGCAGAAAGGAGGCTTCGATCGAGTGCGGAATCAGAGACCCTAAATCACTCAA GGCCTTCAGCTCCCAGTGTCCCAGTCCAGAACGCAGAACCAGCCGACCTAACTGCAGACCTAACTGCAGACCTAACTCCGCCTTCTGCCCCGCAGACCTTCAGG GACTGACTTGGGAACGCGGGGACTGGTGGCGGCAGTTGTGCCCTCCAGAGCGCTCAGAGCGACCTGACCAACCGCCTTCCAACAGCTGGTGAGGCCCTGCCTACCC GCCGCCGTGGAAGGCGTCGGGGACTTGCCGGGTGGCCGGGATTAGCCACTTAGCCCATTAGCCCATTAGCCGAGGGGAGGGTGCCTTGGCGTTGGGGCTGGG TACAGCCCTAGGGCGTGGGGAGGAGGCGGGCGGCTTCCAGACCCGCGGGCCCCATTACGGCCCCTAAACCAGGTCTCCCTG GATTAAGTGCTCACAAGAGAGGTGCCAGGATTCGCAGGATTAACCAACCCGCTCCCCAAGGAGACACTTTCCTTCTCTCCCGAGCACCAGCTCCG TTCTCCAGGGCTTGCTCCTTCACCTGCTTGCCTTCCCGAGCCCAAGGCTGTCTGCCCGCGCCGTTCCCGCCCAAGCCAGTGTTCCCCGCCCAGCTTTCCCCGCCCGCCGAGCACCAAGCTCCGCCAGCGAC GTGACCTCCCCTCCGCAGCCTTTCCCGGACTCCCCATCTGCCGACTCCAGTTTCCGGCGCTCCAGCAGTCCGGCCCCTTCAGGGCACTGCCGGTGAGCGGGGACCCCTCCCTGG CCCGGACCTCCCATGCTCCCGGGACCTCCCATGCTCCCCAGTTCCGGCGCATCAGCGCTCTTCACCAGATGCAGACTCCAGGGATATGCAGGAACCCCCGCTGCT GTTATTTATGAGAGATACCGAGAGAACGGTCTGGACATGCAGAAACCAGAATCTGGACCTTTCAAAACAGGTTAGCTCTGCCCCTCCACGACTCAGAACCCGCTCCGTCTGT CCGAGGACTCTAGTTTTTCAAAACAGGTCTGGACATCTGGAGACACGGGACCCTGGATAACTCAGAAGAGACACTCAAACTCCCAAAGCCATTGCTGGGAAA CTCTCCACGCCACCTGTCCCATCTGCGGGAAAGGAAGGGATAACTCAGAGGAACAGAGTATGTGAGCCTTTGCGAACAAACAAACGTAAGTTA CGGCTTCCCGCCGGCCTCTAGCCGGGTCGCCCCTTGAAAGTGTTTCATAGTCGGGACTTGTATTTTGATCTTAATAAAAATAATAACCCGGGCGACCGCACTCCTCTGT GCTGTTGGCCGGCCCGGGAGGGCCCGCCGCCGAGGGCCGCCGGCCCCAGGTCCAGGGTCAGGCTTCAGGGCTGCCGGCTGCCGGCCGCCGGCTGCTGCGGGCG GGGCGGCCCGGGTGGGGATTGGGGGC |
| 150 | chr15: 87750000- 87751000 | AGTTTGGGGAGCCTTTTCTCCATTTGAGAAAAAACAAACTTACGACCGAGGGGTGAGGGGTTAGGGTTTGGATTGGGGAAAATGTGGTGG GGAGCCCCCGGAAGTGAGGAGGGGCTCCAAGGATTACAGTTTCCTTAGAAATCAATTCATTGTATTTTTATAATT TATTCTAAATCTTTCATGCGAAGAAAGTCAGTAGTAGTAGTAGTGTTAGTACTTGAGTTGAGTTGTGGTGCCCTCCTGATCACACTTGCATCTCTAGTGCCTTAAA |

TABLE 4B-continued

| SEQ ID NO | GENE NAME | SEQUENCE |
|---|---|---|
| | | GGTCTTGGGAATGGAAATATAAAAACTGTCTTCGTGATGCGTCATCTTTATCCCCACCTCCCCACCCATTCCAATATATTTTCTACTTCCAG<br>CCTAAATTCGGAGGCCCCTACCGAGGCCGGCCATGATCTTGAGGGCGCATAGGGAGGCCCTCTGTCCACCCCAGCCTGGTGATG<br>CCGTTCGCTTCTTGTGCCGGTATTGTGCGCTACAGACGCTTTCGGCCTACGAGCTGAGCGTCCAGGCCAGTGCCCTCAACCTCTCAG<br>TAATGTTTACCCGAGGCCGTGTGCAATGGACTATTCCATGGCATTGTCAAGCAGACTCAGGCGCCGCCGCGCGCTCTCGGCCTCCGGCTTGC<br>CAGACTCTGCTGCAAAACCACCTCACCCGTCTCTTTGCCAGGAGACTTGCTCTCTTAATAAATCTCGGCCGCCCCACACTTGCCCTAGACCTGCTCGGTAGA<br>CAGGTCCTGGCAAAAGATGCGAGGAGGAAGACTTGCTTCTCTCTTAATAAATCTCGGCCGCCCCACACTTGCCCTAGACCTGCTCGGTAGA<br>GGACTGGCTGGTGGATGCGCGGTCCAGCCTGCTGACCACCTCTATTTCTCCGACCGCCCCTGATTACCACTTTCGG<br>TTTGCGCTTACATCCGGATGTCGAATTTCCCAGGAATCATAATTATTTATTCTAACCCAAGGTTCAAGAAAAATCT |
| 151 | chr15: 87753000-87754100 | ACATTCCTTCTAAAATGTGGGCTTTCTGTGTACATGGCGCGCCATTCCCAGGACTCGTGTTCCCTGGGAATTCACCCAGGAATACAATC<br>GATTTTCTGAACCTGCGTAAGGCCCACAGGCAGCTCTGAAAAATGAAAGCGTTTGCTAAGTGGGGAGATCTCACGATCGAACGTTTAAAAA<br>TGGCTTTGTCTTCATTCAGCTCTCCCGATTTATTCTGTGTTTTACAAATAGAAGCTCAGAGCTTCTGTCGCCAGTCCTTGCATGACTCATGG<br>CGGTGGCCACACGGTTTCAGGGATACGGATGTTGGAAATCGTGCATATCGGAGTTTCCTAGCACAGTTCCATTTATACTGAACGCA<br>GCCGGCCTGGAAATCCAGCTCGACTTCTGACTTCTGTAATGACGTAGGACCCCTCCGGGGTCTGCGGGACTAGGTTCTGCGAGGACGTGTTCCCGC<br>TCCGATGTGGGAGGCCCTGCGCGGGACTAGGTTCTGACGAGAACGCCAATGCCATGCCGGAGAAGAGACAAGCTCGGCCCCGTCCATCATGCCGGAGAAGAGACAAGCTGTCGCCGGGAT<br>GCCGGGATCCTGGGCGTGCGTCCCAGAGCCTCGCGGTCCATCATGCCGGAGAAGAGAAAATCGGCCGTAGGCCTCCCCCAGTCACTAGGCCGGCCT<br>GGCCCGGAGATCCTCCCAGAGCCCTGCGCGTCCATCATGCCGGAGAAGAGAAGCTCGGCCCTGGAATTCGCTCAAACACAGATG<br>CTCATTTTTGGAATATTCTAGAAAAATTAACAAGATCTTGTTTGTCGTTATGATTCACGGGAGGTAACTGATGGAGGCCATTTACATGAGGG<br>CAGACACTGTGGGCGAAGGTGACTTCTGAGCAGCTAGGCTTTAAAGTAGGAAACGGTCTCCAAATTCCAATATCTCCGGCCTTACCGGTTGCA<br>AATCGGAAAAACCAGAGAACTCTGCTCTGTTCGCGCTTTCGGGCTGCCTCCGGGACTCGCGGAAGCCGCCAAGAGGGCGGGAGTAGGATTCCCT<br>TCAGCCCCGAGCCTTCCTAGTCCTGGAACAAGGCTCCAGGTCGCCCCAGTGCTCGTTTCGGGGCTGCCTCCGGGGACTCGCGGAAGCCGCCAAGAGGGCGGGAGTAGGATTCCCT<br>CCAGCTCCGCAGGGCATC |
| 152 | NR2F2 | TCCTCCTCCGGCCTCAGATGTCGTCCCACCTCTGGAACCTGGAACCTGGCCAGTCCCCAGCGCGGTTCGCCAC<br>CCGGCCGGCCGCCCCTGACACCCGAGTGGTGGAGGAAGGAGCAGCTGGCGGATGGGCCATTGAGAGACTCTTTGAAAATATTAAAAGA<br>CAGGATGGGTAGAGATTTCTCCGGAGAAAGTTCAATCCCGAGGCTCTCGGAGGAGTACCCAGCAGGAGAGAAT<br>GCTACCTGTTTAGGCCACCACTTGGACGAGCTGACACTTGACACTTCCCGGAGGACTGTCGAAAGGACTGCCGGTCATGCCGTTCGGCCGCCTG<br>CAATCCACTCGTTAGGCCGCGCTCCTGCCTGCGGACCAAGCCAGGGACTGCTCTCGGCGGCCGTTCCCACACCGCCCTGCAAGCCTCGGCGCTGCGGCGCAG<br>CCTTCACCCGGCGCCGGACGCACGAAGCCTCCCGGCCGGTGGTCGGGCCGCCCGGCCGGCACTCGAGGCCTGCTCGAGGCCCTCTGAGCCTGCTCCCCTCTGGCCTTGCGCCAAATCC<br>GGACGGAGGCCTGAGCCGGAGCCCCTTCGTCACCCGAGGCCTTGCTGTGAGCCTCCCCCCTCTGAGGCCTGCTGAGCCTCGTCCATCCTTTTCCATCCATCATCTGTTGAAGACACATCTT<br>AAAACACTCCAGCCGGAGTGTCTCTGCAGAGTGTGCCTCTATCCACATAATTTAACAATTCATATTTACCTTCTCCACACAGAGGAAAATC<br>GTTCGAGCCCGGCTATTTGTGTGATCAGTAAATATTAGTGCGGGGTTCCGAGGGGCTCTCCGCCTGCCGGGGGCTTCTCCCCCTCCCAGGCCCTGAATCGATTGCGGGCCACCGGG<br>AGTGCCACACGTCCGGCGGCGGCAAGGCGCCTCCTCCCCGCAGGCCTGAAAATTGCTCTTCCCGAGCCCTGAGCCCCTGAATTGGCTTTTCAACCTTTTACTTTGACATTCAGCCACTTCCCCAGGCTCTAATTC<br>GCAACCAGCTAAGGGGCGGCGCCTAAGGGTCCCCCCTGGCGCGAAAGCCGCCTACCAGCGGCGCCAACGCGGCGCCCCCAGCAAACGCGGCGCCCCC<br>CTCGGCCCCGGGACCACCTATCACAGCCCTGAGGGAGGGGGTGAGACTGCTCCTACTCTGAAGATCAGAAAAGCGCCTGCTGCTGATGCCGGATGCCGGATGGCCGTGGGTGAAGCGT<br>GATGCTCTCCGCCCCGACCCGGCCTTTCCCGACCCCTTCTCCTTCTCCTTCTAAGATCAGAAAAGCGCTTAGCTTGGAATTGTTAG<br>GCTACCCCTTTGCGCGACAAACTCCTCCGACAAAAACTCTCGTTCCTCCTTTCCTTCCTAAGATCAGAAAAGCGCTTAGCTTGGAATTGTTAG<br>TACTTTCCTGCAGAAAAACTCTCCGACAAAACTCTCGTTCCTCCTTTCCTTCCTAAGATCAGAAAAGCGCTTAGCTTGGAATTGTTAG |
| 153 | chr16: 11234300-11234900 | CCTAGGCATTCTCAGCCTCAGCCGTTTGCTGAGGGGCATTTGAGGCCTGCCAGCTAGCCAGCTGCCAGGAGTGTTACTGGGTGAAAAC<br>AGCCAGCCGGGAGACCAGTCTGCTTGTGGCCCGCCAGGGATGGGAAGCAGCAAATGCCACCTTCTGCCTGTCCAGCGTTGCTCCCATC<br>CCTCTTCATGGGGGAACTGGGGCTGCCGGGTTGCCAGGGGTTCAACAAGCGTTATCGTTCCTGGAACTCATGTTCCTCCGCGACTTCCCGAAGACC<br>AAGCCATGTGACGAGACAAGCAGGCCACAAGAAAGAGGTTTCAACAAGCTGCCCCTTCCTCCTCGCTGCTCGGCAGTTCCAACTCGGCGACTTCATCTCAGT<br>GGCTGTGCCTGACGCGGGCGGCTGCCAGCAGGGACAAGGCTGCCCCCTTCCTCCTCGCTGCTTCAGTTCACCGGCACCCCTATCTCAGT<br>CTGACTACCTGGAAGCAGCACTCCACCCTCCAACCCTCCAGCCGGCCCCTCCAGCGGTCCACCGGTCAACCCGGGACCCCTAGGTG<br>CAGGGGCTGCTCCGCCCCAGCCTCTGATGTTCAGGCCGGGCTGCACCAGCCGGGACCCCTAGGTG |

TABLE 4B-continued

| SEQ ID NO | GENE NAME | SEQUENCE |
|---|---|---|
| 154 | SPN | GCACTGGTTCCCCTTTACCTGAGCCAACAACCTCTACCAGGAAGTTTCATCAAGATGTCATCAGTGCCCAGGAAACCCTCATGCAACCAG<br>TCATCCTGCTGTTCCCATAACAGCAAACTCTCTAGGATCCCGACGTGAACAACGACTCCAGAAGAACTCTCCAGAAACCTCCAGTA<br>GGACCAGTGGAGCCCTGTTACCACGGCAGCTAGCTCTCTGGAGACCCCTGTGACCTCTCTGAGACCTCTGAGACTGCCAACTGTCT<br>CTCTGGAGACTTCCAAAGGCACCTCTGACCCCTGAGCCCTCCAGCGGGCCCCTTCCCAGGCTCTTAGCCTGACTATCTACAATGGCCACTGACCCCCTGT<br>TACCATGACAACTGGCTTCTGAGCCTCTGCTGTCCCTGTCCTGACCCAGTGTCCCAGTGACCCAGATGAGAACTCACGAGGCATGCTGCCAGTGGTGCCCTGTGCCCCTGCTG<br>GCGGTCATAGTCCTGTCCTGCTCTCGTCCCTGTCCTGCTGCCCAGAAGGCATGCTGGGCGCCCTGTGTCCTGAGCAGAGGCGGCA<br>AGCGTAACGGGTGGTGACGCCTGGGCTGGGCCAGCCCAGTGCTCCCTGAGGAGGGGCCGTGACAGT |
| 155 | chr16:<br>85469900-<br>85470200 | TGTCCGACAGGCACACACAGAGCGCCGCAGGCGCCCCAGGCGGCCTCATTCTTCACCCCGAGCTCTCCGCAAGGTCGGCGAGGAGCTGGAGCAGC<br>GGGTAGGAGCGGGCGGACCGGGCTCCCCGACGCGTGGGCCGACGTCCATCGACATCCCTACTGCCTGTGAAAACGAGCTCTGTAATCGTGCCGTC<br>AGCGGGGTAACATTGCAGCCTTATGTTTCCTGCCGCTGTTTACCTTCCTGAGCGCGTCCAATGGGGCCCCAGAATCCACACGCTGCCCTGAAGCGG<br>GACGTGACCCTGGGCACCTGTGAGGTCCTGGG |
| 156 | SLFN11 | GTCGGCTCCTGCGCCTCCAACGGGGTGGCCGTTCTCTTCCTGCACCCTCCTTCTCCGGTCGCTCGCCACCTTCCAGATACCCC<br>TCGGAGAGTCCAGCTGAGCTCTCGCCAGAGCTTCCTCGCGTTTGGGCCTCCAACCTCCCCTGTTCTGTTCCAACCTCTGTCTTGCCCAGATCTGGGCTTTCCATCGC<br>CCCAGAAAGTGGGTTTCTGGAGACCAAGGCCAATAATTGAAATTTGGCCTGGCGTGGCCGGTTATTGGGAATGAGGGAACTCGGCTGTCAATCCTCCGGCCTTCAGGGCTTGTG<br>TGCAGATTGGGCCCGCTTGGTTCCTGGCTGGTTTATGGAGGCTGCGGCTGAGGCAGGGCTCCGACAGACCCCGAGCCCCAGCTGCCAGAGTGGGATTT<br>AACGGCGCCGTGCGTGCTTGGTCAACCCGGTAACCGTCAGCTGCGTAGTGATATGAAAAAACCTGCAGCCTTCTGCTTTCTG<br>CCCCGCTGCAGTCTTTAGCACCCGCAGAATTCTGTCCGAGTGTTTGGA |
| 157 | DLX4 | TTTAGTGTGTGCATAAAACATCCCAGTTAATCTCAAATAGACTTTTCTGAGCAGAGCTGAAATTTGCAAGTAATGCAAGAAGACTCGG<br>GAGAGCGTCCCCATGTGGAGACGGGCTGGAGCCAACGGGCCCCACTGCGGGAGGGCTGGGATCCAATCCTCAGAAGTGGTGCTGACCCCAAGACCTC<br>TCCCCTCCTCCTCCCCCGGAGGCTTCTCCAGGGCTTATTTGGGAAATGAGGGGGAACTCAATCCTCGGCTCCCCAGTCCTCAGGGCTTGCTG<br>AGTGAGCGCAAATGGAAGCAAATGAGGGCCAATAATTCAAATTTCAGGAAAAGCTCAAATCGGAGAGGGGGGACGCAGGTTCTTCAGACTGTCCCATT<br>ATCAGAAAGAGAAAGAGGCCCAAATGTGAGGGCGCCAATAATTCAAATTCAGGAAAAGCTCAAATCGGAGAGGGGACGCAGGTCTCTTCAGACTGTCCCATT<br>CTCCAGCCCTGCGAATGCGTGCTTGGTCAACCCGGTAATCCAGGGCGACCCCAGGCGAAGATCTGATTCTTCCTTC<br>CGGCCGCATAGCCCAAACCGATTAATCAGTTTCTTCAACCTGAGTTACTAAGAAGAAAAGGTCTTCAAATAAAACTGAAAATCACTGCGAATGACA<br>ATACTATACTACAAGTTCGTTTTGGGCCGGATGAGCAGAAGCCACCGATAATCCCGAGGGCCGAGTGAGGAGG<br>ACTATGGTCGCGGTGGAATCTTCTGTTCCGCTCAGGGAATCCCGCCAGTGCGCTCTGAGTGCTGGCTCGGGTTACAGACCTCGGCATCC<br>GGCTGCAGGGGCAGACAGAACATCCTCTGTTCCGCTCAGGGCGACACATCCCGCCAGTGCGCTCAGGAGACTGCCGAGAGCACTGCCACTC<br>ACCAAGTGTTAGGGTGCCCGATAGACCCCAGGAGGGCTGGTTCGGAGGAATTCCGGGAAGGTCGGAACTCGGG<br>GTGATCAAACAA |
| 158 | SLC38A10 | CATGGTGCTTCAGGAAGGGGAGGGGGACGAGAGCCCTGGGCTTGGTGTCCACGTGGACAGCTAATGAGCAGCCTTGCCGATGAGGAGCA<br>TGCGTTCCGACGGCGGCCGAATGCGGAAGAGGCCCCGATGACGGCGGATTCTCTCCGCCCTGACCTCTCTCCGCAGATGAGAAACGC<br>GCTGACTTCAGCAGGGTCCCTCCCGAGCGGTCATCTGTGACCCCCCAGAGCCTCGAGATTCTCGAGCGGGATGCCCAGGATGCAGGATGCGGTGCATGTGCAGGAGCGCTGCCCT<br>GAAGTCCCGGCTTCCAAGGCGCACCCAGAGATGCGGTGCATGTGCAGGAGCTTTGGAAAAGCAGGAAAACACAGCCTAGTAACACTATGAATGGTCAAAAAC<br>GGTTTCCTTCCTTACCTTAAACTACTTAGGAAGAAGCACACGCGTTGCCAAACGCCAGA |
| 159 | S1PR4 | GCGCGGGGGCCGGAGGATGGCGGCCTGGGGCCTGCCGGGGCTGTCGTGCCGCCAGCTGCCTGGTGCTGAGAACTTGCT<br>GGTGCTGGCGGCCCATGGGCCCACCAGCCACTGCTGCTGCTGCTGCCGCCACATCACGCTGGTGAACATCACGCTGAGTGACCTGCTCACGG<br>GCGCGGCCAACCTGCTGGCCCGTCGCTGCGCGAAGGCCCGCAACCTTCCTGCAGGGAGCGCTTTGGCCCAGTGGTTCTCTACGGAGGGCCTGCT<br>CTTCACCGCGCTGGCGCCTCCACCTTCACGCCGTCTCTTCAGCCTTCCGCCTGCTGCTCTGCTCCCCCTACTCCAAGCGCGTACATCCTCTTGCTGGATGCGTGCCTTGGTCGCCGGCTGG<br>GGGCCACCAAGAACCAGCCCGTCTTTGACCGCCTTTGACCGCCGCGCGCGCTGCGCTCATGGGGCCATCTTCCAGCGTCAACCCTACTCCAAGCGGTACATCCTCTTCGCCGGCTGG<br>TCCTGGCCCCATCATGGGCCGCGTCCATGGGCGTCTGATGATCCTGGACAGCGAAGGCCAGGCCAGCGGGGCTACATTGCCTGGAACATCACGCTGGTGAACATCACGCTGGCCCCCGCCG<br>CAAGGCCCCGCCGCCCTTGCTGAAGACGGTCTGATGATCCTGCTGTGGGGGCCCACTCTTCGGCCTTCTGGGCCTGTGCTGCCG |

TABLE 4B-continued

| SEQ ID NO | GENE NAME | SEQUENCE |
|---|---|---|
| 160 | MAP2K2 | ACGTCTTTGGCTCCAACCTCTGGGCTCCAGGAGTACCTGCGGGCAGTGACTGGCCGTCCTGGCCTCCTCAACTCGGCGGTCAAC<br>CCCATCATCTACTCCTTCCGCAGTCAGGAAGGTGCAGAGCCGTGCTCAGCTTCCTGCTGCCGGGTGTCTCCGGCTGGGCATGCGAGG<br>GCCCGGGACTGCTGGCCCGGGCGTCGAGGTCACTCAGACCTCCACCACCGACAGCTTCTGAGGCCAAGGGACAGCTTTCCG<br>GCTCCCGCTCGCTCAGCTTTCCGATGCGGGAGCCCCTCGTCCAGCATCTCCAGCGTGCGGAGCATCTGAAGTTGCAGTCTTGCGTGTGGAT<br>GGTGCAGCCACCCGGTGCGTGCCAGGCAGGCCCCTCCTGGGGTACAGGAAGCTGTGTGCACGCAGCCTCGCCTGTATGGGAGCAGGGA<br>ACGGGACAGGCCCCATGTCTTCCCGTGGCCTCTCGGGCTTC |
| 161 | UHRF1 | GGGCGGGGTTGCCACACTGTCTCCCCTTTCTGCATGGGAGGAAGGGGCTCGAGAACTGAGTCAGCCACACAAAACGAGGATGGACAGAACT<br>CCTGAGTAGCGAGGTGCCTGCCGGCCGCGAGGAGGGAAGAGACGAGGAGGAAGAGGAGACCACCATGACA<br>GAGGGGCTGCCTCAGAACCACACAAAGCGCTTCCTCATCCTTTTCCGCCTGGCCTGGCCTGGCGGGCAG<br>ACGCCAGGTCTCCCTGCCAGGCGGGAAAGGGCTCAAGGCGGGTGCTCCTTGCTCGGGTCACATGCTACGTGGGGCCTTGCTCAA<br>ATTCACTTCCTGCCTTCATTACAAAACTGTCAAAGGGATCGCACGTTTGCAGGGTGTCACCCAAGCATTCTGTTTTGCAAACGACCGCTGT<br>GCGGCAGGCGGTCTGATGAGCTTTCGGTGTGGCGGGTCGGCAGCATTTCCTCCGGGGTTTTGAGCTCTGGCCACTTCTCCTTTT<br>GTTCCACCCAATCTCACCCACTTCTGGGCTTCGAGGCCCAGAGTGTCTTAACAAGGGGCACGT |
| 162 | DEDD2 | GAGCGAGACTTTGTCTCAAAAAAAAAAAACCAAATAAATTGAAAGCTGAGAAATTCAGAGCACAAGAAGACAAGCCGCCCCCTCTTTA<br>GCTGTCAACATGGCGGAGCCGTCCCTGGTGACGCAGCCTCCAAAGGCTCCTGCCCTCTGTGCCCTCCACTGACCCTCAGTGGCAGC<br>GACAGTGATCGTCTGGTGTCTTTGTTGGCCGGTTGTGTTGACCCTCACTGACCCCGAAGTGCCGCTCTAGGGTCTGTCCTCAGCGGTGACCCGG<br>CCGGGTCGAAGGCAGAGTTCCGCTGTCACTAGCCCTCTCGTGTGTCTGGGATGCCTCCGCGGCCGTCCACGCACCGCC<br>GCCCCCTCTTGTGTGGGTTCTGTCTCCCGTCTTCTAGGATCCTCCTGCATCCGTTTTCTCCTTTCTCTCCCTTCGTCTGTCTTGCCC<br>GCACCTGAGGTTGTCGCAGAGGCGCTGAGACGGGCCAGAGGCCCAGGAGCTGT |
| 163 | CDC4ZEP1 | TGCTGTCCCGGTCCTGTCGCAGTCCTCCAAAGATGCTAGAGTGACAGTCCTCTTAGGGGTAGAGATGGTCTAGAGGTGCTGGCC<br>CGGAGACTTGGAGGTGGAGGATCAATCCTGCCAGTTCCTGATCAGGAGGCCTCGTGCGGCGCCCCCTCCCATCCAGCAACAG<br>GCGGCGCCCAGCCTCATAGTCAGCCTCATCCACACTGACCACGGCGAACAGCCTCCCGGCGAACAGCTTCCGGTGACCTGAGAACTTG<br>TCAGGAACACGCCCCAGGGCCTGCAGCAGGGCGCCACTCAGGTAGTGCCCCAGAAGGCGTCCAAACACGTCCAGCCTGGGG<br>ATGTCACAAACCACACAGAGCCCAGGTCCCTTGAGCGCCAGCACTGCGGTCGCAGTACTCTCGAACCCGGAGCCGGATGTCGCAGGGAAGGAG<br>CCGCGGATGCCACAGCCCCTGCTCAAGGCTGGCCACTAGAACACACTTATGGGAACGCCACCCTTCCTCCCCC<br>GGATTTGTCAGGGAGGGGGCCCAACACTAGAACACACTTATGGGAACGCCACCCTTCCTCCCTCC |
| 163 | CDC4ZEP1 | TGATGCCCCGGCCCCCAGGGGGGCCAGGAGGCCCCGCCACCATGAGCCTGGGCAAGCTTCTCGCTGTGGGCTGTGTCCAGTTCACAGGG<br>AAAGAGCGGCTGACTGCAGACATGATCAGCCAGGCCACCCACTCGGGACTTCCGCCACACCATGCAGTGGCCCTGGGCGGGATGTCTTCG<br>GGGACACGTCCTTCTCAGCAACACCGTGGCAGCTCCGGAGCACCATCCACCCCGGCCAAGAAGCTGCAGCTG<br>GTGCGGAGGGTGGGGGCGCCCCCGGAGGATGGCATCTCCCCGCCTCCCCCGGCCCATCTCCCCATACTCCAGAA<br>CGCCATCTCCCTGCCCCAGCTCAACCAGCCCGCTCAACCAGCCCGTGTTGGCAAGCTCAGCTTCGCACAGCAGCCACCAGCTCCAC<br>GAACGGCCACTCCAGCTACGGTGAGGGCCTGGGCCATCTTGGCCACTTTTCAGA |

TABLE 4C

| SEQ ID NO | GENE NAME | SEQUENCE |
|---|---|---|
| 164 | chr21: 9906600-9906800 | GGCCGGGCAAAAAGCCCGCGCAACAAAAAGCTGCGCTGACGGCGCGGAAAAGCCGCGCGGCGGAGCCGAGCCAAAA<br>AGCCACGCGTGCGGCGGCCAAACAGCCCGAAAAAGCCGCGTGGCGCGGTGTGGGGCGAAATCAGTGGGACGCAGGGCAATAACACAAAAGC<br>CGCGGCGTGCGGGGCAAAAGCCA |
| 165 | chr21: 9907000-9907400 | TGGCTTTCTGGAGTGTCATGTGATAGGAAATGCAGCCAAAGACAAAAGAAGATGTAAGTAGGCTTGACTCATTGCAGCTAAGAACCCA<br>GATGTTACCTTGAGGGTATTAACTAATAAGCAGTTTAAATCAGATTCGATTTGTTTTGTATGTTCACATTTGGCAGGCATAGA<br>TACTGTTTGAAAAGAGAAAAGTCAGTACATAGAGGTAACAAGCTTAAATATGTGCCAAGTCTAGAAACAAGAGACTAGGGGATAAGGACCT<br>TTCGAAATTAAATGCAAGATTTGAAAACTGATTGGCTGGGGATGAGGCAAAGGCAGGTCTTTAAGGTCAATCCCTGTTTGCTTTAAGTTG<br>TTAGCGGGTGGTTTTATCATATATTGTAGAA |
| 166 | chr21: 9917800-9918450 | TTCCTGGGAATGTCAGCTAACCTGAGCCTAGGGGCCTGAGCCTGAGGGCCCTCCCAGCACAGGGAGGTGCTGCTGTGA<br>CAAGGGGTAGTCTGGCACAGTGCAGGCTACTCCCTAGAAAGATCAGCTTGAATATGCAGGAAGAGCAGGACCCCTCGGGCTGAGGCAGA<br>GGTGGAATGGAAGTGCATGGTGGTAATTTAGTTCTCCAGAGCCAGAGGAGCGGTTGGAATGCTGATGGCCCAAAGGGAAAC<br>CCTGGACTAACCTGCATGGCCTCCTCACTAGTAATTGCGGCTCTCCAGTGCTGTGAGGCCAGGAGTGTTGCCCAATGCTGTC<br>ATCATCCAGTTCACCCCACCCCCATCCAACAGATGAGTATGTCATGCCAATCAGTGTGGTCACCTCATCAGTTGCTCAGTTGTGAAAAGA<br>AATTGTTCAGAAGAAGAGCACTGGGCAAGGGCACTTCCTCCCAGGGCAGAGCCTCCAGCACCAAGAGCAAGAAGCGTCCTGGCACCAGACACTCAGGGACTGAAGG<br>CTGGCAGGGGCCCGCCCAGT |
| 167 | TPTE | TCCCCCAGCTGGGTATAAGCAAACTTTCCTGTCTATGGGCCGCAGAGACCACCTAGTTCCCCGCCAAACTTTACATGATTTTAATT<br>CTCCTGATGAAGATGAGAGATAAGCTGCGCCAACAGAGAGGGCCAGAGGATGGGACTGTCCACGGCAACCCAAACAGAATCCTGTCAGACCTCTGTTGATTCTGTA<br>TACCTCCTTATTGAGAATAAGTCAGTTCTGTTGTAGTAAGAACTTGTGTCCACGGCAACCCAAACAGAATCCTAGCCTCTTGTTGATTCTGTA<br>GAATGGGAATAGAACGAGCTTGCCCACAGACTTGCCAGAGATAATAGGAACACACTTTACACTGTTGTGGACTGTAAACTAGTTCAACCATGTGAAGTCAGTGT<br>AACAGGTGCTGAGGAGGATGTGGAGAGTAATAGGAAGAACACATTTACACTGTTGTGGACTGTAAACTAGTTCAACCATGTGAAGTCAGTGT<br>GGCGATTCCTCAGGGATTCCTAGAACTAGAAATACCATTTGACCCAGCCATCCATTAGCAGAAGTTGGAACCAAGACACCCAAATGTCAACAATGATAGACTG<br>TATACAGACACATGCACACGTATGTTTACTGCACATATACACGTAGGATGATATGCATGAAAAATGATGATCATCAACAATGATAGACTG<br>GATTAAGAAAATGTGGCACATATACACGTATGCAAGACAATAATGCAAACTGCATTGTCAAGGTCATGTCCTTTGTAGGACATGGATGAAAAT<br>GGAAATCATTCTCAGTAAACATCACACTCTGGGGACTGTTGTGGGTGGGGAGGCTGTTTACATATGTTAACTAACCTGCACATTGTGCACATGTAACCTAAAACTTAA<br>GACCCAGGAAGGGGAACATCACACTCTGGGGACTGTTGTGGGTGGGGAGGGGAGGATAGCATTGTGCACATTGTGCACATGTAACCTAAAACTTAA<br>GATGAGGAGTTTGTGGGTCAGCCAGCATGTCACACGTTTACATATGTAACTAACCTGCACATTGTGCACATGTACCCCTAAAACTTAA<br>AGTATAATAAAAAAATACTGTTCTGCCATACAGATACTCATTAAAGATGAGGGCAGAAGAGGGGGGGGGGAGAATGTACCAAAA<br>CCAAAGACCACAGGATAATAACCTCAGAGCCAGAGACTTCAGCTGCCTTTGTGGGTTACAGAGAATAACCAGAGGGCTCAGTTATGCTCTGAATAACTATGTTTGCT<br>TGAAGAAGTTTACATCAAGTGTTCACTGTTCAGCTCTCTTGTGGGTTACAGAGAATAACCAGAGGGCTCAGTTATGCTCTGAATAACTATGTTTGCT<br>TAGTGTTTTCAACATTAAAACAATATTAAATTTCATAAAATAGACAAGGTTGATAGGACTTGGGGGCATAACTCATTGACTCAAGCTATCATTTTATAG<br>GATTGTGAAAAACAAATAGATGAACATTTAAAAATACCTCAGAGAAGAAAGAGATTTTGAATATTCTTACATCAAAGACATGGTA<br>AATGTTAAGGCAATGAATGCTAATTTACCATGATTGATCATTATGCAATGTAAAATGTACTGAAACATCACATTTTAAAAACATGGCAAATA<br>CAATTTATTATGTGCGAATTAAAATTTTGAGTATAAAAACTTCAATTGTAAGAAAACAACCCAACTTTAAAAAACGGGCAAAATA<br>CGTGAACAGATATCTTACTAATAGAAGATTTGCAACTGGCAATGGCAAATTGTTTGACCGTTTCCAACTTGTCCAACTGGCATCGCTGGG<br>TAAAACTACAATAAGAAAACAATGCTGTTCCCAGACCAATTTGTTTGACCGTTTCCAACTTGTCCAACTGGCATCGCTGGG<br>GACCCTACGCCGACGTCCCCCGTCCCCCGCCCCAGACCCCGGCAGGAACCCCAAGCCCAACTTT<br>TCGAACAGCACCCACCGCTCCAGGGCTGAGTGTGACGGCCAAGAGCGGATGCAGCCCGGGATCGCCCGCCCACCTTCCCGTGGGCGGAAGCAGGAGCCA<br>CTAAATCGTCAGCGTGAGTGTGACGGCCAAGAGCGGATGCAGCCCGGGATCGCCCGCCCACCTTCCCGTGGGCGGAAGCAGGAGCCA<br>GCTGGGGAGGGGCGCCTAGAGGCGGCCTCCGCAGGACCCGGCGACCGGCGCCCGCCGCCGGCACTGAGCTAACACCACTCGGGGCGGCGGCGCCCCTTTACCT<br>GGGGCCTTGGGGGCGGGGGGTCCTAGGCCCATTCCTTCCTCACCGGGGGCGGAGGCCTCGAGCTAACACCACTCAGGGAGGTTTTCTCGGCCTTTTGTGCGACACCT<br>GCGGCTCCGGGTCCCAGCTCCATTTCCTTCACCGGGGGCGGAGGCCTCGAGCTAACACCACTCAGGGAGGTTTTCTCGGCCTTTTGTGCGACACCT<br>AGCGGGCGCGGAGGAGGGGCGGGCGACCGGGAGGGAGGCGGAGGGAGGCTCGCGGAGCGCCGGGCGGCCGGGTTCTCGGCCTTTTGTGCGACACCT<br>CCCGGATTCCGCGCCCGACCACCCGGCCCCCCAAAAGACACGGGGAGCACGGGGAGCCCGGCGACCCGCCATCCGCCCGAGCGCCTAGTGCC |

TABLE 4C-continued

| SEQ ID NO | GENE NAME | SEQUENCE |
|---|---|---|
| | | TTCGCGCTCCAAGACCCCCCCCCCAACAAAAAGGAGCTCCCCACCCCCTACCCCCGCCGGAGGACTTAGGGCCTCGGCTCACCTCGG |
| | | GCCCGGAGCTAAGTGACGGCCGCGGGGCTCCCTAGAGCTCCGAGTCCGCAGCCAGTCCGGCCTGGGTAACTGTTGGGTCAGAAACTG |
| | | TTCAGGTAGCAGCTGTTTGTGCCCCTCCCTGGCCCCCCAGTCTCGAGACGCCCCGGCCCTTGAACGCATTTTGAAGCGCCCCGCCCA |
| | | GCGCCCACGTGACTAGCATAGGCGCGCCCCCGTTCCGCCGCGGCCGCCCCTCCCGCAGACTCCGCCTCCCGCGAGCGAGCGAGCGGC |
| | | GCACTACCAGTTCTTGCTCGGCGACTCCGGCGACTAGCCGTGACAGTAGCCGTACCGGGCGGGCCCACCCTCCGCCATCGGCTTAAGT |
| | | GGCGGGCCCGGGTCCTGTCCGCCCCCCCCTCCTGCGAAGGTGTGCCTGGCAGGGAGGCGGGCCTGGGGAGGGAGGGGCCGAACCCTGGGTCA |
| | | ACAGACCCGGGTCCTGTCCGCCCCCCCCTCCTGCGAAGGTGTGCCTGGCAGGGAGGCGGGCCTGGGGAGGGAGGGGCCGAACCCTGGGTCA |
| | | CCCCCGAATTACAAACAAAAACTTAACGCCATTGCTCGCGGTTAGAAGGCAGCTGTGCGTTAGAAGGAAAGAAGCCACGCACCAAGAG |
| | | ACCGCACGCGGCTGGATACACGAACAAACCCAAAATCTCTTTTGAAAGGAAACCAGGCACAGTGGCTCATGCCTATAATCCCAG |
| | | CACTTTCGGGGGCCAAGGCGTCACCTAAACCCGAGAGTTCAAGACCAGCCTGGGCAATACAGCGAAACCCTGTCTCTACGAAAATATAA |
| | | AATTAGCTGGGCATAGGCGTGGACCCAGTGGCCACGTGGCTGCAGCATTTTGAGGCAGGGCCAAGATCACGAGGTCAGG |
| | | AGTTCCAGACCATCCTGGCTAACACAGTGAAACCTTCTCTACTAAAAATACAAAAAATTAGCCGGGCGTGGTGGCAGGTGCCTGTAGT |
| | | CCTAGCTACTTGGGAGGTTGAGGCAGGAGAGAATGGCATGAACTCAGGGAGGCGGAGGCTGCAGTGAGCTGAGATTGCGCCACTGCACTCCAG |
| | | GGCTGAGGTGAGAGGATCTTTGATCTCCGGGTGCAGTGGCCAAGATGGGCATCACCGCAGTGGGCAAGATGCGCAGCAGA |
| | | CCCTGTCTCAAAAAAAAGAGAAAGTGGGAGAAGAAAATGTTCTACGCTAGAAATCAACTTTCTTCTATGCTTTCTTTACTTCACCCTTATAGCTACT |
| | | TAGTAAATCTCACAAATCCTATCCTTCTGATCTCTGAAATGTATGTACCCTTCCCTTTCTATTCTCACCACCATGTTCTATTCTTTGTTCTTTCT |
| | | AGCCTGTGTAATATCTCATAATCGCACCTCCTGCCTTCTGTCTTTCTAGTCAGATACGTTTCCTAATTCTCAATATAACTGTTTCCAATATAACCATCCTG |
| | | CTACTGCTTTGTGTGAAATTCTCCAAAAGAAATTTACTTTACTGGACCCTCTCCCAAGCACTTGGCTAGATAATAATTAAAGAGTGCGGCA |
| | | AGCCAATCTTTCAGCCTGATTCCTCCCCTCAGTCACTCAGTTGTATTTCACAGGAAGCACAGACATTAAATAAATAAAACACAAAAATAGACAAGCA |
| | | CAAAACAAATTGGATTCTCCCCTCAGTCACTCACTCATGGAGTTTGTATTTCACAGGAAGCACAGACATTAAATAAATAAAACACAAAAATAGACAAGCA |
| | | TATAATTACAGTATGTATCCTAGAGAAATATCCTCATGCAGAAGCATACACAGGATGCAGCACTGTTTCCAATAGCGAAAAGCTAGAAAC |
| | | AACCTACATGTTCACCAAGAAATGCCACATACATATCAAATTTACTTTACTATACCAATATCAAAGTTCAGAGTCAGACCGGGTGATCACAACAGTGGTC |
| | | TGGCTCACCTGTAATCCAACACTTTGGAAGCCGAGGCGGGTGATCAGGAGGTCAGGAGTTCAAGACCAGCCTGGCCAACATGGTG |
| | | AAACCCCGTCTCTACTAAAAATACAAAAACAAATTAGCCGGGCGTGGGCCACGCGCCTGTAATCCCAGCTACTTGGGAGGCTGAGGCAGGAG |
| | | AATCGCTTGAACCCTGGAGGCGGAGGTTGCAGTGAGCCGAGATCGCGCCACTGCACTCCAGCCTGGGTGACAGAGCAAGACTCCATCTCA |
| | | G |
| 168 | chr21: 13974500-13976000 | TGTAGGAGTCCTCCGGTGCTCCAGAGCACAGTGAGGTGGGTCCTCCGTGCCATAGTGTAGGGCATGCGGACAGGGATCCT |
| | | GCCCTGCCATAGTCCAGTGCTTGAGTCCGAGTGCCAGTAAGGCAATGCTCCCAATGCTGGAGTTCACGGGCTGTGTGGGGTCCTTTGG |
| | | TGACTTAGTCCAGGGCGTACCAGGCGGGGCTAATCCACAGTTGCCACAGTTGGAGGAAGGTGGTTCCTGCCTTGCTGTAGTCCG |
| | | GGGAGCAGGGCAGGGGCTCCTCTCCCGGTCCTTGTCAGAGTCTCAGGGCTCTCAGGGCGGAGACCCTGCGGAGACGGGGGTTTCCTATGCGATAGCCACG |
| | | GGTCGGTGAAGCCGGTCCGGTCCCAGTGGCCGGTCCTTTGTCCAGGGACGGCGGCAGGGGGACCTGTCCTGCAGTGGACCTGTGGACGGGAGCGGAGGAC |
| | | CTGTCCTCCAGTCCAGTGCCGGTCCTCCAGTGCCTGGAATCAGGTCCAGTGGTCCAGCGGTCCAGGGTGTCCAAGCGCGGTAGTCAGAGAGCGC |
| | | CGTTGGCAGGGGCTCTAGGGGGCAGGGGCAGGGGCAGGGCAGGTCCTCTAGTCAGGAGTCTCTGTGCAGGAGTCAG |
| | | GACGTAGCCGAGGAGTCCTCCAATGCTGGGACGGGGCTCGCGGGCCCGGGTCCCATGCGGGCATCCAGAGTTCAGGTGA |
| | | GGGTCTTGGCGTCCAGTAATCGGGGTCTTCTTCTGTGTCTAGGGGTAGTCCAGGAGTAGTCCAGGGGACGCGTTCAGGTGCCCAGT |
| | | GCCCTGGGCCGGGATCCGGGGTCTCAGGTCCAGTGGGGGCCGGGACGGAGTAGGGCCGGGCCCAAGTTGCCCAGGACCAGTA |
| | | CAGAGGTTCTCCCTGGTCTCAGTCAGGGAGGGCAGGAGTAGTTCAGGGCAGGATCCTCGGGCGGATCCTCGTGCCGTTAGTCCAGGGCT |
| | | CTCTGGGACCCACAGTCCTCCAGGGGTCCGGTAATCCGGGCAGTCCAGAGCGGAGGGCAGGATCGCGGGCATCCCTCCTGTGCCTTAGTCGGCT |
| | | TGGAGGGCGTCGGACTGCTTGCAGTGGCCACAGTCCAAGACATCGCGGCCCCAGTGTCCAGGTGTGGTCCAGGTGTCCAGGGCT |
| | | GAGCCGCGGGACGAGAGGTCTTAGTTCAGGGCCGAGTGGTCTGAGGTCTTCTCCGTGCCAGTGTCCTCAGTGCCTCAGGGCCACGCAGGTGCGGGT |
| | | CCCACTGTGCCTCAGTTCAGGGCCGAGTCCGAGTCTCTTCTCCGTCCAGTCAGGGCTCTAGGGCCTGGAGAGCGGGGATCCT |

TABLE 4C-continued

| SEQ ID NO | GENE NAME | SEQUENCE |
|---|---|---|
| 169 | chr21: 13989500- 13992000 | GGGTTGGTCCTAGAAAGCGTGAGGATCGCCGAGTGCACTGCCTGCCCTCCCAGCTCTAGGGTCCACTCTTCCTTGGCCGACCCAGAGCTCGG GGTTTCAGGCGCTGGGCCCTGCGCAGCTGCCCAGAATAGGCTGAGCGGCCAGGTTCCCGCCCTTGGCAAGGGATCCAGCAGTGGAATCTC ACTGCTGTTGGCTGGCGTCGGGCAAGGTCAGCGGGGTTTCCATCGCTGCTGGGGTGCATCGCCCCTGAGGGTCTCTGGGGTGTAGCTGCAAGTGAGCGGTGG CAGAGACTGGCAGGGCTGGTCCAGACACCCTGAGGGTTCTGAGCGCTGGGATGCTGAGCAGCAGATTCCTGCCCTGCTGCAGCTACAGTCTG CCAGGACGGCGGTTACGAGGGCTAGACTCTGGGTACGCAGCCTGCAGGATGGGCGTGAGCAGCAGAGATGGGGGCTGAGTGTCCCGCCAGCTCATGGGCAGCAGCATCAGTCCAGATCTCTCGCCTGCAATCCCAGCCTATGGAGACCTCCCAGCCTATGGGAGCGACCACCTGACTTAGATGCTTGAG GCATCCGGTCCTCGGGGTTCTTGCTGTCGTCTCGCGGCAGGGGTCTGAGTTGCCTAAGGTGGCTGAGTGCACACGCTTCCACCCAGGGTCCG TGCAGCTGAGTCCGAGGCAGATGCTGTCAGGTGTCTGCAGTGGCATGAGGATCTGTTGGTGCAGATTCCCGCCT TTATTCCTAGGCCGGCTCCCAGATTGCAGGGTTTCGAGGCCGTCGAGTGCCATGGACACATCTGGTTCCGTGCAGATTCCCGCCT CCTGCAGCTGAGAGACTCCAATCTCATAACAGGCCGCTGCAGTGACCGTGCAGGGTCCTCGCCTTGGCAGAGAACAGA GCTGCCACCGCTGCTGCTTCCAGGAGTGTGCAGCTGGCAGCTCAGCTGGACCCTGAGCCCTGAGGCTGAAGGCCTTATTCCAGAAGCCT TGAGGGTCCCGAATGCACCGCCTCCCACCTAAGTTCCGCCTCAGTCTTCCTTGCCTGCTGCAGAGAGTTGGATTGCAGGCGCTGAGGCACAG TGCAGGTGCTGGGATGGGCTAAGCTGCAGGGGAGCCTGGAAGTTTCCGCCTCGGCCGTGGGGCGGGGGCTGCCAGCCTATGCGCCGCCCGC TGGTCATGGGAATCCGCACTGCCGACGCTGCCGTTGCGACCGCTGCTATAGTTCACCGTGCACGTGCAGCGGCCGGC CCTGAGCCCTGACCCACCCGGACCCTGAGCCCTCCCCAGAACGCCGTTCCCGCCCTCTACACGCTGTGGGCCAGATGCCTGCCGATTTGGCCACTAGG TGGGCACTGCGCAGCCTCCCGGAATCCGCTGCAGCCGCCGGGTTTCGAGCCGCCTGGTTGGCCACCGGGAGTCCGGGTTTGCCACACGGTCCCGCCACCCTAGGTCG TGCAGCGGAGCTTTAGACCCAGGGCTGGCAGGGCTGGCCCAGAGCGCTGGGAGTGCAGGGTCCTCCCACCCTAGGTCG CTCTCTTCCTTTCCCTTACCCCTCTGCTGCAGTGGAAGACAGATTACCTGCTCTCTCAACACCATTGCGCTGCTGGAGCCGCCTGAGGCGAGCCCATTGCCACCGTTCCTTCAT AGCAGCCGGATTTCCTCCCTGCTCAGTGGAAGACAGATTACCTGCTCTCTAAACCATTGCGAGCCTCAGGGTCACCAAGTTCACCGTTCCTTCAT GACCGGGAGGGTCAGGGTCAGGTTGCAGGTGGCAGCTGCTGCGGAGCTGTCCGGGACTTCGGGCCCCGGCGTCTGAGGGCCCGGTCCAGCGCCAGTTT CATAGTATCTGATCTTTTGCCCAGGCTGCTGGGGCCTAAGGTCTTTAGGCGCCAGGTGGCAGCTCCATAGCTTCTGGCCCTGCTGCTGACGCTGCTGGTGTGGGACAGG CACGTCTTCCTGCAGCTCGTCGTGCCCTGCTCCCGTGCCATCGGACATGCCACCCTAGGTTACCGTCTTGGCCGGATTGGGATGGGCCACCACTGGAATTAGCCTCTGGTGGTTAGGGCGAGGTTAAGAGGGTCGCCACTCGGGACATGCCACCCTAGGTTCCCCAATTGAGGCTTGGGCTACGGGGTCTGGG GTCAAGGGTTGCCACTGCGAGGCGCCACGGCGGGATGGTCTGAGTGACGTGCTGTGTGTGGGCAGGTTGCTCCGTTCCTTCCTAGATGAGAATGGGGGCACCACTGAATTAGCCTCTGGTGGTAT CTGACCCCTAGGGTGCTGCTGTGTGGGCGGGTCGAGCTGCTCGTGCTGGCGTGGCTGGGCGGTGCCGAGTGCGAGTGCCTCGAAGTCCCATTTGCACGCTGCCATTGCACCGTCCTCCTGGTA C |
| 170 | chr21: 13998500- 14000100 | AAATACTTCTACTGCAAAAAAACAGAATAGTAAATGAATACAGTAAAGTTTAGAATACAAATTCAGTCAAAATCAGCATTTCTATACC CAACAGCATACCATTCGAAAAGAATCAAGAAGAATCAAGAAAACAATCCCATTTAAAATAGCTATTAAAATGCTGGGAATAACATAAGCCAATAAAT ATGTCTAAAATGAAAACTATAAAACATTGATAAAATCAATTGAAAAACAGATTAAAGAATAAAATAGCTATTAAAGGAGTTATCCATTTTATGAATTAGAAGTAT TAATACTGTTAAAAATGACCATATACTCAATCATCAATCAGTCTATAGGTCCAATACATTCTTTAAAACGCTTTTTCGGTTCTGCATGCTGCAGAGATGTTAAAA AAGGTTTTAAAAATCGTTCTGCAGGATGTTTAAAAGGATTTTTAAAACGCTTTTTCGTTCTGCAGGCGAGGCTGTGCCGTGCTCCCGCCGG CCAGTTCCCAGCAGCAGCATTCCGCTCCCTGCTGCGGGAGCCGATCGCCGGGAGGAGCCGATTGGAGGAGGGCGACGAGGCCTTCCCCA GGTCCGGGCCGCCAGTGGCCAGTGCTCCCCAGTGTCGGGCTGCGACTGCCGGATCGCCGGGAGCCTGGAGGCGAGCCGCGGTCAGTGCTCAGTGCTGCCCAGAGC GAGCGAGTACCAGAAAAAGCAGCCGGGCTTCTCCGCTCCGCCGGTGGCCTCCCGGGTCGCCCCTGGGCGCGGGGACCCGGGAGCCCCCCGCTGCC AACGCGCTGGCCAGGCTGGCCGCAGAGAGCTGGAGAGCTGGTGTGCCCCACCGCAGGGCCGCCCAGCGCCGCCAGCGCGGACCCCGGGCCTGCGCCCGGAGAGCTGCCCGGAGAGCTGGTGTGCCCGCCACTGTTCACGCAGGGACTGAGCCGGCCAGCCTGCCCGGCCTGCTGCTGCACAAGCCG CTTGAGGCGCCAGCTGGAGGAGGGGCAGCCTGCTGCTGCTCAGGGAGGGCCAGGCTGCTGCTGGGCGGCGGAGAGCGGCCGGCCGGCTGTCACAAGTGGCT GTGACACTGCCCTGCGGGCTCGGGAGAGGTGCTTCCCGGCAGTGCTGCCCGGGCTGTGTGAGCGCCGAGGCTCAGCCCGAGCCGGCCCTGTCAGGCG GAGCCGCAAGCTGGAGGTGCTGGAGGTGGCTTCAGGGTGCCCGGAGGGCAGGAGGCCTGGCTTCAGGCCGGGAAGCTGATAAGTGACGAAGGCGGGTGCCACA CCCTGCAGTCAGGTGGCAGTCTGTTCAGAGCCCCACATGCGACCGCAACCCACCTGTTTGCCTCTATTGAGGAGTGGGAAGCTGATGAAGTGCGGGGTGCCACA AGGAAAATGCACATGGGAGGACACACCCGGTTACTATTTGAGTGAGCCCAGACAGGAGGAGGCAGCGGTCTGCT |

TABLE 4C-continued

| SEQ ID NO | GENE NAME | SEQUENCE |
|---|---|---|
| 171 | chr21: 14017000-14018500 | TGGGTGGATTGCTTGAGCCCAGGAGTTCGAGACCAGCCTGGACAAAATGGCAGAAACTCCATGTCTACAAAAAATACAAAAATTAGCCGGG<br>CATGATGTTCTGCGCTTCTAGTCCAGCTACTCCAGGAGGCTGAGGATCGCTTGCAGGAGGCGGAGTTTGCAGTGAGCT<br>GAGATGTCACTGCATTCCAGCCTGGGACAGAGCCAGACTCTGTCTCAAAAGAAAAAAAGAAAAAAAGAAAAACGAAATT<br>GTATTCTGAATACATCTTCTAAAGTACTACATTTACTTGCACTATATTAAACTGGTTTTATCCTGACCACATTGTAGGACCACCTTTGCTGAAGATACCACTG<br>TTGTTCTATTTTTTTGTCATCGCTTTTCTCGGTATGAGTGAGGCCATGTCTTCCGCCCAATTCCATCTGTCTAGCCTCTGGCTCTGGTCTTTTTCGAGCCTCTCCAG<br>CCGCAGGTATTCGTCTGGGCTGCAGTGTTGTTGGCTGTGAGAAGGCGGCGCGTGCGAGCAGCCAGCAGAGACTCCTAGTAGCTCA<br>GGCGCTGCCCTGCCCGGATGGGCCCTGCCAGGAGCCTCGGTGTGAGGTACCCTCAGCGTGGCCTTGCTGTGTCCTGCT<br>GCCTGGTTAGAACCCATCCCTCCCTGCCCTGTCTGTGAGAGCTGGCATGTCTGCCGAAGAGGGGCCCATGGAGCCCGGGGCGAA<br>AGGCGGCAGTCACCCTCTGAGGAGGCAGCGCCTCGGGAGGAGGAGCGGCGCGAGGAGCATCTTCCTGACCTGGTAATAATTAGGTGAGAA<br>GAGTGGGAGCGGGATGGGCCTCAGCTGCCAAGCTCGGCCTCCGGGTGTGGGACGTACCCTCAGAGCTGTTATTCCCAGTGAGGAGTGA<br>ACCTGGCCGGGATGGGCCCATCCCTGCCCTGTCTGTGAGAGCTGGGTGCCATGGAGGCCCGGGGCCAA<br>GTGTGCGCCCTTCGCTCCCTGCCCTGTCTGTGAGAGCTGGGTGCCATGGAGGCCCGGGGCGAA<br>CGGTGCCGAGCACATGGGCGGTTGTGAAGGAGCATGACCCGCTCAGGCTGCTGCTCCCAAACACTTACGGT<br>GGATGGTTGGGGCGCTGGCGTAACTCAGGGAGGAACACTGGTCAGGCTGCTGCTCCCAAACGATTACGGT |
| 172 | chr21: 14056400-14058100 | GTCTCTAGGACACCCTAAGATGCGGCAGGGAGACGTGAAGGTTGCGTCACACCCCGCGCTGAACGAACCTTCCGACACCCGTGTGACGCAAGGGCAGGCAGG<br>CTGCTCCAGAAGCTGCTCAGGCCACCTGGACGTGGTGAGGACTGGATGGGAACCTCAGGAAACGAAGACTCCCGTCCCGACGGGACCCGTTGGCTTCGGTCACTT<br>CGCCGCTCGTACGGCCCTGCTGGAGCGGTGTGCCGAGGCAGGCTTGGTTCTCCACGGAACCGCATGGGATCTGAGTCTCCCGACCAACATGAAGACTGCCCAGAGATCGCTGCTTCGGC<br>CGATGAGCGAGACCATGAGGGTTGCGCCCCGCTGTGCCGGACCCTGTGCGAGGCCTTCGTGCTCAAGGGTGGTGCGCTACAAAGGCCACCGTGGTCGGCGA<br>GCACCAGGCCAACCTGAGGTGGCGCTGGGAGCGGCGCCCAGGTGAACCTGGCCCAAGGGCAACACGGCCTGCACCAACCTGTGCCGAGACCAGCAGCTGGA<br>GATCCTGAGCAGGGCCTGTCAGTGCTCAAGGCCATGGAAGACCTGATAGGTCATACGGCATGAGCAGCCCGTTGCTCCGGCGTGACGGGCC<br>ACACCAACATGTGAGTACCTCATCCAGGAGCAGCCTCATGCAGGGGTAGAGCTCAGCTTAGGCTGCCCAAGAA<br>GGCTCCTCCAGCCAGGGGGTGCGCAAGCTGCCATGGAAGCCTTGCACCAGGGGATCTACCTATGTTGATGAATCGAAACTGAAGCCCCAGCTGCCTCTC<br>AGCTGCTGTCCACCAGCCGGGACTGCGGGCCAGCCATGGAGGCTGCCATGGAAGCTCATGGGTCGCCATCGGGTGCCTAGGCTGCTCGCTCGCTGAT<br>GCCCTTAAAACATCTCAGGAGGCGGGGCGACACCAGGAGGTCAACACACCCCAGAGCTCGTACAGGGCGCAGTGTACGCGACTCGGGAATATCGA<br>CTATGACTATTCCAGGAGCATCCCTGTTGGAGTACGCCTGTGGAATTGGGTGAGTACCTGCGATCACCGACGATGAGTGCCTTGTGTGAT<br>CCGGAGCCAATCCGCTTGTGAGTACGCCTGTCTCCTAGGACATGCACCCGCTGACATGCAAAGGCAGCCTGGGCACCAGATCGGCTTTGCAACTGCTGGCCA<br>GTGCTAATCCGTTGTGAGTACGCCCGTGTCCCTAGTACCGCGTGAATGGCCTAGGACCTGCAAAGGCAGCTGCAAGATGTGCCTCAGGACCTGTTTGCAACGACGCTGGCCA<br>CTCGCCAAAAGGGTCCGGAGTGAATGCGCCTGCAGCGTCAGGGACTCTGCCAGCTGCCTCAGGACGTCAGGCAGCCTGTCAACAAGGCGTGGCCA<br>CCTCACCAAAGGGTCCGGAGTGAATGCGCCTGCAGCGTCAGGGACTCTGCCAGCTGCCTCAGGGACGTCAGGGACTGCAAGAAGGCGTGGCCA<br>TCATCCCTCCACCTGCTCTACCTGCTGGAGAAAGTGGAGTGCAACCTGAAGCACCTGAAGCACATCTATCCGCCTGTCA<br>AGTGCGC |
| 173 | chr21: 14070250-14070550 | TAAAAATAAATTGTAATAAATATGCCGGCGGATGCCGGATGAGATGCCGACCCTACCGAGGAGCAGATGGCAGAAACAGAGAAACGACGAG<br>GAGCAGTTCGAATGCCAGGAACGCGTCAAGTGCCAAGTGCCAGGTGCCAGGTGCAGGTGGGGCCCCGAGGAGGAGGAGGACCGGGCCTGGCC<br>AAGGCCGAGGCGTGGCTGCAGGCTGCAGGTCTCGATTTCCCGCGTTCCCGTGTGCTCGTTCTCTTCTTTGCCGGAGCTTTCGCGGACGGCCGCCTCCGGAGGACTTC<br>TGCCAGGATCCGCAACAGGGCAGAGGCTATTATT |
| 174 | chr21: 14119800-14120400 | CGCCACCACGTGCGGGTAGCGCCGCATCGCCCAGCCGTGTTCTTGCTCCGGCCTCCGCCGCCTGTGAACTGGAGCACAG<br>GGACCATAGTTCTGGAAATTTATCCTTTTCTCCATGGATTCAGCAGCAGTGTCTAAAGAAGCAGCAACTGTTTTCAGGCTCTTTTATTAAT<br>ATATAAGGTAAAACATAAAACACTGGACCCAGTGAACCAGTGAATTCAGTTTACAGAACACAACTGTTTTCAGAGCTGTTTGTTAGAGCT<br>ATAAAAGGCCATATATATATTCTGTGGAATTCCCTTTTACTTAAGAATTCATTATCAGCAAGACGAATTAGTTTAAGGAGGCTGTTTGTTAGAGCT<br>GTGGTTGCATTCAAAAATTGGAATAGGAACAATGACTTTATTTATTTGAGATGGAGTCTCGCTCTGTCGCCCAG TABLE 4C-continued

| SEQ ID NO | GENE NAME | SEQUENCE |
|---|---|---|
| 175 | chr21: 14304800-14306100 | GCTGTAGTGCAGTGGCGCGATCTCGGCTCACTGCAACCTCAGCCTCCCGGGTTCAAGCGATTCTCCTGCTTCAGCCTCCTGAGTAGCTGGGA TTACAGGCGCATGCCACCAAGCCCAGCTAATTTTTTGTATT CCCTGAACAGTCAGAGTTTACTGCCCACTTTTGCTGAGGAGAAGCTCCTGAACAACTAGAGAGACTGTGGTTCCCAAAGAGCAGCCTGTA GGCCTGAGGACTGCTCATGACCGGACTGCAGTCCCTGCCTCCGTCCGTCCCTCCTCCGTCCTGCCTCCTTCCGGCCTTCTCTGACTA CCAGATCCAGCAGCGATGACGGCCAACTTGTGAAGCACGACTCCCCTCCTGGATCAGTTTGGCTTGCAGACCAACAACATCAAGTGAGTC CACTTGGATCCCCCTGCAGAGCACGACTCCCCTGCTCTCTGCTGCTGAAGTCCATGGGGAGCTTGCTGCCGGAGATA ACAGGTGTTTCCAGTTGCATGAGGGTGCTGAGGCTCCAGGGAGGACACTGAGAACCAGGGAGCCTCAGATGAGCACCGGGAGG AGCCCTGAGGCCCCAGATGAGCACTGAGGCTGAGGGCCCCAGATGAGCACCTGAGGCCCAGATGAGCACCGGGAGGAGCGTTGAAGCTCCAGATGAGC ACCAGAGAGGAGAGCTGAGGCTCCAGATGAGCCCCAGATGAGCAGTGGGGAGGACAGTGGGGAGAGCCCCAGATGAGCAGTGGGGCG CCCAGATGAGCACCGGGAGGAGGCCCGAGGCTCCAGATGAGGCCGAGGAGCCCAGATGAGCACCGGGAGGAGCCCGAGG GGGCAGGGAGGGCGCCGAGGCCATCCCCCTTGCTCTTGCAGGGTCATGCAGGGGATCGCGAGATCGGCGAGATCAACATCAACACTGACGA GGACAGTGTGAGCGAGCGGGGCTGTGCGGGAGGCGCCCTCGTGGAGCTAGGAACAGTCGCTTTTCTTGACCCTCCCATCATGCCTCCAGCCA TGGGCCCCACATCCTGAACTAAGCCCTGGGGACTCCCTCTGTCTCCCCAGAACCCTCTGGAAACTGACCTTGG CGTTTACTCTGCAGCCCTGCTGCTGCCCAGTGAAGGCCAGAGCCAGGTCGGGGCCTCGCACGACCAGTGCATCCAGCACTTTGATGAACGAGGACATCTCCGAGGACA GCGACACTTGCTGTCTGCGCTCAGATGCCCAGACCCTGCTGTTTGTTATGCCGG CCCCAGAACACCCGTCAGATGCCCAGACCCTGCTGTTTGTTATGCCGG |
| 176 | chr21: 15649340-15649450 | TTTGGGCCACGAGGCAAGTTCAAAGCGGGAGACTTTTGTTTTATAAAATGATGGTGAGCAGCTCCGGTTTATGTCAAACATCAGGGTTTCG TGCAGGATATAAACATTT |
| 177 | C21orf34 | ATTGCCGTACTTTGCTTCCCTTTGTATGTATTCTTGTATGCTGCCGAGTCACTGATGGCTAGCTCGTCTGCAAGTAATTCAAAAATGCTG TTTATGTAGAAAGGAAAGGTAGGGACTTTACCACACTCTGTCATTAAGGAGCAATTGAAGAACTGAGTAAATTACCATATATATT GCCTTTTGTTGTGCGAAAACATGCTAGCACAAACATCTCCTTTGTCAGCCAATGTTACTTCCTTTGTAATAACCATATAGTAGTTGTCT CCACATATGTACAAGAATCCATATTTGTTATAAAACATTGTTCATTATTTATAGGCTGCAAACATTCATAATCTCAAAGACTTTT ACATATCCACTCCACAGCTATTGTTGTTATTATTTGTTATTTTAAAAGTCTTAAATTAAAAAAAAAAATATATATCTGTTGTTGATTTT ATTAAGCAACTTAGGATTTCAACACAGTTTAAATATTGATGACTCAGATCTCGGCAGGTCTTACCATAGAAATGATTGATCTATACAGATTGGTCTCACTCAT AATAAAATTATTAAGCAATTACTTTTTATTAAGAAGTCTTCCTTTGCTTCATTATCACATAGAAGTGGAAAGTCCCCTTTGCTTCTCTGACCAAGGTGGGAAAATGAAGGCATAGA ATACAATCTAGGGCTATTAAAGAATTGCTGGCATTACTTCTCTATCACGTGCTGCCTGCTTCCTGAGGTAGGGAATCCAGG ATGAGACTGCCGAGCTGTTTCCACAACTGGCTCAATGAAGCACAAGACATTTCTTCCGGAAAGATGTCAAACAACTGAGAACAGCCAGAG AGTGAGGGAGGACCAACTGAGAAAATGAGGAGACCCTGAGTAGAGTGAGTCCATGCAAATGCTGATCCAGGTCTCAGAGGGTGGATGC TTTTTTTGCTTCCATCATCTGACCTAAAGGCTAGAGTGAAAGCCAGTGAAAATACCAGCGTCAAATGCTGTCCAGCAGGTCTGCAGCATCAGA TAGACTGTGAGTTAATGTTAATGATGACGCAGTGAAAATACCAGCGTGTGCGCGGCATCCGTCTCAGAGCGCCTCAGTCAGCATCAGA TGCTTTGCCCTCCGTCTCGGTGTCTGTATCGTATCCTGTGTGCCGGGATGTGCGGGCAGCGGTCTCGTCTAGCGAGGAGGGGT GGCGTGTCCAGTGCCGTGAGGCCTAAAAGCCAGTCAGTGAGAGCCAGTAAAATCGACTGATTTCCATCT TTGGAGCATCAGATGTATTCCC |
| 178 | BTG3 | GCAGCCTCCCTCTGAAAAATGTAAGCCATTTCCACTTTGTAAAGCTACGTTTATATTCCACCACGATACGATGGATAAAGAAACCAAGGCA ATTTAATATACGGGTTGGGAAGAAAGTTTTGCTGATGAAGACTACATTAGCCTCCACTCCAGCAAAGCAAAACACTAAAGAAAT GTACTGAATCTTTTAA |
| 179 | CHODL | TGCCTGAGCGCGAGCGCGGCTGCTGCTGTGATCCAGGACCAAGGCCACCGCTCAGCCTCTCCACTTGTCAGAGGCCGGGAAGAGA AGCAAGGCCAACGTGTGGTCCAAGCCGGGCTTCGCTTCTGCTTCGCCGCCCCTAACTTCAGTCCCCAAACG CACCCTGCCGAAGTCTTGAACTCCAGCCCCACATCCAGCCGGGCCAGGCGGCCAGCTCCGCAGGGTCGAAGGCGATGCGCG CAGGGGGTCGGGCAGCTGGGCTCGGGGGCCGGGCGGGCTGGGCGGGCGGAGTAGGGCGGGGAGGACCAGGAGCAGGAGCAGGGCGAGAGGAGGCTGCAGAGTCAGAGTCGGGGCTGC |

TABLE 4C-continued

| SEQ ID NO | GENE NAME | SEQUENCE |
|---|---|---|
| | | GCCCTGGGCAGAGGCCCGCCCTGCTTCTGCTGCTGCCACCGGCCGCGGATGAGCCGTGGTCTGCTGCTGGGC |
| | | GCCGCGCTGCTCTGCGGCCACCGAGGCCTTCTGCGCCGTCAGCGGTGAGTCAGGGGCCGTCTCCCGAAGAACGAGCGGGAG |
| | | AGGGGACCACCGGGGCGGGCCGCGGGAGAAATTGATTGTGCTGCTTCTCCTCTCTAACACACGCAGAGTGATTTCACTTTCTTTGTGAGACCTTGCTTAC |
| | | GAGGCGGGAGGAGCCAGCCTTCTGCTTCATTACGAGCGGCATAGCCTTTTCAGGAGTGATTTCCACTTTCTTTGTGAGAGAGTGACCACAC |
| | | GTAGCTGCGGACCGAGCCAGCCTTCTGCTTCATTACGAGCGGCATAGCCTTTTCAGGAGTGATTTCCACTTTCTTTGTGAGAGAGTGACCACAC |
| 180 | NCAM2 | TTCAATTTACACTGCACACGCGGTACTGGGTGTTCGGGGTAGGCACTGATCTGGGAAGGTCTCCCCCGACCCAACTCATCT |
| | | TTGCACATTTGCAGTCCTTCCGGTGCACTCCGGTCTCTGGCTGTTCGGCGGGATCTGGCCAGTGGACCTGGGACCCACTGGGACCGCAGCGAGTG |
| | | AGGCCAGGAGACTTCAGGCCTTCAGGCGACAGCCGTAGGCTAAGCTGAGGTAAGGCTGAGGTTGAACGGAGAAACACTCTGTACGTTATTTCCGCCACCCTTTTAGC |
| | | GTGTCTCTCCCGTAAGGTGCCGCTCCCAACAGCAATGCCGTGAGGTGTAGAGAAAACACTCTGTACGTTATTTCCGCCACCCTTTAGC |
| | | GCTGAGGACGACAGTGTGACTTTAGGGTACAAGTTGCTTCCCCTGTCGCCCCGGGGGGTGGGCAGGGGACAGCCGC |
| | | GCAAGGGGCCAGCCTGCTCGGGGCACCGCCCCGCTGCTTTGAGGGAGGAGAAGGAGAAGAGTCCACGGAGAGACAAGAATCCCCTCCCCACGCCCAAAA |
| | | GGAATAAGCTGCGGGGCACACCCCGCCCAGATCCCCATTCACGTTGAGCCGGGCGCG |
| 181 | chr21: 23574000-23574600 | TCATTATCCGATTGATTTTCCTGGTATCACATCACTTAAGTTTAAGTAGCTCTTATGTTACTTAGTAATGACTGCAAAACACAGTTGTGATGC |
| | | GGGCAATTTGGATACAACAAAAGAAGCCATTAAGTTTGTTCCTTAGTTAACAGGTGAAAGCTCTCAAGTTATTAAGGATAAAAATGCTAGTA |
| | | TATATATATGTTTGGAACTATACTGCGGATTTTGGATCATATCCGCCATGGATAAGGAGGAATACTATATCAGGTTTGTTTTTAAATTCC |
| | | ATGTCTAATGACTTCGTTATCTAGATCACCTGTAGATCACTGTGTTTTATTGTGAGATTTCCTTGGTTTTTATCTTTTGATTTGTTTTTCATGTTA |
| | | ATACTGAAATTTTTAAAATTGCATATTGTACTTCCTATATGAAAATTTACTATGTATTTTATTTTTTCCTTTTCCTTTTAGGAAGAATTAG |
| | | TTTGTTCCCTGACAGAGTTTAGGATAAGGACAAATTACTTGTCTCTATAAACACTCAGATGTTTTGACCCGGTGTTGTAGGGGTTATCTTTTT |
| | | CTGGTTTTGCATTTTTATTATAGACATAGTGCTT |
| 182 | chr21: 24366920-24367060 | AGAAGAGAAATCCGTAAAGGATGTTGTATTGAGTTTGAGTTTGCAGTTTGACTTGTGTTTGATCTTGCACAGATTTTCTCAGGGCGCCTTAAGACCGGTG |
| | | CCTTGGACTGCCATCTGGGCATAGACAGAAGGGAGCATTTATACGCC |
| 183 | chr21: 25656000-25656900 | CGAAGATGGCGGAGGTGCAGGTCGAGGTCGAGGTGCTCGATGGTCGAGGCCATCTCCTGGTCCGCCTGGCGGCCATCTGGCTAAACAGGTACTG |
| | | CTGGGCCCGAAAGTGGTGCTGCATCAGACATTTCGAAGGCATCAACATTTCTGGCCATTCTACAGAAACAAGTTGAAGTACCTGGTTTCCTCC |
| | | GCAAGCGGGATGAAGCCCACCCACCCTTTCCCGAGGTCCCGAGGTTCTTGGAGCCTGCATCTCTGGCGACCGTGCGAGGTATGCC |
| | | GCCCACAAGACAAGCAGGCGAGGCCAGGCTTGCGCCTCCTGAAGCCTCCTACAAGCAGTGTTTGACCGCCCTTGGCTCACGAGGTTGGCTGAAGT |
| | | GGTGTTCCTGCTCCCTCCCACCGTGGCGTCCTCTGGAAGGCTCGTCTGAAGCAAGATCACCTACACCAGAGTTGGAATAAAAAGCTCATGAGGCTACGG |
| | | ACCAGGCTGACAGCCACCTGGGAGAACATGGGCGCTGCCCTTCCCCATCGTCGCCCTGAATGTACGGGACCTCCGGGGCAGCAGTCGCAGGGCCAGG |
| | | AAACAGGCCGAGAAGAACATGGGCGCTGCCCTTCCCCATCGTCGCCCTGAATGTACGGGACCTCCGGGGCAGCAGTCGCAGGGCCAGG |
| | | TGTTAATTCCTCCGGACACACGAGGAAGCTGGGAGGAGCCAAGGAAGAGTTAGTCACTGCCTCCCGAAGTGCTTGAAAGCACTGTGCAGG |
| | | CAGCCCTCCGGACACACGGAAGCTGGGAGGAGCCAAGGAAGAGTTAGTCACTGCCTCCCGAAGTGCTTGAAAGCACTGTGCAGG |
| | | TGTCATTTATTCTATGACCAATAGGAACCAGTTACTATTAGTGAAAGGGAGCCAGAGATGTATTGAGGGGGCCCTATCTTGTGAGC |
| 184 | MIR155HG | GCTGAAGACCATTTCTCCTTAGGGACCATTCGGTCTCCAGTGCTGGTCTCCAGTGATTCGGTCAAGATCGCCACTTCCCCGACTCAGCCAGCCAGCCAGCCAGCCAGCCAGCCAGCCAGTCGGCGAC |
| | | CTCCCTGAACCAAGGAGAGAGTAGAGACATTCCTCTGCACCCAGTGCAAGAGTCGCCACTTCCCCGACTCAGCCAGCCAGTCGGCGAC |
| | | GTCTGGGCCGTCATTGAAGGTCCATTTGAAGCCTTTCTTTAAGAACAACAAGTTGGAACCACGAGGAAAACAAGCCAGGAAAGTTACACGGC |
| | | GTGTGTTGAGAGAACAAATACACAAAGTTTCCTTAAGAACAATGACCCCAAGTCTAGGTTCCAAGAACAGGGAGAAGGGAAACACCAACTACCCGGGCCTGGGCTTTTC |
| | | GACTTTTCCTTTAAAAGAGAAAAAATGAAAAAAGTTTTCAAGCTAGGTTCCAAGAACAGGCAGGGAGAAGGGGGGCTTGCAGAAAA |
| | | GGGCCCTGGTCGGTTATGAGTCACAAGTGAGTTATAAAAAGGGTATATAAAAGGGTTATATAAAGGCCGCGCTTCGCCCACCTTCAGGACGGTCCCCAGGGCCCCC |
| | | CCCAGCCCCGCCTCCAGCCTCGGGGGACTAGGGCAGGAGCCCGATAGCGGAGCTCCGCCCCGCGGGAGCCAGCAGCCCGGGAACCAAGGAGCGCT |
| | | CCTGGCACTGCAGTCAGTACGCCCGGTTAACTGCGAGGCAAGCGGGGCCGGCCCCCAGCCGTCCCGCCTGCCCCTTGAACCAAGGAGCCGCGGGACTTCGT |
| | | GCGAGGGTCACCCCCGGGTGCCCCTGGGGACTCAGTGGTGTCGCCTGCGCGCAGAGTTCCTTGGATGTTGGTGGGCCTGGATTGGCCCGGGGGCCTGGGATTGCTGTCGCCCTGGAATAATGGCCCTGACCAG |
| | | AAGGAGGGGTGTTCGAACTGTGCAGAGATGGCCAGAGAAGTGTAAACACACTAGAGGGGCAGTGCCCTTAAGGAGCCCGATAATGGCCCTGACCAG |
| | | CTTCCCCTGTTGGAGTGCCCAGAGAATGGCCAGAGAAGTGTAAAACACACTAGAGGGGCAGTGGCAGGAAAAAGAGACTGCCCTTCTTATATTTCG |

TABLE 4C-continued

| SEQ ID NO | GENE NAME | SEQUENCE |
|---|---|---|
| 185 | CYYR1 | ATTTCATTTTGAAAAATAACTACAAATCTATTTTAATTTACAAAGTTAGACTCATAGCATTTAGATATCATGTCTTCATTTAACAGAAGTGAA GATGGAGCAAAGCCTCAATCAGCGTCTGTATTTATTCGCTCCTCGTTGTGCCAGGGTGCGTTTTGCCAGCGCGTTGCCTTTCTTTACTCACA AAACCCCTTGATGTCTCCTCCACGTTTACGAGGGAGAGCCGGATCTTTTGAAGTTGTATCATCTAAAGCAGGTATATTGGGATGACT ATGGATAGAATTTAACCTGAAAACACTGAAGTTGACAGCTGACAAAG |
| 186 | chr21: 26938800-26939200 | CATAACAAGAGTCATTCTAATGTGATTATAAAGGACCCGAAGCTTTGCTTTTAAAATTCAATACTTAGGTAGAAAGAAAATGATAACTTTTCC CTTTGATTTTATTCACTATTTTTATACACTAGCAGCCTGAGACACCGGATTGGAATATCTACGCCTCTTGATGTTACCTGGGCACCACT GCATCACAGTCCT |
| 187 | GRIK1 | AATAGTAATTGCCAACAGTCAAGATATGTACTACCACCACCAAATTCCGTGTATTTGTGATCAAAAGATATACACAGATACTTGAAAACTGATTTC TACGTTGCATATGGGAAAATACCTCATTTTCTCAGCTGTCCATTATTTTGAGATATTATGTGCAGTGATAGTAAGAACAGATTTGGA ACACATCAGCAATAATTTTTCAATCAGATGCTCTGCCAAATGAAAGAATTTGACAGTATCCGACACCCGTACTCATGCTTGGCTTCTGTAG AAACTGGCTTGCAAAGGGCAGCTGGGTACTGTGTTTTGGTACCTCATTCTTTAAACGTATAATGGGAATCTGGTTGGTTCAGGAAAACC CTTGCCTACTTATTATTACTCTGTTTT |
| 188 | chr21: 30741350-30741600 | GGGCCATAGTACTTAATGTATTTTAAACGTTTAAACATTTACTAATATAGAACCTTCTATTGCCTATTTCCTTCGGTTTATTCCCTTCCTTCTGT CATTGAAGAAATGTTCTAGTGGTAGAAATACTCCACGATTGAGAAGAATGTGGGAAGAAAGAGGGCTGGTGGGTAAGAATTGCTCATGA TGTCTCCCTCTGAATTCTGTGCTCTCACAATGACACTCCAATGTGTGTTTGACGCCTGGAAGA |
| 189 | TIAM1 | TGCTTCAACCGGAAATGGTTGAATTACCCTTACAGTGAACCTGATCAGTGGTAACAGGAGATGCTAGAACAGGAAAAGACAAGTTTCCCC TTTCCTCCCTATCCCAATCACTTTGAGGTGTATTTTTCTTGCAACCCTCCAGAGAAGTCGGCAATGTTAACGAGCATGCCTGCCAA GTGGCTTGCCTTATACCTCATTATGAAGTGATACTCAGGGCCACTACAGCCACATCGCACAGCATTGC |
| 190 | TIAM1 | TATGATTCCCTCGATTTCCCTCAATCTTAACCATTGTGATCACAGCAGGAGGGCCAGAAAGTGAGCTTCAGCGTGCCCGGCACCGGACCTCAG CCCTCCCTTAAACTTTCCCTAATCCTCGGAGCTAGTTTGTTACTCAAGTGACTCCACAGTGTTGCCCAAAACGTGAATGTCAAATCCCTCAAGGCAGAAGGCTAT TTCCAAAATCATGCTACTTTTGCCCTACCTTTGCCCAGCTAAGCAACATCACCTCTGTGCCAACAATTGGTACAAGATCAAGGCGCTTCGTTGGCAG CAAGTCAACTTCGGTTTCAGAAGAAGTCACTATTTCCTGAGGTTAAACCACAAGACACCACATTTTAACCCCAAATCT GCCGACTGAGGGTAACCATGATCCTTCCTTCACAGCACC |
| 191 | TIAM1 | TACTAAATCAACCCGAGAACCCGGTCATGGAGAAATAAATGATAGTAATCTATGCTGTCTTCATCGTCTTCCATCACTCACTCTCT TGCTGAACAAGAAAGGGCCACCCATGTAGCAACACATGTAAAGAGCCGGAAGAC |
| 192 | SOD1 | TATTATTTTGTTCAAAGTAGACGGGTATATACTAACATCTGTGGGCAAGTTACCACACGCCACTTAAAACAGGCTAACAGGGTCATATGCCAAA ACGTTCAGGTTTGCATTTTTGAAAAGCTCAGAAGCTCGACAGATGTGTTCCGGCCGATCGTTCCGGCCTCAGTGAGAAGGAAGCAG ATATGACAAATGTCACTTATTTCAGAACTAAAACCCAGAGGAGCAGCCTGAGCCAAAAGGAAGTGATCAATGAAAGACGGTCGA ATCTGCTCACAGGCAAGGGG |
| 193 | HUNK | AAGACCTGGAGTTTCCATTACACCGAATTGGCACTTAATAACTGGCACTTGTCTGGCGACGCATTTCTTAAGCACCACATTTTCGTAAAGTGCTTAAAATT GCTCCAGTAGGCAGGTGCCATGAGGGCACGACTCTGTAGAGGTGTGCAACAACTCTGAACAAAATATACAGAATATTTCAGAACTTTATCA GTAAAATTACAAAACGTGTGCAAGGAAGGTGCTTGTGATAAACACTGTCCCCAGAACCTTAGTGAAGTTACCAACTGTGGAAAATTTTCTCT TGCACTCGGCTTAAAATCAT |
|   | HUNK | GCAGGGGTGACTGGTCCTCTCTCTCGCACCTCGAGAATTCTCTGAAGATCTGAGCCCCGGACGTCGTGCTGCACTGACCGAGAAGC TGGGTTACAAGAACAGCGACGTGATCAACACTGTCTCTCCAACCGCGCCCGCCATCCTGCCATTCACTTCTCTTAAACAAGAAACT GGAGCGCTATTTGTCAGGGGTAAGTGCGACCCTAGAGGCGATCGTCTCTGCTTCGTCTGTGAAAAAGAGCTCCTACCCCAAAGTGCTTCT CAGTTGCTGACACTTGATCCAAGCTGCTAATTAATCTAATGTGAGGCTGAGTTTTCAATGTGGGATAAGTCGTAGCTAAAGCTGAAAAACCTGCTTCT CAGGGAGTGCCTTTATCTGCAATGTTTTCAAAT |

TABLE 4C-continued

| SEQ ID NO | GENE NAME | SEQUENCE |
|---|---|---|
| 194 | chr21: 33272200- 33273300 | AGTAACGGGATCAAATTAATTATTATTTGGTGGCCGCCTCTTCTTCCACCCAAGCCAGCAAGACTCACCCTGGCCCTGCCCC CAGCATTTCAAATGGAATACCTAGGTGGCCCAGGGGACCCCTGACCCCTATATCCTGTTTCTTCCTGCCTTTGCTACTTTCTCCTTG ATAAAAGGAGAGAGTGAGAGATATTAACAAAAACATGCCCCAGGACAATGAAACAACTGGCTTGGCCGCCAGAAATGTATCCTGGT TTTCTAGTGAACTTCTCCCATCAATCTTTCCTTTAACCTCTCTGTTAGTGGAAGCAATAGGAAACACCCCTCCCCTCCCCCTGAGCAAATGCT TCTTTTGACTGGAAACAAAACAGGGGCTCGGCGAAGCTGAGGTGAATCTGGGCTGCATGGCGCCGCACAATGGGCCCTGTTCCC CGGCCCGGGCTTGTGTTTTACAACAGGGGACAGAAAAGTGACAAAGAACCGGGGCGGGGAATTAAAACAAAATGCTCGACTAAA ATCTTCTGTTCCACCACCGGAGGGACAGAAAAGTGACAAAGAACCGGGGCGGGGAATTAAAACAAAATGCTCGACTAAA AAATCTTCATATCTGCATATTCCAGAAAAGCGCTTGTGGAGAAAGGCCTGGAGCCTTCTTTTGTCCCAGATGAAGTACAATAGGCCACAGGGCGG CTGATTTATTGATGAAGCTGAACGACTTGCTGGAGAAAGGCCTGGAGCCTTCTTTTGTCCCAATACCAGCAGCGGCGACGTTTGTGTGAAGATGGCAC AGATCTCTTGTGATGCTCTCGGGTCTCTGCCTTTCTGCCCCTTTCTTCCTTGCCTCCCCAGTATTATGCCAGGGACGTTTGTGTGAAGATGGCAC CTGGGAGACCGGTGACAAGACTGGGCCCTTGAAGAGGCGTATTATGCCAGGGACGTTTGTGTGAAGATGGCAC ACTCCATTTTGTCAATGGCTCTCATCGGCCCAGATAATCGCCCCTGCCTGCCCAGGGGCGCAGCCGGCCGATTCATGCGCCCTCG GAGAAAGTA |
| 195 | OLIG2 | GTCTTTCCGCCCCCTTGTCTAAACTCAAAACCGAGTCCGGGCGCGAGTCTCGAGGGCGCCTGCAGGGCGCGTTGCGGCTGAA CCCATCCGGCACAAACTCGGGCCACTGCCCTGGGCCCACCTGGGGAGTTTGCGCGTGGCCTCCAGCCCGGGCGCCCACGTGGCGGAAG CTTTCCCGGGCGCGGCTGCCAGCCCTGGCTAGGAGCGCTGGAGCGCGCTCCAGGTGCGAGCGCCCATCAGGTGCCCGCCGCCACCATGGATCACCGCCGGTC GCACGTCCCGCCATGGCCCGGGGACCAGGGGCCCCCATCTCCGCGGACCCCTCCGGACCCTCAGTCCCGGACCGCCCGGCTCAGGCGG GAGGGCAGGCGGCTCCCTGAGGGCGTCTGTTGGGGGACCTCGGGGAGCTCAGGGGCCGTCATTACTGATGGCTAGCAGGGGAAACGGGTTGTCACTTCGGCCTC GATATTGGAGAGGGCCGTGAGTGAGTAGTCCAGGGACTGAGTAGTCCAGGCATTTTGAAACTGAATAACCTAGGGAAATTGTAGCACTGAAGCCACGTG ACTGTCTTTGCCTGTGGAAATCTTTGGCGAATCTCTATCAGAGTCTTATCACCAGTCTTATCACCAGTGTGCAGCCCTTCTGTCCT GTCCCTGTTGCTGGGCCCAGGAATGCAAAGCAGTCAGGTCAAGCGAGAATCAAAGCAGTCCAGGCACTCTGCAGCATCTCTGGAGG AAGCCAGACCCTTACACACCCTGAACCCCTGAACCCCTGGAACGGCTTGACAGAACAAGGCTTGACAGATGCTCAGATGAATGCTTCTGCCTCCAGCCCCAGCAATGTGCATTATTTATTATGTCTCCAGGAGTGTGATGGCGAGGCC GGTGGGGGAGGATGGGAAAGCCTGAAGGGCTTAGAGGGGCTGTAGGGCGGCTGGGCCAGCCCAGCGAGCTTGGGACCCC GTAGGCCGGTTAGAGGCTTGAGCTAGGCTTGACTTGATCCCTGACAGGCGAGGGCTGGAGGATGGAAAAGCCCGGGACTGACTAAAACCAGGTGGCCCAGATCTTAA AGAAAACACCATCTGCGGTGAGGGTCCCTCCATGCCCCATATTAATACCACGTGTCAACTACTCCGGCAACAACTGCCCATCCGGTAACCCGGCC CCAGTCGGGTTTTCCCAGTTCACATTATACCAAACGTCTTGCCAGCAGAACTGTTCAGCAATGCATTATTAACCCTTGACCTCCTGCTC TCAGATTAATCACAACTGTCGAAGGGGTGCTTCCAGTGGCTGGCTATCACCAGATCCTTGACCGTGTGTCTAGCATTCTCTGGGG TGGGGGTTGTGGAAGGGAGGTGTAGGATGGAAGCCTCAGCATGTAGGATGAAGCCCTAGCAATTGTGATCCGGTGGGCTGATACTGAAGCCACCCT GCCTTGACCTCAATTTTCAGTATCTTCATCTGTAAATGGAACAACCTTCCCTCCTAGCCTCAAAGGGCTGCTGTCAAGATTGGCTG AGATAGCTGTTTGCAAGCTGAGCTCAATGAAAGTCATTGTGTCCCCTCAGTCCTATCCCAATATCTCTCACTGAGGTGGGGGCA GCTTAACTCAAGGCACTCAAGGATAGCCCAGGAAGAACTCTTCCAGGCGCACTCCAGCTTTCCAGGTGGCTGTTCCTCGCAGGATCTTGAGAAGAGGGTTGACT GGGAGGGGCAGTTGCTGGTTGGGCTTCGTTAGGTTGCATTTTGTTGTTCTTCATTTCCTTTGGTGCTGAGCTTAAGCCAGGCAGCTAGCAGCACCCCTTCTGATTCACAC CCAGGCCTTCCTCCAGTCACTCAGATTGTTAGCAGAAGACAAAAATTACAAGGAGGGCGTCATGTGATTCTTACACACCCAGAGA CACCTTGGAAGCCACACAGGTAGCTTCAAGAGCCAAACCATTTTACCAGCAGAAAGGAAAGGAACAACTGAGATCTCTGAGTCTCT GAGCCCACACTCACCTCCCTGCCACTCCCCTGCAGCACTCGCTGCTGGCAGGATCTAAATTAAACTATGTTCAAGACACCTGCAGTCGTCAAGACACCTCTGTCAGATCCTGCACA TGTCTGTAAAATGGAGTCATACCTTCCCATGGCCGGTAGAGACTAAATTAAACTATGCTGAAGACTCGTCAAGACACCTATATCCCAAGATCCAGA ATTTAGGTTGCCTTCAAGTGCCTTCAGTTGTCATTAGGTGGAAGTCAACACCAATCATTGTAAAAGTGCCATATTGTAAAGTCCACATGTATTTACGACCATGTTTCACATCA GTCCGCATGTGGAAATCTGCACGTGTGTCATCGCAGTATTTCGGCAGTATTATTCGACAGTATTAACCAGCCGTCTGACCAGCGACTCCAGTCAGATCCAGTCATAGCACATGTTTGGTAGCCAACTGTCTCATGACCGAGGAGCGATGCGTGC ACTGCTCCGACCATCTGGAGAGTTCTGACTTCGGGGCGTCATGTAGCGCTAGACGGAGACACCGGAGACCGGAGACCGGAACCGGGATAGCGCATGAGCTGTTCATTCACGACCAGGAGGCTGCGTCTCCGCAAGAACCTCGTTCTGT AATGCTTTTTCTTGCAGAGTTCTGACTTCGCTGCTTCCGGGGCGTCATGTAGCCTGAATGTGAGCAGGAACTCGGAAGCGCAGCCTATTAAAGTCGGGATAGCGCATGAGCTGTTCATTCACGACCAGGAGGCTGCGTCTCCGCAAGAACCTCGTTCTGT TTGGCAGCCAGGCGAGACGCAGCCTGAATGTGAGCAGGAACTCGGAAGCGCAGCCTGATAAAGTCGGGAAGAGGAAGGCCGGGAGGGAC |

TABLE 4C-continued

| SEQ ID NO | GENE NAME | SEQUENCE |
|---|---|---|
| | | CCGGGAAGCAGTGGAAGTCTGCGCCCTGAGCCCCGAGAGCCCCGGTTTGGCACGGGCTCTCCTCCCGGGCCCCGGCGGTCC<br>AACAAAGGCCGGCCGGCCACACCCCCCGGTCTTTTGTGGGAGAGAAACACGGGGAAAAACCTCCATTCCCCAGGAGGAGGGAGGCCAACAGCACCA<br>GGACGCGGGGGCCAACCAGAACTCCCCGAGCCCGGGCCCATTAGCCTCTGCAAATGAGCACTCATTCCCCAGGAGGGCCCAGCT<br>GCGCCGCTGGTTGGGAACCCAGTGCCTCGGAACCCGCCCAGTGCCGCCCAGAGTCTCTGGGACCGGAGGCCCGACAAGTCCTGGG<br>GACGCCTCCAGGACGCACCAGGGCAAGCTTGGCACCAGGGGGATCTAATTCTAGTTATTCTGGGACCGGGTGGGAGGCATAGGAGACA<br>CACCGAGAGGTACTCAGCATCGCCAGGGGGAAGGAGCCCCAGGGAGCACAGACTCCCAGTCCCCAAGCTTCCCAAGCTACTCGG<br>CGACGGGAAGATGTTGAGGGAAGCCTGCCAGGGCCAGCAGCGTCCAGCAGCGTCCACTTGCCTTGCAGGCTCTAGAC<br>TCGCCCATGCCAAGACGGGCCCCCTGACTTTCACCCTGACTCCCAACTCCCAGCCGCTGACCGAGCGCGCAAAGAACCTGAGACCGCT<br>TGCTCTCACCCGCCAAGTCGGTGCAGGACAGACAGCAGTGGGCAGCAGCAAAAAGAAACCGGGTTCCGGACACGTGCCGGCGAC<br>TGGACTAACCTCAGCGCGTTGCAACCAAGGAGCCGCACGTTGCGCCTGCTGGTGTTTATTAGCTGGCAGGCGCACAACTCCGCGC<br>CCCGACTGGGCCCACAGCCCCACAGGGTAGGCCCAGGAGGGCATCTACAAATGCCCGAG<br>CCCTTTCTGATCCCCACCCCCGCTCAGTTCTTTCATGTTTTAAATACATATTTAAACGATGCTGCAGAGCCAGCTGGGAAACACGCGGATTGAAAA<br>ATAATGCTTCAGAAGGCACGAGCTGGGCCTTCAGCGGTCTGGCTTCTACTTGAAGACCAATTATTTACTACTGCTAATTGTTGCTTGT<br>TAGGGGCAATAACCGTACTTGCAATGGCACAGTGTCAAGTCCTAGCATCCCCAGATCTGCAGAAACAAATGTCTGAATTCTACACTGTCCTCAGATAAGGAACCGCAACAAATGTCTGAATTCTCAGAGACTGTGCTGTGC<br>TTTTAAAACCGTACTTGCACAGTGTCAAGTCCTAGCATCCCCAGATCTGCAGAAACAAATGTCTGAATTCTCAGAGACTGTGCTGTGC<br>CCGCGCTGCGCTCACAGTGTCAAGTCCTAGCATCCCCAGATCTGCAGAAACAAATGTCTGAATTCTCAGAGACTGTGCTGTGAGAAATTCAG<br>CTGCTCTGTAAAGCTTAGCAATTTTTCTGTAGGCTTGCTGCCACACGGTCTCTGCAATCTGTAAAATGGGTGAATGCATCCGTA<br>CCTTCAGCTACCTCCGTGAGGTGCTTCCATCTCGGCTAATTCCTCTGGCCCACAGCGTGGAGAAGCCTTGCCCAGGCTGAAACTTCTTT<br>AAACATGTCCCAACGCGTCGCGAGTGTTCCATCTCGGCTAATTCCTCTGGCCCACAGCGTGGAGAAGCCTTGCCCAGGCTGAAACTTCTTT<br>GCAGTTCCAGAAAGCAGGCAGTGGGACGGAAGCAGGTCTTTTGCTAACCTTTTACACGGAGGCCCTGCTTGGACTACAGATGCCAGCGTTGC<br>CCCTGCCCCAAGCTGTGTGATCAACAAAGACGACACTGAAAATACTATCATCCGGCTCCCCTGCTAATAAATGGAGGGGTGTTTA<br>ACTACAGGCACGACCCTGCCCTTCAAAGAACATCTTCTGCAGTCCGTCCGCTCGGAATAACTGTCCTGTACCCACACCATCCTCAACCTAAAGAGA<br>GTTGTGAATTCTTCAAACACTTCTTCTGAGTCCGTCCGCTCGGAATAACTGTCCTGTACCCACACCATCCTCAACCTAAAGAGA<br>CGTACCGGCTGCCGTCCGGAGTTGCAGCCACCGCCATCTCTAGACGCGAGTAGAGCACCAAGATAGTGGGACTTGTGCCTGGGC<br>ATCGTTTACATTTGGGGCCCAAATGCCATGTTGATGAAACAGTGAGATGGAACCAGACGAGGAAAGCT<br>AGGGAGGAGACCCCGGATCTCGGGTCCGCAGGGTTTTCCGCGCGATCCCAACCTGACTCTGTGCCGTATTTTTACAGAAATTTGACCACGTTCCCTT<br>TTGTTAGACTCTGCAGATCTCCAAACCATCCCAAACCTGACTCTGTGCCGTATTTTTACAGAAATTTGACCACGTTCCCTT<br>TCTCCCTTGGTCCCAAGCGCGTCAGCCCTCCCTCAGGGACGCCGCCCATTTGGTTGTGCGAGGAGGCGTGTGCCCGGCCTTGGCGAGTTTCATTGAGC<br>GTCCCCCCAAGAATCTCCCGGCCACGGGCCATTTGGTTGTGCGAGGAGGCGTGTGCCCGGCCTTGGCGAGTTTCATTGAGC<br>GGAATTAGCCCGGATGACATCAGCTTCCACCCGGAGACTTGCTCTCTTGTGCGGCCAGCTGCAGCCCCTCAGGACACGCACATTGTTC<br>CCCGCCCCCGCCTCGCCGTCGCCCGTCGCCCAAGAGGGGACAGCTCCTCAAATGCCATCCAGATCAGGGGTCT<br>TATAGATCGACGCGACACCAGCGCCCGTGCCAGGTTCCTCGGTTCCTCAAATGCCATCCAGATCAGGGGGTCT<br>CCCCGCACACAGCCAGCCCGACTAGATCCCAGGGACACTTTGTCTCTCTTGTGCGGCCAGCTGCAGCCCCTCAGGACACGCACATTGTTC<br>GGATCCCTACTCTGCGGGACACATCAGCTTCCCACCCCCGGTCGCCGTCTGAGCCCTGAGCTCCTCCCCCGGAACAAGGCGAG<br>AAGTCGGAGCCGCAACACAGCTCTTTCTGCCACCAGTCTTCATTCTCCATTGTGCGTGTCAGTCCTAAAGGAAAGGCCCTAAAGGTGCGATGCTTAT<br>CCCGGGCCCGGCTCTGGGTGCCATGTGCGTGTCCCCAAAGAAAAGGCCCTCACTCCCCTGGTGGTCGATGATTAAGGTGCGATGCTTAT<br>CCCGGGCCCGGCTCTGGGTGCCATGTGCGTGTCCCCAAAGAAAAGGCCCTCACTCCCCTGGTGGTCGATGATTAAGGTGCATTCCCACAC<br>CTAACTAGGACCCGAAGCCTCTAGAATGCCACCGTGTGTCGATGATGGTCAGCGGCCGGAGGCCGGTAAGGAGAGGAGCAGAGG<br>GGAGATAGAGAGCTTAATTATAGGTACCCGTGCAGCTAAAAGGAGGGCAGATTAGTACGAGGGGACGAGGAGCCACGGCC<br>ACCTGTGCCGGGACCCCGCTGTGCTGTGTATCGGTCAGGCGGGGAGCAGTTTTCTGCTCTCACTGACTCACTCTCTCTCTCCCTC<br>CTTCCCCTGGGCCATGAGATGCCGGCCTTCACTGGGCCGCTTCATTCTCTCGGAGGACACCTAGGAGGCAGTCCTTCAGGTCCCGAGCTGAGGCCACCGGCTCGCGG<br>AGTAAGGGCAGCAGCGGCAGCGCCTTCACTGGGCCGCTCATTCTCCGTGGACACCTAGGAGGCAGTTCCCCAGAGCGTCTCAAGATCAAC<br>TGCGCGGCCTATGGCTCTCGCGGCTCCGCATCCTCGGGGACCAAGCTAGGAGGCAGTTCCCCAGAGCGTCGCAGCTCGTCG<br>TCTACGTCGTCGCGGGCGCGCGGGCCCATGCTCCACCAAGCTAGGAAAATAACCAGAAAGGCCAGCTCGGGCATGCCGTCGTCG<br>AGCCGAGCGCAAGCGCATGCACGACCTCAACATCGCCATGATGCGCGCCAACTACATCCTCATGCGCCAACTACCTCATGCGCAACTACCTCATGCG<br>CAAGCTTTTCAAGATCGCACCGCTGCTGCTGGGGACGAGATGAAGGCGACTGGTAG |

TABLE 4C-continued

| SEQ ID NO | GENE NAME | SEQUENCE |
|---|---|---|
| 196 | OLIG2 | CGAGATTTACGGGGCCACCACGCTGGCTTCACCCCTGCGGCTCGGCTGCGCGGCACTCCGCCGCTGCCCGCCGCCACCGCG<br>CACCCGGCCAGCAGCCACGCCACCCCGCGGTGCCACCCCATCCTCGCCCGCCGCCGCCCTGCCCAGCGGCTGCTGCCGCCG<br>CTGCAGCCGCGGCTGTGTCGCCGGCCGGCCCTTCAGCGCCGTTCTGCCCGGATCCGGGCTGCCTCATCCGTCACCGCCTACTCAAG<br>TCTCCGTCTGCTGCCGCCGCCCGCCCCGCCCTGGGGCGGCGGGGCGGCCGGGCGGGCGGGCGGAGCGGGGCTTCCAGCACTGGGGCGGCATG<br>CCCTGCCCCTGACCGATGCTGCCAGGTGCGCGGCCCCGACCACCACAGTGTCGGCTATGCGCCGGAGCCAGCCTGCCTGCGCCTCACCTCG<br>ACGCCAAGTGAGCTGTGTGCGAGAGGGGCAGGACATGAGCGAGACATCCAGCATCTGCAACCAAGCAAT<br>TCGGAGCTCTGTGCGAGAGGGCCAGGACATGAGCGAGACATCCAGCATCTGCAACCAAGCAAT<br>GGGGCGCCCACAGAGCAGTGGGAGTGAGGGAGTGCTCTCCGGGCAACTCATCCGACCCCAACCCTCCGGGAAAAGATTCTAAA<br>TAGACATCGTTTATGAAAGGTACCGCTGTGTGCATTCCTACTAGAACTCATCCGACCCCGGGGTAGGGAGGGGACAC<br>AACTTCTTTCCCTGAGACGTGCTGACTGCTGACAGTGGGGCAGCAGCGTTGGGCACCTCGGGGGTGGAGGGGACAC<br>ATTGGGCGCCTTGCTCCTCTCTTGCCGCACAATTGCCCCCCACTGCAGAAGCAACGGCCGACGGCCGACCGCCCTCC<br>AGGGCTGTCCCTGGCCAAGGCCACACAGTTAGTTGGAAGCCGTTCGTGATCAGAGCCTGATGGTCATATCCAATCTCA<br>ATATCTGGGGTCAATCACCACCCTCTAGAACTGGGCCGTTCTCCTGTCTCGTGATTTTGCAGAGAAATATGGTTTCTAATAAATCTGTG<br>GATGTTCCTTCTTCAACAGTATGAGCAAGTTTATAGACATTCAGAGTAGAAACCACTTGTGATTGGAATAACCAAACCTGCCCGATTCAGG<br>GGCGGCTGTGTAGTATTATATTTAAAATAGAACAAGTTGGTTATAAGCACAAAGTGATTGGTTATATTTGGTA<br>CCTGAGAACGTTAACAGAATTAAAGGCAGTGCTGTGAACAGCTAAGCTGTTGCTCACGTGACTGCCAGCCCCATCGAGTCTAAGCCGCTTTGCAGG<br>ATGTGTAAATTATCAATGATGAGGTAAGTGCGCAATGCTAAGCTCTTAAACTGGTAAACTCCTCCGGTCTTTCTCACAACTTGGGGATCGTCCCCA<br>CTCTATTTTGGTTATTTTGCCACGTTTAAACACATGCATTATCTTTCCACCTGTGCCATCCCGGGTCTTTTCACAACTTGGGGATCGTCCCCTATTTTAT<br>GTTTGGCACTAGAGACACATACGCCATTATCTTTCCACCATGCATTACTCTTCCAGTGAGTATTGAGCATTTCCAAAGAACATCAGAGAGCCTCCCGGAGCATCGACTTTG<br>TTTCTGAACTGGGCTTTGTAGCGTCTGCCCGTGTAACAAAACCATTGTCAGTTGAGTATTGAGCATTTTCTGACCTCTGCTGCACACG<br>GGACTTCGAGGGTGAGGGCTGCGCCTCACCACCTTTGGGGCTGGGCTGGGGTTTCAGGCTTCAGTCTTCAGGCTGCTACTACCTGATTTTTGATTTGAGAGCCAGCGTTCC<br>GCTCAGAGCCGCGTCTCCCGTGCAAAGGCTGGAAGCTCCCGTCCCGTTCCCGCTGCCAGATCACCCTCGCAGTCCGTCCGGAGGGAGGGATTGGGGATCCTGCGCCCCTGCAGCGGATTTGGTGCAGATTAATCTCACTACCTTTCGCAGGCGCTCCCTTGATTCTGCGAGCCTAGCGTTCC<br>CCGCCCTTGAGCTGCAAGGATCAGGTTGCTCCGACCTGCCACCTCTGGAGGAGCACCAGCGGCTTTGGCCCTCTGCTCTTTCT<br>CCGGCACGGCCCGCATCCGCCAGGATTGAAGCAGCTGGCTGCCCCAGGAATTTCCTTTGGCGACATTGCAGCTCAGCCTGCGCGCCA<br>CAATCCGTCCACTGGTTGTGGAGACGTTGAGTGGAGGTCCCCAAGGAGACACGAGAGCTTCCAGAACCCGCTACGGCCTTTGCACATCAGGTCCAAAC<br>CCCAAACAGCCTCCAAGGAGCACCAGTCCATGCACCCGAGCCCAAAATCACAGACCCGCTACGGCTTTGCACATCAGCTCCAAAC<br>ACCTGAGTCCACGTGCACAGGCTTCGCACGGGACTCACGCACCTGAGTTGCGCTCACAGATCGCGCTTGCACACG<br>CAAGGGCTAGAACTGCAAAGCAGCGGCCTCTCTGACCGCCTAGCACAGATCGCGCTTCACGAGTTGCACACG<br>GCCCTGTGACCCGGTGCTTCCTTGACCGTGTCCGCCAAGCATCCTGGTTTACCATCCCTAC |
| 197 | RUNX1 | GGACGCGGCCCGCTCTAGAGGCAAGTTCTGGGGCAAGGGAAACCTTTTTCGCTTGTTCCCAATGCATTTCCCGAGATCCACCCAGGGCT<br>CCTGGGGCCACCCCCACCGTGCATCCCCGGAGCGGCTTGGGCCGCTCCACCTTCCAAAGTAGGCTTTTGA<br>CTCCAGGGGAAATAGCAGACTCGGGTGATTTGCCCGTGCGAAAGGTCCAGGAGGGTGCCAGGCTCCTCCGGGTCCGCTTGCCTAAAACCCT<br>AAACCCCGGCAGCGGGGCTTCGGGCTGCGAGTCGGACTCGGGTCTCCCAGGAGGAGTCAAGTTCCTTTATCGAGTAAGGAAAGTTGGTC<br>CCAGGCTTGCACCACCGAGTTTAGCCCTGCAGATCAATCACAGCTTTGTCCTTGACTCAGCTGAGATCGGGGACATTTGGGTTTCCCGGAGCGGCGCAGG<br>AGCCCAGCAAAAGCTGATAGCAATCACAGCTTTTGTCCTTGAAAAGAAGAAGACCAACCCTCGCCCTTCTTACTGAGGATCTAAAATGAATGGAAAGA<br>CTGTTAACTGCCAGCCGGTGCCTCTCCCAGACCCTTAGCGGACCCCATTTTACGGAGCCCATTTTCAAGGACAGCCACAGCGTGTACGAAG<br>TGAGGGGGCTCCTTTCACCCAAGAGCGCTCATTTTAGCCACAATAATGCTAGATTTACTTTTTGTCATAATGCAAAATTAAAAAAAAATACAACGAAGCGATAC<br>CAGTTCATTCCGTAGTGTTTCCTGGAGATTTTCCAAATTTTGTGCGGAGGAGGAGAATTGAAAACGGCTCCACAAGGAATGA<br>AATGTA |

TABLE 4C-continued

| SEQ ID NO | GENE NAME | SEQUENCE |
|---|---|---|
| 198 | RUNX1 | TTTTTAATGCTCAGAGAAGTTCGTATTACTGATTCGGAACACTGAGTTTTTCAGCTCCTGTAAAACTATTTTCAGGTTTATTTCAAGTACATTCTTTA |
| 199 | RUNX1 | CACCCTAGAGGCAAGACGGGTCTGTGTCAAGAGGCTTCCCAGAGAAGTGAAAACTCTGCAGGTGCAGCCGCTGGGAGAGCATCAAGA<br>AGGGCAGGGTGAGGGGCAGGGGGCGAAGGGAGGGGGGGTGAAGCCCGACCTACCCCACCATGAAAACTGATTCCACTACCCCATCTCTG<br>CAAGCGTCCAGAGGCCAATCACGGGCTCTTGAGCAAGATTCAGCAGTCTGGGCTGAGGCCTCCAGATTCTGCACTTCTAACAAGT<br>AAATCAGGCCAATCACGGGCTCTTGAGCAAGATTCAGCAGTCTGGGCTGAGGCCTCCAGATTCTGCACTTCTAACAAGT<br>TCCCAGTTGGTAGTGATGCTGCCAGTCCAAAGACCACACTG |
| 200 | RUNX1 | TGCTTCAGTGGGTAAACTTGACCGCTGAGAAGACAAGCAGGGAGTCGGTCTGCGTGAGATTTTTACCTGTGGTTCTAGGACGCAGAGG<br>CATGTGAGTGTTCAGGCTTTGCATAGACCCTAAGAACAAGGCTACCTAGCCATTTGCAAAAATATGTAGCTGCCGAGG<br>CTTTTCCTCCCCACACTTCTGTCCGACACTGCACTTTTCAAGGGAACCCAAGTTTGGGTTCGCCAAGAATTGTACGTT<br>GCACACCGTGTGTAATAATTCCAGGGAATTCAATCGCATCTGTCTTCCTCCTAAGCAAATTCGGTGGAACCTGGTGTGGTGTGATAGA<br>AAAAGCCCGAGTTCTCTGTGGTAGACACCATCAATTTCATGTGCCAGTCTCAGACTCCCGGCTTGCCTCTCAAGGAAGGAACAATG<br>GTTTGCTTCACTCGTCCTTCCCCCCAATTTCGACATCTGGTATCTGGCTAAAAATGAGTTCCTCTGTGAGAATTGCAT<br>GGACTGATAAAGTACCATCCCAGGAAGAAACAAAGATGCTGTCTTCCCTTTCGGCTACCAGTTGCCCTGGGAGGGAACACGCTGTA<br>AATTATAGGCAGCCAGAAGTGACCCATTGACCACTGCCAGTGCCCAGCTATGGCAACAGGCTGAGAACTCTGGGGAGGAGCCATTTGT<br>TGGCAGGGATGGTGATTCTTCTAGCATCAAGCTCTAAGATGATGACCAAGCTGTATCAAAAGAAATGATATTTTGCTACCTCTCCGGCTTGG<br>GTGAATGATGTGGACAGTTAACCTGGACAGTTTAAACCTTTATGTTGATGAGCTCACTTGAGTGAAATTAACCAGGAAATTGCCAAGATTTCAC<br>TTGGCCCCTCTGACATCAAATCTCAATATTATATTACCAAATTAGAGATTCTAAAGAACCCTGAGTTCTTTCACTGAGGAAGGAGTGGAAA<br>AACCTTTCCAGATGATCCCTTTGAGTCTTGTGCGCAGACTCCAGGGACTGTCCGGAGATAGCCAGACTCCTGCTATTTCCTGATGTCGC<br>ATAGCTCCAGGTGCGTCTCCCATCTTGCATGGGACAGGAGCCCAGGGGGCCAGTAAGGAGAGCCCCAGGTCTGAGGGGTACTGAAAGCAGAGT<br>CAATGGAATGCTTAAAATCTTTTTTCGTATTATTTCGTATTCTGTGTCTGAAGATGCTTCTATACAAATTGCTTCCTGTGAGTTAGCAAACAATACACGTTGTAGCAGCCCAGAGGAATGCAGCCAGGAGCCGT<br>AAAGCCAGGAAGAGATCTTTTTTTCCTGGCGGTTCTCCCGGTGTCTCATGCGGTCCAGTAGAAGAGCACTTGAAAGAGCACTTGAAACTTGAACCTGTCAAGACTAGTACATAACGCAGCTCTGATGATTCAACT<br>TCACTAAAATTCCCTGCTGCCCATCTCCACACACACACACACACACACGGGACCCGAAACATAATAATGAGTCACAGATACAATTTGGGTGTCAGGCATGAGCTGTCAGAGTGC<br>TCTTTCTCTCTCTCTCTCATCAAGTTTTTTAATTTCAGGACCCGAAACATAATAATGAGTCACAGATACAATTTGGGTGTCAGGCATGAGCTG<br>GGCCGCAAGCCCTCTGCATTCCCCTGCTCACTTAGCTTGTATGAATAATAAATACCTTGCCAAACCACTTAGGGTGCTCAGGACGCTGGTCAGAGTGC<br>GCCAGAAAATTAATTAATTCCCAGCCCACACATTTATGTTATTATTTTGTTTTGTTAAGCACAGCCCTCTTTTTACCACGAAAGATACAC<br>GTGCCCACGCACGGCAATGCTTTGAGACATTTTAATTTAACCACAGCTCAACTGCCTTTGTCCATTTCAAGAGGCTGTTTCAAAATGGAGACAGGTT<br>AAGAGCGCACATGCACCAAGCTGGTGCAAGGCTATCGAAGGCAGCTCGTGCAAGCTGGATATGGAGCAGGGAATGCTAACTCGGAGAATGCTAACTCCTATTGCCCTTTTC<br>TTCCACCCTGGCTGTTCCTATTCATAAGCCTGTAATCTAAGCTGCGAGAATGCTAACTCGGAGAATGCTAACTCCTATTGCCCTTTTC<br>CAGAGAGACCCGTATGCCAACATTTGCTTCCTCTTTCTCTTTGAAAGATGCTGTCTCTCTTTGCATTGAGGCTACAAGGAAACCACAG<br>CACAGCCCCATGCTGATGATTTTAACCTACCAAGCTGCTCACTGCTACTCTGCCTTATAGAGACCAGCTGCCTGCCACTTTGGCC<br>GACTTGTAATCATATGCCTCAGTTGAATTCCTCAGAATTAGAAGAACAGGGAACTGGCAGGCACCGAGCATCTCTGCACCGAGGTGAAAC<br>AAGCTGCCATTTCATTACAGGCAAAGTGTCTGAAGCCATGCGTTCGAAGCCATGCTTCTGAAGGCGGGGACACTCTCATGAAGCACTGTGGGTACGAA<br>GGAAATGACTCAAATATGCTGTCTGAAGCAATGCGTTCGCGTCCCCTCAGCCTCCATCCTCTTCCCCCTCTGCCTCTGCGATACCCTCGG<br>TTCGGACGAAAACCAAGACAGTGACTTTCAGCCTCCAGCCATCCTTTGAAAAATGCACCTTTGAAAGATTAAAAGATGTAAAGATTAAAAGACCAGCGGCCGCCGTT<br>GACTCCCCAGCCCTATTAAAAAATGCTCACCGCTGGTCGTCACGCGAAACCCTGTGGTTCTGTGTTCGATTCAGTGTGTTTATGAGGCCCAATCATGTAAGTGATGTCGATACCCTGG<br>GGCTGTGGGTTGGTGATGCTCACCAGGCTACCCACATCTGAGATTGCGGTTTCGAGTCGATACCCAAATCATGTAAGTGATCGATACCCTGG<br>CAGCTTGTCCCCTTTGCACACTGCCAGCCCATCCAACCTTGGTTCTGTCCAATCATGTGGTTCTGTCCAAAGAAGTTTCAATTTTTCTTTTCTGAGCAATGC<br>AACTGTTCCCCTTTGCACACTGCCAGCCCATCCAACTTGGTTCTGTCCAATCATGTGGTTCTGTCCAAAGAAGTTTCAATTTTTCTTTTCTGAGCAATGC<br>CCTTCCTTCCCCTCCCCAGGCTGCCAGCCCTGCCCCTCCCACCCTGCTGCAAGATAGCCGAGTAGACTTGCAAGAGGGGATGTAGAAAAAGTGACT |

TABLE 4C-continued

| SEQ ID NO | GENE NAME | SEQUENCE |
|---|---|---|
| | | CAGTCACTTATTATATCTCAATGGTCTTTGCTGATTTAGTAGTACAACTCGGCTCTGTGTTATTTGTGTTATTTGGAACTACTGATTATTTGATA<br>AAGATTTCATTGCTGCTATTCAATAGTAATTCAACGCTGGCATCAAGCCGTGCTCCGACAGGATGTGATCCATCATTAAAAATGCTAG<br>GCATCAGCTCCGGGAGAGTTAAGTCCTTGGTAACGTCTATCATGGCAATAAGCCTGAATGAAAACTATAAAGGAAAATAAAAATGTTTTG<br>GTGAGAGTCTGACCCCTACAAGCGGGTCTGGCAACTCACAGGTATTTAAAGCCTGGAAAGGAAAGAATTTTACTTTTGAAATAAAAGGACT<br>GTTTTAATGAAACCAAAATTATGTGGTTTATTCCCCTAAATGACAACTTTAGTAGTATCTCTTTCAGTAAAGAGATAAAATCATAGTACA<br>GTCTTAACACACCACACACACACACACCACCACCACACCTTTAGGAAGCTAAAGCAAAGCAGAGAGAATTTCTGTATT<br>TGGGACAACAGTGTGTTACTCTGCAGATGTTTATTTGTATTGTCACTGGAAAGCTCCCGTATTGCCTTTCTCTAGTTCAATTCAAATCA<br>ATAGGCTAATTTACACCTGTAGGTAAAACTACACTTTGAGCACATGAGGATGCCACAATAGAAGGGGAACCAGGAGGAGACACTTCTCCTG<br>GGGCTGACTAATGAATTATTATATAGCCGCGTCTCTACCTTAGAAGACATGCCTGTTTGAAGATGCTAAAACGTCATTTTGTTTGTAGTTCCAAGAT<br>CAAACCACTGTGTCAACACGTTCATTTTCCGGCCACTGGCTTTACCTGCTGACAACATAACCACACAAAGACCCCATAGACCTCATACACGCACACTTAAGC<br>GAAGAAAGCTTATTTTCCTGATTACTACCTTATTCATTTTCCTCTGCTTCCTGCCATATCCAGTCCTGATTCTAAGCTGCAGTAGCTGCAGCAGGCACTTCAGAAA<br>CACATAGGGTCAAGAGAACCTGTGTGATGATGGGTTTCCCTCATCCATCTAATTCACACACACAAGACCCCACAACGATAGTAGCTTCCATGGCACA<br>GGCTGAACTCCCACAACACTCCCTCGGTTTTCCCTGTTTTTGACTAAAGCAGGAATTGAAACTCAAACGACCCGTTTCTTCTTACACTTGT<br>AGTCTTTCAAAAGGAACAGACAACAATTTTTACTTACTCCTGTTTTGACTAAAGCAGGAATTGAAACTCAAACGACCCGTTTCTTCTTACACTTGT<br>GAGAAGTTAGCTGGCCACATGT |
| 201 | chr21:<br>35499200-<br>35499700 | AGGGAAAAGAGATAACGAAAGAAAAGAAGAAAAAAAAGGCCGGCAATTTCATGTACATTTGTTTTGGCATTCGCTGAATTCTAGAGATG<br>AAAACAATCTCCTGCTTTTAATTCAGTCCACGTGCAACAAAGTTGTACGTTGGAGATCTGGCTTTTAATAAGAACGATTAACAAGCGTTTT<br>GATCACAGGAAGTTGAGAGAGTGCTGCTTCTAAGAGAATAACATTGACTGCAGTTAGACGTTCATCTTTCTATCAGCCGTTTA<br>GCAGCCTCTACTTTGATTTGGGGCAAATGCGAGATGGAGCTCCCACACCACCACGTCCGGATATTTCGGGATATTTCTTCTGTT<br>CCAGAGCGCCCTTCCTTCGTCCAGGAGGCAGGCTCTGAGGCCGGTTTCTGGCAAGAGCCCATTGTCGGGATATTTCTTTAGATAGC<br>TTGCAGTCTGGGCTGAGTGGGTGTTCATTCAGATCAACACA |
| 202 | chr21:<br>35822800-<br>35823500 | AGCCTGGCGGCCACCCGCCCTAATTTGAGTCAGGAGCCCTAGGCGCCTCAGCTCTGGGTTGAGTGCCTCCTGTCAGGATGTGAAGC<br>TGCTGTCCCCCCGGGGCCTTCCAGCACTGCTGAGGACTCAGCAGCCTCAGCTCCTCAGGGCTCATTTACAGAGAGCATTCCA<br>GGAATCAGTCAGTGAGGGAAAGGGAAAACGGCGGAGTGACAACACACCTAGAAGTCTCTGCCAGCTTGGGGCCTTGTCAGCTCAC<br>AGCCCATCCTGCTCCTGCCAGAGCGCTCTGGTCCGCGATTGAGGGCCAGAATGGGTCTGTAAATGGGTTAAATGGGTTCAGCCAAAGGCCAAC<br>GTTGTGACTGACTGAGCAAGGCTCTGTAGGGTGCGGGGAGATCGGCGGGATTGAGGCCAGGGAGACGACGGCTGTGTAAATGGGTTAAATGGGTTCAGCCAAAGGCCAAC<br>CACAAGAATTAGCGGCTAGTATTTACCATAACCATATACAAGCATCAGCCTTCCCTCAAATCATCCGAGACCGCTATATCT<br>CTTTATTAAAGCCTGTCAGGGTTTGTTATTGCACAGTTTGGCCTTGACCCCAACTAAACCAGGCTCTTGAGCAAGAACCAAGCAATGCA<br>AGCATTCAGGCAGGACCATTATAACCCTGAGGCCAAAGGCAGAAGGGCAGGAAGAAGAGAGCGTCTTCC |
| 203 | CBR1 | AGACCAGCTCTCGGTCTTCGGCTGGCGGTTCTGCAAAGTCAGGCTAGCTCAGGCTGGCCTCCTCCGCCCACCCCGGAGGTTCCGGTGG<br>GGAGGGGTAGGGATGGTTCAGCCCCGGTCAGCCCTGAACACTCTGAAACTCTGAGACCAAGTCGCGGCCGGGCGTGTAACCACGGGTGC<br>GCCCCCACACGACCCGCCAGAGTCCGCCCATGTCCGGCATCCATGTCCGGGACGCTGGGTGACTGAGGCAACAAGGGCATCGTTCTCCACGCAGGTGTTC<br>CGCCGCCCGCCCATGTCCCGGCATCCATGTCCGGGACGCTGGGTGACTGAGGCAACAAGGGCATCGTGGCCATCGTGGCGA<br>CCTGTGCCCGCCGCCGCTTCCACCAGCTCGGACATCGACGAGTCTGCAGAGCATCCGCGC<br>GGGGCCTGAGCCCTGCCGCGCTTCCACCAGCTCGGACATCGACGAGTCTGCAGAGCATCCGCGC |
| 204 | DOPEY2 | AAACGTTTAAATATATTTCTAAACAGAATGGGCCAATTCAGTCACGTAACTCAGTTGATCTCCATAGCAGAGCAACCCACAAAGACAGAACTG<br>ATTTTTTTCCCATAATCAGGGGTGAAAATATACAACTTGTTTCTGAACCAAAAACCAATTTCTGCAGTTTAAAATGTTCACTGCTAATATG<br>GCCCTGGTAGAAATTATGTAGTTTCTTTTCTTTAAAAAAAAAATTCCTAAGACACTAAATGCTCATCTGGAATGTAG<br>ATTCTGATCCAAAGCAGCTCAGTTAACATAAAAATAAAATTCCACCTGTCTCAGTAGGGCTGAGAGTAGTGTGGGAACCCA<br>GCTTTGGTATGGAGAGTCATGCCCCTTGAACCAGATAGAGACTTGAATAGCCATAGCGCATATTCATGTCTTCTTTTCTGAGACATAAACTCTGATGTAG<br>GAAGTATCACCCTTCTGCACATACCGTGTAACAGGCATGTCATCCCAGCTTGCAGCAGCGCATATTCATGTCTTCTTTTCTGAGACACCCA<br>CTCCATCCTTCTGCCACTCGCATCCTCGATCTTCGATCCTCGAGGTCCAGCTCCTCGTGATCCTTCAGGTCCTGCTGATGAAGAAGTCC<br>ATTCTTCCATAAATAGCATCTTCTGACATCCTTCTGAACACGGGTCCTGAAGCGCACAAGGCGAAGGCACAAGGGCCGTACCGGCTCTTGACTC<br>GATCTCGCGGATGCGGCTGTACTTGTAGAACAGGTTCCTGCCGACAACCGCACCCGCTCCTTCCCCACGTAGATGCACC<br>CGTCCCCCAGCCGCTCGTGTCCGCCCAGCCAACCGCACCCGCTCCTGCCAGCCGCGGACCCTCCGCCG |

TABLE 4C-continued

| SEQ ID NO | GENE NAME | SEQUENCE |
|---|---|---|
| | | TATCGCCGCCGCTGCCGCCTGCCGGCCTGCAGCACGGCTGCCCCCCGACGGCTCTCTCTCTCGCCCAGGCTGGA |
| | | GTGCAGTGGCGTGATCTTGGCTCCTGCCAACCTCTGCCTCCCGGGTTCAAGCGATTCACCTGCCTCAGCCTCCCAAGTAGTGGCATTATA |
| | | GGTGCCCAGTAACCATGCCCGGCTAATTTTTTTTTTTTTTGAGACAGAGTCTTGCTCTGTCGTCCCAGGCTGGAGTGCAGT |
| | | GGCGCGATCTCGGCTCACTGCCTCCTGCCAACCTCCGCCTCCTGGGTTCAAGCGATTCTCCTGCCTCAGCCTCCTGAGTAGCTGGGATTACAGCTATGT |
| | | ACAGCGATGTCTCAAAGATAGGGATTAACAGCACTCTATGTTCATATGTTCATAAAAAGTCCTACACGCGTGATGTACGTCTAGATCTTTC |
| | | CTTTTGTCTCACAGGATATAGCACGGTAGTTACGGATATAGTCTCCGCAGTGACCTTCCCACGTACTGTCCTGCGCATA |
| | | TTTTGTGTCTCAGTTTCCTCATCTTTAAGGTAG |
| 205 | SIM2 | CACGCGCCCCCGGCCTGGCTGGAGGGGCCAACCAGCGGGGCCTTTCTGTAACTTCTCTCTTTAAACTTCCAAT |
| | | GAATGAACGTGCCTCTTCTTACGGATTTGTTTAGATTAGGGATAGGAGATAGATTCCTCGCTTGCAAATAAGACCTCCTATATTAT |
| | | TCAAACCAAGAGTTTGTCTCTTAAAGACATAGACGCCATTCTATGTTAAGGGTTGCTATTACAATTATATATGCTTAGGGAAAA |
| | | AATGTAAGCCCCGTAGTTTGTGCTTTTCGCAGACTGTTTTTCGCGACTCATTAATGACAGAAAGGTTTATCTTAGGTGGATAGGTTTGTTTCTTTAAATGGGATTTTTT |
| | | GGTTCGTGTCTTTGAAGGGCTGTTTCGCGACTTAATCCAGCCACAGCTCTTCCAGATTTCAAGACGGTGTAATTGATGTAACCACTGA |
| | | GGAATTTCAGTGCACACCAGATCAAGACTCTTCCAGCGCCAGGGGATTCCAGATGCTTCTTGGGCCTCTGGAAGCCATGGGATGTTTCCA |
| | | GACCGAAAGGAGGGCTTTTGTCCGGACGGATGTTGAGGCAGTGAGGAGCGAGATGAGGTCGTCGCTGGGCTCCCTTGT |
| | | AGCCCTCTGGGAGAGGAGGCAGGTCGTAGGGGAGGCGGGTGAGGGGGAGCCACCCTCGGGTGCTGAGATGAGTCCCACCCTACTGAAGGTCGGTC |
| | | CGTTGTCCTTTTCCCCAGAATCCATGTGCAAGGTCAGGCTCAAGGGCCACCAGAAGCCTTCTCAGGGACCAGCGAGAAAGAGGAGCAGGCTTTGGGAGAC |
| | | ACTGGATGTTTTGTGTGCATCGTAAGGGCCTCACCCTCGACCCCCAGGTAAAATTAGAAGGAACGTGTGGCAACCCAGGTGCAGCTTTGGTCG |
| | | AGGGAAGGAAAATGCAGGGGAAGGGCTCATCCCCGGGATGCAGGTAGGCGCCGGGGAATTCTTTCAGATAGCCCCAGAACAAAAATCCTCAGCCATGACAATTGGTGACGTTGACTGATGAGC |
| | | CTCGCTCAAGGACTTGCTAGTCACTACCATTAATTAATTACATAACTCGGACAAGGAGACACTGCCTGAGGAGACCCTCTCCACTCCAATCCAGA |
| | | CTTGAGGGGAATTGGAGAATTCCCGACAACAAGTCCAGCAGCTATGGCAAGCAACAAGACGATCAGCTTCAGGCAGCGATGATCAGCCTCAGGACCCTCTTACCCCACAAGCGGCCAGGA |
| | | ACCCGAAGTTATCCCGACAACAAGTCCAGCAGCTATGCAAGCACATGAACACACAAGACGATCAGCTTCAGGCAGCGATGATCAGCTTCAGGACCCTCTTACCCCACAAGCGGCCAGGA |
| | | GGTTGGACTTATCCGCCACCCCGGAGTTTCCATCCTCGACACCACCCTCCTCCCCTGCCAGGAGAGCTGTGTTGCCAGTGGCGCG |
| | | ATGCCTCTGGACTAATGGGGTCTCTAGACGCACAAAGGCAAATCTGCCAGGAGTAACTCCCAGTGAAATAATTTATTAAAAAGACAATAATTGTGACTGCTGTGGACACATGTTG |
| | | ACCAACCTAAAAGAAAGATAGAAGAAATCAGAACATAGGCACGAGAATTAGGCAGGTCCTGGGAGAGATAGGGTTGGACATATATCCCGTATACCCTCTAATTATTGT |
| | | ACTTGAGAAACAGCAAGAAGAATTAGGCTGGGAGCTCTTGGCCTGTCCCGGAACTCAGAAGGAAAAGGAAGGATCATCAGTGAAGCATCTGAAAATAATCATATGTATGC |
| | | AAGCTGTGTGTAATACTGTTTCGAGAGTCAATAATTCTCAGCATCAGCATGCCTTCTCAGAATAACTGATTGCGAAGTTCTTAAACTCCACTTCCGGGGAACGGCGTATAAACCAAATAGGCTCATATATGTGATC |
| | | TACACATGAAAGAGAGATGAAAATCAGGAGAATTCTTCAGGCCAAATCCATGAGATATAAAGATGAAGGACTCAGGAACAGTTGCGCAGCATCTGAAGCGGAAAAT |
| | | TGGGCCAAGCTGCTTCCGACTTTCTGTTGCCTTCGATCTGCCGCACTGCACCATATCATGAACATCAGGCTTTCCCTCTAATCAAGCAATGGGCACTCGAATCAACGCA |
| | | GTCCTGAATTTTCTGTTGCCTTCGATCCCAGCGTGCTGCCCGCAATACCATATCATAACTCGGGCACTGAAGTTCTTAACATCAGGCTTTCCCTCTAATCAAGCAATGGCACCACCT |
| | | CCGAAGTCGCTTCCCGCTGGGGATGATCCAGTAGGCGCCGGCCCGCAATAGCAAGTTGCGGAGCACTGAGCTCGAAGCGGAAAAT |
| | | CCAAGCACGATGTGAGGCCGATCCGGGCCATCTGCCTGCTCGCACGCGAGTGGACACTGCGGGTGGGACACTGCGGGTACTGAGAGTTCCGACCTCAATGCGTCG |
| | | GGTGGGTCTCCACACGGCCCCTTTCAGCCCGACCTGTTCGCCCAGTCCTCCTTTTCGCATCTTCTGAGCGGTGGGCCGTTCAGCCGCCATT |
| | | ACCCGTCTCCTCGGACCTCAGGTGGCGCCTCCCAGTCGGTGCCTCCTTCCGGCCCGCAGCCTTCAGGGCGTAGCTGG |
| | | TAGAACGCTGCCCTCGGACTCGAGCTCCGCCCAATACCTGGAGGGCTGTCCCTTTCCGCCCGGTACTTTCCAATTCAACAGAGCTTCCAGCTTCATATCACCACATA |
| | | ACCGCCGATGCTCTGTGGGTATTAGCTCCTGACCACTCAGTGAGCAACCTCGTAGTTCCCGAGCCCCCAGGGGAGAGCTCCCGGACGGGAGAGCTCCCGGACGGCCCCACCAA |
| | | CGGCCTGTGGGTTTCCTCTTTCTTCACAATTCCAGAGCCCCCAGAGCATCCCTGCTCCTACCTGGGAAACCTGGGATGTGTGTGGATGTGCCTGTATCTTCTGGT |
| | | ACTTTGCGTGGTGCCATCAGGAGCCACAACCACAGCTCGCTGTGCCAGGCCGTTGGGCCTGGAGGTATCCACACCCA |
| | | CGAAGGATGTGCTTGGGGAGCCAGTACACGGCATTGCTCTGCCTCGAACTGCCTCTCTTGCTGTTACCTCGGTTTCTCCCACTTCCA |
| | | GGGAAGATAATGCGCGTTTCCCGTAAAATCCGGAGAATTTGCCTTGAGGAAAGTTTCCTGACCCCAGCGCCCGAGGAGAATTCTCCCGGCTCCAGAGCGCGAAAGATCTCCTGTTTCTCCCACTTCCA |
| | | CTTAGCCATGTTTCTGCGATCTGGTAATCCTTTCGAAGCCCAGAAGCGCCAGGAGCCCGGAGCCGGAGCCGGCCACGCGCCTGAGCGCCTCCCCCAGCCGCCTGTGAGCTGAGCGCTCATAATTGAGGTCGAAGCGTGGGT |
| | | GAGAAACGCATTAATCTCCCGAAGCTCCTTCTCCAGAGGCCCAGGAGTTGAGACCCCGAGCCGGCTCAGCCGCCGAGCGCAGCCGCCCGAGCCGGCCCGAGCGGCGGCCAGCGCCCGGCCACGCGCCTGAGGGCCAGCACCCAGAGCGATCCAACAGAAAGCGCCT |
| | | GGTAGCCTCTAACCCCCTTGGCCAGGCTTGGCATTGGAGACCTCGCCCATGGCCTCAGCGCAGCCATGGCGCAGCCTGCAAGCGTCAAGGAAAGCGCT |
| | | CCTGGATCCGAAACCCCAAAAGGAAAGCCCCAAAGGAAAGCCCGTATTACTCGTGCCTCCGCGCCGCGGTGGCGCCGTGTGGGTGCCGCGCCCTGCGGTTCGGAGCACCCAAGCCGAGC |

TABLE 4C-continued

| SEQ ID NO | GENE NAME | SEQUENCE |
|---|---|---|
| | | CCTGGCCACGATGTGGACTCCGCAAGGGCTAGGACAGGCAGGGGAGAGAGCCCGGGTTTGCGCACACCTTCCAGCCCCTGAGGGAG
CCTGCTCGGCTTCGAACGCCTTCGAACTTTGACTTCAAAGGAGTCCCTGAAAAGTCAGGAGCGCCTGCTGCGACGGCACGGTTGCCGA
AGGCCAGGCCTTCCCGGGCCAGTGGCGAGAGCAGTGACACCGGAGGGGAGGAAGCGGATACTCAGTCCGTCGACGGCGAGTTTCGGAGCAGCAGG
CTCATGATCCTCCAGTCACGCACCCCCATTGCTCCCTGAGCCTCTGTGGCCACACGGCGGAGAGTCCCACATTGATCTCGACGCCAAG
TGCTGACCTCCAGTGCCCTGCCTCGTCTGCCCTGAGCTTCTGCTGCGGAAAGCTCACCTCTGAAAGAGGGTGGGTTATGTGACC
GTAAGGAATTGCCCCGGAGGACTCTGCCGCCACACCCATTTCCAGGCTGCCAGGCCGACACCAGGGAGGCCAGAGGGGGAC
GCCGCTCGCAGGGGACTCTGCCAGGGACTCTGCCGCCACACCCATTTCCAGGCTGCCAGGCCGACACCAGGGAGGCCAGAGGGGGAC
AAAAGGACTCTTTAGTTCCAAAATGACCCTGAAGGAGAGTCCAGAATGCCCAGTGAAGCCCACCTGCCGCCCACCCTGTGACCCTGGCTGCAGCGACCTTGCCCTTAATGCCCAATGC
CTTCTGCCCCATCACCATGGGCCCTGCAATTCCGGCTGCGTGAATCGGCTGCTGCTGAATCGGCTGCCCTGTTTCCGCGCCTGGGA
CCGATTCCTCAAATTCCGGCTGCCTGGACTCCCCGCTGGCCTCCTGCCCTGCGGCCCTCGTCCCTCCTCTGAGAGGCGA
GAGGCCTCACCACTCGGCTGGCCTCCTGCCCCTGAGCGCCCTCACTTCGAGACGCACTTCGAGGTCAGGCGA
CAATCTCTTTGCACCTTAGTGTTTCGAGACACAGAAAGGGCAGAAAGGTCACTTCGAGACGCACTCGAGCGCCAGGACAGCCAGC
GGGGAGGGGGCTCTCCCGGCTTCTCCCGGCTCGGCCAACGAGTCGCGCCGGAGTCGCGCGAGAGCCAGG
AAGGCTCGATCCTCCCCCTCGGCCCGGCCAGCCGCCAGTGCTCCGCCCAGTGACTCCGAGACGCGACTGACCTTCCCGAGAGCCA
CAGGGGAGCTGTGCCGCTAGCCACACATCGCGGCTCGCTGCTGCTCCAGGCACAAGGGAGGCGCCAGGAAGGGCCAGAGAGCGCG
TCCCCGCCGCCAGGCCCAGGGCCAGGGCTGTGACTCACCCCGACCTGTGACTCGGCTGGGCTTGCGCTGACTCGCGGCTGGCTCGCGCCGCC
ACGCGGAGGCGCCTCCCCCCTCCGGGACCCTGACTCCAGGCGCGCCAGTGCCTCCGCCCCAGTGCTGCGGAGCGGCAAGGCTCGCGCCGACACGTGA
TCCGCTCCAGCCCTCCGGTCGCCCAGGACCTGCAGCCGGCCAGTCGCCAGTGCTGCTCCCAGCCAAGGAGGCAGGCAGGAGAGCCAGGAGAGCGGCC
CAGCGGAGTGCTGCGCTAGCCACACATCGCGGCTCCATGCCCCTGGCTGCGTGCCGCCGCCCCCAGGAGGAGGAGGAGCCAGCCGCC
CGGCCGCCGGGACGCCTGGGGAGCCCGGGAGCTTCCCCAGCGAAGCCAGCCGCCAGCCCCCCCCCCCCAGGAGGGTTGCCGGCCTG
CTGTCGCCCTCCGGTTCCAGGGCCCGAGGGGCCTTGCCAGGCCCGGGTGAGGGCGAATTACGAATTGTTCCAGTGACATAATGCCGGCGACTGTTCCAGTGACTCCGCGCCAGCCCGACG
CGCCCCCACCCTCCTGGTCCTTGGTTTGTTTTTTTTCTTCTTTCTTTCGCCCAGTGACATTCTGGTTTGCATTCTGGTTTTCGCCCCCCCTCTCTCCCCT
TCTTCTTCTTTCTTTTCTTTCTTTCTTCTCTTCGCCAATGCATTGTTTCTCCCCTCTTCTGTCCTCCCCTCCTCTCCAGTGCTCCGCCATCA
AGTCCAGCTAGCTGGACAAAAGCCCTCCAATCATCGCGGCCTGCTCGCCAGGTGTCCTCCTTCTCTGGTTCAGCTGTCCAGTGTGTTCGTT
CTTCGGAGTGCTGCGCTAGCCACACATCGCGGCCCGGCGCCAGGCTACCTGAGAATGCTGAAGTACGGGATCACGTGGGGATCGGAGCTCAGGTG
GGCGCCGGGAGCCGCTGGGAGCCCCGGAGCCCAGGGCAGGGAAGGCAGGCCCAGCCCCCCAGCCCCCCCCCCCCCCCG
GCTCCAGAGCTGGGCTGAGGGCGTCGAGGAGGTTGCTCAGGCTCGGGAGGTGAGGCGAATTACGAATTGTCCAGTGACTGATCCCCAGCCGCACG
CCAGGCCAACCTCTTCTCCTCTGTCTGAGAAAGAGGGCGCTGAAAGAGGAGCCGTTGGGACCGTGCCACGCAGCCCCAGCCGCGGAG
GCCGAGTTCTTTCTTTCTTTCTTTCTTTCTTTCTTTCTTTCTTCGCCCAGTGACATTCTGGTTTGCATTCTGGTTTTCGCCCCCCCTCTCTCCCT
TCTTCTTTTTTTTTTTTTTTTTTTTTTTTTTTTTTTTTTTTTTTTTTTTTTTTTTTTTTTTTTTTTTTTTTTTTTTTTTTTTT
CCTCCTTCTTTCCCCATCCTCCTTCTTTGCCTCTTCTTTGCTCTTCTTTATCGCGGGATCACCGCGATCCCAAAGCTCTCTCTCTCTCTCTCTCTT
TCTTCTTCTTTCTTTCTTTCTTTCTTTCTTTCTTTCTTTCTTCTTCCTTCGCCCAGTGACATTCTGGTTTGCATTCTGGTTTTCGCCCCCCCTCTCTCCCT
TGTCTCTTCGAAGGAGGTCAGCTTCAGGCCCTCAGGCTGCGAGTCAGCGGGATCACGGGATCCAAGCACTGCAGGCTGA
GGCCACAGAGCGAACACTTGTCTGACCCCGGCTGTCCTGGGGTGCGGGTGCCAGGAGAGAGACCCCCCCCGCG
TTGCTGAGCTGAGACCCCGGTGAGGGCTGAAAGAGAGCGTGGGAACGGCGTGGGACCCGGCGACCTTTTCGCGCGTTCTTTTTCAGGAATTGA
AAATGTCCAGTGCCAGTGGCCAGGGACGCTGGGACCTGGGACCTGGACAGTGGCTCGGACCGGCTGCTCCAGAAGACATCAGAGCAGCGTTTCCAAGC
AGCGCCGCTTCTGGCCTTCCAGACTCGTCCAGGACTCGGACAGGCCTGGAGACCTCCCTTCTCCGCCCCGTTGCGCGGCTGCCCTGAGGAGAGCCCGCCAG
GTTCGGGTTCGCTGCCCTCTTCCCAGAGGGTCAGGCTCCTCCAGGAGCTCAGGCCCTCAGGAGCTCAGCAGCCAGGCGGCGCCTTGGGGGGCGCGC
TGCTCAGGGTTCCGCCGAGGTCCTGTGGGTCTCTCGGGCCCCCGAGGTCGCTGGGGAGACCCGGCCAGGCGACCAGTGCCAGTTGCCGAGGTAGG
GAGACAACTTCGCCCAGGCACTCACTCGAAATGCCGAAAATGCTGAAAATGCTGAAAGTCGAACCTTTTGGCTTTCCGGAGCTCAAGCAGGTCGGCTCCCGCGCCCCCCGGCCCCGCCAGGAGAAG
GATGATTCCACTCAGTGCTGCGTATTAGGAAGTATTAGAGTAAAGACATTCGTTCTGAGTCCCTTTCTGAGTCTGTTCGAGCTGAAGAGAAAGAGCAGCTGTGTGTGTCTAGTGGTT
TGCTGGGAAGAGCCGTTCCTAACGACTGCAAACAAGGTGAATCCGGACAACAAAGCAGGTGTGGAATCCGGACCACTGACTACTGAGCGGGACCACTGACGTGAGCCACTACTGCTTCTGCCCTGA |

TABLE 4C-continued

| SEQ ID NO | GENE NAME | SEQUENCE |
|---|---|---|
| | | AATAGAAAAAGCCTTCGAAGCAGCAATCAAAGATCAAAGATTCAATGATTTCAATTAAACCAGAAATTAGTAAGGAGGCCGA
GAAGACACGGCTGCTCAGAAGCTGTTCCTGTTGCTCTGTTTGAGGGATTTCCCGGAGAGCCTGTTAAAAGATGTGGTGTACCGCTCAG
CCACCTTTAAACCGCTCTGGGGTCAGGCCTTGAGCAGTCTCAGCAGTGCCTGGCACTGTGGAGCAGTTGGGAGCCTTCCTGTGTGTCTTTTGA
GGGGTGTCCTTCTGGGGTCAGGCCTTGAGCAGTCTGCACTGGTGGCAGTGTTTGGCTCTAGAGTTTGGAAAGGGCCCTGAACCTGTTCGTCCCCTCGG
AAAGGGAAGGGACAGTGCAGTTGGCACTTGGCACTCTCCCTCCTCCATTCGTCGTTTGGCCTCAGTCAGTTGCCAGAGTGACCTGGAGCTGGGCAGA
CTTGGAATTCGTCAGGACAGCAGCCTCTCCGGGGTCTTGGCCTCGCAGTCAGTTTATGCAAACTGAGTCCAGTAGCTCCAAAGAGTGGCA
GGAAGAAGATGCGTTAGAAAGACCTCCATTATGCAAACTGAGTCCAGGGAGGAGATATGGCTGCGAGGGTGCCGGAGGGCTCTCAGATCGCTC
GTGGAGTGGCATCTTGATTGATTTAACCTCTTCAGGAGTTTAGGGCCCAGGTTTAGGCCTCGCGAGGTCTGCAAGCAAGTGCTGGGTAAAGA
GGGCTCTCAAGTGCAAGTGAAGAATTGATCTGCCAAGCAAGTGCTGTCAAAGCAAGTGAATGCTCAGGTGGGTAAAGA
ATCTAGAGACCAGCTTAGGACTCTGGAGGAACATGACACAGGCCTTTCCCAGAGGCTGCCAGCCTCTGTTCCTTTTAACATAGATGATCCTCACTGC
TCATACCCTCGGGAGAAATTAAGGCCAGACATGACACAGGCCTTTCCCAGAGGCTGCCAGCCTCTGTTCCTTTTAACATAGATCCCTGTTAAGACAGA
GGTCCCCTGTGGGGCATGTTCTCACTGCACCCGTGTGAGGAGCAGAGGGCAGCAGGCCTCTCCTGGCCTTTTAACATAGATCCCTGTTAAGACAGA
AAGAGGAAGCAGAGGGGTTCCCTGTGCAGGGCAGGAGGCAGAGGGCAGCAGGCCTAAGCACCCCACTTTGGTAGCCAGTTCAAGGA
CTTGGGGATGTTTTCAACATTTACAGCGAAGTTTGAGGCCGTGAGGTGAGGGGTGAGGTCTTGGAGGGGGAATCTAAGCATTGTTCC
CCATTAGCAATGCAAGGGTTCTGTGATGAAGGGTGAGGTCCCCATATTCCCTGGCTCAAAGGAGTCTGAATGCAGGGATGGAGGACTCACTGCCTGACTT
TATGCCATTCACCCTTCCTGTGAGCTCCCCATATTCCCTGGCTCAAAGGAGTCTGAATGCAGGGATGGAGGACTCACTGCCTGACTT
TGAAGACCCTGCTTCTGGGTGCAAAATACCATAGGAGAATTGATCTCCTTTGACAGTGAACTAATACATTGGAGTAGATAGTGCTGGGAAGAGGACAGG
AGACCACCGGCTGACTTTGACATGGGCTCGAAATTGATAATTGGCCCTGCCAAAGTGTCCCGTTTGAAAACTGTCAAAAGCGTCCTGGGCAG
CTGAGGTCTGATGGTCAGCCAGCCTGGCCATGCCTGACTGCTCTGACTACAGGCAGGATGAGGTCGGCCTCTGCCATCGGAGGTCAGAGGCAG
GCCCTCCACCAGACTCGTTGCTGGGTGCAAACTGGTCTGCACAACCCAAGATGGGTGTGGGTGAAAGAGGGAGAAGAATTGCTACTCCAGAACC
AGGTTGAGTCCTCCCCATCTCCCTTCCCCAACCCAAGATCTTCAAGGTCTGAACCTGTTCCCGGAATCAAAGCGACTTGATTGGAGAGTT
TGTCATTTGCCCACCACACTTCCACCTGAGCACACCACACCCCTATAGAGGCGGCCAGGTTATCTTAGAACCTGTTCCCGGAATCAAAGCGACTTGATTGGAGAGTT
CCCATCACACCACTTCCACCTGAGCACACCACCCCTATAGAGGCGCCAGGTTATCTTAGAACCTGTTCCCGGAATCAAAGCGACTTGATTATTAA
GGGTGAGGAAACTCACCTGTTTAGCAGAACAACGTAGATTTTTACAGACAACGTCTTTGCGGCTTGAGCCGTCCAGCTCGCAGCTGGGATCCAG
GAGGGAAAGCCCAGGCGGCCTGCAGATTCAGCGCGGGCAGTGCGGGGACAATCCGGAAGTGTAGAGGAGGGGACTTGGATCCTGACCCCGGGCGGACCCTCCG
AGGAAGTGGAGCGCGCCGCTGCAGATTCAGCGCGGGCAGTGCGGGGACAATCCGGAAGTGTAGAGGAGGGGACTTGGATCCTGACCCCGGGCGGAATGGGGCAC
CGGCCCTTCGTCTCCTCAGATATACCCGGGCCAGCTTGCGCGACAACCGGGCCAGGCTAGGAGCCTCTTCCTCCCCCATCCCCCCAT
CGGCCCCGGGAGGCTTTCTTGGGGAGAACACGGAGGGCTCGACGCGGAGGATTGAGGCGTCCAGACAACTAGGCGAGAACCTGGCCCCAAATGCGACAATTACTGG
TTCAGGGACCCCGGGGAGAACACGGAGGGCTCGACGCGGAGGATTGAGGCGTCCAGACAACTAGGCGAGAACCTGGCCCCAAATGCGACAATTACTGG
GATCCTTTTGTGGGAAAGGACGTCTAGAGGCTCAAGCTAGGCGTGTCCTAGAGCAACTAGGCGAGAGGAACCTGGCCCCAAATGCGACAATTACTGG
ACGCCCTGCACACAGTCTCCGGCCACTGGTCTCCAAGGGAGACTGTTCCAAGGGAGCAATTCTACCTCCCTTGCACGGGGTCGTGCTGCCTTCTG
GGTCATAAAACGCCCAGGTGGCGGGGTCCAGGTGCGAGCTCTAGGGGTAGCCTCCGTGCCGCACAATTCCTTCGCACTGGAAGGTGCAATCGCCAAGTG
AGGGAGCGGAAGAGGCAGCCGGTCCTGAGATGGCCCGGCAACCGCCGCCGCGTCCACCCGCGCAGTCAGAGGCATCGCCATATGCCGCAGGATCTCTTGGACCTGTTTGCAATCGAAAGTG
AGACCTGAGTCTCAGATGGCCCGGCAACCGCCGCCGCGTCCACCCGCGCAGTCAGAGGCATCGCCGGGGAAGCGACACTCGCGACGCGGG
GCCCGGTGGTAATTGGAGGAGGAGGCGGGCCGGCCGCCGCGCTGGGCGCGCGCTCTTTAATCCACAAAATCCATTTTGGAGGTGAGAATGAGGTCGACCTGCAGCCCGG
CAAACACTCGGGAGACCAGCTCCAGAGGCAGGCGCTTGGAGGCGCTCGCTGGCTTCGGGCTGATTACCCTGATTTCATGAAGGAGTCGGAGGAGGGTGAGCCCTGCACCCA
GGTGGGGCTTCCCAAAACCGTTCCGGGATTTAACCACACTCCAGGTCAGGATCTGAAGAACCGTTTTGTCACCGTTTTTAAGTGCCGGAGGGGCGAGTGAGAGAAT
TTAACCCATTTGATATTCAAGCAAGACTTTGCCCAACCGTGTGCACCCGATGGGAAGAACCGTTTTGTCACCGTTTTTAAGTGCCGGAGGGGCGAGTGAGAGAAT
CGTCTAACCCTGGGTGTTCCTTACGGTCTCCGGGAATGTCCCGCAGGCCCGTGCCCTGAATCAGTACCACCAACGGACCACCGCCACCGCCGGAGGAACTATCTCCCCGTTTGCTCC
CTGGCTCGCCTCGTTATGCGCACGGGCTCCCTTTAGTTCAGCCCCATGAAGGGGAGGTGGCATCTGGGACCTGCATCTGACCTGACACTGGACCCACACTGGGACCCAGGTACCCCAGGACCTCGTGGGCCTGCAGGTCAGGAGGAATGAGG
CAAATAGTCTTCTTGGTGGTGCTGTCTATGGTTCTGTGACCTGACACTGGACCCACACTGGGACCCAGGTACCCCAGGACCTCGTGGGCCTGCAGGTCAGGAGGAATGAGG
TGGAGGCCGTCAGTGTGAGGAAGCCCAGGGAGGGGGACCTGTTGGGGACCAACATGCGACCAACAACCTGCCATCCCTGACTCTCAACGACACAGCGTCCCAGGGAATGAGG
CGCTGGGCGTTCCCTTCCCTTTCCCATTTCTCCTCCCTTTCGGTGAAAGCAGGAAGCCGAAGCCGAAGCCGAAGCCGCAGGGACCGTCCAAGCAGCACACAGCGTCCCACACGTCCT |

TABLE 4C-continued

| SEQ ID NO | GENE NAME | SEQUENCE |
|---|---|---|
| | | GCAGTGCTCTGCAGGGGTGCAGGGAGTCCCCTTCCCCCAGCCGCAACCTCACCTTCCTCACCCCAAGCTCCTCACCCCCTCCGGCAGGAAGGAAACCACAG GCTGGGTTGGGGACCCCTGGTGCTCCAGAGAGCAGCACGTGAGTGCTGGGAGCCGCTGGGAGCTCCAGAGCCGCTAACCCGAGCGCTAGACAGACTCTTCTCACCC CTTATTCTGAAATAAAGCCCTTCTTCGTTACAAATCCTTATTTAGTCTCTGCGTTTAGACCAAAGTAGATTTTATGGCTGAGTGAGTGTATCACTTACAGTAT CAAGACAATTTCTTTCTCGATGGAACAGCTGGCAGCGCCACGGCCCACGGCTAGAGGGCAGGGGTGCTTGGAGGACATCTAGCACCCG TTGGTTTCTGATGGAACAGCTGGCAGCGCCACGGCCCACGGCTAGAGGGCAGGGGTGCTTGGAGGACATCTAGCACCCG ACCACCTCCACCAGGTGCGAAAGGACGTTTGCACCAAATCTCCGCCAAATCCTGGCCCAAATCTCCGCGCAAATGTCCTGTGCCAATGCACTTTGCATGTAGAGCCA CTAAAAGAGAACAAGTTATCTTGAACTGCTGCGGGTATTTGAATCATCAGAAAATTGTCCTGTGCCAATGCACTTTGCATGTAGAGCCA GGGCCTTCGAGGAAGCTTTCAGAGAGATCCCGGAGCCCAGGGCCACGCTCACCGTTAACACTGCACAGGGCAAAGGTGCTCAGGACAACTGCC CCGCCATGGGCTTTGCAAGAGCACCCAGGCCAGAGAACCAGGGCCCAGAGGTGCATCTCTGCGCCTTTTTGGAAATCAGAATTCCTGGGTCCTTAGT TAAGTCTTCTTCACCAAATCCAGGACCGTTGGGTTGCGCCATTGCTCTAACAGTTGTAAATGCTCCCCACGAGGCTGAGG AAGGACCCCTGGTGAGAGCACAGGGAGTGCTCTGCGTGATCACGGTGGTGATGTATTCCGGGATCGTGTATGTGGAATTAGCCACCTCCT CGCTGCCCCGTGGTGGGTGGGGCCCTAATTCCTTGAGCCCAGGAGGAGAAATTAAAGCTCATCCTTTTTAAATTGAGAATAGTGTTTTTTTAACTTT CAGCCAGGATAAGCCCTAATTCCTTGAGCCCAGGAGGAGAAATTAAAGCTCATCCTTTTTAAATTGAGAATAGTGTTTTTTTAACTTT TTTTTTTTTAGGTTTTTAGTTGCGAAGGATTTGTGCCCAGGTGTTGGCGACCAGCCGCTGCCCTCCGAGGTCAGCCAGGGCCCAGGGTCGAG GCCTCCAGAGACCCCAGGGCGTTCCAGGGGCGTTTGCGCCCGCAGGTCCCCGGAGAGGTGGGGCGCCAGGAGGGCAGCCCCGTCCCGGGAGGAGGAGTCTGGG ACCCACTCGTGCCGCTGCCCCAGGGCTGAAGGGCTTTGCCTTCTGTTGGTTCGAGCGCGCTTAGTGAGGGCTCTGCGGCCCCGTCCCTC GTATCCCGCGCTGCCCCAGCCAGCTCTCCTGCCTTTGGTTCGAGCGCGCTTAGTGAGGGCTCTGCGGGGGGTCG GGCTGGGCCTGCCCAGCGTGGGTTTGGGGCCCCAGCGGTTTGGGGGCGCGTTGTCCTCCGGCCAGGTCTGCAGGGGTCGCAGCCAGGGGTG GGAGCTAGGCTCCGTGGGAGACGCGCCTTAGTGAGGCGCTGCAGCCTGGCCCAGCCGAGCAGCCAAGAATTCCGGAGACGTTGGGGTCAGCAGC AGGTGGTGAAGAAGGGGCAGGAGGGCCAGCAGGAGGCCTCCACGGCCTGTTGAGCAGGAGACCCCTTTCAGTTGCGGCCTGT GGCCCATTCGCTCCTCTCCACCGCCGCTCTGCCGCTCTGTGGAGCCTGTGAAGCCAAGGGAGGTAGCGTCGTGGACTTCCCAGAGAGAGCTCACAGGGAGGTAGCGTGCAGGGAGCAGGAAGCAGGGAAAGAAGGAGGGAGG GAAGGAGGGTCCTTGGGGAATATTGCGGGTCAAATGAATTTGCCCCCAGCCTTCTCCCCCAGCCTTCTCCCCTAGCAGTTTACCGAGTTTGCTTCGTCCCTCGTCCAGTTTACCAGATCATAGAGTGAGCCTTTCAAGCCAAGCAGGTAGCAGCGTGGCCACAGGCG CCCGGGCTGCCGAGCCATCGGGCTGCCCAGGGCAAGAGGAAGCATGAGCAGCCATCGGGATCGGCTGCCCAGTAAAGGGGCAAGGGTGCAGGGTCAGGTTAGGAGACGCGTGGGGACAGCCGAGCC GCTCCCAGGCATCGCGGCTGGGCCTGCAGTTTACCGAGTTTGCTTCGTCCCTCGTCCAGTTTACCGATTTGCTTCGTCCCTCGTCCAGTTTCAAGGCAGGTTCCGCCGCGAGCC GCGCCGGGCTCCCTGGACCGGCTCCAGTCGCCACCCGCCTGCCCTGCCCAGCCCCGATCGGCCACCCCCAGGGGACGCCGCAGCAGCGGCTGAGGAGGGGCCAGCCG CCCAGGCCCTTCCACCCCCACCCCTGCTCCCCACTGTGTCCCCCAGCAAAGCGCTAGCATGTCGATGCCGCCTGATGTCCAGGCAGCCAACCCTACCGCTGCTCGCTGCTGC GGGATGGGGTCGTCCCCCAGCGGGCCCCAGGACTCCCCAGGAGCTGCCCAGGAGCTGTGCCAGCCCAGGCCCCACCCCTACCCCGAGCGGGCTGGCAATGTTTGCAAGTGCTTTTCA CCCACACCCGCCAAGGCCCCAGGAGTTCCACCCAGCAGGTTCCGAGCCCTGTGCCCAGGCCTGGAGCGCCAGGGTTTGAGCAGCAGAAATGATTGGGCTGCTCTGAGC ATCTCACTTCCCTCAGCAGGTTCCACCCAGCAGGTTCCGAGCCCTGTGCCCAGGCCTGGAGCGCCAGGGTTTGAGCAGCAGAAATGATTGGGCTGCTCTGAGC TCTGAAGCATTCGGCCCACATTCAGTTCGTGGCAAGCCACATTCAGTCTGCAAGACCCTTTATTGCACTCCCCCTGCAAGACGAGAGCAGCATCTAGAGTGGATTCTGTTTCATTGTTTGTTTTGTTT TTTGTTTGTTTTGTTTTTTGAACGGAGCGAGTCTCACTCTGTCGCCCAGGCTGGAGTGCAATGGCGCGATCTCGGCTCACTGCAACCTCCGCC TCCCGGGTTCAAGCCATCTCCTGTCTCAGCCTCCCGAGTCAGCTGGGATCCACCACTTGCCCCACCTCAGCCTCCTGGATCGCCCCAGTCGGGATTACAGGCGTGAGCCA AGGGGTTTCACCCAGGCTGGCCTTGATTCTGTTTTTAGATCCCAGAGGAGAAATTGAGACACAGAGGACACAGGAGAGGAAATTACATGTCTAAGGTCACAGGAGAGGAAATTGAGACACAGAGGACACAGGAGAGGAAATTGAGTCTAAGGTCACACAG CAAGGGGTGCGAGTAGCCCCCACTGCCCTAGCTGCCCACTAGCTCTAGACCCCCTCTAGAGGACCAACTTGGTGAGGCCTCCGGGCTCTTGCTTG GTTTGGAGCCAGGTCCTTAGGCGCCCCGAGCCGTTTGCGGTCGGTAGCGCCCGGGTAGCCCTGAGCGCCTGCTGCACGCCCGGCGCCCTGAGCCCTGAGCCCCTGACCTGCTTGCCGCTGGCTGCCCTGAGCCCTGAGCCCGTGCCGCTGGCTGGCTGGCTTAG GCAGAGGGGCGCTTGCGGTCGGCCGCCCCGAGCCCTGAGCACAGCCCTGAGCACAGCCCGATTCATTCCCCCCTGTCATTTGTCTCTGCCATGCAAAAATGCCTACC CTGAGAGCCAGGGCTTCTGCATTTCCGCCTCGCATTTGCATTTGTGTTTACTTTAAAATAATAATAAAAAATGCATGCAGCGCCATGACTTAGGTC AGCGAGTCAGCCCGCTAGCTGCCCAGCAGCCCTAGCCCGGGTAGCGCCTGAGCACAGCTCATTCCCCCTGTCATTTGTCTGCCAACTCTCTTGCCCCAAGTGCCCTGTGTCTGTTGTTTATTTTTAAAAT |

TABLE 4C-continued

| SEQ ID NO | GENE NAME | SEQUENCE |
|---|---|---|
| | | GCATGCCTGCGAAGAGAAGACCCGGGAATATTCGAAACCCGAGCTTTTACAACATAAAGCGCATGGTGTGGCCCGGCCAGTAATGG CGCT |
| 206 | HLCS | CAAATCACTTGAACTCAAGTTCAAGACCAGCTCGGGCAACATGGTGAAACCACATTCTACAAAAGTAAAGAAAATTAGCCAGGCATGGTGC TGTGTGCCTGTAGTTCCAGCTACTCCTGGGGAGGTCGAGGCTGCAGTGAGCCACTTGTACTCCAGCCTGGGCGACAGAG CAAGTCCCATCTCAAAAAAAAAAAAAAAAAAAAGCTGGGTGTGGTGCAATGAGCCCAGACACCTCAAGGGCTGAAAAGGAGGATTG CTTGAGCCAGGAGTTCAAGGCTGCAGTGAGCTGCGATCAATCAATGCCACTCCATCCAGCCTGAGCAATGAGTGAGACCTGACTATAT TTAAAAAAAAAAAAATAGGAAGAACAACTCAACCACAGGGCTAGTATGTTACTCGGTTATAAAATGATAAAGCCTAAACAGAGAATTAGC CCGTTTCAGAGAGGCCAAGAACAGATGATACAGCTGAACTGAACTCCTGCCTGTACAGCTCGTTTTCTACAAGATTCCAGACCTGAAG ATGATGGCATCCAGCCCCCATTGAACGCACCTCGAACAAGAAAACGCCGAGTCGTGGAATCGGAAAACCGAGCTCAAGAACCCACGG AATAACTCCCCCTGGGGAATAAAAACAGGAATCCAAGCAGGAATCTGGTAAGTTCTTTAGGAAACCCACTCACGG GCCTGAGTCCCCCTGGAAGCGGCGACTTCGGCCTCCCGCCCCGTCAGGCTCCGGACCGCTGAAACGCACCCAGGGGTGAAGGCTAGTC CTGATACCGGCCGGCAGCCAGATTGCCAGCGAGGCATGGCAGCAAGAGAAGCCCAGGTCGGACAGCGCCCGAGCCACGCCGCAG GCCAAATCTGCCCGCCCCAGCCGCCCCAGGGCATGGGAACGCTGGCCCACAGCGGGATGCCTGCTCCACAGC GCACTTCCGCTGCCTTCCACTGCTGCTCAGGGAGGTATGCTGCTTTCCCCTTGAGACTGCAAACCTTCAAGGGCAGGAAATGGGTCTGTTTTCTGGC TGCCTCATAGGTCAAAGTCACCTCCCAGGGAGGTTGTACTGCTTTCCCCTTGAGACTGCAAACCTTCAAGGGCAGGAAATGGGTCTGTTTTCTGGC AAATAATGAAGTTGGCTTAAGTTTGCTGAATAAAATGAGTGACAGAACAAAGATAGCCACAAAAATGGCACTCCTGATGGGTTATTTGATGAA GGAGGTGCAATGTATGGGCTTAACTAGTTATTCTGGATTTCTTTCCCCATGTTA |
| 207 | DSCR6 | CAAGGCCGGTGCACGCGGGACCCGAGGATTCGGTAGATGTCTCCCGAGAAGACCCCGCTCTTAAGGCGGTGGAAGCCAGAGATTCTCCGA AACCCAGGAATCCGATGCTCCACAAGACCAAAGCCCAGGGCGTGGGAGACCACCACAGAGGGACCGAGAAGCCGGACTCCTCCACATCC CACATCCGGCAGGGAAGCCCAG |
| 208 | DSCR3 | CTGATAATAAAGTTTTACCATTTTATATTTAAAAATGTAAATAATGGAGTTGGGCATGGTGGTTGGGAGGGCATGGTGGAGAATCGCTTGAG CCCAGCTACTCGGGAGGCTGAGGACAGGAGGATCGCTTGACCCTGCCAATATAAAATTAGCCAGGCGTGGTAGCACGCACCTGTAAT CCCAGCTACTCGGGAGGCTGAGGCAGGAGAATCGCTTGAACCCGGGAGGCTGAGACTGAGACTGCGTTACCACTGCACTCCA GCCTGGGTGACAGAGTGAGGTCTGTCTCAAAAAAAAACAAAAAAACAAACAAAACAAATGTTCTGAAAAGTAAAAAAAGGATCAAATATATGTAAAATAGGAAGTGCG GTTTCCCAAAATGAGGTCTGTAAACACGGCAAGTTCCCTCTGAGGCAAGGGACGCAGGTCAGCCACCTAGCCCATGCCACTAGTCAGTAGAACACTGCCCTGTCTGTATAACA CTGCGCTCTGGACAGGCAAACGGCCAAGTCTGCCTGTGTCTGTCGGAGGGGACGCAGGTCAGCCACCTAGCCCATGCCTAACAAGTCAGTTTGT ACCACGCTCTTCCGAAGCGTCTGCCTGTGTCTGTCGGAGGGGACGCAGGTCAGCCACCTAGCCCATGCCTAACAAGTCAGTTTGT TTTCTGAACGGAAGCTTAAACCTAGAAAAGGAACGCGTGAAATGGGAGTGTTAGGGCGTCACAACTCCAGTGTGGTTGAAATGAAAGCAGAAAGCAAATG ACGACCTGATGAAGAAAAAAGGAAGCGGGAATCCAGCTTTTCACAAACCCTGAAATGGGAGTGTTAGGGCGTCAGCCCCAAGCACGGCCCAAGAAGGACTGGAGGGAGG GAAGGGGTGGGCAGGGAGTACCAGAGCGGGGACACGGGGACAAAGGGGACAGCAGGCACCAAGGCGCAAGGAGCCAAGGAAAGTCGGCGT TAGCTGGATTGGAAACAGTCCAGACAGTCCAGCGCCACCAGCCGGCACGATGAACGAACAGACCCGTGAAGAACTAAGCGGCAGAGAACAAGGGGCACCAAGGGGCCACGAGGCAGG GGACAGTGAAGCACCATGCCGGAGATGAGACCCTCGTGAAGAACTAAGCGGCACGAGAGACCGTTCTAGAGAAAACCGTTCTAGGAAGGTTGCTCACATAACCCATACTGCTCACA CAGTGTGTGGCCGGAATGAGACCCTCGTGAAGAACTAAGCGGCACGAGAGACCCGTTCTAGCAGAAAACCGTTCTAGGAAGGTGCCACTGA CTACGAGGTTAACTGCCGGAGATGAGACCCTCGTGAAGAACTAAGCGGCACGAGAGACCGTTCTAGCAGAAAACCGTTCTAGGAAGGTGCCACTGA CCCGGGCCCTCCCCCGGCCGTTCGGCAGCGCAGCAGACTGCGCACACAAAGCGTCTCCGCTGCCATTCACCTTGCGACACAGCCGCCAACCCT CCCAGGCCGGTTCAGCCGTTCACAGAACTGGCGCCAAAAGGAACATGCGATGTGACGTGTTACCTGTTACCTCCTCAGTCTACATATTGTTACCTGAAAA CTGATGAACGCGGTGGGAACCTGGCGCCAAAAGGAACATGCGATGTGACGTGTTACCTGTTCTCAGTCTCTACATATTGTTACCTGAAAA TAAAGTTTTCTCCTTTTTTCTTCTCCTTGTTAACAGGCAGAAGTGTAGGCTGCAGGTTTCGGCCTAAGGAGGAGCAGAAGTGAAGCGACCCGTGC GAGGGGAGACTTAGCAAGCAGCTTGCAGGGGGGGTGAAGTGTGTCAAAGACCAGGCTGAAGCCATTGTCCAGTATCGAAGATCCCAGACCGTGTC CAAGCAGGCTTTACCATGCT |

TABLE 4C-continued

| SEQ ID NO | GENE NAME | SEQUENCE |
|---|---|---|
| 209 | chr21: 37841100-37841800 | TGAGGCTCAAAACAGGTGTCTGTGAGTTTCAAGGCGGTTCACAGGCCGGTCTGTCTCACATGGCCGGACATGCATCCCGGGGCTGCCCTGCCG TGCTGCCCGAGTGCACGGGGATGAGGACCTGACAAGGCCAATTGATCTTGCCGGAGCTTCCTGCGAGCTACTCCAGCGTGAAAATCTTCCAG AAGGATTCTCCACAGGCAAGATCACGCAGGAGGAAAGGCCAAGAAATTTACAGCTTAGCTGATTAATGGGCCAGGCAGTTAAGAGTTCTTGCCAAGCTATGAG CATAATTTATAGTCATCACGGCAGGAGGAAAGGCCACATAACTCACATCCTTAAAGGCCTTAGACACAAGACACGCCGGATCATTTGAAA ACGTCTCCACTCCTGGCCCAAAGAGATCGGCACGTTTCTGGGTATTCTGGTCAAAGAACAGGGAGTCTGGATTAATACACGGCAGAA AAAAGCGAAGAAAGACACCAGTCATATATTTCTGACCGTCATTTCCGTTTGTTCCGAGGGACTTGGTATTTATTTAACCACATTCT CACTTGACACCGCCCCCCCCCAACCTTGTGACAGTTGCACTAGAATGCTCAGCTGAGTCATTTTCATCACATAGATTGAAATGTGCCAGGAAG GCCGTTTATGAGATTGTGAGAAAATGGCACTAGAGAAAGCAGTGTGAAAAGAGGCCTAGAACGT |
| 210 | ERG | TCTCTACATGCTATCTACTAAAAACTTAGGCAGGAAAATGCATCAGACAGACACCCCACAGCGACACAGAGAACCCCACCGGCCATTGCTTTCCA ATCTCCGAAACCTAACCATTGCTGGAGAAATTCTACTCACAGTGCACCAAAGTAGGTATTTATTGAAGATAACATATGTGAACAAA CCAAATTACCCCCATTGAGTTACGTCGCTTCCACTGGAGCACTCAGTTCTCAGCTGTGAGCATCTGGACACTGGCCTGTAAGGAGCCACTGAAGAGCCTCAAATGTCTGACATT CACAAAACCATCTTTTGCTTTGACCCGACCTTCAACCTCTCCGAGTCTGCTGCCTTTCTGACACACATCCAGGCACGTTAGGGATAG TTAGAGAATCTGAAAATTCAGAAAATGCCTTCCAAAGTAATCCACAGCACTCAACAGTGAATTTAGAAACCCCAATTTTTT CTGAGTTTGAAGTTTTTAAGCCTTGCGGATGGTTGGAGTAGGAAAAA |
| 211 | chr21: 39278700-39279800 | TCAGACAAGCTCTGTGCAGTCGAATTTTTTAAAGATGCACTGTCACTTGAGGAAGACAGGTGATCTTCCTGCGGCACAAATAGAAGCAAAG AGATTTCTCTTCTCTGTCTGTAGAGCAACAATTGATAATGCCGATAATCTTCCACCAAATTGGCAGCAGTAGGCTGCCCGAAGGCAGCAG GCATATTCGTCTTTGTGACTTCCCTGGAATGTTTTACTATGATGCTGTCACATTTCAAAATTATATTGCTTAAAAAAAATCAACGCCACCGCAGGCTGCCCCCA CAGCTTTGCTCTGCCAGGCTCCTGGGCCAGCCTCTCCTGCCAGGCCACAGGGCAGAGTTCTTGGACAGGAGGCAGCAGCCTTCCAGGTTGCCTAG CGGTCCCTGGGCCAAAGCAGTTATGATGAGCTGGGAGCCCGAAACACATACGGCGAAAATGTTGCCAAAGAGTCTTCCATATCAGAAATGCACTTTTATCATGTCAAGAG GAAGCCCCCAAAGACAGTTATGATAGAGCTGGGAGCCCGAAACACATACGGCGAAAATGTTGCCAAAGAGTCTTCCATATCAGAAATGCACTTTTATCATGTCAAGAG ATGCAGGACAGCTGTTCAAGGACCCAAGCTCGGTGCTGACCGGAACACAGACCAGATGTTTGCGGAGGCAAGCCTCACCCAACATCTGCCCAGAGATCATCCCTGCTTG AAGATGCAGGGACCTGTTCAAGGACCCAAGCTCGGTGCTGACCGGAACACAGACCAGATGTTTGCGGAGGCAAGCCTCACCCAACATCTGCCCAGAGATCATCCCTGCTTG TCTAAGCCGGCTGCCTCTCGTGACCTGTTCACAGATAGACTGAGTTCCCGGTGGGTGCCACAGACAATTAGCTGGGCTGCCTCACATGTAATCTAATT GGGAAGGCCTGGGTTCACAGATAGACTGAGTTCCCGGTGGGTGCCACAGACAATTAGCTGGGCTGCCTCACATGTAATCTAATT ACAGGGGAAACAGGCTCAAACACCGGTGATAAGCGCCAACTGTTTCGGTGACTCTGTAATTTTCCTATTAATTTTCTCCATAACG CAC |
| 212 | C21orf129 | GTTGCCTCGGATATGCTTATATCAAAAACTTACGTGCACTGTCACTTACCTAGCATTTGCATTTCACTGCATTTCTGTGTGGTAACCGAC TGCCACCCGACATGCGTGTTTACTTCCTTATTCTCACGCAGTTGCCACATTCAACATACCGACCCTGCAGTGCAAATATTGCCGGTGGATCCTGACT TCCTCGTTGGACACCCTACTGTGTCGGGAAAAACAACAACGACCCTGAAGGAAACCATGAGT |
| 213 | C2CD2 | TCATAAATATTTCCAAATGTATTCTCTATTTGTCTTACAGAGTCTAACAGACATAAATAGCGAATTGAAGGTTCTGTCTTAAAACCAGCAGAA AGAAAACAATGACCAGAAAAAAAAAACAATTGTCTTTGGCTTCCAAGAACAATCGGATTTCAACTGGAACCACAGATGTCCGTTGAT AGAAGCGACTACTTTTTAGCTCTGGAGGACGACAAAAGCAGCCCCTCGATAGCCGTCCTGTGGGTGTCACAGCGAGGTCGCTGGCCACATCAGGT ACCAGAGCCAGCCGCCGCCCCTACCTTGGGAGGGCAGCCCCTGTACAACCTGTACAACCGAGGAAAACACGCGGAACTAGCAACGTAGGAG GGTTAAGGCGAGTTGGGAGGGCAGTCTCGGCTGCCTGGCTGCTGCAGGTCGCACTCGTAGGACGTCTACGTGTAA TTGAGAAAAAATAAGACAAAAATAACTTACTGTGCAGGCAATTAATTCTGTCAAGAGGATCCTCTTAAGTTAAAGGGAATGAGCATGAGA TGAAGAGAAGTAAGAGGCAGAAGAATTATGCAAGAGGCAACATCAGAGTGGA |
| 214 | UMODL1 | ACGCCGAGCCGCCTCTGCAGGGAGAAACCGAAGCAGAGATGGTGATGAGAATAACATCCAACCCTGAGTGCTACTCTAACCTGCCAGAGGCGG AGGGTTCTCAGTGAGATGAAAGCATTACAGATGCGTTAGATCTAAGGAGGGGCCTGCAGATGCGCAGCTGGCAGAGAAACCAGGAGG GGCTGAACTGCAGTGCCGACCGTCAGTCGAATCAGTTCACCGACAGCCTTGGGACATTCACCTTGGCGCTCCACAACCTGTCAGA AATGCCCCCAAGCCCAAAGGCGTCGAGAGAATGGCCAGGTTGTTTCAGGATTGACACATATCCTAATGTACAAGTCAGCCACCACCCCAC GTCACTGAGCCGTCTCTTGTGTTTCACCCAAATAAACTCTGCGGAACTGGGCGGACTCGCAGGACTCGCTAGGAGCTTCAGTGTAA CAGAGGGCAGAGCAGAAGTGGATGGTGAGAAGAGCCAATGAGGGGCCCCGTGAGAGTGAGCAAGGCTGCACCCCTAACCGACGTCCTGGGC |

TABLE 4C-continued

| SEQ ID NO | GENE NAME | SEQUENCE |
|---|---|---|
| | | TACTGTACAAACAAAGACCTGGGAGGCTGAACAACAGACCTGCACTCTCTCGCAGCTCGAGGCTGCAGTCTGAAATCGAGG<br>GGCTGACAGCGCTGGTTTCCTCTGGAGCTGGAGCAGAAACCGTTCAGCCTCTCCCAGGCTCCTGGGTGAGCCCTTCCTGGCATC<br>CCGGGCTCATTGTAGATGATCACTCCAATCTCCATGGCTTCCAGGGCTTCTTCATCTCTCTCCTCTCCTCTTTTGTAA<br>GGATGCCAGTCAGTTGGATTTAGGTTCACCTTAAATCCAGGATGATCTCATCAGATACATCTGCAAAAGACCCTTTTCCAAGTAAGTTGA<br>CATTCACAGGTACCTGGGGTTAGGATTGGACATATCTTTGCAGGGGTGCAGGGGGCTGCCACTGACCTGTCAACCTTGCTGCCCTCGGAGTCC<br>CCAAGGGCCCTTCACTTTCACTTCCATTGGCAAGCTGGTGTTTGAGGGGTGCTGGTGGACACCTTGCTGCCCTCGGAGTCC<br>CCCCTGGTGTCCCCAACAGATTCTAAGCTGTTTCCTGGGAGCCAGGCATTGCAGGGGATTTTTAAAGAGCTTCCCAGCAGGTGAG<br>CAGCCTTTCATGGGTATCAGGAGAGACCTTCCTGGCAAATGTGTGAAGGTCCTTCAGACCCTGCAGAATCCCTCCTTAAGACTCTGGGACT<br>GGCTGCTCACCTGATCGTTAGGACAGGAGCAGTGGAAACCTTGGCTTGGACCTGCTTGGCTGCCCAACTGGGAATTCCCCCTTCCCCAGCCTTTGCCT<br>GTGCACCCAAGGAGTATCGTGAACATTGCTCCAACTGGCCTTCTGCAATTAAAGACAGCCCTTGCAACAGCCTCCCA<br>GAATTAGAGGGGCTGGAGAGCCACTGCAATTAAAGACAGCGTGTGCACACCCTTCAGCAGAGTTTA<br>TGGGTGAGCAGAGCAAACAAGAGATGCTCAGCGCTCAGGTCTCTGGGATGTGTGGGCTGACTCGTACATTAGGATGTGTCAATCTGAATGAGAGTTTA<br>CGTTATATGGATGCCTTGGGGCTTCGGGGTGAGCAGCAGCTGTACGGAGCCCAGGTGAATGTCCCAAGGCTGCTGGTGAATCAGATCC<br>CTGGCGTTCTCCGTTGGACAGTTCTCCTGGCAGTTTCTGCCGGCCGTGTCCTCTGCAGTTGATCTGATTGGATTAATATTTG<br>AATCAATAGACTGAGTCAAGCAGAGATGTGGGTGGGCCTCATGCAAGTCAGCTGAAGCCCTGAAGCGCCTCATGCGAAAAGGCTGCAAAGGCTGCCCCCTTCCCCG<br>AGGAGGAGGAGAAC |
| 215 | UMODL1/<br>C21orf128 | CACATTTCAGAGCTGAGTGCTGTGCGGCAGGTCTTCCTGAGCTGTGCCAGTGATGTGACGCCTCAGGCCGT<br>GCATGGGCCGGGAGGCGGCCCTGCCTGGGAGGCAGCACATTTGATATTACTCGGCAAAAAAACGAAAACAAAAGAGCTCTCTGAAGAAGAAAG<br>GGGGCACCGGGATCTGTAGAGAAGACATTTGATATTACTCGGCAAAAAAACGAAAACAAAAGAGCTCTCTGAAGAAGAAAG<br>GTATTTGCGCTGTGTCCACCTAGAAATATGTTGGCCACACAGCATTCAGGAGGACATTCAGGAGGACATTCAGGAGACAGTTCGTCTCCGGTGCGTCC<br>ACATGTCCTGGGGTTCCTGCCCAGTCACGGTGGGCTGTAGGTGGCCATGTGGCCATGTTTCCCCAGGAGGTACGTACCATGTGCTG<br>GGGCCCTGGGGTTCCTGCGGCCTGCCTGCCGGCCCCGCCAGTCACGGTGGGCTGTAGGTGGCCATGTGGCCATGTTTCCCCAGGAGGTACGTACCATGTGCTG<br>GGAGGCTTGAGGCTGAGCCGCCGCCCAGCAGCGGACTGCCCTGACACGCGAGCGGCCAAACCTCCTGC |
| 216 | ABCG1 | CAGGCTTGAGCGCTGGTGACTGGGAGACCCCGGAATGGAATGGGAATGAATGCCTCAAATGCTGGTGTGGTGTCCGAGGGGAACGCCCGGGGTG<br>TGTTGGAGTCTGCGCCCCTGTGGCTTCGACGCTTCGCGGGGACTGCGGGTGCTTCCAGACTTCCAGTTTAAATCAGAGAGGTGTGTCCACG<br>AAAAGAGTCAAACTAAAACATT |
| 217 | chr21:<br>42598300-<br>42599600 | AACGAGACAGTGCAAAAAGCCGCTGCTGGTGACTGCAGTCGGCATGCAGACTCGGGCTGCCCTCCCACTTGCACGTGATCCACTGAAGACAAGCT<br>GCCTCTGTACTCACGCTCGCCCCGCCTCCCCCATGCGCTCCCCCATGAGTCACTCGAGTCGATAACAGATTGTTTTTTTTTTTTGTTGTGTTTTTG<br>AGCACAATAACCTCGCCCCGCCTCCCCCATGAGTCACTCGAGTCGATAACAGATAACAGTTTTGTTTTGTTTTGTTTTG<br>TTTGTTTTGAGACGGGGTCTCGCTCTGTTGCCCAGGCTCGAGTGCAATGAGCGCGATCTCGGCTCACAACCTCCGCCTCCCGGGTTCA<br>AGAGATTCTTCTGCCTCAGCTGCCTCAGCCTGGACTACAGGCGCGTGCCACCATCACCCAGCCTCAGCTAACTTTTGTATTTTTAGTAGAGACAGG<br>GTTTCATTATATATATTGGCCAGGCAATTTGATGACCCATCCCCCTGCTGTGGGAAAAGGCTGGGCACCCCACACTCAGGCGTGAG<br>TGGCTCGGAATCGCTGCAGGCGCCGCGGCACCCCTCGTCAGAGTCGAGAATCCATGCAGAGCGCGCCACATCCAGAGCGCTC<br>ACTCCAGCATCCATGCAGCCGCCCGCGGCACACCCCCTCGTCAGAGTCTCAGAGTCATGAAGTGCGCAGCACCCCCACACCGAGTGCTCCAGAATCCACG<br>CAGAATCCATGAAGCACCGCACCCCACTCCTCGTCATAGCGTTCTAGAATCATGCAGCCAGCGCAGAGCCCCAGCACACCCCACACCGAGTGCTCCAGAATCACG<br>CCGTGCAGCGAGCGACATCCTTCGCATAGCGTTCTAGAATCATGCAGCCAGCAGCAGCCCCAGCAGCCCCAGCGAGATGGTGATGTCTGCAAAAGGCCATGCCTTC<br>CTGCAACGTGGCATCCTTTATCGAGCGGCTCCATGCAGCCCAGCCCCAGCAGCCAGCGAGATGGTGATGTCTGCAAAAGGCCATGCCTTC<br>ATAAATCTGAAAATTGAAAACATCCTTCTACTTATATCCTTACAACCCACCATTCAAGCTGTAGAAGCCTTTCTGAACCCCAAGCAGAAG<br>GATATCCAAAATGTAAAAACGTGGGGCCT |

TABLE 4C-continued

| SEQ ID NO | GENE NAME | SEQUENCE |
|---|---|---|
| 218 | chr21: 42910000- 42911000 | ATAGTGCGACTGTTCCGAAGTCTTTATCACAGTTACTGGTGATGCTTTTTTCCAGATGTCTTCTGACGTGCACCCATGAAGGGCTCCACCTGA GAGTGCCAGGGTCTCCCTGGGATGGGAGGCTGAGGGGGTCCTTGCCGTCCTGGGCCTCCCAAGCAGCCATAGGAACAATAGGGTGATG GGGCCCCAGAGATAGAGGCCAGTGACAGCAGCCGCTTTGAACCCCTCACAGGCCCTTGGCAGGGATGGGACCTGCCTCCCCACGG ACGGAGATGGGGCTGCTGCTGCAGGTGAGAGGAAGGACGTGTTGGCAGTCCTGTGACTCCCGGCCGGGGCATCTGGGCTGCACCCAGCGA CCGGCTCTGCTTGTAACAGACAAGTGCACAAGGCCTGCAAGGCGCGCAGCCCGGTGAAGGCACAGCGGCCATGCTGGGCCCGAAGT GCCGCCCATACACGTGGAGATGCCGGCCAAGCACTTCTCCAGTCTTCTTTAAGTGTTCCCAGAAATGTGACCACCAAATCTGAGAGCACCCGACAG TAAGCCAGAGGACCTTGATGTGAGATCCAGCACGGTGTGTGGGGGCGACTGTGGTTCACTCTCGTGGAAGGGAGGCACTCCGGGGCTTGCTCACCAGGT CGTGGTGCACATCCACGGCCGTCACAGCTGTAAGCTGCCAGTCCAGCAGTCCCAGCCGAGGGACAGCCAGTCCTGACATCCCTAAAAGGTCACTGTGCTGGGCCA ATGTCCCCAGTCAGTGACTGACAGAGACCCGCTCCTGCCCTGTCCCGAGGGCTCCTCCCCGCCTGCCCCCTGCTGAGCACGC GGGTGGGCGAGCCTCAGCAGAGACCCGCTCTAGACCCTGGTGGCTCCAGGCCCCGGGGTG CCAGAGGGAGCTGCTTG |
| 219 | PDE9A | CACTTGAAAAGCACAACTTCATGTGCCAAAGCTCTGACACGCTCCACTGAGGAGGCCGTGGCAGGGCTGCCAAGTACCGAGTTCCAAG CCGTTGTTATTTGAGAGGCTGTGCCCCCCGCCATGAGACCAGGTGGGGGCATAAGTGACACAGGATGACTGGCCAAAGGTGAGGAC GATCACTTACCTCACAGGATGATGCTGTAAAGCTCTGTGACCGTCCACAGTGGAGACCAGGCTGCCACCAGGTGGGTGCACCAGACTCTCCAACGAACAATAGCAC ATGCCCCTGGGGTGTCTGACCCGGCTGCCGGCAGCCAGCAGCCCGAAGGGGAGGAGGAGCCTGGGTGCACCAGACTCTCTCAATAAGCAGCAGCAGCACTGCC CTTAACAGATGAAAGCGTGGCTTGGAACTCACTTCCAACGAAACAATAGCAC |
| 220 | PDE9A | AGCACCCTTCCTACCCCACCCTCCCATTCCTGCCATCCCAGGGTCCAGGGAGCCCAGATTCCAGGGAGGAAGGGTTGCATTAGCTCCCACTCG AGCACCCTTCCTACCCCACCCTCCCATTCCTGCCATCCCAGGGTCCAGGAGCCCAGATTCCAGGGAGGAAGGGTTGCATTAGCTCCCACTCG GGTGGCGGAAGGGTCATGTTCATGCAGACTGCTTCGCAGGCGAGAGTGCTTCAGGACGATTACAGGAGCAGATGCCAACTGGCAGAGG CCTTCAGAAATGCCCCTGTGATCCATTATTATACAGTGGAGATTGGCCTCAGACACTAGCAGTGAGACCTGAGAGAAGCGAAGCTACCAGAAGAACAATGACAAGA CCCTGTGATCCATTATTATACAGTGGAGATTGGCCTCAGACACTAGCAGTGAGACCTGAGAGAAGCGAAGCTACCAGAAGAACAATGACAAGA GTATGAGCACAGCAGTCAGACCATGACAATGCCCTTGCGGAGGCCCGATGCGAGATGCCGGCAGTGTCCAGCCGCATCTACCAGCCTGAGGAATGGGCCTGA ATCCCACCGTGGAGGCTGAGGCTGTTCAGAGAGTTATCAGAGCTGCTCCCCGACGGGCCACATCAAGTCCCTCGCAGC GTCGGGAGGAATTCCACCGGATTATCGAGACTGCTCCCCGTGTTAACGATTATCCGCAGATCCCCCAGAGACCAGGCCCTGAGCAAATG CTCTGGCCAGCGGCTGAGCCCTTCAAGGACTCCATTGCTTGCGAAAAGATTCCACCCGTCTGAGGATGGAGTCAAAATCTGAGGCTGAAATCC TGAGGCCCCACCCGGTATCAAGGACTCCAAAGCCTTTAAAACAACAGAGAAAACGATTATCTCGCAGCTCTGGGGATCGCTGTGCGTGGGCTGCAGCAGTTTG AGGGTGCGGCAGGGCTAAAGCCCCGCCGGCCGCAGGAGTCCCCGGAGATTCCCTCCTTCCTGTGCCTCTTCCAGCTGCTGTGGGCTGCCAGCAGTTTG GGAATTGCGGCCCGCCATCACACCACATTTGATTGATATTAACTCATGCCAATGTTAGGCAAGTGCCCCTCAAATCCTTCCACTTAACAGACATTTATTGA AGGTTCCTGTGTGCGGGCCCAAGAGAAGGGA |
| 221 | PDE9A | GAATGTTCAAAGAAGAAGAGCCCTCCTTGCCTTCTTCACCCCATGCCCCTCCGACTGGGGTTCTGTAGACCCCAAAGTAAGTCC GCCACACCGGAAGGAAGTGAGTTACACAGGGCCCACATGGGAACCGCTTTTTGTCCTGTCTTGGGAAAATGGCCACGACCCCAGCC CAGGCCTCTGCCACGCCACA |
| 222 | PDE9A | CCATCTTCCTAGGCCTGCGTTCCCCCACACCCGGGACTTGTGCTGGAAGGAACTGCGTTGGCAGCCAGGAGCCCGGGAAACTGTCC AGGGAGGCATCCTCGCGATGAAGGCGGGGCCTCGGCGTGCCCCGTTCCGCGCTCTGTTCCGCGCTCTGTTCCGCGCTCTGAGAAGCCCACCCTTCACCGA GCTCGAAATAACCCCCCGGAGAGCCGAGACTCATGCCGGACAAGATGCGTAACCCGGCGATTCACCGCGGGCCCCAGG GCCCCGGCCTGGGAGCGACCGCGCCCATCCCGCCGTAGGTGGTGTTTCTCTGCAGCGAGGTTCGTCATTCAGCCTCGTCATCATTCAGCCTCAGTCCCAAATACCGAAAGGCAGTCTT ATCCTCAACGGTTTCTGTGTGATGAGTTTCACTCTTGTTGCCCAGGTGAGTCGCGATATGCCACCACCGCCTGCAACCTCCGCGTCTCCCTG TTTTTTTTTTTGAGACCGAGTTTCACTCTTGTTGCCCAGGTGAGTCGCGATATGCCACCACCGCCTGCAACCTCCGTCTCCCTG GCTCAAGCGATTCTCCCGGCTCAGCCTCCCGAGTAGCTGGGATTACAGACGGGATGGTCCATGCCACCAGCCTGGCTAATTTTTTGTATTTTAGTAG AGACGGGGTTTCACCATGTTGGCCAGGATCGATCCTCAGGTGATCCACCCGCCTGCCCAAATGCTGGGATTAC AGGCGTGAGCCACCGCCGCCCGGCCTTTTTTCTTTTGAAGTTAATGAACTTGATTTATTTATTTACAGAATAGCCCCATGAGA |

TABLE 4C-continued

| SEQ ID NO | GENE NAME | SEQUENCE |
|---|---|---|
| | | TACTTGAAGACCCGGTGCCAAGCGACAGTGTTGACCCCAGGTGTCAGTCCTGCCTGCCCCTTCACCATAACC ATGTCACGGACAGGCGTTGGGCAAGGAGCTGTCTATTTTCACAACTTCTTTCACACATGACACATTTTCACCACCCGT ATGCATCAACAAATGAAAAGATGAGCCTGTGACATTCCGTGCGTAGTTACAACCTTTCTTTCAAAACGAACCTTCAGTTGGAGCCG AAGCGGAAGCACGTGGCGTCTGACGCACGCCCGCCCTCGCTGCAACGCACCGGACGCCTGCCTCGGTGAGTGCGCCTGCGGCCCGG GCAAGTACTGCAACTCCAGCGACATCATGCGACCTGTTCTGATGCTGCACCGGCCTGCCTGCCCTGCGGCCTGCCTTCCCGGCTTCTACAA TGACGCCACGCGGCCTCTCCGCCTTTGGAGTGATGGCTGGAGGGCGCCTGAAAGAGGCCTGAAAGGCCACCCGCCTCTACAA GGGCTCTTCGAAATCAATCAATCCGAGAATCCGAGGCTCAGCCGCCTCCCGGCCCTCCTGCTCCACCAGTGATGGCTGTGT CCACAAGGAGGAAAACCGTCGGGCTGAATTAAACAGAACCCGCCCCCTCTAAGAGTGTTGGGTTTTTCTGCCGGCGCTGTCTCACACCTGT AATCCCAACACACCAACTTTGAGAGGCTGGACCAGGTGGGCACAGATCACACCTGAGGTCAGGAGGTTCGAGACCAGT |
| 223 | PDE9A | AGGCAGCAGGGTTAGGACTTCAACATACAACTTTGGGGGGAGATGTACTTCAGCCCATAACACCGTGGGAGGATAACACCGATTTC AGAGCTTGCAGAGGAAGCGCCCAGGAACGCTGTGAGACATCAGCCCAGGTGCCTGTCAGGGACACCCGCGGGGGCACCTG GCCCATCTGAGTAACGGAGGGCATCCGCCACTTCCCCCAGGAGTACATTTTTAGAACCCAGCGCCATAAACCAAAGACAAGGAGACTT CCTGGTGCCCCGTCAGCTTCTGAGGCGACGTTCTCCGGCTGCAGCCCTCCCCTGTAGGTGAGAAGACAGTAAATGGGACTC TTGCTTCCAAAACGGAACCAGGGTAAAAATTCTCAAGCGTT |
| 224 | chr21: 43130800-43131500 | TGCTGCACCCCCGCTGCCCCTCCTCCCGCTGCCCGGCCAGCACCACTTCTCACCCGGGCCCCTCTGCTCACAGCGCTCCCCGGCCTCT CCCCAGGGGGCCCAGGACATGGCCCTGAAAGCCTAGCCGTTTGAACCTTCCGGCCTCAGCCCCTCCCCCACCCTCCGCCTCT GCCAACCCCTGGCCCTGCCCTGCCCTCTGTCCCCTGTGCGCCGCCCAGACTTGGGGTCGCCCCAGACTGGGCTGTGCTGGGGT CCTGGCCGGCTGTGCCGCTGTGCCCCACCCCAGGTTTCTGTGCAGCCGGAAGCCTCGTCGGCCGGATGGCGAGGTCTGTGCCTTCCAG CTGCTTCCCTGCGGCCACCCCCAGGTTTCTGTGCAGCCGGAAGCCTCTGTCGTGCGCGGGTGATCCACCATGGCGTGGGCCCAGGAG GCACGGGATCTGTCTCGCCCCTGGTCTGCTGCCCCCCTGGGTCTGTTTAGTTCTCATCACCAGCAGCTGACTAGGGCCTGTCCTTCTGCCT CCTTCCAGCCCCTGCACTACCACTTCCCCGAGGTGCTGTCATTGTTAGCTGGGCCCTCAGCCTCCG |
| 225 | U2AF1 | TTAAAGGGAGTGGTTGTATGAGAGTTCCTCCAGTCAAAGGTGTGCAGCTGGGAAGCCACCCCACCTAAAGGGAGGAGCTGACAACTG TCCACACTGAACACTGAACACTGAACACCTCACTCAGATCCTGAACTGAAACTGACATCCGAGACCTCCCTCCATAAGCCCCAAGTACGCCGTCTGAGTTAACTGAACTCAGGCCTGGG AGGCTTTCCAAGTTGACTGACTTGACTCAGCTTTGAACTGAATGACCGTACCATGACAACACCCTGATGAAAAGCTAAACTGAGCCAATTATTCA ACAGTAAAATTCAGTTGGTCTCACTCA |
| 226 | U2AF1 | TGCTACCAGCGTCTGCTCTTGGGCTTGGACAAGTCACCCTGGCAAGTGCATCTGTAATGATGACAATGCCAATGCAATGCTGTTCTGAGA GTCAGACAGAACGTATGTGTCTTCACATATGCTCATGAAGTCTCATGAAATATCTGAAGTAATCAATTCCTCAGGCACCATTCAGAGTCTCT AAACGCATGACAACCAGACCAACAGGAGTGTTCAAAAATAGGTCTGAAGTAAAATCAATTCCTCGGTCTCAATACACTGAAAACAAACTATTA GGGACTGACCGAACCACCTTAGGAACCAGCAATCATGCCTGTCGCCAGCAATGTCAGGAGGAAGCCGATCTCTGATGAAT AATCCAGATCCATATCCAATGGAACCAGCAATCATGCCTGTGCCAGCAATGTCAGGAGGAAGCCGATCTCTGATGAAT |
| 227 | chr21: 43446600-43447600 | CAGGTGCCGGCCACCACCCGGCTAATTTTGTGTTTTTAGTGGAGACAGGGTTTCCCATGTTGGCCGGCTGGTCTCAAACTCCTGAC CTCATGTGATCACCCGCCTCGGCCTTCCAAAGTGCTGGGATTACAAGGCCTGACCGCCCGGCCCAAGAGTGAAGTCTGATAGCTG GGTAAGAAAGCCGTGGGAACAGCCGGTTCAGACACGCTGGGTCTAAGACGTCTGCCTGCTCGCGCATCCAATGGGAGCCG TGGAGAAGCCAGGCGAGTGCTAGGGCGGCACCCGAGCCCGGGGATGAGGTCAACCGCTGATGAGGTCAAGTGTGACGG AAGTAGAGGATGCAAGCACCCAGCACCCGAGCCCGGGGATGAGGTCAACCGCTGATGAGGTCAAGTGTGACGG CTGGAGACCAGTGGAGCCAGTGAGAGACATTTGGTGGAGTCATGGGGCCACAGCCTGATTGGTGAGAACAGGAAATTGCAGATGG GCCTGCGGCCCCTGGCTCCCGATACTCCAGGACTGGCTGCCCAGGAACCACTGGGGCCTCTACCTGGAACCACAGCCCCGCCGCTGTC ACTCGGTATCCAGTTACCCTGGGGGAACCACTGGGGCCTTTCAGTAACAGAGTGTTAGGGACACGGGTGGCGTTGAAAGGCCTAAGGT GGACTGCATGCCCGTGGGGGACCTGAGGGCTTGTAGGCCCCAGGGCGTAAGCATCTCTAACAGGGCAGCAGCCACTCATTTAGCACAGGAGAG GCGGTTGTTTTAGATTGGGGTGGTGAGGGCCCCAGGGGCGTAAGCATCTCTAACAGGGCAGCAGCCACTCATTTAGCACAGGAGAG GCGTCCAGCGTTTCGTGGGCT |

TABLE 4C-continued

| SEQ ID NO | GENE NAME | SEQUENCE |
|---|---|---|
| 228 | CRYAA | ACCCAACCACAGCCTCCTCTCTGAGCCACGGTGAGCGGTGCAGGTTCTGTTGTTCTGGAGGGCCTGAGTCCCACCCAGCACCTCATAA<br>ACAGGGTCCTCCCCAGGCTGCTGCAGTAGGCATCACCCAGGGTGCAAAATGCCTCAGGGAGCCCAAGGCTGAGCCAGTGAGTGAGA<br>AGGAGCATGTGGAAGTGCGTTTTGGAGAGGCAGCAGCTGCCGACGTGTCAGCAGCTGCCCGGCCGTTCTAGAGACAGCATGACACCAAGGG<br>CAGTGACCTCATTCCACAGGCTGAGTCCAGGCAGCCAAGCATCACCAGCCAGCGATTGACCCTAACGACCAACCAACCCGTAAC<br>GACCCCTCCTACCATAACCAGTAGCCAGCCAGCCCATAACCCAATTCTATAACCAGCCACCTGACCATAGCCAAACAACCAGCCG<br>GCCCACCAGTAGCATTCAGCCCTGGTGTGTGGAGGAGAGGCCGAAGCATCTCTGTTCTGATAACCGGACCCGCC<br>GCCCCGAAAGCTTGCCCACCTTGGTGTGTGGAGGAGAGGCCGAAGCATCTCTGTTCTGATAACCGGACCCGCC<br>TGTCTCTGCCAACCCCAGCAGGGACGCACTTCTCCCGGAGGACTCCACCGTGAAGGTGCAGGACGACTTTGTGAGATCCACGGAAAGCACAA<br>CGTCATTCTCCGATGTGAACGAGGCCCAGGTGAGCCACTGTGATGGTGTTCCCCGAGGACCCCGAATCAGCCTGCTTTTCCCAGGGAG<br>GGGCCGTGCCACCTGACACACGCCAGCCCATTCCCAGGCCGAGGAGGTCACCATTCCCAGGATCTCAGGTTAGGG<br>TCCCTTCCCGGGCTGCACCCAGCCGTCGCCAGTCGTACATCTTCACATGAACCCTGTCACCTGGTGTCTTAGAAAGAACCCAGGAAGTGGGA<br>GTGCCCCGGGTGGCCGCCTCTAGCCACCTTCACAGACAGCAGTTTGGAACCAGTGTCCTCATTATTCAGGGACGCTGGGAACAA<br>TTGGAATGCTTTACAGGACATTGACACCTTCGCCTCCACACAGCACTTTGGAACCAGTGTCCTCATTATTCAGGGACGCTGGGAACAA<br>GGGGGTCCTCAGCCTGCTGGGTCCCACAGCTAGTACCCGGCAGTGGACGGGAGCTTCTCCCACAGTCACCCTGATGCACCCCTCTTG<br>CTCGGCTGGAGCCTCGAGTCTCCGTGTGTTGAGGAGCCGGGACTGGAGGCAGAGTGGAAGGTGGAACTCTTAGCCAAAGTCTT<br>GAGTCATGGAGCTGTCACAGATGGACAGTGCCCCGCCAGTGGGGCTGGAGAGCAGAGTGGAAGGTGGAACTCTTAGCCAAAGTCTT<br>GGTTTCTTTTGGCCAGGTCTCCTTTCAATGCTGGAGAAGGTGCTGGCCAGGTGAACGCTGAACCTCCATGTCGCCCCTCCCTC<br>GCCTGGGCCCGGTAAAGCCCCACGTAGCCCACAGCCAGCTGGAACATGCTTCCTGAGCTCGGTGGCTCTTGGTCTTTGCACCCAGTGAG<br>GAGGAGTCAGCCCAGGGAGCTGAGTCTGCGGAGCAGTCCTGCGGGGTTAGGGCGTCCAGGGACTGGAAGCATGTGGCGGGCCTGGTCTGCACCCGCCTCCCTGTGAGAGCCCCGACTGTCG<br>TGCAGAGACCTGGGCTAGAGCAGTCCTGCCGAGCAATGCCCAAGATCGAGAATAGCCCGCAGTGGCCTGAACCATCTGCTGCGGAGCCAT<br>TTTTGGAGTGAAGCCATGGAGCGGAGAGAAGCCCACTCGGCTCCTGGTCTCTCCCTGGTGCCTGGCCTCTCGGCTGGCCTGCCCATC<br>ATGGGGAGCACCCCTGAGGGCGGGGGGTGTCTCAGGGTGTCCCCAGGGTGTCCCAGACCCCGACACCCAGTGCGCGAGTGACCCAGCCACCTCCGGCCAGTGCCTCTGCA<br>AGCAGCCAGGAGAGCTTAGGGTTCAGGGCTCCAGGGCGTCCCAGACCCCGACACCCAGTGGCGAGTAACCGACCACCTACTCCAACTCCTTTAGATA<br>GCAGCCTGGCTCCCCTGGGGCTCCCCTGGCCGCCTCCACACACTTCTGAGGTCTCCAGGGCGTTGGACCTCCCATCAGGGCGGGCGCCACGTTCGTCACCTGGGGC<br>CACCTGAGCCTCCTCCTCCGCGGCAGCCCTCCACCAGACCAGTGATAACAGCAGGTGATACAACCGACCCACACGGGCCGCGTCCATGCGCCTGAGCGCCCTCAGGGGCCTGGGCTGATAGCACAGCAGCC<br>GCCCAGGAGGGGGAGACAGCGGGGTCTCTCCGTCTCGCCGTTGACCCCGTGAACGCATGG |
| 229 | chr21: 43545000-43546000 | TTTTTGTGTTTTTAGTAGAGATGGGATTTCACCATGTTGGCCAGGCTGGTCTCAAACTCCTGGCCTCATGCAATCCTCCTGCCTCAGTAGTA<br>GTAGTTGGGATTACAGGTGTGAGCTGCCATGCCCAGCTGACTCTTCAGCGAGCAGCAGTGAGGCCTCAGAGACTGTGACTCTGGCGGTGAG<br>GAGCGGGCATGGCGCCGTCAGGACAGGCCGGGAGGAGCTGACTCTTCAGCGGACAGCCCTTCCTGAGGCCAAACAGGAGGGCCTT<br>TGGAGCCCGGCGCTCAGGACAGGCCGCTGCCGCCGGCAGCCCGGGCCAGTCCCACCACTTTTCCACACTTTTCCAAGAGCGGAGTTCGCCAGAGC<br>TGTTGTTTCAGGATAAAAAATGCCGGGTGCCGGGTCCCCGTCCCCGCTGCCTGACGACGCATTCCGGAGCCCCCCTTGGGAAGCTGCCTGCTGGCTCTCCCA<br>CCCACCCGAAGCCGGGCTTTCGACAGGCGGTGCCACGAGGGGCTCCACGGGGCATGCTCATCCTACGTGACTGCGAAGACCAGTAGACAAGCCAGTAGACAAGTG<br>TGCCTGGGCGCCAGCTCAGGACGCTCAGGAGCTGGAGCCTGTCTGTCTGAAACAGAGGGTGAATCAGGTTCAACGGCAAGCTG<br>AACAGGGTGCTGTTTCAGCCTGACAACCCAGGGTCTGACAACCTGGTCGTGAACAGAGGGTGAATCAGGGTTCGAGCAAGCTGCAGCACA<br>GCACAGGACCCCGCCTTGGAACCTGGGCGCCCGGGGGCTGCGAGCCAGGGCGGTTCCCTCAGGCCTGGGCGCGCTGCGTGCTGCTCCCG<br>CCACCCCGTCAGCGCACCACCAGATTGCGGGGCTGGCTGACTTGTTCTCAAACCTGACCCGAGTGAGTGCAGCTGCCTGCTGAGACCGGAGCTGCTGAGACGAGCAG<br>TGCAGGTGAATCAGCAT |

TABLE 4C-continued

| SEQ ID NO | GENE NAME | SEQUENCE |
|---|---|---|
| 230 | chr21: 43606000-43606500 | TCCTTATTTTTAGTTCTCAAGCCCTGTAGGGTGTGTTTCGGTCGCAGTTGTTTTGGGTCGTGTGTCCTACCCTCCTCAGTTCCAGTGCTCTG TTCAGGAGAGCTGCCTGGGGCCGGGACTTCTGAAACACTGAGCCACAGCCCGGCCTTGGGTTCACCGCCGCTCTTTG TGTGTGATGTCCTGGAATAGGCCCGTGCACGTTCAGATGACACTGCACATATAAATACTTGAGCCGAGAACAGGATGGGGGGAGG AGGGGAGGGCAGAACGTACCAGCAGCAGAGTCACTGTGATGCCTTCGTAAGTTGCATGGAAGGTTTTAAACCTAGCCTGCCGAG CAGCCCTCTCCTGTCCGGGAGAACGATGGGGAGGAGAGCTGGCGTTCAGCTTTCATCACTGAGCCCGTTCCTTCTTCCGGCCCCGAGG GCCTGTCCATGATCACACTTTGTCTGTTTCGGGGGTGGCCCTGTGAC |
| 231 | chr21: 43643000-43644300 | CAAGCCTTGTGGTAGGGACCAGTTCAGATGAGAGTAAACAGGAAGACAGCTTTCGGCCTGCAGGCCGTGCACCTCCGTGCCGGTGAGTGTGAGCGTGT GTGCGTGTGCACGTGTCAGATGTGTGTGACAGTGTGTGAGGTCCTGACCCCCTGCAGGTGACCCTCAGCCAGCCCAG GGCTGCCCCCACTTCTCCCCGTGACACACTACTCATTTGGGTGAACTGGGGGGCAGTGGGGGGTGCTTTGGGGGCACACT TCGACCCCCTCTCTCCAGGCCAGGCTCAGTTCTCGAGCCTCTGCCAGCTGGTGCCGACGTGGTCCGGAGTGACGTGAG GGTTCATGACCCAGGTGTGGGCAGCCAGCCCCCTTCACGGGGAGGCCACCTGCCACAGTGCCTGGGAATTTAGGTCGGCACTGCCG ATATGTCGCCTTCCAAAGGCGGGGCCGGGCTCCGTGACCGGGACCAGTGAGGCAGTGAGGGAACTCCCAGGCTCCTGTCCCAGGAAGCCAGCCCGCGAGC GCATCTGCTGGCTGACTGGGACGTGTAGTGACCCAGTGAGGAACCAGTGCCCCCCTTGCCTGTGTCCTCACAGACTCCTTCTCCAGGGAGCTGCC AGGCTGCACCCCCGGGTGCTGGGATCGGGAGGGGGTGCCCGACACGCTCTCTCTGAGGCTCTGAGGGCTGAGGGGCCTGGACACCAGGCCTGGCTTCTGGCC ACAGGGTGGGCGCAGGGGCCCTGCTCACTGGAGCCCCTGGAACTGAGAGACTTCCCGGCCCCTCCTCCGCCCG GCTCCGACCACCCTGCTACTGTGACTTCCTGCCCCGACTCGCTTGCCAGCTGGGGGCAAACATCTTTGGGGTTTTCACTTCCC TCTTTCCCAAGTGGGGACCCGGCCCCTGCCCAGGGCACAGGGCAGGAAACGCTCGTGTGGGACGTCTGTCGTTCTAAGTACAAGGTCAGGAGAGGAGCCCCC CTTGGGGCAGGCCGGCCGGGGAGGAGGCACAGGGGCAGGGGCAGGGAAACCGCAGTCAGCCA |
| 232 | C21orf125 | GCCCACTGTGGGGTGCGCCCCTGTCGTGTTGTGCGTGAGGCGTGAGTGTCTGGAGTGGGAGCATGAGTGTGTG CCACGGGCCTGCTGTTGGGTCTGGAGGCCACGGTTGCCCCTGAAGGGACTGCAAGCTCTTTTTGATTGTATTGAGAAGTCTA TACAGGAAGAAATTAAACCG |
| 233 | C21orf125 | AGCGCCCAGCGCAGGGCCGGACCCAGAGTGGACTCTACCGTGGGGCTGCCTCAAAGAAATCTCAGCAAACAGGAAGCCAGCCACC CGTGCAGCCATGGGCCAGGAGGCCCAGGTCATTTGGGCCATTTTTCTGTGCTAACAGCCCAGATGGAGCCATAGCCTC AACCTCTGTTCTGATAACACCAAGTGGGACGCGGAGCCATGGCAGGGACATGCAAATGGCAAATGGTCAAATGGCTCAAAGAGCCCTGAGGCTCAGCCTGGGTCTGGATG CCTTTCTAATTCAGGGCCTGTGTTCCATAAATGGTCATAAATGCTCAGATCAGCCCAGCGCTCCTCTATCAGCCGCTGGGCTTCCGT ACCGCCACACAGCCACATACCCGTTCCAGGACGTGGGCAGTGCTTCTCCCAGCCTGAAAGCTGCACCTCCGATCCTCCGGCTCGCGCCCGAACCGCCTC TCTCGTGTCCGAGGAGCCAATTCGGCCAAGGAGCTACCCTTCCCAAGGGGAGTACCTCCATTTCACCTCCATTTCTTGTAGAGAAGAAACATTTCTGACAGCAAG GAAGATTCTAATTTGAAAAGCAAGTGATTCATCTCCGTAGCCAAGGCAAGCAGTGCCAAACAGCAGCCGTTACCAGTCTGGGTGGGGGCCCGAGCTG GGGAGCTGGTCTTCCTGGGAGGGCAAGAAGGCAGCCATGCTCCATCTTTGGTGATAAATGAGAGTTCCATCGGGTGCCACCCTG CTGCCCGTAGCTGCTGCAGCCCTTTCTGCAGCCTTGCCAAGTGCTCTCGTCCAAGTCCTCCTGCCGGTCCGAAGAGCGAAGATGCTGGGACCCAGCCCAGCTGTCAGGGGTCT TGTGACGGGAGCAGAGAAGACTCCACAGTTAAAACTCCACGCCACAGGAGATCGCAGGTAAGCTGCTGGCTGCACCAGGTGTGCTAAATGGATTAAA CCAATCCCAG |
| 234 | HSF2BP | GGAACGGAGGAGCCCCAGCCCAAACCTCCCAGAATTTGCGCAGTATTCCGGCCTAGAGAGCGAGGAGTGCCTTGGCGAGTCCCTC TTTGGCTCTTCTGGCTTAGCCGGGGTTTTAACTTGTTATCTGCAAAGCAGAAGAAGTCAGCCCTGATGTAAGTGTCAAGTAAATAAA TCGATGGGTTCCTCTTTCCTGTTTGGCGAGGAAGAATGCTACACATAAGGGGACAGTGCGTTCAAATGGCCAGTCTTTGCTGGAAACCTCGCCTCCGC GCGCCTTTCCTCCTCGGATTCCCGCCCTACTGTGAAGCGCTATGTGAGTGACCTAGTCATTAACTTGTCCCTAGCAGCCCCTAGACAACTGA GCGGAGCAACTGAGATAACCCCAAGCCCAAAGCTGAGATAATCCCCTCATTACGTTAGGGTGAATTTTGTCAACAGGCACCGTGCCTAGACAACTGA ATGGCCTCGGGTTTAGATGAACCCAAAGCGCCTGGACGCCGGTCCCAATGGCTCTAGTCATTTCTTCCCCTCTTGCCTGCACCAGGGCTCCGGGATTAGGAGCACCGGGCACCAGGCACGCGCGAAGC GCGGTGCTCGCCAGGCTGGAGGAGGCCCGGGGCGCCTTGCACTGCACCCGTCAACAGGCCCGCCTTTCCTTCCAGTTCCACCCG AGCCTCTGCCACGCTGAAGGAGGGCAGCGAGCCCTCCAACACTCCACGCAGCCACCCGCCCGCCAAGGTCCACAGCGGTCGAGGAGCCGGCGAGGAAGCCGGCCTTTCCTTCCAGTTCCACCCG GGCCCCCGGGGCTCCACAGTTAAAACTCCACGCCACGAGATCGCAGGTAAGCTGCTGGCTGCACCAGGTGTGCTAAATGGATTAAA |

TABLE 4C-continued

| SEQ ID NO | GENE NAME | SEQUENCE |
|---|---|---|
| | | GATCCTGACCGTGCAAGCCGTGGCCAGGCCGGCTGGCTCAAGCCTGTAATCCAGCGATCAGGAGGCCCGCGGGAGGATTGTTGAGCCCAAG |
| | | AGTTTGAGACCAGCTTGGGCAACAGTTGAGAACATAGCGAGACACCGTCTCTCAAAAAAATAACAAATAGTGGGCGTGATGGCGCCTGTAGTCTC |
| | | AGCTACTTGGGCGGTCAGAGGTCGGGAGGATCAGATCAGTTCGGGAGGCTGAGGCTGCAGCAGGATCGAGCCAAGATCGCCAC |
| | | TGCATTCCAGCCTGGGCGACAGAGGGAGACCCTGTCTCAAAGACAAACAAACAAAAATCTAGACACCGTTTACAAACAGCCTTCCGTCTCTTCCTG |
| | | GTCAAGTCCTAACCCTGCCTCCGCGTCTACAGCCTGATTTTGCAACCGAAAGGCAGCGCCGGCCGGCCACGTGCACACGGGCTGG |
| | | GCCGCTCCGCCAGCTGCCAGGGCCACTGCCGCCGCTCACT |
| 235 | AGPAT3 | CGCACACACAGCACAGACGCCTGCATCTTCCCATGCGTGGTTTCTGCTCTTGCCTCTGGTTTTGTTTCACTTCCGTCGAGTTTTTGGT |
| | | GGTGTTGAGCGGATAGCCGGGAAGTTGGAGTTTCTTGTGCCGCCTCGTGCTCTGTATCTAAGATCCTCAGGCTGCTCTTTT |
| | | TGGGTAAGGTCTGTTGCTTTCTCTAGGAACAGTGACGTGCAGAGCCCGTGGCCCCTCTCTCTGTCCCAGACCCAAGCTGTTTCCTCTCC |
| | | CCACTCCCGGCACCCTGCGGGCAAG |
| 236 | chr21:<br>44446500-<br>44447500 | CACAGCCCAGCTTCAAGCCTGGCCGACCAGGGCTTTGGCATGAAGACCCGGCAGGGCTGTGCTGGAATCCACCCGGAAGTTT |
| | | CCTGCCCCTTGGGCTGCCCACCAGGTCCCCTTTGCTCTGATCAAGCTGACAAAGGCCAGCAATCGGGCAAAACGCACACGCACAGCGCCAACGC |
| | | AAGCTGGGATGTCAGACGTTGGACAAGCAGGAGAAGAAGAAGAGAAGCCATTCGGGACACACTCGGAGAAGTCGGGAAGAAGGGCG |
| | | ACAGGCACCTCTCTGTGGACAAGCAGACTGGGCGCCCGAGATTCCGCATAGATGCCCTGCTGCTCCCACGACGGTCCTGCC |
| | | CAGTCCGGTCCCCTCACCTCTGTCTGGGTCTCTTCTGTTGCCCAGAGCTCTCCACTCCTGAGCTCCCGGTTGACTCTCACG |
| | | ACTGCACCAGCCTCTCCCCAAGACGCCTGGAACGCTGGAAAACAACCTCCTTCTCCAGCCCTCTGCGCTTCAAGCAAATCCGTTC |
| | | CTCCAGGAGATGATGCAACACATCCTTGTTGGAGCCCAGAGAAGTGCCTCTCGGCTGATGCAGCCCAGAGAATAGCCCGTTCTCTTCGGG |
| | | AGTGGCTTCCCTGAACTAAGGACAGAGACTTTGTCTTCATCATGTGAGCTCGGCAGCCGGTGTTGGGCTGGGCTGGTGCGTGGG |
| | | TGCAGGCCCGATGCCCAGAGCCCCATTAGCCCTGGGAGCCATGGCAAACCCCCCATGCGTCGGTCAGAGTGCGTCAAACTCGGAGCGTCCTT |
| | | CTCTGGAAACGAAT |
| 237 | TRPM2 | GGGAGGGGGCGTGGCCAGCAGCCTGGGTGGGGCTGAGCCAGGGCGATCGCCACCCGGATCCGAGCTTTAGCACTTTGAGTCCCT |
| | | GTACTCAGAGGTTCCTGCAGCCCGGAATCCCACTGTCGTGTGTCCCTGGCAGTCCTGCTTCCCAAGCTTCTCCCAGCTTCTCCAGCTTCTCCAAGGTTGAG |
| | | GACGAGCACTCCTCTGCCCCTGATTAACTGACGCAGGAGAAGCAGTTGCTTTAATCCGGAGCCTTGAGTTGGACAGATAGATAGTCATTC |
| | | AACCAGATTTTCCAAGGACACACTAACTTTGTATCCCGAGGGTGATGCGTGTGCCCCTGAATCCACGTTGTGCAGGAAAGCCCAGGGAACACTGCCT |
| | | GTGACTCACTGACGCAGGTTCCCTTGTTACCCCAGAGGGTGATTTACTCCTGACAGTGACACGGACACTGTGCTCATTCCCGGCG |
| | | GGCAGAGACACTCCCAGATGCCCACGAGGGGGCCAGCAAGCACTGCCA |
| 238 | C21orf29 | CTGCAGGACCTGCTCGTTCACAGATGTTCTCTAGAAGCAGAAGCTGTTTCTTGTTGCAAACAAATTTGCTGTGTCCTGTCTTTAGGAGTCTC |
| | | ACCTGAATTTACCAAGGATGCATCTGTGCTTGCAGCTGGGATGGCTCGGTTTGAGGGTCGTCGGTTTGAGGAGCGGCTCGAAGCGATCCTTCTCCCCAG |
| | | GAGCCCCACCTGCCAGCTGTCAGCCCACATCTCAAGATGAGGGAAATGGAGTCGAAGCCATGCGAAGCACGCAGGCGTCCTGCTG |
| | | ACATGCCAGGCGGGTGCTCCTGTATTCAGCAGCCGTGGCCAGTTCAGGCAGCCAGAGGGGCCTCATCCGGTGCTTCC |
| | | CTGCAGGCAGTGTGGGGCCGGCCTGTGGGCCATGGGGCCCTTGGGCCTCCTACTCCTTCGGTCAGTCAGGTGACATCTGGAGCCACTCCATTAATGGTGGGTTA |
| | | AGGGCGGGCAGAGCCCATGCAGCCCGTGCCAGCTCCTGCCGGAGGACGAGGACGCCCCTGTGATC |
| | | TGATTTGGTTCCCATGCAGCCCGTGCCAGCTCCTGCCGGAGGACGAGGACGGCCTGTGATC |
| 239 | C21orf29 | AAGAGGAAATTCCCACCTTAATAAATTTGGTCAGACCGGTTGATCTCAAACCCTGTCTCCTGATAAGATGTTATCAATGACAATGTGCCC |
| | | GAAACTTCATTAGCAATTTAATTTCACCCACACTATTCGCACACCTTCCCTTTTGAAACTTCCTGTGATATTCTATTACCTGT |
| | | TAAGTACTTGCTGTCTGTCCAACGATCCTAGGATCGGGCTGTGATGTCCCCCGGACCGCCCAGCTTGCTCTCTTTGTACCTCTGTCCCTTTATTTCTCAAG |
| | | GGGCATCACAGATCCTACCAACGTGCGATCTGATGGTCAGGATCTAGAAAATAGAAAAGAACCTACGTGATTATCGGGCAGTCCAGATGCAGATGCAGATG |
| | | CCAGTCGATGCTTAGGAAAATAGAAAGAACCCTTCCCAGTGCCCACCAACCGGCGCCTCCACCTACGCCAGCCCCCTGCTGCTGCTAGTG |
| | | CGAGCACAGGTCCTCGTAGAAACTTCAGAAACATGCACCGGCAAACCGGCAAACCGCACACCCATGCACACCAAGGAAGGTGGCTGCGTCCAGGGTTCTTA |
| | | CACCGATGCATGCCATCCAAACGCACACACCGCACAACAAACATGGACCTACCACACACACCGCACAAGCGC |
| | | GTGCACCCCATGCCACGCACCCACACCGCGCACCACACCGTGCGCGCCACCACGTGACACACCAC |

TABLE 4C-continued

| SEQ ID NO | GENE NAME | SEQUENCE |
|---|---|---|
| | | GCGTACACCACCACGCGCACACACCGTCGTCCCAGCCGTCGAGAACGATCTCCCTGAGTCCCGACCCACGCAGCACTC
GCTAAACGCTTCCCACGCAGTCGTTTTCTGGGTTGCGCTTCACCCACTTCTCAGAGGGGCGGGGCGAGGTGTCGGGATGA
GCAGCTCCGGGCCTCAGGGGTCGCCCCGCCAGGGGAGGCTGTTTCTTTCTGTTTTCTGCGCCCCTGAGCCCTGACAGTGCCAAGCTGCCCATGG
CCGACTAGGTCACCCTAGAAGCGGAGGCGAGCTTCTCTTCTGTTTTCTGCGCGCCCCTGAGCCCTGACAGTGCCAAGCTGCCCATGG
GATTGGATTCGCCAGAGCCTCTACGCAGACCCCACCAGGCCAAAGCCAACCCAGCCCCACCTTGGTGTTGGGATGAAAAG
TGAGCCATCGAGAGATGGGGTCCCCGGGAATTGCGCCGCACGATCAAGGCGGGCTGGGATCAGGTTGTGGATCAGGAGAATCCGTGGGGATCCATTATCAGTT
GTGTGGGGTTGGGCGAGCACCCCACCTGCCTCCCACTCCTGCCCGCTCCACCCTGCCCGCCCACCGCGGAAGCCCACTGACGCGATTTGGGATTTAAGACGGGG
TGACAGCCAGGAGGACCGCACTGCCTGCCCCTGCCCGACGCGGATCAGGGGCGCGATCAGGGCGAAGGTGAGGGGATCTGTGCAGAGATCATCCACCAGGAAGAT
GGGGTGGGAAAGGACCCGGGGTGGGGGGCGAGAGGGGCGCAGAGACACAGGTGCAGGGACCTGGAGGGGATCCCAGGCCCCGGGGCCCT
AGGCCGAGCCACGCAGCTCGGGGGCCGCGAGGAGGGCGTTCAGATGGGAGCCTAGTCCAGACCCGTCGGGGCCT
CGTGTGCGCCTCGTTATCCTGAACCAGAGAGGCTGAGATGACCATGGGGGCGAGCGTGAGACCCTGGCTGTCTGAGCGGAACCGTAGTGCCTTATAGTTAGAATTTATAA
CTCAGCCCTAAAGCTAAACATTCTTTATTTCGCGTTCAGGAGTCCCAGGAGTGACCCGCTCCAGACGCAGGAATGAGGGGGTCCTTAACT
AAGGAAAGGCCTGGCCACTGACAATTGCGCTTCAGGAGTCCCAGGAGTGACCCGCTCCAGACGCAGGAATGAGGGGGTCCTTAACT
CTGAGATTTGTTTTCTGAGAGCAAAGTGATGGGTGACAAGTGCAAGGCTGGCAAGGCTTCGGCTCATTCATTCTATAGGTGCGGCCATTCATTTCAGAACATGA
ATGGATTCAGTAATAAACATGATAGAAAAATGCCACAAGCCCTAGGCCATGGAGTGGACAGTCTGTCCCCAGTGTGTCCCTCA
GCCTCGGTTCCCCGCGTGCACACACACACACACACGCCGGAGCCCTGGCTGCCTCTGGCTGCCTAGCCTGTGCCCCCCGATTCCCCCTCCC
CGCCCCGCGCGCTGCACACACACACACACACGCCGGAGCCCTGGCTGCCTCTGGCTGCCTAGCCTGTGCCCCCGATGAGATATGAGAGAGCG
AGCGAGGAGGACGACGCAGCTCCGTGACCAGTGTGCCAAGTGTGCCAAGTGTGGGGTAACCCGGGGTATTGGGGTAACAGGCTGGAGCT
CAGATCCCTCCCCCAGCCTCCCCAGCAGGGGGACTGCAGCTCCAGCCTGGGTCTGAGTGGGGAGCTGGGCTG
CGGGGTCAGGAATGGGCACACTTCCTAACTGCAGGAGCACTGAGGAGGACCTCCGCCAAGGACCTCCGCCAAGGACTCTCCCAGCAGCACGCACGCACCGAAGAGTGTCGCTGCTGGCAC
ACAGCCTTCCAGGAGCCGGATCTTGGAGACCTCCGCCAAGGACCTCCGCCAAGGACTCTCCCAGCACTCACACTCCCTTAGGCGCTCAGAGGACA
GAGGTTGAGGGCAGACTCCTGGAGCACCCAGTGAGGTCAAGTAGGAGGGCTGGGCTGGAAGTCAAATCGCGCAAAACCTCCCCAACCTCCTATTGCAAAGAGCT
CCAGCCAGCAGCTCCACACCCCAGGCCTGATCTTTTAAGATGCAAATCTCGCCCATCATTATTTCTCGGGTCTCCAGCTCCAGCCTTCC
CACACTGCCCGTCCCTCCCCAGGCCTGTCTCCCTGAGCCCTGCAGCTGCCAGGCACGGAGCCAGGGACCTGTGCCACATCCCGGGGTGGGCACCG
TGCAGTCGCAGTTTGGCCAAGTTGCAGTCGCAAGTCCAGGACTCCCCCGAATGCTGTCCCTGACACCTGCAGGGACGACTCAGCACCATGCTGCCACATCCCGGGGTGGGCACCG
CGGGCAGACTCAGTTTGGCCAAGTTGCAGTCGCAAGTCCAGGACTCCCCCGAATGCTGTCCCTGACACCTGCAGGCCTGCCACATCCCGGGGTGGGCACCG
CCTTTCCTGGCGTGATCGTGACCAAACCTAGGGGAGGAAGGGAGTGAATGACACTCCAGGACAGGGCGTAACACTCCAGGGAGGACGGACAGCCCTGAGGCCTCACTGAG
CAGGGTCCGCGTGACCGGTCCCGACTCCAGCTCCAGCCTTGATCTCCTGTCCACATGGAGTGGGTTGCTCTGAATGAGGGGTGCCGAGCCTAGGG
CTCGCATCCTGCAGCTCCACGGGATCTCCACGGGATCTCCTGCCTTGATCTCCTGTCCACATGGAGTGGGTTGCTCTGAATGAGGGGTGCCGAGCCTAGGG
CAGATGGCTCCCACGGAGCTCCTGGGAGCACCACCAGCCACCAGCAGCAGCCTTCGCGACAACACCTCCAGGGCTGAGCGCTGGGCTGAAATCCCAGCCCA
GCGACCCCACTCTCTGCGGCCATCACCAGCAGCAGCAGCCTTCGCGACAACACCTCCAGGGCTGAGCGCCGGCTGAAATCCCAGCCCA
CACTGAGGCCTTCCTACTGTGCCAGTCAGTGCCAGAGTAGCACCAGGCTTGTAAACACCAGCCTCGGCTGCAATGAGGCGAGAGCGCCGAAAATCCCAGCCCA
CACTTCCCCAAAGCCTGGCAGCTGGACACCTCCAGACTCCAGACTTGACAACTCAGAAGAGGCGAGAGGGGGGTCCTGGGAGAGAGAGCCGAAAATCAAAG
CAGGTTCCCCCCTGCCAAAGCCTGGCAGACTGGACACCTTGAAATAGCCAGATCCATGGGCCATGGGCCGACAGGCGATGAGAAAGCTGAGACGCCCTGGGAGAGCCGCCTGTGACCTGCGG
GTCAACCACCCGCGCGCCGCGGTCCCACCGCGGCCAGCCGGGCACAGCTCAGGGAGGCACAGCTCAGGAGGCGATGAGAAAGCTGAGACGCCTCACGCCCGGCGGTG
CTTCACGCCACACCGGACACAGCCCAGCCAGCTGACTTCTACAGAACCAAGTGACTTCTACAGAACCAAGTGACTTCGAACTGAAGCCCTGGTCTCCTTATGCTAGTCTTTGGAGCGTTCC
TGCTTCCCAAACGGAATGACTACTACTGGAACCAAGTGACTTCATCTGCGGCCGGTCTGGGATTTATAAACTGGCTCATCTTTAACATTTGCAACGTAG
CTTCAGGGAGGAGGGGGACTCCTGGAGCACATCACCAGGCTTTTATTAAATAACTGTATTTATTATATGCAGGTTGATTCTGTTCCTGAGCTAAAGGGAACATGAAAATA
CATGCTGACTGACTACTGATACTGACTCCAGGGCCATGCTGCGCTGCCCTGAAGCCAGGGTGACTCCGACGAGTGCTCTGCGGGGATTCTCGACTTGACTGATGACATGCAGGGGGGA
GAAAGGCTGGCCCCGCCCCTCCATGCGCAGGAGGTGCCGACCCGAGGGTGCTGCGCCTGGGCTGTCCGACAAGCTGACCTTGCCCAAGATGGGCAGACGCTCAGGACGCAGTAAATTGGCAC
CCCACCCCAGCTCCCAGCCCCCAGCCCCCACCCGCACGGACAGGTGGCCGCCCTCTGAGTGCAGGCGGTGTTCCATATGTGCCATGTCCCACGGTTATGGCCAGGAAGTCCAGCACGTTATGAC
GTGCCATCCGAGCAGGAGAGCTTGGGCCCGGTGCCCCGGCCGCGGGGTGACAGCGGGGTGACTTCATCTTATTCCAGGGAACCAAGGATGCATGATTTGCAAACAAAAC
CAGAAGCCAAGCCATCTCCTGCCTCCGATAGCCGTGCGAGCCTGAGTGCTGAG |

TABLE 4C-continued

| SEQ ID NO | GENE NAME | SEQUENCE |
|---|---|---|
| 240 | ITGB2 | CAGGAACCACGGGACCTGCTGCTCCTAGCGGCCCTGTTCCACCCTTGGCCGCGCTCGCAAATGTTTAGGCTTCATAAGGTTTGCCCAGGGTCA<br>CAAATTTAACTCACGAACAATGAAACATCAGCGACCATGATTTTCGAGCCTCGTGGTTCACCCTCCTCCTGCCCTTTCCTGCATGGGC<br>AGCAGCAGGGTGAGGAGCTGCTCTCCCACACTGGGGAACGTGGGGACCCAGGTGGAGTCCCTCAGACGACCAGGGAGCGCCCTGGACTACCCCCCCACACA<br>GCGCCTGACAGAGCCCCCACCTCGGGTGCATCCAGGTTTCCGGAAATCAGCTGCTTCCCGACCTGGTTCTGAAACTGGTTGGAGTTGTTGGTCAGC<br>TTCAGCACGTGCCTGAAGCAGCACGGGGCTGCACTCTTCTCCTTGTGGGGACATGGGTTTCGCAGCTTATCAGGGTGCCGTTCACG<br>AACGGCAGCACGGTCTGTCTCCACGAAGACCCCAAGCCTGCACGGGCACATGAGGGGCTGG |
| 241 | ITGB2 | TGCGTTTAGTGTAAAAATATCAGGTGTGCTCGACGGAGTGAAAAATCACAGGCTCACGGAGCCGGAGGCCTGCTGCCCTGCCCTCTT<br>GTTTGATGAGGAAATGGCGACCCGCAAGAAGAGTAGCAGCAGCAGCAGATGTAGCCACCGGCATCCGTGGGGCATCCGTGGGGCTGCTTCCCAGGG<br>CCCTCGCCAAGCCAGACCTAGAGAGTGTTGATCCCAAGTAGGACAGGCCGAGGGGAGTCAGTG<br>GGCGAAACTGGCCGCATGTCTGGGTACAACTGCTCAGGGTTTCTCATCTGCTGAATCACCCAAGCTAGGTTCTGAAGCCAGGCCTGAGTGA<br>GCAGGACTGGAGCAGGATTCTGGGAACAATCTTTTCCCTCC |
| 242 | POFUT2 | GCTGGGGAACTGAAGGAAGGGCTGTGAGCCTGGACCCTGGGCCTGTCAGGGCCGACCGCTGGGTGATGCAGAGGCCACT<br>CCACCTCCCCAGGTCCAGCCTCATCCGGCAACCTGGGAGCCTGGGAGCCTGGAGCCCTGCTGTCCTCATGGG<br>GCCCCTCCAGGTCCTTGGGCTCCAGTGCGGGACAGTGGCTGTGAGATCTGACCCTCCCCGTTCCCCACCAAGTAGGAGAGAAACCCCG<br>GAGCATGAGCCTTCTTCGCCGTCCCGGGGACTCTTGCTAGCTGTAACGAAGCCACAGAGCTGTGGCTTTTCCCTTCAGCTCTAGGAAAGGTT<br>CTTCACAGGAAGCCAGTGACCATGGACCAGATCTGTAGCTCTGGGCTTGGGCTCTGAGAGGCATCAGACTCAGACGCCCTCCGCCTGCCAGCTCCAGACATTCC<br>ATCTGCCCTGACAGAGATCTCCGGAGGCCCAGCTTCAAAGACAATTCCACACGGCCAAGCCACCCTGCCTGCCGGTGGGAGCAG<br>AGCCCTTGCACTGCAGCCTGGGCTCAGGGGCTCTGGGGCTGGGCACAGCAGTGGCAGGGGCCAGGGCAGGAGCCTGAGAAGCGCACCAACC<br>CGCGTCTTAGAACCTCCCCTCCGGAGCTTGCTCACACAGCCTCAGTGCTGTGTCTTGGGGGAAGAAGTCCGCCACCA<br>GACCGCAGAGCCCGCAGCCTGGGCTGGCCGCTTCACGCGTGCTGCAAGCTCCCTGCGGCTGGCGCTGTGTTGA<br>GGGTTCTGGCCTTGACCCACATCTGGGGACCCCAGTGTCGAAGATCTGGGCCTTATAGACCAGGTGAGGAGGCCAGAGCTGGCCAGAGAAGCTCAGG<br>CACCTTTGTAGAGTGGAAACCTTGTAGAGACTGCAGCAAGGCCATTCTCTTGAGACCTCAGGTGAGAGGGCCGCCCAGAA<br>CCAAGGAGCAGCGGAGAATTTGCACTCAGCAAGGCCCATGTCATGGGCGCCCATGCCGCCCAGCACACCAGCCCCCTCTCCACGGTCTTCCC<br>CCGCGGGGGCACGTGGGGCGGCTGCAGGGTGCATCCAGGGCGCCTCACCTGCTGTTTGCAGGCACGGCGATGCCCTTGTGTCAAGTGTGGGAAA<br>CACGCGTTCCCGCGGATCAGAGCAGCCTCACGGTGTCACCTCGGGATGCTCTTTCTGTTTCAATAGCTGTGGGAAA<br>GCTCAATCGGTTCCCGAAGATGTGCAGCAATGACAAGGCCTTCTTAGAACCTTCTGCCATCTCAGACAGGAGGG<br>AGCCGAGCAGGCGGAGATTTGCACTAGGAAGCCAGGTGGCGCATCCGGCGCCTAATGATTAACGCCCCTCCGTCTTCC<br>GGCCCCAACCCCCTCCCCGGTCATCCACCTCGGGTGCAGGGTCCCTGGGCTCCACCCCGGCCCAGGTCCAACA<br>GACCAAAGCTGGCCCGACCCCAGAAGAATGAAACACCTTCTGCACACAGTCTGACTGCTGTCCGTGGTCCTGTTCCGCAAGGTTGAGCTGTG<br>TCTAGATAGCAAAACTAAGTGCTCAGGAGACCACCTTCTGCACACAGTCTGAGCTGCACGTGCTAATGATTAACGCCCCTCCGTCTGTGG<br>TTCCAGAGACATGGCTCCTGCCGGTGATGAACAGGCCCCTGAGGGGGCCTGAGCTGCAGGGCTGTAATGATTAACGCCCCTCCGTCTGTGG<br>CCGGTTTCTCAAATGCCTCCTGACGATTGCGC |
| 243 | chr21: 45571500-45573700 | GGCCTGAGGAGTGAGTCAAACCGTGCAAACCCTGCCCACTCCCACTCTGTTTGGGAAGCACCTGCTGTGTGCGCAGGCGCTGCCTTGGTGTCTGGGGAT<br>AGACCATGGGAGGAAGAAACACACAGGGGAAGCGGCCAGGCAGAGACCCAAGGCAGAACACAC<br>CCACACAGTGGCGTAATGACAGTGCTTATGGTGGGACCTGGCTGCACAGCAGGGGATGTTCAGGTGACACTGGGGCAC<br>GGAGACCCAGGGAGGGAGTGGATTGACAGAGGGGCAGCGCTGGAGAGAGCCCGAGGCTGAGGTGCGGGAAGGAGGAGGCTGCC<br>GCAGAGGCGCAGAGAGCTTTGCCAGGTGTTGCAGAGACGTGCTGGATGCTCCAGAGTGCCAACCCCAGGGGAGT<br>AGAAGGATCTGGGCTGCCAGATGCCCTGGGGTTGCAGAGCTGCTCAGGGCTGCCACGGGCTGTCGTGCCACGCTGGGACCTGGAGGTGTGAG<br>GGGCCTGGGCCAGGTGCCCGGGAGCTCTCCCGAGCTGGGCACGCGCAATGAAGTGGGCGGGTTCTGGATGGTG<br>GAGGTGTCTGTTTTGCTCGTGAGCGGGAGCAATGGAGGGCACCGCTCAATGGTGATCCACTCCCCAGATGTGTGAAGCCCTCGGCACCAA<br>ACAGGATGGAGTTGAGTTCCAGGAGCTCCAGGGTGGCTTGGGCAACAGCCTCCCACTCCCAGATGTGTGGAAGCCCTCGGCACCAA<br>GCCTCAGCCTCTCCATCTGTGAAATGAGACAACTGCACTGGACTTGCAGGCGTGCCATGAGGGTGATGCGATCAGAAGGGGTGAGGTC |

TABLE 4C-continued

| SEQ ID NO | GENE NAME | SEQUENCE |
|---|---|---|
| | | CTGAACGCCCCGGGGTCGGGGTCTCACAGCAGAGCTTAGCTGGTGTCGGCATCTCCTCAGCTCCTCGAGCGCCCAGTCC<br>TGCCACCTGTCTCAAGTCTGCACTGTCCCAAGGCCCACGAGGAGTCCCTTGTGCCCCAGCTTCCTGACGCGCCCAGCCACCGT<br>CCTTGTGTGAGGTGGACACTCCTTCTGACACCGCCCCCACGGGAAGAGTAGTAACTTGGGTGTCGGGTAGTTGCCATGGAACGGGCAGTAATGCCC<br>GTCCTTGTGTGAGGTGGACACTCCTTCTGACACCGCCCCCACGGGAAGAGTAGTAACTTGGGTGTCGGGTAGTTGCCATGGAACGGGCAGTAATGCCC<br>AGGTATTGCCGTGGCAACCGTATCGACATGGCCATCGACACCGCGCTCCTGCCTGAGGGCGTGCCTCATGGAAAGCTACCTGTGCCCCTGCCGTGTTAGCTA<br>GGCCTCAATGTGTTCCAGTATCTGAAGCACCGCTTGCTCCATCGTGTCACCCATTACCAGGGCGACTTCGGGTCCTT<br>TCCAGCCATCATTGTCCATGCCACACTGGCCACCAGCTGTGTGTGCTTGCCCAGTCTCACCCAGTGCTTCACCCTCTGGGAT<br>AAACCAGGCACGTGGCGCCGCCCATTTTCCACCCGCCAGCCGTGGAGGAGTGCCCAGCCTTGCAGGAAAACAGCTCTCATGCCAGC<br>AGCCGAGACATCCTATTCAAGTTTTCTCAGGGCTGCCAGCACAAATGCTGACATGCCCGGCGGCTTCCTCAGCAGACCGTTGTTTCTCTGCGT<br>CCTGGAGGCTGGAGACTGCCCCCGTGTGCAGGCCCGTGTCCTCCCTCCCCCCGTATAAGGACTGCCTCCCCTAAGGA<br>GGTCCTCCAGAGGCCACCCTCCTGCCCGTGTTTAAAAGCTGTCTCCAAATACAGTCACCTTCGGGGTGAGCCCAGCCTGCAGGAGTCCCCTGGTTGA<br>CTGAATTTTACCTTACTGACACCGCTCAGCCCTCAGCCCCATAAGCTGTCTCCAAATACAGTCACCTTCGGGGTGAGCCCAGCCTGCAGGAGTCCCCTGGTTGA<br>GGGGACACCGCTCAGCCCTCAGCCCCTAACGACCCTCAGCCTGCTTCCAGCCGCCACTTGTGCTT<br>TGTCTGCTGTGGCCACGGCAGCCCCTCAGCCTGCTTCCAGCCGCCACTTGTGCTT |
| 244 | chr21: 45609000-45610600 | GGGGAGTCTCCAGGGGCTGGAGCCTGGAGCGTGAGCTGAGCTTTGCCTTCAGGGAAGCTGTGACCCCACGGGTGCTGCCCAGAGAGATCGGGCCAGGTGGA<br>TTCTTCAGAGACACCCGTGAAGCTGAGCTGAGCTTTGCCTTCAGGGAAGCTGTGACCCCACGGGTGCTGCCCAGAGAGATCGGGCCAGGTGGA<br>GCCAAGATGGACATTGGAATTCCCCCGACCAAAGGGCCCGGACCAAAGCCGAGCTGCTCTGTCTGATGAATGGTCAGTTTGCTTTTCT<br>CCTGAAAACAGAGCAGTGATCCGCCAGCCTAATTCGACAGAGGATGCTGCAATGCCAGAGATGGAGACGGATGGTGAGAATGAGGCTGTGGGCGGAAGAGC<br>AGATGGGACTCGCCAGCATCTCGCCAGCAGGGCCGCTATTGCCCCTGAGTTGGGCACGTCCCAGGAGTCCGGCTGGGAGACAAGGGCCTCCTTCAA<br>CAATGCTGCCAGGCGATTTCTGCCGCCCCGCAGATCTGAGGAGCCTGACAGGCGACCAGCGTCACCGGGCCATAGTGAGCGGCCAAGCCAGCGTCA<br>GCCCGCTCCCTGTCAAACCCGGAGAGCCTCAGCCTCTGACCTGAGGTCACCCAGCGCGTCACCGGGCCATAGTGAGCGGCCAAGCCAGCGTCA<br>CCCGGACCATAGTGAGGCGCCAAGCCAAGCCTTGGTCTGCCAGAGGCGCCCCAGCCTCCACTCCCCAGCCCTCACTCCCCAGCAAGGATTTCTGGGTCCCAGTCCTGAGCGC<br>CAGTGTCACCGGCCATAGTGAGCGGCCAAGCCTTGGTCTGCCAGAGGCGCCCCAGCCTCCACTCCCCAGCAAGGATTTCTGGGTCCCAGTCCTGAGCGC<br>AGCACACGGTTTACACCAGGCTTGGGAGGGAAGGCCAAGGCTGGGAGGGGAAGGGCAAGGCTGGGAGGGGATCCTAACAGGGCGGGATCCTAACAGGGCCGTTCATCCACGGAGGAGCCGAATTCATCACCGGAGGAGCCGTTCACCCAGAGGACC<br>AGAGGAACTGAGAGACCCCAGGGCGGGATCCTAACAGGGCCGGATCCTAACAGGGCCGTTGATTGCTCCAACAGGGCGCCTAATTCGACAGAGCCAGTCCCTGAGGACTGGAATGAGCTGCCCCGAGGACTGTCCTGCTC<br>CGGAGCTTCTCCAGGTGGCCATCCGGAGAGACCCAGGAGCCTGTAATTGCTCCAACAGGGCGCCTGTTGTGACTGGGGACCAGCCTGTTGTCACTGAGCTGGGCCGGTGGAGGAGGAGG<br>TGACTCCAGGTGTGCCAGGCCGTCTGGTTTTCTTGGCGCCGCAGCCGGCCGGTGGAGGGACCTGCTCCAGCCTGGGACCAGCCTGTGAATCTGAATTGAATCTAATTCCCGTCGTCGTTCAAAGCCCATGAGCCTGCATGAGCCCATGAGCCCATGAGCCCATGAGCCAGGAGGTGTGGGACCTGGAACGGAGGTTCTTATGACATCAGGAGTTTTATCCCTCACGTCAG<br>GGGACCCTCCCAAGCACGTTTGGAAGGCCAAGGCCAAGCCGGTGGATCACGAGGTCAGGGGTTCGAGACCAGCCAACATGCAA<br>AGTTCCTTTATCTTGAATGGCCTTTTGGGGATTTTCACAGATTCTGAGTTCAAAGCCCATGAGCCTGTTCTTATGACATCAGGAGTTTTATCCCTCACGTCAG<br>ATTCCTCACCGCATTCCTCTGTAAACCAGGCTGTTGGCACCCATGAGCCTGTCTTATGACATCAGGAGTTTTATCCCTCACGTCAG<br>AAATCAGGTTGCCAGGCCGTTCGTTTTCTTGGCGCCGCAGCCGGTTGCTATAGAAGAAAACTGAAGGGCCAGGTGCGGTGGCTCACA<br>CCTGTAATCCCAGCACTTTGGAAGGCCAAGGCCAAGCCGGTGATCACGAGGTCAGGGGTTCGAGACCAGCCAACATGCAA |
| 245 | COL18A1 | GCTCCTCCAGGGAGGTTCGGGGGCCCTTTGCTTCGGGACTTGGGCAGCAGGAAGGAAACATCCTGGGGGCCTGTGTGACCCCATCC<br>TCCCCAGGGTGGTCTGCAGGGGACACTGTTTTCCAAAGCAAAGCCAGCGCCAGGCGCCAGGATCCAGAGATCCACATTTATCC<br>CAAGTTAGAACAGCACATCGTGCTGCAAACTTCATTCGACTTCGGCCGTCAGTGGGGCTGAGTGTGACTCCTCTGGTTTTAGAGAGCACTGCCCCGCCCC<br>GCATCCCTGTCCTGTTCCCCACCTTTTCCACCCTTTCAGCACCCTTTTCCACCCTTTTCACCCTTTCAGCATTTAGTTTGAGTACAGCATTTAGTTTGAGTGATCAGCATTTAGTTTGAGTGATCATTTAGCATTAGGGCTGAGCTCATTTAGCATTTAGTTTGAGTGATCATTTGACTTAGTTGAGTGATCAGCATTTAGTTTGAGTGATCAGCATTTAGTTTGAGTGATCAGCATTTAGTTTGAGTGATCAGCATTTAGTTTGAGTGATCAGCATTTAGTTTGAGTGATCTTACACCGGGTT<br>TTTTCTTTTTTGAGACAGAGTCTCGCTCTGTCGCCCAGGGCTGGACTCGCAGGTGGGTGACTGGGTGAATTCGACCTGAATTCGACCTACTTT<br>CAAGCGATTCACCATGTTGGCCAGGCTGGTCTGAACTCCTGAGTAGCTGGGATTACAGGCGCCCACCACCACCTGCCTGGCCTCCAAAGTGCTGGGATTACAGGT<br>GTGAGCCACCGAGCCTGGCCTGGCGAGTTATTTTGGAGAGCCAGCCTGTGGGCAGCCTCGGGCTTCAGCGTGGCAGCCTGGAAGCCCTGGAAGCCCCGGAAACCCT<br>CGTCCACACCTCCGCCAGGTGCAGAGTGCAGAGCCAACCCCTGCCCCATCACGTTCGGCCTCGGGCCTGGAAGCCCTGGAAGCCCCGGAAACCCT<br>GCCACGCCCGAGTGCGAGACGGCAGGTCCCTTGCGTGGGCGAGACGCCCGAGCCCTGCCCCATCCCGGTGGGGCCTCATTCCTGGGGGCCTCGTTCAGCAGTT<br>GCGACACTGTGGCTGCATCCTCTGCAGACACTTGCCCATTCTGGGGCCTCGTCTGCCCGGTTGGAAGGAGCTCCTTGTTGAGGGGTCTGGAGGGA<br>GGCCTTGAGGTACCCATGCTGCGGGGTGCGGGCCCTTGCGTGGGCGAGACGCCCGAGCCCTGCCCCATCACCGTCCCGGTGGGGCCTCATTCCTGGGGCCCCGGTGGGCCTCGTCTGCCCGGTTGAGCTGCTCACTCCAGAG<br>GAGGGGATGCGGGGTGCGGGCCGTGCACACAGGTGCTCAGGACGCCAGGGTCTCAGGACGCCAGGGGCTGTCCCAGGGCTGCTCACTCCAGAGG |

TABLE 4C-continued

| SEQ ID NO | GENE NAME | SEQUENCE |
|---|---|---|
| | | GCAGACTCCTGAGGTGCAGACACCCCAGCTTCACGCTCACACTTCTGAAGGCGATGTCTGTGCGTTTGCTTTCTGCTGCAGTTTAAAAAG
CCGGGCTCTCCGGAGCGTGTAGGGCTGTCAGCTCACTGGAGTATATCTGGAATATCTGGACTCAGTGTTAATGGCAGCCACCGGGCGTGGCCCAG
CTTTCTGTCTCCGTGGGTGCCCCTGGAGGCTTCCTGAGGCTTTCTTCTCTCCGACCTTTAAATCACAGTGTCACCTCCCCGTGTGT
CCTGCCAGTGGCCCCTGGAGGCTTCCTGAGGCTTTGGCTCCCACCAGCTCCCATGTTCTTTAAGGCTGGCATTGAATCAGGAGGCCAGATGTGGCC
CCTAGTAACTCACCAGCAGTCCTGGAGCGTGTCCCGGTGCGTCTGCGACACCACCAGCCCCATGGCTCTGCCCTTGTCCGGCCACCCCCTGCTCT
ACTGAACCAGACTGTGCCCCGGTGCGTCTGCGACACCACCAGCCCCATGGCTCTGCCCTTGTCCGGCCACCCCCTGCTCT
TGACCTCACACCTCTGCCGTGTCTGCCGCTGTCTGACACACCAGCCCCATGGCTCTGCCCTTGTCCGGCCACCCCCTGCTCT
GGGTGTTGAGGTCTCTGTGCATTCATGCTGGCCATCACGTGCGTGCCCATGAGCTCCCTGACCTGACTGCGGACTGCAGGACTGAGAACCA
GTCTGCCCGGCCGGCCGGCCGGCCAGCATTCATGCTGGCCATCACGTGCGTGCCCATGAGCTCCCTGACCTGACTGCGGACTGAGAACCA
GCCGAAGGGGGCGAGGCTCCGGGAATGCGCCGAGCCCAACTGGTGACTGCGGCGTAATGAGCCCAGGAGCTCATACACCCG
GGGCCTGACTGAGTCCAGGACTGTCTGCCCTGCCCTGCTGCCTGTGCCTGCCCTGCCCTGCCCGGCCCGGAGGACAC
GAGGCCCCTGGGTCACAGCCAGCCTACTCCCTCCTGCCCACGCTCCGCCACACGTCCCATGGCCACCACCTCCTCCCATGAAGC
CTTCCTGACTGCCCCATCCCTCCTGGGCCAGCTGAGTGTCGCATCTGAGTGCTGGCCTCCAGGGCTCCTGGGCTCCTGCAGGCAGGC
GGCCCTCTGGGCTTCGGGGCTCTCAGAGTTTGAGGAGCCCGTGGGTGAGGGGCTGGCCTCAAAGACCAGCAGCGTGACGGCGTGGCC
GAGACTGGCTGAGCCCGCTCTGAGGAAGGGGGCCAGGGGCGTCAGGAGCAGCCAGTTCAGTGACCTTCACCTGGCATTTCCATCTTTGAAGGA
AAGGATGGGGGTCTCGGGATCTTTAACTTTTTTAAGTTGAGGTGAAATTCACAACGCATAAAATTAACATCTTAAAGCGAACATTCGTGACATT
CTGAAACGATTGGATTCTTTAACTTTTTTAAGTTGAGGTGAAATTCACAACGCATAAAATTAACATCTTAAAGCGAACATTCGTGACATT
TAGTACAGCCAGAAGCGTGTGCAGCCATCACCACTGCCACCTCTAGAACATTTCACACGCCGAGAGAGGAGCCCTTGGGCCATCACCCA
GCCACCGCCCGGCCCAAGAACCTGCGAGTCCACTTTGCCCTGGATCGGCGGTTCTGGACTATAGGCGGCGGTCTCCAGGTGGTTCCCGCAGTGCG
AGGCCTTTGTTTCGGGCTCCTCCACAAGCCTCACGTTTCCAGGTACGTCGTGTGTTGTGCAGACCCACATTCATCCCTTTCATGGGT
GTGTAATAGTCCACCATAGATTCTCTACGTTTTTAATTGAACATGTTTATGTGCCTGAGGCTTCGACTCGAGACTATAGCTTCGCTTTCTTTCT
TTTCTTTTTTTTTTTTAATTGAAACATTTCAGCCAGGCTCCCAAGATGAAAGGCCAGAGTCTCCAGGTCCAGCTTGTTCAGTGCACAGTTGGGGAGC
CCCAGGTCCAACTGATCTCTTTGCCCTGCGTGCTGCAGGACTATAGGCGGCGGTCACACCCTCTGGGCCTCCGCCCCCCCAATTTTTGTATTTAG
TAGAGATGGGGTTTCATCATGTTGGCCAGGATGGTCTCGATCTTCCAGGTCTTCTTTAACTGCATCCTGAGGGATCTGAGAGTCTTTCCCTGCCTGCTCCGGGATTA
CAGGCGTGAGCGCACCGCGCCCAGGCCTCCCCAAGATGAAAGGCCAGAGTCCCAGGCATGGGCGTTGCAGGTGCACAGCAGGAGGAAGCCGAGGAGC
CTTTGGAAAACATTTCAGCCAGGCGTCAGCCGGTGCTGCAGGTGCTGCCACCACTGTGCACCCAGCCTCGGCTGCACAGAAGACATGGCCCAGG
TGTGGGAGTGTCGTCGCCCGCCAGTCCATTCCATCATTCAGTCAGTGCACCCACTGTGCACCCAGCCTCGGCTGCACAGAAGACATGGCCCAGG
ACGTTGATTGGCAGTGCCCGCCAGTCCATTCCATCATTCAGTCAGTGCACCCACTGTGCACCCAGCCTCGGCTGCACAGAAGACATGGCCCAGG
AAGGCTCCACTTCCTGTCTCCCTCTCCCAGGACGTGGAGCGTGCCCACCTCATGATGGGAGCCTGACTGCGGGTGACGAGCAGCTCTGGAGGCAGCTCTTAGTTTTGAGTTTCTGAGCTAATGAACA
TGCTCATGAGCAGGCGGCAGGATCCCAGGACGTGTCCTGGAGCTGAGCAGCGAGCAGCAGCTCCCACCTCCTCTGGGCCCATGTGCACGGGACCTGGG
ATCCCTCCAGGCCATGTGAAAGCCAGCCTGCTGCAGATCCTGTCTTGCCAGGACAGGTGTCTCTACAGCGGTGTCAGGCAGGAGCAGGAGCAGCGTCCAGCAGTCTGGCCAGGCAGCAGCAGTTCGCGCAGCAGCAGTCCAGCAGCAGCAGTGGCAGCCAGGCTGTGTTCCAGCTCCAGCAGCGTCGTCAGCCTGCAGCAGCAGCAGCAGGCAGCCAGCAGCAGAGCCAGCAGCAGCAGAGCAGCAGCAGAGCAGCAGCAGCAGAGCAGCAGCAGCAGCAGCAGCAGCAGCAGCAGCAGCAGCAGCAGCAGCAGCAGCAGCAGCAGCAGCAGCAG |

TABLE 4C-continued

| SEQ ID NO | GENE NAME | SEQUENCE |
|---|---|---|
| | | GCCCAGGGGAGGTGGGCAGGCAGGACCCGGCCGGCCCAGGGAGGGGGCAGGCAGGACCCGGCGGCCCAGGGAGGGGGCAGGCA<br>GGACCCGGCGGCCCAGGGAGGGGGCAGGCTGGCGGCCCAGGACTCGACGATTCTGACGATTGTAGACCAGGCCCTGGGGGTC<br>AGGGGTGGAGGCCAGGCCAGGAGACCCCCAAGGACAATCCAGCTGGCTCTCGCGGTGTTGTCTCCCATTTGAGACAATTGGCACA<br>GAGGGGCCAGCAGGCCCTGCGCGACCGTCTAAGCCGCGACGTGTGGGTGGTGTAAGCCGCGACGTGTGCCCATGTGGGGCAGCAGAGCCCCTGCTCTCAGCTCTCGGGTACAGCG<br>GGGTACCAGGCAGGCCGTGGGTGGTGGTGTAACAAGGTGTCACTGCTCTGCCAAGGCAGCCCCATCCTATTAGCTACTTTCCGGGACACTTTAAGACAGACAGGACACAGGTTGAA<br>GCTCTCATTCCTGCCCCATTGCTAACAAGGTGTCATAAGGTCTAACAAGGTGTCATAAGGTCTCTTGCCCACTCGTGCCCACTCGTCCCCTCCCAGCAGGGCCTTCCCTGGGAGCCACATTCCAGGTCTCAG<br>GAGCCCCTGCTGTGGGCTGCAGCACAGATGGAAGAAGTTCAGGACACAGATGGAAGAAGTTCAGGACACAGATTCAGGACACAGAAGTTCAGGACAGAGTCAGGAGTCGCCGGGGACCCCCCTGGGCGCCGGGAC<br>CTTCATGGGGGTCCTGAAGGTCAGAGTCTGACAGTCGCGTGCAGAGCGCGCTTCCGGGACGCGCTCCGCTGCCCACCCCCTCCCTGCCATTTTCCCACCCCCTCCCTGTGGGGACCACATTCATCACCCCACCCCCCCATTTTTGGGTGAGAACCCCCTCGAG<br>TGAGAGTCTGTGGCAGGCAGCCTTCAGGCGCTCCCCCTCCATGTGCATTGGGCAGCTGCCGCTCCATGTTTGGGTGATGGTGTCCATTGATTGCCTCCAGG<br>TTTAAATCAGGTGGATATTTACCTAGCGCTGTCAGGCCCTGGACCATCTGAGAGTGGGATGGACTGGGGTGCTCAGCTGAGGCTC<br>TGCAGACACAGCCCCTGGGCTATGCAGAGCCCTGTGCAGTCAGAGCATCTGGACCATACTGCTGGGGTTCAGAGCGCGGCAGCAATGC<br>TCCTAACATCGCCAGGCATCTCAGAGCCTGTGCCAGTCAGAGCATCTGGACCATACTGCTGGGGTTCAGAGCGCGGACAATGGC |
| 246 | COL18A1 | TGCCACCACATTCTTCAGTAGAGCTTCTCTTCTCTGCTTCGGGCGGAAGCCTGCAGGACCCAGACAGCCAAG<br>GACTCTGCCCCGCCAAGCACGCGGCCTCCAAGCTCCAGGTCCTCGCCGGGACACGCACGCCACTCTGCAGTCACACTTTAACCAG<br>GGCTCCCTGGGCAAGCACGCGGCCTCCAAGCTCCAGGTCCTGCCAGCGCGGCGACACGCACGGCAGCGCACTGTCTCAGGTCCAGCGCACTGTCTCAGGTCGACTAATAACTCTCAGGTCCGCAG<br>GGACAGCGGGCAGCCTCCCACCTGCTCTGCCCCGCTGCCTGGGACCCGCTGCCAGCTGGACGCGCACGCCAGCTGGCTGCGTCTGCCCAAGCCCAAGCCCCTGCTGCTGCCGCGATCTGCGGGCTGCCTGGGATCACGCCTGTCGCGGGCCAGATCGCGGGGCAGTGCACCCCACAGCCAGCTCCTGCCCTGCCATGCCCGAGCCCCCATCGCATGCCCGAGATCCTGCCAGGATCCTGCCCCCTGCCATGCCCGAGATCCTGGGGGCAGTGCAGCACACAGTTGGGGGCCAGGATGTGGGGGCAGTGCAGCACACAGTTGGGGGCCAGGATGGGGGCCAGGATGTGGGGGCAGTGCAGCACACAGTGGGCAGTTCCACCCGACGAGACGACGCCAGCTTCCGGGGGAGGATGGGCCGCCTCGGCGGGTCAGTGCAGAGTGGAGAGCCTGGGGGCTGCAGGTGCGTCCAGTTGGGGCAGCAGCTGGAGCTGGCTGGGCCAAAGTGGAGGAGCAGCCTGGGACGGAAGGAAAGGGGGGAACTGAGGCCTGGAGGAAACTGAGGCCTGGAGGGACTCTTTGCAG<br>CATTTTAGCGCATTAGTCCCCAGGGCCCGGGCAGTTCCCCATTGCTGAGAGGCAGGAAGGCCCGGGGCTGCCCGGAGATACCCGACATCCGCCGCATGCCCCGCATGCCCATCCAGAGAGGCAGCGCAGCAGCAGCAAGTGGGACCAGGGAAAACTGAGGCTGCGGGCAGTGGC<br>GTGACTCACCCCAGGGAGCCAGATTCCGGTCAGGTTGGGCTGCATGAGCCTGCGGGCCAGCTGCCAGCTGGTCATGAGCCTGTCGGTGCATCTGCCTGGTCATGAGCCTGTCGGGATGCCAGCGGGCCTGGGCTGCATGTTGCATTCACCACGCGTTCACCACGCGCGGTTGGGCAGGCCTACCAGGCTGCGGAGGCTGCAGGAGTCGAGCTGGAGAGACGACACGCCAGGTAGGCCAGTGCAGAGTCTGATGCGGGTCTTCATGTGGGAGGTCTTCCTTGGACCGCTGCCTCCGCTGCCTACCAGCGTGGGGACCAGGAGGTCGGACCAGGAGGTCGCAG<br>GGCCGTCTGCAGGGAGCTTTCATGTCCCCCTCCGCCAATCCTGAGACACACAGTGGGGCGGCCGGGGGCCGCTTCTGGGCCC<br>AGGGGACGTTGCCCCATCACCGTGTGGCCTGCCTTGTTGCCTCGCCTGCCTTGTGCTGGCGCATGCCGTGTGGGGCAGGAAGGAGGAGAGGAGAGTAGACCGGGCCCC<br>ACCTCCTGCAGGGGCCAGGGCCAGCCAGAAAGGACCCCAGACCCCTCCTCTGTGTCCGGGAGTAGACGGGGCCCC |
| 247 | COL18A1 | GGGCTCCACAGCGGCCTGTCTCCTCACAGGGTCTCAGCCCAGTCTGCTCTCACTCATTTCTGATTCATTCTTTCATTCAGCCAGTCAATAGT<br>CATGCCCCTCCTGCTCGCCGTGGTGGCCATGGATATTGCCCTGGGTAACACACACAGCCTGGCCCTGTGGAGCAGACAGCCA<br>TGTGGACAGGCTGTCAGGTGCAATGCCAGGCTGGGTCAGAGGGCCGTGAGGGCCGTGAGGCCCAGGAAAGTGCAGAATCAATAGGGGGCAT<br>CCCGACTGGGGTCCAGGCCTGCAGGATTTCTAGGGTGGAGGTCACCTCGAGGGAGACAGAGCCCTGGGAGATTAGAA<br>GGTCGAAGGTCCCCGTGTTGAGGTCAGGGGCTCCGGAGCGCGGCAAAGGAGGAGGCAGGTCAGGCACGTGGTGAGTGATTG<br>CTCGGCTTCTACCACCCCCAGGGAGCCAGCCCAGAGTCGGGAGCGCAGCTCCTGCCAGTTCAGAGCCCGATCCGGGATCCGGATCCGGATCCTCTCACCCAGCC<br>TGCTGCTCTACCACCCCAGGGAGCCAGCCCAGAGTCGGGAGCGCAGCTCCTGCCAGTTCAGAGCCCGATCCGGATCCCTCTCACCCAGCC<br>CAGAGGAGGACACAGATGGAGGAGGGGCACCCGGAGGGTTCCCCGACCAGGCTCCACCTGCAGGACAATGAAGTGG<br>CCGCCTTGCAGCATGACATCTGGGCTGCAGCCCTCGCTGCCACGACAGCCCTGCCCGGAGCAGCCCTGGCAGGACCCCGGGCCCTGGGCGG<br>GGCCAGATGACAATCCTGGCCAGCCCCACGACTCAGCGCCTGCCGGACTTGCAGGCCCGGACTTGCAGGCCCGAGCTGGAGCTGGAGTGCCCCCAAAGTGGGCTTGGCTCCAT<br>CTAGCCCCCTCAGGGCTCTCGGGCACTCAGGGCGGCTTGCCTCCGCCTTGCGGCTTGCCTGCCTCCGGCTCATGATGGTGGTCGGGGTCTG<br>GCGGGCTCAGGGCCACTCAGGGCGGCCTACCTCCGCCTTGGCGGCAGCAGCAGCAGCAGCAGCTGGCCAAGCAGTGTCATGAAAGTTCCAGCCGCTC<br>ACATCCTTGAGGAACCGGCTCAGCCCCGTCTACCCCAGTGCTCAGTTGGGGCCACCCAGGGGCCACCGCCTCCGGGCACGCGATGC<br>GGGGCTGTCCTCGGGCCCCCAGTGTGTCACTTGCACTGGGCCGTCACGCAGCGGGCAGCCCCTCCCGCGCCCCCTCTCCCCGAGCCCCCTCTCCCCGCCCCCTCCCCCAGCCTGCGCGCCCCCTCCCCCAGCCTGCGCGGGGC<br>CGGGGCTGTGCCCGGGGGCTGGGTGCAGGGCCAGCGTGGGACGTGGGACACAGCCCTGACGCCCCCGGAGTAGACGCGGTT |

TABLE 4C-continued

| SEQ ID NO | GENE NAME | SEQUENCE |
|---|---|---|
| 248 | chr21: 45885000- 45887000 | GCCTCAACAGCCCCCTGTCAGGCGGCATGCGGGGCATCCGCGGGGCCGACTTCCAGTGCTTCCAGCAGGCGCGGGGCCGTGGGGCTG CGGGCACCTTCCCGCCTCTCCTGCTCCGCGCTGCTCCAGGACGTGTACGACGTCTACGCGGCCGCAGCCGTGCCTGCCATCGTC AACCTCAAGGTGGGTCAGTCCAGTCCGAGGGCGCGGGCTCCTCGGCCACTGGTCACTTGACCTCTGGGGTGAACTCCAGGGGAGCTCC CTCTAGGGCTCCTCTGGAGGCCACCATGTTACAGACACTGGCCGCTAGGCTGCACTTCAGGGACTCCAGGCTCCGGTGGTCACACCCTCC AGGCTCAGGCCAGGCCTCTGCATCCTCTGGGCACTGCCACGTCCCACGTCGCCATGAGGCCCCCATGAGGCCCCCCTGACCCCGC TCCCCCGGCAGTGCTCCCCATGCTGCTGATGGGCTCGAGCAAGTGCTCACAGTGATAGGCCTCACATACAAGCCTGAATCAGGA ACCGTCCTTTGGGCCTCTAGTGCATGCGGGGCTGGTGGCCCTGCCA |
| 248 | | GCTTGGAGTGTAGTCCTGCTGAGGACCAGAGACCCACACTCCACCCAGATCTCCACCAGACTCGGATCTCCTCCCCAGCAGGGGATGAGGCCCTG CCCTGGGAGTGCTGGTTATGTGGAAGGGCTGTTACTGTTGTCCCACACTTTAGCCAGGCTAATGTGGACTTAACGCATTCACGAGTTTCAGCCTTACAAGGTTTGACGTTAATTA CTATTATGAATTGCTTTCTGTGTTACTGTTTTTCCCCACACTTTAGCCAGGCTAATGTGGACTACAGAGGCCCTCGCCCTGCCCCCCTCCAG ATGTCCCAGCCCATGACAAGCAGGAAGGCCGGGTGCTGGGAGACTTCCTGGGAGACTCTGAGCAGCTAATGTGGGCTCTGATCTGAGCCCTGACGATGATAACCTGC CTTCCCGATTTCCAAACCCACAGCAAGACACCCCGAGCTCAGGAGCCAGGAAACTTCGACTGGAGCCGGGGCACTTCTGACGGACAAGCAGCACCCTGA CGCCATGAGAGGGTGGAGACAGTGAGCTGCTGCGCTGGGGCGTCGAGGCGGGCAAGCCCAGAGACCCAGAGCCGGATCAGCGTGTCAAGA TGCAGGCCCAGCTGCTGCCGCCCCTGGCTGTTTCACAGGGTTGGCAGGAGCGCAGGCCGAGGGTCTTTAGGGTCTAACGCTGCC CTGAAAACACTATCATTACTTCCTATGACTAATCTGTGTCTTTCACGCGTCGAGCGCCAGCCTCCAGTCCAGCCGTCCCCACAGAGTCT GGGTCCCCTGCCCTGCCCCGCAGAGTCTGGGCTGTGCAGAGCGCCGTCGCAGTATCCCCATTCACGACGTAGAGCCCCTCTTTCTAAAAACAGAGTCT CACGATGTTTCCCGGCGGGTCTTCCAACCGCCTGGGCTCAGGCGATCCTCCCCGGAAGTGCTGGAAGGCCGGGGTTGGCCGTTGGGATTAAGGGCGAGCC ACCGCGGCCCGCCCTCCCGCCCCCAATTCTCCCCGAAACGCGCCAAGCAGGGTTCGCCAAGCACAGGTGTCGAACCCCCCGCCCCCACTCC ACATTCCCTCGCCCCTGCCCGACACTCCGCCGTAGCTCGCCGAGACTCTCCAGGCACTGGAGCGCTTCCCGCCGACGTTCCACCCAGCTCTTCCACGACGGGCCC TAAGGTTGTCTTTTAAATGACAAGGCCCGGAACGTTCCGCCTCGAGGCTGACTCGCCCGTCGCCTCACCTCTTCCTCGACCACCTCCACCCCACCCCAGTGCAGCCTGCTGCGACGGGGCTCG GGGGGCCCGCTGGGGTCTTTGACGCTGTGACTGCAGTGAGGCTGCTGCGGGGCGATCCCGAGGCTTGGAGTCTCGGGCCTGAGGACGCTTGTCCTCCACCCGCG CGGAACCCAAGGCTTAGGGCGCACCCCAAGCCGGAGGTCGACCCGGGCGACGGGGAAAACGGGCGGCGGCGCAAGCGGACCCGCCGCCACGACGAGGGCCCCGGCC TTTCTCCGCTCAGCCCCCTTCCCGCTCAGCCGCCGAGCGCGGGGCGCTCAGCGCGCGGAAAACCCCCGGCGCGGGGCGCGGGGGTCCGGGGAA AGGACCCGCCCTGCCCGAGCCGGGGGGCCGCCAGAGCGGGGCGCAGCCCGGCCCCGGGCCGGCGAGCCCGGGCTGCAGCCGGGGGGGAGGACG GCCCTTGCCCTGCCCGAGCCCGGGGGCGCGGGCGCTCAGCGCGCGGACCCCCCGCCCGCGGGGAACGCGCCGGGGGCCCCCAGTGCCGGGGAGCCCCCC GTACCGGGAAAAACGGCGCGGAGCGGAACAG |
| 249 | PCBP3 | TGGAGCAATCCCAGAGAGGCTGAGGTGTTCAGGCTGGCCTGGCCCTGAGCCTGTTCAGAAGCCGTGAAGCGTCAGCTCCTCCACACCCT CTCCCCGCTGCCAGAGCTCCAGCACCCCTCCCGCTTCCCTGTGCTCCTGCTCCTGCCCACCCCGCCCCTGTCTCACGGG TGCAGAACATATCCGCAGGAGTAATTAACACAGCAGGACTGGAGGCTTGTTGGTTTCTCCATGGTATTTAAATAATTGGGC CAGAACATATCCGCAGGAGTAATTAACACAGCAGGACTGGAGGCTTGTTGGTTTGCTGTATTAAAAAACAGTGGATTAAATTAATGGGC ATGGGAAGACTATTCAGTGAAAGACATCGTCATTGAGTCATTGGAGTATCTGTTTTTTGGGAGGGCATCGTTTTGGACAGAGGCATGTGGAAGCGCAACCGCG AGCACGCAGCATAGAAGCGTGGTGGCTGTTTAACGTGGCTGCCCGCTGCCCGTGTCGGGGCACAAGCGACATCCTCCAGGACCGAAGGCGAACGCAACGCG AGCGATGACAAAACGCGGACCCCACGAATCCGCGAATGAAGAGCACCACCACCAGAAACAGAAATACGATGACCCGA AAGACTTCCCGATGGTAGTCACCAGCATACAGGACCTGACACGGGCGGGGTGCGGGCAGGGTGCGCGTACGGGTCCCTGGCGACCTGC TACCCTGCCTACCCGATTCACCGACCGTGTTGTGCAGACATGGTCGGCGCTGACATGGTTGCGGCACTGGTTATCAGAGAGAAGGAAATCT CCAGGAATCTGCCGGCCGTAGGCTGCAGGAGATCGCCGGCCGCTGCCCATTCGTGGAGGACAGTGCCATTCGTCATGAACGACCAAGTCC GGCTGCGGCCACAGAAGACTCGCCCTGCCCACCCTGGACGACGAGGAATTCTGCTTCATGTGTAAGGAGGAGGATTAGTGGCCAGTGCCATCCACAGCAG AAGGGCGGGCAGCCAGGAATTCAGAAATGTTTACTTTGAGTCAAAAGCTGGACAAAAAGGCAAGCCAGTATCCAGCCGCTGCACA CACAGCGGGGACAGAGTTCTCAGAAATGTTTGAGTCAAAAGCTGGACAAAAAGGCAAGCCAGATAGTGTGCTGAAGAGGCCAGGTGG GAGGCTGCAGCCAGGGTGCGGCAATCGCCGAGGCCAGTGGACGCAAGCCAGATAGTGGCCATACGCAAGCCTGAGGCCAGTGG ACATCAAACCGTCACTTCAGATCGTCAGCTTGGTTATGCCGCTGCGTGCGTGTCACTGCCGCTTCAGATCAAGTCACCAGAAGTACACCTGGAATGTGGT |

TABLE 4C-continued

| SEQ ID NO | GENE NAME | SEQUENCE |
|---|---|---|
| | | GTTTACGCAGAACAAAGCGGGTGCCTCGGAGGAGAGAGAGCCTAGGACAGCAGGGGCACCTCCGGTGTGGTGCCAGGGTTGCAGGGTG<br>CTTCCTCTGTCTGCGCGGTTTCAGAGCCCCAGGGTCCTGCCTGCCCGGTCCTGCCGCCATCCTGCTCCGCCGCCGAA<br>TCTCAGCCTGAACAGCTTCGCTGCTGTGTTGTGACTATTTGTTCTTTTTTTTTTTAAATCGCCACTGAGCCTTAAGGCGTCTGGCCC<br>GCGCATTGAGGAATCCACAGTTCCGGGGTCTCGGGGTCTCCGGCCTTCAGCCTGCCCAGCTCCCTGCTTCAGCCTGCAGCCTGCCCGTCAGCCCCGTTCAGCCTGACCCCCCGTTCACCGGAAACTGCAG<br>CCCAGACAGCTTCCTGCCCCTGTGTACTGACAGGAGCCCCGCAGGAGCTGGGCTTTGGGCAGCTCGTGTGAGCTCCTCACCCA<br>AGCCAGGGCTTCCTGCCCCTGTGTACTGACAGGAGCCCCGCAGGAGCTGGGCTTTGGGCAGCTCGTGTGAGCACTCTCTTTCAG<br>ATCCTGCCACAGCAAAGCTCACAGAGACTCACTTCTTCCCATTGGAATTCACTAAGACAAATTCAACAATTCAGACCCCAGCTGAGGTT<br>TATTTTATGGATTTTACCTGTGCGTATTAGGGTTGTTGTGTTTATGAATAAAGTGTGCTTCTGGCAAGTAGAAATACAGAGCTTGTCTTTCA<br>CCCAAGATATCTGAACTTTCCAATGCAGTAAAATCAATAAACAACAAACAAATTAAAACATTAAACATTAAACATTAAAATAGAGGCAGGCTGAT<br>GGGAGGTTGTGGGATTAACAGGCCGTCAGCGATTGAAGCTGCGCACATCGTCGGGATGCTGCGGGAGGATTCGTCTAATCCGGG<br>AGCATCTGGCTGGGCAGTGGGCAGCGTCTGCAGTCGTGGCTGTCGGGCTATCTCAGCTCATCTTCAGGTATGAAGGTTGTGGCCTTGCTTCCCCCATCAGGCTGCC<br>CCACCCTGGACCCCACCCAGACCCTCCCGGGCACCCTGGCAGTGCGCTGTCCCTGGGACTGCGACTGTGCAGTGAGCGTGAGCGCTGCTC<br>CTGCTCCTGCTCCTCGCCTCCCACCCTCCCATCCTCCTCCATCATGTGTCAACATGTGGGCTGCAGCCTCAGCCTGCAGGACGCTGTC<br>AGTGCAGCTCCTCAGTGGCCAGG |
| 250 | PCBP3 | ATCTTGTCTTCTTGTCCCAGTCCTGGAACCAGCCACTGCCCCAGCAGCTCTCTGTGTGTGGCATGTTCTGGAAGCCAGGATGCATGGT<br>GCTTCCTGGGCGTCTGGGGTGTGTCCAGCTCCGAGCTGCTCCCCGAGTTCTTCCTGCTCAGGTGTGCACCAGGAGGAATCCA<br>GTTCAGCTCCCCTATATGTGCGTGCCCCAGTTCCAGCCCGCCGGAGGAGGCTGCGGAGGCTCTGAGCTCTAGCCACAGCAGCTGGCACATCCTAGATTT<br>CCGGGAAGACACCGGCCTCCTCCCAGGGGAAGGTGGTGCCAAGGCGCATGGTAAATGGGCTCTTGTGAGGCAGGTGCACGGCCCCATCTCAGCAGCAGG<br>TCTCAACTGTGGGTGTCAGGAGCCACTCTGTGGGGAGCCATGAGTGCCATGATTGACGGAGGCCTCCCTGCACCATCCCTATGGTCTCCTCTGCACAAC<br>GCCATGCCACCCAGCTGCACCTCTGTGGGGAGGTGCCATGATTGACGGAGGCCTCCCTGCACACCATCCTCATGGTCTCCTCTGCACACGTCT<br>GTCCCTCACAGCCTCCCCTCCTCTCTCTCCCCACCGGGCCCCCTCTGCACCCGGCTCCTCCACAGCCTCCCTCCTCCCAGCCCTCC<br>CCCTCCTCCATCCTCACAGACCCCTTGCTCTCGCCATCCTCACGGGCCCCCTCCACGGGCCCCCTCTACACACTGTCTGCCCAGCCCTCCC<br>TCTACACGCCATCCTCCACAGCCTCCCCTCCTCTCTCCCCACCGGGCCCCCTCTGCACGGCCCCCTCTGCACGCAGCCTCCTCACGGGCCCCCTTGCC<br>GCACACCGTCCTCACAGGCCTCCCCTCCTCTCTCCCCACCGGGCCCCCTCTGCATGCCGTGACAGGGAGATACTGGGCACTCAGCCCAGCGGGGAACGTGTCCC<br>ACGGCCGTCCTCACAGGCCTCCCATCCAGACTGCAGCATCTGGGCAGCATCTTCCAGCCTGCCGTGGAATAGGAGTCACGGAGCAA<br>GCCGCTCCTCACGGCCTCCCATCCAGACTGCAGCATCTGGGCAGCATCTTCCAGCCTGCCGTTGGAATAGGAGTCACGGAGCAA<br>GTCCTCACGCCCCACAGTAGACTCAGCTCGTCAGTGAACTGTGGCAGCATCTGGGCAGCATCTGGGCAGCATCTCCAGCCTCAGCCTGCCAGGAGTCATG<br>GAAACTGCCTTGGGCTCCGCATCAGAAGCTGCAGCATCTGGGCAGCATCGGGCAGCATCGGGCAGCATGTCCTCTGAGTCTCCCGGGAGTCATG<br>TTGCAGCTGTAAGGTTCTCACACAATTGAAGAGGCTTTATTTTCTCACATTTCTCTGTAGCCTGAGTGCATG<br>GGTGATGCCCCTGAGTTATTATCAGGGGCTCAGTTTATTATCAGGGGCTCGTATGGGCAGCAGCATCATACGGGAAGTAGGCAGGTTCGGTAGTGTCGTCGTGTCTGCTCAGGTGG<br>GCGCCAAGGAAGACCACACCGGGAAGTCCCTTCGGGCTCGTATGGGCAGCAGCATCATACGGGAAGTAGGCAGGTTCGGTAGTGTCGCCACCAGAGATTCTGATTTCCCT<br>TCTTCATGCACACCGGGAAGTCCCTTCGGGCTCGTATGGGCAGCAGCATCATACGGGAAGTAGGCAGGTTCGTGCCACCAGAGATTCGATTCCCTCTCC<br>TGCTTATGACATACATCTTTCTGATTTTTTTTTTCTGCAGGAAGTTGGAACATCATCGGAGCATCATCGGGAAGTAATTATTGATTGAATCTGCCTCT<br>CCTGGGCTCTGTAAGGGATGTGAGGATGGGAGATGGGAGATGGGAGATGGGAGATGGGAGAGGGGTACTAGGTGGCACCAGTAGGTGCGCTTGTGTGG<br>TGGTCTGTGTTCATGAAGACAGGACCTCACCTCAGCTGGTCACCTCTGTATGCTGTATGACATTGAAGCTGTCCTTCTTTCCGGTTGGCTGAGG<br>GGAAGGGGTCACTCAGCTGGTCACCTCTGTATGCTGTATGACATTGAAGCTGTCCTTCTTTCCGGTTGGCTGGCTGAGG<br>GAATGATTTCTCACGCCCTTCTTCAGCCGCCTGTAGTTCGGGTTCAGTTGGAAGCCCAGTTGGAAGCCCAGTGGTCGTCCCGGAAGTAAGGCCCAGTTGGAAGCCCAGACAATTCTT<br>TCCAAATCAGGGCTGGCCGGGAAGTAAGGCCCAGTTGGAAGCCGTCCCGGGAGCAGTGAGGGCCACCTCCTGTC<br>TTCATCACATTTTCACCGCTTCCGGGTCCTTCCCCTCAGTCCCACTGCCCACCATGCCCACCATGGGGCGCC |

TABLE 4C-continued

| SEQ ID NO | GENE NAME | SEQUENCE |
|---|---|---|
| 251 | COL6A1 | GCTGGACACCTCTGAGAGCCTGGCCTGAGGCTGAAGCCCTACGGGGCCCTTCCTCCTGTGGACAAAGTCAAGTCCTTCACCAAGCGCTTCATCGA<br>CAACCTGAGGGACCAGGTAGGAGGGACCGCCCCGTGACCTCTCTGGGCCTCTTGGAGGGAGGGTGGGGCCCCAGGGGA<br>ACACGGGTGCGACGGCCCTCAACCTTCCTAAGGTGAGCTGCTTGGCGAGCGTGCCCTGACCTTCCCAGAGTGAGCTGGTTTGAGACCCTGCTCGGCCGG<br>GGCCCTTTCCGCGCGCCCCTCCAGAGTGAGCTGGTTCTGAGCCTCTCCAGCGCCTTCCAGAGTGAGCTCCGCAGGCTGAGCTGAGCCTGCTCGCGGGG<br>GTGGCACCTGTTCAGCAGGGCCGAGGTGACAGTGAGGCTGCAGGGCCCTCACTCAACCCTGACCTGACCCTGGTTTGTTCCGTGGCAGTGAGAGCC<br>CACTGGGCCCAGACACCAGTCCTTGCCTGGATCGACCGCCCTCGTCCCCAGACCTGGAGGGTGTCCTCTGACCGGGGCCCCAGGCT<br>TCTACCTGGGTCCTGGATCCACGTTCTGAAGCTCCCCTCCTGCTCCCCACCCTTCGTCTGCTTCCTCCATCTGTGCTGTGCTGAGGACAGACCCGGGAGACGACAGCC<br>TGGTTCTGGGCTTGGAACACGGCACCCTCGTGAGGGGGGCACTGAGACCTGGCATGTAGAACGGGCTCCCCACTGAGACGGGTCCTGCAGTGGGACACAGC<br>GGTCCTGTGGGTGCACAGGCCCGTCGACAGGGCCCGCTGAGGGGGGGACACCCTGACTGAGAACGGGCTCCCCACTGAGACGGGTCCTGCAGTGGGACACAGC<br>TTAGCCCGCGTAGGAACCCCCGTCCTCTGCCCTGACCTTCTGACTGGCCCTGGGCTGGGGCCCGGAGGGCACCAGAAGGGGCACAGTCAGA<br>GGCTCGCCGTAACGACCAGGGTGACCTTCCAGCCGCTCCAGCAGGCCATTGGTACCAGGAAACCCTGAGCTTAGTGGACAT<br>GGCCAGGCCCGTGCGGCAGTGTTTGGGGGGGTCTGCTGTGATGGAGGGGCCGCCCAGCGCTCCCCGA<br>GTCGCCCTTGTTGCTTTACTCAGTCTCCCCATGACTCAGTTTCCCACCTGTGAAATGGGCGGAGTCATCCCATGTCGCTGCCACTGGA<br>TCCTGCAGGGCGCCGTGGCTCACTCTGCTGAATGGATGGAGGGTGGGTGGGAGGAGGTGGGCCTCCAGGCTGGGGCAGAGCAGA<br>CCCCTGAGAGGCTTCAGGTGCTTCAGAGGGCCTGCAGGGGGCTTCCTGGTGCCTCCTGCAATCCCCAGTGCTCACTGTCATGTCTG<br>CCCCACTGCAGGCCCAAGGACCCCCAGCAGGGCCCACACTCAGGGCTCGGGGCCTGAGGGCCTGGGTCTGAGACGCCAGGTC<br>GCTTGCTGGCCACACCGCCTGTCCATCTGGGTGACGTCCGCGCCTCCAGGGCCTGGGACGTAGGCGATGGCCGCCCCGACGCCTTCAGGGCGCCCCCGCCGT<br>GGGTGGGGCAGCCTGCAGTACCGCTGTGACCGGCGAAACCTGTGTGGAACGCCAGGCCGGCTCTGTACTACAGTGACGAGGTGGAGATCATCCA<br>AGGCCTCTATCAAGAAGGGGCTGGAGCAGCTCCCTCCGGGCGTCTGGGTGAGTGCCCCCAGCTCAAGTACTTTGGAAGGCACTCACGCGTGTGTACCCAG<br>CCTGGGCCTGGGGGTTGGCCTGGGTCCTCTTGTGCGGCTTCAGCTGCAGGAGGTGCACGGCCTCCCTGACCCACTT<br>TGTGCGGCAAAGAGAGACAGAGACAGAGACAGAGAGTGACAGAGGAGAAAACAGAGGAGAAGCAGAGGGAGAACACAGAGACCAAGCAGGGCTAG<br>GATPAGAGACAGAGACAGAGAGAGACAGAGACCGGAACAGAGAGTGACAGAGGAGCAGAGAGAGACAGAGAAGCAGAAACAGAGGACAGAGAG<br>ACACAGAGAGACAGAGACACAGAGAGAGAGACAGGGCGAACAGAGACAGAGACAGAGCAGACAGAAACAGAGGAGACAGAGACAGAGAGACAGAGG<br>GACAGAGACAGGCGAAGAGAGAGACAGGGAGAGAGACAAAGAGAGGACAGAGACAGAATAGAGACAGACAGAGGACAGAGACAGAAACAAAGACAGT<br>AGAGAGACAGAGACAGAGACAGAGACAGAAACAGAGACAGATAGAGACAGGGGCAGAGAAGCAGAGAAGCAGAGAGGGCAGAGGACAGACAGAGCT<br>CAGAGACAGACAGGGGAAACAGAGGCAGAGACTGAGAGACGTGAGAGACAGAGACAGGGCAGGGGCCATCACCACCAAGCAGGGCTAG<br>ACAGCGAAACAGAGAGACATACAGACCCGGAACATGCGCTTTCTCAGGGGGCAGAGAGCAGAGAAGCAGAGGAGACAGAGAAGCAGAGATAG<br>CAGGGACAGAGACAGAGACAGAATAGAGACCAGAGGAGACAGAGAAGCCAGAGAAGACAGAGGAGACAGAGACAGGGAGACAGAGACAGGACAGAGAA<br>AAGCAGAGAGACCGGAAACAGAGGCAGAGACGGGGTGGTTTTCTGGACCTCCCCACACCAGCCTCTCCCCAGAGGTCGTCTCAGAGGGCA<br>CAGAGACACCGGTGTGCCGGACAATTCCCTTTCCAATGGTGTGCCACTTCCAGAGTTGGTGCCAAGCTGGGACCTGGGGGACTTGG<br>AGTCTCAGGAAGTCCCCTAAATGAGCTCCCCTTCTGGCCAGATGCTCAGGCGTCCAGCAGGCTGCCCGACTGCCTGCGATACTGCCCT<br>CAGACACGACTCCCTGCTCCCACTTTCCCTTCGGGGGTTGATTTGGGGCATTCAGGGATCGCCGGCGGCCCCATCGGAGGCGCACGCTCCCTGCCACC<br>AAGAGCCACGTCCGGCAGCCTTGAGTTGAGAGCCCGCCCAAGGGCGTAGGAGCAACCAGGGACCTGCGCCGAGGTCTTTCCATGGTGAGGTTCTTTTCAGTAACCCCACCGTATA<br>GCCAGGATCAGCAAAGACAAAGAGAGGGCCGGCTCCCCCTCCCCCAGTGCCCTCCGGTGACGCCAGCACGCTCCCGAGACCACTCGACGGACTCCCCA<br>CCTAGTCTCGAGTCTCCACGGCCTCCCCTTCCCTCTCCAAAGTGGGGGCTGGAGAGAATAAGTACCTGATTGTGACCGGCAC<br>CCCCTGGAGGGCTACAAGGAACCCTGTGGGGCACCCGGGCCTGGAGGATCTGTGAACGAGGCCAAGCACCTGGGCGTCAAAGTCTTCTCGGTGC<br>CATCACACCCGTCTTTTGGTCTCGGGAGGTGGGTTCTCCAGCGCGCCCTTGCCCCTGAGGAGCCACCCTTGCCCCTGGTGCCTCAGCCACCCTGAA<br>TGGGACCGTCCTTTGCCCAGCCTCCGCCGTCTGAGCATCATCGCCACGGAACCACCACGCACTGCGCAACTTCACCGGGCTGACTGGGCCAGAGCCG |

TABLE 4C-continued

| SEQ ID NO | GENE NAME | SEQUENCE |
|---|---|---|
| | | CGACGCAAGGAGGAGCCATCAGCCAGACCATCGACACCATCGTGGACATGATCGTGAGGCCCTGCCTCCAGGACGCGGGAGGCCCGCG |
| | | CGGCCCGACGGTGGAAAGTAATTCGCGTTTCCATTTCTTTCTCAGAAAATAACGTGGAGCAAGTGGTAAGAGCCTCCCCCACCACCCCCC |
| | | AGCCGTGAGTCTGCACACGTCCACCACGTCCACCTGTGTTCAGGACGCATGTCTCTATGCATATCCGCCACTGCCCGGACAC |
| | | ATGTCCCCTGCGTCTGCCCGTGTGCCGGATGTGTGCCCCTGCGTCTGCCACCTGTGTTCTGCCCATGTGCTTCTGCCAGCCGTATGTCCCCAGCCGTGTCCCAC |
| | | CGCCTGTGCGTCCATCCATGCTTTCCCCCACAGTGCTGTCGTCTGCCCATGTCCATGTGAATGCCAGGTCAGTGCTCAGGTGTCCCCGACCCCTGACCC |
| | | TGACTCGTCTCCATGCTTTGCCCCCACAGTGCTGTCGTCTGCCCATGTCCATGTGAATGCCAGGTCAGTGCTCAGGTGTCCCCGACCCCTGACCC |
| | | CTGGAACCTGAGTCTGGGCTCGGCCCTGACCTGCAAGAGGACCTCCGGGGCTCCAAGGGAGGTCCAGATGAGGGG |
| | | CTTTGAGGTGAGTGGTGACTCAGAGGGGACGGCGGGGTCCAGATGAGGGGACGCGCGGGGTCCAGATGAGGGGACGCGGGGTCCAGATGAGGGGACGGCGGGAGTCCAG |
| | | GTCCACCATGAGATGAGATCCAGAGGGGACGCGGGGTCCAGATGAGGGGACGCGGGGTCCAGATGAGGGGAC |
| | | ATGGAGGGGATGCGGGGTCCAGATGGAGGGGACGCGGGGTCCAGATGGAGGGGAC |
| | | GTCCAGATGGAGGGGACGCGGGGTCCAGATGGAGGGGACGCGGGGTCCAGATGGAGGGGAC |
| | | GGCGGGAGTCCGGGGCTCCAGATGGAGGGGACGCGGGGTCCAGATGGAGGGGAC |
| | | GGGGACTTCGGGGCTCCAGATGGAGGGGACGCGGGGTCCAGATGGAGGGGAC |
| | | AGATGGAGGGGACGCGGGGTCCAGATGGAGGGGACGCGGGGTCCAGATGGAGGGGAC |
| | | GGGGTCCAGATGGAGGGGACGCGGGGTCCAGATGGAGGGGACGCGGGGTCCAGA |
| | | GACGGCGGGAGTCCAGATGGAGGGGTCCAGATGGAGGGGAC |
| | | TGGAGGGGACGCGGGGTCCAGATGGAGGGGACGCGGGGTCCAGATGGAGGGGACGCGGGGACTCCAGA |
| | | CAGGGTGTGGACTGTCCCGGGGAGTGTCCGGGGCTGCCCCTTCTCGAGGGTGTCTGTCCCCTGCTTCTGTGGCTCAC |
| | | TTCTGAGGTAGGAGGGTGAGAATGTGGGTCCCCTGCTTCTGTGGCTCAC |
| 252 | COL6A1 | GGCCGGGAGGCGGGAGGCTCCCCCAAGAGTAAAAGCCTTTCTGACGTGCCAGACGCGGCCCTGACTGTCTAACTGACTCTTCT |
| | | CTTCTCTTCAGTTTGCTGTGGTGAACCAGGCTGTGGTGAACCAGGCTCTAGCTCGTGAACACGGCCGGAGCGCAGGGTCCCACA |
| | | CATGTCACAGGACCACATGGCCATCTGCCACCTCTGGCCTCTCCCGCCCAGCTCCCCTGCCGTCCTGCCCTGCTCACCTGCTCCAAGCCAGCA |
| | | GGGTTCCCCGGGTGTTGGCTGGGCTGTGCCACCTCGGGCTGGGGGGTCTGGGGGGTCCTTACGGGGCAGCCTTTTACGGGGCAGCCTTTCATGGGAG |
| | | TCTGCCCACAGCCCCACCCTAGCCTGCTGAGACGGGAGACCCCAAACGTGTCAGTGAGATGTGGCAGCAGAGGAGGGGCCAAGGAGGGGCCCATGGAGG |
| | | GGGTGGGCTTTTCTGAGGTCTTCAGGCACTGGAGGGAGGGAGGGAGGCGTGCTCTGGACCCTTGGACCTTCAAGGGTGGGAGAATGCAAGGTGCTCAAGTGGGGCCATGGAGGGGGGCAAGGACCTC |
| | | TGTTCGTCTGCTGGACGACTCAGAGAGCATTGGCCTGCCCCCGCGTCCGGCCTCCAGGCCTTCGTCGTCAAGGTCATCGACCGGCTGAGCC |
| | | GGGACGAGCTGTCAAGGTGAGGCCTCAAGGTGAACGACGGGCCCGCCGCCGCCGCCCTGCCCGGACTCCAAGAGCATCGGCTGCCGGAGCG |
| | | CCTCCAGCTCCACCTGGCGAGCCTGGCCATCTGTATACAAGAGGCCCCAGATGATGCCCTACTCTGCAGGATGCTCCCCTCTCTTGAAGGGCGTAGTC |
| | | TGGGGTCCTGAGTGCTGAGGTGTGGGCTTGTCCTGGTGTGGGCTTGTCCTCGTGTCTCCTCGTGACAACCCAGCCTCCAGCCTTTCATCCACCAAGAAGATTGTTTGCAGGGTAC |
| | | CCAGGTCCCCGGGGCTGTGCCAGCCAGGGCACCGAGCCACCCTCTGGGCACCCCAGGTCCCCTGCAGGCAGGGAAGGCTACCCATGCTCAGTCCCCACTCCATGTGCCTCCAGCCAATAGAGTCACCCTTGG |
| | | CCAGAGCCATGCCAGGACCTGGGGCAGCACCTGGGACCTTGCGAGGCTCCAGGTCCGCCCGAAGCTGGCGGCCCCGTGAGGGCCGGGGCACCTTC |
| | | GAAGCTTATGCGGACCTGGCCTGGAGACGAGAGCAGCGGACCTGGCCTGGAGCGGACCTGGGGCCCCACAGTTCCAGCCGGGTGTGG |
| | | TGCAGTACAGACAGAGACCAGGACACTGAGAAGCCTCCAGCAGTGCTCAAGGAGCTCCAAGGAGCTCAAGGAGTGAGTGCCC |
| | | CACCCGGCCAGGACCCTCCACCAACCGGCACTACACGCCAGGTGCCCAGGGCCACCCCCAGGTGTCCCAGGGCAGCTGCCCTGACCCTCGGCC |
| | | CGCCGGACCAGGGCCTGGGCCCAGGACCCTTGCCTCCCCTCTGCCCCTATGCAGAGCCATCAAGAGCCATCGCCCTGGTCATCACGGGCGCT |
| | | ACGGGAGGCCCTTCAAGGACCCTACACGCGGCCAGGTGACCTCCAACCTGCTGCTCAACCTGGCAGCTCCACGGGCCCCC |
| | | CAGACACTAGAGGCGCCCCACCACACCACCCAGCAGGGCCGCCCACCCAGGCCCGCCCTCAGGGCATCCAGCCGGCTCCACCTGCCCCC |
| | | GCCTAGGGCGCCCGGCCAGCCAGGGTGCCTTGTCCCAGGAGAAAGACACGGTGGCCTCCCAGGGCCACCAGGGCAGGACCTCAGGTCTGTCCCCA |
| | | CAGTGGTCTCCGGGCATCAAAGACACCTCCTGGTTGACGTGTTTGACTTCATCCCAGGCTCAGACCAGCTCAGACCAGCTGGAGGATGCCTTCTGGAGGATGCCTTCTGAAAGAATGTCACCGCCCAGATCT |
| | | GCATAGGTCGCGCCATGGCTCCCAGGTGCCACCCGGCAGTCCCAGGAGTCGCGGCCCCGTCCTAGGTGCACGCGGGGCCGGCCTCAGTCCCAGGAGATCTGCGTAGGT |
| | | GCACGCGGGCCGCCGCCCGGGCCTCCGGGCAGTCCCAGAGCCCTCCTCCCCGGGCACTGTTACCTCGTAGTTCACGCGGGGCCTCACCCCCTGTGCTTCGGCGGAGTGTAGGTGCGCA |
| | | GGCGCCCAGGGCTGCTCCAAGGCATCCTCCTCCCCGGGCATCCTCCTCCCCGGGCACGGCCACCCCTGTGCTTCGGCGGAGTGTAGGTGCGCCCT |
| | | TCTCCTTGCGGGGTTATAGGTGGAGCAGTGGGCTCACACTGCCACCGTGGTGGGCAGGACGACCACCGTGGTGGGCAGGACGCCACCTGGAGGCTCTGTGACA |
| | | AGTAGTACCTCCGCGGCCAGGGCGCGGGGAGACACGTGGGGAGGAGGAGGAGGCACCGTGGGAGGAGGGAGCACCTGTCGAGGAGGGAGCACCTGTCGAGGAGGCTCGGGAGGAG |

TABLE 4C-continued

| SEQ ID NO | GENE NAME | SEQUENCE |
|---|---|---|
| | | GGCCTGGCGGTACGAGAGTAGTGCATGGCTCACTCCGGTGCTGAGCACCACCGTGCCCTGCCTGTGCCCTCTCTGGGAGCTTAGACGCTCT |
| | | CTGCCGGCCCCACTGCCGCGCTCATCACCAGGGCTCATGCTAACGGCTGCCCAGTCACGTTCTCCTCCCGGCTGAC |
| | | ATCACCATCTGCTGGACGCGTCCGCCAGCCCCCACGACGTGCGGGTTGCCGTGCCACCAACTTGACACCACCAAGCGCTTGCAGGCGCCAAGGCTTCGCCAAGCGCTTGCCGAGCGCTT |
| | | CCTCACAGCGGGCAGGACGGACCCCGCCACGACGTGCGGGTTGCCGTGCCACCAACTTGACACCACCAAGCGCTTCAGCGGCCACGGCCCAGAGCG |
| | | GGCGTCGCTGCAGTTCCTGCAGAACTACGGCCGAGGCCTCGTCCAGTGCCGTCGATGCCATGGACTTATCAACGACGCCACCGACGTCAACGA |
| | | TGCCCTGGGCTATGTGACCCCGTTCTACCGGAGAAGGCCGTGCAGGAAGCATGCAGGCATCAGAGGCTGCTGCTTCTCAGATGGCAACTCGCA |
| | | GGGCGCCACCCCGCTGCCATGCAGAGAAGGCCGTGCAGGAAGCCGTGCAGGGCATCAGATCTTCGTGTGTCGTGGGCGCCAG |
| | | GTGAATGAGCCCCACATCCGTGTCCGCGGTGCTTCCACCAGTCGTCCTGGCGCTAGCCACCCTGCACGCCGGCACCA |
| | | CAGCTACCAGGCCCTGCTCCCACCCCTCCACTCATCACTAACACAGAGTAAAAATGTGATGCGAATTTTCCGACCAACCTGATTTCGCTAGATTTTTTTTT |
| | | AAGGAAAAGCTTGGAAAGCCTGTGCAAGACCTCTCCGGGGTCTCCGAGGTCTCCTGAGTTGGCATCACCTGCG |
| | | CAGGGCCCTCGGGGCTCAGCCCTGAGCTAGTGCTCACCTGGGTTCCCACCCCGGGCTCTCTGCCCTCGGGGGCTGTGCCCGCCCTCCTCTGC |
| | | CCCTCTGGGGCTCAGCCCTGAGCTGGCTCACCTGTGCATCCCACCAGCTACTCCACCAGTCCTGAGCAAGACGCCCTTCGGGGCTGTGCCGCACTAGCCTCC |
| | | CTGCCAGCTCCTTCCCTAGGCACCCTGTGCTGCATCCACCACCAGCTACTCTACCAACTCTACAATTAACTCAAAGCAAGCTCTTCTCCTCAGCTTG |
| | | TCTCCTCTGTCCCCATAGCTGGTTTCCACCATTGTCCGGCGTCGTGTCTGTTCTGTTCTGTTGCGGACTGCGGAGGAGCCGTGTTGCAGACGACTGACCATAAATCTCGGCGACTCGGACTGAGAGTACT |
| | | GGGCAGCCATTGGCCTCTGTCTGTTTGGGAAACCAAGGTCAGGAGGCCGTTGCAGACATAAATCTCGGCGACTCGGACCTCAGAGAGTACT |
| | | AGGTCTGCTGTGACCGGCTGGACTGCCCTACGCCTGGAGTTAACGGTCGTCATCCCTCCCCTGCGAAGACACGTCTTCAATCTTACCATGTTGCTGACTTTTTGGGGGGGGC |
| | | CGCAGGGGCGCTGGCTGACTCAAGACCCTGAGATTAACGGTGTCTACTAGAAAACACGCAAACCTCTCTTCCTCAGAATAGTGATGTGTTGCA |
| | | TGGACATGAGAGCCCCTTGCTGCCACAGAGGGCTGTGTCTTACTAGAAAACACGCAAACCTCTCTTCCTCAGAATAGTGATGTGTTGAC |
| | | GTTTTATCAAAGGCCCCTCTCCCTGTGGTTATCTCCCCACAAAGTAAAAATCTGCCGTGCCGTGTGCCCAAAGGAGCAGTCAAGGAGGTTGGGGGGC |
| | | AGTTTTCACTCTCTGCTCACCCCATCACCACAGTCCAGCCAGACGAACCAGTCCAGCGACAGAACCAGTCCAGCGACTGCTGCCTTGGCTACAGCTGTCCATCATGCC |
| | | GTGTGCGTGCGTGCCTCACTCCAAACCCCCATCACCACAGTCCAGCCAGACGAACCAGTCCAGCGACAGAACCAGAGCTGAGAAGGCAACACCACCCTGGCTTTGGGGT |
| | | CCTTATCCTGCGTCGGTGACATGGAGACCAGCATGCATCGCACGGCAACATCCACCGAGGCCCCTCAACCACAGAGCCCGGCCACAGTTCTCAGGCTTCTGGTAC |
| | | CGGGAGCAGATCAGGCTCAGTGGGCTGCTGGGGCCGGACAGTTGAGATACTCGGGGCCCATAGGAGGGCCGGACAGTTCTTCCAGCGAAGTTCCACCTTGGGCAGAG |
| | | TGAAATACCCCTGGAGCTCGAAAGGGGGAGTTGAGATACTCGGGGGCCAGAGCAGAAGGGCCGGAAGCAGCGAGGCAGCTAAGAGGATCGGCCGGGCCGGGCT |
| | | GAAGAAGTTCTTGGGAGGCTCCACCTTTGGGGGCAGGAAGCAAGGAAGCAGAGAGGCCGGAAGCAGCGAGCTAAGAGGATCGGCCGAGGGCTGGGCT |
| | | GTTAGTGCCCCCTGAATCCAGATCCGGGGTTGCACGCTGTTCTCAGCCCTGAAGGCTTCCTGAAGCCCTTCACCTGCCGGCAGACCCCCGAGCCCCCTCAG |
| | | GGAGGAGGGCAGCAGGATGGGCCGGAGTGCTGAGGGTGGGGCCCGAGGAAAATGCTGGGAAATGCTGGGGACCCTGCATTTCCG |
| | | GTGCCACAGGCAGGGACACGCTTCGCTCGATGCGTCGCAAGCACTAGCCGGGCAGACGGGCCCCGGGGCAGACCCAGTGGGGGCCGGTGGCGGTGG |
| | | TTTCAGGTGGGAACAAGCCGCCCCCTCAGGGTAGGAGACGGGCCCGGGGCAGACGGGCCCGGGGCAGACGGGCAGTGAGGCCGTGG |
| | | GCAGATGCAGTGAGGCGTGGGCGGGGGCGCCCCGGAGGCCCGGGGCACGACGCAGTGAGGCCGTGGGCCCGGGGTAGTGCA |
| | | GCCGGCCCGGAGAGCCAGGCGGTGGGCGGGGCAGCGCAGACGCAGTGACATGCAGTGAGGCCGTGGGCCCGGGGTAGTGCA |
| | | GTAGGTGTGGGCGGGGCCCGGAGCGGGTGGCGGGGGCAGTGAGGTGGTGAGGCAGCGAACCCAGTCCGGGCAGACCCAGTGAGGCCG |
| | | GGCAGCAGCAGTGAGGCGTGGGCGGGGCTGGGCGGGTGAGGCCCGGGGTGGGCGGGGCCCAGAGGGCAGGGCTGGACTCAGTGAGGGCAG |
| | | TGGGCGGGGCGGGGGGCCGGAGGCCAGAGTGGGCGGGGCAGACGCAGTGAGGGCCCGGGGCAGAGCCAGTGAGGCAGTTGCCAG |
| | | CGCAGTGAGGCGGTGGGCGGGGCCCCGGAGCCAGATGCTCGCAGTGAGGCTCGCGGCCCCCTGGCGGACGCAGTGAGGCAGTTGCCAG |
| | | CCTCTCTCAGCTGCCTCATGGGATTCGCACTCGGCTGTGGAGCCTCCCCGTCCCCCAGGCTACCCCAGTTGCTTGCCGGACAAGGCTGGACTTGGCCAGCGGACAGTCCCTCACG |
| | | GGCTGAGGCCCACACTCTGCTGTGAGCCCGGCTACTTCCCATCCCAGTTGCTTGCCGGACAAGGCTGGACTTGGCCAGCGGACAGTCCCTGCCCAGCCCCCGCCCCCAGCCCCGC |
| | | ACACAGTCCTCCCCTGTAAGCTGCGTAAGGACTCCATGCCACCACCAGTGAAGGAGGTTGCGGGGAGCCAGGCCCAGCCCCTCTGTGCCCA |
| | | GTCCCGGCTTCCTCCCCTGTAAGCTCTCTGGCAGGGGCTGGGAGGGAGCCGCTGGTGGGACCAGGAGAGCCGCCCTCAGGGA |
| | | CACGGCCCGGCCGCCATGCCTGCCGCCATTGCTCCCGGAGGGTCTGGGGCCCGCCGTGTCTTCACGACCTCTCCGGGTACCCCTGGG |
| | | CCCTGGTGAGAGGGTCTCTCCAAGTGCTCTCTATGAGGGTGGGGCCCCTGTTTCCCAAGTCTCCGCGACGAGGAGGTCCGGGGTACCCCTGGGTCACCCCTGGG |
| | | CTGCACACTGGGTTCAGGGGGTTCAGGGGTCACCAGGATTCTACCAGGATTCACCAGGTACTGCACAGAGCCTCGCGCCGAGGGCCGGTTCCCGGGGGTCACCCCTGGGTCACCCCTGGG |
| | | GCGCAGGCCATTCCCATCCCCAAGCCTCTGCGCCACCGCAGATCCCCAACGCCGGCCGCGGAGGACCCCACGGCCGGGTTGCCATGCA |
| | | GAACCCCAGGCTCCATCCATCCATCTTGTAGAAAACTGAGGCACCAGAGGGACAACACTCCTCTGGTCTCACACTGCACTTCTGTAAGGCCGAGCCGGGCCAGACTC |
| | | CAAGGTCCCGGCTTCCATCTTGTAGAAACTGAGGCACCCGTGGCACAGCCTCAGCCCTGCTCCCTGCCCTCCTCCAGCACCACCACCACCCACCTCCCCAC |
| | | TGGACTGACACCTGGCCAGGCTCCGGACACCGTGGCACAGCCTCAGCCCTGCTCCCTGCCCTCCTCCAGCACCCTCCCCAGCTCC |

TABLE 4C-continued

| SEQ ID NO | GENE NAME | SEQUENCE |
|---|---|---|
| 253 | chr21: 46280500- 46283000 | CATGTGCAGTCCTGCCTCAGGCCTGCTGGAGGCCCCTGCGGCCCCAAATAATCAGACAATTCAACAGCAAAACTACTTTTTCAGGCTGGCAGG ACTCTGGGCAACCCCTGCAACAGCCTGGCCCTATCACAGCCACCCTGCTTGCCAGGCACGGAGACCCCACCATCAGGTCCCAGCCT TGGTTCATCCCCAAGCACCCTGTGTTGTTGGAGGATGGCTGGCTGCTGAGCCCTGCATCC |
| 254 | COL6A2 | AGGGCGTTTGGGAACACCCCTCCCGGAGGGGTGAGGCGGCCAGCCTGCGGCTGCCAGGAGGACACAGTTCTGCTGCGGAACCTGCAG ACATGGCCATAACAGGGCCAGTGCTCGGGGCCCACAGCTGGACCCACATGGCCCACCCTGCTCACCTCCTCCAGGGCAGGCTTCAGGGC CTCGACCCTAGAGGCTGCCCTCCTCGGTTCTGCTCATGGACGCGGCCAGCCTGTGACCAGGCAGTGTGACGAGTTCACGAAGCTCAGGATG ACCCCGCTCTGCGCCCCTTCCCAGCATTCCAGACGCTCTTGGCCCTGAAAACGAGGCATCGCCAGAGCATCCCACTTCCTCCGA AGCTGCCGTCTGGGGACGCGTCGGAGACACAGAATTCAGAGTCTGGGCTTGCCCTGAGATACTGATGGCTGCCAGGGGCACAGAGACCCGTCC TGACAGAGCGTGTGAGGCGCTGTGAGGGCCTGAGGAGGCAGTGGGGCCTCCAGCTGGTGAGCAGC TGGAGCGAGGGGGCCGGGCTGACCTGTGATGGTGCTCAGCCAGGAGGCCGGCACCCCAGATAACCCCAAAGAACTGCAGGCCCTGAGC AGTCAGGAGGCCGGGCTGACCTGTGGGGCCGGGGACGGCAGGGGAGGTGCTCCGTGCTCCTTGGGCAGTGCTCGGGGGTGTAACAACGCCAAGACGCAT CTGAAGGTGGAAAGGCCTCACACATTCTCCCCGGCTGCTTCGTGTCACGTCAGCGCCCTACATTCAAACAAAAGTGCAATTTGAAAATGTAGTCCAAGGTTTTCTGGTGCGG AAATGGCCAGGCCAGGCCGGGCCCGGCCGGCCAGGCCTTGGTGTCTTCGTGCAAGGGCAGCAGGCGTCAGGGCCCATGACCTCACAGGCTTCTC CTCTGTCCTCGGGGCTTCAGCACCTGCAGCCGCTCGATGCGCATGCGCCCGCCGATTCCCTGGCGTTCCCTGCCATGGGGTTTCCAAAGTGTG TGCTCAGAGGACAGTTTCCTCCAGGATGACCTGTCAGTGGCTCGCGGGCGTGTGGGCCCGGTCTGGGTCTGAATGCTTCT AACGATTTACCCAGTTCCTTTCTCCACTCAAGGAGGCGTTTGCTGAACTGACGTCCACTCGACTGTCTCCAGGACATGCGCCACAGGGACAGA CGGGGTCTCCCTGTGGCGTGAACTGACGTCCCAGGCGTCCACTCGACTGTCTCCAGGACACACCCTATCCAGGCAGAGAGGCCTATCGAGGGCTGATGGTGGTG ACAGCCCTCCGGGGCTTGTGCCTGGAAGATGCACCCAGGGCAGGATGCATGATCAGCCACAGGGGCTCAGGGCTTCAGGCTTGCAGATGGCAGTGAGCAGTC CTGGGGGTGCAGTTTCACCAACAGAATCCGTTTGGAAGGGACCTGTCCCACCAGGGGCTGACGGAGGACTCACCCCTGTGGCTGCCACCAGGTAGCCGC GCTCCACACCTGCTCAACCCAGTCACTGAACCTGAAAATCCTTTCTTTCGTTGTTATTCATGTATTCACAGAGTGACGCTCCGTGTTCGTTCAGCCTCCAGGCCTGCAGAAGCTGCATCT CAGCCCTGGCTTTGACTTCTGCCTGGAGAGATGCACCCAGGCAGGGGATTCATGCCCATGCCGTTCCTGCTTCCACGACCAGAGTGC CTTTCCCGGACTGAGAGCCCGGCCAGGCCCCGAGAGTGAGAGACAGAGTGTTTTGACCACAGTGATCAACACGAGCCCGTGGG |
| 254 | COL6A2 | AAGAAAGGCCAGACCGGACACGGCTGGCTCACCGTGGTCAATCTCTACTAAAAATACAAAAATTAGCCGGCCTGTGGCAGGCACCTGTAATC TCCAGCTAATCTGGGAGGCTGAGGCAGGAGGATCACTTGAACCTGGGAGGCGGGGCTGAGATGACCCGCCACTGCACTCC AGCCTGGGTGAGGGAGGCCAGACTGTCTGCCTCCCTGTGGCTCCTGGCCTATTTCACGTTTATGCAAAGTCGGGCGCCTGGACTGGGGGCCTGATGCGGGGCTCACCCGCCACAAG CAGGGGCTTCCGGTGCGTGCTATGGAAGACGGACAGTGAGTGTGCATCGAGTCCCTGCCTGTGATGGGCCTGGGGACCTGGGCAGGGGAGGAAG CAAACACCCAGCGCCTGCCTTTCTGGGCAGCTGGGCGGCATCCTGGGGTCAGAGGTCAGAGAACGTCAGATGCCATCCAGAGAGTGCGGGGA GCCTGCTCTTAGAAGGCGGCATCCTGGGGTCAGAGGTGAGAGAACGTCAGATGCCATCCAGAGAGTGCGGGGA |
| 255 | COL6A2 | GGGTGAATGAGTAGTATGGATAGATGTATGGCTGAGTGAGGTGGGTAGGTGGGTGAGTGAGCAGTGTGTTGTTAGGATGATGG CTGAATGAATGAGTGGGGGGATGGATGGGTAGTGGGTTATGTATGGATGGGTGAGTGAGTGATGGGTGGGTGATGAATGGGTGCATAAA GGATGGATGGATGAATGAGTTAGTGAGTTGGCAGATGAGATGAGATGGGTATGTGATGATGGGTAGTGAGTGGGTAGGATGG ATGGTTGGGTAGGTGATGGGTGATGAGTGGGTATGTGAGTGATGGGCAGTGAGGATGGGTGGGATGAGGTAGTGGGGGCAGTGAAGATGGGTAGAGGATGATGGGTGATGGATGGGTGGGATGGATGAGGAATGA GGATGGAGTGAGTGGGTGGGTGGGTGGTGCAGTGGGGGATGGATAGGATAGGATAGGGTAAGTAGGTGGGTCAGTGAGGTGATGATGGGTGGGATGGGTAGTGATGATGA CGGACAGGTGAGTGGGTGGCAGTGGGTGGATGATGGGTGATGGGTAAGTGAGTGGATAGATGATGGGTGGGTGATAGGAATGGGTGGGTGGGTAGGATGATGGGTAGGATGATGATGGGTGAGGATGGGGTGATGAATGA GATGGGTTAGTGGGTGATGATGGGTGGCAGTGGGTGGCAGTGGGTGATGATGGGTGGCAGTGGGGATGGATGGGTAACTGGGGTGACTGGGGTTAGTGATGGGTTAGTGGTTAGTGGTTAGTGGTGATAGA |

TABLE 4C-continued

| SEQ ID NO | GENE NAME | SEQUENCE |
|---|---|---|
| | | TGGATGGGTGATTGGGCGAATGGGTGGATGGTGGAGTTGGTGGTGGTACATGATATAATGGGTGAATACCCATGA<br>TTGAATGAGCTGTTTTGGCTGCTATTTCTGGACACCCAGCTCTGCCAGGCCTGCGTGGAGCCTCGTGACGGTGGCCA<br>CTCATGGCCTTTCTAGCTCTGGTGCCAGCATAGGGAAGGAGGAGGGCACCTCGTCTTCTACTCCTTGACCTGTTAGCCCCCCCGC<br>CAAGGGAGGAGACCCGTGTTGGGACAGCACAGGGGCCCTGTCTGTGCAGGGACTGTCCCTGGGGCCACTGAAGCCCACTGTTCTTG<br>TTCCTTTCTCAGGCGGATCCTGGTCCCCCTGGTGAGCCAGGCCCTGGGGGCCAAGAGAGTCCCAGGACCCCAGGAGGTAGGTTGGTGGCCA<br>GTCCCCATGCCTCTCCCCCAACCCTGCCAGGCCAACAACACACAGCCAAGCCTGTGGTTCTGCCACGGTGACCCACGTATCAGTGGGCAGT<br>GGCCTGGGAGAGACTCAGCACCCTTGGCCCTAGGCTTGGGCCCTCCTTCTCCAGGTGAGCCCGGCCGCCCCTGGAGA<br>CCCCGGTCTCACCGTAGGTGTCATGGGCAGAATCAGTGGAGGAGTCAGAGGGCAAGGTTGGTGCAAAACTAGACACCAAGAGCAGGGGTGGGGAA<br>GGTCAGCTGGCACGGTCAGAGAGGCAAGATCAGTGGAGGAGGTTGGTAGGGACAGGACCCTCAGAGAGCAGCTCCCCCATGGCTGCCTTCCACAGTGGG<br>GCAAGGTTGGTGGGGGAGGAGGGTGGGCAGGAGTCTGGGTGGGAAGTTCGTGGGGAGTCGTGCCTGCCGTGTGCATT<br>CTGGAATCTCCCGGGACCCCCAGGACCTTGCTGTGGAAATCTTCTGGGGACCCCTGGTGCTCCTGGGTGGGGGCCCATGTGACAC<br>GCAGGAGTGTGACCTCATGACCTACGTCAGCAGGCTGGTCATGCTGGTGCTGGCCTGTGGCCCCTGGAGGCTGGAGGTCTCCCGGTAC<br>CGGGTGGAGGGCGGAGGTGCCACCCCCCCGGGATGACCCTGGGCGTGGGTGGACCTGGAACGCCCTGGGTCATCGACAGCTCGAGGACATT<br>GGGTACACCAACTTCACACGTGGAAGACTTCGTCATCAACAGGCTGGGTGCCATGCTGTTGCCTACGACCCTAAGGACCCCCAAGTCGAGACA<br>GGTCAGCCGGGCCAGGGGCTGCAGCATTGCCGGGGCCGGGTCCAGGCCCTGGGGAGGCCGATGAGAGATGGGAGAAGTCCAGACGCGTCC<br>CTCCAACGAGGGCCCTGCATGCTCGGGGATCCCCAGAGTCCCGGGACACTGGGCAACGACGACCTCACGCGTCGGCTTGCAGGGACGCGT<br>GTGGCGCTGGTGCAGTACAGGCCACAGAGGCCACCCCTTTGAGGCCATCACAGCTGGAGCCTGACGTATCGAACGATCCAGCTGGAGCCTGTGAGCTTCAAGGA<br>GGCTGTCAAGAACCCTGAGTGGATTGCGGCGGCAGTCGCGCAGGAAGACCCTGTTGCCTACGACCCGCCTCATCAAGGAGAGCCCG<br>GCGCCAGAGAGACACCTGTGTTTGGCGTGTGCAGCATTGGGGAGTGCCCACGACGGGCCCGGAGTCACCCTCGGCGCTGTGCG<br>ACCGCGACGTCACAGTGACGGCCATGCAGTGAACGGCTTCCCTGCCAGATCAGTGACGCTGTTTCGACCTGGTCGCTGAGGAGTTCATCGATGACATGGAGGACGTCCTCTGCCCGGGTG<br>AGCCACAGCAGGTGCGCAACATGACGCGTCGGATTGCCCAGAAGCAGGTTAATGCAGGGACCACCGTAGTCAGCCCACCACCCAGACTACAAAGCAGCCCTGGTGTC<br>CCCCCGAGGCCAGGCGCCCGGCGAGAGCAGTCGGCGCCAGGAGGAGCAGGCTGGGAGGCAGCGTCCCAGGAACGCAGGAACGATCAGAGGCCATGAGG<br>ATGCCCCAGGATGCAGCACAGGGGAGGAGGGGCTTGGGGAAGGCAGGCTGTTGAGGCCACTGGTCTTGAAGGCCCACCATGGGCCTTGCAGTCTCCCTCAGCTGCCGC<br>TGGGTGCTGCTAGCCTGGCCGTCGGCCGTGCTGCCTGGCCGTGCATGTGCCATCGGAGGAAGCCCTGGATTCAGTGAGTGAAACATCCCGGGTGAAGCACTGACA<br>CAGCTTCCCATGGCCTCTGCCACCGACCAGTCTTGCTCCAACCCTGGCCTCTCGGAGCTGCCTCTGACGTGCGGTTCTACATCTCTGGAGTGGGAGCCA<br>CCCCAGCACCAGCAGTCTTGCTCCAACCCTGGCCTCTCGGAGCTGCCTCTGACGTGCGGTTCTACATCTCTGGAGTGGGAGCCA<br>TGTCCCGACATGTGCCCCACGTGGCCAGTGGCCTTCCCACGTGGGAGCTCTGCAGGCTCTGCTGGACGTGTGCCCCCATGGTGCAC<br>TGCTGCACCGTACCTGGGCCTACGGCTCACCTGGGCCCACAGAGAGAGCTCCCGGGAGGCGTTAGGAGACACACAGGGAGGAAACTCAGGGTCTGCGGTACGAAGTCAGCG<br>GTAGGGATGCCATGGACACAGGGTGGGAGACAGGGTCCGACCTGGAGGACCCTGAGGACCCAGTGCGGAGTCTGCATTCACAGG<br>CTTCCTCAGCACCTGCGCGGGTCGTGCCTTCCCATGGGAGCCTCGTTCATGGGAGCCCATGGGTGGGTGGCACTGAGCCACATTCACAGG<br>CCCTGAGGCTGCCCAGCAGGGAGGAGAGCCATGGCTCCAGGCCAGGCTGCAGGCCTCAGACCGGTCTGCCACAGAGAACCTAGGCTTGCACCTGG<br>GTCTGGCTGCCCCTTCAGCAGGCTGCATGTGGGCCAGCCTCTGCCCTGCCCCACAACAGTGGGCTGTGCTTCTGCGCCAAGGTGCAGGCGTCCTCCCCAG<br>GGTCCACATCAGCAGCAGGGGCACCTGGACCTGGGCAGCTCCAGGCAGGAAGCAGACAGATCATGGGGTGGTGCATCAGGCCATGCTTCCTGATGGGCCA<br>GGGAAGTCTCGGGAGCATGGAGTCAGCCCCATTGCTTTCCCCTGCCACTCCAGGTGCAGGCTGGAGTGCATGGCATGCTTGCAGGATGTGGCGAAACCAGCCCAGGCGGAGGA<br>GTCCAGGCGTGAGTGCCGCCTATGGCTTCCCACGTGAAGCTGCTTCAGGGCTGTATCGTGCAGGACCTGACAGTAGACGCCAGGAGCATCCAGCTCTGTGATGTCACGTGACCT<br>TTCCTCTTTAGCCTGGCTCTATCATTGTAGTGTGGAGTTAGTCACACGTTGGCCTCATTGAATTTCAGTGTTGACGTTGAGCCAGCCTGCTTGCGCTTATCGGCGA<br>TAAACCACCTGCCGTGTGGTGTTTTCTTTCTCGACTTGTTATGCACTGTTCTTGGCCTGGCTCAGGCCTGACCTGCTGGGCACCCTGGCCTCCTATCGGCGA<br>CATCAGCCTGCACTTCCCCTCGCCCATCCTCCCTGGGACCCACATCGATGGCTCGTGTGGCCTGACCAGCATCGCGCTGCCATCCCCGGCCAGCTGCCTAGGGAAAGCAGAGGAGA<br>AGACAGCTGACATGGGAGTGAGCCATCCTTCTCCTCCCACTTCCCTGAGCCTTCCAGGAGCTTGACCATCCTCTTCCAGCCGCTTATAAGTGAAGCAGCCGTGCTGGAGCACCCCTCCCC<br>GTCCAGGAGGCCCTTGAAGTCTGACACCTCATCCCGACACTCAGACGCCTTCCCAGGCTCATCCTTCCACCCAGCCTCTCTAAATCGGCTCTTGACCTCCCACCATCCCAGGCCACCCTGCCTTCCAGCCCAGGCCACGAGCATCTCCTGGGCTGTTTCAATTTCAAATGAACTGAACTCGACCTTGTGGCT<br>CTCGGCCGCCCTGACACCTCATCCCGACACTCAGACGCTTAAATCGGCTCTTCCACCCAGCCTGTCCACCCCAAGCCAGCCTTCCAATTCAACGGCCACCCCTGGGCCAGCCCGAT<br>CAGGAGATGCAGCAGGGACAGTGTTAAATCGGCTTTAAATCGGCTTTAGTAGTCCCAGCCTGTTTCCAATTTCAAAGTGAACTCGACCTCGGGCACTGGGTGG<br>ACACCACCTGGCTGGGCATCCGGGGACCCAGAGGGTGCTGGAGACAACAAACCACAGGCCAGCAGGCCAGAAGCCAGGGAGGA<br>GGAGTTCTCAGTTGCGTGGGAGCCAGGAGGTGCTGGAAGGGTCTGAAGGCAGTCAGGGCCAATCAGCGAT |

TABLE 4C-continued

| SEQ ID NO | GENE NAME | SEQUENCE |
|---|---|---|
| | | AAGAGCTGCATAGGGGCCACAGGCTAACCTGAGCTCCAGTCGTGTGAAGAAAAGGCAGAGACGTTGCAGAGGCCAGTCTGCTCAGGG
GAAGACAGTTCTGGGTGTAGAGACTCACATCCCAGAGAGGCTTGAGGAAGGGTTTACCACCGAAGCAGTTTCTCAGGGGGCTCTTGAGGG
GTGCTGGGGTCTTCCTGCGACGGGCCTGCGGCACTGGAAGCCCTACTGGAGTTTGCCTGTCTCCGCACAGTTTGACGAGCTG
TTTTGTGCTGAAAGGTTTTCTCGGGGTCCGTGGTGTCCCCAAAGGTGCCACCGTGCCCTGAGCTCCCTGACCAGCTTCCTGTCCCT
GTGCTCACTGCCCCCACGGCTCCTGCCAGCGGCTGCCCAGCCACACACCCGCTCACTCATTCTCCTACCGACTCGCCAGCCCAAATGCCG
CTCTTCACTCTGGCCTCTGACGGGCTGCCTGAGCAGGTCTAGGCGAGTCTTCCGCACCGAGGAGGGAGTCTTCTCTGGACGCTCC
CTTGCAGATGCACCGCTGGCGTGGAGGCCTCTTCCTCCGCACGAAGACCTTCGTCCCAGCGAGACCCCGGCCACCTTCCCAGGACCAT
TCCCCTGATCCAACAGTTGCTAAACGCACGGAGTCACCGAGACCCGGGTCACTCCAGCTGGTGGCCGTGCTGGTCTACACCGC
CGAGCGGGCCAAGTTCGCCACCCGGGATTGAGCGCGGAGCCGGACTGATGGAGCGTGTTCATTGACACCTTAAGCTGTGCACAGGACATCG
TGGGGGACCCCGAGACCGCTGGCCCTTCGTCTAAAGCCCGGGCACCCCAGCGGGCTGGGCCTCCGTGCCACACTAGCTTCCC
AGGGCTGCCCCCGACAGGCTGGCTCTCAGTGGGGACAGAGATCTACAGTGGAATCGGCCGAATCCTCCTACGTCCTCTTCCAGGGCTCTG
GGCAGCTCCCAGCCTCCATGCTGGTGGCCCACCGTGTCCCTTGCTGCGGCTGCATCTTCCAGTCTCCTCCGTCTTCCTGTGGCCG
CTCTCTTTGCTGCATCAGGTCACCCTCAGGTCCGGCACCCGGCAGCTCAGGGCCCAAGTCCAGAATGACCTCCGAAGACCCTTAACTCACTCCGTCTGCAGA
GTCCCTTCTTTGCTGCATCAGGTGCATCCTTCCACACGCTCAGGTTGGGGTGTGAAGTCTTTGGAGGCCCTTACTTAGCGCCCAGCTGGG
CTGCCGTCTGTGGGATGTGGGCTCTGCGGAGAGGATGTTCCAGCAGGTTCCAGCGAGCCTCGGAA
ACAGGCCCCAGAGAGCTGGTGAGCCTCGCTGGTGGGTGTGGGAAGCTGGACACCTGCGCCAGTCGTATCGCCCACCGCCCCACTGTCC
AGTGAAGGCTTCCGGTTGGGCAGCAGATAGTCCTGGGGAAGCTGGAGTCACAACAGCTCCAGCCTCCCTGCCCTCCCGGCGCACACGAGCTT
GTAGGGCGGCCACAGTCCCCAGGGGCCAAAAACCAGTGCCCCAAAAACCAGCTCGCCTCTCTCCCATATGTTTGG
AGTCGGGAGCATCCACCAGGAGCTCTGCGGTTCTGCAGAGGACTGAGCAGAGAATCCAGGGGTCCACAATGTTGGAGCGGCA
GGGATCACCATCAAAGGAGGCGCTCGCTGGTGGGAGCCCAGCCGAGTCTGTCCCGAGGCGAGCTCGACTGACCCCGACCCCCATCCAGCCCTGTC
GGGCCACGGCTGTGACATTCTCAGGGGCCAGTTCTGTCCCCCACACTGCACAGCTCTCAGCCTCCCGGCGCAGGCTGGTGTCCCACTGTGGGG
ATGAAGGATCCTCCACAGGAGGAGGAGAGTCCACAGATCTCAGCTTCACCAGCCTGCCTCCCTCCATAGTATCTGCCCATCTATCTGCCGCAGCTT
CCCCGTCTCCCCAGGCCCCACCAGGACACTCGATGATAATGCAACACCAGTCGCCCCAAAACCAGCGCTTGTGCTGTCTCCATATGTTTGG
AGTCGGGAGCATCCACCAGGAGCATCCGCTCTGGCTGCTCAGAGACTGAGCAGCGTGCCCAGCTCTACCGGGTTTCGACATTTAAGCCGTTCCTAGG
TGGTGGCCCTTAACAGGCGCGGCTCCATGTCGCTCGCAGCCGGTTCGTGACGTGGACGGTGTGGGTGAGGTTCAGCCGGCTCCAGCGTCGTG
CGTTGCTCAGAGCGGCCTGCCATGTCTCAAGCCGTTCTGTGAAGGCTGCCGTGCAGCCTGAGGGTCACCGCTGCCTCCTGTGCATTCTGGGGTCACT
GCTCCGGGTCACCAGGCGTCCAGGGGTTGGGCTGCGACGTGTGAGAAGCACAGAACCGAGTTTCGGCCCTGTCTGTCCCCCATCCAGGAG
TACCAGCTGACAGTCAGGGTTGGTCAAGGCCAAGTCCACAGAGCCAGGGTCGACTATGGCAGGGATCAGCCAGGTCACGCCAGCAGTGTTCGAGCAGCTCTGGGA
CTGAGGTCTTGTGAAGGCCACAGTGGCTTGGTTGTGGTATGGCCAGGAACTACAGGCCCACCCGATGCCCAGGGCTGGTGACACCCAGGCAGT
GGGGGCCCCACTTGGTAACAGAGTCATAGGGCCAGAAGCAGACCCACCTCGGCTGCCACAGCCAGCCTGGCTGTGCCCCTGCCACTGCTCCCA
CCATGGCCAATCAGAAGAGTCAGGGCTCCTGCGTTCTGCTGGCCAGTCAGTGACCACTACCAGCCCAGCCAGCTGAAACTCTCTGGGA
CCCAGCGATTGAGGGGTCAGGGTCAGGCATGAAAGGATGCTTTGGGCCTCTGGGCTGGGGCAGCGGATGGCTGTCCAGACAGTGGCCCCTTTTGTGG
GCAGCAAATTCTTGAGCCATGAAAGGATGCTTTTGGGCCTGGGGAGGCCAGCCGTGTCCAGGAGGATGGTGCGCTCAGCAGGTGAC
AGGGCCTCGGGGGTCTGTGTCAGGGTCAGGCTGGGAGCGCGCCGGCCCAGTGGCGGCGCCTGGAAAGTGTCTTG
GGCTAAGGACCACCCAGGCTGCACCTGGCACACACCCGCCAGCTGCCAGTGGTCTGTGAGGTTGCAGGCAGGGTGCGAATGGAA
GGGCACAGTGCCGGGCCACGCTGGACCAGAGAGAGAGCGCCGAGCGGCTGGCCGCGCCCTCCAGCCCTCGTCCCCAGAGACTGTCCGT
GCACAGTGCACGGAGCAGGCGGCCGTGAGAGCGGCCATCGTCGCTCTGCTGGACGGCTCCGAGCGGCGGTGGTGAGGCAGAGAACTTCCACAGGCCCGGC
GCTTCGTGGAGCAGCAGGTGCCGCGCCCTTCCGCCCTGAGCCACCATCCACGCCCTGACCACGCTGGCGCTGCAGTTTGG
TGGCCCGGCGAGCCAGGCGCTTTGCGCTGAGCCATCAATGCCATCGTGCCAGCCCGTGCGGGGCGCCGTGCTGGCACGCGAGCT
CCTTCTCGTCGTTTCCGCGACGTGTTTGGGCAGCCGGTCACGACAGTCTGACACAGTCTGCGTCACACGCTCAAGCGCAAGACAGTGTACCCA
GTCCTTCTGCTGCGTGTCACGGTGCTGGGCAGCATGGACAGTGCTCACCACGCTGCAGCCGGTGCGGGGCACTCCATGCGCCAGGAGCAGAAGGAC
TATGACAGCCTGGCCCACCCCGCGTTCCTGCGATGCTGTCTCAGCCGTCACCACGGCTGCTCACCCACGCTCCTCCACCGCAGCGACGCCCTGCAC
TGAGCCCACCCATGTTGCGGGTTCCCCATGGCTCTAAGCGCGGTTCCCCGGAGCCCCGGCCCTGCGCCAAGGTCTGACTCAGCCGCACCACTCCCCGAGCCCTGACCAATAAAGGCTTTGAACCATT
GCTGCCTGCTGCAGCCTGAGCTTCTGTGCCAGGAGAGACGCTCAAAGGTGCTTTGGCCAGGAGGGAACACTTCAGCTGTCGCTCGCCA
CCAGGGTCAATGGCCTGTCCCCGGGCCTGCCAGCCTGCTGACCTCTAGGACATCAACTCCAGGGTGCTGCCTGACCCGCCGTCAGACCCACCA |

TABLE 4C-continued

| SEQ ID NO | GENE NAME | SEQUENCE |
|---|---|---|
| | | GCCTTGATCAGCAAACTCTCCCTTCCAGCCCCAGCCCAGCCCCAAAGTGCTCTAAGAAGTGTCACCATGCTGAGGGTCTTCTGTGGGTGA CGCATGATTAACACTAGACGGGAGACAGCAGCAGTGCTGAGCCTGAACCAGTGCTGTTGTGTTCTGTGTGGAGATCTCAGTGAGTTTTGCTGTGTTCAGACCCC AGGGTCCTTCAGGCTCAGCTCAGAGACCCCACAGTGAACACTACCAGTTCGGCCACAGGCCTGAGGCTGCACCTGACCTGACAGGAGTGGCTTGGTGGCC ATCAGGGCACCACAGACACAGCTTGAACACTACCAGTTCGGCCACAGGCCTGAGGCATCAGCCGGCCATGCTTCCTCTGAGGG CTAGAGGAGGACTAGAACAGCCTGCCCCGGCCTCTCCACCAGGGTTCCTAGAATACCTCACCTAAGTACAGTGGACCAGGCTCAGCTGTCCTGATCCTCTGATCTCTGATAAGGATACAAGTCACCACAC TGGACTGGGGCTCAGCCTGCTCTAGAATACCTCACCTAAGTACAGTGGACCAGGCTCAGCCTGCTCAGCCTTGACCAGGCTCAGCCTGCTCAGCCTTGACCAGGCTCAGCCTATTCCGGATGAGCTCACCCGAGTC GGACCAGAGATCAGCCTATCCTGGGATAAGCTCACCCGAGTCACCCGAGTCGACCTGGATAAGCTCACCCGAGTCACCCGAGTCGACCTGGATAAGCTCACCCGAGTC |
| 256 | C21orf56 | GACACTTCCATGACTGCAGCTGACCAGTCCACCTGCCAGCGGTTGACAACTCCGCAGCGACCTCAGCGACCGAAGGGAGGGGGCCT CACCTGAGGGCAACAGCAGAACCCACCCACACCCTGGTCTTGCTTTACTCAGAACTCGAGGGTGTGAAAGGTGCCCGTGACCTCCCGCATCAGGG AGCTGGCCGCCCACCCTGACTCCCGGGGAGCAGCCCTCCATCTACCAGGCCATCTGAGCTGGCGCGCCTCACCTC CGCTCCCCGGGAGCCGGCTCAGGGTAGGACATGCCCCTGCTTCTTCAGGAGGCGCACCTGCTTCTCGCTCAGGACCGGCTCATCAGCTGCC CAGCCGCCGCAGCATCTGATTCTCCTTCAGGAGGCGCACCTGCTTCTTCAGGACCGGCTCAGAGACCCAGAGACCGGCTCATCAGCTGCC GCCTTCAGCCATGCGGGTGCCTCCTGTCCCTCACGGCCTTCCACGCCTTGATGCAGCCCAGCCTTGATGTCACTGCCCTAGTGATGAGGTGCCAGCACCCT AGAACAGCCCAGGACCGAGTTCCGTAGCCACCACCGAGTTCCGTAGCCACCACCGAGCGCCACGAGGCAGCCAGCCTTGATGTGAGCGGTGCACAGGCAGCACTCCCACATTATGACC GCCTGCCCCCGCGATGCTCATGCCCCGTTGAGGCAGTGAAGCTGGAGCTGCGCAGCTGCAGCTGGAGCGCGCCAGCCAGCCTCCACATTATGACC AGGGCCCCGAGAATGCCAAGGACATTAGCAGCTACGGACGTTAGGCACTGTACTGTACTCCAAGAGGGGCGTCCAAGCACTCCCCATTGA |
| 257 | C21orf57 | AGTGGAGGTTGCAGTGAGCCCCTCCTCCCCTCCGTTCCCCCATGCCCCCCCTTTCTCCTCCCACTCCCTCCCGAG GCCCCGCTTATTCTCCCGGCTGGGCCGTTCCGTTCGTGCACTCGCTCAGCTCAGCTCCGTTCAGGTTCTGTGAAGGTGCCCGGTCCCCCGCCTTCG GCTGAGCTAGAGCCGCGCGCGGGCCGCGGGCCGCTTCCCCCAAACCGTGTGGGAGGGCATCCCGAGGAGGCGACCCCAGAGAGTGGGGCG CGGACACCTTCCCTGGGAGGGCCAG |
| 258 | C21orf57 | CCTTCCAGATGTTCCAGAGAGGAGAAGGCGGTGCTGGACGAGCTGGGCGACGCACGGCTCAGCCCCGGCTGACCCGGGCCT CTTCGGAGGGAGCTGAGGGCGTTCCTTCTGAAAGCGGAACCTCCTTATTCTTCACGTTGCATGGGTATTTTCGTTATTGTAAATAAACGGTTCCGAGCC AATAACGAATGAACGAAAGCGTACGAGGGGAACCTCCTTATTCTTCACGTTGCATGGGTATTTTCGTTATTGTAAATAAACGGTTCCGAGCC GTGGCATCGAGAGGGCGTCTGGAGTTCAGGGACACGCGTCTGGAGTTCAGGGACACGCGTCTGGAGTTCAGGGACACGCTCCGCCCTTCAAGGG GGTCCCTGCCCGGACCCTGCCCGGACGAGGGCTCGAGGAGGAAGGGGCTCGGAGAGGAAGGGGCTCGGAGCCCGCAGCCGCGCCAGCCGCTGCCAGCCGCTGCAGCCGCTGCAGCCGCTGCAGCCGCTGTCCTCCGTAGAAAAGCTTGC GTCAGTATTTCCTGCTTTTACCTTCCTGAG |
| 259 | C21orf57 | CAGTATTTCCTGCTTTTACCTCCTGAGTATTGGAATATTCGAGTAAACCCTGGAGTTTCAGCGCCACGCCGCTCTTCATCAGGCAGCG CGTGCGGAGCGCCTGGTTCCCCGGAGCCGGGCCCCCGGACCCGCCGGTTGAGCCAGGCCGTGCCCGCCGCTGCCCAGCCGCTGCCCAGCCGCTGCCCAGCCGCTGCCCAGCCGCTGCCCAGCCGCTGCCCAGCCAGCACCTCA GAGACCTGCCTGGAGTTCTAAAGCTCGGGCTACTACAATTCTGCTCATCTGTTTGCTCTGTGAATGATTCAGGGACATGAAAATGCCTTCC CACTGACTTGCGTCTCCGTCTTAGCCTGGACTTGTCCCCTTGGGAACACGGGCCCAGGCCCCTCTGTTCCTGAAGT |

TABLE 4C-continued

| SEQ ID NO | GENE NAME | SEQUENCE |
|---|---|---|
| 260 | C21orf58 | ATGTCTCAGGGAAGAAGCAGGGGACCCTGAATAAAGTTTCCGTTTTCCTATTGTTAAAGTGATAGAGCATTATAGGACCAGAGAACAG<br>GTGTGTCTGTACACTGCTGTCCAGGTCCCCGGGGCAGGCTCCGTCGCCCCCCCCCGGGCGCCCCTGAGCCCGT<br>CTGCACACGGTGCGGGTCCCCGGGGCGCGCCCCTGAGCCCGTCTGCACACGGTGCGGGTCCCCGGGGCGCGCCCTGAGCCCGTCTGCA<br>CACGGTGCGGGTCCCCGGGGCGCGCCCTGAGCCCGTCTGTACACGGTGCGGGTCCCCGGGGCGCGCCCTGAGTCTCTACTAAAATACAAAAAT<br>TGCGGGTCCCCGGGGCGCGCCCTGAGCCCGTCTGTACACGGTGCGGGTCCCCGGGGCGCGCCCTGAGTCTCTACTAAAATACAAAAAT<br>TAGCCAGGCGTGGTTCAAGCCTGTAATCCCAGCTCCTTGGAGG |
| 261 | PRMT2 | CATACATGGTTATTAGAAAAGGCATTCATCCAAATGTGGTGCTCTGCTTCAGGAGGCCAAGGAGGAGGATTA<br>CTTGAGCCTAAGAGTTTGAGACCGTAGCCAGCTGGGCAACACAAGACCTTGCCTCTACAAAACTTAAAAACTAGCTGGTATGATGGTGCAC<br>ACCTGTAGTCCCAGCTACTTGGGAGGCCGAGGCGGGAGGATCGCTTGAGGTTCAGAGTTCGAGACCAGCCTGGCCAACATGATGAAACC<br>CCGTTCTACTAAAAATACAAAAATTAGCCGAGCGTGGTGGTGTGCGCCTGTAATCCCAGCTACTCAGGAGGCTGAGGCAGGAGAATCACT<br>TGAACCCGGGAGGCGGAGGTTGCCATGAGCCGAGATCACGTCACTGCACTCCAGCCTGGGTGACAGAGCACAAAGACAGGCATGACTTT<br>GTACTTAACTGTCTCAGCTTTGTAATCACTGGGGGCCCTGGGCGGGTCTGTGCGCCTGTGCCTGCTGGGCCTCGTGGCCTCGTGGCCCCG<br>AGGTGAGCAATGATGCAGAGGGCTCTGTGCGCCGGAAGGCGGCCACCCGCGGCGGATCCGGCAGCTCCCAGCGGTTCCAGCGCCCGCTCT<br>GGAAGGTGCGCAGCCCCCCACCGCGGAAGGCGGCCACCGCGGAAGGCGGCCACCGCGGAAGGCGACCCCTGCCGTCCCAGGAGGGGTCTGCGCCCGAGGGTCGCCCAGCGCGTCTGCAGGCAGGCGGAGACGGTGGGCCTAAGACGCGCCTTGCCGGGTTCCCGGTCCCTTCGAGGACTGT<br>GCTCGGGCAGCCAGGGGACGGGTTCAGGAGCGTCAGGAGCGTCCGTGAGCCTAAGACGCGCCTTGCCGGGTTCCCGGTCCCTTCCTGAGGACTGT<br>AGGTATTAGGAACCGTGCCACAAATCTGTAGGTTTTCCTCCAGGAGCTCCAAACCGGACGGTTTTCTCCGAGGACTGT<br>GTTCAGACAGATACTGGTTCCTTATCCGCAGTGTCGCGCGCTCGCAGTGTCGCAAGTGTCAGCATAAGCGCCGGAATTCGGAAAGCCCTG<br>CGTCCGTGACGACCCACTTGGAAGGAGTTGGGAGAGATTCCTTGCCCCACGCCGACGCTTCCCTGTGTCCTTCCGAGCCGCTCGGA<br>AAGCCCAGACCTAACCCGTCTCCTTTCTCCCCCGCGCTCCCATGCAGAACTCCGCCCGTTCCTGGAGGGAAGCCGCGAGGCGTGGGA<br>GAGGCACGTCTCCCGTGAGCAAAGAGTCTTCCTGCAGCGCGCCGGACGCGTGGGCCGACAGGGAGGCTGCCGGGGCAGGGCGGAGA<br>GGACCCGCCCACTCGGGTCCCAGCCCGTAACACTCAGGACCGCCCAGCCGGAGCTCCAGCCCGAGAGTCTCGACCCCTTCTGAGGACCCCTGGGGGA<br>GCTTATTGCGGTTCTTTTGCAAATACCCGCTGCCTGCCTTATTACTCTTAATTCTGCCCAGCTGTGTGAAATGCTTCAGGTGTGCGCCCTTGGGAGCCGAGGT<br>GAACGCATGCCTGTCCAGGAGCCTTTATTTACTCTTAATTCTGCCCACCACCCAGGGTGACAGCTGAGATGCGCCTTCTCAGGGTGGAGCCTTCCTCGTTTT<br>GTTACATAAATCATGGAAAATGCCTTCTGTCCAGCCCCTAACACTCAGGAAACAATAAGGACATACAAAAACATTAATAAAATAAAGGAACATAAGAAAACTTAAAAACATTAATAAATAAGGACATAGATTCTACTCCCAGGGTGGAGCCTTCCTCGTTTT<br>CCAGAGCTGCTTGTTGAGTCTTCTGAAGTTCATAAATGCCAACAATGCTCACCTTGGCATGCAGGTGGAGGCCAGGTGGAAGCTTT<br>TGTTTTCATTCATTCCTAGTGTTCATAAATGCCAACAATCCAAGTATTGCCATGTCAGCAACACATTCCTACTTTAAGTTTATGAAGTTAATTGAAGTAGTGGAGAACAAAA<br>AGCACAACAAACACAAAATCCAAGTATTGCCATGTCAGCAACACATTCCTACTTTAAGTTTATGAAGTTAATTGAAGTAGTGGAGAACAAAA<br>GTGGATGTGGGCAG |

Example 4

Fetal DNA Quantification Using Massively Parallel Shotgun Sequencing

In this example, fetal-specific DNA methylation markers were utilized to quantify the fraction of circulating cell-free fetal DNA in maternal plasma, using a massively parallel shotgun sequencing (MPSS) platform. For this Example, four types of DNA markers were assayed: 1) fetal-specific methylation markers which allowed selective enrichment and subsequent quantification of fetal DNA (e.g., SOX14, TBX), 2) Y-chromosome markers which confirmed fetal DNA quantification (for samples with a male fetus; e.g., SRY1, SRY2, UTY), 3) total markers avoid of restriction sites which were used to quantify total cell-free DNA, including fetal and maternal DNA (e.g., ALB, APOE, RNAseP, and 4) digestion control markers which monitored the completeness of restriction digestion and hence the accuracy of methylation marker-based fetal quantification (e.g., LDHA, POPS).

Methylation-Specific Restriction Digestion

Fetal methylation DNA markers were enriched by selective digestion of unmethylated maternal DNA, using methylation-sensitive restriction enzymes. Digestion was performed according to the parameters specified in Table 5 below.

TABLE 5

Methylation-specific restriction digestion

| Reagent | Concentration in reaction | Reagent Volume (μL) for n = 1 |
|---|---|---|
| H2O | N/A | 16.7 |
| 10× PCR Buffer (20 mM MgCl2, Roche) | 1 | 3.5 |
| 25 mM MgCl2 (Roche) | 2 | 2.8 |
| ExoI [U/μl] (NEB) | 0.2857 | 0.5 |
| HhaI [U/μl] (NEB) | 0.2857 | 0.5 |
| HpaII [U/μl] (NEB) | 1.4285 | 1 |
| DNA [μl] | | 10 |
| Final Vol: | | 35 |

Reaction conditions:

| Digestion | 41° C. 60' |
|---|---|
| Inactivation | 98° C. 10' |

Competitive PCR

The digested samples were amplified by PCR together with known copy numbers of competitor oligonucleotides. The competitors were synthetic oligonucleotides having the same nucleotide sequences as the target DNA, except for one base difference at the synthetic target site, which differentiated the target DNA from the competitor. Competitive PCR using target-specific primers allowed for independent quantification of each marker. Competitive PCR was performed according to the parameters specified in Table 6 below.

TABLE 6

PCR amplification

| Reagent | Concentration in reaction | Reagent Volume (μL) for n = 1 |
|---|---|---|
| Water, HPLC grade | N/A | 6.64 |
| 10× PCR Buffer (20 mM MgCL2, Roche) | 1× (2 mM MgCl2) | 1.5 |
| 25 mM MgCl2 (Roche) | 2 mM | 1.2 |
| dNTPs (25 mM, Roche) | 500 μM | 1 |
| PCR primer (1 uM each) | 0.1 μM | 5 |
| FASTSTART PCR Enzyme (5 U/μl, Roche) | 0.1 U/μl | 1 |
| Competitor MIX (8000/800 c/ul)(1:0.1 c/ul) | | 0.38 |
| DNA (from restriction digestion) | | 35 |
| Total | | 50 |

PCR Cycling conditions:

| 95° C., 5 min | |
|---|---|
| 95° C., 45 sec | 35 cycles |
| 60° C., 30 sec | |
| 72° C., 45 sec | |
| 72° C., 3 min | |
| 4° C. hold | |

Adaptor Oligonucleotide Ligation

Illumina adaptor oligonucleotides (TRUSEQ adaptors) were ligated to the amplicons generated in the competitive PCR described above. The adaptor-ligated amplicons were subsequently sequenced using the Illumina HISEQ 2000 platform (Illumina, San Diego Calif.). Two different ligation-based approaches were used to flank the amplicons with the adaptors. The ligation procedure was optimized to maximize the amount of double ligation products (i.e., adaptor oligonucleotides ligated to both ends of the amplicon), and minimize single ligation and/or empty ligation (i.e., two adaptor oligonucleotides ligate to each other without amplicon insertion).

Direct Ligation of Adaptors

Figure 21:
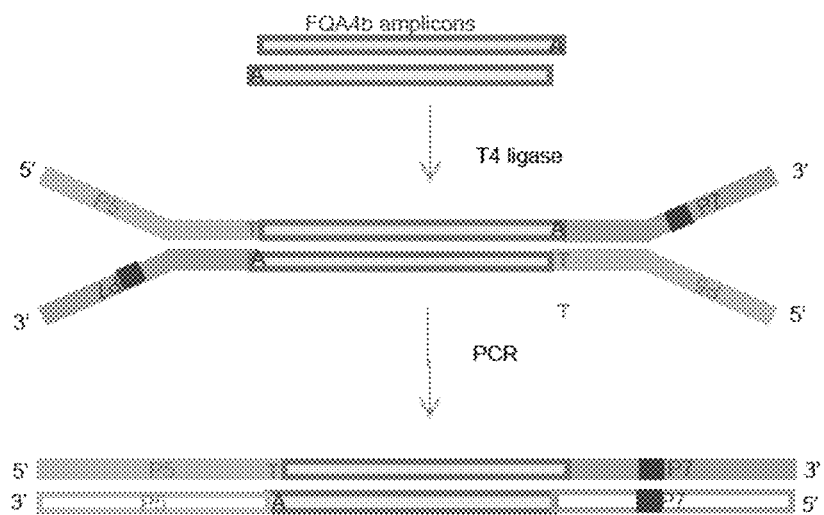
FIG. 21 shows a scheme for ligating a PCR amplicon with Illumina sequencing adaptors.
Figure 22:
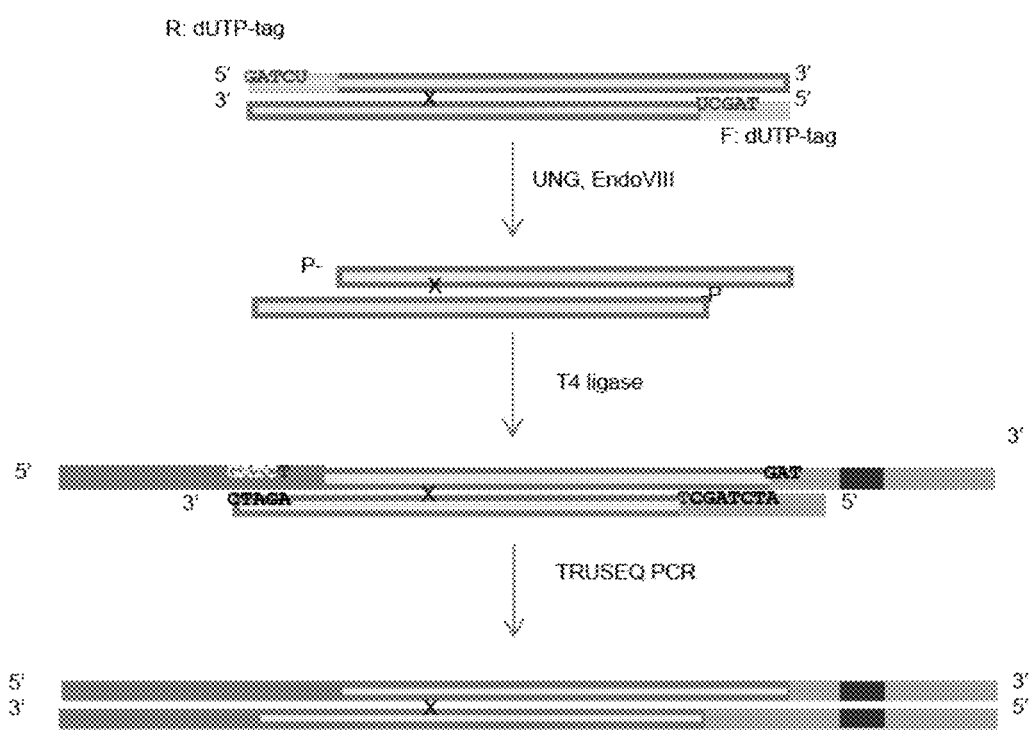
FIG. 22 shows a modified ligation scheme.

To render the PCR amplicons compatible for MPSS, the amplicons (which had 3' adenine (A) overhangs generated by Taq polymerase during the PCR reaction) were ligated to adaptor oligonucleotides having 3' thymine (T) overhangs (see FIG. 21). Prior to the ligation reaction, AMPURE XP beads at 2-fold volume of PCR reaction volume were used to remove single-stranded primers and amplicons generated by asymmetric PCR. Cleaned amplicons were quantified by Agilent Bioanalyzer and mixed with Illumina TRUSEQ library adaptors at an 8:1 ratio. 2 μL of T4 DNA ligase (Enzymatics) and 17.5 μL of 2× ligase buffer (Enzymatics) were added, and the ligation reaction was carried out at room temperature for 15 minutes.

Unidirectional Adaptor Ligation

In some cases, a modified protocol to improve ligation efficiency and to ensure unidirectional ligation was used. Single base overhang ligation can be less efficient compared to ligation of longer cohesive ends. Additionally, using single base overhang ligation, PCR amplicons can ligate with Illumina TRUSEQ adaptors in either orientation such that, when the ligated product were sequenced, only about half of the sequence reads covered the target sites for copy number calculation. Modifications of the ligation procedure were thus developed to overcome such limitations. First, tag sequences that were 5 nucleotides long were designed to replace the original tag sequence (10 nucleotides long) in the PCR primers (for the competitive PCR above; provided in Table 7 below). The tags were of different sequences for reverse or forward PCR primers and each had a deoxyuridine at the junction between tag sequence and target-specific sequence. The modified primers were used at equal molar ratio in the competitive PCR reaction above.

After PCR amplification, the tags were cleaved from the amplicons by uracil N-glycosylase (UNG; UDG) and EndoVIII digestion, creating a 5 base overhang that selectively ligated the PCR amplicon to universal or indexed adaptors (provided in Table 7 below) with high efficiency (see FIG. 22). Specifically, 1 µL UDG (5 U/µL, NEB) and 5 µL EndoVIII (10 U/µL, NEB) were added to each reaction and incubated at 37° C. for 30 minutes. The reaction was stopped by heating at 95° C. for 10 minutes to inactivate UDG, after which it was gradually cooled to 25° C. The amplicons were cleaned by AMPURE XP beads prior to the ligation reaction.

TABLE 7

Primer and adaptor sequences

| Target | Forward_Primer (SEQ ID NOS 350-362) | Reverse_Primer (SEQ ID NOS 363-375) |
|---|---|---|
| ALB | TAGCUGCGTAGCAACCTGTTACATATT | GATCUATACTGAGCAAAGGCAATCAAC |
| APOE | TAGCUCAGTTTCTCCTTCCCCAGAC | GATCUGAATGTGACCAGCAACGCAG |
| RNAseP | TAGCUGGTCAGCTCTTCCCTTCATC | GATCUCCTCCCACATGTAATGTGTTG |
| CDC42EP1 | TAGCUAGCTGGTGCGGAGGGTGGG | GATCUATGGGGGAGATGGCCGGTGGA |
| LDHA | TAGCUGGCCTTTGCAACAAGGATCAC | GATCUCGCAATACTAGAAACCAGGGC |
| MGC15523 | TAGCUTCTGGTGACCCCCGCGCTTC | GATCUCATCTCTGGGTGCGCCTTG |
| POP5 | TAGCUCCCTCCACATCCCGCCATC | GATCUCAGCCGCCTGCTCCATCG |
| SOX14 | TAGCUACGGAATCCCGGCTCTGTG | GATCUCCTTCCTAGTGTGAGAACCG |
| SPN | TAGCUGGCCCTGCTGGCGGTCATA | GATCUTGCTCAGCACGAGGGCCCCA |
| SRY1 | TAGCUAGCAACGGGACCGCTACAG | GATCUTCTAGGTAGGTCTTTGTAGCC |
| SRY2 | TAGCUTAAGTTTCGAACTCTGGCACC | GATCUGAAGCATATGATTGCATTGTCAA |
| TBX3 | TAGCUCTCCTCTTTGTCTCTGCGTG | GATCUTTAATCACCCAGCGCATGGC |
| UTY | TAGCUTGATGCCCGATGCCGCCCTT | GATCUGTCTGTGCTGGGTGTTTTGC |

Adaptors (SEQ ID NOS 376-378)

| | |
|---|---|
| Universal_adaptor | AATGATACGGCGACCACCGAGATCTACACTCTTTCCCTACACGACGCTCTTCCGATCT |
| Index_linker | GCTCTTCCGATCTATAGCT |
| Index_adaptor | 5'phos/<br>GATCGGAAGAGCACACGTCTGAACTCCAGTCAC<u>AGTCAA</u>CAATCTCGTATGCCGTCTTCTGCTTG |

TABLE 8

PCR amplification of ligation products

| Reagent | Reagent Volume (µL) for n = 1 |
|---|---|
| Water, HPLC grade | 11 |
| TRUSEQ PCR master mix | 20 |
| TRUSEQ PCR primers | 4 |
| Ligation product | 5 |
| Total | 40 |

TABLE 8-continued

PCR amplification of ligation products

| Reagent | Reagent Volume (µL) for n = 1 |
|---|---|
| PCR Cycling conditions | |
| 98° C., 5 min | |
| 98° C., 10 sec | 10 cycles |
| 65° C., 30 sec | |
| 72° C., 30 sec | |
| 72° C., 3 min | |
| 4° C. hold | |

Pre-annealed index adaptor and index-linker was prepared by mixing at equal molar ratio, heating to 95° C. for 5 minutes, and gradually cooled to 25° C. Universal adaptor and pre-annealed index adaptor at equal molar ratio were mixed with the UDG/EndoVIII-digested PCR amplicons (having 5 nucleotide overhangs). The ratio of adaptor to amplicon varied from 8:1 to 2:1. 2 µL of T4 DNA ligase (Enzymatics) and 17.5 µL of 2× ligase buffer (Enzymatics) were added, and the ligation reaction was carried out at room temperature for 15 minutes.

For both ligation approaches, the ligated product (5 µL) was amplified using Illumina TRUSEQ PCR mixture and primers as specified in Table 8 below. Amplified libraries were purified using AMPURE XP beads to remove free primers/adaptors and DNA fragments of smaller size.

Amplified libraries were retained on an Illumina flow cell and bridge amplified to generate clusters for subsequent sequencing on Illumina's HISEQ 2000. Use of indexed adaptors allowed for sequencing of multiple samples in a single lane on the flow cell.

Nucleotide Sequence Read Analysis and Fetal DNA Quantification

Nucleotide sequence reads were analyzed and used to calculate copy number of individual markers and fetal percentage. 50 base pair (bp) nucleotide sequence reads were uniquely aligned to expected chromosome positions, allowing up to 5 mismatches outside the target sites/synthetic target sites. Reads having quality score greater than 13 at the target site with expected target DNA or competitor alleles were used to calculate the copy number of each marker. Specifically, the following formula was used:

$$\text{Copy}(DNA) = \text{Copy}(comp) \times \frac{\text{Read Counts(expected } DNA \text{ allele)}}{\text{Read Counts(expected } comp \text{ allele)}}$$

Fetal DNA, Y-chromosome DNA and total DNA copy numbers were represented by the mean value of methylation markers, Y-markers and total DNA markers, respectively. Fetal percentage was calculated according to the following formulas:

$$\text{Fetal Protection(methyl)} = \frac{\text{mean copy number (methylation markers)}}{\text{mean copy number(total markers)}}$$

and $$\text{Fetal Protection}(Y) = 2 \times \frac{\text{mean copy number}(Y \text{ markers})}{\text{mean copy number(total markers)}}$$

Digestion efficiency was calculated by $$\text{digestion efficiency} = 1 - \frac{\text{mean copy number(digestion markers)}}{\text{mean copy number(total markers)}}$$

Results

Figure 23:
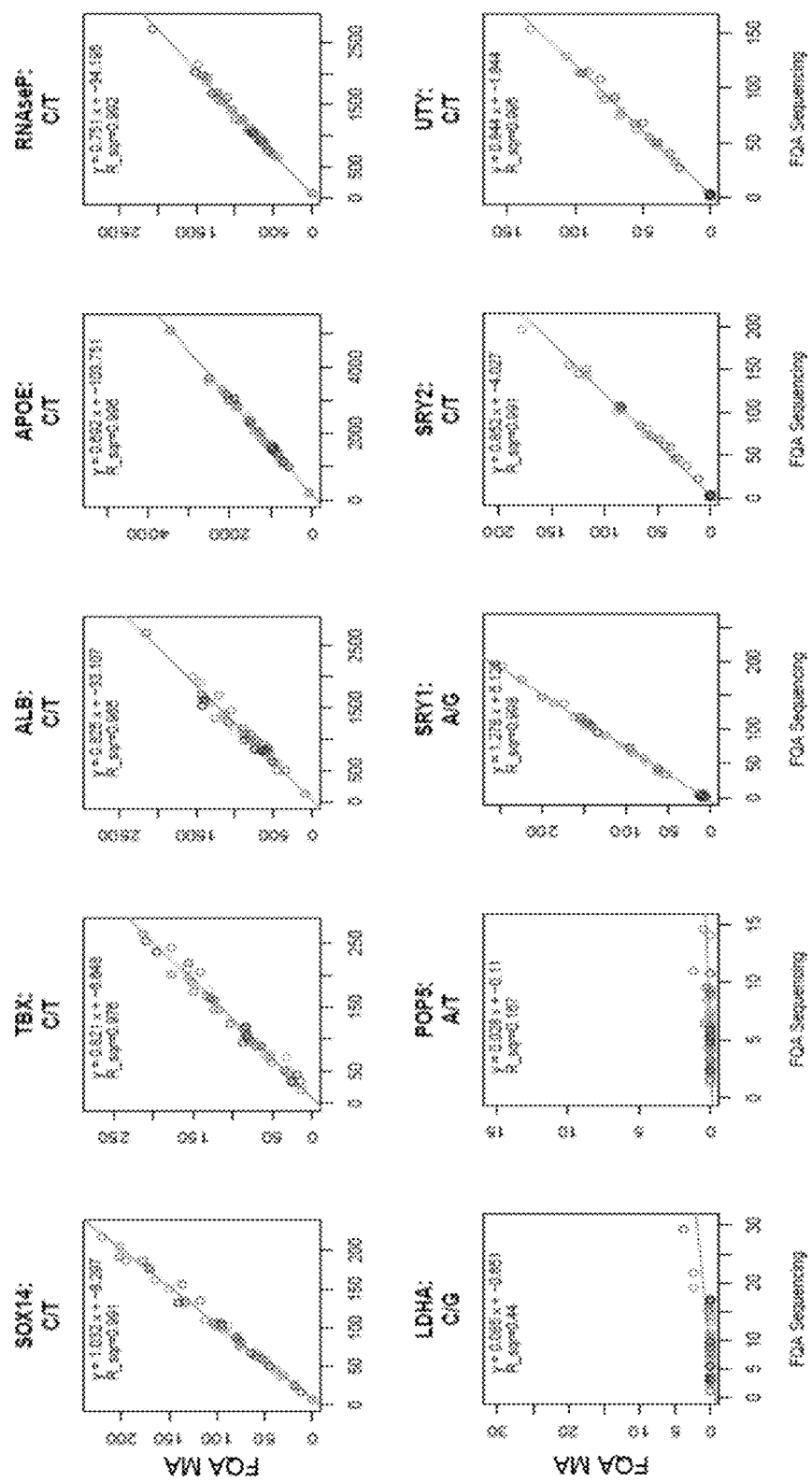
FIG. 23 shows a comparison of copy numbers of individual markers determined by a fetal quantification assay using MPSS (FQA Sequencing; x-axis) with those obtained by a fetal quantification assay using MASSARRAY (FQA MA; y-axis). The results from both methods were highly correlated ($R^2 > 0.97$). In some cases, platform-specific allele bias resulted in slight copy number differences and slopes of the linear fit which deviated from 1.
Figure 24:
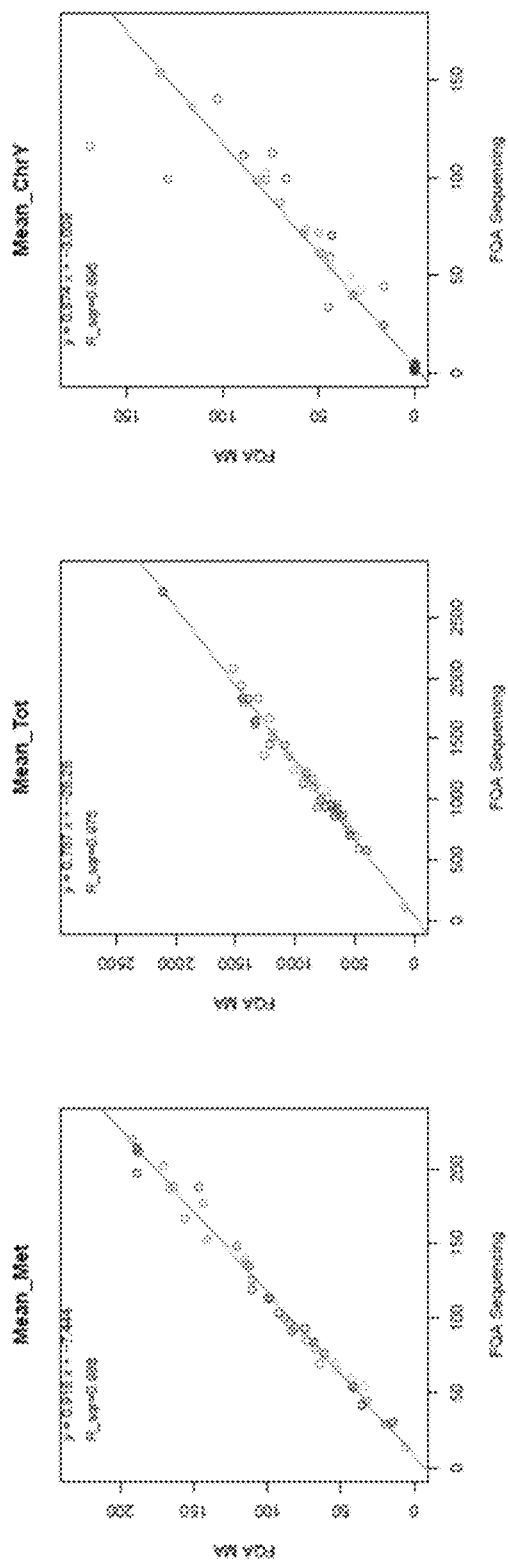
FIG. 24 shows a comparison of mean copy numbers for each of the marker groups determined by a fetal quantification assay using MPSS (FQA Sequencing; x-axis) with those obtained by a fetal quantification assay using MASSARRAY (FQA MA; y-axis).
Figure 25:
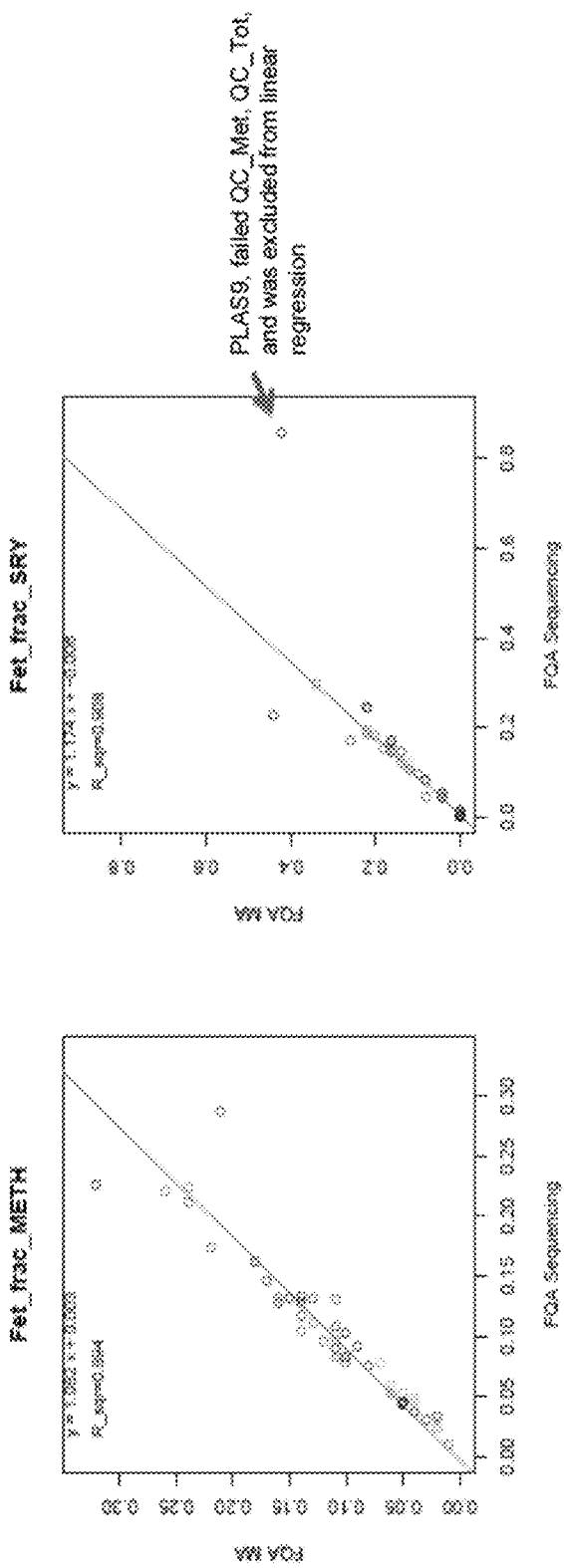
FIG. 25 shows a comparison of fetal fractions derived from either methylation (left) or Y-chromosome markers determined by a fetal quantification assay using MPSS (FQA Sequencing; x-axis) with those obtained by a fetal quantification assay using MASSARRAY (FQA MA; y-axis).

The fetal DNA quantification method using MPSS described in this Example was applied to ccfDNA extracted from 48 plasma samples from pregnant women. The results were compared to those obtained from another method that used mass spectrometry (e.g., MASSARRAY) as a detection method instead of MPSS. The results from both methods were highly correlated (see FIGS. 23 and 24). With exception of digestion markers (LDHA and POPS, which were detected at higher levels by the MPSS method), the $R^2$ values were in the range of 0.965-0.998. The fetal fractions derived from methylation markers also were highly correlated between MPSS and mass spectrometry methods (see FIG. 25).

Example 5

SNP Allele Frequency Based Method for Fetal Fraction Quantification

In this example, single nucleotide polymorphism (SNP) markers were utilized to detect and quantify circulating cell-free (CCF) fetal DNA in maternal plasma (i.e. fetal fraction). In some cases, fetal fraction was determined by measuring single nucleotide polymorphism alleles using a single tube multiplex PCR for amplicon sequencing via massively parallel shotgun sequencing (MPSS). Advantages of this methodology include, for example: 1) the ability to detect CCF fraction of DNA from both male and female fetuses without prior knowledge of maternal or paternal SNP genotypes; 2) a simplified workflow that generates MPSS ready products without the need for traditional library generation and 3) an ability to perform MPSS fetal fraction quantification on samples multiplexed with genomic libraries on the same flow cell lane.

Materials and Methods

CCF DNA was extracted from 4 mL plasma from 46 pregnant women using QIAAMP Circulating Nucleic Acid kit in an elution volume of 55 μl. DNA also was extracted from maternal buffy coat samples for confirmation of maternal genotypes. Gestational age at collection ranged from 10-17 weeks. Maternal age ranged from 18-42 years. Ethnic background of samples included African American, Asian, Caucasian and Hispanic ethnicities. 15 μl of CCF DNA underwent PCR for each SNP panel using a single tube multiplex of forward and reverse PCR primers that included adapter sequences to allow secondary amplification with universal PCR primers designed to incorporate index tags. Amplicon libraries with index tags were clustered on the cBOT and sequenced on the HiSeq 2000 for 36 cycles or 27 cycles to generate amplicon sequence reads and 7 cycles to determine the index tag sequence. Reads were aligned to the human genome (hg19) and matched read counts for expected SNP alleles were used to calculate the allele ratio of each SNP within each CCF DNA. 15 μl of CCF DNA also was used for quantification of fetal fraction by fetal specific methylation patterns for comparison with SNP based quantification.

Detection of Paternally Inherited Alleles

Figure 27:
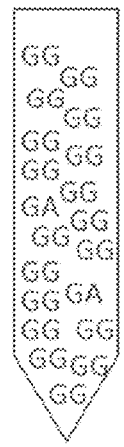
FIG. 27 illustrates a possible distribution of maternal and paternal alleles.

CCF fetal DNA in maternal plasma contains both maternally and paternally inherited DNA (e.g., SNP alleles). Detection of paternal SNP alleles not present in the maternal genome can allow confirmation of the presence of fetal DNA. Additionally, quantification of paternal:maternal SNP allele ratios can provide for a determination of fetal DNA fraction in maternal plasma. The likelihood of detecting a paternally inherited allele at a single locus is dependent upon allele frequency and individual inheritance patterns. FIG. 26, for example, provides a summary of expected genotypes and the associated population frequency of each genotype based a SNP having a minor allele population frequency of 0.4. A SNP with a high minor allele frequency may increase the chance that paternal and maternal alleles will differ at a given SNP locus. Provided enough SNPs are interrogated, a high probability can be established that the fetus will contain some paternal alleles that differ from the maternal alleles. Thus, use of multiple SNP alleles increases the likelihood of informative fetal and maternal genotype combinations. Often, no prior knowledge of the paternal genotypes is required because paternal alleles can be inferred by the presence of non-maternal alleles in the maternal/fetal cell free DNA mixture. FIGS. 27 and 28 show how fetal fraction can be calculated using SNP allele frequency.

SNP Panels

High minor allele frequency SNPs that contain only 2 known alleles were identified. Two panels of SNPs were generated: a 67 SNP panel (SNP panel 1) and an 86 SNP panel (SNP panel 2). Individual SNP identifiers for each panel are provided in Table 9A and Table 10A below. Tables 9B and 10B include chromosome identity for each SNP.

TABLE 9A

| SNP Panel 1 |
| --- |
| rs10413687 |
| rs10949838 |
| rs1115649 |
| rs11207002 |
| rs11632601 |
| rs11971741 |
| rs12660563 |
| rs13155942 |
| rs1444647 |
| rs1572801 |
| rs17773922 |
| rs1797700 |
| rs1921681 |
| rs1958312 |
| rs196008 |
| rs2001778 |
| rs2323659 |
| rs2427099 |
| rs243992 |
| rs251344 |
| rs254264 |
| rs2827530 |
| rs290387 |
| rs321949 |
| rs348971 |
| rs390316 |
| rs3944117 |
| rs425002 |

TABLE 9A-continued

SNP Panel 1 rs432586
rs444016
rs4453265
rs447247
rs4745577
rs484312
rs499946
rs500090
rs500399
rs505349
rs505662
rs516084
rs517316
rs517914
rs522810
rs531423
rs537330
rs539344
rs551372
rs567681
rs585487
rs600933
rs619208
rs622994
rs639298
rs642449
rs6700732
rs677866
rs683922
rs686851
rs6941942
rs7045684
rs7176924
rs7525374
rs870429
rs949312
rs9563831
rs970022
rs985462

TABLE 9B

SNP Panel 1

| SNP_ID | Chromosome |
| --- | --- |
| rs10413687 | chr19 |
| rs10949838 | chr7 |
| rs1115649 | chr21 |
| rs11207002 | chr1 |
| rs11632601 | chr15 |
| rs11971741 | chr7 |
| rs12660563 | chr6 |
| rs13155942 | chr5 |
| rs1444647 | chr12 |
| rs1572801 | chr6 |
| rs17773922 | chr19 |
| rs1797700 | chr12 |
| rs1921681 | chr4 |
| rs1958312 | chr14 |
| rs196008 | chr16 |
| rs2001778 | chr11 |
| rs2323659 | chr17 |
| rs2427099 | chr20 |
| rs243992 | chr4 |
| rs251344 | chr5 |
| rs254264 | chr19 |
| rs2827530 | chr21 |
| rs290387 | chr20 |
| rs321949 | chr19 |
| rs348971 | chr2 |
| rs390316 | chr14 |
| rs3944117 | chr7 |
| rs425002 | chr4 |
| rs432586 | chr12 |

TABLE 9B-continued

SNP Panel 1

| SNP_ID | Chromosome |
| --- | --- |
| rs444016 | chr5 |
| rs4453265 | chr11 |
| rs447247 | chr6 |
| rs4745577 | chr9 |
| rs484312 | chr13 |
| rs499946 | chr7 |
| rs500090 | chr11 |
| rs500399 | chr10 |
| rs505349 | chr11 |
| rs505662 | chr6 |
| rs516084 | chr1 |
| rs517316 | chr1 |
| rs517914 | chr4 |
| rs522810 | chr13 |
| rs531423 | chr1 |
| rs537330 | chr8 |
| rs539344 | chr19 |
| rs551372 | chr11 |
| rs567681 | chr11 |
| rs585487 | chr19 |
| rs600933 | chr1 |
| rs619208 | chr11 |
| rs622994 | chr13 |
| rs639298 | chr1 |
| rs642449 | chr1 |
| rs6700732 | chr1 |
| rs677866 | chr13 |
| rs683922 | chr15 |
| rs686851 | chr6 |
| rs6941942 | chr6 |
| rs7045684 | chr9 |
| rs7176924 | chr15 |
| rs7525374 | chr1 |
| rs870429 | chr3 |
| rs949312 | chr18 |
| rs9563831 | chr13 |
| rs970022 | chr4 |
| rs985462 | chr10 |

TABLE 10A

SNP Panel 2 rs1005241
rs1006101
rs10745725
rs10776856
rs10790342
rs11076499
rs11103233
rs11133637
rs11974817
rs12102203
rs12261
rs12460763
rs12543040
rs12695642
rs13137088
rs13139573
rs1327501
rs13438255
rs1360258
rs1421062
rs1432515
rs1452396
rs1518040
rs16853186
rs1712497
rs1792205
rs1863452
rs1991899
rs2022958
rs2099875

TABLE 10A-continued

SNP Panel 2 rs2108825
rs2132237
rs2195979
rs2248173
rs2250246
rs2268697
rs2270893
rs244887
rs2736966
rs2851428
rs2906237
rs2929724
rs3742257
rs3764584
rs3814332
rs4131376
rs4363444
rs4461567
rs4467511
rs4559013
rs4714802
rs4775899
rs4817609
rs488446
rs4950877
rs530913
rs6020434
rs6442703
rs6487229
rs6537064
rs6654065
rs6576533
rs6661105
rs669161
rs6703320
rs675828
rs6814242
rs6989344
rs7120590
rs7131676
rs7214164
rs747583
rs768255
rs768708
rs7828904
rs7899772
rs7900911
rs7925270
rs7975781
rs8111589
rs849084
rs873870
rs9386151
rs9504197
rs9690525
rs9909561

TABLE 10B

SNP Panel 2

| SNP_ID | Chromosome |
|---|---|
| rs1518040 | chr1 |
| rs16853186 | chr1 |
| rs2268697 | chr1 |
| rs3814332 | chr1 |
| rs4363444 | chr1 |
| rs4950877 | chr1 |
| rs6661105 | chr1 |
| rs6703320 | chr1 |
| rs1432515 | chr2 |
| rs12695642 | chr3 |
| rs2132237 | chr3 |
| rs6442703 | chr3 |

TABLE 10B-continued

SNP Panel 2

| SNP_ID | Chromosome |
|---|---|
| rs13137088 | chr4 |
| rs13139573 | chr4 |
| rs1452396 | chr4 |
| rs1712497 | chr4 |
| rs4461567 | chr4 |
| rs4467511 | chr4 |
| rs6537064 | chr4 |
| rs6814242 | chr4 |
| rs747583 | chr4 |
| rs1006101 | chr5 |
| rs11133637 | chr5 |
| rs2929724 | chr5 |
| rs4559013 | chr5 |
| rs4714802 | chr6 |
| rs669161 | chr6 |
| rs9386151 | chr6 |
| rs9504197 | chr6 |
| rs11974817 | chr7 |
| rs13438255 | chr7 |
| rs2736966 | chr7 |
| rs2906237 | chr7 |
| rs4131376 | chr7 |
| rs849084 | chr7 |
| rs9690525 | chr7 |
| rs12543040 | chr8 |
| rs1863452 | chr8 |
| rs2022958 | chr8 |
| rs6989344 | chr8 |
| rs7828904 | chr8 |
| rs10776856 | chr9 |
| rs11103233 | chr9 |
| rs1327501 | chr9 |
| rs1360258 | chr9 |
| rs1421062 | chr10 |
| rs2248173 | chr10 |
| rs768255 | chr10 |
| rs7899772 | chr10 |
| rs7900911 | chr10 |
| rs10790342 | chr11 |
| rs1792205 | chr11 |
| rs1991899 | chr11 |
| rs2099875 | chr11 |
| rs2851428 | chr11 |
| rs488446 | chr11 |
| rs7120590 | chr11 |
| rs7131676 | chr11 |
| rs768708 | chr11 |
| rs7925270 | chr11 |
| rs10745725 | chr12 |
| rs2250246 | chr12 |
| rs2270893 | chr12 |
| rs6487229 | chr12 |
| rs7975781 | chr12 |
| rs12261 | chr13 |
| rs3742257 | chr13 |
| rs675828 | chr13 |
| rs12102203 | chr15 |
| rs4775899 | chr15 |
| rs6576533 | chr15 |
| rs11076499 | chr16 |
| rs244887 | chr16 |
| rs654065 | chr16 |
| rs7214164 | chr17 |
| rs9909561 | chr17 |
| rs12460763 | chr19 |
| rs2108825 | chr19 |
| rs2195979 | chr19 |
| rs3764584 | chr19 |
| rs8111589 | chr19 |
| rs873870 | chr19 |
| rs530913 | chr20 |
| rs6020434 | chr20 |
| rs4817609 | chr21 |
| rs1005241 | chr22 |

Generation of Illumina Sequencer Ready Amplicons

For SNP panel 1, PCR primers were designed to amplify the 67 targeted SNPs plus a flanking region of 35 base pairs (bp) surrounding the SNP site. The 67 targeted regions were amplified in a single multiplex reaction. For SNP panel 2, PCR primers were designed to amplify the 86 targeted SNPs plus a flanking region of 26 base pairs (bp) surrounding the SNP site. The 86 targeted regions were amplified in a single multiplex reaction.

Figure 29:
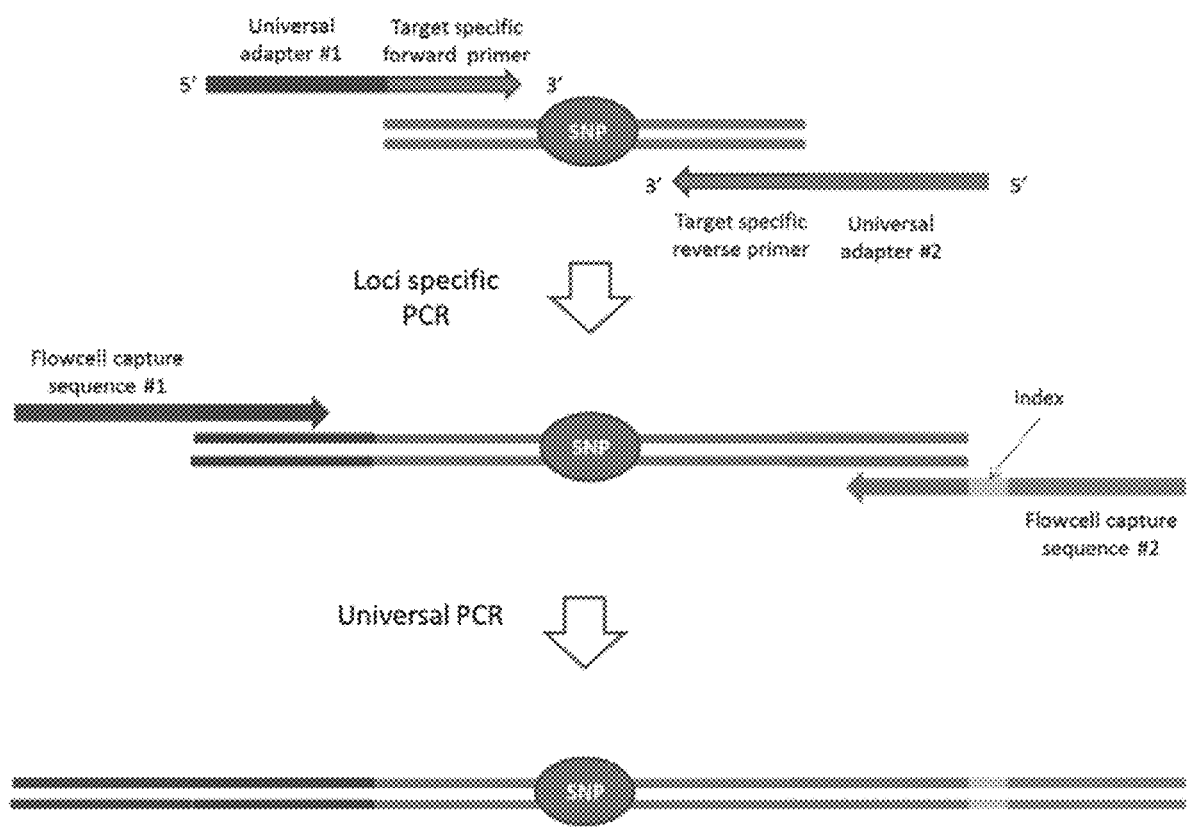
FIG. 29 illustrates a scheme for multiplexed amplicon library generation and sequencing.

PCR primers were modified such that Illumina sequencing adapters could be added via universal tag sequences incorporated onto the 5' end of the SNP-specific PCR primers. Illumina tags were added using two separate PCR reactions (see FIG. 29 and Table 11 below): 1) a loci-specific PCR which incorporated a section of the Illumina sequencing adapters followed by 2) a universal PCR whose primers annealed to the tags in the loci-specific PCR to complete the addition of the adapters whilst allowing the addition of a sample specific index sequence via the reverse primer in the universal PCR. A 3$^{rd}$ single cycle PCR was performed to remove heteroduplex secondary structure that can arise in the amplicons during the universal PCR stage due to cross-annealing of shared adapter sequences between different amplicons in the same multiplex. Loci-specific PCR and universal PCR were performed under standard conditions using primers synthesized from Integrated DNA Technologies (IDT; Coralville, Iowa) with no special modifications.

and variant alleles at target SNP position. The frequency of each SNP allele was determined by counting the number of reads having the allele of interest and dividing it by the total number of reads for each SNP locus (i.e., (# reads allele 1)/(# reads allele 1+# reads allele 2)). Based on the frequency value generated from this data, the sequenced genotypes were assigned as Type 0 non-informative genotypes, Type 1 informative genotypes or Type 2 informative genotypes. A Type 0 non-informative genotype is a fetal genotype that cannot be distinguished from the maternal genotype because the fetus has the same genotype as the mother (e.g., mother is "Aa" and fetus is "Aa"). A Type I informative genotype is the situation where the mother is homozygous (AA) and the fetus is heterozygous (Aa). This genotype is informative because allele "a" is from the father. The frequency of a Type 1 informative allele can be indicative of the percentage fetal DNA in the mixture. A Type 2 informative genotype is the situation where the mother is heterozygous (Aa) and the fetus is homozygous (AA). The genotype is informative because the frequency of the maternal allele "a" will deviate from the expected Mendelian frequency of 0.5 when there is fetal DNA contributing additional "A" alleles. This deviation in value from 0.5 can be used to compute the fetal fraction.

Allele frequencies for each of the SNPs was calculated for each sample based on the number of reads containing each allele, as described above. Variation of expected allele

TABLE 11

Sequencing adaptors, loci specific PCR primer tags and universal PCR primer tags
(SEQ ID NOS 379-386)

| Name | Sequence |
|---|---|
| TRUSEQ P5 Adapter | 5'-AATGATACGGCGACCACCGAGATCTACACTCTTTCCCTACACGA CGCTCTTCCGATCT- 3' |
| TRUSEQ Read 1 sequencing primer | 5'-ACACTCTTTCCCTACACGACGCTCTTCCGATCT-3' |
| TRUSEQ P7 adapter, Index 13 | GATCGGAAGAGCACACGTCTGAACTCCAGTCAC<u>AGTCAA</u>ATCTC GTATGCCGTCTTCTGCTTG-3' |
| TRUSEQ index read primer | 5'-GATCGGAAGAGCACACGTCTGAACTCCAGTCAC-3' |
| Loci PCR forward tag | 5'-TCTTTCCCTACACGACGCTCTTCCGATCT-3' |
| Loci PCR reverse tag | 5'-GTGACTGGAGTTCAGACGTGTGCTCTTCCGATCT-3' |
| UNIV PCR forward primer | 5'-AATGATACGGCGACCACCGAGATCTACACTCTTTCCCTACACGA CGCTC-3' |
| UNIV PCR reverse index 13 primer | 5'-CAAGCAGAAGACGGCATACGAGAT<u>TTGAC</u>TGTGACTGGAGTTCA GACGTG-3' |

Amplicon Sequencing by Numina NGS

Universal PCR products were quantified using standard DNA fragment analysis methods such as Caliper LabChip GX or Agilent Bioanalyzer. The sequencer-ready amplicons from up to 12 samples were pooled and sequenced on an Illumina HISEQ apparatus. For SNP panel 1, 36 cycles were used to sequence the target SNP plus the 35 bp flanking region. For SNP panel 2, 27 cycles were used to sequence the target SNP plus the 26 bp flanking region. Samples were de-mulitplexed using a 6 bp index identifier incorporated at the universal PCR stage.

Assignment of Informative Alleles and Fetal Fraction Determination

Reads were aligned to the human genome (hg19) with up to 3 mismatches in each read to allow for sequencing error frequency could be due to the presence of fetal DNA with a different paternal allele or could be due to mis-incorporated sequences by the Illumina Sequencer (e.g., background noise). In some cases, the amount of background noise associated with each particular SNP amplicon was determined to establish a dynamic cutoff value for each SNP. Maternal DNA (i.e. buffy coat) samples were sequenced and the deviations from the expected Mendelian ratios of 1 for homozygotes and 0.5 for heterozygotes were observed. From these values a median-adjusted deviation (MAD score) was identified for each SNP assay. In some cases, a genotype was identified as being a Type I informative genotype when the paternal allele frequency measured was greater than 3×MAD score. In some cases, multiple Type 1 informative genotypes were identified and an average allele frequency was determined. Fetal fraction was calculated by multiplying the average Type 1 informative allele frequency by 2. For example, an average informative allele frequency of 4.15% indicated a fetal fraction of 8.3%. Fetal Fraction also can be calculated from Type 2 informative genotypes by determining maternal allele "a" frequencies deviating from 0.5 by greater than 3×MAD, for example. Fetal fraction can be identified by multiplying this deviation by 2.

Figure 30:
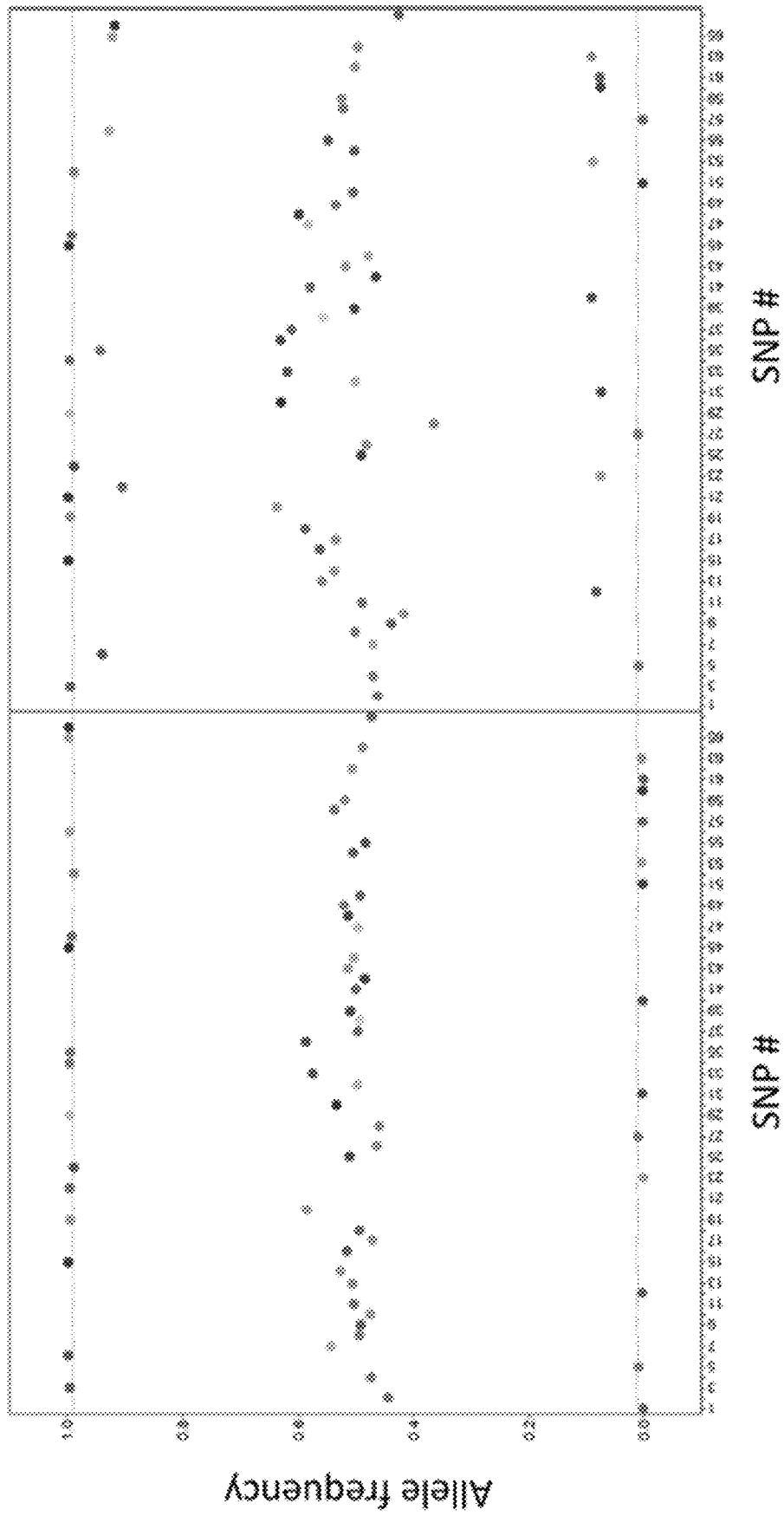
FIG. 30 shows allele frequencies per SNP for a particular sample.
Figure 31:
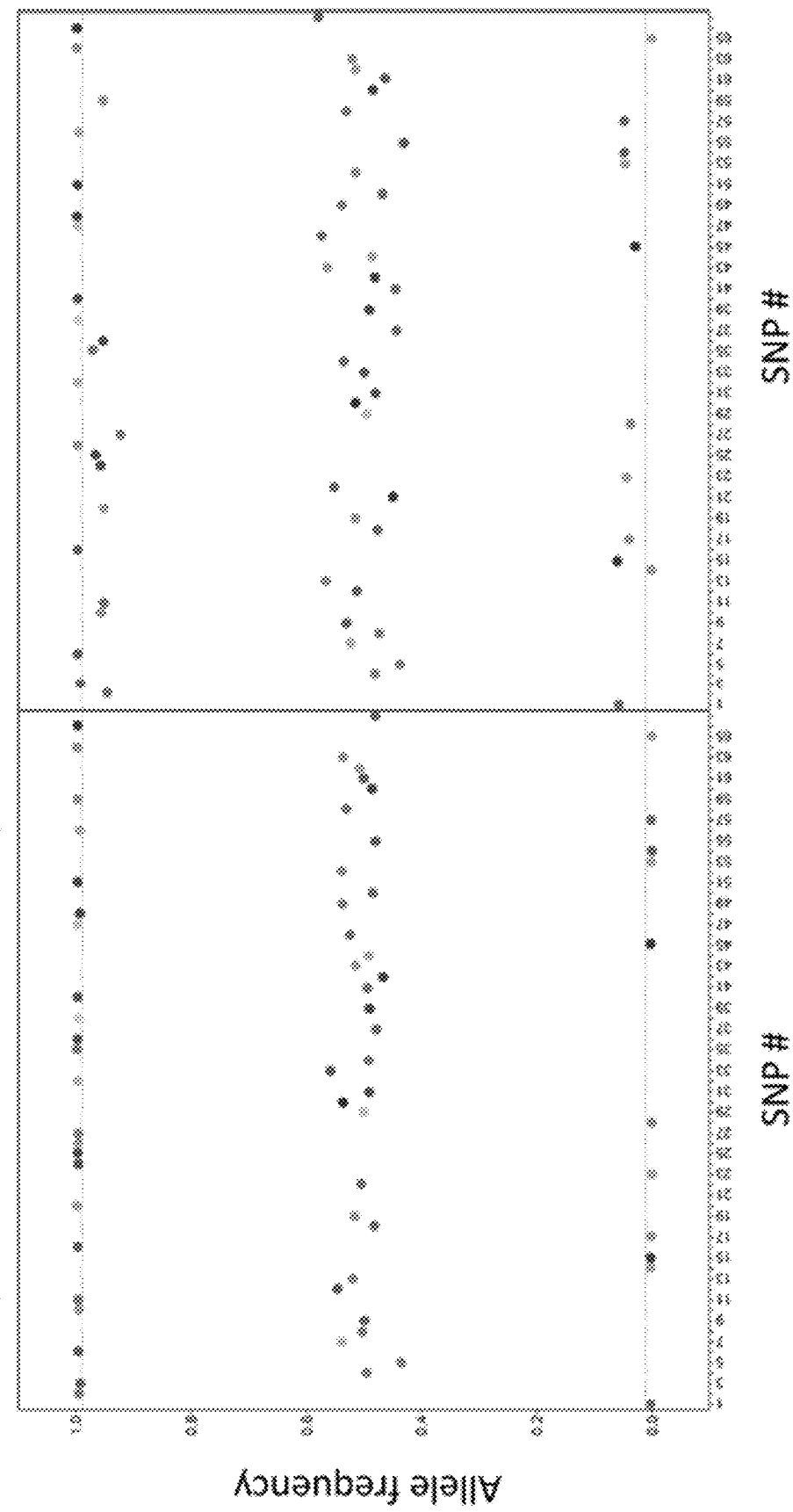
FIG. 31 shows allele frequencies per SNP for a particular sample.
Figure 32:
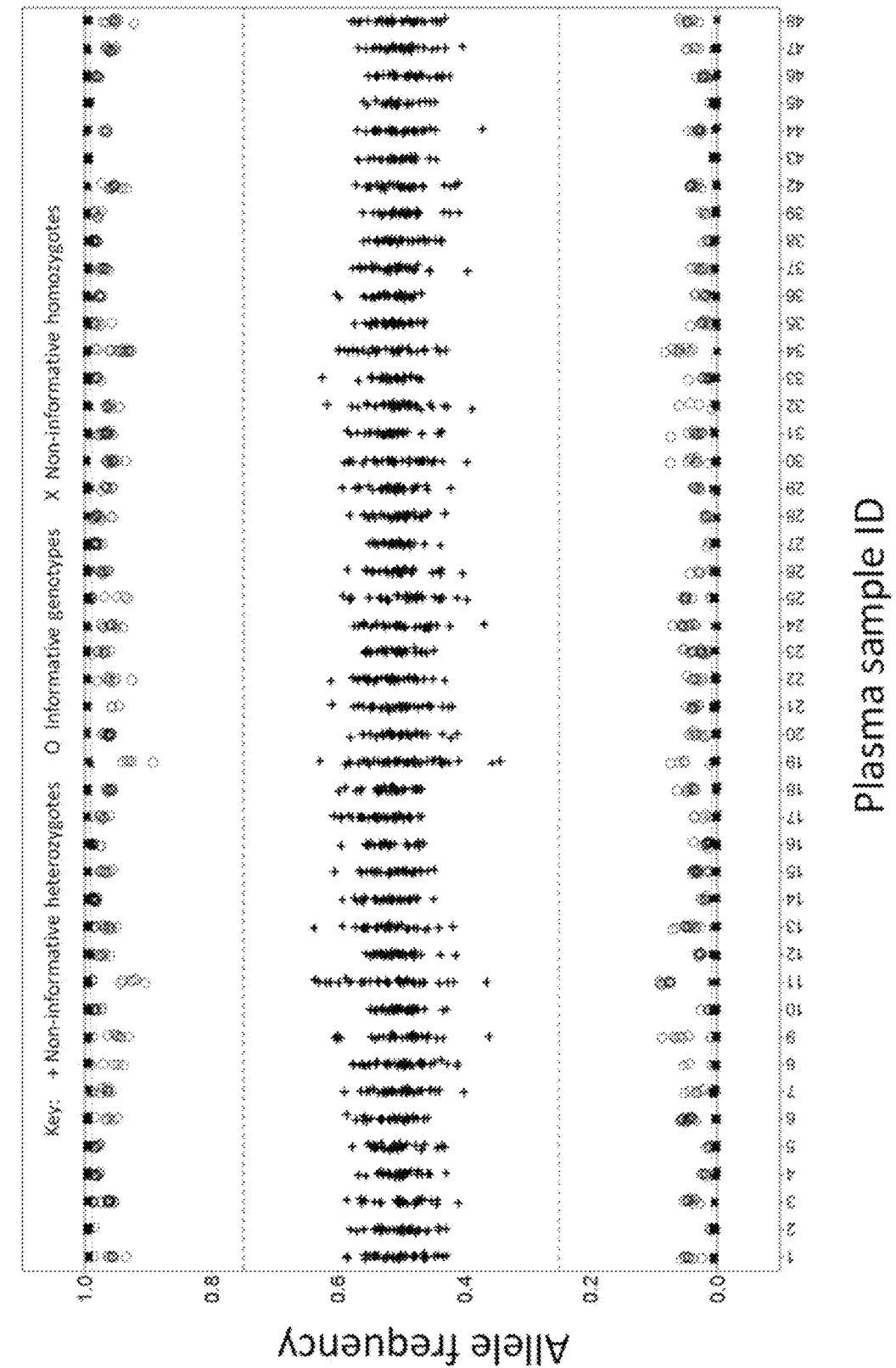
FIG. 32 shows allele frequencies per sample for a collection of 46 samples.
Figure 33:
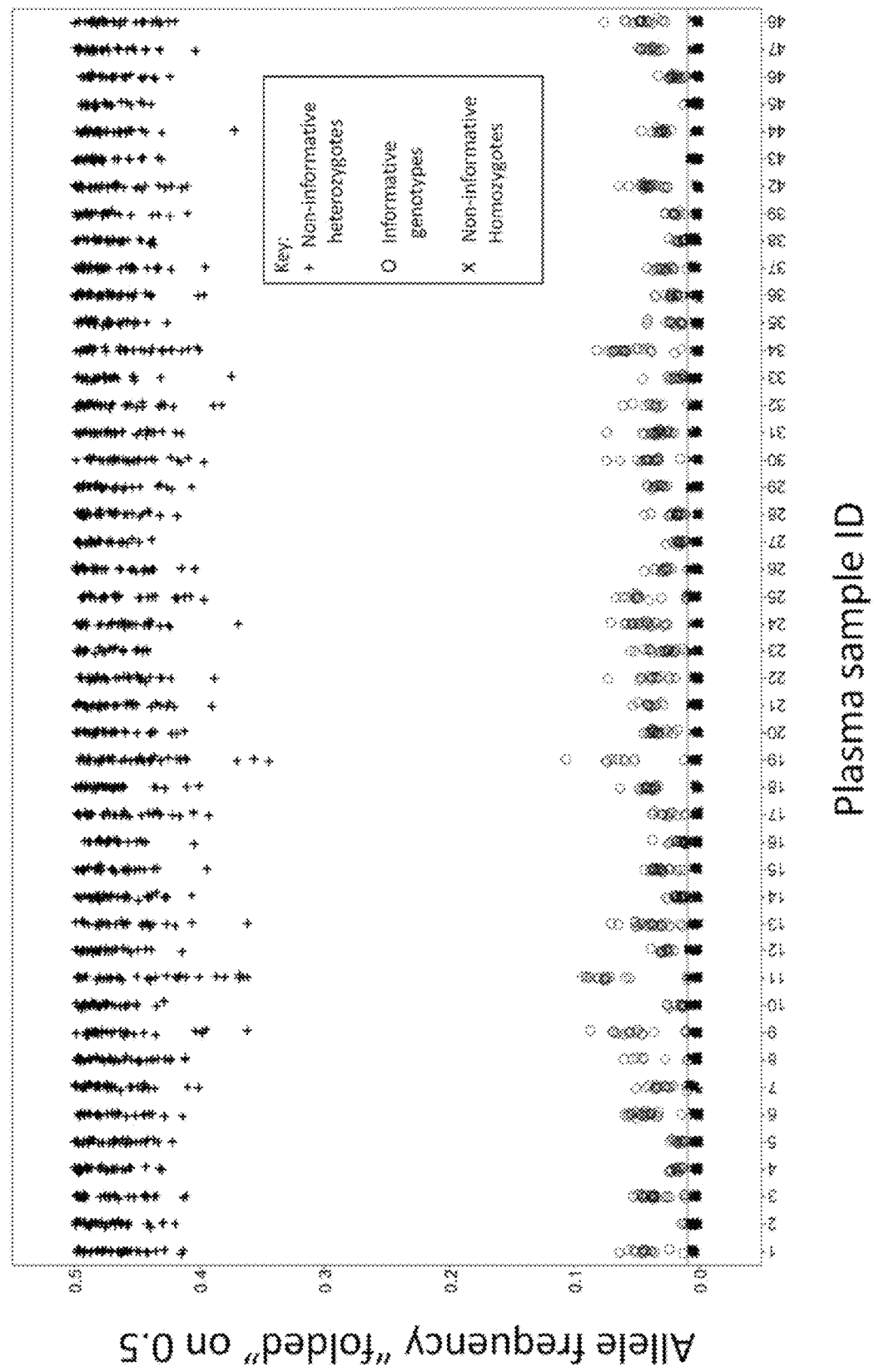
FIG. 33 shows allele frequencies per sample (folded on 0.5) for a collection of 46 samples.
Figure 34:
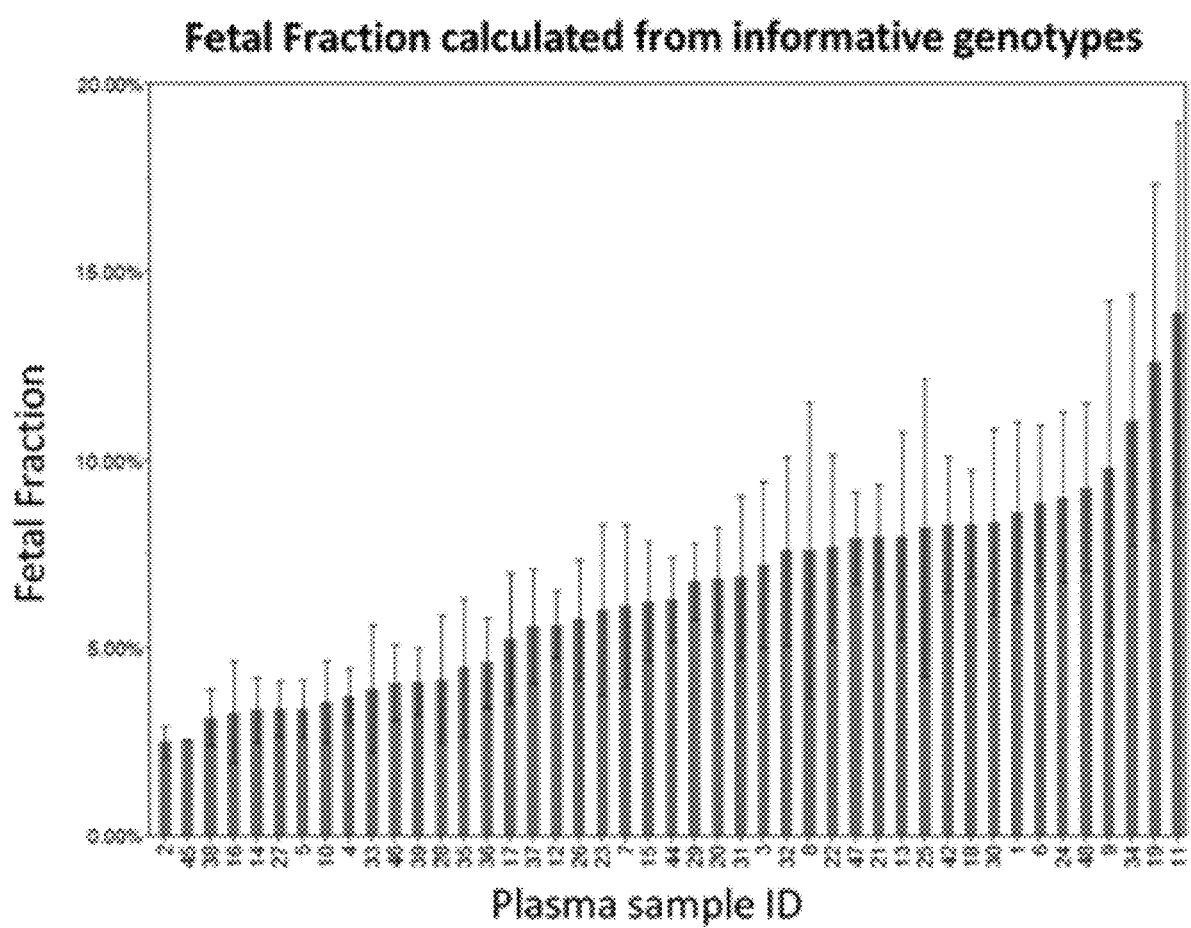
FIG. 34 shows fetal fraction values calculated from informative genotypes for each sample.

In some cases, informative genotypes were assigned without prior knowledge of maternal or paternal genotypes. Allele frequencies for each SNP (of SNP panel 1) were plotted as shown in FIG. 30 and FIG. 31 for two of the 46 samples tested. Homozygous allele frequencies in maternal buffy coat were close to 0 or 1. Type 1 informative SNPs were identified by allele frequencies that deviated from the expected allele frequency of 0 or 1 due to the presence of a paternal allele from the fetus. The size of the deviation was dependent on the size of the fetal fraction of CCF DNA. A maximum background allele frequency of 0.007 was observed for maternal buffy coat DNA. For this approach, a fixed cutoff frequency value of 0.01 was used to distinguish non-informative homozygotes from informative genotypes in plasma samples (see FIGS. 32 and 33, showing the assignment of certain Type 1 informative genotypes). A fixed cutoff value of 0.25 was used to distinguish non-informative heterozygotes from other genotypes. Fetal fractions were calculated for 46 plasma samples by taking the mean of the informative genotype allele frequencies and multiplying this value by 2. Informative genotypes assigned per sample ranged from 1 to 26. Fetal fractions ranged from 2.5% to 14% (see FIG. 34).

Figure 35:
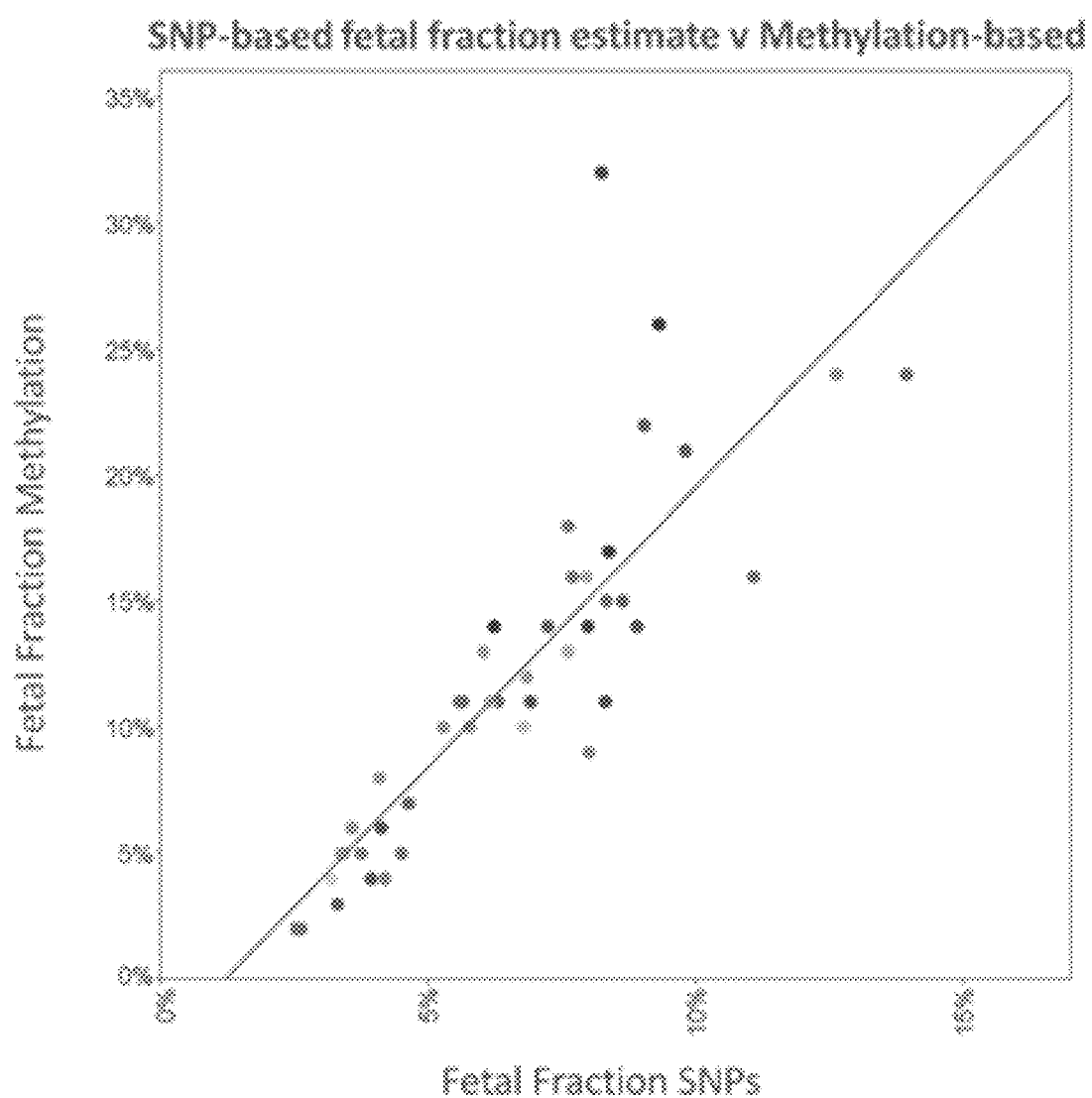
FIG. 35 shows a correlation plot for SNP-based fetal fraction estimates versus methylation-based fetal fraction estimates.

To assess performance of the above method, fetal fractions also were determined for the 46 plasma samples using a differential methylation-based fetal quantifier assay. SNP-based fetal fraction estimates showed a linear association with the methylation-based estimates ($r^2$=0.72). FIG. 35 shows linear regression of fetal fraction estimate methods as a diagonal line.

Amplicon Sequence Coverage

Figure 36:
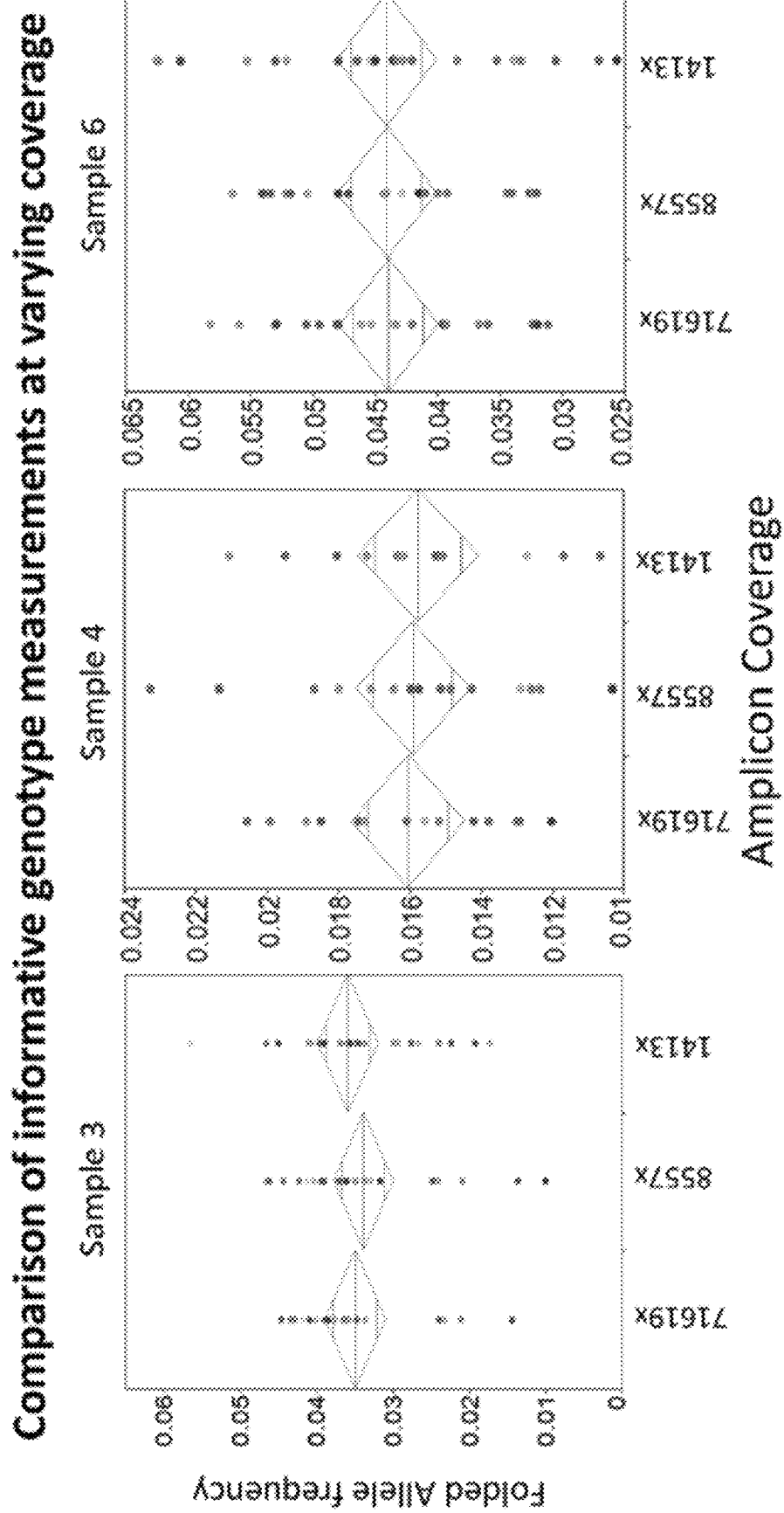
FIG. 36 shows a comparison of informative genotype measurements at varying sequencing coverage.

Various amounts of SNP amplicon libraries were combined (i.e. diluted) with TRUSEQ libraries to demonstrate that allele frequency determinations can be made at varying levels of amplicon sequence coverage. SNP amplicon libraries from 6 plasma samples and 6 buffy coat samples were combined with 11 TRUSEQ libraries and co-sequenced on a HISEQ 2000 apparatus in the same flowcell lane. Percent (%) of SNP amplicon library combined with TRUSEQ libraries ranged from 50% to 0.8%. After alignment coverage per SNP for each amplicon library ranged from 71619× per SNP (50% amplicon library) to 1413× per SNP (0.8% amplicon library). Fetal fraction estimates were not significantly different even at lowest coverage level (see FIG. 36). These findings indicate that less than 1% of the flowcell clusters on a HISEQ 2000 apparatus can be used to co-sequence amplicon libraries and that high levels of sample multiplexing (e.g., greater than 96) can be achieved.

Example 6

Examples of Embodiments

Provided hereafter are non-limiting examples of certain embodiments of the technology.

A1. A method for determining the amount of fetal nucleic acid in a sample comprising:
(a) contacting a sample nucleic acid with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid;
(b) contacting under amplification conditions the differentially modified sample nucleic acid with:
(i) a first set of amplification primers that specifically amplify a first region in sample nucleic acid comprising one or more loci that are differentially methylated between the fetal nucleic acid and maternal nucleic acid, and
(ii) a second set of amplification primers that amplify a second region in the sample nucleic acid allowing for a determination of total nucleic acid in the sample, wherein the first region and the second region are different, thereby generating fetal nucleic acid amplification products and total nucleic acid amplification products;
(c) incorporating adaptor oligonucleotides into the amplification products in (b); thereby generating adaptor-modified amplification products;
(d) obtaining nucleotide sequences of the adaptor-modified amplification products in (c) by a sequencing process, thereby generating sequence reads;
(e) quantifying the sequence reads; and
(f) determining the amount of fetal nucleic acid in the sample based on a quantification of the sequence reads in (e).

A2. The method of embodiment A1, wherein the first region comprises one or more loci which each contain a restriction site for a methylation-sensitive restriction enzyme.

A3. The method of embodiment A2, wherein the one or more agents that differentially modify methylated nucleic acid and unmethylated nucleic acid comprise one or more methylation sensitive restriction enzymes.

A4. The method of embodiment A2 or A3, wherein the second region comprises one or more loci which do not contain a restriction site for a methylation-sensitive restriction enzyme.

A5. The method of embodiment A1, wherein the one or more agents that differentially modify methylated nucleic acid and unmethylated nucleic acid comprise bisulfite.

A6. The method of any one of embodiments A1 to A5, wherein the adaptor oligonucleotides are incorporated into the amplification products by ligation.

A7. The method of embodiment A6, wherein the ligation is unidirectional ligation.

A8. The method of any one of embodiments A1 to A5, wherein the adaptor oligonucleotides are incorporated into the amplification products using amplification primers comprising the adaptor oligonucleotide sequences.

A9. The method of any one of embodiments A1 to A8, wherein the adaptor oligonucleotides comprise one or more index sequences.

A10. The method of embodiment A9, wherein the one or more index sequences comprise a sample-specific index.

A11. The method of embodiment A9, wherein the one or more index sequences comprise an aliquot-specific index.

A12. The method of any one of embodiments A1 to A11, wherein at least one of the one or more loci in the first region comprises a nucleotide sequence selected from among SEQ ID NOs:1-261, or a fragment thereof.

A13. The method of embodiment A12, wherein at least one of the one or more loci in the first region comprises a nucleotide sequence selected from among SEQ ID NOs:1-89, or a fragment thereof.

A14. The method of embodiment A12, wherein at least one of the one or more loci in the first region comprises a nucleotide sequence selected from among SEQ ID NOs:90-261, or a fragment thereof.

A15. The method of embodiment A12, wherein at least one of the one or more loci in the first region comprises a nucleotide sequence selected from among SEQ ID NOs:1-59 and SEQ ID NOs:86-89, or a fragment thereof.

A16. The method of embodiment A12, wherein at least one of the one or more loci in the first region comprises a nucleotide sequence selected from among SEQ ID NOs:1-59, or a fragment thereof.

A17. The method of embodiment A12, wherein at least one of the one or more loci in the first region comprises a nucleotide sequence selected from among SEQ ID NO:42, SEQ ID NO:52, SEQ ID NO:154, SEQ ID NO:158 and SEQ ID NO:163.

A18. The method of any one of embodiments A1 to A17, wherein the sequencing process is a sequencing by synthesis method.

A19. The method of any one of embodiments A1 to A18, wherein the sequencing process is a reversible terminator-based sequencing method.

A20. The method of any one of embodiments A1 to A19, wherein the amount of fetal nucleic acid determined is the fraction of fetal nucleic acid in the sample based on the amount of each of the fetal nucleic acid amplification products and total nucleic acid amplification products.

A21. The method of embodiment A20, wherein the fraction of fetal nucleic acid is a ratio of fetal nucleic acid amplification product amount to total nucleic acid amplification product amount.

A22. The method of any one of embodiments A1 to A21, further comprising contacting under amplification conditions the nucleic acid sample with a third set of amplification primers that amplify a third region in the sample nucleic acid allowing for a determination of the presence or absence of fetal specific nucleic acid.

A23. The method of embodiment A22, wherein the fetal specific nucleic acid is Y chromosome nucleic acid.

A24. The method of embodiment A23, wherein the third region comprises one or more loci within chromosome Y.

A25. The method of any one of embodiments A3 to A24, further comprising contacting under amplification conditions the nucleic acid sample with a fourth set of amplification primers that amplify a fourth region in the sample nucleic acid allowing for a determination of the amount of digested or undigested nucleic acid, as an indicator of digestion efficiency.

A26. The method of embodiment A25, wherein the fourth region comprises one or more loci present in both fetal nucleic acid and maternal nucleic acid and unmethylated in both fetal nucleic acid and maternal nucleic acid.

A27. The method of any one of embodiments A1 to A26, further comprising contacting under amplification conditions the nucleic acid sample with a predetermined copy number of one or more first competitor oligonucleotides that compete with the first region for hybridization of primers of the first amplification primer set.

A28. The method of any one of embodiments A1 to A27, further comprising contacting under amplification conditions the nucleic acid sample with a predetermined copy number of one or more second competitor oligonucleotides that compete with the second region for hybridization of primers of the second amplification primer set.

A29. The method of any one of embodiments A22 to A28, further comprising contacting under amplification conditions the nucleic acid sample with a predetermined copy number of one or more third competitor oligonucleotides that compete with the third region for hybridization of primers of the third amplification primer set.

A30. The method of any one of embodiments A25 to A29, further comprising contacting under amplification conditions the nucleic acid sample with a predetermined copy number of one or more fourth competitor oligonucleotides that compete with the fourth region for hybridization of primers of the fourth amplification primer set.

A31. The method of any one of embodiments A27 to A30, wherein the amount of fetal nucleic acid determined is the copy number of fetal nucleic acid based on the amount of competitor oligonucleotide used.

A32. The method of any one of embodiments A1 to A26, wherein the amount of fetal nucleic acid determined is the copy number of fetal nucleic acid based on a quantification of sequence reads.

A33. The method of any one of embodiments A1 to A32, wherein the sample nucleic acid is extracellular nucleic acid.

A34. The method of any one of embodiments A1 to A33, wherein the nucleic acid sample is obtained from a pregnant female subject.

A35. The method of embodiment A34, wherein the subject is human.

A36. The method of any one of embodiments A1 to A35, wherein the sample nucleic acid is from plasma or serum.

A37. The method of any one of embodiments A1 to A36, wherein two or more independent loci in the first region are assayed.

A38. The method of any one of embodiments A1 to A37, wherein the amount of fetal nucleic acid is substantially equal to the amount of fetal nucleic acid determined using a mass spectrometry method.

A39. The method of any one of embodiments A1 to A38, wherein the amount of fetal nucleic acid is determined with an $R^2$ value of 0.97 or greater when compared to an amount of fetal nucleic acid determined using a mass spectrometry method.

B1. A method for determining the amount of fetal nucleic acid in a sample comprising:
 (a) contacting a sample nucleic acid with one or more methylation sensitive restriction enzymes, which sample nucleic acid comprises differentially methylated fetal nucleic acid and maternal nucleic acid, the combination of the fetal nucleic acid and the maternal nucleic acid comprising total nucleic acid in the sample, thereby generating differentially digested sample nucleic acid;
 (b) contacting under amplification conditions the digested sample nucleic acid with:
  (i) a first set of amplification primers that specifically amplify a first region in sample nucleic acid comprising one or more loci that are differentially methylated between the fetal nucleic acid and maternal nucleic acid, and
  (ii) a second set of amplification primers that amplify a second region in the sample nucleic acid allowing for a determination of total nucleic acid in the sample, wherein the first region and the second region are different, thereby generating fetal nucleic acid amplification products and total nucleic acid amplification products;

(c) incorporating adaptor oligonucleotides into the amplification products in (b); thereby generating adaptor-modified amplification products;

(d) obtaining nucleotide sequences of the adaptor-modified amplification products in (c) by a sequencing process, thereby generating sequence reads;

(e) quantifying the sequence reads; and (f) determining the amount of fetal nucleic acid in the sample based on a quantification of the sequence reads in (e).

B2. The method of embodiment B1, wherein the adaptor oligonucleotides are incorporated into the amplification products by ligation.

B3. The method of embodiment B2, wherein the ligation is unidirectional ligation.

B4. The method of any one of embodiments B1 to B3, wherein the adaptor oligonucleotides are incorporated into the amplification products using amplification primers comprising the adaptor oligonucleotide sequences.

B5. The method of any one of embodiments B1 to B4, wherein the adaptor oligonucleotides comprise one or more index sequences.

B6. The method of embodiment B5, wherein the one or more index sequences comprise a sample-specific index.

B7. The method of embodiment B5, wherein the one or more index sequences comprise an aliquot-specific index.

B8. The method of any one of embodiments B1 to B7, wherein at least one of the one or more loci in the first region comprises a nucleotide sequence selected from among SEQ ID NOs:1-261, or a fragment thereof.

B9. The method of embodiment B8, wherein at least one of the one or more loci in the first region comprises a nucleotide sequence selected from among SEQ ID NOs:1-89, or a fragment thereof.

B10. The method of embodiment B8, wherein at least one of the one or more loci in the first region comprises a nucleotide sequence selected from among SEQ ID NOs:90-261, or a fragment thereof.

B11. The method of embodiment B8, wherein at least one of the one or more loci in the first region comprises a nucleotide sequence selected from among SEQ ID NOs:1-59 and SEQ ID NOs:86-89, or a fragment thereof.

B12. The method of embodiment B8, wherein at least one of the one or more loci in the first region comprises a nucleotide sequence selected from among SEQ ID NOs:1-59, or a fragment thereof.

B13. The method of embodiment B8, wherein at least one of the one or more loci in the first region comprises a nucleotide sequence selected from among SEQ ID NO:42, SEQ ID NO:52, SEQ ID NO:154, SEQ ID NO:158 and SEQ ID NO:163.

B14. The method of any one of embodiments B1 to B13, wherein the sequencing process is a sequencing by synthesis method.

B15. The method of any one of embodiments B1 to B13, wherein the sequencing process is a reversible terminator-based sequencing method.

B16. The method of any one of embodiments B1 to B15, wherein the amount of fetal nucleic acid determined is the fraction of fetal nucleic acid in the sample based on the amount of each of the fetal nucleic acid amplification products and total nucleic acid amplification products.

B17. The method of embodiment B16, wherein the fraction of fetal nucleic acid is a ratio of fetal nucleic acid amplification product amount to total nucleic acid amplification product amount.

B18. The method of any one of embodiments B1 to B17, further comprising contacting under amplification conditions the nucleic acid sample with a third set of amplification primers that amplify a third region in the sample nucleic acid allowing for a determination of the presence or absence of fetal specific nucleic acid.

B19. The method of embodiment B18, wherein the fetal specific nucleic acid is Y chromosome nucleic acid.

B20. The method of embodiment B19, wherein the third region comprises one or more loci within chromosome Y.

B21. The method of any one of embodiments B1 to B20, further comprising contacting under amplification conditions the nucleic acid sample with a fourth set of amplification primers that amplify a fourth region in the sample nucleic acid allowing for a determination of the amount of digested or undigested nucleic acid, as an indicator of digestion efficiency.

B22. The method of embodiment B21, wherein the fourth region comprises one or more loci present in both fetal nucleic acid and maternal nucleic acid and unmethylated in both fetal nucleic acid and maternal nucleic acid.

B23. The method of any one of embodiments B1 to B22, further comprising contacting under amplification conditions the nucleic acid sample with a predetermined copy number of one or more first competitor oligonucleotides that compete with the first region for hybridization of primers of the first amplification primer set.

B24. The method of any one of embodiments B1 to B23, further comprising contacting under amplification conditions the nucleic acid sample with a predetermined copy number of one or more second competitor oligonucleotides that compete with the second region for hybridization of primers of the second amplification primer set.

B25. The method of any one of embodiments B18 to B24, further comprising contacting under amplification conditions the nucleic acid sample with a predetermined copy number of one or more third competitor oligonucleotides that compete with the third region for hybridization of primers of the third amplification primer set.

B26. The method of any one of embodiments B21 to B25, further comprising contacting under amplification conditions the nucleic acid sample with a predetermined copy number of one or more fourth competitor oligonucleotides that compete with the fourth region for hybridization of primers of the fourth amplification primer set.

B27. The method of any one of embodiments B23 to B26, wherein the amount of fetal nucleic acid determined is the copy number of fetal nucleic acid based on the amount of competitor oligonucleotide used.

B28. The method of any one of embodiments B1 to B27, wherein the amount of fetal nucleic acid determined is the copy number of fetal nucleic acid based on a quantification of sequence reads.

B29. The method of any one of embodiments B1 to B28, wherein the sample nucleic acid is extracellular nucleic acid.

B30. The method of any one of embodiments B1 to B29, wherein the nucleic acid sample is obtained from a pregnant female subject.

B31. The method of embodiment B30, wherein the subject is human.

B32. The method of any one of embodiments B1 to B31, wherein the sample nucleic acid is from plasma or serum.

B33. The method of any one of embodiments B1 to B32, wherein two or more independent loci in the first region are assayed.

B34. The method of any one of embodiments B1 to B33, wherein the amount of fetal nucleic acid is substantially equal to the amount of fetal nucleic acid determined using a mass spectrometry method.

B35. The method of any one of embodiments B1 to B34, wherein the amount of fetal nucleic acid is determined with an $R^2$ value of 0.97 or greater when compared to an amount of fetal nucleic acid determined using a mass spectrometry method.

C1. A method for determining the copy number of fetal nucleic acid in a sample comprising:
  (a) contacting a sample nucleic acid with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid;
  (b) contacting under amplification conditions the differentially modified sample nucleic acid with:
    (i) a first set of amplification primers that specifically amplify a first region in sample nucleic acid comprising one or more loci that are differentially methylated between the fetal nucleic acid and maternal nucleic acid, and
    (ii) a predetermined copy number of one or more first competitor oligonucleotides that compete with the first region for hybridization of primers of the first amplification primer set, thereby generating fetal nucleic acid amplification products and competitor amplification products;
  (c) incorporating adaptor oligonucleotides into the amplification products in (b); thereby generating adaptor-modified amplification products;
  (d) obtaining nucleotide sequences of the adaptor-modified amplification products in (c) by a sequencing process, thereby generating sequence reads;
  (e) quantifying the sequence reads; and
  (f) determining the copy number of fetal nucleic acid in the sample based on a quantification of the sequence reads in (e) and the amount of competitor oligonucleotide used.

C2. The method of embodiment C1, wherein the first region comprises one or more loci which each contain a restriction site for a methylation-sensitive restriction enzyme.

C3. The method of embodiment C2, wherein the one or more agents that differentially modify methylated nucleic acid and unmethylated nucleic acid comprise one or more methylation sensitive restriction enzymes.

C4. The method of embodiment C1, wherein the one or more agents that differentially modify methylated nucleic acid and unmethylated nucleic acid comprise bisulfite.

C5. The method of any one of embodiments C1 to C4, wherein the adaptor oligonucleotides are incorporated into the amplification products by ligation.

C6. The method of embodiment C5, wherein the ligation is unidirectional ligation.

C7. The method of any one of embodiments C1 to C4, wherein the adaptor oligonucleotides are incorporated into the amplification products using amplification primers comprising the adaptor oligonucleotide sequences.

C8. The method of any one of embodiments C1 to C7, wherein the adaptor oligonucleotides comprise one or more index sequences.

C9. The method of embodiment C8, wherein the one or more index sequences comprise a sample-specific index.

C10. The method of embodiment C8, wherein the one or more index sequences comprise an aliquot-specific index.

C11. The method of any one of embodiments C1 to C10, wherein at least one of the one or more loci in the first region comprises a nucleotide sequence selected from among SEQ ID NOs:1-261, or a fragment thereof.

C12. The method of embodiment C11, wherein at least one of the one or more loci in the first region comprises a nucleotide sequence selected from among SEQ ID NOs:1-89, or a fragment thereof.

C13. The method of embodiment C11, wherein at least one of the one or more loci in the first region comprises a nucleotide sequence selected from among SEQ ID NOs:90-261, or a fragment thereof.

C14. The method of embodiment C11, wherein at least one of the one or more loci in the first region comprises a nucleotide sequence selected from among SEQ ID NOs:1-59 and SEQ ID NOs:86-89, or a fragment thereof.

C15. The method of embodiment C11, wherein at least one of the one or more loci in the first region comprises a nucleotide sequence selected from among SEQ ID NOs:1-59, or a fragment thereof.

C16. The method of embodiment C11, wherein at least one of the one or more loci in the first region comprises a nucleotide sequence selected from among SEQ ID NO:42, SEQ ID NO:52, SEQ ID NO:154, SEQ ID NO:158 and SEQ ID NO:163.

C17. The method of any one of embodiments C1 to C16, wherein the sequencing process is a sequencing by synthesis method.

C18. The method of any one of embodiments C1 to C16, wherein the sequencing process is a reversible terminator-based sequencing method.

C19 The method of any one of embodiments C1 to C18, further comprising contacting under amplification conditions the nucleic acid sample with a second set of amplification primers that amplify a second region in the sample nucleic acid allowing for a determination of total nucleic acid in the sample, wherein the first region and the second region are different.

C20. The method of embodiment C19, wherein the second region comprises one or more loci which do not contain a restriction site for a methylation-sensitive restriction enzyme.

C21. The method of any one of embodiments C1 to C20, further comprising contacting under amplification conditions the nucleic acid sample with a third set of amplification primers that amplify a third region in the sample nucleic acid allowing for a determination of the presence or absence of fetal specific nucleic acid.

C22. The method of embodiment C21, wherein the fetal specific nucleic acid is Y chromosome nucleic acid.

C23. The method of embodiment C22, wherein the third region comprises one or more loci within chromosome Y.

C24. The method of any one of embodiments C3 to C23, further comprising contacting under amplification conditions the nucleic acid sample with a fourth set of amplification primers that amplify a fourth region in the sample nucleic acid allowing for a determination of the amount of digested or undigested nucleic acid, as an indicator of digestion efficiency.

C25. The method of embodiment C24, wherein the fourth region comprises one or more loci present in both fetal nucleic acid and maternal nucleic acid and unmethylated in both fetal nucleic acid and maternal nucleic acid.

C26. The method of any one of embodiments C19 to C25, further comprising contacting under amplification conditions the nucleic acid sample with a predetermined copy number of one or more second competitor oligonucleotides that compete with the second region for hybridization of primers of the second amplification primer set.

C27. The method of any one of embodiments C21 to C26, further comprising contacting under amplification conditions the nucleic acid sample with a predetermined copy number of one or more third competitor oligonucleotides that compete with the third region for hybridization of primers of the third amplification primer set.

C28. The method of any one of embodiments C24 to C27, further comprising contacting under amplification conditions the nucleic acid sample with a predetermined copy number of one or more fourth competitor oligonucleotides that compete with the fourth region for hybridization of primers of the fourth amplification primer set.

C29. The method of any one of embodiments C1 to C28, wherein the sample nucleic acid is extracellular nucleic acid.

C30. The method of any one of embodiments C1 to C29, wherein the nucleic acid sample is obtained from a pregnant female subject.

C31. The method of embodiment C30, wherein the subject is human.

C32. The method of any one of embodiments C1 to C31, wherein the sample nucleic acid is from plasma or serum.

C33. The method of any one of embodiments C1 to C32, wherein two or more independent loci in the first region are assayed.

C34. The method of any one of embodiments C1 to C33, wherein the copy number of fetal nucleic acid is substantially equal to the copy number of fetal nucleic acid determined using a mass spectrometry method.

C35. The method of any one of embodiments C1 to C34, wherein the copy number of fetal nucleic acid is determined with an $R^2$ value of 0.97 or greater when compared to a copy number of fetal nucleic acid determined using a mass spectrometry method.

D1. A method for detecting the presence or absence of a fetal aneuploidy in a sample comprising:
(a) contacting a sample nucleic acid with one or more agents that differentially modify methylated nucleic acid and unmethylated nucleic acid, which sample nucleic acid comprises differentially methylated fetal nucleic acid and maternal nucleic acid, the combination of the fetal nucleic acid and the maternal nucleic acid comprising total nucleic acid in the sample, thereby generating differentially modified sample nucleic acid;
(b) contacting under amplification conditions the differentially modified sample nucleic acid with:
(i) a first set of amplification primers that specifically amplify one or more loci in a target chromosome that are differentially methylated between the fetal nucleic acid and maternal nucleic acid, and
(ii) a second set of amplification primers that specifically amplify one or more loci in a reference chromosome that are differentially methylated between the fetal nucleic acid and maternal nucleic acid, thereby generating target chromosome amplification products and reference chromosome amplification products;
(c) incorporating adaptor oligonucleotides into the amplification products in (b); thereby generating adaptor-modified amplification products;
(d) obtaining nucleotide sequences of the adaptor-modified amplification products in (c) by a sequencing process, thereby generating sequence reads;
(e) quantifying the sequence reads; and
(f) detecting the presence or absence of a fetal aneuploidy in the sample based on a quantification of the sequence reads in (e).

D2. The method of embodiment D1, wherein the target chromosome comprises one or more loci which each contain a restriction site for a methylation-sensitive restriction enzyme.

D3. The method of embodiment D1 or D2, wherein the reference chromosome comprises one or more loci which each contain a restriction site for a methylation-sensitive restriction enzyme.

D4. The method of embodiment D2 or D3, wherein the one or more agents that differentially modify methylated nucleic acid and unmethylated nucleic acid comprise one or more methylation sensitive restriction enzymes.

D5. The method of embodiment D1, wherein the one or more agents that differentially modify methylated nucleic acid and unmethylated nucleic acid comprise bisulfite.

D6. The method of any one of embodiments D1 to D5, wherein the adaptor oligonucleotides are incorporated into the amplification products by ligation.

D7. The method of embodiment D6, wherein the ligation is unidirectional ligation.

D8. The method of any one of embodiments D1 to D5, wherein the adaptor oligonucleotides are incorporated into the amplification products using amplification primers comprising the adaptor oligonucleotide sequences.

D9. The method of any one of embodiments D1 to D8, wherein the adaptor oligonucleotides comprise one or more index sequences.

D10. The method of embodiment D9, wherein the one or more index sequences comprise a sample-specific index.

D11. The method of embodiment D9, wherein the one or more index sequences comprise an aliquot-specific index.

D12. The method of any one of embodiments D1 to D11, wherein at least one of the one or more loci in the target chromosome comprises a nucleotide sequence selected from among SEQ ID NOs:1-261, or a fragment thereof.

D13. The method of embodiment D12, wherein at least one of the one or more loci in the target chromosome comprises a nucleotide sequence selected from among SEQ ID NOs:1-89, or a fragment thereof.

D14. The method of embodiment D12, wherein at least one of the one or more loci in the target chromosome comprises a nucleotide sequence selected from among SEQ ID NOs:90-261, or a fragment thereof.

D15. The method of embodiment D12, wherein at least one of the one or more loci in target chromosome comprises a nucleotide sequence selected from among SEQ ID NOs:1-59 and SEQ ID NOs:86-89, or a fragment thereof.

D16. The method of embodiment D12, wherein at least one of the one or more loci in the target chromosome comprises a nucleotide sequence selected from among SEQ ID NOs:1-59, or a fragment thereof.

D17. The method of embodiment D12, wherein at least one of the one or more loci in the target chromosome comprises a nucleotide sequence selected from among SEQ ID NO:42, SEQ ID NO:52, SEQ ID NO:154, SEQ ID NO:158 and SEQ ID NO:163.

D18. The method of any one of embodiments D1 to D17, wherein at least one of the one or more loci in the reference chromosome comprises a nucleotide sequence selected from among SEQ ID NOs:1-261, or a fragment thereof.

D19. The method of embodiment D18, wherein at least one of the one or more loci in the reference chromosome comprises a nucleotide sequence selected from among SEQ ID NOs:1-89, or a fragment thereof.

D20. The method of embodiment D18, wherein at least one of the one or more loci in the reference chromosome comprises a nucleotide sequence selected from among SEQ ID NOs:90-261, or a fragment thereof.

D21. The method of embodiment D18, wherein at least one of the one or more loci in reference chromosome comprises a nucleotide sequence selected from among SEQ ID NOs:1-59 and SEQ ID NOs:86-89, or a fragment thereof.

D22. The method of embodiment D18, wherein at least one of the one or more loci in the reference chromosome comprises a nucleotide sequence selected from among SEQ ID NOs:1-59, or a fragment thereof.

D23. The method of embodiment D18, wherein at least one of the one or more loci in the reference chromosome comprises a nucleotide sequence selected from among SEQ ID NO:42, SEQ ID NO:52, SEQ ID NO:154, SEQ ID NO:158 and SEQ ID NO:163.

D24. The method of any one of embodiments D1 to D23, wherein the sequencing process is a sequencing by synthesis method.

D25. The method of any one of embodiments D1 to D23, wherein the sequencing process is a reversible terminator-based sequencing method.

D26. The method of any one of embodiments D1 to D25, further comprising contacting under amplification conditions the nucleic acid sample with a predetermined copy number of one or more first competitor oligonucleotides that compete with the target chromosome for hybridization of primers of the first amplification primer set.

D27. The method of any one of embodiments D1 to D26, further comprising contacting under amplification conditions the nucleic acid sample with a predetermined copy number of one or more second competitor oligonucleotides that compete with the reference chromosome for hybridization of primers of the second amplification primer set.

D28. The method of any one of embodiments D1 to D27, wherein the sample nucleic acid is extracellular nucleic acid.

D29. The method of any one of embodiments D1 to D28, wherein the nucleic acid sample is obtained from a pregnant female subject.

D30. The method of embodiment D29, wherein the subject is human.

D31. The method of any one of embodiments D1 to D30, wherein the sample nucleic acid is from plasma or serum.

D32. The method of any one of embodiments D1 to D31, wherein two or more independent loci in the target chromosome are assayed.

D33. The method of any one of embodiments D1 to D32, wherein two or more independent loci in the reference chromosome are assayed.

D34. The method of any one of embodiments D1 to D33, wherein the target chromosome is chromosome 13.

D35. The method of any one of embodiments D1 to D33, wherein the target chromosome is chromosome 18.

D36. The method of any one of embodiments D1 to D33, wherein the target chromosome is chromosome 21.

E1. A method for determining fetal fraction in a sample comprising:
(a) enriching a sample nucleic acid for a plurality of polymorphic nucleic acid targets, which sample nucleic acid comprises fetal nucleic acid and maternal nucleic acid;
(b) obtaining nucleotide sequences for some or all of the nucleic acid targets by a sequencing process;
(c) analyzing the nucleotide sequences of (b); and
(d) determining fetal fraction based on the analysis of (c), wherein the polymorphic nucleic acid targets and number thereof result in at least five polymorphic nucleic acid targets being informative for determining the fetal fraction for at least 90% of samples.

E2. The method of embodiment E1, wherein the enriching comprises amplifying the plurality of polymorphic nucleic acid targets.

E3. The method of embodiment E1 or E2, wherein the enriching comprises generating amplification products in an amplification reaction.

E4. The method of embodiment E3, wherein the amplification reaction is performed in a single vessel.

E5. The method of any one of embodiments E1 to E4, wherein the maternal genotype and the paternal genotype at each of the polymorphic nucleic acid targets are not known prior to (a).

E5.1 The method of any one of embodiments E1 to E5, wherein polymorphic nucleic acid targets having a minor allele population frequency of about 40% or more are selected.

E6. The method of any one of embodiments E1 to E5.1, comprising determining an allele frequency in the sample for each of the polymorphic nucleic acid targets.

E7. The method of embodiment E6, wherein determining which polymorphic nucleic acid targets are informative comprises identifying informative genotypes by comparing each allele frequency to one or more fixed cutoff frequencies.

E7.1 The method of embodiment E7, wherein the fixed cutoff for identifying informative genotypes from non-informative homozygotes is about a 1% or greater shift in allele frequency.

E7.2 The method of embodiment E7, wherein the fixed cutoff for identifying informative genotypes from non-informative homozygotes is about a 2% or greater shift in allele frequency.

E7.3 The method of embodiment E7, wherein the fixed cutoff for identifying informative genotypes from non-informative heterozygotes is about a 25% or greater shift in allele frequency.

E7.4 The method of embodiment E7, wherein the fixed cutoff for identifying informative genotypes from non-informative heterozygotes is about a 50% or greater shift in allele frequency.

E8. The method of embodiment E6, wherein determining which polymorphic nucleic acid targets are informative comprises identifying informative genotypes by comparing each allele frequency to one or more target-specific cutoff frequencies.

E9. The method of embodiment E8, wherein the one or more target-specific cutoff frequencies are determined for each polymorphic nucleic acid target.

E10. The method of embodiment E8 or E9, wherein each target-specific cutoff frequency is determined based on the allele frequency variance for the corresponding polymorphic nucleic acid target.

E11. The method of any one of embodiments E6 to E10, further comprising determining an allele frequency mean.

E12. The method of embodiment E11, wherein fetal fraction is determined based, in part, on the allele frequency mean.

E13. The method of any one of embodiments E1 to E12, wherein the fetal genotype at one or more informative polymorphic nucleic acid targets is heterozygous.

E14. The method of any one of embodiments E1 to E13, wherein the fetal genotype at one or more informative polymorphic nucleic acid targets is homozygous.

E15. The method of any one of embodiments E1 to E14, wherein fetal fraction is determined with a coefficient of variance (CV) of 0.20 or less.

E16. The method of embodiment E15, wherein fetal fraction is determined with a coefficient of variance (CV) of 0.10 or less.

E17. The method of embodiment E16, wherein fetal fraction is determined with a coefficient of variance (CV) of 0.05 or less.

E18. The method of any one of embodiments E1 to E17, wherein the polymorphic nucleic acid targets each comprise at least one single nucleotide polymorphism (SNP).

E19. The method of embodiment E18, wherein the SNPs are selected from:
rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, rs985462, rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

E20. The method of embodiment E19, wherein the SNPs are selected from:
rs10413687, rs10949838, rs1115649, rs11207002, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs516084, rs517316, rs517914, rs522810, rs531423, rs537330, rs539344, rs551372, rs567681, rs585487, rs600933, rs619208, rs622994, rs639298, rs642449, rs6700732, rs677866, rs683922, rs686851, rs6941942, rs7045684, rs7176924, rs7525374, rs870429, rs949312, rs9563831, rs970022, and rs985462.

E21. The method of embodiment E19, wherein the SNPs are selected from:
rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

E22. The method of any one of embodiments E1 to E21, wherein the polymorphic nucleic acid targets and number thereof result in at least five polymorphic nucleic acid targets being informative for determining the fetal fraction for at least 95% of samples.

E23. The method of embodiment E22, wherein the polymorphic nucleic acid targets and number thereof result in at least five polymorphic nucleic acid targets being informative for determining the fetal fraction for at least 99% of samples.

E24. The method of any one of embodiments E1 to E21, wherein the polymorphic nucleic acid targets and number thereof result in at least ten polymorphic nucleic acid targets being informative for determining the fetal fraction for at least 90% of samples.

E25. The method of embodiment E24, wherein the polymorphic nucleic acid targets and number thereof result in at least ten polymorphic nucleic acid targets being informative for determining the fetal fraction for at least 95% of samples.

E26. The method of embodiment E25, wherein the polymorphic nucleic acid targets and number thereof result in at least ten polymorphic nucleic acid targets being informative for determining the fetal fraction for at least 99% of samples.

E27. The method of any one of embodiments E1 to E26, wherein 10 or more polymorphic nucleic acid targets are enriched.

E27.1 The method of embodiment E27, wherein about 40 to about 100 polymorphic nucleic acid targets are enriched.

E28. The method of embodiment E27, wherein 50 or more polymorphic nucleic acid targets are enriched.

E29. The method of embodiment E28, wherein 100 or more polymorphic nucleic acid targets are enriched.

E30. The method of embodiment E29, wherein 500 or more polymorphic nucleic acid targets are enriched.

E31. The method of any one of embodiments E1 to E30, wherein the sequencing process comprises a sequencing by synthesis method.

E31.1 The method of embodiment E31, wherein the sequencing by synthesis method comprises a plurality of synthesis cycles.

E31.2 The method of embodiment E31.1, wherein the sequencing by synthesis method comprises about 36 cycles.

E31.3 The method of embodiment E31.1, wherein the sequencing by synthesis method comprises about 27 cycles.

E32. The method of any one of embodiments E1 to E30, wherein the sequencing process comprises a sequencing by ligation method.

E33. The method of any one of embodiments E1 to E30, wherein the sequencing process comprises a single molecule sequencing method.

E34. The method of any one of embodiments E1 to E33, wherein the sequencing process comprises sequencing a plurality of samples in a single compartment.

E35. The method of embodiment E34, wherein the fetal fraction is determined for 10 or more samples.

E36. The method of embodiment E35, wherein the fetal fraction is determined for 100 or more samples.

E37. The method of embodiment E36, wherein the fetal fraction is determined for 1000 or more samples.

E38. The method of any one of embodiments E1 to E37, wherein the sample nucleic acid is cell-free DNA.

E39. The method of any one of embodiments E1 to E38, wherein the sample nucleic acid is obtained from a pregnant female subject.

E40. The method of embodiment E39, wherein the subject is human.

E41. The method of any one of embodiments E1 to E40, wherein the sample nucleic acid is from plasma or serum.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. An in vitro method for measuring a fraction of fetally-derived alleles in a sample comprising:
   (a) amplifying in a single reaction at least 40 polymorphic nucleic acid targets in a sample nucleic acid from a subject, thereby generating amplification products, wherein the sample nucleic acid comprises fetal nucleic acid and maternal nucleic acid, wherein the polymorphic nucleic acid targets comprise the single nucleotide polymorphisms of rs11207002, rs516084, rs517316, rs531423, rs600933, rs639298, rs642449, rs6700732, and rs7525374, wherein the maternal genotype and the paternal genotype for each polymorphic nucleic acid target are not known, and wherein each of the polymorphic nucleic acid targets have a minor allele frequency of at least 40% in the general population, and wherein at least five of the polymorphic nucleic acid targets are informative for measuring fetally-derived alleles in the sample;
   (b) sequencing the amplified nucleic acid targets by sequencing by synthesis to obtain sequence reads of the nucleic acid targets; and
   (c) measuring, from the sequence reads from (b), the fraction of fetally-derived alleles of the nucleic acid targets.

2. The method of claim 1, wherein the sequencing by synthesis method comprises about 36 cycles or about 27 cycles.

3. The method of claim 1, wherein the sample nucleic acid is cell-free DNA.

4. The method of claim 1, wherein the sample nucleic acid is from plasma or serum.

5. The method of claim 1, wherein the the polymorphic nucleic acid targets of step (a) further comprise at least one single nucleotide polymorphism (SNP) selected from the group consisting of rs10413687, rs10949838, rs1115649, rs11632601, rs11971741, rs12660563, rs13155942, rs1444647, rs1572801, rs17773922, rs1797700, rs1921681, rs1958312, rs196008, rs2001778, rs2323659, rs2427099, rs243992, rs251344, rs254264, rs2827530, rs290387, rs321949, rs348971, rs390316, rs3944117, rs425002, rs432586, rs444016, rs4453265, rs447247, rs4745577, rs484312, rs499946, rs500090, rs500399, rs505349, rs505662, rs517914, rs522810, rs537330, rs539344, rs551372, rs567681, rs585487, rs619208, rs622994, rs677866, rs683922, rs686851, rs6941942, rs7045684, rs7176924, rs870429, rs949312, rs9563831, rs970022, rs985462, or all of the polymorphic nucleic acid targets amplified in a single reaction comprise at least one single nucleotidepolymorphism (SNP) selected from the group consisting of rs1005241, rs1006101, rs10745725, rs10776856, rs10790342, rs11076499, rs11103233, rs11133637, rs11974817, rs12102203, rs12261, rs12460763, rs12543040, rs12695642, rs13137088, rs13139573, rs1327501, rs13438255, rs1360258, rs1421062, rs1432515, rs1452396, rs1518040, rs16853186, rs1712497, rs1792205, rs1863452, rs1991899, rs2022958, rs2099875, rs2108825, rs2132237, rs2195979, rs2248173, rs2250246, rs2268697, rs2270893, rs244887, rs2736966, rs2851428, rs2906237, rs2929724, rs3742257, rs3764584, rs3814332, rs4131376, rs4363444, rs4461567, rs4467511, rs4559013, rs4714802, rs4775899, rs4817609, rs488446, rs4950877, rs530913, rs6020434, rs6442703, rs6487229, rs6537064, rs654065, rs6576533, rs6661105, rs669161, rs6703320, rs675828, rs6814242, rs6989344, rs7120590, rs7131676, rs7214164, rs747583, rs768255, rs768708, rs7828904, rs7899772, rs7900911, rs7925270, rs7975781, rs8111589, rs849084, rs873870, rs9386151, rs9504197, rs9690525, and rs9909561.

* * * * *